United States Patent
Zhuo et al.

(10) Patent No.: US 11,130,769 B2
(45) Date of Patent: Sep. 28, 2021

(54) SPIRO-SULFONAMIDE DERIVATIVES AS INHIBITORS OF MYELOID CELL LEUKEMIA-1 (MCL-1) PROTEIN

(71) Applicant: Prelude Therapeutics Incorporated, Wilmington, DE (US)

(72) Inventors: Jincong Zhuo, Garnet Valley, PA (US); Raul Leal, Newark, DE (US); Rupa Shetty, Blue Bell, PA (US); Juan Luengo, Phoenixville, PA (US); Andrew Paul Combs, Kenneth Square, PA (US); Peng Wei, Hockessin, DE (US)

(73) Assignee: Prelude Therapeutics, Incorporated, Wilmington, DE (US)

( * ) Notice: Subject to any disclaimer, the term of this patent is extended or adjusted under 35 U.S.C. 154(b) by 0 days.

(21) Appl. No.: 16/679,105

(22) Filed: Nov. 8, 2019

(65) Prior Publication Data

US 2020/0148705 A1    May 14, 2020

Related U.S. Application Data

(60) Provisional application No. 62/758,202, filed on Nov. 9, 2018, provisional application No. 62/907,451, filed on Sep. 27, 2019, provisional application No. 62/909,635, filed on Oct. 2, 2019.

(51) Int. Cl.
| | |
|---|---|
| A61K 31/553 | (2006.01) |
| A61P 35/00 | (2006.01) |
| C07D 498/10 | (2006.01) |
| C07D 498/20 | (2006.01) |
| C07D 513/10 | (2006.01) |
| C07D 513/20 | (2006.01) |
| C07D 515/10 | (2006.01) |
| C07D 515/20 | (2006.01) |
| C07D 267/16 | (2006.01) |
| C07D 413/06 | (2006.01) |
| C07D 413/12 | (2006.01) |
| C07D 417/12 | (2006.01) |

(52) U.S. Cl.
CPC ......... *C07D 515/10* (2013.01); *C07D 267/16* (2013.01); *C07D 413/06* (2013.01); *C07D 413/12* (2013.01); *C07D 417/12* (2013.01); *C07D 513/10* (2013.01); *C07D 513/20* (2013.01)

(58) Field of Classification Search
CPC ..... A61K 31/553; A61P 35/00; C07D 498/10; C07D 498/20; C07D 513/10; C07D 513/20; C07D 515/10; C07D 515/20
See application file for complete search history.

(56) References Cited

FOREIGN PATENT DOCUMENTS

| WO | 2016033486 A1 | 3/2016 |
| WO | 2017147410 A1 | 8/2017 |
| WO | 2018183418 A1 | 10/2018 |

OTHER PUBLICATIONS

Boezio et al., "1,2,4-Triazolsulfone: A novel isosteric replacement of acylsulfonamides in the context of Nav 1.7 Inhibition" Bioorganic & Medicinal Chemistry Letters, XP085402234, vol. 28, 2018, pp. 2103-2108.
International Search Report and Written Opinion issued in PCT/US2019/060638, dated Feb. 27, 2020.
Caenepeel et al., "AMG 176, a Selective MCL1 Inhibitor, is Effective in Hematologic Cancer Models Alone and in Combination with Established Therapies" Cancer Discovery, Dec. 2018, pp. 1582-1597.

*Primary Examiner* — Brenda L Coleman
(74) *Attorney, Agent, or Firm* — BakerHostetler

(57) ABSTRACT

The disclosure is directed to compounds of Formula I

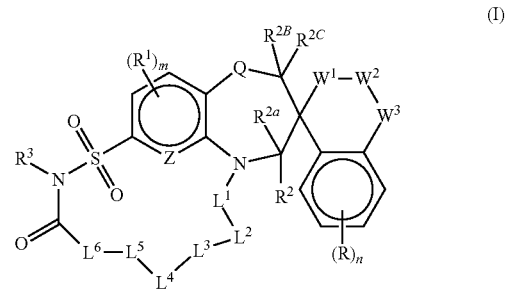

Pharmaceutical compositions comprising compounds of Formula I as well as methods of their use and preparation, are also described.

31 Claims, 1 Drawing Sheet

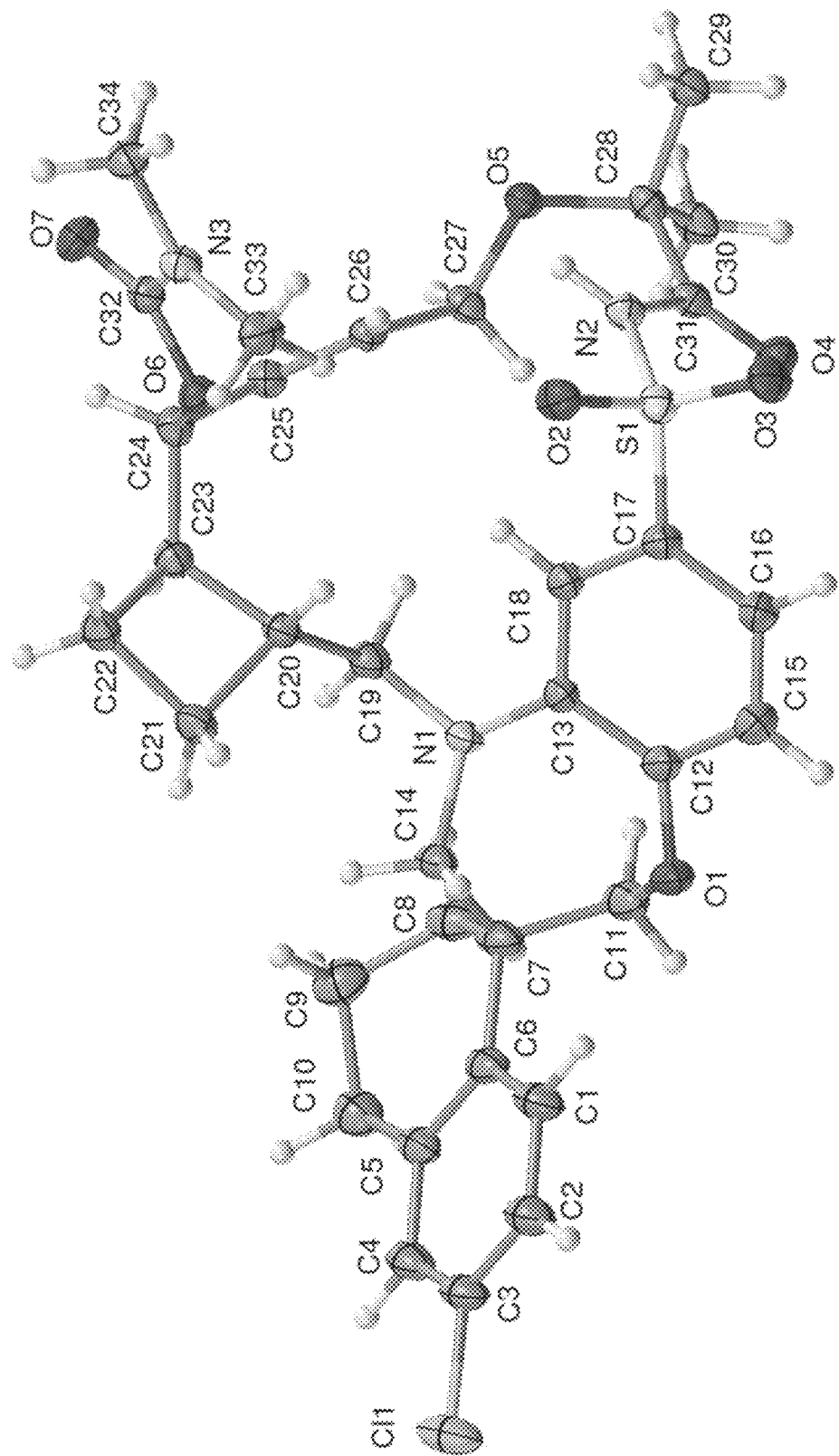

SPIRO-SULFONAMIDE DERIVATIVES AS INHIBITORS OF MYELOID CELL LEUKEMIA-1 (MCL-1) PROTEIN

CROSS-REFERENCE TO RELATED APPLICATIONS

This application claims the benefit of priority to U.S. Provisional Application No. 62/758,202, filed on Nov. 9, 2018; U.S. Provisional Application No. 62/907,451, filed on Sep. 27, 2019; and U.S. Provisional Application No. 62/909,635, filed on Oct. 2, 2019. Each of these applications is incorporated by reference in its entirety herein.

TECHNICAL FIELD

The disclosure is directed to MCL-1 inhibitors and methods of their use.

BACKGROUND

Apoptosis (programmed cell death) is a highly conserved cellular process that is required for embryonic development and normal tissue homeostasis (Ashkenazi A. et al., Nat. Rev. Drug Discov. 2017, 16, 273-284). Apoptotic-type cell death involves morphological changes such as condensation of the nucleus, DNA fragmentation as well as biochemical phenomena such as the activation of caspases which cause damage to key structural components of the cell, resulting in its disassembly and death. Regulation of the process of apoptosis is complex and involves the activation or repression of several intracellular signaling pathways (Cory S. et al., Nature Review Cancer 2002, 2, 647-656; Thomas L. W. et al., FEBS Lett. 2010, 584, 2981-2989; Adams J. M. et al., Oncogene 2007, 26, 1324-1337)

The Bcl-2 protein family, which includes both pro-apoptotic and anti-apoptotic members, plays a pivotal role in the regulation of the apoptosis process (Youle R. J. et al., Nat. Rev. Mol. Cell Biol. 2008, 9, 47-59; Kelly G. L. et al., Adv. Cancer Res. 2011, 111, 39-96). Bcl-2, Bcl-XL, Bcl-W, Mcl-1 and A1 are anti-apoptotic proteins and they share a common BH regions. In contrast, the pro-apoptotic family members are divided into two groups. The multi-region pro-apoptotic proteins, such as Bax, Bak and Bok, are conventionally thought to have BH1-3 regions, whereas the BH3-only proteins are proposed to share homology in the BH3 region only. Members of BH3-only proteins include Bad, Bim, Bid, Noxa, Puma, Bik/Blk, Bmf, Hrk/DP5, Beclin-1 and Mule (Xu G. et al., Bioorg. Med. Chem. 2017, 25, 5548-5556; Hardwick J. M. et al., Cell. 2009, 138, 404; Reed J. C., Cell Death Differ. 2018, 25, 3-6; Kang M. H. et al., Clin Cancer Res 2009, 15, 1126-1132). The pro-apoptotic members (such as BAX and BAK), upon activation, form a homo-oligomer in the outer mitochondrial membrane that leads to pore formation and the escape of mitochondrial contents, a step into triggering apoptosis. Antiapoptotic members of the Bcl-2 family (such as Bcl-2, Bcl-XL, and Mcl-1) block the activity of BAX and BAK. In normal cells, this process is tightly regulated. Abnormal cells can dysregulate this process to avoid cell death. One of the ways that cancer cells can accomplish this is by upregulating the antiapoptotic members of the Bcl-2 family of proteins. Overexpression or up-regulation of the anti-apoptotic Bcl-2 family proteins enhance cancer cell survival and cause resistance to a variety of anticancer therapies.

Aberrant expression or function of the proteins responsible for apoptotic signaling contributes to numerous human pathologies including auto-immune diseases, neurodegeneration (such as Parkinson's disease, Alzheimer's disease and ischaemia), inflammatory diseases, viral infections and cancer (such as colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, pancreatic cancer, etc.) (Hanahan D. et al., Cell 2000, 100. 57-70). Herein, it is prospective to target key apoptosis regulators for cancer treatment (Kale J. et al., Cell Death Differ. 2018, 25, 65-80; Vogler M. et al., Cell Death Differ. 2009, 16, 360-367).

By overexpressing one or more of these pro-survival proteins, cancer cells can evade elimination by normal physiological processes and thus gain a survival advantage. Myeloid Cell Leukemia-1 (Mcl-1) is a member of the pro-survival Bcl-2 family of proteins. Mcl-1 has the distinct trait of being essential for embryonic development as well as the survival of all hematopoietic lineages and progenitor populations. Mcl-1 is one of the most common genetic aberrations in human cancer and is highly expressed in many tumor types. Mcl-1 overexpression in human cancers is associated with high tumor grade and poor survival (Beroukhim R. et al., Nature 2010, 463, 899-905). Mcl-1 overexpression prevents cancer cells from undergoing programmed cell death (apoptosis), allowing the cells to survive despite widespread genetic damage. Further, its amplification is associated with both intrinsic and acquired resistance to a wide variety of antitumorigenic agents including chemotherapeutic agents such as microtubule binding agents, paclitaxel and gemcitabine, as well as apoptosis-inducing agents such as TRAIL, the Bcl-2 inhibitor, venetoclax, and the Bcl-2/Bcl-XL dual inhibitor navitoclax. Not only do gene silencing approaches that specifically target Mcl-1 circumvent this resistance phenotype, but certain cancer cell types frequently undergo cell death in response to Mcl-1 silencing, indicating a dependence on Mcl-1 for survival. Consequently, approaches that inhibit Mcl-1 function are of considerable interest for cancer therapy (Wertz I. E et al., Nature 2011, 471, 110-114; Zhang B. et al., Blood 2002, 99, 1885-1893).

SUMMARY

The disclosure is directed to compounds of Formula I:

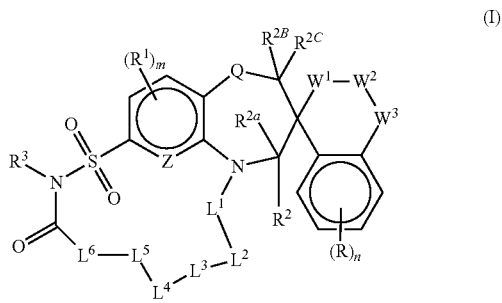

or a pharmaceutically acceptable salt or solvate thereof; wherein
Z is CH or N;
Q is —O—, —S—, —S(O)—, or —S(O)$_2$—;
the moiety —W$^1$—W$^2$—W$^3$— is —CR$^2$R$^{2A}$—CR$^2$R$^{2A}$—CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —NR$^{2B}$—CR$^{2B}$R$^{2C}$—

$CR^2R^{2A}$—, —$CR^2R^{2A}$—$CR^{2B}R^{2C}$—$NR^{2B}$, —S—$CR^{2B}R^{2C}$—$CR^2R^{2A}$, or —$CR^2R^{2A}$—$CR^{2B}R^{2C}$—S—;

$L^1$ is absent or is optionally substituted —$C_1$-$C_6$alkylene-;

$L^2$ is absent or is optionally substituted cycloalkylene, optionally substituted heterocycloalkylene, optionally substituted arylene, or optionally substituted heteroarylene;

$L^3$ is absent, or is —$(CR^4R^5)_p$—, —$(CR^4R^5)_p$O—, —O—, —S—, —S(O)—, —S(O)$_2$—, —C(=O)—, —$NR^6$—, —OC(=O)—, —C(=O)O—, —$NR^{6A}$C(O)—, —C(=O)$NR^{6A}$—, —OC(=O)N($R^{6A}$)—, —$NR^{6A}$C(O)O—, —S(=O)$NR^{6A}$—, —$NR^{6A}$S(O)—, —S(=O)$_2NR^{6A}$—, or —$NR^{6A}$S(O)$_2$—;

$L^4$ is absent, or is —$(CR^4R^5)_p Q^1(CR^4R^5)_q$—, wherein $Q^1$ is absent, —$CR^{4A}$=$CR^{4B}$—, —O—, —S—, —S(O)—, —S(O)$_2$—, —C(=O)—, —$NR^6$—, —OC(=O)—, —C(=O)O—, —$NR^{6A}$C(O)—, —C(=O)$NR^{6A}$—, —$NR^{6A}$C(O)$R^{6B}$—, —OC(=O)N($R^{6A}$)—, —$NR^{6A}$C(O)O—, —S(=O)$NR^{6A}$—, —$NR^{6A}$S(O)—, —S(=O)$_2NR^{6A}$—, or —$NR^{6A}$S(O)$_2$—; or is —$(CR^4R^5)_p$—$(CR^{4A}$=$CR^{4B})$—$(CR^4R^5)_q$—O—;

$L^5$ is absent, or is —$C_1$-$C_6$ alkylene-, —$C_2$-$C_6$ alkenylene-, —$C_2$-$C_6$ alkynylene-, -arylene-, -heteroarylene-, -cycloalkenylene-, -cycloalkylene-, -heterocycloalkylene-, wherein said $C_1$-$C_6$ alkylene, $C_2$-$C_6$ alkenylene, $C_2$-$C_6$ alkynylene, arylene, heteroarylene, cycloalkenylene, cycloalkylene, or heterocycloalkylene groups are optionally substituted;

$L^6$ is absent, or is —$(CR^7R^8)_s$—, —$(CR^7R^8)_sO(CR^7R^8)_t$—, —$(CR^7R^8)_sNR^9(CR^7R^8)_t$—, —$(CR^7R^8)_sS(CR^7R^8)_t$—, —$(CR^7R^8)_sS(O)(CR^7R^8)_t$—, —$(CR^7R^8)_sS(O)_2(CR^7R^8)_t$—, —$(CR^7R^8)_sNR^{9A}C(O)(CR^7R^8)_t$—, —$(CR^7R^8)_sOC(O)NR^{9A}(CR^7R^8)_t$—, —$(CR^7R^8)_sNR^{9A}C(O)O(CR^7R^8)_t$—, —$(CR^7R^8)_sNR^{9A}C(O)NR^{9B}(CR^7R^8)_t$—, —$(CR^7R^8)_sNR^{9A}S(O)(CR^7R^8)_t$—, —$(CR^7R^8)_sNR^{9A}S(O)_2(CR^7R^8)_t$—; —$(CR^7R^8)_s$—$CR^{4A}$=$CR^{4B}$—$(CR^7R^8)_t$—, —$(CR^7R^8)_sC(=O)(CR^7R^8)_t$—; —$(CR^7R^8)_sC(=O)(CR^7R^8)_t$-O—, or —$(CR^7R^8)_sC(=O)(CR^7R^8)_t$-$NR^6$—;

each n is independently 0-3;
each m is independently 0-2;
each p is independently 0-4;
each q is independently 0-4;
each s is independently 0-3;
each t is independently 0-4;
each R is independently -D, -halo, —CN, —$NO_2$, —$C_1$-$C_6$alkyl, —$C_2$-$C_6$alkenyl, —$C_1$-$C_6$alkoxy, -cycloalkyl, —$OR^a$, —$SR^a$, —$C(O)R^b$, —$C(O)OR^a$, —$NR^cR^d$, —$C(O)NR^cR^d$, or —$S(O)_2R^a$; wherein said —$C_1$-$C_6$alkyl, —$C_2$-$C_6$alkenyl, —$C_1$-$C_6$alkoxy, or -cycloalkyl is optionally substituted;

each $R^1$ is independently -D, -halo, —CN, —$NO_2$, —$C_1$-$C_6$alkyl, —$C_2$-$C_6$alkenyl, —$C_2$-$C_6$alkynyl, —$OR^a$, —$SR^a$, —$NR^cR^d$, —$C(O)R^b$, —$OC(O)R^b$, —$C(O)OR^a$, —$C(O)NR^cR^d$, —$S(O)_2R^a$; -aryl, -heteroaryl, -cycloalkyl, or -heterocycloalkyl, wherein said —$C_1$-$C_6$alkyl, —$C_2$-$C_6$alkenyl, —$C_2$-$C_6$alkynyl, -cycloalkyl, -heterocycloalkyl, -aryl, or -heteroaryl is optionally substituted;

each $R^2$, $R^{2A}$, or $R^{2a}$ is independently H, D, halo, $OR^a$, optionally substituted $C_1$-$C_6$alkyl, or $R^2$ and $R^{2A}$ that are attached to the same carbon atom may, together with the carbon atom to which they are both attached, form an optionally substituted cycloalkyl ring;

each $R^{2B}$ and $R^{2C}$ is independently H, D, optionally substituted $C_1$-$C_6$alkyl, or $R^{2B}$ and $R^{2C}$ may, together with the carbon atom to which they are both attached, form an optionally substituted cycloalkyl ring;

$R^3$ is H, D, —$C_1$-$C_6$alkyl, —$C_3$-$C_6$alkenyl, —$C_3$-$C_6$alkynyl, cycloalkyl, heterocycloalkyl, $C(O)R^b$, $C(O)OR^a$, or $C(O)NR^cR^d$; wherein said $C_1$-$C_6$alkyl, —$C_3$-$C_6$alkenyl, —$C_3$-$C_6$alkynyl, cycloalkyl, or heterocycloalkyl is optionally substituted; or $R^3$ is —$C_1$-$C_6$alkyl substituted at the $C_1$ carbon atom with —$OR^{3A}$ wherein $R^{3A}$ is $C_1$-$C_6$alkyl, —$PO_3H$, —$C(O)OR^{2C}$, or —$C(O)NR^{3A}R^{3B}$ wherein $R^{3A}$ and $R^{3B}$ are each independently H, D, optionally substituted $C_1$-$C_6$alkyl;

each $R^4$ or $R^7$ is independently H, D, halo, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^a$, —$C(O)OR^a$, —$C(O)NR^cR^d$, —$S(O)R^b$, or —$S(O)_2R^b$, wherein said $C_1$-$C_6$alkyl, —$C_2$-$C_6$alkenyl, —$C_2$-$C_6$alkynyl, aryl, heteroaryl, cycloalkyl, cycloalkenyl, heterocycloalkenyl, or heterocycloalkyl is optionally substituted;

each $R^{4A}$ or $R^{4B}$ is independently H, D, -Me, —$CF_3$ or —F;

each $R^5$ or $R^8$ is independently H, D, fluoro, —$C_1$-$C_6$alkyl, —$C_2$-$C_6$alkenyl, —$C_2$-$C_6$alkynyl, —$C(O)R^b$, —$C(O)OR^a$, —$C(O)NR^cR^d$, aryl, heteroaryl, cycloalkyl, cycloalkenyl, heterocycloalkyl, or heterocycloalkenyl, wherein said $C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl is optionally substituted;

or $R^4$ and $R^5$ together with the C atom to which they are attached form a cycloalkyl, cycloalkenyl, heterocycloalkyl, or heterocycloalkenyl ring, each optionally substituted;

or an $R^4$ and an $R^5$ attached to adjacent carbon atoms, together with the C atoms to which they are attached, form a cycloalkyl, cycloalkenyl, heterocycloalkyl, or heterocycloalkenyl ring, each optionally substituted;

or $R^7$ and $R^8$ together with the C atom to which they are both attached form a cycloalkyl, cycloalkenyl, heterocycloalkyl, or heterocycloalkenyl ring, each optionally substituted, each optionally substituted;

or an $R^7$ and an $R^8$ attached to adjacent carbon atoms, together with the C atoms to which they are attached, form a cycloalkyl, cycloalkenyl, heterocycloalkyl, or heterocycloalkenyl ring, each optionally substituted;

each $R^6$ or $R^9$ is independently H, D, —$C_1$-$C_6$alkyl, —$C_2$-$C_6$alkenyl, —$C_2$-$C_6$alkynyl, —$OC_1$-$C_6$alkyl, —$C(O)R^b$, —$C(O)OR^a$, —$C(O)NR^cR^d$, —$S(O)R^b$ or —$S(O)_2R^b$, aryl, heteroaryl, cycloalkyl, cycloalkenyl, heterocycloalkyl, or heterocycloalkenyl group, wherein said $C_1$-$C_6$alkyl, —$C_2$-$C_6$alkenyl, —$C_2$-$C_6$alkynyl, —$OC_1$-$C_6$alkyl, aryl, heteroaryl, cycloalkyl, cycloalkenyl, heterocycloalkyl, or heterocycloalkenyl ring, is optionally substituted;

or $R^9$ together with an $R^7$ or an $R^8$ forms an optionally substituted heterocyclic alkylene;

each $R^{6A}$, $R^{6B}$, $R^{9A}$, or $R^{9B}$ is independently H, D, —$C_1$-$C_6$alkyl, —$C_2$-$C_6$alkenyl, —$C_2$-$C_6$alkynyl, cycloalkyl, cycloalkenyl, heterocycloalkyl, or heterocycloalkenyl, wherein said $C_1$-$C_6$alkyl, —$C_2$-$C_6$alkenyl, —$C_2$-$C_6$alkynyl, cycloalkyl, cycloalkenyl, heterocycloalkyl, or heterocycloalkenyl is optionally substituted;

or $R^{6A}$ and $R^{6B}$ together with the N atoms to which they are attached form an optionally substituted heterocycloalkyl or heterocycloalkenyl ring;

or $R^{9A}$ and $R^{9B}$ together with the N atoms to which they are attached form an optionally substituted heterocycloalkyl or heterocycloalkenyl ring;

each $R^a$ is independently H, D, —C(O)$R^b$, —C(O)O$R^c$, —C(O)N$R^cR^d$, —P(O$R^c$)$_2$, —P(O)$R^cR^b$, P(O)O$R^c$O$R^b$, —S(O)$R^b$, —S(O)N$R^cR^d$, —S(O)$_2R^b$, —S(O)$_2$N$R^cR^d$, —B(O$R^c$)(O$R^b$), Si$R^b_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl wherein said $C_1$-$C_{10}$ alkyl, $C_2$-$C_{10}$ alkenyl, $C_2$-$C_{10}$ alkynyl, aryl, cycloalkyl, cycloalkenyl, heteroaryl, heterocycloalkyl, or heterocycloalkenyl is optionally substituted;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl wherein said —$C_1$-$C_6$ alkyl, —$C_2$-$C_6$ alkenyl, —$C_2$-$C_6$ alkynyl, aryl, cycloalkyl, cycloalkeneyl, heteroaryl, heterocycloalkyl, or heterocycloalkenyl is optionally substituted;

each $R^c$ or $R^d$ is independently H, D, —$C_1$-$C_{10}$ alkyl, —$C_2$-$C_6$ alkenyl, —$C_2$-$C_6$ alkynyl, —O$C_1$-$C_6$alkyl, —O-cycloalkyl, aryl, heteroaryl, cycloalkyl, cycloalkenyl, heteroaryl, heterocycloalkyl, or heterocycloalkenyl, wherein said $C_1$-$C_{10}$ alkyl, $C_2$-$C_6$ alkenyl, $C_2$-$C_6$ alkynyl, —O$C_1$-$C_6$alkyl, —O-cycloalkyl, aryl, heteroaryl, cycloalkyl, cycloalkenyl, heterocycloalkyl, or heterocycloalkenyl are each optionally substituted;

or $R^c$ and $R^d$, together with the N atom to which they are both attached, form an optionally substituted monocyclic or multicyclic heterocycloalkyl, or optionally substituted monocyclic or multicyclic heterocycloalkenyl group.

Stereoisomers of the compounds of Formula I and the pharmaceutical salts and solvates thereof, are also contemplated, described, and encompassed herein. Methods of using compounds of Formula I are described, as well as pharmaceutical compositions including the compounds of Formula I.

BRIEF DESCRIPTION OF THE DRAWINGS

The FIGURE shows an ORTEP representation of the compound of Example 34.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like.

The term "haloalkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group, wherein one or more of the hydrogen atoms in the group have been replaced by a halogen atom. Examples of haloalkyl groups include trifluoromethyl (—$CF_3$, $C_1$haloalkyl), trifluoroethyl (—$CH_2CF_3$, $C_2$haloalkyl), and the like.

The term "alkylene" when used alone or as part of a substituent group, refers to an alkyl diradical, i.e., a straight- or branched-chain hydrocarbon group having from 1 to 12 carbon atoms ("$C_1$-$C_{12}$"), preferably 1 to 6 carbons atoms ("$C_1$-$C_6$"), in the group, wherein the group is directly attached to two other variable groups.

As used herein, "cycloalkyl" refers to non-aromatic cyclic hydrocarbons including cyclized alkyl and/or alkenyl groups. Cycloalkyl groups thus also encompass cycloalkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (C3-10). In some embodiments, the cycloalkyl is a C3-10 monocyclic or bicyclic cycloalkyl. In some embodiments, the cycloalkyl is a $C_{3-10}$ monocyclic or bicyclic cycloalkyl which is optionally substituted by $CH_2F$, $CHF_2$, $CF_3$, and $CF_2CF_3$. In some embodiments, the cycloalkyl is a $C_{3-7}$ monocyclic cycloalkyl. In some embodiments, the cycloalkyl is a C4-10 spirocycle or bridged cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl. In some embodiments, cycloalkyl are cyclic-containing, non-aromatic hydrocarbon groups having from 3 to 12 carbon atoms ("$C_3$-$C_{12}$"), preferably from 3 to 6 carbon atoms ("$C_3$-$C_6$"). Examples of cycloalkyl groups include, for example, cyclopropyl ($C_3$; 3-membered), cyclobutyl ($C_4$; 4-membered), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "cycloalkylene" when used alone or as part of a substituent group refers to a cycloalkyl diradical, i.e., a cyclic-containing, non-aromatic hydrocarbon group having from 3 to 14 carbon atoms ("$C_3$-$C_{14}$"; or 3-14 membered), for example 3 to 12 carbon atoms ("$C_3$-$C_{12}$"), preferably from preferably from 3 to 7 carbon atoms ("$C_3$-$C_7$", or 3-7 membered) or 3 to 6 carbon atoms ("$C_3$-$C_6$"), wherein the group is directly attached to two other variable groups. Cycloalkylene groups include spirocycloalkylene groups.

The term "cycloalkenylene" refers to a cycloalkenylene diradical.

The term "spirocycloalkyl" when used alone or as part of a substituent group refers to a non-aromatic hydrocarbon group containing two cycloalkyl rings, and wherein the two cycloalyl rings share a single carbon atom in common.

The term "spirocycloalkylene" when used alone or as part of a substituent group refers to a spirocycloalkyl diradical, i.e., a non-aromatic hydrocarbon group containing two cycloalkyl rings, and wherein the two cycloalyl rings share a single carbon atom in common, and wherein the group is directly attached to two other variable groups.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)2, etc.). Heterocycloalkyl groups include monocyclic and polycyclic (e.g., having 2 fused rings) systems. Included in heterocycloalkyl are monocyclic and polycyclic 3-10, 4-10, 3-7, 4-7, and 5-6 membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

In some embodiments, heterocycloalkyl refers to any three to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "heterocycloalkylene" when used alone or as part of a substituent group refers to a heterocycloalkyl diradical. In some embodiments heterocycloalkylene any three to ten membered monocyclic or bicyclic, saturated ring structure containing at least one heteroatom selected from the group consisting of O, N and S, wherein the ring structure is directly attached to two other variable groups.

In some embodiments, the term "spiroheterocycloalkyl" when used alone or as part of a substituent group refers to a non-aromatic group containing two rings, at least one of which is a heterocycloalkyl ring, and wherein the two rings share a single carbon atom in common.

In some embodiments, the term "spirocycloalkylene" when used alone or as part of a substituent group refers to a spirocycloalkyl diradical. In some embodiments, spirocycloalkylene is a non-aromatic group containing two rings, at least one of which is a heterocycloalkyl ring, and wherein the two rings share a single carbon atom in common, and wherein the group is directly attached to two other variable groups.

The term "alkenyl" when used alone or as part of a substituent group refers to a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon double bond. Examples of alkenyl groups include vinyl (—CH=CH$_2$; $C_2$alkenyl), allyl (—CH$_2$—CH=CH$_2$; $C_3$alkenyl), propenyl (—CH=CHCH$_3$; $C_3$alkenyl); isopropenyl (—C(CH$_3$)=CH$_2$; $C_3$alkenyl), butenyl (—CH=CHCH$_2$CH$_3$; $C_4$alkenyl), sec-butenyl (—C(CH$_3$)=CHCH$_3$; $C_4$alkenyl), iso-butenyl (—CH=C(CH$_3$)$_2$; $C_4$alkenyl), 2-butenyl (—CH$_2$CH=CHCH$_3$; $C_4$alkyl), pentenyl (CH=CHCH$_2$CH$_2$CH$_3$ or CH$_2$=CHCH$_2$CH$_2$CH$_2$—; $C_5$alkenyl), and the like.

The term "alkenylene" when used alone or as part of a substituent group refers to a alkenyl diradical, i.e., a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon double bond, and wherein the group is directly attached to two other variable groups.

The term "alkynyl" when used alone or as part of a substituent group refers to a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon triple bond. Examples of alkynyl groups include ethynyl (—C≡CH; $C_2$alkynyl), propragyl (—CH$_2$—CH≡CH; $C_3$alkynyl), and the like.

The term "alkynylene" when used alone or as part of a substituent group refers to an alkynyl diradical, i.e., a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon triple bond, and wherein the group is directly attached to two other variable groups.

The term "aryl" when used alone or as part of a substituent group refers to a monocyclic all carbon aromatic ring or a multicyclic all carbon ring system wherein the rings are aromatic. Thus, aryl also includes multiple condensed ring systems (e.g., ring systems comprising 2, 3 or 4 aryl rings) having about 9 to 14 carbon atoms. In some embodiments, "aryl" refers to a mono- or bicyclic-aromatic hydrocarbon ring structure having 6 or 10 carbon atoms in the ring, wherein one or more of the carbon atoms in the ring is optionally substituted. Exemplary substituents include halogen atoms, —$C_1$-$C_3$ alkyl groups, and $C_1$-$C_3$haloalkyl groups. Halogen atoms include chlorine, fluorine, bromine, and iodine. $C_1$-$C_3$haloalkyl groups include, for example, —$CF_3$, —$CH_2CF_3$, and the like.

The term "arylene" when used alone or as part of a substituent group refers to an aryl diradical. In some embodiments, "arylene" refers to a mono- or bicyclic-aromatic hydrocarbon ring structure having 6 or 10 carbon atoms in the ring, wherein one or more of the carbon atoms in the ring is optionally substituted, and wherein the ring structure is directly attached to two other variable groups.

The term "heteroaryl" when used alone or as part of a substituent group, the term "heteroaryl" as used herein refers to a monocyclic aromatic ring that has at least one atom other than carbon in the ring, wherein the atom is selected from the group consisting of oxygen, nitrogen and sulfur; "heteroaryl" also includes multicyclic ring systems that have at least one such aromatic ring. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. "Heteroaryl" also includes multiple condensed ring systems (e.g., ring systems comprising 2, 3 or 4 rings) wherein a heteroaryl group is condensed with one or more rings selected from heteroaryls or aryls. Thus, a heteroaryl (a single aromatic ring or multiple condensed ring system) has about 1-20 carbon atoms and about 1-6 heteroatoms within the heteroaryl ring system. A heteroaryl (a monocyclic aromatic ring or multicyclic condensed ring system) can also have about 5 to 12 or about 5 to 10 members within the heteroaryl ring. The rings of a multicyclic ring system can be connected to each other via fused, spiro and bridged bonds when allowed by valency requirements. In some embodiments, "heteroaryl" refers to a mono- or bicyclic-aromatic ring structure including carbon atoms as well as up to four heteroatoms selected from nitrogen, oxygen, and sulfur. In such embodiments, heteroaryl rings can include a total of 5, 6, 9, or 10 ring atoms. The heteroaryl moiety can be optionally substituted. Exemplary substituents include halogen atoms; —$C_1$-$C_3$ alkyl groups, and $C_1$-$C_3$haloalkyl groups. Halogen atoms include chlorine, fluorine, bromine, and iodine.

The term "heteroarylene" when used alone or as part of a substituent group refers to a heteroaryl diradical. In some embodiments, heteroarylene is a mono- or bicyclic-aromatic ring structure including carbon atoms as well as up to four heteroatoms selected from nitrogen, oxygen, and sulfur, wherein the ring structure is directly attached to two other variable groups.

The term "halo" refers to a halogen substituent (i.e., —F, —Cl, —Br, or —I).

The term "oxo" refers to an oxygen substituent that is connected by a double bond (i.e., =O).

The term "alkoxy" when used alone or as part of a substituent group refers to an oxygen radical attached to an alkyl group by a single bond. Examples of alkoxy groups include methoxy (—$OCH_3$), ethoxy (—$OCH_2CH_3$), isopropoxy (—$OCH(CH_3)_2$) and the like.

The term "haloalkoxy" when used alone or as part of a substituent group refers to an oxygen radical attached to a haloalkyl group by a single bond. Examples of haloalkoxy groups include —$OCF_3$, —$OCH_2CF_3$, —$OCH(CF_3)_2$, and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond. In some aspects, the $C_1$-$C_6$alk can be substituted with one or more substituents.

In some embodiments wherein a group is described as "optionally substituted" (e.g., when a $C_1$-$C_6$alkyl, —$C_1$-$C_6$alkylene-, $C_1$-$C_{10}$ alkyl, —$C_2$-$C_{10}$alkenyl, —$C_2$-$C_{10}$alkynyl, —$C_2$-$C_6$ alkenylene-, —$C_2$-$C_6$ alkynylene-, cycloalkyl, cycloalkylene, heterocycloalkyl, heterocycloalkylene, aryl, arylene, heteroaryl, or heteroarylene group is optionally substituted), the optional substituent may be one or more of D, halo, oxo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl-$NR^{c1}R^{d1}$, —$(CH_2CH_2O)_oC_1$-$C_6$alkyl wherein o is 1-10; $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, CN, $NO_2$, $N_3$, $OR^{a1}$, $SR^{a1}$, $C(O)R^{b1}$, $C(O)NR^{c1}R^{d1}$, —$CH_2C(O)NR^{c1}R^{d1}$, $C(O)OR^{a1}$, $OC(O)R^{b1}$, $OC(O)NR^{c1}R^{d1}$, —$NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, >SO(=$NR^{b1}$); $S(O)NR^{c1}R^{d1}$, $S(O)_2R^{b1}$, $NR^{c1}S(O)_2R^{b1}$, $S(O)_2NR^{c1}R^{d1}$; aryl, heteroaryl, spirocycloalkyl, spiroheterocycloalkyl, cycloalkyl, or heterocycloalkyl, wherein the aryl, heteroaryl, spirocycloalkyl, spiroheterocycloalkyl, cycloalkyl, or heterocycloalkyl are optionally substituted with D, halo, oxo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl-$NR^{c1}R^{d1}$, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, CN, $NO_2$, $N_3$, $OR^{a1}$, $SR^{a1}$, $C(O)R^{b1}$, $C(O)NR^{c1}R^{d1}$, —$CH_2C(O)NR^{c1}R^{d1}$, $C(O)OR^{a1}$, $OC(O)R^{b1}$, $OC(O)NR^{c1}R^{d1}$, —$NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$.

In these optional substituents, each $R^{a1}$ is independently H, D, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl, wherein said $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In these optional substituents each $R^{b1}$ is independently H, D, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl, wherein said $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In these optional substituents $R^{c1}$ or $R^{d}1$ is independently H, $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, $C_1$-$C_6$ haloalkoxy, hydroxyalkyl, cyanoalkyl, aryl, heteroaryl, $C(O)OR^{a1}$, $C(O)R^{b1}$, $S(O)_2R^{b1}$, alkoxyalkyl, and alkoxyalkoxy;

Alternatively, in some embodiments, these optional substituents $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, $C_1$-$C_6$ haloalkoxy, hydroxyalkyl, cyanoalkyl, aryl, heteroaryl, $C(O)OR^{a1}$, $C(O)R^{b1}$, $S(O)_2R^{b1}$, alkoxyalkyl, and alkoxyalkoxy;

In these optional substituents $R^{e1}$ is independently H, $C_1$-$C_6$ alkyl, $C_1$-$C_6$ haloalkyl, $C_2$-$C_6$ alkenyl, ($C_1$-$C_6$ alkoxy)-$C_1$-$C_6$ alkyl, $C_2$-$C_6$ alkynyl, aryl, cycloalkyl, heteroaryl, heterocycloalkyl, arylalkyl, cycloalkylalkyl, heteroarylalkyl, or heterocycloalkylalkyl.

In these optional substituents $R^{f1}$ is independently H, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, or heterocycloalkyl.

In these optional substituents $R^{g1}$ is independently H, CN, or $NO_2$.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I or Formula II as described herein, as well as their respective subgenera, which expression includes the stereoisomers (e.g., entaniomers, diastereomers) and constitutional isomers (e.g., tautomers) of compounds of Formula I or Formula II as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

In some aspects, the disclosure is directed to a compound of Formula I:

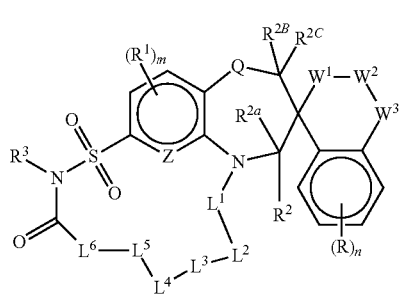

(I)

or a pharmaceutically acceptable salt or solvate thereof.

In some aspects, Z in Formula I is CH or N. In some embodiments, Z is CH. In other embodiments, Z is N.

In some aspects, Q in Formula I is —O—, —S—, —S(O)—, or —S(O)$_2$—. In some embodiments, Q is —O—. In some embodiments, Q is —S—. In some embodiments, Q is —S(O)—. In some embodiments, Q is —S(O)$_2$—.

In some aspects, the moiety —W$^1$—W$^2$—W$^3$ in Formula I is —CR$^2$R$^{2A}$—CR$^2$R$^{2A}$—CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —NR$^{2B}$—CR$^{2B}$R$^{2C}$—CR$^2$R$^{2A}$—, —CR$^2$R$^{2A}$—CR$^{2B}$R$^{2C}$—NR$^{2B}$—, —S—CR$^{2B}$R$^{2C}$—CR$^2$R$^{2A}$, or —CR$^2$R$^{2A}$—CR$^{2B}$R$^{2C}$—S—.

In some embodiments, the moiety —W$^1$—W$^2$—W$^3$ in Formula I is —CR$^2$R$^{2A}$—CR$^2$R$^{2A}$—CR$^2$R$^{2A}$—. In some embodiments, the moiety —W$^1$—W$^2$—W$^3$ in Formula I is —O—CR$^{2B}$R$^{2C}$—CR$^2$R$^{2A}$—. In some embodiments, the moiety —W$^1$—W$^2$—W$^3$ in Formula I —CR$^2$R$^{2A}$—CR$^{2B}$R$^{2C}$—O—. In some embodiments, the moiety —W$^1$—W$^2$—W$^3$ in Formula I is —NR$^{2B}$—CR$^{2B}$R$^{2C}$—CR$^2$R$^{2A}$—. In some embodiments, the moiety —W$^1$—W$^2$—W$^3$ in Formula I —CR$^2$R$^{2A}$—CR$^{2B}$R$^{2C}$—NR$^{2B}$—. In some embodiments, the moiety —W$^1$—W$^2$—W$^3$ in Formula I is —S—CR$^{2B}$R$^{2C}$—CR$^2$R$^{2A}$. In some embodiments, the moiety —W$^1$—W$^2$—W$^3$ in Formula I is —CR$^2$R$^{2A}$—CR$^{2B}$R$^{2C}$—S—.

In some aspects, L$^1$ in Formula I is absent, or is —C$_1$-C$_6$alkylene-, for example, —C$_1$alkylene, —C$_2$alkylene, —C$_3$alkylene, —C$_4$alkylene, —C$_5$alkylene, or —C$_6$alkylene, wherein the C$_1$-C$_6$alkylene is optionally substituted. In some embodiments, L$^1$ in Formula I is —C$_1$-C$_6$alkylene-, for example, —C$_1$alkylene, —C$_2$alkylene, —C$_3$alkylene, —C$_4$alkylene, —C$_5$alkylene, or —C$_6$alkylene, wherein the C$_1$-C$_6$alkylene is optionally substituted. In some embodiments, L$^1$ in Formula I is optionally substituted —C$_1$alkylene. In some embodiments, L$^1$ in Formula I is —CH$_2$—.

In some aspects, L$^2$ in Formula I is optionally substituted cycloalkylene, optionally substituted heterocycloalkylene, optionally substituted arylene, or optionally substituted heteroarylene.

In some embodiments, L$^2$ in Formula I is 3-7 membered cycloalkylene, 4-7 membered heterocycloalkylene, arylene, or heteroarylene; each optionally substituted.

In some embodiments, L$^2$ is optionally substituted cycloalkylene or optionally substituted heterocycloalkylene.

In some embodiments, L$^2$ is optionally substituted cyclobutylene or optionally substituted pyrrolidinyl.

In some embodiments, L$^2$ in Formula I is 3-7 membered cycloalkylene, for example, 3-membered cycloalkylene, 4-membered cycloalkylene, 5-membered cycloalkylene, 6-membered cycloalkylene, or 7-membered cycloalkylene. In some embodiments, L$^2$ is 4-membered cycloalkylene. In some embodiments, L$^2$ is cyclobutylenyl.

In some embodiments, L$^2$ in Formula I is 4-7 membered heterocycloalkylene, for example, 4-membered heterocycloalkylene, 5-membered heterocycloalkylene, 6-membered heterocycloalkylene, or 7-membered heterocycloalkylene. In some embodiments, L$^2$ in Formula I is 5-membered heterocycloalkylene. In some embodiments, L$^2$ is pyrrolidinyl.

In other embodiments, L$^2$ in Formula I is heteroarylene. In some embodiments, the heteroarylene is pyrazolyl.

In some aspects, L$^3$ in Formula I is absent, or is —(CR$^4$R$^5$)$_p$—, —(CR$^4$R$^5$)$_p$O—, —O—, —S—, —S(O)—, —S(O)$_2$—, —C(=O)—, —NR$^6$—, —OC(=O)—, —C(=O)O—, —NR$^{6A}$C(O)—, —C(=O)NR$^{6A}$—, —OC(=O)N(R$^{6A}$)—, —NR$^{6A}$C(O)O—, —S(=O)NR$^{6A}$—, —NR$^{6A}$S(O)—, —S(=O)$_2$NR$^{6A}$—, or —NR$^{6A}$S(O)$_2$—.

In some embodiments, L$^3$ in Formula I is absent. In some embodiments, L$^3$ is —(CR$^4$R$^5$)$_p$—. In some embodiments, L$^3$ is —(CR$^4$R$^5$)$_p$O—. In some embodiments, L$^3$ is —O—. In some embodiments, L$^3$ is —S—. In some embodiments, L$^3$ is —S(O)—. In some embodiments, L$^3$ is —S(O)$_2$—. In some embodiments, L$^3$ is —C(=O)—. In some embodiments, L$^3$ is —NR$^6$—. In some embodiments, L$^3$ is —OC(=O)—. In some embodiments, L$^3$ is —C(=O)O—. In some embodiments, L$^3$ is —NR$^{6A}$C(O). In some embodiments, L$^3$ is —C(=O)NR$^{6A}$—. In some embodiments, L$^3$ is —OC(=O)N(R$^{6A}$)—. In some embodiments, L$^3$ is —NR$^{6A}$C(O)O—. In some embodiments, L$^3$ is —S(=O)NR$^{6A}$—. In some embodiments, L$^3$ is —NR$^{6A}$S(O)—. In some embodiments, L$^3$ is —S(=O)$_2$NR$^{6A}$—. In some embodiments, L$^3$ is —NR$^{6A}$S(O)$_2$—.

In some aspects, L$^4$ in Formula I is absent, or is —(CR$^4$R$^5$)$_p$Q$^1$(CR$^4$R$^5$)$_q$—, wherein Q$^1$ is absent, —CR$^{4A}$=CR$^{4B}$—, —O—, —S—, —S(O)—, —S(O)$_2$—, —C(=O)—, —NR$^6$—, —OC(=O)—, —C(=O)O—, —NR$^{6A}$C(O)—, —C(=O)NR$^{6A}$—, —NR$^{6A}$C(O)R$^{6B}$—, —OC(=O)N(R$^{6A}$)—, —NR$^{6A}$C(O)O—, —S(=O)NR$^{6A}$—, —NR$^{6A}$S(O)—, —S(=O)$_2$NR$^{6A}$—, or —NR$^{6A}$S(O)$_2$—; or is —(CR$^4$R$^5$)$_p$—(CR$^{4A}$=CR$^{4B}$)—(CR$^4$R$^5$)$_q$—O—.

In some embodiments, $L^4$ in Formula I is absent. In other embodiments, $L^4$ in Formula I is $-(CR^4R^5)_p-(CR^{4A}=CR^{4B})-(CR^4R^5)_q-$. In other embodiments, $L^4$ in Formula I is $-(CR^4R^5)_p-O-(CR^4R^5)_q-$. In other embodiments, $L^4$ in Formula I is $-(CR^4R^5)_p-S-(CR^4R^5)_q-$. In other embodiments, $L^4$ in Formula I is $-(CR^4R^5)_p-S(O)-(CR^4R^5)_q-$. In other embodiments, $L^4$ in Formula I is $-(CR^4R^5)_p-S(O)_2-(CR^4R^5)_q-$. In other embodiments, $L^4$ in Formula I is $-(CR^4R^5)_p-C(=O)-(CR^4R^5)_q-$. In other embodiments, $L^4$ in Formula I is $-(CR^4R^5)_p-NR^6-(CR^4R^5)_q-$. In other embodiments, $L^4$ in Formula I is $-(CR^4R^5)_p-OC(=O)-(CR^4R^5)_q-$. In other embodiments, $L^4$ in Formula I is $-(CR^4R^5)_p-C(=O)O-(CR^4R^5)_q-$. In other embodiments, $L^4$ in Formula I is $-(CR^4R^5)_p-NR^{6A}C(O)-(CR^4R^5)_q-$. In other embodiments, $L^4$ in Formula I is $-(CR^4R^5)_p-C(=O)NR^{6A}-(CR^4R^5)_q-$. In other embodiments, $L^4$ in Formula I is $-(CR^4R^5)_p-NR^{6A}C(O)R^{6B}-(CR^4R^5)_q-$. In other embodiments, $L^4$ in Formula I is $-(CR^4R^5)_p-OC(=O)N(R^{6A})-(CR^4R^5)_q-$. In other embodiments, $L^4$ in Formula I is $-(CR^4R^5)_p-NR^{6A}C(O)O-(CR^4R^5)_q-$. In other embodiments, $L^4$ in Formula I is $-(CR^4R^5)_p-S(=O)NR^{6A}-(CR^4R^5)_q-$. In other embodiments, $L^4$ in Formula I is $-(CR^4R^5)_p-NR^{6A}S(O)-(CR^4R^5)_q-$. In other embodiments, $L^4$ in Formula I is $-(CR^4R^5)_p-S(=O)_2NR^{6A}-(CR^4R^5)_q-$. In other embodiments, $L^4$ in Formula I is $-(CR^4R^5)_p-NR^{6A}S(O)_2-(CR^4R^5)_q-$. In some embodiments, $L^4$ is $-(CR^4R^5)_p-(CR^{4A}=CR^{4B})-(CR^4R^5)_q-O-$.

In some aspects, $L^5$ in Formula I is absent, or is $-C_1-C_6$ alkylene-, $-C_2-C_6$ alkenylene-, $-C_2-C_6$ alkynylene-, -arylene-, -heteroarylene-, -cycloalkenylene-, -cycloalkylene-, -heterocycloalkylene-, wherein the $C_1-C_6$ alkylene, $C_2-C_6$ alkenylene, $C_2-C_6$ alkynylene, arylene, heteroarylene, cycloalkenylene, cycloalkylene, or heterocycloalkylene groups are optionally substituted.

In some embodiments, $L^5$ in Formula I is absent. In other embodiments, $L^5$ in Formula I is $C_1-C_6$ alkylene, for example, $C_1$alkylene, $C_2$alkylene, $C_3$alkylene, $C_4$alkylene, $C_5$alkylene, or $C_6$alkylene, each optionally substituted.

In other embodiments, $L^5$ in Formula I is $C_2-C_6$ alkenylene, for example, $C_2$alkenylene, $C_3$alkenylene, $C_4$alkenylene, $C_5$alkenylene, or $C_6$alkenylene, each optionally substituted.

In other embodiments, $L^5$ in Formula I is $C_2-C_6$ alkynylene, for example, $C_2$alkynylene, $C_3$alkynylene, $C_4$alkynylene, $C_5$alkynylene, or $C_6$alkynylene, each optionally substituted.

In other embodiments, $L^5$ in Formula I is an optionally substituted arylene. In some embodiments, $L^5$ in Formula I is a 6- to 10-membered arylene, for example phenylene or naphthylene. In some embodiments, $L^5$ in Formula I is a phenylene.

In other embodiments, $L^5$ in Formula I is an optionally substituted heteroarylene. In some embodiments, $L^5$ in Formula I is a 5- to 10-membered heteroarylene, for example, pyrazolyl, thiazolyl, imidazolyl, or pyridinyl. In some embodiments, $L^5$ in Formula I is pyrazolyl. In other embodiments, $L^5$ in Formula I is thiazolyl. In other embodiments, $L^5$ in Formula I is imidazolyl. In some embodiments, $L^5$ in Formula I is pyridinyl.

In other embodiments, $L^5$ in Formula I is an optionally substituted cycloalkenylene. In some embodiments, $L^5$ in Formula I is a 3- to 12-membered cycloalkenylene, for example, cyclohexenyl.

In other embodiments, $L^5$ in Formula I is an optionally substituted cycloalkylene. In some embodiments, $L^5$ in Formula I is a 3- to 7-membered monocyclic cycloalkylene, for example, cyclopentanyl, cyclohexanyl, and the like. In some embodiments, $L^5$ in Formula I is cyclopentanyl.

In other embodiments, $L^5$ in Formula I is a 6- to 12-membered bicyclic cycloalkylene.

In other embodiments, $L^5$ in Formula I is an optionally substituted heterocycloalkylene. In some embodiments, $L^5$ in Formula I is an optionally substituted 3- to 7-membered monocyclic heterocycloalkylene group, for example, pyrrolidinyl, tetrahydrofuranyl, piperidinyl, piperazinyl, and the like. In some embodiments, $L^5$ in Formula I is pyrrolidinyl. In some embodiments, $L^5$ in Formula I is tetrahydrofuranyl. In some embodiments, $L^5$ in Formula I is piperidinyl. In some embodiments, $L^5$ in Formula I is piperazinyl.

In other embodiments, $L^5$ in Formula I is an optionally substituted 6- to 12-membered bicyclic heterocycloalkylene group.

In some embodiments, $L^5$ is absent, or is $-C_1-C_6$ alkylene-, $-C_2-C_6$ alkenylene-, $-C_2-C_6$ alkynylene-, a 6- to 10-membered arylene, 5- to 10-membered heteroarylene, a 3- to 12-membered cycloalkenylene, a 3- to 7-membered monocyclic cycloalkylene, or 6- to 12 bicyclic cycloalkylene, a 3- to 7-membered monocyclic heterocycloalkylene, or 6- to 12-membered bicyclic heterocycloalkylene group.

In some aspects, $L^6$ in Formula I is absent, or is $(CR^7R^8)_s$, $(CR^7R^8)_sO(CR^7R^8)_t$, $(CR^7R^8)_sNR^9(CR^7R^8)_t$, $(CR^7R^8)_sS(CR^7R^8)_t$, $(CR^7R^8)_sS(O)(CR^7R^8)_t$, $(CR^7R^8)_sS(O)_2(CR^7R^8)_t$, $(CR^7R^8)_sNR^{9A}C(O)(CR^7R^8)_t$, $(CR^7R^8)_sOC(O)NR^{9A}(CR^7R^8)_t$, $(CR^7R^8)_sNR^{9A}C(O)O(CR^7R^8)_t$, $(CR^7R^8)_sNR^{9A}C(O)NR^{9B}(CR^7R^8)_t$, $(CR^7R^8)_sNR^{9A}S(O)(CR^7R^8)_t$, $(CR^7R^8)_sNR^{9A}S(O)_2(CR^7R^8)_t$; $-(CR^7R^8)_s-CR^{4A}=CR^{4B}-(CR^7R^8)_t$, $(CR^7R^8)_sC(=O)(CR^7R^8)_t$; $-(CR^7R^8)_sC(=O)(CR^7R^8)t-O-$, or $-(CR^7R^8)_sC(=O)(CR^7R^8)t-NR^6-$.

In some embodiments, $L^6$ in Formula I is absent. In other embodiments, $L^6$ in Formula I is $(CR^7R^8)_s$. In other embodiments, $L^6$ in Formula I is $(CR^7R^8)_sO(CR^7R^8)_t$. In other embodiments, $L^6$ in Formula I is $(CR^7R^8)_sNR^9(CR^7R^8)_t$. In other embodiments, $L^6$ in Formula I is $(CR^7R^8)_sS(CR^7R^8)_t$. In other embodiments, $L^6$ in Formula I is $(CR^7R^8)_sS(O)(CR^7R^8)_t$. In other embodiments, $L^6$ in Formula I is $(CR^7R^8)_s S(O)_2(CR^7R^8)_t$. In other embodiments, $L^6$ in Formula I is $(CR^7R^8)_sNR^{9A}C(O)(CR^7R^8)_t$. In other embodiments, $L^6$ in Formula I is $(CR^7R^8)_sOC(O)NR^{9A}(CR^7R^8)_t$. In other embodiments, $L^6$ in Formula I is $(CR^7R^8)_sNR^{9A}C(O)O(CR^7R^8)_t$. In other embodiments, $L^6$ in Formula I is $(CR^7R^8)_sNR^{9A}C(O)NR^{9B}(CR^7R^8)_t$. In other embodiments, $L^6$ in Formula I is $(CR^7R^8)_sNR^{9A}S(O)(CR^7R^8)_t$. In other embodiments, $L^6$ in Formula I is $(CR^7R^8)_sNR^{9A}S(O)_2(CR^7R^8)_t$. In other embodiments, $L^6$ in Formula I is $-(CR^7R^8)_s-CR^{4A}=CR^{4B}-(CR^7R^8)_t$. In other embodiments, $L^6$ in Formula I is $(CR^7R^8)_sC(=O)(CR^7R^8)_t$. In other embodiments, $L^6$ in Formula I is $-(CR^7R^8)_sC(=O)(CR^7R^8)t-O-$. In other embodiments, $L^6$ in Formula I is $-(CR^7R^8)_sC(=O)(CR^7R^8)t-NR^6-$.

In some embodiments, $L^6$ is absent, or is $-(CR^7R^8)_s-$, $-O(CR^7R^8)_t-$, $-NR^9(CR^7R^8)_t-$, $-S(CR^7R^8)_t-$, $-S(O)(CR^7R^8)_t-$, $-S(O)_2(CR^7R^8)_t-$, $-NR^{9A}C(O)(CR^7R^8)_t-$, $-C(O)NR^{9A}(CR^7R^8)_t-$, $-R^{9A}C(O)O(CR^7R^8)_t-$, $-NR^{9A}C(O)NR^{9B}(CR^7R^8)_t-$, $-NR^{9A}S(O)(CR^7R^8)_t-$, $-NR^{9A}S(O)_2(CR^7R^8)_t-$; $-CR^{4A}=CR^{4B}-(CR^7R^8)_t-$, $-C(=O)(CR^7R^8)_t-$; $-C(=O)(CR^7R^8)_t-O-$, or $-C(=O)(CR^7R^8)t-NR^6-$.

In some aspects, in Formula I, each n is independently 0-3. In some embodiments, n=0. In other embodiments, n=1. In other embodiments, n=2. In other embodiments, n=3.

In some aspects, in Formula I, each m is independently 0-2. In some embodiments, m=0. In other embodiments, m=1. In other embodiments, m=2.

In some aspects, in Formula I, each p is independently 0-4. In some embodiments, p=0. In other embodiments, p=1. In other embodiments, p=2. In other embodiments, p=3. In other embodiments, p=4.

In some aspects, in Formula I, each q is independently 0-4. In some embodiments, q=0. In other embodiments, q=1. In other embodiments, q=2. In other embodiments, q=3. In yet other embodiments, q=4.

In some aspects, in Formula I, each s is independently 0-3. In some embodiments, s=0. In other embodiments, s=1. In other embodiments, s=2. In other embodiments, s=3.

In some aspects, in Formula I, each t is independently 0-4. In some embodiments, t=0. In other embodiments, t=1. In other embodiments, t=2. In other embodiments, t=3. In other embodiments, t=4.

In some aspects, each R in Formula I is independently -D, -halo, —CN, —NO$_2$, —C$_1$-C$_6$alkyl, —C$_2$-C$_6$alkenyl, —C$_1$-C$_6$alkoxy, -cycloalkyl, —OR$^a$, —SR$^a$, —C(O)R$^b$, —C(O)OR$^a$, —NR$^c$R$^d$, —C(O)NR$^c$R$^d$, or —S(O)$_2$R$^a$; wherein said —C$_1$-C$_6$alkyl, —C$_2$-C$_6$alkenyl, —C$_1$-C$_6$alkoxy, or -cycloalkyl is optionally substituted.

In some embodiments, R is halo, for example, Cl or F. In some embodiments, R is —SR$^a$, for example —SCH$_3$. In other embodiments, R is —C$_1$-C$_6$alkyl, for example —CH$_3$.

In some aspects, each R$^1$ in Formula I is independently -D, -halo, —CN, —NO$_2$, —C$_1$-C$_6$alkyl, —C$_2$-C$_6$alkenyl, —C$_2$-C$_6$alkynyl, —OR$^a$, —SR$^a$, —NR$^c$R$^d$, —C(O)R$^b$, —OC(O)R$^b$, —C(O)OR$^a$, —C(O)NR$^c$R$^d$, —S(O)$_2$R$^a$; -aryl, -heteroaryl, -cycloalkyl, or -heterocycloalkyl, wherein the —C$_1$-C$_6$alkyl, —C$_2$-C$_6$alkenyl, —C$_2$-C$_6$alkynyl, -cycloalkyl, -heterocycloalkyl, -aryl, or -heteroaryl is optionally substituted.

In some embodiments, R$^1$ in Formula I is halo, for example, Cl or F. In other embodiments, R$^1$ in Formula I is —C$_1$-C$_6$alkyl substituted with fluorine, for example —CF$_3$. In other embodiments, R$^1$ in Formula I is —C$_1$-C$_6$alkyl, for example, —C$_6$alkyl, —C$_5$alkyl, —C$_4$alkyl, —C$_3$alkyl, —C$_2$alkyl, —C$_1$alkyl. In some embodiments, R$^1$ in Formula I is —C$_1$alkyl substituted with —CN. In other embodiments, R$^1$ in Formula I is cycloalkyl, for example, cyclopropane, cyclobutane, cyclopentane, and the like. In other embodiments, R$^1$ in Formula I is cyclopropane substituted with —CN.

In some aspects, each R$^2$, R$^{2A}$, or R$^{2a}$ is independently H, D, halo, OR$^a$, optionally substituted C$_1$-C$_6$alkyl, or R$^2$ and R$^{2A}$ that are attached to the same carbon atom may, together with the carbon atom to which they are both attached, form an optionally substituted cycloalkyl ring.

In some embodiments, R$^2$, R$^{2A}$, and R$^{2a}$ in Formula I are each H.

In other embodiments, R$^2$, R$^{2A}$, or R$^{2a}$ in Formula I is C$_1$-C$_6$alkyl, for example —CH$_3$ or —CH$_2$CH$_3$.

In other embodiments, R$^2$ and R$^{2A}$ that are attached to the same carbon atom, together with the carbon atom to which they are both attached, form an optionally substituted 3-6 membered cycloalkyl ring. In some embodiments, R$^2$ and R$^{2A}$ that are attached to the same carbon atom, together with the carbon atom to which they are both attached, form a cyclopropane ring.

In other aspects, R$^2$ and R$^{2a}$ that are attached to the same carbon atom, together with the carbon atom to which they are both attached, form an optionally substituted 3-6 membered cycloalkyl ring. In some embodiments, R$^2$ and R$^{2a}$ that are attached to the same carbon atom, together with the carbon atom to which they are both attached, form a cyclopropane ring.

In some aspects, each R$^{2B}$ and R$^{2C}$ in Formula I is independently H, D, optionally substituted C$_1$-C$_6$alkyl, or R$^{2B}$ and R$^{2C}$ may, together with the carbon atom to which they are both attached, form an optionally substituted cycloalkyl ring.

In some embodiments, R$^{2B}$ and R$^{2C}$ in Formula I are each H.

In other embodiments, R$^{2B}$ and R$^{2C}$ that are attached to the same carbon atom together with the carbon atom to which they are both attached, form a cyclopropane ring.

In some aspects, R$^3$ in Formula I is H, D, —C$_1$-C$_6$alkyl, —C$_3$-C$_6$alkenyl, —C$_3$-C$_6$alkynyl, cycloalkyl, heterocycloalkyl, C(O)R$^b$, C(O)OR$^a$, or C(O)NR$^c$R$^d$; wherein said C$_1$-C$_6$alkyl, —C$_3$-C$_6$alkenyl, —C$_3$-C$_6$alkynyl, cycloalkyl, or heterocycloalkyl is optionally substituted; or R$^3$ is —C$_1$-C$_6$alkyl substituted at the C$_1$ carbon atom with —OR$^{3A}$ wherein R$^{3A}$ is C$_1$-C$_6$alkyl, —PO$_3$H, —C(O)OR$^{2C}$, or —C(O)NR$^{3A}$R$^{3B}$ wherein R$^{3A}$ and R$^{3B}$ are each independently H, D, optionally substituted C$_1$-C$_6$alkyl.

In some embodiments, R$^3$ in Formula I is H. In other embodiments, R$^3$ in Formula I is —C$_1$-C$_6$alkyl, for example, C$_6$alkyl, C$_5$alkyl, C$_4$alkyl, C$_3$alkyl, C$_2$alkyl, C$_1$alkyl, —CH$_3$, and the like.

In some aspects, each R$^4$ or R$^7$ in Formula I is independently H, D, halo, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^a$, —C(O)OR$^a$, —C(O)NR$^c$R$^d$, —S(O)R$^b$, or —S(O)$_2$R$^b$, wherein said C$_1$-C$_6$alkyl, —C$_2$-C$_6$alkenyl, —C$_2$-C$_6$alkynyl, aryl, heteroaryl, cycloalkyl, or heterocycloalkyl is optionally substituted.

In some embodiments, R$^4$ is Formula I is H. In some embodiments, R$^4$ is Formula I is —OH. In other embodiments, R$^4$ in Formula I is —C$_1$-C$_6$alkyl, for example, C$_6$alkyl, C$_5$alkyl, C$_4$alkyl, C$_3$alkyl, C$_2$alkyl, C$_1$alkyl, —CH$_3$, and the like. In other embodiments, R$^4$ is Formula I is —OR$^a$, for example, —OCH$_3$.

In some embodiments, R$^7$ in Formula I is H. In other embodiments, R$^7$ in Formula I is —C$_1$-C$_6$alkyl, for example, C$_6$alkyl, C$_5$alkyl, C$_4$alkyl, C$_3$alkyl, C$_2$alkyl, C$_1$alkyl, —CH$_3$, and the like. In some embodiments, R$^7$ in Formula I is —CH$_3$. In other embodiments, R$^7$ in Formula I is —OR$^a$, for example, —OCH$_3$.

In some aspects, each R$^{4A}$ or R$^{4B}$ in Formula I is independently H, D, -Me, —CF$_3$ or —F. In some embodiments, R$^{4A}$ is H. In some embodiments, R$^{4B}$ is H.

In some aspects, each R$^5$ or R$^8$ in Formula I is independently H, D, fluoro, —C$_1$-C$_6$alkyl, —C$_2$-C$_6$alkenyl, —C$_2$-C$_6$alkynyl, —C(O)R$^b$, —C(O)OR$^a$, —C(O)NR$^c$R$^d$, aryl, heteroaryl, cycloalkyl, cycloalkenyl, heterocycloalkyl, or heterocycloalkenyl, wherein the C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl is optionally substituted.

In some embodiments, R$^5$ in Formula I is H. In other embodiments, R$^5$ in Formula I is —C$_1$-C$_6$alkyl, for example, C$_6$alkyl, C$_5$alkyl, C$_4$alkyl, C$_3$alkyl, C$_2$alkyl, C$_1$alkyl, —CH$_3$, and the like. In some embodiments, R$^5$ in Formula I is —CH$_3$.

In some embodiments, R$^8$ in Formula I is H. In other embodiments, R$^8$ in Formula I is —C$_1$-C$_6$alkyl, for example, $C_6$alkyl, $C_5$alkyl, $C_4$alkyl, $C_3$alkyl, $C_2$alkyl, $C_1$alkyl, —$CH_3$, and the like. In some embodiments, $R^8$ in Formula I is —$CH_3$.

In some embodiments each $R^7$ and each $R^8$ is independently, optionally substituted cycloalkyl, optionally substituted heterocycloalkyl, or optionally substituted —$C_1$-$C_6$alkyl.

In other embodiments, each $R^7$ and each $R^8$ is independently H, optionally substituted 3-7 membered cycloalkyl, 4-7 membered heterocycloalkyl, or optionally substituted —$C_1$-$C_6$alkyl.

In other embodiments, each $R^7$ and each $R^8$ is independently H, —$CH_3$, -cyclopropyl, —$CH_2CH_3$, or —$CH(CH_3)_2$.

In other embodiments, each $R^7$ and each $R^8$ is independently H, or a —$C_1$-$C_6$alkyl group optionally substituted with —OH, optionally substituted —$OC_1$-$C_6$alkyl, optionally substituted —$(CH_2CH_2O)_oC_1$-$C_6$alkyl wherein o is 1-10, or —$C(O)NR^{c1}R^{d1}$ wherein $R^{c1}$ and $R^{d1}$ are independently H, optionally substituted —$C_1$-$C_6$alkyl, optionally substituted cycloalkyl, or optionally substituted heterocycloalkyl.

In other embodiments, each $R^7$ and each $R^8$ is independently H, or —$C_1$-$C_6$alkyl group is optionally substituted with —OH, —$OC_1$-$C_6$alkyl, —$(CH_2CH_2O)_oC_1$-$C_6$alkyl wherein o is 1-10, or —$C(O)NR^{c1}R^{d1}$ wherein $R^{c1}$ and $R^{d1}$ are independently H, $C_1$-$C_6$alkyl, or 4-7 membered heterocycloalkyl; or wherein or $R^{c1}$ and $R^{d1}$, together with the N atom to which they are both attached, form a multicyclic 4-7 membered heterocycloalkyl ring optionally substituted with halo, —$OC_1$-$C_6$alkyl, or —$C_1$-$C_6$alkyl optionally substituted with —OH or —$OC_1$-$C_6$alkyl.

In some aspects, $R^4$ and $R^5$ together with the C atom to which they are attached form a cycloalkyl, cycloalkenyl, heterocycloalkyl, or heterocycloalkenyl ring, each optionally substituted.

In other aspects, $R^4$ and an $R^5$ attached to adjacent carbon atoms, together with the C atoms to which they are attached, form a cycloalkyl, cycloalkenyl, heterocycloalkyl, or heterocycloalkenyl ring, each optionally substituted.

In some embodiments, each $R^7$ and each $R^8$ is independently H, optionally substituted cycloalkyl, optionally substituted heterocycloalkyl, or optionally substituted —$C_1$-$C_6$alkyl; or $R^7$ and $R^8$ attached to the same carbon atom, together with that carbon atom, form an optionally substituted cycloalkyl ring or an optionally substituted heterocycloalkyl ring; or $R^7$ and $R^8$ attached to adjacent carbon atoms, together with those carbon atoms, form an optionally substituted cycloalkyl ring or and optionally substituted heterocycloalkyl ring.

In some embodiments, each $R^7$ and each $R^8$ is independently H, optionally substituted 3-7 membered cycloalkyl, 4-7 membered heterocycloalkyl, or optionally substituted —$C_1$-$C_6$alkyl; or wherein $R^7$ and $R^8$ attached to the same carbon atom, together with that carbon atom, form an optionally substituted 3-7 membered cycloalkyl ring or an optionally substituted 4-7 membered heterocycloalkyl ring; or $R^7$ and $R^8$ attached to adjacent carbon atoms, together with those carbon atoms, form an optionally substituted 3-7 membered cycloalkyl ring or an optionally substituted 4-7 membered heterocycloalkyl ring.

In some embodiments, $R^7$ and $R^8$ attached to the same carbon atom, together with that carbon atom, form a 3-7 membered cycloalkyl ring or 4-7 membered heterocycloalkyl ring; or $R^7$ and $R^8$ attached to adjacent carbon atoms, together with the atoms to which they are attached, form a 3-7 membered cycloalkyl ring or 4-7 membered heterocycloalkyl ring.

In some embodiments, $R^7$ or $R^8$ are each independently H, —$CH_3$, -cyclopropyl, —$CH_2CH_3$, or —$CH(CH_3)_2$.

In some embodiments, $R^7$ and $R^8$ attached to the same carbon atom, together with that carbon atom, form a cyclopropyl ring, a cyclobutyl ring, or azetidinyl ring.

In some embodiments, each $R^7$ and each $R^8$ is independently H, or a —$C_1$-$C_6$alkyl group optionally substituted with —OH; optionally substituted —$OC_1$-$C_6$alkyl; optionally substituted —$(CH_2CH_2O)_oC_1$-$C_6$alkyl wherein o is 1-10; or —$C(O)NR^{c1}R^{d1}$ wherein $R^{c1}$ and $R^{d1}$ are independently H, optionally substituted —$C_1$-$C_6$alkyl, optionally substituted cycloalkyl, or optionally substituted heterocycloalkyl; or wherein or $R^{c1}$ and $R^{d1}$, together with the N atom to which they are both attached, form an optionally substituted monocyclic or multicyclic heterocycloalkyl ring.

In some embodiments, the —$C_1$-$C_6$alkyl group is optionally substituted with —OH; —$OC_1$-$C_6$alkyl; —$(CH_2CH_2O)_oC_1$-$C_6$alkyl wherein o is 1-10; or —$C(O)NR^{c1}R^{d1}$ wherein $R^{c1}$ and $R^{d1}$ are independently H, $C_1$-$C_6$alkyl, or 4-7 membered heterocycloalkyl; or wherein or $R^{c1}$ and $R^{d1}$, together with the N atom to which they are both attached, form a monocyclic or multicyclic 4-7 membered heterocycloalkyl ring optionally substituted with halo; —$OC_1$-$C_6$alkyl; or —$C_1$-$C_6$alkyl optionally substituted with —OH or —$OC_1$-$C_6$alkyl.

In some aspects, $R^7$ and $R^8$ together with the C atom to which they are both attached form a cycloalkyl, cycloalkenyl, heterocycloalkyl, or heterocycloalkenyl ring, each optionally substituted, each optionally substituted.

In some embodiments, $R^7$ and $R^8$ together with the C atom to which they are both attached form a cycloalkyl ring, for example, a cyclopropyl ring, a cyclobutyl ring, or a cyclopentyl ring.

In some embodiments, $R^7$ and $R^8$ attached to the same carbon atom, together with that carbon atom, form an optionally substituted cycloalkyl ring or an optionally substituted heterocycloalkyl ring.

In other embodiments, $R^7$ and $R^8$ attached to adjacent carbon atoms, together with those carbon atoms, form an optionally substituted cycloalkyl ring or and optionally substituted heterocycloalkyl ring.

In other embodiments, $R^7$ and $R^8$ attached to the same carbon atom, together with that carbon atom, form an optionally substituted 3-7 membered cycloalkyl ring or an optionally substituted 4-7 membered heterocycloalkyl ring;

In other embodiments, $R^7$ and $R^8$ attached to adjacent carbon atoms, together with those carbon atoms, form an optionally substituted 3-7 membered cycloalkyl ring or an optionally substituted 4-7 membered heterocycloalkyl ring.

In other embodiments, $R^7$ and $R^8$ attached to adjacent carbon atoms, together with the atoms to which they are attached, form a 3-7 membered cycloalkyl ring or 4-7 membered heterocycloalkyl ring.

In other embodiments, $R^7$ and $R^8$ attached to the same carbon atom, together with that carbon atom, form a cyclopropyl ring, a cyclobutyl ring, or azetidinyl ring.

In some aspects, an $R^7$ and an $R^8$ attached to adjacent carbon atoms, together with the C atoms to which they are attached, form a cycloalkyl, cycloalkenyl, heterocycloalkyl, or heterocycloalkenyl ring, each optionally substituted.

In some aspects, each $R^6$ or $R^9$ is independently H, D, —$C_1$-$C_6$alkyl, —$C_2$-$C_6$alkenyl, —$C_2$-$C_6$alkynyl, —$OC_1$-$C_6$alkyl, —$C(O)R^b$, —$C(O)OR^a$, —$C(O)NR^cR^d$, —$S(O)R^b$ or —$S(O)_2R^b$, aryl, heteroaryl, cycloalkyl, cycloalkenyl, heterocycloalkyl, or heterocycloalkenyl group, wherein the $C_1$-$C_6$alkyl, —$C_2$-$C_6$alkenyl, —$C_2$-$C_6$alkynyl, —$OC_1$-$C_6$alkyl, aryl, heteroaryl, cycloalkyl, cycloalkenyl, heterocycloalkyl, or heterocycloalkenyl ring, is optionally substituted.

In some embodiments, $R^6$ is H. In other embodiments, $R^6$ is —$C_1$-$C_6$alkyl, for example, —$CH_3$ or —$CH_2CH_3$.

In some embodiments, $R^9$ is H; optionally substituted —$C_1$-$C_6$alkyl; optionally substituted —$C(O)OC_1$-$C_6$alkyl; optionally substituted —$SO_2C_1$-$C_6$alkyl; optionally substituted —$C(O)C_1$-$C_6$alkyl; optionally substituted —$C(O)NR^cR^d$; or wherein $R^9$ together with either $R^7$ or $R^8$ form an optionally substituted heterocyclic alkylene.

In some embodiments, $R^9$ is H; —$C_1$-$C_6$alkyl, optionally substituted with deuterium; —$C(O)OC_1$-$C_6$alkyl; —$SO_2C_1$-$C_6$alkyl; —$C(O)C_1$-$C_6$alkyl; or wherein $R^9$ together with either $R^7$ or $R^8$ forms an optionally heterocyclic alkylene.

In other embodiments, $R^9$ is H; —$C_1$-$C_6$alkyl, optionally substituted with deuterium; —$C(O)OC_1$-$C_6$alkyl; —$SO_2C_1$-$C_6$alkyl; —$C(O)C_1$-$C_6$alkyl.

In yet other embodiments, $R^9$ is H; —$CH_3$; —$CH_2CH_3$, —$CH_2CH_2CH_3$, -$CD_3$, —$C(O)OCH_3$; —$C(O)OC(CH_3)_3$, —$SO_2CH_3$; or —$C(O)CH_3$.

In some aspects, $R^9$ together with either an $R^7$ or an $R^{8'}$ forms an optionally substituted heterocyclic alkylene. In some embodiments, $R^9$ together with either $R^7$ or $R^8$ form a heterocyclic alkylene. In some embodiments, $R^9$ together with either an $R^7$ or an $R^{8'}$ forms a $C_3$-$C_9$ heterocyclic alkylene.

In some aspects, each $R^{6A}$, $R^{6B}$, $R^{9A}$, or $R^{9B}$ in Formula I is independently H, D, —$C_1$-$C_6$alkyl, —$C_2$-$C_6$alkenyl, —$C_2$-$C_6$alkynyl, cycloalkyl, cycloalkenyl, heterocycloalkyl, or heterocycloalkenyl, wherein the $C_1$-$C_6$alkyl, —$C_2$-$C_6$alkenyl, —$C_2$-$C_6$alkynyl, cycloalkyl, cycloalkenyl, heterocycloalkyl, or heterocycloalkenyl is optionally substituted.

In some aspects, $R^{6A}$ and $R^{6B}$ together with the N atoms to which they are attached form an optionally substituted heterocycloalkyl or heterocycloalkenyl ring.

In some aspects, $R^{9A}$ and $R^{9B}$ together with the N atoms to which they are attached form an optionally substituted heterocycloalkyl or heterocycloalkenyl ring;

In some aspects, each $R^a$ in Formula I is independently H, D, —$C(O)R^b$, —$C(O)OR^c$, —$C(O)NR^cR^d$, —$P(OR^c)_2$, —$P(O)R^cR^b$, —$P(O)OR^cOR^b$, —$S(O)R^b$, —$S(O)NR^cR^d$, —$S(O)_2R^b$, —$S(O)_2NR^cR^d$, —$B(OR^c)(OR^b)$, $SiR^b_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl wherein said $C_1$-$C_{10}$ alkyl, $C_2$-$C_{10}$ alkenyl, $C_2$-$C_{10}$ alkynyl, aryl, cycloalkyl, cycloalkenyl, heteroaryl, heterocycloalkyl, or heterocycloalkenyl is optionally substituted.

In some embodiments, $R^a$ is H, —$C(O)R^b$, —$C(O)NR^cR^d$, optionally substituted $C_1$-$C_{10}$alkyl, optionally substituted $C_2$-$C_{10}$alkenyl, optionally substituted $C_2$-$C_{10}$ alkynyl, optionally substituted aryl, optionally substituted cycloalkyl, optionally substituted heteroaryl, or optionally substituted heterocycloalkyl In some embodiments, $R^a$ is H, —$C(O)R^b$, —$C(O)NR^cR^d$, or optionally substituted $C_1$-$C_{10}$alkyl.

In some embodiments, $R^a$ is H.

In some embodiments, $R^a$ is —$C(O)R^b$.

In some embodiments, $R^a$ is —$C(O)R^b$ wherein $R^b$ is optionally substituted —$C_1$-$C_6$alkyl.

In some embodiments, $R^a$ is —$C(O)R^b$ wherein $R^b$ is —$C_1$-$C_6$alkyl.

In some embodiments, $R^a$ is —$C(O)R^b$ wherein $R^b$ is —$CH_3$.

In some embodiments, $R^a$ is —$C(O)NR^cR^d$.

In some embodiments, $R^a$ is —$C(O)NR^cR^d$ wherein $R^c$ and $R^d$ are independently H; optionally substituted —$OC_1$-$C_6$alkyl; optionally substituted cycloalkyl; optionally substituted —$C_1$-$C_6$alkyl, or optionally substituted heterocycloalkyl.

In some embodiments, $R^a$ is —$C(O)NR^cR^d$ wherein $R^c$ and $R^d$ are independently H; optionally substituted 3-7 membered cycloalkyl; —$OC_1$-$C_6$alkyl; or —$C_1$-$C_6$alkyl optionally substituted with deuterium, halo, optionally substituted cycloalkyl, optionally substituted —$OC_1$-$C_6$alkyl, —$NR^{c1}R^{d1}$ wherein $R^{c1}$ and $R^{d1}$ are independently H or optionally substituted —$C_1$-$C_6$alkyl, optionally substituted 4-7 membered heterocycloalkyl, or optionally substituted 5-6 membered heteroaryl; or optionally substituted 4-7 membered heterocycloalkyl.

In some embodiments, $R^a$ is —$C(O)NR^cR^d$ wherein $R^c$ and $R^d$ are independently H; 3-7 membered cycloalkyl; —$C_1$-$C_6$alkyl optionally substituted with deuterium, halo, —$OC_1$-$C_6$alkyl, cycloalkyl, —$NR^{c1}R^{d1}$ wherein $R^{c1}$ and $R^{d1}$ are independently H or —$C_1$-$C_6$alkyl, 4-7 membered heterocycloalkyl (optionally substituted with halo, —$C_1$-$C_6$alkyl, —OH, or —$OC_1$-$C_6$alkyl), or -5-6 membered heteroaryl, —$OC_1$-$C_6$alkyl; or -4-7 membered heterocycloalkyl optionally substituted with —$C_1$-$C_6$alkyl or —OH.

In some embodiments, $R^a$ is —$C(O)NR^cR^d$ wherein $R^c$ and $R^d$, together with the nitrogen atom to which they are both attached, form an optionally substituted monocyclic or multicyclic heterocycloalkyl group.

In some embodiments, $R^a$ is —$C(O)NR^cR^d$ wherein $R^c$ and $R^d$, together with the nitrogen atom to which they are both attached, form a monocyclic or multicyclic heterocycloalkyl group optionally substituted with -halo, —OH, optionally substituted -4-7 membered heterocycle, optionally substituted 5-6 membered heteroaryl, optionally substituted —$OC_1$-$C_6$alkyl, optionally substituted —$C_1$-$C_6$alkyl; or —$NR^{c1}R^{d1}$ wherein $R^{c1}$ and $R^{d1}$ are independently H or optionally substituted $C_1$-$C_6$alkyl.

In some embodiments, $R^a$ is —$C(O)NR^cR^d$ wherein $R^c$ and $R^d$, together with the nitrogen atom to which they are both attached, form a monocyclic or multicyclic-4-10 membered heterocycloalkyl group optionally substituted with -halo, —OH, -4-7 membered heterocycle, 5-6 membered heteroaryl, —$OC_1$-$C_6$alkyl, —$C_1$-$C_6$alkyl (optionally substituted with —OH, —$OC_1$-$C_6$alkyl, or $NR^{c1}R^{d1}$, wherein $R^{c1}$ and $R^{d1}$ are independently H or $C_1$-$C_6$alkyl); or —$NR^{c1}R^{d1}$, wherein $R^{c1}$ and $R^{d1}$ are independently H or $C_1$-$C_6$alkyl.

In some embodiments, $R^a$ is optionally substituted —$C_1$-$C_{10}$alkyl.

In some embodiments, $R^a$ is —$C_1$-$C_{10}$alkyl optionally substituted with —$C(O)NR^{c1}R^{d1}$, wherein $R^{c1}$ and $R^{d1}$ are independently H, optionally substituted $C_1$-$C_6$alkyl, or optionally substituted heterocyclyl; or wherein or $R^{c1}$ and $R^{d1}$, together with the N atom to which they are both attached, form an optionally substituted monocyclic or multicyclic-4-10 membered heterocycloalkyl group; —$NR^{c1}R^{d1}$ wherein $R^{c1}$ and $R^{d1}$ are independently H, optionally substituted $C_1$-$C_6$alkyl, optionally substituted cycloalkyl, or optionally substituted heterocycloalkyl; optionally substituted heteroaryl; —$C(O)OH$; or optionally substituted -heterocycloalkyl.

In some embodiments, $R^a$ is —$C_1$-$C_{10}$alkyl optionally substituted with —$C(O)NR^{c1}R^{d1}$, wherein $R^{c1}$ and $R^{d1}$ are independently H, $C_1$-$C_6$alkyl, or 4-7 membered heterocycloalkyl; or wherein or R$^{c1}$ and R$^{d1}$, together with the N atom to which they are both attached, form a monocyclic or multicyclic-4-10 membered heterocycloalkyl group (optionally substituted with halo, —OC$_1$-C$_6$alkyl, or —C$_1$-C$_6$alkyl optionally substituted with —OH or —OC$_1$-C$_6$alkyl); —NR$^{c1}$R$^{d1}$ wherein R$^{c1}$ and R$^{d1}$ are independently H, or optionally substituted C$_1$-C$_6$alkyl; —C$_4$-C$_5$heteroaryl; —C(O)OH; or -4-7 membered heterocycloalkyl optionally substituted with halo, C$_1$-C$_6$alkyl, or —OC$_1$-C$_6$alkyl.

In some embodiments, R$^a$ is —C(O)NR$^c$R$^d$ wherein R$^c$ and R$^d$ are independently H; —OCH$_3$, —CH$_3$, -CD$_3$, —CH$_2$CH$_2$OCH$_3$, —CH$_2$CH$_3$, —CH$_2$-cyclopropyl, -cyclobutyl, cyclopropyl, —CH(CH$_3$)$_2$, —CH$_2$—CH(CH$_3$)$_2$, —CH$_2$CH$_2$NH$_2$, —CH$_2$CH$_2$N(CH$_3$)$_2$, —CH$_2$CH$_2$NH (CH$_3$), —CH$_2$CHF$_2$,

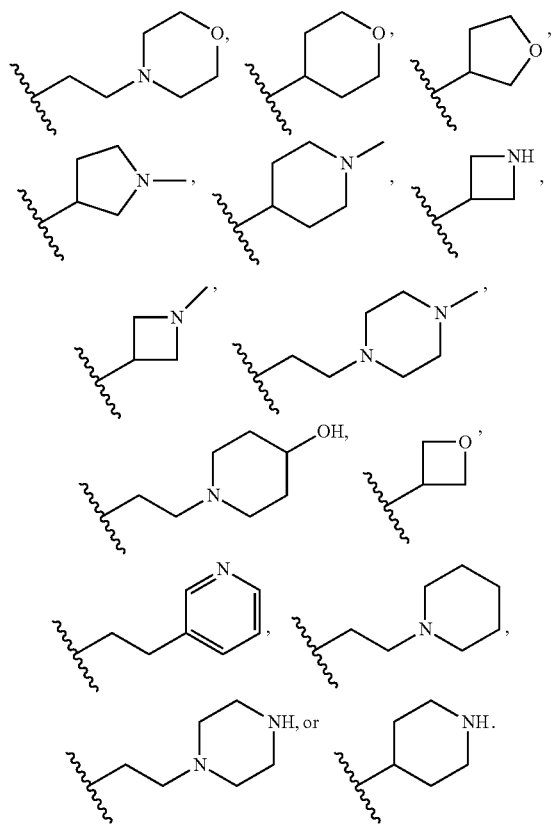

In some embodiments, R$^a$ is —C(O)NR$^c$R$^d$ wherein R$^c$ and R$^d$, together with the nitrogen atom to which they are both attached, are

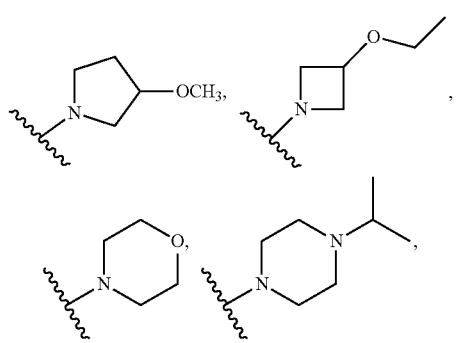

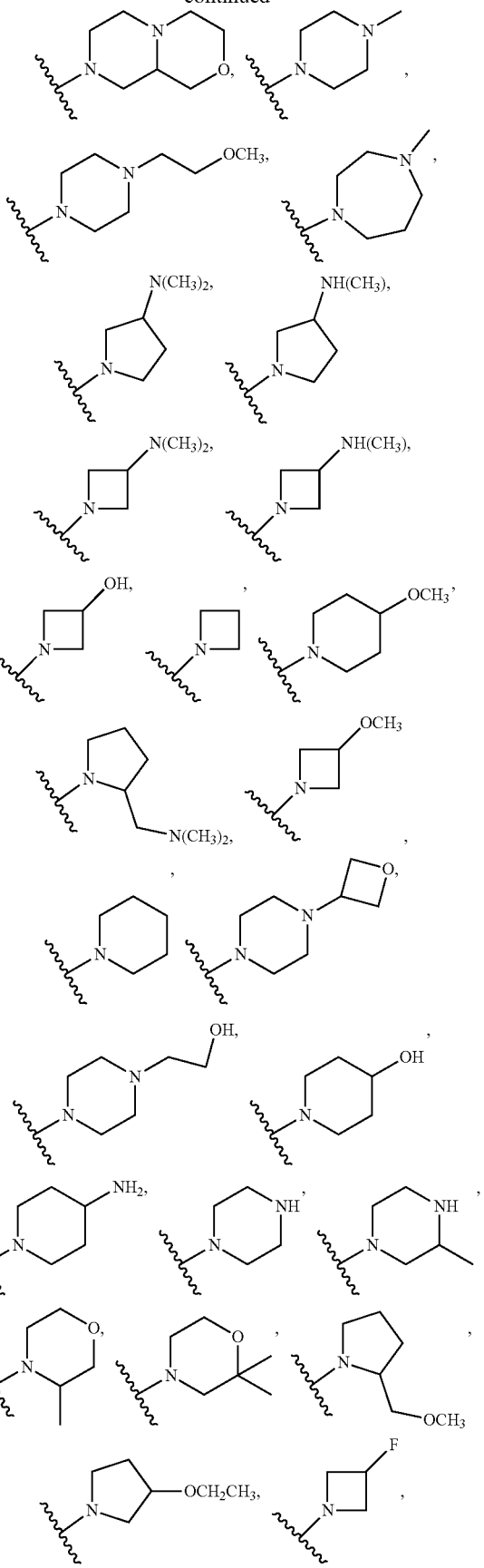

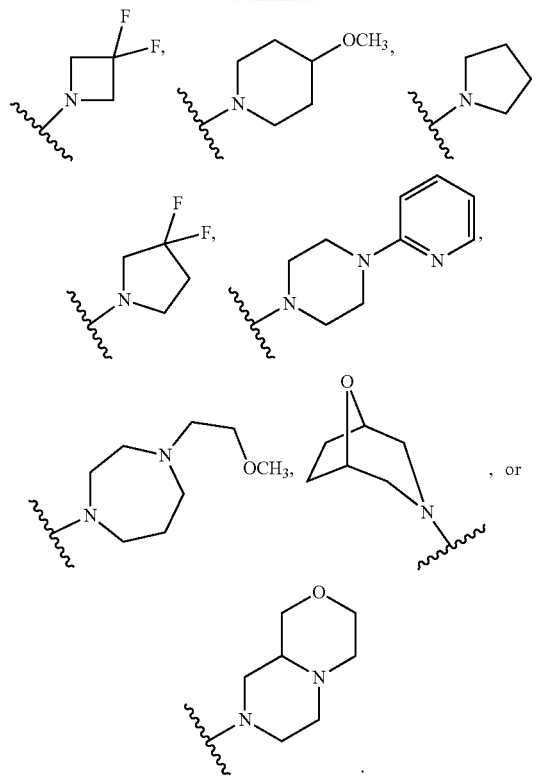

In some embodiments, R$^a$ is —C$_1$-C$_6$alkyl optionally substituted with —N(CH$_3$)$_2$, —CO$_2$H, —CONH$_2$, —CON(CH$_3$)(CH$_2$CH$_2$OCH$_3$),

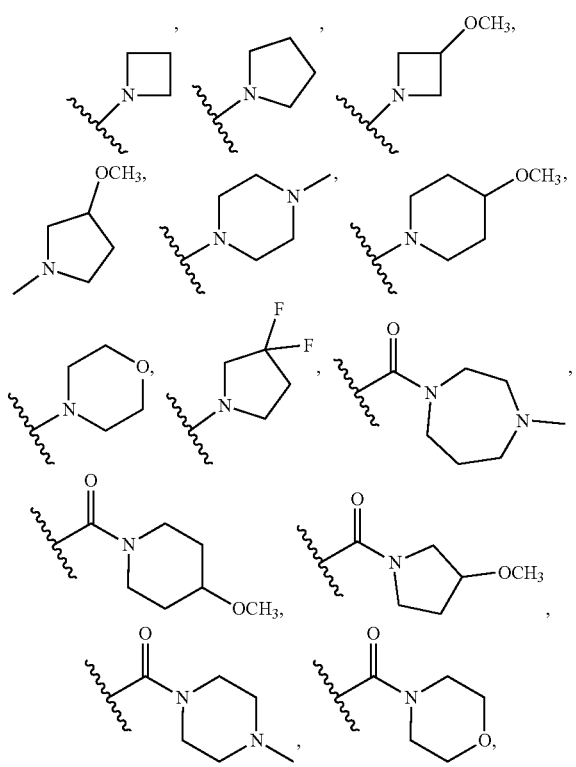

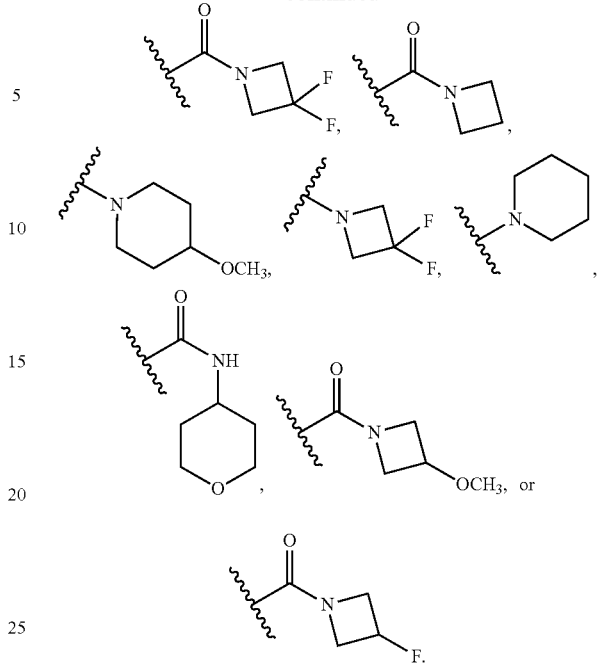

In some aspects, each R$^b$ in Formula I is independently H, D, —C$_1$-C$_6$ alkyl, —C$_2$-C$_6$ alkenyl, —C$_2$-C$_6$ alkynyl, aryl, cycloalkyl, cycloalkenyl, heteroaryl, heterocycloalkyl, or heterocycloalkenyl wherein the —C$_1$-C$_6$ alkyl, —C$_2$-C$_6$ alkenyl, —C$_2$-C$_6$ alkynyl, aryl, cycloalkyl, cycloalkeneyl, heteroaryl, heterocycloalkyl, or heterocycloalkenyl is optionally substituted.

In some aspects, each R$^c$ or R$^d$ in Formula I is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, heteroaryl, cycloalkyl, cycloalkenyl, heterocycloalkyl, or heterocycloalkenyl, wherein the C$_1$-C$_{10}$ alkyl, C$_2$-C$_6$ alkenyl, C$_2$-C$_6$ alkynyl, —OC$_1$-C$_6$alkyl, —O-cycloalkyl, aryl, heteroaryl, cycloalkyl, cycloalkenyl, heterocycloalkyl, or heterocycloalkenyl are each optionally substituted.

In some aspects, R$^c$ and R$^d$, together with the N atom to which they are both attached, form an optionally substituted monocyclic or multicyclic heterocycloalkyl, or optionally substituted monocyclic or multicyclic heterocycloalkenyl group.

In some embodiments, compounds of Formula I are those having the Formula IA-0:

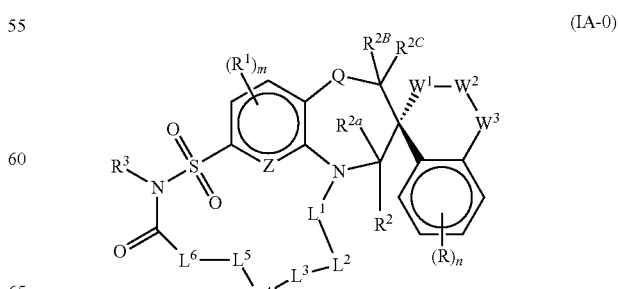

(IA-0)

In some embodiments, compounds of Formula I are those having the Formula IA:

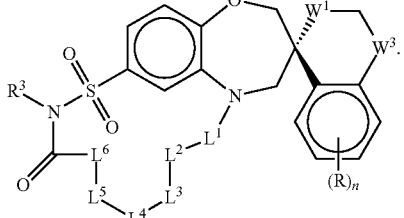

(IA)

In some embodiments, the compounds of Formula IA are those wherein $W^1$ is —$CH_2$— and $W^3$ is —O—, or $W^1$ is —O— and $W^3$ is —$CH_2$—, or $W^1$ is —$CH_2$— and $W^3$ is —S—, or $W^1$ is —S— and $W^3$ is —$CH_2$—, or $W^1$ is —$CH_2$— and $W^3$ is —$NR^{2B}$—, or $W^1$ is —$NR^{2B}$— and $W^3$ is —$CH_2$—, or $W^1$ is —$CH_2$— and $W^3$ is —$CH_2$—.

In other embodiments, the compounds of Formula I are those having Formula IA-1:

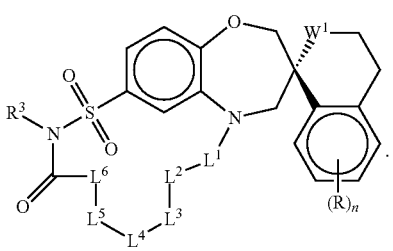

(IA-1)

In some embodiments, the compounds of Formula IA-1 are those wherein $W^1$ is —$CH_2$— or —O—.

In some embodiments, the compounds of Formula I are those having the Formula IA-2:

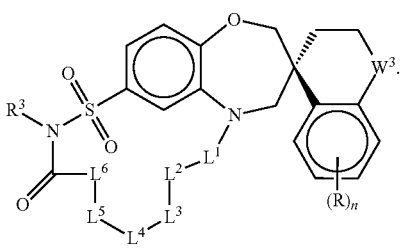

(IA-2)

In some embodiments, the compound of formula IA-2 are those wherein $W^3$ is —$CH_2$— or —O—.

In some embodiments, the compounds of Formula I are those of Formula IA-3 wherein $W^1$ is —$CH_2$— and $W^3$ is O, or $W^1$ is —O— and $W^3$ is —$CH_2$—, or $W^1$ is —$CH_2$— and $W^3$ is —$CH_2$—:

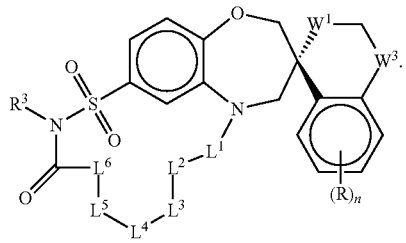

(IA-3)

In some embodiments, the compounds of Formula I are compound of Formula IA-4:

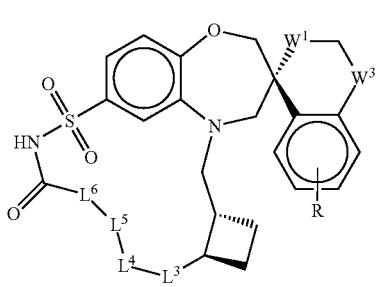

(IA-4)

or a pharmaceutically acceptable salt or solvate thereof; wherein $W^1$ is —$CH_2$— and $W^3$ is O, or $W^1$ is —O— and $W^3$ is —$CH_2$—, or $W^1$ is —$CH_2$— and $W^3$ is —$CH_2$—; $L^3$ is absent, or is —$(CR^4R^5)_p$—; $L^4$ is absent, or —$(CR^4R^5)_p Q^1(CR^4R^5)_q$—, wherein $Q^1$ is absent, —$CR^{4A}$=$CR^{4B}$—, —O—, —S—, —S(O)—, —$S(O)_2$—, —C(=O)—, —$NR^6$—, —OC(=O)—, —C(=O)O—, —$NR^{6A}$C(O), —C(=O)$NR^{6A}$—, —$NR^{6A}$C(O)$R^{6B}$—, —OC(=O)N($R^{6A}$)—, —$NR^{6A}$C(O)O—, —S(=O)$NR^{6A}$—, —$NR^{6A}$S(O)—, —$S(=O)_2NR^{6A}$—, or —$NR^{6A}S(O)_2$—; $L^5$ is absent, or is a 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group, wherein the 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group is optionally substituted; and $L^6$ is absent, or is $(CR^7R^8)_s$, —$O(CR^7R^8)_t$—, —$NR^9(CR^7R^8)_t$—, —$S(CR^7R^8)_t$—, —S(O)$(CR^7R^8)_t$—, —$S(O)_2(CR^7R^8)_t$—, —$NR^{9A}C(O)(CR^7R^8)_t$—, —C(O)$NR^{9A}(CR^7R^8)_t$—, —$R^{9A}C(O)O(CR^7R^8)_t$—, —$NR^{9A}C(O)NR^{9B}(CR^7R^8)_t$—, —$NR^{9A}S(O)(CR^7R^8)_t$—, —$NR^{9A}S(O)_2(CR^7R^8)_t$; —$CR^{4A}$=$CR^{4B}$—$(CR^7R^8)_t$—, —C(=O)$(CR^7R^8)_t$; —C(=O)$(CR^7R^8)$t-O—, or —C(=O)$(CR^7R^8)$t-$NR^6$—.

In some embodiments of the compounds of Formula I or Formula IA-4, $L^3$ absent; $L^4$ is —$(CR^4R^5)_pQ^1(CR^4R^5)_q$—, wherein $Q^1$ is absent, —$CR^{4A}$=$CR^{4B}$—, —O—, —S—, —S(O)—, —$S(O)_2$—, —C(=O)—, —$NR^6$—, —OC(=O)—, —C(=O)O—, —$NR^{6A}$C(O), —C(=O)$NR^{6A}$—, —$NR^{6A}$C(O)$R^{6B}$—, —OC(=O)N($R^{6A}$)—, —$NR^{6A}$C(O)O—, —S(=O)$NR^{6A}$—, —$NR^{6A}$S(O)—, —$S(=O)_2NR^{6A}$—, or —$NR^{6A}S(O)_2$—; and $L^5$ is absent.

In some embodiments of the compounds of Formula I or Formula IA-4, L⁶ is absent, or is —(CR⁷R⁸)$_s$—, —O(CR⁷R⁸)$_t$—, —NR⁹(CR⁷R⁸)$_t$—, —S(CR⁷R⁸)$_t$—, —S(O)(CR⁷R⁸)$_t$—, —S(O)₂(CR⁷R⁸)$_t$—, —NR$^{9A}$C(O)(CR⁷R⁸)$_t$—, —C(O)NR$^{9A}$(CR⁷R⁸)$_t$—, —R$^{9A}$C(O)O(CR⁷R⁸)$_t$—, —NR$^{9A}$C(O)NR$^{9B}$(CR⁷R⁸)$_t$—, —NR$^{9A}$S(O)(CR⁷R⁸)$_t$—, —NR$^{9A}$S(O)₂(CR⁷R⁸)$_t$—; —CR$^{4A}$=CR$^{4B}$—(CR⁷R⁸)$_t$—, —C(=O)(CR⁷R⁸)$_t$—; —C(=O)(CR⁷R⁸)t-O—, or —C(=O)(CR⁷R⁸)t-NR⁶—.

In other embodiments of the compounds of Formula I or Formula IA-4, Q¹ is —CR$^{4A}$=CR$^{4B}$—; and L⁶ is absent, —O(CR⁷R⁸)$_t$, or —NR⁹(CR⁷R⁸)$_t$;

In other embodiments of the compounds of Formula I or Formula IA-4, p=1; q=1-4; and t=1.

In other embodiments of the compounds for Formula I or Formula IA-4, L³ absent; L⁴ is —(CR⁴R⁵)$_p$Q¹(CR⁴R⁵)$_q$—, wherein Q¹ is absent, —CR$^{4A}$=CR$^{4B}$—, —O—, —S—, —S(O)—, —S(O)₂—, —C(=O)—, —NR⁶—, —OC(=O)—, —C(=O)O—, —NR$^{6A}$C(O), —C(=O)NR$^{6A}$—, —NR$^{6A}$C(O)R$^{6B}$—, —OC(=O)N(R$^{6A}$)—, —NR$^{6A}$C(O)O—, —S(=O)NR$^{6A}$—, —NR$^{6A}$S(O)—, —S(=O)₂NR$^{6A}$—, or —NR$^{6A}$S(=O)₂—; L⁵ is a 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group, wherein the 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group is optionally substituted; and L⁶ is absent, or is (CR⁷R⁸)$_s$.

In other embodiments, the compounds of Formula I or Formula IA-4 are those wherein Q¹ is —CR$^{4A}$=CR$^{4B}$—, —O—, —S—, —S(O)—, —S(O)₂—, —C(=O)—, —OC(=O)—, —C(=O)O—, —OC(=O)N(R$^{6A}$)—, or —NR$^{6A}$C(O)O—; L⁵ is a 6- to 10-membered arylene, 5- to 10-membered heteroarylene, a 3- to 7-membered monocyclic cycloalkylene, a 3- to 7-membered monocyclic heterocycloalkylene, wherein the 6- to 10-membered arylene, 5- to 10-membered heteroarylene, a 3- to 7-membered monocyclic cycloalkylene, a 3- to 7-membered monocyclic heterocycloalkylene is optionally substituted; and L⁶ is absent, or is (CR⁷R⁸)$_s$.

In some embodiments, the compounds of Formula I or Formula IA-4 are those wherein L⁴ is —(CR⁴R⁵)$_p$Q¹(CR⁴R⁵)$_q$— wherein p=1; q=1-3, Q¹ is absent, or —CR$^{4A}$=CR$^{4B}$—; L⁶ is (CR⁷R⁸)$_s$ wherein s=1-2, —O(CR⁷R⁸)$_t$, —NR⁹(CR⁷R⁸)$_t$, —S(CR⁷R⁸)$_t$, —S(O)(CR⁷R⁸)$_t$, or —S(O)₂(CR⁷R⁸)$_t$, wherein t=1.

In some embodiments, the compounds of Formula I are those of Formula IA-5

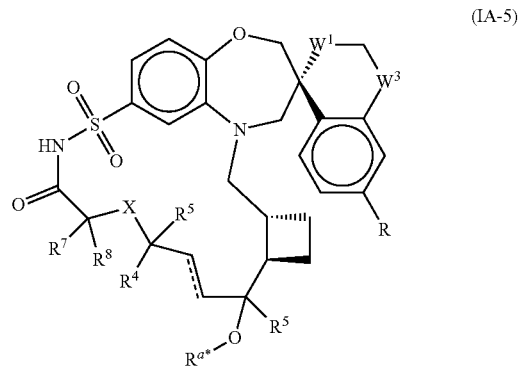

(IA-5)

wherein X is O, NR⁹, CR⁷R⁸, S, S(O), SO₂; R is halo or C₁-C₆alkyl; ===== represents a carbon-carbon single bond in which each carbon atom in the bond is substituted with R⁴ and R⁵, an (E)-carbon-carbon double bond substituted with R$^{4A}$ and R$^{4B}$, or a (Z)-carbon-carbon double bond substituted with R$^{4A}$ and R$^{4B}$; and R$^{a*}$ is R$^a$ wherein R$^a$ is H, —C(O)R$^b$, —C(O)OR$^c$, —C(O)NR$^c$R$^d$, P(OR$^c$)₂, P(O)R$^c$R$^b$, P(O)OR$^c$OR$^b$, S(O)R$^b$, S(O)NR$^c$R$^d$, S(O)₂R$^b$, S(O)₂NR$^c$R$^d$, B(OR$^c$)(OR$^b$), SiR$^b$₃, C₁-C₁₀alkyl, C₂-C₁₀ alkenyl, C₂-C₁₀ alkynyl, aryl, cycloalkyl, heteroaryl, or heterocycloalkyl, wherein said C₁-C₁₀ alkyl, C₂-C₁₀alkenyl, C₂-C₁₀ alkynyl, aryl, cycloalkyl, heteroaryl, or heterocycloalkyl is optionally substituted.

In some embodiments of the compound Formula IA-5, ===== represents a carbon-carbon single bond in which each carbon atom in the bond is substituted with R⁴ and R⁵.

In other embodiments of the compound Formula IA-5, ===== represents a carbon-carbon double bond.

In some embodiments of the compound Formula IA-5, X is O, NR⁹, or CR⁷R⁸.

In some embodiments of the compound Formula IA-5, R$^{a*}$ is R$^a$ wherein R$^a$ is H, —C(O)R$^b$, —C(O)NR$^c$R$^d$, or optionally substituted C₁-C₁₀alkyl, optionally substituted C₂-C₁₀alkenyl, optionally substituted C₂-C₁₀ alkynyl, optionally substituted aryl, optionally substituted cycloalkyl, optionally substituted heteroaryl, or optionally substituted heterocycloalkyl.

In some aspects, the compounds of Formula I are those of Formula IA-6:

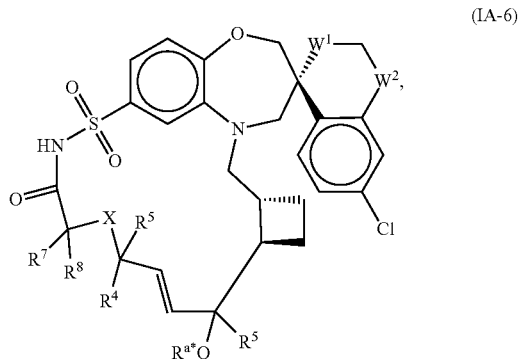

(IA-6)

or a pharmaceutically acceptable salt or solvate thereof; wherein X is —O—, —NR⁹—, or —CR⁷R⁸—; and W¹ is —CH₂— and W³ is O, or W¹ is —O— and W³ is —CH₂—, or W¹ is —CH₂— and W³ is —CH₂; R$^{a*}$ is R$^a$.

In some embodiments, the compounds of Formula IA-6 are those wherein X is —CR$^7$R$^8$—.

In other embodiments, the compounds of Formula IA-6 are those wherein X is —O—.

In some embodiments, the compounds of Formula IA-6 are those wherein X is —NR$^9$—.

In some embodiments X is —NR$^9$— wherein R$^9$ is H; optionally substituted —C$_1$-C$_6$alkyl; optionally substituted —C(O)OC$_1$-C$_6$alkyl; optionally substituted —SO$_2$C$_1$-C$_6$alkyl; optionally substituted —C(O)C$_1$-C$_6$alkyl; optionally substituted —C(O)NR$^c$R$^d$; or wherein R$^9$ together with either R$^7$ or R$^8$ form an optionally substituted C$_1$-C$_6$alkylene group.

In other embodiments, X is —NR$^9$— wherein R$^9$ is H; —C$_1$-C$_6$alkyl, optionally substituted with deuterium; —C(O)OC$_1$-C$_6$alkyl; —SO$_2$C$_1$-C$_6$alkyl; —C(O)C$_1$-C$_6$alkyl; or wherein R$^9$ together with either R$^7$ or R$^8$ form a C$_1$-C$_6$alkylene group.

In some embodiments, the compounds of Formula IA-6 are those having the structure (IA-7):

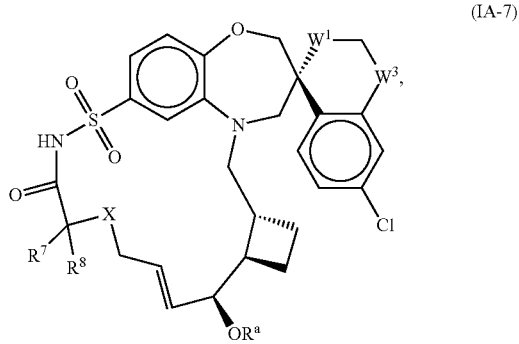

(IA-7)

wherein W$^1$ is —CH$_2$— and W$^3$ is —O—; or W$^1$ is —O— and W$^3$ is —CH$_2$—; or W$^1$ is —CH$_2$— and W$^3$ is —CH$_2$—.

In some embodiments, the compounds of Formula IA-7 are those wherein W$^1$ is —CH$_2$— and W$^3$ is —CH$_2$—.

In some embodiments, the compounds of Formula I are those of Formula IA-8

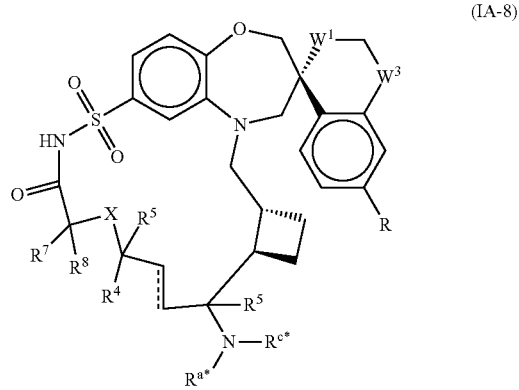

(IA-8)

wherein X is O, NR$^9$, CR$^7$R$^8$, S, S(O), SO$_2$; W$^1$ is —CH$_2$— and W$^3$ is O, or W$^1$ is —O— and W$^3$ is —CH$_2$—, or W$^1$ is —CH$_2$— and W$^3$ is —CH$_2$—; R is halo or C$_1$-C$_6$alkyl; ----- represents a carbon-carbon single bond in which each carbon atom in the bond is substituted with R$^4$ and R$^5$, an (E)-carbon-carbon double bond, or a (Z)-carbon-carbon double bond; and R$^{a*}$ is R$^a$ wherein R$^a$ is H, —C(O)R$^b$, —C(O)OR$^c$, —C(O)NR$^c$R$^d$, P(OR$^c$)$_2$, P(O)R$^c$R$^b$, P(O)OR$^c$OR$^b$, S(O)R$^b$, S(O)NR$^c$R$^d$, S(O)$_2$R$^b$, S(O)$_2$NR$^c$R$^d$, B(OR$^c$)(OR$^b$), SiR$^b$$_3$, C$_1$-C$_{10}$alkyl, C$_2$-C$_{10}$ alkenyl, C$_2$-C$_{10}$ alkynyl, aryl, cycloalkyl, heteroaryl, or heterocycloalkyl, wherein said C$_1$-C$_{10}$ alkyl, C$_2$-C$_{10}$alkenyl, C$_2$-C$_{10}$ alkynyl, aryl, cycloalkyl, heteroaryl, or heterocycloalkyl is optionally substituted; and R$^{c*}$ is R$^c$ wherein R$^c$ is H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, heteroaryl, cycloalkyl, cycloalkenyl, heterocycloalkyl, or heterocycloalkenyl, wherein said C$_1$-C$_{10}$ alkyl, C$_2$-C$_6$ alkenyl, C$_2$-C$_6$ alkynyl, —OC$_1$-C$_6$alkyl, —O-cycloalkyl, aryl, heteroaryl, cycloalkyl, cycloalkenyl, heterocycloalkyl, or heterocycloalkenyl are each optionally substituted.

In some embodiments of the compound Formula IA-8, ----- represents a carbon-carbon single bond in which each carbon atom in the bond is substituted with R$^4$ and R$^5$.

In other embodiments of the compound Formula IA-8, ----- represents a carbon-carbon double bond.

In other embodiments of the compound Formula IA-8, ----- represents a (E)-carbon-carbon double bond substituted with R$^{4A}$ and R$^{4B}$.

In some embodiments of the compound of Formula IA-8, R$^{a*}$ is R$^a$ and R$^{c*}$ is R$^c$.

In other embodiments of the compound Formula IA-8, R$^{a*}$ is R$^a$ wherein R$^a$ is H, —C(O)R$^b$, —C(O)OR$^c$, —C(O)NR$^c$R$^d$, —S(O)$_2$R$^b$, or optionally substituted C$_1$-C$_{10}$alkyl; and R$^{c*}$ is R wherein R$^c$ is H or optionally substituted C$_1$-C$_{10}$alkyl.

In other embodiments of the compound Formula IA-8, R is —Cl.

In other embodiments of the compound Formula IA-8, each R$^4$ and R$^5$ is independently H or C$_1$-C$_6$alkyl.

In some embodiments of the compound of Formula IA-8, X is O, NR$^9$, or CR$^7$R$^8$.

In some aspects, the compounds of Formula I are those of Formula IA-9:

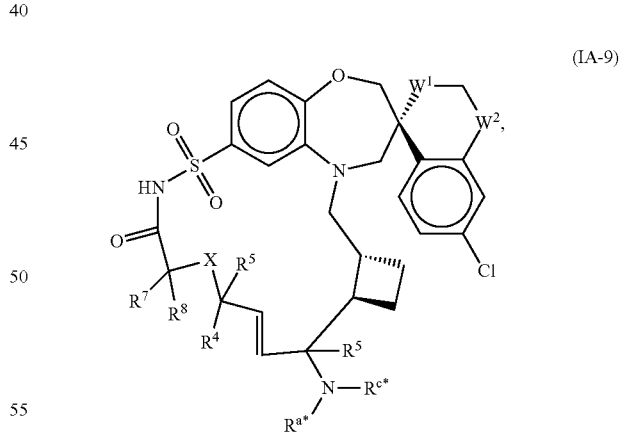

(IA-9)

or a pharmaceutically acceptable salt or solvate thereof; wherein X is —O—, —NR$^9$—, or —CR$^7$R$^8$—; and $^1$ is —CH$_2$— and W$^3$ is O, or W$^1$ is —O— and W$^3$ is —CH$_2$—, or W$^1$ is —CH$_2$— and W$^3$ is —CH$_2$—; R$^{a*}$ is R$^a$ and R$^{c*}$ is R$^c$.

In other embodiments of the compound Formula IA-9, R$^{a*}$ is R$^a$ wherein R$^a$ is H, —C(O)R$^b$, —C(O)OR$^c$, —C(O)NR$^c$R$^d$, —S(O)$_2$R$^b$, or optionally substituted C$_1$-C$_{10}$alkyl; and R$^{c*}$ is R$^c$ wherein R$^c$ is H or optionally substituted C$_1$-C$_{10}$alkyl.

In some embodiments, the compounds of Formula IA-9 are those wherein X is —CR$^7$R$^8$—.

In other embodiments, the compounds of Formula IA-9 are those wherein X is —O—.

In some embodiments, the compounds of Formula IA-9 are those wherein X is —NR$^9$—.

In some embodiments, X is —NR$^9$— wherein R$^9$ is H; optionally substituted —C$_1$-C$_6$alkyl; optionally substituted —C(O)OC$_1$-C$_6$alkyl; optionally substituted —SO$_2$C$_1$-C$_6$alkyl; optionally substituted —C(O)C$_1$-C$_6$alkyl; optionally substituted —C(O)NR$^c$R$^d$; or wherein R$^9$ together with either R$^7$ or R$^8$ form an optionally substituted C$_1$-C$_6$alkylene group.

In other embodiments, X is —NR$^9$— wherein R$^9$ is H; —C$_1$-C$_6$alkyl, optionally substituted with deuterium; —C(O)OC$_1$-C$_6$alkyl; —SO$_2$C$_1$-C$_6$alkyl; —C(O)C$_1$-C$_6$alkyl; or wherein R$^9$ together with either R$^7$ or R$^8$ form a C$_1$-C$_6$alkylene group.

In some embodiments, the compounds of Formula IA-9 are those having the structure (IA-10):

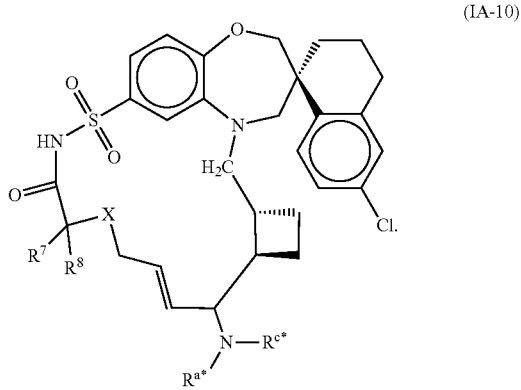

(IA-10)

In some aspects, the disclosure is directed to compounds of Formula II:

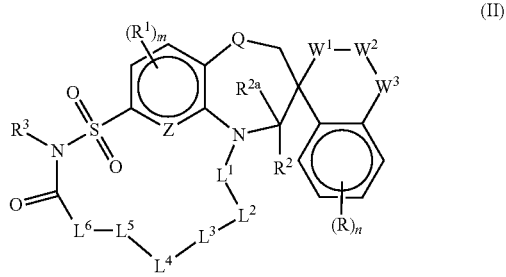

(II)

or a pharmaceutically acceptable salt or solvate thereof.

In some aspects, Z in Formula II is C or N. In some embodiments, Z is C. In other embodiments, Z is N.

In some aspects, Q in Formula II is —O—, —S—, —S(O)—, or —S(O)$_2$—. In some embodiments, Q is —O—. In some embodiments, Q is —S—. In some embodiments, Q is —S(O)—. In some embodiments, Q is —S(O)$_2$—.

In some aspects, the moiety —W$^1$—W$^2$—W$^3$ in Formula II is —CR$^2$R$^{2A}$—CR$^2$R$^{2A}$—CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —S—CR$^{2B}$R$^{2C}$—CR$^2$R$^{2A}$—, or —CR$^2$R$^{2A}$—CR$^{2B}$R$^{2C}$—S—.

In some embodiments, the moiety —W$^1$—W$^2$—W$^3$ in Formula II is —CR$^2$R$^{2A}$—CR$^2$R$^{2A}$—CR$^2$R$^{2A}$—. In some embodiments, the moiety —W$^1$—W$^2$—W$^3$ in Formula II is —O—CR$^{2B}$R$^{2C}$—CR$^2$R$^{2A}$—. In some embodiments, the moiety —W$^1$—W$^2$—W$^3$ in Formula II —CR$^2$R$^{2A}$—CR$^{2B}$R$^{2C}$—O—. In some embodiments, the moiety —W$^1$—W$^2$—W$^3$ in Formula II is —S—CR$^{2B}$R$^{2C}$—CR$^2$R$^{2A}$. In some embodiments, the moiety —W$^1$—W$^2$—W$^3$ in Formula II is —CR$^2$R$^{2A}$—CR$^{2B}$R$^{2C}$—S—.

In some aspects, L$^1$ in Formula II is —C$_1$-C$_6$alkylene-, for example, —C$_1$alkylene, —C$_2$alkylene, —C$_3$alkylene, —C$_4$alkylene, —C$_5$alkylene, or —C$_6$alkylene, wherein the C$_1$-C$_6$alkylene is optionally substituted with 1, 2, or 3 substituents independently selected from halo, oxo, CN, OR$^{a1}$, SR$^{a1}$, NR$^{c1}$C(O)R$^{b1}$, NR$^{c1}$C(O)OR$^{a1}$, and NR$^{c1}$S(O)$_2$ R$^{b1}$. In some embodiments, L$^1$ in Formula II is —C$_1$alkylene. In some embodiments, L$^1$ in Formula II is —CH$_2$—.

In some aspects, L$^2$ in Formula II is C$_3$-C$_7$cycloalkylene, C$_4$-C$_7$heterocycloalkylene, or heteroarylene; wherein the C$_3$-C$_7$cycloalkylene, C$_4$-C$_7$heterocycloalkylene, or heteroarylene is optionally substituted with 1, 2, or 3 substituents independently selected from halo, C$_1$-C$_6$ alkyl, C$_2$-C$_6$ alkenyl, C$_2$-C$_6$ alkynyl, C$_1$-C$_6$ haloalkyl, oxo, CN, NO$_2$, N$_3$, OR$^{a2}$, SR$^{a2}$, C(O)R$^{b2}$, C(O)NR$^{c2}$R$^{d2}$, C(O)OR$^{a2}$, OC(O) R$^{b2}$, NR$^{c2}$R$^{d2}$ NR$^{c2}$C(O)R$^{b2}$ NR$^{c2}$C(O)OR$^{a2}$, P(O) OR$^{e1}$OR$^{f1}$, S(O)$_2$R$^{a2}$, NR$^{c2}$S(O)$_2$R$^{b2}$, and S(O)$_2$NR$^{c2}$R$^{d2}$.

In some embodiments, L$^2$ in Formula II is C$_3$-C$_7$cycloalkylene, for example, C$_3$cycloalkylene, C$_4$cycloalkylene, C$_5$cycloalkylene, C$_6$cycloalkylene, or C$_7$cycloalkylene. In some embodiments, L$^2$ is C$_4$cycloalkylene. In some embodiments, L$^2$ is cyclobutylenyl.

In some embodiments, L$^2$ in Formula II is C$_4$-C$_7$heterocycloalkylene, for example, C$_4$heterocycloalkylene, C$_5$heterocycloalkylene, C$_6$heterocycloalkylene, or C$_7$heterocycloalkylene. In some embodiments, L$^2$ in Formula II is C$_4$heterocycloalkylene. In some embodiments, L$^2$ is pyrrolidinyl.

In other embodiments, L$^2$ in Formula II is heteroarylene. In some embodiments, the heteroarylene is pyrazolyl.

In some aspects, L$^3$ in Formula II is absent, or is —(CR$^4$R$^5$)$_p$—, —(CR$^4$R$^5$)$_p$O—, —O—, —S—, —S(O)—, —S(O)$_2$—, —C(=O)—, —NR$^6$—, —OC(=O)—, —C(=O)O—, —NR$^{6A}$C(O), —C(=O)NR$^{6A}$—, —OC(=O)N(R$^{6A}$)—, —NR$^{6A}$C(O)O—, —S(=O)NR$^{6A}$—, —NR$^{6A}$S(O)—, —S(=O)$_2$NR$^{6A}$—, or —NR$^{6A}$S(O)$_2$—.

In some embodiments, L$^3$ in Formula II is absent. In some embodiments, L$^3$ is —(CR$^4$R$^5$)$_p$—. In some embodiments, L$^3$ is —(CR$^4$R$^5$)$_p$O—. In some embodiments, L$^3$ is —O—. In some embodiments, L$^3$ is —S—. In some embodiments, L$^3$ is —S(O)—. In some embodiments, L$^3$ is —S(O)$_2$—. In some embodiments, L$^3$ is —C(=O)—. In some embodiments, L$^3$ is —NR$^6$—. In some embodiments, L$^3$ is —OC(=O)—. In some embodiments, L$^3$ is —C(=O)O—. In some embodiments, L$^3$ is —NR$^{6A}$C(O). In some embodiments, L$^3$ is —C(=O)NR$^{6A}$—. In some embodiments, L$^3$ is —OC(=O)N(R$^{6A}$)—. In some embodiments, L$^3$ is —NR$^{6A}$C(O)O—. In some embodiments, L$^3$ is —S(=O) NR$^{6A}$—. In some embodiments, L$^3$ is —NR$^{6A}$S(O)—. In some embodiments, L$^3$ is —S(=O)$_2$NR$^{6A}$—. In some embodiments, L$^3$ is —NR$^{6A}$S(O)$_2$—.

In some aspects, L$^4$ in Formula II is absent, or is —(CR$^4$R$^5$)$_p$Q$^1$(CR$^4$R$^5$)$_q$—, wherein Q$^1$ is —CR$^{4A}$=CR$^{4B}$—, —O—, —S—, —S(O)—, —S(O)$_2$—, —C(=O)—, —NR$^6$—, —OC(=O)—, —C(=O)O—, —NR$^{6A}$C(O), —C(=O)NR$^{6A}$—, —NR$^{6A}$C(O)R$^{6B}$—, —OC(=O)N($R^{6A}$)—, —$NR^{6A}$C(O)O—, —S(=O) $NR^{6A}$—, —$NR^{6A}$S(O)—, —S(=O)$_2NR^{6A}$—, or —$NR^{6A}$S(O)$_2$—; or is —$(CR^4R^5)_p$—$(CR^{4A}$=$CR^{4B})$—$(CR^4R^5)_q$—O—.

In some embodiments, $L^4$ in Formula II is absent. In other embodiments, $L^4$ in Formula II is —$(CR^4R^5)_p$—$(CR^{4A}$=$CR^{4B})$—$(CR^4R^5)_q$—. In other embodiments, $L^4$ in Formula II is —$(CR^4R^5)_p$—O—$(CR^4R^5)_q$—. In other embodiments, $L^4$ in Formula II is —$(CR^4R^5)_p$—S—$(CR^4R^5)_q$—. In other embodiments, $L^4$ in Formula II is —$(CR^4R^5)_p$—S(O)—$(CR^4R^5)_q$—. In other embodiments, $L^4$ in Formula II is —$(CR^4R^5)_p$—S(O)$_2$—$(CR^4R^5)_q$—. In other embodiments, $L^4$ in Formula II is —$(CR^4R^5)_p$—C(=O)—$(CR^4R^5)_q$—. In other embodiments, $L^4$ in Formula II is —$(CR^4R^5)_p$—$NR^6$—$(CR^4R^5)_q$—. In other embodiments, $L^4$ in Formula II is —$(CR^4R^5)_p$—OC(=O)—$(CR^4R^5)_q$—. In other embodiments, $L^4$ in Formula II is —$(CR^4R^5)_p$—C(=O)O—$(CR^4R^5)_q$—. In other embodiments, $L^4$ in Formula II is —$(CR^4R^5)_p$—$NR^{6A}$C(O)—$(CR^4R^5)_q$—. In other embodiments, $L^4$ in Formula II is —$(CR^4R^5)_p$—C(=O)$NR^{6A}$—$(CR^4R^5)_q$—. In other embodiments, $L^4$ in Formula II is —$(CR^4R^5)_p$—$NR^{6A}$C(O)$R^{6B}$—$(CR^4R^5)_q$—. In other embodiments, $L^4$ in Formula II is —$(CR^4R^5)_p$—OC(=O)N($R^{6A}$)—$(CR^4R^5)_q$—. In other embodiments, $L^4$ in Formula II is —$(CR^4R^5)_p$—$NR^{6A}$C(O)O—$(CR^4R^5)_q$—. In other embodiments, $L^4$ in Formula II is —$(CR^4R^5)_p$—S(=O)$NR^{6A}$—$(CR^4R^5)_q$—. In other embodiments, $L^4$ in Formula II is —$(CR^4R^5)_p$—$NR^{6A}$S(O)—$(CR^4R^5)_q$—. In other embodiments, $L^4$ in Formula II is —$(CR^4R^5)_p$—S(=O)$_2NR^{6A}$—$(CR^4R^5)_q$—. In other embodiments, $L^4$ in Formula II is —$(CR^4R^5)_p$—$NR^{6A}$S(O)$_2$—$(CR^4R^5)_q$—. In some embodiments, $L^4$ is —$(CR^4R^5)_p$—$(CR^{4A}$=$CR^{4B})$—$(CR^4R^5)_q$—O—.

In some aspects, $L^5$ in Formula II is absent, or is $C_1$-$C_6$ alkylene, $C_2$-$C_6$ alkenylene, $C_{2-6}$ alkynylene, a 6- to 10-membered arylene, 5- to 10-membered heteroarylene, a 5- to 12-membered spirocycloalkylene, a 5- to 12-membered spiroheterocycloalkylene, a 3- to 12-membered cycloalkenylene, a 3- to 7-membered monocyclic cycloalkylene, or a 6- to 12-membered bicyclic cycloalkylene, or a 3- to 7-membered monocyclic heterocycloalkylene or a 6 to 12-membered bicyclic heterocycloalkylene group, wherein the heteroarylene, spiroheterocycloalkylene or heterocycloalkylene group have 1, 2, 3 or 4, heteroatoms independently selected from O, N or S; wherein the cycloalkylene, spirocycloalkylene, spiroheterocycloalkylene, and heterocycloalkylene groups may include a C=O group; wherein the spiroheterocycloalkylene, and heterocycloalkylene groups may include a S=O or SO$_2$; wherein said $C_1$-$C_6$ alkylene, $C_2$-$C_6$ alkenylene, $C_2$-$C_6$ alkynylene, cycloalkylene, spirocycloalkylene, heterocycloalkylene, spiroheterocycloalkylene, arylene or heteroarylene are optionally substituted by 1, 2, 3, 4 or 5 substituents independently selected from halo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl $NR^{c3}R^{d3}$, $C_2$-$C_6$ alkenyl $NR^{c3}R^{d3}$, $C_2$-$C_6$ alkynyl $NR^{c3}R^{d3}$, $OC_2$—$C_6$ alkyl $NR^{c3}R^{d3}$, CN, $NO_2$, $N_3$, $OR^{a3}$, $SR^{a3}$, $C(O)R^{b3}$, $C(O)NR^{c3}R^{d3}$, —$CH_2C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, C(=$NR^{g1}$)$NR^{c2}R^{d2}$ $NR^{c3}$C(=$NR^{g1}$)$NR^{c3}R^{d3}$, P($R^{f2}$)$_2$, P($OR^{e2}$)$_2$, P(O)$R^{e2}R^{f2}$, P(O)$OR^{e2}OR^{f2}$, S(O)$R^{b3}$, S(O)$NR^{c3}R^{d3}$, S(O)$_2R^{b3}$, $NR^{c3}$S(O)$_2R^{b3}$, and S(O)$_2NR^{c3}R^{d3}$.

In some embodiments, $L^5$ in Formula II is absent. In other embodiments, $L^5$ in Formula II is $C_1$-$C_6$ alkylene, for example, $C_1$alkylene, $C_2$alkylene, $C_3$alkylene, $C_4$alkylene, $C_5$alkylene, or $C_6$alkylene.

In other embodiments, $L^5$ in Formula II is $C_2$-$C_6$ alkenylene, for example, $C_2$alkenylene, $C_3$alkenylene, $C_4$alkenylene, $C_5$alkenylene, or $C_6$alkenylene.

In other embodiments, $L^5$ in Formula II is $C_2$-$C_6$ alkynylene, for example, $C_2$alkynylene, $C_3$alkynylene, $C_4$alkynylene, $C_5$alkynylene, or $C_6$alkynylene.

In other embodiments, $L^5$ in Formula II is a 6- to 10-membered arylene, for example phenylene or naphthylene. In some embodiments, $L^5$ in Formula II is a phenylene.

In other embodiments, $L^5$ in Formula II is a 5- to 10-membered heteroarylene, for example, pyrazolyl, thiazolyl, imidazolyl, or pyridinyl. In some embodiments, $L^5$ in Formula II is pyrazolyl. In some embodiments, $L^5$ in Formula II is thiazolyl. In some embodiments, $L^5$ in Formula II is imidazolyl. In some embodiments, $L^5$ in Formula II is pyridinyl.

In other embodiments, $L^5$ in Formula II is a 5- to 12-membered spirocycloalkylene, for example, spiro[3.4]octane, or spiro[3.3]heptane.

In other embodiments, $L^5$ in Formula II is a 5- to 12-membered spiroheterocycloalkylene, for example, 2,6-diazaspiro [3.4]octane, 2-azaspiro[3.4]octane, or 2-azaspiro[3.3]heptane. In some embodiments, $L^5$ in Formula II is 2,6-diazaspiro[3.4]octane. In some embodiments, $L^5$ in Formula II is 2-azaspiro[3.4]octane. In some embodiments, $L^5$ in Formula II is 2-azaspiro[3.3]heptane.

In other embodiments, $L^5$ in Formula II is a 3- to 12-membered cycloalkenylene, for example, cyclohexenyl.

In other embodiments, $L^5$ in Formula II is a 3- to 7-membered monocyclic cycloalkylene, for example, cyclopentanyl, cyclohexanyl, and the like. In some embodiments, $L^5$ in Formula II is cyclopentanyl.

In other embodiments, $L^5$ in Formula II is a 6- to 12-membered bicyclic cycloalkylene.

In other embodiments, $L^5$ in Formula II is a 3- to 7-membered monocyclic heterocycloalkylene group, for example, pyrrolidinyl, tetrahydrofuranyl, piperidinyl, piperazinyl, and the like. In some embodiments, $L^5$ in Formula II is pyrrolidinyl. In some embodiments, $L^5$ in Formula II is tetrahydrofuranyl. In some embodiments, $L^5$ in Formula II is piperidinyl. In some embodiments, $L^5$ in Formula II is piperazinyl.

In other embodiments, $L^5$ in Formula II is a 6- to 12-membered bicyclic heterocycloalkylene group.

In some aspects, $L^6$ in Formula II is absent, or is ($CR^7R^8$)$_s$, ($CR^7R^8$)$_s$O($CR^7R^8$)$_t$, ($CR^7R^8$)$_s$$NR^9$($CR^7R^8$)$_t$, ($CR^7R^8$)$_s$S($CR^7R^8$)$_t$, ($CR^7R^8$)$_s$S(O)($CR^7R^8$)$_t$, ($CR^7R^8$)$_s$S(O)$_2$($CR^7R^8$)$_t$, ($CR^7R^8$)$_s$$NR^{9A}$C(O)($CR^7R^8$)$_t$, ($CR^7R^8$)$_s$OC(O)$NR^{9A}$($CR^7R^8$)$_t$, ($CR^7R^8$)$_s$$NR^{9A}$C(O)O($CR^7R^8$)$_t$, ($CR^7R^8$)$_s$$NR^{9A}$C(O)$NR^{9B}$($CR^7R^8$)$_t$, ($CR^7R^8$)$_s$$NR^{9A}$S(O)($CR^7R^8$)$_t$, ($CR^7R^8$)$_s$$NR^{9A}$S(O)$_2$($CR^7R^8$)$_t$; —($CR^7R^8$)$_s$—$CR^{4A}$=$CR^{4B}$—($CR^7R^8$)$_t$, ($CR^7R^8$)$_s$C(=O)($CR^7R^8$)$_t$; —($CR^7R^8$)$_s$C(=O)($CR^7R^8$)t-O—, or —($CR^7R^8$)$_s$C(=O)($CR^7R^8$)t-$NR^6$—.

In some embodiments, $L^6$ in Formula II is absent. In other embodiments, $L^6$ in Formula II is ($CR^7R^8$)$_s$. In other embodiments, $L^6$ in Formula II is ($CR^7R^8$)$_s$O($CR^7R^8$)$_t$. In other embodiments, $L^6$ in Formula II is ($CR^7R^8$)$_s$$NR^9$($CR^7R^8$)$_t$. In other embodiments, $L^6$ in Formula II is ($CR^7R^8$)$_s$S($CR^7R^8$)$_t$. In other embodiments, $L^6$ in Formula II is ($CR^7R^8$)$_s$S(O)($CR^7R^8$)$_t$. In other embodiments, $L^6$ in Formula II is ($CR^7R^8$)$_s$S(O)$_2$($CR^7R^8$)$_t$. In other embodiments, $L^6$ in Formula II is ($CR^7R^8$)$_s$$NR^{9A}$C(O)($CR^7R^8$)$_t$. In other embodiments, $L^6$ in Formula II is ($CR^7R^8$)$_s$OC(O)$NR^{9A}$($CR^7R^8$)$_t$. In other embodiments, $L^6$ in Formula II is ($CR^7R^8$)$_s$$NR^{9A}$C(O)O($CR^7R^8$)$_t$. In other embodiments, $L^6$ in Formula II is ($CR^7R^8$)$_s$$NR^{9A}$C(O)$NR^{9B}$($CR^7R^8$)$_t$. In other embodiments, $L^6$ in Formula II is ($CR^7R^8$)$_s$$NR^{9A}$S(O)($CR^7R^8$)$_t$. In other embodiments, $L^6$ in Formula II is $(CR^7R^8)_sNR^{9A}S(O)_2(CR^7R^8)_t$. In other embodiments, $L^6$ in Formula II is $-(CR^7R^8)_s-CR^{4A}=CR^{4B}-(CR^7R^8)_t$. In other embodiments, $L^6$ in Formula II is $(CR^7R^8)_sC(=O)(CR^7R^8)_t$. In other embodiments, $L^6$ in Formula II is $-(CR^7R^8)_sC(=O)(CR^7R^8)t-O-$. In other embodiments, $L^6$ in Formula II is $-(CR^7R^8)_sC(=O)(CR^7R^8)t-NR^6-$.

In some aspects, in Formula II, n=0-3. In some embodiments, n=0. In other embodiments, n=1. In other embodiments, n=2. In other embodiments, n=3.

In some aspects, in Formula II, m=0-2. In some embodiments, m=0. In other embodiments, m=1. In other embodiments, m=2.

In some aspects, in Formula II, o=1-3. In some embodiments, o=0. In other embodiments, o=1. In other embodiments, o=2. In other embodiments, o=3.

In some aspects, in Formula II, p=0-4. In some embodiments, p=0. In other embodiments, p=1. In other embodiments, p=2. In other embodiments, p=3. In other embodiments, p=$^4$.

In some aspects, in Formula II, q=0-3. In some embodiments, q=0. In other embodiments, q=1. In other embodiments, q=2. In other embodiments, q=3.

In some aspects, in Formula II, s=0-3. In some embodiments, s=0. In other embodiments, s=1. In other embodiments, s=2. In other embodiments, s=3.

In some aspects, in Formula II, t=0-4. In some embodiments, t=0. In other embodiments, t=1. In other embodiments, t=2. In other embodiments, t=3. In other embodiments, t=4.

In some aspects, each R in Formula II is independently selected from halo, CN, $-NO_2$, $C_1$-$C_6$alkyl, $C_2$-$C_6$alkenyl, $C_1$-$C_6$haloalkyl, $C_1$-$C_6$alkoxy, $-(CH_2CH_2O)_oR^a$, $C_1$-$C_6$haloalkoxy, $C_3$-$C_6$cycloalkyl, $OR^a$, $SR^a$, $C(O)R^b$, $C(O)OR^a$, $NR^cR^d$, $C(O)NR^cR^d$, and $S(O)_2R^a$; wherein said $C_1$-$C_6$alkyl or $C_3$-$C_6$cycloalkyl is optionally substituted by 1, 2, or 3 substituents independently selected from halo, CN, $OR^{a1}$, $NR^{c1}R^{d1}$ and $C(O)NR^{c1}R^{d1}$.

In some embodiments, R is halo, for example, Cl or F. In some embodiments, R is $-SR^a$, for example $-SCH_3$.

In some aspects, each $R^1$ in Formula II is independently selected from halo, $-CN$, Nitro, $-C_1$-$C_6$alkyl, $-C_2$-$C_6$alkenyl, $-C_2$-$C_6$alkynyl, $C_1$-$C_6$haloalkyl, $-(CH_2CH_2O)_o R^a$, $-C_1$-$C_6$alkyl$C_3$-$C_7$cycloalkyl, $OR^a$, $SR^a$, $NR^cR^d$, $C(O)R^b$, $OC(O)R^b$, $C(O)OR^a$, $C(O)NR^cR^d$, or $S(O)_2R^a$; aryl, heteroaryl, spirocycloalkyl, spiroheterocycloalkyl, cycloalkyl, or heterocycloalkyl group, wherein the heteroaryl, spiroheterocycloalkyl or heterocycloalkyl group have 1, 2, 3 or 4, heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$; wherein said $C_1$-$C_6$alkyl, $-C_2$-$C_6$alkenyl, $-C_2$-$C_6$alkynyl, cycloalkyl, spirocycloalkyl, spiroheterocycloalkyl, and heterocycloalkyl is optionally substituted with 1, 2, or 3 substituents independently selected from halo, $C_1$-$C_6$ alkyl, $C_2$-$C_6$ alkenyl, $C_2$-$C_6$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^1$ in Formula II is halo, for example, Cl or F. In other embodiments, $R^1$ in Formula II is $-C_1$-$C_6$haloalkyl, for example $-CF_3$. In other embodiments, $R^1$ in Formula II is $-C_1$-$C_6$alkyl, for example, $-C_6$alkyl, $-C_5$alkyl, $-C_4$alkyl, $-C_3$alkyl, $-C_2$alkyl, $-C_1$alkyl. In some embodiments, $R^1$ in Formula II is $-C_1$alkyl substituted with $-CN$. In other embodiments, $R^1$ in Formula II is cycloalkyl, for example, cyclopropane, cyclobutane, cyclopentane, and the like. In other embodiments, $R^1$ in Formula II is cyclopropane substituted with $-CN$.

In some aspects, $R^2$ and $R^{2A}$ in Formula II are each independently H, halo, $OR^a$, $C_1$-$C_6$alkyl, $C_1$-$C_6$haloalkyl. In some embodiments, $R^2$ and $R^{2A}$ in Formula II are each H.

In other aspects, $R^2$ and $R^{2A}$ that are attached to the same carbon atom, together with the carbon atom to which they are both attached, form an optionally substituted $C_3$-$C_6$cycloalkyl ring. In some embodiments, $R^2$ and $R^{2A}$ that are attached to the same carbon atom, together with the carbon atom to which they are both attached, form a cyclopropane ring.

In some aspects, $R^2$ and $R^{2a}$ in Formula II are each independently H, halo, $OR^a$, $C_1$-$C_6$alkyl, $C_1$-$C_6$haloalkyl. In some embodiments, $R^2$ and $R^{2a}$ in Formula II are each H.

In other aspects, $R^2$ and $R^{2a}$ that are attached to the same carbon atom, together with the carbon atom to which they are both attached, form an optionally substituted $C_3$-$C_6$cycloalkyl ring. In some embodiments, $R^2$ and $R^{2a}$ that are attached to the same carbon atom, together with the carbon atom to which they are both attached, form a cyclopropane ring.

In some aspects, $R^{2B}$ and $R^{2C}$ in Formula II are each independently H, $C_1$-$C_6$alkyl, or $C_1$-$C_6$haloalkyl. In some embodiments, $R^{2B}$ and $R^{2C}$ in Formula II are each H.

In some aspects, $R^{2B}$ and $R^{2C}$ may, together with the carbon atom to which they are both attached, form an optionally substituted $C_3$-$C_6$cycloalkyl ring. In some embodiments, $R^{2B}$ and $R^{2C}$ that are attached to the same carbon atom together with the carbon atom to which they are both attached, form a cyclopropane ring.

In some aspects, $R^3$ in Formula II is H, $-C_1$-$C_6$alkyl, $-C_3$-$C_6$alkenyl, $-C_3$-$C_6$alkynyl, $-(CH_2CH_2O)_oR^a$, $-C_3$-$C_7$cycloalkyl, $-C_3$-$C_7$heterocycloalkyl, $-C_1$-$C_6$alkyl$C_3$-$C_7$cycloalkyl, $-C_1$-$C_6$alkyl$C_3$-$C_7$heterocycloalkyl, $C(O)R^b$, $C(O)OR^a$, or $C(O)NR^cR^d$; wherein the $C_1$-$C_6$alkyl, $-C_3$-$C_6$alkenyl, $-C_3$-$C_6$alkynyl, cycloalkyl, and heterocycloalkyl is optionally substituted with 1, 2, or 3 substituents independently selected from OH, halo, $C_{1-6}$ alkyl, CN, $-OP(O)OR^{e3}OR$, and $OR^{a4}$.

In some embodiments, $R^3$ in Formula II is H. In other embodiments, $R^3$ in Formula II is $-C_1$-$C_6$alkyl, for example, $C_6$alkyl, $C_5$alkyl, $C_4$alkyl, $C_3$alkyl, $C_2$alkyl, $C_1$alkyl, $-CH_3$, and the like.

In some aspects, $R^4$ and $R^7$ in Formula II are independently selected from H, halo, OH, CN, $NO_2$, $-C_1$-$C_6$alkyl, $-C_2$-$C_6$alkenyl, $-C_2$-$C_6$alkynyl, $-C_1$-$C_6$haloalkyl, $-(CH_2CH_2O)_oR^a$, $C_3$-$C_7$cycloalkyl, $-C_1$-$C_6$alkyl$C_3$-$C_7$cycloalkyl, cyano$C_1$-$C_6$alkyl-, heterocycloalkyl, $C_1$-$C_6$alk-$NR^cR^d$, $OR^a$, $SR^a$, $NR^cR^d$, $C(O)R^b$, $OC(O)R^a$, $C(O)OR^a$, $C(O)NR^cR^d$, and $S(O)_2R^a$, wherein said $C_1$-$C_6$alkyl, $C_3$-$C_7$cycloalkyl, heterocycloalkyl, or $-C_1$-$C_6$alkyl$C_3$-$C_7$cycloalkyl is optionally substituted with 1, 2, or 3 substituents independently selected from halo, $C_1$-$C_6$ alkyl, $C_2$-$C_6$ alkenyl, $C_2$-$C_6$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^4$ is Formula II is H. In other embodiments, $R^4$ in Formula II is $-C_1$-$C_6$alkyl, for example, $C_6$alkyl, $C_5$alkyl, $C_4$alkyl, $C_3$alkyl, $C_2$alkyl, $C_1$alkyl, —$CH_3$, and the like. In other embodiments, $R^4$ is Formula II is —$OR^a$, for example, —$OCH_3$.

In some embodiments, $R^7$ in Formula II is H. In other embodiments, $R^7$ in Formula II is —$C_1$-$C_6$alkyl, for example, $C_6$alkyl, $C_5$alkyl, $C_4$alkyl, $C_3$alkyl, $C_2$alkyl, $C_1$alkyl, —$CH_3$, and the like. In other embodiments, $R^7$ is Formula II is —$OR^a$, for example, —$OCH_3$.

In some aspects, $R^{4A}$ and $R^{4B}$ in Formula II are independently selected from H, Me, $CF_3$ and F. In some embodiments, $R^{4A}$ is H. In some embodiments, $R^{4B}$ is H.

In some aspects, $R^5$ and $R^8$ in Formula II are independently selected from H, halo, OH, CN, $NO_2$, —$C_1$-$C_6$alkyl, —$C_2$-$C_6$alkenyl, —$C_2$-$C_6$alkynyl, —$C_1$-$C_6$haloalkyl, —$(CH_2CH_2O)_oR^a$, —$C_1$-$C_6$alkyl$C_3$-$C_7$cycloalkyl, cyano$C_1$-$C_6$alkyl-, $C_1$-$C_6$alk-$NR^cR^d$, $OR^c$, $SR^c$, $NR^cR^d$, $C(O)R^c$, $OC(O)R^c$, $C(O)OR^c$, $C(O)NR^cR^d$, $S(O)R^c$, $S(O)_2R^c$, aryl, heteroaryl, spirocycloalkyl, spiroheterocycloalkyl, cycloalkyl, and heterocycloalkyl group, wherein the heteroaryl, spiroheterocycloalkyl or heterocycloalkyl group have 1, 2, 3 or 4, heteroatoms independently selected from O, N and S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$, wherein said $C_1$-$C_6$alkyl, —$C_2$-$C_6$alkenyl, —$C_2$-$C_6$alkynyl, or —$C_1$-$C_6$alkyl$C_3$-$C_7$cycloalkyl, cycloalkyl, spirocycloalkyl, spiroheterocycloalkyl, and heterocycloalkyl is optionally substituted with 1, 2, or 3 substituents independently selected from $R^{10}$, halo, $C_1$-$C_6$ alkyl, $C_2$-$C_6$ alkenyl, $C_2$-$C_6$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$ $NR^{c4}C(O)NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^5$ in Formula II is H. In other embodiments, $R^5$ in Formula II is —$C_1$-$C_6$alkyl, for example, $C_6$alkyl, $C_5$alkyl, $C_4$alkyl, $C_3$alkyl, $C_2$alkyl, $C_1$alkyl, —$CH_3$, and the like. In other embodiments, $R^5$ in Formula II is —$OR^a$, for example, —$OCH_3$.

In some embodiments, $R^8$ in Formula II is H. In other embodiments, $R^8$ in Formula II is —$C_1$-$C_6$alkyl, for example, $C_6$alkyl, $C_5$alkyl, $C_4$alkyl, $C_3$alkyl, $C_2$alkyl, $C_1$alkyl, —$CH_3$, and the like. In other embodiments, $R^8$ in Formula II is —$OR^a$, for example, —$OCH_3$.

In some embodiments, $R^4$ and $R^5$ in Formula II, together with the carbon atom to which they are both attached form a 3, 4, 5, 6, or 7-membered cycloalkyl, heterocycloalkyl or spiroheterocycloalkyl ring, each optionally substituted by 1, 2, or 3 substituents independently selected from halo, OH, $C_1$-$C_6$ alkyl, $C_2$-$C_6$ alkenyl, $C_2$-$C_6$ alkynyl, $C_1$-$C_6$ alkoxy, alkoxyalkyl, cyanoalkyl, heterocycloalkyl, cycloalkyl, $C_1$-$C_6$ haloalkyl, CN, and $NO_2$.

In some embodiments, $R^7$ and $R^8$ in Formula II, together with the carbon atom to which they are both attached form a 3, 4, 5, 6, or 7-membered cycloalkyl, heterocycloalkyl or spiroheterocycloalkyl ring, each optionally substituted by 1, 2, or 3 substituents independently selected from halo, OH, $C_1$-$C_6$ alkyl, $C_2$-$C_6$ alkenyl, $C_2$-$C_6$ alkynyl, $C_1$-$C_6$ alkoxy, alkoxyalkyl, cyanoalkyl, heterocycloalkyl, cycloalkyl, $C_{1-6}$ haloalkyl, CN, and $NO_2$.

In some aspects, $R^6$ and $R^9$ in Formula II are independently selected from H, —$C_1$-$C_6$alkyl, —$C_2$-$C_6$alkenyl, —$C_2$-$C_6$alkynyl, —$C_1$-$C_6$haloalkyl, —$(CH_2CH_2O)_oR^a$, —$C_1$-$C_6$alkyl$C_3$-$C_7$cycloalkyl, cyano$C_1$-$C_6$alkyl-, $C_1$-$C_6$alk-$NR^cR^d$, $C(O)R^b$, $C(O)OR^b$, $C(O)NR^cR^d$, $S(O)R^b$, $S(O)_2R^b$, aryl, heteroaryl, spirocycloalkyl, spiroheterocycloalkyl, cycloalkyl, and heterocycloalkyl group, wherein the heteroaryl, spiroheterocycloalkyl or heterocycloalkyl group have 1, 2, 3 or 4, heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$, wherein said $C_1$-$C_6$alkyl, —$C_2$-$C_6$alkenyl, —$C_2$-$C_6$alkynyl, —$C_1$-$C_6$alkyl$C_3$-$C_7$cycloalkyl, aryl, heteroaryl, cycloalkyl, spirocycloalkyl, spiroheterocycloalkyl, and heterocycloalkyl is optionally substituted with 1, 2, or 3 substituents independently selected from halo, $C_1$-$C_6$ alkyl, $C_2$-$C_6$ alkenyl, $C_2$-$C_6$ alkynyl, CN, $N_3$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^6$ in Formula II is H. In other embodiments, $R^6$ in Formula II is —$C_1$-$C_6$alkyl, for example, $C_6$alkyl, $C_5$alkyl, $C_4$alkyl, $C_3$alkyl, $C_2$alkyl, or $C_1$alkyl.

In some embodiments, $R^9$ in Formula II is H. In other embodiments, $R^6$ in Formula II is —$C_1$-$C_6$alkyl, for example, $C_6$alkyl, $C_5$alkyl, $C_4$alkyl, $C_3$alkyl, $C_2$alkyl, or $C_1$alkyl.

In some aspects, $R^{10}$ in Formula II is aryl, heteroaryl, spirocycloalkyl, spiroheterocycloalkyl, cycloalkyl, or heterocycloalkyl group, wherein the heteroaryl, spiroheterocycloalkyl or heterocycloalkyl group have 1, 2, 3 or 4, heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$, wherein said aryl, cycloalkyl, cycloalkenyl, spirocycloalkyl, spiroheterocycloalkyl, heteroaryl, and heterocycloalkyl is optionally substituted with 1, 2, or 3 substituents independently selected from halo, $C_1$-$C_6$alkyl, —$C_2$-$C_6$alkenyl, —$C_2$-$C_6$alkynyl, —$CH_2CH_2OR^a$, CN, $N_3$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$ $NR^{c4}C(O)NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some aspects $R^{6A}$, $R^{6B}$, $R^{9A}$, and $R^{9B}$ in Formula II are each independently H, $C_1$-$C_6$alkyl, —$C_2$-$C_6$alkenyl, —$C_2$-$C_6$alkynyl, —$(CH_2CH_2O)_oR^a$, $C_3$-$C_7$cycloalkyl, —$C_1$-$C_6$alkyl$C_3$-$C_7$cycloalkyl, $C_4$-$C_7$heterocycloalkyl, —$C_1$-$C_6$alkyl$C_4$-$C_7$heterocycloalkyl, wherein said $C_1$-$C_6$alkyl, —$C_2$-$C_6$alkenyl, —$C_2$-$C_6$alkynyl, —$C_3$-$C_7$cycloalkyl, —$C_1$-$C_6$alkyl$C_3$-$C_7$cycloalkyl, —$C_4$-$C_7$heterocycloalkyl, —$C_1$-$C_6$alkyl$C_3$-$C_7$heterocycloalkyl is optionally substituted with 1, 2, or 3 substituents independently selected from halo, $C_1$-$C_6$ alkyl, $C_2$-$C_6$ alkenyl, $C_2$-$C_6$ alkynyl, CN, $N_3$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)$ $NR^{c4}R^{d4}$, $NR^{c4}C(O)OR^{a4}$, $P(OR^{e3})_2$, $P(O)R^{e3}R^{f3}$, $P(O)OR^{e3}OR^{f3}$, $S(O)R^{b4}$, $S(O)NR^{c4}R^{d4}$ $S(O)_2R^{b4}$, $NR^{c4}S(O)_2R^{b4}$, and $S(O)_2NR^{c4}R^{d4}$.

In some embodiments, $R^{6A}$ and $R^{6B}$ in Formula II, together with the N atom to which they are attached form a 5, 6, 7, 8 or 9-membered heterocycloalkyl ring or spiroheterocycloalkyl ring, each optionally substituted by 1, 2, or 3 substituents independently selected from halo, OH, $C_1$-$C_6$ alkyl, $C_2$-$C_6$ alkenyl, $C_2$-$C_6$ alkynyl, $C_1$-$C_6$ alkoxy, alkoxyalkyl, cyanoalkyl, heterocycloalkyl, cycloalkyl, $C_1$-$C_6$ haloalkyl, CN, and $NO_2$.

In some embodiments, $R^{9A}$ and $R^{9B}$ in Formula II, together with the N atom to which they are attached form a 5, 6, 7, 8 or 9-membered heterocycloalkyl ring or spiroheterocycloalkyl ring, each optionally substituted by 1, 2, or 3 substituents independently selected from halo, OH, $C_1$-$C_6$ alkyl, $C_2$-$C_6$ alkenyl, $C_2$-$C_6$ alkynyl, $C_1$-$C_6$ alkoxy, alkoxyalkyl, cyanoalkyl, heterocycloalkyl, cycloalkyl, $C_1$-$C_6$ haloalkyl, CN, and $NO_2$.

In some aspects, $R^a$, $R^{a1}$, $R^{a2}$, $R^{a3}$, and $R^{a4}$ in Formula II are independently H, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, and heterocycloalkylalkyl, wherein said $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some embodiments, $R^a$ is H. In other embodiments, $R^a$ is —$C_1$-$C_6$ alkyl, for example $C_6$alkyl, $C_5$alkyl, $C_4$alkyl, $C_3$alkyl, $C_2$alkyl, or $C_1$alkyl. In some embodiments, $R^a$ is —$CH_3$.

In some aspects, $R^b$, $R^{b1}$, $R^{b2}$, $R^{b3}$, and $R^{b4}$ in Formula II are independently H, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl, wherein said $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^c$ and $R^d$ in Formula II are independently H, $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy, or heterocycloalkyl group.

In some embodiments, $R^c$ and $R^d$ in Formula II, together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{c1}$ and $R^{d1}$ in Formula II are independently H, $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some embodiments, $R^{c1}$ and $R^{d1}$ in Formula II, together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{c2}$ and $R^{d2}$ in Formula II are independently H, $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, $C_1$-$C_6$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy.

In some aspects, $R^{c2}$ and $R^{d2}$ in Formula II, together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, $C_1$-$C_6$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy.

In some aspects, $R^{c3}$ and $R^{d3}$ in Formula II are independently H, $C_{1-10}$ alkyl, $C_{1-6}$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{c3}$ and $R^{d3}$ in Formula II together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{c4}$ and $R^{d4}$ in Formula II are independently H, $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl, wherein said $C_1$-$C_{10}$ alkyl, $C_1$-$C_6$ haloalkyl, $C_2$-$C_6$ alkenyl, $C_2$-$C_6$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{c4}$ and $R^{d4}$ in Formula II together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_1$-$C_6$ alkyl, $C_1$-$C_6$ alkoxy, $C_1$-$C_6$ haloalkyl, and $C_1$-$C_6$ haloalkoxy.

In some aspects, $R^{e1}$, $R^{e2}$, and $R^{e3}$ in Formula II are independently H, $C_1$-$C_6$ alkyl, $C_1$-$C_6$ haloalkyl, $C_2$-$C_6$ alkenyl, ($C_1$-$C_6$ alkoxy)-$C_1$-$C_6$ alkyl, $C_2$-$C_6$ alkynyl, aryl, cycloalkyl, heteroaryl, heterocycloalkyl, arylalkyl, cycloalkylalkyl, heteroarylalkyl, or heterocycloalkylalkyl.

In some aspects, $R^{f1}$, $R^{f2}$, and $R^{f3}$ in Formula II are independently selected from H, $C_1$-$C_6$ alkyl, $C_1$-$C_6$ haloalkyl, $C_2$-$C_6$ alkenyl, $C_2$-$C_6$ alkynyl, aryl, cycloalkyl, heteroaryl, and heterocycloalkyl.

In some aspects, $R^{g1}$ in Formula II is H, CN, or $NO_2$.

In some aspects, the disclosure is directed to compounds of Formula IIA:

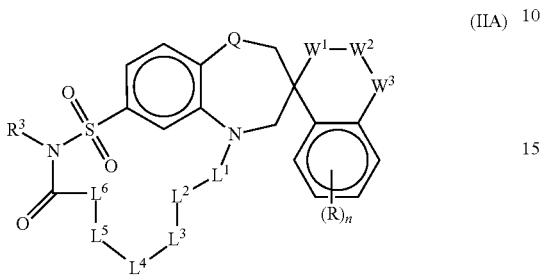

(IIA)

or a pharmaceutically acceptable salt or solvate thereof; wherein

Q is —O—, —S—, —S(O)—, or —S(O)$_2$—;

R is halo; n=1;

the moiety —$W^1$—$W^2$—$W^3$— is —$CR^2R^{2A}$—$CR^2R^{2A}$—$CR^2R^{2A}$—, —O—$CR^{2B}R^{2C}$—$CR^2R^{2A}$—, —$CR^2R^{2A}$—$CR^{2B}R^{2C}$—O—, —S—$CR^{2B}R^{2C}$—$CR^2R^{2A}$—, or —$CR^2R^{2A}$—$CR^{2B}R^{2C}$—S—;

$R^2$ and $R^{2A}$ are each independently H, halo, or $C_1$-$C_6$alkyl, or $R^2$ and $R^{2A}$ that are attached to the same carbon atom may, together with the carbon atom to which they are both attached, form a $C_3$-$C_6$cycloalkyl ring;

$R^{2B}$ and $R^{2C}$ are each independently H or $C_1$-$C_6$alkyl, or $R^{2B}$ and $R^{2C}$ may, together with the carbon atom to which they are both attached, form a $C_3$-$C_6$cycloalkyl ring;

$R^3$ is H or $C_1$-$C_6$alkyl;

$L^1$ is —$C_1$-$C_6$alkylene-;

$L^2$ is $C_3$-$C_7$ cycloalkylene, $C_4$-$C_7$ heterocycloalkylene or heteroarylene;

$L^3$ is absent, or is —$NR^{6A}S(O)$—, —$S(=O)_2NR^{6A}$—, —$NR^{6A}S(O)_2$—, —$(CR^4R^5)_p$—, —$(CR^4R^5)_pO$—, —$NR^{6A}C(O)$, —$C(=O)NR^{6A}$—;

$L^4$ is absent, —$(CR^4R^5)_p$—$(CR^{4A}=CR^{4B})$—$(CR^4R^5)_q$—O—, or —$(CR^4R^5)_pQ^1(CR^4R^5)_q$—, wherein $Q^1$ is —$CR^{4A}=CR^{4B}$—, or —O—, —S—, —S(O)—, —S(O)$_2$—, —$NR^6$—, —$NR^{6A}C(O)$, or —$C(=O)NR^{6A}$—;

$L^5$ is absent, or is a 6-10 membered arylene or 5-10 membered heteroarylene, wherein said heteroarylene is optionally substituted with $C_1$-$C_6$ alkyl, $OC_2$—$C_6$ alkyl $NR^{c3}R^{d3}$, or —$C_1$-$C_6$ alkyl-$C(O)NR^{c3}R^{d3}$;

$L^6$ is absent, or is —$(CR^7R^8)_s$—;

p=0-4; q=0-3; s=1;

each $R^4$ is independently H, OH, —$C_1$-$C_6$alkyl, or —$OC_1$-$C_6$alkyl, each $R^5$ is independently selected from is H, OH, —$C_1$-$C_6$alkyl, or —$OC_1$-$C_6$alkyl;

each $R^6$ is independently selected from is H or —$C_1$-$C_6$alkyl;

each $R^{6A}$ is independently selected from H, or $C_1$-$C_6$alkyl;

each $R^7$ is H, —$C_1$-$C_6$alkyl, or —$OC_1$-$C_6$alkyl;

each $R^{4A}$ and $R^{4B}$ is independently H, Me, $CF_3$ or F; and each $R^8$ is H, —$C_1$-$C_6$alkyl, or —$OC_1$-$C_6$alkyl;

$R^{c3}$ and $R^{d3}$ together with the N atom to which they are attached form a 4-, 5-, 6- or 7-membered heterocycloalkyl group optionally substituted with 1, 2, or 3 substituents independently selected from OH, $C_1$-$C_6$ alkyl, $C_1$-$C_6$ alkoxy, or $C_1$-$C_6$ alk-$C_1$-$C_6$ alkoxy.

In some aspects, the disclosure is directed to compounds of Formula IIA-1:

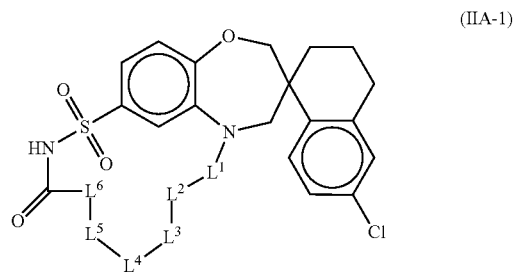

(IIA-1)

or a pharmaceutically acceptable salt or solvate thereof; wherein $L^2$ is $C_4$ cycloalkylene, $C_5$ heterocycloalkylene or heteroarylene;

$L^3$ is absent, or is —$NR^{6A}S(O)$—, —$S(=O)_2NR^{6A}$—, —$NR^{6A}S(O)_2$—, —$(CR^4R^5)_p$—, —$(CR^4R^5)_pO$—, —$NR^{6A}C(O)$, —$C(=O)NR^{6A}$—;

$L^4$ is absent, —$(CR^4R^5)_p$—$(CR^{4A}=CR^{4B})$—$(CR^4R^5)_q$—O—, or —$(CR^4R^5)_pQ^1(CR^4R^5)_q$—, wherein $Q^1$ is —$CR^{4A}=CR^{4B}$—, or —O—, —S—, —S(O)—, —S(O)$_2$—, —$NR^6$—, —$NR^{6A}C(O)$, or —$C(=O)NR^{6A}$—;

$L^5$ is absent, a 6-membered arylene, or a 5- or 6-membered heteroarylene, wherein said heteroarylene is optionally substituted with —$C_1$-$C_6$ alkyl, $OC_{2-6}$ alkyl $NR^{c3}R^{d3}$, or —$C_1$-$C_6$ alkyl-$C(O)NR^{c3}R^{d3}$;

$L^6$ is absent, or is —$(CR^7R^8)_s$—;

p=0-4; and q=0-3; s=1;

each $R^4$ is independently selected from H, OH, —$C_1$-$C_6$alkyl, and —$OC_1$-$C_6$alkyl, each $R^5$ is independently selected from H, OH, —$C_1$-$C_6$alkyl, and —$OC_1$-$C_6$alkyl;

each $R^6$ is independently selected from H and —$C_1$-$C_6$alkyl;

each $R^{6A}$ is independently selected from H, and $C_1$-$C_6$alkyl;

each $R^7$ is H, —$C_1$-$C_6$alkyl, or —$OC_1$-$C_6$alkyl;

each $R^{4A}$ and $R^{4B}$ is independently H, Me, $CF_3$ or F; and each $R^8$ is H, —$C_1$-$C_6$alkyl, or —$OC_1$-$C_6$alkyl;

$R^{c3}$ and $R^{d3}$ together with the N atom to which they are attached form a 4-, 5-, 6- or 7-membered heterocycloalkyl group optionally substituted with 1, 2, or 3 substituents independently selected from OH, $C_1$-$C_6$ alkyl, $C_1$-$C_6$ alkoxy, or $C_1$-$C_6$ alk-$C_1$-$C_6$ alkoxy.

In some embodiments, the compounds of Formula IIA-1 are those wherein $L^2$ is heteroarylene, $L^3$ is absent, $L^4$ is —$(CR^4R^5)_pQ^1(CR^4R^5)_q$—, wherein $Q^1$ is —$CR^{4A}=CR^{4B}$—; $L^5$ is absent, $L^6$ is absent, p=1; and q=3, $R^4$ and $R^5$ are H; $R^{4A}$ and $R^{4B}$ are H.

In some aspects, the disclosure is directed to compounds of Formula IIA-2:

(IIA-2)

or a pharmaceutically acceptable salt or solvate thereof; wherein
$L^3$ is absent, or is —NR$^{6A}$S(O)—, —S(=O)$_2$NR$^{6A}$—, —NR$^{6A}$S(O)$_2$—, —(CR$^4$R$^5$)$_p$—, —(CR$^4$R$^5$)$_p$O—, —NR$^{6A}$C(O), —C(=O)NR$^{6A}$—;
$L^4$ is absent, —(CR$^4$R$^5$)$_p$—(CR$^{4A}$=CR$^{4B}$)—(CR$^4$R$^5$)$_q$— O—, or —(CR$^4$R$^5$)$_p$Q$^1$(CR$^4$R$^5$)$_q$—, wherein Q$^1$ is —CR$^{4A}$=CR$^{4B}$—, or —O—, —S—, —S(O)—, —S(O)$_2$—, —NR$^6$—, —NR$^{6A}$C(O), or —C(=O)NR$^{6A}$—;
$L^5$ is 6-membered arylene or 5- or 6-membered heteroarylene, wherein said heteroarylene is optionally substituted with —C$_1$-C$_6$ alkyl, —OC$_2$-C$_6$alkyl NR$^{c3}$R$^{d3}$, or —C$_1$-C$_6$ alkyl-C(O)NR$^{c3}$R$^{d3}$;
$L^6$ is absent, or is —(CR$^7$R$^8$)$_s$—;
p=0-4; q=0-3; and s=1;
each R$^4$ is independently H, OH, or —OC$_1$-C$_6$alkyl;
each R$^5$ is independently selected from is H, OH, or —OC$_1$-C$_6$alkyl;
each R$^6$ is independently selected from is H or —C$_1$-C$_6$alkyl;
each R$^{6A}$ is independently selected from H or C$_1$alkyl;
each R$^7$ is H, —C$_1$alkyl, or —OC$_1$alkyl;
each R$^{4A}$ and R$^{4B}$ is H;
each R$^8$ is H, —C$_1$alkyl, or —OC$_1$alkyl;
R$^{c3}$ and R$^{d3}$ together with the N atom to which they are attached form a 6-membered heterocycloalkyl group optionally substituted with —C$_1$-C$_6$ alkoxy or —C$_1$-C$_6$ alk-C$_1$-C$_6$ alkoxy.

In some aspects, the disclosure is directed to compounds of Formula IIA-3:

(IIA-3)

or a pharmaceutically acceptable salt or solvate thereof; wherein
$L^3$ is absent, or is —NR$^{6A}$S(O)—, —S(=O)$_2$NR$^{6A}$—, —NR$^{6A}$S(O)$_2$—, —(CR$^4$R$^5$)$_p$—, —(CR$^4$R$^5$)$_p$O—, —NR$^{6A}$C(O), —C(=O)NR$^{6A}$—;
$L^4$ is absent, —(CR$^4$R$^5$)$_p$—(CR$^{4A}$=CR$^{4B}$)—(CR$^4$R$^5$)$_q$— O—, or —(CR$^4$R$^5$)$_p$Q$^1$(CR$^4$R$^5$)$_q$—, wherein Q$^1$ is —CR$^{4A}$=CR$^{4B}$—, or —O—, —S—, —S(O)—, —S(O)$_2$—, —NR$^6$—, —NR$^{6A}$C(O), or —C(=O)NR$^{6A}$—;

$L^5$ is phenyl;
$L^6$ is —(CR$^7$R$^8$)$_s$—;
p=0-4; q=0-3; and s=1
each R$^4$ is independently H, OH, or —OC$_1$-C$_6$alkyl;
each R$^5$ is independently selected from is H, OH, or —OC$_1$-C$_6$alkyl;
each R$^6$ is independently selected from is H or —C$_1$-C$_6$alkyl;
each R$^{6A}$ is independently selected from H or C$_1$alkyl;
each R$^7$ is H, —C$_1$alkyl, or —OC$_1$alkyl;
each R$^{4A}$ and R$^{4B}$ is H;
each R$^8$ is H, —C$_1$alkyl, or —OC$_1$alkyl.

In some embodiments, the compounds of Formula IIA-3 are those wherein
$L^3$ is absent,
$L^4$ is —(CR$^4$R$^5$)$_p$Q$^1$(CR$^4$R$^5$)$_q$—, wherein Q$^1$ is —O— or —S—,
$L^5$ is phenyl;
$L^6$ is —(CR$^7$R$^8$)$_s$—;
p=1-2; q=0-1; and s=1-2;
each R$^4$ is independently H, OH, or —OC$_1$-C$_6$alkyl;
each R$^5$ is independently selected from is H, OH, or —OC$_1$-C$_6$alkyl;
each R$^7$ is H, —C$_1$alkyl, or —OC$_1$alkyl; and
each R$^8$ is H, —C$_1$alkyl, or —OC$_1$alkyl.

In other embodiments, the compounds of Formula IIA-3 are those wherein
$L^3$ is absent;
$L^4$ is —(CR$^4$R$^5$)$_p$Q$^1$(CR$^4$R$^5$)$_q$—, wherein Q$^1$ is —O— or —S—;
$L^5$ is phenyl;
$L^6$ is —(CR$^7$R$^8$)$_s$—;
p=1; q=0; and s=1
each R$^4$ is independently H, OH, or —OC$_1$-C$_6$alkyl;
each R$^5$ is independently selected from is H, OH, or —OC$_1$-C$_6$alkyl;
each R$^7$ is H, —C$_1$alkyl, or —OC$_1$alkyl; and
each R$^8$ is H, —C$_1$alkyl, or —OC$_1$alkyl.

In other embodiments, the compounds of Formula IIA-3 are those wherein L$^3$ is absent; L$^4$ is —(CR$^4$R$^5$)$_p$Q$^1$(CR$^4$R$^5$)$_q$—, wherein Q$^1$ is —O— or —S—; L$^5$ is phenyl; L$^6$ is —(CR$^7$R$^8$)$_s$—; p=1; q=0; and s=1; each R$^4$ is H; each R$^5$ is H; R$^7$ is H; and R$^8$ is H.

In some aspects, the disclosure is directed to compounds of Formula IIB:

(IIB)

or a pharmaceutically acceptable salt or solvate thereof; wherein
Q is —O—, —S—, —S(O)—, or —S(O)$_2$—;
the moiety —W$^1$—W$^2$—W$^3$— is —CR$^2$R$^{2A}$—CR$^2$R$^{2A}$— CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —S—CR$^{2B}$R$^{2C}$— CR$^2$R$^{2A}$, or —CR$^2$R$^{2A}$—CR$^{2B}$R$^{2C}$—S—;

R² and R²ᴬ are each independently H, halo, C₁-C₆alkyl, or R² and R²ᴬ that are attached to the same carbon atom may, together with the carbon atom to which they are both attached, form a C₃-C₆cycloalkyl ring;

R²ᴮ and R²ᶜ are each independently H or C₁-C₆alkyl, or R²ᴮ and R²ᶜ may, together with the carbon atom to which they are both attached, form a C₃-C₆cycloalkyl ring;

R is halo, —S—C₁-C₆alkyl, or —O—C₁-C₆alkyl;

n=1 or 2;

R¹ is halo, —CH₂—CN, —C₁-C₆haloalkyl, —OC₁-C₆haloalkyl, —OC₁-C₆haloalkyl, —C₁-C₆alk-OH, —C₁-C₆alk-O—C₁-C₆alkyl, —O—C₁-C₆alk-O—C₁-C₆alkyl, —C₁-C₆alk-O—C₃-C₆cycloalkyl, —C₁-C₆alk-O—C₁-C₆haloalkyl, or

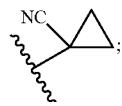

m=1 or 2

L³ is absent, or is —NR⁶S(O)—, —S(=O)₂NR⁶—, —NR⁶S(O)₂—;

L⁴ is —(CR⁴R⁵)ₚ, (CR⁴R⁵)ₚ—CR⁴ᴬ=CR⁴ᴮ—(CR⁴R⁵)ᵩ, (CR⁴R⁵)ₚO(CR⁴R⁵)ᵩ, (CR⁴R⁵)ₚ—S(=O)₂NR⁶ᴬ—(CR⁴R⁵)ᵩ, (CR⁴R⁵)ₚS(CR⁴R⁵)ᵩ, (CR⁴R⁵)ₚS(O)(CR⁴R⁵)ᵩ, (CR⁴R⁵)ₚS(O)₂(CR⁴R⁵)ᵩ, (CR⁴R⁵)ₚC(O)NR⁶ᴬ(CR⁴R⁵)ᵩ, (CR⁴R⁵)ₚNR⁶ᴬC(O)(CR⁴R⁵)ᵩ, or —(CR⁴R⁵)ₚ—(CR⁴ᴬ=CR⁴ᴮ)—(CR⁴R⁵)ᵩ—O—;

wherein each occurrence of p or q is independently p=0-2 and q=1-5;

L⁵ is absent,

L⁶ is absent, or is (CR⁷R⁸)ₛO(CR⁷R⁸)ₜ, (CR⁷R⁸)ₛNR⁹(CR⁷R⁸)ₜ, (CR⁷R⁸)ₛS(CR⁷R⁸)ₜ, (CR⁷R⁸)ₛS(O)(CR⁷R⁸)ₜ, or (CR⁷R⁸)ₛS(O)₂(CR⁷R⁸)ₜ;

wherein each occurrence of s or t is independently s=0-2 and t=0-2;

each R⁴ and each R⁷ is independently selected from H, OH, C₁-C₆alkyl, C₁-C₆haloalkyl, —OC₁-C₆alkyl, —C₃-C₇cycloalkyl, —OC₃-C₇cycloalkyl, —CH₂—CN, —CN, —N(CH₃)₂,

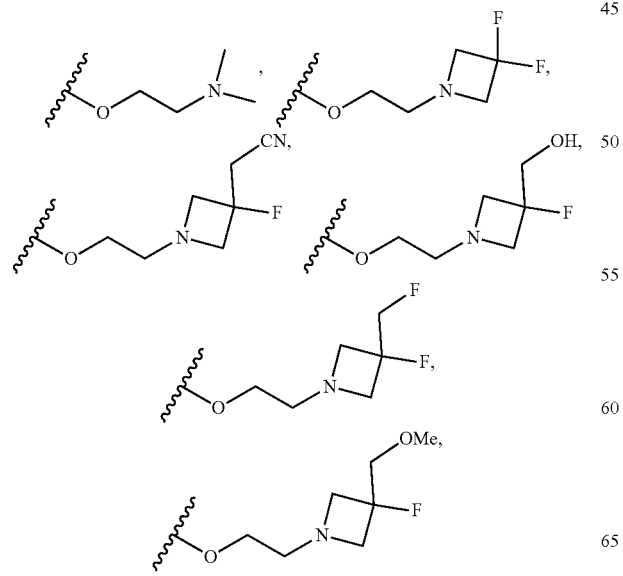

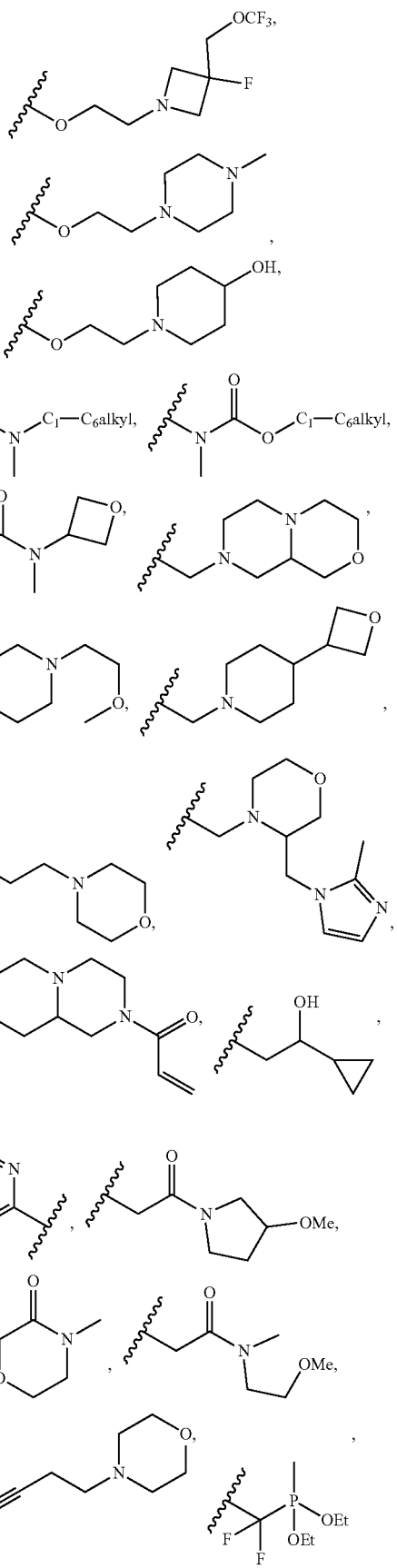

-continued

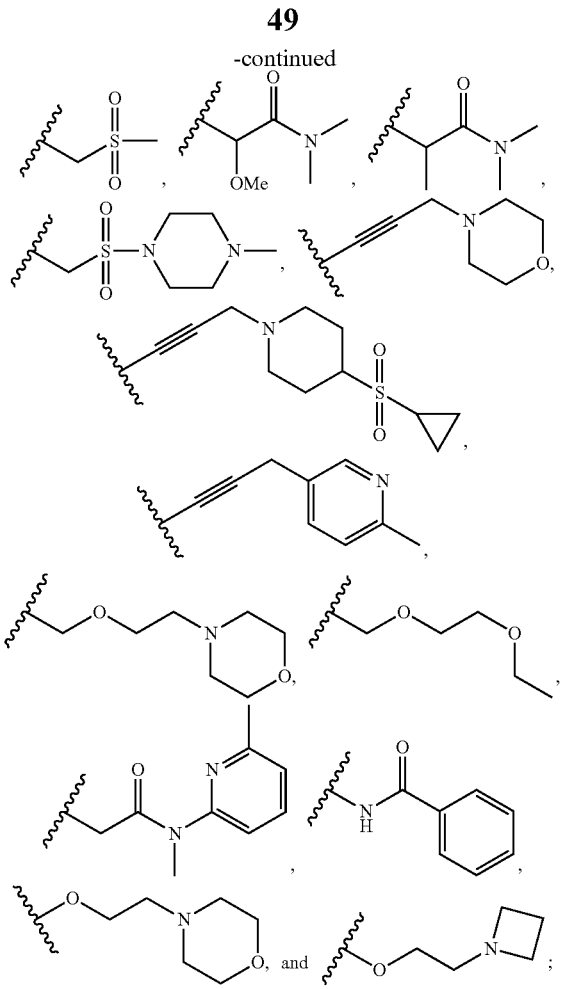

each $R^5$ and each $R^8$ is independently selected from H, OH, —CH$_2$OH, C$_1$-C$_6$alkyl, —OC$_1$-C$_6$alkyl, —C$_3$-C$_7$cycloalkyl, and —OC$_3$-C$_7$cycloalkyl;

wherein one $R^4$ and $R^5$ together with the C atom to which they are both attached may optionally form a 3, 4, 5, or 6-membered cycloalkyl ring,

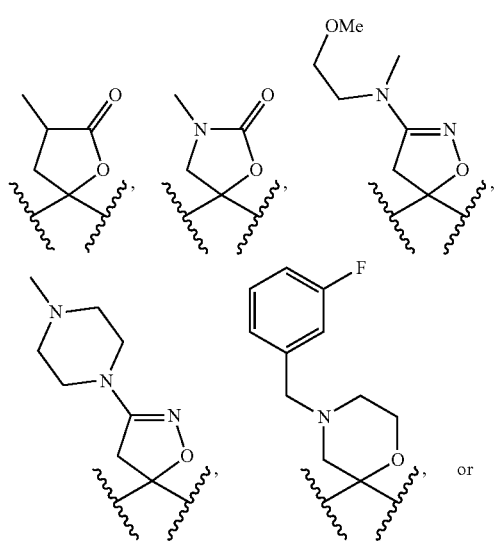

-continued

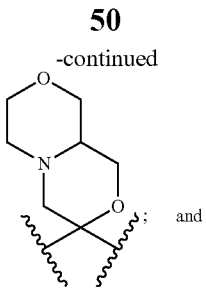

and each $R^9$ is independently H or —C$_1$-C$_6$alkyl.
and each $R^{4A}$ and each $R^{4B}$ is independently selected from H, Me, CF$_3$, and F.

In some aspects, the disclosure is directed to compounds of Formula IIB-1:

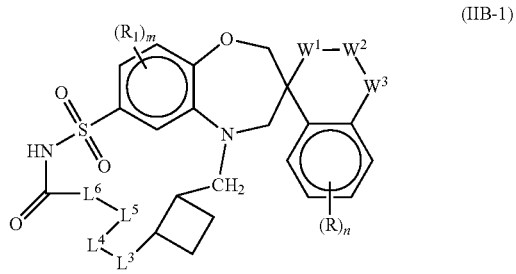

(IIB-1)

or a pharmaceutically acceptable salt or solvate thereof; wherein the moiety —W$^1$—W$^2$—W$^3$— is —CR$^2$R$^{2A}$—CR$^2$R$^{2A}$—CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —S—CR$^{2B}$R$^{2C}$—CR$^2$R$^{2A}$, or —CR$^2$R$^{2A}$—CR$^{2B}$R$^{2C}$—S—;

$R^2$ and $R^{2A}$ are each independently H, halo, C$_1$-C$_6$alkyl, or $R^2$ and $R^{2A}$ that are attached to the same carbon atom may, together with the carbon atom to which they are both attached, form a C$_3$-C$_6$spirocycloalkyl ring;

$R^{2B}$ and $R^{2C}$ are each independently H or C$_1$-C$_6$alkyl, or $R^{2B}$ and $R^{2C}$ may, together with the carbon atom to which they are both attached, form a C$_3$-C$_6$spirocycloalkyl ring;

R is halo, —S—C$_1$-C$_6$alkyl, or —O—C$_1$-C$_6$alkyl;

n=1 or 2;

$R^1$ is halo, —CH$_2$—CN, —C$_1$-C$_6$haloalkyl, —OC$_1$-C$_6$haloalkyl, —OC$_1$-C$_6$haloalkyl, —C$_1$-C$_6$alk-OH, —C$_1$-C$_6$alk-O—C$_1$-C$_6$alkyl, —O—C$_1$-C$_6$alk-O—C$_1$-C$_6$alkyl, —C$_1$-C$_6$alk-O—C$_3$-C$_6$cycloalkyl, —C$_1$-C$_6$alk-O—C$_1$-C$_6$haloalkyl, or

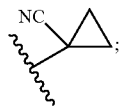

m=1 or 2

$L^3$ is absent, or is —NR$^6$S(O)—, —S(=O)$_2$NR$^6$—, —NR$^6$S(O)$_2$—, $L^4$ is —(CR$^4$R$^5$)$_p$, (CR$^4$R$^5$)$_p$—CR$^{4A}$=CR$^{4B}$—(CR$^4$R$^5$)$_q$, (CR$^4$R$^5$)$_p$O(CR$^4$R$^5$)$_q$, (CR$^4$R$^5$)$_p$—S(=O)$_2$NR$^{6A}$—(CR$^4$R$^5$)$_q$, (CR$^4$R$^5$)$_p$S(CR$^4$R$^5$)$_q$, (CR$^4$R$^5$)$_p$S(O) (CR$^4$R$^5$)$_q$, (CR$^4$R$^5$)$_p$S(O)$_2$(CR$^4$R$^5$)$_q$, (CR$^4$R$^5$)$_p$C(O)NR$^{6A}$(CR$^4$R$^5$)$_q$, (CR$^4$R$^5$)$_p$NR$^{6A}$C(O)(CR$^4$R$^5$)$_q$, or —(CR$^4$R$^5$)$_p$—(CR$^{4A}$=CR$^{4B}$)—(CR$^4$R$^5$)$_q$—O—;

wherein each occurrence of p or q is independently p=0-2 and q=1-5;

$L^5$ is absent, $L^6$ is absent, or is $(CR^7R^8)_sO(CR^7R^8)_t$, $(CR^7R^8)_sNR^9(CR^7R^8)_t$, $(CR^7R^8)_sS(CR^7R^8)_t$, $(CR^7R^8)_sS(O)(CR^7R^8)_t$, or $(CR^7R^8)_sS(O)_2(CR^7R^8)_t$;

wherein each occurrence of s or t is independently s=0-2 and t=0-2;

each $R^4$ and each $R^7$ is independently selected from H, OH, $C_1$-$C_6$alkyl, $C_1$-$C_6$haloalkyl, —$OC_1$-$C_6$alkyl, —$C_3$-$C_7$cycloalkyl, —$OC_3$-$C_7$cycloalkyl, —$CH_2$—CN, —CN, —$N(CH_3)_2$,

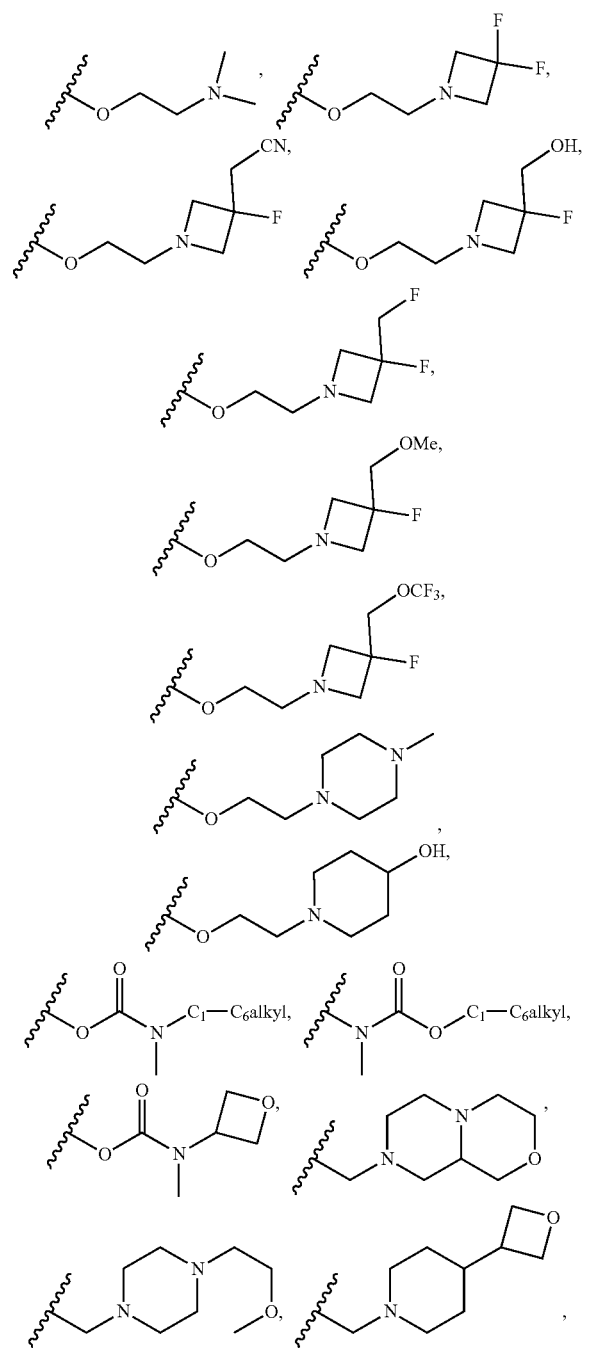

-continued

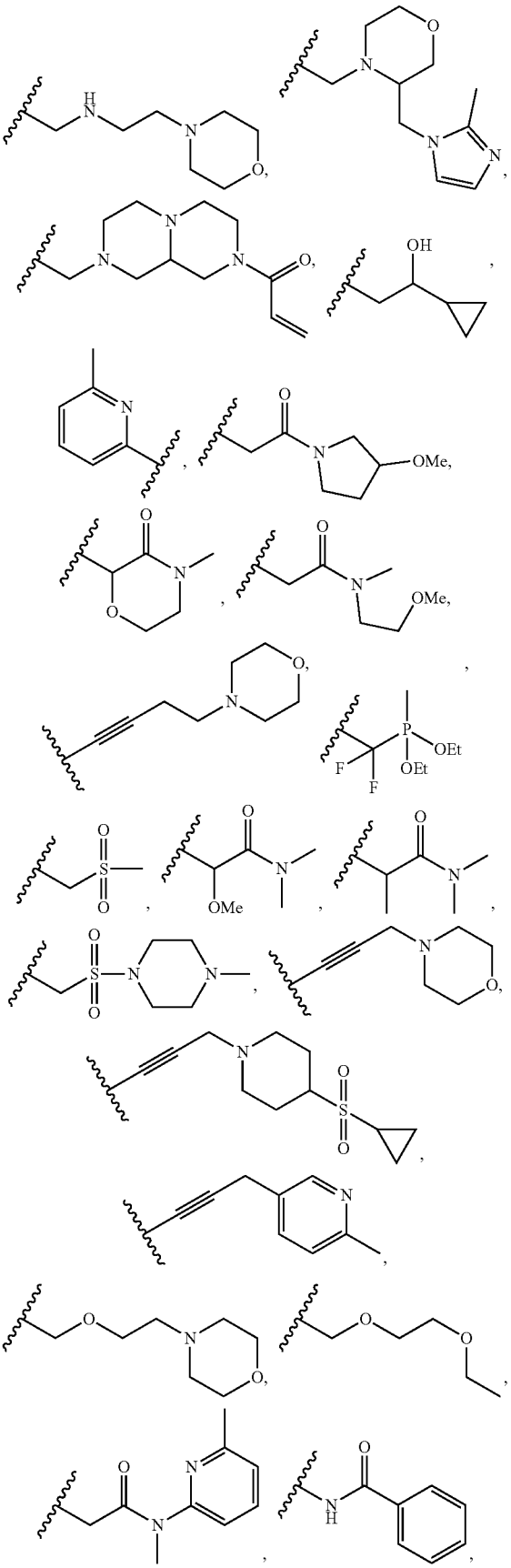

-continued

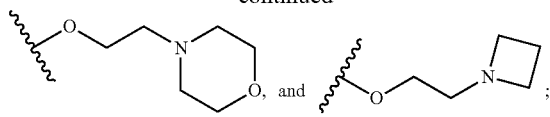

each $R^5$ and each $R^8$ is independently selected from H, OH, —CH$_2$OH, C$_1$-C$_6$alkyl, —OC$_1$-C$_6$alkyl, —C$_3$-C$_7$cycloalkyl, and —OC$_3$-C$_7$cycloalkyl;

wherein one $R^4$ and $R^5$ together with the C atom to which they are both attached may optionally form a 3, 4, 5, or 6-membered cycloalkyl ring,

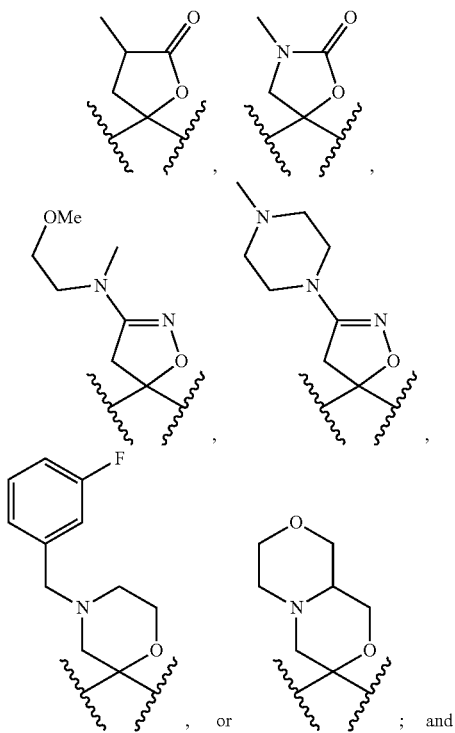

each $R^9$ is independently H or —C$_1$-C$_6$alkyl.
and each $R^{4A}$ and each $R^{4B}$ is independently selected from H, Me, CF$_3$, or F.

In some aspects, the disclosure is directed to compounds of Formula IIB-2:

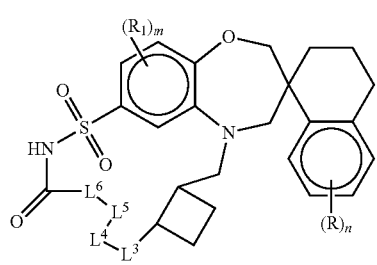

(IIB-2)

or a pharmaceutically acceptable salt or solvate thereof; wherein

R is halo, —S—C$_1$-C$_6$alkyl, or —O—C$_1$-C$_6$alkyl;
n=1 or 2;

$R^1$ is halo, —CH$_2$—CN, —C$_1$-C$_6$haloalkyl, —OC$_1$-C$_6$haloalkyl, —OC$_1$-C$_6$haloalkyl, —C$_1$-C$_6$alk-OH, —C$_1$-C$_6$alk-O—C$_1$-C$_6$alkyl, —O—C$_1$-C$_6$alk-O—C$_1$-C$_6$alkyl, —C$_1$-C$_6$alk-O—C$_3$-C$_6$cycloalkyl, —C$_1$-C$_6$alk-O—C$_1$-C$_6$haloalkyl, or

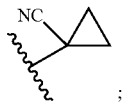 [SMILES: *C1(C#N)CC1]

m=1 or 2

$L^3$ is absent, or is —NR$^6$S(O)—, —S(=O)$_2$NR$^6$—, —NR$^6$S(O)$_2$—, $L^4$ is —(CR$^4$R$^5$)$_p$, (CR$^4$R$^5$)$_p$—CR$^{4A}$=CR$^{4B}$—(CR$^4$R$^5$)$_q$, (CR$^4$R$^5$)$_p$O(CR$^4$R$^5$)$_q$, (CR$^4$R$^5$)$_p$—S(=O)$_2$NR$^{6A}$—(CR$^4$R$^5$)$_q$, (CR$^4$R$^5$)$_p$S(CR$^4$R$^5$)$_q$, (CR$^4$R$^5$)$_p$S(O) (CR$^4$R$^5$)$_q$, (CR$^4$R$^5$)$_p$S(O)$_2$(CR$^4$R$^5$)$_q$, (CR$^4$R$^5$)$_p$C(O) NR$^{6A}$(CR$^4$R$^5$)$_q$, (CR$^4$R$^5$)$_p$NR$^{6A}$C(O)(CR$^4$R$^5$)$_q$, or —(CR$^4$R$^5$)$_p$—(CR$^{4A}$=CR$^{4B}$)—(CR$^4$R$^5$)$_q$—O—;

wherein each occurrence of p or q is independently p=0-2 and q=1-5;

$L^5$ is absent, $L^6$ is absent, or is (CR$^7$R$^8$)$_s$O(CR$^7$R$^8$)$_t$, (CR$^7$R$^8$)$_s$NR$^9$ (CR$^7$R$^8$)$_t$, (CR$^7$R$^8$)$_s$S(CR$^7$R$^8$)$_t$, (CR$^7$R$^8$)$_s$S(O)(CR$^7$R$^8$)$_t$, or (CR$^7$R$^8$)$_s$S(O)$_2$(CR$^7$R$^8$)$_t$;

wherein each occurrence of s or t is independently s=0-2 and t=0-2;

each $R^4$ and each $R^7$ is independently selected from H, OH, C$_1$-C$_6$alkyl, C$_1$-C$_6$haloalkyl, —OC$_1$-C$_6$alkyl, —C$_3$-C$_7$cycloalkyl, —OC$_3$-C$_7$cycloalkyl, —CH$_2$—CN, —CN, —N(CH$_3$)$_2$,

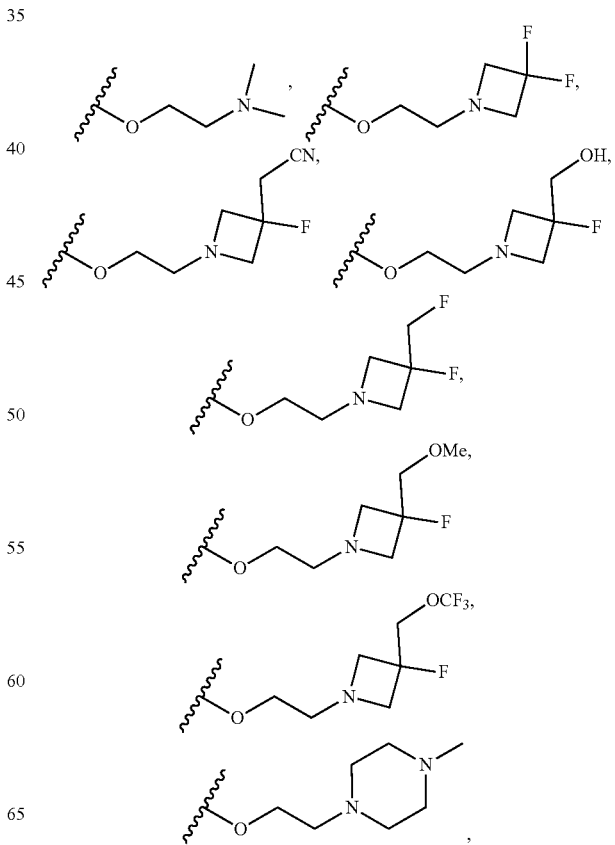

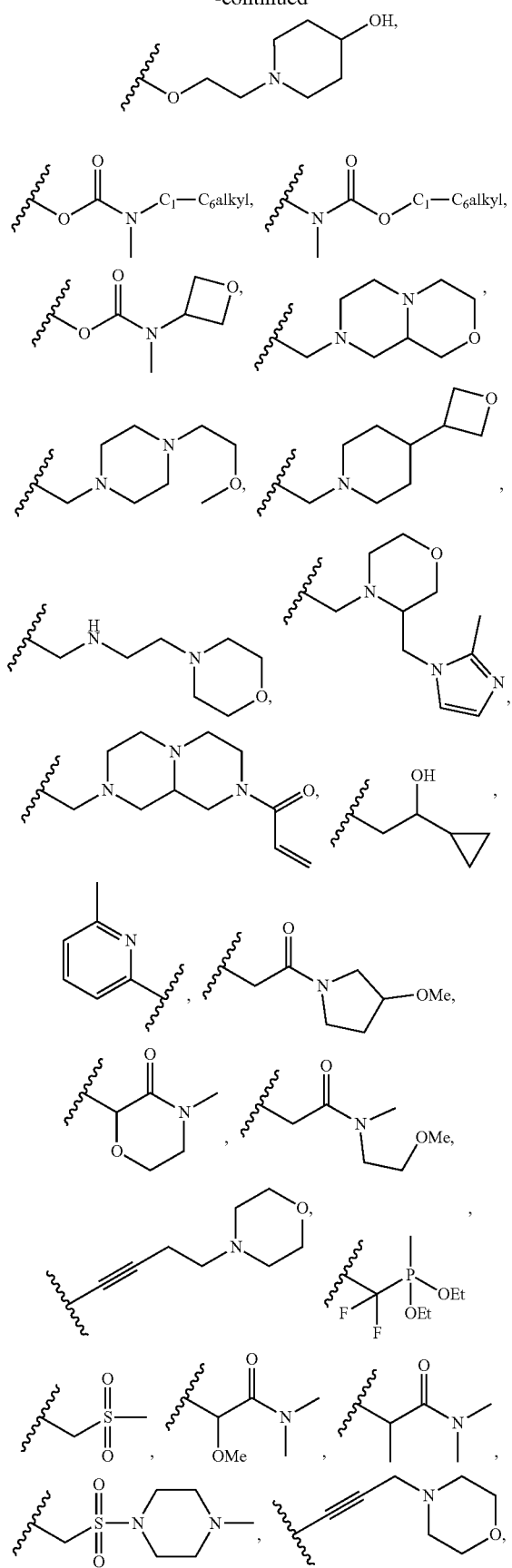
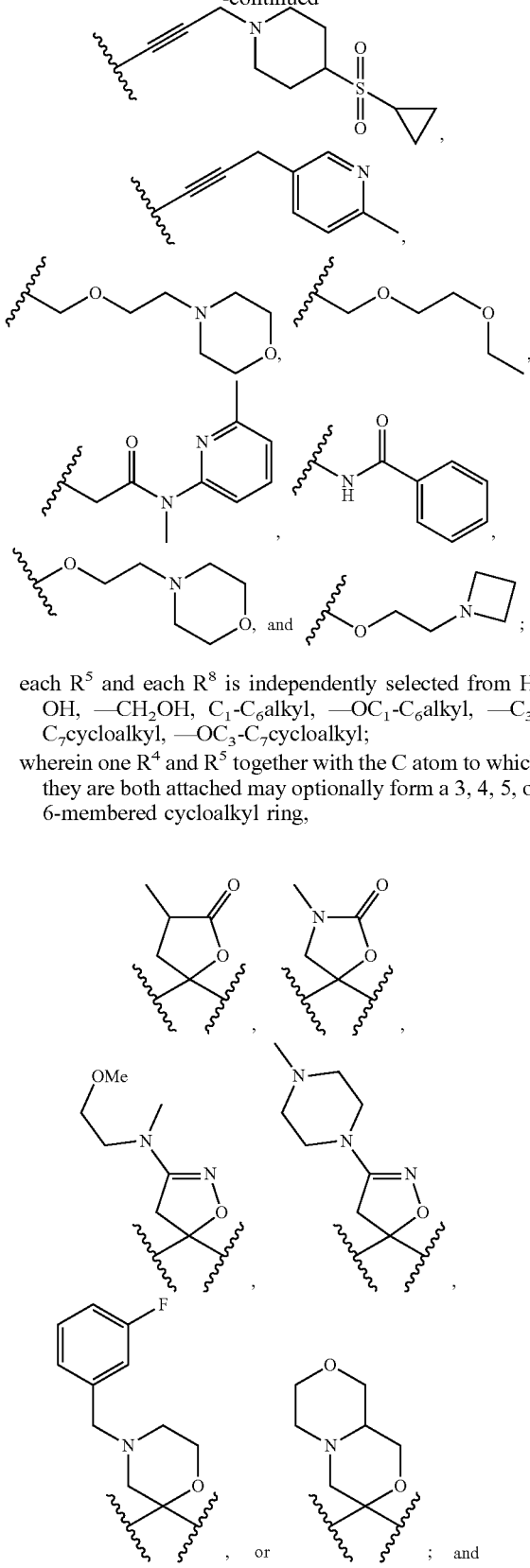
each R[5] and each R[8] is independently selected from H, OH, —CH$_2$OH, C$_1$-C$_6$alkyl, —OC$_1$-C$_6$alkyl, —C$_3$-C$_7$cycloalkyl, —OC$_3$-C$_7$cycloalkyl;
wherein one R[4] and R[5] together with the C atom to which they are both attached may optionally form a 3, 4, 5, or 6-membered cycloalkyl ring,
each R[9] is independently H or —C$_1$-C$_6$alkyl.
and each R[4A] and each R[4B] is independently selected from H, Me, CF$_3$, or F.

In some aspects, the disclosure is directed to compounds of Formula IIB-3:

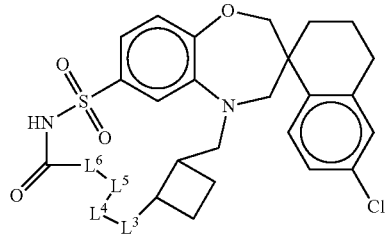

(IIB-3)

or a pharmaceutically acceptable salt or solvate thereof; wherein
- $L^3$ is absent, or is —$NR^6S(O)$—, —$S(=O)_2NR^6$—, —$NR^6S(O)_2$—,
- $L^4$ is —$(CR^4R^5)_p$, $(CR^4R^5)_p$—$CR^{4B}$=$CR^{4B}$—$(CR^4R^5)_q$, $(CR^4R^5)_pO(CR^4R^5)_q$, $(CR^4R^5)_p$—$S(=O)_2NR^{6A}$— $(CR^4R^5)_q$, $(CR^4R^5)_pS(CR^4R^5)_q$, $(CR^4R^5)_pS(O)(CR^4R^5)_q$, $(CR^4R^5)_pS(O)_2(CR^4R^5)_q$, $(CR^4R^5)_pC(O)NR^{6A}(CR^4R^5)_q$, $(CR^4R^5)_pNR^{6A}C(O)(CR^4R^5)_q$, or —$(CR^4R^5)_p$—$(CR^{4A}$=$CR^{4B}$)—$(CR^4R^5)_q$—O—;
- wherein each occurrence of p or q is independently p=0-2 and q=1-5;
- $L^5$ is absent,
- $L^6$ is absent, or is $(CR^7R^8)_sO(CR^7R^8)_t$, $(CR^7R^8)_sNR^9(CR^7R^8)_t$, $(CR^7R^8)_sS(CR^7R^8)_t$, $(CR^7R^8)_sS(O)(CR^7R^8)_t$, or $(CR^7R^8)_sS(O)_2(CR^7R^8)_t$;
- wherein each occurrence of s or t is independently s=0-2 and t=0-2;
- each $R^4$ and each $R^7$ is independently selected from H, OH, $C_1$-$C_6$alkyl, $C_1$-$C_6$haloalkyl, —$OC_1$-$C_6$alkyl, —$C_3$-$C_7$cycloalkyl, and —$OC_3$-$C_7$cycloalkyl;
- each $R^5$ and each $R^8$ is independently selected from H, OH, —$CH_2OH$, $C_1$-$C_6$alkyl, —$OC_1$-$C_6$alkyl, —$C_3$-$C_7$cycloalkyl, and —$OC_3$-$C_7$cycloalkyl;
- wherein one $R^4$ and $R^5$ together with the C atom to which they are both attached may form a 3, 4, 5, or 6-membered cycloalkyl ring; and
- each $R^{4A}$ and each $R^{4B}$ is independently selected from H, Me, $CF_3$ and F; and
- each $R^9$ is independently H or —$C_1$-$C_6$alkyl.

In some aspects, the disclosure is directed to compounds of Formula IIB-4:

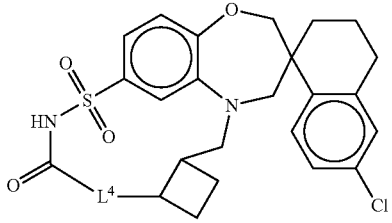

(IIB-4)

or a pharmaceutically acceptable salt or solvate thereof; wherein
- $L^4$ is —$(CR^4R^5)_p$—$CR^{4A}$=$CR^{4B}$—$(CR^4R^5)_q$—;
- p=1 and q=1-4.

each $R^4$ is independently selected from H, OH, $C_1$-$C_6$alkyl, $C_1$-$C_6$haloalkyl, —$OC_1$-$C_6$alkyl, —$C_3$-$C_7$cycloalkyl, —$OC_3$-$C_7$cycloalkyl, —$CH_2$—CN, —CN, —$N(CH_3)_2$,

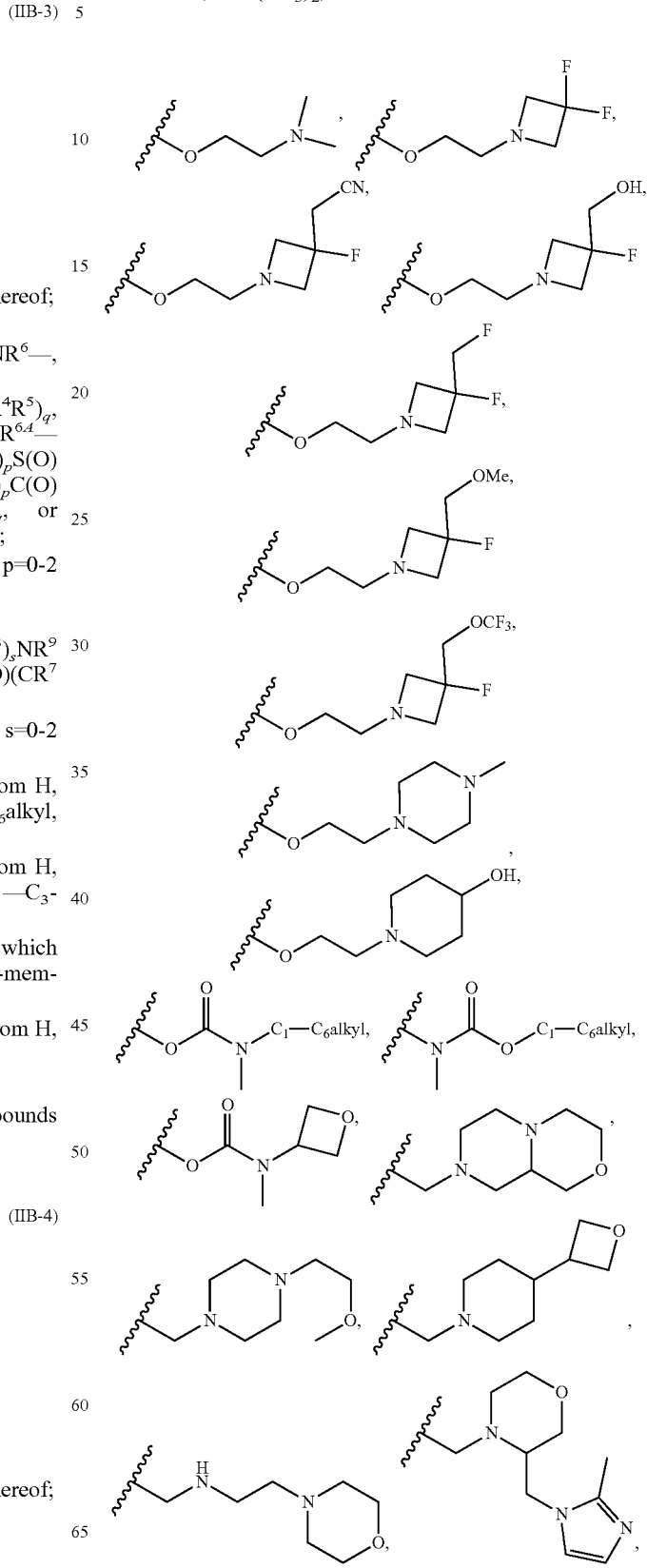

-continued each R⁵ is independently selected from H, OH, —CH₂OH, C₁-C₆alkyl, —OC₁-C₆alkyl, —C₃-C₇cycloalkyl, and —OC₃-C₇cycloalkyl;
and each $R^{4A}$ and each $R^{4B}$ is independently selected from H, Me, and F.

In some aspects, the disclosure is directed to compounds of Formula IIB-5:

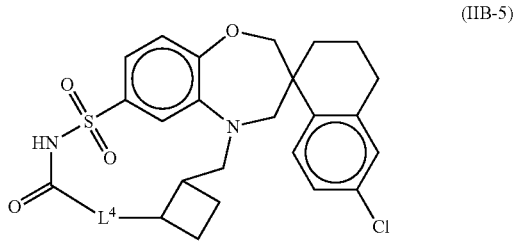

(IIB-5)

or a pharmaceutically acceptable salt or solvate thereof; wherein $L^4$ is —$(CR^4R^5)_p$—$CR^{4A}$=$CR^{4B}$—$(CR^4R^5)_q$—;

p=1 and q=1-4;

R⁴ is independently H, or —C₁-C₆alkyl;

R⁵ is independently H, or C₁-C₆alkyl;

wherein one R⁴ and one R⁵, together with the carbon atom to which they are both attached, are

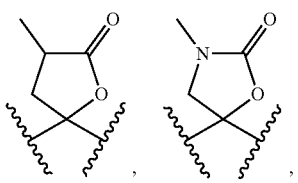

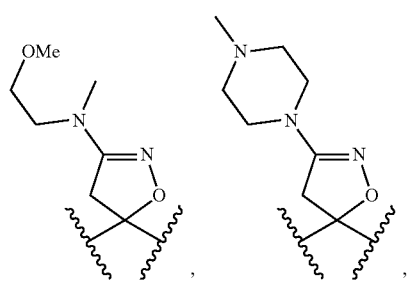

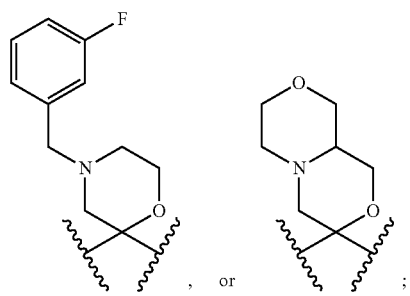

and each $R^{4A}$ and each $R^{4B}$ is independently selected from H, Me, or F.

In some aspects, the disclosure is directed to compounds of Formula IIB-6:

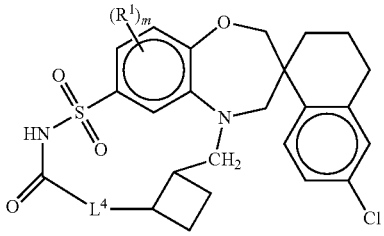

(IIB-6)

or a pharmaceutically acceptable salt or solvate thereof; wherein $R^1$ is halo, —CH$_2$—CN, —C$_1$-C$_6$haloalkyl, —OC$_1$-C$_6$haloalkyl, —OC$_1$-C$_6$haloalkyl, —C$_1$-C$_6$alk-OH, —C$_1$-C$_6$alk-O—C$_1$-C$_6$alkyl, —O—C$_1$-C$_6$alk-O—C$_1$-C$_6$alkyl, —C$_1$-C$_6$alk-O—C$_3$-C$_6$cycloalkyl, —C$_1$-C$_6$alk-O—C$_1$-C$_6$haloalkyl, or

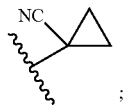

;

m=1 or 2;

$L^4$ is —(CR$^4$R$^5$)$_p$—CR$^{4A}$=CR$^{4B}$—(CR$^4$R$^5$)$_q$—;

p=1 and q=1-4;

$R^4$ is independently H, —OC$_1$-C$_6$alkyl, or —C$_1$-C$_6$alkyl;

$R^5$ is independently H, —OC$_1$-C$_6$alkyl, or —C$_1$-C$_6$alkyl;

$R^{4A}$ and $R^{4B}$ are H.

In some aspects, the disclosure is directed to compounds of Formula IIB-7:

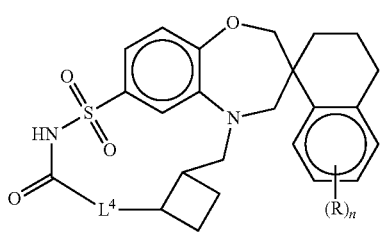

(IIB-7)

or a pharmaceutically acceptable salt or solvate thereof; wherein

R is halo, —S—C$_1$-C$_6$alkyl, or —O—C$_1$-C$_6$alkyl;

n=1 or 2;

$L^4$ is —(CR$^4$R$^5$)$_p$—CR$^{4A}$=CR$^{4B}$—(CR$^4$R$^5$)$_q$—;

p=1 and q=1-4;

$R^4$ is independently H, —OC$_1$-C$_6$alkyl, or —C$_1$-C$_6$alkyl;

$R^5$ is independently H, —OC$_1$-C$_6$alkyl, or —C$_1$-C$_6$alkyl;

$R^{4A}$ and $R^{4B}$ are H.

The disclosure is directed to compounds of Formula IIC:

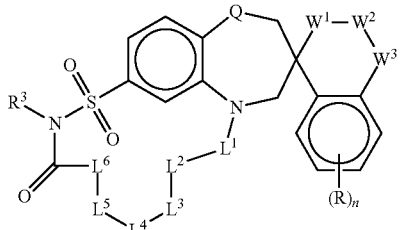

IIC or a pharmaceutically acceptable salt or solvate thereof; wherein

Q is —O—, or —S—;

R is halo; n=1;

the moiety —W$^1$—W$^2$—W$^3$ is —CH$_2$—CH$_2$—CH$_2$—, —O—CH$_2$—CH$_2$—, or —CH$_2$—CH$_2$—O—;

$R^3$ is H, or C$_1$-C$_6$alkyl;

$L^1$ is —C$_1$-C$_6$alkylene-;

$L^2$ is C$_3$-C$_7$cycloalkyl, or C$_4$-C$_7$heterocycloalkylene;

$L^3$ is absent, or is —(CR$^4$R$^5$)$_p$—, —(CR$^4$R$^5$)$_p$O—, —S(O)$_2$—, —C(=O)—, —NR$^6$—;

$L^4$ is absent or is —(CR$^4$R$^5$)$_p$—CR$^{4A}$=CR$^{4B}$—(CR$^4$R$^5$)$_q$, —(CR$^4$R$^5$)$_p$O(CR$^4$R$^5$)$_q$—;

$L^5$ is a 6-membered arylene, 5-membered heteroarylene, 7- to 10-membered spirocycloalkylene, 7- to 10-spiroheterocycloalkylene, 3- to 7-membered monocyclic cycloalkylene, 3- to 7-membered cycloalkenylene, or a 4- to 7-membered monocyclic heterocycloalkylene group, wherein the spiroheterocycloalkylene or heterocycloalkylene groups have 1, 2, 3 or 4, heteroatoms independently selected from O, or N;

$L^6$ is absent, or is —(CR$^7$R$^8$)$_s$, (CR$^7$R$^8$)$_s$O(CR$^7$R$^8$)$_t$, —(CR$^7$R$^8$)$_a$—CR$^{4A}$=CR$^{4B}$—(CR$^7$R$^8$)$_c$, (CR$^7$R$^8$)$_s$C(=O)(CR$^7$R$^8$)$_t$; —(CR$^7$R$^8$)$_s$C(=O)(CR$^7$R$^8$)$_t$—O—, or —(CR$^7$R$^8$)$_s$C(=O)(CR$^7$R$^8$)$_t$—NR$^6$—;

each $R^4$ is independently H, OH, or —OC$_1$-C$_6$alkyl;

each $R^5$ is independently selected from is H, OH, or —OC$_1$-C$_6$alkyl;

or $R^4$ and $R^5$ together with the C atom to which they are both attached may form a 3, 4, 5, 6, or 7-membered cycloalkyl ring;

each $R^6$ is independently selected from is H or —C$_1$-C$_6$alkyl, each $R^7$ is H, OH, —C$_1$-C$_6$alkyl, or —OC$_1$-C$_6$alkyl, each $R^8$ is H, OH, —C$_1$-C$_6$alkyl, or —OC$_1$-C$_6$alkyl;

or $R^7$ and $R^8$ together with the C atom to which they are both attached may form a 3, 4, 5, 6, or 7-membered cycloalkyl ring;

each $R^{4A}$ and each $R^{4B}$ is independently H, or —OC$_1$-C$_6$alkyl;

a=0-1; c=0-3; p=0-3; s=0-2, t=0-5; and q=0-2;

In some aspects, the disclosure is directed to compounds of Formula IIC-1:

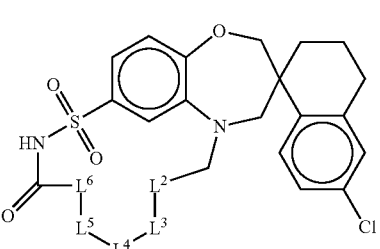

(IIC-1)

or a pharmaceutically acceptable salt or solvate thereof; wherein
$L^2$ is $C_3$-$C_6$cycloalkylene, or heterocycloalkylene;
$L^3$ is absent, or is —$(CR^4R^5)_p$—, —$(CR^4R^5)_pO$—, —$S(O)_2$—, —$C(\!\!=\!\!O)$—, —$NR^6$—;
$L^4$ is absent or is —$(CR^4R^5)_p$—$CR^{4A}\!\!=\!\!CR^{4B}$—$(CR^4R^5)_q$, —$(CR^4R^5)_pO(CR^4R^5)_q$—;
$L^5$ is a 6-membered arylene, or 5-membered heteroarylene, 7- to 10-membered spirocycloalkylene, 7- to 10-spiroheterocycloalkylene, 3- to 7-membered cycloalkylene, 3- to 7-membered cycloalkenylene, or a 4- to 7-membered heterocycloalkylene group, wherein the spiroheterocycloalkylene or heterocycloalkylene groups have 1, 2, 3 or 4, heteroatoms independently selected from O, or N;
$L^6$ is absent, —$(CR^7R^8)_s$, $(CR^7R^8)_sO(CR^7R^8)_t$, —$(CR^7R^8)_a$—$CR^{4A}\!\!=\!\!CR^{4B}$—$(CR^7R^8)_c$, $(CR^7R^8)_sC(\!\!=\!\!O)(CR^7R^8)_t$; —$(CR^7R^8)_sC(\!\!=\!\!O)(CR^7R^8)_t$—O—, or —$(CR^7R^8)_sC(\!\!=\!\!O)(CR^7R^8)_t$—$NR^6$—;
a=0-1; c=0-3; p=0-3; s=0-2, t=0-5; and q=0-2;
each $R^4$ is independently H, OH, or —$OC_1$-$C_6$alkyl;
each $R^5$ is independently selected from is H, OH, or —$OC_1$-$C_6$alkyl;
or $R^4$ and $R^5$ together with the C atom to which they are both attached may form a 3, 4, 5, 6, or 7-membered cycloalkyl ring;
each $R^{4A}$ and each $R^{4B}$ is independently H, or —$OC_1$-$C_6$alkyl;
each $R^6$ is independently selected from is H or —$C_1$-$C_6$alkyl;
each $R^7$ is H, OH, —$C_1$-$C_6$alkyl, or —$OC_1$-$C_6$alkyl;
each $R^8$ is H, OH, —$C_1$-$C_6$alkyl, or —$OC_1$-$C_6$alkyl;
or $R^7$ and $R^8$ together with the C atom to which they are both attached may form a 3, 4, 5, 6, or 7-membered cycloalkyl ring.

In some aspects, the disclosure is directed to compounds of Formula IIC-2:

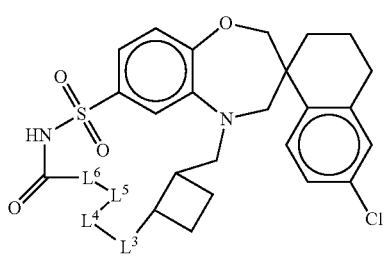

(IIC-2)

or a pharmaceutically acceptable salt or solvate thereof; wherein
$L^3$ is absent, or is —$(CR^4R^5)_p$—, —$(CR^4R^5)_pO$—, —$S(O)_2$—, —$C(\!\!=\!\!O)$—, —$NR^6$—;
$L^4$ is absent or is —$(CR^4R^5)_p$—$CR^{4A}\!\!=\!\!CR^{4B}$—$(CR^4R^5)_q$, —$(CR^4R^5)_pO(CR^4R^5)_q$—;
$L^5$ is a 7- to 10-membered spirocycloalkylene, 7- to 10-spiroheterocycloalkylene, 3- to 7-membered cycloalkylene, 3- to 7-membered cycloalkenylene, or a 4- to 7-membered heterocycloalkylene group, wherein the spiroheterocycloalkylene or heterocycloalkylene groups have 1, 2, 3 or 4, heteroatoms independently selected from O, or N;
$L^6$ is absent, or is —$(CR^7R^8)_s$—, $(CR^7R^8)_sO(CR^7R^8)_t$, or $(CR^7R^8)_sC(\!\!=\!\!O)(CR^7R^8)_t$;

a=0-1; c=0-3; n=1; p=0-1; s=0-2; t=0-2; and q=0-2;
each $R^4$ is independently H, OH, or —$OC_1$-$C_6$alkyl;
each $R^{4A}$ and each $R^{4B}$ is independently H, or —$OC_1$-$C_6$alkyl;
each $R^5$ is independently selected from is H, OH, or —$OC_1$-$C_6$alkyl;
each $R^6$ is independently selected from is H or —$C_1$-$C_6$alkyl,
each $R^7$ is independently H, —$C_1$-$C_6$alkyl, or —$OC_1$-$C_6$alkyl; and
each $R^8$ is independently H, —$C_1$-$C_6$alkyl, or —$OC_1$-$C_6$alkyl.

In some aspects, the disclosure is directed to compounds of Formula IIC-3:

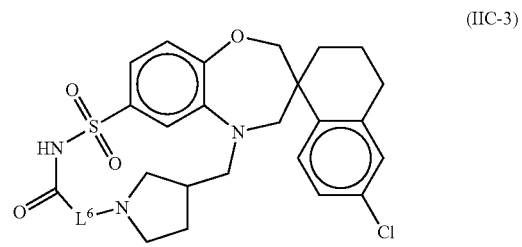

(IIC-3)

or a pharmaceutically acceptable salt or solvate thereof; wherein
$L^6$ is —$(CR^7R^8)_a$—$CR^{4A}\!\!=\!\!CR^{4B}$—$(CR^7R^8)_c$, $(CR^7R^8)_sC(\!\!=\!\!O)(CR^7R^8)_t$; —$(CR^7R^8)_sC(\!\!=\!\!O)(CR^7R^8)_t$—O—, or —$(CR^7R^8)_sC(\!\!=\!\!O)(CR^7R^8)_t$—$NR^6$—;
a=0-1; c=1-3; n=1; s=0-2, t=0-5;
each $R^4$ is independently H, OH, or —$OC_1$-$C_6$alkyl;
each $R^{4A}$ and each $R^{4B}$ is H;
each $R^5$ is independently selected from is H, OH, or —$OC_1$-$C_6$alkyl;
each $R^6$ is independently selected from is H or —$C_1$-$C_6$alkyl,
each $R^7$ is independently H, —$C_1$-$C_6$alkyl, or —$OC_1$-$C_6$alkyl,
each $R^8$ is independently H, —$C_1$-$C_6$alkyl, or —$OC_1$-$C_6$alkyl;
or $R^7$ and $R^8$, together with the carbon atom to which they are attached, for a $C_3$-$C_6$ cycloalyl ring.

It will be apparent that the compounds of Formula I and Formula II, including all subgenera described herein, have multiple stereogenic centers. As a result, there exist multiple stereoisomers (enantiomers and diastereomers) of the compounds of Formula I and Formula II (subgenera described herein). The present disclosure contemplates and encompasses each stereoisomer of any compound of Formula I and Formula II (and subgenera described herein), as well as mixtures of said stereoisomers.

Pharmaceutically acceptable salts and solvates of the compounds of Formula I and Formula II (including all subgenera described herein) are also within the scope of the disclosure.

Isotopic variants of the compounds of Formula I and Formula II (including all subgenera described herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention;

optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100%, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

In some embodiments, the compounds or pharmaceutical composition of the present invention are administered by intravenous injection.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash.

In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a MCL-1 inhibitor with an IC50 value of about or less than a predetermined value, as ascertained in an in vitro assay. In some embodiments, the MCL-1 inhibitor inhibits MCL-1 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 $\mu$M or less, 1.1 $\mu$M or less, 1.2 $\mu$M or less, 1.3 $\mu$M or less, 1.4 $\mu$M or less, 1.5 $\mu$M or less, 1.6 $\mu$M or less, 1.7 $\mu$M or less, 1.8 $\mu$M or less, 1.9 $\mu$M or less, 2 $\mu$M or less, 5 $\mu$M or less, 10 $\mu$M or less, 15 $\mu$M or less, 20 $\mu$M or less, 25 $\mu$M or less, 30 $\mu$M or less, 40 $\mu$M or less, 50 $\mu$M, 60 $\mu$M, 70 $\mu$M, 80 $\mu$M, 90 $\mu$M, 100 $\mu$M, 200 $\mu$M, 300 $\mu$M, 400 $\mu$M, or 500 $\mu$M, or less, (or a number in the range defined by and including any two numbers above).

In some embodiments, the MCL-1 inhibitor selectively inhibits MCL-1 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other MCL-1s.

In some embodiments, the MCL-1 inhibitor selectively inhibits MCL-1 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 $\mu$M, 1.1 $\mu$M, 1.2 $\mu$M, 1.3 $\mu$M, 1.4 $\mu$M, 1.5 $\mu$M, 1.6 $\mu$M, 1.7 $\mu$M, 1.8 $\mu$M, 1.9 $\mu$M, 2 $\mu$M, 5 $\mu$M, 10 $\mu$M, 15 $\mu$M, 20 $\mu$M, 25 $\mu$M, 30 $\mu$M, 40 $\mu$M, 50 $\mu$M, 60 $\mu$M, 70 $\mu$M, 80 $\mu$M, 90 $\mu$M, 100 $\mu$M, 200 $\mu$M, 300 $\mu$M, 400 $\mu$M, or 500 $\mu$M (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other MCL-1s.

The subject methods are useful for treating a disease condition associated with MCL-1. Any disease condition that results directly or indirectly from an abnormal activity or expression level of MCL-1 can be an intended disease condition.

Different disease conditions associated with MCL-1 have been reported. MCL-1 has been implicated, for example, auto-immune diseases, neurodegeneration (such as Parkinson's disease, Alzheimer's disease and ischaemia), inflammatory diseases, viral infections and cancer such as, for example, colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS) or epidermoid cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

Compounds of the disclosure also include, for example, the compounds and genera identified in Tables A, B, and C.

TABLE A

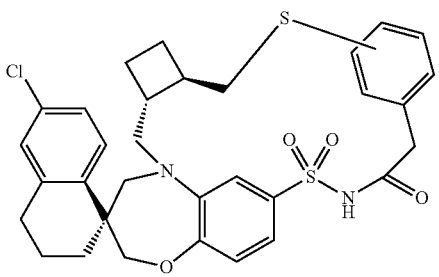

TABLE A-continued
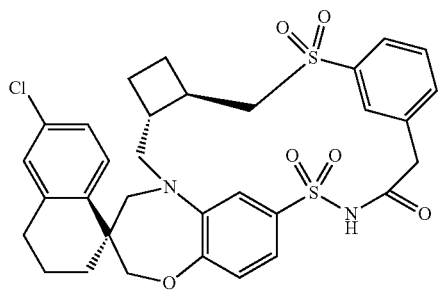
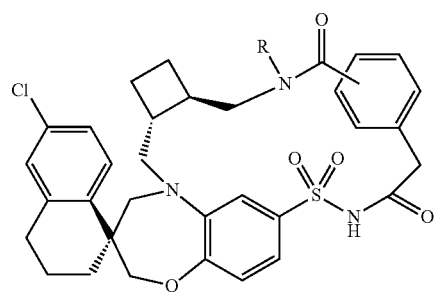
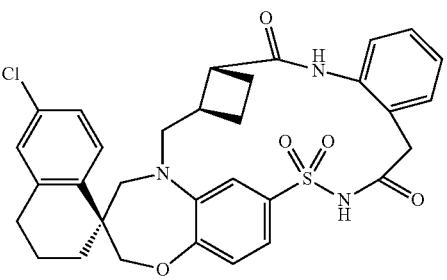 [SMILES: O=C1Cc2ccccc2NC(=O)[C@@H]2CC[C@H]2CN2C[C@@]3(CCCc4cc(Cl)ccc43)COc3ccc(cc32)S(=O)(=O)N1]
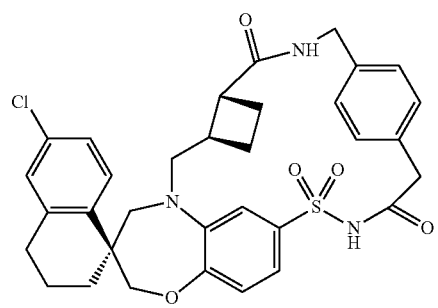 [SMILES: O=C1Cc2ccc(cc2)CNC(=O)[C@@H]2CC[C@H]2CN2C[C@@]3(CCCc4cc(Cl)ccc43)COc3ccc(cc32)S(=O)(=O)N1]
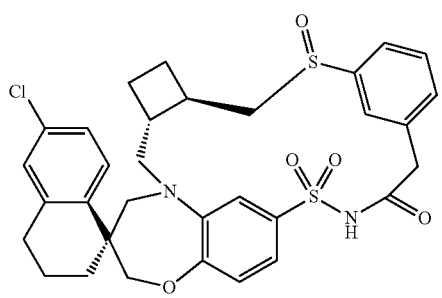

TABLE A-continued
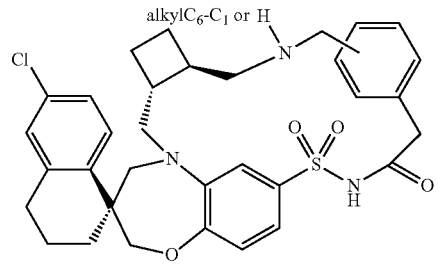
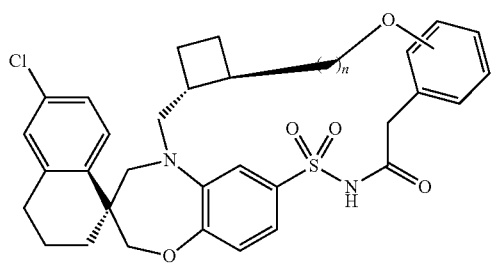
n = 1, 2, 3, or 4
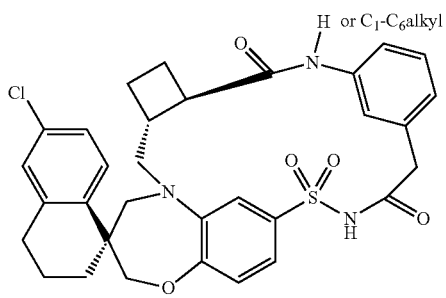
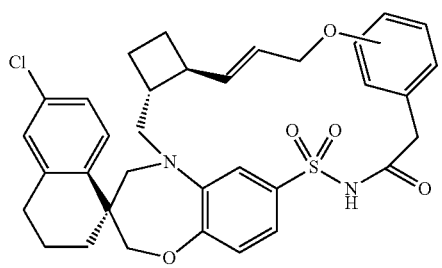
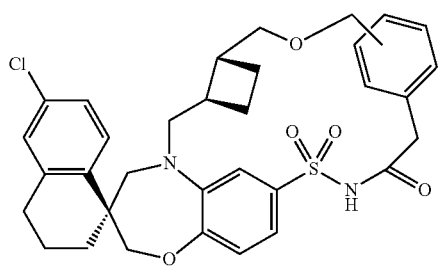

TABLE A-continued
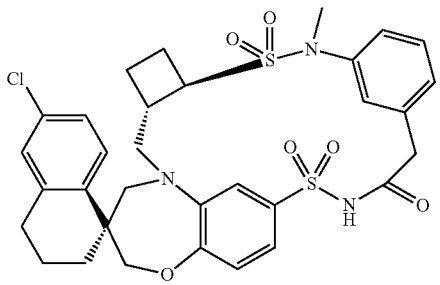
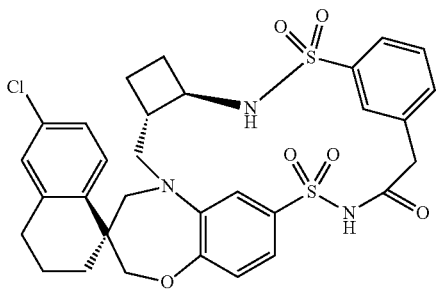
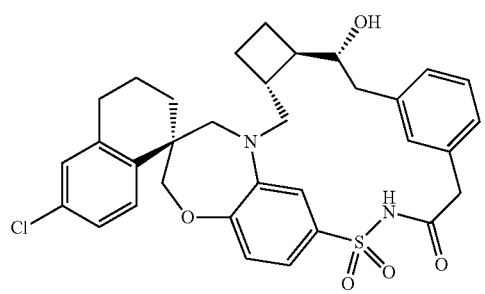 [SMILES: O=C1Cc2cccc(c2)C[C@@H](O)[C@@H]2CC[C@H]2CN2C[C@@]3(CCCc4cc(Cl)ccc43)COc3ccc(cc32)S(=O)(=O)N1]
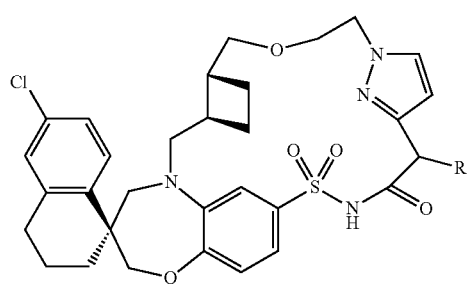
R = H, or C₁-C₆alkyl
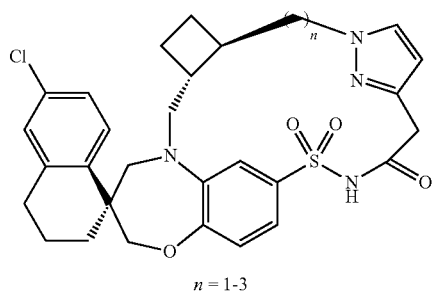
n = 1-3

TABLE A-continued
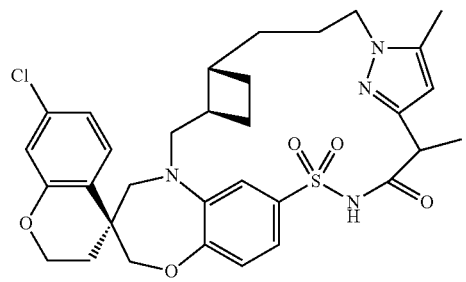
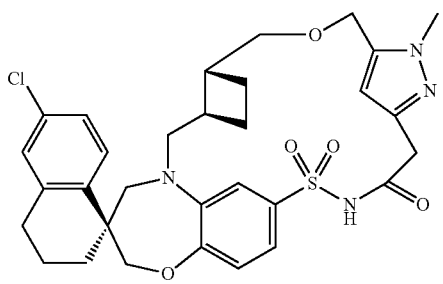 [SMILES: Cn1nc2cc1COC[C@@H]1CC[C@H]1CN1C[C@@]3(CCCc4cc(Cl)ccc43)COc3ccc(cc31)S(=O)(=O)NC(=O)C2]
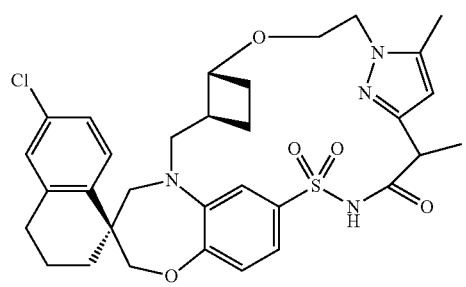 [SMILES: Cc1cc2nn1CCO[C@@H]1CC[C@H]1CN1C[C@@]3(CCCc4cc(Cl)ccc43)COc3ccc(cc31)S(=O)(=O)NC(=O)C2C]
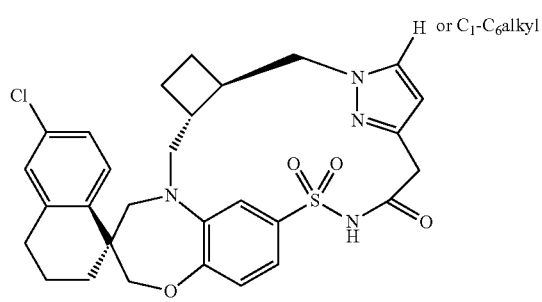
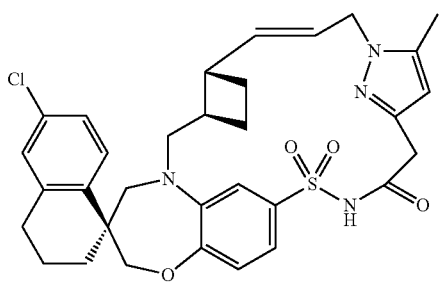 [SMILES: Cc1cc2nn1C/C=C/[C@@H]1CC[C@H]1CN1C[C@@]3(CCCc4cc(Cl)ccc43)COc3ccc(cc31)S(=O)(=O)NC(=O)C2]

TABLE A-continued
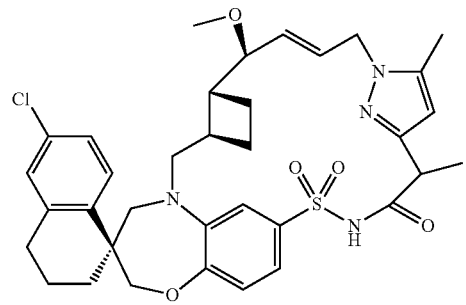 [SMILES: CO[C@H]1/C=C/Cn2nc(cc2C)C(C)C(=O)NS(=O)(=O)c2ccc3c(c2)N(C[C@@H]2CC[C@H]21)C[C@@]1(CCCc2cc(Cl)ccc21)CO3]
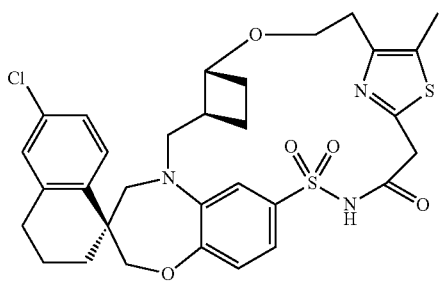 [SMILES: Cc1sc2nc1CCO[C@@H]1CC[C@H]1CN1C[C@@]3(CCCc4cc(Cl)ccc43)COc3ccc(cc31)S(=O)(=O)NC(=O)C2]
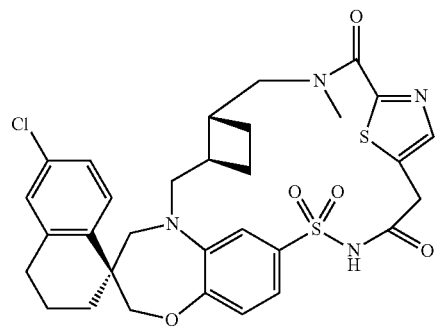 [SMILES: CN1C[C@@H]2CC[C@H]2CN2C[C@@]3(CCCc4cc(Cl)ccc43)COc3ccc(cc32)S(=O)(=O)NC(=O)CC2=CN=C(S2)C1=O]
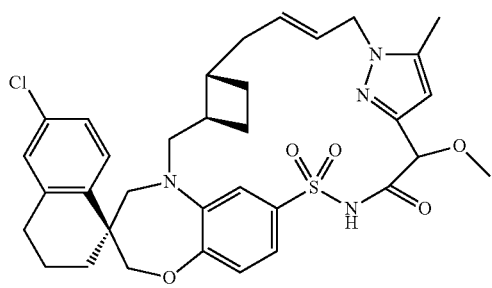 [SMILES: COC1C(=O)NS(=O)(=O)c2ccc3c(c2)N(C[C@@H]2CC[C@H]2C/C=C/Cn2nc1cc2C)C[C@@]1(CCCc2cc(Cl)ccc21)CO3]
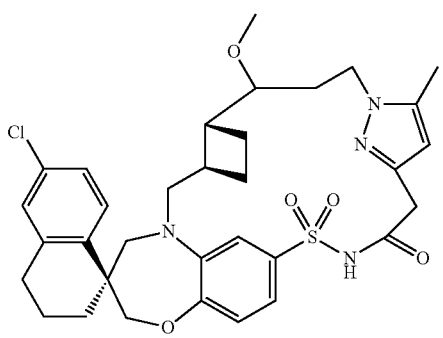 [SMILES: COC1CCn2nc(cc2C)CC(=O)NS(=O)(=O)c2ccc3c(c2)N(C[C@@H]2CC[C@@H]12)C[C@@]1(CCCc2cc(Cl)ccc21)CO3]

TABLE A-continued
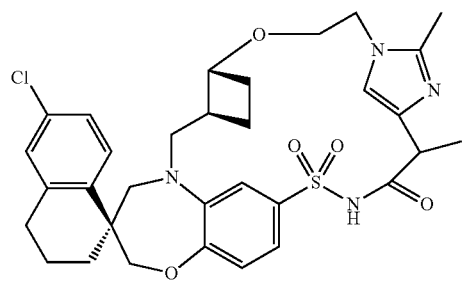
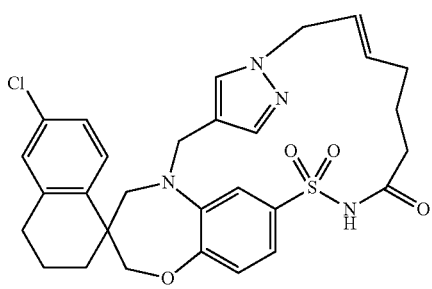 [SMILES: O=C1CCC/C=C/Cn2cc(cn2)CN2CC3(CCCc4cc(Cl)ccc43)COc3ccc(cc32)S(=O)(=O)N1]
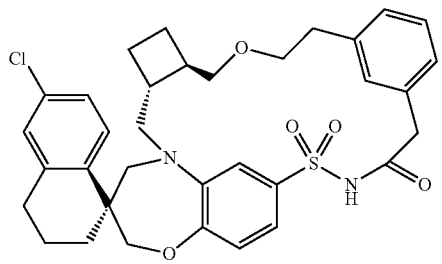
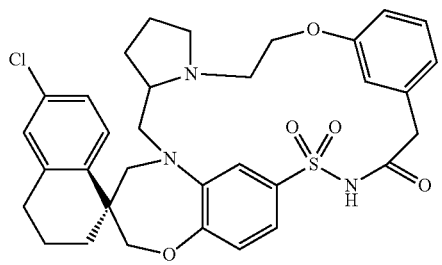
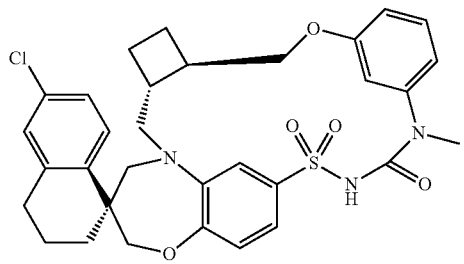

TABLE A-continued
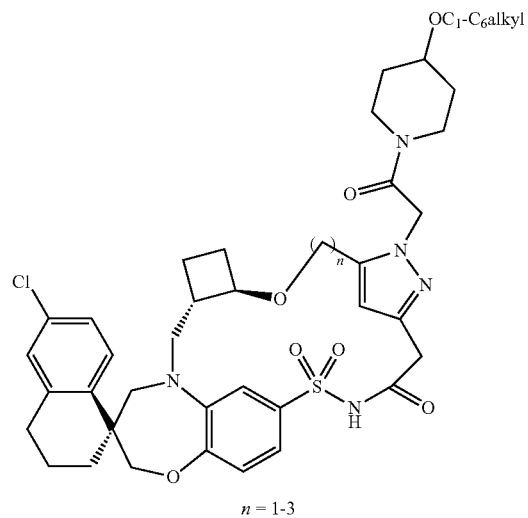
n = 1-3
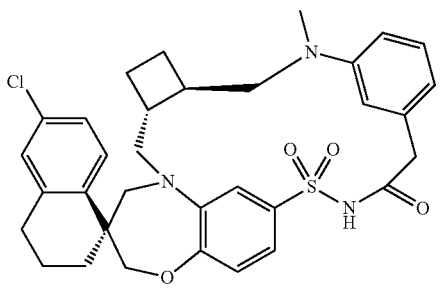
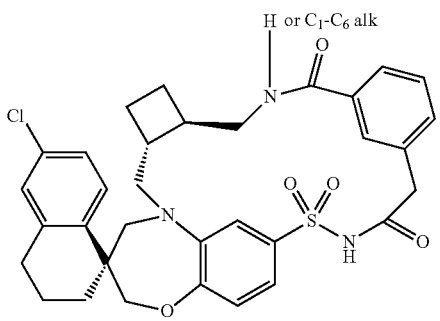
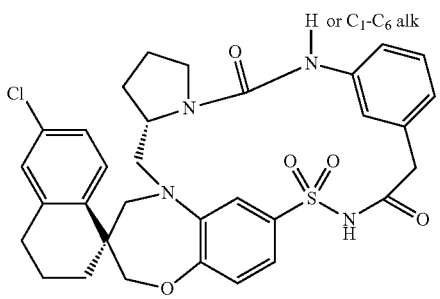

TABLE A-continued
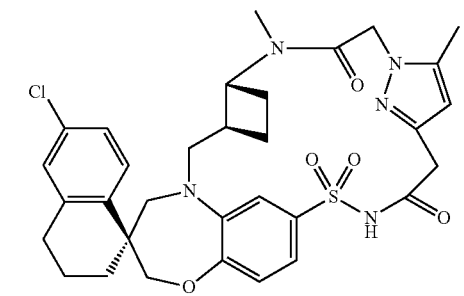 [SMILES: Cc1cc2nn1CC(=O)N(C)[C@@H]1CC[C@H]1CN1C[C@@]3(CCCc4cc(Cl)ccc43)COc3ccc(cc31)S(=O)(=O)NC(=O)C2]
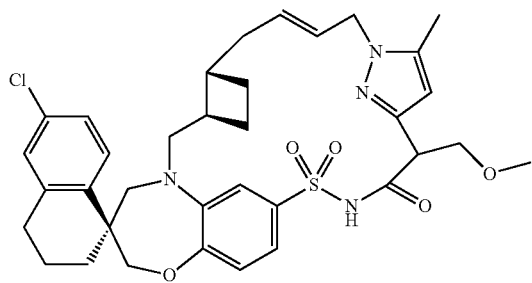 [SMILES: COCC1C(=O)NS(=O)(=O)c2ccc3c(c2)N(C[C@@H]2CC[C@H]2C/C=C/Cn2nc1cc2C)C[C@@]1(CCCc2cc(Cl)ccc21)CO3]
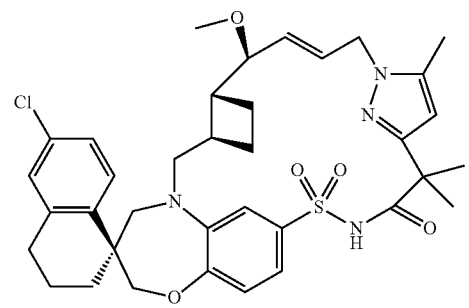 [SMILES: CO[C@H]1/C=C/Cn2nc(cc2C)C(C)(C)C(=O)NS(=O)(=O)c2ccc3c(c2)N(C[C@@H]2CC[C@H]21)C[C@@]1(CCCc2cc(Cl)ccc21)CO3]
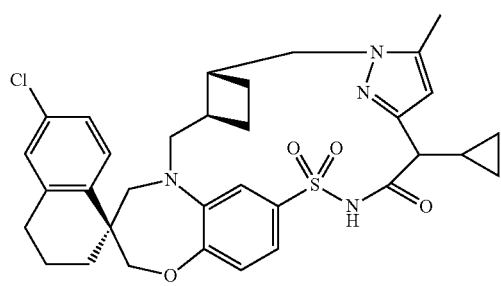 [SMILES: Cc1cc2nn1C[C@@H]1CC[C@H]1CN1C[C@@]3(CCCc4cc(Cl)ccc43)COc3ccc(cc31)S(=O)(=O)NC(=O)C2C1CC1]
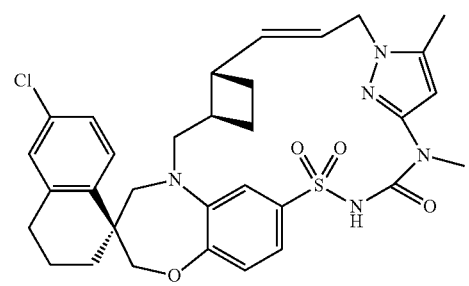 [SMILES: Cc1cc2nn1C/C=C/[C@@H]1CC[C@H]1CN1C[C@@]3(CCCc4cc(Cl)ccc43)COc3ccc(cc31)S(=O)(=O)NC(=O)N2C]

TABLE A-continued
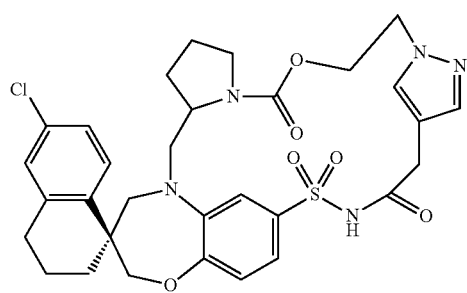 [SMILES: O=C1Cc2cnn(c2)CCOC(=O)N2CCCC2CN2C[C@@]3(CCCc4cc(Cl)ccc43)COc3ccc(cc32)S(=O)(=O)N1]
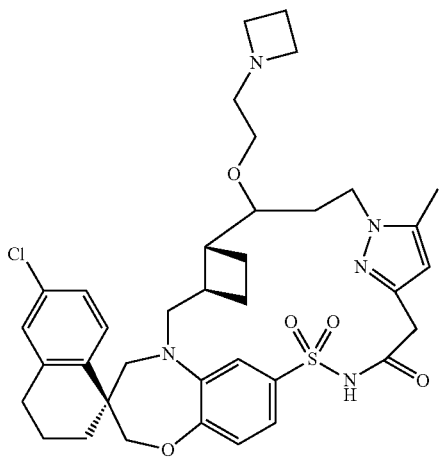 [SMILES: Cc1cc2nn1CCC(OCCN1CCC1)[C@@H]1CC[C@H]1CN1C[C@@]3(CCCc4cc(Cl)ccc43)COc3ccc(cc31)S(=O)(=O)NC(=O)C2]
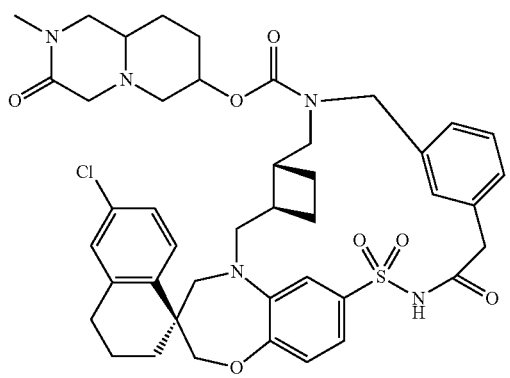 [SMILES: CN1CC2CCC(OC(=O)N3Cc4cccc(c4)CC(=O)NS(=O)(=O)c4ccc5c(c4)N(C[C@@H]4CC[C@H]4C3)C[C@@]3(CCCc4cc(Cl)ccc43)CO5)CN2CC1=O]
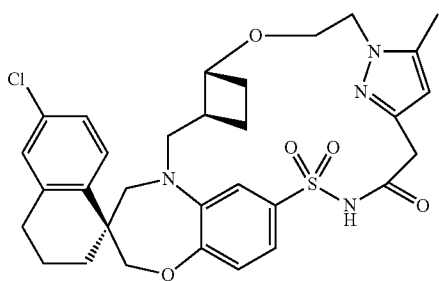 [SMILES: Cc1cc2nn1CCO[C@@H]1CC[C@H]1CN1C[C@@]3(CCCc4cc(Cl)ccc43)COc3ccc(cc31)S(=O)(=O)NC(=O)C2]

TABLE A-continued
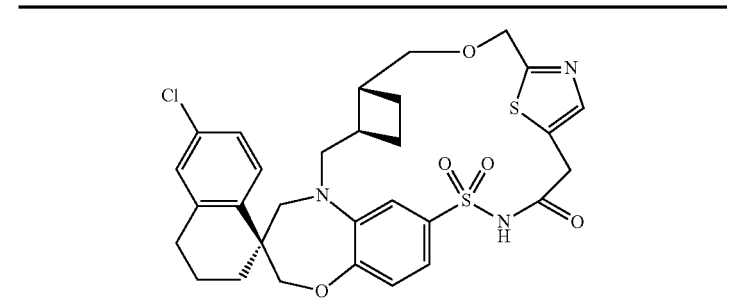
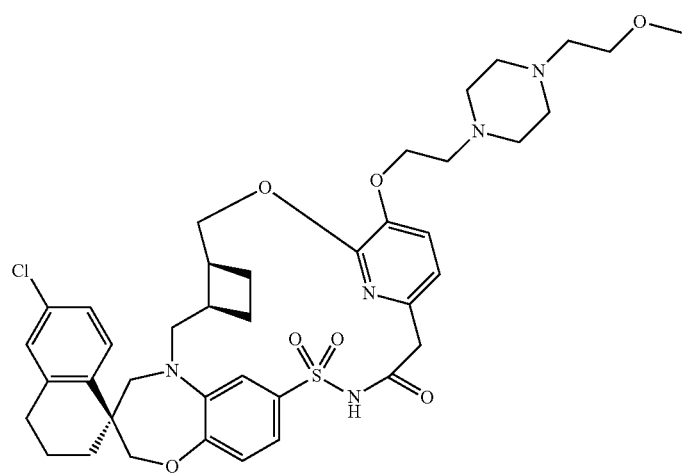 [SMILES: COCCN1CCN(CCOc2ccc3nc2OC[C@H]2CC[C@H]2CN2C[C@@]4(CCCc5cc(Cl)ccc54)COc4ccc(cc42)S(=O)(=O)NC(=O)C3)CC1]
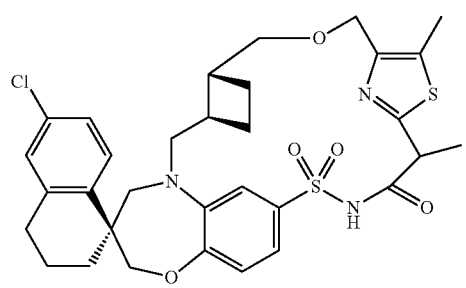 [SMILES: Cc1sc2nc1COC[C@@H]1CC[C@H]1CN1C[C@@]3(CCCc4cc(Cl)ccc43)COc3ccc(cc31)S(=O)(=O)NC(=O)C2C]
TABLE B
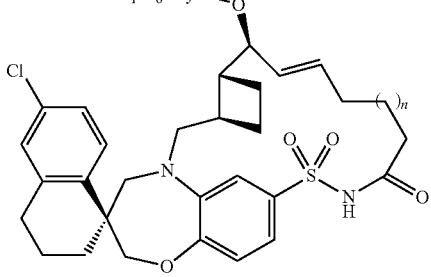
n = 0, 1 or 2

TABLE B-continued
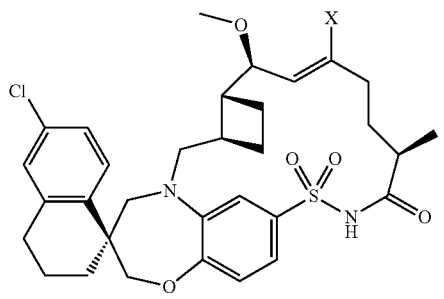
X = H, Me, F
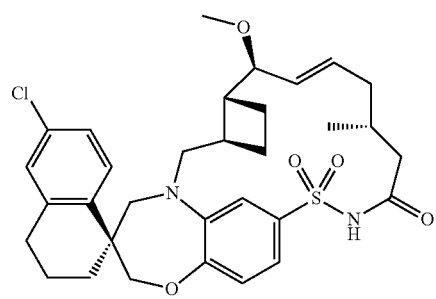 [SMILES: CO[C@H]1/C=C/C[C@@H](C)CC(=O)NS(=O)(=O)c2ccc3c(c2)N(C[C@@H]2CC[C@H]21)C[C@@]1(CCCc2cc(Cl)ccc21)CO3]
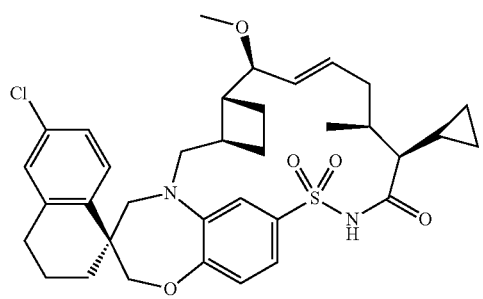 [SMILES: CO[C@H]1/C=C/C[C@H](C)[C@@H](C2CC2)C(=O)NS(=O)(=O)c2ccc3c(c2)N(C[C@@H]2CC[C@H]21)C[C@@]1(CCCc2cc(Cl)ccc21)CO3]
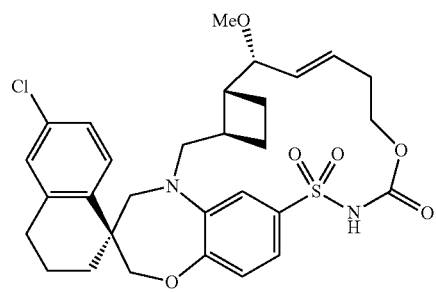 [SMILES: CO[C@@H]1/C=C/CCOC(=O)NS(=O)(=O)c2ccc3c(c2)N(C[C@@H]2CC[C@H]21)C[C@@]1(CCCc2cc(Cl)ccc21)CO3]
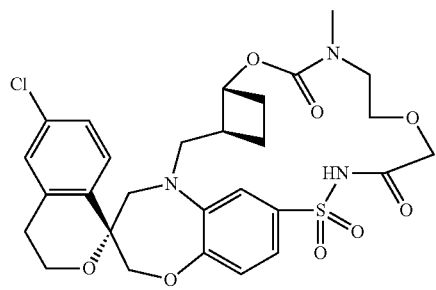 [SMILES: CN1CCOCC(=O)NS(=O)(=O)c2ccc3c(c2)N(C[C@@H]2CC[C@H]2OC1=O)C[C@]1(CO3)OCCc2cc(Cl)ccc21]

TABLE B-continued
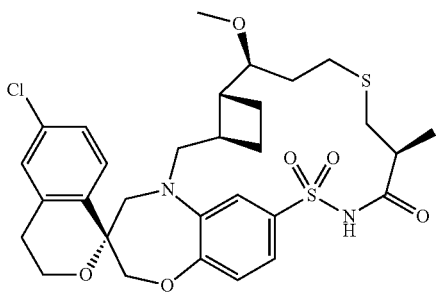 [SMILES: CO[C@H]1CCSC[C@@H](C)C(=O)NS(=O)(=O)c2ccc3c(c2)N(C[C@@H]2CC[C@H]21)C[C@]1(CO3)OCCc2cc(Cl)ccc21]
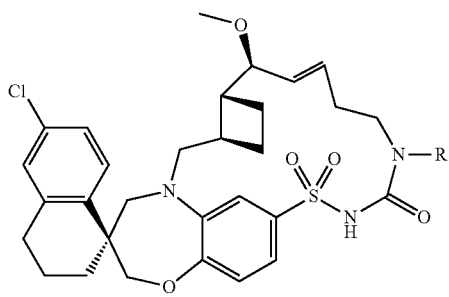
R = H or C$_1$-C$_6$alkyl
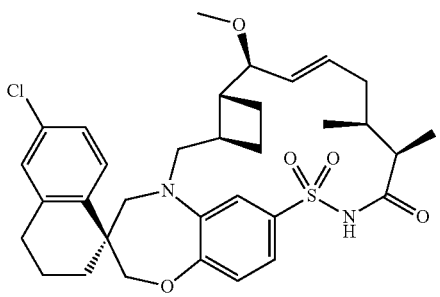 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
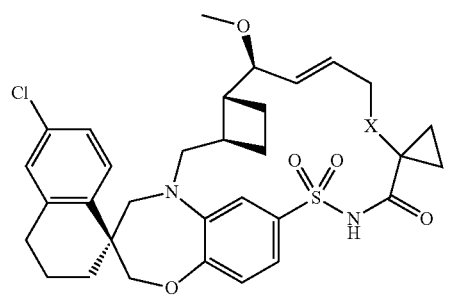
X = CHR, O, S, S(O)$_2$, NR
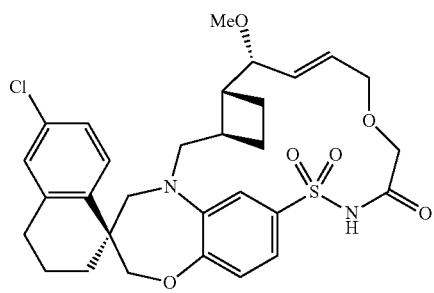 [SMILES: CO[C@@H]1/C=C/COCC(=O)NS(=O)(=O)c2ccc3c(c2)N(C[C@@H]2CC[C@H]21)C[C@@]1(CCCc2cc(Cl)ccc21)CO3]

TABLE B-continued
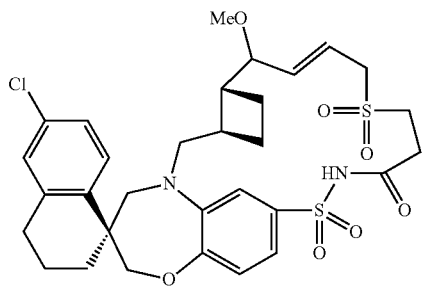 [SMILES: COC1/C=C/CS(=O)(=O)CCC(=O)NS(=O)(=O)c2ccc3c(c2)N(C[C@@H]2CC[C@@H]12)C[C@@]1(CCCc2cc(Cl)ccc21)CO3]
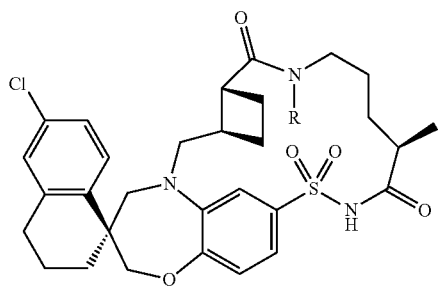
R = H or C₁-C₆alkyl
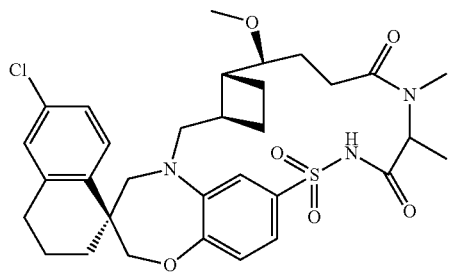 [SMILES: CO[C@H]1CCC(=O)N(C)C(C)C(=O)NS(=O)(=O)c2ccc3c(c2)N(C[C@@H]2CC[C@H]21)C[C@@]1(CCCc2cc(Cl)ccc21)CO3]
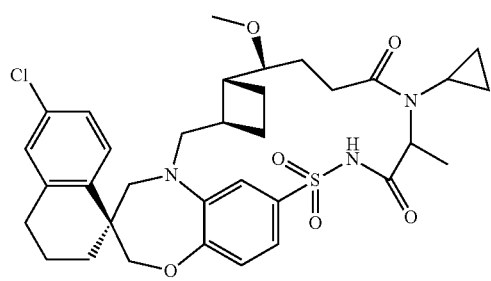 [SMILES: CO[C@H]1CCC(=O)N(C2CC2)C(C)C(=O)NS(=O)(=O)c2ccc3c(c2)N(C[C@@H]2CC[C@H]21)C[C@@]1(CCCc2cc(Cl)ccc21)CO3]
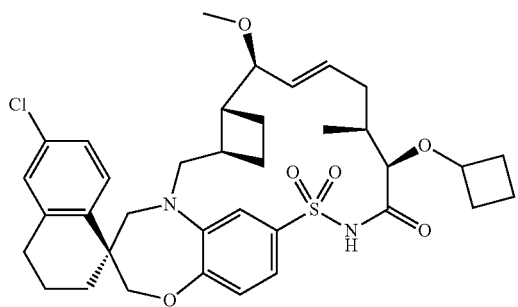 [SMILES: CO[C@H]1/C=C/C[C@H](C)[C@@H](OC2CCC2)C(=O)NS(=O)(=O)c2ccc3c(c2)N(C[C@@H]2CC[C@H]21)C[C@@]1(CCCc2cc(Cl)ccc21)CO3]

TABLE B-continued
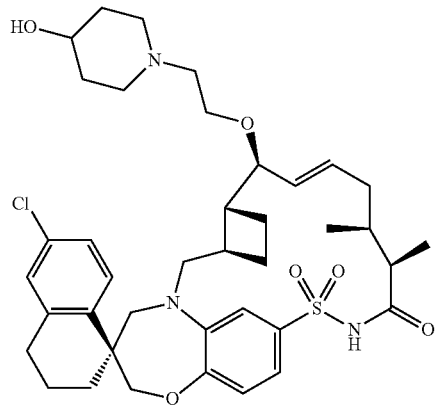
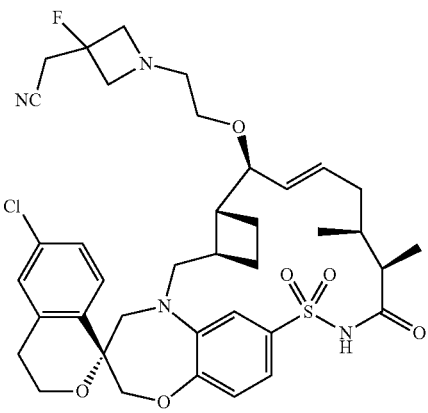 [SMILES: C[C@H]1C/C=C/[C@H](OCCN2CC(F)(CC#N)C2)[C@@H]2CC[C@H]2CN2C[C@]3(COc4ccc(cc42)S(=O)(=O)NC(=O)[C@@H]1C)OCCc1cc(Cl)ccc13]
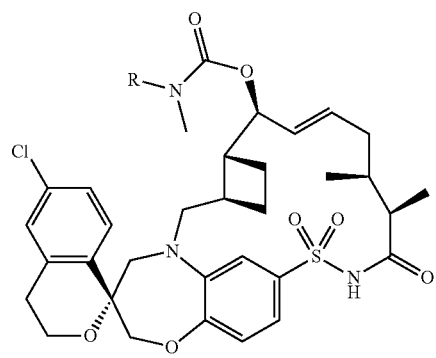
R = alkyl, cyclic alkyl, heterocyclic alkyl
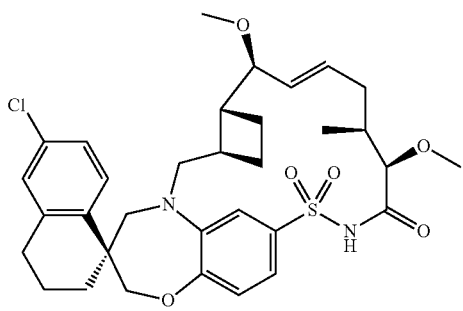 [SMILES: CO[C@H]1/C=C/C[C@H](C)[C@@H](OC)C(=O)NS(=O)(=O)c2ccc3c(c2)N(C[C@@H]2CC[C@H]21)C[C@@]1(CCCc2cc(Cl)ccc21)CO3]

TABLE B-continued
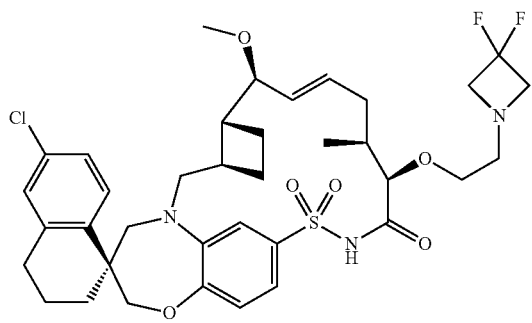 [SMILES: CO[C@H]1/C=C/C[C@H](C)[C@@H](OCCN2CC(F)(F)C2)C(=O)NS(=O)(=O)c2ccc3c(c2)N(C[C@@H]2CC[C@H]21)C[C@@]1(CCCc2cc(Cl)ccc21)CO3]
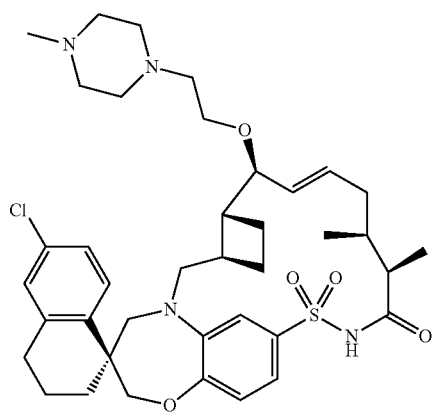 [SMILES: C[C@H]1C/C=C/[C@H](OCCN2CCN(C)CC2)[C@@H]2CC[C@H]2CN2C[C@@]3(CCCc4cc(Cl)ccc43)COc3ccc(cc32)S(=O)(=O)NC(=O)[C@@H]1C]
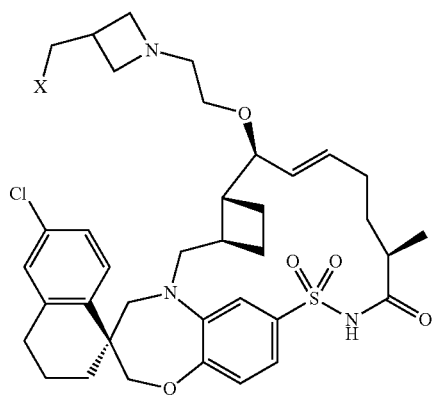
X = OH, F, OMe, OCF₃
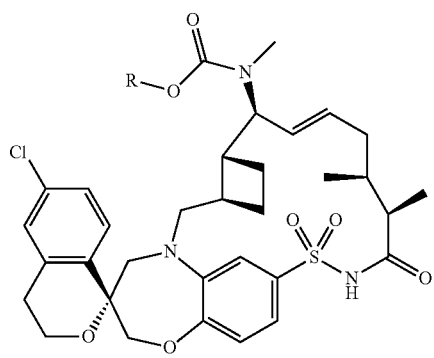
R = alkyl, cyclic alkyl, heterocyclic alkyl TABLE B-continued
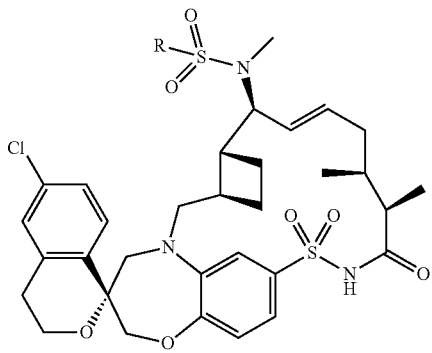
R = alkyl, cyclic alkyl, heterocyclic alkyl
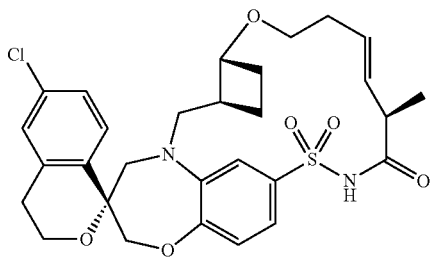
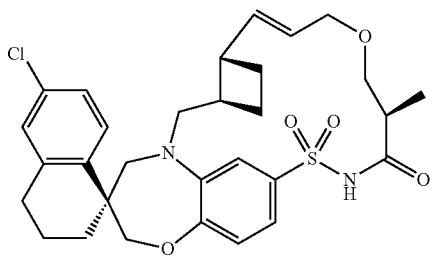 [SMILES: C[C@@H]1COC/C=C/[C@@H]2CC[C@H]2CN2C[C@@]3(CCCc4cc(Cl)ccc43)COc3ccc(cc32)S(=O)(=O)NC1=O]
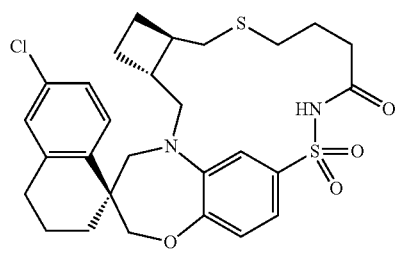 [SMILES: O=C1CCCSC[C@@H]2CC[C@H]2CN2C[C@@]3(CCCc4cc(Cl)ccc43)COc3ccc(cc32)S(=O)(=O)N1]
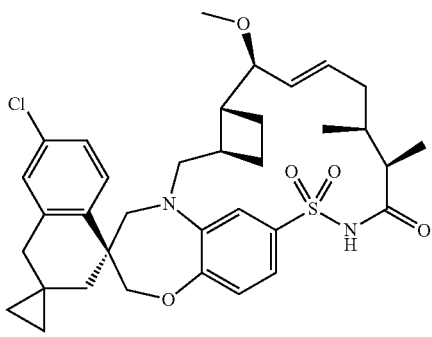 [SMILES: CO[C@H]1/C=C/C[C@H](C)[C@@H](C)C(=O)NS(=O)(=O)c2ccc3c(c2)N(C[C@@H]2CC[C@H]21)C[C@]1(CO3)CC2(CC2)Cc2cc(Cl)ccc21]

TABLE B-continued
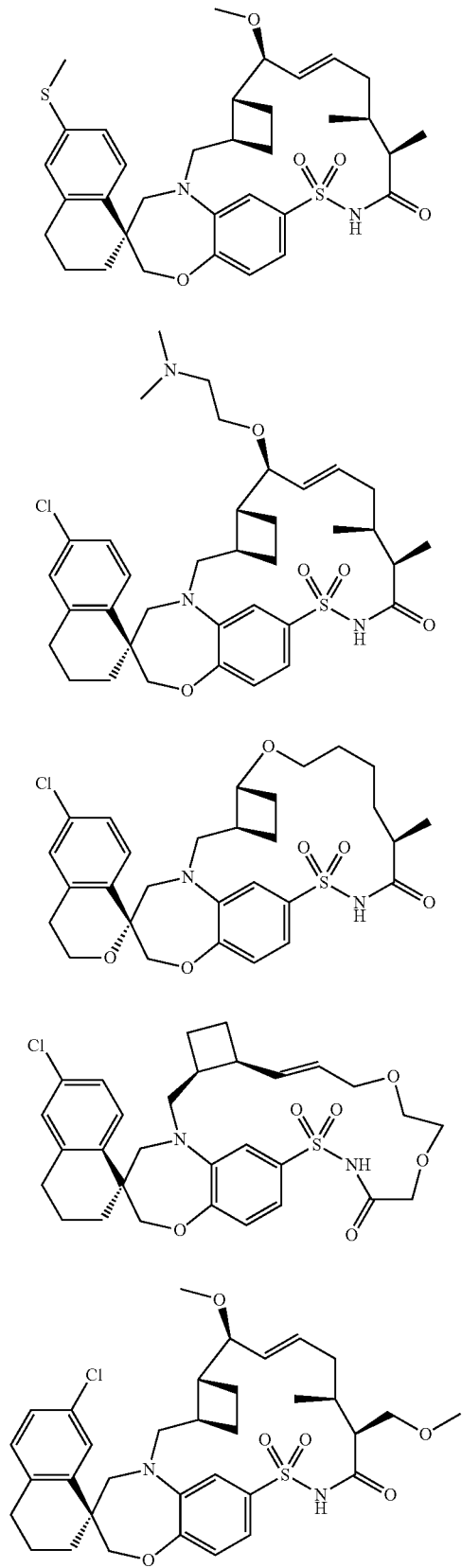

TABLE B-continued
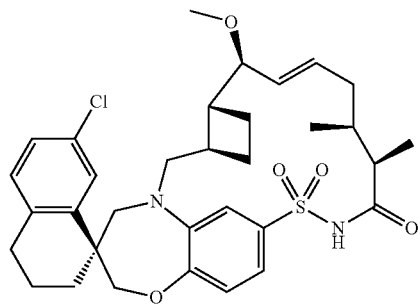 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCCc2ccc(Cl)cc21)CO3]
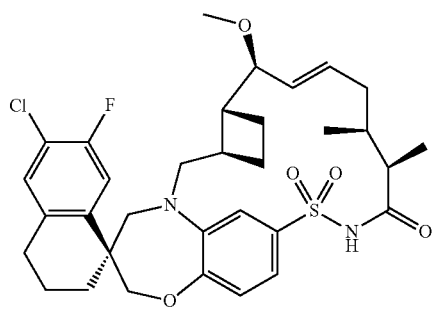 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCCc2cc(Cl)c(F)cc21)CO3]
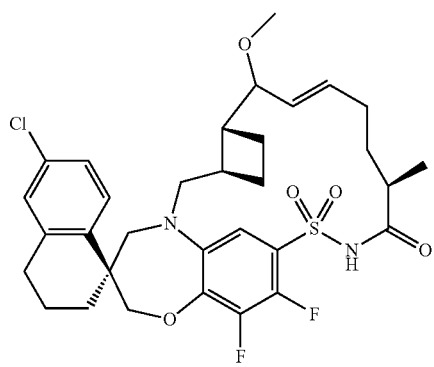 [SMILES: COC1/C=C/CC[C@@H](C)C(=O)NS(=O)(=O)c2cc3c(c(F)c2F)OC[C@]2(CCCc4cc(Cl)ccc42)CN3C[C@@H]2CC[C@@H]12]
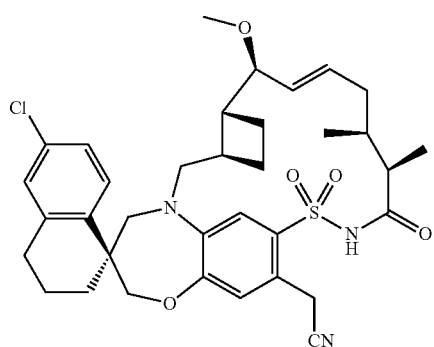 [SMILES: CO[C@H]1/C=C/C[C@H](C)[C@@H](C)C(=O)NS(=O)(=O)c2cc3c(cc2CC#N)OC[C@]2(CCCc4cc(Cl)ccc42)CN3C[C@@H]2CC[C@H]21]

TABLE B-continued
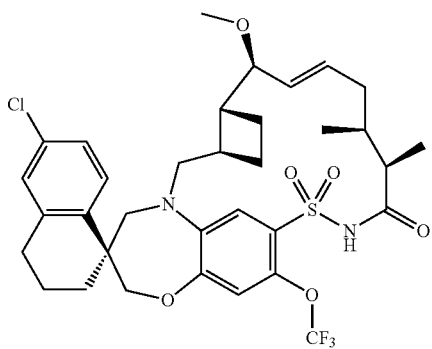 [SMILES: CO[C@H]1/C=C/C[C@H](C)[C@@H](C)C(=O)NS(=O)(=O)c2cc3c(cc2OC(F)(F)F)OC[C@]2(CCCc4cc(Cl)ccc42)CN3C[C@@H]2CC[C@H]21]
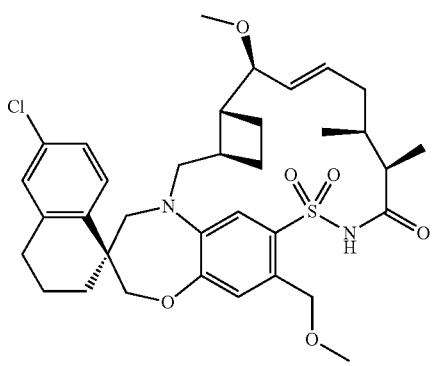 [SMILES: COCc1cc2c3cc1S(=O)(=O)NC(=O)[C@H](C)[C@@H](C)C/C=C/[C@H](OC)[C@@H]1CC[C@H]1CN3C[C@@]1(CCCc3cc(Cl)ccc31)CO2]
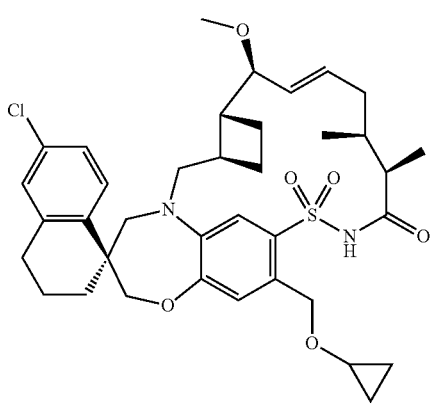 [SMILES: CO[C@H]1/C=C/C[C@H](C)[C@@H](C)C(=O)NS(=O)(=O)c2cc3c(cc2COC2CC2)OC[C@]2(CCCc4cc(Cl)ccc42)CN3C[C@@H]2CC[C@H]21]
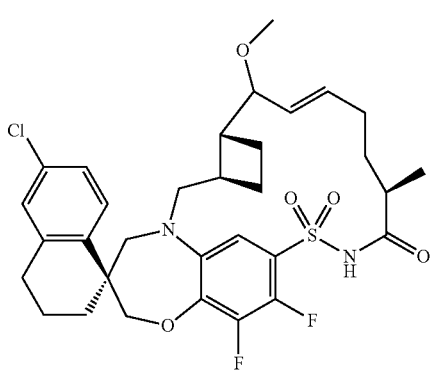 [SMILES: COC1/C=C/CC[C@@H](C)C(=O)NS(=O)(=O)c2cc3c(c(F)c2F)OC[C@]2(CCCc4cc(Cl)ccc42)CN3C[C@@H]2CC[C@@H]12]

TABLE B-continued
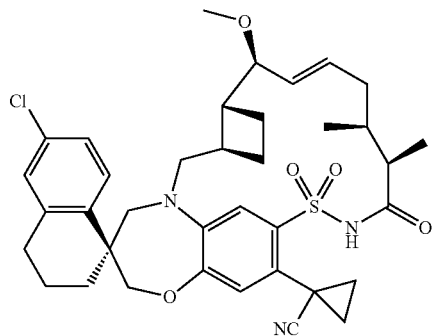 [SMILES: CO[C@H]1/C=C/C[C@H](C)[C@@H](C)C(=O)NS(=O)(=O)c2cc3c(cc2C2(C#N)CC2)OC[C@]2(CCCc4cc(Cl)ccc42)CN3C[C@@H]2CC[C@H]21]
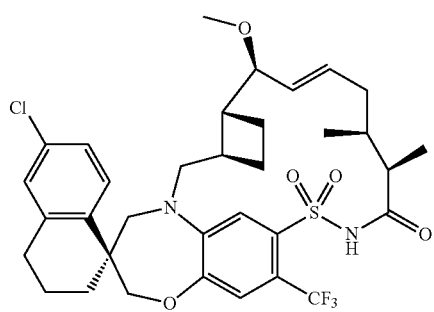 [SMILES: CO[C@H]1/C=C/C[C@H](C)[C@@H](C)C(=O)NS(=O)(=O)c2cc3c(cc2C(F)(F)F)OC[C@]2(CCCc4cc(Cl)ccc42)CN3C[C@@H]2CC[C@H]21]
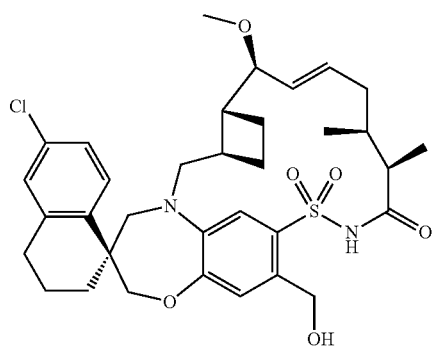
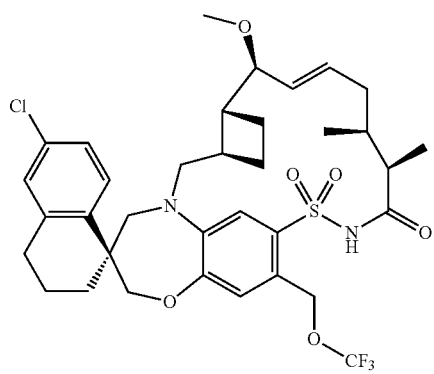 [SMILES: CO[C@H]1/C=C/C[C@H](C)[C@@H](C)C(=O)NS(=O)(=O)c2cc3c(cc2COC(F)(F)F)OC[C@]2(CCCc4cc(Cl)ccc42)CN3C[C@@H]2CC[C@H]21]

TABLE B-continued
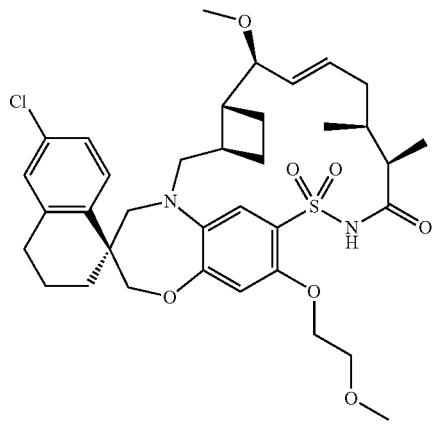 [SMILES: COCCOc1cc2c3cc1S(=O)(=O)NC(=O)[C@H](C)[C@@H](C)C/C=C/[C@H](OC)[C@@H]1CC[C@H]1CN3C[C@@]1(CCCc3cc(Cl)ccc31)CO2]
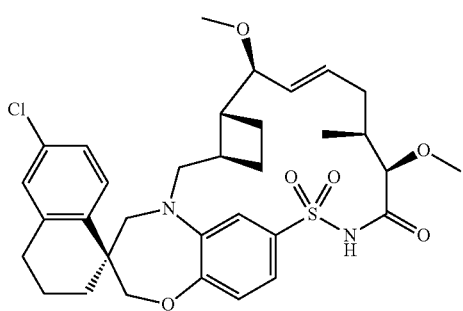 [SMILES: CO[C@H]1/C=C/C[C@H](C)[C@@H](OC)C(=O)NS(=O)(=O)c2ccc3c(c2)N(C[C@@H]2CC[C@H]21)C[C@@]1(CCCc2cc(Cl)ccc21)CO3]
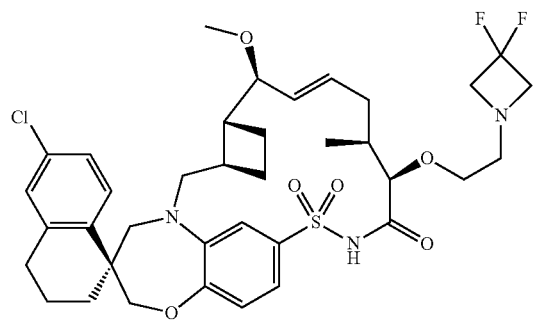 [SMILES: CO[C@H]1/C=C/C[C@H](C)[C@@H](OCCN2CC(F)(F)C2)C(=O)NS(=O)(=O)c2ccc3c(c2)N(C[C@@H]2CC[C@H]21)C[C@@]1(CCCc2cc(Cl)ccc21)CO3]
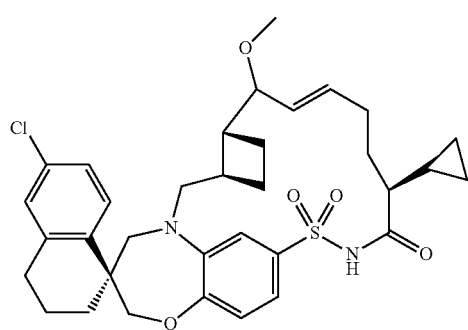 [SMILES: COC1/C=C/CC[C@@H](C2CC2)C(=O)NS(=O)(=O)c2ccc3c(c2)N(C[C@@H]2CC[C@@H]12)C[C@@]1(CCCc2cc(Cl)ccc21)CO3]

TABLE B-continued
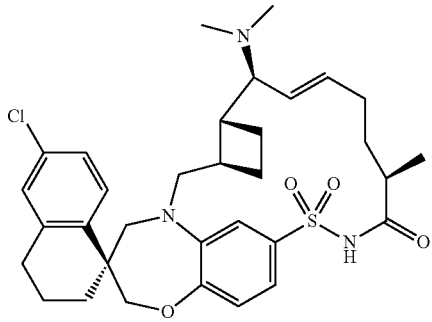 [SMILES: C[C@@H]1CC/C=C/[C@H](N(C)C)[C@@H]2CC[C@H]2CN2C[C@@]3(CCCc4cc(Cl)ccc43)COc3ccc(cc32)S(=O)(=O)NC1=O]
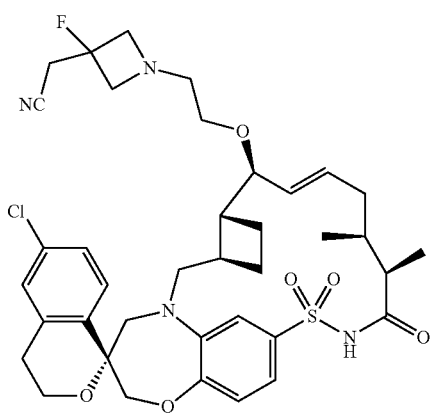 [SMILES: C[C@H]1C/C=C/[C@H](OCCN2CC(F)(CC#N)C2)[C@@H]2CC[C@H]2CN2C[C@]3(COc4ccc(cc42)S(=O)(=O)NC(=O)[C@@H]1C)OCCc1cc(Cl)ccc13]
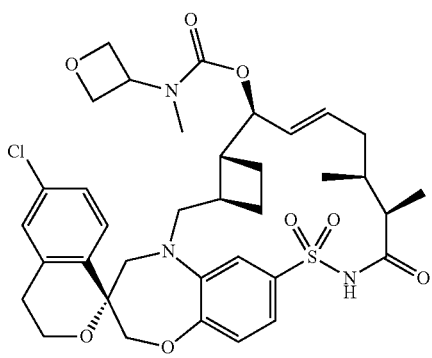 [SMILES: C[C@H]1C/C=C/[C@H](OC(=O)N(C)C2COC2)[C@@H]2CC[C@H]2CN2C[C@]3(COc4ccc(cc42)S(=O)(=O)NC(=O)[C@@H]1C)OCCc1cc(Cl)ccc13]
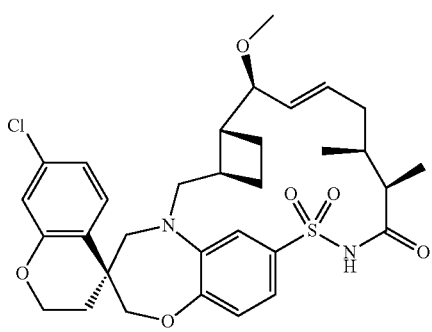 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCOc2cc(Cl)ccc21)CO3]

TABLE B-continued
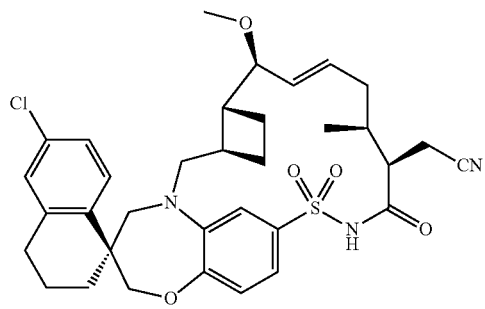 [SMILES: CO[C@H]1/C=C/C[C@H](C)[C@@H](CC#N)C(=O)NS(=O)(=O)c2ccc3c(c2)N(C[C@@H]2CC[C@H]21)C[C@@]1(CCCc2cc(Cl)ccc21)CO3]
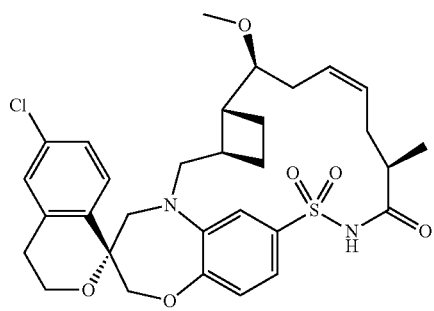 [SMILES: CO[C@H]1C/C=C\C[C@@H](C)C(=O)NS(=O)(=O)c2ccc3c(c2)N(C[C@@H]2CC[C@H]21)C[C@]1(CO3)OCCc2cc(Cl)ccc21]
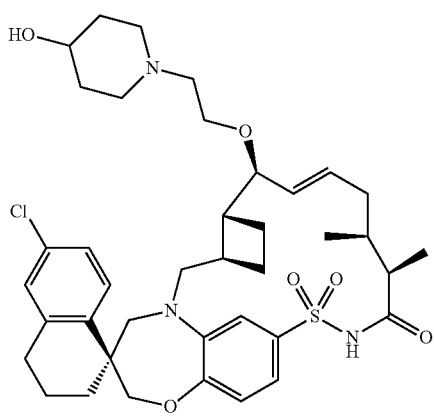
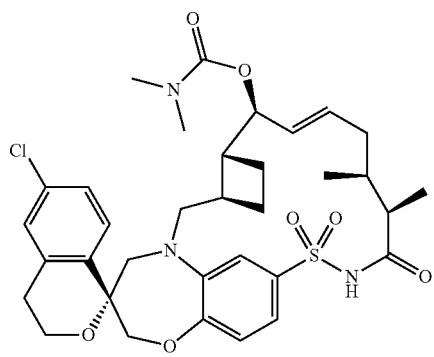 [SMILES: C[C@H]1C/C=C/[C@H](OC(=O)N(C)C)[C@@H]2CC[C@H]2CN2C[C@]3(COc4ccc(cc42)S(=O)(=O)NC(=O)[C@@H]1C)OCCc1cc(Cl)ccc13]

TABLE B-continued
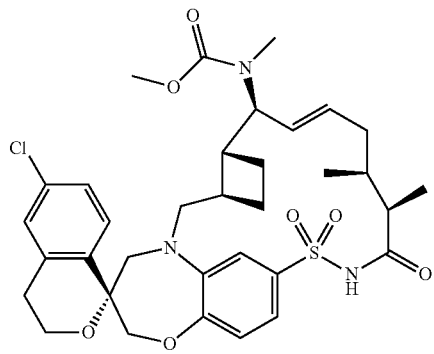 [SMILES: COC(=O)N(C)[C@H]1/C=C/C[C@H](C)[C@@H](C)C(=O)NS(=O)(=O)c2ccc3c(c2)N(C[C@@H]2CC[C@H]21)C[C@]1(CO3)OCCc2cc(Cl)ccc21]
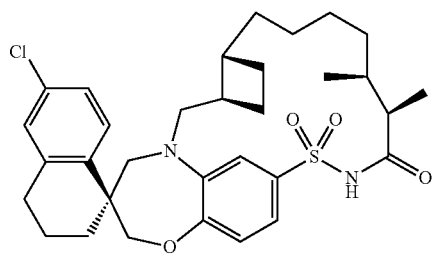 [SMILES: C[C@H]1CCCC[C@@H]2CC[C@H]2CN2C[C@@]3(CCCc4cc(Cl)ccc43)COc3ccc(cc32)S(=O)(=O)NC(=O)[C@@H]1C]
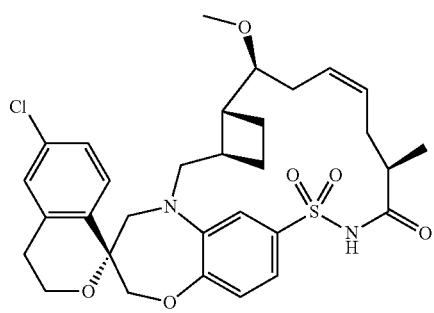 [SMILES: CO[C@H]1C/C=C\C[C@@H](C)C(=O)NS(=O)(=O)c2ccc3c(c2)N(C[C@@H]2CC[C@H]21)C[C@]1(CO3)OCCc2cc(Cl)ccc21]
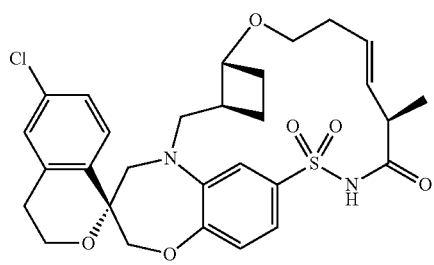 [SMILES: C[C@@H]1/C=C/CCO[C@@H]2CC[C@H]2CN2C[C@]3(COc4ccc(cc42)S(=O)(=O)NC1=O)OCCc1cc(Cl)ccc13]
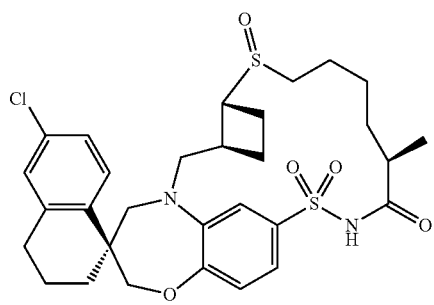 [SMILES: C[C@@H]1CCCCS(=O)[C@@H]2CC[C@H]2CN2C[C@@]3(CCCc4cc(Cl)ccc43)COc3ccc(cc32)S(=O)(=O)NC1=O]

TABLE B-continued
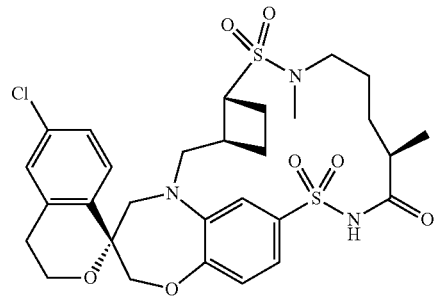 [SMILES: C[C@@H]1CCCN(C)S(=O)(=O)[C@@H]2CC[C@H]2CN2C[C@]3(COc4ccc(cc42)S(=O)(=O)NC1=O)OCCc1cc(Cl)ccc13]
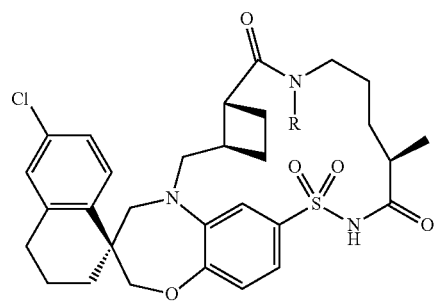
R = H or C$_1$-C$_6$alkyl
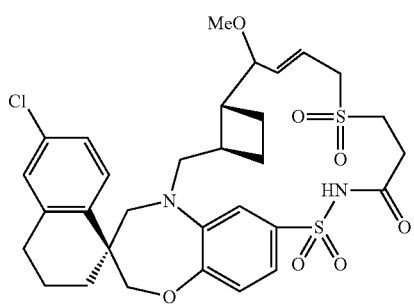 [SMILES: COC1/C=C/CS(=O)(=O)CCC(=O)NS(=O)(=O)c2ccc3c(c2)N(C[C@@H]2CC[C@@H]12)C[C@@]1(CCCc2cc(Cl)ccc21)CO3]
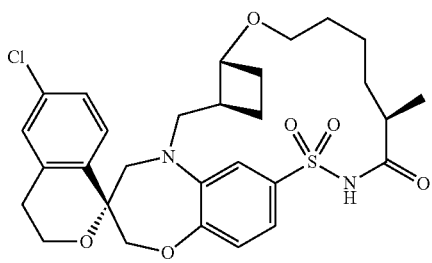 [SMILES: C[C@@H]1CCCCO[C@@H]2CC[C@H]2CN2C[C@]3(COc4ccc(cc42)S(=O)(=O)NC1=O)OCCc1cc(Cl)ccc13]
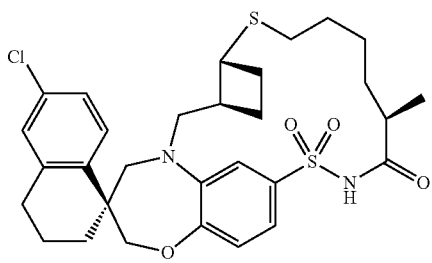

TABLE B-continued
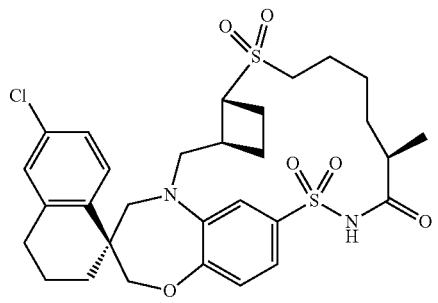 [SMILES: C[C@@H]1CCCCS(=O)(=O)[C@@H]2CC[C@H]2CN2C[C@@]3(CCCc4cc(Cl)ccc43)COc3ccc(cc32)S(=O)(=O)NC1=O]
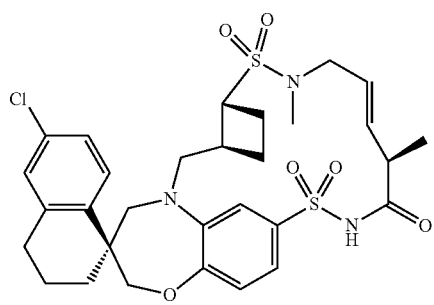 [SMILES: C[C@@H]1/C=C/CN(C)S(=O)(=O)[C@@H]2CC[C@H]2CN2C[C@@]3(CCCc4cc(Cl)ccc43)COc3ccc(cc32)S(=O)(=O)NC1=O]
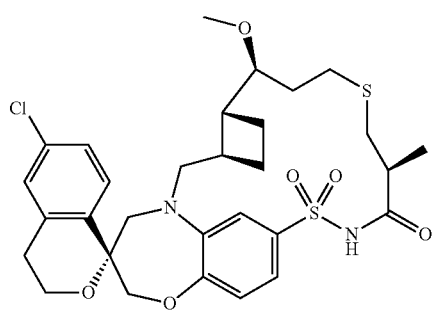 [SMILES: CO[C@H]1CCSC[C@@H](C)C(=O)NS(=O)(=O)c2ccc3c(c2)N(C[C@@H]2CC[C@H]21)C[C@]1(CO3)OCCc2cc(Cl)ccc21]
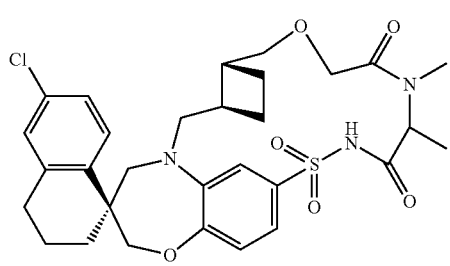 [SMILES: CC1C(=O)NS(=O)(=O)c2ccc3c(c2)N(C[C@@H]2CC[C@H]2COCC(=O)N1C)C[C@@]1(CCCc2cc(Cl)ccc21)CO3]
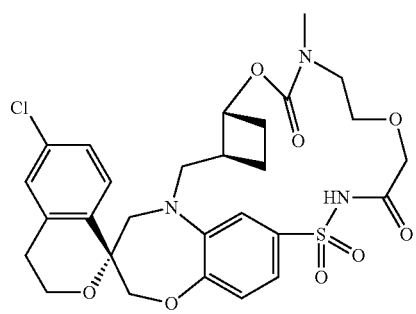 [SMILES: CN1CCOCC(=O)NS(=O)(=O)c2ccc3c(c2)N(C[C@@H]2CC[C@H]2OC1=O)C[C@]1(CO3)OCCc2cc(Cl)ccc21]

TABLE B-continued
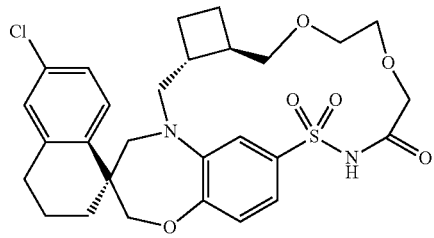
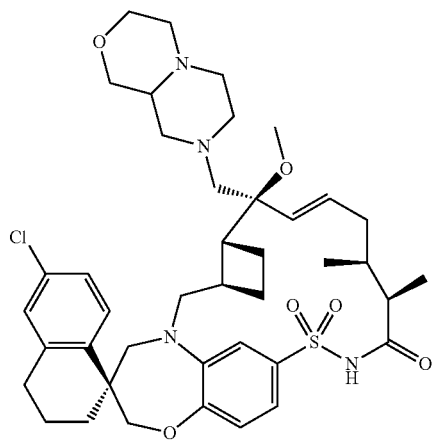 [SMILES: CO[C@@]1(CN2CCN3CCOCC3C2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
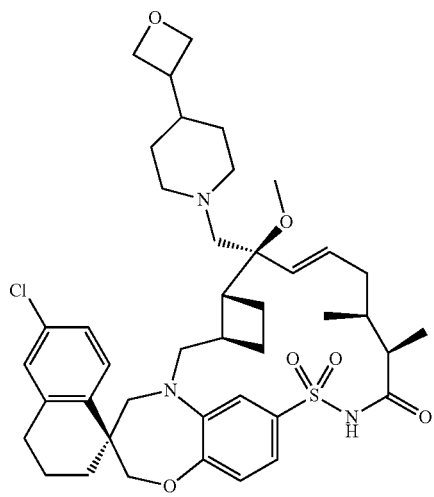 [SMILES: CO[C@@]1(CN2CCC(C3COC3)CC2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
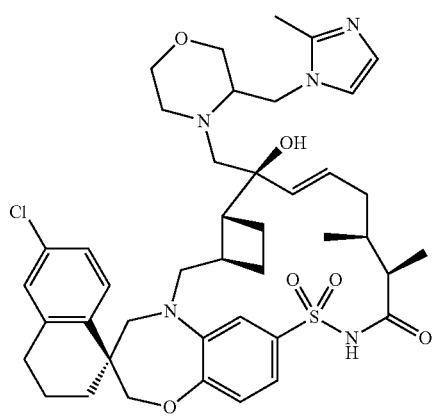 [SMILES: Cc1nccn1CC1COCCN1C[C@]1(O)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]

TABLE B-continued
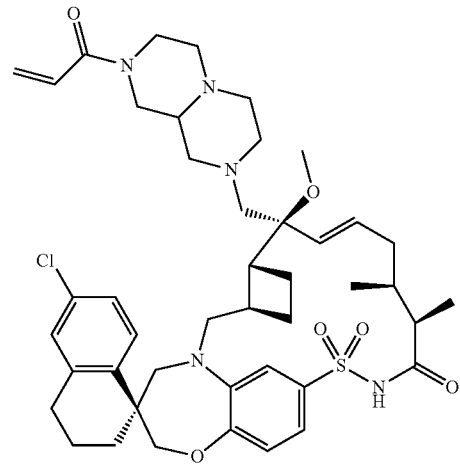 [SMILES: C=CC(=O)N1CCN2CCN(C[C@]3(OC)/C=C/C[C@H](C)[C@@H](C)C(=O)NS(=O)(=O)c4ccc5c(c4)N(C[C@@H]4CC[C@H]43)C[C@@]3(CCCc4cc(Cl)ccc43)CO5)CC2C1]
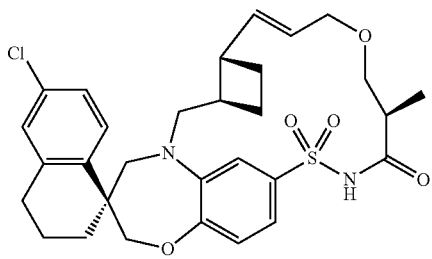 [SMILES: C[C@@H]1COC/C=C/[C@@H]2CC[C@H]2CN2C[C@@]3(CCCc4cc(Cl)ccc43)COc3ccc(cc32)S(=O)(=O)NC1=O]
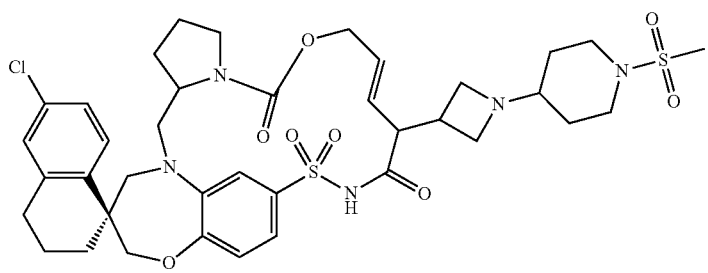 [SMILES: CS(=O)(=O)N1CCC(N2CC(C3/C=C/COC(=O)N4CCCC4CN4C[C@@]5(CCCc6cc(Cl)ccc65)COc5ccc(cc54)S(=O)(=O)NC3=O)C2)CC1]
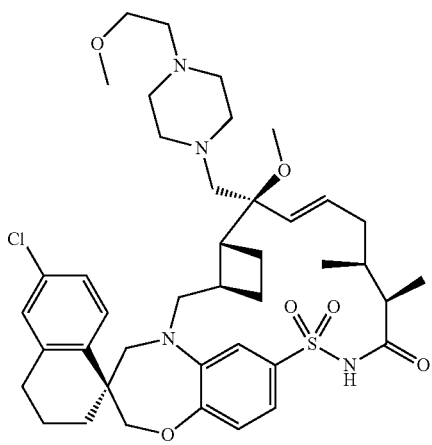 [SMILES: COCCN1CCN(C[C@]2(OC)/C=C/C[C@H](C)[C@@H](C)C(=O)NS(=O)(=O)c3ccc4c(c3)N(C[C@@H]3CC[C@H]32)C[C@@]2(CCCc3cc(Cl)ccc32)CO4)CC1]

TABLE B-continued
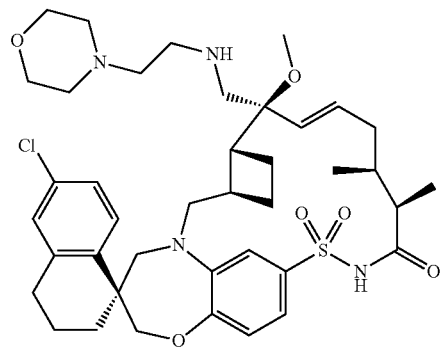 [SMILES: CO[C@@]1(CNCCN2CCOCC2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
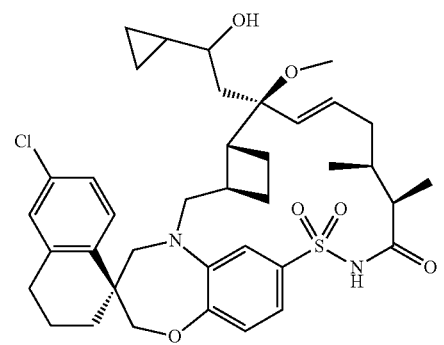 [SMILES: CO[C@@]1(CC(O)C2CC2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
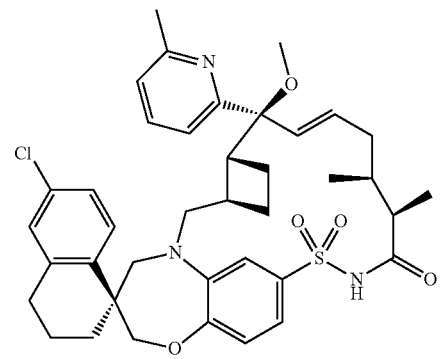 [SMILES: CO[C@@]1(c2cccc(C)n2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
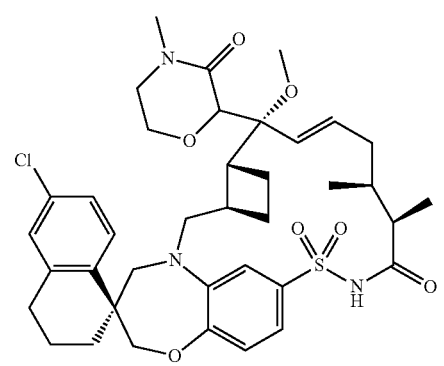 [SMILES: CO[C@]1(C2OCCN(C)C2=O)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]

TABLE B-continued
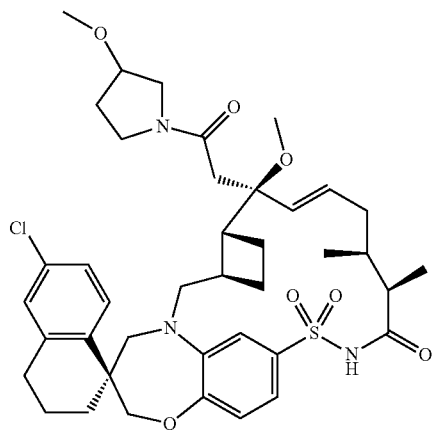 [SMILES: COC1CCN(C(=O)C[C@]2(OC)/C=C/C[C@H](C)[C@@H](C)C(=O)NS(=O)(=O)c3ccc4c(c3)N(C[C@@H]3CC[C@H]32)C[C@@]2(CCCc3cc(Cl)ccc32)CO4)C1]
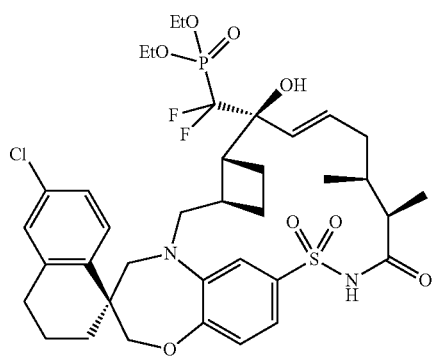 [SMILES: CCOP(=O)(OCC)C(F)(F)[C@]1(O)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
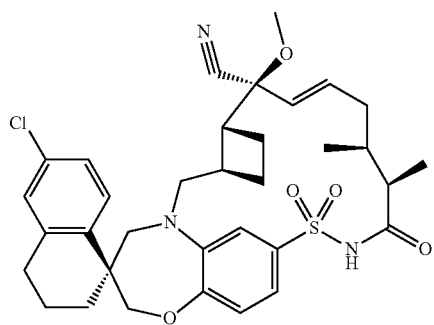 [SMILES: CO[C@@]1(C#N)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
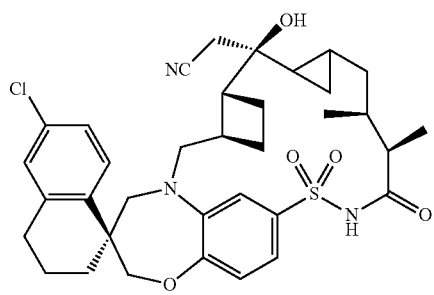 [SMILES: C[C@H]1CC2CC2[C@@](O)(CC#N)[C@@H]2CC[C@H]2CN2C[C@@]3(CCCc4cc(Cl)ccc43)COc3ccc(cc32)S(=O)(=O)NC(=O)[C@@H]1C]

TABLE B-continued
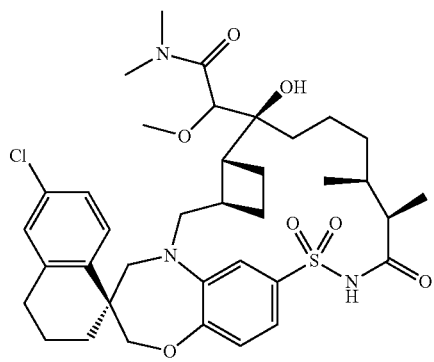 [SMILES: COC(C(=O)N(C)C)[C@]1(O)CCC[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
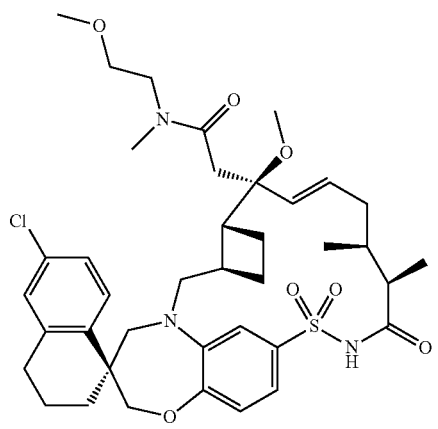 [SMILES: COCCN(C)C(=O)C[C@]1(OC)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
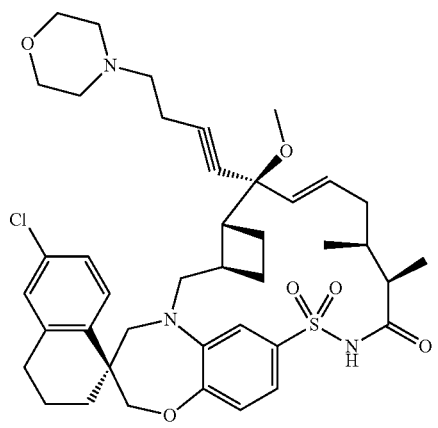 [SMILES: CO[C@@]1(C#CCCN2CCOCC2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
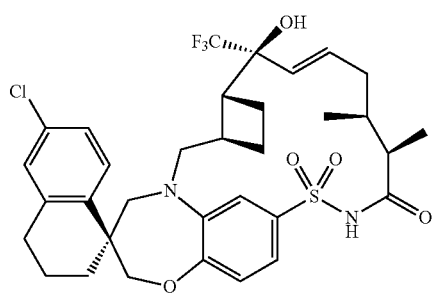 [SMILES: C[C@H]1C/C=C/[C@@](O)(C(F)(F)F)[C@@H]2CC[C@H]2CN2C[C@@]3(CCCc4cc(Cl)ccc43)COc3ccc(cc32)S(=O)(=O)NC(=O)[C@@H]1C]

TABLE B-continued
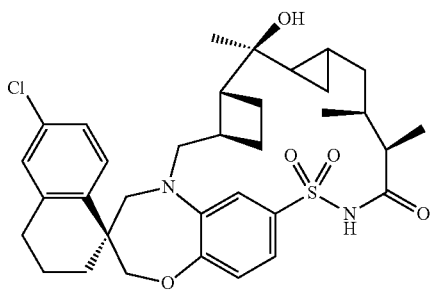 [SMILES: C[C@H]1CC2CC2[C@](C)(O)[C@@H]2CC[C@H]2CN2C[C@@]3(CCCc4cc(Cl)ccc43)COc3ccc(cc32)S(=O)(=O)NC(=O)[C@@H]1C]
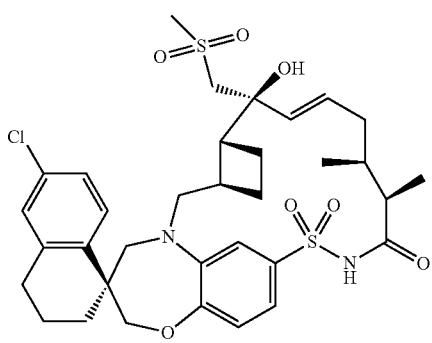 [SMILES: C[C@H]1C/C=C/[C@@](O)(CS(C)(=O)=O)[C@@H]2CC[C@H]2CN2C[C@@]3(CCCc4cc(Cl)ccc43)COc3ccc(cc32)S(=O)(=O)NC(=O)[C@@H]1C]
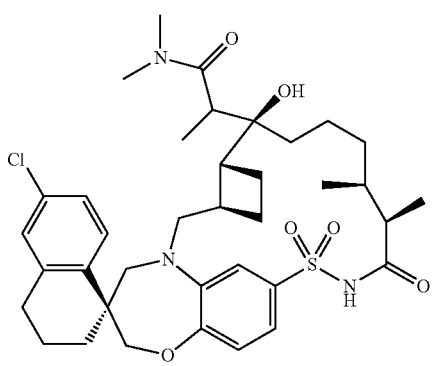 [SMILES: CC(C(=O)N(C)C)[C@]1(O)CCC[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
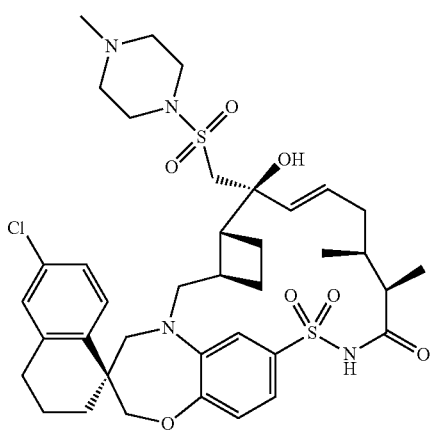 [SMILES: C[C@H]1C/C=C/[C@@](O)(CS(=O)(=O)N2CCN(C)CC2)[C@@H]2CC[C@H]2CN2C[C@@]3(CCCc4cc(Cl)ccc43)COc3ccc(cc32)S(=O)(=O)NC(=O)[C@@H]1C]

TABLE B-continued
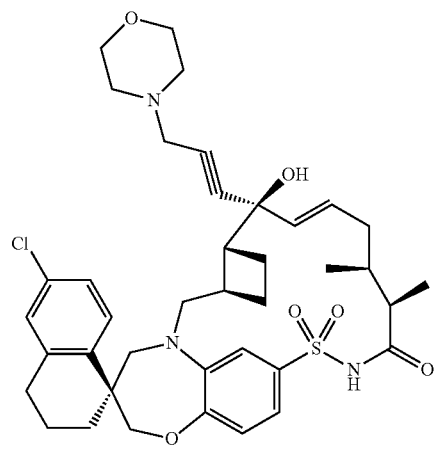 [SMILES: C[C@H]1C/C=C/[C@@](O)(C#CCN2CCOCC2)[C@@H]2CC[C@H]2CN2C[C@@]3(CCCc4cc(Cl)ccc43)COc3ccc(cc32)S(=O)(=O)NC(=O)[C@@H]1C]
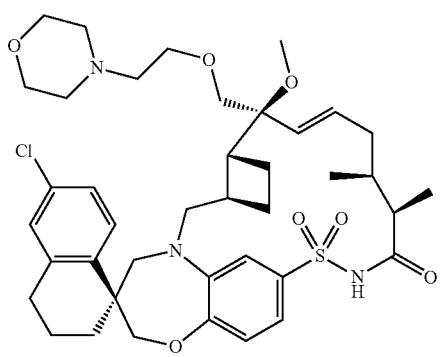 [SMILES: CO[C@@]1(COCCN2CCOCC2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
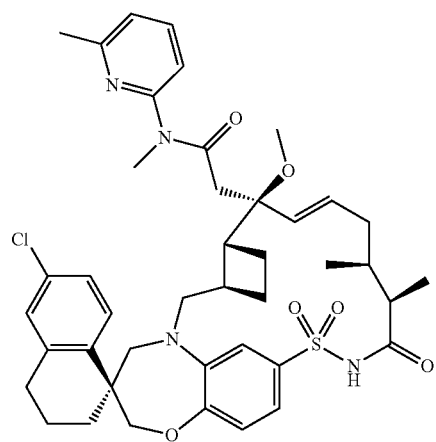 [SMILES: CO[C@@]1(CC(=O)N(C)c2cccc(C)n2)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]

TABLE B-continued
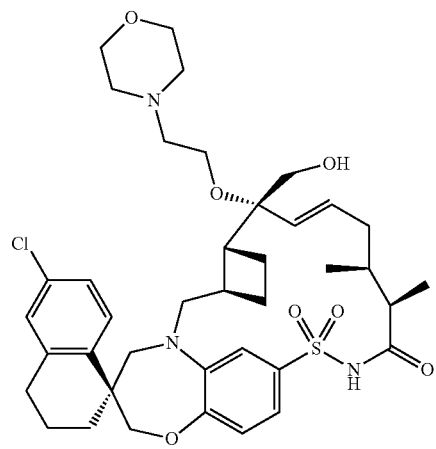 [SMILES: C[C@H]1C/C=C/[C@@](CO)(OCCN2CCOCC2)[C@@H]2CC[C@H]2CN2C[C@@]3(CCCc4cc(Cl)ccc43)COc3ccc(cc32)S(=O)(=O)NC(=O)[C@@H]1C]
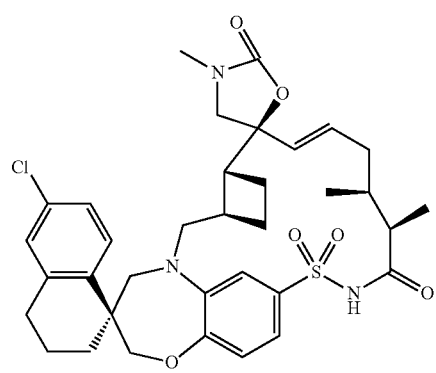 [SMILES: C[C@H]1C/C=C/[C@@]2(CN(C)C(=O)O2)[C@@H]2CC[C@H]2CN2C[C@@]3(CCCc4cc(Cl)ccc43)COc3ccc(cc32)S(=O)(=O)NC(=O)[C@@H]1C]
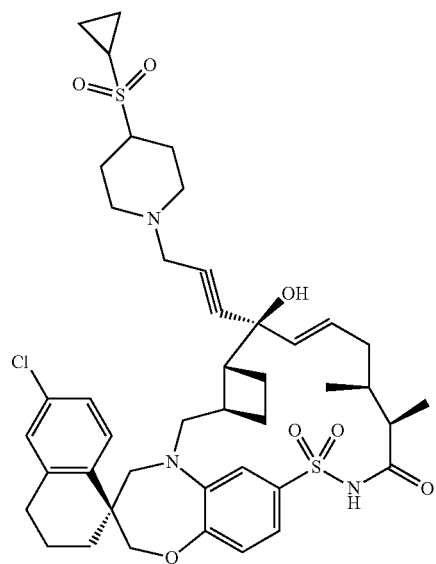 [SMILES: C[C@H]1C/C=C/[C@@](O)(C#CCN2CCC(S(=O)(=O)C3CC3)CC2)[C@@H]2CC[C@H]2CN2C[C@@]3(CCCc4cc(Cl)ccc43)COc3ccc(cc32)S(=O)(=O)NC(=O)[C@@H]1C]

TABLE B-continued
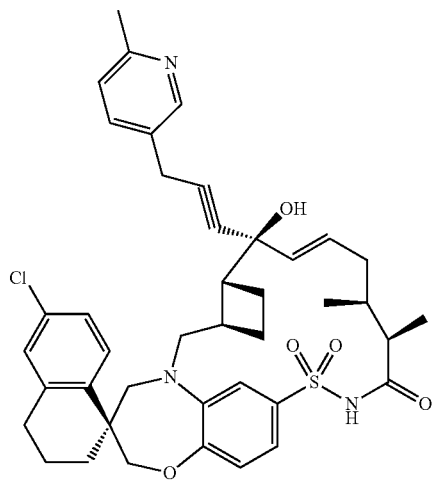 [SMILES: Cc1ccc(CC#C[C@]2(O)/C=C/C[C@H](C)[C@@H](C)C(=O)NS(=O)(=O)c3ccc4c(c3)N(C[C@@H]3CC[C@H]32)C[C@@]2(CCCc3cc(Cl)ccc32)CO4)cn1]
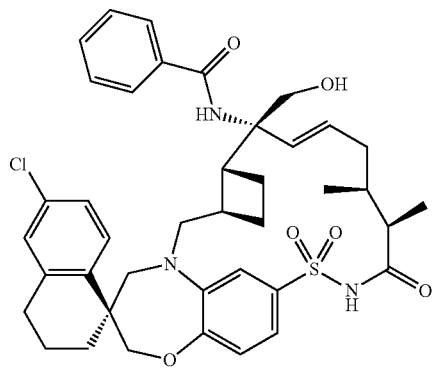 [SMILES: C[C@H]1C/C=C/[C@@](CO)(NC(=O)c2ccccc2)[C@@H]2CC[C@H]2CN2C[C@@]3(CCCc4cc(Cl)ccc43)COc3ccc(cc32)S(=O)(=O)NC(=O)[C@@H]1C]
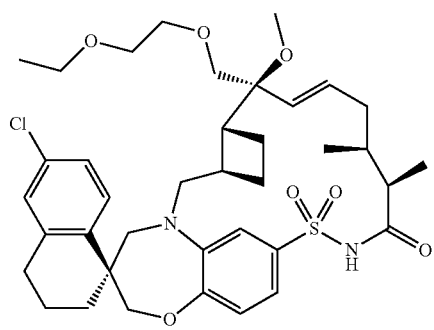 [SMILES: CCOCCOC[C@]1(OC)/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
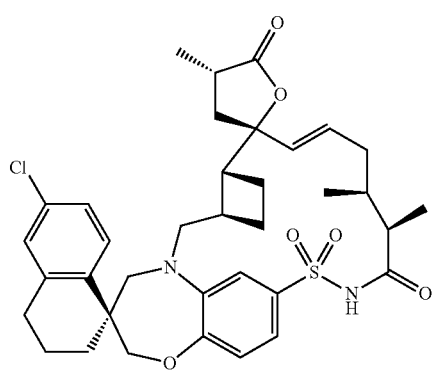 [SMILES: C[C@H]1C[C@]2(/C=C/C[C@H](C)[C@@H](C)C(=O)NS(=O)(=O)c3ccc4c(c3)N(C[C@@H]3CC[C@H]32)C[C@@]2(CCCc3cc(Cl)ccc32)CO4)OC1=O]

TABLE B-continued
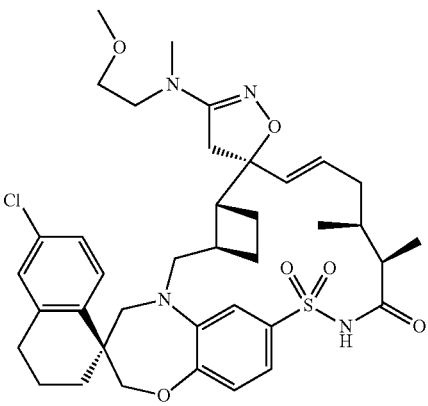 [SMILES: COCCN(C)C1=NO[C@]2(/C=C/C[C@H](C)[C@@H](C)C(=O)NS(=O)(=O)c3ccc4c(c3)N(C[C@@H]3CC[C@H]32)C[C@@]2(CCCc3cc(Cl)ccc32)CO4)C1]
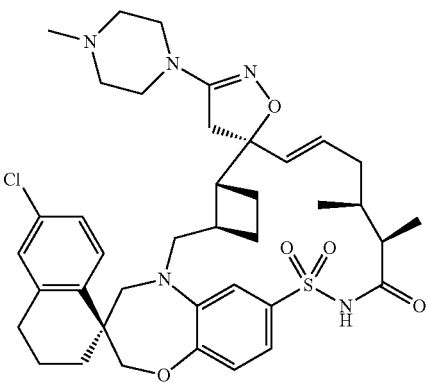 [SMILES: C[C@H]1C/C=C/[C@@]2(CC(N3CCN(C)CC3)=NO2)[C@@H]2CC[C@H]2CN2C[C@@]3(CCCc4cc(Cl)ccc43)COc3ccc(cc32)S(=O)(=O)NC(=O)[C@@H]1C]
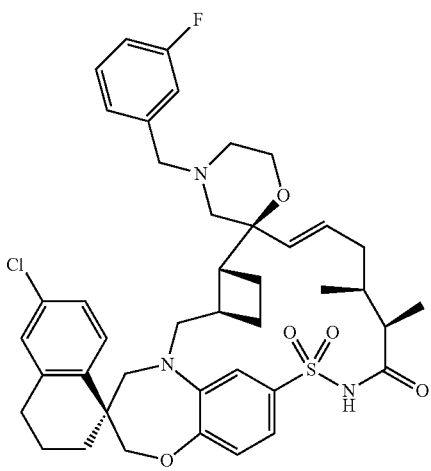 [SMILES: C[C@H]1C/C=C/[C@@]2(CN(Cc3cccc(F)c3)CCO2)[C@@H]2CC[C@H]2CN2C[C@@]3(CCCc4cc(Cl)ccc43)COc3ccc(cc32)S(=O)(=O)NC(=O)[C@@H]1C]
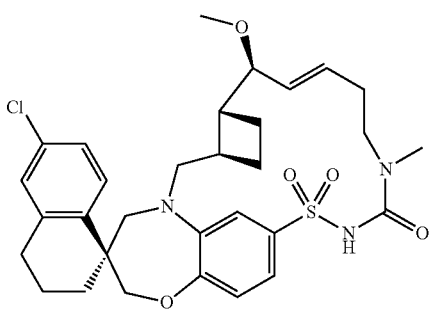 [SMILES: CO[C@H]1/C=C/CCN(C)C(=O)NS(=O)(=O)c2ccc3c(c2)N(C[C@@H]2CC[C@H]21)C[C@@]1(CCCc2cc(Cl)ccc21)CO3]

TABLE B-continued
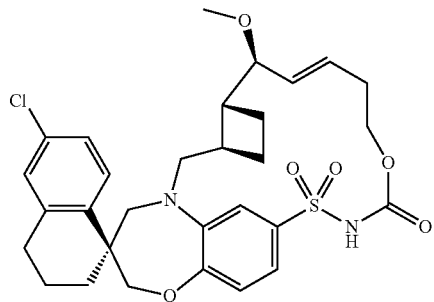 [SMILES: CO[C@H]1/C=C/CCOC(=O)NS(=O)(=O)c2ccc3c(c2)N(C[C@@H]2CC[C@H]21)C[C@@]1(CCCc2cc(Cl)ccc21)CO3]
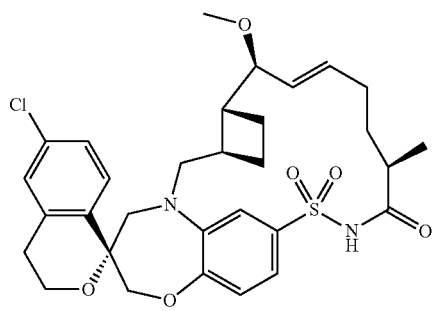 [SMILES: CO[C@H]1/C=C/CC[C@@H](C)C(=O)NS(=O)(=O)c2ccc3c(c2)N(C[C@@H]2CC[C@H]21)C[C@]1(CO3)OCCc2cc(Cl)ccc21]
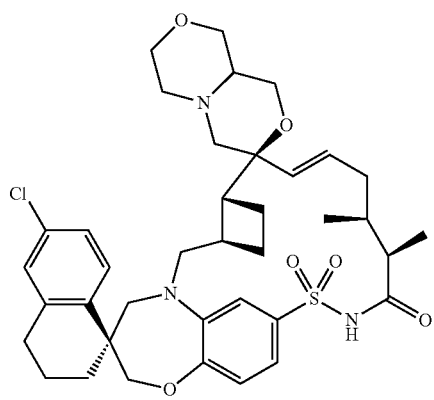
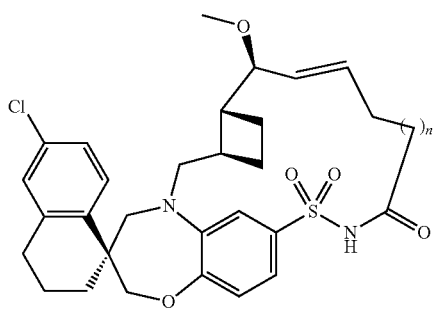
n = 1, 2, 3

TABLE B-continued
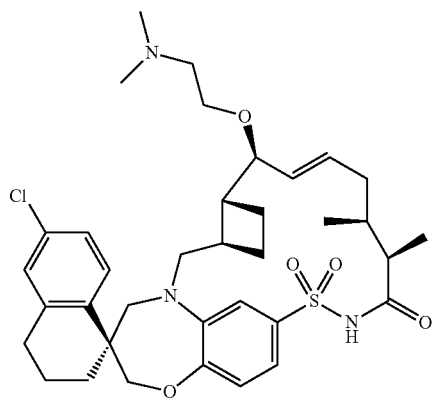 [SMILES: C[C@H]1C/C=C/[C@H](OCCN(C)C)[C@@H]2CC[C@H]2CN2C[C@@]3(CCCc4cc(Cl)ccc43)COc3ccc(cc32)S(=O)(=O)NC(=O)[C@@H]1C]
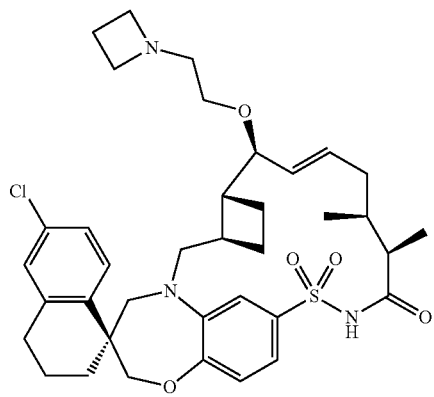 [SMILES: C[C@H]1C/C=C/[C@H](OCCN2CCC2)[C@@H]2CC[C@H]2CN2C[C@@]3(CCCc4cc(Cl)ccc43)COc3ccc(cc32)S(=O)(=O)NC(=O)[C@@H]1C]
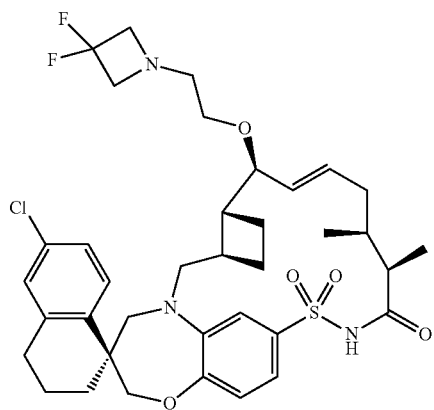 [SMILES: C[C@H]1C/C=C/[C@H](OCCN2CC(F)(F)C2)[C@@H]2CC[C@H]2CN2C[C@@]3(CCCc4cc(Cl)ccc43)COc3ccc(cc32)S(=O)(=O)NC(=O)[C@@H]1C]
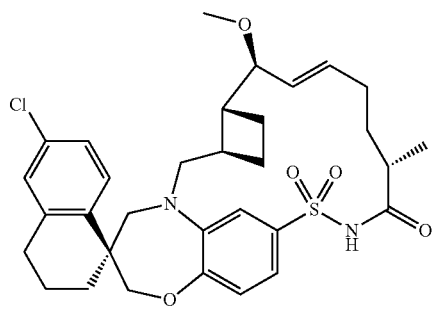

TABLE B-continued
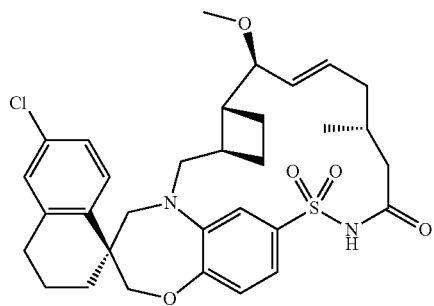 [SMILES: CO[C@H]1/C=C/C[C@@H](C)CC(=O)NS(=O)(=O)c2ccc3c(c2)N(C[C@@H]2CC[C@H]21)C[C@@]1(CCCc2cc(Cl)ccc21)CO3]
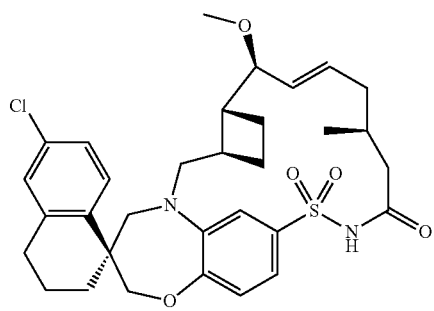 [SMILES: CO[C@H]1/C=C/C[C@H](C)CC(=O)NS(=O)(=O)c2ccc3c(c2)N(C[C@@H]2CC[C@H]21)C[C@@]1(CCCc2cc(Cl)ccc21)CO3]
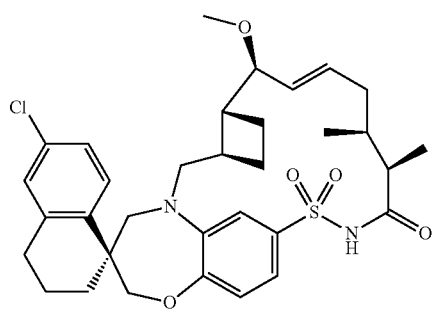 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]
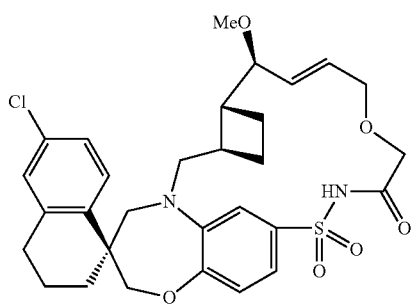 [SMILES: CO[C@H]1/C=C/COCC(=O)NS(=O)(=O)c2ccc3c(c2)N(C[C@@H]2CC[C@H]21)C[C@@]1(CCCc2cc(Cl)ccc21)CO3]
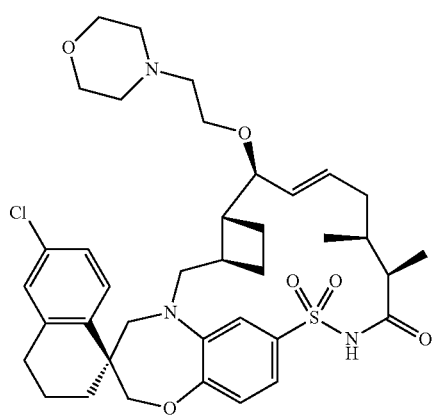 [SMILES: C[C@H]1C/C=C/[C@H](OCCN2CCOCC2)[C@@H]2CC[C@H]2CN2C[C@@]3(CCCc4cc(Cl)ccc43)COc3ccc(cc32)S(=O)(=O)NC(=O)[C@@H]1C]

TABLE B-continued
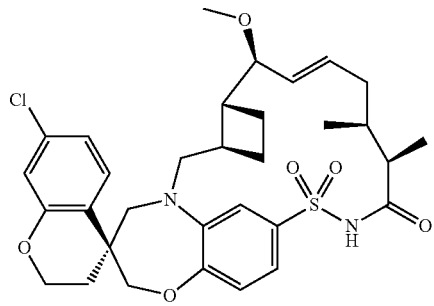 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCOc2cc(Cl)ccc21)CO3]
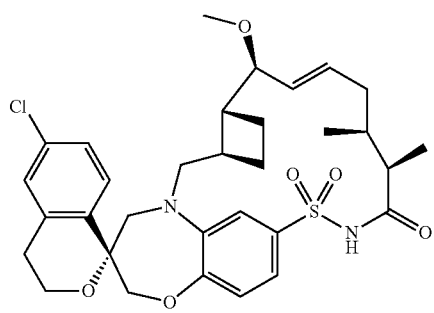 [SMILES: CO[C@H]1/C=C/C[C@H](C)[C@@H](C)C(=O)NS(=O)(=O)c2ccc3c(c2)N(C[C@@H]2CC[C@H]21)C[C@]1(CO3)OCCc2cc(Cl)ccc21]
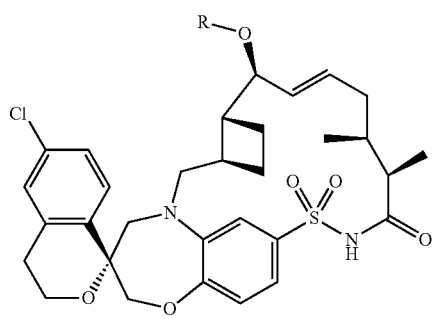
R = H or C$_1$-C$_6$alkyl
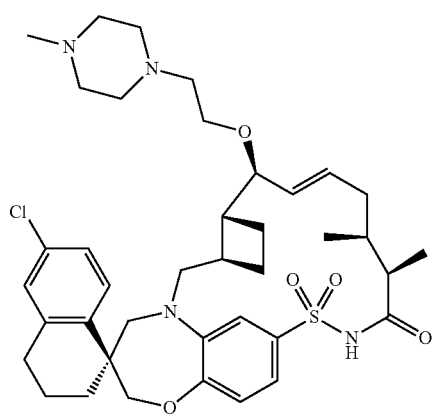 [SMILES: C[C@H]1C/C=C/[C@H](OCCN2CCN(C)CC2)[C@@H]2CC[C@H]2CN2C[C@@]3(CCCc4cc(Cl)ccc43)COc3ccc(cc32)S(=O)(=O)NC(=O)[C@@H]1C]

TABLE B-continued
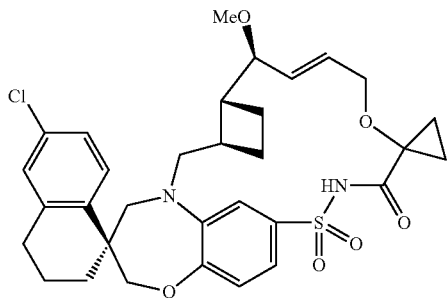 [SMILES: CO[C@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]
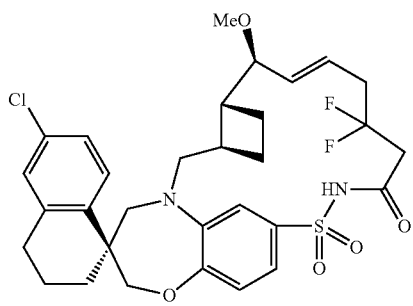 [SMILES: CO[C@H]1/C=C/CC(F)(F)CC(=O)NS(=O)(=O)c2ccc3c(c2)N(C[C@@H]2CC[C@H]21)C[C@@]1(CCCc2cc(Cl)ccc21)CO3]
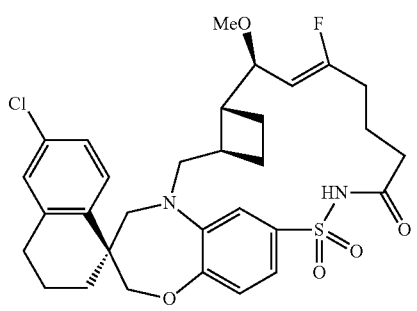 [SMILES: CO[C@H]1/C=C(\F)CCCC(=O)NS(=O)(=O)c2ccc3c(c2)N(C[C@@H]2CC[C@H]21)C[C@@]1(CCCc2cc(Cl)ccc21)CO3]
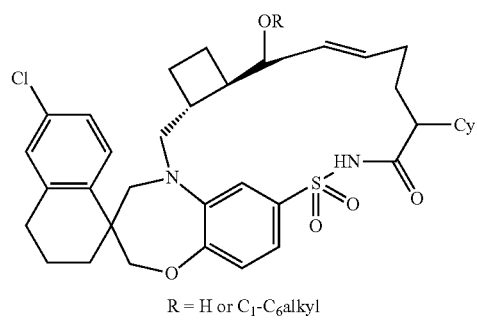
R = H or C$_1$-C$_6$alkyl
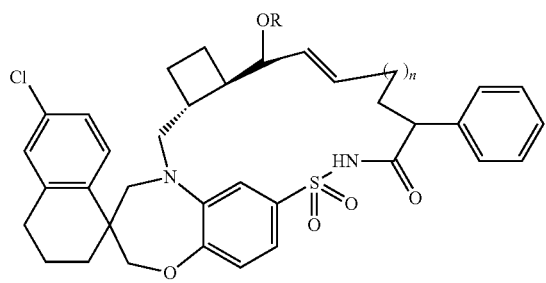
R = H or C$_1$-C$_6$alkyl
n = 0-3

TABLE C
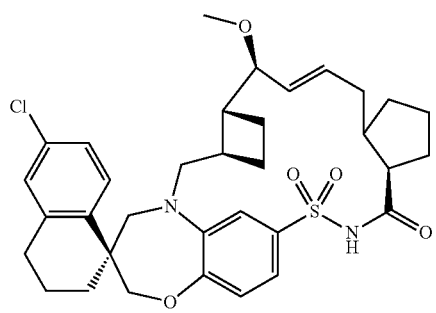
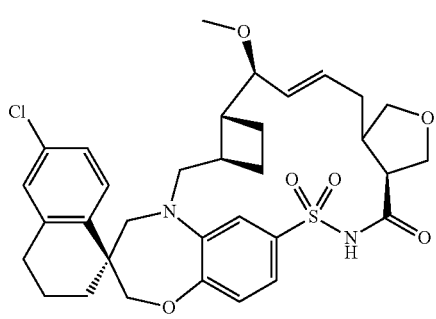 [SMILES: CO[C@H]1/C=C/CC2COC[C@H]2C(=O)NS(=O)(=O)c2ccc3c(c2)N(C[C@@H]2CC[C@H]21)C[C@@]1(CCCc2cc(Cl)ccc21)CO3]
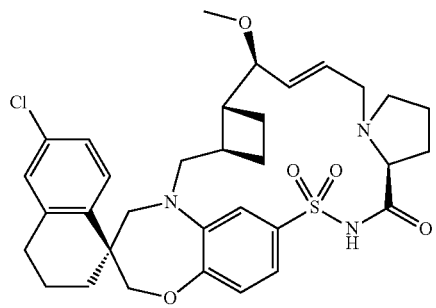 [SMILES: CO[C@H]1/C=C/CN2CCC[C@H]2C(=O)NS(=O)(=O)c2ccc3c(c2)N(C[C@@H]2CC[C@H]21)C[C@@]1(CCCc2cc(Cl)ccc21)CO3]
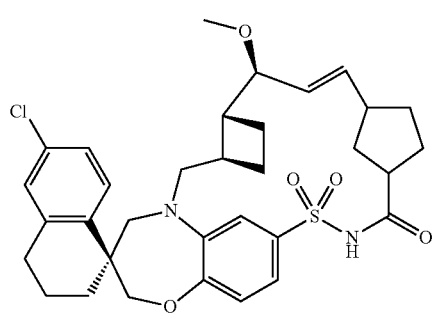 [SMILES: CO[C@H]1/C=C/C2CCC(C2)C(=O)NS(=O)(=O)c2ccc3c(c2)N(C[C@@H]2CC[C@H]21)C[C@@]1(CCCc2cc(Cl)ccc21)CO3]
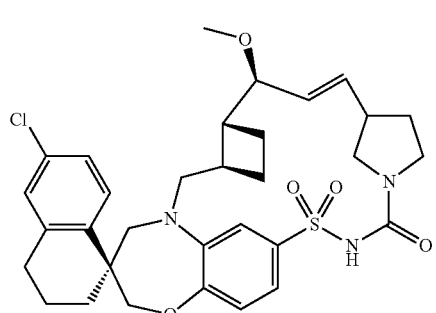
TABLE C-continued
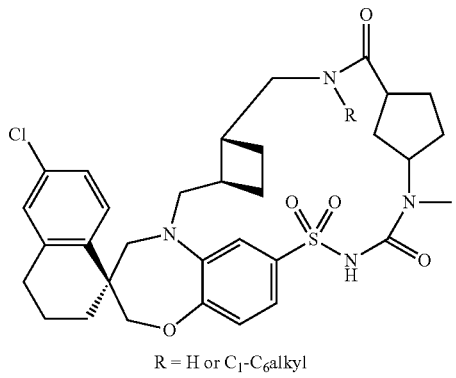
R = H or C$_1$-C$_6$alkyl
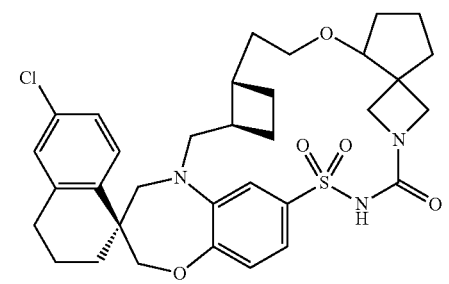 [SMILES: O=C1NS(=O)(=O)c2ccc3c(c2)N(C[C@@H]2CC[C@H]2CCOC2CCCC24CN1C4)C[C@@]1(CCCc2cc(Cl)ccc21)CO3]
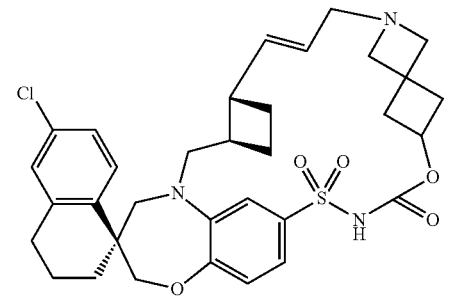 [SMILES: O=C1NS(=O)(=O)c2ccc3c(c2)N(C[C@@H]2CC[C@H]2/C=C/CN2CC4(CC(C4)O1)C2)C[C@@]1(CCCc2cc(Cl)ccc21)CO3]
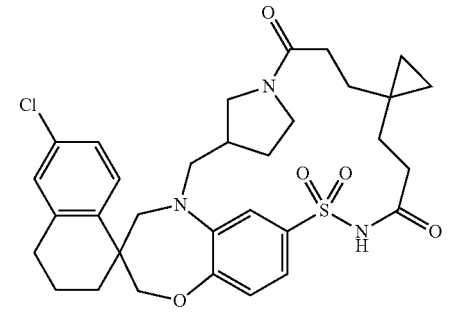 [SMILES: O=C1CCC2(CCC(=O)N3CCC(C3)CN3CC4(CCCc5cc(Cl)ccc54)COc4ccc(cc43)S(=O)(=O)N1)CC2]
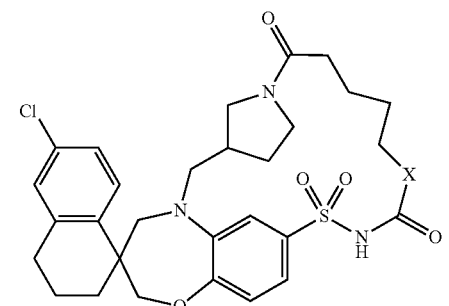
X = CH$_2$, O, NR TABLE C-continued
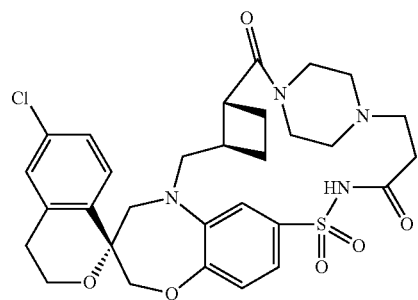 [SMILES: O=C1CCN2CCN(CC2)C(=O)[C@@H]2CC[C@H]2CN2C[C@]3(COc4ccc(cc42)S(=O)(=O)N1)OCCc1cc(Cl)ccc13]
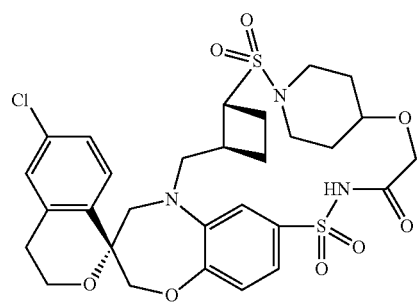 [SMILES: O=C1COC2CCN(CC2)S(=O)(=O)[C@@H]2CC[C@H]2CN2C[C@]3(COc4ccc(cc42)S(=O)(=O)N1)OCCc1cc(Cl)ccc13]
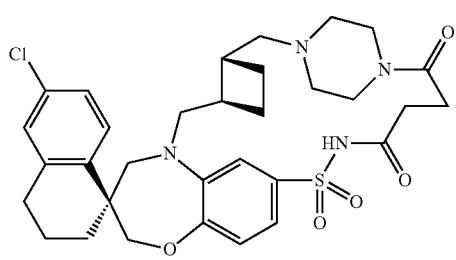 [SMILES: O=C1CCC(=O)N2CCN(CC2)C[C@@H]2CC[C@H]2CN2C[C@@]3(CCCc4cc(Cl)ccc43)COc3ccc(cc32)S(=O)(=O)N1]
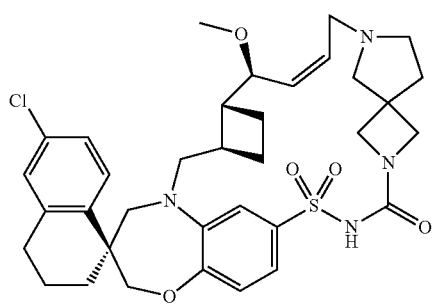 [SMILES: CO[C@H]1/C=C\CN2CCC3(C2)CN(C3)C(=O)NS(=O)(=O)c2ccc3c(c2)N(C[C@@H]2CC[C@H]21)C[C@@]1(CCCc2cc(Cl)ccc21)CO3]
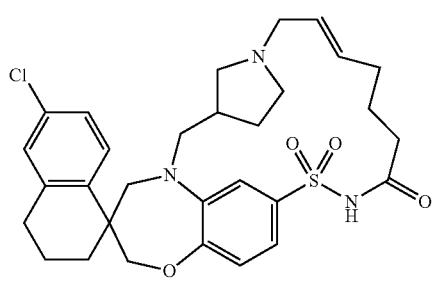 [SMILES: O=C1CCC/C=C/CN2CCC(C2)CN2CC3(CCCc4cc(Cl)ccc43)COc3ccc(cc32)S(=O)(=O)N1]
TABLE C-continued
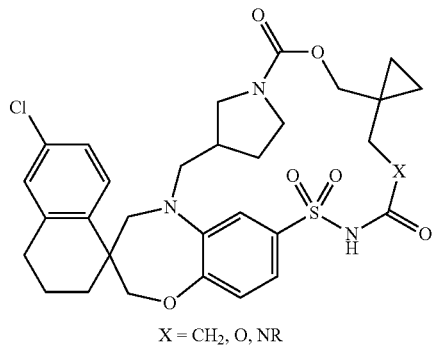
X = CH$_2$, O, NR
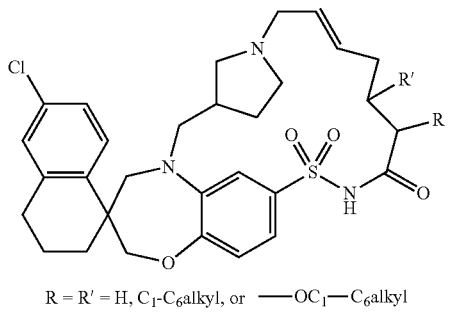
R = R' = H, C$_1$-C$_6$alkyl, or —OC$_1$—C$_6$alkyl
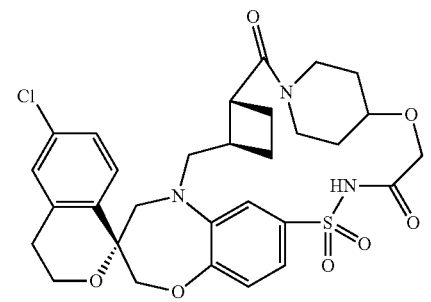 [SMILES: O=C1COC2CCN(CC2)C(=O)[C@@H]2CC[C@H]2CN2C[C@]3(COc4ccc(cc42)S(=O)(=O)N1)OCCc1cc(Cl)ccc13]
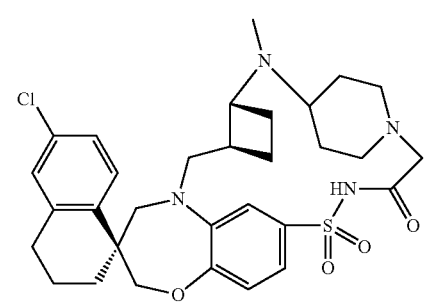 [SMILES: CN1C2CCN(CC2)CC(=O)NS(=O)(=O)c2ccc3c(c2)N(C[C@@H]2CC[C@H]21)C[C@@]1(CCCc2cc(Cl)ccc21)CO3]
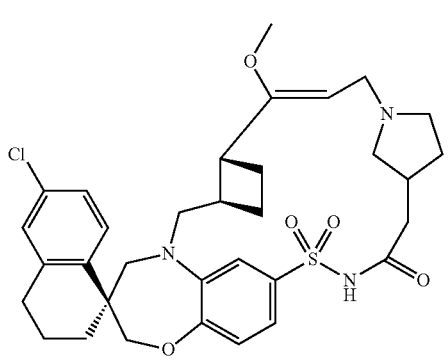 [SMILES: CO/C1=C\CN2CCC(CC(=O)NS(=O)(=O)c3ccc4c(c3)N(C[C@@H]3CC[C@@H]13)C[C@@]1(CCCc3cc(Cl)ccc31)CO4)C2]

TABLE C-continued

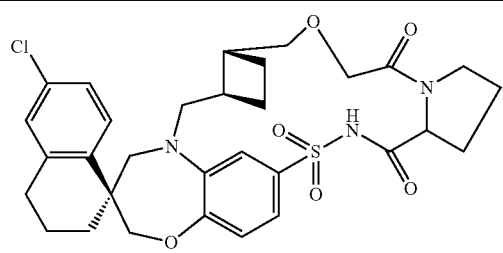

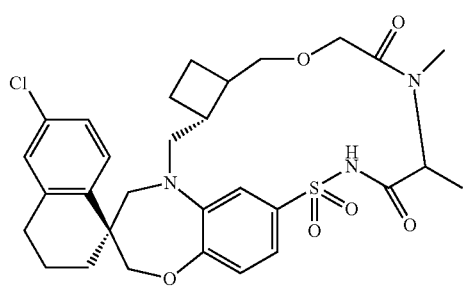 [SMILES: CC1C(=O)NS(=O)(=O)c2ccc3c(c2)N(C[C@@H]2CCC2COCC(=O)N1C)C[C@@]1(CCCc2cc(Cl)ccc21)CO3]

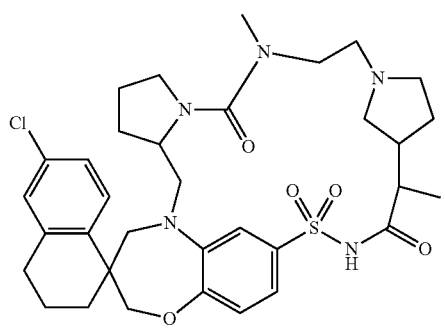 [SMILES: CC1C(=O)NS(=O)(=O)c2ccc3c(c2)N(CC2CCCN2C(=O)N(C)CCN2CCC1C2)CC1(CCCc2cc(Cl)ccc21)CO3]

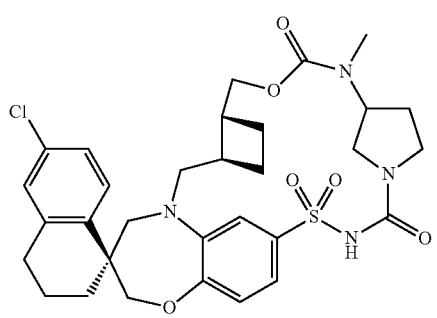 [SMILES: CN1C(=O)OC[C@@H]2CC[C@H]2CN2C[C@@]3(CCCc4cc(Cl)ccc43)COc3ccc(cc32)S(=O)(=O)NC(=O)N2CCC1C2]

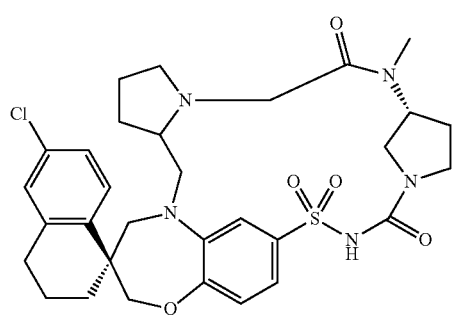 [SMILES: CN1C(=O)CN2CCCC2CN2C[C@@]3(CCCc4cc(Cl)ccc43)COc3ccc(cc32)S(=O)(=O)NC(=O)N2CC[C@@H]1C2]

TABLE C-continued

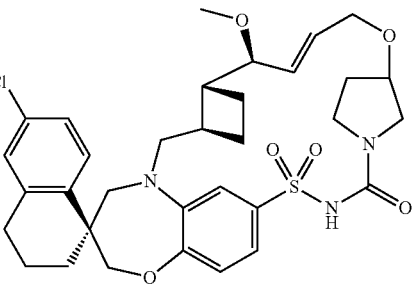

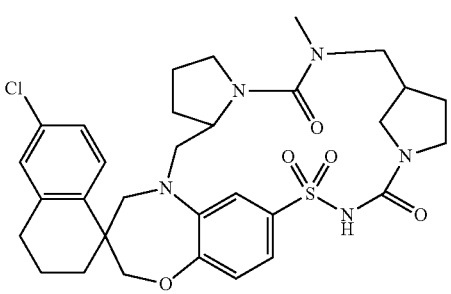 [SMILES: CN1CC2CCN(C2)C(=O)NS(=O)(=O)c2ccc3c(c2)N(CC2CCCN2C1=O)CC1(CCCc2cc(Cl)ccc21)CO3]

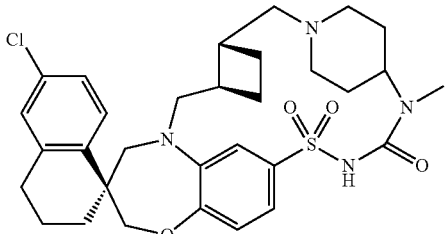

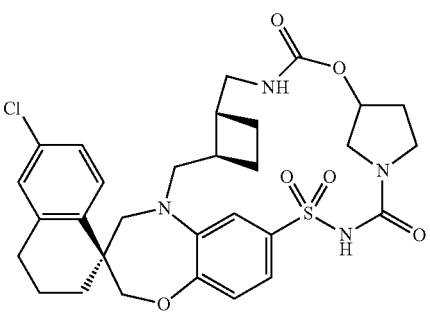 [SMILES: O=C1NC[C@@H]2CC[C@H]2CN2C[C@@]3(CCCc4cc(Cl)ccc43)COc3ccc(cc32)S(=O)(=O)NC(=O)N2CCC(C2)O1]

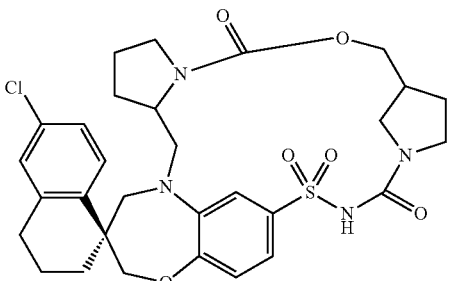

Compounds of the disclosure also include, for example, the compounds described as Examples below.

Synthesis

Compounds of the invention can be prepared according to numerous preparatory routes known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Example synthetic methods for preparing compounds of the invention are provided in the Schemes below.

A series of 1,3-diol derivatives of formula 4 (n=0, 1, 2) can be prepared by the methods outlined in Scheme 1. Johnson-Corey-Chaykovsky reaction of the substituted ketone 1 with sulfur ylide can form the corresponding epoxide 2 which can be converted to the aldehyde 3 under Lewis acid (e.g., boron trifluoride diethyl etherate or $TiCl_4$). The aldehyde 3 can be transformed to the 1,3-diol derivative 4 by treatment with formaldehyde under basic conditions (e.g., KOH).

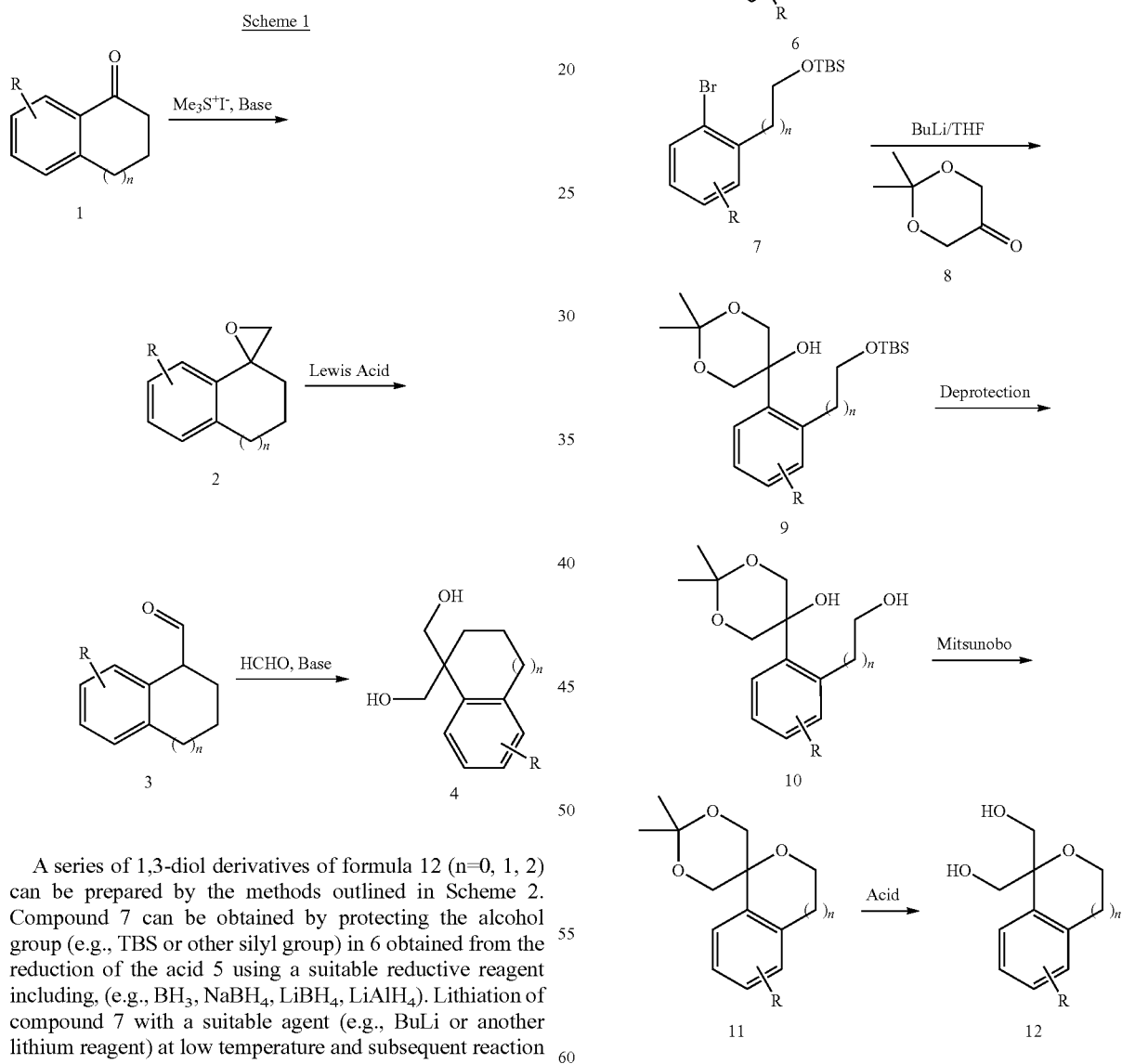

A series of 1,3-diol derivatives of formula 12 (n=0, 1, 2) can be prepared by the methods outlined in Scheme 2. Compound 7 can be obtained by protecting the alcohol group (e.g., TBS or other silyl group) in 6 obtained from the reduction of the acid 5 using a suitable reductive reagent including, (e.g., $BH_3$, $NaBH_4$, $LiBH_4$, $LiAlH_4$). Lithiation of compound 7 with a suitable agent (e.g., BuLi or another lithium reagent) at low temperature and subsequent reaction of the intermediate with the ketone 8 can afford the alcohol derivative 9. Removal of the protecting group (e.g., TBAF removal of TBS group) followed by intra-molecular Mitsunobo reaction (e.g., DEAD and triphenylphospine) can yield the cyclic ether 11. Removal of the protecting group by treatment of 11 with acid (e.g. pTSA or HCl) can provide the 1,3-diol derivative 12.

A series of spiro-sulfonamide derivatives of formula 22 (X=$CH_2$, O; n=0, 1, 2) can be prepared by the methods outlined in Scheme 3. Mono-protection of the hydroxyl group 13 can be achieved by reaction of 4 or 12 with substituted benzoyl chloride in the presence of a base (e.g., TEA, DIEA, or NaOH). Oxidation of the hydroxyl group of 13 using a suitable oxidant (e.g., Dess-Martin or Swern oxidation conditions) can afford the corresponding aldehyde 14 which can be transformed into compound 15 by reaction with trimethyl orthoformate in the presence of p-toluenesulfonic acid (p-TsOH). Reaction of compound 15 with 4-fluoro-3-nitrobenzenesulfonamide 16 in the presence of base (e.g., potassium tert-butoxide, sodium tert-butoxide, LiHMDS or NaLiHMDS) can afford the corresponding compound 17. De-protection of the acetal group in 17 to the aldehyde 18 can be achieved under acid conditions (e.g., Amberlyst, p-TsOH, HCl in dioxane or TFA). Reduction of the nitro group in 18 using a suitable reducing agent (e.g., iron in acetic acid, iron and $NH_4Cl$ in ethanol) can yield the imine intermediate 19 which can be further reduced to the amine derivative 20 by using suitable reductive reagent (e.g., $NaBH_4$ or $NaBH(OAc)_3$). Alternatively, the amine derivative 20 can be obtained by direct hydrogenation of the nitro compound 18 in the presence of a palladium catalyst (e.g., Pd/C or $Pd(OH)_2$/C in an appropriate solvent such as methanol or ethanol). Reductive amination of the amine derivative 20 can afford the corresponding derivative 21 which can be transformed into the desired product 22 by reaction with the suitable acid using standard amide coupling conditions (e.g., EDCI, CDI, BOP, HATU or HBTU in the presence of a suitable base, TEA or DIEA).

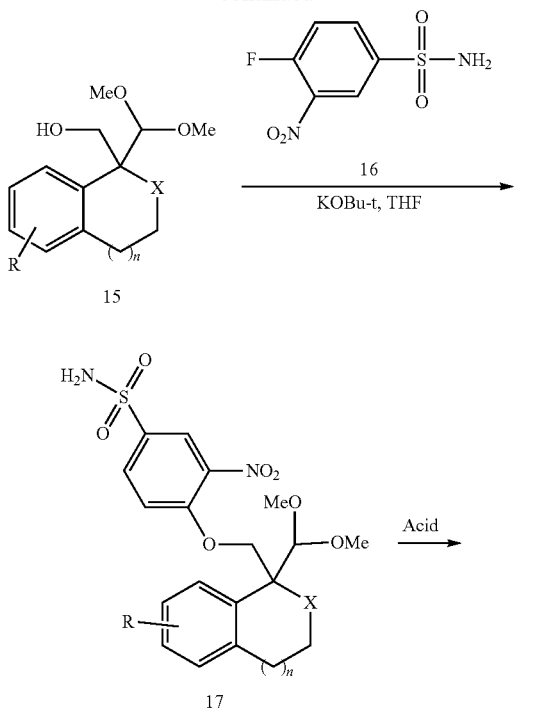

175

-continued

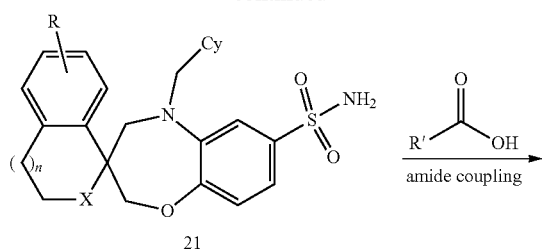

21

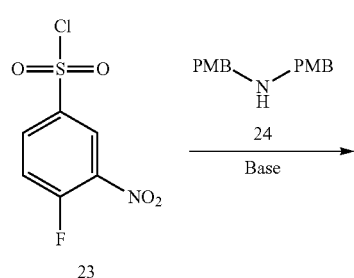

22

Alternatively, a series of sulfonamide derivatives of formula 21 (X=CH$_2$, O; n=0, 1, 2) can be prepared by the methods outlined in Scheme 4. Reaction of the sulfonyl chloride 23 with bis-(4-mothoxybenzyl)-amine (PMB)$_2$NH 24 can form the corresponding sulfonamide 25 which can be transformed into the derivative 30 in a similar manner as described for compound 15 to compound 21 in the scheme 3. The removal of the PMB protecting groups in 30 to afford the sulfonamide derivative 21 can be achieved by using acid (e.g., TFA in DCM) or hydrogenation conditions (e.g., palladium catalyzed hydrogenation Pd/C with H$_2$).

Scheme 4

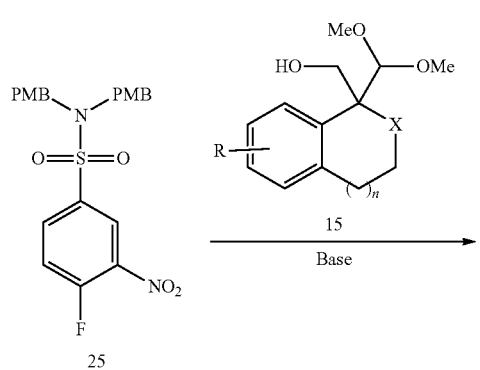

176

-continued

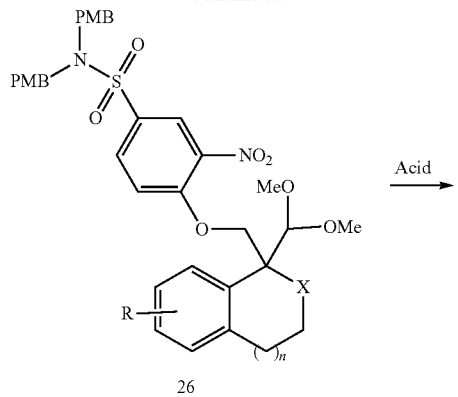

26

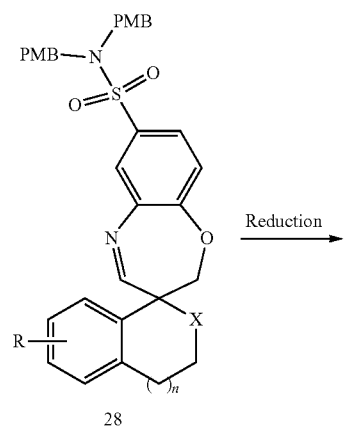

27

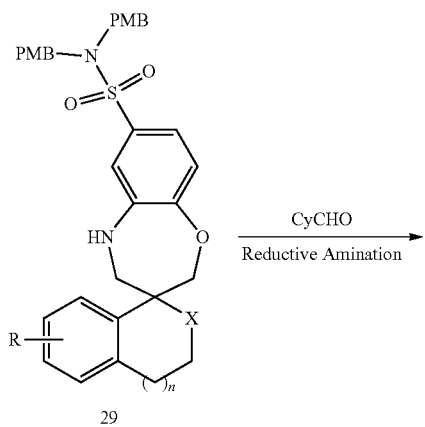

28

29

-continued

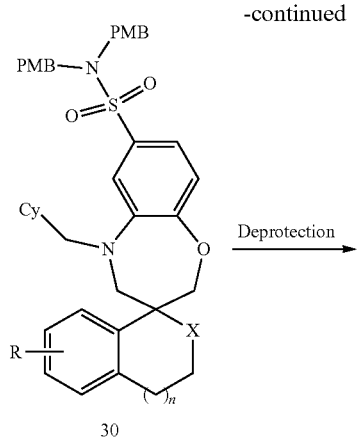 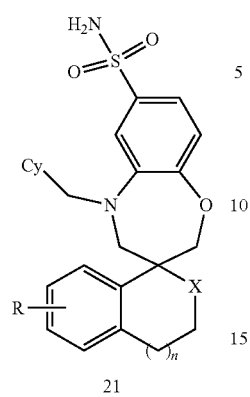

30          21

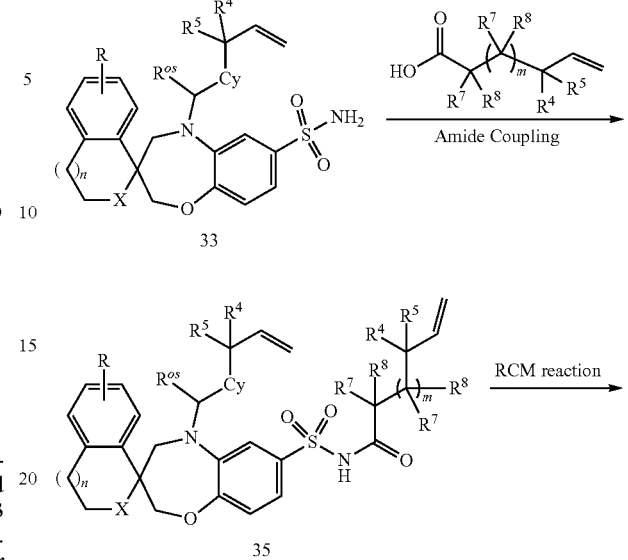

33

35

A series of macro-cyclic sulfonamide derivatives of formula 36 (X=CH$_2$, O; n=0, 1, 2; m=0, 1, 2) can be prepared by the methods outlined in Scheme 5. The sulfonamide 33 can be obtained by the removal of the protecting groups (e.g. PMB) in 32 under acid conditions (e.g. TFA, HCl) or hydrogenation conditions (e.g., palladium catalyzed hydrogenation Pd/C with H$_2$) following the reductive amination of the sulfonamide 29 with the appropriate aldehyde or ketone 31 (R$^{os}$=optional substituent) under suitable conditions (e.g. imine formation followed by treatment with a suitable reducing agent, such as NaBH$_3$(CN) or NaBH(OAc)$_3$). The amide coupling of the sulfonamide 33 with the suitable acid 34 using a coupling agent (e.g. EDC, DCC, or HATU) in the presence of a suitable base (e.g. TEA or DIEA) can yield the macrocyclic precursor 35 which can be then be converted to the corresponding macrocyclic-sulfonamide derivative 36 using a suitable ring closing metathesis (RCM) catalyst (e.g. Grubbs catalyst, Grubbs-II catalyst, Grubbs-III catalyst, Hoveyda-Grubbs catalyst or Zhan catalyst 1B) under standard reaction conditions.

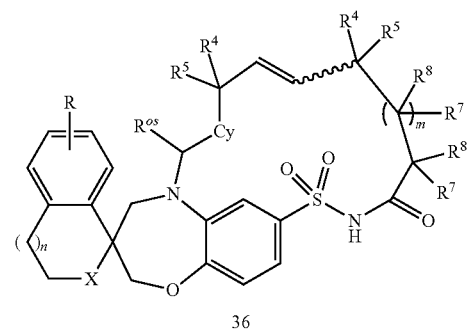

36

Similarly, a series of macrocyclic sulfonamide derivatives of formula 39 (X=CH$_2$, O; n=0, 1, 2; m=0, 1, 2) can be prepared by the methods outlined in Scheme 6. The amide coupling of the sulfonamide 33 with the appropriate acid 37 using a coupling agent (e.g. EDC, DCC, or HATU) in the presence of a suitable base (e.g. TEA or DIEA) can provide the sulfonamide derivative 38 which can be then converted to the corresponding macrocyclic sulfonamide derivative 39 in the presence of an RCM catalyst as described in Scheme 4.

Scheme 5

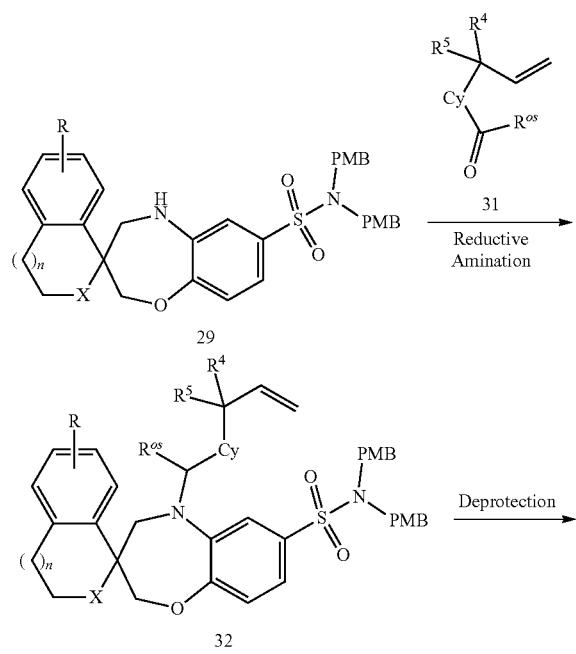

Scheme 6

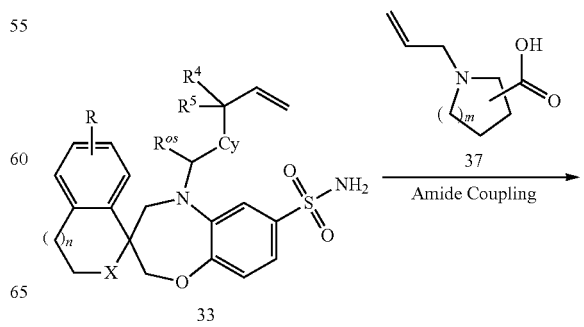

-continued

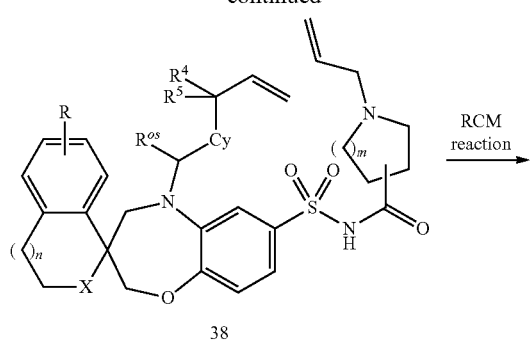

38

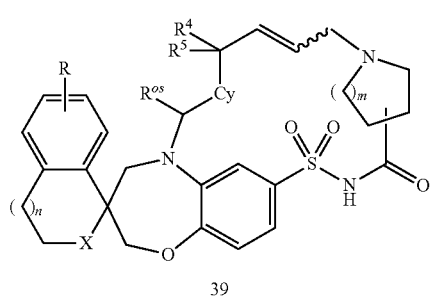

39

A series of macrocyclic sulfonyl carbamate derivatives of formula 42 (X=CH₂, O; n=0, 1, 2; m=0, 1, 2) can be prepared similar methods outlined in Scheme 7. The sulfonamide 33 can react with the appropriate chloroformate derivative 40 in the presence of a suitable base (e.g. DIEA, TEA, or NaOH) to produce the corresponding sulfonyl carbamate 41 which can be transformed into the desired macrocycle of formula 42 in the presence of an RCM catalyst as described in Scheme 4.

Scheme 7

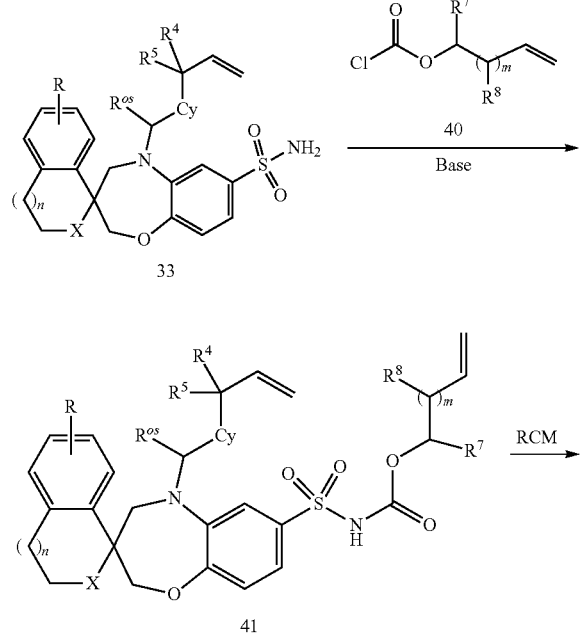

-continued

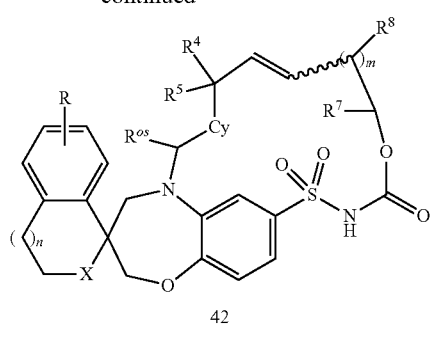

42

Alternatively, the macrocyclic sulfonamide derivatives of formula 36 (X=CH₂, O; n=0, 1, 2; m=0, 1, 2) can be prepared by the methods outlined in Scheme 8. Intermolecular olefin metathesis reaction of compound 33 with the vinyl derivative 43 in the presence of suitable olefin metathesis catalyst, (e.g., Grubbs catalyst, Grubbs-II catalyst, Grubbs-III catalyst, Hoveyda-Grubbs catalyst or Zhan catalyst 1B under suitable reaction conditions) can provide the corresponding olefin compound 44 which can be then hydrolyzed under basic conditions (e.g., LiOH or NaOH) to provide the corresponding acid 45. Intra-molecular amide formation of 45 can afford compound 36 using a suitable amide coupling reagent (e.g., EDCI, CDI, BOP, HATU, or HBTU) and base (e.g., DMAP, Et₃N, or Hunig's base).

Scheme 8

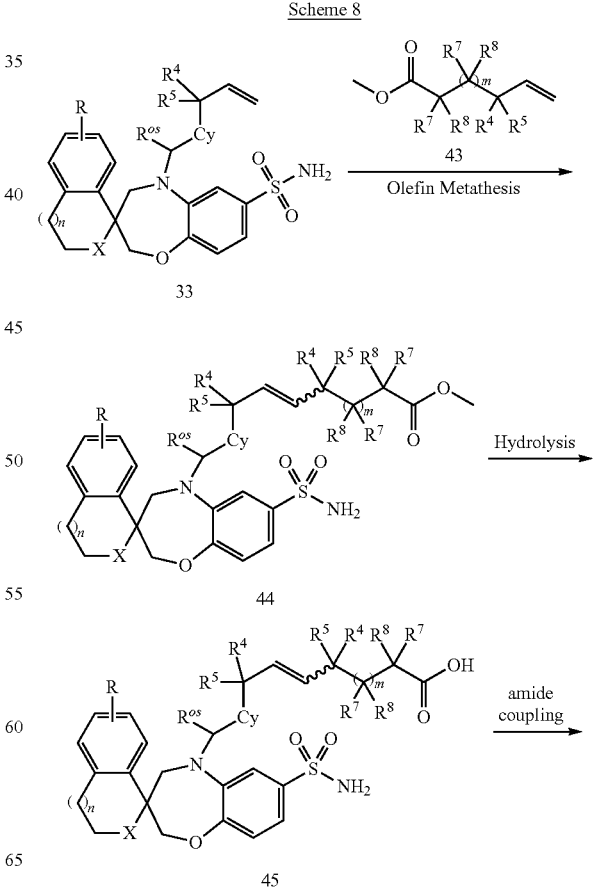

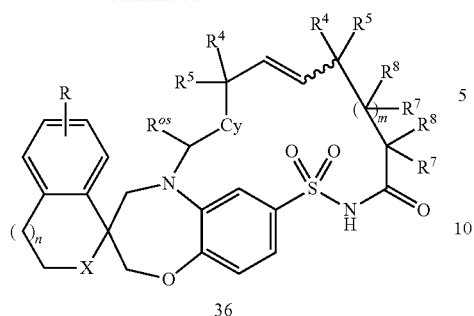

36

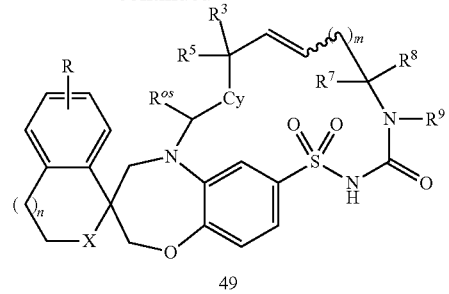

49

In a similar manner, a series of macrocyclic sulfonyl urea derivatives of formula 49 (X=CH$_2$, O; n=0, 1, 2; m=0, 1, 2) can be prepared by the methods outlined in Scheme 9. Grubbs metathesis reaction of compound 33 with the vinyl derivative 46 can provide the corresponding olefin compound 47. Removal the protecting Boc-group in 47 by using acid (e.g., TFA in DCM, HCl in dioxane) can afford the corresponding amine 48. Treatment of 48 with a suitable reagent such as CDI, phosgene or triphosgene and a base (e.g., DMAP, Et$_3$N, or Hunig's base) can provide the macrocyclic sulfonyl urea derivative 49.

Alternatively, a series of macro-cyclic sulfonyl urea derivatives of formula 49 (X=CH$_2$, O; n=0, 1, 2; m=0, 1, 2) can be prepared by the methods outlined in Scheme 10. The sulfonyl urea derivatives 49 can be obtained by treatment of the sulfonamide 33 with diphenyl carbonate or 4-nitrophenyl chloroformate in the presence of DMAP and triethylamine or Hunig's base, follow by the addition of the appropriate amine 50. Alternatively, treatment of the amine 50 with phosgene, or triphosgene to form the corresponding carbamoyl chloride which can react with the sulfonamide 33 to afford the sulfonyl urea derivatives 51. RCM reaction of 51 using methods described above can afford macrocycles of formula 49.

Scheme 9

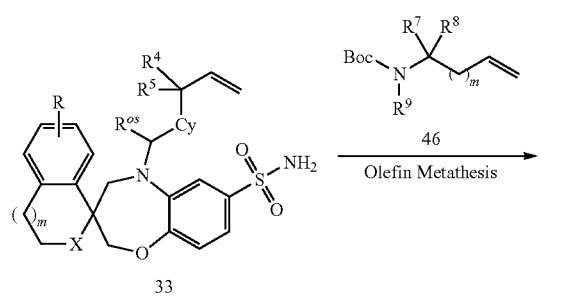

Scheme 10

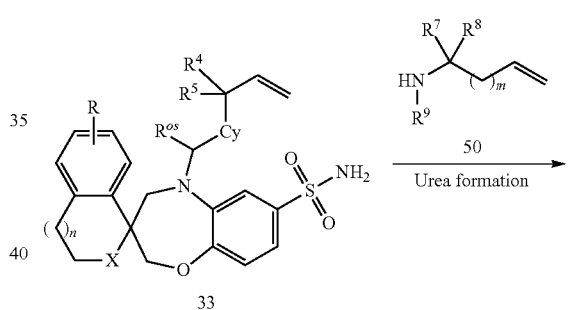

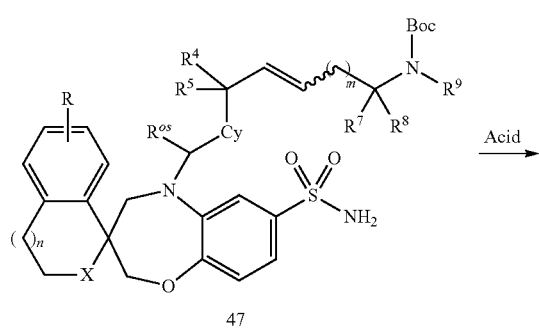

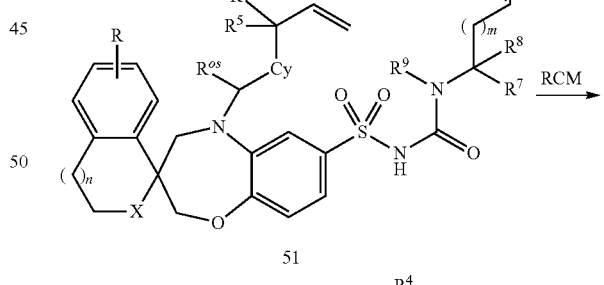

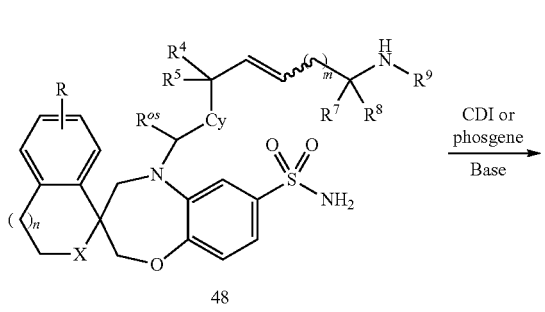

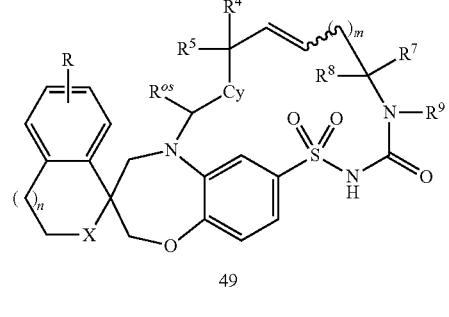

A series of macrocyclic sulfonamide derivatives of formula 59 (X=CH$_2$, O; n=0, 1, 2) can be prepared by the methods outlined in Scheme 10. The alcohol derivative 54 can be obtained by hydrolysis of the acetate ester 53 which can be produced by the reductive amination of 29 with the aldehyde 52. Mitsunobo reaction (e.g., DEAD and triphenylphospine) of compound 54 with ester 55 (R$^{os}$=optional substituent) can yield the ether derivative 56. Removal of the PMB groups in 56 under acid conditions (e.g. TFA, HCl) or hydrogenation conditions (e.g., palladium catalyzed hydrogenation Pd/C with H$_2$) can give 57, and hydrolysis of the ester group in 57 under basic conditions (e.g., LiOH or NaOH in water/THF) can afford the sulfonamide-acid derivative 58. Intra-molecular amide formation of 58 can form the macro-cyclic sulfonamide derivative 59 by methods provided above.

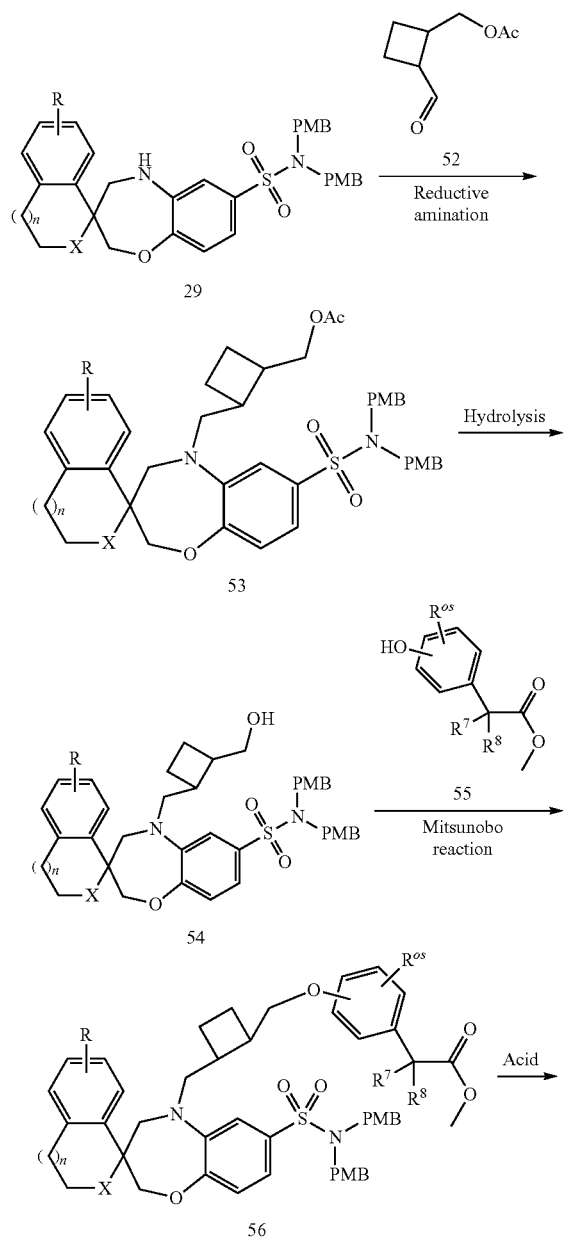

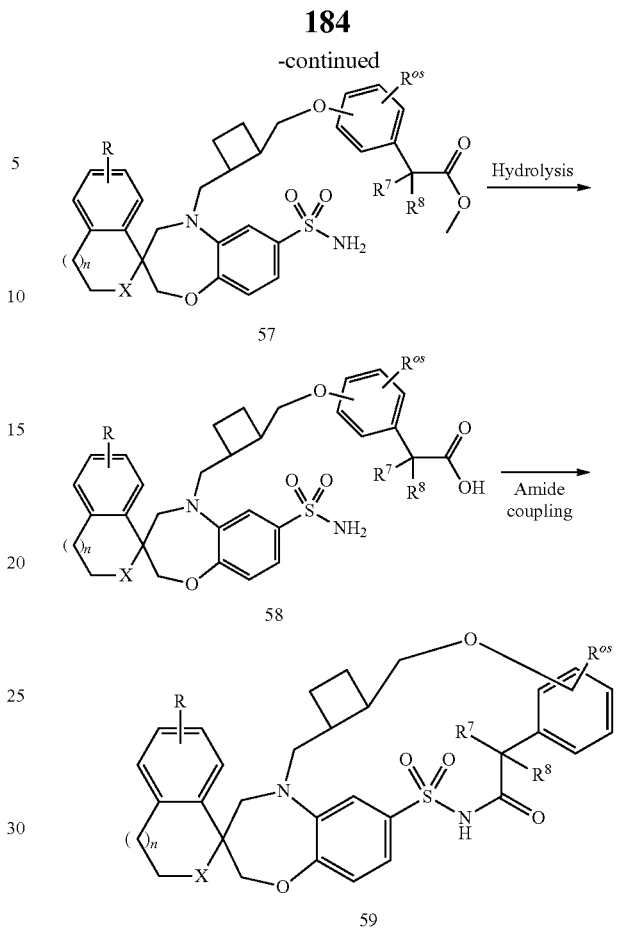

A series of spiro-cyclic sulfonamide derivatives of formula 60 can be prepared by the methods outlined in Scheme 12. Alkylation of phenol compound 61 with a bromide 62 can give the corresponding ether 63 in the presence of a base (e.g., NaH or NaOH) which can react with diethyl malonate 64 or other dialkyl malonate in the presence of a suitable palladium catalyst (e.g., Pd(PtButyl)$_3$ or other Pd catalyst) to afford the malonate derivative 65. 1,3-diol derivative 67 can be obtained by reduction (e.g., DIBAL, LAH, or NaBH$_4$) of the diethyl ester 66 provided by treatment of the malonate derivative 65 with 4-nitrobenzenesulfonyl fluoride in the presence of a base (e.g., DBU or DIEA). Asymmetric mono-protecting of the OH-group 68 can be achieved by reaction of 67 with substituted benzoyl chloride in the presence of a suitable chiral catalyst, such as (R,R)-Kang Catalyst. Dess-Martin oxidation or Swern oxidation of the hydroxyl group of 68 can afford the corresponding aldehyde 69 which can be transformed to compound 70 by reaction with trimethyl orthoformate in the presence of acid (e.g., p-TsOH in methanol). Hydrolysis of compound 70 can yield the alcohol 71 which can be transformed into the spiro-cyclic sulfonamide derivatives 60 in a similar manner as the those described above for compound 15 to compound 20 in Scheme 3. Reaction of the alcohol 71 with 4-fluoro-3-nitrobenzenesulfonamide 25 in the presence of base (e.g., potassium tert-butoxide, sodium tert-butoxide, LiHMDS or NaLiHMDS) can afford the corresponding compound 72. De-protection of the acetal group in 72 to the aldehyde 73 can be achieved under acid conditions (e.g., Amberlyst, p-TsOH, HCl in dioxane or TFA). Reduction of the nitro group in 73 by using a suitable reducing agent (e.g., iron in acetic acid, iron or zinc and NH$_4$Cl in ethanol) followed by further reduction of the imine formed in situ with suitable reductive reagent (e.g., NaBH₄ or NaBH(OAc)) can afford the spiro-cyclic sulfonamide derivatives of formula 60.
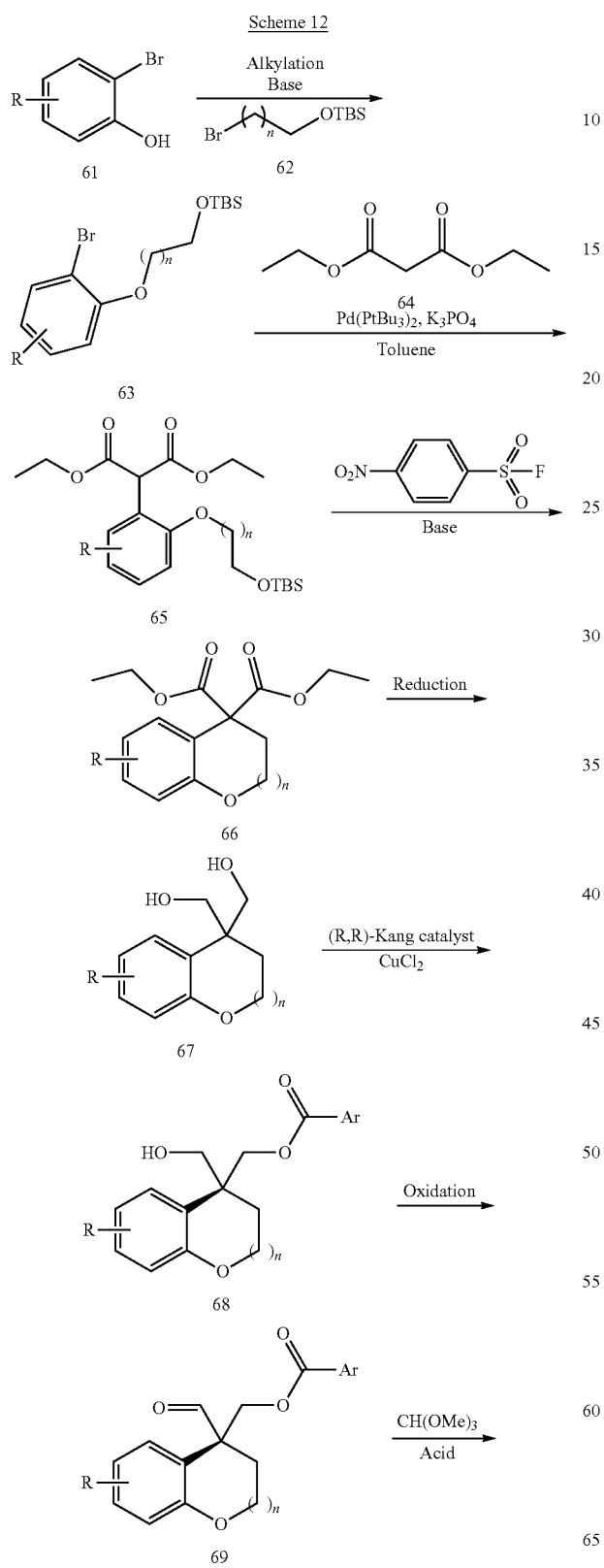
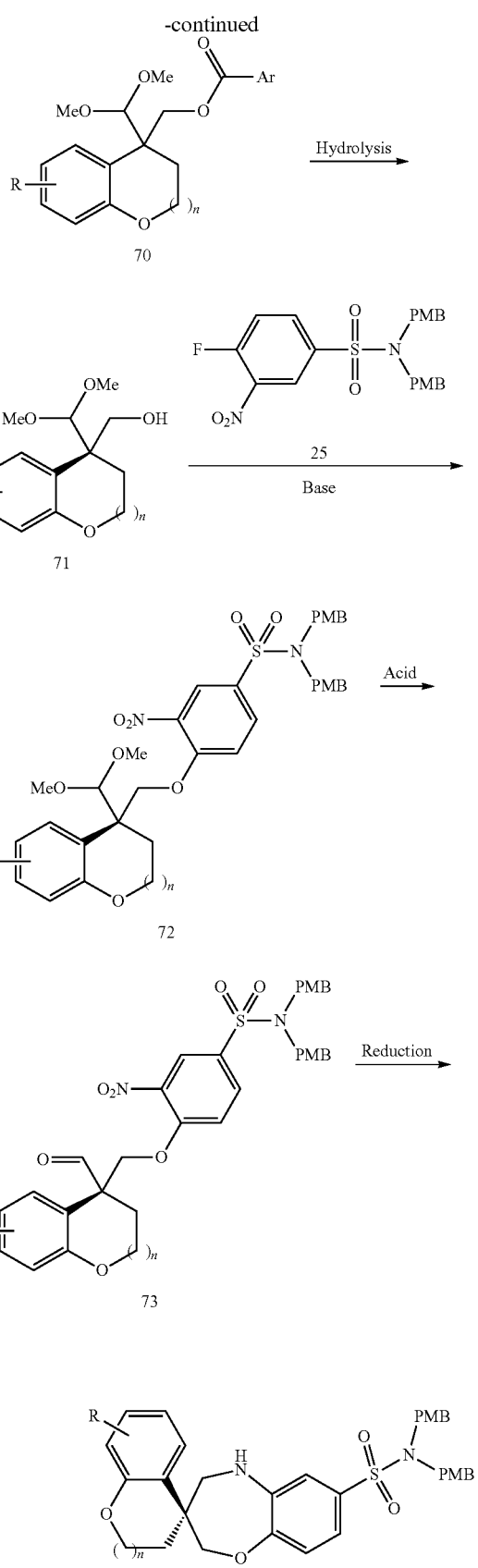

A series of allyl alcohol derivatives of formula 81 or 82 can be prepared by the methods outlined in Scheme 13. Reductive amination of the spiro-sulfonamide 74 with aldehyde 75 using reductive agent (e.g., NaBH$_4$, NaBH(OAc)$_3$, or NaBCNH$_3$) can afford the corresponding product 76 which can be transformed into the alcohol 77 under saponification conditions (e.g. acid or base). Swern oxidation or Dess-Martin oxidation of the alcohol 77 can afford the aldehyde 78. Alkylation of 78 with a suitable reagent (e.g., vinylmagnesium bromide or vinyllithium) can yield a mixture of the allyl alcohol 79 and 80. The diastereomers can be separated by chromatography (e.g., silica gel column, or preparative HPLC on a C18 column, or by SFC using a suitable column) using suitable conditions. Removal of the protecting group PMB in 79 or 80 under acid conditions (e.g., TFA in DCM or HCl in dioxane or phosphoric acid in water) can produce the 81 or 82, respectively.

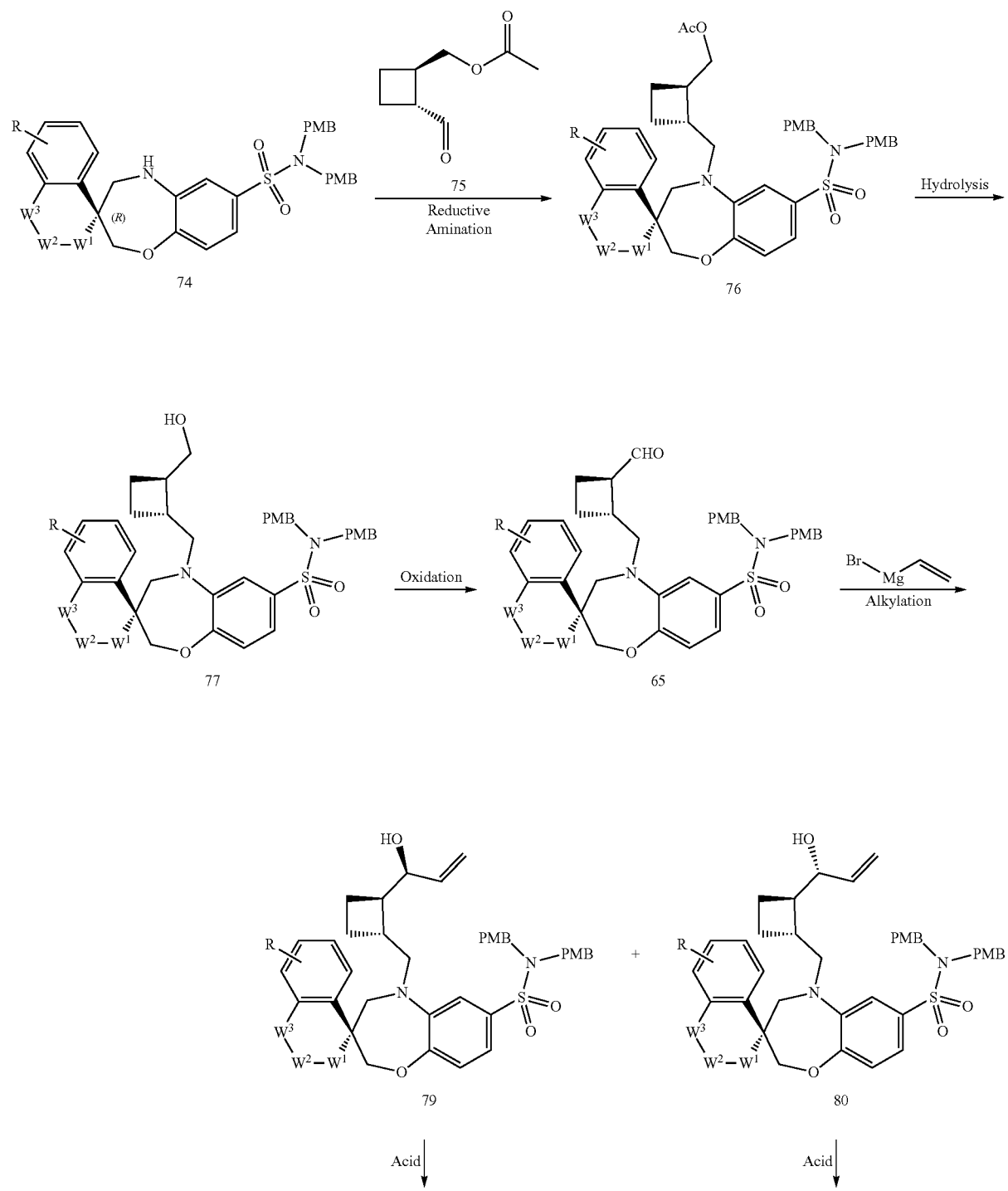

Scheme 13

-continued

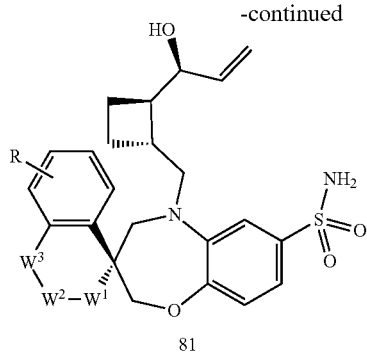

81

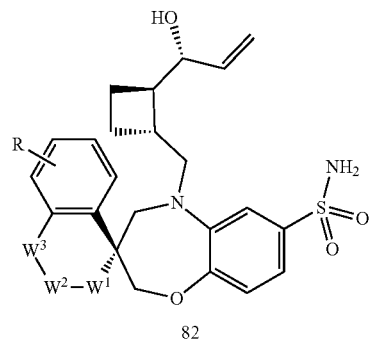

82

Alternatively, the allyl alcohol derivatives of formula 81 or 82 can be prepared by the methods outlined in Scheme 14 via reductive amination of the spiro-sulfonamide 74 with the aldehyde 85 or 86 by methods described in Scheme 13.

Oxidation of 83 or 84 under suitable conditions (e.g., Dess-Martin or Swern conditions) can afford the 85 or 86, respectively.

Scheme 14

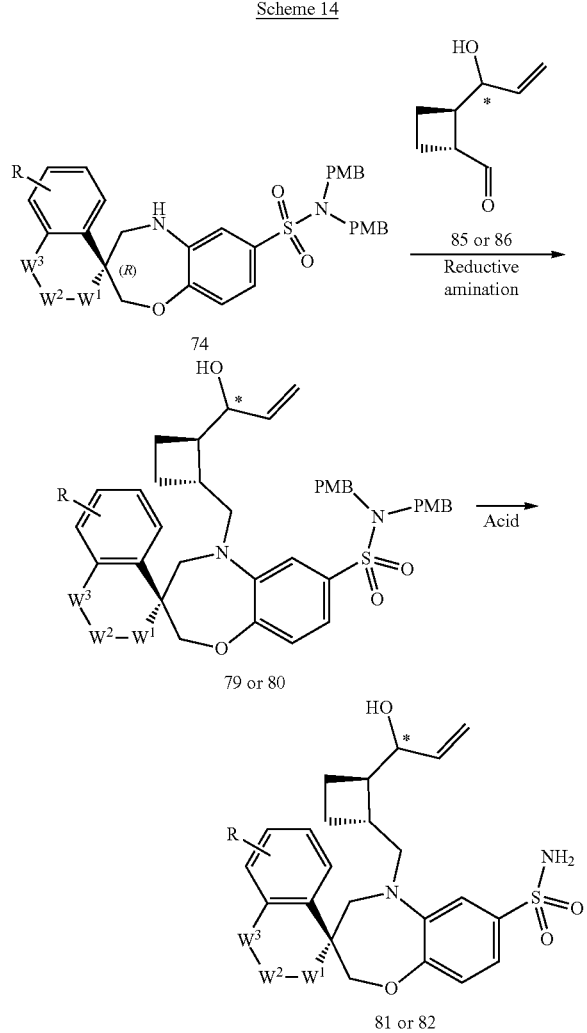

Scheme 15

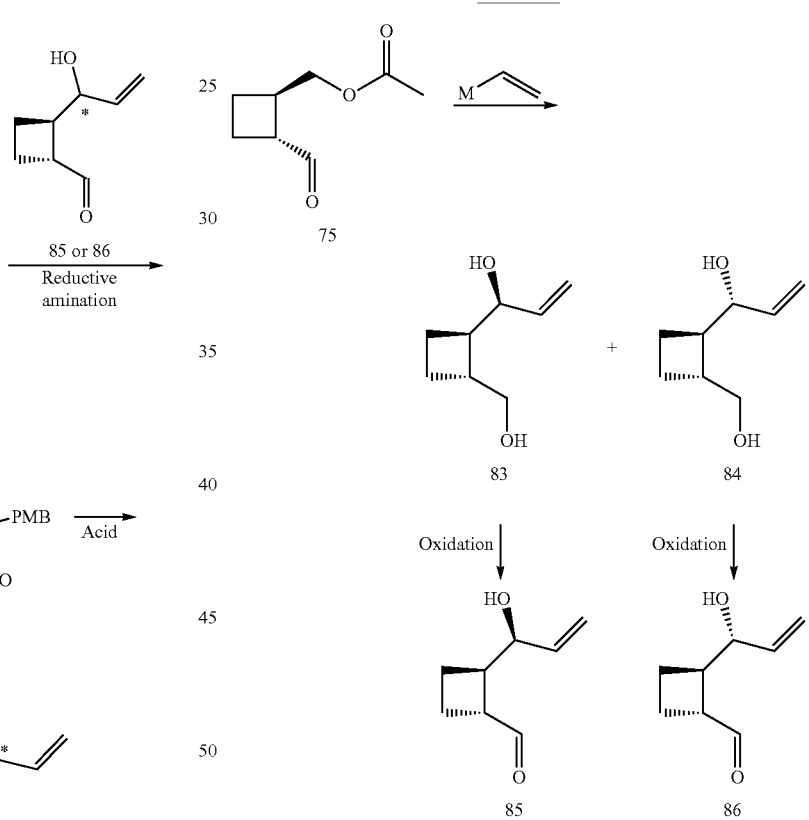

The aldehyde 85 or 86 can be prepared by the methods outlined in Scheme 15. Alkylation of 75 with a suitable agent (e.g., vinylmagnesium bromide or vinyllithium) can produce a mixture of the allyl alcohol 83 or 84 that can be separated by chromatographic methods as described above.

A series of carbamate derivatives of formula 92 can be prepared by the methods outlined in Scheme 16. Reaction of the allyl alcohol 81 or 82 with acid 87 can yield the amide 88 under amide coupling conditions (e.g., BOP, HATU, HBTU, or EDCI, and an organic base such as DMAP, Et$_3$N, or Hunig's base). Hydrolysis under basic conditions (e.g., LiOH or NaOH) of 88 can give the alcohol 89. Macrocyclic alcohol 90 can be obtained by a RCM reaction of 89 using RCM reaction conditions described above. Macrocyclic alcohol 90 can be transformed into the desired carbamate derivative 92 by reaction with a suitable dialkylcarbamoyl chloride 93, or by reaction with diphenyl carbonate or CDI followed by treatment with suitable amine R$^c$R$^d$NH.

Scheme 16

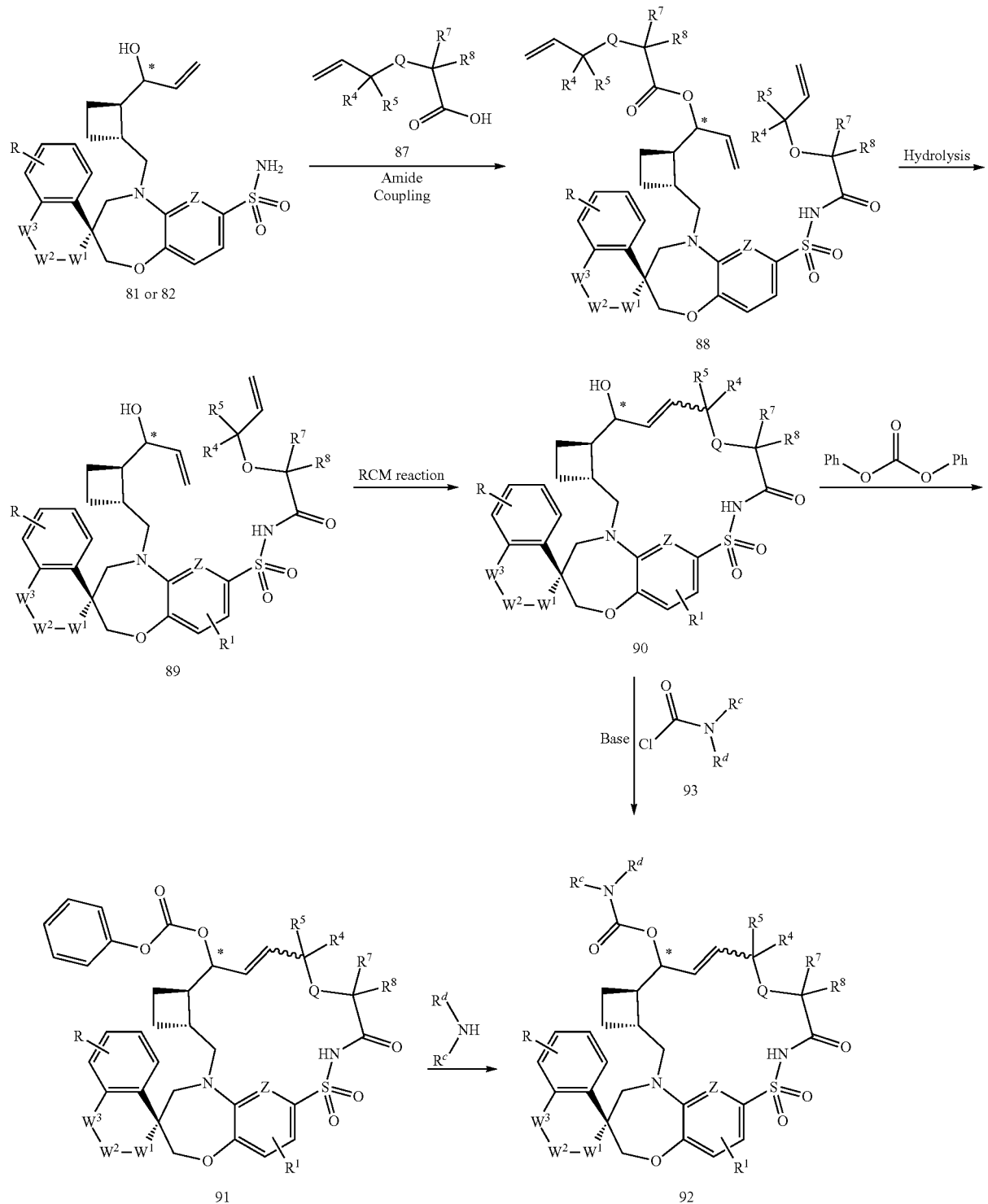

Alternative, a series of carbamate derivatives of formula 98 can be prepared by the methods outlined in Scheme 17. Reaction of the allyl alcohol 81 or 82 with 3-allyl-oxazolidine-2,5-dione 94 in the presence of a suitable base (e.g., DBU or DIEA) can afford the amide 95 which can undergo a RCM reaction to yield the corresponding macrocycles 96. Reductive amination of 96 with an aldehyde RCHO with a suitable reducing agent (e.g., $NaBH_3(CN)$ or $NaBH(OAc)_3$) can afford 97 which can be transformed into the desired carbamate derivative 98 by methods similar to those shown for conversion of 90 to 92 as described in Scheme 16.

Scheme 17

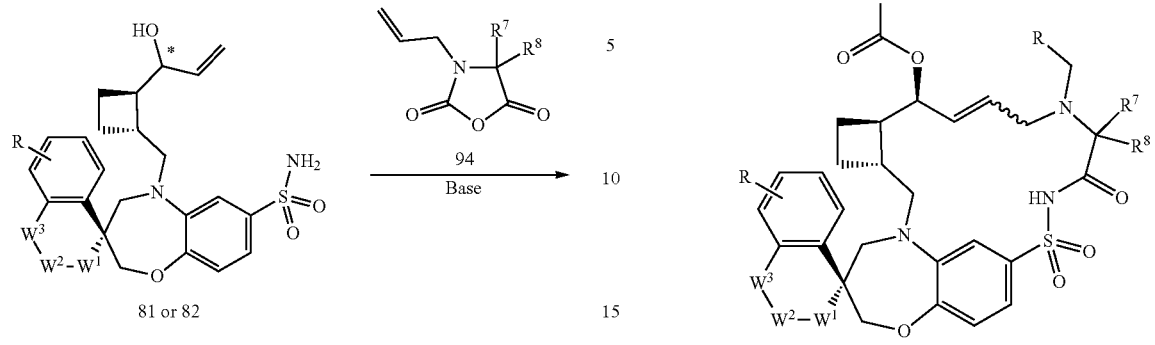

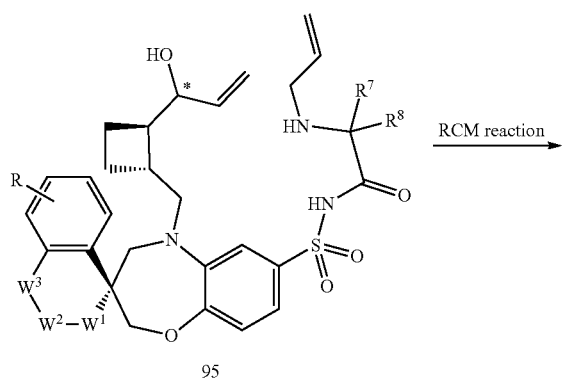

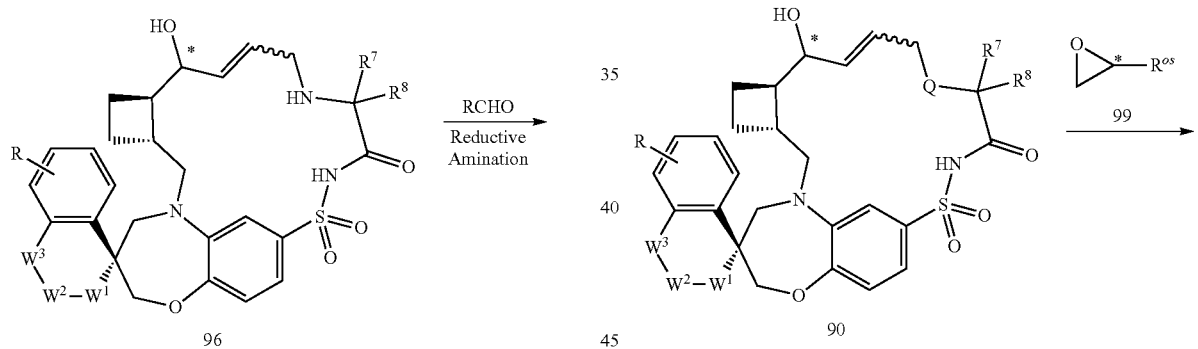

A series of 2-aminoethylene ether of formula 102 can be prepared by the methods outlined in Scheme 18. Epoxide opening of compound 99 ($R^{os}$=optional substituent) with macrocyclic alcohol 90 can give the corresponding alcohol 100 which can be transformed into the ether 102 by a two-step process of activation of the alcohol (e.g., mesylation or tosylation) to yield 101 with a leaving group (Lg) and then displacement of the Lg with an amine $R^cR^dNH$ to afford 102.

Scheme 18

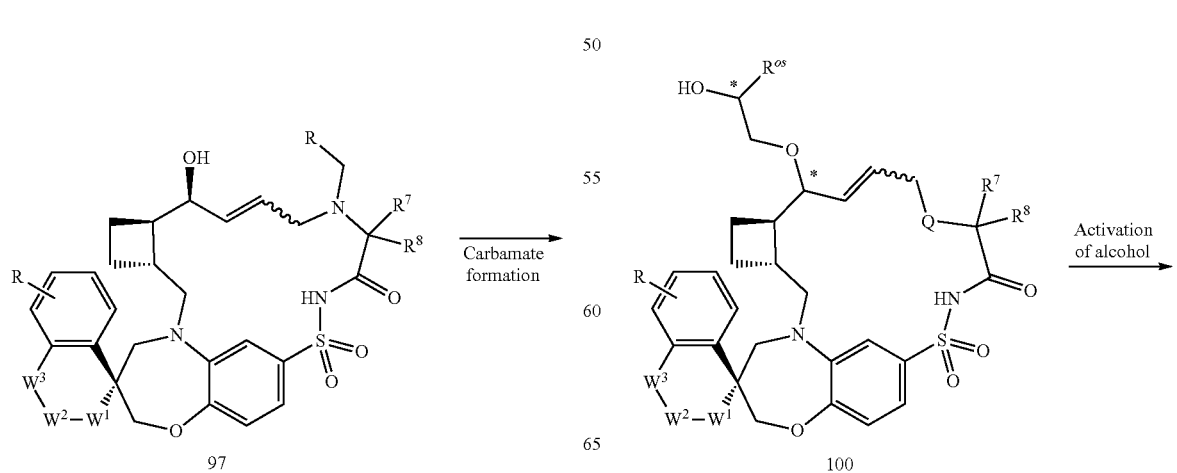

195
-continued

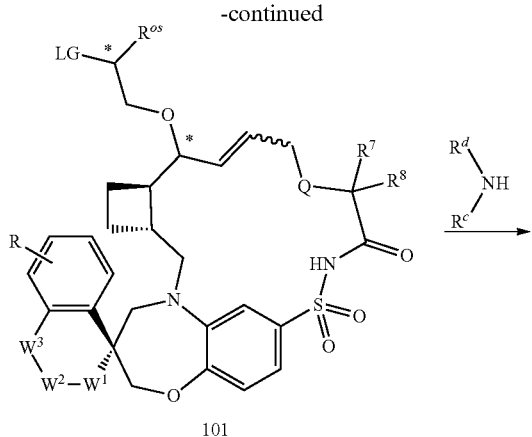
101

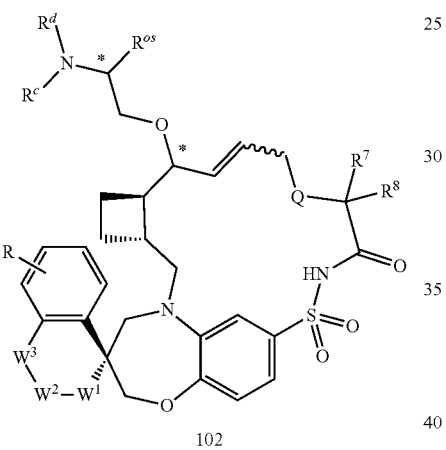
102

In a similar manner, a series of aminoalkylene ether of formula 105 can be prepared by the methods outlined in Scheme 19. Reaction of the macrocyclic alcohol 90 with bromoalkyl trifluoromethanesulfonate 103 ($R^{os}$=optional substituent, n=1-5) can give the bromide 104 which can be converted to the aminoalkylene ether 105 by reaction with a suitable amine $R^cR^dNH$.

Scheme 19

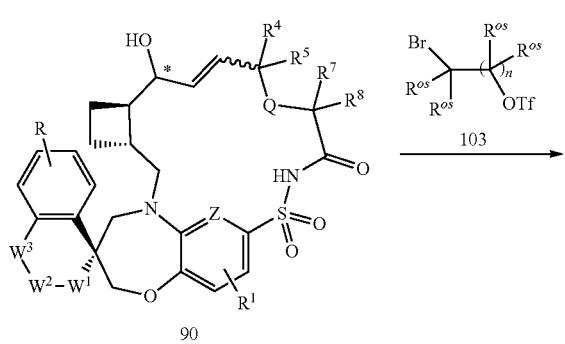

196
-continued

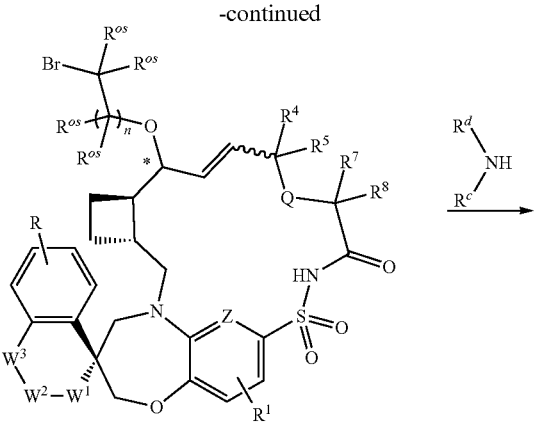
104

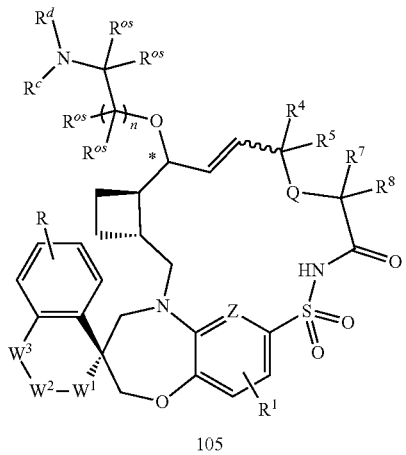
105

A series of 2-aminoethylene ether of formula 110 and amide derivative of formula 111 can be prepared by the methods outlined in Scheme 20. Reaction of the macrocyclic alcohol 90 with substituted 2-bromoacetic acid 106 ($R^{os}$=optional substituent) using a suitable base (e.g. NaH or DBU) can give the acid 107 which can be converted to the isobutyl carbonic anhydride 108 by treatment with isobutyl chloroformate. Reduction of the anhydride 108 with a suitable reducing agent (e.g., DIBAL or $NaBH_4$) at low temperature can provide the aldehyde 109 which can be transformed into the 2-aminoethylene ether 110 by reductive amination with $R^cR^dNH$ using reductive agent (e.g., $NaBH_4$, $NaBH(OAc)_3$, or $NaBCNH_3$). Alternatively, reaction of the anhydride 108 with amine $R^cR^dNH$ can yield the corresponding amide 111.

Scheme 20
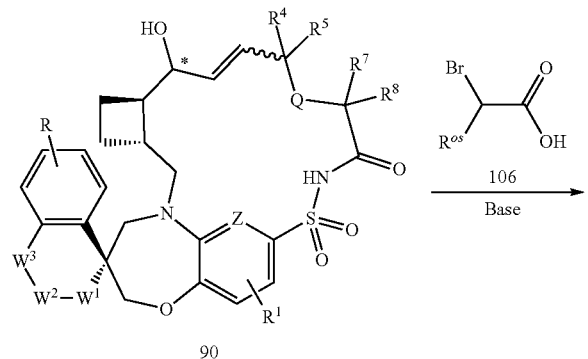
90
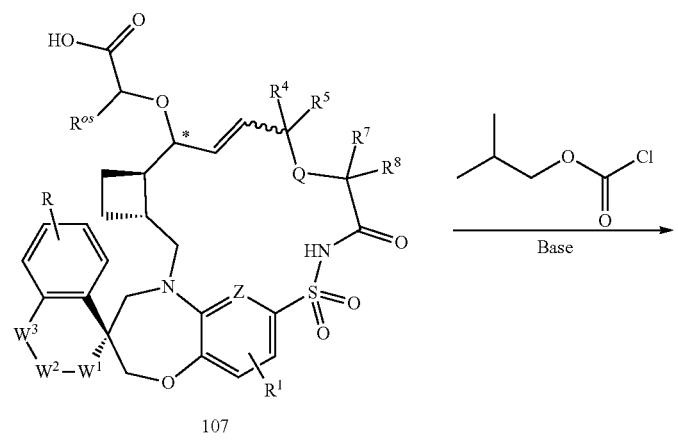
107
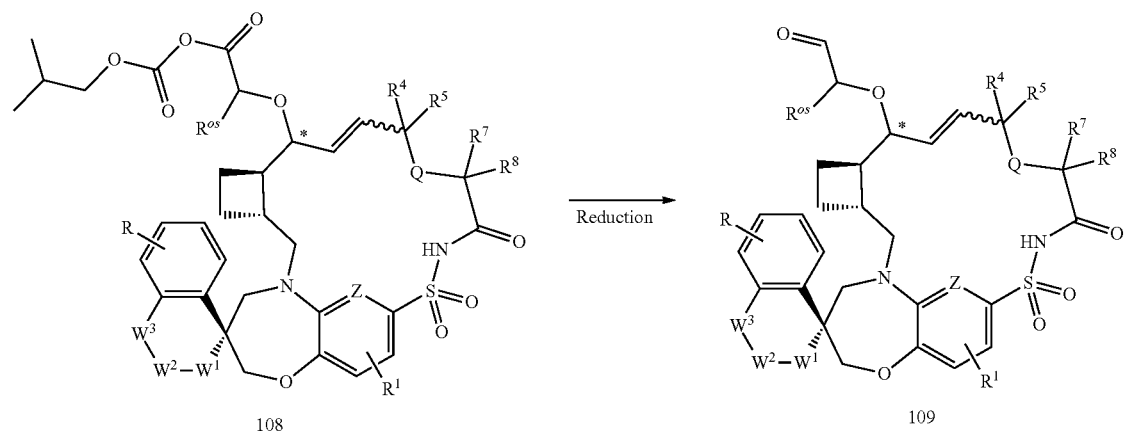
108    109

199 200

-continued

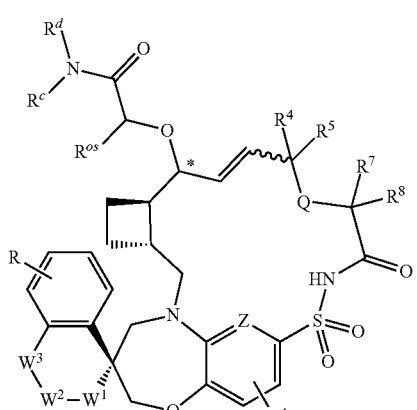

111

Intermediate 1

6'-Chlorospiro[4,5-dihydro-2H-1,5-benzoxazepine-3,1'-tetralin]-7-sulfonamide

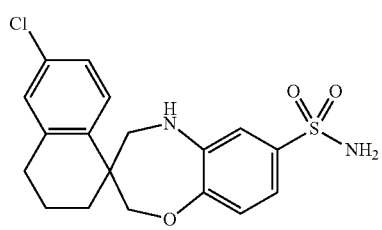

Step 1: 6'-chlorospiro[oxirane-2,1'-tetralin]

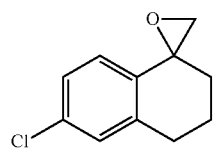 [SMILES: Clc1ccc2c(c1)CCCC21CO1]

To a solution of 6-chlorotetralin-1-one (10.0 g, 55.3 mmol) in DMSO (100 mL) was added trimethylsulfonium iodide (12.4 g, 60.9 mmol) and hydroxypotassium (6.21 g, 110 mmol), the mixture was stirred at 25° C. for 24 hours. The mixture was added to ice water (500 mL), extracted with MTBE (400 mL×3), combined the organic phases, washed with brine (500 mL×2), dried over Na$_2$SO$_4$, filtered and concentrated in vacuum to give 6'-chlorospiro[oxirane-2,1'-tetralin] (10.0 g, 51.3 mmol, 92% yield).

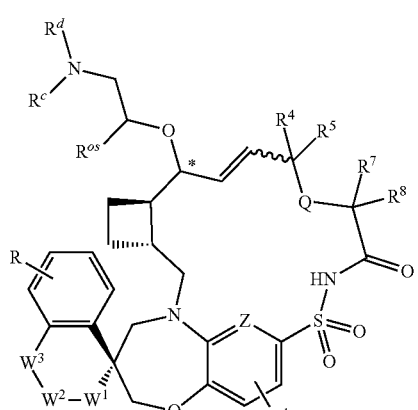

110

Step 2: 6-chlorotetralin-1-carbaldehyde

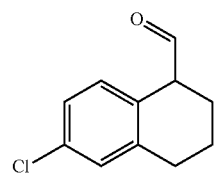 [SMILES: O=CC1CCCc2cc(Cl)ccc21]

To a solution of 6'-chlorospiro[oxirane-2,1'-tetralin] (10.0 g, 51.3 mmol) in THF (160 mL) was added Boron trifluoride etherate (364 mg, 2.57 mmol) at −8° C., the solution was stirred at −8° C. for 10 mins. The reaction was quenched with sat. NaHCO$_3$ (200 mL) at −8° C., extracted the aqueous with MTBE (400 mL×2), combined the organic phases, washed with brine (400 mL), dried over Na$_2$SO$_4$, filtered and concentrated in vacuum to give 6-chlorotetralin-1-carbaldehyde (11.40 g, 70% purity, 40.995 mmol, 79% yield).

Step 3: [6-chloro-1-(hydroxymethyl)tetralin-1-yl]methanol

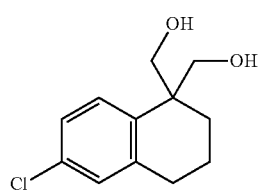 [SMILES: OCC1(CO)CCCc2cc(Cl)ccc21]

To a solution of 6-chlorotetralin-1-carbaldehyde (11.4 g, 70% purity, 41 mmol) in 2-(2-hydroxyethoxy)ethanol (80 mL, 41 mmol) was added paraformaldehyde (56 mL, 41 mmol), then potassium hydroxide (56 mL, 41 mmol) was added to the mixture at 5° C. The reaction mixture was stirred at 45° C. for 1 h. The reaction mixture was added brine (250 mL), extracted with DCM (300 mL×3), combined the organic phases, dried over Na$_2$SO$_4$, filtered and concentrated in vacuum, the residue was purified by silica gel column chromatography (PE:EA=1.5:1) to give [6-chloro-1-(hydroxymethyl)tetralin-1-yl]methanol (11.2 g, 75% purity, 90% yield). H NMR (400 MHz, CDCl$_3$): δ 7.31-7.34 (m, 2H), 7.11-7.14 (m, 2H), 3.87-3.91 (m, 2H), 3.72-3.76 (m, 2H), 2.73-2.76 (m, 2H), 2.11-2.15 (m, 2H), 1.89-1.92 (m, 2H), 1.79-1.83 (m, 2H).

Step 4: 6-chloro-1-(hydroxymethyl)tetralin-1-yl] methyl Benzoate

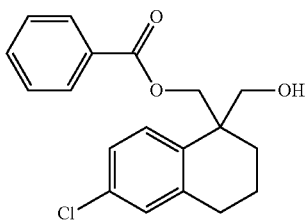 [SMILES: O=C(OCC1(CO)CCCc2cc(Cl)ccc21)c1ccccc1]

To a solution of [6-chloro-1-(hydroxymethyl)tetralin-1-yl]methanol (11.2 g, 37 mmol) in DCM (150 mL) was added benzoyl chloride (6.26 g, 44 mmol) at 0° C., following by drop-wise addition of DIPEA (7.4 mL, 44 mmol). The mixture stirred at 25° C. 16 h. Added DCM (150 mL) to the mixture, washed with sat. NH$_4$Cl (100 mL) and brine (100 mL), dried over Na$_2$SO$_4$, filtered and concentrated in vacuum, the residue was purified by silica gel column chromatography (PE:EA=9:1) to give 11.65 g of racemic product. $^1$H NMR (400 MHz, CDCl$_3$): δ 8.00-8.02 (m, 2H), 7.57-7.61 (m, 1H), 7.44-7.48 (m, 3H), 7.14-7.16 (m, 2H), 4.48 (s, 2H), 3.74-3.82 (m, 2H), 2.78-2.81 (m, 2H), 1.83-1.95 (m, 4H).

Step 5. (6-chloro-1-formyl-tetralin-1-yl)methyl Benzoate

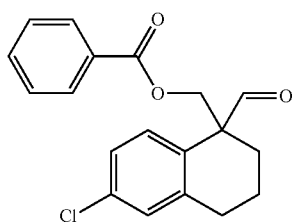 [SMILES: O=CC1(COC(=O)c2ccccc2)CCCc2cc(Cl)ccc21]

To a solution of [6-chloro-1-(hydroxymethyl)tetralin-1-yl]methyl benzoate (1.48 g, 4.47 mmol) in DCM (25 mL) was added Dess-Martin periodinane (2.84 g, 6.7 mmol) at 0° C., then the mixture was stirred at 25° C. for 1 h. To the reaction mixture was added a 1:1 mixture of 10% Na$_2$S$_2$O$_3$/sat. NaHCO$_3$ solution (100 mL). The mixture was extracted with DCM (100 mL×2). The combined organic phases were washed with brine (15 mL), dried over Na$_2$SO$_4$, filtered and concentrated under reduced pressure. The residue was purified by FC on a silica gel column to give (6-chloro-1-formyl-tetralin-1-yl)methyl benzoate (1.24 g, 84% yield). $^1$H NMR (400 MHz, CDCl$_3$): δ 9.61 (s, 1H), 7.94-7.96 (m, 2H), 7.54-7.58 (m, 1H), 7.41-7.45 (m, 2H), 7.15-7.21 (m, 3H), 4.75 (d, J=11.6 Hz, 1H), 4.55 (d, J=11.6 Hz, 1H), 2.81-2.85 (m, 2H), 2.19-2.23 (m, 1H), 2.00-2.06 (m, 1H), 1.89-1.95 (m, 2H).

Step 6. [6-chloro-1-(dimethoxymethyl)tetralin-1-yl] methanol

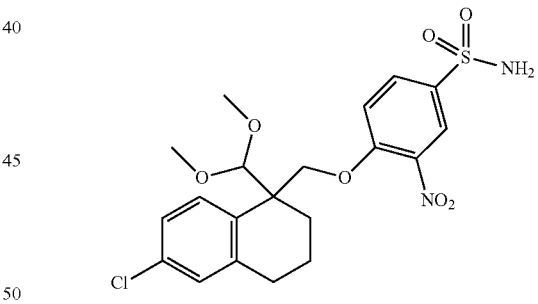

To a solution of (6-chloro-1-formyl-tetralin-1-yl)methyl benzoate (1.24 g, 3.77 mmol) in methanol (25 mL) were added p-TsOH H$_2$O (35 mg, 0.19 mmol) and trimethyl orthoformate (1.2 g, 11.3 mmol). The mixture was stirred at 70° C. for 4 h., then concentrated to 50% volume. The residue was diluted with THF (25 mL) and 1 N NaOH (25 mL) was added. The resulting reaction mixture was stirred at 40° C. 4 h. The solvent was removed. The residue was extracted with EA (20 mL×3). The combined organic layers were washed with 1 N NaOH (50 mL) and brine (100 mL), dried over Na$_2$SO$_4$, and concentrated under vacuum. The residue was purified by FC on a silica gel column (PE:EA=9:1) to give [6-chloro-1-(dimethoxymethyl)tetralin-1-yl] methanol (0.98 g, 96% yield). $^1$H NMR (400 MHz, CDCl$_3$): δ 7.35 (d, J=8.4 Hz, 1H), 7.10-7.13 (m, 2H), 4.49 (s, 1H), 3.90 (dd, J=3.8, 11.2 Hz, 1H), 3.53 (dd, J=8.4, 11.2 Hz, 1H), 3.46 (s, 3H), 3.33 (s, 3H), 2.68-2.76 (m, 2H), 1.99-2.06 (m, 1H), 1.89-1.96 (m, 1H), 1.70-1.86 (m, 2H).

Step 7: 4-[[6-chloro-1-(dimethoxymethyl)tetralin-1-yl]methoxy]-3-nitro-benzenesulfonamide A 100 mL flask with septum containing a mixture of [6-chloro-1-(dimethoxymethyl)tetralin-1-yl]methanol (818 mg, 3.02 mmol) and potassium t-butoxide (779 mg, 6.94 mmol) under N$_2$ was charged with THF (22 mL) giving a tan solution. The solution was stirred for 5 min at 0° C., followed by addition at 0° C. of a solution of 4-Fluoro-3-nitrobenzenesulfonamide (731 mg, 3.32 mmol) in THF (4 mL) over 8 min. The reaction was stirred at 0° C. for 20 min. The reaction mixture was quenched with sat. NH$_4$Cl (10 mL). The reaction mixture was diluted with water (80 mL) and sat. NH$_4$Cl (10 mL), and extracted with EtOAc (100 mL). The organic layer was washed with water (70 mL) and sat. NH$_4$Cl (10 mL), and brine (50 mL). The aqueous layers were combined, and back-extracted with EtOAc (60 mL), washed with water (60 mL), and brine (30 mL). The organic layers were combined, dried over Na$_2$SO$_4$, and filtered and concentrated under reduced pressure to afford 4-[[6-chloro-1-(dimethoxymethyl)tetralin-1-yl]methoxy]-3-nitro-benzenesulfonamide as a yellow foam (1.52 g) and was used directly in the next reaction without further purification. R$_f$=0.36 (1:1 hexanes:EtOAc); $^1$H NMR (500 MHz, DMSO-d$_6$) δ 8.28 (d, J=2.3 Hz, 1H), 8.01 (dd, J=2.4, 8.9 Hz, 1H), 7.60 (dd, J=8.7, 16.3 Hz, 2H), 7.50 (s, 2H), 7.19-7.11 (m, 2H), 4.63 (s, 1H), 4.38-4.26 (m, 2H), 3.38 (s, 3H), 3.29 (s, 3H), 2.70 (d, J=6.2 Hz, 2H), 2.04-1.94 (m, 1H), 1.90-1.79 (m, 2H), 1.77-1.67 (m, 1H).

Step 8: 4-[(6-chloro-1-formyl-tetralin-1-yl)methoxy]-3-nitro-benzenesulfonamide

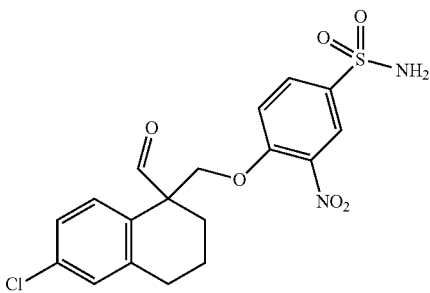 [SMILES: NS(=O)(=O)c1ccc(OCC2(C=O)CCCc3cc(Cl)ccc32)c([N+](=O)[O-])c1]

The Amberlyst 16 wet catalyst was rinsed with acetone and dried under high vacuum before use. A 500 mL RBF with septum containing crude 4-[[6-chloro-1-(dimethoxymethyl)tetralin-1-yl]methoxy]-3-nitro-benzenesulfonamide (1.42 g, 3.02 mmol) and pre-treated Amberlyst 16 wet (1 g, ~7.44 mmol) under N$_2$ was charged with acetone (30 mL). The reaction mixture was heated at 50° C. for 2 h., filtered through cotton and rinsed with DCM. The filtrate was concentrated under reduced pressure to afford 4-[(6-chloro-1-formyl-tetralin-1-yl)methoxy]-3-nitro-benzenesulfonamide as an orange/brown oil (1.7 g) which was used directly in the next reaction without further purification. R$_f$=0.31 (1:1 hexanes:EtOAc); $^1$H NMR (500 MHz, DMSO-d$_6$) δ 9.65 (s, 1H), 8.27 (d, J=2.4 Hz, 1H), 8.03 (dd, J=2.4, 8.9 Hz, 1H), 7.63 (d, J=9.0 Hz, 1H), 7.50 (s, 2H), 7.35-7.29 (m, 2H), 7.26 (dd, J=2.4, 8.4 Hz, 1H), 4.77 (d, J=9.6 Hz, 1H), 4.47 (d, J=9.6 Hz, 1H), 2.78 (t, J=6.3 Hz, 2H), 2.19 (ddd, J=3.0, 8.9, 13.2 Hz, 1H), 1.99 (ddd, J=2.8, 8.1, 13.5 Hz, 1H), 1.89-1.80 (m, 1H), 1.80-1.70 (m, 1H).

Step 9: 6'-chlorospiro[4,5-dihydro-2H-1,5-benzoxazepine-3,1'-tetralin]-7-sulfonamide

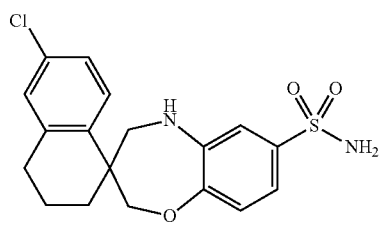 [SMILES: NS(=O)(=O)c1ccc2c(c1)NCC1(CCCc3cc(Cl)ccc31)CO2]

A solution of crude 4-[(6-chloro-1-formyl-tetralin-1-yl)methoxy]-3-nitro-benzenesulfonamide (assumed 3.02 mmol) in acetic acid (50 mL) was charged with iron powder (1.69 g, 30.2 mmol). The mixture was heated at 70° C. for 3 h. The mixture was charged with Celite, diluted with DCM (50 mL), filtered through a Celite plug, and rinsed with DCM to yield crude 6'-chlorospiro[2H-1,5-benzoxazepine-3,1'-tetralin]-7-sulfonamide. R$_f$=0.24 (1:1 EtOAc/hexanes); LCMS calculated for C$_{18}$H$_{18}$ClN$_2$O$_3$S (M+H)$^+$: m/z=377.07/379.07; found: 377.0/379.0.

The filtrate was concentrated under reduced pressure, dissolved in DCM (30 mL), cooled to 0° C., and charged with sodium triacetoxyborohydride (1.99 g, 9.44 mmol) over 1 min. The reaction mixture was stirred at 0° C. for 1 min, then stirred at RT for 80 min. The reaction mixture was quenched with 10% citric acid (30 mL), diluted with water (30 mL), and extracted with EtOAc (125 mL). The organic layer was washed with 10% citric acid (10 mL) and water (40 mL), washed with brine (2×40 mL), dried over Na$_2$SO$_4$, and filtered. The filtrate was concentrated under reduced pressure to yield 6'-chlorospiro[4,5-dihydro-2H-1,5-benzoxazepine-3,1'-tetralin]-7-sulfonamide (1.24 g, 2.61 mmol, 86% yield) as a light tan foam. R$_f$=0.45 (1:1 EtOAc/hexanes). LCMS calculated for C$_{18}$H$_{20}$ClN$_2$O$_3$S (M+H)$^+$: m/z=379.09/379.08; found: 379.0/381.0; $^1$H NMR (500 MHz, DMSO-d$_6$) δ 7.81 (d, J=8.5 Hz, 1H), 7.26 (dd, J=2.4, 8.5 Hz, 1H), 7.18 (dd, J=2.3, 15.2 Hz, 2H), 7.13 (s, 2H), 7.02 (dd, J=2.3, 8.4 Hz, 1H), 6.92 (d, J=8.4 Hz, 1H), 6.20 (t, J=4.1 Hz, 1H), 4.08 (q, J=12.2 Hz, 2H), 3.23 (dd, J=4.7, 13.7 Hz, 1H), 2.77-2.65 (m, 2H), 1.87-1.66 (m, 3H), 1.55 (ddd, J=2.9, 9.7, 12.7 Hz, 1H).

Intermediate 2

(3S)-6'-Chloro-N,N-bis[(4-methoxyphenyl)methyl]spiro[4,5-dihydro-2H-1,5-benzoxazepine-3,1'-tetralin]-7-sulfonamide

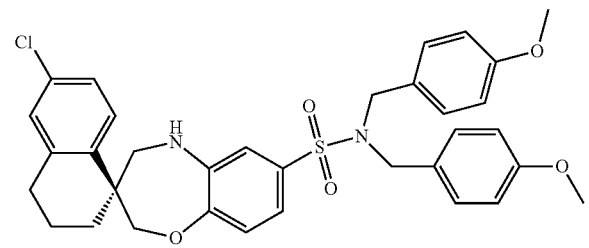 [SMILES: COc1ccc(CN(Cc2ccc(OC)cc2)S(=O)(=O)c2ccc3c(c2)NC[C@@]2(CCCc4cc(Cl)ccc42)CO3)cc1]

Step 1: 4-fluoro-N,N-bis[(4-methoxyphenyl)methyl]-3-nitro-benzenesulfonamide

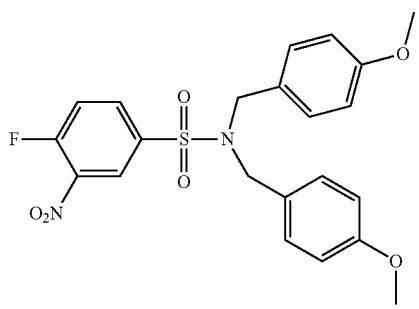 [SMILES: COc1ccc(CN(Cc2ccc(OC)cc2)S(=O)(=O)c2ccc(F)c([N+](=O)[O-])c2)cc1]

To a cooled (−35° C.) solution of 4-Fluoro-3-nitrobenzenesulfonyl chloride (4.89 g, 20.42 mmol) in THF (50 mL) was added Triethylamine (3.13 mL, 22.46 mmol), followed by addition of Bis-(4-methoxybenzyl)amine (4.97 mL, 20.7 mmol) in THF (50 mL) solution over 30 min. while the temperature was kept at −35° C. After completion of the addition, the temperature was allowed slowly to warm to 0° C. over 1 h., and the mixture was stirred at 0° C. for an additional hour. The mixture was neutralized with 1 N HCl to pH about 4-5 and diluted with EtOAc (100 mL). The organic layer was separated, washed with 1 N HCl (10 mL), 7.5% NaHCO$_3$ aqueous solution (20 mL), and brine, dried over Na$_2$SO$_4$, filtered, and concentrated under reduced pressure. The residue was treated with DCM (30 mL), and hexane was added to the suspension until it became cloudy. The resulting suspension was sonicated for 2 min. and left at r.t. for 1 h. The mixture was filtered, and washed with hexane to afford the desired title product (6.85 g) without further purification. The mother liquid was concentrated under reduced pressure. The residue was treated with DCM (5 mL) and hexane was added as the procedures mentioned above to afford the additional 0.51 g of the title product. Total product 4-fluoro-N,N-bis[(4-methoxyphenyl)methyl]-3-nitro-benzenesulfonamide obtained is 7.36 g (78%). $^1$H NMR (400 MHz, DMSO-d$_6$): δ 8.18-8.23 (m, 2H), 7.75-7.79 (q, 1H), 7.08 (d, 4H), 6.81 (d, 4H), 4.31 (s, 4H), 3.71 (s, 6H). $^{19}$F NMR (376 MHz, DMSO-d$_6$): δ −112.54 (s, 1F). LCMS calculated for C$_{22}$H$_{22}$FN$_2$O$_6$S (M+H)$^+$: m/z=461.11; found: 461.1.

Step 2: [(1S)-6-chloro-1-(hydroxymethyl)tetralin-1-yl]methyl benzoate and [(1R)-6-chloro-1-(hydroxymethyl)tetralin-1-yl]methyl Benzoate

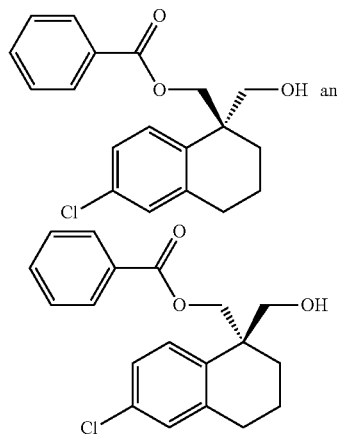

Racemic product 6-chloro-1-(hydroxymethyl)tetralin-1-yl]methyl benzoate (intermediate 1, Step 4) was separated by Waters-SFC80 instrument under the separation conditions: Column: AD-H (2.5*25 cm, 10 um); Mobile phase A: Supercritical CO$_2$, Mobile phase B: EtOH, A:B=80/20 at 60 mL/min; Circle Time: 15 min; Sample preparation: Ethanol; Injection Volume: 0.8 mL; Detector Wavelength: 214 nm; Column temperature: 25° C.; Back pressure: 100 bar. The separated products were determined by chiral HPLC. Chiral HPLC conditions: Chiral Column: AD-H, 5 um, 4.6 mm×250 mm (Daicel); Mobile phase: Supercritical CO$_2$/EtOH/DEA 70/30/0.06; Flow rate: 2.0 mL/min and Run time: 12 min. to afford [(1S)-6-chloro-1-(hydroxymethyl)tetralin-1-yl]methyl benzoate (P1, Retention time=4.952 min.) and [(1R)-6-chloro-1-(hydroxymethyl)tetralin-1-yl]methyl benzoate (P2, Retention time=6.410 min.). $^1$H NMR (400 MHz, CDCl$_3$): δ 8.00-8.02 (m, 2H), 7.57-7.61 (m, 1H), 7.44-7.48 (m, 3H), 7.14-7.16 (m, 2H), 4.48 (s, 2H), 3.74-3.82 (m, 2H), 2.78-2.81 (m, 2H), 1.83-1.95 (m, 4H).

Step 3: [(1R)-6-chloro-1-formyl-tetralin-1-yl]methyl Benzoate

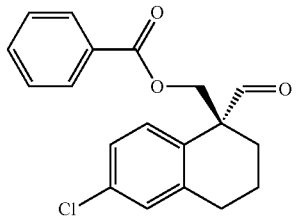 [SMILES: O=C[C@]1(COC(=O)c2ccccc2)CCCc2cc(Cl)ccc21]

This compound was prepared using procedures analogous to those described for Intermediate 1 using [(1S)-6-chloro-1-(hydroxymethyl)tetralin-1-yl]methyl benzoate (Step 2, P1) to replace the racemic [6-chloro-1-(hydroxymethyl)tetralin-1-yl]methyl benzoate in Step 5. $^1$H NMR (400 MHz, CDCl$_3$): δ 9.61 (s, 1H), 7.94-7.96 (m, 2H), 7.55-7.58 (m, 1H), 7.41-7.45 (m, 2H), 7.15-7.20 (m, 3H), 4.73-4.76 (d, 1H), 4.53-4.56 (d, 1H), 2.82-2.85 (m, 2H), 2.20-2.26 (m, 1H), 2.01-2.07 (m, 1H), 1.90-1.96 (m, 2H).

Step 4. [(1R)-6-chloro-1-(dimethoxymethyl)tetralin-1-yl]methanol

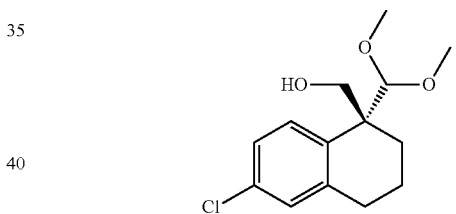

Method A: This compound was prepared using procedures analogous to those described for Intermediate 1 using [(1R)-6-chloro-1-formyl-tetralin-1-yl]methyl benzoate to replace the racemic (6-chloro-1-formyl-tetralin-1-yl)methyl benzoate in Step 6. $^1$H NMR (400 MHz, CDCl$_3$+D$_2$O): δ 7.34-7.36 (m, 1H), 7.10-7.12 (m, 2H), 4.49 (s, 1H), 3.89-3.91 (d, 1H), 3.50-3.53 (m, 1H), 3.46 (s, 3H), 3.33 (s, 3H), 2.68-2.76 (m, 2H), 1.99-2.06 (m, 1H), 1.89-1.96 (m, 1H), 1.70-1.86 (m, 2H).

Method B: The racemic (6-chloro-1-formyl-tetralin-1-yl)methyl benzoate (Intermediate 1 Step 6) was separated by chiral column on Berger MG2 Preparative SFC instrument under the separation conditions: Column: ChiralPak IC (2×25 cm); Mobile phase A: i-PrOH, Mobile phase B: Supercritical CO$_2$, A:B=1/3 at 60 mL/min; Circle Time (Run Time): 5 min injection intervals; Sample preparation: 20 mg/mL iPrOH/DCM; Injection Volume: 0.5 mL; Detector Wavelength: 220 nm; Column temperature: 30° C.; Back pressure: 100 bar. The separated products were determined by chiral HPLC on Berger Analytical SFC. Chiral HPLC conditions: Chiral Column: ChiralPak IC, 5 um, 4.6 mm×250 mm (Daicel); Mobile phase: i-PrOH/Supercritical CO$_2$/EtOH 1/3; Flow rate: 3.0 mL/min and Run time: 7 min.; Detector Wavelength (UV length): 220 nm, 254 nm, and 280 nm; Column temperature: 30° C.; Back pressure: 120 bar. to afford [(1S)-6-chloro-1-(dimethoxymethyl)tetralin-1-yl]methanol (P1, Retention time=1.96 min.) and [(1R)-6-chloro-1-(dimethoxymethyl)tetralin-1-yl]methanol (P2, Retention time=2.69 min.)

Step 5: N,N-bis[(4-methoxyphenyl)methyl]-3-nitro-4-[[(1R)-6-chloro-1-(dimethoxymethyl)-tetralin-1-yl]methoxy]benzenesulfonamide

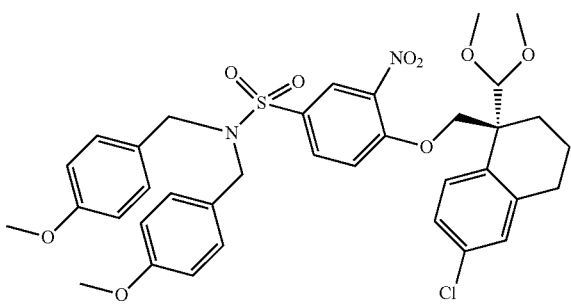 [SMILES: COc1ccc(CN(Cc2ccc(OC)cc2)S(=O)(=O)c2ccc(OC[C@@]3(C(OC)OC)CCCc4cc(Cl)ccc43)c([N+](=O)[O-])c2)cc1]

To a solution of [(1R)-6-chloro-1-(dimethoxymethyl)tetralin-1-yl]methanol (2.96 g, 10.93 mmol, P2) in THF (50 mL) was drop-wised add LiHMDS (11.5 mL, 11.4 mmol) under N₂ atmosphere at −40° C., the solution was stirred at −40° C. for 5 mins, then dropwise added 4-fluoro-N,N-bis[(4-methoxyphenyl)methyl]-3-nitro-benzenesulfonamide (7.55 g, 16.4 mmol) (Step 1) in THF (30 mL). The solution was stirred for 5 min. under −40° C., then the mixture was stirred at r.t. for 1 h. The reaction was cooled with ice-water bath, and quenched with sat. NH₄Cl aqueous solution (100 mL). The mixture was extracted with EtOAc (100 mL×3). The combined organic layers were washed with sat. NH₄Cl solution and brine, dried over Na₂SO₄, filtered and concentrated in vacuum. The residue was purified by flash chromatography on a silica gel column eluting with ethyl acetate (EA) and petroleum ether (PE) to give N,N-bis[(4-methoxyphenyl)methyl]-3-nitro-4-[[(1R)-6-chloro-1-(dimethoxymethyl)tetralin-1-yl]methoxy]benzenesulfonamide (6.41 g, 82% yield). $^1$H NMR (400 MHz, DMSO-d₆): δ 8.06-8.07 (m, 1H), 7.97-8.00 (m, 1H), 7.60-7.62 (m, 1H), 7.49-7.51 (m, 1H), 7.14-7.17 (m, 2H), 6.99-7.07 (m, 4H), 6.77-6.79 (m, 4H), 4.62 (s, 1H), 4.27-4.36 (m, 2H), 4.24 (s, 4H), 3.70 (s, 6H), 3.39 (s, 3H), 3.30 (s, 3H), 2.68-2.71 (m, 2H), 1.98-2.00 (m, 1H), 1.81-1.85 (m, 2H), 1.71-1.73 (m, 1H).

Step 6: N,N-bis[(4-methoxyphenyl)methyl]-3-nitro-4-[[(1R)-6-chloro-1-formyl-tetralin-1-yl]methoxy]benzenesulfonamide

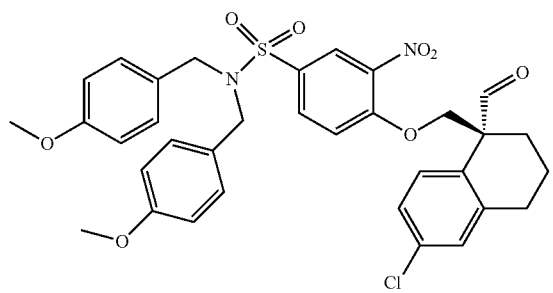 [SMILES: COc1ccc(CN(Cc2ccc(OC)cc2)S(=O)(=O)c2ccc(OC[C@@]3(C=O)CCCc4cc(Cl)ccc43)c([N+](=O)[O-])c2)cc1]

To a solution of N,N-bis[(4-methoxyphenyl)methyl]-3-nitro-4-[[(1R)-6-chloro-1-(dimethoxymethyl)tetralin-1-yl]methoxy]benzenesulfonamide (6.11 g, 8.59 mmol) in THF (80 mL) and water (20 mL) was added p-TsOH—H₂O (3.27 g, 17.18 mmol), the mixture was stirred at 70° C. for 16 h. The mixture was cooled to 0° C., and sat. NaHCO₃ aqueous (100 mL) was added. The mixture was extracted with EA (100 mL×3). The combined organic layers were dried over Na₂SO₄, filtered and concentrated under reduced pressure. The residue was purified by flash chromatography on a silica gel column eluting with EA and to give N,N-bis[(4-methoxyphenyl)methyl]-3-nitro-4-[[(1R)-6-chloro-1-formyl-tetralin-1-yl]methoxy]benzenesulfonamide (6.11 g, 85% purity, 91% yield).

Step 7: (S)-6'-chloro-N,N-bis(4-methoxybenzyl)-3',4'-dihydro-2H,2'H-spiro[benzo[b][1,4]oxazepine-3,1'-naphthalene]-7-sulfonamide

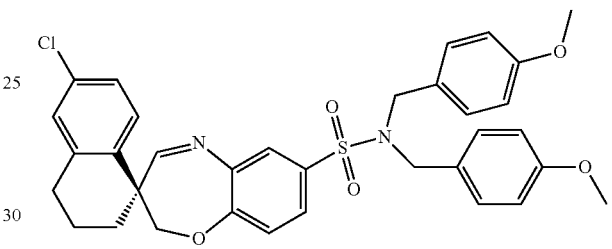

To a solution of N,N-bis[(4-methoxyphenyl)methyl]-3-nitro-4-[[(1R)-6-chloro-1-formyl-tetralin-1-yl]methoxy]benzenesulfonamide (6.11 g, 7.81 mmol) in ethanol (40 mL) and water (20 mL) was added iron powder (2.18 g, 39 mmol) and NH₄Cl (827 mg, 15.6 mmol), the mixture was stirred at 100° C. for 3 h. LCMS showed the reaction completed. The mixture was filtered. The filtrate was added H₂O (20 mL), extracted with EA (30 mL×3). The combined organic layers were dried over Na₂SO₄, filtered and concentrated under reduced pressure to give (S)-6'-chloro-N,N-bis(4-methoxybenzyl)-3',4'-dihydro-2H,2'H-spiro[benzo[b][1,4]oxazepine-3,1'-naphthalene]-7-sulfonamide (6.11 g, 70% purity, 86% yield) which was directly used in next step reaction without further purification. LCMS calculated for C₃₄H₃₄ClN₂O₅S (M+H)⁺: m/z=617.18; found: 617.3.

Step 8: (3S)-6'-chloro-N,N-bis[(4-methoxyphenyl)methyl]spiro[4,5-dihydro-2H-1,5-benzoxazepine-3,1'-tetralin]-7-sulfonamide

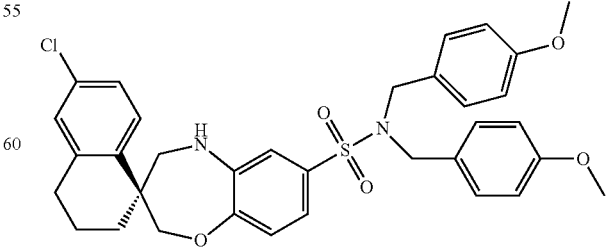

To a solution of (S)-6'-chloro-N,N-bis(4-methoxybenzyl)-3',4'-dihydro-2H,2'H-spiro[benzo[b][1,4]oxazepine-3,1'- naphthalene]-7-sulfonamide (6.11 g, 6.73 mmol) (crude product from Step 7, 70% purity) in DCM (80 mL) was portion-wise added NaBH(OAc)$_3$ (7.14 g, 33.67 mmol). The mixture was stirred at 25° C. for 16 h. LCMS showed the reaction worked well. The reaction was added sat. NaHCO$_3$ aqueous (80 mL), extracted with DCM (100 mL×3), dried over Na$_2$SO$_4$, filtered and concentrated under reduced pressure. The residue was purified by flash chromatography on a silica gel column eluting with EA and PE to give (3S)-6'-chloro-N,N-bis[(4-methoxyphenyl)methyl]spiro[4,5-dihydro-2H-1,5-benzoxazepine-3,1'-tetralin]-7-sulfonamide (2.30 g, 53% yield). LCMS calculated for C$_{34}$H$_{36}$ClN$_2$O$_5$S (M+H)$^+$: m/z=619.2; found: 619.3. $^1$H NMR (400 MHz, DMSO-d$_6$): δ 7.81-7.83 (m, 1H), 7.24-7.28 (m, 2H), 7.17-7.18 (m, 1H), 6.95-7.06 (m, 6H), 6.78-6.80 (m, 4H), 6.20 (s, 1H), 4.15 (m, 4H), 4.08-4.14 (m, 2H), 3.68 (s, 6H), 3.30-3.36 (m, 1H), 3.23-3.27 (m, 1H), 2.71-2.75 (m, 2H), 1.76-1.86 (m, 3H), 1.56-1.61 (m, 1H).

Intermediate 3

(3S)-6'-Chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide And Intermediate 4

(3S)-6'-Chloro-5-[[(1R,2R)-2-[(1R)-1-hydroxyallyl]cyclobutyl]methyl]spiro[2,4-dihydro-1,5-benzoxazepine-3,1'-tetralin]-7-sulfonamide Intermediate 3

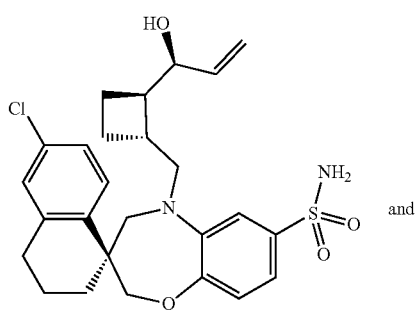

and

Intermediate 4

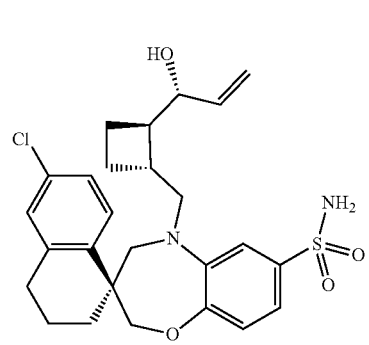

Step 1: [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl Acetate

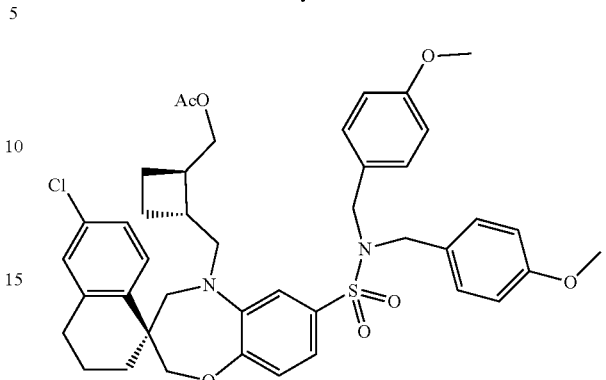

2,2,2-trifluoroacetic acid (7.0 mL, 92 mmol) was dropwise added to a stirred solution of sodium borohydride (3.48 g, 92.0 mmol) in DCM (200 mL) at 0° C. The resulting mixture was stirred at 0° C. for 10 min. A solution of (3S)-6'-chloro-N,N-bis[(4-methoxyphenyl)methyl]spiro[4,5-dihydro-2H-1,5-benzoxazepine-3,1'-tetralin]-7-sulfonamide (28.5 g, 46.03 mmol) and [(1R,2R)-2-formylcyclobutyl]methyl acetate (8.63 g, 55.24 mmol) in 200 mL DCM was then dropwise added at 0° C. The resulting mixture was stirred at room temperature for overnight. The reaction was monitored by LC-MS. Another 2 equivalents of sodium borohydride (3.48 g, 92.06 mmol) and 2,2,2-trifluoroacetic acid (7.04 mL, 92.06 mmol) were added to the mixture, followed by the stirring for 3 h. The reaction was quenched by addition of methanol (30 mL), and followed by addition of saturated NaHCO$_3$ solution (300 mL) slowly. The resulting mixture was extracted with DCM (300 mL×3). The combined organic layers were dried over Na$_2$SO$_4$, filtered and concentrated under reduced pressure. The residue was purified by flash chromatography on a silica gel column using EtOAc/Heptanes (5-40%) to afford the desired product [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl acetate (34.5 g, 45.4 mmol, 98% yield) as a white solid. LC-MS calc. for C$_{40}$H$_{43}$ClN$_2$O$_6$S [M+H]$^+$: m/z=759.28/760.28; Found 759.67/760.64.

Step 2: (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide

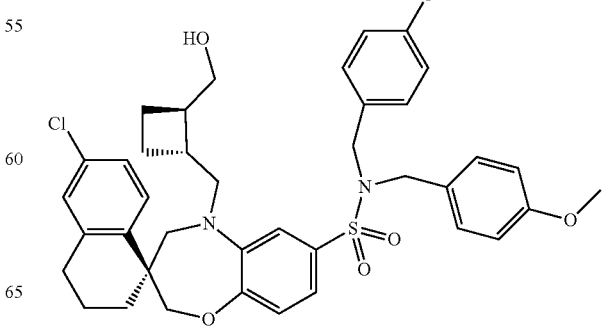

To a solution of [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl acetate (54.0 g, 71.1 mmol) in THF (500 mL), methanol (500 mL) and water (500 mL) was added lithium hydroxide monohydrate (14.9 g, 355 mmol). The mixture was stirred at r.t. overnight. The solvent was removed, and the aqueous layer was extracted with DCM (100 mL×3). The combined organic layers were dried over $Na_2SO_4$, filtered and concentrated under reduced pressure to afford (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide (52 g, 101% yield) as white solid which was directly used for the next step without further purification. LC-MS calc. for $C_{40}H_{45}ClN_2O_6S$ [M+H]$^+$: m/z=717.27/718.27; Found 717.6/718.6.

Step 3: (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide

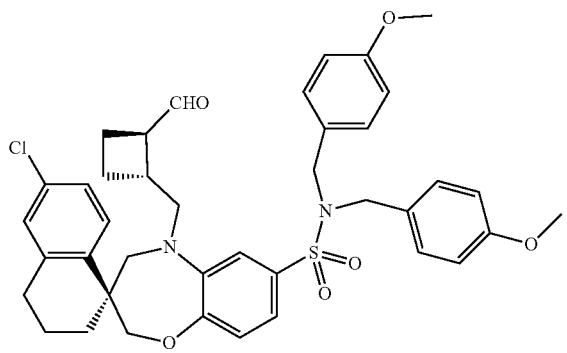 [SMILES: COc1ccc(CN(Cc2ccc(OC)cc2)S(=O)(=O)c2ccc3c(c2)N(C[C@@H]2CC[C@H]2C=O)C[C@@]2(CCCc4cc(Cl)ccc42)CO3)cc1]

DMSO (20.5 mL, 289 mmol) was slowly added to a cooled (−78° C.) solution of oxalyl chloride (12.4 mL, 144.9 mmol) in DCM (1000 mL). Gas was produced during this addition. The mixture was stirred at −78° C. for 30 min. Then a solution of (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide (52.0 g, 72.4 mmol) in DCM (50 mL) was added over 5 min. The resulting mixture was stirred at −78° C. for 40 min. Then triethylamine (101 mL, 724 mmol) was added. The solution was stirred at −78° C. for additional 10 min, and allowed to warm slowly to 0° C. After the starting material was consumed, water (150 mL) was added. The organic layer were separated. The aqueous layer was extracted with DCM (300 mL×3). The combined organic layers were dried over sodium sulfate and concentrated. The residue was purified by flash chromatography on a silica gel column with EtOAc/Heptanes (5-50%) to afford (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide (43 g, 83% yield) as a white solid. LC-MS calc. for $C_{40}H_{43}ClN_2O_6S$ [M+H]$^+$: m/z=715.25/716.26; Found 715.7/716.7.

Step 4: (3S)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-tetralin]-7-sulfonamide and (3S)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-tetralin]-7-sulfonamide

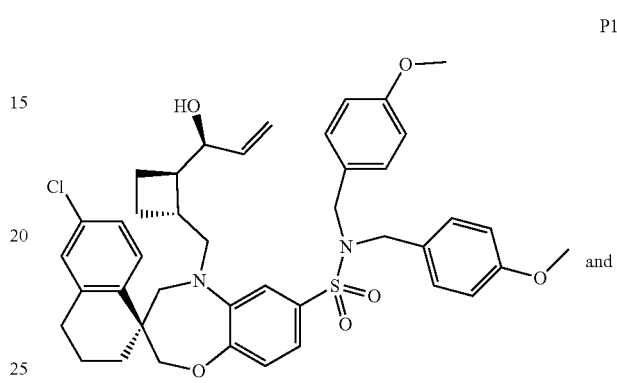

P1 and

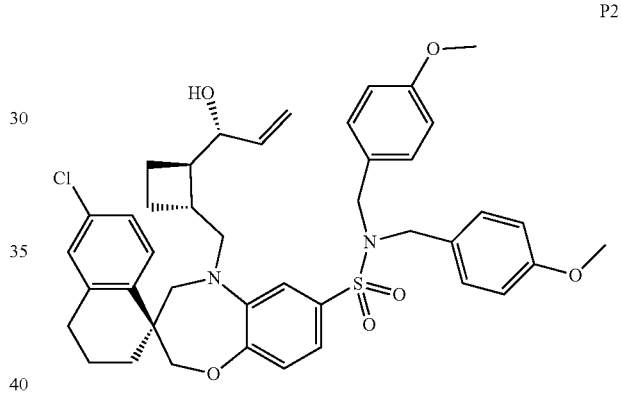

P2

Vinylmagnesium bromide (1.0 M solution in THF, 300 mL, 300 mmol) was diluted with THF (200 mL) in a 3 necked round bottom flack under nitrogen. (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide (43.0 g, 60.1 mmol) dissolved in THF (400 mL) was introduced dropwise through a dropping funnel over 2 hours at room temperature. The reaction was monitored by LC-MS. After the starting material was consumed, the reaction was then quenched by addition of sat. aqueous solution $NH_4Cl$ (300 mL) at 0° C. The organic layer was then separated, and the aqueous layer was extracted with ethyl acetate (300 mL×2). The combined organic layers were dried over $Na_2SO_4$, filtered and concentrated under reduced pressure. The residue was purified by flash chromatography on a silica gel column using EtOAc/Heptanes (5-40%) to afford two products: P1 (the earlier eluted product: 24.3 g, 40%) and P2 (the latter eluted product: 20 g, 33%).

P1 was assigned as (3S)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Rt=4.43 min from LC-MS). LC-MS calc. for $C_{42}H_{48}ClN_2O_6S$ [M+H]$^+$: m/z=743.28/744.29; Found 743.76/744.78. $^1$H NMR (300 MHz, $CDCl_3$) δ 7.76 (t, J=7.2 Hz, 1H), 7.53 (d, J=1.9 Hz, 1H), 7.24-7.14

(m, 2H), 7.12 (d, J=2.0 Hz, 1H), 7.03-6.97 (m, 5H), 6.79 (t, J=5.7 Hz, 4H), 5.84-5.69 (m, 1H), 5.16 (d, J=17.2 Hz, 1H), 5.05 (d, J=10.4 Hz, 1H), 4.26 (t, J=5.6 Hz, 4H), 4.13 (s, 2H), 3.97 (d, J=4.4 Hz, 1H), 3.80 (d, J=1.8 Hz, 6H), 3.74 (d, J=6.2 Hz, 1H), 3.26 (d, J=14.2 Hz, 1H), 3.09 (dd, J=15.0, 9.3 Hz, 1H), 2.93 (d, J=4.2 Hz, 1H), 2.83-2.75 (m, 2H), 2.48-2.35 (m, 1H), 2.10-1.92 (m, 4H), 1.82 (m, 3H), 1.50 (m, 2H).

And P2 was assigned as (3S)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Rt=4.13 min from LC-MS). LC-MS calc. for $C_{42}H_{48}ClN_2O_6S$ [M+H]$^+$: m/z=743.28/745.29; Found 743.8/745.8. $^1$H NMR (300 MHz, CDCl$_3$) δ 7.75-7.68 (m, 1H), 7.24-7.14 (m, 3H), 7.12 (d, J=2.0 Hz, 1H), 7.01 (t, J=8.3 Hz, 5H), 6.79 (d, J=8.7 Hz, 4H), 5.85 (ddd, J=17.0, 10.4, 6.4 Hz, 1H), 5.29 (dd, J=17.2, 1.2 Hz, 1H), 5.17-5.08 (m, 1H), 4.26 (d, J=8.4 Hz, 4H), 4.14 (d, J=8.0 Hz, 3H), 3.81 (s, 6H), 3.69 (d, J=14.3 Hz, 1H), 3.59 (d, J=12.9 Hz, 1H), 3.31 (d, J=14.3 Hz, 1H), 3.15 (dd, J=14.9, 9.0 Hz, 1H), 2.84-2.76 (m, 2H), 2.67-2.56 (m, 1H), 2.23-2.09 (m, 2H), 2.03 (m, 2H), 1.86-1.73 (m, 3H), 1.59-1.46 (m, 2H).

Step 5: (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Intermediate 3)

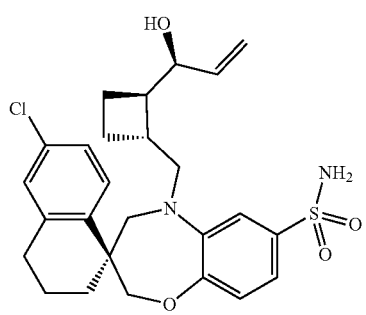

Intermediate 3

To a solution of (3S)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-tetralin]-7-sulfonamide (24.3 g, 32.6 mmol, P1, Step 4) and anisole (23.7 mL, 218 mmol) in DCM (240 mL) was added 2,2,2-trifluoroacetic acid (243 mL). The mixture was stirred overnight. The reaction was monitored by LC-MS. Solvents were removed under reduced pressure. The residue was diluted with DCM (200 mL). The mixture was washed with saturated aqueous NaHCO$_3$ solution (200 mL×3) and brine, dried over Na$_2$SO$_4$, filtered and concentrated under reduced pressure. The residue was purified by flash chromatography on a silica gel column with EA/heptane (5%-70%) to afford (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (15.7 g, 31.2 mmol, 95% yield) as a pale white solid. LC-MS calc. for $C_{26}H_{32}ClN_2O_4S$ [M+H]$^+$: m/z=503.17/505.17; Found 503.5/505.5; $^1$H NMR (300 MHz, CDCl$_3$) δ 7.74 (d, J=8.5 Hz, 1H), 7.55 (d, J=1.8 Hz, 1H), 7.21 (dd, J=11.4, 4.2 Hz, 2H), 7.12-7.08 (m, 2H), 6.97-6.94 (m, 1H), 6.85 (d, J=8.6 Hz, 1H), 5.90-5.76 (m, 1H), 5.25 (d, J=17.2 Hz, 1H), 5.16-5.08 (m, 1H), 4.11 (s, 2H), 3.88 (d, J=5.1 Hz, 1H), 3.81 (s, 2H), 3.27 (d, J=14.3 Hz, 1H), 3.14 (m, 1H), 2.84-2.75 (m, 2H), 2.51 (dd, J=16.9, 8.5 Hz, 1H), 2.08 (m, 3H), 1.90 (dd, J=15.8, 5.6 Hz, 2H), 1.63 (m, 3H), 1.45 (t, J=12.1 Hz, 1H).

Step 6: (3S)-6'-chloro-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Intermediate 4)

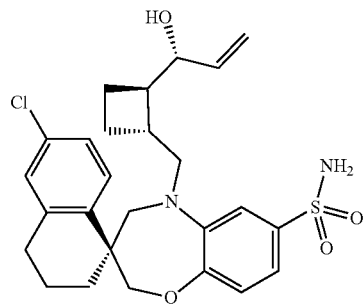

Intermediate 4

This compound was prepared using procedures analogous to those described for step 5 using P2 Step 4. LC-MS calc. for $C_{26}H_{32}ClN_2O_4S$ [M+H]$^+$: m/z=503.17/505.17; Found 503.5/505.5; $^1$H NMR (300 MHz, CDCl$_3$) δ 7.72 (d, J=8.5 Hz, 1H), 7.27-7.16 (m, 3H), 7.12 (s, 1H), 6.99-6.94 (m, 1H), 5.94-5.79 (m, 1H), 5.31 (d, J=17.2 Hz, 1H), 5.19 (d, J=10.5 Hz, 1H), 4.34-4.26 (m, 1H), 4.15-4.08 (m, 2H), 3.70 (d, J=14.5 Hz, 2H), 3.28 (d, J=14.2 Hz, 1H), 3.16 (dd, J=15.1, 9.0 Hz, 1H), 2.79 (dd, J=9.3, 5.0 Hz, 2H), 2.75-2.65 (m, 1H), 2.31-2.21 (m, 1H), 2.05-1.88 (m, 3H), 1.80-1.71 (m, 2H), 1.71-1.59 (m, 2H), 1.50 (t, J=11.4 Hz, 1H).

Intermediate 5

[(1S)-1-[(1R,2R)-2-[[(3S)-6'-Chloro-7-sulfamoyl-spiro[2,4-dihydro-1,5-benzoxazepine-3,1'-tetralin]-5-yl]methyl]cyclobutyl]allyl] Acetate

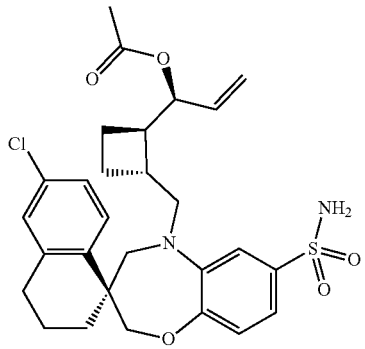 [SMILES: C=C[C@H](OC(C)=O)[C@@H]1CC[C@H]1CN1C[C@@]2(CCCc3cc(Cl)ccc32)COc2ccc(S(N)(=O)=O)cc21]

Step 1: [(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl] Acetate

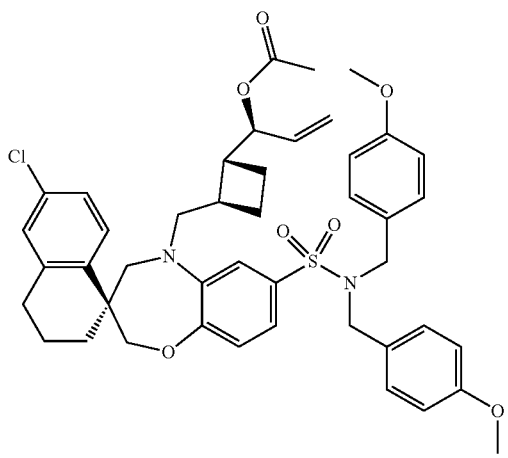 [SMILES: C=C[C@H](OC(C)=O)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

To a stirred solution of (3S)-6'-chloro-5-[[(1R,2R)-2-[(1S)-1-hydroxyallyl]cyclobutyl]methyl]-N,N-bis[(4-methoxyphenyl)methyl]spiro[2,4-dihydro-1,5-benzoxazepine-3,1'-tetralin]-7-sulfonamide (1.20 g, 1.61 mmol, Intermediate 3 and 4, Step 4, P1) in DCM (40 mL) was added DMAP (39 mg, 0.32 mmol), triethylamine (0.27 mL, 2.1 mmol) and Ac₂O (0.18 mL, 1.8 mmol).The reaction mixture was then stirred at r.t. for 6 h. The reaction was diluted with DCM (40 mL), washed with water (30 mL) and brine. The combined organic layers were dried over Na₂SO₄, filtered and the filtrate was concentrated under reduced pressure to afford the desired product (1.26 g) as a light orange colored solid. LC-MS calc. for $C_{44}H_{50}ClN_2O_7S$ [M+H]⁺: m/z=785.29/787.29. Found: 785.2/787.4.

Step 2: [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] Acetate To a stirred solution of [(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl] acetate (1.26 g, 1.6 mmol) in DCM (20 mL) was added TFA (20 mL, 137 mmol) dropwise. The reaction was stirred at 40° C. overnight. LC-MS showed the starting material was consumed. The reaction was cooled to r.t. and slowly poured into a 120 mL of saturated K₂CO₃ solution under an ice bath. The mixture was extracted with DCM (30 mL×3). The combined organic layers were dried over sodium sulfate and concentrated under reduced pressure. The crude product was purified by flash chromatography on a silica gel column (12 g) using EtOAc/Hetpanes (2% to 50%) to afford [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] acetate (680 mg, 77% yield). LC-MS calc. for $C_{28}H_{34}ClN_2O_5S$ [M+H]⁺: mz=545.18/547.18. Found: 544.8/546.4.

Intermediate 6

[(1R)-1-[(1R,2R)-2-[[(3S)-6'-Chloro-7-sulfamoyl-spiro[2,4-dihydro-1,5-benzoxazepine-3,1'-tetralin]-5-yl]methyl]cyclobutyl]allyl] Acetate

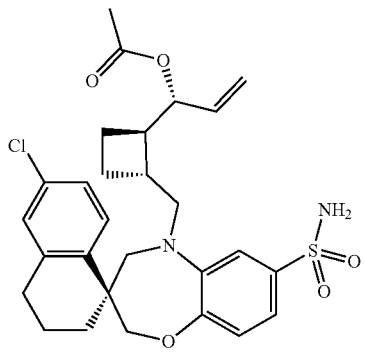 [SMILES: C=C[C@@H](OC(C)=O)[C@@H]1CC[C@H]1CN1C[C@@]2(CCCc3cc(Cl)ccc32)COc2ccc(S(N)(=O)=O)cc21]

This compound was prepared using procedures analogous to those described for Intermediate 5 using (3S)-6'-chloro-5-[[(1R,2R)-2-[(1R)-1-hydroxyallyl]cyclobutyl]methyl]-N,N-bis[(4-methoxyphenyl)methyl]spiro[2,4-dihydro-1,5-benzoxazepine-3,1'-tetralin]-7-sulfonamide (Intermediate 3 and 4, Step 4, P2) in Step 1. LC-MS calc. for $C_{28}H_{34}ClN_2O_5S$ [M+H]⁺: m/z=545.18/547.18. Found: 544.8/546.6.

Intermediate 7

(3R)-6'-Chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide

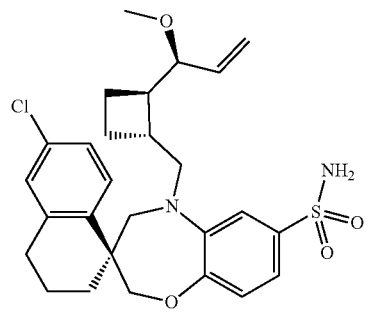 [SMILES: C=C[C@H](OC)[C@@H]1CC[C@H]1CN1C[C@@]2(CCCc3cc(Cl)ccc32)COc2ccc(S(N)(=O)=O)cc21]

Step 1: (3S)-6'-chloro-N,N-bis[(4-methoxyphenyl)methyl]-5-[[(1R,2R)-2-[(1S)-1-methoxyallyl]cyclobutyl]methyl]spiro[2,4-dihydro-1,5-benzoxazepine-3,1'-tetralin]-7-sulfonamide

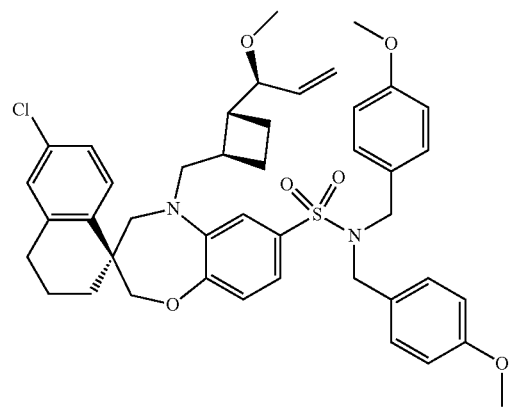 [SMILES: C=C[C@H](OC)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

To a cooled (ice-water bath) solution of (3S)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-tetralin]-7-sulfonamide (3.2 g, 4.3 mmol, Intermediate 3 and 4, Step 4, P1) in THF (70 mL) was added sodium hydride (0.52 g, 12.9 mmol). The mixture was stirred for 5 min., then iodomethane (0.8 mL, 12.9 mmol) was added. The mixture was stirred at 50° C. overnight. The reaction was quenched by addition of saturated aqueous ammonium chloride (70 mL) and water (70 mL). The mixture was extracted with EA (70 mL×3). The combined organic layers were washed with brine, dried over sodium sulfate, filtered and concentrated under reduced pressure to afford the crude product (3S)-6'-chloro-N,N-bis[(4-methoxyphenyl)methyl]-5-[[(1R,2R)-2-[(1S)-1-methoxyallyl]cyclobutyl]methyl]spiro[2,4-dihydro-1,5-benzoxazepine-3,1'-tetralin]-7-sulfonamide (3.1 g, 95% yield) which was directly used in next step directly without further purification. LC-MS calc. for $C_{43}H_{50}ClN_2O_6S$ [M+H]$^+$: m/z=757.3/759.3. Found: 757.0/759.4.

Step 2: (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide This compound was prepared using procedures analogous to those described for Intermediate 5 Step 2 using (3S)-6'-chloro-N,N-bis[(4-methoxyphenyl)methyl]-5-[[(1R,2R)-2-[(1S)-1-methoxyallyl]cyclobutyl]methyl]spiro[2,4-dihydro-1,5-benzoxazepine-3,1'-tetralin]-7-sulfonamide. LC-MS calc. for $C_{27}H_{34}ClN_2O_4S$ [M+H]$^+$: m/z=517.2/519.2. Found: 516.8/518.7.

Intermediate 8

(3S)-6'-Chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide

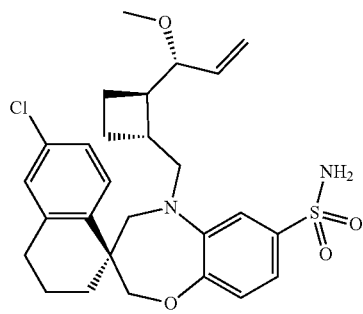 [SMILES: C=C[C@@H](OC)[C@@H]1CC[C@H]1CN1C[C@@]2(CCCc3cc(Cl)ccc32)COc2ccc(S(N)(=O)=O)cc21]

This compound was prepared using procedures analogous to those described for Intermediate 7 using (3S)-6'-chloro-5-[[(1R,2R)-2-[(1R)-1-hydroxyallyl]cyclobutyl]methyl]-N,N-bis[(4-methoxyphenyl)methyl]spiro[2,4-dihydro-1,5-benzoxazepine-3,1'-tetralin]-7-sulfonamide (Intermediate 3 and 4, Step 4, P2) in Step 1. LC-MS calc. for $C_{27}H_{35}ClN_2O_4S$ [M+H]$^+$: m/z=517.2/519.2. Found: 516.8/518.5.

Intermediate 9

[(1S)-1-[(1R,2R)-2-[[(3S)-6'-Chloro-7-sulfamoyl-spiro[2,4-dihydro-1,5-benzoxazepine-3,1'-tetralin]-5-yl]methyl]cyclobutyl]allyl] N,N-dimethylcarbamate

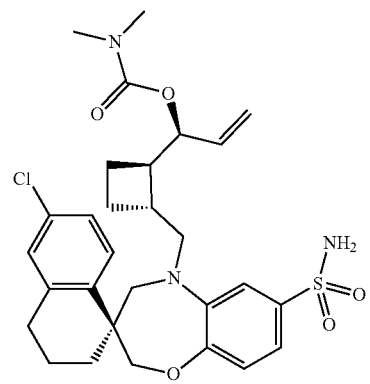 [SMILES: C=C[C@H](OC(=O)N(C)C)[C@@H]1CC[C@H]1CN1C[C@@]2(CCCc3cc(Cl)ccc32)COc2ccc(S(N)(=O)=O)cc21]

Step 1: [(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl] N,N-dimethylcarbamate

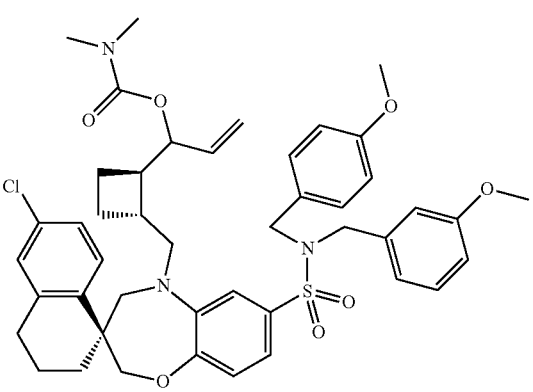 [SMILES: C=CC(OC(=O)N(C)C)[C@@H]1CC[C@H]1CN1C[C@@]2(CCCc3cc(Cl)ccc32)COc2ccc(S(=O)(=O)N(Cc3ccc(OC)cc3)Cc3cccc(OC)c3)cc21]

To a stirred solution of (3S)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-tetralin]-7-sulfonamide (0.8 g, 1.08 mmol, Intermediate 3 and 4, Step 4, P1) in THF (10 mL)/Toluene (10 mL) was added N,N-dimethylcarbamoyl chloride (1.16 g, 10.7 mmol). The resulting mixture was cooled to −78° C. and KHMDS (8.15 mL, 0.5 M in Toluene) was added dropwise over 10 min. The reaction was stirred at −78° C. for 10 min. Then the solution was slowly warmed up to r.t. and stirred for 1 h. LC-MS showed the consumption of starting material and the formation of desired product. The reaction was quenched with saturated ammonium chloride solution (20 mL) and extracted with EtOAc (20 mL×3). The combined organic layers were dried over sodium sulfate, filtered and concentrated under reduced pressure. The residue was purified by flash chromatography on a silica gel column (20 g) using EtOAc/Heptanes (10% to 60%) to afford [(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl] N,N- dimethylcarbamate (0.69 g, 78% yield) as a white solid. LC-MS calc. for $C_{45}H_{53}ClN_3O_7S$ [M+H]⁺: m/z=814.3/816.3; Found: 814.8/816.9.

Step 2. [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate This compound was prepared using procedures analogous to those described for Intermediate 5 Step 2. LC-MS calc. for $C_{29}H_{37}ClN_3O_5S$ [M+H]⁺: m/z=574.2/576.2; Found: 574.6/576.5.

Intermediate 10

[(1R)-1-[(1R,2R)-2-[[(3S)-6'-Chloro-7-sulfamoyl-spiro[2,4-dihydro-1,5-benzoxazepine-3,1'-tetralin]-5-yl]methyl]cyclobutyl]allyl] N,N-dimethylcarbamate

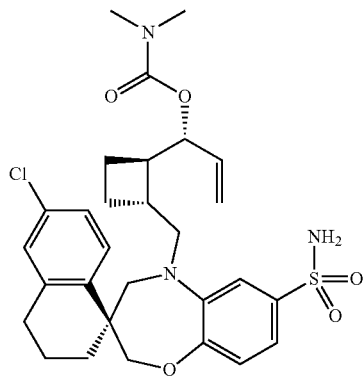 [SMILES: C=C[C@@H](OC(=O)N(C)C)[C@@H]1CC[C@H]1CN1C[C@@]2(CCCc3cc(Cl)ccc32)COc2ccc(S(N)(=O)=O)cc21]

Step 1: [(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl] N,N-dimethylcarbamate

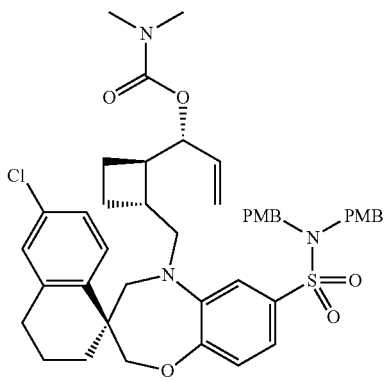

This compound was prepared using procedures analogous to those described for Intermediate 9 Step 1 using (3S)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Intermediate 3 and 4, Step 4 P2) and N,N-dimethylcarbamoyl chloride. LC-MS calc. for $C_{45}H_{53}ClN_3O_7S$ [M+H]⁺: m/z=814.3/816.3; Found: 814.7/816.1.

Step 2: [(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate

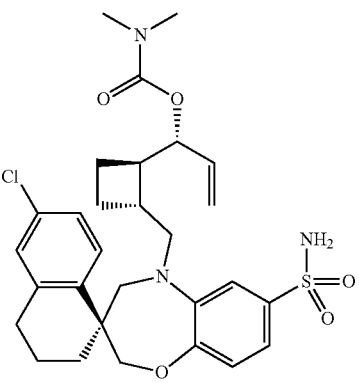 [SMILES: C=C[C@@H](OC(=O)N(C)C)[C@@H]1CC[C@H]1CN1C[C@@]2(CCCc3cc(Cl)ccc32)COc2ccc(S(N)(=O)=O)cc21]

This compound was prepared using procedures analogous to those described for Intermediate 5 Step 2. LC-MS calc. for $C_{29}H_{37}ClN_3O_5S$ [M+H]⁺: m/z=574.2/576.2; Found: 574.8/576.7.

Intermediate 11

(S)-7'-Chloro-N,N-bis(4-methoxybenzyl)-4,5-dihydro-2H-spiro[benzo[b][1,4]oxazepine-3,4'-chromane]-7-sulfonamide

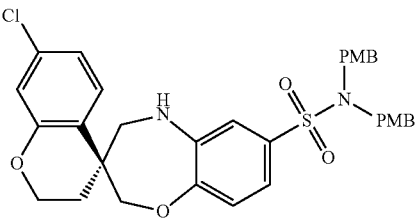

Step 1: (2-(2-bromo-5-chlorophenoxy)ethoxy)(tert-butyl)dimethylsilane

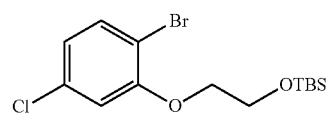 [SMILES: CC(C)(C)[Si](C)(C)OCCOc1cc(Cl)ccc1Br]

To a solution of 2-bromo-5-chlorophenol (20.0 g, 96.4 mmol) in NMP (100 mL) was added $K_2CO_3$ (26.6 g, 192 mmol) and 2-bromoethoxy-tert-butyldimethylsilane (22.7 mL, 106 mmol). The resulting suspension was stirred at 90° C. for 5 h. After cooling to r.t., the suspension was diluted with water (150 mL), and extracted with ethyl acetate (3×150 mL). The combined organic layers were washed with water (150 mL), brine (150 mL) and dried over Na₂SO₄, filtered and concentrated under reduced pressure. The residue was purified by column chromatography on a silica gel column with PE/EA (5%) to afford 2-(2-bromo-5-chloro-phenoxy)ethoxy-tert-butyl-dimethyl-silane (32 g, 90% yield) as light yellow oil. ¹H NMR (400 MHz, DMSO-d₆) δ 7.58 (d, J=8.4 Hz, 1H), 7.24 (d, J=2.4 Hz, 1H), 6.95 (dd, J=8.4, 2.4 Hz, 1H), 4.18-4.16 (m, 2H), 3.94-3.93 (m, 2H), 0.86 (s, 9H), 0.06 (s, 6H).

Step 2: diethyl 2-(2-(2-((tert-butyldimethylsilyl)oxy)ethoxy)-4-chlorophenyl)malonate

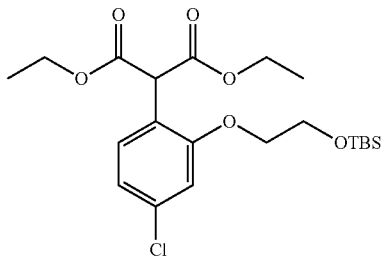 [SMILES: CCOC(=O)C(C(=O)OCC)c1ccc(Cl)cc1OCCO[Si](C)(C)C(C)(C)C]

To a suspension of K₃PO₄ (21.35 g, 100.6 mmol) and bis(tri-tert-butylphosphine)palladium(0) (1.70 g, 3.34 mmol) in toluene (100 mL), was added 2-(2-bromo-5-chloro-phenoxy)ethoxy-tert-butyl-dimethyl-silane (12.2 g, 33.3 mmol), followed by the addition of diethyl malonate (10.68 g, 66.7 mmol). The resulting suspension was heated at 85° C. for 6 h. under an atmosphere of argon, and then cooled to r.t. The mixture was filtered through a pad of Celite and the filtrate was concentrated under reduced pressure. The residue was purified by column chromatography on a silica gel column with Hexane/EA (0-10%) to afford diethyl 2-[2-[2-[tert-butyl(dimethyl)silyl]oxyethoxy]-4-chloro-phenyl]propanedioate (7.3 g, 49.2% yield) as a clear oil. ¹H NMR: (400 MHz, CDCl₃) δ 7.30 (d, J=8.2 Hz, 1H), 6.96 (dd, J=8.3, 2.0 Hz, 1H), 6.92 (d, J=2.0 Hz, 1H), 5.11 (s, 1H), 4.27-4.15 (m, 4H), 4.04 (t, J=5.0 Hz, 2H), 3.94 (t, J=5.1 Hz, 2H), 1.26 (t, J=7.2 Hz, 6H), 0.91 (s, 9H), 0.09 (s, 6H).

Step 3: diethyl 7-chlorochromane-4,4-dicarboxylate

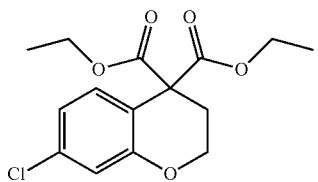 [SMILES: CCOC(=O)C1(C(=O)OCC)CCOc2cc(Cl)ccc21]

To a solution of diethyl 2-[2-[2-[tert-butyl(dimethyl)silyl]oxyethoxy]-4-chloro-phenyl]propanedioate (9.53 g, 21.4 mmol) and DBU (6.52 g, 42.8 mmol) in MeCN (200 mL) under N₂ atmosphere was added 4-nitrobenzenesulfonyl fluoride (8.79 g, 42.8 mmol). The resulting solution was stirred at 70° C. for 24 h. After cooling, the solution was concentrated at 35° C. under reduced pressure to remove MeCN. The residue was diluted with water (120 mL) and extracted with ethyl acetate (3×100 mL). The combined organic layers were washed with water (100 mL), 1 N HCl (100 mL), followed by NaHCO₃ (500 mL) solution and brine (100 mL). The organic layers were dried over Na₂SO₄, filtered, and concentrated under reduced pressure. The residue was purified by column chromatography on a silica gel column with Hexane/EA (0-10%) (R_f=0.4 in 10% ethyl acetate in hexane) to afford diethyl 7-chlorochromane-4,4-dicarboxylate (7.400 g, 110.5% yield). ¹H NMR: (400 MHz, CDCl₃) δ 7.36 (d, J=8.4 Hz, 1H), 6.90 (dd, J=2.0 Hz, 8.4 Hz, 1H), 6.86 (d, J=2.4 Hz, 1H), 4.28-4.19 (m, 6H), 2.54-2.51 (m, 2H), 1.27 (t, J=7.2 Hz, 6H).

Step 4: [7-chloro-4-(hydroxymethyl)chroman-4-yl]methanol

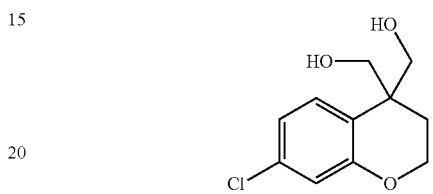

To a solution of diethyl 7-chlorochromane-4,4-dicarboxylate (6.30 g, 20.1 mmol) in THF (25 mL) was added diisobutylaluminum hydride (201.4 mL, 201 mmol, 1 M in THF) dropwise at 0° C. The reaction mixture was stirred at r.t. for 18 h. Then it was quenched by the addition of saturated solution of NH₄Cl (200 mL) and extracted with ethyl acetate (3×280 mL). The combined organic layers were concentrated under reduced pressure. The crude material was dissolved in THF (100 mL) and water (200 mL), and sodium borohydride (4.4 g, 114.8 mmol) was added. The reaction was stirred at r.t. for 3 h., and then quenched with saturated NH₄Cl solution (75 mL). The mixture was extracted with ethyl acetate (2×60 mL). The combined organic layers were dried over sodium sulfate, filtered and concentrated under reduced pressure. The residue was purified by column chromatography on a silica gel column with Hexane/EA (0-70%) to afford [7-chloro-4-(hydroxymethyl)chroman-4-yl]methanol (2.80 g, 61% yield). ¹H NMR: (400 MHz, CDCl₃) δ 7.23 (d, J=9.2 Hz, 1H), 6.87-6.85 (m, 2H), 4.21 (t, J=5.2 Hz, 2H), 3.97 (d, J=10.8 Hz, 2H), 3.78 (d, J=10.8 Hz, 2H), 2.09 (t, J=5.2 Hz, 2H).

Step 5: (S)-(7-chloro-4-(hydroxymethyl)chroman-4-yl)methyl 4-bromobenzoate

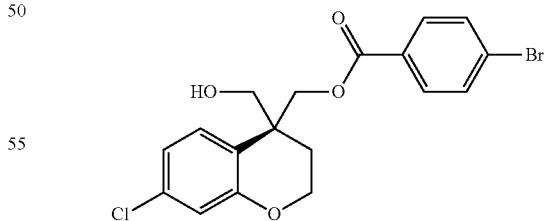

To a solution of 2,6-bis((R)-5,5-dibutyl-4-phenyl-4,5-dihydrooxazol-2-yl)pyridine (934 mg, 1.57 mmol) in dry DCM (3 mL) was added CuCl₂ (211 mg, 1.57 mmol) and the resulting green solution was stirred at r.t. for 3 h. This solution was added to a solution of [7-chloro-4-(hydroxymethyl)chroman-4-yl]methanol (3.60 g, 15.74 mmol) in dry DCM (60 mL). The resulting solution was cooled to −78° C. A solution of 4-bromobenzoyl chloride (4.15 g, 18.8 mmol)

in DCM (5 mL) was then added slowly, followed by the dropwise addition of DIPEA (3.29 mL, 18.8 mmol). The resulting reaction mixture was stirred at −78° C. for 2 h. and then quenched with $KH_2PO_4/H_3PO_4$ buffer solution (70 mL, pH~3). The reaction was diluted with ethyl acetate (150 mL) and the layers were separated. The organic phase was washed with pH~3 buffer (1×50 mL), saturated $NaHCO_3$ (2×50 mL) and brine (1×50 mL), dried over sodium sulfate, filtered and concentrated under reduced pressure The residue was purified by column chromatography on a silica gel column eiuting with 100% DCM to afford [(4S)-7-chloro-4-(hydroxymethyl)chroman-4-yl]methyl 4-bromobenzoate (4.10 g, 63% yield) (e.r.=92:8). The chiral HPLC: Chiral Column: AD, 2.5 um, 3.0 mm×150 mm; Mobile phase A: Supercritical $CO_2$, Mobile phase B: MeOH (with 0.1% DEA), A:B=50:50; Run time: 20 min.; Detector Wavelength: 254 nm, Instrument: Waters Acouity $UPC^2$. $^1H$ NMR: (400 MHz, $CDCl_3$) δ 7.86 (d, J=8.0 Hz, 1H), 7.84 (s, 1H), 7.60 (d, J=8.4 Hz, 2H), 7.32 (d, J=8.0 Hz, 1H), 6.88 (d, J=8.4 Hz, 2H), 4.53 (d, J=6.0 Hz, 2H), 4.23 (d, J=6.0 Hz, 2H), 3.80 (s, 2H), 2.16-2.09 (m, 1H), 2.02-1.97 (m, 1H).

Step 6: (R)-(7-chloro-4-formylchroman-4-yl)methyl 4-bromobenzoate (GXL002-55-1)

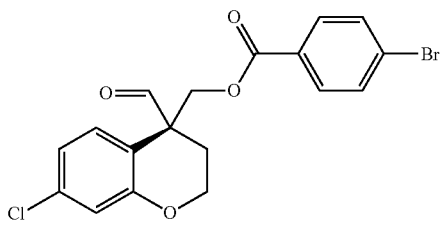 [SMILES: O=C[C@]1(COC(=O)c2ccc(Br)cc2)CCOc2cc(Cl)ccc21]

Dess-Martin periodinane (5.07 g, 11.95 mmol) was added to a stirring solution of [(4S)-7-chloro-4-(hydroxymethyl)chroman-4-yl]methyl 4-bromobenzoate (4.10 g, 9.96 mmol) in DCM (130 mL) at 10° C. After addition, the cooling bath was removed and the reaction mixture was stirred for 30 min. at ambient temperature. Water (17 ml) was then added slowly and the reaction mixture was stirred further at ambient temperature for 30 min. The reaction was cooled to 0° C., quenched with a 1:1 mixture of 10% $Na_2S_2O_3$ and saturated $NaHCO_3$ (20 mL) solution and stirred further at r.t. for 1 h. The solution was then diluted with ethyl acetate (700 mL) and the aqueous phase was separated. The organic phase was washed with 1:1 mixture of 10% $Na_2S_2O_3$/saturated $NaHCO_3$ solution (200 mL) and brine (20 mL), dried over sodium sulfate, filtered, and concentrated under reduced pressure The residue was purified by column chromatography on a silica gel column with eluting with ethylacetate in hexanes (10%) to afford [(4R)-7-chloro-4-formyl-chroman-4-yl]methyl 4-bromobenzoate (3.0 g, 73% yield). $^1H$ NMR: (400 MHz, $CDCl_3$) δ 9.60 (s, 1H), 77.81 (d, J=6.8 Hz, 2H) 7.58 (d, J=8.4 Hz, 2H), 7.13 (dd, J=1.2 Hz, 7.6 Hz, 1H), 6.94 (d, J=8.4 Hz, 2H), 4.84 (d, J=11.2 Hz, 1H), 4.54 (d, J=11.2 Hz, 1H), 4.27-4.24 (m, 2H), 2.52-2.46 (m, 1H), 2.12-2.06 (m, 1H).

Step 7: (R)-(7-chloro-4-(dimethoxymethyl)chroman-4-yl)methyl 4-bromobenzoate

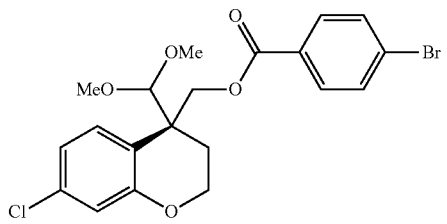 [SMILES: COC(OC)[C@]1(COC(=O)c2ccc(Br)cc2)CCOc2cc(Cl)ccc21]

To a mixture of [(4R)-7-chloro-4-formyl-chroman-4-yl] methyl 4-bromobenzoate (3.0 g, 7.3 mmol) and trimethyl orthoformate (2.33 g, 21.9 mmol) in anhydrous MeOH (10 mL) was added p-toluenesulfonic acid (63 mg, 0.37 mmol). The reaction was refluxed for 6 h., and concentrated under reduced pressure. The residue was purified by column chromatography on a silica gel column with eluting with ethyl acetate/hexane (10%) to afford [(4R)-7-chloro-4-(dimethoxymethyl)chroman-4-yl]methyl 4-bromobenzoate (2.5 g, 74% yield) as a colorless oil. $^1H$ NMR (400 MHz, $CDCl_3$) δ 7.75 (d, J=8.4 Hz, 1H), 7.74 (s, 1H), 7.56 (d, J=8.4 Hz, 2H), 7.37 (d, J=8.4 Hz, 1H), 6.87-6.83 (m, 1H), 6.51 (d, J=4.4 Hz, 1H), 4.53-4.49 (m, 2H), 4.32-4.29 (m, 1H), 4.20-4.18 (m, 1H), 3.45 (s, 3H), 3.30 (s, 3H), 2.34-2.29 (m, 1H), 2.02-1.97 (m, 1H).

Step 8: (R)-(7-chloro-4-(dimethoxymethyl)chroman-4-yl)methanol

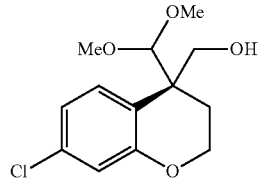 [SMILES: COC(OC)[C@]1(CO)CCOc2cc(Cl)ccc21]

To a mixture of [(4R)-7-chloro-4-(dimethoxymethyl) chroman-4-yl]methyl 4-bromobenzoate (2.50 g, 5.49 mmol) in water (17 mL) and THF (34 mL) was added NaOH (658 mg, 16.4 mmol). The resulting mixture was stirred at r.t. overnight, and then concentrated under reduced pressure. The residue was diluted with EtOAc (50 mL) and washed with water (10 mL), 1 N NaOH (10 mL), water (10 mL) and brine. The organic layer was dried over sodium sulfate, filtered and concentrated under reduced pressure. The residue was purified by column chromatography on a silica gel column eluting with PE:EA (2:1) to afford [(4R)-7-chloro-4-(dimethoxymethyl)chroman-4-yl]methanol (1.50 g, 100% yield) as a colorless oil. $^1H$ NMR (400 MHz, $CDCl_3$) δ 7.28-7.26 (m, 1H), 6.86-6.84 (m, 2H), 4.48 (s, 1H), 4.29-4.23 (m, 1H), 4.66-4.11 (m, 1H), 3.98 (d, J=11.2 Hz, 1H), 3.56 (d, J=11.2 Hz, 1H), 3.48 (s, 3H), 3.36 (s, 3H), 2.26-2.20 (m, 1H), 2.08-1.97 (m, 1H).

Step 9: N,N-bis[(4-methoxyphenyl)methyl]-3-nitro-4-[[(4R)-7-chloro-4-(dimethoxymethyl)chroman-4-yl]methoxy]benzenesulfinamide

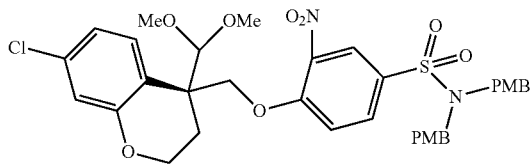

To a solution of [(4R)-7-chloro-4-(dimethoxymethyl)chroman-4-yl]methanol (1.50 g, 5.5 mmol) in anhydrous THF (50 mL) was added KOBu-t (1.23 g, 11 mmol). After stirring for 5 min at r.t., a solution of 4-fluoro-N,N-bis[(4-methoxyphenyl)methyl]-3-nitro-benzenesulfonamide (3.04 g, 6.6 mmol, Intermediate 2 Step 1) in THF (30 mL) was added dropwise and the resulting mixture was stirred at r.t. for 3 h. The reaction was quenched with saturated NH$_4$Cl solution (50 mL) and extracted with ethyl acetate (3×100 mL). The combined organic layers were washed with NH$_4$Cl (50 mL) and brine (50 mL), dried over sodium sulfate, filtered and concentrated under reduced pressure. The residue was purified by column chromatography on a silica gel column eluting with ethyl acetate/hexane (20%) to afford N,N-bis[(4-methoxyphenyl)methyl]-3-nitro-4-[[(4R)-7-chloro-4-(dimethoxymethyl)chroman-4-yl]methoxy]benzenesulfonamide (3.35 g, 85% yield) as a yellow semi-solid. $^1$H NMR (400 MHz, CDCl$_3$) δ 8.04 (d, J=2.4 Hz, 1H), 7.78 (dd, J=2.4, 8.8 Hz, 1H), 7.51 (d, J=8.8 Hz, 1H), 7.00-6.97 (m, 5H), 6.82-6.79 (m, 2H), 6.73-6.70 (m, 4H), 4.68 (s, 1H), 4.28-4.21 (m, 8H), 3.72 (s, 6H), 3.42 (s, 3H), 3.25 (s, 3H), 2.31-2.25 (m, 1H), 1.97-1.84 (m, 1H).

Step 10: (R)-4-((7-chloro-4-formylchroman-4-yl)methoxy)-N,N-bis(4-methoxybenzyl)-3-nitrobenzenesulfonamide

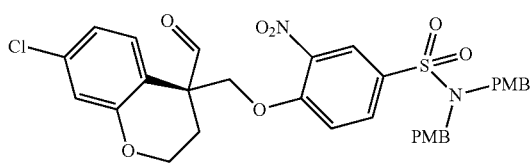

To a solution of N,N-bis[(4-methoxyphenyl)methyl]-3-nitro-4-[[(4R)-7-chloro-4-(dimethoxymethyl)chroman-4-yl]methoxy]benzenesulfonamide (3.35 g, 4.7 mmol) in 1,4-Dioxane (50 mL) and water (17 mL) was added TsOH (1.79 g, 9.39 mmol). The resulting solution was stirred at 105° C. overnight. The reaction was diluted with ethyl acetate (50 mL) and washed with sat. NaHCO$_3$ solution (15 mL), water (15 mL) and brine (15 mL). The organic layer was dried over Na$_2$SO$_4$, filtered and concentrated under reduced pressure. The residue was purified by column chromatography on a silica gel column eluting with PE:EA (2:1) to afford N,N-bis[(4-methoxyphenyl)methyl]-3-nitro-4-[[(4R)-7-chloro-4-formyl-chroman-4-yl]methoxy]benzenesulfonamide (2.50 g, 79% yield) as a yellow oil. $^1$H NMR (400 MHz, CDCl$_3$) δ 9.51 (s, 1H), 8.09 (d, J=2.4 Hz, 1H), 6.89-7.86 (m, 1H), 7.12 (d, J=9.2 Hz, 1H), 7.08-7.03 (m, 5H), 6.99-6.93 (m, 2H), 6.81-6.78 (m, 4H), 4.71 (d, J=9.2 Hz, 1H), 4.37-4.35 (m, 1H), 4.30-4.23 (m, 6H), 3.79 (s, 6H), 2.54-2.47 (m, 1H), 2.42-2.36 (m, 1H).

Step 11: (S)-7'-chloro-N,N-bis(4-methoxybenzyl)-4,5-dihydro-2H-spiro[benzo[b][1,4]oxazepine-3,4'-chromane]-7-sulfonamide

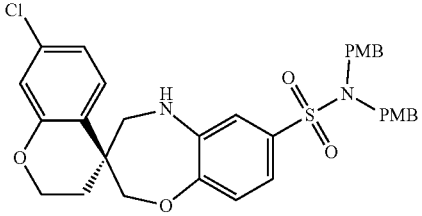

To a solution of N,N-bis[(4-methoxyphenyl)methyl]-3-nitro-4-[[(4R)-7-chloro-4-formyl-chroman-4-yl]methoxy]benzenesulfonamide (2.50 g, 3.75 mmol) and NH$_4$Cl (1.99 g, 37.4 mmol) in ethanol (30 mL) was added zinc (2.45 g, 37.4 mmol) and the resulting solution was stirred at 80° C. under N$_2$ atmosphere overnight. After cooling, the mixture was filtered through a pad of celite. The filtrate was concentrated under reduced pressure. The residue was purified by column chromatography on a silica gel column eluting with PE:EA (2:1) to afford (3S)-7'-chloro-N,N-bis[(4-methoxyphenyl)methyl]spiro[4,5-dihydro-2H-1,5-benzoxazepine-3,4'-chromane]-7-sulfonamide (1.44 g, 58% yield) as a white solid. LC-MS calc. for C$_{33}$H$_{34}$ClN$_2$O$_6$S [M+H]$^+$: m/z=621.17/623.17; Found: 621.2/623.2. $^1$H NMR (400 MHz, CDCl$_3$) δ 7.71 (d, J=8.4 Hz, 1H), 7.21-7.18 (m, 1H), 7.04-6.93 (m, 6H), 6.91 (m, 1H), 6.85 (d, J=2.4 Hz, 1H), 6.78-6.75 (m, 4H), 4.23-4.10 (m, 8H), 3.78 (s, 6H), 3.53 (d, J=12.8 Hz, 1H), 3.40 (d, J=12.8 Hz, 1H), 2.05-2.00 (m, 1H), 1.96-1.92 (m, 1H).

Intermediate 12

(3S)-7'-Chloro-5-[[(1R,2R)-2-[(1S)-1-hydroxyallyl]cyclobutyl]methyl]spiro[2,4-dihydro-1,5-benzoxazepine-3,4'-chromane]-7-sulfonamide And Intermediate 13

(3S)-7'-chloro-5-[[(1R,2R)-2-[(1R)-1-hydroxyallyl]cyclobutyl]methyl]spiro[2,4-dihydro-1,5-benzoxazepine-3,4'-chromane]-7-sulfonamide Intermediate 12

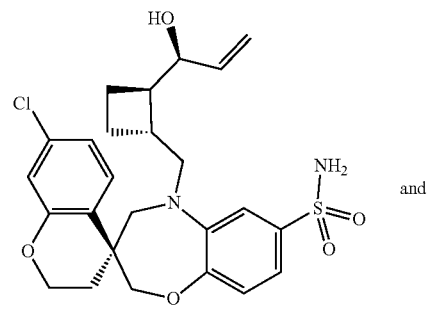

and

Intermediate 13

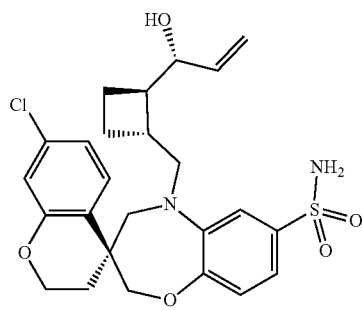

Step 1: (3S)-7'-chloro-N,N-bis[(4-methoxyphenyl)methyl]-5-[[(1R,2R)-2-formylcyclobutyl]methyl]spiro[2,4-dihydro-1,5-benzoxazepine-3,4'-chromane]-7-sulfonamide

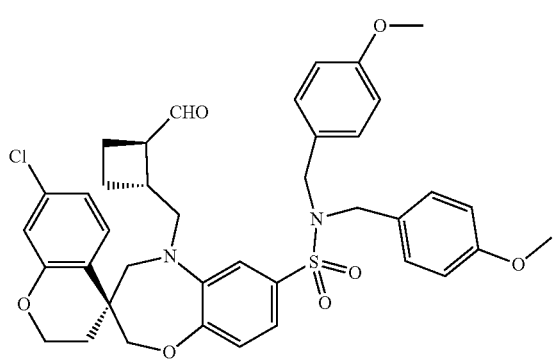 [SMILES: COc1ccc(CN(Cc2ccc(OC)cc2)S(=O)(=O)c2ccc3c(c2)N(C[C@@H]2CC[C@H]2C=O)C[C@@]2(CCOc4cc(Cl)ccc42)CO3)cc1]

This compound was prepared using procedures analogous to those described for Intermediate 3 Step 1-3 using (3S)-7'-chloro-N,N-bis[(4-methoxyphenyl)methyl]spiro[4,5-dihydro-2H-1,5-benzoxazepine-3,4'-chromane]-7-sulfonamide (Intermediate 11) and [(1R,2R)-2-formylcyclobutyl]methyl acetate in Step 1. LC-MS: calc. for $C_{39}H_{42}ClN_2O_7S$ [M+H]$^+$: m/z=717.3/719.3; Found: 717.4/719.2.

Step 2. (3S)-7'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,4'-chromane]-7-sulfonamide and (3S)-7'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,4'-chromane]-7-sulfonamide

P1

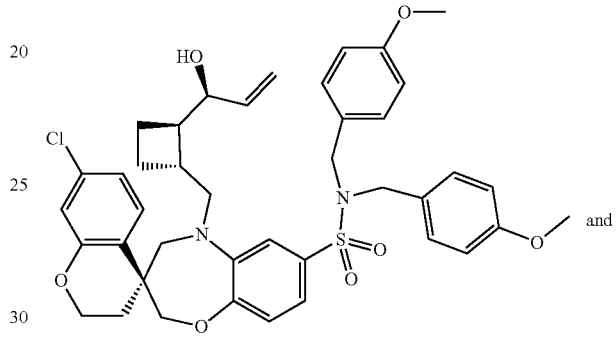

and

P2

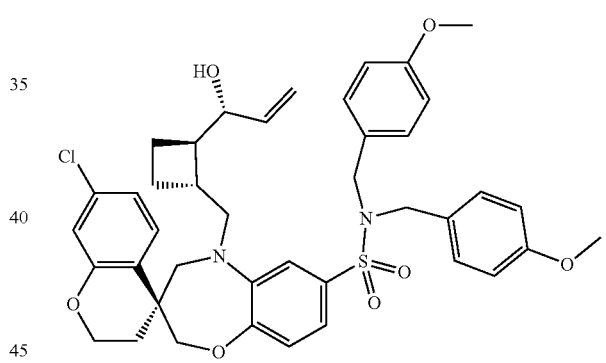

This compound was prepared using procedures analogous to those described for Intermediate 3 Step 4 using vinylmagnesium bromide (1.0 M solution THF solution). The reaction was quenched with sat. NH$_4$Cl solution (300 mL) and extracted with (EA 300 mL×3). The organic layer was concentrated and purified by flash chromatography on a silica gel column eluting with EA/Hep (20% to 50%) to afford the two products: P1 (the earlier eluted product) which was assigned to (3S)-7'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,4'-chromane]-7-sulfonamide. LC-MS calc. for $C_{41}H_{46}ClN_2O_7S$ [M+H]$^+$: m/z=745.3/747.3; Found: 745.5/747.4.

And P2 (the latter eluted product) was assigned to (3S)-7'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,4'-chromane]-7-sulfonamide. LC-MS calc. for $C_{41}H_{46}ClN_2O_7S$ [M+H]$^+$: m/z=745.3/747.3; Found: 745.5/747.4.

Step 3. (3S)-7'-chloro-5-[[(1R,2R)-2-[(1S)-1-hydroxyallyl]cyclobutyl]methyl]spiro[2,4-dihydro-1,5-benzoxazepine-3,4'-chromane]-7-sulfonamide (Intermediate 12)

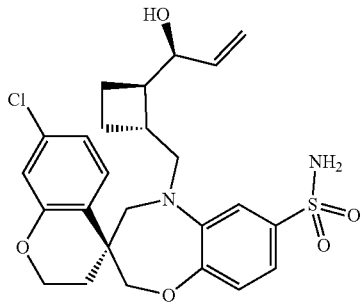 [SMILES: C=C[C@H](O)[C@@H]1CC[C@H]1CN1C[C@@]2(CCOc3cc(Cl)ccc32)COc2ccc(S(N)(=O)=O)cc21]

This compound was prepared using procedures analogous to those described for Intermediate 3 Step 5 using (3S)-7'-chloro-5-[[(1R,2R)-2-[(1S)-1-hydroxyallyl]cyclobutyl]methyl]-N,N-bis[(4-methoxyphenyl)methyl]spiro[2,4-dihydro-1,5-benzoxazepine-3,4'-chromane]-7-sulfonamide (P1 Step 2). LC-MS: calcd. for $C_{25}H_{30}ClN_2O_5S$ [M+H]$^+$: m/z=505.0/507.0; Found: 505.1/507.0.

Step 4. (3S)-7'-chloro-5-[[(1R,2R)-2-[(1R)-1-hydroxyallyl]cyclobutyl]methyl]spiro[2,4-dihydro-1,5-benzoxazepine-3,4'-chromane]-7-sulfonamide (Intermediate 13)

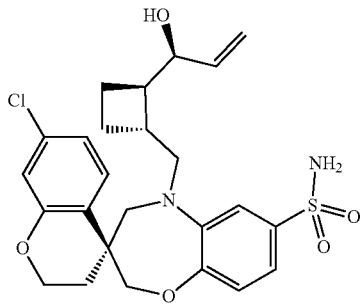 [SMILES: C=C[C@H](O)[C@@H]1CC[C@H]1CN1C[C@@]2(CCOc3cc(Cl)ccc32)COc2ccc(S(N)(=O)=O)cc21]

This compound was prepared using procedures analogous to those described for Intermediate 3 Step 5 using (3S)-7'-chloro-5-[[(1R,2R)-2-[(1R)-1-hydroxyallyl]cyclobutyl]methyl]-N,N-bis[(4-methoxyphenyl)methyl]spiro[2,4-dihydro-1,5-benzoxazepine-3,4'-chromane]-7-sulfonamide (P2 Step 2). LC-MS: calc. for $C_{25}H_{30}ClN_2O_5S$ [M+H]$^+$: m/z=505.0/507.0; Found: 505.1/507.0.

Intermediate 14

(R)-6'-Chloro-N,N-bis(4-methoxybenzyl)-4,5-dihydro-2H-spiro[benzo[b][1,4]oxazepine-3,1'-isochroman]-7-sulfonamide

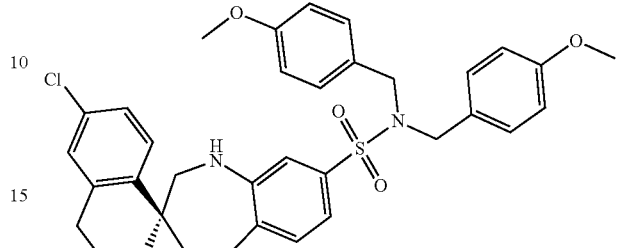

Step 1: 2-(2-bromo-5-chlorophenyl)ethanol (LGY001-54-1)

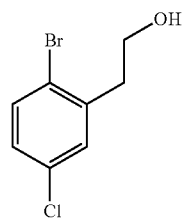 [SMILES: OCCc1cc(Cl)ccc1Br]

To a suspension of 2-(2-bromo-5-chloro-phenyl)acetic acid (60.0 g, 240 mmol) in THF (300 mL) was added BH$_3$-THF (760 mL, 760 mmol) at 0° C. The reaction mixture was stirred at 25° C. for 4 h., and then quenched by MeOH (300 mL) under N$_2$ at 0° C. The mixture was concentrated to give crude product which was diluted with DCM (100 mL) and washed with 1 M HCl and brine. The organic layer was dried over anhydrous Na$_2$SO$_4$, filtered and concentrated under reduce pressure to afforded 2-(2-bromo-5-chloro-phenyl)ethanol (60 g, 84% yield) as a colorless oil which was used for the next step directly. $^1$H NMR: (400 MHz, CDCl$_3$) δ 7.46 (d, J=8.4 Hz, 1H), 7.27 (d, J=2.8 Hz, 1H), 7.07 (dd, J=2.8 Hz, 8.8 Hz, 1H), 3.86 (t, J=6.4 Hz, 2H), 2.97 (t, J=6.4 Hz, 2H), 1.88 (s, 1H).

Step 2. (2-bromo-5-chlorophenethoxy)(tert-butyl)dimethylsilane

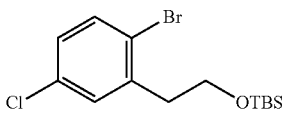 [SMILES: CC(C)(C)[Si](C)(C)OCCc1cc(Cl)ccc1Br]

tert-Butylchlorodimethylsilane (25.34 g, 168 mmol) was slowly added to a solution of imidazole (17.34 g, 254 mmol) and 2-(2-bromo-5-chloro-phenyl)ethanol (60.0 g, 254 mmol) in dry DCM (400 mL) at 0° C. over 30 min. After addition, the reaction mixture was stirred at r.t. for 18 h., and treated with 5% of NaHCO$_3$ aqueous. The mixture was extracted with EA (200 mL×3). The combined organic layers were washed with brine (100 mL), dried over anhydrous Na$_2$SO$_4$, filtered and concentrated under reduced pressure. The residue was purified by column chromatography on a silica gel column eluting with PE:EA (0-10%) to give 2-(2-bromo-5-chloro-phenyl)ethoxy-tert-butyl-dimethyl-silane (61 g, 68% yield) as an colorless oil. ¹H NMR (400 MHz, CDCl₃) δ 7.48 (d, J=8.4 Hz, 1H), 7.30 (d, J=2.8 Hz, 1H), 7.09 (dd, J=8.4, 2.8 Hz, 1H), 3.85 (t, J=6.4 Hz, 2H), 2.97 (t, J=6.4 Hz, 2H), 0.90 (s, 9H), 0.00 (s, 6H).

Step 3: 5-(2-(2-((tert-butyldimethylsilyl)oxy)ethyl)-4-chlorophenyl)-2,2-dimethyl-1,3-dioxan-5-ol

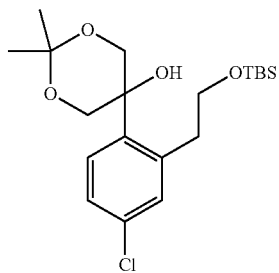 [SMILES: CC1(C)OCC(O)(c2ccc(Cl)cc2CCO[Si](C)(C)C(C)(C)C)CO1]

To a solution of 2-(2-bromo-5-chloro-phenyl)ethoxy-tert-butyl-dimethyl-silane (40.0 g, 114 mmol) in THF (400 mL) was added n-BuLi (54.8 mL, 137 mmol) (2.5 M in hexane) at −78° C. dropwised, and stirred at this temperature for 30 min. To the reaction mixture was added 2,2-dimethyl-1,3-dioxan-5-one (20.8 g, 160 mmol) in THF (15 mL), stirred at −78° C. to −15 OC for 4 h. The mixture was quenched by sat. NH₄Cl (150 mL), and extracted with EA (150 mL×3). The combined organic layers were dried over Na₂SO₄, filtered and concentrated under reduced pressure. The residue was purified by flash chromatography on a silica gel column eluting with PE/EA (2-10%) to give 5-[2-[2-[tert-butyl(dimethyl)silyl]oxyethyl]-4-chloro-phenyl]-2,2-dimethyl-1,3-dioxan-5-ol (30 g, 65% yield) as a colorless oil. ¹H NMR (400 MHz, CDCl₃) δ 7.65 (d, J=8.4 Hz, 1H), 7.33-7.18 (m, 2H), 4.84 (s, 1H), 4.18 (d, J=11.6 Hz, 2H), 4.03 (d, J=11.6 Hz, 2H), 3.97 (t, J=6.0 Hz, 2H), 3.24 (t, J=6.0 Hz, 2H), 1.62 (s, 3H), 1.52 (s, 3H), 0.88 (s, 9H), 0.01 (s, 6H).

Step 4: 5-(4-chloro-2-(2-hydroxyethyl)phenyl)-2,2-dimethyl-1,3-dioxan-5-ol (LGY001-75-1)

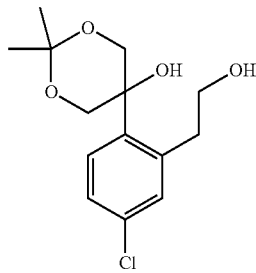 [SMILES: CC1(C)OCC(O)(c2ccc(Cl)cc2CCO)CO1]

To a solution of 5-[2-[2-[tert-butyl(dimethyl)silyl]oxyethyl]-4-chloro-phenyl]-2,2-dimethyl-1,3-dioxan-5-ol (30.0 g, 74.8 mmol) in THF (150 mL) was slowly added TBAF (97 mL, 97 mmol) (1 M in THF) at 0° C. After addition, the mixture was stirred at 25° C. for 1 h., and diluted with EtOAc (150 mL). The mixture was washed with brine (50 mL) and H₂O (50 mL×3), dried over Na₂SO₄, filtered and concentrated under reduced pressure. The residue was purified by flash chromatography on a silica gel column with PE/EA (10-50%) to give 5-(4-chloro-2-(2-hydroxyethyl)phenyl)-2,2-dimethyl-1,3-dioxan-5-ol (21 g, 97% yield) as a colorless oil. TLC (PE/EA=2/1, R_f=0.2). ¹H NMR (400 MHz, DMSO-d₆) δ 7.61 (d, J=8.4 Hz, 1H), 7.31 (d, J=2.4 Hz, 1H), 7.22 (dd, J=8.4, 2.4 Hz, 1H), 5.44 (s, 1H), 4.75 (t, J=5.0 Hz, 1H), 4.03 (d, J=11.6 Hz, 2H), 3.84 (d, J=11.6 Hz, 2H), 3.62 (dd, J=12.0, 6.8 Hz, 2H), 3.04 (t, J=6.8 Hz, 2H), 1.44 (s, 3H), 1.28 (s, 3H).

Step 5: 6'-chloro-2,2-dimethylspiro[[1,3]dioxane-5,1'-isochroman] (LGY001-80-1)

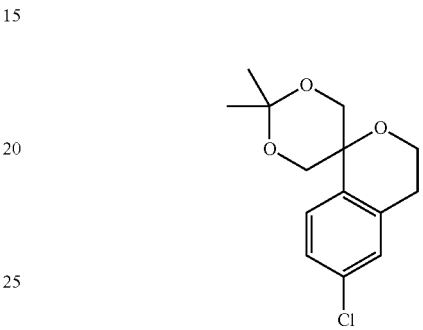

To a solution of 5-[4-chloro-2-(2-hydroxyethyl)phenyl]-2,2-dimethyl-1,3-dioxan-5-ol (42.0 g, 146 mmol) in THF (150 mL) was added Ph₃P (69.15 g, 263 mmol), and followed by DIAD (52.27 mL, 263.64 mmol) at 0° C. dropwise. The mixture was stirred at 0° C. for 1 h. and 25° C. for 2 h. The reaction was concentrated under reduced pressure. The residue was purified by flash chromatography on a silica gel column with PE/EA (5%) to give (27 g, 68.6% yield) as colorless oil. ¹H NMR (400 MHz, DMSO-d₆) δ 7.53 (d, J=8.4 Hz, 1H), 7.29-7.25 (m, 2H), 3.92 (d, J=12.4 Hz, 2H), 3.84 (t, J=5.6 Hz, 2H), 3.77 (d, J=12.4 Hz, 2H), 2.75 (t, J=5.6 Hz, 2H), 1.51 (s, 3H), 1.35 (s, 3H).

Step 6: (6-chloroisochroman-1,1-diyl)dimethanol (LGY001-82-1)

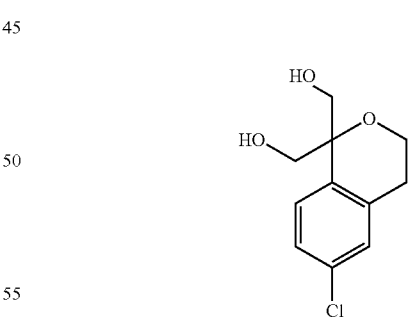

To a solution of 6'-chloro-2,2-dimethyl-spiro[1,3-dioxane-5,1'-isochromane] (17.0 g, 63.2 mmol) in methanol (25 mL) was added TsOH (0.6 g, 3.16 mmol) and stirred at 25° C. for 18 h. The mixture was quenched by NaHCO₃ aqueous (20 mL), and extracted with EtOAc (100 mL×3). The combined organic layers were washed with brine and water, dried over Na₂SO₄, filtered and concentrated under reduced pressure to give (6-chloroisochroman-1,1-diyl)dimethanol (7.6 g, 52.5% yield) as a white solid which was used for next step directly. TLC (silica gel, PE/EA=1/1, R.f.=0.4). ¹H NMR (400 MHz, CDCl₃) δ 7.20 (dd, J=8.4, 2.4 Hz, 1H), 7.16 (d, J=2.4 Hz, 1H), 7.10 (d, J=8.4 Hz, 1H), 4.01 (t, J=5.6 Hz, 1H), 3.91-3.83 (m, 4H), 2.84 (t, J=5.6 Hz, 1H), 2.20 (s, 2H).

Step 7: (R)-(6-chloro-1-(hydroxymethyl)isochroman-1-yl)methyl 4-bromobenzoate (LGY001-98-1)

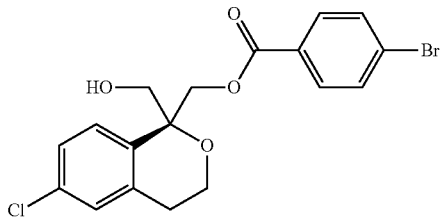 [SMILES: O=C(OC[C@@]1(CO)OCCc2cc(Cl)ccc21)c1ccc(Br)cc1]

To a solution of R,R-Kang catalyst (2,6-bis((R)-5,5-dibutyl-4-phenyl-4,5-dihydrooxazol-2-yl)pyridine) (908.93 mg, 1.53 mmol) in dry DCM (25 mL) was added Copper(II) chloride (205.79 mg, 1.53 mmol). The resulting green solution was stirred at ambient temperature for 3 h. This solution was transferred via cannula to a solution of 4-bromobenzoyl chloride (5.76 g, 26.2 mmol) in dry DCM (25 mL). The resulting solution was cooled to −78° C. and light green colored precipitation was observed in the reaction after some time. A solution of [6-chloro-1-(hydroxymethyl)isochroman-1-yl]methanol (5.0 g, 21.87 mmol)) in DCM (25 mL) was then added slowly (over 10 min.), followed by the dropwise addition of DIPEA (3.81 mL, 21.8 mmol). The resulting mixture was stirred at −78° C. for 2 h., and quenched by KH₂PO₄ sat. aqueous solution (100 mL) and allowed to warm to ambient temperature with vigorous stirring. The reaction was diluted with ethyl acetate (400 mL) and the layers were separated. The organic phase was washed with pH~3 buffer (1×50 mL), saturated NaHCO₃ (2×100 mL), and brine (100 mL), dried over sodium sulfate, filtered and concentrated under reduced pressure The crude material was purified by flash chromatography on a silica gel column eluting with EA/PE (5-10%) to give (R)-(6-chloro-1-(hydroxymethyl)isochroman-1-yl)methyl 4-bromobenzoate (5.1 g, 56% yield). The chiral HPLC showed (e.e=93%): Chiral Column: AD, 2.5 um, 3.0 mm×150 mm; Mobile phase A: Supercritical CO₂, Mobile phase B: MeOH (with 0.1% DEA), A:B=50:50; Run time: 18 min.; Detector Wavelength: 254 nm, Instrument: Waters Acouity UPC². ¹H NMR (400 MHz, CDCl₃) δ 7.79 (d, J=8.4 Hz, 2H), 7.57 (d, J=8.4 Hz, 2H), 7.26-7.16 (m, 3H), 4.72 (d, J=12.0 Hz, 1H), 4.56 (d, J=12.0 Hz, 1H), 4.13-3.96 (m, 2H), 3.98-3.84 (m, 2H), 2.88-2.78 (m, 2H).

Step 8: (S)-(6-chloro-1-formylisochroman-1-yl)methyl 4-bromobenzoate (LGY001-100-1)

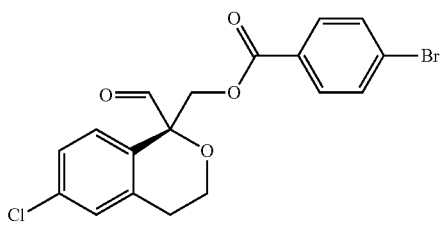

To a solution of (R)-(6-chloro-1-(hydroxymethyl)isochroman-1-yl)methyl 4-bromobenzoate (2.6 g, 6.32 mmol) in DCM (35 mL) was added Dess-Martin periodinane (3.48 g, 8.21 mmol) at 10° C. After addition, the cooling bath was removed. The reaction mixture was stirred for 2 h. at ambient temperature. The reaction was then cooled to 0° C., and diluted with ethyl acetate (100 mL), quenched with a 1:1 mixture of 10% Na₂S₂O₃ and saturated NaHCO₃ (100 mL) solution and stirred at r.t. for an additional 0.5 h. The aqueous phase was separated. The organic phase was washed with brine (100 mL), dried over sodium sulfate, filtered, and concentrated under reduced pressure. The crude material was purified by flash chromatography on a silica gel column eluting with ethyl acetate in hexanes (10%) to afforded [(S)-6-chloro-1-formyl-isochroman-1-yl]methyl 4-bromobenzoate (2.00 g, 77% yield) as light yellow oil. R_f=0.5 in 10% ethyl acetate in hexane. ¹H NMR (400 MHz, CDCl₃) δ 9.68 (s, 1H), 7.81 (d, J=8.4 Hz, 2H), 7.56 (d, J=8.4 Hz, 2H), 7.26 (m, 2H), 7.21 (s, 1H), 4.85 (d, J=11.6 Hz, 1H), 4.67 (d, J=11.6 Hz, 1H), 4.26-4.12 (m, 1H), 4.09 (m, 1H), 2.98-2.78 (m, 2H).

Step 9: (S)-(6-chloro-1-(dimethoxymethyl)isochroman-1-yl)methanol (LGY001-91-1)

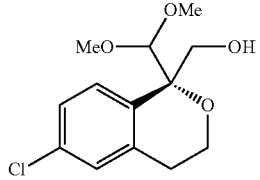 [SMILES: COC(OC)[C@]1(CO)OCCc2cc(Cl)ccc21]

To a solution of (S)-(6-chloro-1-formylisochroman-1-yl) methyl 4-bromobenzoate (700.0 mg, 1.71 mmol) in anhydrous methanol (15 mL), TsOH (16.25 mg, 0.09 mmol) and trimethyl orthoformate (217 mg, 2.05 mmol) were added and the reaction mixture was refluxed for 4 h. The reaction mixture was then concentrated to 50% volume, diluted with THF (12 mL) and added NaOH (273 mg, 6.83 mmol) in water (2 mL). The resulting mixture was stirred at r.t. overnight, concentrated under reduced pressure. The residue was diluted with diethyl ether (50 mL). The aqueous layer was separated, and the organic layer was washed with 1 N NaOH (10 mL). The combined aqueous layers were extracted with diethyl ether (20 mL). The combined organic layers were washed with 1 N NaOH (10 mL) and brine, dried over sodium sulfate and concentrated under reduced pressure. The crude material was purified by flash chromatography on a silica gel column eluting with ethyl acetate/hexane (20%) to afford (S)-(6-chloro-1-(dimethoxymethyl)isochroman-1-yl)methanol (320 mg, 68% yield) as a colorless oil. ¹H NMR (400 MHz, CDCl₃) δ 7.40 (d, J=8.5 Hz, 1H), 7.18-7.03 (m, 2H), 4.16-4.13 (m, 1H), 3.96-3.93 (m, 2H), 3.70 (d, J=11.6 Hz, 1H), 3.54 (s, 3H), 3.48 (s, 3H), 2.90-2.69 (m, 2H).

Step 10: (S)-4-((6-chloro-1-(dimethoxymethyl)isochroman-1-yl)methoxy)-N,N-bis(4-methoxybenzyl)-3-nitrobenzenesulfonamide

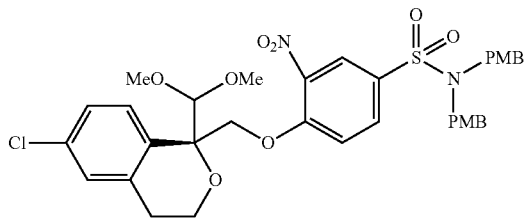

To a solution of tert-butoxypotassium (987.47 mg, 8.8 mmol) in anhydrous THF (3 mL) was cooled to 0° C. and a solution of (S)-(6-chloro-1-(dimethoxymethyl)isochroman-1-yl)methanol (2.0 g, 7.33 mmol) in THF (5 mL) was added dropwise. After 5 min., 4-fluoro-N,N-bis[(4-methoxyphenyl)methyl]-3-nitro-benzenesulfonamide (4390 mg, 9.53 mmol) (1 M in THF) was added dropwise via syringe and the resulting mixture was warmed to r.t. After 1 h the reaction was cooled to 0° C., quenched with saturated NH$_4$Cl solution (10 mL) and extracted with ethyl acetate (50 mL). The combined organic layers were washed with NH$_4$Cl (10 mL), brine (20 mL), dried over sodium sulfate, filtered and concentrated under reduced pressure. The crude material was purified by flash chromatography on a silica gel column eluting with ethyl acetate/PE (25%) (TLC R$_f$=0.5 in 30% ethyl acetate in hexane) to afford (S)-4-((6-chloro-1-(dimethoxymethyl)isochroman-1-yl)methoxy)-N,N-bis(4-methoxybenzyl)-3-nitrobenzenesulfonamide (4.2007 g, 80% yield) as a yellow semi-solid. $^1$H NMR (400 MHz, CDCl$_3$) δ 8.10 (d, J=2.4 Hz, 1H), 7.85 (dd, J=8.8, 2.4 Hz, 1H), 7.50 (d, J=8.6 Hz, 1H), 7.21-7.16 (m, 2H), 7.09-7.04 (m, 5H), 6.82-6.76 (m, 4H), 4.71 (s, 1H), 4.38 (s, 2H), 4.27 (s, 4H), 4.18-4.13 (m, 1H), 4.02-3.92 (m, 1H), 3.79 (s, 6H), 3.54 (d, J=2.0 Hz, 3H), 3.50 (s, 3H), 2.83 (m, 2H).

Step 11: (S)-4-((6-chloro-1-formylisochroman-1-yl)methoxy)-N,N-bis(4-methoxybenzyl)-3-nitrobenzenesulfonamide

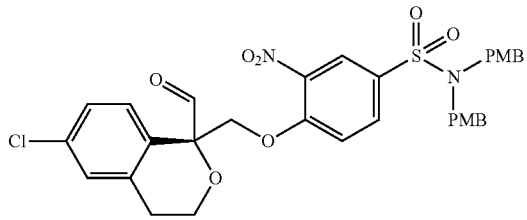

To a solution (S)-4-((6-chloro-1-(dimethoxymethyl)isochroman-1-yl)methoxy)-N,N-bis(4-methoxybenzyl)-3-nitrobenzenesulfonamide (3.5 g, 4.91 mmol) in 1,4-dioxane (30 mL) was added TsOH (2.53 g, 14.72 mmol) and the suspension was heated to 110° C. for 18 h. Upon completion, the mixture was cooled to r.t., and concentrated under reduced pressure. The residue was dissolved in EtOAc (100 mL) and washed by NaHCO$_3$ (100 mL). The organic layer was concentrated to give (S)-4-((6-chloro-1-formylisochroman-1-yl)methoxy)-N,N-bis(4-methoxybenzyl)-3-nitrobenzenesulfonamide (3.2 g, 78.2% yield) which was used directly in next step. $^1$H NMR (400 MHz, CDCl$_3$) δ 9.71 (s, 1H), 8.06 (d, J=2.4 Hz, 1H), 7.85 (dd, J=8.8, 2.4 Hz, 1H), 7.26-7.45 (m, 3H), 7.10-7.03 (m, 5H), 6.81-6.77 (m, 4H), 4.59-4.48 (m, 2H), 4.26 (s, 4H), 4.16-4.07 (m, 2H), 3.79 (s, 6H), 3.02-2.85 (m, 2H).

Step 12: (R)-6'-chloro-N,N-bis(4-methoxybenzyl)-4,5-dihydro-2H-spiro[benzo[b][1,4]oxazepine-3,1'-isochroman]-7-sulfonamide

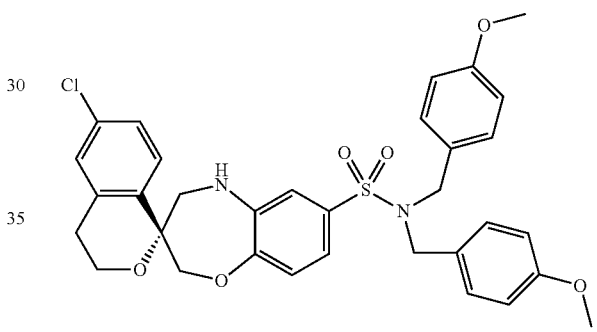

To a solution (S)-4-((6-chloro-1-formylisochroman-1-yl)methoxy)-N,N-bis(4-methoxybenzyl)-3-nitrobenzenesulfonamide (500 mg, 0.75 mmol) in acetic acid (8 mL) was added iron powder (3382 mg, 14.9 mmol) and the suspension was heated to 40° C. for 12 h. Upon completion, the suspension was cooled to r.t. The solid was filtered off and the filtrate was concentrated under reduced pressure. The residue was diluted with DCE (10 mL). To the solution was added NaHB(OAc)$_3$ (795 mg, 3.75 mmol). The reaction mixture was stirred at r.t. for 3 h., and MeOH (10 mL) was added. The resulting mixture was stirred for 1 h., and then concentrated under reduced pressure. The residue was purified by flash chromatograph on a silica gel column to afford (R)-6'-chloro-N,N-bis(4-methoxybenzyl)-4,5-dihydro-2H-spiro[benzo[b][1,4]oxazepine-3,1'-isochroman]-7-sulfonamide (70 mg, 14% yield). LC-MS calc. for C$_{33}$H$_{34}$ClN$_2$O$_6$S [M+H]$^+$: m/z=621.18/623.18; Found: 621.1/623.0. $^1$H NMR (400 MHz, CDCl$_3$) δ 7.62 (d, J=8.4 Hz, 1H), 7.25-7.21 (m, 2H), 7.20 (d, J=2.0 Hz, 1H), 7.08 (d, J=2.4 Hz, 1H), 7.02-6.99 (m, 5H), 6.80-6.76 (m, 4H), 4.38 (dd, J=41.2, 12.6 Hz, 2H), 4.24 (s, 4H), 3.99 (t, J=5.6 Hz, 2H), 3.78-3.75 (m, 7H), 3.51 (d, J=14.0 Hz, 1H), 2.85 (t, J=5.2 Hz, 2H).

Intermediate 15

(3R)-6'-Chloro-5-[[(1R,2R)-2-[(1S)-1-hydroxyallyl]cyclobutyl]methyl]spiro[2,4-dihydro-1,5-benzoxazepine-3,1'-isochromane]-7-sulfonamide And

Intermediate 16

(3R)-6'-chloro-5-[[(1R,2R)-2-[(1R)-1-hydroxyallyl]cyclobutyl]methyl]spiro[2,4-dihydro-1,5-benzoxazepine-3,1'-isochromane]-7-sulfonamide Intermediate 15

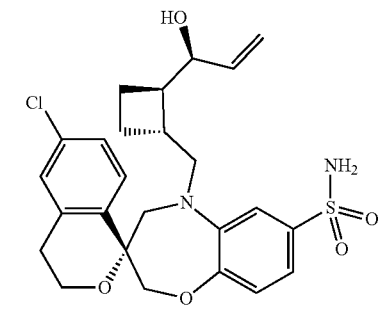

and

Intermediate 16

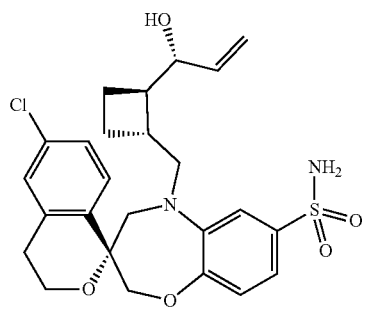

Step 1: (3R)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-isochromane]-7-sulfonamide

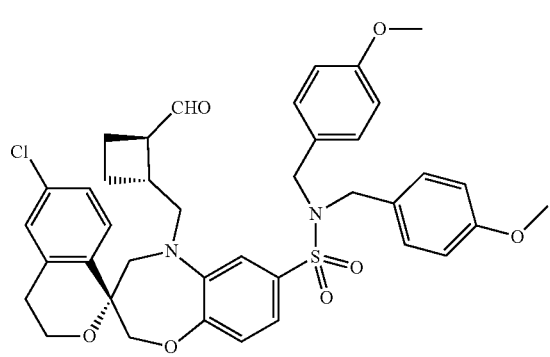 [SMILES: COc1ccc(CN(Cc2ccc(OC)cc2)S(=O)(=O)c2ccc3c(c2)N(C[C@@H]2CC[C@H]2C=O)C[C@]2(CO3)OCCc3cc(Cl)ccc32)cc1]

This compound was prepared using procedures analogous to those described for Intermediate 3 Step 1-3 using (R)-6'-chloro-N,N-bis(4-methoxybenzyl)-4,5-dihydro-2H-spiro[benzo[b][1,4]oxazepine-3,1'-isochroman]-7-sulfonamide (Intermediate 14) and [(1R,2R)-2-formylcyclobutyl]methyl acetate in Step 1. LC-MS: calc. for $C_{39}H_{42}ClN_2O_7S$ [M+H]$^+$: m/z=717.3/719.3; Found: 717.3/719.3.

Step 2. (3R)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-isochromane]-7-sulfonamide and (3R)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-isochromane]-7-sulfonamide

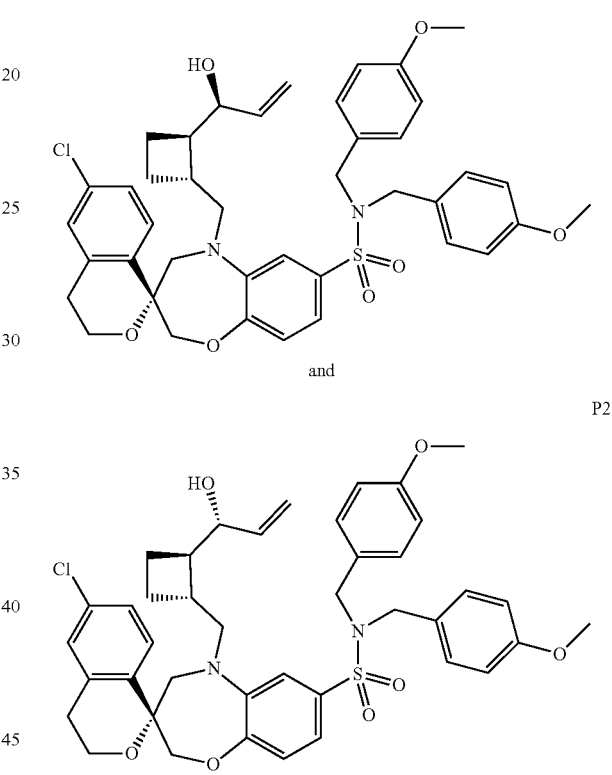

This compound was prepared using procedures analogous to those described for Intermediate 3 Step 4 using vinylmagnesium bromide (1.0 M solution THF solution). The reaction was quenched with sat. NH$_4$Cl solution (300 mL) and extracted with (EA 300 mL×3). The organic layer was concentrated and purified by flash chromatography on a silica gel column eluting with EA/Hep (20% to 50%) to afford the two products: P1 (the earlier eluted product) which was assigned to (3R)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-isochromane]-7-sulfonamide. LC-MS calc. for $C_{41}H_{46}ClN_2O_7S$ [M+H]$^+$: m/z=745.3/747.3; Found: 745.5/747.4.

And P2 (the latter eluted product) was assigned to (3R)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-isochromane]-7-sulfonamide. LC-MS calc. for $C_{41}H_{46}ClN_2O_7S$ [M+H]$^+$: m/z=745.3/747.3; Found: 745.5/747.4.

Step 3: (3R)-6'-chloro-5-[[(1R,2R)-2-[(S)-1-hydroxyallyl]cyclobutyl]methyl]spiro[2,4-dihydro-1,5-benzoxazepine-3,1'-isochromane]-7-sulfonamide (Intermediate 15)

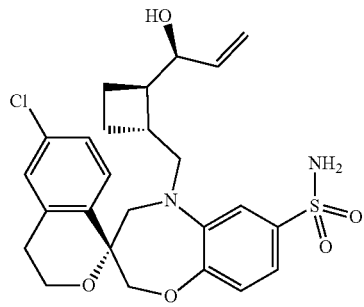 [SMILES: C=C[C@H](O)[C@@H]1CC[C@H]1CN1C[C@]2(COc3ccc(S(N)(=O)=O)cc31)OCCc1cc(Cl)ccc12]

This compound was prepared using procedures analogous to those described for Intermediate 3 Step 5 using (3R)-6'-chloro-N,N-bis[(4-methoxyphenyl)methyl]-5-[[(1R,2R)-2-[(1S)-1-hydroxyallyl]cyclobutyl]methyl]spiro[2,4-dihydro-1,5-benzoxazepine-3,1'-isochromane]-7-sulfonamide (P1 Step 2). LC-MS: calcd. for $C_{25}H_{30}ClN_2O_5S$ [M+H]$^+$: m/z=505.0/507.0; Found: 505.1/507.0.

Step 4. (3R)-6'-chloro-5-[[(1R,2R)-2-[(1R)-1-hydroxyallyl]cyclobutyl]methyl]spiro[2,4-dihydro-1,5-benzoxazepine-3,1'-isochromane]-7-sulfonamide (Intermediate 16)

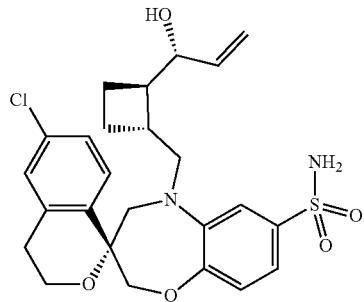 [SMILES: C=C[C@@H](O)[C@@H]1CC[C@H]1CN1C[C@]2(COc3ccc(S(N)(=O)=O)cc31)OCCc1cc(Cl)ccc12]

This compound was prepared using procedures analogous to those described for Intermediate 3 Step 5 using (3R)-6'-chloro-N,N-bis[(4-methoxyphenyl)methyl]-5-[[(1R,2R)-2-[(1R)-1-hydroxyallyl]cyclobutyl]methyl]spiro[2,4-dihydro-1,5-benzoxazepine-3,1'-isochromane]-7-sulfonamide (P2 Step 2). LC-MS: calc. for $C_{25}H_{30}ClN_2O_5S$ [M+H]$^+$: m/z=505.0/507.0; Found: 505.1/507.0.

Example 1

N-[6'-Chloro-5-(cyclobutylmethyl)spiro[2,4-dihydro-1,5-benzoxazepine-3,1'-tetralin]-7-yl]sulfonylacetamide

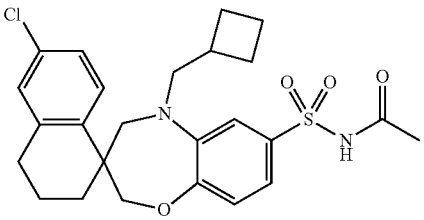 [SMILES: CC(=O)NS(=O)(=O)c1ccc2c(c1)N(CC1CCC1)CC1(CCCc3cc(Cl)ccc31)CO2]

Step 1: 6'-chloro-5-(cyclobutylmethyl)spiro[2,4-dihydro-1,5-benzoxazepine-3,1'-tetralin]-7-sulfonamide

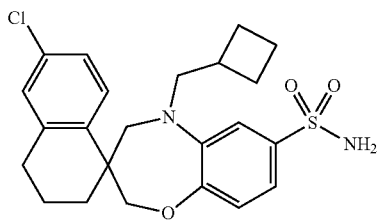 [SMILES: NS(=O)(=O)c1ccc2c(c1)N(CC1CCC1)CC1(CCCc3cc(Cl)ccc31)CO2]

A 20 mL vial with septum under $N_2$ containing a solution of ~80% pure 6'-chlorospiro[4,5-dihydro-2H-1,5-benzoxazepine-3,1'-tetralin]-7-sulfonamide (Intermediate 1, 400 mg, 0.84 mmol) in DCM (9 mL) and 2,2,2-trifluoroacetic acid (TFA) (1.5 mL, 19.6 mmol) was charged with cyclobutanecarboxaldehyde (very impure, 262 µL, 3.36 mmol). The solution was stirred at RT for 30 min. The reaction vessel was then placed at 0° C. in an ice-water bath, and charged with sodium borohydride (100 mg, 2.64 mmol) in small portions over 2 min. The reaction was stirred at 0° C. for 1 h. The reaction was quenched by dumping it into sat. NaHCO$_3$ (20 mL, caution: gas evolution), diluting with water (30 mL) and extracting with EtOAc (60 mL). The organic layer was washed with water (20 mL) and sat. NaHCO$_3$ (20 mL), brine (30 mL), dried over Na$_2$SO$_4$, and filtered. The filtrate was concentrated to afford a yellow gum, then turned into a yellow/white solid by repeated concentration after dissolving in DCM and triturating with hexanes. Solids were mostly dissolved in hot DCM (~10 mL), then charged with hexanes until a cloudy color appeared. The resulting suspension was let cool to RT, then cooled to 0° C. After 2 h, a white/grey precipitate formed. The supernatant was decanted, and the precipitate was washed twice more with DCM/hexanes (2×2 mL, 2:1 ratio). The precipitate was dried under reduced pressure to yield 6'-chloro-5-(cyclobutylmethyl)spiro[2,4-dihydro-1,5-benzoxazepine-3,1'-tetralin]-7-sulfonamide (105 mg, 27.9% yield) as a grey solid.

The remaining filtrates were combined, dry loaded on Celite, and purified by FCC (40 g SiO$_2$, 0-50% EtOAc in hexanes). Fractions containing pure desired product by TLC were combined and concentrated under reduced pressure and heat (~50° C.) to yield 6'-chloro-5-(cyclobutylmethyl)

spiro[2,4-dihydro-1,5-benzoxazepine-3,1'-tetralin]-7-sulfonamide (93.8 mg, 24.8% yield) as a white solid. Combined yield of 52.7%. $R_f$=0.28 (2:1 hexanes:EtOAc); LCMS calculated for $C_{23}H_{28}ClN_2O_3S$ (M+H)$^+$: m/z=447.15/449.15; found: 447.0/449.0; $^1$H NMR (500 MHz, CDCl$_3$) δ 7.67 (d, J=8.5 Hz, 1H), 7.24 (dd, J=2.2, 8.3 Hz, 1H), 7.19-7.14 (m, 2H), 7.09 (d, J=2.3 Hz, 1H), 6.97 (d, J=8.2 Hz, 1H), 4.74 (s, 2H), 4.11 (ABq, 2H), 3.60 (dd, J=1.2, 14.4 Hz, 1H), 3.40-3.26 (m, 3H), 2.84-2.74 (m, 2H), 2.74-2.64 (m, 1H), 2.14-2.04 (m, 2H), 1.97-1.76 (m, 7H), 1.61-1.53 (m, 1H).

Step 2: N-[6'-chloro-5-(cyclobutylmethyl)spiro[2,4-dihydro-1,5-benzoxazepine-3,1'-tetralin]-7-yl]sulfonylacetamide

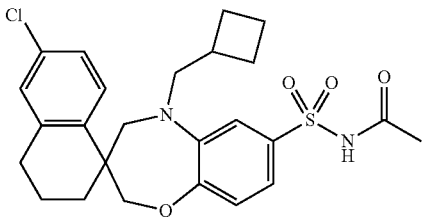 [SMILES: CC(=O)NS(=O)(=O)c1ccc2c(c1)N(CC1CCC1)CC1(CCCc3cc(Cl)ccc31)CO2]

A 2 mL microwave vial with septum containing a mixture of solid 6'-chloro-5-(cyclobutylmethyl)spiro[2,4-dihydro-1,5-benzoxazepine-3,1'-tetralin]-7-sulfonamide (18 mg, 0.04 mmol), 4-(dimethylamino)pyridine (0.74 mg, 0.01 mmol), and DCM (1 mL) under $N_2$ was charged with acetyl chloride (5.75 uL, 0.08 mmol), followed by N,N-Diisopropylethylamine (17.54 uL, 0.10 mmol) at r.t. (white vapors appeared). The mixture was shaken then stirred vigorously at 45° C. for 30 min, and shaken occasionally until all solids were dissolved. The reaction solution was quenched by addition of sat. NH$_4$Cl (3 mL). The mixture was extracted with DCM (3 mL), washed with water (2 mL) and sat. NH$_4$Cl (2 mL), brine (4 mL), dried over Na$_2$SO$_4$, and filtered. The filtrate was concentrated under reduced pressure. The residue was purified by FCC (12 g SiO$_2$, 0→35% EtOAc in hexanes, wet-loaded in DCM). Fractions containing pure product were combined, and concentrated under reduced pressure and heat (~75° C.) to yield 98% pure N-[6'-chloro-5-(cyclobutylmethyl)spiro[2,4-dihydro-1,5-benzoxazepine-3,1'-tetralin]-7-yl]sulfonylacetamide (14.2 mg, 70.6% yield) as a white solid after scratching. LCMS calculated for $C_{25}H_{30}ClN_4O_4S$ (M+H)$^+$: m/z=489.15/491.15; found: 489.0/491.0. $^1$H NMR (500 MHz, CDCl$_3$) δ 7.88 (s, 1H), 7.67 (d, J=8.5 Hz, 1H), 7.32 (dd, J=2.2, 8.3 Hz, 1H), 7.29 (d, J=2.3 Hz, 1H), 7.17 (dd, J=2.3, 8.5 Hz, 1H), 7.09 (d, J=2.3 Hz, 1H), 6.98 (d, J=8.4 Hz, 1H), 4.13 (s, 2H), 3.60 (d, J=14.7 Hz, 1H), 3.39-3.29 (m, 3H), 2.82-2.74 (m, 2H), 2.70 (dt, J=7.3, 14.0 Hz, 1H), 2.17-2.06 (m, 5H), 1.96-1.71 (m, 8H).

Example 2

N-[6'-Chloro-5-(cyclopropylmethyl)spiro[2,4-dihydro-1,5-benzoxazepine-3,1'-tetralin]-7-yl]sulfonylacetamide

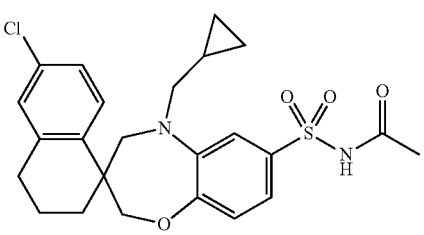 [SMILES: CC(=O)NS(=O)(=O)c1ccc2c(c1)N(CC1CC1)CC1(CCCc3cc(Cl)ccc31)CO2]

Step 1: 6'-chloro-5-(cyclopropylmethyl)spiro[2,4-dihydro-1,5-benzoxazepine-3,1'-tetralin]-7-sulfonamide

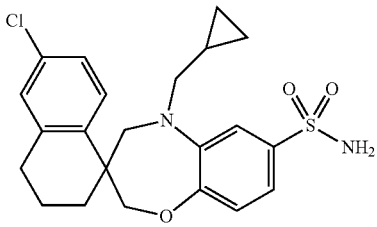 [SMILES: NS(=O)(=O)c1ccc2c(c1)N(CC1CC1)CC1(CCCc3cc(Cl)ccc31)CO2]

To a solution of 6'-chlorospiro[4,5-dihydro-2H-1,5-benzoxazepine-3,1'-tetralin]-7-sulfonamide (Intermediate 1, 60 mg, 0.16 mmol) in TFA (0.18 mL, 2.38 mmol) and DCM (1 mL) was added cyclopropylcarboxaldehyde (16.65 mg, 0.24 mmol). The mixture was stirred at r.t. for 15 min., then the mixture was cooled by ice-water bath, and sodium borohydride (15 mg, 0.40 mmol) was added slowly (over 15 min). The mixture was stirred at 0° C. for 1 h., then the volatiles were removed under reduced pressure. The residue was diluted with AcOEt (5 mL), and washed with sat. NaHCO$_3$ solution (2 mL×2), and brine. The organics was dried over Na$_2$SO$_4$, filtered and concentrated under reduced pressure to afford the crude product 6'-chloro-5-(cyclopropylmethyl)spiro[2,4-dihydro-1,5-benzoxazepine-3,1'-tetralin]-7-sulfonamide (49 mg, 71%) was directly used in next step reaction without further purification. LCMS calculated for $C_{22}H_{26}ClN_2O_3S$ (M+H)$^+$: m/z=433.13/435.12; found: 433.0/435.0.

Step 2: N-[6'-chloro-5-(cyclopropylmethyl)spiro[2,4-dihydro-1,5-benzoxazepine-3,1'-tetralin]-7-yl]sulfonylacetamide

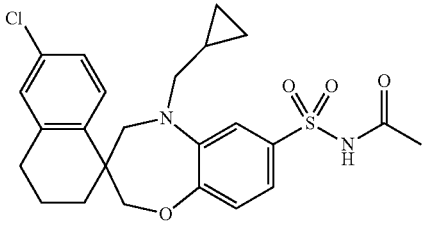 [SMILES: CC(=O)NS(=O)(=O)c1ccc2c(c1)N(CC1CC1)CC1(CCCc3cc(Cl)ccc31)CO2]

To a mixture of 6'-chloro-5-(cyclopropylmethyl)spiro[2,4-dihydro-1,5-benzoxazepine-3,1'-tetralin]-7-sulfonamide (21 mg, 0.05 mmol), acetic acid (0.01 mL, 0.10 mmol) and 4-(dimethylamino)pyridine (12.2 mg, 0.10 mmol) in DCM (2 mL) was added 1-ethyl-3-(3-dimethylaminopropyl)carbodiimide hydrochloride (19.1 mg, 0.10 mmol) at r.t. The mixture was stirred at r.t. overnight. The mixture was concentrated under reduced pressure. The residue was purified by FC on a silica gel column eluting with EtOAc/Hex (0-60%) (both contains 0.3% AcOH) to afford the desired product as white solid. LCMS calculated for $C_{24}H_{28}ClN_2O_4S$ $(M+H)^+$: m/z=475.14/476.14; found: 475.0/477.0. $^1H$ NMR (500 MHz, DMSO-$d_6$) δ 11.90 (s, 1H), 7.67 (d, J=8.5 Hz, 1H), 7.37 (d, J=2.2 Hz, 1H), 7.24 (dd, J=2.4, 8.5 Hz, 1H), 7.19 (dd, J=2.2, 8.3 Hz, 1H), 7.17 (d, J=2.4 Hz, 1H), 7.02 (d, J=8.3 Hz, 1H), 4.09 (s, 2H), 3.56 (d, J=14.4 Hz, 1H), 3.45 (d, J=14.4 Hz, 1H), 3.28 (s, 1H), 3.21 (dd, J=5.9, 14.8 Hz, 1H), 3.09 (dd, J=6.7, 14.8 Hz, 1H), 2.79-2.64 (m, 2H), 2.04-1.91 (m, 1H), 1.90 (s, 3H), 1.76 (d, J=14.5 Hz, 2H), 1.48 (m, 1H), 1.09-0.99 (m, 1H), 0.51 (dq, J=2.1, 8.2 Hz, 2H), 0.33-0.28 (m, 1H), 0.27-0.21 (m, 1H).

Example 3

N-[6'-Chloro-5-(cyclohexylmethyl)spiro[2,4-dihydro-1,5-benzoxazepine-3,1'-tetralin]-7-yl]sulfonylacetamide

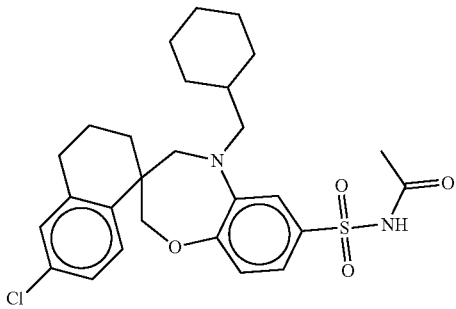

This compound was prepared using procedures analogous to those described for Example 2 using cyclohexanecarboxaldehyde to replace cyclopropylcarboxaldehyde in Step I. LCMS calculated for $C_{27}H_{34}ClN_2O_4S$ $(M+H)^+$: m/z=517.18/519.18; found: 517.1/519.1. $^1H$ NMR (500 MHz, DMSO-$d_6$) δ 11.92 (s, 1H), 7.62 (d, J=8.5 Hz, 1H), 7.23 (dt, J=2.6, 5.8 Hz, 2H), 7.19-7.13 (m, 2H), 7.00 (d, J=8.3 Hz, 1H), 4.08 (q, J=12.2 Hz, 2H), 3.61 (d, J=14.4 Hz, 1H), 3.34 (d, J=14.2 Hz, 1H), 3.18 (dd, J=6.4, 14.8 Hz, 1H), 3.07 (dd, J=7.4, 14.8 Hz, 1H), 2.81-2.64 (m, 2H), 1.99-1.92 (m, 1H), 1.91 (s, 3H), 1.79 (m, 3H), 1.75-1.63 (m, 4H), 1.63-1.56 (m, 1H), 1.52 (m, 1H), 1.13 (m, 3H), 0.96 (m, 2H).

Example 4

N-(5-Benzyl-6'-chloro-spiro[2,4-dihydro-1,5-benzoxazepine-3,1'-tetralin]-7-yl)sulfonylacetamide

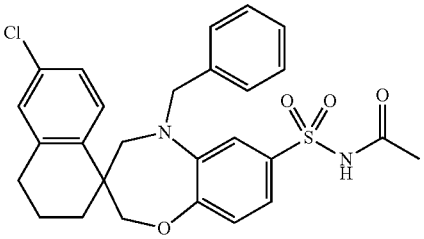 [SMILES: CC(=O)NS(=O)(=O)c1ccc2c(c1)N(Cc1ccccc1)CC1(CCCc3cc(Cl)ccc31)CO2]

This compound was prepared using procedures analogous to those described for Example 2 using benzaldehyde to replace cyclopropylcarboxaldehyde in Step I. LCMS calculated for $C_{27}H_{28}ClN_2O_4S$ $(M+H)^+$: m/z=511.14/513.14; found: 511.0/513.0. $^1H$ NMR (500 MHz, DMSO-$d_6$) δ 11.77 (s, 1H), 7.70 (d, J=8.6 Hz, 1H), 7.31 (dd, J=6.8, 8.5 Hz, 2H), 7.27-7.17 (m, 5H), 7.14 (d, J=2.3 Hz, 1H), 7.09-7.01 (m, 2H), 4.64-4.53 (m, 2H), 4.26-4.14 (m, 2H), 3.75 (d, J=14.5 Hz, 1H), 3.41 (d, J=14.4 Hz, 1H), 2.72-2.64 (m, 2H), 1.95 (m, 1H), 1.77 (s, 3H), 1.66 (m, 2H), 1.51 (t, J=12.3 Hz, 1H), 1.22 (m, 2H).

Example 5

N-[6'-Chloro-5-(cyclobutylmethyl)spiro[2,4-dihydro-1,5-benzoxazepine-3,1'-tetralin]-7-yl]sulfonyl-2-phenyl-acetamide

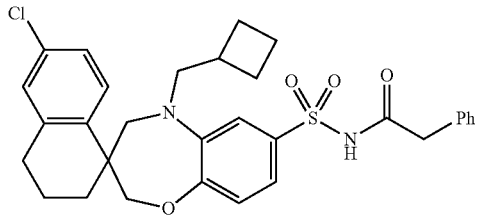 [SMILES: O=C(Cc1ccccc1)NS(=O)(=O)c1ccc2c(c1)N(CC1CCC1)CC1(CCCc3cc(Cl)ccc31)CO2]

A 4 mL vial with septum containing a suspension of 6'-chloro-5-(cyclobutylmethyl)spiro[2,4-dihydro-1,5-benzoxazepine-3,1'-tetralin]-7-sulfonamide (Example 1 Step 1, 40 mg, 0.09 mmol) and 4-(dimethylamino)pyridine (1.5 mg, 0.01 mmol) in DCM (2 mL) and N,N-diisopropylethylamine (40 μL, 0.23 mmol) under $N_2$ was charged with phenylacetyl chloride (18 μL, 0.14 mmol). The vial was heated at 40° C. for 30 min. The reaction mixture was charged with additional phenylacetyl chloride (23 μL, 0.17 mmol) and N,N-diisopropylethylamine (60 uL, 0.34 mmol), and heated at 40° C. for 1 h. The reaction mixture was diluted with EtOAc (40 mL), washed with sat. $NH_4Cl$ (20 mL), water (20 mL) and sat. $NH_4Cl$ (20 mL), and brine (30 mL). The organic layer was dried over $Na_2SO_4$, filtered, concentrated under reduced pressure, and purified by FCC (30 g C18, 10→100% MeCN in water, wet-loaded in DMSO). The fraction containing pure desired product was lyophilized, then further dried under reduced pressure and heat (60° C.) to yield N-[6'-chloro-5-(cyclobutylmethyl)spiro[2,4-dihydro-1,5-benzoxazepine-3,1'-tetralin]-7-yl]sulfonyl-2-phenyl-acetamide (21.5 mg, 97% purity, 41% yield) as a white solid. LCMS calculated for $C_{31}H_{34}ClN_2O_4S$ (M+H)$^+$: m/z=565.19/567.19; found: 565.2/567.1. $^1$H NMR (500 MHz, CDCl$_3$) δ 7.76 (s, 1H), 7.67 (d, J=8.5 Hz, 1H), 7.41-7.30 (m, 3H), 7.30-7.26 (m, 2H), 7.20-7.14 (m, 3H), 7.09 (d, J=2.3 Hz, 1H), 6.95 (d, J=8.8 Hz, 1H), 4.13 (s, 2H), 3.63 (s, 2H), 3.59 (d, J=14.3 Hz, 1H), 3.38-3.26 (m, 3H), 2.83-2.71 (m, 2H), 2.68 (p, J=7.2 Hz, 1H), 2.13-2.04 (m, 2H), 1.97-1.71 (m, 8H).

Example 6

N-[6'-Chloro-5-(cyclobutylmethyl)spiro[2,4-dihydro-1,5-benzoxazepine-3,1'-tetralin]-7-yl]sulfonyl-2-methyl-propanamide

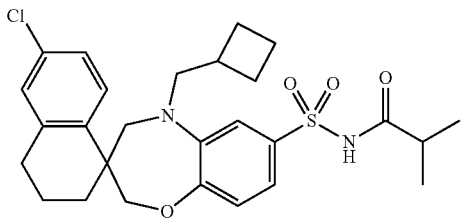 [SMILES: CC(C)C(=O)NS(=O)(=O)c1ccc2c(c1)N(CC1CCC1)CC1(CCCc3cc(Cl)ccc31)CO2]

This compound was prepared using procedures analogous to those described for Example 5 using isobutyryl chloride to replace phenylacetyl chloride. The product was purified by FCC (12 g SiO$_2$, 0→20% EtOAc in hexanes with 0.3% AcOH, wet-loaded in DCM to afford N-[6'-chloro-5-(cyclobutylmethyl)spiro[2,4-dihydro-1,5-benzoxazepine-3,1'-tetralin]-7-yl]sulfonyl-2-methyl-propanamide as a white solid. R$_f$=0.40 (2:1 hexanes:EtOAc). LCMS calculated for $C_{27}H_{34}ClN_2O_4S$ (M+H)$^+$: m/z=517.19/517.19; found: 517.1/519.1. $^1$H NMR (500 MHz, CDCl$_3$) δ 7.91 (s, 1H), 7.67 (d, J=8.5 Hz, 1H), 7.33 (dq, J=2.2, 4.4 Hz, 2H), 7.17 (dd, J=2.4, 8.5 Hz, 1H), 7.09 (d, J=2.3 Hz, 1H), 6.98-6.95 (m, 1H), 4.13 (s, 2H), 3.60 (d, J=14.3 Hz, 1H), 3.39-3.29 (m, 3H), 2.82-2.66 (m, 3H), 2.43 (hept, J=6.9 Hz, 1H), 2.16-2.06 (m, 2H), 1.97-1.73 (m, 8H), 1.16 (d, J=6.9 Hz, 6H).

Example 7

4-Chloro-N-[6'-chloro-5-(cyclobutylmethyl)spiro[2,4-dihydro-1,5-benzoxazepine-3,1'-tetralin]-7-yl]sulfonyl-benzamide

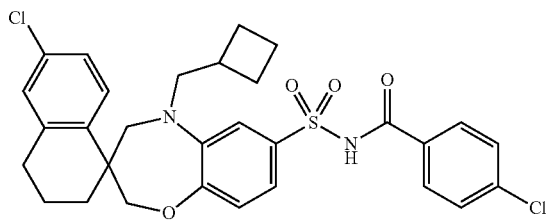 [SMILES: O=C(NS(=O)(=O)c1ccc2c(c1)N(CC1CCC1)CC1(CCCc3cc(Cl)ccc31)CO2)c1ccc(Cl)cc1]

This compound was prepared using procedures analogous to those described for Example 5 using 4-chlorobenzoyl chloride to replace phenylacetyl chloride. The product was purified by FCC (12 g SiO$_2$, 0→20% EtOAc in hexanes with 0.3% AcOH, wet-loaded in DCM to afford 4-chloro-N-[6'-chloro-5-(cyclobutylmethyl)spiro[2,4-dihydro-1,5-benzoxazepine-3,1'-tetralin]-7-yl]sulfonyl-benzamide as a white solid. R$_f$=0.25 (2:1 hexanes:EtOAc); LCMS calculated for $C_{30}H_{31}Cl_2N_2O_4S$ (M+H)$^+$: m/z=585.14/587.13; found: 585.1/587.1; $^1$H NMR (500 MHz, CDCl$_3$) δ 8.72 (s, 1H), 7.74 (dt, J=2.0, 2.4, 8.6 Hz, 2H), 7.66 (d, J=8.5 Hz, 1H), 7.48-7.39 (m, 4H), 7.16 (dd, J=2.3, 8.5 Hz, 1H), 7.09 (d, J=2.3 Hz, 1H), 7.01-6.96 (m, 1H), 4.13 (s, 2H), 3.60 (d, J=14.4 Hz, 1H), 3.42-3.29 (m, 3H), 2.74 (dq, J=5.5, 6.1, 17.8 Hz, 3H), 2.16-2.06 (m, 2H), 1.98-1.70 (m, 8H).

Example 8

N-[6'-Chloro-5-[[rac-(2S,6R)-2,6-dimethyltetrahydropyran-4-yl]methyl]spiro[2,4-dihydro-1,5-benzoxazepine-3,1'-tetralin]-7-yl]sulfonylacetamide

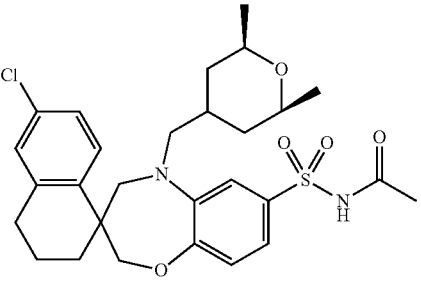 [SMILES: CC(=O)NS(=O)(=O)c1ccc2c(c1)N(CC1C[C@@H](C)O[C@@H](C)C1)CC1(CCCc3cc(Cl)ccc31)CO2]

This compound was prepared using procedures analogous to those described for Example 2 using (2R,6S)-2,6-dimethyltetrahydro-2H-pyran-4-carbaldehyde to replace cyclopropylcarboxaldehyde in Step I. LCMS calculated for $C_{28}H_{36}ClN_2O_5S$ (M+H)$^+$: m/z=547.2/549.19; found: 547.2/549.1. $^1$H NMR (500 MHz, DMSO-d$_6$) δ 11.91 (s, 1H), 7.62 (d, J=8.5 Hz, 1H), 7.24 (dd, J=2.2, 9.9 Hz, 2H), 7.17 (d, J=2.4 Hz, 1H), 7.15 (dd, J=2.1, 8.3 Hz, 1H), 7.00 (d, J=8.3 Hz, 1H), 4.12-4.04 (m, 2H), 3.64 (d, J=14.4 Hz, 1H), 3.30 (m, 2H) overlap with water signal, 3.16 (qd, J=6.8, 14.8 Hz, 2H), 2.81-2.65 (m, 2H), 2.13 (s, 1H), 2.02-1.92 (m, 2H), 1.90 (s, 3H), 1.85-1.73 (m, 2H), 1.62 (t, J=10.6 Hz, 2H), 1.54-1.40 (m, 2H), 1.05 (dd, J=4.4, 6.2 Hz, 6H), 0.90-0.77 (m, 3H).

Example 9

N-[6'-Chloro-5-[(1-methylpyrazol-4-yl)methyl]spiro[2,4-dihydro-1,5-benzoxazepine-3,1'-tetralin]-7-yl]sulfonylacetamide

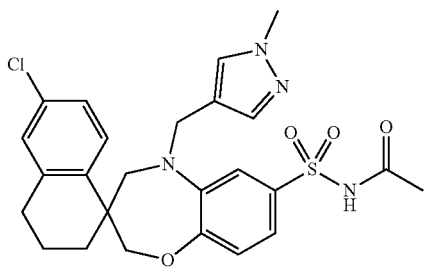 [SMILES: CC(=O)NS(=O)(=O)c1ccc2c(c1)N(Cc1cnn(C)c1)CC1(CCCc3cc(Cl)ccc31)CO2]

This compound was prepared using procedures analogous to those described for Example 2 using 1-methyl-1H-pyrazole-4carboxaldehyde to replace cyclopropylcarboxaldehyde in Step I. LCMS calculated for $C_{25}H_{28}ClN_4O_4S$ (M+H)$^+$: m/z=515.14/517.14; found: 515.2.0/517.1. $^1$H NMR (500 MHz, DMSO-d$_6$) δ 11.90 (s, 1H), 7.68 (d, J=8.6 Hz, 1H), 7.65 (s, 1H), 7.38 (s, 1H), 7.33 (d, J=2.2 Hz, 1H), 7.23 (dd, J=2.4, 8.6 Hz, 1H), 7.20-7.14 (m, 2H), 7.00 (d, J=8.3 Hz, 1H), 4.32 (s, 2H), 4.13 (s, 2H), 3.74 (s, 3H), 3.49 (d, J=14.1 Hz, 1H), 3.35 (d, J=14.2 Hz, 1H), 2.69 (d, J=16.0 Hz, 2H), 2.04-1.94 (m, 2H), 1.87 (s, 3H), 1.48 (m, 2H).

Example 10

N-[5-[(1-Allylpyrazol-4-yl)methyl]-6'-chloro-spiro[2,4-dihydro-1,5-benzoxazepine-3,1'-tetralin]-7-yl]sulfonylhex-5-enamide

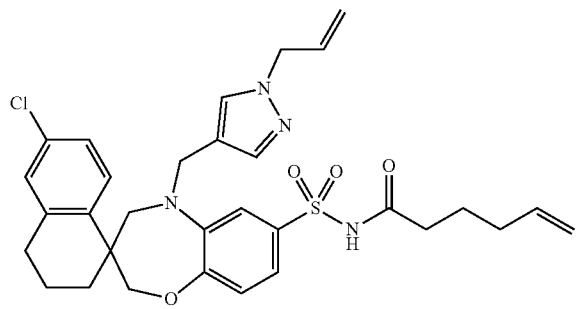 [SMILES: C=CCCCC(=O)NS(=O)(=O)c1ccc2c(c1)N(Cc1cnn(CC=C)c1)CC1(CCCc3cc(Cl)ccc31)CO2]

Step 1: 5-[(1-allylpyrazol-4-yl)methyl]-6'-chloro-spiro[2,4-dihydro-1,5-benzoxazepine-3,1'-tetralin]-7-sulfonamide

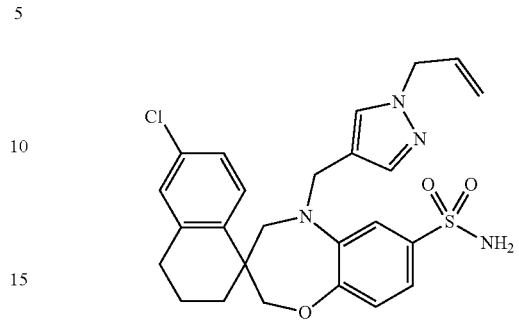

This compound was prepared using procedures analogous to those described for Example 2 using 1-allylpyrazole-4-carbaldehyde to replace cyclopropylcarboxaldehyde in Step I. LCMS calculated for $C_{25}H_{28}ClN_4O_3S$ (M+H)$^+$: m/z=499.15/501.15; found: 499.1/501.0. $^1$H NMR (500 MHz, DMSO-d$_6$) δ 7.66 (t, J=4.3 Hz, 2H), 7.42 (s, 1H), 7.34 (d, J=2.1 Hz, 1H), 7.23 (dd, J=2.4, 8.5 Hz, 1H), 7.19-7.14 (m, 3H), 7.11 (dd, J=2.1, 8.3 Hz, 1H), 6.97 (d, J=8.2 Hz, 1H), 5.94 (ddt, J=5.7, 10.1, 17.2 Hz, 1H), 5.16-5.02 (m, 2H), 4.66 (dt, J=1.6, 5.7 Hz, 2H), 4.39-4.28 (m, 2H), 4.08 (s, 2H), 3.47 (d, J=14.2 Hz, 1H), 3.34 (d, J=15.4 Hz, 1H), 2.69 (dt, J=5.7, 10.1 Hz, 2H), 2.02-1.94 (m, 2H), 1.92-1.84 (m, 1H), 1.67 (d, J=29.4 Hz, 2H), 1.52-1.40 (m, 2H), 1.27 (d, J=13.9 Hz, 2H), 1.16 (t, J=7.3 Hz, 1H), 0.84 (t, J=6.8 Hz, 1H).

Step 2: N-[5-[(1-allylpyrazol-4-yl)methyl]-6'-chloro-spiro[2,4-dihydro-1,5-benzoxazepine-3,1'-tetralin]-7-yl]sulfonylhex-5-enamide

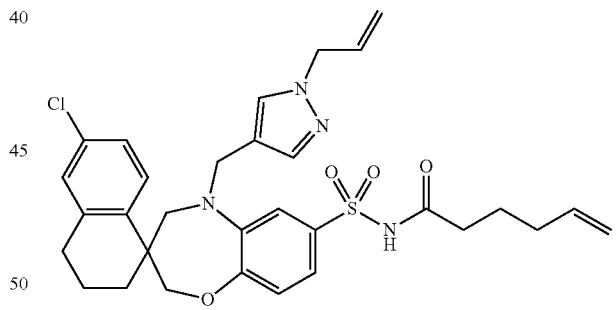

This compound was prepared using procedures analogous to those described for Example 2 using 5-hexenoic acid to replace acetic acid in Step 2. LCMS calculated for $C_{31}H_{36}ClN_4O_4S$ (M+H)$^+$: m/z=595.21/597.20; found: 595.3/597.2. $^1$H NMR (500 MHz, DMSO-d$_6$) δ 11.87 (s, 1H), 7.69 (s, 1H), 7.67 (d, J=8.5 Hz, 1H), 7.43 (s, 1H), 7.35 (d, J=2.2 Hz, 1H), 7.23 (dd, J=2.3, 8.5 Hz, 1H), 7.18 (dd, J=2.2, 8.2 Hz, 1H), 7.16 (d, J=2.4 Hz, 1H), 7.01 (d, J=8.3 Hz, 1H), 5.94 (ddt, J=5.7, 10.2, 17.1 Hz, 1H), 5.71 (ddt, J=6.5, 10.1, 16.9 Hz, 1H), 5.12 (dq, J=1.5, 10.2 Hz, 1H), 5.05 (dq, J=1.6, 17.0 Hz, 1H), 4.97-4.88 (m, 2H), 4.65 (dt, J=1.6, 5.8 Hz, 2H), 4.33 (s, 2H), 4.12 (s, 2H), 3.49 (d, J=14.3 Hz, 1H), 3.35 (d, J=14.3 Hz, 1H), 2.69 (m, 2H), 2.17 (t, J=7.4 Hz, 2H), 2.03-1.94 (m, 2H), 1.94-1.83 (m, 2H), 1.50 (p, J=7.4 Hz, 4H).

Example 11

(4'Z,5'E)-6-Chloro-3,4-dihydro-2H-spiro[naphthalene-1,3'-13-thia-12-aza-1(5,7)-benzo[b][1,4]oxazepina-3(4,1)-pyrazolacyclotridecaphanen]-5'-en-11'-one 13',13'-dioxide and (4'Z,5'Z)-6-chloro-3,4-dihydro-2H-spiro[naphthalene-1,3'-13-thia-12-aza-1(5,7)-benzo[b][1,4]oxazepina-3(4,1)-pyrazolacyclotridecaphanen]-5'-en-11'-one 13',13'-dioxide

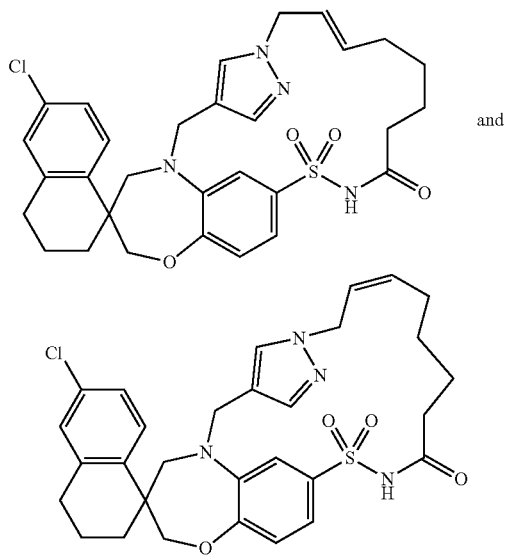

and

A solution of N-[5-[(1-allylpyrazol-4-yl)methyl]-6'-chloro-spiro[2,4-dihydro-1,5-benzoxazepine-3,1'-tetralin]-7-yl]sulfonylhex-5-enamide (Example 10, Step 2, 42 mg, 0.07 mmol) in toluene (50 mL) was evacuated and re-charged with nitrogen for three cycles. To the solution was added (1,3-dimesitylimidazolidin-2-ylidene)(2-isopropoxybenzylidene)ruthenium(VI) chloride (Hoveyda-Grubbs II, 8.84 mg, 0.01 mmol) in toluene (5 mL). The mixture was then heated at 105° C. for 2 h. Additional Hoveyda-Grubbs II (8.84 mg, 0.01 mmol) was added. The system was evacuated and re-charged with nitrogen for three cycles. The mixture was heated at 105° C. overnight. The mixture was concentrated under reduced pressure. The residue was purified by FC on a silica gel column eluting with EtOAc/Hex (0-60%) (both contains 0.1% AcOH). The desired fractions were collected and concentrated under reduced pressure. The residue was further purified by RP FC on $C_{18}$ eluting with MeCN/water (10-80%) (both contains 0.2% AcOH) to afford the desired product as slight brown solid which contained 1 eq. AcOH. Based on 1H NMR spectrum, the ratio of the cis- and trans-isomers is about 1:4. Some signals from the cis-isomer could not be distinguished and overlaps with those for the trans-isomer. LCMS calculated for $C_{29}H_{32}ClN_4O_4S$ $(M+H)^+$: m/z=567.18/569.17; found: 567.1/569.1. $^1$H NMR (500 MHz, Methanol-$d_4$) δ 7.78 (d, J=8.6 Hz, 1H), 7.46 (d, J=13.9 Hz, 2H), 7.32 (dd, J=2.2, 8.3 Hz, 1H), 7.18 (dd, J=2.4, 8.5 Hz, 1H), 7.11 (dd, J=2.3, 5.0 Hz, 2H), 6.98 (d, J=8.4 Hz, 1H), 5.51 (dt, J=6.2, 14.9 Hz, 0.81H for the 1H in trans-isomer), 5.42 (dt, J=6.9, 14.9 Hz, 0.81H for the 1H in trans-isomer), 5.35 (tt, J=5.0, 1.5 Hz, 0.48H for the 2H in cis-isomer) 4.62-4.56 (m, 2H from trans and 4H from cis), 4.51 (d, J=4.7 Hz, 2H), 4.23 (d, J=4.2 Hz, 2H), 3.79-3.70 (m, 1H), 3.46 (d, J=14.6 Hz, 1H), 2.78 (d, J=5.8 Hz, 2H, overlaps with 2H for cis-isomer), 2.21-2.16 (m, 2H, overlaps with 2H for cis-isomer), 2.03 (m, 2H, overlaps with 2H for cis-isomer), 1.97 (s, 2H, AcOH signal), 1.91-1.85 (m, 2H), 1.68-1.57 (m, 4H).

Example 12

N-[(3S)-6'-Chloro-5-(cyclobutylmethyl)spiro[2,4-dihydro-1,5-benzoxazepine-3,1'-tetralin]-7-yl]sulfonylacetamide

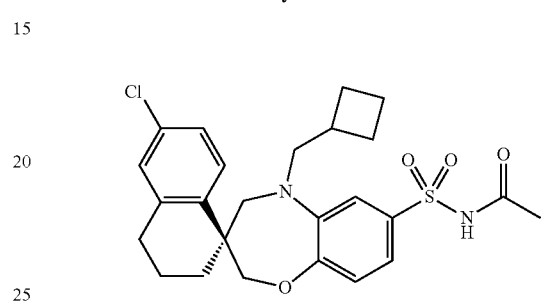

Step 1: (3S)-6'-chloro-5-(cyclobutylmethyl)-N,N-bis[(4-methoxyphenyl)methyl]spiro[2,4-dihydro-1,5-benzoxazepine-3,1'-tetralin]-7-sulfonamide

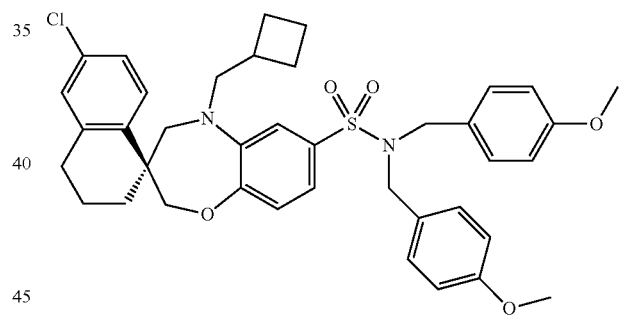

To a solution of rac-(3S)-6'-chloro-N,N-bis[(4-methoxyphenyl)methyl]spiro[4,5-dihydro-2H-1,5-benzoxazepine-3,1'-tetralin]-7-sulfonamide (Intermediate 2, 46 mg, 0.07 mmol) in TFA (0.06 mL, 0.74 mmol) and DCM (2 mL) was added cyclobutanecarboxaldehyde (12.5 mg, 0.15 mmol) The mixture was stirred at r.t. for 15 min., then the mixture was cooled by ice-water bath, and sodium borohydride (8.43 mg, 0.22 mmol) was added slowly (over 15 min). The mixture was stirred at 0° C. for 1 h., then the volatile was removed under reduced pressure. The residue was diluted with AcOEt (5 mL) and washed with sat. NaHCO$_3$ solution (2 mL×2), and brine. The organics was dried over Na$_2$SO$_4$, filtered and concentrated under reduced pressure. The residue was purified by FC on a silica gel column with EtOAc in hexane (0-50%) to afford the desired product (3S)-6'-chloro-5-(cyclobutylmethyl)-N,N-bis[(4-methoxyphenyl)methyl]spiro[2,4-dihydro-1,5-benzoxazepine-3,1'-tetralin]-7-sulfonamide. LCMS calculated for $C_{39}H_{44}ClN_2O_5S$ $(M+H)^+$: m/z=687.26/689.26; found: 688.7.2/689.2.

Step 2: (3S)-6'-chloro-5-(cyclobutylmethyl)spiro[2,4-dihydro-1,5-benzoxazepine-3,1'-tetralin]-7-sulfonamide

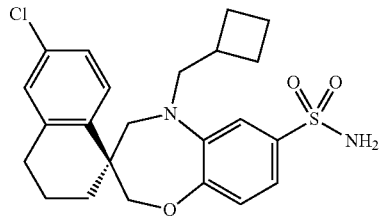 [SMILES: NS(=O)(=O)c1ccc2c(c1)N(CC1CCC1)C[C@@]1(CCCc3cc(Cl)ccc31)CO2]

To a solution of (3S)-6'-chloro-5-(cyclobutylmethyl)-N,N-bis[(4-methoxyphenyl)methyl]spiro[2,4-dihydro-1,5-benzoxazepine-3,1'-tetralin]-7-sulfonamide (48 mg, 0.07 mmol) in DCM (1 mL) was added TFA (0.8 mL, 10.4 mmol). The mixture was stirred at r.t. overnight. and diluted with DCM (5 mL) and carefully neutralized with 7.5% NaHCO$_3$ solution to about pH 8. The organic layer was separated. The aqueous layer was extracted with DCM (3 mL). The combined organic layers were washed with 7.5% NaHCO$_3$ solution (2 mL), and water (2 mL), dried over Na$_2$SO$_4$, filtered, and concentrated under reduced pressure to afford (3S)-6'-chloro-5-(cyclobutylmethyl)spiro[2,4-dihydro-1,5-benzoxazepine-3,1'-tetralin]-7-sulfonamide which was directly used in next step reaction without further purification. LCMS calculated for C$_{23}$H$_{28}$ClN$_2$O$_3$S (M+H)$^+$: m/z=447.14/449.14; found: 447.0/449.0.

Step 3: N-[(3S)-6'-chloro-5-(cyclobutylmethyl)spiro[2,4-dihydro-1,5-benzoxazepine-3,1'-tetralin]-7-yl]sulfonylacetamide

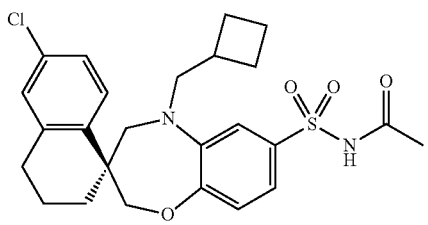 [SMILES: CC(=O)NS(=O)(=O)c1ccc2c(c1)N(CC1CCC1)C[C@@]1(CCCc3cc(Cl)ccc31)CO2]

To a mixture of (3S)-6'-chloro-5-(cyclobutylmethyl)spiro[2,4-dihydro-1,5-benzoxazepine-3,1'-tetralin]-7-sulfonamide (15 mg, 0.03 mmol), acetic acid (0.5 mL, 0.07 mmol) and 4-(dimethylamino)pyridine (8.2 mg, 0.07 mmol) in DCM (1 mL) was added 1-ethyl-3-(3-dimethylaminopropyl) carbodiimide hydrochloride (12.8 mg, 0.07 mmol) at r.t. The mixture was stirred at r.t. for 1 h. The mixture was concentrated under reduced pressure. The residue was purified by FC on a silica gel column eluting with EtOAc/Hex (0-50%). The desired fractions were collected and concentrated under reduced pressure. The residue was diluted with MeCN and water, and was lyophilized to afford the desired product as white solid. LCMS calculated for C$_{25}$H$_{30}$ClN$_4$O$_4$S (M+H)$^+$: m/z=489.15/491.15; found: 489.1/491.1. $^1$H NMR (500 MHz, DMSO-d$_6$) δ 11.90 (s, 1H), 7.63 (d, J=8.6 Hz, 1H), 7.23 (dd, J=2.4, 8.5 Hz, 1H), 7.20-7.15 (m, 3H), 7.03-6.98 (m, 1H), 4.07 (s, 2H), 3.52 (d, J=14.3 Hz, 1H), 3.23-3.36 (m, 3H, overlap with water), 2.80-2.58 (m, 3H), 2.08-1.95 (m, 2H), 1.92 (s, 3H), 1.91-1.84 (m, 1H), 1.77 (m, 6H), 1.51 m, 1H).

Example 13

N-[(3S)-6'-Chloro-5-(cyclobutylmethyl)spiro[2,4-dihydro-1,5-benzoxazepine-3,1'-tetralin]-7-yl]sulfonylcyclopentanecarboxamide

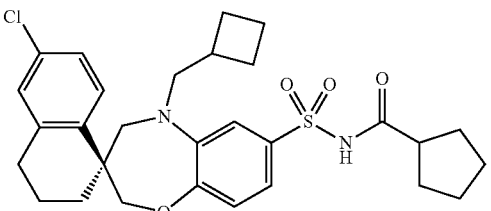

To a mixture of (3S)-6'-chloro-5-(cyclobutylmethyl)spiro[2,4-dihydro-1,5-benzoxazepine-3,1'-tetralin]-7-sulfonamide (15 mg, 0.03 mmol), 4-(dimethylamino)pyridine (8.2 mg, 0.07 mmol) and N,N-Diisopropylethylamine (0.01 mL, 0.07 mmol) in DCM (1 mL) was added cyclopentanecarbonyl chloride (6.67 mg, 0.05 mmol) at r.t. The mixture was stirred at r.t. for 2 h. The mixture was concentrated under reduced pressure. The residue was purified by FCC on a silica gel column eluting with EtOAc/Hex (0-50%). The desired fractions were collected and concentrated under reduced pressure. The residue was diluted with MeCN and water and was lyophilized to afford the desired product as white solid. LCMS calculated for C$_{29}$H$_{36}$ClN$_4$O$_3$S (M+H)$^+$: m/z=543.2/545.2; found: 543.1/545.1. $^1$H NMR (500 MHz, DMSO-d$_6$) δ 11.87 (s, 1H), 7.63 (d, J=8.5 Hz, 1H), 7.23 (dd, J=2.4, 8.5 Hz, 1H), 7.19-7.13 (m, 3H), 6.98 (d, J=8.7 Hz, 1H), 4.06 (s, 2H), 3.51 (d, J=14.3 Hz, 1H), 3.29-3.21 (m, 3H), 2.81-2.57 (m, 4H), 2.00 (d, J=6.9 Hz, 2H), 1.90 (d, J=13.9 Hz, 1H), 1.84-1.68 (m, 8H), 1.50 (d, J=29.6 Hz, 7H).

Example 14

Benzyl N-[6'-chloro-5-(cyclobutylmethyl)spiro[2,4-dihydro-1,5-benzoxazepine-3,1'-tetralin]-7-yl]sulfonylcarbamate

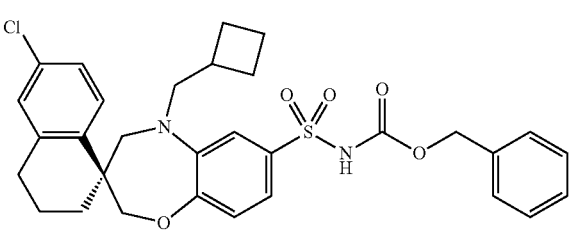 [SMILES: O=C(NS(=O)(=O)c1ccc2c(c1)N(CC1CCC1)C[C@@]1(CCCc3cc(Cl)ccc31)CO2)OCc1ccccc1]

To a mixture of 6'-chloro-5-(cyclobutylmethyl)spiro[2,4-dihydro-1,5-benzoxazepine-3,1'-tetralin]-7-sulfonamide (15.0 mg, 0.03 mmol), Benzyl chloroformate (8.2 mg, 0.07 mmol) and N,N-Diisopropylethylamine (0.01 mL, 0.07 mmol) in DCM (1 mL) was added Benzyl chloroformate (6.67 mg, 0.04 mmol) at r.t. The mixture was stirred at r.t. for 2 h. The mixture was concentrated under reduced pressure. The residue was purified by FC on a silica gel column eluting with EtOAc/Hex (0-50%). The desired fractions were collected and concentrated under reduced pressure. The residue was diluted with MeCN and water, and was lyophilized to afford the desired product as white solid. LCMS calculated for $C_{31}H_{34}ClN_2O_5S$ (M+H)$^+$: m/z=581.18/583.18; found: 581.3/583.3. $^1$H NMR (500 MHz, Acetonitrile-d$_3$) δ 9.05 (sbr, 1H), 7.72 (d, J=8.5 Hz, 1H), 7.41-7.32 (m, 3H), 7.32-7.27 (m, 2H), 7.27-7.16 (m, 4H), 6.98 (d, J=8.3 Hz, 1H), 5.12 (s, 2H), 4.14 (s, 2H), 3.64-3.56 (m, 1H), 3.39-3.32 (m, 2H), 3.28 (dd, J=6.1, 14.9 Hz, 1H), 2.86-2.73 (m, 2H), 2.66 (p, J=7.3 Hz, 1H), 2.09-2.02 (m, 3H), 1.92-1.75 (m, 6H), 1.58 m, 1H).

Example 15

2-(1,5-Dimethylpyrazol-3-yl)-N-[(3S)-6'-chloro-5-(cyclobutylmethyl)spiro[2,4-dihydro-1,5-benzoxazepine-3,1'-tetralin]-7-yl]sulfonyl-acetamide

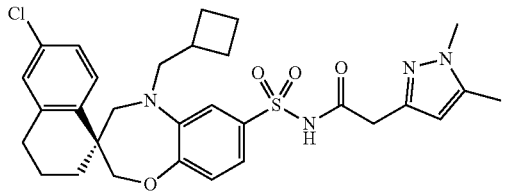 [SMILES: Cc1cc(CC(=O)NS(=O)(=O)c2ccc3c(c2)N(CC2CCC2)C[C@@]2(CCCc4cc(Cl)ccc42)CO3)nn1C]

This compound was prepared using procedures analogous to those described for Example 12 using 2-(1,5-dimethylpyrazol-3-yl)acetic acid to replace acetic acid in Step 3. LCMS calculated for $C_{30}H_{36}ClN_4O_4S$ (M+H)$^+$: m/z=583.21/585.21; found: 583.2/585.2. $^1$H NMR (500 MHz, Chloroform-d) δ 7.67 (d, J=8.5 Hz, 1H), 7.38-7.32 (m, 2H), 7.17 (dd, J=2.3, 8.5 Hz, 1H), 7.09 (d, J=2.3 Hz, 1H), 6.95 (d, J=8.9 Hz, 1H), 5.95 (s, 1H), 4.12 (s, 2H), 3.81 (d, J=8.3 Hz, 3H), 3.61 (s, 2H), 3.38-3.30 (m, 2H), 2.80-2.65 (m, 2H), 2.33-2.20 (m, 5H), 2.16-2.05 (m, 3H), 1.99-1.71 (m, 8H).

Example 16

N-[(3S)-6'-Chloro-5-(cyclobutylmethyl)spiro[2,4-dihydro-1,5-benzoxazepine-3,1'-tetralin]-7-yl]sulfonyl-2-thiazol-2-yl-acetamide

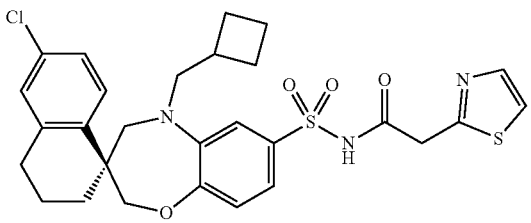 [SMILES: O=C(Cc1nccs1)NS(=O)(=O)c1ccc2c(c1)N(CC1CCC1)C[C@@]1(CCCc3cc(Cl)ccc31)CO2]

This compound was prepared using procedures analogous to those described for Example 12 using 2-(4-thiazolyl)acetic acid to replace acetic acid in Step 3. LCMS calculated for $C_{28}H_{31}ClN_3O_4S_2$ (M+H)$^+$: m/z=571.14/573.14; found: 571.2/573.2. $^1$H NMR (500 MHz, DMSO-d6) δ 12.33 (s, 1H), 9.00 (d, J=2.0 Hz, 1H), 7.68-7.61 (m, 2H), 7.50-7.39 (m, 2H), 7.24 (dd, J=2.4, 8.5 Hz, 1H), 7.21-7.14 (m, 2H), 6.98 (d, J=8.8 Hz, 1H), 4.06 (s, 2H), 3.51 (d, J=14.3 Hz, 1H), 2.82-2.58 (m, 4H), 2.06-1.67 (m, 12H), 1.52 (dd, J=7.0, 14.2 Hz, 1H).

Example 17

2-(6-Methyl-3-pyridyl)-N-[(3S)-6'-chloro-5-(cyclobutylmethyl)spiro[2,4-dihydro-1,5-benzoxazepine-3,1'-tetralin]-7-yl]sulfonyl-acetamide

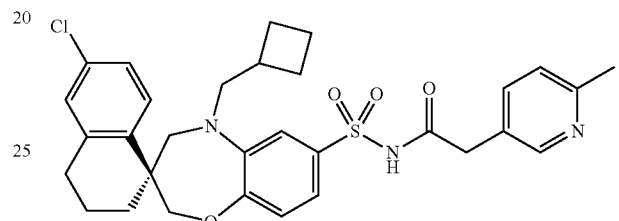

This compound was prepared using procedures analogous to those described for Example 12 using 2-(6-methylpyridin-3-yl)acetic acid to replace acetic acid in Step 3. LCMS calculated for $C_{31}H_{35}ClN_3O_4S$ (M+H)$^+$: m/z=580.2/582.20; found: 580.3/582.3. $^1$H NMR (500 MHz, DMSO-d$_6$) δ 12.33 (s, 1H), 8.51 (s, 1H), 8.00 (s, 1H), 7.63 (d, J=8.5 Hz, 2H), 7.29-7.15 (m, 4H), 7.01 (d, J=8.2 Hz, 1H), 4.11-4.03 (m, 2H), 3.77 (s, 2H), 3.51 (d, J=14.3 Hz, 1H), 3.35-3.20 (m, 3H), 2.82-2.67 (m, 2H), 2.58 (s, 3H), 2.04-1.66 (m, 11H), 1.50 (dd, J=5.5, 12.2 Hz, 1H).

Example 18

(3R,6R,24S)-6'-Chloro-17,17-dioxo-spiro[8,22-dioxa-17λ^6-thia-1,16-diazapentacyclo[16.7.2.1^9,13.0^3,6.0^21,26]octacosa-9(28),10,12,18(27),19,21(26)-hexaene-24,1'-tetralin]-15-one

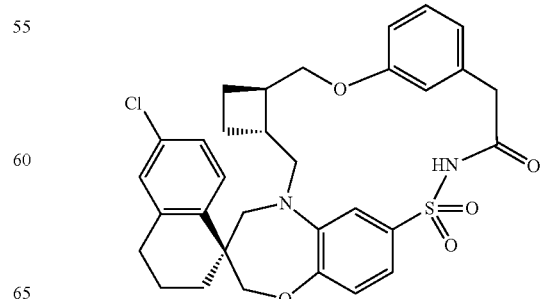

Step 1: [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl acetate

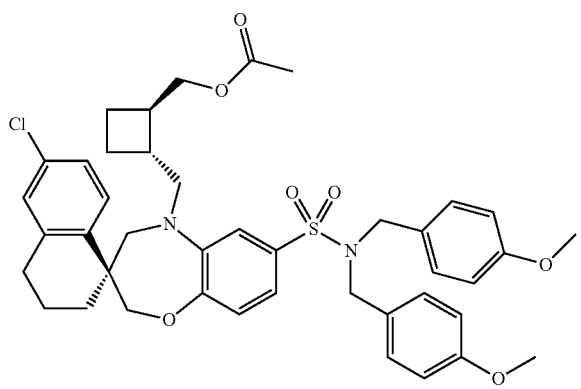 [SMILES: COc1ccc(CN(Cc2ccc(OC)cc2)S(=O)(=O)c2ccc3c(c2)N(C[C@@H]2CC[C@H]2COC(C)=O)C[C@@]2(CCCc4cc(Cl)ccc42)CO3)cc1]

To a solution of (3S)-6'-chloro-N,N-bis[(4-methoxyphenyl)methyl]spiro[4,5-dihydro-2H-1,5-benzoxazepine-3,1'-tetralin]-7-sulfonamide (Intermediate 2, 1.20 g, 1.94 mmol) and [(1R,2R)-2-formylcyclobutyl]methyl acetate (0.333 g, 2.13 mmol) in DCM (25 mL) was added 2,2,2-trifluoroacetic acid; TFA (1.2 mL, 15.68 mmol, 8 eq.). The mixture was stirred for 5 min., and then cooled with ice-water bath. To the cooled solution was added sodium borohydride (146.64 mg, 3.88 mmol) in small portion-wise over 15 min. The mixture was stirred at 0° C. for 1.5 h. and was quenched by addition of methanol (1 mL). The reaction mixture was then carefully neutralized with 7.5% NaHCO$_3$ aq. solution to about pH 8. The organic layer was separated and washed with water, dried over Na$_2$SO$_4$, filtered and concentrated under reduced pressure to afford the desired crude product (1.63 g, 90% purity) without further purification. LCMS: m/z=781.3 (M+Na)$^+$.

Step 2: (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide

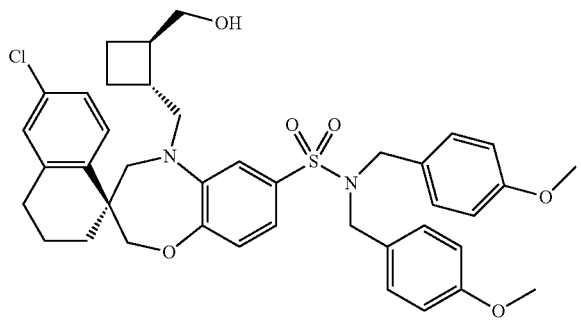 [SMILES: COc1ccc(CN(Cc2ccc(OC)cc2)S(=O)(=O)c2ccc3c(c2)N(C[C@@H]2CC[C@H]2CO)C[C@@]2(CCCc4cc(Cl)ccc42)CO3)cc1]

To a solution of [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl acetate (1635.0 mg, 1.94 mmol, 90% pure) in methanol (5 mL) and THF (5 mL) was added a solution of lithium hydroxide (100 mg, 4.0 mmol) in water (5 mL). The mixture was stirred at r.t overnight. The volatiles were removed under reduced pressure. The residue was neutralized with 1 N HCl aqueous solution to about pH 7. The mixture was extracted with ethyl acetate (3×5 mL). The combined organic layers were washed with water and brine, dried over Na$_2$SO$_4$, filtered, and concentrated under reduced pressure. The residue was purified by flash chromatography on a silica gel column with ethyl acetate in hexane (0-50%) to afford the desired product (1.21 g, 87%).

Step 3: methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]phenyl]acetate

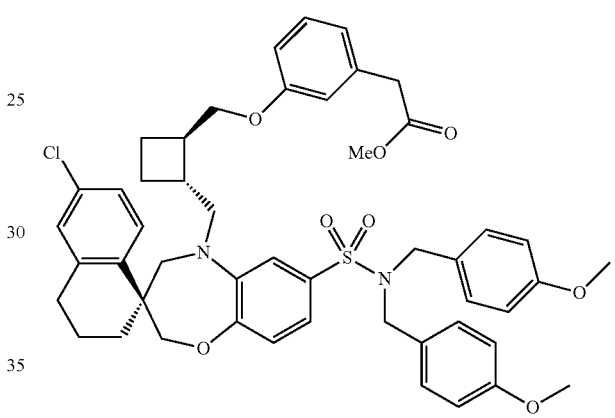

A 4 mL vial with septum containing triphenylphosphine (36.0 mg, 0.14 mmol) and vacuum-dried (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide (60.9 mg, 0.08 mmol) was charged with 3-hydroxyphenylacetic acid methyl ester (13.5 uL, 0.09 mmol) followed by diisopropyl azodicarboxylate (24.0 µL, 0.12 mmol) dropwise over 1 min at r.t. The reaction mixture was stirred at r.t. for 2 h. The vial was then charged with additional triphenylphosphine (16.5 mg, 0.06 mmol), diisopropyl azodicarboxylate (15.0 µL, 0.08 mmol), and 3-hydroxyphenylacetic acid methyl ester (6.0 µL, 0.04 mmol). The solution was stirred at r.t. for an additional 1 h., then quenched with 2 drops water. The solution was dried under reduced pressure and purified by FCC (12 g SiO$_2$, 0→35% EtOAc in hexanes, wet-loaded in DCM). Fractions containing desired product were combined and concentrated under reduced pressure and heat (~100 OC) to yield methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]phenyl]acetate (53.6 mg, 0.0619 mmol, 72.9% yield) as a slightly white/hazy clear glass. $R_f$=0.30 (2:1 hexanes:EtOAc); LCMS calcd for C$_{49}$H$_{54}$ClN$_2$O$_8$S (M+H)$^+$: m/z=865.33; found: 865.2.

Step 4: methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl]acetate

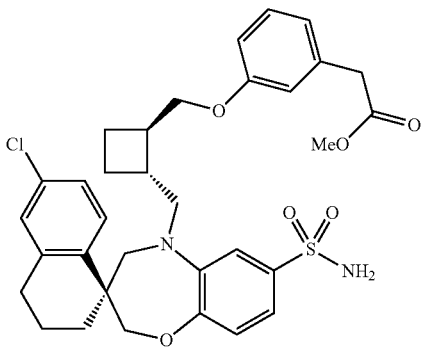 [SMILES: COC(=O)Cc1cccc(OC[C@@H]2CC[C@H]2CN2C[C@@]3(CCCc4cc(Cl)ccc43)COc3ccc(S(N)(=O)=O)cc32)c1]

A 4 mL vial with septum containing methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]phenyl]acetate (50.0 mg, 0.06 mmol) under $N_2$ was charged with DCM (1 mL) followed by TFA (1.0 mL, 0.06 mmol) and stirred at r.t. overnight. The purple reaction mixture was concentrated under reduced pressure, neutralized with sat. sodium bicarbonate (10 mL), diluted with water (30 mL) and extracted with EtOAc (40 mL). The organic layer was washed with water (40 mL), brine (20 mL), and dried over $Na_2SO_4$. The organic layer was filtered, concentrated under reduced pressure, and heat (~50° C.) to yield methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl]acetate (44.1 mg) as a yellow gum. LCMS calculated for $C_{33}H_{38}ClN_2O_6S$ $(M+H)^+$: m/z=625.21; found: 625.4.

Step 5: 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl] acetic Acid

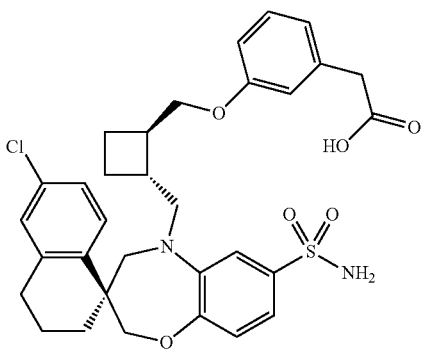 [SMILES: NS(=O)(=O)c1ccc2c(c1)N(C[C@@H]1CC[C@H]1COc1cccc(CC(=O)O)c1)C[C@@]1(CCCc3cc(Cl)ccc31)CO2]

A 20 mL vial containing methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl]acetate (40 mg, 0.06 mmol) and lithium hydroxide (8.2 mg, 0.33 mmol) was charged with THF (900 μL) and water (300 μL). The vial was purged with $N_2$ and stirred at r.t. for 2 h. The reaction mixture was diluted with EtOAc (30 mL), washed twice with 0.1 M HCl (5 mL) and brine (20 mL), and washed with brine (20 mL). The organic layer was dried over $Na_2SO_4$, filtered, concentrated under reduced pressure and heat (~60° C.) to yield crude 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl]acetic acid (37 mg, 0.061 mmol, 95% yield) as an off-white glass. LCMS calculated for $C_{32}H_{36}ClN_2O_5S$ $(M+H)^+$: m/z=611.20; found: 611.3.

Step 6: (3R,6R,24S)-6'-chloro-17,17-dioxo-spiro[8,22-dioxa-17λ^6-thia-1,16-diazapentacyclo[16.7.2.1^9,13.0^3,6.0^21,26]octacosa-9(28),10,12,18(27),19,21(26)-hexaene-24,1'-tetralin]-15-one

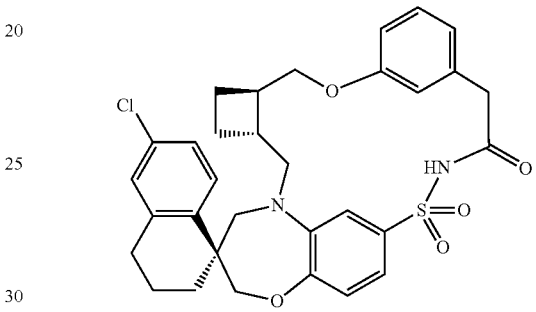

A 20 mL vial with septum containing 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]phenyl]acetic acid (26 mg, 0.04 mmol) in DCM (3 mL) was charged with 1-ethyl-3-(3-dimethylaminopropyl)carbodiimide hydrochloride (25 mg, 0.13 mmol) and 4-(dimethylamino)pyridine (25 mg, 0.20 mmol) in one portion. The reaction mixture was stirred at r.t. for 2 h. The reaction mixture was quenched with 2 drops of water. The reaction mixture was then diluted with EtOAc (30 mL), washed twice with 0.1 M HCl (3 mL) and water (20 mL), and brine (20 mL). The organic layer was dried over $Na_2SO_4$, filtered, concentrated under reduced pressure, and purified by FCC (12 g $SiO_2$, 0→40% EtOAc in hexanes, wet-loaded in DCM+hexanes). Fractions containing mostly product were combined and re-purified by FCC (15.5 g C18, 40→95% MeCN in $H_2O$, wet-loaded in DMSO). Fraction of high purity were combined, and concentrated under reduced pressure and heat (~60° C.) to yield 96.3% pure (3R,6R,24S)-6'-chloro-17,17-dioxo-spiro[8,22-dioxa-17λ^6-thia-1,16-diazapentacyclo[16.7.2.1^9,13.0^3,6.0^21,26]octacosa-9(28),10,12,18(27),19,21(26)-hexaene-24,1'-tetralin]-15-one (8.1 mg, 0.013 mmol, 30% yield) as an off-white solid. $R_f$=0.54 (1:2 hexanes:EtOAc). LCMS calculated for $C_{32}H_{34}ClN_2O_5S$ $(M+H)^+$: m/z=593.19; found: 593.1; $^1H$ NMR (500 MHz, Acetonitrile-$d_3$) δ 9.40 (s, 1H), 7.66 (d, J=8.5 Hz, 1H), 7.20 (dd, J=2.4, 8.5 Hz, 1H), 7.16 (d, J=2.3 Hz, 1H), 7.13 (dd, J=2.2, 8.3 Hz, 1H), 7.09 (t, J=7.9 Hz, 1H), 6.92 (d, J=2.2 Hz, 1H), 6.83 (t, J=2.1 Hz, 1H), 6.78-6.71 (m, 2H), 6.67 (d, J=7.4 Hz, 1H), 4.13-4.02 (m, 4H), 3.46 (d, J=14.5 Hz, 1H), 3.41 (s, 2H), 3.32 (dd, J=5.4, 14.7 Hz, 2H), 3.19 (dd, J=9.5, 14.7 Hz, 1H), 2.84-2.70 (m, 2H), 2.64 (h, J=7.5, 8.5 Hz, 1H), 2.60-2.51 (m, 1H), 2.03-1.95 (m, 3H), 1.88-1.78 (m, 3H), 1.65-1.55 (m, 2H).

Example 19

2-Pyridin-4-yl-N-[(3S)-6'-chloro-5-(cyclobutylmethyl)spiro[2,4-dihydro-1,5-benzoxazepine-3,1'-tetralin]-7-yl]sulfonyl-acetamide

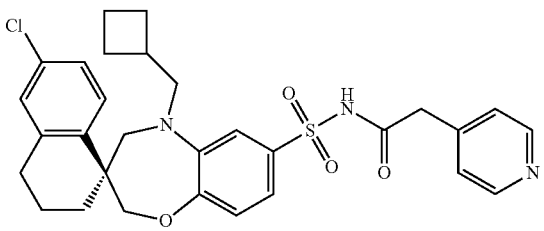 [SMILES: O=C(Cc1ccncc1)NS(=O)(=O)c1ccc2c(c1)N(CC1CCC1)C[C@@]1(CCCc3cc(Cl)ccc31)CO2]

This compound was prepared using procedures analogous to those described for Example 12 using 2-(pyridin-4-yl)acetic acid to replace acetic acid in Step 3. LCMS calculated for $C_{30}H_{33}ClN_3O_4S$ (M+H)$^+$: m/z=566.18; found: 566.1. $^1$H NMR (500 MHz, DMSO-d$_6$) δ 12.20 (s, 1H), 8.55 (d, J=5.2 Hz, 1H), 7.62 (d, J=8.6 Hz, 1H), 7.35 (s, 1H), 7.27-7.13 (m, 2H), 7.00 (d, J=8.3 Hz, 1H), 4.06 (s, 1H), 3.71 (s, 1H), 2.82-2.65 (m, 1H), 2.02-1.86 (m, 2H), 1.84-1.68 (m, 4H), 1.50 (d, J=6.8 Hz, 1H).

Example 20

3-Pyridin-4-yl-N-[rac-(3S)-6'-chloro-5-(cyclobutylmethyl)spiro[2,4-dihydro-1,5-benzoxazepine-3,1'-tetralin]-7-yl]sulfonyl-propanamide

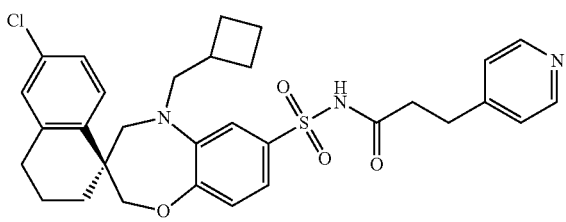 [SMILES: O=C(CCc1ccncc1)NS(=O)(=O)c1ccc2c(c1)N(CC1CCC1)C[C@@]1(CCCc3cc(Cl)ccc31)CO2]

This compound was prepared using procedures analogous to those described for Example 12 using 2-(pyridin-4-yl)acetic acid to replace acetic acid in Step 3. LCMS calculated for $C_{31}H_{35}ClN_3O_4S$ (M+H)$^+$: m/z=580.2; found: 580.2. $^1$H NMR (500 MHz, DMSO-d$_6$) δ 12.33 (s, 1H), 8.51 (s, 1H), 8.00 (s, 1H), 7.63 (d, J=8.5 Hz, 2H), 7.29-7.15 (m, 5H), 7.01 (d, J=8.2 Hz, 1H), 4.11-4.03 (m, 2H), 3.77 (s, 2H), 3.51 (d, J=14.3 Hz, 1H), 3.35-3.20 (m, 3H), 2.82-2.67 (m, 2H), 2.58 (s, 4H), 2.04-1.66 (m, 10H), 1.50 (dd, J=5.5, 12.2 Hz, 1H).

Example 21 tert-Butyl 4-[[6'-chloro-5-(cyclobutylmethyl)spiro[2,4-dihydro-1,5-benzoxazepine-3,1'-tetralin]-7-yl]sulfonylcarbamoyl]piperidine-1-carboxylate

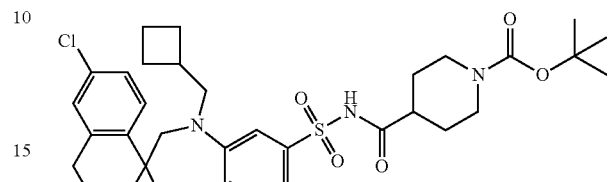

This compound was prepared using procedures analogous to those described for Example 2 using N-Boc-isonipecotic acid to replace acetic acid in Step 2. LCMS calculated for $C_{34}H_{45}ClN_3O_6S$ (M+H)$^+$: m/z=658.26; found: 657.9.

Example 22 tert-Butyl 4-[2-[[6'-chloro-5-(cyclobutylmethyl)spiro[2,4-dihydro-1,5-benzoxazepine-3,1'-tetralin]-7-yl]sulfonylamino]-2-oxo-ethyl]piperidine-1-carboxylate

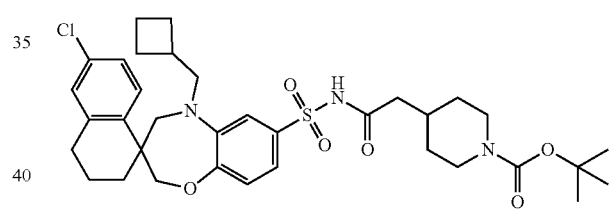

This compound was prepared using procedures analogous to those described for Example 2 using 2-(1-tert-butoxycarbonyl-4-piperidyl)acetic acid to replace acetic acid in Step 2. LCMS calculated for $C_{35}H_{47}ClN_3O_6S$ (M+H)$^+$: m/z=672.28; found: 671.9.

Example 23 tert-Butyl (3S)-3-[[6'-chloro-5-(cyclobutylmethyl)spiro[2,4-dihydro-1,5-benzoxazepine-3,1'-tetralin]-7-yl]sulfonylcarbamoyloxy]piperidine-1-carboxylate

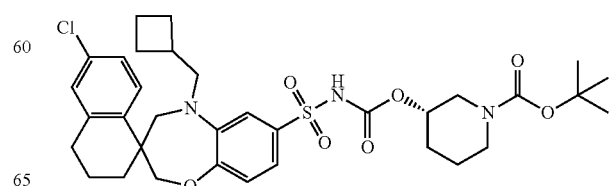

Step 1: Tert-Butyl (3S)-3-chlorocarbonyloxypiperidine-1-carboxylate

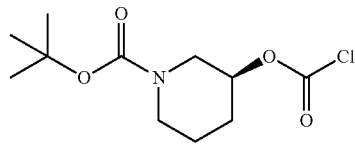 [SMILES: CC(C)(C)OC(=O)N1CCC[C@H](OC(=O)Cl)C1]

A solution of tert-butyl (3S)-3-hydroxypiperidine-1-carboxylate (2.01 g, 9.99 mmol) in DCM (20 mL) was cooled to 0° C. and a freshly prepared solution of triphosgene (1.48 g, 4.99 mmol) in 5 mL of DCM was added dropwise over 5 minutes. The mixture was stirred at this temperature for 30 min., then pyridine (0.81 mL, 9.9 mmol) was added dropwise. The mixture was kept stirring at 0° C. for 1 h. Water (30 mL) was added to the mixture and the layers were separated. The organic layer was dried over sodium sulfate and concentrated under reduced pressure to afford the crude product tert-butyl (3S)-3-chlorocarbonyloxypiperidine-1-carboxylate (1.8 g, 68% yield) which was used in next step without further purification.

Step 2: Tert-Butyl (3S)-3-[[6'-chloro-5-(cyclobutylmethyl)spiro[2,4-dihydro-1,5-benzoxazepine-3,1'-tetralin]-7-yl]sulfonylcarbamoyloxy]piperidine-1-carboxylate A solution of 6'-chloro-5-(cyclobutylmethyl)spiro[2,4-dihydro-1,5-benzoxazepine-3,1'-tetralin]-7-sulfonamide (Example 1, Step 1, 15 mg, 0.03 mmol) and potassium carbonate (13.8 mg, 0.10 mmol) in acetone (2 mL) was stirred for 5 min in a sealed tube. Then a solution of tert-butyl (3S)-3-chlorocarbonyloxypiperidine-1-carboxylate (13.3 mg, 0.05 mmol) in acetone was added. The resulting mixture was stirred at 60° C. overnight, and poured into water (5 mL) and extracted with DCM (5 mL×3). The combined organic layer were dried over sodium sulfate, filtered and concentrated under reduced pressure. The crude product was purified by prep-HPLC on C18 column to afford desired product tert-butyl (3S)-3-[[6'-chloro-5-(cyclobutylmethyl)spiro[2,4-dihydro-1,5-benzoxazepine-3,1'-tetralin]-7-yl]sulfonylcarbamoyloxy]piperidine-1-carboxylate (12.1 mg, 53% yield) as a white solid. LCMS calculated for $C_{34}H_{45}ClN_3O_7S$ $(M+H)^+$: m/z=674.26; found: 673.9.

Example 24

N-[6'-Chloro-5-(cyclobutylmethyl)spiro[2,4-dihydro-1,5-benzoxazepine-3,1'-tetralin]-7-yl]sulfonylpyrrolidine-1-carboxamide

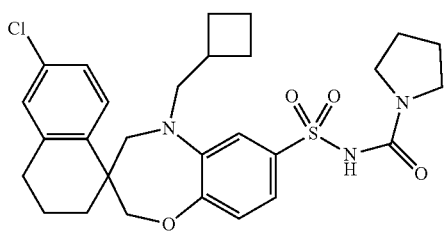 [SMILES: O=C(NS(=O)(=O)c1ccc2c(c1)N(CC1CCC1)CC1(CCCc3cc(Cl)ccc31)CO2)N1CCCC1]

To a solution of pyrrolidine (23.8 mg, 0.34 mmol) in THF (2 mL) was added triphosgene (49.7 mg, 0.17 mmol). The mixture was kept stirring at r.t. for 2 hrs. Then pyridine was added to the solution. The mixture was further kept stirring at r.t. for 1 h. Then the whole solution was transferred to a solution of 6'-chloro-5-(cyclobutylmethyl)spiro[2,4-dihydro-1,5-benzoxazepine-3,1'-tetralin]-7-sulfonamide (Example 1, Step 1, 15.0 mg, 0.03 mmol) and potassium carbonate (4.64 mg, 0.03 mmol) in acetone. The mixture was kept stirring at reflux overnight. The mixture was poured into water (5 mL) and the pH of aqueous was adjusted to 7-8 by adding saturated potassium bicarbonate solution. The aqueous layer was extracted with DCM (5 mL×3). The combined organic layer was dried over sodium sulfate and concentrated. The crude product was further purified prep HPLC on C18 column to afford N-[6'-chloro-5-(cyclobutylmethyl)spiro[2,4-dihydro-1,5-benzoxazepine-3,1'-tetralin]-7-yl]sulfonylpyrrolidine-1-carboxamide (9 mg, 47% yield) as a yellow solid. LCMS calculated for $C_{28}H_{35}ClN_3O_4S$ $(M+H)^+$: m/z=544.20; found: 543.8.

Example 25

(1S,1'R,2'R)-6-Chloro-3,4-dihydro-2H-spiro[naphthalene-1,3'-5,10-dithia-9-aza-1(5,7)-benzo[b][1,4]oxazepina-6(1,3)-benzena-3(1,2)-cyclobutanacyclodecaphan]-8'-one 10',10'-dioxide

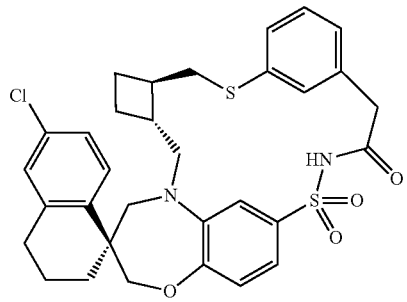

Step 1: [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl] methyl 4-methylbenzenesulfonate

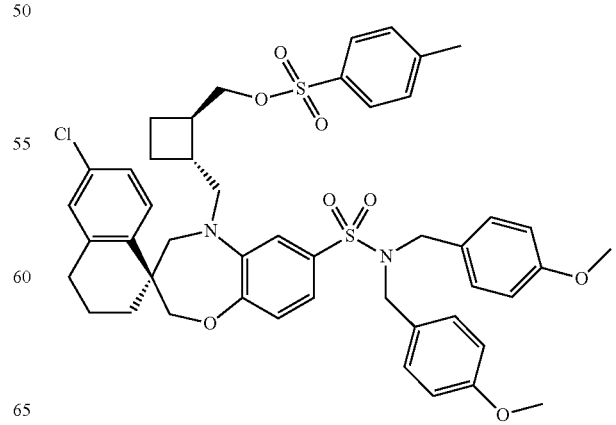

To a mixture of (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide (Example 18, Step 2, 44.0 mg, 0.06 mmol), tosyl chloride (16.2 mg, 0.08 mmol) in DCM (0.5 mL) was added TEA (22 uL, 0.16 mmol) at r.t. The reaction mixture was stirred at r.t. for 22 h. The additional tosyl chloride (21.2 mg, 0.11 mmol) and TEA (70 μL, 0.50 mmol) were added, and the reaction mixture was stirred for an additional 3 d at r.t. The reaction mixture was diluted with EtOAc (30 mL), washed with sat. NH₄Cl (15 mL) and water (15 mL), 0.05N HCl (30 mL), sat. NaHCO₃ (2×20 mL), and brine (20 mL). The organic layer was dried over Na₂SO₄, filtered, concentrated under reduced pressure to yield crude [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl 4-methylbenzenesulfonate (65.8 mg) which was directly used in next step reaction without further purification.

Step 2: methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methylsulfanyl]phenyl]acetate

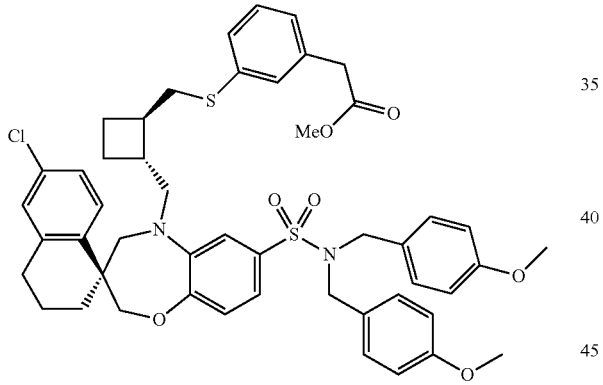

A mixture of [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl 4-methylbenzenesulfonate (65.8 mg), methyl 2-(3-sulfanylphenyl)acetate (26.3 mg, 0.12 mmol), and potassium carbonate (21.5 mg, 0.15 mmol) was purged with N₂, and charged with DMF (400 μL). The mixture was stirred at r.t. overnight. LCMS analysis to form two major products. The reaction mixture was diluted with EtOAc (30 mL), washed with 0.1 N HCl (3 mL) and water (30 mL), sat. NaHCO₃ (30 mL), and brine (20 mL). The organic layer was dried over Na₂SO₄, filtered, concentrated under reduced pressure to yield crude methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methylsulfanyl]phenyl]acetate (74 mg) as a brown solid. $R_f$=0.34 (2:1 hexanes:EtOAc)

Step 3: methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methylsulfanyl]phenyl]acetate

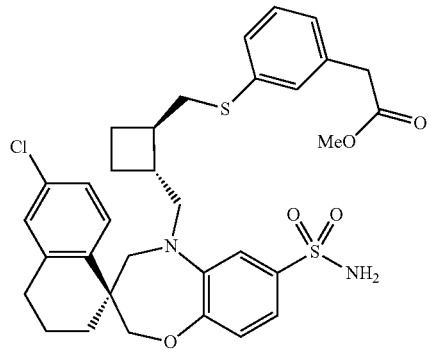 [SMILES: COC(=O)Cc1cccc(SC[C@@H]2CC[C@H]2CN2C[C@@]3(CCCc4cc(Cl)ccc43)COc3ccc(S(N)(=O)=O)cc32)c1]

A solution of methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methylsulfanyl]phenyl]acetate (74 mg) in DCM (1.3 mL) and TFA (1.3 mL) was stirred at r.t. for 18 h. The volatiles were removed under reduced pressure. The residue was co-evaporated with DCM twice under reduced pressure, and purified by FCC (12 g SiO₂, 10→35% EtOAc in hexanes, wet-loaded in DCM) to yield methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methylsulfanyl]phenyl]acetate (19.3 mg with ~80% pure) as a white solid. $R_f$=0.18 (2:1 hexanes:EtOAc); LCMS m/z calcd for $C_{33}H_{38}ClN_2O_5S_2$ (M+H)⁺: m/z=641.19/643.19; found: 641.2/643.1.

Step 4: 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methylsulfanyl]phenyl]acetic Acid

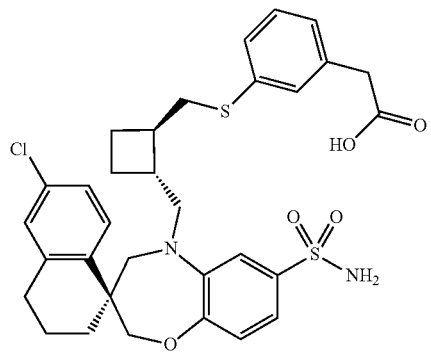 [SMILES: NS(=O)(=O)c1ccc2c(c1)N(C[C@@H]1CC[C@H]1CSc1cccc(CC(=O)O)c1)C[C@@]1(CCCc3cc(Cl)ccc31)CO2]

Methyl 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl sulfanyl]phenyl]acetate (19.0 mg, 0.02 mmol) in THF (400 uL) was treated with lithium hydroxide (6.0 mg, 0.24 mmol) in water (130 μL) at r.t. The reaction mixture was stirred at r.t. for 4 h. The mixture was diluted with EtOAc (20 mL), washed with water (5 mL), 0.1

N HCl (4 mL), and brine (15 mL). The aqueous layer was separated and extracted again with EtOAc (20 mL). The combined organic layers were dried over Na$_2$SO$_4$, filtered, and concentrated under reduced pressure to yield 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methylsulfanyl]phenyl]acetic acid (29 mg) as an opaque yellow gum. LCMS m/z calcd for C$_{32}$H$_{36}$ClN$_2$O$_5$S$_2$ (M+H)$^+$: m/z=627.17/629.17; found: 627.1/629.1.

Step 5: (1S,1'R, 2'R)-6-chloro-3,4-dihydro-2H-spiro [naphthalene-1,3'-5,10-dithia-9-aza-1(5,7)-benzo[b] [1,4]oxazepina-6(1,3)-benzena-3(1,2)-cyclobutana-cyclodecaphan]-8'-one 10',10'-dioxide A solution of 2-[3-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl sulfanyl]phenyl]acetic acid (29 mg) and 1-ethyl-3-(3-dimethylaminopropyl)carbodiimide hydrochloride (26.0 mg, 0.14 mmol) in DCM (1.5 mL) was charged with 4-(dimethylamino)pyridine (27.0 mg, 0.22 mmol). The mixture was purged with N$_2$ and stirred at r.t. for 20 h. The reaction mixture was diluted with EtOAc (30 mL), washed twice with 1 N HCl (3 mL) and brine (20 mL). The aqueous layers were combined and back-extracted with DCM (3×20 mL). The organic combined layers were dried over Na$_2$SO$_4$, and filtered, and concentrated under reduced pressure. The residue was purified by FCC (15.5 g C18, 20→100% MeCN in H$_2$O, wet-loaded in DMSO). Fractions containing clean desired product were combined and concentrated under reduced pressure to yield (1S,1'R,2'R)-6-chloro-3,4-dihydro-2H-spiro[naphthalene-1,3'-5,10-dithia-9-aza-1(5,7)-benzo[b][1,4]oxazepina-6(1,3)-benzena-3(1,2)-cyclobutanacyclodecaphan]-8'-one 10',10'-dioxide (5.5 mg) as a white solid. LCMS m/z calcd for C$_{32}$H$_{34}$ClN$_2$O$_4$S$_2$ (M+H)$^+$: m/z=609.16/611.16; found: 609.0/611.0. $^1$H NMR (500 MHz, Chloroform-d) δ 7.88 (s, 1H), 7.72 (d, J=8.5 Hz, 1H), 7.45 (dd, J=2.1, 8.4 Hz, 1H), 7.28 (d, J=4.2 Hz, 2H), 7.21 (dd, J=2.3, 8.5 Hz, 1H), 7.12 (d, J=2.2 Hz, 1H), 7.07 (s, 1H), 7.03 (t, J=4.7 Hz, 1H), 6.97 (d, J=8.3 Hz, 1H), 6.86 (d, J=2.2 Hz, 1H), 4.23 (d, J=12.1 Hz, 1H), 4.08 (d, J=12.0 Hz, 1H), 3.61 (ABq, 2H, J$_{AB}$=14.8 Hz, Δδ$_{AB}$=0.017 Hz), 3.46 (d, J=14.4 Hz, 1H), 3.38-3.27 (m, 2H), 3.07 (dt, J=6.8, 13.6 Hz, 2H), 2.84-2.73 (m, 3H), 2.26 (ddd, J=7.7, 15.0, 31.3 Hz, 2H), 2.06 (dtd, J=2.6, 8.0, 10.9 Hz, 1H), 1.98-1.75 (m, 3H), 1.66 (p, J=9.0 Hz, 2H), 1.61-1.48 (m, 2H).

Example 26

(3R,6R,7R,8E,23S)-6'-Chloro-7-methoxy-13,13-(1,3-propylene)-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

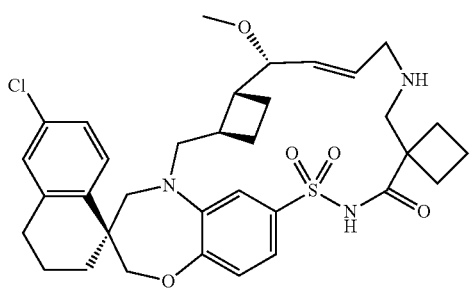

Step 1: 1-[(tert-butoxycarbonylamino)methyl]cyclobutanecarboxylic Acid

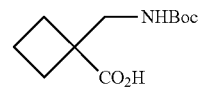

To a suspension of 1-(aminomethyl)cyclobutanecarboxylic acid hydrochloride salt (500 mg, 3.02 mmol) and sodium bicarbonate (1014 mg, 12.0 mmol) in THF (5 mL) and water (5 mL) was added di-tert-butyl dicarbonate (790 mg, 3.62 mmol). The resulting mixture was heated at 40° C. for 3 h. The reaction was acidified with 0.5 N HCl (to pH 4-5) and extracted with MTBE. The combined organic layers were washed with brine, dried over Na$_2$SO$_4$, filtered and concentrated under reduced pressure. The residue was purified by flash chromatography on a silica gel column with EtOAc/Hept (15% to 40%) to afford 1-[(tert-butoxycarbonylamino)methyl]cyclobutanecarboxylic acid (520 mg, 75% yield). LCMS: calc. for C$_{11}$H$_{18}$NO$_4$ (M−H)$^−$: m/z=228.12; Found: 228.17.

Step 2: 1-[[allyl(tert-butoxycarbonyl)amino]methyl] cyclobutanecarboxylic Acid

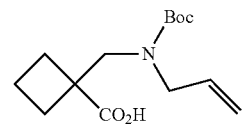

To a solution of 1-[(tert-butoxycarbonylamino)methyl] cyclobutanecarboxylic acid (520 mg, 2.27 mmol) in THF (10 mL) was slowly added sodium hydride (272 mg, 6.8 mmol) at r.t. After 20 min, allyl bromide (411 mg, 3.4 mmol) was added in one portion. The resulting slurry was heated to a gentle reflux for 48 h. The reaction was cool to r.t., concentrated under reduced pressure, charged with EtOAc, and acidified with 0.5 N HCl (to pH 4-5). The layers were separated, and the aqueous phase was extracted with EtOAc. The combined organic layers were washed with brine, dried over Na$_2$SO$_4$, and concentrated under reduced pressure The residue was purified by flash chromatography on a silica gel column with EtOAc/Hept (10% to 30%) to afford 1-[[allyl(tert-butoxycarbonyl)amino]methyl]cyclobutanecarboxylic acid (203 mg, 33% yield) as a yellow oil. LCMS: calc. for C$_{14}$H$_{22}$NO$_4$ (M−H)$^−$: m/z=268.16, Found: 268.13.

Step 3: tert-butyl N-allyl-N-[[1-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylcarbamoyl]cyclobutyl]methyl]carbamate

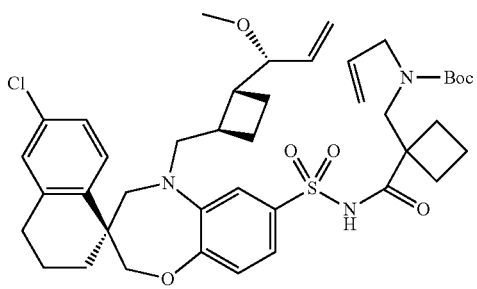

A mixture of (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (120.0 mg, 0.23 mmol, Intermediate 8), 1-[[allyl(tert-butoxycarbonyl)amino]methyl]cyclobutanecarboxylic acid (125 mg, 0.46 mmol), DMAP (170 mg, 1.39 mmol) and EDCI (0.27 mL, 1.39 mmol) was stirred at r.t. for 4 h. The reaction was diluted with CH$_2$Cl$_2$ and washed with 0.5 N HCl. The organic phase was dried over Na$_2$SO$_4$, filtered and concentrated under reduced pressure. The residue was purified by flash chromatography on a silica gel column (12 g) using EtOAc/Heptanes (5% to 50%) to afford tert-butyl N-allyl-N-[[1-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylcarbamoyl]cyclobutyl]methyl]carbamate (180 mg) as a colorless oil. LCMS: calc. for C$_{41}$H$_{55}$ClN$_3$O$_7$S [M+H]$^+$: m/z=768.34/770.34; Found: 768.14/770.47.

Step 4: (3R,6R,7R,8E,23S)-6'-chloro-7-methoxy-11-(tert-butoxycarbonyl)-13,13-(1,3-propylene)-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

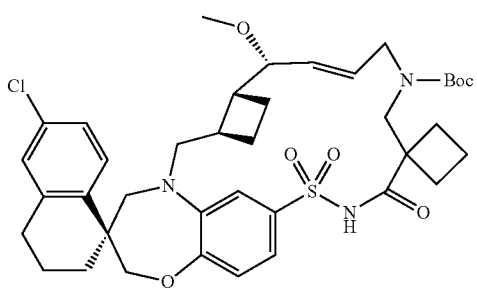

A solution of tert-butyl N-allyl-N-[[1-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylcarbamoyl]cyclobutyl]methyl]carbamate (180 mg, 0.23 mmol) in DCE (90 mL) was bubbled with N$_2$ for 10 min. (1,3-Dimesitylimidazolidin-2-ylidene)(2-isopropoxybenzylidene)ruthenium(VI) chloride; Hoveyda-Grubbs II (29.3 mg, 0.05 mmol) was added and the resulting greenish solution was further bubbled with N$_2$ for 5 min, and was heated to reflux under N$_2$ for 16 h. LC-MS analysis indicated the completion of reaction. The reaction was allowed to cool to r.t. while being exposed to air. The reaction was concentrated under reduced pressure, and the residue was purified by flash chromatography on a silica gel column (12 g) using EtOAc/Heptanes (5% to 60%) to afford (3R,6R,7R,8E,23S)-6'-chloro-7-methoxy-11-(tert-butoxycarbonyl)-13,13-(1,3-propylene)-16,16-dioxo-spiro[21-oxa-16-thia-1,11,15-triazatetracyclo[15.7.2.03,6.020,25]hexacosa[8,17(26), 18,20 (25)]tetraene-23,1'-tetralin]-14-one (140 mg, 80% yield). LC-MS: [M+H]$^+$ calc. for C$_{39}$H$_{51}$ClN$_3$O$_7$S: 740.31/742.31; Found: 739.96/742.29.

Step 5: (3R,6R,7R,8E,23S)-6'-chloro-7-methoxy-13,13-(1,3-propylene)-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

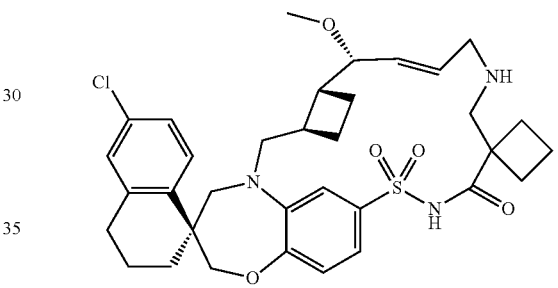

(3R,6R,7R,8E,23S)-6'-Chloro-7-methoxy-11-(tert-butoxycarbonyl)-13,13-(1,3-propylene)-16,16-dioxo-spiro[21-oxa-16-thia-1,11,15-triazatetracyclo[15.7.2.03,6.020,25]hexacosa[8,17(26), 18,20(25)]tetraene-23,1'-tetralin]-14-one (140.0 mg, 0.19 mmol) in 2 N HCl in EtOAc (3 mL) was stirred at r.t. overnight. The reaction was diluted with EtOAc, washed with saturated aqueous NaHCO$_3$ solution and brine, dried over Na$_2$SO$_4$, filtered and concentrated under reduced pressure to afford the crude product (120 mg). 40 mg of the crude product was purified by prep-HPLC on C18 column (30×250 mm, 10 m) with 20 to 100% ACN/H$_2$O to afford the desired (3R,6R,7R,8E,23S)-6'-chloro-7-methoxy-13,13-(1,3-propylene)-16,16-dioxo-spiro[21-oxa-16-thia-1,11,15-triazatetracyclo[15.7.2.03,6.020,25]hexacosa[8,17(26), 18,20(25)]tetraene-23,1'-tetralin]-14-one (19 mg) as a white solid. LCMS: calc. for C$_{34}$H$_{43}$ClN$_3$O$_5$S [M+H]$^+$: m/z=640.26/642.26; Found: 639.96/642.23. $^1$H NMR (600 MHz, CDCl$_3$) δ 7.69 (d, J=8.5 Hz, 1H), 7.50 (d, J=8.3 Hz, 1H), 7.27 (d, 1H, overlapped with CDCl$_3$), 7.17 (dd, J=8.5, 2.3 Hz, 1H), 7.07 (d, J=2.3 Hz, 1H), 6.96 (d, J=8.3 Hz, 1H), 5.90 (app s, 1H), 5.62 (dd, J=15.6, 8.0 Hz, 1H), 4.07 (t, J=9.3 Hz, 2H), 3.74 (d, J=14.4 Hz, 1H), 3.54 (app s, 1H), 3.41 (app s, 1H), 3.28 (d, J=14.6 Hz, 1H), 3.25 (s, 3H), 3.18-3.10 (m, 1H), 3.02 (d, J=13.4 Hz, 1H), 2.89-2.71 (m, 2H), 2.63-2.42 (m, 2H), 2.26 (app s, 1H), 2.09-1.77 (m, 8H), 1.62-1.50 (m, 9H).

Example 27

(3R,6R,7R,8E,23S)-6'-Chloro-7-methoxy-11-methyl-13,13-(1,3-propylene)-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

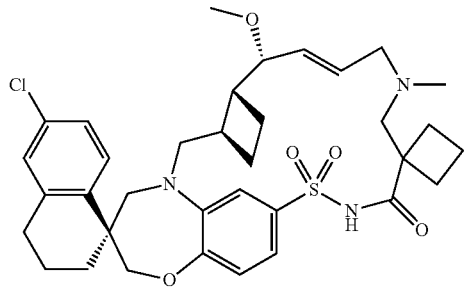 [SMILES: CO[C@@H]1/C=C/CN(C)CC2(CCC2)C(=O)NS(=O)(=O)c2ccc3c(c2)N(C[C@@H]2CC[C@H]21)C[C@@]1(CCCc2cc(Cl)ccc21)CO3]

To a solution of (3R,6R,7R,8E,23S)-6'-chloro-7-methoxy-13,13-(1,3-propylene)-16,16-dioxo-spiro[21-oxa-16-thia-1,11,15-triazatetracyclo[15.7.2.03,6.020,25]hexacosa[8,17(26), 18,20(25)]tetraene-23,1'-tetralin]-14-one (40.0 mg, 0.06 mmol, Example 26) in DCM (5 mL) was added acetic acid (0.02 mL, 0.31 mmol) and formaldehyde solution (37% wt %, 51 mg, 0.625 mmol HCHO). After 2 h, the reaction mixture was cooled at 0° C. and sodium borohydride (47.2 mg, 1.25 mmol) was added in portions. The reaction was stirred at r.t. for 3 h, and diluted with DCM and water, filtered through a pad of Celite. The organic layer was washed with saturated aqueous NaHCO$_3$ solution and brine, dried over Na$_2$SO$_4$, filtered and concentrated under reduced pressure. The residue was purified by prep-HPLC on C18 column (30×250 mm, 10 m) with 20 to 100% ACN/H$_2$O to afford (3R,6R,7R,8E,23S)-6'-chloro-7-methoxy-11-methyl-13,13-(1,3-propylene)-16,16-dioxo-spiro[21-oxa-16-thia-1,11,15-triazatetracyclo[15.7.2.03, 6.020,25]hexacosa[8,17(26), 18,20(25)]tetraene-23,1'-tetralin]-14-one (20 mg, 48.9% yield). LCMS: calc. for C$_{35}$H$_{45}$ClN$_3$O$_5$S [M+H]$^+$: m/z=654.28/656.27; Found: 654.02/656.36. $^1$H NMR (600 MHz, CDCl$_3$) δ 13.75 (br s, 1H), 7.70 (d, J=8.5 Hz, 1H), 7.54 (dd, J=8.3, 2.1 Hz, 1H), 7.17 (dd, J=8.5, 2.3 Hz, 1H), 7.07 (d, J=2.3 Hz, 1H), 6.97 (d, J=8.3 Hz, 1H), 6.95 (br s, 1H), 6.12-6.03 (m, 1H), 5.53 (dd, J=15.8, 8.8 Hz, 1H), 4.06 (s, 2H), 3.72 (d, J=14.6 Hz, 1H), 3.60 (t, J=8.5 Hz, 1H), 3.52 (q, J=12.8, 11.3 Hz, 1H), 3.31 (d, J=14.7 Hz, 1H), 3.28 (s, 3H), 3.19 (q, J=13.4, 9.2 Hz, 1H), 3.09 (t, J=11.4 Hz, 1H), 2.96 (dd, J=15.1, 11.2 Hz, 1H), 2.87 (d, J=13.8 Hz, 1H), 2.83-2.66 (m, 3H), 2.60-2.52 (m, 1H), 2.45 (app s, 5H), 2.15-1.58 (m, 13H).

Example 28

(3R,6R,7S,8E,22S)-6'-Chloro-7-methoxy-12,12-ethylene-15,15-dioxo-spiro[[11,20]dioxa-15-thia-1,14-diazatetracyclo[14.7.2.03,6.019,24]pentacosa[8,16(25),17,19(24)]tetraene-22,1'-tetralin]-13-one

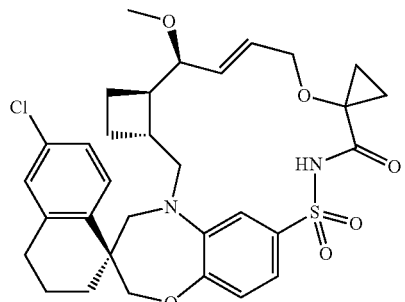

Step 1: methyl 1-(allyloxy)cyclopropane-1-carboxylate

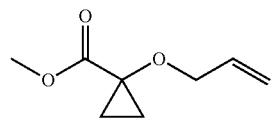

NaH (1.03 g, 25.84 mmol) washed by ether (30 mL) was added in one portion to a solution of methyl 1-hydroxycyclopropanecarboxylate (2.0 g, 17.22 mmol) in THF (20 mL). The reaction mixture was stirred at r.t. for 1 h. Allyl bromide (2.08 g, 17.2 mmol) was added, and the reaction mixture was stirred at r.t. for 14 h., then quenched with saturated aqueous NH$_4$Cl (20 mL). The resulting mixture was extracted with ether (3×30 mL). The combined organic layers were washed with brine, dried over anhydrous Na$_2$SO$_4$, and filtered. The filtrate was concentrated by decompression distillation at 0° C. to give methyl 1-(allyloxy)cyclopropane-1-carboxylate (1.2 g, 44% yield) as colorless oil. $^1$H NMR (400 MHz, DMSO-d$_6$) δ 5.91-5.83 (m, 1H), 5.24-5.19 (m, 1H), 5.12-5.09 (m, 1H), 4.096-4.06 (m, 2H), 3.65 (s, 3H), 1.19-1.17 (m, 4H).

Step 2: 1-(allyloxy)cyclopropane-1-carboxylic Acid

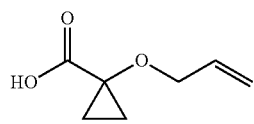

NaOH (1.5 g, 37.5 mmol) was added to a solution of methyl 1-allyloxycyclopropanecarboxylate (1.2 g, 7.68 mmol) in methanol (5 mL) and water (5 mL). The reaction mixture was stirred at r.t. for 14 h. To the reaction mixture was added 20 mL of water. The resulting mixture was extracted with DCM (3×20 mL), then adjusted with HCl (3 M) to pH 2-3, extracted with DCM (5 mL×3). The combined organic layers were dried over anhydrous Na₂SO₄ and filtered. The filtrate was concentrated to give the crude product 1-allyloxycyclopropanecarboxylic acid (369 mg, 34% yield) which was used directly in next step reaction without further purification. ¹H NMR (400 MHz, DMSO-d₆) δ 12.54 (br s, 1H), 5.92-5.82 (m, 1H), 5.20 (ddd, J=17.3, 3.8, 1.8 Hz, 1H), 5.09 (ddd, J=10.5, 3.4, 1.5 Hz, 1H), 4.07 (dt, J=5.4, 1.6 Hz, 2H), 1.15-1.14 (m, 2H), 1.11-1.09 (m, 1H).

Step 3: (3R,6R,7S,8E,22S)-6'-chloro-7-methoxy-12,12-ethylene-15,15-dioxo-spiro[[11,20]dioxa-15-thia-1,14-diazatetracyclo[14.7.2.03,6.019,24]pentacosa[8,16(25),7,19(24)]tetraene-22,1'-tetralin]-13-one This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and 1-(allyloxy)cyclopropane-1-carboxylic acid in Step 3. LC-MS calc. for C₃₂H₃₈ClN₂O₆S [M+H]⁺: m/z=613.2/615.2. Found: 612.8/615.1. ¹H NMR (600 MHz, DMSO-d₆) δ 11.73 (s, 1H), 7.58 (d, J=8.4 Hz, 1H), 7.33 (d, J=15.7 Hz, 1H), 7.27-7.19 (m, 3H), 7.08 (d, J=14.5 Hz, 1H), 5.66-5.57 (m, 1H), 5.09-5.01 (m, 1H), 4.14 (d, J=11.9 Hz, 1H), 4.09-4.03 (m, 1H), 4.00 (d, J=12.0 Hz, 1H), 3.93 (dd, J=12.7, 9.3 Hz, 1H), 3.52 (d, J=14.2 Hz, 1H), 3.33-3.28 (m, 2H), 3.16-3.05 (m, 2H), 3.02 (s, 3H), 2.84-2.71 (m, 2H), 2.11-2.05 (m, 1H), 2.06-1.97 (m, 1H), 1.88-1.80 (m, 3H), 1.78-1.72 (m, 3H), 1.56 (q, J=9.3 Hz, 1H), 1.40-1.37 (m, 1H), 1.27-1.23 (m, 2H), 1.07-1.05 (m, 2H).

Example 29

(3R,6R,7R,8E,22S)-6'-Chloro-7-methoxy-12,12-ethylene-15,15-dioxo-spiro[[11,20]dioxa-15-thia-1,14-diazatetracyclo[14.7.2.03,6.019,24]pentacosa[8,16(25),17,19(24)]tetraene-22,1'-tetralin]-13-one

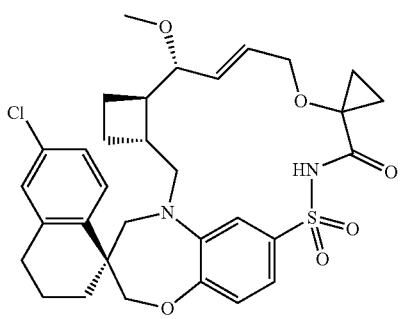 [SMILES: CO[C@@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-(allyloxy)cyclopropane-1-carboxylic acid in Step 3. LC-MS calc. for C₃₂H₃₈ClN₂O₆S [M+H]⁺: m/z=613.2/615.2. Found: 613.2/615.1. ¹H NMR (600 MHz, DMSO-d₆) 11.79 (s, 1H), 7.67 (d, J=8.5 Hz, 1H), 7.30 (dd, J=8.5, 2.3 Hz, 1H), 7.25 (d, J=8.4 Hz, 1H), 7.21-7.20 (m, 2H), 7.05 (d, J=8.2 Hz, 1H), 5.67-5.63 (m, 1H), 5.40 (dd, J=15.4, 8.5 Hz, 1H), 4.16-4.05 (m, 3H), 3.80 (dd, J=13.1, 7.2 Hz, 1H), 3.63-3.57 (m, 2H), 3.09-3.05 (m, 4H), 2.83-2.80 (m, 1H), 2.75-2.69 (m, 1H), 2.64-2.59 (m, 1H), 2.29-2.27 (m, 1H), 2.00 (d, J=13.7 Hz, 1H), 1.88-1.82 (m, 3H), 1.76-1.61 (m, 3H), 1.44-1.41 (m, 1H), 1.26-1.14 (m, 3H), 1.06-1.04 (m, 1H).

Example 30

(3R,6R,7R,8E,22S)-6'-Chloro-7-methoxy-12,12-dimethyl-15,15-dioxo-spiro[[11,20]dioxa-15-thia-1,14-diazatetracyclo[14.7.2.03,6.019,24]pentacosa[8,16(25),17,19(24)]tetraene-22,1'-tetralin]-13-one

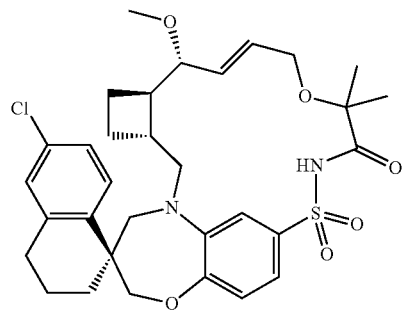 [SMILES: CO[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: 2-allyloxy-2-methyl-propanoic Acid

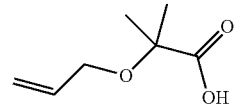

This compound was prepared using procedures analogous to those described for Example 28 Step 1-2 using ethyl 2-hydroxy-2-methyl-propanoate to replace methyl 1-hydroxycyclopropanecarboxylate in Step 1.

Step 2: (3R,6R,7R,8E,22S)-6'-chloro-7-methoxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-(allyloxy)cyclopropane-1-carboxylic acid in Step 3. LC-MS calc. for C₃₂H₄₀ClN₂O₆S [M+H]⁺: m/z=615.22/617.22. Found: 614.8/617.1. ¹H-NMR (600 MHz, CDCl₃) δ 9.07 (s, 1H), 7.67 (d, J=8.5 Hz, 1H), 7.51 (d, J=8.2 Hz, 1H), 7.17 (d, J=8.5 Hz, 1H), 7.08 (d, J=2.0 Hz, 1H), 6.99 (dd, J=8.7, 5.1 Hz, 2H), 5.83 (d, J=15.4 Hz, 1H), 5.53 (dd, J=15.6, 8.5 Hz, 1H), 4.11 (dt, J=21.2, 7.1 Hz, 3H), 3.77 (d, J=12.2 Hz, 1H), 3.72 (d, J=14.7 Hz, 1H), 3.59-3.44 (m, 2H), 3.33 (d, J=14.7 Hz, 1H), 3.27 (s, 3H), 3.07 (dd, J=15.0, 9.9 Hz, 1H), 2.84-2.67 (m, 2H), 2.58-2.44 (m, 1H), 2.25-2.13 (m, 1H), 2.04-1.89 (m, 4H), 1.87-1.77 (m, 1H), 1.65-1.52 (m, 3H), 1.42 (s, 3H), 1.38 (s, 3H).

Example 31

(3R,6R,7R,8E,22S)-6'-Chloro-7-methoxy-12,12-(1,3-propylene)-15,15-dioxo-spiro[11,20-dioxa-15-thia-1,14-diazatetracyclo[14.7.2.0³,⁶.0¹⁹,²⁴]pentacosa[8,16(25),17,19(24)]tetraene-22,1'-tetralin]-13-one

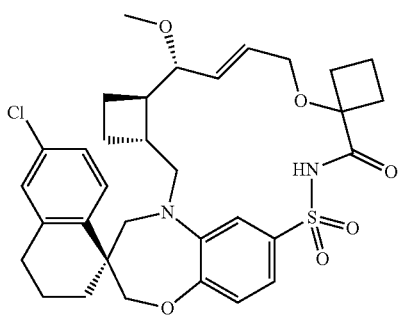 [SMILES: CO[C@@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3]

Step 1: ethyl 1-hydroxycyclobutanecarboxylate

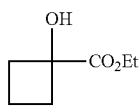

To a solution of ethyl 1-aminocyclobutanecarboxylate hydrochloride (501.2 mg, 2.79 mmol) in aqueous sulfuric acid (11.2 mL, 5.6 mmol) at 0° C. was dropwise added a solution of sodium nitrite (980 mg, 14 mmol) in water (3 mL). The reaction was stirred at 0° C. for 1 h and allowed to warm to r.t. After 24 h., the reaction was extracted with MTBE. The combined organic layers were washed with brine, dried over $Na_2SO_4$, filtered and concentrated in vacuo to give ethyl 1-hydroxycyclobutane-1-carboxylate as colorless oil (240 mg). The crude product was used in next step without further purification. TLC: $R_f$=0.38 (3:7 EtOAc/Hept).

Step 2: 1-allyloxycyclobutanecarboxylic Acid

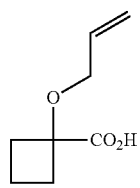

This compound was prepared using procedures analogous to those described for Example 28 Step 1-2 using ethyl 1-hydroxycyclobutane-1-carboxylate to replace methyl 1-hydroxycyclopropanecarboxylate in Step 1. LC-MS calc. for $C_8H_{11}O_3$ [M−H]⁻: m/z=155.1; Found: 155.1.

Step 3: (3R,6R,7R,8E,22S)-6'-chloro-7-methoxy-12,12-(1,3-propylene)-15,15-dioxo-spiro[11,20-dioxa-15-thia-1,14-diazatetracyclo[14.7.2.0³,⁶.0¹⁹,²⁴]pentacosa[8,16(25), 17, 19(24)]tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-allyloxycyclobutanecarboxylic acid in Step 3. LC-MS calc. for $C_{33}H_{40}ClN_2O_6S$ [M+H]⁺: m/z=627.23/629.23. Found: 626.9/629.0. ¹H-NMR (400 MHz, CDCl₃) δ 10.13 (s, 1H), 7.73 (d, J=8.5 Hz, 1H), 7.53 (d, J=8.5 Hz, 1H), 7.23 (s, 1H), 7.20 (d, J=10.1 Hz, 1H), 7.10 (s, 1H), 6.97 (d, J=8.3 Hz, 1H), 5.90-5.79 (m, 2H), 4.29-3.63 (m, 8H), 3.33 (s, 3H), 3.27 (d, J=14.5 Hz, 1H), 3.00 (dd, J=15.2, 10.5 Hz, 1H), 2.84-2.72 (m, 2H), 2.70-2.59 (m, 1H), 2.37 (s, 2H), 2.10-1.16 (m, 12H).

Example 32

(3R,6R,7S,8E,22S)-6'-Chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one and

Example 33

(3R,6R,7S,8Z,22S)-6'-Chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one Example 32

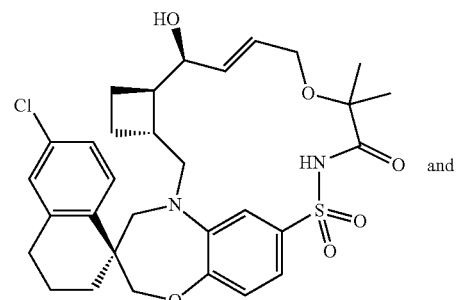

and

Example 33

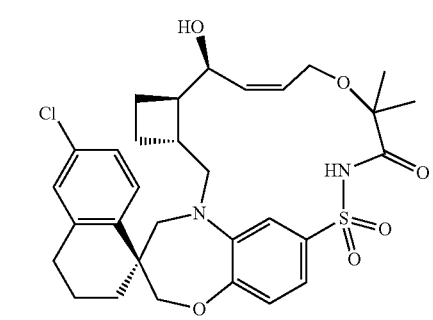

Step 1: [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]allyl] 2-allyloxy-2-methyl-propanoate

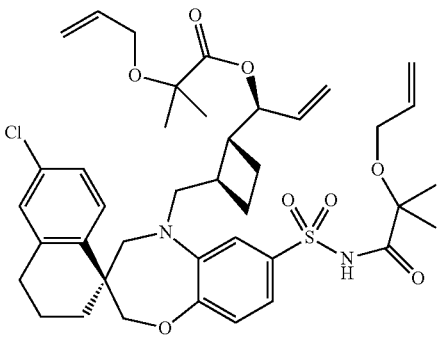 [SMILES: C=CCOC(C)(C)C(=O)NS(=O)(=O)c1ccc2c(c1)N(C[C@@H]1CC[C@H]1[C@H](C=C)OC(=O)C(C)(C)OCC=C)C[C@@]1(CCCc3cc(Cl)ccc31)CO2]

A solution of (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (200.0 mg, 0.40 mmol, Intermediate 3), 2-allyloxy-2-methyl-propanoic acid (171.96 mg, 1.19 mmol, Example 30, Step 1), EDCI (0.47 mL, 2.39 mmol), and DMAP (291.43 mg, 2.39 mmol) in DCM (4 mL) was stirred at r.t. for 16 h. LC-MS indicated the completion of reaction. The reaction was diluted with DCM and washed with 0.5 N HCl. The organic phase was dried over Na$_2$SO$_4$ and concentrated under reduced pressure. The residue was purified by flash chromatography on a silica gel column (12 g) with EtOAc/Heptanes (10% to 20%) to afford [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]allyl] 2-allyloxy-2-methyl-propanoate (300 mg, 99.9% yield). LC-MS: calc. for C$_{40}$H$_{52}$ClN$_2$O$_8$S [M+H]$^+$: m/z=755.31/757.31; Found: 755.1/757.4.

Step 2: 2-allyloxy-2-methyl-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-propanamide

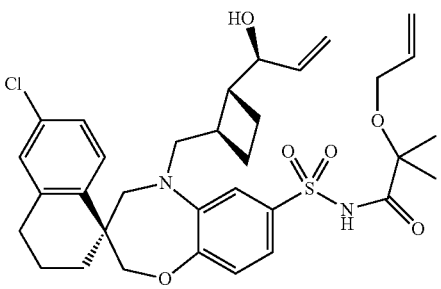 [SMILES: C=CCOC(C)(C)C(=O)NS(=O)(=O)c1ccc2c(c1)N(C[C@@H]1CC[C@H]1[C@@H](O)C=C)C[C@@]1(CCCc3cc(Cl)ccc31)CO2]

A solution of [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]allyl] 2-allyloxy-2-methyl-propanoate (300 mg, 0.40 mmol) and lithium hydroxide monohydrate (83.3 mg, 1.99 mmol) in THF/MeOH/H$_2$O (0.3 mL each) was heated at 45° C. for 4 h. LC-MS indicated the completion of reaction. The reaction was adjusted with 1 N HCl to pH 3-4 and extracted with DCM. The combined organic layers were washed with saturated aqueous NaHCO$_3$ solution and brine, dried over Na$_2$SO$_4$, filtered and concentrated under reduced pressure to afford 2-allyloxy-2-methyl-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-propanamide (175 mg, 70% yield), which was used without further purifications. LCMS: calc. for C$_{33}$H$_{42}$ClN$_2$O$_6$S [M+H]$^+$: m/z=629.24/631.24; Found: 628.9/631.2.

Step 3. (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one A solution of 2-allyloxy-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-2-methyl-propanamide (1.40 g, 2.23 mmol) in DCE (1230 mL) was bubbled with N$_2$ for 10 min. 1,3-Bis(2,4,6-trimethylphenyl)-4,5-dihydroimidazol-2-ylidene[2-(i-propoxy)-5-(N,N-dimethyl aminosulfonyl)phenyl]methyleneruthenium(II) dichloride (Zhan Catalyst 1B) (326 mg, 0.45 mmol) was added and the resulting greenish solution was further bubbled with N$_2$ for 5 min., and was heated at 40° C. under N$_2$ for 2 h. The reaction was concentrated under reduced pressure, and the residue purified by flash column chromatography on a silica gel column with EtOAc/Hept (10% to 70%) to afford two products: P1 (the earlier eluted product, 160 mg, 11% yield) and P2 (the latter eluted product, 647 mg, 47% yield).

P2 was assigned to (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 32). HPLC: major product, C18 column (4.6×150 mm, 100 Å); flow rate=1 mL/min; mobile phase: 90% MeCN/H$_2$O (with 0.1% HCO$_2$H) 10 min λ=220 nm. tR=3.2 min. LC-MS calc. for C$_{31}$H$_{38}$ClN$_2$O$_6$S [M+H]$^+$: m/z=601.21/603.21; Found 601.6/603.6; $^1$H NMR (300 MHz, CDCl$_3$) δ 9.15 (s, 1H), 7.69 (d, J=8.5 Hz, 1H), 7.53 (dd, J=8.3, 2.1 Hz, 1H), 7.20 (dd, J=8.6, 2.2 Hz, 1H), 7.12 (s, 1H), 7.06 (d, J=1.8 Hz, 1H), 7.02 (d, J=8.3 Hz, 1H), 5.84-5.72 (m, 2H), 4.24 (d, J=3.3 Hz, 1H), 4.13 (t, J=7.2 Hz, 2H), 4.00 (dd, J=13.2, 4.5 Hz, 1H), 3.88 (d, J=12.5 Hz, 1H), 3.72 (d, J=14.6 Hz, 1H), 3.40-3.24 (m, 3H), 2.84-2.71 (m, 3H), 2.43-2.33 (m, 1H), 2.01 (d, J=15.5 Hz, 2H), 1.94-1.81 (m, 4H), 1.75-1.58 (m, 2H), 1.54 (d, J=14.5 Hz, 1H), 1.45 (s, 3H), 1.41 (s, 3H).

And P1 to (3R,6R,7S,8Z,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 33). P1: minor product, C18 column (4.6×150 mm, 100 Å); flow rate=1 mL/min; mobile phase: 90% MeCN/H$_2$O (with 0.1% HCO$_2$H) 10 min λ=220 nm. tR=4.3 min. LC-MS calc. for C$_{31}$H$_{38}$ClN$_2$O$_6$S [M+H]$^+$: m/z=601.21/603.21; Found 601.6/603.6; $^1$H NMR (300 MHz, CDCl$_3$) δ 9.22 (s, 1H), 7.68 (t, J=8.3 Hz, 1H), 7.55 (dd, J=8.4, 2.1 Hz, 1H), 7.20 (dd, J=8.5, 2.1 Hz, 1H), 7.13 (dd, J=9.6, 2.0 Hz, 2H), 7.03 (d, J=8.4 Hz, 1H), 5.92-5.75 (m, 2H), 4.22-4.14 (m, 1H), 4.00 (dd, J=13.4, 4.9 Hz, 1H), 3.89 (dd, J=13.3, 2.9 Hz, 1H), 3.81-3.61 (m, 4H), 3.33 (d, J=14.5 Hz, 1H), 3.15 (dd, J=15.1, 9.2 Hz, 1H), 2.79 (d, J=9.2 Hz, 2H), 2.53 (d, J=5.2

Hz, 1H), 2.33-2.22 (m, 1H), 2.08-1.92 (m, 4H), 1.81 (dd, J=35.4, 6.4 Hz, 2H), 1.71-1.57 (m, 2H), 1.45 (s, 3H), 1.42 (s, 3H).

Example 34

[(3R,6R,7S,8E,22S)-6'-Chloro-12,12-dimethyl-3,5,5-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate

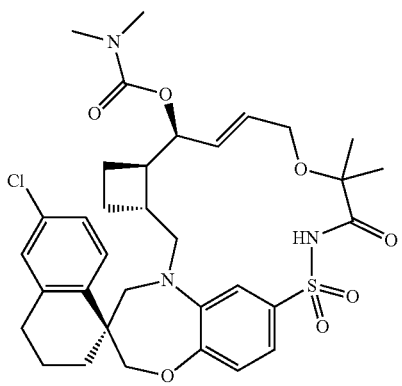 [SMILES: CN(C)C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (13.0 mg, 0.02 mmol, Example 32) in THF (0.5 mL) was added sodium hydride (4.3 mg, 0.11 mmol) at r.t. After 10 min, N,N-dimethylcarbamoyl chloride (4.6 mg, 0.04 mmol) was added, and followed by DMAP (5.3 mg, 0.04 mmol). The mixture was stirred at r.t. for 6 h., and diluted with DCM and acidified with 0.5 N HCl to pH 5-6. The organic phase was separated, washed with water and brine, dried over $Na_2SO_4$, filtered and concentrated under reduced pressure. The residue was purified by prep-HPLC on C18 column (30×250 mm, 10 m) with 20 to 100% ACN/$H_2O$ to afford [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate (6 mg, 38% yield) as a white solid. LCMS: calc. for $C_{34}H_{43}ClN_3O_7S$ [M+H]$^+$: m/z=672.25/674.25; Found: 672.45/674.37. $^1$H NMR (600 MHz, CDCl$_3$) δ 9.08 (br s, 1H), 7.67 (d, J=8.5 Hz, 1H), 7.49 (dd, J=8.3, 2.2 Hz, 1H), 7.17 (dd, J=8.5, 2.4 Hz, 1H), 7.08 (d, J=2.2 Hz, 1H), 7.04-6.95 (m, 2H), 5.86-5.78 (m, 1H), 5.74-5.67 (m, 1H), 5.30 (t, J=4.5 Hz, 1H), 4.15 (d, J=12.2 Hz, 1H), 4.12-4.05 (m, 2H), 3.76-3.72 (m, 1H), 3.70 (d, J=14.8 Hz, 1H), 3.43 (dd, J=15.1, 4.7 Hz, 1H), 3.37 (d, J=14.7 Hz, 1H), 3.21 (dd, J=15.1, 9.3 Hz, 1H), 2.95 (d, J=14.6 Hz, 6H), 2.83-2.73 (m, 3H), 2.37 (dtd, J=15.2, 10.2, 9.7, 5.5 Hz, 1H), 2.06-1.90 (m, 3H), 1.88-1.77 (m, 3H), 1.67-1.60 (m, 2H), 1.56 (s, 2H), 1.43 (s, 6H).

Example 35

[(3R,6R,7S,8Z,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate

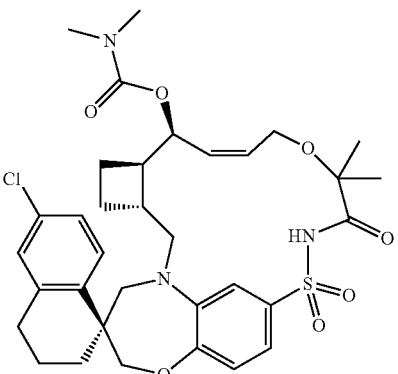

This compound was prepared using procedures analogous to those described for Example 34 using (3R,6R,7S,8Z,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 33) and N,N-dimethylcarbamoyl chloride. LC-MS calc. for $C_{34}H_{43}ClN_3O_7S$ [M+H]$^+$: m/z=672.24/674.24; Found: 672.6/674.6.

Example 36

(3R,6R,7R,8E,22S)-6'-Chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

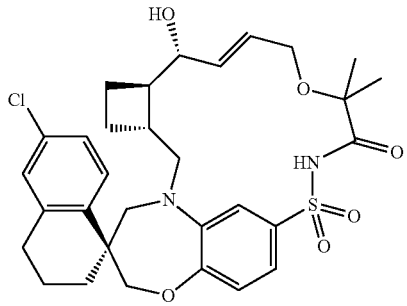 [SMILES: CC1(C)OC/C=C/[C@@H](O)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 32 using (3S)-6'-chloro-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Intermediate 8) to replace (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Intermediate 7) in Step 2. LC-MS calc. for $C_{31}H_{38}ClN_2O_6S$ [M+H]$^+$: m/z=601.21/603.21; Found: 600.9/602.8. $^1$H NMR (600 MHz, DMSO-d$_6$) δ 11.87 (s, 1H), 7.64 (d, J=8.5 Hz, 1H), 7.26 (dd, J=14.2, 5.6 Hz, 2H), 7.18 (d, J=1.9 Hz, 1H), 7.01 (d, J=8.3 Hz, 1H), 6.89 (s, 1H), 5.83 (d, J=12.7 Hz, 1H), 5.49 (dd, J=15.6, 7.9 Hz, 1H), 4.85 (d, J=4.0 Hz, 1H), 4.09 (dd, J=29.6, 12.2 Hz, 2H), 3.99 (dd, J=13.4, 7.4 Hz, 1H), 3.74 (dd, J=11.8, 8.0 Hz, 1H), 3.60 (d, J=14.6 Hz, 1H), 3.45 (d, J=12.5 Hz, 1H), 3.38 (dd, J=21.8, 9.7 Hz, 2H), 3.08 (dd, J=14.8, 10.0 Hz, 1H), 2.81 (d, J=16.9 Hz, 1H), 2.75-2.67 (m, 1H), 2.37-2.30 (m, 1H), 2.03-1.77 (m, 6H), 1.63 (ddd, J=30.2, 19.2, 10.3 Hz, 2H), 1.44 (dd, J=19.1, 9.3 Hz, 1H), 1.34 (s, 3H), 1.21 (s, 3H) ppm.

Example 37

[(3R,6R,7R,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N,N-dimethylcarbamate

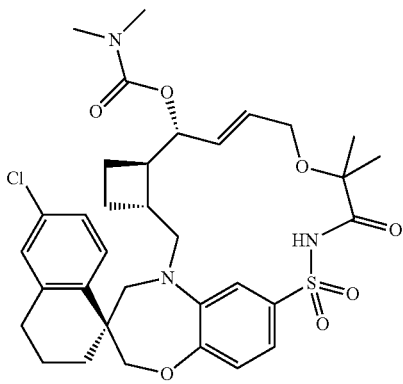 [SMILES: CN(C)C(=O)O[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 34 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 36) and N,N-dimethylcarbamoyl chloride. LC-MS calc. for $C_{34}H_{43}ClN_3O_7S$ [M+H]⁺: m/z=672.24/674.24; Found: 672.0/674.2. ¹H NMR (600 MHz, CDCl₃) δ 9.27 (br s, 1H), 7.69 (d, J=8.5 Hz, 1H), 7.52 (dd, J=8.3, 2.2 Hz, 1H), 7.18 (dd, J=8.5, 2.4 Hz, 1H), 7.08 (d, J=2.3 Hz, 1H), 7.04 (d, J=2.2 Hz, 1H), 7.00 (d, J=8.3 Hz, 1H), 5.85 (dt, J=15.6, 4.2 Hz, 1H), 5.80-5.73 (m, 1H), 5.08 (dd, J=7.9, 5.0 Hz, 1H), 4.11 (d, J=12.1 Hz, 1H), 4.06 (d, J=12.1 Hz, 1H), 4.05-3.96 (m, 2H), 3.79 (d, J=14.5 Hz, 1H), 3.73 (dd, J=15.2, 3.8 Hz, 1H), 3.27 (d, J=14.5 Hz, 1H), 3.08 (dd, J=15.3, 9.8 Hz, 1H), 2.96 (s, 3H), 2.92 (s, 3H), 2.77 (dddd, J=22.3, 16.7, 11.4, 4.6 Hz, 3H), 2.54 (td, J=13.0, 11.6, 6.5 Hz, 1H), 2.41 (qd, J=9.4, 4.9 Hz, 1H), 2.05-1.78 (m, 6H), 1.66 (tq, J=14.6, 7.5, 6.4 Hz, 2H), 1.55 (qd, J=10.4, 8.5 Hz, 1H), 1.40 (s, 3H), 1.36 (s, 3H).

Example 38

(3R,6R,7R,8E,22S)-6'-Chloro-7-hydroxy-12,12-ethylene-15,15-dioxo-spiro[11,20-dioxa-15-thia-1,14-diazatetracyclo[14.7.2.03,6.019,24]pentacosa[8,16(25),17,19(24)]tetraene-22,1'-tetralin]-13-one

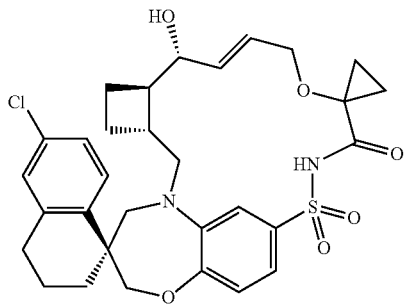 [SMILES: O=C1NS(=O)(=O)c2ccc3c(c2)N(C[C@@H]2CC[C@H]2[C@H](O)/C=C/COC12CC2)C[C@@]1(CCCc2cc(Cl)ccc21)CO3]

This compound was prepared using procedures analogous to those described for Example 32 using (3S)-6'-chloro-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Intermediate 4) and 1-allyloxycyclopropanecarboxylic acid (Example 28, Step 2) in Step 1. LCMS: calc. for $C_{31}H_{36}ClN_2O_6S$ [M+H]⁺: m/z=599.20/601.19; Found: 599.4/601.5. ¹H NMR (600 MHz, DMSO-d₆) δ 11.68 (br, 1H), 7.67 (d, J=8.5 Hz, 1H), 7.29 (dd, J=8.5, 2.3 Hz, 1H), 7.27-7.15 (m, 3H), 7.01 (dd, J=12.3, 5.6 Hz, 1H), 5.58-5.47 (m, 2H), 4.76 (d, J=4.5 Hz, 1H), 4.10 (d, J=12.0 Hz, 1H), 4.04-3.95 (m, 2H), 3.84-3.76 (m, 1H), 3.69-3.57 (m, 2H), 3.03 (d, J=14.5 Hz, 1H), 2.86-2.77 (m, 1H), 2.70 (dt, J=16.9, 8.6 Hz, 1H), 2.05-1.95 (m, 2H), 1.87-1.78 (m, 3H), 1.74-1.68 (m, 2H), 1.62-1.58 (m, 1H), 1.49-1.45 (m, 1H), 1.41 (td, J=15.3, 8.3 Hz, 1H), 1.32-1.10 (m, 6H).

Example 39

[(3R,6R,7R,8E,22S)-6'-Chloro-12,12-ethylene-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate

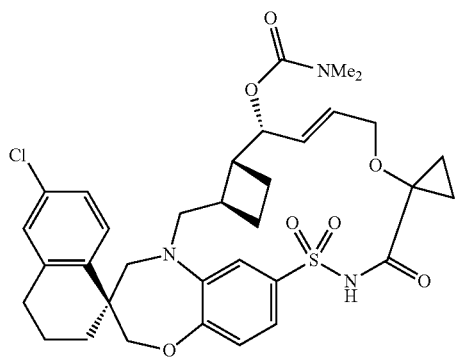 [SMILES: CN(C)C(=O)O[C@@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 34 using (3R,6R,7R,8E,22S)-6'-Chloro-7-hydroxy-12,12-ethylene-15,15-dioxospiro[11,20-dioxa-15-thia-1,14-diazatetracyclo[14.7.2.0³,⁶.0¹⁹,²⁴]pentacosa[8,16(25),17,19(24)]tetraene-22,1'-tetralin]-13-one (Example 38) and N,N-dimethylcarbamoyl chloride. LCMS: calc. for C₃₄H₄₁ClN₃O₇S [M+H]⁺: m/z=670.24/672.23; Found: 670.84/672.86. ¹H NMR (600 MHz, CDCl₃) δ 9.04 (s, 1H), 7.71 (d, J=8.5 Hz, 1H), 7.49 (dd, J=8.3, 2.1 Hz, 1H), 7.29 (d, J=2.2 Hz, 1H), 7.18 (dd, J=8.5, 2.3 Hz, 1H), 7.08 (d, J=2.3 Hz, 1H), 7.01 (d, J=8.3 Hz, 1H), 5.71 (app q, J=2.6 Hz, 2H), 4.88 (d, J=3.0 Hz, 1H), 4.13 (d, J=12.1 Hz, 1H), 4.05-3.99 (m, 2H), 3.96-3.91 (m, 1H), 3.85 (d, J=14.4 Hz, 1H), 3.82-3.76 (m, 1H), 3.18 (d, J=14.5 Hz, 1H), 3.06 (dd, J=15.3, 5.7 Hz, 1H), 2.91 (s, 3H), 2.84 (s, 3H), 2.76 (dt, J=11.0, 5.4 Hz, 2H), 2.56 (tt, J=10.7, 5.2 Hz, 2H), 2.03-1.85 (m, 4H), 1.83-1.63 (m, 2H), 1.72-1.64 (m, 1H), 1.44 (td, J=13.6, 13.1, 2.6 Hz, 1H), 1.38 (q, J=3.2 Hz, 2H), 1.24-1.19 (m, 1H), 1.18-1.11 (m, 1H).

Example 40

(3R,6R,7S,8E,22S)-6'-Chloro-7-hydroxy-12,12-ethylene-15,15-dioxo-spiro[11,20-dioxa-15-thia-1,14-diazatetracyclo[14.7.2.0³,⁶.0¹⁹,²⁴]pentacosa[8,16(25),17,19(24)]tetraene-22,1'-tetralin]-13-one

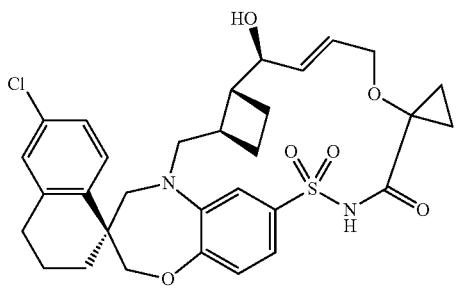 [SMILES: O=C1NS(=O)(=O)c2ccc3c(c2)N(C[C@@H]2CC[C@H]2[C@@H](O)/C=C/COC12CC2)C[C@@]1(CCCc2cc(Cl)ccc21)CO3]

This compound was prepared using procedures analogous to those described for Example 32 using (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Intermediate 3) and 1-allyloxycyclopropanecarboxylic acid (Example 28, Step 2) in Step 1. LCMS: calc. for C₃₁H₃₆ClN₂O₆S [M+H]⁺: m/z=599.20/601.19; Found: 599.7/601.6. ¹H NMR (300 MHz, CDCl₃) δ 9.09 (s, 1H), 7.67 (d, J=8.5 Hz, 1H), 7.52 (d, J=8.2 Hz, 1H), 7.31 (s, 1H), 7.18 (d, J=8.6 Hz, 1H), 7.10 (d, J=1.9 Hz, 1H), 7.02 (d, J=8.4 Hz, 1H), 5.86 (dd, J=15.5, 4.2 Hz, 1H), 5.69-5.51 (m, 1H), 4.19-4.02 (m, 3H), 3.96 (dd, J=12.0, 6.7 Hz, 2H), 3.74 (d, J=14.5 Hz, 1H), 3.54 (dd, J=15.0, 8.1 Hz, 1H), 3.33 (dd, J=17.5, 7.5 Hz, 2H), 2.79 (dd, J=9.1, 5.2 Hz, 2H), 2.64 (dd, J=14.6, 8.3 Hz, 1H), 2.55-2.41 (m, 1H), 2.10-1.77 (m, 3H), 1.65 (ddd, J=35.5, 23.7, 11.9 Hz, 3H), 1.51-1.41 (m, 2H), 1.41-1.31 (m, 2H), 1.23 (ddd, J=17.1, 9.8, 5.4 Hz, 3H).

Example 41

[(3R,6R,7S,8E,22S)-6'-Chloro-12,12-ethylene-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate

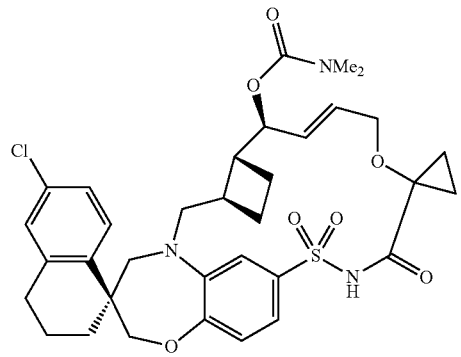 [SMILES: CN(C)C(=O)O[C@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 34 using (3R,6R,7S,8E,22S)-6'-Chloro-7-hydroxy-12,12-ethylene-15,15-dioxo-spiro[11,20-dioxa-15-thia-1,14-diazatetracyclo[14.7.2.03,6.0-19,24]pentacosa[8,16(25),17,19(24)]tetraene-22,1'-tetralin]-13-one (Example 40) and N,N-dimethylcarbamoyl chloride. LCMS: calc. for C₃₄H₄₁ClN₃O₇S [M+H]⁺: m/z= 670.24/672.23; Found: 670.84/672.73. ¹H NMR (600 MHz, CDCl₃) δ 9.16 (s, 1H), 7.65 (d, J=8.5 Hz, 1H), 7.45 (dd, J=8.3, 2.2 Hz, 1H), 7.25 (d, J=2.3 Hz, 1H), 7.16 (dd, J=8.5, 2.4 Hz, 1H), 7.07 (d, J=2.3 Hz, 1H), 6.96 (d, J=8.3 Hz, 1H), 5.79-5.65 (m, 2H), 5.21-5.17 (m, 1H), 4.15 (d, J=12.2 Hz, 1H), 4.10 (d, J=12.1 Hz, 1H), 4.06-3.98 (m, 2H), 3.63 (d, J=14.7 Hz, 1H), 3.54 (dd, J=15.3, 7.6 Hz, 1H), 3.31 (d, J=14.7 Hz, 1H), 3.22 (dd, J=15.2, 6.5 Hz, 1H), 2.85 (s, 3H), 2.82-2.71 (m, 3H), 2.63 (s, 3H), 2.55 (qd, J=8.8, 6.2 Hz, 1H), 2.09-1.87 (m, 4H), 1.78 (tdd, J=20.5, 10.8, 6.3 Hz, 2H), 1.63 (p, J=9.8 Hz, 1H), 1.50-1.42 (m, 1H), 1.41-1.33 (m, 2H), 1.30-1.23 (m, 1H), 1.20-1.12 (m, 1H).

Example 42

(3R,6R,7R,8E,22S)-6'-Chloro-7-methoxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one

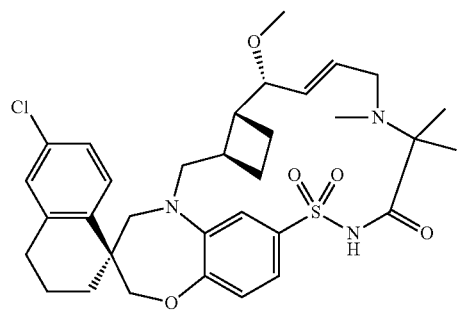 [SMILES: CO[C@@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3]

Step 1: 2-[allyl(tert-butoxycarbonyl)amino]-2-methyl-propanoic acid

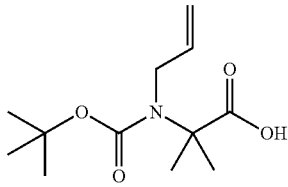 [SMILES: C=CCN(C(=O)OC(C)(C)C)C(C)(C)C(=O)O]

To a stirred solution of 2-((tert-butoxycarbonyl)amino)-2-methylpropanoic acid (2.0 g, 9.84 mmol) in THF (40 mL) was added sodium hydride (0.98 g, 24.6 mmol) in portions under an ice bath. The resulting solution was stirred at r.t. for 10 minutes. Then Allyl bromide (2.13 mL, 24.6 mmol) was added. The reaction was stirred at 50° C. for 24 h. The reaction was quenched with saturated NH$_4$Cl solution (40 mL). The mixture was extracted with EtOAc (40 mL×3). The combined organic layers were dried over sodium sulfate and concentrated under reduced pressure. The residue was purified by flash chromatography on a silica gel column (40 g) with EtOAc/Heptanes (5% to 80%) to afford 2-[allyl(tert-butoxycarbonyl)amino]-2-methyl-propanoic acid (1.6 g, 66% yield) as a white solid. LC-MS calc. for C$_{12}$H$_{20}$NO$_4$ [M−H]$^-$: m/z=242.1; Found: 242.1.

Step 2: tert-butyl N-[1,1-dimethyl-2-oxo-2-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylamino]ethyl]carbamate

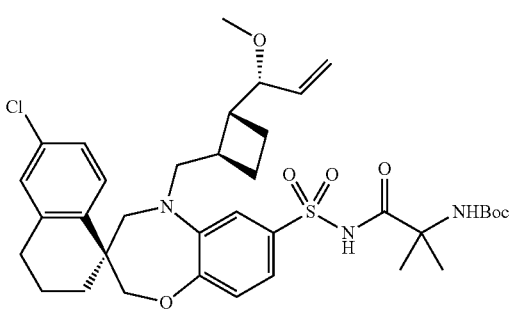 [SMILES: C=C[C@@H](OC)[C@@H]1CC[C@H]1CN1C[C@@]2(CCCc3cc(Cl)ccc32)COc2ccc(S(=O)(=O)NC(=O)C(C)(C)NC(=O)OC(C)(C)C)cc21]

To a stirred solution of 2-((tert-butoxycarbonyl)amino)-2-methylpropanoic acid (176.87 mg, 0.87 mmol) in DCM (5 mL) was added DMAP (212 mg, 1.74 mmol) followed by EDCI (135 mg, 0.87 mmol). The resulting mixture was stirred at r.t. for 10 min. Then (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (150.0 mg, 0.29 mmol, Intermediate 8) was added. The reaction was stirred at 40° C. for 8 h. LC-MS showed full conversion of starting material. The reaction was quenched by HCl (1 M, 10 mL), and was extracted with DCM (10 mL×2). The combined organic layers were dried over sodium sulfate and concentrated under reduced pressure. The residue was purified by flash chromatography on a silica gel column (20 g) with EtOAc/Heptanes (10% to 80%) to afford tert-butyl N-[1,1-dimethyl-2-oxo-2-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylamino]ethyl]carbamate (159 mg, 78% yield) as a yellow liquid. LC-MS calc. for C$_{36}$H$_{49}$ClN$_3$O$_7$S [M+H]$^+$: m/z=702.3/704.3; Found: 702.0/704.3.

Step 3: 2-amino-2-methyl-N-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-propanamide

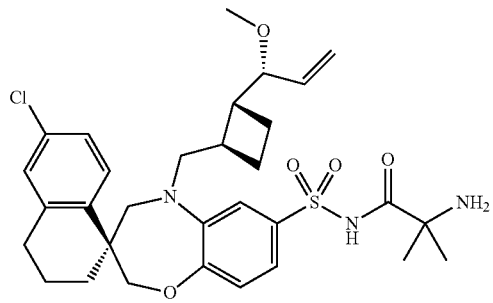 [SMILES: C=C[C@@H](OC)[C@@H]1CC[C@H]1CN1C[C@@]2(CCCc3cc(Cl)ccc32)COc2ccc(S(=O)(=O)NC(=O)C(C)(C)N)cc21]

tert-Butyl N-[1,1-dimethyl-2-oxo-2-[[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonylamino]ethyl]carbamate (230 mg, 0.33 mmol) was treated with 2M HCl in EA (10.0 mL, 0.33 mmol) at r.t. for 2 h. The solvent was evaporated under reduced pressure to afford the crude product as HCl salt which was used in next step without further purification. LC-MS calc. for C$_{31}$H$_{41}$ClN$_3$O$_5$S [M+H]$^+$: m/z=602.2/604.2; Found: 602.0/604.2.

Step 4: 2-(allylamino)-2-methyl-N-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-propanamide

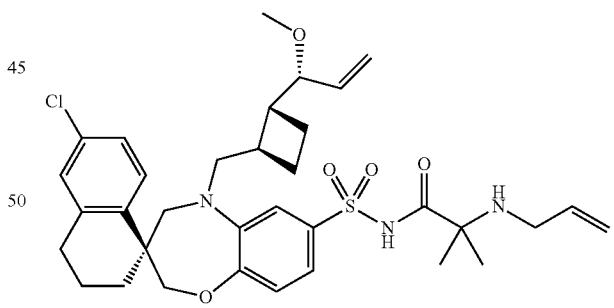

To a stirred solution of 2-amino-2-methyl-N-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-propanamide hydrochloride (180 mg, 0.28 mmol) in DMF (5 mL) was added sodium hydride (45 mg, 1.13 mmol). The resulting mixture was stirred at r.t. for 5 min. Then allyl bromide (0.02 mL, 0.28 mmol) was added. The reaction was stirred at r.t. for 48 h. LC-MS showed unreacted starting material (~15%), desired product (~60%) and dialkylation product (25%). The reaction was quenched by adding water (20 mL). EtOAc (20 mL) was added and the layers were separated. The organic layer was washed with water (20 mL), dried over sodium sulfate, filtered and concentrated under reduced pressure The residue was purified by flash chromatography on a silica gel column (20 g) with EtOAc/Heptanes (30% to 100%) to afford 2-(allylamino)-2-methyl-N-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-propanamide (57.5 mg, 31.7% yield) as a white solid. LC-MS calc. for $C_{34}H_{45}ClN_3O_5S$ [M+H]$^+$: 642.3/644.3; Found: 642.5/644.2.

Step 5: (3R,6R,7R,8E,22S)-6'-chloro-7-methoxy-12, 12-dimethyl-15,15-dioxo-spiro[20-oxa-15-thia-1,11, 14-triazatetracyclo[14.7.2.03,6.019,24]pentacosa-8, 16,18,24-tetraene-22,1'-tetralin]-13-one

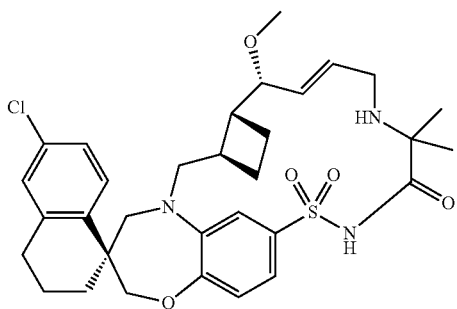 [SMILES: CO[C@@H]1/C=C/CNC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 4 using 2-(allylamino)-2-methyl-N-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-propanamide.
LC-MS calc. for $C_{32}H_{41}ClN_3O_5S$ [M+H]$^+$: 614.2/616.2; Found: 614.3/616.3.

Step 6: (3R,6R,7R,8E,22S)-6'-chloro-7-methoxy-11, 12,12-trimethyl-15,15-dioxo-spiro[20-oxa-15-thia-1, 11,14-triazatetracyclo[14.7.2.03,6.019,24]pentacosa-8,16,18,24-tetraene-22,1'-tetralin]-13-one This compound was prepared using procedures analogous to those described for Example 27 using (3R,6R,7R,8E, 22S)-6'-chloro-7-methoxy-12,12-dimethyl-15,15-dioxo-spiro[20-oxa-15-thia-1,11,14-triazatetracyclo[14.7.2.03, 6.019,24]pentacosa-8,16,18,24-tetraene-22,1'-tetralin]-13-one. LC-MS calc. for $C_{33}H_{43}ClN_3O_5S$ [M+H]$^+$: m/z=628.3/630.3; Found: 628.0/630.2. $^1$H NMR (600 MHz, DMSO-d$_6$) δ 9.13 (s, 1H), 7.64 (d, J=8.5 Hz, 1H), 7.25 (dd, J=8.5, 2.4 Hz, 1H), 7.17 (d, J=2.4 Hz, 1H), 7.10 (d, J=8.2 Hz, 1H), 6.83 (d, J=8.2 Hz, 1H), 6.74-6.70 (m, 1H), 6.27 (dd, J=12.4, 6.4 Hz, 1H), 5.62-5.57 (m, 1H), 4.04-3.95 (m, 2H), 3.56 (d, J=14.5 Hz, 1H), 3.53-3.37 (m, 2H), 3.21 (s, 3H), 3.01 (dd, J=15.2, 11.0 Hz, 1H), 2.80 (dt, J=17.0, 4.3 Hz, 1H), 2.71 (ddd, J=16.8, 10.4, 6.5 Hz, 1H), 2.65-2.55 (m, 2H), 2.49-2.25 (m, 3H), 2.03-1.90 (m, 3H), 1.87-1.81 (m, 1H), 1.77-1.70 (m, 2H), 1.54-1.31 (m, 4H), 1.31-1.04 (m, 6H).

Example 43

(3R,6R,7S,8E,22S)-6'-Chloro-7-hydroxy-11,12,12-trimethyl-15,15-dioxo-spiro[20-oxa-15-thia-1,11,14-triazatetracyclo[14.7.2.03,6.019,24]pentacosa-8,16, 18,24-tetraene-22,1'-tetralin]-13-one

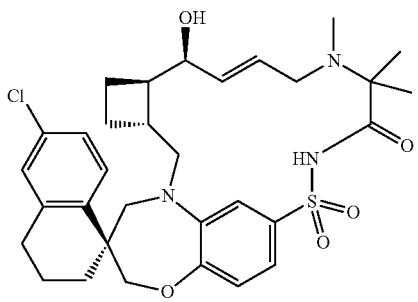 [SMILES: CN1C/C=C/[C@H](O)[C@@H]2CC[C@H]2CN2C[C@@]3(CCCc4cc(Cl)ccc43)COc3ccc(cc32)S(=O)(=O)NC(=O)C1(C)C]

Step 1: 3-allyl-4,4-dimethyl-oxazolidine-2,5-dione

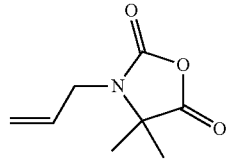

To a solution of 2-[allyl(tert-butoxycarbonyl)amino]-2-methyl-propanoic acid (4.79 g, 19.6 mmol, Example 83 Step 1) in ethyl acetate (25 mL) was added t-butylchlorodiphenylsilane (3.26 g, 21.6 mmol) at 0° C. followed by addition of triethylamine (TEA) (2.74 mL, 19.6 mmol). White precipitate was formed immediately. The reaction was stirred at 0° C. for 30 min. The white solid was filtered off and rinsed with EtOAc. The filtrate was concentrated under reduced pressure. The residue was dissolved in DCM (25 mL) and followed by addition of oxalyl chloride (2.1 mL, 24 mmol) and DMF (10 drops). Gas was evolved and the reaction was stirred at r.t. overnight. TLC showed a new spot (R$_f$=0.6, EA:Heptane=1:1) formed. The reaction was concentrated and co-evaporated THF 3 times to remove excess oxalyl chloride. The residue was treated with THF (30 mL) and filtered to provide a stock solution of the desired product (about 0.66 M with 98.6% purity showed by GC at 8.93 min.) which was directly used in next step reaction without further purification.

Step 2: 2-(allylamino)-2-methyl-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-propanamide

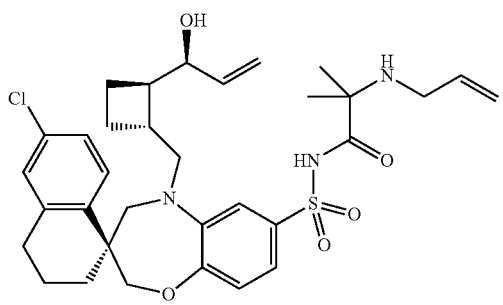 [SMILES: C=CCNC(C)(C)C(=O)NS(=O)(=O)c1ccc2c(c1)N(C[C@@H]1CC[C@H]1[C@@H](O)C=C)C[C@@]1(CCCc3cc(Cl)ccc31)CO2]

To a solution of (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (500.0 mg, 0.99 mmol, Intermediate 3) and 3-allyl-4,4-dimethyl-oxazolidine-2,5-dione (3.01 mL, 1.99 mmol) in THF (5 mL) was added 1,8-diazabicyclo[5.4.0]undec-7-ene (298 μL, 1.99 mmol). The resulting mixture was heated to 65° C. for 2 h. The reaction was cooled to r.t. Methanol (8 mL) and water (8 mL) were added, followed by addition of lithium hydroxide monohydrate (500 mg, 11.9 mmol). The reaction was heated to 45° C. for 3 h. THF was removed under reduced pressure. The residue was re-dissolved in DCM, and was quenched with sat. NH$_4$Cl aq. (5 mL). The mixture was extracted with DCM (5 mL×2). The combined organic layers were dried over Na$_2$SO$_4$, filtered and concentrated under reduced pressure. The residue was purified by flash chromatography on a silica gel column (20 g) with EtOAc/Heptanes (20% to 100%) then MeOH/EtOAc (0% to 50%) to afford 2-(allylamino)-2-methyl-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-propanamide (490 mg, 78.5% yield). LC-MS calc. for C$_{33}$H$_{43}$ClN$_3$O$_5$S [M+H]$^+$: m/z=628.3/630.3; Found: 628.8/630.8.

Step 3: (3R,6R,7S,8E,22S)-6'-chloro-7-hydroxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

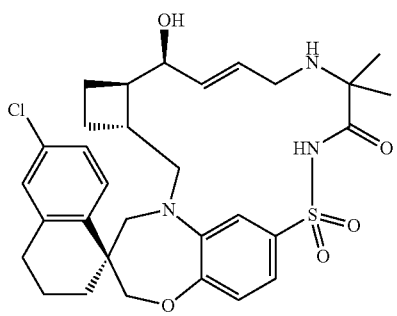 [SMILES: CC1(C)NC/C=C/[C@H](O)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 26 Step 4 using 2-(allylamino)-2-methyl-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-propanamide. LC-MS calc. for C$_{31}$H$_{39}$ClN$_3$O$_5$S [M+H]$^+$: m/z=600.2/602.2; Found: 600.7/602.7.

Step 4: (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one This compound was prepared using procedures analogous to those described for Example 27 using (3R,6R,7S,8E,22S)-6'-chloro-7-hydroxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one and formaldehyde aqueous solution. LC-MS calc. for C$_{32}$H$_{41}$ClN$_3$O$_5$S [M+H]$^+$: m/z=614.24/616.24; Found: 614.8/616.8. $^1$H NMR (600 MHz, DMSO-d$_6$) δ 7.63 (d, J=8.6 Hz, 1H), 7.25 (dd, J=8.5, 2.4 Hz, 1H), 7.17 (d, J=2.3 Hz, 1H), 7.14-7.10 (m, 1H), 7.08 (br, 1H), 6.86-6.84 (m, 2H), 5.79-5.73 (m, 1H), 5.37-5.31 (m, 1H), 4.09 (d, J=19.1 Hz, 1H), 3.51 (d, J=14.6 Hz, 1H), 3.07 (t, J=12.7 Hz, 1H), 2.84-2.76 (m, 1H), 2.71 (ddd, J=16.8, 10.8, 6.1 Hz, 1H), 2.64-2.60 (m, 1H), 2.17 (d, J=11.4 Hz, 1H), 2.04-2.00 (m, 2H), 1.89-1.82 (m, 3H), 1.67-1.61 (m, 2H), 1.47-1.41 (m, 3H), 1.35-1.33 (m, 2H), 1.27-1.22 (m, 10H), 0.89-0.81 (m, 2H).

Example 44

[(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

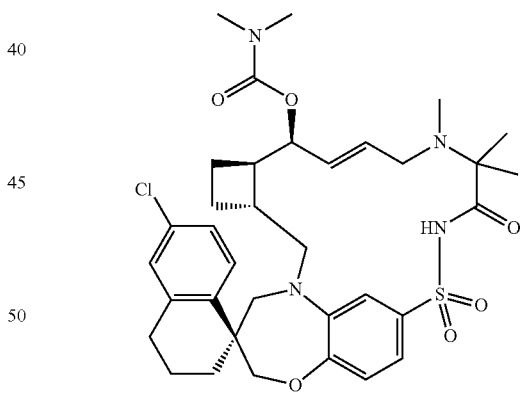

This compound was prepared using procedures analogous to those described for Example 34 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 43) and N,N-dimethylcarbamoyl chloride. LC-MS calc. for C$_{35}$H$_{46}$ClN$_4$O$_6$S [M+H]$^+$: m/z=685.3/687.3; Found: 685.3/687.3. $^1$H NMR (400 MHz, DMSO-d$_6$) δ 9.02 (s, 1H), 7.64 (d, J=8.5 Hz, 1H), 7.26 (dd, J=8.5, 2.4 Hz, 1H), 7.17 (d, J=2.3 Hz, 1H), 7.10 (dd, J=8.1, 1.9 Hz, 1H), 6.84 (d, J=8.2 Hz, 1H), 6.77-6.73 (m, 1H), 6.62-6.59 (m, 1H), 6.29-6.26 (m, 1H), 5.91-5.83 (m, 1H), 4.15-3.92 (m, 3H), 3.56 (d, J=14.6 Hz, 1H), 3.29 (d, J=14.4 Hz, 2H), 3.02 (s, 3H), 2.86 (s, 3H), 2.75-2.65 (m, 2H), 2.57-2.51 (m, 4H), 2.43-2.26 (m, 3H), 2.08-1.79 (m, 4H), 1.68 (dt, J=17.5, 8.3 Hz, 2H), 1.57 (t, J=9.0 Hz, 2H), 1.36 (s, 3H), 1.18 (s, 3H).

Example 45

[(3R,6R,7S,8E,22S)-6'-Chloro-12,12-dimethyl-13,15,15-trioxo-11-(trideuteriomethyl)spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

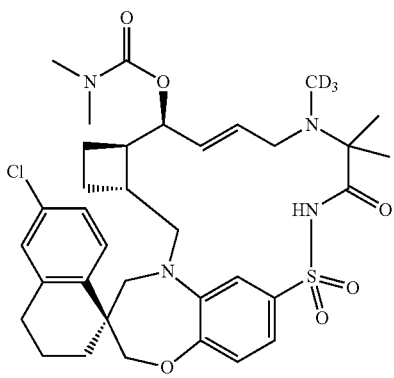 [SMILES: [2H]C([2H])([2H])N1C/C=C/[C@H](OC(=O)N(C)C)[C@@H]2CC[C@H]2CN2C[C@@]3(CCCc4cc(Cl)ccc43)COc3ccc(cc32)S(=O)(=O)NC(=O)C1(C)C]

Step 1: (3R,6R,7S,8E,22S)-6'-chloro-7-hydroxy-12,12-dimethyl-15,15-dioxo-11-(trideuteriomethyl)spiro[20-oxa-15-thia-1,11,14-triazatetracyclo[14.7.2.03,6.019,24]pentacosa-8,16,18,24-tetraene-22,1'-tetralin]-13-one

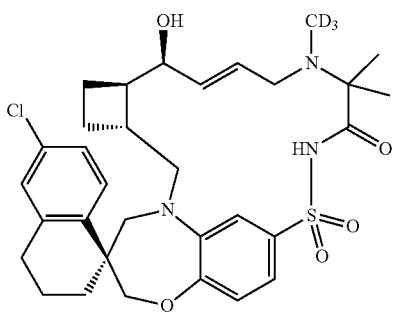 [SMILES: [2H]C([2H])([2H])N1C/C=C/[C@H](O)[C@@H]2CC[C@H]2CN2C[C@@]3(CCCc4cc(Cl)ccc43)COc3ccc(cc32)S(=O)(=O)NC(=O)C1(C)C]

To solution of (3R,6R,7S,8E,22S)-6'-chloro-7-hydroxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (425 mg, 0.71 mmol, Example 43) in DCE (10 mL) was added formaldehyde-d2 solution (~20 wt. % in D₂O) (113 mg, 3.54 mmol). The mixture was stirred at 20° C. for 2 h. LC-MS analysis indicated the starting material was consumed and the iminium intermediate was formed. Sodium cyanoborodeuteride (233 mg, 3.54 mmol) was then added the reaction was stirred for 4 h. LC-MS analysis indicated the reaction was complete. The reaction was quenched with 1M HCl aq. solution (20 mL), and extracted with DCM (20 mL×2). The combined organic layers were dried over Na₂SO₄, filtered and concentrated under reduced pressure to afford (3R,6R,7S,8E,22S)-6'-chloro-7-hydroxy-12,12-dimethyl-15,15-dioxo-11-(trideuteriomethyl)spiro[20-oxa-15-thia-1,11,14-triazatetracyclo[14.7.2.03,6.019,24]pentacosa-8,16,18,24-tetraene-22,1'-tetralin]-13-one (393 mg, 89.9% yield) as a light brown colored solid. LC-MS: calc. for $C_{32}H_{38}D_3ClN_3O_5S$ [M+H]⁺: m/z=617.26/619.26; Found: 617.3/619.1.

Step 2: [(3R,6R,7S,8E,22S)-6'-chloro-12,12-dimethyl-13,15,15-trioxo-11-(trideuteriomethyl)spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate This compound was prepared using procedures analogous to those described for Example 34 (3R,6R,7S,8E,22S)-6'-chloro-7-hydroxy-12,12-dimethyl-15,15-dioxo-11-(trideuteriomethyl)spiro[20-oxa-15-thia-1,11,14-triazatetracyclo[14.7.2.03,6.019,24]pentacosa-8,16,18,24-tetraene-22,1'-tetralin]-13-one and N,N-dimethylcarbamoyl chloride. LC-MS calc. for $C_{35}H_{43}ClD_3N_3O_6S$ [M+H]⁺: m/z=688.29/690.29; Found 688.5/690.3. ¹H NMR (499 MHz, DMSO-d₆) δ 7.62 (d, J=8.6 Hz, 1H), 7.23 (dd, J=8.5, 2.4 Hz, 1H), 7.15 (d, J=2.4 Hz, 1H), 7.09 (dd, J=8.1, 1.9 Hz, 1H), 6.82 (d, J=8.2 Hz, 1H), 6.75 (s, 1H), 6.23 (s, 1H), 5.82 (d, J=15.8 Hz, 1H), 5.22 (s, 1H), 3.98 (q, J=12.2 Hz, 2H), 3.54 (d, J=14.5 Hz, 2H), 3.40 (t, J=11.6 Hz, 3H), 3.06 (dd, J=15.1, 10.8 Hz, 1H), 3.00 (s, 3H), 2.84 (s, 3H), 2.78 (dt, J=16.8, 4.5 Hz, 1H), 2.69 (ddd, J=16.4, 10.6, 5.9 Hz, 2H), 2.39-2.28 (m, 1H), 2.02-1.93 (m, 1H), 1.93-1.76 (m, 3H), 1.68 (dt, J=17.7, 8.4 Hz, 2H), 1.63-1.52 (m, 1H), 1.47-1.36 (m, 1H), 1.34 (s, 3H), 1.16 (s, 3H).

Example 46

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 4-(2-methoxyethyl)piperazine-1-carboxylate

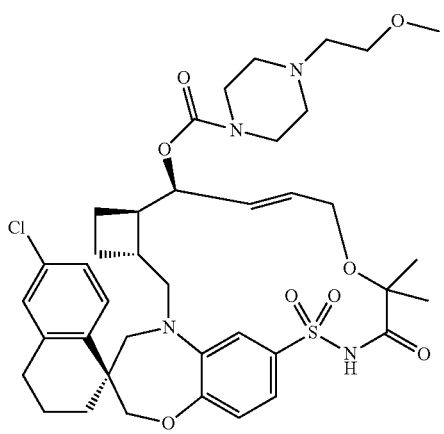 [SMILES: COCCN1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

Step 1: phenyl [(3R,6R,7S,8E,22S)-6'-chloro-12,12-dimethyl-13,15,15-trioxo-spiro[11,20-dioxa-15-thia-1,14-diazatetracyclo-[14.7.2.03,6.019,24]pentacosa-8,16,18,24-tetraene-22,1'-tetralin]-7-yl]carbonate

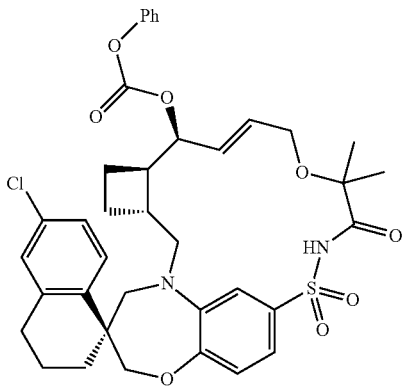 [SMILES: CC1(C)OC/C=C/[C@H](OC(=O)Oc2ccccc2)[C@@H]2CC[C@H]2CN2C[C@@]3(CCCc4cc(Cl)ccc43)COc3ccc(cc32)S(=O)(=O)NC1=O]

To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (2.8 g, 4.66 mmol, Example 32) and phenyl chloroformate (3.64 g, 23.2 mmol) in ACN (60 mL) was added pyridine (3.77 mL, 46.5 mmol). The mixture was stirred at r.t. for 1 h. The reaction was monitored by LC-MS. The mixture was carefully neutralized with 0.5 N HCl (80 mL), and extracted with ethyl acetate (40 mL×2). The organic layer was washed with saturated NaHCO$_3$ (80 mL), dried over Na$_2$SO$_4$, filtered and concentrated under reduced pressure. The residue was purified by flash chromatography on a silica gel column with EtOAc/10% DCM in Heptanes (5-65%) to afford the desired product phenyl [(3R,6R,7S,8E,22S)-6'-chloro-12,12-dimethyl-13,15,15-trioxo-spiro[11,20-dioxa-15-thia-1,14-diazatetracyclo[14.7.2.0~3,6.0~19,24]pentacosa-8,16,18,24-tetraene-22,1'-tetralin]-7-yl] carbonate (1.24 g, 36.9% yield). LC-MS calc. for C$_{38}$H$_{42}$ClN$_2$O$_8$S [M+H]$^+$: m/z=721.23.21/723.23; Found 721.8/723.8.

Step 2: [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 4-(2-methoxyethyl)piperazine-1-carboxylate To a solution of phenyl [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] carbonate (20.0 mg, 0.03 mmol) in MeCN (0.50 mL) was added 1-(2-methoxyethyl)piperazine (12.0 mg, 0.08 mmol). The reaction was heated to 80° C. for 2 h. The reaction was cooled to r.t. and concentrated under reduced pressure. The residue was re-dissolved in DCM (2 mL) and washed with 0.5 N HCl aq. (2 mL). Aqueous layer was extracted with DCM (2 mL) one more time. The combined organic layers were dried over Na$_2$SO$_4$, filtered and the filtrate was concentrated under reduced pressure. The residue was purified by prep-HPLC on C18 column (21.2×150 mm, 5 m) using MeCN/H$_2$O (20% to 100% over 18 min) to afford [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 4-(2-methoxyethyl)piperazine-1-carboxylate (10.6 mg, 48.7% yield). LC-MS calc. for C$_{39}$H$_{52}$ClN$_4$O$_8$S [M+H]$^+$: m/z=771.32/773.32; Found: 771.8/773.8. $^1$H NMR (300 MHz, CDCl$_3$) δ 7.68 (d, J=8.5 Hz, 1H), 7.50 (dd, J=8.3, 2.1 Hz, 1H), 7.19 (dd, J=8.5, 2.2 Hz, 1H), 7.10 (d, J=2.1 Hz, 1H), 7.02-6.95 (m, 2H), 5.88-5.75 (m, 1H), 5.70 (dd, J=15.7, 4.9 Hz, 1H), 5.34 (s, 1H), 4.11 (dt, J=11.6, 9.0 Hz, 3H), 3.81-3.65 (m, 3H), 3.62-3.43 (m, 5H), 3.43-3.31 (m, 4H), 3.22 (dd, J=15.1, 9.1 Hz, 1H), 2.85-2.67 (m, 2H), 2.60 (t, J=5.5 Hz, 3H), 2.38 (d, J=3.8 Hz, 2H), 2.08-1.89 (m, 5H), 1.89-1.71 (m, 4H), 1.63 (t, J=9.4 Hz, 2H), 1.50 (d, J=12.5 Hz, 2H), 1.44 (s, 3H), 1.37 (s, 3H).

Example 47

[(3R,6R,7S,8E,22S)-6'-Chloro-12,12-dimethyl-13,15,15-trioxo-spiro[11,20-dioxa-thia-1,14-diazatetracyclo[14.7.2.03,6.019,24]pentacosa-8,16,18,24-tetraene-22,1'-tetralin]-7-yl] N,N-bis(trideuteriomethyl)carbamate

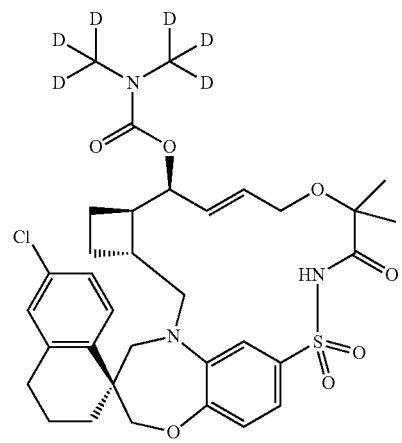 [SMILES: [2H]C([2H])([2H])N(C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3)C([2H])([2H])[2H]]

To a solution of DIPEA (232 mg, 1.8 mmol) in MeCN (3 mL) was added 1,1,1-trideuterio-N-(trideuteriomethyl)methanamine hydrochloride (0.3 mL, 1.8 mmol). The resulting mixture was stirred for 5 min at r.t. [(3R,6R,7S,8E,22S)-6'-chloro-12,12-dimethyl-13,15,15-trioxo-spiro[11,20-dioxa-thia-1,14-diazatetracyclo[14.7.2.03,6.019,24]pentacosa-8,16,18,24-tetraene-22,1'-tetralin]-7-yl] phenyl carbonate (260 mg, 0.36 mmol, Example 46 Step 1) was then added to the reaction mixture and the resulting solution was stirred at 65° C. for 4 h. LCMS analysis indicated the reaction was complete. The reaction mixture was concentrated under reduced pressure and the residue was purified by prep-HPLC. The desired fractions were collected and concentrated under reduced pressure to afford [(3R,6R,7S,8E,22S)-6'-chloro-12,12-dimethyl-13,15,15-trioxo-spiro[11,20-dioxa-thia-1,14-diazatetracyclo[14.7.2.03,6.019,24]pentacosa-8,16,18,24-tetraene-22,1'-tetralin]-7-yl] N,N-bis(trideuteriomethyl)carbamate (202 mg, 82.6% yield) as a white solid. LC-MS: calc. for C$_{34}$H$_{36}$D$_6$ClN$_3$O$_7$S [M+H]$^+$: m/z=678.3/680.3; Found 678.4/680.4. $^1$H NMR (300 MHz, CDCl$_3$) δ 9.14 (s, 1H), 7.68 (d, J=8.5 Hz, 1H), 7.50 (dd, J=8.3, 2.2 Hz, 1H), 7.19 (dd, J=8.5, 2.4 Hz, 1H), 7.10 (d, J=2.3 Hz, 1H), 7.02-6.94 (m, 2H), 5.97-5.58 (m, 2H), 5.30 (d, J=5.0 Hz, 1H), 4.17-4.04 (m, 3H), 3.79-3.63 (m, 3H), 3.50-3.32 (m, 2H), 3.19 (dd, J=14.5, 4.9 Hz, 1H), 2.78 (t, J=5.5 Hz, 3H), 2.38 (qd, J=9.0, 3.6 Hz, 1H), 2.06-1.90 (m, 3H), 1.83 (q, J=8.9 Hz, 3H), 1.64 (p, J=9.7 Hz, 1H), 1.45 (s, 3H), 1.37 (s, 3H).

Example 48

[(3R,6R,7R,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

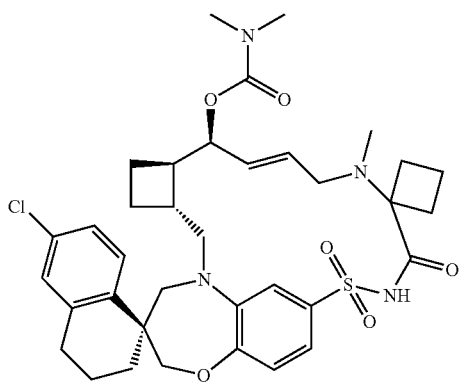 [SMILES: CN(C)C(=O)O[C@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3]

Step 1: (3S)-6'-chloro-5-[[(1R,2R)-2-[(S)-1-[tert-butyl(dimethyl)silyl]oxyallyl]cyclobutyl]methyl]spiro[2,4-dihydro-1,5-benzoxazepine-3,1'-tetralin]-7-sulfonamide

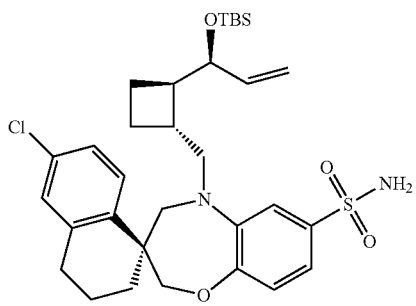 [SMILES: C=C[C@H](O[Si](C)(C)C(C)(C)C)[C@@H]1CC[C@H]1CN1C[C@@]2(CCCc3cc(Cl)ccc32)COc2ccc(S(N)(=O)=O)cc21]

To a stirred solution of (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (300 mg, 0.60 mmol) in DMF (3 mL) was added TBSCl (269 mg, 1.79 mmol) followed by imidazole (243 mg, 3.58 mmol). The resulting mixture was stirred at r.t. for 4 h. HCl (aq, 0.5 M, 10 mL) was added followed by 10 mL of EtOAc. The layers were separated, and the organic layer was washed with 10 mL of HCl (0.5 M). The organic layer was dried over sodium sulfate and concentrated under reduced pressure The residue was purified by flash chromatography on a silica gel column (12 g) using 2% to 35% EtOAc/Heptanes. The desired fractions were collected to afford (3S)-6'-chloro-5-[[(1R,2R)-2-[(1S)-1-[tert-butyl(dimethyl)silyl]oxyallyl]cyclobutyl]methyl]spiro[2,4-dihydro-1,5-benzoxazepine-3,1'-tetralin]-7-sulfonamide (260 mg, 70% yield) as a white solid. LC-MS calc. for $C_{32}H_{46}ClN_2O_4SiS[M+H]^+$: m/z=617.3/619.3; Found: 617.8/619.4.

Step 2: tert-butyl N-allyl-N-[1-[[(3S)-6'-chloro-5-[[(1R,2R)-2-[(1S)-1-[tert-butyl(dimethyl)silyl]oxyallyl]cyclobutyl]methyl]spiro[2,4-dihydro-1,5-benzoxazepine-3,1'-tetralin]-7-yl]sulfonylcarbamoyl]cyclobutyl]carbamate

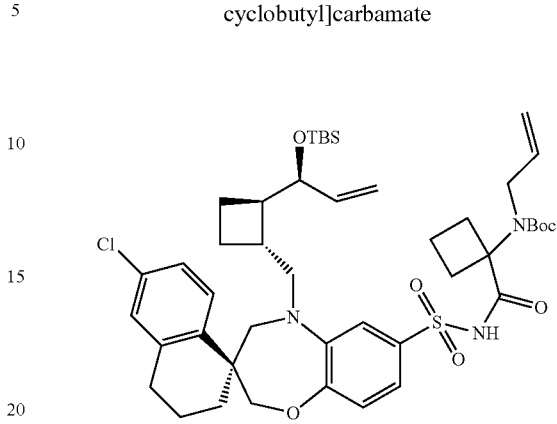

To a stirred solution of (3S)-6'-chloro-5-[[(1R,2R)-2-[(1S)-1-[tert-butyl(dimethyl)silyl]oxyallyl]cyclobutyl]methyl]spiro[2,4-dihydro-1,5-benzoxazepine-3,1'-tetralin]-7-sulfonamide (260 mg, 0.42 mmol) in DCM (10 mL) was added 1-[allyl(tert-butoxycarbonyl)amino]cyclobutanecarboxylic acid (322 mg, 1.26 mmol), 4-(dimethylamino)pyridine (308 mg, 2.53 mmol) and EDCI (0.25 mL, 1.26 mmol) successively. The resulting mixture was stirred at r.t. for 48 hours. HCl (1 M, 30 mL) was added followed by 30 mL of DCM. The layers were separated, and the aqueous layer was extracted with DCM. The combined organic layers were dried over sodium sulfate and concentrated under reduced pressure The residue was purified by flash chromatography on a silica gel column (12 g) using EtOAc/Heptanes (5% to 80%). The desired fractions were collected to afford tert-butyl N-allyl-N-[1-[[(3S)-6'-chloro-5-[[(1R,2R)-2-[(1S)-1-[tert-butyl(dimethyl)silyl]oxyallyl]cyclobutyl]methyl]spiro[2,4-dihydro-1,5-benzoxazepine-3,1'-tetralin]-7-yl]sulfonylcarbamoyl]cyclobutyl]carbamate (190 mg, 53% yield) as a white solid. LC-MS calc. for $C_{45}H_{65}ClN_3O_7SiS$ $[M+H]^+$: m/z=854.4/856.4; Found: 855.0/857.1.

Step 3: tert-butyl N-allyl-N-[1-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylcarbamoyl]cyclobutyl]carbamate

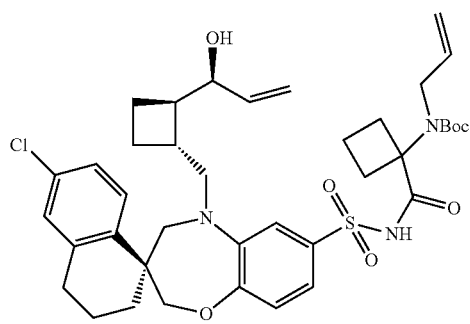 [SMILES: C=CCN(C(=O)OC(C)(C)C)C1(C(=O)NS(=O)(=O)c2ccc3c(c2)N(C[C@@H]2CC[C@H]2[C@@H](O)C=C)C[C@@]2(CCCc4cc(Cl)ccc42)CO3)CCC1]

A solution of tert-butyl N-allyl-N-[1-[[(3S)-6'-chloro-5-[[(1R,2R)-2-[(1S)-1-[tert-butyl(dimethyl)silyl]oxyallyl]cyclobutyl]methyl]spiro[2,4-dihydro-1,5-benzoxazepine-3,1'-tetralin]-7-yl]sulfonylcarbamoyl]cyclobutyl]carbamate (190 mg, 0.22 mmol) in THF (3 mL) and tetrabutylammonium fluoride solution (3.0 mL, 0.22 mmol, 1 M in THF) was stirred at r.t. overnight. The reaction was quenched by adding 10 mL of saturated NH$_4$Cl solution followed by 10 mL of EtOAc. The layers were separated and the aqueous layer was extracted with EtOAc (10 mL×3). The combined organic layers were washed with brine, dried over sodium sulfate and concentrated under reduced pressure The residue was purified by flash chromatography on a silica gel column (20 g) using 10% to 100% EtOAc/Heptanes then 0% to 50% MeOH/EtOAc. The desired fractions were collected to afford tert-butyl N-allyl-N-[1-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylcarbamoyl]cyclobutyl]carbamate (101 mg, 61% yield) as a white solid. LC-MS: calcd. For C$_{39}$H$_{51}$ClN$_3$O$_7$S [M+H]$^+$: m/z=740.3/742.3; Found: 740.8/743.0.

Step 4: (3R,6R,7S,8E,22S)-6'-chloro-7-hydroxy-11-tert-butoxycarbonyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

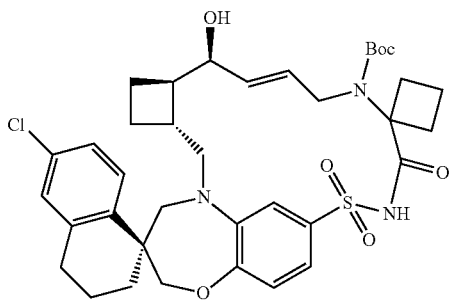 [SMILES: CC(C)(C)OC(=O)N1C/C=C/[C@H](O)[C@@H]2CC[C@H]2CN2C[C@@]3(CCCc4cc(Cl)ccc43)COc3ccc(cc32)S(=O)(=O)NC(=O)C12CCC2]

To a stirred solution of tert-butyl N-allyl-N-[1-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylcarbamoyl]cyclobutyl]carbamate (60 mg, 0.08 mmol) in DCE (80 mL) was bubbled with nitrogen for 20 minutes. Then 1,3-Bis(2,4,6-trimethylphenyl)-4,5-dihydroimidazol-2-ylidene[2-(i-propoxy)-5-(N,N-dimethyl aminosulfonyl)phenyl]methyleneruthenium(II) dichloride (resin supported) Zhan Catalyst II (11.8 mg, 0.02 mmol) was added under nitrogen. The resulting mixture was further bubbled with nitrogen for 20 minutes. Then the reaction was stirred at 60° C. under nitrogen for 3 hours. LC-MS showed the consumption of the starting material and the formation of desired product. The reaction was cooled to r.t. and stirred under air for 30 minutes to deactivate the catalyst. The solution was concentrated under reduced pressure. The residue was purified by flash chromatography on a silica gel column (12 g) using 20% to 100% EtOAc/Heptanes. The desired fractions were collected to afford (3R,6R,7S,8E,22S)-6'-chloro-7-hydroxy-11-tert-butoxycarbonyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (54 mg, 93% yield) as a white solid. LC-MS calc. for C$_{37}$H$_{47}$ClN$_3$O$_7$S [M+H]$^+$: m/z=712.3/714.3; Found: 712.9/714.6.

Step 5. (3R,6R,7S,8E,22S)-6'-chloro-7-hydroxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

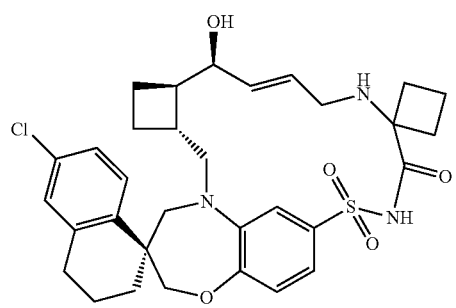 [SMILES: O=C1NS(=O)(=O)c2ccc3c(c2)N(C[C@@H]2CC[C@H]2[C@@H](O)/C=C/CNC12CCC2)C[C@@]1(CCCc2cc(Cl)ccc21)CO3]

To a stirred solution of (3R,6R,7S,8E,22S)-6'-chloro-7-hydroxy-11-tert-butoxycarbonyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (45.0 mg, 0.06 mmol) in DCM (3 mL) was added phosphoric acid (3.0 mL, 43.8 mmol). The resulting mixture was stirred at r.t. for 48 h. The solution was slowly poured into saturated NaHCO$_3$ solution (20 mL) under an ice bath. The mixture was extracted with DCM (10 mL×3). The combined organic layers were washed with brine, dried over sodium sulfate, filtered and concentrated under reduced pressure The crude product (3R,6R,7S,8E,22S)-6'-chloro-7-hydroxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (37 mg, quantitative yield) was used in next step without further purification. LC-MS calc. for C$_{32}$H$_{39}$ClN$_3$O$_5$S [M+H]: m/z=612.2/614.2; Found: 612.8/614.6.

Step 6. (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

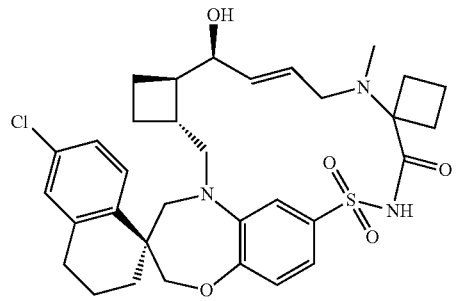 [SMILES: CN1C/C=C/[C@H](O)[C@@H]2CC[C@H]2CN2C[C@@]3(CCCc4cc(Cl)ccc43)COc3ccc(cc32)S(=O)(=O)NC(=O)C12CCC2]

This compound was prepared using procedures analogous to those described for Example 27 using (3R,6R,7S,8E,22S)-6'-chloro-7-hydroxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one. LC-MS calc. for $C_{33}H_{41}ClN_3O_5S$ [M+H]$^+$: m/z=626.2/628.2; Found: 626.9/628.8. $^1$H NMR (499 MHz, DMSO-$d_6$) δ 7.61 (d, J=8.5 Hz, 1H), 7.23 (dd, J=8.5, 2.4 Hz, 1H), 7.20 (dd, J=8.2, 2.0 Hz, 1H), 7.18 (d, J=2.4 Hz, 1H), 6.99-6.95 (m, 1H), 6.88 (d, J=8.2 Hz, 1H), 5.64-5.56 (m, 1H), 4.84-4.77 (m, 1H), 4.06 (d, J=12.1 Hz, 1H), 4.00-3.84 (m, 2H), 3.49 (d, J=14.3 Hz, 1H), 2.89-2.57 (m, 6H), 2.39-2.21 (m, 4H), 2.07-1.96 (m, 2H), 1.86-1.77 (m, 6H), 1.70-1.64 (m, 1H), 1.61-1.54 (m, 2H), 1.47 (q, J=7.2 Hz, 1H), 1.30-1.23 (m, 5H), 0.89-0.84 (m, 1H).

Step 7: [(3R,6R,7R,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate This compound was prepared using procedures analogous to those described for Example 34 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one and N,N-dimethylcarbamoyl chloride. LC-MS calc. for $C_{36}H_{46}ClN_4O_6S$ [M+H]$^+$: m/z=697.3/699.3; Found: 697.9/699.7. $^1$H NMR (300 MHz, CDCl$_3$) δ 7.67 (d, J=8.5 Hz, 1H), 7.49 (dd, J=8.3, 2.1 Hz, 1H), 7.16 (dd, J=8.5, 2.3 Hz, 1H), 7.06 (d, J=2.3 Hz, 1H), 6.96 (d, J=8.4 Hz, 1H), 6.85 (d, J=2.3 Hz, 1H), 5.79-5.59 (m, 2H), 5.28 (s, 1H), 4.29-3.97 (m, 2H), 3.70 (d, J=14.7 Hz, 1H), 3.53-3.26 (m, 2H), 3.04 (s, 3H), 2.95 (s, 3H), 2.89-2.57 (m, 6H), 2.40 (s, 3H), 2.27 (ddt, J=11.9, 8.2, 3.2 Hz, 2H), 2.19-1.90 (m, 7H), 1.87-1.73 (m, 3H), 1.73-1.55 (m, 3H), 1.41 (t, J=11.8 Hz, 1H).

Example 49

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3,3-difluoroazetidine-1-carboxylate

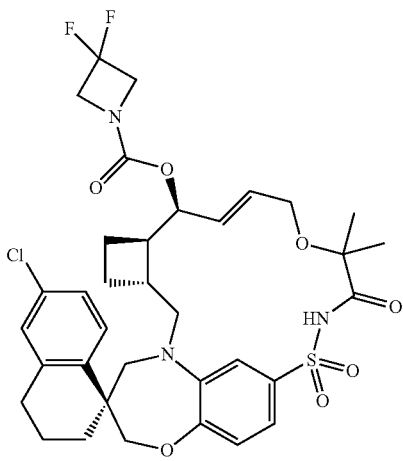 [SMILES: CC1(C)OC/C=C/[C@H](OC(=O)N2CC(F)(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 3,3-difluoroazetidine hydrochloride and N,N-diisopropylethylamine to replace 1-(2-methoxyethyl)piperazine in Step 2. LC-MS calc. for $C_{35}H_{41}C_1F_2N_3O_7S$ [M+H]$^+$: m/z=720.22/722.22; Found 720.8/722.89. $^1$H NMR (300 MHz, CDCl$_3$) δ 7.69 (d, J=8.5 Hz, 1H), 7.50 (d, J=8.2 Hz, 1H), 7.19 (dd, J=8.5, 2.2 Hz, 1H), 7.10 (d, J=2.1 Hz, 1H), 7.05-6.94 (m, 2H), 5.82 (m, 1H), 5.71 (m, 1H), 5.28 (s, 1H), 4.32 (m, 2H), 4.18-4.05 (m, 3H), 3.81-3.68 (m, 2H), 3.47-3.32 (m, 2H), 3.23 (m, 1H), 2.85-2.69 (m, 3H), 2.46-2.35 (m, 1H), 2.01 (m, 3H), 1.90-1.76 (m, 4H), 1.71-1.58 (m, 3H), 1.46-1.58 (m, 1H), 1.45 (s, 3H), 1.37 (s, 3H).

Example 50

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methylcarbamate

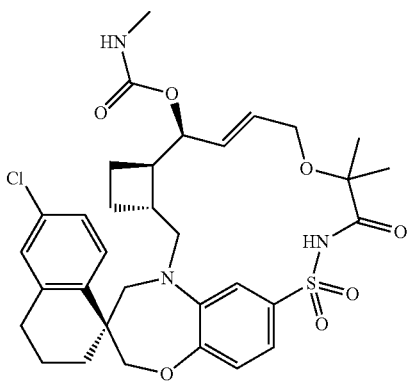 [SMILES: CNC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using methylamine to replace 1-(2-methoxyethyl)piperazine in Step 2. LC-MS calc. for $C_{33}H_{41}ClN_3O_7S$ [M+H]$^+$: m/z=658.23/660.23; Found 658.7/660.7. $^1$H NMR (300 MHz, CDCl$_3$) δ 7.68 (d, J=8.5 Hz, 1H), 7.51 (dd, J=8.3, 1.9 Hz, 1H), 7.19 (dd, J=8.5, 2.2 Hz, 1H), 7.10 (d, J=2.1 Hz, 1H), 7.08-7.02 (m, 1H), 7.00 (d, J=8.3 Hz, 1H), 5.88-5.65 (m, 2H), 5.24 (s, 1H), 4.86 (s, 1H), 4.20-4.05 (m, 3H), 3.74 (m, 2H), 3.47 (dd, J=15.1, 4.8 Hz, 1H), 3.34 (d, J=14.6 Hz, 1H), 3.17 (m, 1H), 2.80 (m, 6H), 2.42-2.32 (m, 1H), 1.98 (m, 4H), 1.81 (m, 3H), 1.64 (m, 2H), 1.44 (s, 3H), 1.38 (s, 3H).

Example 51

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 4-methoxypiperidine-1-carboxylate

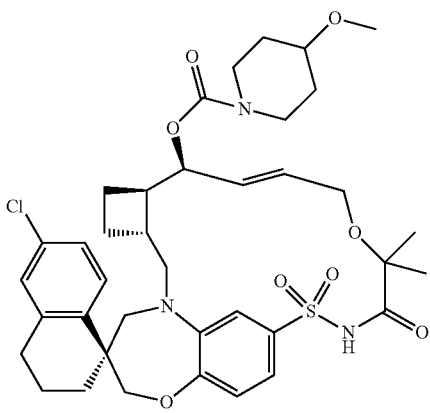 [SMILES: COC1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using 4-methoxypiperidine to replace 1-(2-methoxyethyl)piperazine in Step 2. LC-MS calc. for $C_{38}H_{49}ClN_3O_8S$ [M+H]$^+$: m/z=742.29/744.29; Found: 742.7/744.8. $^1$H NMR (300 MHz, CDCl$_3$) δ 9.08 (s, 1H), 7.68 (d, J=8.5 Hz, 1H), 7.50 (d, J=8.2 Hz, 1H), 7.19 (dd, J=8.5, 2.2 Hz, 1H), 7.10 (d, J=2.1 Hz, 1H), 6.99 (d, J=8.2 Hz, 2H), 5.73 (t, J=20.2 Hz, 2H), 5.32 (d, J=3.8 Hz, 1H), 4.22-3.98 (m, 3H), 3.92-3.64 (m, 5H), 3.51-3.29 (m, 6H), 3.22 (dd, J=14.5, 8.9 Hz, 4H), 2.79 (d, J=4.1 Hz, 3H), 2.39 (d, J=6.8 Hz, 1H), 2.10-1.46 (m, 10H), 1.44 (s, 3H), 1.37 (s, 3H).

Example 52

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-(dimethylamino)azetidine-1-carboxylate

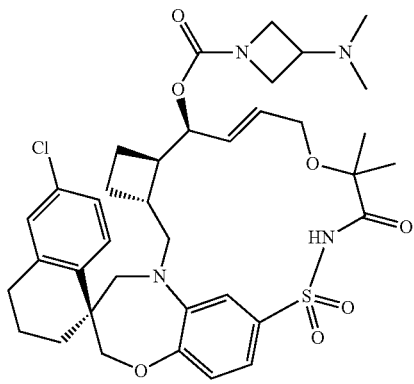 [SMILES: CN(C)C1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using N,N-dimethylazetidin-3-amine dihydrochloride salt and Hunig's base to replace 1-(2-methoxyethyl)piperazine in Step 2. LC-MS calc. for $C_{37}H_{48}ClN_4O_7S$ [M+H]$^+$: m/z=727.3/729.3; Found: 727.6/729.6. $^1$H NMR (300 MHz, CDCl$_3$) δ 7.69 (d, J=8.5 Hz, 1H), 7.51-7.40 (m, 1H), 7.18 (dd, J=8.5, 2.3 Hz, 1H), 7.09 (d, J=2.3 Hz, 1H), 6.96 (d, J=8.3 Hz, 1H), 5.81-5.59 (m, 1H), 5.15 (s, 1H), 4.29 (s, 1H), 4.11 (q, J=11.4, 10.7 Hz, 4H), 3.85 (dd, J=9.1, 4.9 Hz, 2H), 3.71 (d, J=14.6 Hz, 2H), 3.40 (t, J=17.2 Hz, 2H), 2.97 (s, 5H), 2.80 (s, 3H), 2.21 (s, 6H), 1.99 (d, J=16.0 Hz, 3H), 1.90-1.73 (m, 3H), 1.73-1.58 (m, 2H), 1.46 (s, 3H), 1.34 (s, 3H).

Example 53

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3R)-3-(dimethylamino)pyrrolidine-1-carboxylate

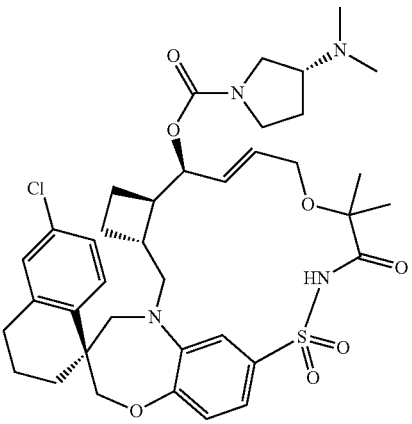 [SMILES: CN(C)[C@@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3R)-N,N-dimethylpyrrolidin-3-amine to replace 1-(2-methoxyethyl)piperazine in Step 2. LC-MS calc. for $C_{38}H_{50}ClN_4O_7S$ [M+H]$^+$: m/z=741.3/743.3; Found: 741.4/743.2. $^1$H NMR (499 MHz, DMSO-d$_6$) δ 7.67 (d, J=8.5 Hz, 1H), 7.27 (dd, J=8.4, 2.3 Hz, 1H), 7.18 (d, J=2.4 Hz, 1H), 7.11 (dd, J=8.1, 1.9 Hz, 1H), 6.92-6.80 (m, 2H), 6.23 (dd, J=16.5, 7.7 Hz, 1H), 5.54 (dd, J=16.0, 4.1 Hz, 1H), 5.10 (d, J=40.1 Hz, 1H), 4.02 (d, J=7.7 Hz, 3H), 3.88 (dd, J=13.5, 8.0 Hz, 1H), 3.57 (dt, J=12.3, 4.5 Hz, 4H), 3.34-3.26 (m, 4H), 3.08 (td, J=15.2, 9.8 Hz, 2H), 2.75 (dddd, J=33.6, 16.8, 11.5, 5.3 Hz, 3H), 2.39 (d, J=23.1 Hz, 6H), 2.16-1.76 (m, 6H), 1.74-1.56 (m, 3H), 1.49-1.36 (m, 1H), 1.23 (d, J=2.4 Hz, 3H), 1.12 (s, 3H).

Example 54

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] 4-methyl-1,4-diazepane-1-carboxylate

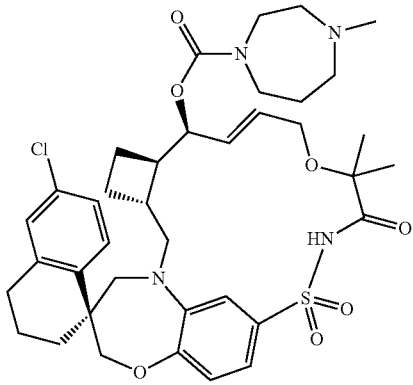 [SMILES: CN1CCCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using 1-methyl-1,4-diazepane to replace 1-(2-methoxyethyl)piperazine in Step 2. LC-MS calc. for $C_{38}H_{50}ClN_4O_7S$ [M+H]$^+$: m/z=741.3/743.3; Found: 741.4/743.2. $^1$H NMR (300 MHz, CDCl$_3$) δ 7.69 (dd, J=8.5, 3.6 Hz, 1H), 7.54-7.37 (m, 1H), 7.18 (dd, J=8.5, 2.3 Hz, 1H), 7.08 (d, J=2.3 Hz, 1H), 7.02-6.84 (m, 2H), 6.26-5.60 (m, 1H), 5.28 (s, 1H), 4.31 (d, J=12.4 Hz, 1H), 4.21-3.96 (m, 4H), 3.72 (d, J=14.5 Hz, 2H), 3.52-3.01 (m, 10H), 2.92-2.48 (m, 8H), 2.43 (s, 1H), 2.24 (t, J=9.9 Hz, 1H), 2.06-1.75 (m, 7H), 1.42 (s, 3H), 1.34 (s, 3H).

Example 55

[(3R,6R,7S,8E,22S)-6'-Chloro-12,12-dimethyl-13, 15,15-trioxo-spiro[11,20-dioxa-15-thia-1,14-diaza-tetracyclo[14.7.2.0~3,6.0~19,24]pentacosa-8,16,18, 24-tetraene-22,1'-tetralin]-7-yl] N-[2-(dimethylamino)ethyl]-N-methyl-carbamate

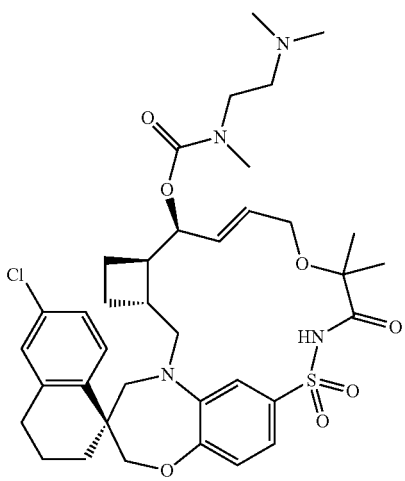 [SMILES: CN(C)CCN(C)C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using N,N,N'-trimethyl-ethylenediamine to replace 1-(2-methoxyethyl)piperazine in Step 2. LC-MS calc. for $C_{37}H_{50}ClN_4O_7S$ [M+H]$^+$: m/z=729.31/731.31; Found: 729.5/731.5. $^1$H NMR (500 MHz, DMSO-d$_6$) δ 11.62 (s, 1H), 9.39 (s, 1H), 7.64 (d, J=8.4 Hz, 1H), 7.26 (dd, J=8.5, 2.3 Hz, 2H), 7.19 (d, J=2.2 Hz, 1H), 7.02 (d, J=8.2 Hz, 1H), 6.94 (s, 1H), 6.59 (d, J=61.5 Hz, 1H), 5.71 (s, 2H), 5.24 (d, J=88.7 Hz, 1H), 4.34-3.89 (m, 3H), 3.56 (d, J=14.4 Hz, 2H), 3.02-2.62 (m, 13H), 2.12-1.44 (m, 10H), 1.39 (s, 3H), 1.24 (s, 6H).

Example 56

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] 3-methoxyazetidine-1-carboxylate

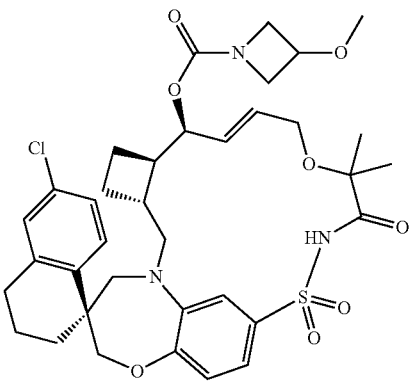 [SMILES: COC1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using 3-methoxyazetidine to replace 1-(2-methoxyethyl)piperazine in Step 2. LC-MS calc. for $C_{36}H_{45}ClN_3O_8S$ [M+H]$^+$: m/z=714.25/716.25; Found: 714.5/716.5. $^1$H NMR (499 MHz, DMSO-d$_6$) δ 7.71 (d, J=8.5 Hz, 1H), 7.30 (dd, J=8.5, 2.5 Hz, 1H), 7.21 (d, J=2.4 Hz, 1H), 7.12 (dd, J=8.2, 1.9 Hz, 1H), 6.94-6.80 (m, 2H), 6.30 (d, J=12.0 Hz, 1H), 5.51 (ddd, J=16.0, 3.7, 1.7 Hz, 1H), 5.05 (s, 1H), 4.25 (s, 1H), 4.17-4.10 (m, 1H), 4.08-3.99 (m, 2H), 3.87 (dd, J=13.5, 7.8 Hz, 1H), 3.78 (d, J=7.9 Hz, 1H), 3.65-3.53 (m, 2H), 3.38 (s, 2H), 3.32 (d, J=14.3 Hz, 2H), 3.26 (s, 3H), 3.10 (dd, J=14.9, 10.1 Hz, 1H), 2.89-2.67 (m, 3H), 2.33 (td, J=8.8, 2.8 Hz, 1H), 2.06-1.97 (m, 1H), 1.92-1.83 (m, 3H), 1.69 (ddt, J=17.6, 12.7, 8.1 Hz, 3H), 1.47 (td, J=13.2, 12.1, 3.9 Hz, 1H), 1.30 (s, 1H), 1.24 (s, 3H), 1.13 (s, 3H).

Example 57

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-ethoxyazetidine-1-carboxylate

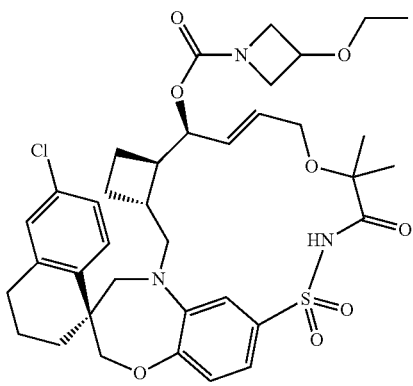 [SMILES: CCOC1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using 3-ethoxyazetidine to replace 1-(2-methoxyethyl)piperazine in Step 2. LC-MS calc. for $C_{37}H_{47}ClN_3O_8S$ [M+H]$^+$: m/z=728.27/730.27; Found: 728.5/730.5. $^1$H NMR (499 MHz, DMSO-d$_6$) δ 7.66 (d, J=8.6 Hz, 1H), 7.25 (dd, J=8.5, 2.4 Hz, 1H), 7.16 (d, J=2.4 Hz, 1H), 7.06 (dd, J=8.1, 1.9 Hz, 1H), 6.85 (d, J=2.0 Hz, 1H), 6.79 (d, J=8.1 Hz, 1H), 6.24 (d, J=13.1 Hz, 1H), 5.46 (dt, J=16.1, 2.9 Hz, 1H), 5.00 (s, 1H), 4.28 (q, J=5.3 Hz, 1H), 4.09 (dd, J=9.3, 6.5 Hz, 2H), 4.03-3.93 (m, 2H), 3.85-3.64 (m, 3H), 3.60-3.47 (m, 2H), 3.39 (d, J=6.9 Hz, 1H), 3.26 (d, J=14.3 Hz, 2H), 3.04 (dd, J=14.8, 10.1 Hz, 1H), 2.86-2.60 (m, 3H), 2.28 (qd, J=9.2, 3.0 Hz, 1H), 2.03-1.91 (m, 1H), 1.88-1.75 (m, 3H), 1.71-1.56 (m, 3H), 1.41 (td, J=13.1, 12.2, 4.3 Hz, 1H), 1.30-1.21 (m, 1H), 1.18 (s, 3H), 1.13 (t, J=7.5 Hz, 3H), 1.08 (s, 3H).

Example 58

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3R)-3-methoxypyrrolidine-1-carboxylate

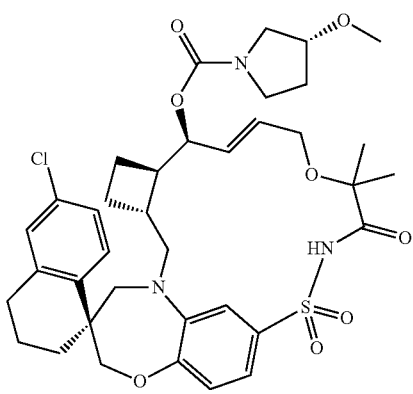 [SMILES: CO[C@@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3R)-3-methoxypyrrolidine to replace 1-(2-methoxyethyl)piperazine in Step 2. LC-MS calc. for $C_{37}H_{47}ClN_3O_8S$ [M+H]$^+$: m/z=728.27/730.27; Found: 728.5/730.5. $^1$H NMR (300 MHz, CDCl$_3$) δ 7.68 (d, J=8.5 Hz, 1H), 7.37 (dd, J=8.3, 1.9 Hz, 1H), 7.13 (dd, J=8.4, 2.3 Hz, 1H), 7.06 (d, J=2.3 Hz, 1H), 6.96 (t, J=3.1 Hz, 1H), 6.87 (dd, J=8.3, 3.2 Hz, 1H), 6.08 (d, J=23.0 Hz, 1H), 5.69 (dt, J=15.3, 6.5 Hz, 1H), 5.19 (d, J=15.8 Hz, 1H), 4.08-3.92 (m, 3H), 3.82 (d, J=6.9 Hz, 1H), 3.69-3.58 (m, 2H), 3.48 (dt, J=19.4, 8.9 Hz, 3H), 3.35-3.24 (m, 4H), 3.17-3.05 (m, 2H), 2.75 (s, 3H), 2.56 (q, J=7.2 Hz, 1H), 2.31 (t, J=9.7 Hz, 1H), 2.01-1.89 (m, 3H), 1.78 (s, 3H), 1.60 (t, J=9.1 Hz, 1H), 1.39-1.30 (m, 10H).

Example 59

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3R)-3-ethoxypyrrolidine-1-carboxylate

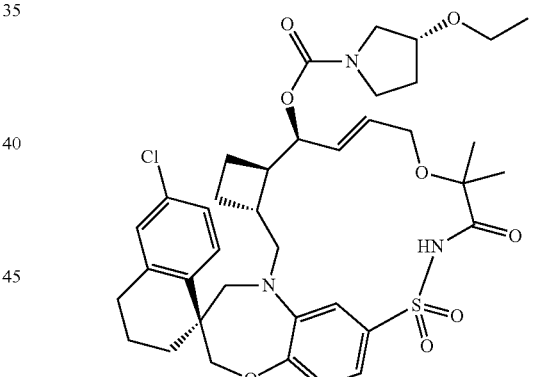

This compound was prepared using procedures analogous to those described for Example 46 using (3R)-3-ethoxypyrrolidine to replace 1-(2-methoxyethyl)piperazine in Step 2. LC-MS calc. for $C_{38}H_{49}ClN_3O_8S$ [M+H]$^+$: m/z=742.29/744.28; Found: 742.6/744.6. $^1$H NMR (300 MHz, CDCl$_3$) δ 7.69 (d, J=8.5 Hz, 1H), 7.37-7.28 (m, 1H), 7.12 (dd, J=8.4, 2.3 Hz, 1H), 7.06 (d, J=2.2 Hz, 1H), 7.00 (d, J=3.4 Hz, 1H), 6.80 (d, J=8.2 Hz, 1H), 6.34-6.07 (m, 1H), 5.70 (dt, J=15.5, 8.1 Hz, 1H), 5.13 (s, 1H), 4.07-3.86 (m, 4H), 3.67-3.38 (m, 7H), 3.22 (d, J=14.4 Hz, 1H), 3.05 (p, J=8.8 Hz, 1H), 2.76-2.74 (m, 2H), 2.68-2.50 (m, 1H), 2.23-2.19 (m, 6H), 2.02-1.70 (m, 8H), 1.63-1.53 (m, 1H), 1.35-1.25 (m, 8H).

Example 60

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] 4-(2-methoxyethyl)-1,4-diazepane-1-carboxylate

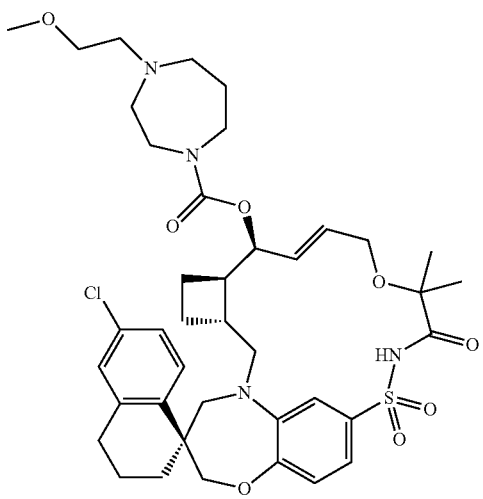 [SMILES: COCCN1CCCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using 1-(2-methoxyethyl)-1,4-diazepane to replace 1-(2-methoxyethyl)piperazine in Step 2. LC-MS calc. for $C_{40}H_{54}ClN_4O_8S$ [M+H]⁺: m/z=785.33/787.32; Found: 785.5/787.4; ¹H NMR (300 MHz, CDCl₃) δ 9.29 (s, 1H, NH), 7.68 (dd, J=8.5, 5.1 Hz, 1H), 7.47 (dd, J=7.1, 5.2 Hz, 1H), 7.19 (d, J=8.4 Hz, 1H), 7.10 (d, J=2.0 Hz, 1H), 7.00 (d, J=8.3 Hz, 1H), 6.87 (d, J=10.0 Hz, 1H), 5.90 (s, 2H), 5.27 (s, 1H), 4.13 (m, 4H), 3.75 (m, 9H), 3.47 (d, J=15.0 Hz, 2H), 3.35 (d, J=12.2 Hz, 6H), 3.25-3.16 (m, 2H), 2.79 (d, J=4.2 Hz, 4H), 2.36 (d, J=8.0 Hz, 2H), 1.98 (d, J=11.1 Hz, 2H), 1.91-1.76 (m, 4H), 1.76-1.63 (m, 2H), 1.46 (s, 3H), 1.36 (d, J=2.4 Hz, 3H).

Example 61

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-[(3S)-tetrahydrofuran-3-yl]carbamate

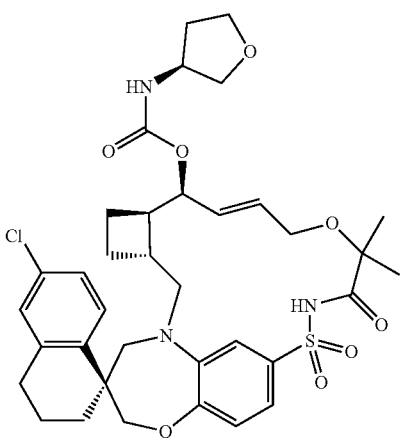 [SMILES: CC1(C)OC/C=C/[C@H](OC(=O)N[C@H]2CCOC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using (3S)-tetrahydrofuran-3-amine to replace 1-(2-methoxyethyl)piperazine in Step 2. LC-MS calc. for $C_{36}H_{45}ClN_3O_8S$ [M+H]⁺: m/z=714.2; Found: 714.4. ¹H NMR (300 MHz, CDCl₃) δ 9.85 (s, 1H), 7.68 (d, J=8.5 Hz, 1H), 7.52 (dd, J=8.3, 2.1 Hz, 1H), 7.19 (dd, J=8.5, 2.4 Hz, 1H), 7.09 (d, J=2.3 Hz, 1H), 7.00 (d, J=8.4 Hz, 2H), 6.02 (m, 1H), 5.65 (m, 2H), 5.17 (s, 1H), 4.27 (m, 2H), 4.21-4.03 (m, 2H), 3.99 (d, J=9.7 Hz, 1H), 3.81-3.59 (m, 6H), 3.47-3.28 (m, 2H), 3.08 (dd, J=15.0, 10.2 Hz, 1H), 2.96-2.69 (m, 3H), 2.37-2.19 (m, 2H), 1.93 (m, 7H), 1.67-1.54 (m, 1H), 1.47 (s, 3H), 1.34 (s, 3H).

Example 62

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-[(3R)-tetrahydrofuran-3-yl]carbamate

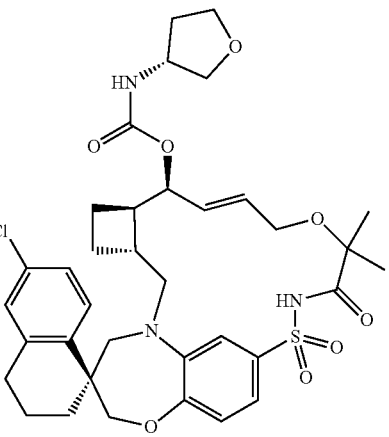

This compound was prepared using procedures analogous to those described for Example 46 using (3R)-tetrahydrofuran-3-amine to replace 1-(2-methoxyethyl)piperazine in Step 2. LC-MS calc. for $C_{36}H_{45}ClN_3O_8S$ [M+H]⁺: m/z=714.2; Found: 714.4. ¹H NMR (300 MHz, CDCl₃) δ 9.08 (s, 1H), 7.68 (d, J=8.5 Hz, 1H), 7.51 (dd, J=8.3, 2.0 Hz, 1H), 7.19 (dd, J=8.5, 2.4 Hz, 1H), 7.10 (d, J=2.3 Hz, 1H), 7.07-6.96 (m, 2H), 5.87-5.61 (m, 2H), 5.18 (s, 1H), 4.36-4.01 (m, 6H), 3.97 m, 1H), 3.91-3.66 (m, 5H), 3.47 (dd, J=15.3, 5.0 Hz, 1H), 3.33 (d, J=14.6 Hz, 1H), 3.18 (dd, J=15.2, 8.5 Hz, 1H), 2.78 (m, 3H), 2.48-2.34 (m, 1H), 2.32-2.19 (m, 1H), 2.09-1.70 (m, 7H), 1.63 (t, J=9.4 Hz, 1H), 1.44 (s, 3H), 1.38 (s, 3H).

Example 63

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methoxy-N-methyl-carbamate

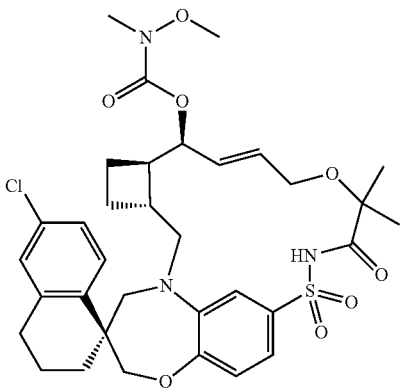 [SMILES: CON(C)C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: N-methoxy-N-methyl-carbamoyl Chloride

To a solution of N,O-dimethylhydroxylamine hydrochloride (500 mg, 8.19 mmol) in DCM (10 mL) was added triphosgene (2429 mg, 8.19 mmol), followed by potassium carbonate (4525 mg, 32.7 mmol). The mixture was stirred at r.t. for 1 h. NMR showed that the starting material was consumed. The reaction was then added $H_2O$ (15 mL) and extracted with DCM (10 mL×3). The combined organic layers were dried over $Na_2SO_4$, filtered and concentrated under reduced pressure. The resulting residue N-methoxy-N-methyl-carbamoyl chloride (600 mg, 59% yield) was directly used in the following step without further purification.

Step 2: [(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methoxy-N-methyl-carbamate To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one (40.0 mg, 0.07 mmol, Example 32) and N-methoxy-N-methyl-carbamoyl chloride (41 mg, 0.33 mmol) in toluene (2 mL) was dropwise added KHMDS (0.8 mL, 3.53 mmol) at −30° C. The mixture was then warmed to r.t. and stirred for 4 h. LC-MS showed that most of the starting material was consumed. The mixture was then added 1 N HCl (5 mL) and extracted with ethyl acetate (5 mL×3). The combined organic layers were dried over $Na_2SO_4$, filtered and concentrated under reduced pressure. The residue was purified by prep-HPLC on a C18 column using $H_2O$/ACN (20-100%) to afford the desired product [(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methoxy-N-methyl-carbamate (19.7 mg, 43% yield). LC-MS calc. for $C_{34}H_{43}ClN_3O_8S$ [M+H]⁺: m/z=688.24/690.24; Found: 688.4/690.5; ¹H NMR (300 MHz, $CDCl_3$) δ 9.09 (s, 1H, NH), 7.69 (t, J=7.0 Hz, 1H), 7.51 (dd, J=8.3, 2.0 Hz, 1H), 7.19 (dd, J=8.5, 2.0 Hz, 1H), 7.10 (d, J=1.9 Hz, 1H), 7.01 (dd, J=8.7, 3.2 Hz, 2H), 5.90-5.79 (m, 1H), 5.70 (dd, J=15.6, 5.6 Hz, 1H), 5.32 (d, J=4.0 Hz, 1H), 4.14 (q, J=12.2 Hz, 2H), 4.04 (dd, J=13.9, 5.6 Hz, 1H), 3.77 (d, J=9.1 Hz, 1H), 3.72 (d, J=3.3 Hz, 4H), 3.44-3.34 (m, 2H), 3.28 (dd, J=13.8, 7.7 Hz, 1H), 3.19 (s, 3H), 2.79 (d, J=4.6 Hz, 3H), 2.49-2.39 (m, 1H), 2.00 (dd, J=11.5, 3.6 Hz, 2H), 1.84 (dd, J=16.9, 8.9 Hz, 3H), 1.66-1.60 (m, 3H), 1.45-1.41 (s, 3H), 1.37 (s, 3H).

Example 64

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate

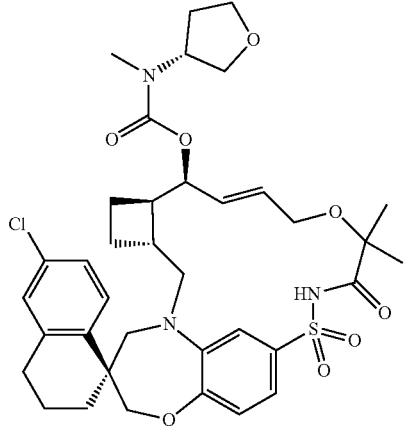 [SMILES: CN(C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3)[C@@H]1CCOC1]

This compound was prepared using procedures analogous to those described for Example 63 using (3R,6R,7S,8E,22S)-6'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one (Example 32) in Step 2 and (3R)-N-methyltetrahydrofuran-3-amine hydrochloride in Step 1. LC-MS calc. for $C_{37}H_{47}ClN_3O_8S$ [M+H]⁺: m/z=728.27/730.27; Found: 728.4/730.3. ¹H NMR (300 MHz, $CDCl_3$) δ 9.11 (s, 1H), 7.68 (d, J=8.5 Hz, 1H), 7.50 (dd, J=8.3, 2.2 Hz, 1H), 7.19 (dd, J=8.5, 2.4 Hz, 1H), 7.10 (d, J=2.3 Hz, 1H), 7.00 (d, J=8.4 Hz, 1H), 6.96 (d, J=2.3 Hz, 1H), 5.83 (d, J=4.3 Hz, 1H), 5.73 (dd, J=15.8, 5.3 Hz, 1H), 5.35 (d, J=5.7 Hz, 1H), 4.93 (s, 1H), 4.14 (d, J=6.5 Hz, 2H), 4.08 (d, J=5.4 Hz, 1H), 3.77 (d, J=5.1 Hz, 2H), 3.71 (s, 1H), 3.49-3.34 (m, 2H), 3.23 (dd, J=15.1, 9.4 Hz, 1H), 2.92 (s, 3H), 2.83-2.75 (m, 3H), 2.44-2.36 (m, 1H), 2.28-2.16 (m, 4H), 2.05-1.95 (m, 3H), 1.89-1.75 (m, 4H), 1.65 (t, J=9.4 Hz, 2H), 1.44 (d, J=4.2 Hz, 3H), 1.37 (s, 3H).

Example 65

(3R,6R,7S,8E,22S)-6'-Chloro-7-[2-(dimethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

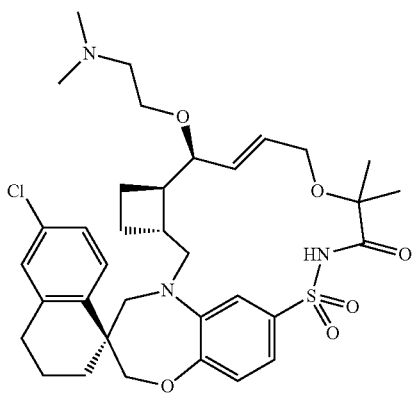 [SMILES: CN(C)CCO[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: ethyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetate

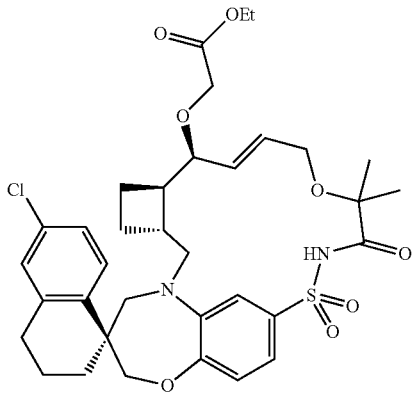 [SMILES: CC1(C)OC/C=C/[C@H](OCC(=O)O)[C@@H]2CC[C@H]2CN2C[C@@]3(CCCc4cc(Cl)ccc43)COc3ccc(cc32)S(=O)(=O)NC1=O]

To a cooled (ice-bath) solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (1.0 g, 1.66 mmol, Example 32) in THF (10 mL) was added sodium hydride (199 mg, 8.32 mmol). After stirring 10 mins at r.t., ethyl bromoacetate (1111 mg, 6.65 mmol) was added. The resulting mixture was stirred at r.t. overnight. The reaction was monitored by LC-MS and quenched with a mixture of cold 1 N HCl aq. (50 mL) and DCM (50 mL). The aqueous layer was extracted with DCM (50 mL). The combined organic layers were dried over $Na_2SO_4$, filtered and concentrated under reduced pressure. The residue was purified by flash chromatography on a silica gel column (20 g) using EA/Heptane (5%-80%) to afford the desired product ethyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetate (600 mg, 52.4% yield). LC-MS calc. for $C_{35}H_{44}ClN_2O_8S$ [M+H]$^+$: m/z=687.20; Found: 687.72.

Step 2: 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetic Acid

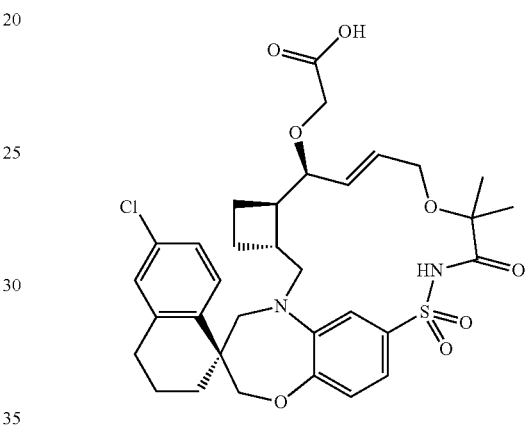

To a solution of ethyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetate (600 mg, 0.87 mmol) in THF (10 mL) and water (10 mL) was added lithium hydroxide monohydrate (183.18 mg, 4.37 mmol). The mixture was stirred at r.t. for 1 h. The mixture was then was quenched with 1N HCl (50 mL), extracted with EA (50 mL×2). The combined organic layers were dried over $Na_2SO_4$, filtered and concentrated under reduced pressure to afford 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]oxyacetic acid (400 mg, 70% yield) which was directly used in next step without purification. LC-MS calc. for $C_{33}H_{40}ClN_2O_6S$ [M+H]$^+$: m/z=659.22; Found: 659.70. 1H NMR (300 MHz, CDCl$_3$) δ 9.24 (s, 1H, NH), 7.64 (t, J=6.0 Hz, 1H), 7.49 (dd, J=8.3, 2.0 Hz, 1H), 7.18 (dd, J=8.5, 2.2 Hz, 1H), 7.10 (d, J=2.1 Hz, 1H), 7.05 (d, J=2.0 Hz, 1H), 7.02-6.98 (m, 1H), 5.73-5.59 (m, 2H), 4.15-4.03 (m, 4H), 3.94-3.83 (m, 3H), 3.68 (d, J=14.7 Hz, 1H), 3.36 (dd, J=14.4, 8.5 Hz, 3H), 2.85-2.72 (m, 3H), 2.45-2.35 (m, 1H), 2.02 (t, J=7.9 Hz, 3H), 1.95-1.75 (m, 3H), 1.64 (t, J=8.8 Hz, 1H), 1.54 (d, J=11.7 Hz, 1H), 1.46-1.41 (m, 3H), 1.39 (s, 3H).

Step 3: isobutoxycarbonyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetate

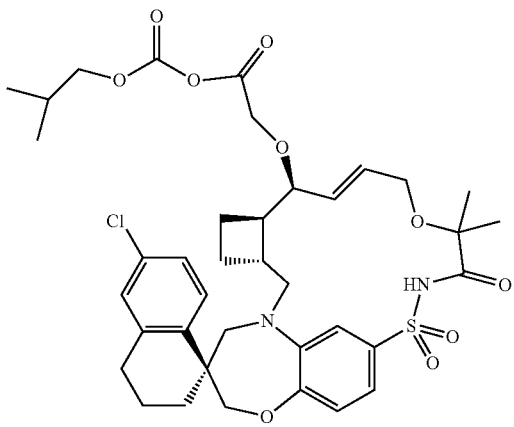 [SMILES: CC(C)COC(=O)OC(=O)CO[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

To a solution 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetic acid (400 mg, 0.60 mmol) in THF (16 mL) cooled with an ice-bath was added triethylamine (0.33 mL, 2.38 mmol) and isobutyl chloroformate (0.27 mL, 2.09 mmol). The reaction mixture was stirred at r.t. for 60 min. and monitored by LC-MS. When LC-MS shows complete reaction, the crude was directly used in further step without work-up and purification. LC-MS calc. for $C_{38}H_{48}ClN_2O_{10}S$ $[M+H]^+$: m/z=759.27; Found: 759.87.

Step 4: 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetaldehyde

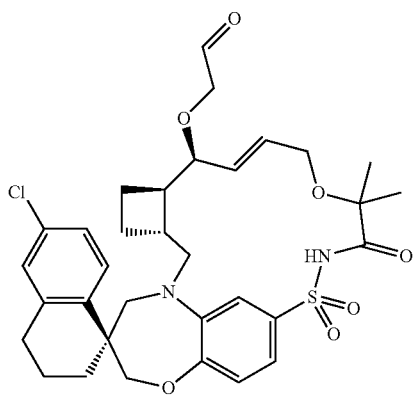 [SMILES: CC1(C)OC/C=C/[C@H](OCC=O)[C@@H]2CC[C@H]2CN2C[C@@]3(CCCc4cc(Cl)ccc43)COc3ccc(cc32)S(=O)(=O)NC1=O]

To a solution of isobutoxycarbonyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24] pentacosa-8,16,18,24-tetraene-22,1'-tetralin]-7-yl] oxyacetate (456.0 mg, 0.60 mmol) in THF (16 mL) at −78° C. was added diisobutylaluminum hydride (4.0 mL, 6.0 mmol, 1.5 M in toluene). The reaction was stirred for 30 mins at −78° C. The reaction mixture was quenched with 10% Rochelle's salt aqueous solution (40 mL) and the mixture was stirred at r.t. for 1 h. The layers were separated, and the aqueous layer was extracted with EA (2×50 mL). The combined organic layers were dried over $Na_2SO_4$, filtered and the filtrate was concentrated under reduced pressure to afford 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetaldehyde (400 mg, 60%) which was directly used in next step without purification. LC-MS calc. for $C_{33}H_{40}ClN_2O_6S$ $[M+H]^+$: m/z=643.22; Found: 643.5.

Step 5: (3R,6R,7S,8E,22S)-6'-chloro-7-[2-(dimethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one To a solution of 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetaldehyde (235 mg, 0.37 mmol, 60%) in DCE (5 mL) was added dimethylamine in THF (750.0 μL, 1.5 mmol, 2.0 M THF solution). The mixture was stirred at r.t. for 5 min., followed by adding of sodium triacetoxyborohydride (316 mg, 1.5 mmol). The mixture was then stirred at r.t. for additional 30 min. LC-MS showed that the starting material was consumed. The reaction was quenched by 1N HCl (10 mL) and extracted with DCM (2×10 mL). The combined organic layers were dried over $Na_2SO_4$, filtered and concentrated under reduced pressure. The residue was purified by prep-HPLC on a C18 column using $H_2O$/ACN (20-100%) to afford the desired product (3R,6R,7S,8E,22S)-6'-chloro-7-[2-(dimethylamino) ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (73 mg, 46% yield). LC-MS calc. for $C_{35}H_{47}ClN_3O_6S$ $[M+H]^+$: m/z=672.28; Found: 672.4. $^1H$ NMR (300 MHz, DMSO-$d_6$) δ 9.42 (s, 1H, NH), 7.61 (d, J=8.5 Hz, 1H), 7.33-7.16 (m, 3H), 7.03 (t, J=7.5 Hz, 2H), 5.59 (dd, J=15.6, 6.7 Hz, 1H), 5.43 (d, J=14.1 Hz, 1H), 4.08 (dd, J=19.7, 12.1 Hz, 2H), 3.91 (dd, J=14.3, 6.0 Hz, 1H), 3.67-3.60 (m, 2H), 3.32 (m, 5H), 3.15 (dd, J=14.5, 7.5 Hz, 2H), 2.79 (s, 9H), 2.43 (d, J=8.5 Hz, 2H), 1.97 (d, J=10.0 Hz, 1H), 1.86 (t, J=12.2 Hz, 4H), 1.71 (d, J=8.4 Hz, 1H), 1.58 (d, J=9.0 Hz, 2H), 1.43-1.31 (m, 3H), 1.24 (s, 3H).

Example 66

(3R,6R,7S,8E,22S)-6'-Chloro-12,12-dimethyl-15,15-dioxo-7-(2-pyrrolidin-1-ylethoxy)spiro[11,20-dioxa-15-thia-1,14-diazatetracyclo[14.7.2.03,6.019,24]pentacosa-8,16,18,24-tetraene-22,1'-tetralin]-13-one

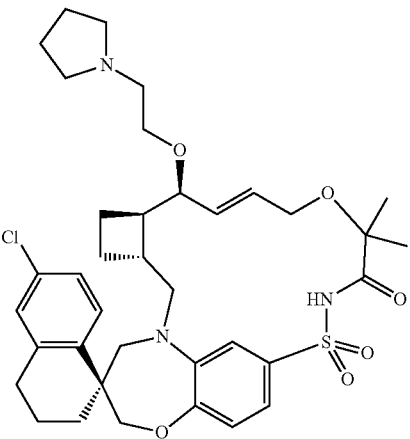 [SMILES: CC1(C)OC/C=C/[C@H](OCCN2CCCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using pyrrolidine to replace dimethylamine in THF (2.0 M) in Step 5. LC-MS calc. for $C_{37}H_{49}ClN_3O_6S$ [M+H]$^+$: m/z=698.30/700.29; Found: 698.5/700.7; $^1$H NMR (300 MHz, DMSO-d$_6$) δ 9.56 (s, 1H, NH), 7.66-7.56 (m, 1H), 7.25 (m, 3H), 7.03 (dd, J=9.5, 6.1 Hz, 2H), 5.58 (dd, J=15.5, 6.9 Hz, 1H), 5.40 (d, J=13.6 Hz, 1H), 4.08 (dd, J=19.3, 12.1 Hz, 2H), 3.88 (dd, J=14.4, 6.0 Hz, 1H), 3.66-3.58 (m, 2H), 3.32 (d, J=14.9 Hz, 8H), 3.15 (dd, J=14.5, 7.9 Hz, 2H), 3.04 (s, 3H), 2.79-2.62 (m, 3H), 1.97 (d, J=5.4 Hz, 3H), 1.87 (dd, J=18.6, 5.1 Hz, 6H), 1.72 (d, J=8.4 Hz, 1H), 1.63-1.52 (m, 2H), 1.43-1.30 (m, 3H), 1.24 (s, 3H).

Example 67

(3R,6R,7R,8E,23S)-6'-Chloro-7-methoxy-11-methoxycarbonyl-13,13-(1,3-propylene)-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

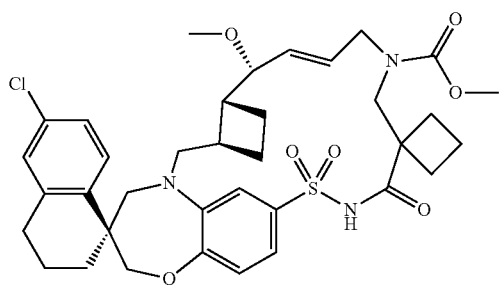 [SMILES: COC(=O)N1C/C=C/[C@@H](OC)[C@@H]2CC[C@H]2CN2C[C@@]3(CCCc4cc(Cl)ccc43)COc3ccc(cc32)S(=O)(=O)NC(=O)C2(CCC2)C1]

To a solution of (3R,6R,7R,8E,23S)-6'-chloro-7-methoxy-13,13-(1,3-propylene)-16,16-dioxo-spiro[21-oxa-16-thia-1,11,15-triazatetracyclo[15.7.2.03,6.020,25]hexacosa[8,17(26), 18,20(25)]tetraene-23,1'-tetralin]-14-one (8.0 mg, 0.01 mmol, Example 26) and triethylamine (0.01 mL, 0.06 mmol) in DCM (1 mL) was added methyl carbonochloridate (4.72 mg, 0.05 mmol) in one portion at r.t. After 10 min, LC-MS indicated the completion of reaction. The reaction was diluted with DCM, washed with saturated aqueous NaHCO$_3$ solution and brine, dried over Na$_2$SO$_4$, filtered and concentrated under reduced pressure to afford the desired product (3R,6R,7R,8E,23S)-6'-chloro-7-methoxy-11-methoxycarbonyl-13,13-(1,3-propylene)-16,16-dioxo-spiro[21-oxa-16-thia-1,11,15-triazatetracyclo[15.7.2.03,6.020,25]hexacosa[8,17(26), 18,20(25)]tetraene-23,1'-tetralin]-14-one (8 mg, 89.9% yield). LCMS: calc. for $C_{36}H_{45}ClN_3O_7S$ [M+H]$^+$: m/z=698.27/700.26; Found: 697.97/700.24. $^1$H NMR (600 MHz, CDCl$_3$) δ 7.66 (d, J=8.5 Hz, 1H), 7.43 (d, J=5.8 Hz, 1H), 7.29 (dd, J=8.3, 2.1 Hz, 1H), 7.16 (dd, J=8.5, 2.4 Hz, 1H), 7.08 (d, J=2.3 Hz, 1H), 6.90 (d, J=8.2 Hz, 1H), 5.40-5.32 (m, 1H), 5.12 (app s, 1H), 4.18 (d, J=12.0 Hz, 1H), 4.04 (d, J=11.9 Hz, 1H), 3.94-3.81 (m, 2H), 3.67 (app s, 6H), 3.58-3.49 (m, 2H), 3.43-3.21 (m, 4H), 3.15 (m, 1H), 2.84-2.68 (m, 3H), 2.54-2.30 (m, 3H), 2.12-1.77 (m, 9H), 1.63 (ddt, J=26.9, 18.3, 9.5 Hz, 2H), 1.47 (t, J=12.8 Hz, 1H). The sulfonamide NH was not observed due to solvent exchange.

Example 68

(3R,6R,7R,8E,23S)-6'-Chloro-7-methoxy-13,13-dimethyl-16,16-dioxo-spiro[21-oxa-16-thia-1,11,15-triazatetracyclo[15.7.2.03,6.020,25]hexacosa[8,17(26),18,20(25)]tetraene-23,1'-tetralin]-14-one

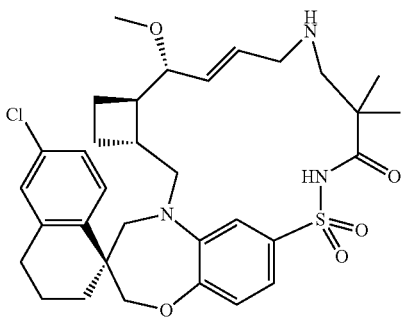 [SMILES: CO[C@@H]1/C=C/CNCC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 using 3-[(tert-butoxycarbonylamino)-2,2-dimethyl-propanoic acid to replace 1-[(tert-butoxycarbonylamino)methyl]cyclobutanecarboxylic acid in Step 2. LCMS: calc. for $C_{33}H_{43}ClN_3O_5S$ [M+H]$^+$: m/z=628.25/630.25; Found: 628.0/630.2. $^1$H NMR (300 MHz, CDCl$_3$) δ 8.07 (s, 1H), 7.72 (d, J=8.5 Hz, 1H), 7.43 (dd, J=8.3, 1.7 Hz, 1H), 7.19 (dd, J=8.5, 2.1 Hz, 1H), 7.08 (s, 2H), 6.94 (d, J=8.3 Hz, 1H), 5.99 (dt, J=15.6, 5.5 Hz, 1H), 5.64 (dd, J=15.6, 7.7 Hz, 1H), 4.12-3.99 (m, 2H), 3.81-3.61 (m, 3H), 3.57 (t, J=7.3 Hz, 1H), 3.46 (dd, J=14.8, 4.5 Hz, 1H), 3.27 (s, 3H), 3.01 (dd, J=15.0, 10.3 Hz, 1H), 2.81 (dd, J=24.0, 11.2 Hz, 3H), 2.72-2.52 (m, 2H), 2.32-2.15 (m, 1H), 1.90 (ddd, J=33.7, 25.8, 12.0 Hz, 5H), 1.77-1.54 (m, 4H), 1.40 (t, J=12.1 Hz, 1H), 1.16 (s, 3H), 1.11 (s, 3H).

Example 69

(3R,6R,7R,8E,22S)-6'-Chloro-7-methoxy-12,12-ethylene-15,15-dioxo-spiro[[20]oxa[15]thia-1,14-diazatetracyclo[14.7.2.03,6.019,24]pentacosa[8,16(25),17,19(24)]tetraene-22,1'-tetralin]-13-one and

Example 70

(3R,6R,7R,8Z,22S)-6'-chloro-7-methoxy-12,12-ethylene-15,15-dioxo-spiro[20-oxa-15-thia-1,14-diazatetracyclo[14.7.2.03,6.019,24]pentacosa[8,16(25),17,19(24)]tetraene-22,1'-tetralin]-13-one Example 69

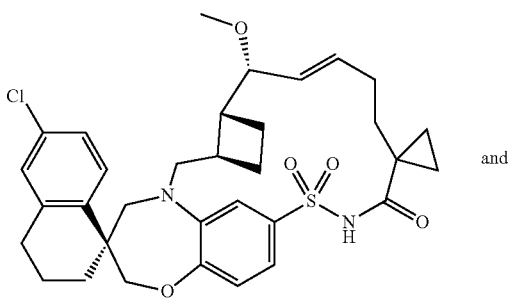

and

Example 70

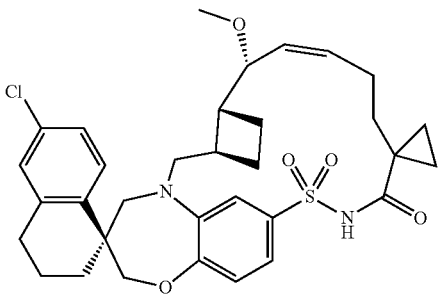

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-but-3-enylcyclopropanecarboxylic acid in Step 3. The major product was assigned to Example 69 (3R,6R,7R,8E,22S)-6'-chloro-7-methoxy-12,12-ethylene-15,15-dioxo-spiro[20-oxa-15-thia-1,14-diazatetracyclo[14.7.2.03,6.019,24]pentacosa[8,16(25),17,19(24)]tetraene-22,1'-tetralin]-13-one. LC-MS calc. for $C_{33}H_{40}ClN_2O_5S$ [M+H]$^+$: m/z=611.23/613.23; Found: 611.0/612.8. Analytic HPLC: C18 column (4.6×150 mm, 100 Å); flow rate=1 mL/min; mobile phase: 5% MeCN/H$_2$O (with 0.1% HCO$_2$H) 1 min, 5% to 95% 7 min, 95% 5 min. λ=230 nm. $t_R$=4.6 min. $^1$H NMR: (600 MHz, CDCl$_3$) δ 8.18 (br s, 1H), 7.69 (d, J=8.5 Hz, 1H), 7.49 (dd, J=8.3, 2.1 Hz, 1H), 7.41 (d, J=2.2 Hz, 1H), 7.18 (dd, J=8.5, 2.3 Hz, 1H), 7.08 (d, J=2.3 Hz, 1H), 7.00 (d, J=8.3 Hz, 1H), 5.30 (ddd, J=14.9, 9.9, 4.7 Hz, 1H), 5.08 (dd, J=15.2, 9.0 Hz, 1H), 4.18-4.07 (m, 2H), 3.68-3.56 (m, 2H), 3.32 (d, J=14.5 Hz, 1H), 3.15-3.11 (m, 1H), 3.09 (s, 3H), 2.97 (dd, J=8.8, 2.7 Hz, 1H), 2.82-2.69 (m, 3H), 2.46-2.36 (m, 1H), 2.24-2.14 (m, 1H), 2.09-1.98 (m, 2H), 1.93-1.53 (m, 9H), 1.43 (t, J=13.1 Hz, 1H), 1.39-1.19 (m, 3H).

And the minor peak was assigned to Example 70 (3R,6R,7R,8Z,22S)-6'-chloro-7-methoxy-12,12-ethylene-15,15-dioxo-spiro[20-oxa-15-thia-1,14-diazatetracyclo[14.7.2.03,6.019,24]pentacosa[8,16(25),17,19(24)]tetraene-22,1'-tetralin]-13-one. LC-MS calc. for $C_{33}H_{40}ClN_2O_5S$ [M+H]$^+$: m/z=611.23/613.23; Found: 611.0/613.1. Analytic HPLC: C18 column (4.6×150 mm, 100 Å); flow rate=1 mL/min; mobile phase: 5% MeCN/H$_2$O (with 0.1% HCO$_2$H) 1 min, 5% to 95% 7 min, 95% 5 min. λ=230 nm. $t_R$=4.1 min (minor product). $^1$H NMR: (600 MHz, CDCl$_3$) δ 8.14 (br s, 1H), 7.67 (d, J=8.5 Hz, 1H), 7.47-7.45 (m, 1H), 7.33 (d, J=2.2 Hz, 1H), 7.17 (dd, J=8.5, 2.3 Hz, 1H), 7.08 (d, J=2.3 Hz, 1H), 6.99 (d, J=8.3 Hz, 1H), 5.40 (td, J=10.7, 3.9 Hz, 1H), 5.07 (t, J=10.4 Hz, 1H), 4.15-4.05 (m, 2H), 3.74-3.58 (m, 3H), 3.40 (d, J=14.7 Hz, 1H), 3.28 (dd, J=14.8, 5.3 Hz, 1H), 3.15 (s, 3H), 2.77 (dddd, J=22.5, 16.6, 11.0, 4.9 Hz, 3H), 2.35 (t, J=7.5 Hz, 1H), 2.26-2.18 (m, 1H), 2.10-1.75 (m, 8H), 1.68-1.52 (m, 3H), 1.48 (t, J=12.8 Hz, 1H), 1.34 (dt, J=10.3, 5.7 Hz, 2H), 1.15 (ddd, J=9.7, 6.5, 4.3 Hz, 1H).

Example 71

(3R,6R,7R,8E,11S,22S)-6'-Chloro-7-methoxy-11-methyl-15,15-dioxo-spiro[20-oxa-15-thia-1,14-diazatetracyclo[14.7.2.03,6.019,24]pentacosa-8,16(25),17,19(24)-tetraene-22,1'-tetralin]-13-one

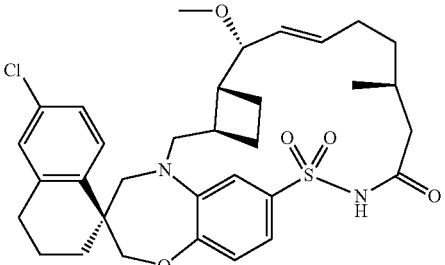

Step 1: (R,E)-3-(but-2-enoyl)-4-phenyloxazolidin-2-one

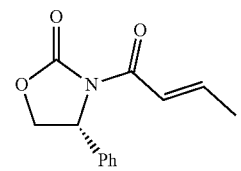 [SMILES: C/C=C/C(=O)N1C(=O)OC[C@H]1c1ccccc1]

To a solution of (R)-(+)-4-Phenyl-1,3-oxazolidin-2-one (20.0 g, 122 mmol) in THF (400 mL) was added n-BuLi (53.9 mL, 134 mmol) slowly at −78° C. The reaction solution was stirred at −78° C. for 20 min. Then (E)-but-2-enoyl chloride (14.09 g, 134 mmol) was added slowly. The reaction solution was stirred at −78° C. for 0.5 h and then at 0° C. for 15 mins. The reaction was quenched with saturated NH$_4$Cl solution (20 mL), extracted with EA (200 mL). The organic layer was dried over Na$_2$SO$_4$, filtered and concentrated to give crude mixture which was purified by flash chromatography on a silica gel column with PE/EA=10/1 to give (4R)-4-phenyl-3-[(E)-but-2-enoyl]oxazolidin-2-one (33 g, 58% yield). LC-MS calc. for $C_{13}H_{14}NO_3$ [M+H]$^+$ m/z=232.09; Found: 232.0. $^1$H NMR: (400 MHz, CDCl$_3$) δ 7.43-7.28 (m, 6H), 7.16-7.07 (m, 1H), 5.51 (dd, J=8.8, 4.0 Hz, 1H), 4.72 (t, J=8.8 Hz, 1H), 4.30 (dd, J=8.8, 4.0, Hz, 1H), 1.96 (dd, J=6.8, 1.6 Hz, 3H).

Step 2: (4R)-4-phenyl-3-[(3S)-3-methylhex-5-enoyl]oxazolidin-2-one

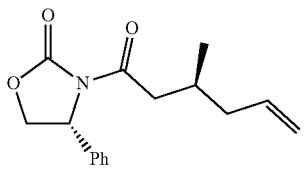 [SMILES: C=CC[C@H](C)CC(=O)N1C(=O)OC[C@H]1c1ccccc1]

To a solution of (4R)-4-phenyl-3-[(E)-but-2-enoyl]oxazolidin-2-one (11.5 g, 49.73 mmol) in DCM (400 mL) was added TiCl$_4$ (28.3 g, 149.19 mmol) at −78° C. under N$_2$. The solution was stirred at −78° C. for 20 min. Then allyltrimethylsilane (17.0 g, 149 mmol) was added slowly at −78° C. After the addition the reaction solution was stirred at −78° C. for 4 h., and quenched with saturated sodium bicarbonate solution. The organic layer was separated, and the aqueous layer was extracted with EA (200 mL×2). The combined organic layers were dried over Na$_2$SO$_4$, filtered and concentrated under reduced pressure. The residue was purified by flash chromatography on a silica gel column with PE/EA=10/1 to give (4R)-4-phenyl-3-[(3S)-3-methylhex-5-enoyl]oxazolidin-2-one (5.33 g, 39% yield). The product was purified by recrystallization (n-pentane/Et$_2$O=60/1 with trace CH$_2$Cl$_2$ at 0° C.) to give (R)-3-((S)-3-methylhex-5-enoyl)-4-phenyloxazolidin-2-one (3 g with dr=97/3). LC-MS calc. for $C_{16}H_{20}NO_3$ [M+H]$^+$ m/z=2734.14; Found: 274.0. $^1$H NMR: (400 MHz, CDCl$_3$) δ 7.41-7.27 (m, 5H), 5.79-5.69 (m, 1H), 5.43 (dd, J=8.4, 3.6 Hz, 1H), 5.01-4.95 (m, 2H), 4.71-4.66 (m, 1H), 4.29-4.25 (m, 1H), 3.03-2.68 (m, 2H), 2.15-1.91 (m, 3H), 0.92 (d, J=6.4 Hz, 3H).

Step 3: (S)-3-methylhex-5-enoic acid

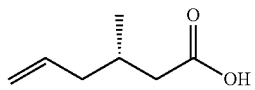

To a solution of (4R)-4-phenyl-3-[(3S)-3-methylhex-5-enoyl]oxazolidin-2-one (1.6 g, 5.85 mmol) in THF (25 mL) and water (5 mL) was added hydrogen peroxide (2.35 mL, 23 mmol) and LiOH—H$_2$O (0.49 g, 11 mmol) at 0° C. Then the reaction solution was stirred at 0° C. for 1 h. The reaction mixture was concentrated under reduced pressure. The residue was extracted with DCM. The aqueous solution was adjusted pH to 1 with HCl (2 N) and extracted with DCM. The combined organic layers were dried over Na$_2$SO$_4$, filtered and concentrated to give (3S)-3-methylhex-5-enoic acid (600 mg, 80.0% yield). [Ca]$^{20}$D=−4.5 (c=0.79, CHCl$_3$) {lit. [α]$^{22}$$_D$=−2.8 (c=1.00, CHCl$_3$), Ref: Angew. Chem., 2009, 48, 8780-8783}. $^1$H NMR: (400 MHz, CDCl$_3$) δ 5.74-5.83 (m, 1H), 5.04-5.08 (m, 2H), 2.40-2.44 (m, 1H), 2.03-2.20 (m, 4H), 1.01 (d, J=6.4 Hz, 3H).

Step 4. (3R,6R,7R,8E,11S,22S)-6'-chloro-7-methoxy-11-methyl-15,15-dioxo-spiro[20-oxa-15-thia-1,14-diazatetracyclo[14.7.2.03,6.019,24]pentacosa-8,16(25),17,19(24)-tetraene-22,1'-tetralin]-13-one This compound was prepared using procedures analogous to those described for Example 30 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (3S)-3-methylhex-5-enoic acid in Step 3. LC-MS calc. for $C_{32}H_{40}ClN_2O_5S$ [M+H]$^+$: m/z=599.2/601.2; Found 598.9/600.5. $^1$H NMR (600 MHz, DMSO-d$_6$) 11.76 (s, 1H), 7.58 (d, J=8.5 Hz, 1H), 7.16 (dd, J=8.3, 2.1 Hz, 1H), 7.13 (d, J=2.2 Hz, 1H), 7.11 (d, J=2.4 Hz, 1H), 6.94 (d, J=8.3 Hz, 1H), 5.13-5.06 (m, 1H), 4.78 (dd, J=15.3, 9.0 Hz, 1H), 4.93-3.96 (m, 2H), 3.43 (d, J=14.3 Hz, 2H), 3.01 (dd, J=15.0, 5.3 Hz, 1H), 2.87 (s, 3H), 2.71-2.68 (m, 2H), 2.64-2.56 (m, 2H), 2.21-2.19 (m, 1H), 2.05-1.87 (m, 5H), 1.76-1.64 (m, 4H), 1.54-1.44 (m, 3H), 1.38-1.31 (m, 1H), 0.80 (d, J=6.3 Hz, 3H).

Example 72

(3R,6R,7R,8E,12R,22S)-6'-Chloro-7-methoxy-12-methyl-15,15-dioxo-spiro[20-oxa-15-thia-1,14-diazatetracyclo[14.7.2.03,6.019,24]pentacosa-8,16(25),17,19(24)-tetraene-22,1'-tetralin]-13-one

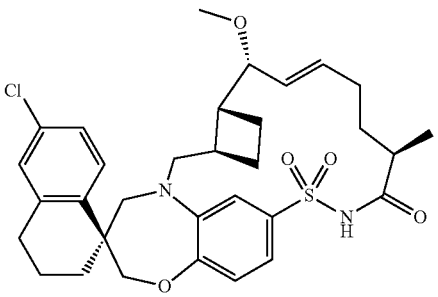 [SMILES: CO[C@@H]1/C=C/CC[C@@H](C)C(=O)NS(=O)(=O)c2ccc3c(c2)N(C[C@@H]2CC[C@H]21)C[C@@]1(CCCc2cc(Cl)ccc21)CO3]

Step 1: hex-5-enoyl chloride

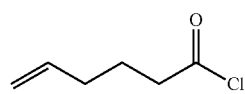

To the solution of hex-5-enoic acid (1.0 g, 8.76 mmol) in DCM (10 mL) was added oxalyl chloride (0.62 mL, 8.76 mmol) and DMF (0.10 mL) in one portion. The reaction mixture was stirred at r.t. for 1 h., and concentrated to give hex-5-enoyl chloride (1.16 g, 94.7% yield) which was directly used in next step reaction without further purification.

Step 2. (S)-4-benzyl-3-(hex-5-enoyl)oxazolidin-2-one

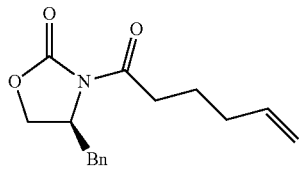 [SMILES: C=CCCCC(=O)N1C(=O)OC[C@@H]1Cc1ccccc1]

To a solution of (4R)-4-benzyloxazolidin-2-one (1.55 g, 8.75 mmol) in THF (10 mL) was added LiCl (370 mg, 8.75 mmol) and triethylamine (2.65 g, 26.25 mmol) slowly at 0° C. The reaction solution was stirred at 0° C. for 20 min. Then hex-5-enoyl chloride (1.16 g, 8.75 mmol) was added slowly, and stirred at r.t. overnight. The reaction solution was quenched with water (20 mL) and extracted with EA (40 mL). The organic layer was washed with saturated NaHCO$_3$ solution, dried over Na$_2$SO$_4$, filtered and concentrated to give crude mixture which was purified by flash chromatography on a silica gel column with PE/EA=10/1 to give (4R)-4-benzyl-3-hex-5-enoyl-oxazolidin-2-one (500 mg, 21% yield) as a white oil. $^1$H NMR (400 MHz, CDCl$_3$) δ 7.37-7.27 (m, 3H), 7.24-7.17 (m, 2H), 5.83 (ddt, J=16.9, 10.2, 6.7 Hz, 1H), 5.13-4.95 (m, 2H), 4.68 (ddd, J=10.6, 6.9, 3.3 Hz, 1H), 4.27-4.07 (m, 2H), 3.30 (dd, J=13.4, 3.3 Hz, 1H), 3.07-2.85 (m, 2H), 2.76 (dt, J=18.7, 9.3 Hz, 1H), 2.16 (q, J=7.3 Hz, 2H), 1.89-1.74 (m, 2H).

Step 3: (R)-4-benzyl-3-((R)-2-methylhex-5-enoyl)oxazolidin-2-one

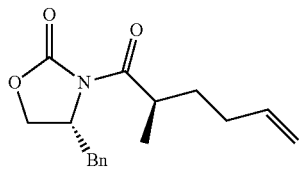 [SMILES: C=CCC[C@@H](C)C(=O)N1C(=O)OC[C@H]1Cc1ccccc1]

To a solution of (4R)-4-benzyl-3-hex-5-enoyl-oxazolidin-2-one (500.0 mg, 1.83 mmol) in THF (5 mL) was added NaHMDS (2.5 mL, 1.0 M THF solution, 2.5 mmol) slowly at −78° C. After stirring at −78° C. for 1 h. Iodomethane (778 mg, 5.49 mmol) was added slowly. The mixture was stirred at −78° C. for additional 3 h. The mixture was quenched with CH$_3$COOH (0.1 mL) and warmed up to r.t. Then water (15 mL) was added and extracted with EA (2×20 mL). The organic layer was dried over Na$_2$SO$_4$, filtered and concentrated under reduced pressure. The resulting mixture was purified by flash chromatography on a silica gel column with PE/EA=10/1 to give (4R)-4-benzyl-3-[(2R)-2-methylhex-5-enoyl]oxazolidin-2-one (200 mg, 38% yield) as a white oil. $^1$H NMR (400 MHz, CDCl$_3$) δ 7.36-7.27 (m, 3H), 7.23-7.20 (m, 2H), 5.84-5.74 (m, 1H), 4.70-4.64 (m, 1H), 4.22-4.13 (m, 2H), 3.76-3.71 (m, 1H), 3.26 (dd, J=13.4, 3.3 Hz, 1H), 2.77 (dd, J=13.3, 9.6 Hz, 1H), 2.12-2.06 (m, 2H), 1.93-1.84 (m, 1H), 1.55-1.48 (m, 1H), 1.24 (d, J=6.9 Hz, 3H).

Step 4: (R)-2-methylhex-5-enoic acid

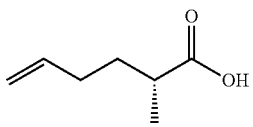

This compound was prepared using procedures analogous to those described for Example 41 using (4R)-4-benzyl-3-[(2R)-2-methylhex-5-enoyl]oxazolidin-2-one to replace (4R)-4-phenyl-3-[(3S)-3-methylhex-5-enoyl]oxazolidin-2-one in Step 3. [α]$_D$$^{20}$ −23.5 (c 0.79, CHCl$_3$) (lit. [α]$_D$$^{23}$ −25.0 (c 1.07, CHCl$_3$)). (Ref: Tetrahedron 2007 vol. 63 #26 p. 5754-5767). $^1$H NMR (400 MHz, CDCl$_3$) δ 5.79 (ddt, J=16.9, 10.2, 6.6 Hz, 1H), 5.14-4.86 (m, 2H), 2.58-2.44 (m, 1H), 2.16-2.02 (m, 2H), 1.89-1.71 (m, 1H), 1.53 (dt, J=13.9, 7.6 Hz, 1H), 1.25-1.12 (m, 3H). $^{13}$C NMR: (100 MHz, CDCl$_3$) δ 183.2, 137.7, 115.2, 38.7, 32.5, 31.2, 16.8.

Step 5: (3R,6R,7R,8E,12R,22S)-6'-Chloro-7-methoxy-12-methyl-15,15-dioxo-spiro[20-oxa-15-thia-1,14-diazatetracyclo[14.7.2.0$^{3,6}$.0$^{19,24}$]pentacosa-8,16(25),17,19(24)-tetraene-22,1'-tetralin]-13-one This compound was prepared using procedures analogous to those described for Example 30 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and using (R)-2-methylhex-5-enoic acid in Step 3. LC-MS calc. for C$_{32}$H$_{40}$ClN$_2$O$_5$S [M+H]$^+$: m/z=599.2/601.2; Found: 599.0/600.9. $^1$H NMR (600 MHz, DMSO-d$_6$) δ 11.82 (s, 1H), 7.69 (d, J=8.5 Hz, 1H), 7.31-7.23 (m, 3H), 7.20 (d, J=2.4 Hz, 1H), 7.04 (d, J=8.2 Hz, 1H), 5.26-5.11 (m, 1H), 5.01-4.91 (m, 1H), 4.16 (d, J=12.3 Hz, 1H), 4.01 (d, J=12.3 Hz, 1H), 3.57-3.46 (m, 2H), 3.29 (d, J=14.3 Hz, 1H), 3.05-2.99 (m, 1H), 2.98 (s, 3H), 2.83-2.78 (m, 1H), 2.74-2.68 (m, 1H), 2.22-2.17 (m, 1H), 2.11-2.07 (m, 1H), 2.00 (dt, J=18.9, 6.8 Hz, 1H), 1.93 (d, J=14.0 Hz, 1H), 1.86-1.67 (m, 6H), 1.59-1.51 (m, 2H), 1.44 (td, J=14.9, 6.6 Hz, 2H), 1.34 (dd, J=7.9, 4.4 Hz, 2H), 1.00 (d, J=6.5 Hz, 3H).

Example 73

(3R,6R,7R,8E,23S)-6'-Chloro-7-methoxy-16,16-dioxo-spiro[21-oxa-16-thia-1,15-diazatetracyclo[15.7.2.0$^{3,6}$.0$^{20,25}$]hexacosa-8,17,19,25-tetraene-23,1'-tetralin]-14-one

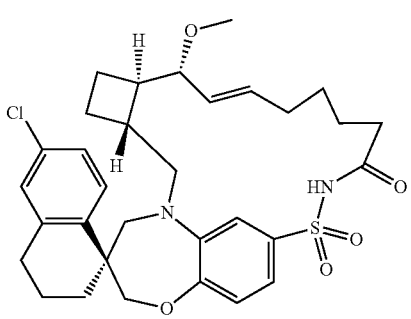 [SMILES: CO[C@@H]1/C=C/CCCCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and hept-6-enoic acid in Step 3. LC-MS calc. for $C_{32}H_{40}ClN_2O_5S$ [M+H]$^+$: m/z=599.23/601.22; Found: 599.0/600.8. $^1$H NMR (400 MHz, DMSO-d$_6$) δ 11.96 (s, 1H), 7.66 (d, J=8.5 Hz, 1H), 7.29-7.24 (m, 2H), 7.21 (d, J=2.4 Hz, 1H), 7.13 (d, J=2.3 Hz, 1H), 7.02 (d, J=8.3 Hz, 1H), 5.60 (dt, J=15.6, 6.3 Hz, 1H), 5.09 (dd, J=15.6, 8.2 Hz, 1H), 4.21 (d, J=12.1 Hz, 1H), 4.12 (d, J=12.1 Hz, 1H), 3.34-3.30 (m, 1H), 3.27-3.18 (m, 2H), 3.08 (s, 3H), 2.81-2.66 (m, 3H), 2.41 (q, J=7.8 Hz, 1H), 2.29-2.08 (m, 4H), 2.03-1.91 (m, 3H), 1.88-1.92 (m, 4H), 1.61-1.45 (m, 4H), 1.45-1.37 (m, 1H), 1.25-1.20 (m, 3H), 1.15-1.06 (m, 1H).

Example 74

(3R,6R,7R,8E,21S)-6'-Chloro-7-methoxy-14,14-dioxo-spiro[19-oxa-14-thia-1,13-diazatetracyclo[13.7.2.03,6.018,23]tetracosa-8,15,17,23-tetraene-21,1'-tetralin]-12-one

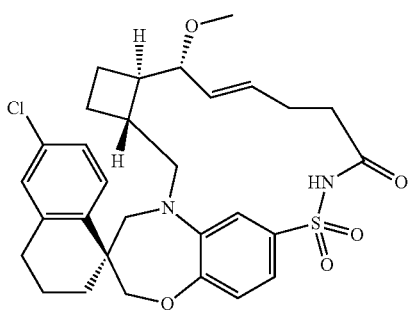 [SMILES: CO[C@@H]1/C=C/CCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 30 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and pent-4-enoic acid in Step 3. LC-MS calc. for $C_{30}H_{36}ClN_2O_5S$ [M+H]$^+$: m/z=571.20/573.19; Found: 570.9/572.7. $^1$H NMR (600 MHz, MeOH-d$_4$) δ 7.63 (d, J=8.3 Hz, 1H), 7.27-7.21 (m, 1H), 7.13 (d, J=2.2 Hz, 1H), 7.09-7.06 (m, 1H), 7.02 (d, J=2.5 Hz, 1H), 6.89 (d, J=8.3 Hz, 1H), 5.05 (s, 1H), 4.91 (dd, J=15.6, 8.2 Hz, 1H), 4.33-4.28 (m, 1H), 3.99-3.96 (m, 1H), 3.66-3.61 (m, 1H), 3.56-3.50 (m, 1H), 3.34-3.27 (m, 3H), 3.02 (s, 3H), 2.78-2.71 (m, 4H), 2.31-2.28 (m, 2H), 2.15-2.02 (m, 3H), 1.85-1.78 (m, 6H), 1.61 (dt, J=10.9, 9.0 Hz, 1H), 1.54-1.43 (m, 3H).

Example 75

(3R,6R,7S,8E,21S)-6'-Chloro-7-methoxy-14,14-dioxo-spiro[19-oxa-14-thia-1,13-diazatetracyclo[13.7.2.0~3,6.0~18,23]tetracosa-8,15,17,23-tetraene-21,1'-tetralin]-12-one

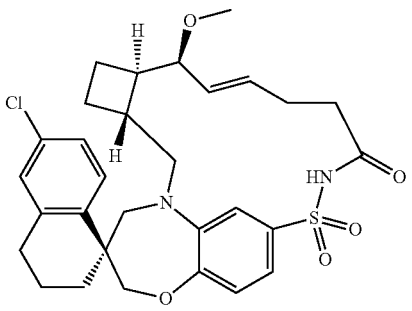 [SMILES: CO[C@H]1/C=C/CCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and pent-4-enoic acid in Step 3. LC-MS calc. for $C_{30}H_{36}ClN_2O_5S$ [M+H]$^+$: m/z=571.20/573.19; Found: 570.9/572.8. $^1$H NMR (600 MHz, Methanol-d$_4$) δ 7.49 (d, J=8.4 Hz, 1H), 7.38 (dd, J=8.3, 2.2 Hz, 1H), 7.04 (ddd, J=12.3, 7.4, 2.3 Hz, 3H), 6.95 (d, J=8.3 Hz, 1H), 5.28 (dd, J=15.6, 8.6 Hz, 1H), 4.54 (t, J=11.8 Hz, 1H), 4.15 (d, J=11.9 Hz, 1H), 3.95 (d, J=11.9 Hz, 1H), 3.60 (dd, J=14.1, 3.3 Hz, 1H), 3.46 (d, J=14.2 Hz, 1H), 3.27 (dd, J=8.7, 2.5 Hz, 1H), 3.04 (s, 3H), 2.88 (dd, J=14.2, 11.1 Hz, 1H), 2.79-2.61 (m, 2H), 2.50 (qd, J=8.3, 4.0 Hz, 2H), 2.41 (dt, J=14.7, 4.4 Hz, 1H), 2.34-2.22 (m, 1H), 2.19-2.03 (m, 3H), 1.92-1.78 (m, 3H), 1.74-1.59 (m, 3H), 1.47 (dq, J=13.0, 9.9, 9.5 Hz, 1H), 1.25-1.17 (m, 1H).

Example 76

(3R,6R,7R,21S)-6'-Chloro-7-methoxy-14,14-dioxo-spiro[19-oxa-14-thia-1,13-diazatetracyclo[13.7.2.03,6.018,23]tetracosa-15,17,23-triene-21,1'-tetralin]-12-one

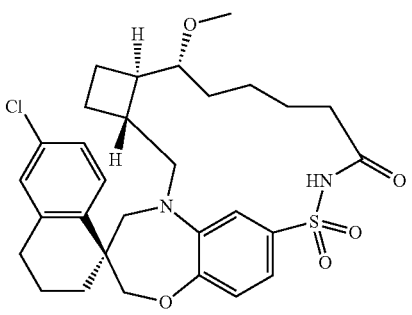 [SMILES: CO[C@@H]1CCCCC(=O)NS(=O)(=O)c2ccc3c(c2)N(C[C@@H]2CC[C@H]21)C[C@@]1(CCCc2cc(Cl)ccc21)CO3]

To a stirred solution of (3R,6R,7R,8E,21S)-6'-chloro-7-methoxy-14,14-dioxo-spiro[19-oxa-14-thia-1,13-diazatetracyclo[13.7.2.03,6.018,23]tetracosa-8,15,17,23-tetraene-21,1'-tetralin]-12-one (Example 74, 7.9 mg, 0.01 mmol) was added platinum(IV) oxide anhydrous (0.63 mg). The reaction flask was charged with hydrogen and the reaction mixture was stirred at 20° C. with a hydrogen balloon. LC-MS showed full conversion of starting material after 3 h. The solution was filtered through a pad of Celite and concentrated under reduced pressure The crude product was further purified by Prep-HPLC to afford (3R,6R,7R,21S)-6'-chloro-7-methoxy-14,14-dioxo-spiro[19-oxa-14-thia-1,13-diazatetracyclo[13.7.2.03,6.018,23]tetracosa-15,17,23-triene-21,1'-tetralin]-12-one (2.9 mg, 28.2% yield) as a white solid. LC-MS calc. for $C_{30}H_{38}ClN_2O_5S$ $[M+H]^+$: m/z=573.21/575.20; Found: 572.8/574.6.

Example 77

(3R,6R,7S,21S)-6'-Chloro-7-methoxy-14,14-dioxo-spiro[19-oxa-14-thia-1,13-diazatetracyclo[13.7.2.03,6.018,23]tetracosa-15,17,23-triene-21,1'-tetralin]-12-one

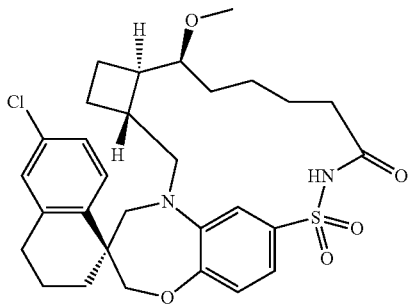 [SMILES: CO[C@H]1CCCCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using (3R,6R,7S,8E,21S)-6'-chloro-7-methoxy-14,14-dioxo-spiro[19-oxa-14-thia-1,13-diazatetracyclo[13.7.2.03,6.018,23]tetracosa-8,15,17,23-tetraene-21,1'-tetralin]-12-one (Example 51). LC-MS calc. for $C_{30}H_{38}ClN_2O_5S$ $[M+H]^+$: m/z=573.21/575.20; Found: 572.8/574.8.

Example 78

(3R,6R,7R,8E,1S,12R,22S)-6'-Chloro-7-methoxy-11,12-dimethyl-15,15-dioxo-spiro[20-oxa-15-thia-1,14-diazatetracyclo[14.7.2.03,6.019,24]pentacosa-8,16,18,24-tetraene-22,1'-tetralin]-13-one

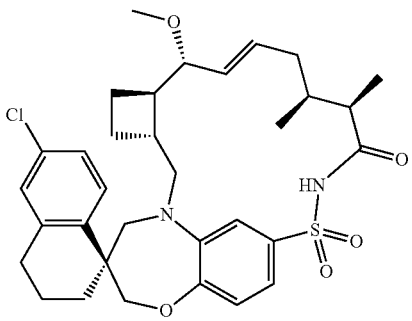 [SMILES: CO[C@@H]1/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]

Step 1: (R)-3-((2R,3S)-2,3-dimethylhex-5-enoyl)-4-phenyloxazolidin-2-one

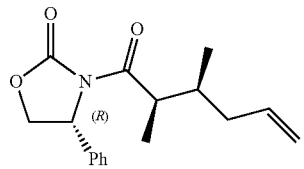

To a solution of LiHMDS, 1 M in THF (30.7 mL, 39.9 mmol) in THF (10 mL) was slowly added (R)-3-((S)-3-methylhex-5-enoyl)-4-phenyloxazolidin-2-one (5.46 g, 19.9 mmol, Example 71, Step 2) in THF (1 mL) at −78° C. The mixture was stirred at −78° C. for 1 h. Iodomethane (2.5 mL, 39 mmol) was added slowly. The mixture was stirred at −78° C. for 3 h. Then the mixture was stirred at −35° C. overnight. The mixture was quenched with saturated $NH_4Cl$ solution. The organic layer was separated, and the aqueous layer was extracted with EA (3×20 mL). The combined organic layers were dried over $Na_2SO_4$, filtered and concentrated to give crude solid. The crude solid was purified by flash chromatography on a silica gel column with PE/EA=10/1 to give (R)-3-((2R,3S)-2,3-dimethylhex-5-enoyl)-4-phenyloxazolidin-2-one (1.4 g, 24% yield) as a white solid. $^1H$ NMR: (400 MHz, $CDCl_3$) δ 7.40-7.27 (m, 1H), 5.82-5.75 (m, 1H), 5.41 (dd, J=3.6 Hz, 8.8 Hz, 1H), 5.02 (t, J=6.8 Hz, 2H), 4.66 (d, J=8.8 Hz, 1H), 4.24 (dd, J=3.6 Hz, 8.8 Hz, 1H), 3.74-3.69 (m, 1H), 2.14-2.09 (m, 1H), 2.01-1.95 (m, 2H), 1.03 (d, J=6.8 Hz, 3H), 0.88 (d, J=6.4 Hz, 3H). $^{13}C$ NMR: (100 MHz, $CDCl_3$) δ 176.3, 153.4, 139.4, 137.1, 129.2, 128.6, 125.7, 116.1, 69.7, 57.8, 41.9, 40.0, 34.5, 15.5, 13.3.

Step 2: (2R,3S)-2,3-dimethylhex-5-enoic acid

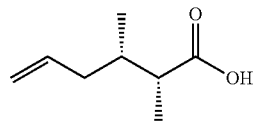

This compound was prepared using procedures analogous to those described for Example 71 using (R)-3-((2R,3S)-2,3-dimethylhex-5-enoyl)-4-phenyloxazolidin-2-one to replace (4R)-4-phenyl-3-[(3S)-3-methylhex-5-enoyl]oxazolidin-2-one in Step 3. dr=97:3. $[α]^{22}_D$=−33.8 (c=0.94, $CHCl_3$). $^1H$ NMR: (400 MHz, $CDCl_3$) δ 11.2 (br s, 1H), 5.82-5.73 (m, 1H), 5.06-5.01 (m, 2H), 2.49-2.42 (m, 1H), 2.14-2.09 (m, 1H), 2.04-1.96 (m, 2H), 1.10 (d, J=6.8 Hz, 3H), 0.90 (d, J=6.4 Hz, 3H).

Step 3: (3R,6R,7R,8E,11S,12R,22S)-6'-chloro-7-methoxy-11,12-dimethyl-15,15-dioxo-spiro[20-oxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2R,3S)-2,3-dimethylhex-5-enoic in Step 3. LC-MS calc. for $C_{33}H_{42}ClN_2O_5S$ [M+H]$^+$: m/z=613.25/615.25; Found: 612.9/615.0. $^1$H NMR (400 MHz, DMSO-d$_6$) δ 11.78 (s, 1H), 7.66 (d, J=8.5 Hz, 1H), 7.28 (dd, J=8.5, 2.5 Hz, 1H), 7.27-7.18 (m, 2H), 7.16 (s, 1H), 7.03 (d, J=8.2 Hz, 1H), 5.60-5.51 (m, 1H), 5.08-4.97 (m, 1H), 4.20 (d, J=12.1 Hz, 1H), 4.04 (d, J=12.6 Hz, 1H), 3.27 (d, J=14.0 Hz, 2H), 3.03 (s, 3H), 2.86-2.62 (m, 4H), 2.24-1.98 (m, 4H), 1.95-1.72 (m, 6H), 1.65-1.40 (m, 5H), 1.24 (d, J=3.0 Hz, 3H), 0.84 (d, J=4.2 Hz, 3H).

Example 79

(3R,6R,7S,8E,11S,12R,22S)-6'-Chloro-7-methoxy-11,12-dimethyl-15,15-dioxo-spiro[20-oxa-15-thia-1,14-diazatetracyclo[14.7.2.0$^{3,6}$.0$^{19,24}$]pentacosa-8,16,18,24-tetraene-22,1'-tetralin]-13-one

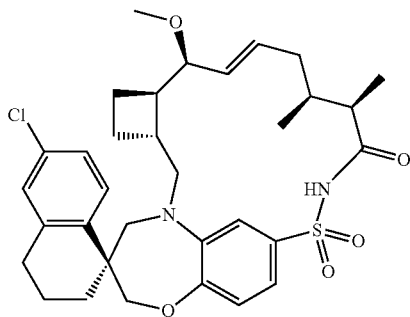 [SMILES: CO[C@H]1/C=C/C[C@H](C)[C@@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and (2R,3S)-2,3-dimethylhex-5-enoic acid (Example 47 Step 2) in Step 3. LC-MS calc. for $C_{33}H_{42}ClN_2O_5S$ [M+H]$^+$: m/z=613.25/615.25; Found: 613.0/615.0. $^1$H NMR (600 MHz, MeOH-d$_4$) δ 7.61 (d, J=8.6 Hz, 1H), 7.46-7.41 (m, 2H), 7.19-7.14 (m, 2H), 7.05 (d, J=8.3 Hz, 1H), 5.41-5.33 (m, 2H), 5.17 (s, 1H), 4.23 (d, J=11.8 Hz, 1H), 4.07 (d, J=12.0 Hz, 1H), 3.60 (d, J=12.2 Hz, 1H), 3.53 (d, J=14.3 Hz, 2H), 3.17 (s, 3H), 2.86-2.79 (m, 3H), 2.25-2.18 (m, 3H), 2.05 (d, J=7.0 Hz, 3H), 1.94 (d, J=7.5 Hz, 2H), 1.80 (d, J=15.9 Hz, 2H), 1.63 (d, J=6.0 Hz, 2H), 1.34-1.28 (m, 6H), 1.16 (d, J=6.9 Hz, 3H).

Example 80

(3R,6R,7S,8E,22S)-6'-Chloro-7-methoxy-15,15-dioxo-spiro[20-oxa-15-thia-1,14-diazatetracyclo[14.7.2.0$^{3,6}$.0$^{19,24}$]pentacosa-8,16(25),17,19(24)-tetraene-22,1'-tetralin]-13-one

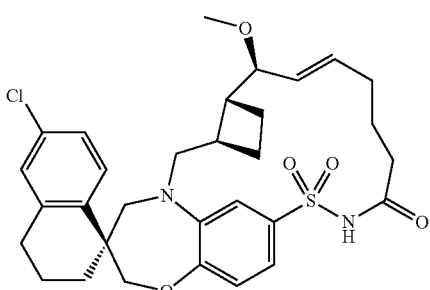

This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and hex-5-enoic acid in Step 3. LC-MS calc. for $C_{31}H_{38}ClN_2O_5S$ [M+H]$^+$: m/z=585.21/587.21; Found: 585.0/586.9. $^1$H NMR (600 MHz, DMSO-d$_6$) 11.76 (s, 1H), 7.58 (d, J=8.5 Hz, 1H), 7.16 (dd, J=8.3, 2.1 Hz, 1H), 7.13 (d, J=2.2 Hz, 1H), 7.11 (d, J=2.4 Hz, 1H), 6.94 (d, J=8.3 Hz, 1H), 5.13-5.06 (m, 1H), 4.78 (dd, J=15.3, 9.0 Hz, 1H), 4.93-3.96 (m, 2H), 3.43 (d, J=14.3 Hz, 2H), 3.01 (dd, J=15.0, 5.3 Hz, 1H), 2.87 (s, 3H), 2.71-2.68 (m, 2H), 2.64-2.56 (m, 2H), 2.21-2.19 (m, 1H), 2.05-1.87 (m, 5H), 1.76-1.64 (m, 4H), 1.54-1.44 (m, 3H), 1.38-1.31 (m, 1H), 0.80 (d, J=6.3 Hz, 3H).

Example 81

(3R,6R,7S,8E,12R,22S)-6'-Chloro-7-methoxy-12-methyl-15,15-dioxo-spiro[20-oxa-15-thia-1,14-diazatetracyclo[14.7.2.0$^{3,6}$.0$^{19,24}$]pentacosa-8,16(25),17,19(24)-tetraene-22,1'-tetralin]-13-one

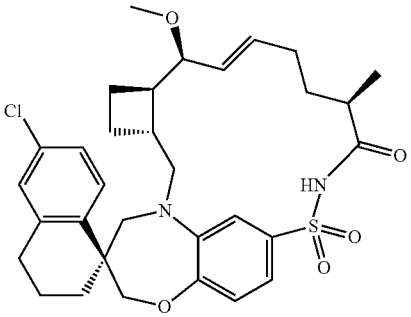 [SMILES: CO[C@H]1/C=C/CC[C@@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 30 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and (R)-2-methylhex-5-enoic acid (Example 72, Step 4) in Step 3. LC-MS calc. for $C_{32}H_{40}ClN_2O_5S$ [M+H]$^+$: m/z=599.2/601.2; Found: 599.4/601.5. $^1$H NMR (600 MHz, MeOH-d$_4$) δ 7.58 (d, J=8.4 Hz, 1H), 7.51 (d, J=2.3 Hz, 1H), 7.44 (dd, J=8.4, 2.2 Hz, 1H), 7.20-7.13 (m, 2H), 7.08 (d, J=8.3 Hz, 1H), 5.12 (dd, J=15.4, 8.3 Hz, 1H), 4.99-4.89 (m, 1H), 4.25 (d, J=12.0 Hz, 1H), 4.04 (d, J=11.9 Hz, 1H), 3.68 (dd, J=14.6, 4.3 Hz, 1H), 3.53 (d, J=14.3 Hz, 1H), 3.29 (dd, J=8.9, 2.7 Hz, 1H), 3.13 (s, 3H), 2.88-2.80 (m, 3H), 2.57 (tt, J=9.0, 4.5 Hz, 1H), 2.35 (ddd, J=10.5, 6.7, 3.0 Hz, 1H), 2.21 (dt, J=9.6, 3.3 Hz, 1H), 2.09-1.98 (m, 2H), 1.99-1.90 (m, 2H), 1.88-1.73 (m, 5H), 1.64-1.53 (m, 3H), 1.17 (d, J=7.0 Hz, 3H).

Example 82

(3R,6R,7S,8E,11S,22S)-6'-Chloro-7-methoxy-11-methyl-15,15-dioxo-spiro[20-oxa-15-thia-1,14-diazatetracyclo[14.7.2.0³,⁶.0¹⁹,²⁴]pentacosa-8,16(25),17,19(24)-tetraene-22,1'-tetralin]-13-one

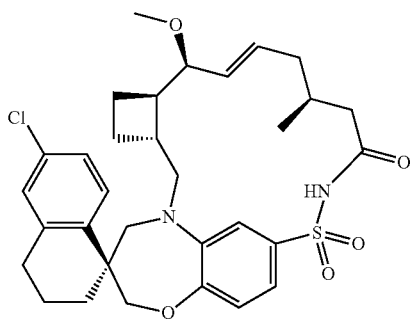 [SMILES: CO[C@H]1/C=C/C[C@H](C)CC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 30 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and (S)-3-methylhex-5-enoic acid (Example 71, Step 3) in Step 3. LC-MS calc. for $C_{32}H_{40}ClN_2O_5S$ [M+H]⁺: m/z=599.2/601.2; Found: 599.3/601.1 ¹H NMR (600 MHz, MeOH-d₄) δ 7.59 (d, J=8.4 Hz, 1H), 7.48-7.41 (m, 2H), 7.18-7.14 (m, 2H), 7.08 (d, J=8.2 Hz, 1H), 5.17 (dd, J=15.4, 7.9 Hz, 1H), 5.09-5.02 (m, 1H), 4.27 (d, J=11.9 Hz, 1H), 4.03 (d, J=11.9 Hz, 1H), 3.74-3.67 (m, 1H), 3.36 (d, J=10.2 Hz, 1H), 3.14 (s, 3H), 3.06 (dd, J=14.1, 11.4 Hz, 1H), 2.87-2.74 (m, 3H), 2.63-2.58 (m, 1H), 2.39 (dd, J=14.7, 2.6 Hz, 1H), 2.25-2.19 (m, 1H), 2.13-1.92 (m, 7H), 1.87-1.67 (m, 5H), 1.62-1.57 (m, 2H), 1.01 (d, J=6.6 Hz, 3H).

Example 83

(3R,6R,7S,8E,23S)-6'-Chloro-7-methoxy-16,16-dioxo-spiro[21-oxa-16-thia-1,15-diazatetracyclo[15.7.2.0³,⁶.0²⁰,²⁵]hexacosa-8,17,19,25-tetraene-23,1'-tetralin]-14-one

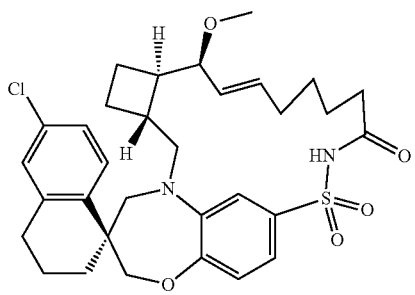 [SMILES: CO[C@H]1/C=C/CCCCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 30 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and hept-6-enoic acid in Step 3. LC-MS calc. for $C_{32}H_{40}ClN_2O_5S$ [M+H]⁺: m/z=599.23/601.23; Found: 598.8/601.1. ¹H NMR (400 MHz, DMSO-d₆) δ 12.00 (s, 1H), 7.59-7.54 (m, 1H), 7.36 (dd, J=8.4, 2.1 Hz, 1H), 7.27 (d, J=2.3 Hz, 1H), 7.24-7.20 (m, 2H), 7.11 (d, J=8.3 Hz, 1H), 5.13 (dd, J=15.6, 8.0 Hz, 1H), 4.85 (ddd, J=14.9, 8.2, 5.2 Hz, 1H), 4.20 (d, J=11.9 Hz, 1H), 3.99 (d, J=12.0 Hz, 1H), 3.61 (dd, J=8.0, 3.5 Hz, 1H), 3.55 (dd, J=14.0, 2.9 Hz, 1H), 3.34-3.24 (m, 2H), 3.10 (s, 3H), 3.04-2.98 (m, 1H), 2.79-2.72 (m, 2H), 2.45 (dt, J=8.6, 4.4 Hz, 1H), 2.40-2.33 (m, 1H), 2.26 (ddd, J=12.4, 8.0, 3.9 Hz, 1H), 2.11 (ddd, J=13.0, 6.3, 3.0 Hz, 1H), 2.06-1.98 (m, 1H), 1.94-1.91 (m, 1H), 1.88-1.70 (m, 5H), 1.70-1.62 (m, 2H), 1.58-1.47 (m, 3H), 1.39 (td, J=9.1, 4.8 Hz, 1H), 1.17-1.10 (m, 1H).

Example 84

(3R,6R,7S,8E,11R,22S)-6'-Chloro-7-methoxy-11-methyl-15,15-dioxo-spiro[20-oxa-15-thia-1,14-diazatetracyclo[14.7.2.0³,⁶.0¹⁹,²⁴]pentacosa-8,16(25),17,19(24)-tetraene-22,1'-tetralin]-13-one

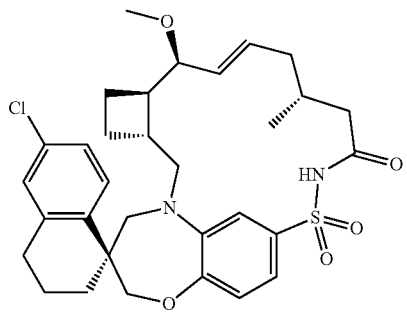 [SMILES: CO[C@H]1/C=C/C[C@@H](C)CC(=O)NS(=O)(=O)c2ccc3c(c2)N(C[C@@H]2CC[C@H]21)C[C@@]1(CCCc2cc(Cl)ccc21)CO3]

Step 1: (R)-3-methylhex-5-enoic acid

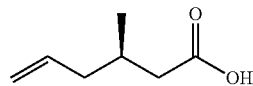

This compound was prepared using procedures analogous to those described for Example 71 Step 1-3 using (S)-(+)-4-Phenyl-1,3-oxazolidin-2-one to replace (R)-(+)-4-Phenyl-1,3-oxazolidin-2-one in Step 1. [α]²⁰D=+3.6 (c=0.74, CHCl₃). ¹H NMR: (400 MHz, CDCl₃) δ 5.83-5.74 (m, 1H), 5.10-5.04 (m, 2H), 2.44-2.40 (m, 1H), 2.23-2.03 (m, 4H), 1.01 (d, J=6.0 Hz, 3H).

Step 2: (3R,6R,7S,8E,11R,22S)-6'-chloro-7-methoxy-11-methyl-15,15-dioxo-spiro[20-oxa-15-thia-1,14-diazatetracyclo[14.7.2.0³,⁶.0¹⁹,²⁴]pentacosa-8,16(25), 17,19(24)-tetraene-22,1'-tetralin]-13-one This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and (R)-3-methylhex-5-enoic acid in Step 3. LC-MS calc. for $C_{32}H_{40}ClN_2O_5S$ [M+H]⁺: m/z=599.2/601.2; Found: 599.0/601.0. ¹H NMR (600 MHz, DMSO-d$_6$) δ 11.94 (s, 1H), 7.61 (d, J=8.5 Hz, 1H), 7.27 (dd, J=8.3, 2.1 Hz, 1H), 7.23 (dd, J=8.4, 2.5 Hz, 1H), 7.21 (d, J=2.5 Hz, 1H), 7.07 (d, J=8.3 Hz, 1H), 7.03 (d, J=2.2 Hz, 1H), 5.14-5.06 (m, 2H), 4.13 (d, J=12.1 Hz, 1H), 4.04 (d, J=12.1 Hz, 1H), 3.52 (dd, J=14.5, 6.4 Hz, 2H), 3.43-3.37 (m, 1H), 3.22-3.13 (m, 1H), 3.07 (s, 3H), 2.80-2.71 (m, 3H), 2.45-2.41 (m, 1H), 2.21 (dd, J=16.7, 7.8 Hz, 1H), 2.18-2.12 (m, 2H), 2.02-1.94 (m, 4H), 1.89-1.82 (m, 3H), 1.78-1.71 (m, 2H), 1.66 (t, J=11.2 Hz, 1H), 1.55 (p, J=9.2 Hz, 1H), 0.89 (d, J=6.9 Hz, 3H).

Example 85

(3R,6R,7S,8E,12S,22S)-6'-Chloro-7-methoxy-12-methyl-15,15-dioxo-spiro[20-oxa-15-thia-1,14-diazatetracyclo[14.7.2.0³,⁶.0¹⁹,²⁴]pentacosa-8,16(25),17,19(24)-tetraene-22,1'-tetralin]-13-one

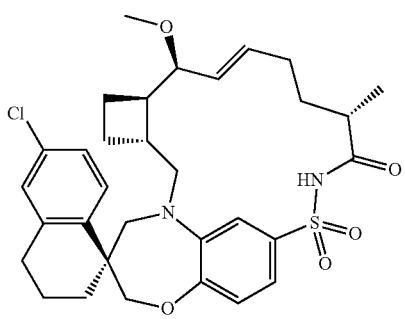 [SMILES: CO[C@H]1/C=C/CC[C@H](C)C(=O)NS(=O)(=O)c2ccc3c(c2)N(C[C@@H]2CC[C@H]21)C[C@@]1(CCCc2cc(Cl)ccc21)CO3]

Step 1: (2S)-2-methylhex-5-enoic acid

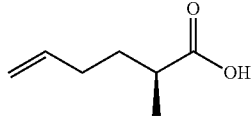

This compound was prepared using procedures analogous to those described for Example 72 Step 2-4 using (4S)-4-benzyl-3-hex-5-enoyl-oxazolidin-2-one to replace (4R)-4-benzyl-3-hex-5-enoyl-oxazolidin-2-one in Step 2. $^1$H NMR (400 MHz, CDCl$_3$) 5.76-5.86 (m, 1H), 4.99-5.09 (m, 2H), 2.50-2.55 (m, 1H), 2.11-2.16 (m, 2H), 1.79-1.88 (m, 1H), 1.51-1.59 (m, 1H), 1.22 (d, J=7.2 Hz, 3H).

Step 2: (3R,6R,7S,8E,12S,22S)-6'-chloro-7-methoxy-12-methyl-15,15-dioxo-spiro[20-oxa-15-thia-1,14-diazatetracyclo[14.7.2.0³,⁶.0¹⁹,²⁴]pentacosa-8,16(25),17,19(24)-tetraene-22,1'-tetralin]-13-one This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and (2S)-2-methylhex-5-enoic acid in Step 3. LC-MS calc. for C$_{32}$H$_{40}$ClN$_2$O$_5$S [M+H]$^+$: m/z=599.2/601.2; Found: 598.9/600.9. $^1$H NMR (400 MHz, DMSO-d$_6$) δ 11.94 (s, 1H), 7.62 (d, J=8.5 Hz, 1H), 7.31 (d, J=8.5 Hz, 1H), 7.27-7.19 (m, 2H), 7.06 (d, J=8.3 Hz, 1H), 7.00 (d, J=2.1 Hz, 1H), 5.18-5.07 (m, 2H), 4.16 (d, J=12.1 Hz, 1H), 4.04 (d, J=12.0 Hz, 1H), 3.54-3.43 (m, 3H), 3.07 (s, 3H), 2.82-2.74 (m, 2H), 2.01 (m, J=14.4, 6.7 Hz, 2H), 1.93-1.79 (m, 5H), 1.73-1.65 (m, 4H), 1.54-1.45 (m, 3H), 1.33-1.17 (m, 4H), 0.96 (d, J=6.8 Hz, 3H).

Example 86

(3R,6R,7R,8E,22S)-6'-Chloro-7-methoxy-12,12-(1,3-propylene)-15,15-dioxo-spiro[[20]oxa-15-thia-1,14-diazatetracyclo[14.7.2.0³,⁶.0¹⁹,²⁴]pentacosa[8,16(25),17,19(24)]tetraene-22,1'-tetralin]-13-one

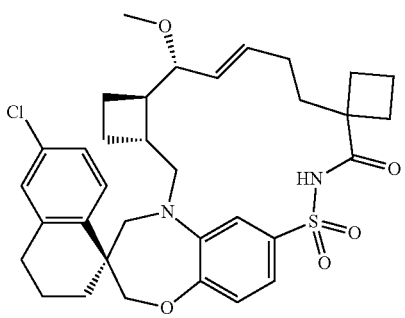 [SMILES: CO[C@@H]1/C=C/CCC2(CCC2)C(=O)NS(=O)(=O)c2ccc3c(c2)N(C[C@@H]2CC[C@H]21)C[C@@]1(CCCc2cc(Cl)ccc21)CO3]

Step 1: ethyl 1-but-3-enylcyclobutanecarboxylate

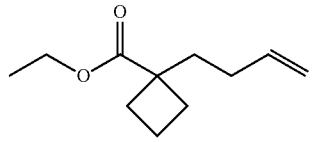

To a solution of diisopropylamine (4.86 g, 48. mmol) in THF (25 mL) was added n-butyllithium (18.3 mL, 45 mmol, 2.5 M in hexane) at −65° C. slowly. After addition, the reaction mixture was allowed to warm slowly to −10° C. and then cooled back to −65° C. Ethyl cyclobutanecarboxylate (5.6 g, 43 mmol) was added dropwise. The resulting mixture was stirred at −65° C. for 1 h., and then 4-bromobut-1-ene (7.08 g, 52 mmol) in N-[bis(dimethylamino)phosphoryl]-N-methyl-methanamine (10 mL, 43 mmol) was added. The reaction was stirred at ambient temperature overnight. The mixture was quenched with water at 0° C., and extracted with MTBE (2×20 mL). The combined organic layers were dried over Na$_2$SO$_4$, filtered and concentrated under reduced pressure. The residue was purified by flash chromatography on a silica gel column to afford ethyl 1-but-3-enylcyclobutanecarboxylate (7.78 g, 97% yield).

Step 2: 1-(but-3-en-1-yl)cyclobutane-1-carboxylic acid

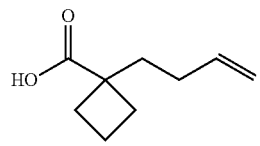

Ethyl 1-but-3-enylcyclobutanecarboxylate (240.0 mg, 1.32 mmol) in methanol (2 mL) and water (2 mL) was treated with lithium hydroxide monohydrate (226 mg, 5.2 mmol). The reaction was heated and stirred at 50° C. over weekend. After cooling, the reaction was adjusted with 1 N HCl to pH about 2. The mixture was extracted with EA (2×10 mL). The combined organic layers were dried over Na$_2$SO$_4$, filtered and concentrated under reduced pressure. The residue was purified by flash chromatography on a silica gel column to afford pure 1-but-3-enylcyclobutanecarboxylic acid (128.7 mg, 63% yield). LC-MS calc. for C$_8$H$_{13}$O$_2$ [M-H]$^-$: m/z=153.1; Found: 153.0.

Step 3: (3R,6R,7R,8E,22S)-6'-Chloro-7-m ethoxy-12,12-(1,3-propylene)-15,15-dioxo-spiro[20-oxa-15-thia-1,14-diazatetracyclo[14.7.2.0$^{3,6}$.0$^{19,24}$]pentacosa[8,16(25), 17, 19(24)]tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-(but-3-en-1-yl)cyclobutane-1-carboxylic acid in Step 3. LC-MS calc. for C$_{34}$H$_{42}$ClN$_2$O$_5$S [M+H]$^+$: m/z=625.24/627.24; Found: 625.0/627.3. $^1$H NMR (400 MHz, CDCl$_3$) δ 7.71 (d, J=8.5 Hz, 1H), 7.58 (dd, J=8.4, 2.1 Hz, 1H), 7.35 (d, J=1.7 Hz, 1H), 7.18 (dd, J=8.5, 2.2 Hz, 1H), 7.11 (d, J=2.1 Hz, 1H), 7.04 (d, J=8.4 Hz, 1H), 5.27-5.15 (m, 1H), 4.86 (dd, J=15.1, 9.1 Hz, 1H), 4.26 (d, J=11.7 Hz, 1H), 4.15 (d, J=11.9 Hz, 1H), 3.58 (d, J=14.4 Hz, 2H), 3.31 (ddd, J=35.6, 22.1, 11.1 Hz, 3H), 3.11 (d, J=13.4 Hz, 2H), 3.01 (d, J=6.7 Hz, 2H), 2.84-2.70 (m, 2H), 2.63 (d, J=22.6 Hz, 1H), 2.51 (dt, J=16.4, 9.1 Hz, 2H), 2.41-2.29 (m, 2H), 2.13-1.74 (m, 10H), 1.56 (ddd, J=27.7, 19.1, 11.5 Hz, 5H).

Example 87

(3R,6R,7R,8E,11S,12S,22S)-6'-Chloro-7-methoxy-12-(methoxymethyl)-11-methyl-15,15-dioxo-spiro[20-oxa-15-thia-1,14-diazatetracyclo[14.7.2.0$^{3,6}$.0$^{19,24}$]pentacosa-8,16,18,24-tetraene-22,1'-tetralin]-13-one

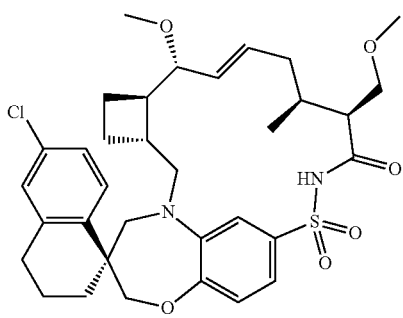 [SMILES: COC[C@H]1C(=O)NS(=O)(=O)c2ccc3c(c2)N(C[C@@H]2CC[C@H]2[C@H](OC)/C=C/C[C@@H]1C)C[C@@]1(CCCc2cc(Cl)ccc21)CO3]

Step 1: (R)-3-((2S,3S)-2-(methoxymethyl)-3-methylhex-5-enoyl)-4-phenyloxazolidin-2-one

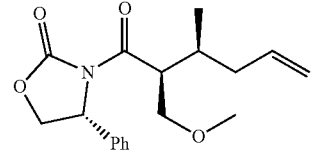 [SMILES: C=CC[C@H](C)[C@@H](COC)C(=O)N1C(=O)OC[C@H]1c1ccccc1]

To a solution of LiHMDS, 1M in THF (179 mL, 179 mmol) was slowly added (4R)-4-phenyl-3-[(3S)-3-methylhex-5-enoyl]oxazolidin-2-one (27.3 g, 99 mmol, Example 41, Step 2) in THF (30 mL) at −78° C. After stirring at −78° C. for 2 h., bromo(methoxy)methane (11 mL, 179 mmol) was slowly added. The reaction mixture was stirred at −78° C. for additional 3 h., and then stirred at −30° C. overnight. The mixture was quenched with saturated NH$_4$Cl aqueous solution. The organic layer was separated and the aqueous layer was extracted with EA (50 mL×3). The combined organic layers were dried over Na$_2$SO$_4$, filtered and concentrated under reduced pressure The residue solid was purified by silica gel with PE/EA=10/1 to give (R)-3-((2S,3S)-2-(methoxymethyl)-3-methylhex-5-enoyl)-4-phenyloxazolidin-2-one (11.6 g, 36% yield). $^1$H NMR (400 MHz, CDCl$_3$) δ 7.38-7.27 (m, 5H), 5.80-5.70 (m, 1H), 5.48 (dd, J=8.8, 4.1 Hz, 1H), 5.04-4.99 (m, 2H), 4.65 (t, J=8.8 Hz, 1H), 4.22-4.15 (m, 2H), 3.60-3.50 (m, 2H), 3.16 (s, 3H), 2.20-2.12 (m, 1H), 2.05-1.95 (m, 2H), 0.92 (d, J=8.4 Hz, 3H).

Step 2: (2S,3S)-2-(methoxymethyl)-3-methylhex-5-enoic acid

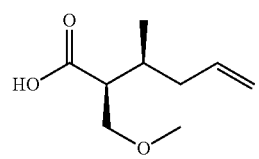

This compound was prepared using procedures analogous to those described for Example 71, Step 3 using (4R)-4-phenyl-3-[(2S,3S)-2-(methoxymethyl)-3-methyl-hex-5-enoyl]oxazolidin-2-one. $^1$H NMR (400 MHz, CDCl$_3$) 5.81-5.71 (m, 1H), 5.07-5.03 (m, 2H), 3.65 (t, J=9.2 Hz, 1H), 3.57-3.54 (m, 1H), 3.12 (s, 3H), 2.64-2.59 (m, 1H), 2.22-2.18 (m, 1H), 2.18-1.97 (m, 1H), 2.06-1.95 (m, 2H), 0.95 (d, J=6.6 Hz, 3H).

Step 3: (3R,6R,7R,8E,11S,12S,22S)-6'-Chloro-7-methoxy-12-(methoxymethyl)-11-methyl-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2S,3S)-2-(methoxymethyl)-3-methylhex-5-enoic acid in Step 3. LC-MS calc. for $C_{34}H_{44}ClN_2O_6S$ [M+H]$^+$: m/z=643.25/645.25; Found: 642.9/645.2. $^1$H NMR (400 MHz, DMSO-d$_6$) δ 11.89 (s, 1H), 7.66 (d, J=8.5 Hz, 1H), 7.28 (dd, J=8.5, 2.4 Hz, 1H), 7.22 (d, J=2.3 Hz, 2H), 7.14 (s, 1H), 7.03 (d, J=8.2 Hz, 1H), 5.60-5.52 (m, 1H), 5.08-4.99 (m, 1H), 4.19-4.12 (m, 4H), 3.45 (t, J=9.2 Hz, 2H), 3.33-3.25 (m, 2H), 3.19-3.11 (m, 3H), 3.04 (s, 3H), 2.86-2.65 (m, 4H), 2.55 (s, 3H), 2.09 (q, J=6.2, 5.2 Hz, 2H), 2.01 (q, J=6.8, 6.1 Hz, 1H), 1.88-1.80 (m, 5H), 1.64-1.36 (m, 5H).

Example 88

(3R,6R,7R,8E,11S,12S,22S)-6'-Chloro-7-hydroxy-12-(methoxymethyl)-11-methyl-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one

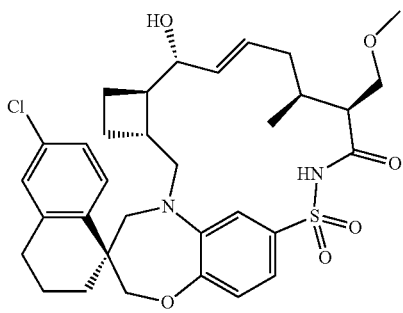 [SMILES: COC[C@H]1C(=O)NS(=O)(=O)c2ccc3c(c2)N(C[C@@H]2CC[C@H]2[C@H](O)/C=C/C[C@@H]1C)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1R)-1-hydroxyallyl]cyclobutyl]methyl]spiro[2,4-dihydro-1,5-benzoxazepine-3,1'-tetralin]-7-sulfonamide (Intermediate 4) and (2S,3S)-2-(methoxymethyl)-3-methylhex-5-enoic acid in Step 3. LC-MS calc. for $C_{33}H_{42}ClN_2O_6S$ [M+H]$^+$: m/z=629.2/631.2; Found: 628.9/631.1. $^1$H NMR (600 MHz, DMSO-d$_6$) δ 11.69 (s, 1H), 7.65 (d, J=8.5 Hz, 2H), 7.32-7.19 (m, 4H), 7.15 (s, 1H), 7.00 (d, J=7.7 Hz, 1H), 5.52 (s, 1H), 5.27 (s, 1H), 4.53 (d, J=3.4 Hz, 1H), 4.27-3.93 (m, 3H), 3.55 (s, 2H), 3.43 (t, J=9.2 Hz, 2H), 3.34 (s, 12H), 3.21 (dd, J=32.9, 8.9 Hz, 5H), 2.94 (d, J=11.3 Hz, 1H), 2.85-2.68 (m, 3H), 2.11-1.97 (m, 3H), 1.90 (d, J=13.2 Hz, 2H), 1.79 (d, J=19.7 Hz, 5H), 1.66-1.36 (m, 5H), 0.60 (s, 4H).

Example 89

(3R,6R,7R,8E,11S,12R,22S)-6'-Chloro-7-methoxy-12-(2-methoxyethyl)-1-methyl-15,15-dioxo-spiro[20-oxa-15-thia-1,14-diazatetracyclo[14.7.2.0³,6.0¹⁹,²⁴]pentacosa-8,16,18,24-tetraene-22,1'-tetralin]-13-one

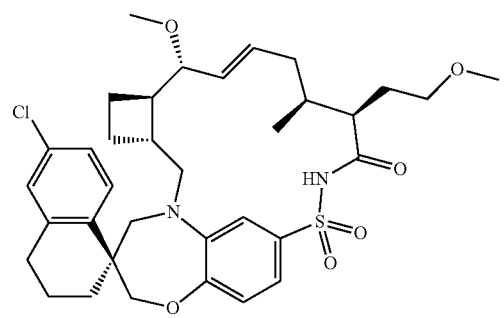 [SMILES: COCC[C@H]1C(=O)NS(=O)(=O)c2ccc3c(c2)N(C[C@@H]2CC[C@H]2[C@H](OC)/C=C/C[C@@H]1C)C[C@@]1(CCCc2cc(Cl)ccc21)CO3]

Step 1: tert-butyl (3R,4S)-4-methyl-3-((R)-2-oxo-4-phenyloxazolidine-3-carbonyl)hept-6-enoate

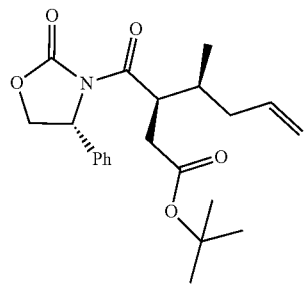 [SMILES: C=CC[C@H](C)[C@@H](CC(=O)OC(C)(C)C)C(=O)N1C(=O)OC[C@H]1c1ccccc1]

To a mixture of (4R)-4-phenyl-3-[(3S)-3-methylhex-5-enoyl]oxazolidin-2-one (Example 71 Step 2, 20.0 g, 73.2 mmol) in THF (150 mL) at −78° C. was added the solution of NaHMDS (2 M in THF) (54.8 mL, 109 mmol) dropwise. The mixture was stirred at −78° C. for 3.5 h. Then t-butyl bromoacetate (21.4 g, 109 nmmol) was added dropwise. The mixture was stirred at −78° C. for 30 min., and then allowed to warm to −40° C. and stirred at −40° C. for 1 h. The mixture was quenched with 50 mL of saturated NH$_4$Cl aqueous solution, extracted with ethyl acetate (3×200 mL). The organic layer was dried and concentrated under reduced pressure. The residue was purified by flash chromatography on a silica gel column with PE/EA=10:1 to get tert-butyl-(3R,4S)-4-methyl-3-[-(4R)-2-oxo-4-phenyl-oxazolidine-3-carbonyl]hept-6-enoate (8 g, 27.2% yield) as white solid. $^1$H NMR (400 MHz, CDCl$_3$) δ 7.41-7.27 (m, 5H), 5.89-5.70 (m, 1H), 5.45-5.35 (m, 1H), 5.09-4.96 (m, 2H), 4.75-4.61 (m, 1H), 4.29-4.20 (m, 2H), 2.67 (dd, J=16.9, 11.7 Hz, 1H), 2.30 (dd, J=16.9, 3.4 Hz, 1H), 2.18 (dd, J=15.5, 8.6 Hz, 1H), 2.08-1.93 (m, 2H), 1.32-1.19 (m, 9H), 0.87 (dd, J=19.0, 6.6 Hz, 3H).

Step 2: (3R,4S)-4-methyl-3-((4R)-2-oxo-4-phenyloxazolidine-3-carbonyl)hept-6-enoic acid

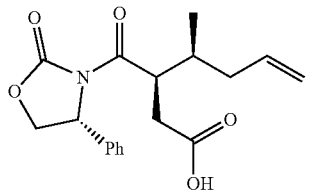 [SMILES: C=CC[C@H](C)[C@@H](CC(=O)O)C(=O)N1C(=O)OC[C@H]1c1ccccc1]

To a mixture of tert-butyl-(3R,4S)-4-methyl-3-[(4R)-2-oxo-4-phenyl-oxazolidine-3-carbonyl]hept-6-enoate (9.6 g, 24.7 mmol) in 50 mL of DCM was added trifluoroacetic acid (73 mL, 991 mmol). The mixture was stirred at r.t. for 12 h. LC-MS showed the reaction was complete. The mixture was concentrated under reduced pressure. To the residue was added water (60 mL). The mixture was adjusted to pH~7 with saturated NaHCO₃ aqueous solution (100 mL), and extracted with ethyl acetate (100 mL). The organic layer was dried and concentrated under reduced pressure. The residue was purified by flash chromatography on a silica gel column with PE/EA=2:1 to afford (3R,4S)-4-methyl-3-[(4R)-2-oxo-4-phenyl-oxazolidine-3-carbonyl]hept-6-enoic acid (6.6 g, 79% yield) as a pale yellow solid. LC-MS calc. for $C_{18}H_{22}N_{O5}$ [M+H]⁺: m/z=332.14; Found: 332.2. ¹H NMR (400 MHz, DMSO-d₆) δ 12.17 (s, 1H), 7.26-7.36 (m, 5H), 5.74-5.84 (m, 1H), 5.49 (dd, J=2.8, 8.4 Hz, 1H), 5.01-5.08 (m, 2H), 4.76 (t, J=8.4 Hz, 1H), 4.17 (dt, J=3.2, 11.6 Hz, 1H), 4.10 (dd, J=2.8, 8.8 Hz, 1H), 2.54 (dd, J=12.0, 17.2 Hz, 1H), 2.34 (dd, J=3.2, 17.2 Hz, 1H), 1.99-2.13 (m, 3H), 0.76 (d, J=6.4 Hz, 3H).

Step 3: (4R)-4-phenyl-3-[(2R,3S)-2-(2-hydroxyethyl)-3-methyl-hex-5-enoyl]oxazolidin-2-one

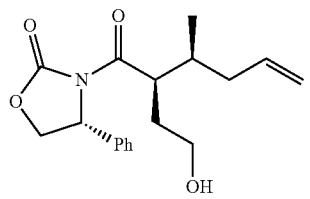 [SMILES: C=CC[C@H](C)[C@@H](CCO)C(=O)N1C(=O)OC[C@H]1c1ccccc1]

To a mixture of (3R,4S)-4-methyl-3-[(4R)-2-oxo-4-phenyl-oxazolidine-3-carbonyl]hept-6-enoic acid (3.0 g, 9.05 mmol) and triethylamine (3.7 g, 36 mmol) in 100 mL of dry THF at −40° C. was added isobutyl chloroformate (2.47 g, 18.11 mmol). The mixture was stirred at −40° C. for 1 h. Then sodium borohydride (1.37 g, 36.21 mmol) in 30 mL of water was added. The mixture was stirred at −40° C. for 2 h. The reaction mixture was treated with 3 N HCl (80 mL) and allowed to warm to r.t. The organic solvent was removed under reduced pressure, and the aqueous solution was extracted with DCM (100 mL). The organic layer was dried and concentrated to afford the crude product (4R)-4-phenyl-3-[(2R,3S)-2-(2-hydroxyethyl)-3-methyl-hex-5-enoyl]oxazolidin-2-one (5.6 g) which was directly used in next step reaction without further purification. LC-MS calc. for $C_{18}H_{24}NO_4$ [M+H]⁺: m/z=318.16; Found: 318.2.

Step 4: (4R)-4-phenyl-3-[(2R,3S)-2-(2-methoxyethyl)-3-methyl-hex-5-enoyl]oxazolidin-2-one

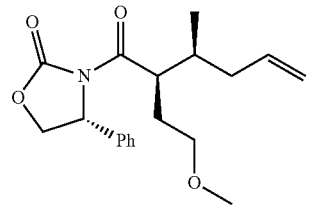 [SMILES: C=CC[C@H](C)[C@@H](CCOC)C(=O)N1C(=O)OC[C@H]1c1ccccc1]

To a mixture of (4R)-4-phenyl-3-[(2R,3S)-2-(2-hydroxyethyl)-3-methyl-hex-5-enoyl]oxazolidin-2-one (600 mg, 1.89 mmol) in 20 mL of dry DCM was added trimethyloxonium tetrafluoroborate (279 mg, 1.89 mmol) and proton sponge (1,8-bis(dimethylamino)naphthalene) (405 mg, 1.89 mmol). The mixture was stirred at r.t. for 2 d. The mixture was concentrated under reduced pressure and the residue was dissolved in ethyl acetate (50 mL). The mixture was washed with 3 M HCl (30 mL). The organic layer was dried over Na₂SO₄, filtered and concentrated under reduced pressure The residue was purified by flash chromatography on a silica gel column with PE/EA=10:1 to afford (4R)-4-phenyl-3-[(2R,3S)-2-(2-methoxyethyl)-3-methyl-hex-5-enoyl]oxazolidin-2-one (320 mg, 50% yield) as a colorless oil. LC-MS calc. for $C_{19}H_{26}NO_4$ [M+H]⁺: m/z=332.18; Found: 332.2.

Step 5: (2R,3S)-2-(2-methoxyethyl)-3-methylhex-5-enoic acid (HHC001-80-1)

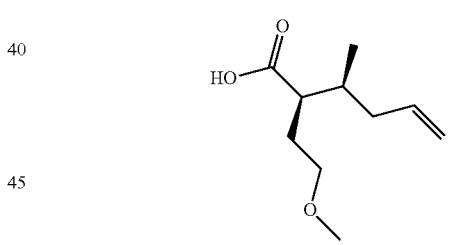

To a mixture of (4R)-4-phenyl-3-[(2R,3S)-2-(2-methoxyethyl)-3-methyl-hex-5-enoyl]oxazolidin-2-one (320 mg, 0.97 mmol) in 15 mL of THF and 3 mL of water at 0° C. was added hydrogen peroxide (30% in water) (0.39 mL, 3.8 mmol) and lithium hydroxide (46 mg, 1.9 mmol). The mixture was stirred at 0° C. for 1 h and then allowed to warm to r.t. and stirred at r.t. for 12 h. The organic solvent was removed and the aqueous solution was added 10 mL of water, adjusted to pH 3.0 with con. HCl, extracted with ethyl acetate (30 mL). The organic layer was dried and concentrated to get (2R,3S)-2-(2-methoxyethyl)-3-methyl-hex-5-enoic acid (90 mg, 47% yield) as a colorless oil. LC-MS calc. for $C_{10}H_{19}O_3$ [M+H]⁺: m/z=187.13; Found: 169.2 ([M−H₂O+H]⁺). ¹H NMR (400 MHz, CDCl₃) δ 0.94 (d, J=6.4 Hz, 3H), 1.71-1.79 (m, 1H), 1.85-1.92 (m, 1H), 1.93-2.01 (m, 2H), 2.13-2.21 (m, 1H), 2.44-2.49 (m, 1H), 3.33 (s, 3H), 3.37-3.47 (m, 2H), 5.02 (s, 1H), 5.05-5.06 (m, 1H), 5.71-5.82 (m, 1H).

Step 6: (3R,6R,7R,8E,11S,12R,22S)-6'-chloro-7-methoxy-12-(2-methoxyethyl)-11-methyl-15,15-dioxo-spiro[20-oxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2R,3S)-2-(2-methoxyethyl)-3-methyl-hex-5-enoic acid in Step 3. LC-MS calc. for $C_{35}H_{46}ClN_2O_6S$ [M+H]$^+$: m/z=657.28/659.28; Found: 657.1/658.8.

Example 90

(3R,6R,7R,8E,11S,12R,22S)-6'-Chloro-12-[2-(3,3-difluoroazetidin-1-yl)-2-oxo-ethyl]-7-methoxy-11-methyl-15,15-dioxo-spiro[20-oxa-15-thia-1,14-diazatetracyclo[14.7.2.03,6.019,24]pentacosa-8,16,18,24-tetraene-22,1'-tetralin]-13-one

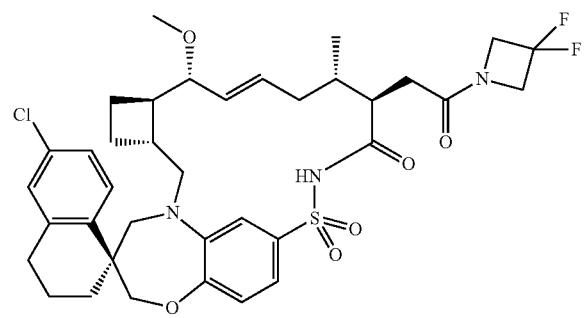 [SMILES: CO[C@@H]1/C=C/C[C@H](C)[C@@H](CC(=O)N2CC(F)(F)C2)C(=O)NS(=O)(=O)c2ccc3c(c2)N(C[C@@H]2CC[C@H]21)C[C@@]1(CCCc2cc(Cl)ccc21)CO3]

Step 1: (2R,3S)-2-(2-(tert-butoxy)-2-oxoethyl)-3-methylhex-5-enoic acid

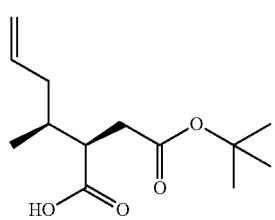 [SMILES: C=CC[C@H](C)[C@@H](CC(=O)OC(C)(C)C)C(=O)O]

This compound was prepared using procedures analogous to those described for Example 71 Step 3 using tert-butyl (3R,4S)-4-methyl-3-((R)-2-oxo-4-phenyloxazolidine-3-carbonyl)hept-6-enoate (Example 89 Step 1). $^1$H NMR (400 MHz, CDCl$_3$) δ 0.91 (d, J=6.4 Hz, 3H), 1.44 (s, 9H), 1.94-2.08 (m, 2H), 2.10-2.16 (m, 1H), 2.31 (dd, J=4.0 Hz, 16.8 Hz, 1H), 2.61 (m, J=11.2 Hz, 16.8 Hz, 1H), 2.88 (m, J=4.0 Hz, 11.2 Hz, 1H), 5.02-5.03 (m, 1H), 5.06 (m, J=1.2 Hz, 1H), 5.71-5.81 (m, 1H).

Step 2: tert-butyl 2-[(3R,6R,7R,8E,11S,12R,22S)-6'-chloro-7-methoxy-11-methyl-13,15,15-trioxo-spiro[20-oxa-15-thia-1,14 diazatetracyclo[14.7.2.03,6.019,24]pentacosa-8,16,18,24-tetraene-22,1'-tetralin]-12-yl]acetate

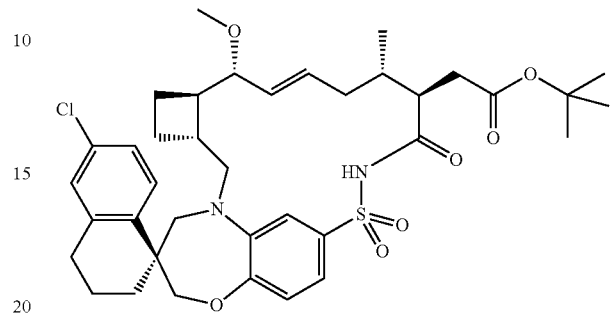

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2R,3S)-2-(2-(tert-butoxy)-2-oxoethyl)-3-methylhex-5-enoic acid in Step 3. LC-MS calc. for $C_{35}H_{50}ClN_2O_7S$ [M+H]$^+$: m/z=713.3/715.3; Found: 712.9/715.2.

Step 3: 2-[(3R,6R,7R,8E,11S,12R,22S)-6'-chloro-7-methoxy-11-methyl-13,15,15-trioxo-spiro[20-oxa-15-thia-1,14-diazatetracyclo[14.7.2.03,6.019,24]pentacosa-8,16,18,24-tetraene-22,1'-tetralin]-12-yl]acetic acid

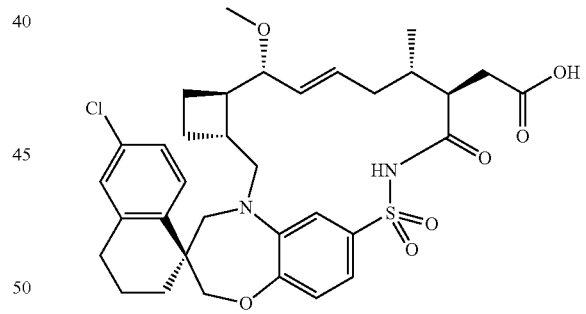

A solution of tert-butyl 2-[(3R,6R,7R,8E,11 S, 12R,22S)-6'-chloro-7-methoxy-11-methyl-13,15,15-trioxo-spiro[20-oxa-15-thia-1,14-diazatetracyclo[14.7.2.03,6.019,24]pentacosa-8,16,18,24-tetraene-22,1'-tetralin]-12-yl]acetate (25.0 mg, 0.04 mmol) in CH$_2$Cl$_2$ (1 mL) at 0° C. was treated with 2,2,2-trifluoroacetic acid (TFA) (0.5 mL) drop-wise. The reaction was stirred at r.t. overnight. The volatile components are removed under vacuum to afford the crude product 2-[(3R,6R,7R,8E,11S,12R,22S)-6'-chloro-7-methoxy-11-methyl-13,15,15-trioxo-spiro[20-oxa-15-thia-1,14-diazatetracyclo[14.7.2.03,6.019,24]pentacosa-8,16,18,24-tetraene-22,1'-tetralin]-12-yl]acetic acid (21 mg) which was directly used in next step without further purification. LC-MS: calc. for $C_{34}H_{42}ClN_2O_7S$ [M+H]$^+$: m/z=657.2/659.2; Found: 657.0/659.3.

Step 4: (3R,6R,7R,8E,11S,12R,22S)-6'-chloro-12-[2-(3,3-difluoroazetidin-1-yl)-2-oxo-ethyl]-7-methoxy-11-methyl-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one A mixture of 2-[(3R,6R,7R,8E,11S,12R,22S)-6'-chloro-7-methoxy-11-methyl-13,15,15-trioxo-spiro[20-oxa-15-thia-1,14-diazatetracyclo[14.7.2.0³,⁶.0¹⁹,²⁴]pentacosa-8,16,18,24-tetraene-22,1'-tetralin]-12-yl]acetic acid (20.0 mg, 0.03 mmol), 3,3-difluoroazetidine hydrochloride (7.94 mg, 0.06 mmol), and HATU (34.71 mg, 0.09 mmol) in DCM (1 mL) was stirred at 0° C. for 1 h., and then diisopropylethylamine (11.78 mg, 0.09 mmol) was added. The mixture was stirred at r.t. overnight. LC-MS analysis indicated complete conversion. The reaction was quenched with 0.5M HCl (1.0 mL) and volatile components were removed under reduced pressure. The residue was purified by prep-HPLC on a C18 column with ACN and water to afforded (3R,6R,7R,8E,11S,12R,22S)-6'-chloro-12-[2-(3,3-difluoroazetidin-1-yl)-2-oxo-ethyl]-7-methoxy-11-methyl-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one (2 mg, 9.0% yield). LC-MS calc. for $C_{37}H_{45}ClF_2N_3O_6S$ [M+H]⁺: m/z=732.2/734.2; Found: 732.0/734.3.

Example 91

2-[(3R,6R,7R,8E,11S,12R,22S)-6'-Chloro-7-methoxy-11-methyl-13,15,15-trioxo-spiro[20-oxa-15-thia-1,14-diazatetracyclo[14.7.2.0³,⁶.0¹⁹,²⁴]pentacosa-8,16,18,24-tetraene-22,1'-tetralin]-12-yl]-N,N-dimethyl-acetamide

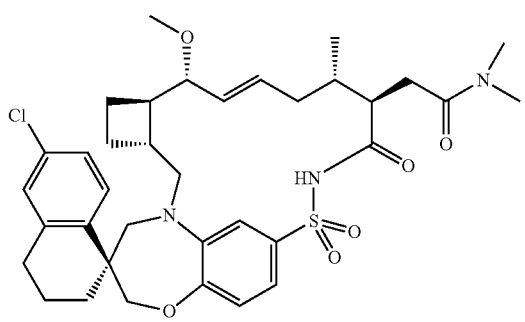 [SMILES: CO[C@@H]1/C=C/C[C@H](C)[C@@H](CC(=O)N(C)C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 149 Step 4 using dimethylamine HCl salt. LC-MS: calc. for $C_{36}H_{47}ClN_3O_6S$ [M+H]⁺= 684.2/686.2; Found: 684.0/686.3.

Example 92

(3R,6R,7R,8E,11S,12R,22S)-6'-Chloro-7-methoxy-11-methyl-12-(2-morpholino-2-oxo-ethyl)-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one

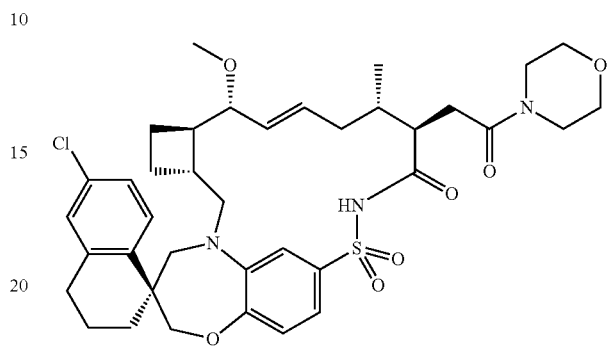

This compound was prepared using procedures analogous to those described for Example 149 Step 4 using morpholine. LC-MS: calc. for $C_{38}H_{49}ClN_3O_7S$ [M+H]⁺=726.3/728.3; Found: 726.7/728.1.

Example 93

(3R,6R,7R,8E,11S,12S,22S)-6'-chloro-7-methoxy-12-(2-methoxyethoxymethyl)-11-methyl-15,15-dioxo-spiro[20-oxa-15-thia-1,14-diazatetracyclo[14.7.2.0³,⁶.0¹⁹,²⁴]pentacosa-8,16,18,24-tetraene-22,1'-tetralin]-13-one

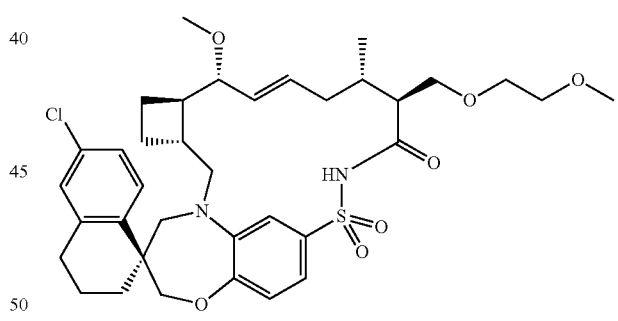

Step 1: (2S,3S)-2-(2-methoxyethoxymethyl)-3-methyl-hex-5-enoic acid

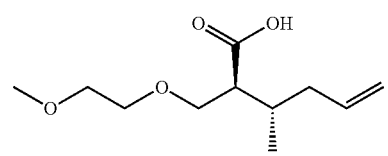

This compound was prepared using procedures analogous to those described for Example 88 Step 1-2 using (4R)-4-phenyl-3-[(3S)-3-methylhex-5-enoyl]oxazolidin-2-one (Example 86 Step 2) and 1-(chloromethoxy)-2-methoxy-ethane in Step 1. ¹H NMR (400 MHz, CDCl₃) δ 5.81-5.72 (m, 1H), 5.06-5.03 (m, 2H), 3.74 (t, J=9.2 Hz 1H), 3.67-3.60 (m, 3H), 3.56-3.52 (m, 2H), 3.38 (s, 3H), 2.67-2.65 (m, 1H), 2.21-2.19 (m, 1H), 2.03-1.96 (m, 2H), 0.96 (d, J=6.4 Hz, 3H).

Step 2: (3R,6R,7R,8E,11S,12S,22S)-6'-chloro-7-methoxy-12-(2-methoxyethoxymethyl)-11-methyl-15,15-dioxo-spiro[20-oxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2S,3S)-2-(2-methoxyethoxymethyl)-3-methyl-hex-5-enoic acid in Step 3. LC-MS calc. for C₃₆H₄₇ClN₂O₇S [M+H]⁺: m/z=687.28/689.28; Found:

Example 94

(3R,6R,7R,8E,11S,12S,22S)-6'-Chloro-12-(hydroxymethyl)-7-methoxy-11-methyl-15,15-dioxo-spiro[20-oxa-15-thia-1,14-diazatetracyclo[14.7.2.03,6.019,24]pentacosa-8,16,18,24-tetraene-22,1'-tetralin]-13-one

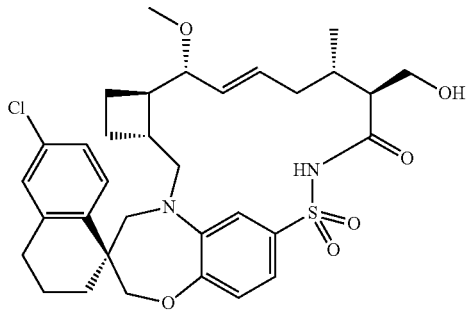 [SMILES: CO[C@@H]1/C=C/C[C@H](C)[C@@H](CO)C(=O)NS(=O)(=O)c2ccc3c(c2)N(C[C@@H]2CC[C@H]21)C[C@@]1(CCCc2cc(Cl)ccc21)CO3]

Step 1: (2S,3S)-3-methyl-2-((2-(trimethylsilyl)ethoxy)methyl)hex-5-enoic acid

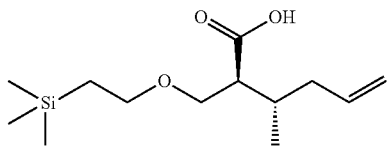 [SMILES: C=CC[C@H](C)[C@@H](COCC[Si](C)(C)C)C(=O)O]

This compound was prepared using procedures analogous to those described for Example 88 Step 1-2 using (4R)-4-phenyl-3-[(3S)-3-methylhex-5-enoyl]oxazolidin-2-one (Example 86 Step 2) and (2-(chloromethoxy)ethyl)trimethylsilane in Step 1. ¹H NMR (400 MHz, CDCl₃) δ 5.78-5.71 (m, 1H), 5.06-5.02 (m, 2H), 3.66-3.51 (m, 4H), 2.60-2.57 (m, 1H), 2.30-2.11 (m, 1H), 2.03-1.96 (m, 2H), 1.01-0.85 (m, 5H), 0.01 (s, 9H).

Step 2: (3R,6R,7R,8E,11S,12S,22S)-6'-chloro-7-methoxy-11-methyl-15,15-dioxo-12-(2-trimethylsilylethoxymethyl)spiro[20-oxa-15-thia-1,14-diazatetracyclo[14.7.2.03,6.019,24]pentacosa-8,16,18,24-tetraene-22,1'-tetralin]-13-one

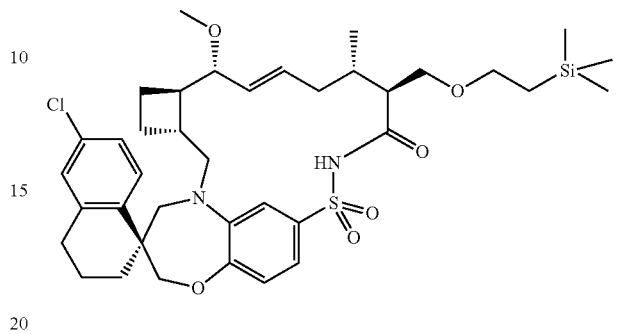

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2S,3S)-3-methyl-2-((2-(trimethylsilyl)ethoxy)methyl)hex-5-enoic acid in Step 3. LC-MS calc. for C₃₈H₅₄ClN₂O₆SiS [M+H]⁺: m/z=729.31; Found: 729.7.

Step 3: (3R,6R,7R,8E,11S,12S,22S)-6'-chloro-12-(hydroxymethyl)-7-methoxy-11-methyl-15,15-dioxo-spiro[20-oxa-15-thia-1,14-diazatetracyclo[14.7.2.03,6.019,24]pentacosa-8,16,18,24-tetraene-22,1'-tetralin]-13-one To a solution of (3R,6R,7R,8E,11S,12S,22S)-6'-chloro-7-methoxy-11-methyl-15,15-dioxo-12-(2-trimethylsilylethoxymethyl)spiro[20-oxa-15-thia-1,14-diazatetracyclo[14.7.2.03,6.019,24]pentacosa-8,16,18,24-tetraene-22,1'-tetralin]-13-one (10 mg) in DCM (1 mL) was added 50% TFA (1 mL). The resulting mixture was stirred at r.t. for 2 h. The mixture was concentrated under reduced pressure. The residue was purified on C18 column with MeCN/H₂O (30-100%) to afford the desired product (5 mg). LC-MS calc. for C₃₃H₄₂ClN₂O₆S [M+H]⁺: m/z=629.24; Found: 629.0.

Example 95

(3R,6R,7R,8E,12S,22S)-6'-Chloro-12-(hydroxymethyl)-7-methoxy-15,15-dioxo-spiro[20-oxa-15-thia-1,14-diazatetracyclo[14.7.2.03,6.019,24]pentacosa-8,16,18,24-tetraene-22,1'-tetralin]-13-one

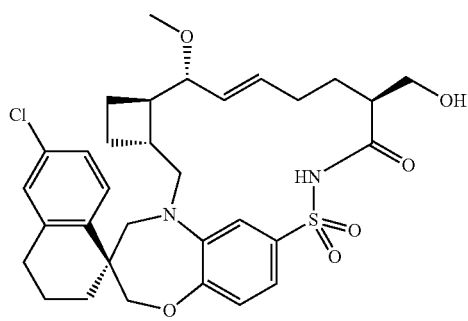 [SMILES: CO[C@@H]1/C=C/CC[C@@H](CO)C(=O)NS(=O)(=O)c2ccc3c(c2)N(C[C@@H]2CC[C@H]21)C[C@@]1(CCCc2cc(Cl)ccc21)CO3]

Step 1: (4R)-3-hex-5-enoyl-4-phenyl-oxazolidin-2-one

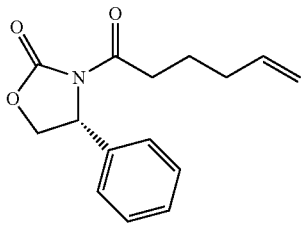 [SMILES: C=CCCCC(=O)N1C(=O)OC[C@H]1c1ccccc1]

To a solution of (R)-(−)-phenyl-2-oxazolidinone (15.0 g, 93 mmol) in THF (500 mL) was added n-BuLi (80.9 mL, 202 mmol) slowly at −78° C. The reaction solution was stirred at −78° C. for 20 min. Then hex-5-enoyl chloride (26.8 g, 202 mmol) was added slowly. The reaction was stirred at −78° C. for 0.5 h and allowed to warm to ambient temperature overnight. The reaction was quenched with saturated NH$_4$Cl solution (100 mL), and extracted with EA (100 mL×2). The organic layer was dried over Na$_2$SO$_4$, filtered and concentrated under reduced pressure to give crude mixture which was purified by flash chromatography on a silica gel column with PE/EA (10/1) to give (4R)-3-hex-5-enoyl-4-phenyl-oxazolidin-2-one (15 g, 31% yield). $^1$H NMR: (400 MHz, CDCl$_3$) 7.29-7.43 (m, 5H), 5.73-5.83 (m, 1H), 5.43-5.46 (m, 1H), 4.96-5.04 (m, 2H), 4.71 (t, J=8.8 Hz, 1H), 4.28-4.31 (m, 1H), 2.95-2.99 (m, 2H), 2.06-2.12 (m, 2H), 1.70-1.77 (m, 2H).

Step 2: (S)-2-((2-(trimethylsilyl)ethoxy)methyl)hex-5-enoic acid

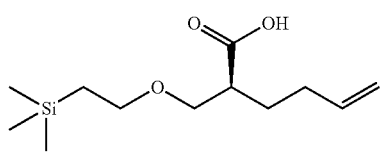 [SMILES: C=CCC[C@@H](COCC[Si](C)(C)C)C(=O)O]

This compound was prepared using procedures analogous to those described for Example 88 Step 1-2 using (4R)-3-hex-5-enoyl-4-phenyl-oxazolidin-2-one and (2-(chloromethoxy)ethyl)trimethylsilane in Step 1. $^1$H NMR (400 MHz, CDCl$_3$) δ 5.78 (ddt, J=16.9, 10.2, 6.6 Hz, 1H), 5.09-4.88 (m, 2H), 3.58-3.39 (m, 4H), 2.67 (ddd, J=15.5, 7.8, 5.6 Hz, 1H), 2.23-2.07 (m, 2H), 1.81 (ddd, J=21.5, 11.5, 5.8 Hz, 1H), 1.68-1.52 (m, 1H), 0.99-0.81 (m, 2H), 0.04-−0.01 (m, 9H).

Step 3: (3R,6R,7R,8E,12S,22S)-6'-chloro-12-(hydroxymethyl)-7-methoxy-15,15-dioxo-spiro[20-oxa-15-thia-1,14-diazatetracyclo[14.7.2.0$^{3,6}$.0$^{19,24}$]pentacosa-8,16,18,24-tetraene-22,1'-tetralin]-13-one This compound was prepared using procedures analogous to those described for Example 94 Step 2-3 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (S)-2-((2-(trimethylsilyl)ethoxy)methyl)hex-5-enoic acid. LC-MS calc. for C$_{32}$H$_{40}$ClN$_2$O$_6$S [M+H]$^+$: m/z=615.22; Found: 615.0.

Example 96

(3R,6R,7R,8E,12S,22S)-6'-Chloro-12-(methoxymethyl)-7-methoxy-15,15-dioxo-spiro[20-oxa-15-thia-1,14-diazatetracyclo[14.7.2.0$^{3,6}$.0$^{19,24}$]pentacosa-8,16,18,24-tetraene-22,1'-tetralin]-13-one

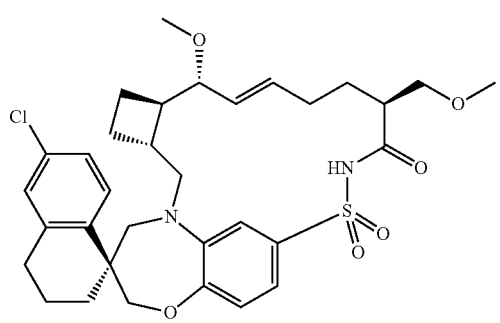 [SMILES: COC[C@@H]1CC/C=C/[C@@H](OC)[C@@H]2CC[C@H]2CN2C[C@@]3(CCCc4cc(Cl)ccc43)COc3ccc(cc32)S(=O)(=O)NC1=O]

Step 1: (S)-2-(methoxymethyl)hex-5-enoic acid

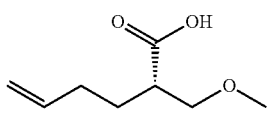

This compound was prepared using procedures analogous to those described for Example 88 Step 1-2 using (4R)-3-hex-5-enoyl-4-phenyl-oxazolidin-2-one and bromo(methoxy)methane in Step 1. $^1$H NMR (400 MHz, CDCl$_3$) δ 5.84-5.74 (m, 1H), 5.08-4.98 (m, 2H), 3.59 (dd, J=9.2, 8.0 Hz, 1H), 3.52 (dd, J=9.2, 5.2 Hz, 1H), 3.37 (s, 3H), 2.74-2.67 (m, 2H), 2.17-2.10 (m, 2H), 1.85-1.74 (m, 1H), 1.66-1.57 (m, 1H).

Step 2: (3R,6R,7R,8E,12S,22S)-6'-chloro-12-(methoxymethyl)-7-methoxy-15,15-dioxo-spiro[20-oxa-15-thia-1,14-diazatetracyclo[14.7.2.0$^{3,6}$.0$^{19,24}$]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (S)-2-(methoxymethyl)hex-5-enoic acid in Step 3. LC-MS calc. for C$_{33}$H$_{42}$ClN$_2$O$_6$S [M+H]$^+$: m/z=629.24/631.24; Found:

Example 97

(3R,6R,7R,8E,12S,22S)-6'-Chloro-12-((2-methoxy-ethoxy)methyl)-7-methoxy-15,15-dioxo-spiro[20-oxa-15-thia-1,14-diazatetracyclo[14.7.2.03,6.019,24]pentacosa-8,16,18,24-tetraene-22,1'-tetralin]-13-one

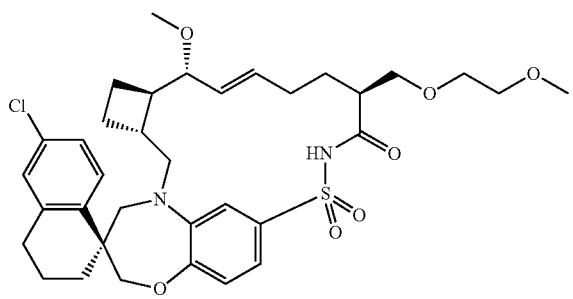 [SMILES: COCCOC[C@@H]1CC/C=C/[C@@H](OC)[C@@H]2CC[C@H]2CN2C[C@@]3(CCCc4cc(Cl)ccc43)COc3ccc(cc32)S(=O)(=O)NC1=O]

Step 1: (S)-2-((2-methoxyethoxy)methyl)hex-5-enoic acid

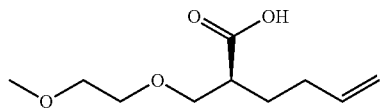

This compound was prepared using procedures analogous to those described for Example 88 Step 1-2 using (4R)-3-hex-5-enoyl-4-phenyl-oxazolidin-2-one and 1-(chloromethoxy)-2-methoxyethane in Step 1. $^1$H NMR (400 MHz, CDCl$_3$) δ 5.85-5.75 (m, 1H), 5.09-4.98 (m, 2H), 3.72-3.69 (m, 1H), 3.67-3.60 (m, 3H), 3.56-3.52 (m, 2H), 3.36 (s, 3H), 2.78-2.71 (m, 1H), 2.19-2.09 (m, 2H), 1.81-1.71 (m, 1H), 1.69-1.59 (m, 1H).

Step 2: (3R,6R,7R,8E,12S,22S)-6'-chloro-12-((2-methoxyethoxy)methyl)-7-methoxy-15,15-dioxo-spiro[20-oxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (S)-2-((2-methoxyethoxy)methyl)hex-5-enoic acid in Step 3. LC-MS calc. for C$_{35}$H$_{46}$ClN$_2$O$_7$S [M+H]$^+$: m/z=673.26/675.26; Found:

Example 98

(3R,6R,24S)-6'-Chloro-8,8,17,17-tetraoxo-spiro[22-oxa-8,17-dithia-1,16-diazapentacyclo[16.7.2.19,13.03,6.021,26]octacosa-9(28),10,12,18(27),19,21(26)-hexaene-24,1'-tetralin]-15-one

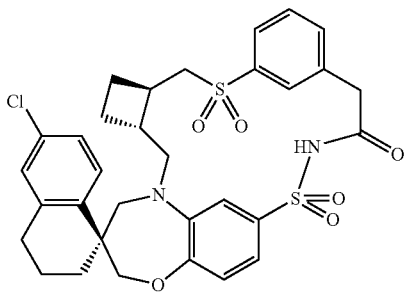 [SMILES: O=C1Cc2cccc(c2)S(=O)(=O)C[C@@H]2CC[C@H]2CN2C[C@@]3(CCCc4cc(Cl)ccc43)COc3ccc(cc32)S(=O)(=O)N1]

To a solution of (3R,6R,24S)-6'-chloro-17,17-dioxo-spiro[22-oxa-8,17-dithia-1,16-diazapentacyclo[16.7.2.19,13.03,6.021,26]octacosa-9(28), 10,12,18(27), 19,21(26)-hexaene-24,1'-tetralin]-15-one (3.5 mg, Example 25) in DCM (0.50 mL) was added m-CPBA (77 wt %) (2.0 mg, 0.01 mmol) under N$_2$, and stirred at r.t. for 18 h. The reaction mixture was concentrated under reduced pressure. The residue (white solid) was purified by FCC (15.5 g C18, 20→100% MeCN in H$_2$O, wet-loaded in DMSO). Fractions containing pure product were combined and concentrated under reduced pressure to afford (3R,6R,24S)-6'-chloro-8,8,17,17-tetraoxo-spiro[22-oxa-8,17-dithia-1,16-diazapentacyclo[16.7.2.19,13.03,6.021,26]octacosa-9(28),10,12,18(27),19, 21(26)-hexaene-24,1'-tetralin]-15-one (1.66 mg) as a white solid. LCMS m/z calc. for C$_{32}$H$_{34}$ClN$_2$O$_6$S$_2$ [M+H]$^+$: m/z=641.15/643.15; Found: 641.1/643.1.

Example 99

(3R,6R,10E,23S)-6'-Chloro-16,16-dioxo-spiro[8,21-dioxa-16-thia-1,15-diazatetracyclo[15.7.2.03,6.020,25]hexacosa-10,17(26),18,20(25)-tetraene-23,1'-tetralin]-14-one

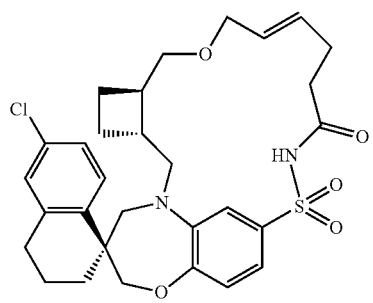 [SMILES: O=C1CC/C=C/COC[C@@H]2CC[C@H]2CN2C[C@@]3(CCCc4cc(Cl)ccc43)COc3ccc(cc32)S(=O)(=O)N1]

347

Step 1: (3S)-6'-chloro-N,N-bis[(4-methoxyphenyl)
methyl]-5-[[(1R,2R)-2-(allyloxymethyl)cyclobutyl]
methyl]spiro[2,4-dihydro-1,5-benzoxazepine-3,1'-
tetralin]-7-sulfonamide

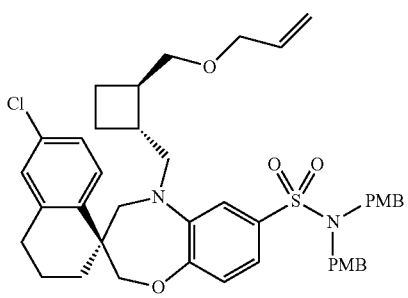

A solution of (3S)-6'-chloro-N,N-bis[(4-methoxyphenyl)
methyl]-5-[[(1R,2R)-2-(hydroxymethyl)cyclobutyl]methyl]
spiro[2,4-dihydro-1,5-benzoxazepine-3,1'-tetralin]-7-sulfonamide (56.8 mg, 0.08 mmol, Example 18 Step 2) in DMF (0.5 mL) was charged with sodium hydride (60% dispersion in mineral oil, 14 mg, 0.36 mmol) (caution: evolves $H_2$) at r.t. and was purged with $N_2$. After 1 min., the mixture was charged with allyl bromide (27 uL, 0.32 mmol) and stirred at r.t. for 22 h. The reaction mixture was quenched with water (1 mL) (caution: evolves $H_2$), diluted with sat. $NH_4Cl$ (20 mL) and extracted with EtOAc (30 mL). The organic layer was separated, washed with water (2×20 mL) and brine (2×20 mL). The organic layer was dried over $Na_2SO_4$, filtered, concentrated under reduced pressure to yield (3S)-6'-chloro-N,N-bis[(4-methoxyphenyl)methyl]-5-[[(1R,2R)-2-(allyloxymethyl)cyclobutyl]methyl]spiro[2,4-dihydro-1,5-benzoxazepine-3,1'-tetralin]-7-sulfonamide (67 mg) without further purification.

Step 2: (3S)-6'-chloro-5-[[(1R,2R)-2-(allyloxymethyl)cyclobutyl]methyl]spiro[2,4-dihydro-1,5-benzoxazepine-3,1'-tetralin]-7-sulfonamide

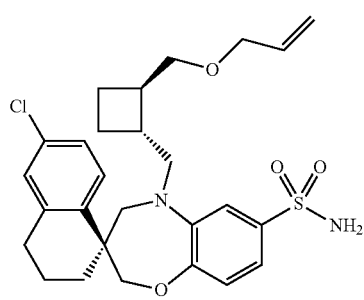 [SMILES: C=CCOC[C@@H]1CC[C@H]1CN1C[C@@]2(CCCc3cc(Cl)ccc32)COc2ccc(S(N)(=O)=O)cc21]

The crude (3S)-6'-chloro-N,N-bis[(4-methoxyphenyl)methyl]-5-[[(1R,2R)-2-(allyloxymethyl)cyclobutyl]methyl]spiro[2,4-dihydro-1,5-benzoxazepine-3,1'-tetralin]-7-sulfonamide (67 mg) was dissolved in DCM (800 μL). The flask was purged with $N_2$, then charged with TFA (800 μL), and stirred at r.t. for 22 h. The reaction mixture was co-evaporated with DCM twice under reduced pressure, and diluted with EtOAc (30 mL), washed with sat. $NaHCO_3$ (20 mL), water (20 mL), and brine (20 mL). The organic layer was dried over $Na_2SO_4$, filtered, concentrated under reduced pressure to yield (3S)-6'-chloro-5-[[(1R,2R)-2-(allyloxymethyl)cyclobutyl]methyl]spiro[2,4-dihydro-1,5-benzoxazepine-3,1'-tetralin]-7-sulfonamide (62.1 mg) as a yellow/white solid. LCMS m/z calc. for $C_{27}H_{34}ClN_2O_4S$ $[M+H]^+$: m/z=517.19/519.19; Found: 517.1/519.2.

Step 3: N-[(3S)-6'-chloro-5-[[(1R,2R)-2-(allyloxymethyl)cyclobutyl]methyl]spiro[2,4-dihydro-1,5-benzoxazepine-3,1'-tetralin]-7-yl]sulfonylpent-4-enamide

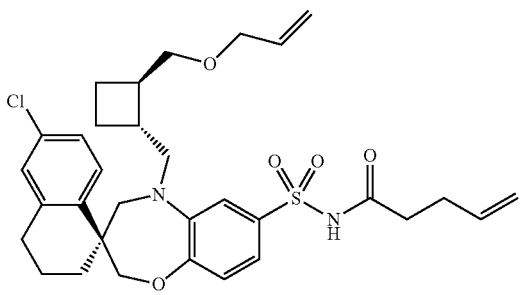 [SMILES: C=CCCC(=O)NS(=O)(=O)c1ccc2c(c1)N(C[C@@H]1CC[C@H]1COCC=C)C[C@@]1(CCCc3cc(Cl)ccc31)CO2]

A mixture of (3S)-6'-chloro-5-[[(1R,2R)-2-(allyloxymethyl)cyclobutyl]methyl]spiro[2,4-dihydro-1,5-benzoxazepine-3,1'-tetralin]-7-sulfonamide (40.95 mg, 0.08 mmol), 4-(dimethylamino)pyridine (DMAP) (48.38 mg, 0.40 mmol), and 1-ethyl-3-(3-dimethylaminopropyl)carbodiimide hydrochloride (EDCI) (53.14 mg, 0.28 mmol) under $N_2$ was dissolved in DCM (1 mL). To the solution was added 4-pentenoic acid (24 uL, 0.24 mmol). The mixture was stirred at r.t. for 2.5 h. The reaction mixture was diluted with EtOAc (30 mL), washed twice with brine (20 mL) and 0.1 N HCl (5 mL), and washed with brine (20 mL). The organic layer was dried over $Na_2SO_4$, filtered, and concentrated under reduced pressure to yield N-[(3S)-6'-chloro-5-[[(1R,2R)-2-(allyloxymethyl)cyclobutyl]methyl]spiro[2,4-dihydro-1,5-benzoxazepine-3,1'-tetralin]-7-yl]sulfonylpent-4-enamide (36 mg, 76% yield) as a clear yellow glass (36 mg). $R_f$=0.44 (2:1 hexanes:EtOAc); LCMS m/z calc. for $C_{32}H_{40}ClN_2O_5S$ $[M+H]^+$: m/z=599.23/601.23; Found: 599.3/601.2.

Step 4: (3R,6R,10E,23S)-6'-chloro-16,16-dioxospiro[8,21-dioxa-16-thia-1,15-diazatetracyclo[15.7.2.03,6.020,25]hexacosa-10,17(26),18,20(25)-tetraene-23,1'-tetralin]-14-one A solution of N-[(3S)-6'-chloro-5-[[(1R,2R)-2-(allyloxymethyl)cyclobutyl]methyl]spiro[2,4-dihydro-1,5-benzoxazepine-3,1'-tetralin]-7-yl]sulfonylpent-4-enamide (28.0 mg, 0.05 mmol) in DCM (2 mL) was purged with $N_2$ and was charged with a solution of (1,3-dimesitylimidazolidin-2-ylidene)(2-isopropoxybenzylidene)ruthenium(VI) chloride (Hoveyda-Grubbs II) (2.9 mg) in DCM (1 mL). The reaction mixture was stirred at r.t. for 1 d. The reaction mixture was charged with 3 drops DMSO, concentrated under reduced pressure, and purified by FCC (15.5 g C18, 40→100% MeCN in $H_2O$, wet-loaded in DMSO). Fractions containing pure product were combined and concentrated under reduced pressure and heat (~50° C.) to yield the desired (3R,6R,10E,23S)-6'-chloro-16,16-dioxo-spiro[8,21-dioxa-16-thia-1,15-diazatetracyclo[15.7.2.03,6.020,25]hexacosa-10,17(26),18,20(25)-tetraene-23,1'-tetralin]-14-one (14.4 mg, 51% yield) as a white solid. LCMS m/z calc.

for $C_{30}H_{35}ClN_2O_5S$ [M+H]$^+$: m/z=571.20/573.20; Found: 571.1/573.0; $^1$H NMR (500 MHz, MeCN-d$_3$) δ 9.31 (s, 1H), 7.66 (d, J=8.4 Hz, 1H), 7.36 (dd, J=2.2, 8.4 Hz, 1H), 7.20 (d, J=2.2 Hz, 1H), 7.19-7.13 (m, 2H), 6.98 (d, J=8.4 Hz, 1H), 5.48-5.38 (m, 1H), 4.95 (dt, J=5.5, 15.8 Hz, 1H), 4.35 (d, J=11.9 Hz, 1H), 4.02 (d, J=11.9 Hz, 1H), 3.64 (dd, J=5.9, 13.0 Hz, 1H), 3.59 (dd, J=4.6, 14.4 Hz, 1H), 3.54 (dt, J=1.5, 5.0, 12.7 Hz, 1H), 3.50 (d, J=14.6 Hz, 1H), 3.35 (d, J=14.4 Hz, 1H), 3.29 (dd, J=6.3, 9.8 Hz, 1H), 3.19 (dd, J=4.1, 9.8 Hz, 1H), 3.08 (dd, J=10.5, 14.5 Hz, 1H), 2.85 (td, J=4.3, 9.4 Hz, 1H), 2.77 (q, J=6.6, 7.8 Hz, 2H), 2.46-2.40 (m, 1H), 2.40-2.34 (m, 1H), 2.27-2.18 (m, 3H), 2.08-2.04 (m, 1H), 2.01-1.96 (m, 1H), 1.88-1.82 (m, 3H), 1.71-1.52 (m, 3H).

Example 100

(3R,6R,7S,8E,15S,24S)-6'-Chloro-7-methoxy-17,17-dioxo-spiro[22-oxa-17-thia-1,11-diazapentacyclo[16.7.2.0³,⁶.0¹¹,¹⁵.0²¹,²⁶]heptacosa-8,18,20,26-tetraene-24,1'-tetralin]-16-one

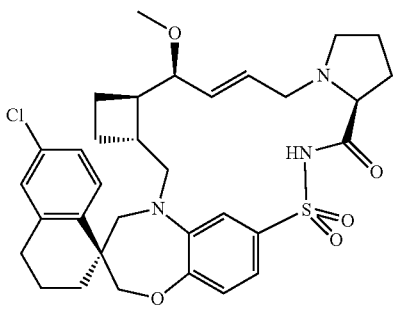 [SMILES: CO[C@H]1/C=C/CN2CCC[C@H]2C(=O)NS(=O)(=O)c2ccc3c(c2)N(C[C@@H]2CC[C@H]21)C[C@@]1(CCCc2cc(Cl)ccc21)CO3]

Step 1: Methyl allyl-L-prolinate

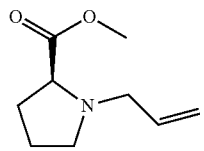

To a solution of L-proline methyl ester hydrochloride (6.64 g, 40.0 mmol) in DMF (80 mL) was added Et$_3$N (223 mL, 160 mmol) and Allyl bromide (9.7 g, 80 mmol) at 0° C. The mixture was stirred at ambient temperature for 12 h. The reaction mixture was poured into water, and extracted with ethyl acetate (3×30 mL). The combined organic layers were washed with brine, dried over anhydrous Na$_2$SO$_4$, and evaporated under reduced pressure. The residue was purified by flash chromatography on a silica gel column (EtOAc/hexane=1:3) to give methyl (2S)-1-allylpyrrolidine-2-carboxylate (5.4 g, 79% yield) as a colorless liquid. $^1$H NMR (400 MHz, CDCl$_3$) δ 6.04-5.94 (m, 1H), 5.20 (dd, J=16.8, 1.6 Hz, 1H), 5.16 (d, J=10.0 Hz, 1H), 3.71 (s, 3H), 3.33-3.28 (m, 1H), 3.16-3.11 (m, 3H), 2.39-2.37 (m, 1H), 2.17-2.04 (m, 1H), 1.95-1.90 (m, 2H), 1.82-1.79 (m, 1H).

Step 2: (2S)-1-allylpyrrolidine-2-carboxylic acid HCl salt

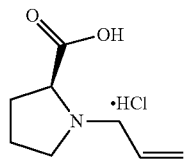

To a solution of methyl (2S)-1-allylpyrrolidine-2-carboxylate (2.0 g, 11 mmol) in THF (10 mL) and water (5 mL) was added NaOH (945 mg, 23 mmol). After stirring for 18 h at rt., the reaction mixture was added water (10 mL) and washed with ethyl acetate (2×20 mL). The aqueous layer was acidified with 1 N HCl (10 mL) and washed with ethyl acetate (10 mL). The aqueous layer was concentrated under reduced pressure. The residue was dissolved in DCM/MeOH (1:1, 20 mL). The salt was removed by filtration and the filtrate was evaporated under reduced pressure to afford (2S)-1-allylpyrrolidine-2-carboxylic acid HCl salt (1.9 g, 84% yield) as a white solid. $[α]_D^{20}$=−74.0 (c=1.0, MeOH). $^1$H NMR (400 MHz, MeOH-d$_4$) δ 5.98-5.94 (m, 1H), 5.60 (dd, J=17.2, 1.2 Hz, 1H), 5.51 (d, J=10.0 Hz, 1H), 4.09-4.05 (m, 1H), 3.95-3.90 (m, 1H), 3.86-3.81 (m, 1H), 3.74-3.68 (m, 1H), 3.23-3.18 (m, 1H), 2.54-2.48 (m, 1H), 2.20-2.11 (m, 2H), 2.03-1.96 (m, 1H).

Step 3: (3R,6R,7S,8E,15S,24S)-6'-Chloro-7-methoxy-17,17-dioxo-spiro[22-oxa-17-thia-1,11-diazapentacyclo[16.7.2.0³,⁶.0¹¹,¹⁵.0²¹,²⁶]heptacosa-8,18,20,26-tetraene-24,1'-tetralin]-16-one This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and allylpyrrolidine-2-carboxylic acid in Step 3. LC-MS calc. for $C_{33}H_{41}ClN_3O_5S$ [M+H]$^+$: m/z=626.24/628.24; Found: 626.0/628.0. $^1$H NMR (600 MHz, DMSO-d$_6$) δ 8.85 (s, 1H), 7.61 (d, J=8.5 Hz, 1H), 7.27 (d, J=2.0 Hz, 1H), 7.24 (dd, J=8.5, 2.4 Hz, 1H), 7.19 (d, J=2.4 Hz, 1H), 7.12 (dd, J=8.2, 1.9 Hz, 1H), 6.86 (d, J=8.2 Hz, 1H), 5.71 (dd, J=15.4, 6.5 Hz, 1H), 5.14-5.00 (m, 1H), 4.02 (d, J=12.0 Hz, 1H), 3.97 (d, J=12.1 Hz, 1H), 3.77 (d, J=8.7 Hz, 2H), 3.59 (d, J=18.3 Hz, 2H), 3.54 (d, J=14.2 Hz, 1H), 3.39 (dd, J=14.4, 5.4 Hz, 1H), 3.26 (d, J=14.4 Hz, 2H), 3.03 (s, 3H), 2.86-2.78 (m, 1H), 2.77-2.70 (m, 2H), 2.45-2.38 (m, 1H), 2.34-2.30 (m, 1H), 2.08-1.93 (m, 5H), 1.88-1.80 (m, 3H), 1.79-1.71 (m, 2H), 1.63-1.44 (m, 3H).

Example 101

(3R,6R,11R,24S)-6'-Chloro-10-methyl-17,17-dioxo-spiro[8,22-dioxa-17-thia-1,10,14,16-tetrazapentacyclo[16.7.2.1¹¹,¹⁴.0³,⁶.0²¹,²⁶]octacosa-18(27),19,21(26)-triene-24,1'-tetralin]-9,15-dione

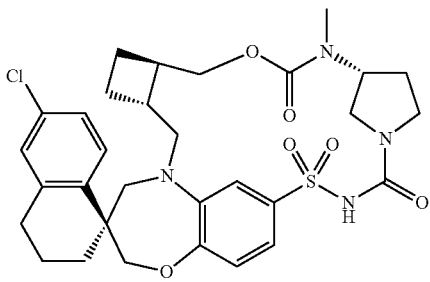 [SMILES: CN1C(=O)OC[C@@H]2CC[C@H]2CN2C[C@@]3(CCCc4cc(Cl)ccc43)COc3ccc(cc32)S(=O)(=O)NC(=O)N2CC[C@@H]1C2]

Step 1: [(1R, 2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl] methyl carbonochloridate

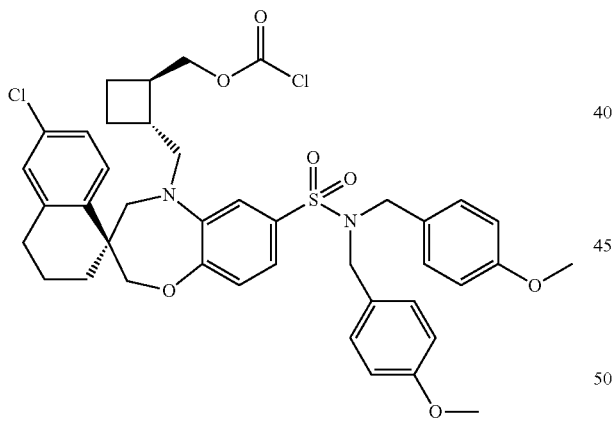

To a solution of (3S)-6'-chloro-N,N-bis[(4-methoxyphenyl)methyl]-5-[[(1R,2R)-2-(hydroxymethyl)cyclobutyl]methyl]spiro[2,4-dihydro-1,5-benzoxazepine-3,1'-tetralin]-7-sulfonamide (300.0 mg, 0.42 mmol, Intermediate 3 Step 2) in DCM (5 mL) was added triphosgene (62 mg, 0.21 mmol) and pyridine (0.03 mL, 0.42 mmol) at r.t. The reaction was stirred for 1 h. Water was added and extracted with DCM. The combined organic layers were dried over Na₂SO₄, filtered and concentrated under reduced pressure. The residue was used directly without further purification.

Step 2: tert-butyl (3R)-3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxycarbonylamino]pyrrolidine-1-carboxylate

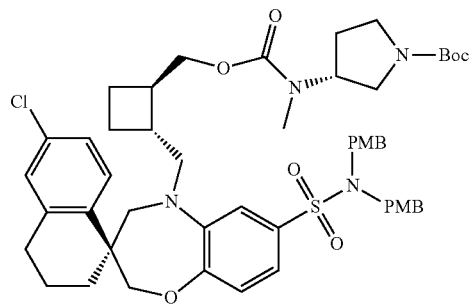

To a solution of [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methyl carbonochloridate (161 mg, 0.21 mmol) in MeCN (2 mL) was added potassium carbonate (285 mg, 2.07 mmol) and tert-butyl (3R)-3-(methylamino)pyrrolidine-1-carboxylate (124 mg, 0.62 mmol). The reaction mixture was stirred at r.t. for 2 d. After the reaction was completed, Water was added and extracted with EtOAc. The combined organic layers were dried over Na₂SO₄, filtered and concentrated under reduced pressure. The residue was purified by flash chromatography on a silica gel column with EtOAc in Hexane (0-50%) to afford tert-butyl (3R)-3-[[(1R,2R)-2-[[rac-(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxycarbonylamino]pyrrolidine-1-carboxylate (105 mg, 54% yield)

Step 3: [(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl N-methyl-N-[(3R)-pyrrolidin-3-yl]carbamate

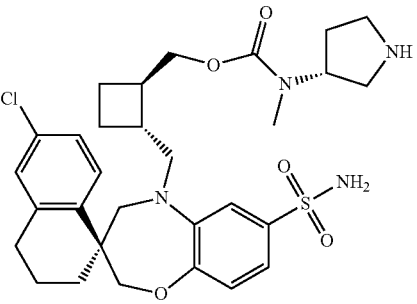 [SMILES: CN(C(=O)OC[C@@H]1CC[C@H]1CN1C[C@@]2(CCCc3cc(Cl)ccc32)COc2ccc(S(N)(=O)=O)cc21)[C@@H]1CCNC1]

To a solution of tert-butyl (3R)-3-[methyl-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxycarbonyl]amino]pyrrolidine-1-carboxylate (105.0 mg, 0.11 mmol) in DCM (0.50 mL) was added 2,2,2-trifluoroacetic acid (1.0 mL, 13.07 mmol). The reaction mixture was stirred at r.t. overnight. The mixture was neutralized by sat. NaHCO₃ aq. and extracted with DCM. The combined organic layers were dried over Na$_2$SO$_4$, filtered and evaporated under reduced pressure. The residue was purified by prep-HPLC with MeCN/H$_2$O to afford [(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl N-methyl-N-[(3R)-pyrrolidin-3-yl]carbamate (47.5 mg, 70.78% yield).

Step 4: [(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl N-methyl-N-[(3R)-1-(pyrrole-1-carbonyl)pyrrolidin-3-yl]carbamate

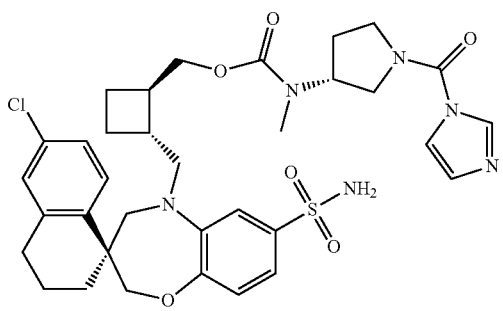 [SMILES: CN(C(=O)OC[C@@H]1CC[C@H]1CN1C[C@@]2(CCCc3cc(Cl)ccc32)COc2ccc(S(N)(=O)=O)cc21)[C@@H]1CCN(C(=O)n2ccnc2)C1]

To a solution of [(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl N-methyl-N-[(3R)-pyrrolidin-3-yl]carbamate (47.4 mg, 0.08 mmol) in THF (0.50 mL) was added 1,1'-carbonyldiimidazole (14.0 mg, 0.09 mmol). The reaction was heated to 55° C. for 30 min. The resulting mixture was quenched with water and extracted with EtOAc. The combined organic layers were dried over Na$_2$SO$_4$, filtered and evaporated under reduced pressure to afford the crude product which was used directly in next step without further purification.

Step 5: (3R,6R,11R,24S)-6'-chloro-10-methyl-17,17-dioxo-spiro[8,22-dioxa-17-thia-1,10,14,16-tetrazapentacyclo[16.7.2.111,14.03,6.021,26]octacosa-18(27),19,21(26)-triene-24,1'-tetralin]-9,15-dione To a solution of [(1R,2R)-2-[[(3S)-6'-chloro-7-sulfamoyl-spiro[2,4-dihydro-1,5-benzoxazepine-3,1'-tetralin]-5-yl]methyl]cyclobutyl]methyl N-methyl-N-[(3R)-1-(pyrrole-1-carbonyl)pyrrolidin-3-yl]carbamate (52.2 mg, 0.07 mmol) in MeCN (0.50 mL) was added 1,8-diazabicyclo[5.4.0]undec-7-ene (DBU) (34.24 mg, 0.22 mmol). The reaction was heated to 85° C. overnight. The reaction was quenched with water (2 mL) and the mixture was extracted with DCM (2×2 mL). The combined organic layers were dried over Na$_2$SO$_4$, filtered and evaporated under reduced pressure. The residue was purified by prep-HPLC on C18 column (30×250 mm, 10 µm) using MeCN/H$_2$O (20% to 100%) to afford (3R,6R,11R,24S)-6'-chloro-10-methyl-17,17-dioxo-spiro[8,22-dioxa-17-thia-1,10,14,16-tetrazapentacyclo[16.7.2.111,14.03,6.021,26]octacosa-18(27),19,21(26)-triene-24,1'-tetralin]-9,15-dione (7 mg, 14% yield). LC-MS: calc. for C$_{31}$H$_{38}$ClN$_4$O$_6$S [M+H]$^+$: m/z=629.21/631.21; Found: 628.9/631.1. $^1$H NMR (400 MHz, DMSO-d$_6$) δ 7.66 (d, J=8.4 Hz, 1H), 7.30-7.21 (m, 1H), 7.19 (d, J=2.1 Hz, 1H), 7.11 (d, J=18.0 Hz, 1H), 6.93 (d, J=7.8 Hz, 1H), 6.57 (s, 1H), 4.21-3.90 (m, 4H), 3.88-3.29 (m, 10H), 3.23 (dd, J=25.3, 21.5 Hz, 3H), 2.87-2.56 (m, 4H), 2.40-1.74 (m, 6H), 1.58 (d, J=47.6 Hz, 3H).

Example 102

(3R,6R,11R,24S)-6'-Chloro-17,17-dioxo-spiro[8,22-dioxa-17-thia-1,10,14,16-tetrazapentacyclo[16.7.2.111,14.03,6.021,26]octacosa-18(27),19,21(26)-triene-24,1'-tetralin]-9,15-dione

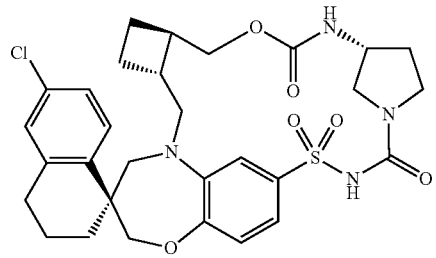 [SMILES: O=C1N[C@@H]2CCN(C2)C(=O)NS(=O)(=O)c2ccc3c(c2)N(C[C@@H]2CC[C@H]2CO1)C[C@@]1(CCCc2cc(Cl)ccc21)CO3]

This compound was prepared using procedures analogous to those described for Example 101 Step 2-5 using tert-butyl (3R)-3-aminopyrrolidine-1-carboxylate to replace (3R)-3-(methylamino)pyrrolidine-1-carboxylate in Step 2. LC-MS calc. for C$_{30}$H$_{36}$ClN$_4$O$_6$S [M+H]$^+$: 615.22/617.22; Found: 614.9/616.7. $^1$H NMR (400 MHz, DMSO-d$_6$) δ 7.65 (d, J=8.1 Hz, 1H), 7.26 (d, J=8.8 Hz, 1H), 7.20 (s, 1H), 7.12 (s, 1H), 6.97 (dd, J=16.3, 8.5 Hz, 1H), 6.82 (d, J=8.7 Hz, 1H), 6.57 (s, 1H), 4.22 (s, 1H), 4.05 (s, 1H), 3.80 (d, J=16.1 Hz, 1H), 3.71 (d, J=2.6 Hz, 1H), 3.12 (s, 2H), 2.84-2.62 (m, 2H), 2.37-2.27 (m, 1H), 1.68 (ddd, J=134.6, 64.0, 36.5 Hz, 10H).

Example 103

(3R,6R,11S,24S)-6'-Chloro-10-methyl-17,17-dioxo-spiro[8,22-dioxa-17λˆ6-thia-1,10,14,16-tetrazapentacyclo[16.7.2.1ˆ11,14.0ˆ3,6.0ˆ21,26]octacosa-18,20,26-triene-24,1'-tetralin]-9,15-dione

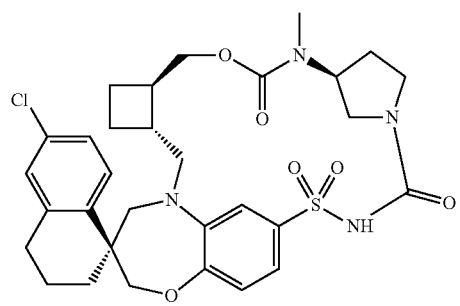 [SMILES: CN1C(=O)OC[C@@H]2CC[C@H]2CN2C[C@@]3(CCCc4cc(Cl)ccc43)COc3ccc(cc32)S(=O)(=O)NC(=O)N2CC[C@H]1C2]

This compound was prepared using procedures analogous to those described for Example 101 Step 2-5 using (3S)-3-(methylamino)pyrrolidine-1-carboxylate to replace (3R)-3-(methylamino)pyrrolidine-1-carboxylate in Step 2. LC-MS: calc. for C$_{31}$H$_{38}$ClN$_4$O$_6$S [M+H]$^+$: m/z=629.2/631.2; Found: 628.9/631.1. $^1$H NMR (600 MHz, MeOH-d$_4$) δ 7.72 (d, J=8.5 Hz, 1H), 7.32 (d, J=6.4 Hz, 1H), 7.21-7.18 (m, 1H), 7.17 (s, 1H), 7.14 (s, 1H), 6.96 (d, J=8.0 Hz, 1H), 4.24-4.03 (m, 6H), 3.71 (s, 2H), 3.62-3.36 (m, 3H), 2.94 (s, 2H), 2.81 (dt, J=16.9, 13.1 Hz, 3H), 2.70 (s, 1H), 2.46 (s, 1H), 2.22-2.09 (m, 3H), 2.00 (s, 2H), 1.91 (d, J=6.6 Hz, 3H), 1.67 (d, J=28.3 Hz, 3H), 1.33 (d, J=27.8 Hz, 2H).

Example 104

(3R,6R,24S)-6'-Chloro-17,17-dioxo-spiro[8,22-dioxa-17-thia-1,11,16-triazapentacyclo[16.7.2.19, 13.03,6.021,26]octacosa-9(28),10,12,18(27),19,21 (26)-hexaene-24,1'-tetralin]-15-one (PRT1001203)

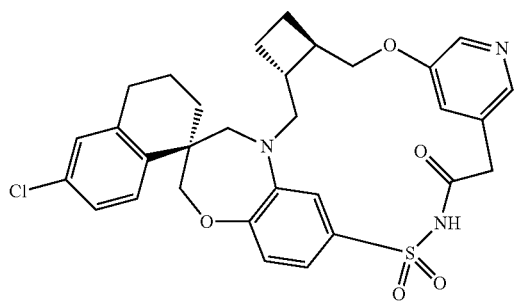 [SMILES: O=C1Cc2cncc(c2)OC[C@@H]2CC[C@H]2CN2C[C@@]3(CCCc4cc(Cl)ccc43)COc3ccc(cc32)S(=O)(=O)N1]

Step 1: (3S)-5-[[2-(bromomethyl)cyclobutyl] methyl]-6'-chloro-N,N-bis[(4-methoxyphenyl) methyl]spiro[2,4-dihydro-1,5-benzoxazepine-3,1'-tetralin]-7-sulfonamide

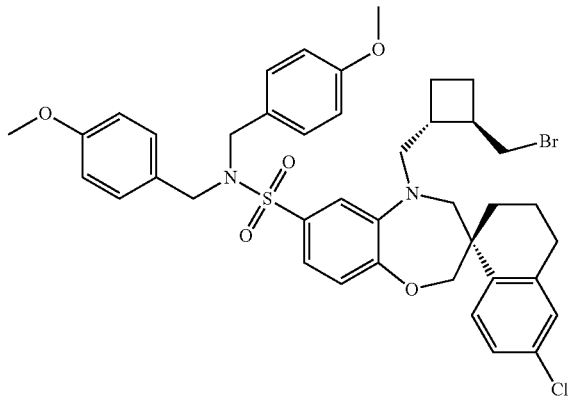 [SMILES: COc1ccc(CN(Cc2ccc(OC)cc2)S(=O)(=O)c2ccc3c(c2)N(C[C@@H]2CC[C@H]2CBr)C[C@@]2(CCCc4cc(Cl)ccc42)CO3)cc1]

To a solution of CBr$_4$ (388.35 mg, 1.17 mmol) in DCM (25 mL) under an atmosphere of nitrogen was added triphenylphosphine (307 mg, 1.17 mmol) and stirred for 30 mins. To this was added the (3S)-6'-chloro-5-[[2-(hydroxymethyl) cyclobutyl]methyl]-N,N-bis[(4-methoxyphenyl)methyl] spiro[2,4-dihydro-1,5-benzoxazepine-3,1'-tetralin]-7-sulfonamide (Example 18, Step 2, 420 mg, 0.59 mmol). The reaction was stirred at r.t. for 14 h. The reaction mixture was concentrated under reduced pressure. The residue was purified by flash chromatography on a silica gel column using 0-30% EtOAc in hexane to give (3S)-5-[[2-(bromomethyl) cyclobutyl]methyl]-6'-chloro-N,N-bi s[(4-methoxyphenyl) methyl]spiro[2,4-dihydro-1,5-benzoxazepine-3,1'-tetralin]-7-sulfonamide (300 mg, 65% yield). $^1$H NMR (500 MHz, CDCl$_3$) δ 7.67 (d, J=8.5 Hz, 1H), 7.24-7.08 (m, 3H), 7.06-6.96 (m, 6H), 6.84-6.75 (m, 4H), 4.29 (d, J=5.7 Hz, 4H), 4.11 (d, J=1.7 Hz, 2H), 3.79 (d, J=7.5 Hz, 8H), 3.70-3.55 (m, 2H), 3.40-3.19 (m, 4H), 2.78 (d, J=12.2 Hz, 2H), 2.46-2.29 (m, 2H), 2.05-1.80 (m, 4H), 1.70-1.48 (m, 2H).

Step 2: Methyl 2-[5-[[[(JR, 2R)-2-[[(3S)-7-[bis[(4-methoxyphenyl)methyl]sulfamoyl]-6'-chloro-spiro[2, 4-dihydro-1,5-benzoxazepine-3,1'-tetralin]-5-yl] methyl]cyclobutyl]methoxy]-3-pyridyl]acetate

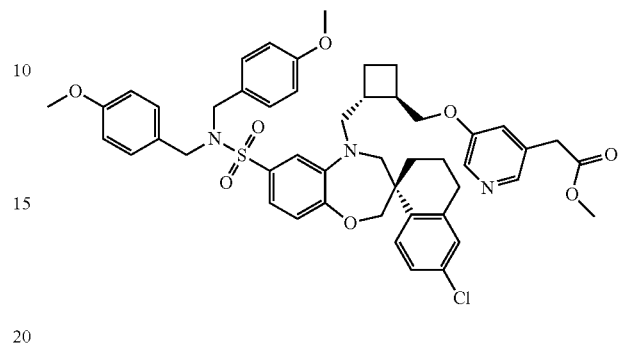

To (3S)-5-[[2-(bromomethyl)cyclobutyl]methyl]-6'-chloro-N,N-bis[(4-methoxyphenyl)methyl]spiro[2,4-dihydro-1,5-benzoxazepine-3,1'-tetralin]-7-sulfonamide (300.0 mg, 0.38 mmol) in MeCN (20 mL) was added the potassium carbonate (215 mg, 1.54 mmol), and methyl 2-(5-hydroxy-3-pyridyl)acetate (128 mg, 0.77 mmol). The reaction was heated at 80° C. overnight, filtered and concentrated under reduced pressure The residue was purified by flash chromatography on a silica gel column using 0-40% EtOAc in hexane to give methyl 2-[5-[[(1R,2R)-2-[[(3S)-7-[bis[(4-methoxyphenyl)methyl]sulfamoyl]-6'-chloro-spiro [2,4-dihydro-1,5-benzoxazepine-3,1'-tetralin]-5-yl]methyl] cyclobutyl]methoxy]-3-pyridyl]acetate (170 mg, 51% yield). LC-MS calc. for C$_{48}$H$_{53}$ClN$_3$O$_8$S [M+H]$^+$: m/z=866.3; found 866.5. $^1$H NMR (500 MHz, CDCl$_3$) δ 8.13 (s, 2H), 7.68 (d, J=8.4 Hz, 1H), 7.47 (s, 1H), 7.19 (dd, J=2.3, 8.5 Hz, 1H), 7.15-7.10 (m, 2H), 7.05 (d, J=2.1 Hz, 1H), 6.98 (d, J=8.2 Hz, 1H), 6.93 (d, J=8.7 Hz, 4H), 6.76 (d, J=8.6 Hz, 4H), 4.13 (d, J=15.2 Hz, 8H), 3.99-3.90 (m, 2H), 3.78 (s, 7H), 3.71 (s, 4H), 3.64 (s, 4H), 3.34-3.19 (m, 2H), 2.79 (s, 2H), 2.49 (s, 2H).

Step 3: Methyl 2-[5-[[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl] acetate

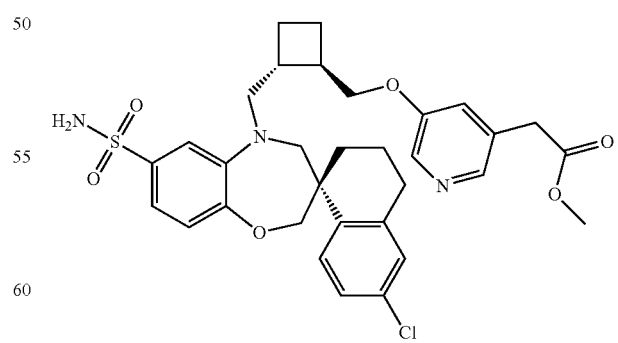

To methyl 2-[5-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl] methoxy]-3-pyridyl]acetate (170 mg, 0.20 mmol) in DCM (3 mL) was added the 2,2,2-trifluoroacetic acid (TFA) (1.5 mL). The reaction stirred at r.t. for 16 h. The reaction was concentrated under vacuum, extracted with DCM, the organic layer was washed with water, saturated sodium bicarbonate, and dried over sodium sulfate. The DCM layer was filtered, concentrated under reduced pressure, and purified by flash chromatography on a silica gel column using 0-10% methanol in DCM to give methyl 2-[5-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl]acetate (99 mg, 80.6% yield).

Step 4: 2-[5-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl]acetic acid

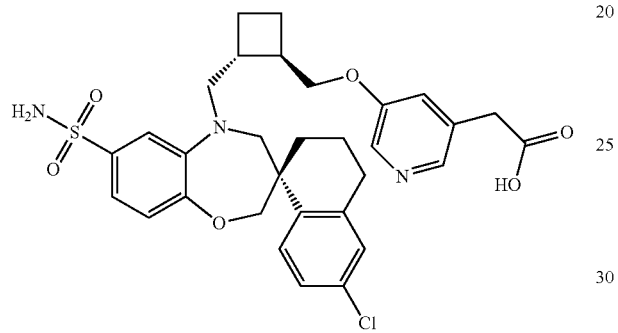

To methyl 2-[5-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl]acetate (99.0 mg, 0.16 mmol) in THF (3 mL) and water (3 mL) was added the lithium hydroxide (18.0 mg, 0.72 mmol) and stirred at r.t. for 2 h. The reaction mixture was concentrated and the residue neutralized with 0.25 N HCl, extracted with ethyl acetate. The combined organic layers were washed with water, brine, dried over sodium sulfate, filtered and concentrated to give 2-[5-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl]acetic acid (92 mg, 80% yield). LC-MS calc. for $C_{33}H_{35}ClF_3N_3O_8S$ [M+H]$^+$: m/z=612.2; found 612.4.

Step 5: (3R,6R,24S)-6'-chloro-17,17-dioxo-spiro[8,22-dioxa-17-thia-1,11,16-triazapentacyclo[16.7.2.19,13.03,6.021,26]octacosa-9(28), 10,12,18(27),19,21(26)-hexaene-24,1'-tetralin]-15-one To 2-[5-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]-3-pyridyl]acetic acid (72.0 mg, 0.12 mmol) in DCM (9 mL) and DMF (1 mL) was added the EDCI (67 mg, 0.35 mmol) and DMAP (67 mg, 0.55 mmol) and stirred at r.t. for 16 h. The reaction was diluted with water, extracted with ethyl acetate. The ethyl acetate layer was washed with water brine, dried over sodium sulfate, filtered and concentrated under reduced pressure The residue was purified by flash chromatography on a silica gel column using 0-15% MeOH in DCM to give (3R,6R,24S)-6'-chloro-17,17-dioxo-spiro[8,22-dioxa-17-thia-1,11,16-triazapentacyclo[16.7.2.19,13.03,6.021,26]octacosa-9(28), 10,12,18(27), 19,21(26)-hexaene-24,1'-tetralin]-15-one (20 mg, 28% yield). LC-MS calc. for $C_{31}H_{33}ClN_3O_5S$ [M+H]$^+$: m/z=594.2; Found 594.3. $^1$H NMR (500 MHz, MeCN-d$_3$) δ 8.04 (d, J=2.6 Hz, 1H), 7.90 (d, J=1.7 Hz, 1H), 7.68 (d, J=8.5 Hz, 1H), 7.30 (t, J=2.2 Hz, 1H), 7.23-7.07 (m, 3H), 6.98 (d, J=2.2 Hz, 1H), 6.75 (d, J=8.3 Hz, 1H), 4.17-3.98 (m, 4H), 3.53 (d, J=14.5 Hz, 1H), 3.45-3.20 (m, 7H), 2.84-2.69 (m, 3H), 2.55 (d, J=12.0 Hz, 3H), 1.90-1.47 (m, 5H).

Example 105

(3R,6R,24S)-6'-Chloro-11-(2-morpholinoethoxy)-17, 17-dioxo-spiro[8,22-dioxa-17-thia-1,16-diazapentacyclo[16.7.2.19,13.03,6.021,26]octacosa-9(28),10, 12,18(27),19,21(26)-hexaene-24,1'-tetralin]-15-one

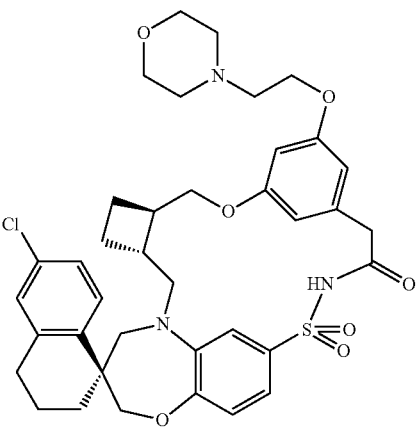 [SMILES: O=C1Cc2cc(OCCN3CCOCC3)cc(c2)OC[C@@H]2CC[C@H]2CN2C[C@@]3(CCCc4cc(Cl)ccc43)COc3ccc(cc32)S(=O)(=O)N1]

Step 1: methyl 2-[3-[[(1R,2R)-2-[[(3S)-7-[bis[(4-methoxyphenyl)methyl]sulfamoyl]-6'-chloro-spiro[2, 4-dihydro-1,5-benzoxazepine-3,1'-tetralin]-5-yl] methyl]cyclobutyl]methoxy]-5-hydroxy-phenyl] acetate

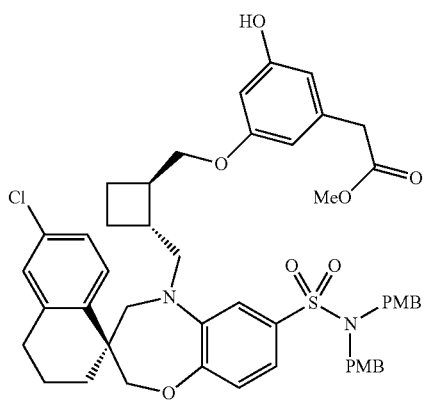

This compound was prepared using procedure analogous to that described for Example 18 Step 3 using methyl 2-(3,5-dihydroxyphenyl)acetate to replace methyl 3-hydroxyphenylacetate. R$_f$=0.73 (1:1 hexanes:EtOAc).

359

Step 2: methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]-5-(2-morpholinoethoxy)phenyl]acetate

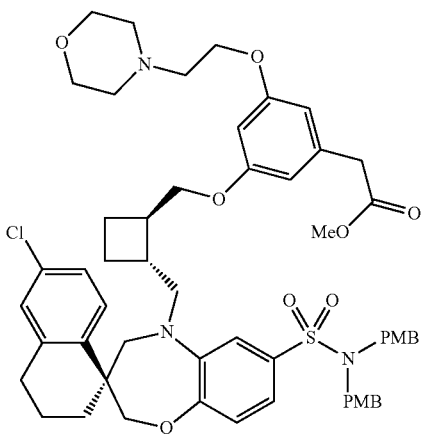

A mixture of methyl 2-[3-hydroxy-5-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]phenyl]acetate (72 mg, 0.08 mmol), and triphenylphosphine (37.0 mg, 0.14 mmol) were evacuated and recharged with $N_2$ (×2). Then N-(2-hydroxyethyl)morpholine (15.0 µL, 0.12 mmol) in DCM (3 mL) was added. To the mixture was added a solution of di-tert-butyl azodicarboxylate (25.0 mg, 0.11 mmol) in DCM (850 µL) dropwise over 2 min at r.t. The reaction mixture was stirred at r.t. overnight. An additional triphenylphosphine (9.0 mg, 0.03 mmol) was added, followed by diisopropyl azodicarboxylate (9.0 µL, 0.05 mmol). The mixture was stirred at r.t. for 1 h., concentrated under reduced pressure and purified by flash chromatography on a silica gel column with EtOAc in hexanes (10-100%) and then MeOH in DCM (2%) (with 0.2% $NH_4OH$) to afford methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]-5-(2-morpholinoethoxy)phenyl]acetate (44 mg, 54% yield). LCMS m/z calc. for $C_{55}H_{65}ClN_3O_{10}S$ [M+H]$^+$: m/z=994.41; Found: 994.5.

Step 3: (3R,6R,24S)-6'-chloro-11-(2-morpholinoethoxy)-17,17-dioxo-spiro[8,22-dioxa-17-thia-1,16-diazapentacyclo[16.7.2.19,13.03, 6.021, 26]octacosa-9(28), 10,12,18(27),19,21(26)-hexaene-24,1'-tetralin]-15-one This compound was prepared as TFA salt using procedures analogous to those described for Example 18 Step 4-6 using methyl 2-[3-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]-5-(2-morpholinoethoxy)phenyl]acetate. LCMS m/z calc. for $C_{38}H_{45}ClN_3O_7S$ [M+H]$^+$: m/z=722.27; found: 722.5. $^1$H NMR (500 MHz, DMSO-d$_6$) δ 12.05 (s, 1H), 9.94 (s, 1H), 7.60 (d, J=8.6 Hz, 1H), 7.27 (dd, J=2.4, 8.5 Hz, 1H), 7.21 (d, J=2.3 Hz, 1H), 7.07 (dd, J=2.1, 8.3 Hz, 1H), 6.92-6.86 (m, 1H), 6.82 (d, J=8.3 Hz, 1H), 6.64 (s, 1H), 6.51 (bs, 2H), 6.35 (d, J=2.2 Hz, 1H), 6.28 (s, 1H), 4.21 (q, J=5.0,

360

6.2 Hz, 2H), 4.11-4.03 (m, 2H), 4.03-3.95 (m, 4H), 3.74-3.65 (m, 2H), 3.48 (d, J=7.8 Hz, 1H), 3.41 (t, J=13.7 Hz, 1H), 3.39-3.25 (m, 4H), 3.20 (q, J=11.5, 14.9 Hz, 3H), 2.83-2.69 (m, 2H), 2.63 (s, 1H), 2.01-1.86 (m, 3H), 1.83-1.73 (m, 3H), 1.60 (q, J=10.4 Hz, 1H), 1.56-1.49 (m, 1H).

Example 106

(3R,6R,7R,8E,22S)-6'-Chloro-7-methoxy-15,15-dioxo-spiro[20-oxa-15-thia-1,12,14-triazatetracyclo[14.7.2.03,6.019,24]pentacosa-8,16,18,24-tetraene-22,1'-tetralin]-13-one

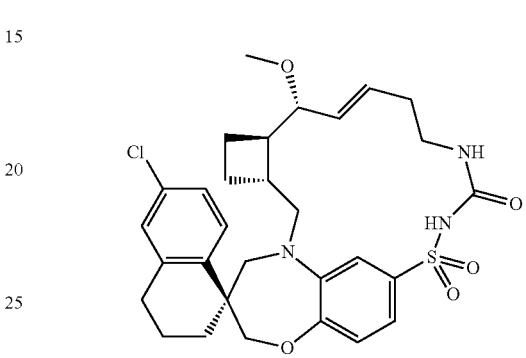

Step 1: 1-but-3-enyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea

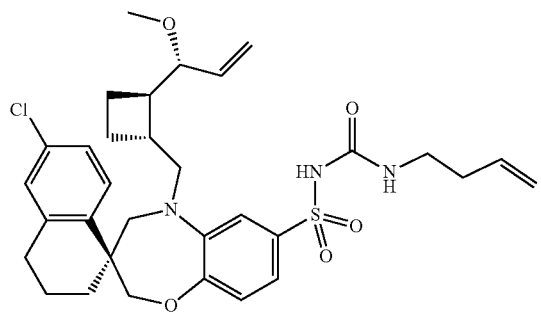 [SMILES: C=CCCNC(=O)NS(=O)(=O)c1ccc2c(c1)N(C[C@@H]1CC[C@H]1[C@@H](C=C)OC)C[C@@]1(CCCc3cc(Cl)ccc31)CO2]

To a stirred solution of (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (100 mg, 0.19 mmol, Intermediate 8) in MeCN (3 mL) was added TEA (0.1 mL, 0.58 mmol) and phenyl chloroformate (0.07 mL, 0.58 mmol). The resulting mixture was stirred at r.t. for 10 min. LCMS indicated the starting material was consumed. But-3-en-1-amine (16.5 mg, 0.23 mmol) was then added to the reaction mixture and the resulting solution was stirred overnight. The reaction was quenched by water (5 mL), extracted with EtOAc (3×10 mL). The combined organic layers were dried over $Na_2SO_4$, filtered and concentrated under reduced pressure. The residue was purified by flash chromatography on a silica gel column (12 g) using EtOAc/Heptanes (2% to 60%) to afford 1-but-3-enyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea (91 mg, 76% yield) as a white solid. LC-MS calc. for $C_{32}H_{41}ClN_3O_5S$ $[M+H]^+$: m/z=614.25/616.25. Found: 613.9/615.4.

Step 2: (3R,6R,7R,8E,22S)-6'-chloro-7-methoxy-15,15-dioxo-spiro[20-oxa-15-thia-1,12,14-triazatetracyclo[14.7.2.0³,⁶.0¹⁹,²⁴]pentacosa-8,16,18,24-tetraene-22,1'-tetralin]-13-one A solution of 1-but-3-enyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea (91.0 mg, 0.15 mmol) in DCE (100 mL) was bubbled with $N_2$ for 30 min. Hoveyda-Grubbs II (18.5 mg, 0.03 mmol) was added and the reaction mixture was further bubbled with $N_2$ for 30 min., and was stirred at 80° C. under $N_2$ overnight. The reaction was concentrated under reduced pressure, and the residue was purified by flash chromatography on a silica gel column (12 g) using EtOAc/Heptanes (2% to 60%). The desired fractions were collected, concentrated under reduced pressure, and further purified by Prep-HPLC on C18 column (30×250 mm, 10 m) with 20 to 100% $CH_3CN/H_2O$ ($t_R$=23 min) to afford (3R,6R,7R,8E,22S)-6'-chloro-7-methoxy-15,15-dioxo-spiro[20-oxa-15-thia-1,12,14-triazatetracyclo[14.7.2.0³,⁶.0¹⁹,²⁴]pentacosa-8,16,18,24-tetraene-22,1'-tetralin]-13-one (38 mg, 43% yield) as a white solid. LC-MS calc. for $C_{30}H_{37}ClN_3O_5S$ $[M+H]^+$: m/z=586.21/588.21; Found 586.1/587.9. $^1H$ NMR (600 MHz, $CDCl_3$) δ 7.68 (d, J=8.5 Hz, 1H), 7.18 (dt, J=8.7, 2.4 Hz, 1H), 7.08 (d, J=2.1 Hz, 1H), 7.02 (s, 1H), 6.99 (s, 1H), 6.96 (d, J=8.3 Hz, 1H), 5.88 (dt, J=14.2, 6.5 Hz, 1H), 5.48 (dd, J=15.7, 8.3 Hz, 1H), 4.09 (s, 2H), 3.80 (d, J=14.6 Hz, 1H), 3.67 (d, J=15.0 Hz, 1H), 3.49 (t, J=8.2 Hz, 2H), 3.42-3.30 (m, 2H), 3.26 (s, 3H), 3.02 (dd, J=15.1, 10.7 Hz, 1H), 2.89-2.67 (m, 2H), 2.57 (d, J=10.2 Hz, 1H), 2.38 (s, 2H), 2.29-2.12 (m, 1H), 2.10-1.91 (m, 3H), 1.84 (d, J=12.9 Hz, 1H), 1.67 (p, J=9.5 Hz, 3H), 1.42 (t, J=13.1 Hz, 1H), 1.39-1.21 (m, 2H).

Example 107

(3R,6R,7R,8E,22S)-6'-Chloro-7-methoxy-12-methyl-15,15-dioxo-spiro[20-oxa-15-thia-1,12,14-triazatetracyclo[14.7.2.0³,⁶.0¹⁹,²⁴]pentacosa-8,16,18,24-tetraene-22,1'-tetralin]-13-one

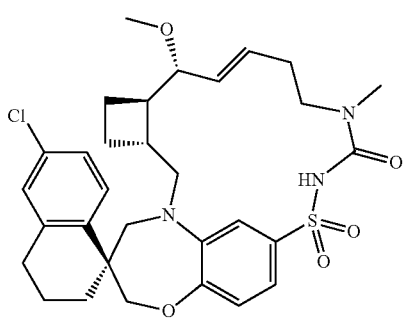 [SMILES: CO[C@@H]1/C=C/CCN(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 106 using N-methylbut-3-en-1-amine hydrochloride to replace but-3-en-1-amine in Step 1. LC-MS calc. for $C_{31}H_{39}ClN_3O_5S$ $[M+H]^+$: m/z=600.22/602.22; Found 600.1/602.0. $^1H$ NMR (600 MHz, $CDCl_3$) δ 7.69 (d, J=8.5 Hz, 1H), 7.52-7.30 (m, 2H), 7.19 (dd, J=8.5, 2.4 Hz, 1H), 7.08 (t, J=1.6 Hz, 1H), 6.97 (d, J=8.3 Hz, 1H), 5.53-5.11 (m, 2H), 4.13 (d, J=12.2 Hz, 1H), 4.03 (d, J=12.1 Hz, 1H), 3.76-3.58 (m, 3H), 3.31 (d, J=14.6 Hz, 1H), 3.17-3.00 (m, 5H), 2.85 (s, 3H), 2.82-2.68 (m, 3H), 2.43-2.15 (m, 3H), 2.02-1.94 (m, 1H), 1.91-1.69 (m, 5H), 1.43 (q, J=16.1, 11.8 Hz, 2H), 1.36-1.18 (m, 1H).

Example 108

(3R,6R,7R,8E,21S)-6'-Chloro-7-methoxy-11-methyl-14,14-dioxo-spiro[19-oxa-14-thia-1,11,13-triazatetracyclo[3.7.2.0³,⁶.0¹⁸,²³]tetracosa-8,15,17,23-tetraene-21,1'-tetralin]-12-one

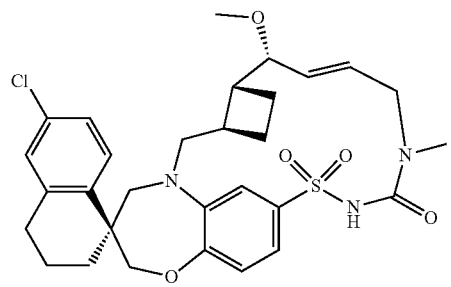

This compound was prepared using procedures analogous to those described for Example 106 using N-methylprop-2-en-1-amine hydrochloride to replace but-3-en-1-amine in Step 1. LC-MS: calc. for $C_{30}H_{37}ClN_3O_5S$ $[M+H]^+$: m/z=586.2/588.2; Found: 586.0/587.8. $^1H$ NMR (600 MHz, $CDCl_3$) δ 7.69 (d, J=8.5 Hz, 1H), 7.48-7.32 (m, 1H), 7.22-7.13 (m, 1H), 7.07 (d, J=2.2 Hz, 1H), 7.01 (s, 1H), 6.93 (s, 1H), 5.85 (d, J=16.0 Hz, 1H), 5.69 (s, 1H), 4.25 (d, J=18.4 Hz, 1H), 4.07 (s, 2H), 3.76 (d, J=14.4 Hz, 3H), 3.61 (t, J=7.0 Hz, 1H), 3.32-3.22 (m, 4H), 3.13-2.95 (m, 3H), 2.85-2.67 (m, 2H), 2.52 (t, J=8.9 Hz, 1H), 2.09-1.97 (m, 2H), 1.91 (s, 2H), 1.87-1.76 (m, 1H), 1.66 (p, J=9.4 Hz, 2H), 1.57-1.46 (m, 1H), 1.40 (t, J=13.0 Hz, 1H), 1.28-1.22 (m, 1H).

Example 109

(3R,6R,8E,22S)-6'-Chloro-7-hydroxy-7-[(4-isopropylpiperazin-1-yl)methyl]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one

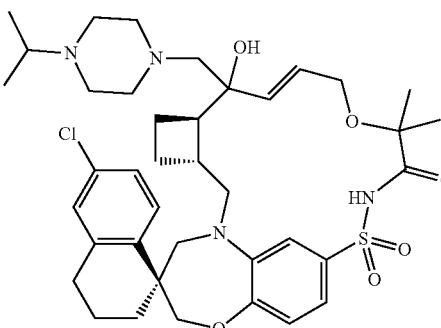

363

Step 1: (3R,6R,8E,22S)-6'-chloro-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-7,13-dione

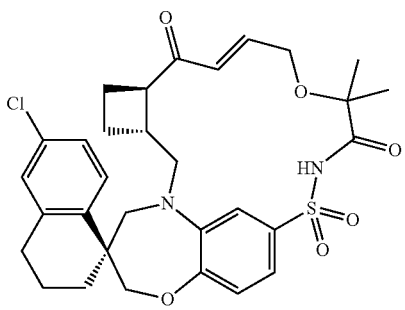 [SMILES: CC1(C)OC/C=C/C(=O)[C@@H]2CC[C@H]2CN2C[C@@]3(CCCc4cc(Cl)ccc43)COc3ccc(cc32)S(=O)(=O)NC1=O]

To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (175 mg, 0.29 mmol, Example 32) in DCM (17 mL) was added Dess-Martin periodinane (144 mg, 0.34 mmol) at 0° C. (ice-water bath). The mixture was stirred at r.t. for 30 min., and then quenched with 10% sodium thiosulfate (5 mL) and stirred for additional 30 min. The resulting mixture was extracted with DCM (10 mL×2). The combined organic layers were washed with saturated NaHCO$_3$ (10 mL), dried over Na$_2$SO$_4$, filtered and concentrated under reduced pressure. The residue was purified by flash chromatography on a silica gel column with EtOAc/Heptanes (5-90%) to afford the desired product (3R,6R,8E,22S)-6'-chloro-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-7,13-dione (100 mg, 57% yield). LC-MS calc. for C$_{31}$H$_{36}$ClN$_2$O$_6$S [M+H]$^+$: m/z=599.19/601.19; Found 599.5/601.5.

Step 2: (3R,6R,8E,22S)-6'-chloro-7,7-(1-oxa-ethylene)-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

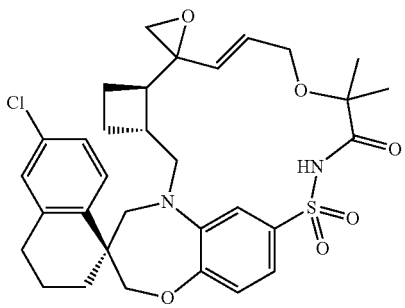 [SMILES: CC1(C)OC/C=C/C2(CO2)[C@@H]2CC[C@H]2CN2C[C@@]3(CCCc4cc(Cl)ccc43)COc3ccc(cc32)S(=O)(=O)NC1=O]

To a solution of (3R,6R,8E,22S)-6'-chloro-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-7,13-dione (100 mg, 0.17 mmol) in DMSO (8 mL) and THF (2 mL) was added trimethylsulfonium iodide (51 mg, 0.25 mmol), followed by potassium t-butoxide (1.0M in THF) (46 mg, 0.42 mmol) at 0° C. in ice-water bath. The mixture was then stirred at r.t. for 3 h. The reaction was monitored by LC-MS. The reaction was quenched with 1 drop acetic acid and stirred for 1 min. The mixture was poured into ethyl acetate (20 mL) and washed with water (20 mL). The aqueous layer was extracted with EA (20 mL×2). The combined organic layers were washed with water (50 mL), brine (50 mL) and dried over Na$_2$SO$_4$, filtered and concentrated under reduced pressure. The residue was purified by flash chromatography on a silica gel column with EtOAc/Heptanes (5-90%) to afford the desired product (3R,6R,8E,22S)-6'-chloro-7,7-(1-oxa-ethylene)-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (50 mg, 48% yield). LC-MS calc. for C$_{32}$H$_{38}$ClN$_2$O$_6$S [M+H]$^+$: m/z=613.21/615.20; Found 613.7/615.7.

Step 3: (3R,6R,8E,22S)-6'-chloro-7-hydroxy-7-[(4-isopropylpiperazin-1-yl)methyl]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one To a solution of (3R,6R,8E,22S)-6'-chloro-7,7-(1-oxa-ethylene)-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (10.0 mg, 0.02 mmol) and 1-isopropylpiperazine (3.1 mg, 0.02 mmol) in THF (2 mL) was added potassium t-butoxide (1.0 M in THF) (3.6 mg, 0.03 mmol). The mixture was stirred at 65° C. for 3 d. and monitored by LC-MS. The reaction mixture was neutralized with 1-2 drops of 2 N HCl in ethyl acetate. The solvent was then removed and the residue was purified through Prep-HPLC on C18 column to afford (3R,6R,8E,22S)-6'-chloro-7-hydroxy-7-[(4-isopropylpiperazin-1-yl)methyl]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (2.8 mg, 23% yield) as a white solid. LC-MS calc. for C$_{39}$H$_{54}$ClN$_4$O$_6$S [M+H]$^+$: m/z=741.34/743.33; Found 741.8/743.8.

Example 110

(3R,6R,22S)-6'-Chloro-8,12,12-trimethyl-15,15-dioxo-spiro[11,20-dioxa-thia-1,8,14-triazatetracyclo[14.7.2.03,6.019,24]pentacosa-16(25),17,19(24)-triene-22,1'-tetralin]-7,13-dione

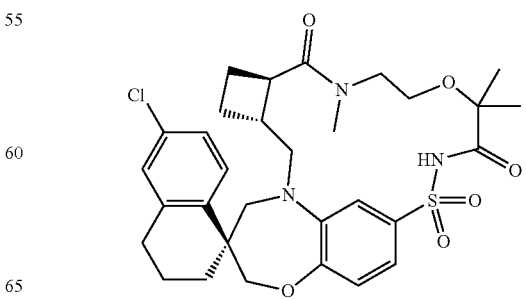

365

Step 1: 2-[2-[tert-butoxycarbonyl(methyl)amino]ethoxy]-2-methyl-propanoic acid

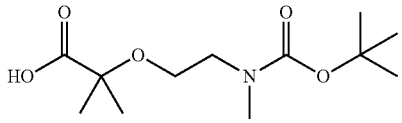 [SMILES: CN(CCOC(C)(C)C(=O)O)C(=O)OC(C)(C)C]

To a stirred solution of 2-bromo-2-methyl-propanoic acid (500 mg, 2.99 mmol) in MeCN (3 mL) was added tert-butyl N-(2-hydroxyethyl)-N-methyl-carbamate (786 mg, 4.49 mmol) and DIPEA (1.15 mL, 6.59 mmol) at 40° C. The resulting solution was stirred at 40° C. for 3 h. LC-MS analysis indicated the reaction was complete. The reaction mixture was adjusted with 1 N HCl to pH 1-2, and then extracted with EtOAc (2×20 mL). The combined organic layers were dried over $Na_2SO_4$, filtered and concentrated under reduced pressure to afford 2-[2-[tert-butoxycarbonyl(methyl)amino]ethoxy]-2-methyl-propanoic acid (160 mg, 20% yield) as a colorless oil. LC-MS calc. for $C_{12}H_{22}NO_5$ [M−H]⁻: m/z=260.3; Found: 260.2.

Step 2: (1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarboxylic acid

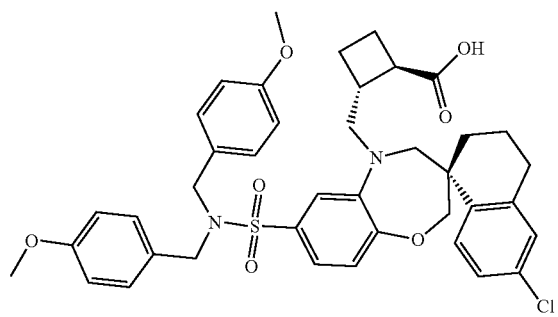 [SMILES: COc1ccc(CN(Cc2ccc(OC)cc2)S(=O)(=O)c2ccc3c(c2)N(C[C@@H]2CC[C@H]2C(=O)O)C[C@@]2(CCCc4cc(Cl)ccc42)CO3)cc1]

To a suspension of (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide (1450.0 mg, 2.03 mmol, Intermediate 3 Step 3) in 1-butanol (5 mL) and 2-methylbut-2-ene (5.0 mL, 47.2 mmol) was added sodium chlorite (458 mg, 4.05 mmol) and the solution of sodium phosphate monobasic monohydrate (559 mg, 4.05 mmol) in water (5 mL). The reaction was stirred at r.t. for 3 h. LC-MS showed reaction was completed. The reaction was quenched with 10% $Na_2S_2O_3$ aq. (5 mL) and the mixture was extracted with EtOAc (2×2 mL). The combined organic layers were dried over $Na_2SO_4$, filtered and concentrated under reduced pressure to afford the crude product (500 mg) which was used directly in next step reaction without further purification.

366

Step 3: methyl (1R,2R)-2-[[rac-(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarboxylate

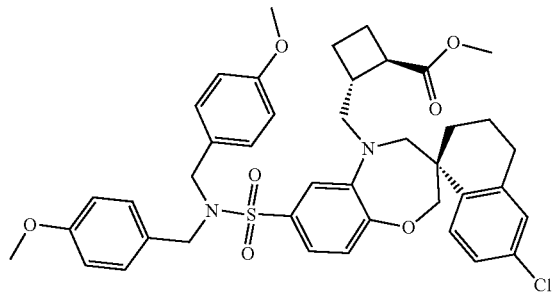 [SMILES: COC(=O)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

To a solution of (1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarboxylic acid (500 mg, 0.68 mmol) in DMF (5 mL) was added iodomethane (116 mg, 0.82 mmol) and potassium carbonate (141 mg, 1.03 mmol). The reaction was stirred overnight and then quenched with water (20 mL), and extracted with MTBE (2×10 mL). The combined organic layers were dried over $Na_2SO_4$, filtered and concentrated under reduced pressure to afford the crude product which was used without further purification.

Step 4: methyl (1R,2R)-2-[[(3S)-6'-chloro-7-sulfamoyl-spiro[2,4-dihydro-1,5-benzoxazepine-3,1'-tetralin]-5-yl]methyl]cyclobutanecarboxylate

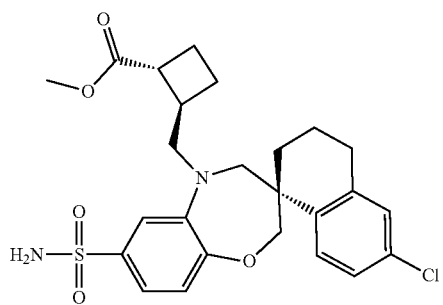 [SMILES: COC(=O)[C@@H]1CC[C@H]1CN1C[C@@]2(CCCc3cc(Cl)ccc32)COc2ccc(S(N)(=O)=O)cc21]

To a solution of methyl (1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarboxylate (850 mg, 1.14 mmol) in DCM (2 mL) was added anisole (0.5 mL, 4.6 mmol) and 2,2,2-trifluoroacetic acid (TFA) (2.0 mL, 26.14 mmol). The reaction was stirred at r.t. overnight. Upon completion of the reaction, the mixture was concentrated under reduced pressure. The residue was re-dissolved in DCM and washed with sat. $Na_2CO_3$ aq. The organic layer was dried over $Na_2SO_4$, filtered and concentrated under reduced pressure to afford the crude product which was used without further purification.

Step 5: methyl (1R,2R)-2-[[(3S)-7-[[2-[2-[tert-butoxycarbonyl(methyl)amino]ethoxy]-2-methyl-propanoyl]sulfamoyl]-6'-chloro-spiro[2,4-dihydro-1,5-benzoxazepine-3,1'-tetralin]-5-yl]methyl]cyclobutanecarboxylate

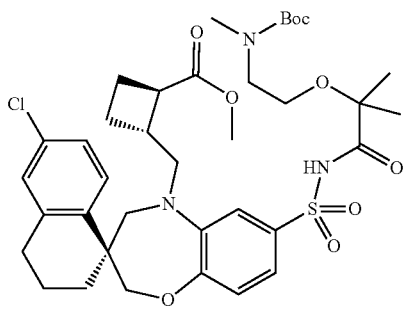 [SMILES: COC(=O)[C@@H]1CC[C@H]1CN1C[C@@]2(CCCc3cc(Cl)ccc32)COc2ccc(S(=O)(=O)NC(=O)C(C)(C)OCCN(C)C(=O)OC(C)(C)C)cc21]

To a stirred solution of methyl (1R,2R)-2-[[(3S)-6'-chloro-7-sulfamoyl-spiro[2,4-dihydro-1,5-benzoxazepine-3,1'-tetralin]-5-yl]methyl] (50 mg, 0.10 mmol) in DCM (1 mL) was added DMAP (48 mg, 0.40 mmol) and EDCI (38 mg, 0.20 mmol) at 20° C. The resulting solution was stirred at 20° C. for 3 h. LCMS analysis indicated the reaction was complete. The reaction mixture was quenched with 1 N HCl solution and extracted with EtOAc (5 mL×3). The combined organic layers were dried over sodium sulfate, filtered and concentrated under reduced pressure The residue was purified by flash chromatography on a silica gel column using EtOAc/Heptanes (5-90%) to afford methyl (1R,2R)-2-[[(3S)-7-[[2-[2-[tert-butoxycarbonyl(methyl)amino]ethoxy]-2-methyl-propanoyl]sulfamoyl]-6'-chloro-spiro[2,4-dihydro-1,5-benzoxazepine-3,1'-tetralin]-5-yl]methyl]cyclobutanecarboxylate (37 mg, 50% yield) as a light orange solid. LC-MS calc. for $C_{37}H_{51}ClN_3O_9S$ $[M+H]^+$: m/z=748.3/750.3; Found: 748.5/750.3.

Step 6: methyl (1R,2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylate

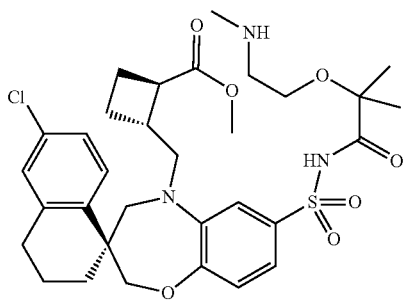 [SMILES: CNCCOC(C)(C)C(=O)NS(=O)(=O)c1ccc2c(c1)N(C[C@@H]1CC[C@H]1C(=O)OC)C[C@@]1(CCCc3cc(Cl)ccc31)CO2]

To a solution of methyl (1R,2R)-2-[[(3S)-7-[[2-[2-[tert-butoxycarbonyl(methyl)amino]ethoxy]-2-methyl-propanoyl]sulfamoyl]-6'-chloro-spiro[2,4-dihydro-1,5-benzoxazepine-3,1'-tetralin]-5-yl]methyl]cyclobutanecarboxylate (40 mg, 0.05 mmol) in DCM (0.50 mL) was added phosphoric acid (0.67 mL, 11 mmol). The resulting solution was vigorously stirred at 40° C. for 3 h. LCMS analysis indicated the reaction was complete. The reaction mixture was quenched with 1 M NaOH aqueous solution to pH 8 and extracted with 2×4 mL DCM. The combined organic layers were concentrated under reduced pressure to afford methyl (1R,2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylate (19 mg, 55% yield) as a white solid. LC-MS calc. for $C_{32}H_{43}ClN_3O_7S$ $[M+H]^+$: m/z=648.2/650.2; Found: 648.3/650.3 Step 7: (JR, 2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylic acid

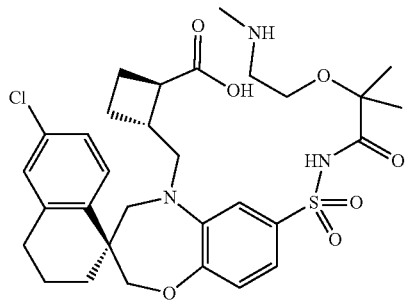 [SMILES: CNCCOC(C)(C)C(=O)NS(=O)(=O)c1ccc2c(c1)N(C[C@@H]1CC[C@H]1C(=O)O)C[C@@]1(CCCc3cc(Cl)ccc31)CO2]

To a solution of methyl (1R,2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylate (19.0 mg, 0.03 mmol) in methanol (0.50 mL) and THF (0.50 mL) was added lithium hydroxide monohydrate (3.7 mg, 0.09 mmol) in water (0.50 mL). The resulting solution was stirred at 40° C. for 2 h. LCMS analysis indicated the reaction was complete. The reaction mixture was quenched with 1 M HCl aqueous solution to pH 5-6 and extracted with EtOAc (2×10 mL). The combined organic layers were concentrated under reduced pressure to afford (1R,2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylic acid (16 mg, 86% yield) as a white solid. LC-MS calc. for $C_{31}H_{41}ClN_3O_7S$ $[M+H]^+$: m/z=634.2/636.2; Found: 634.6/636.7.

Step 8: (3R,6R,22S)-6'-chloro-8,12,12-trimethyl-15,15-dioxo-spiro[11,20-dioxa-thia-1,8,14-triazatetracyclo[14.7.2.0³,⁶.0¹⁹,²⁴]pentacosa-16(25),17,19(24)-triene-22,1'-tetralin]-7,13-dione To a solution of (1R,2R)-2-[[(3S)-6'-chloro-7-[[2-methyl-2-[2-(methylamino)ethoxy]propanoyl]sulfamoyl]spiro[2,4-dihydro-1,5-benzoxazepine-3,1'-tetralin]-5-yl]methyl]cyclobutanecarboxylic acid (16 mg, 0.03 mmol) in DMF (5 mL) was added HATU (2.1 mg, 0.05 mmol) and DIPEA (0.01 mL, 0.05 mmol). The resulting solution was stirred at 20° C. for 1 h. LCMS analysis indicated the reaction was complete. The reaction mixture was quenched with water and extracted with EtOAc (2×10 mL). The combined organic layers were concentrated under reduced pressure and the residue was purified by prep-HPLC on C18 column (30×250 mm, 10 μm) using MeCN/H$_2$O (20 to 100%) to afford (3R,6R,22S)-6'-chloro-8,12,12-trimethyl-15,15-dioxo-spiro[11,20-dioxa-thia-1,8,14-triazatetracyclo[14.7.2.03,6.019,24]pentacosa-16(25),17,19(24)-triene-22,1'-tetralin]-7,13-dione (4 mg, 25% yield) as a white solid. LC-MS calc. for C$_{31}$H$_{39}$ClN$_3$O$_6$S [M+H]$^+$: m/z=616.2/618.2; Found 616.6/618.6. $^1$H NMR (300 MHz, CDCl$_3$) δ 7.74 (d, J=8.5 Hz, 1H), 7.51-7.31 (m, 2H), 7.22-7.04 (m, 2H), 6.94 (d, J=8.4 Hz, 1H), 4.10 (s, 2H), 4.03-3.89 (m, 1H), 3.89-3.77 (m, 1H), 3.73-3.63 (m, 1H), 3.56 (t, J=6.5 Hz, 1H), 3.29 (d, J=14.5 Hz, 2H), 3.11 (s, 5H), 2.77 (q, J=5.5, 5.0 Hz, 2H), 2.30-2.15 (m, 1H), 2.06-1.67 (m, 9H), 1.41 (s, 3H), 1.34 (s, 3H).

Example 111

(3R,6R,7S,8E,22S)-6'-Chloro-7-methoxy-15,15-dioxo-spiro[[11,20]dioxa[15]thia-1,14-diazatetracyclo[14.7.2.03,6.019,24]pentacosa[8,16(25),17,19(24)]tetraene-22,1'-tetralin]-13-one

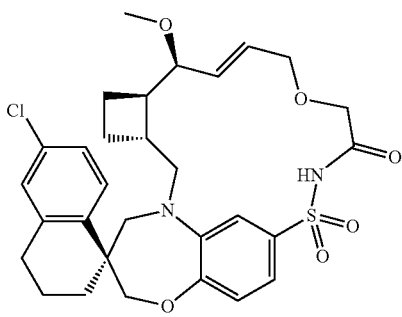 [SMILES: CO[C@H]1/C=C/COCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and 2-(allyloxy)acetic acid in Step 3. LC-MS calc. for C$_{30}$H$_{36}$ClN$_2$O$_6$S [M+H]$^+$: m/z=587.19/589.19; Found: 586.8/588.9. $^1$H NMR (600 MHz, DMSO-d$_6$) δ 12.01 (s, 1H), 7.62 (d, J=8.5 Hz, 1H), 7.29 (dd, J=8.3, 2.1 Hz, 1H), 7.24 (dd, J=8.5, 2.4 Hz, 1H), 7.21 (d, J=2.4 Hz, 1H), 7.10 (d, J=2.2 Hz, 1H), 7.06 (d, J=8.3 Hz, 1H), 5.43 (ddt, J=15.6, 7.6, 1.4 Hz, 1H), 5.20-5.09 (m, 1H), 4.13 (d, J=12.0 Hz, 1H), 4.06 (d, J=12.0 Hz, 1H), 4.01-3.90 (m, 4H), 3.55-3.47 (m, 2H), 3.39 (dd, J=7.5, 3.1 Hz, 1H), 3.20-3.12 (m, 1H), 3.05 (s, 3H), 2.80-2.73 (m, 2H), 2.02 (ddd, J=14.2, 6.4, 2.8 Hz, 1H), 1.91 (ddt, J=11.2, 7.6, 3.8 Hz, 1H), 1.89-1.80 (m, 2H), 1.79-1.71 (m, 2H), 1.66 (ddd, J=13.8, 10.3, 3.2 Hz, 1H), 1.58-1.50 (m, 1H), 1.30-1.20 (m, 3H).

Example 112

(3R,6R,7R,8E,22S)-6'-Chloro-7-methoxy-15,15-dioxo-spiro[[11,20]dioxa[15]thia-1,14-diazatetracyclo[14.7.2.03,6.019,24]pentacosa[8,16(25),17,19(24)]tetraene-22,1'-tetralin]-13-one

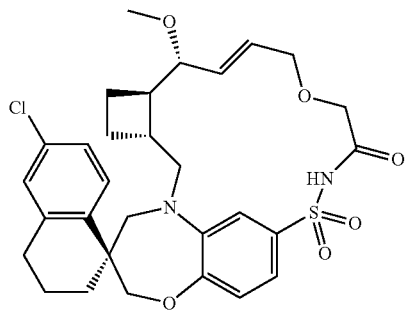 [SMILES: CO[C@@H]1/C=C/COCC(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 2-(allyloxy)acetic acid in Step 3. LC-MS calc. for C$_{30}$H$_{36}$ClN$_2$O$_6$S [M+H]$^+$: m/z=587.19/589.19; Found: 586.8/589.0. $^1$H NMR (600 MHz, CDCl$_3$) δ 7.69 (d, J=8.5 Hz, 1H), 7.26-7.21 (m, 1H), 7.13 (d, J=8.3 Hz, 1H), 7.07 (s, 1H), 6.83 (d, J=63.8 Hz, 1H), 6.05 (s, 1H), 5.34 (qd, J=11.1, 6.0 Hz, 1H), 5.17 (dd, J=99.9, 13.5 Hz, 1H), 4.52 (s, 1H), 4.19-3.88 (m, 4H), 3.78 (dt, J=31.6, 15.8 Hz, 2H), 3.34 (s, 3H), 3.28 (d, J=14.7 Hz, 1H), 3.00 (dd, J=29.7, 15.2 Hz, 1H), 2.83-2.68 (m, 2H), 2.64 (s, 1H), 2.33 (d, J=31.7 Hz, 2H), 2.08-1.95 (m, 3H), 1.74-1.54 (m, 3H), 1.34 (dd, J=28.1, 12.4 Hz, 3H).

Example 113

[(3R,6R,7S,8E,12S,22S)-6'-Chloro-12-methyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] acetate

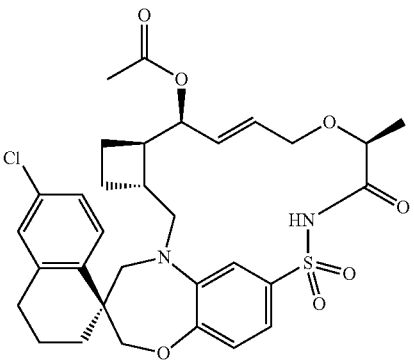 [SMILES: CC(=O)O[C@H]1/C=C/CO[C@@H](C)C(=O)NS(=O)(=O)c2ccc3c(c2)N(C[C@@H]2CC[C@H]21)C[C@@]1(CCCc2cc(Cl)ccc21)CO3]

Step 1: (2S)-2-allyloxypropanoic Acid

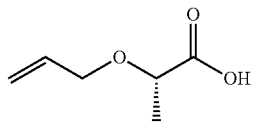

This compound was prepared using procedures analogous to those described for Example 28 Step 1-2 using ethyl (2S)-2-hydroxypropanoate to replace methyl 1-hydroxycyclopropanecarboxylate in Step 1. TLC $R_f$=0.25 (EA:Hep=2:1).

Step 2. [(3R,6R,7S,8E,12S,22S)-6'-chloro-12-methyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] acetate This compound was prepared using procedures analogous to those described for Example 26 Step 3-4 using [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] acetate (Intermediate 5) and (2S)-2-allyloxypropanoic acid in Step 3. LC-MS calc. for $C_{32}H_{38}ClN_2O_7S$ [M+H]$^+$: m/z=629.20/631.20; Found: 629.0/630.8. $^1$H NMR (600 MHz, CDCl$_3$) δ 8.95 (s, 1H), 7.66 (d, J=8.5 Hz, 1H), 7.55-7.48 (m, 1H), 7.17 (dd, J=8.5, 2.3 Hz, 1H), 7.12 (d, J=2.2 Hz, 1H), 7.09 (d, J=2.3 Hz, 1H), 6.99 (d, J=8.3 Hz, 1H), 5.59 (q, J=3.7 Hz, 2H), 5.41-5.28 (m, 1H), 5.21 (t, J=4.3 Hz, 1H), 4.39-4.29 (m, 1H), 4.24 (d, J=12.2 Hz, 1H), 4.13 (d, J=12.2 Hz, 1H), 3.83-3.70 (m, 2H), 3.66 (d, J=14.6 Hz, 1H), 3.48-3.31 (m, 2H), 3.23 (dd, J=15.0, 8.1 Hz, 1H), 2.87-2.72 (m, 3H), 2.53 (dt, J=13.7, 8.8 Hz, 1H), 2.07 (s, 3H), 2.07-1.72 (m, 5H), 1.60 (td, J=18.9, 17.8, 11.1 Hz, 2H), 1.41 (d, J=6.8 Hz, 3H).

Example 114

(3R,6R,7R,8E,12S,22S)-6'-Chloro-7-methoxy-12-methyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

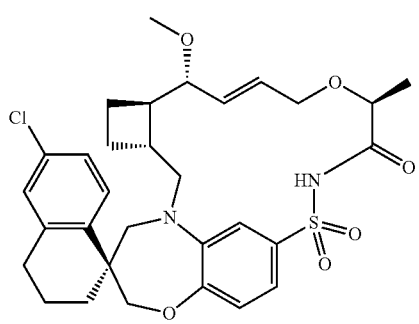 [SMILES: CO[C@@H]1/C=C/CO[C@@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2S)-2-allyloxypropanoic acid (Example 113 Step 1) in Step 3. LC-MS calc. for $C_{33}H_{38}ClN_2O_6S$ [M+H]$^+$: m/z=601.2/603.2; Found: 601.0/602.8. $^1$H NMR (400 MHz, DMSO-d$_6$) δ 12.00 (s, 1H), 7.63 (dd, J=30.8, 26.0 Hz, 1H), 7.29 (dd, J=8.5, 2.2 Hz, 1H), 7.26-7.21 (m, 3H), 7.05 (d, J=7.4 Hz, 1H), 5.38-5.20 (m, 1H), 4.21 (d, J=12.9 Hz, 1H), 4.11 (d, J=12.2 Hz, 1H), 4.01 (d, J=12.3 Hz, 1H), 3.80-3.52 (m, 4H), 3.07-2.94 (m, 3H), 2.87-2.65 (m, 3H), 2.33 (dd, J=11.1, 9.2 Hz, 1H), 2.05-1.92 (m, 1H), 1.88-1.54 (m, 6H), 1.42 (dd, J=22.3, 11.3 Hz, 1H), 1.30-1.21 (m, 5H) ppm.

Example 115

(3R,6R,7R,8E,12R,22S)-6'-Chloro-7-methoxy-12-methyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

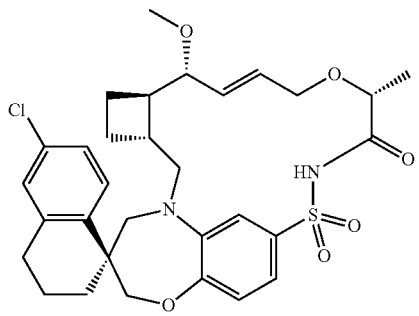 [SMILES: CO[C@@H]1/C=C/CO[C@H](C)C(=O)NS(=O)(=O)c2ccc3c(c2)N(C[C@@H]2CC[C@H]21)C[C@@]1(CCCc2cc(Cl)ccc21)CO3]

Step 1: (2R)-2-allyloxypropanoic acid

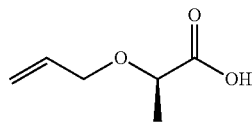

This compound was prepared using procedures analogous to those described for Example 28 Step 1-2 using ethyl (2R)-2-hydroxypropanoate to replace methyl 1-hydroxycyclopropanecarboxylate in Step 1. TLC $R_f$=0.3 (50% EA in Hep).

Step 2: (3R,6R,7R,8E,12R,22S)-6'-chloro-7-methoxy-12-methyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2R)-2-allyloxypropanoic acid in Step 3. LC-MS calc. for $C_{33}H_{38}ClN_2O_6S$ [M+H]$^+$: m/z=601.2/603.2; Found: 600.8/603.0. $^1$H NMR (400 MHz, DMSO-d$_6$) δ 12.09 (s, 1H), 7.67 (d, J=8.6 Hz, 1H), 7.30-7.23 (m, 2H), 7.19 (d, J=2.2 Hz, 1H), 7.02 (d, J=8.3 Hz, 2H), 5.70-5.61 (m, 1H), 5.13 (dd, J=15.6, 8.0 Hz, 1H), 4.25 (d, J=12.1 Hz, 1H), 4.06 (d, J=12.1 Hz, 1H), 3.97 (dd, J=12.8, 6.2 Hz, 2H), 3.78 (dd, J=14.4, 6.8 Hz, 1H), 3.52 (d, J=14.4 Hz, 1H), 3.39 (t, J=6.5 Hz, 2H), 3.30

(d, J=7.3 Hz, 2H), 3.09 (s, 2H), 2.84-2.65 (m, 3H), 2.30 (dd, J=16.0, 10.6 Hz, 2H), 2.06-1.96 (m, 2H), 1.95-1.76 (m, 4H), 1.62-1.42 (m, 4H), 1.24 (d, J=6.6 Hz, 3H).

Example 116

(3R,6R,7R,8E,22S)-6'-Chloro-7-methoxy-12,12-(1,3-propylene)-15,15-dioxo-spiro[[20]oxa-15-thia-1,11,14-triazatetracyclo[14.7.2.0³,⁶.0¹⁹,²⁴]pentacosa[8,16(25),17,19(24)]tetraene-22,1'-tetralin]-13-one

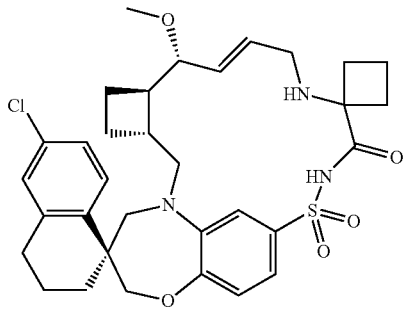 [SMILES: CO[C@@H]1/C=C/CNC2(CCC2)C(=O)NS(=O)(=O)c2ccc3c(c2)N(C[C@@H]2CC[C@H]21)C[C@@]1(CCCc2cc(Cl)ccc21)CO3]

Step 1: ethyl 1-(tert-butoxycarbonylamino)cyclobutanecarboxylate

To a solution of ethyl 1-aminocyclobutanecarboxylate hydrochloride (1.00 g, 5.57 mmol) and sodium bicarbonate (1.43 g, 16.7 mmol) in THF (5 mL) and water (5 mL) was added di-tert butyl dicarbonate (1.46 g, 6.68 mmol). The resulting mixture was stirred at r.t. for 10 min. and briefly heated in a hot water bath at 50° C. for 10 min. diluted with water, and extracted with MTBE. The combined organic layers were washed with brine, dried over $Na_2SO_4$, filtered and concentrated under reduced pressure to afford the crude product which was used without further purifications. LC-MS calc. for $C_{12}H_{22}N_{04}$ [M+H]⁺: m/z=244.15; Found 244.0.

Step 2: ethyl 1-[allyl(tert-butoxycarbonyl)amino]cyclobutanecarboxylate

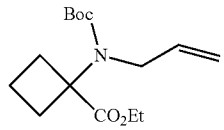 [SMILES: C=CCN(C(=O)OC(C)(C)C)C1(C(=O)OCC)CCC1]

To a suspension of sodium hydride (60%, 446 mg, 11.5 mmol) in DMF (15 mL) was added ethyl 1-(tert-butoxycarbonylamino)cyclobutanecarboxylate (1.35 g, 5.57 mmol) in DMF (5 mL) at 0° C. After 20 min., allyl bromide (1.01 g, 8.36 mmol) was added in one portion. The reaction was stirred at ambient temperature overnight, quenched with saturated aqueous $NH_4Cl$ and extracted with EtOAc. The combined organic layers were washed with water and brine, dried over $Na_2SO_4$, filtered and concentrated under reduced pressure. The residue was purified by flash chromatography on a silica gel column (3% to 8% EtOAc/Hept) to afford ethyl 1-[allyl(tert-butoxycarbonyl)amino]cyclobutanecarboxylate (1.42 g, 90% yield) as a colorless oil. TLC (10% EtOAc/Hept) $R_f$=0.48.

Step 3: 1-[allyl(tert-butoxycarbonyl)amino]cyclobutanecarboxylic acid

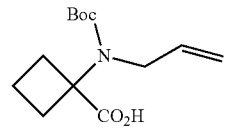

A solution of ethyl 1-[allyl(tert-butoxycarbonyl)amino]cyclobutanecarboxylate (1.40 g, 4.94 mmol) and lithium hydroxide monohydrate (1.03 g, 24.7 mmol) in MeOH/THF/$H_2O$ (5 mL, 5 mL, 8 mL) was heated at 45° C. overnight. The reaction was cooled to 0° C., acidified with 2 N HCl, and extracted with EtOAc. The combined organic layers were washed with brine, dried over $Na_2SO_4$, filtered and concentrated under reduced pressure The residue was purified by flash chromatography on a silica gel column (10% to 30% EtOAc/Hept) to afford 1-[allyl(tert-butoxycarbonyl)amino]cyclobutanecarboxylic acid (0.790 g, 62.6% yield). LC-MS calc. for $C_{13}H_{20}NO_4$ [M–H]⁻: m/z=254.14; Found 254.1.

Step 4. (3R,6R,7R,8E,22S)-6'-chloro-7-methoxy-12,12-(1,3-propylene)-15,15-dioxo-spiro[20-oxa-15-thia-1,11,14-triazatetracyclo[14.7.2.0³,⁶.0¹⁹,²⁴]pentacosa[8,16(25),17,19(24)]tetraene-22,1'-tetralin]-13-one This compound was prepared using procedures analogous to those described for Example 26 Step 3-5 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-[allyl(tert-butoxycarbonyl)amino]cyclobutanecarboxylic acid in Step 3. LC-MS calc. for $C_{33}H_{41}ClN_3O_5S$ [M+H]⁺: m/z=626.24/628.24; Found: 626.0/628.2. ¹H NMR (600 MHz, CDCl₃) δ 7.68 (d, J=8.5 Hz, 1H), 7.42 (dd, J=8.6, 2.1 Hz, 1H), 7.26 (app s, 1H, overlapped with CHCl₃), 7.17 (dd, J=8.5, 2.3 Hz, 1H), 7.08 (d, J=2.3 Hz, 1H), 6.97 (d, J=8.3 Hz, 1H), 5.37-5.24 (m, 2H), 4.11 (d, J=12.1 Hz, 1H), 4.06 (d, J=12.2 Hz, 1H), 3.70 (d, J=14.6 Hz, 1H), 3.65 (dd, J=14.4, 7.0 Hz, 1H), 3.40 (dd, J=14.7, 4.3 Hz, 1H), 3.31 (d, J=14.6 Hz, 1H), 3.13 (s, 3H), 3.09 (d, J=5.6 Hz, 1H), 3.02 (dd, J=15.1, 7.1 Hz, 1H), 2.94 (d, J=13.1 Hz, 1H), 2.82-2.71 (m, 2H), 2.59 (dqd, J=16.2, 8.8, 8.2, 2.6 Hz, 2H), 2.45 (tt, J=8.4, 3.3 Hz, 1H), 2.28 (d, J=8.1 Hz, 1H), 2.08-1.77 (m, 10H), 1.76-1.69 (m, 1H), 1.68-1.60 (m, 1H), 1.44-1.37 (m, 1H).

Example 117

(3R,6R,7R,8E,12S,22S)-6'-Chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one

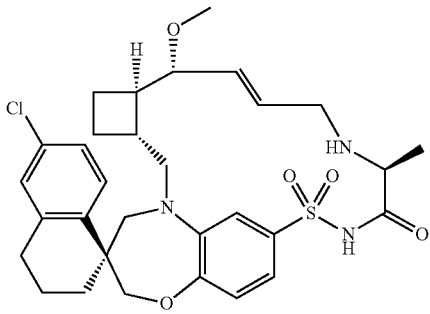 [SMILES: CO[C@@H]1/C=C/CN[C@@H](C)C(=O)NS(=O)(=O)c2ccc3c(c2)N(C[C@@H]2CC[C@H]21)C[C@@]1(CCCc2cc(Cl)ccc21)CO3]

Step 1: (2S)-2-[allyl(tert-butoxycarbonyl)amino]propanoic acid

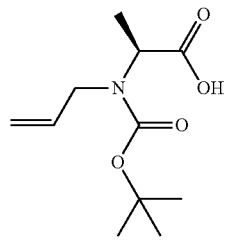 [SMILES: C=CCN(C(=O)OC(C)(C)C)[C@@H](C)C(=O)O]

This compound was prepared using procedures analogous to those described for Example 116 Step 2-3 using methyl (2S)-2-(tert-butoxycarbonylamino)propanoate to replace ethyl 1-(tert-butoxycarbonylamino)cyclobutanecarboxylate in Step 2.

Step 2: tert-butyl N-allyl-N-[(1S)-1-methyl-2-oxo-2-[[(3S)-6'-chloro-5-[[(1R,2R)-2-[(JR)-1-methoxyallyl]cyclobutyl]methyl]spiro[2,4-dihydro-1,5-benzoxazepine-3,1'-tetralin]-7-yl]sulfonylamino]ethyl]carbamate

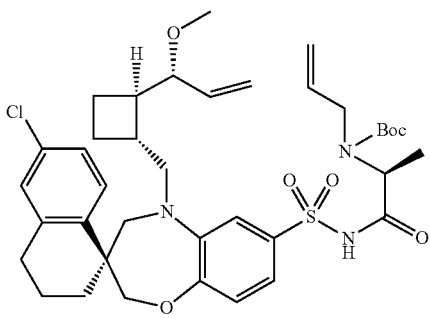 [SMILES: C=CCN(C(=O)OC(C)(C)C)[C@@H](C)C(=O)NS(=O)(=O)c1ccc2c(c1)N(C[C@@H]1CC[C@H]1[C@@H](C=C)OC)C[C@@]1(CCCc3cc(Cl)ccc31)CO2]

This compound was prepared using procedures analogous to those described for Example 26 Step 3 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (2S)-2-[allyl(tert-butoxycarbonyl)amino]propanoic acid.

Step 3: tert-butyl (3R,6R,7R,8E,12S,22S)-6'-chloro-7-methoxy-12-methyl-13,15,15-trioxo-spiro[20-oxa-15-thia-1,11,14-triazatetracyclo[14.7.2.03,6.019,24] pentacosa-8,16(25),7,19(24)-tetraene-22,1'-tetralin]-11-carboxylate and tert-butyl (3R,6R,7R,8Z,12S,22S)-6'-chloro-7-methoxy-12-methyl-13,15,15-trioxo-spiro[20-oxa-15-thia-1,11,14-triazatetracyclo[14.7.2.03,6.019,24] pentacosa-8,16(25), 17, 19(24)-tetraene-22,1'-tetralin]-11-carboxylate

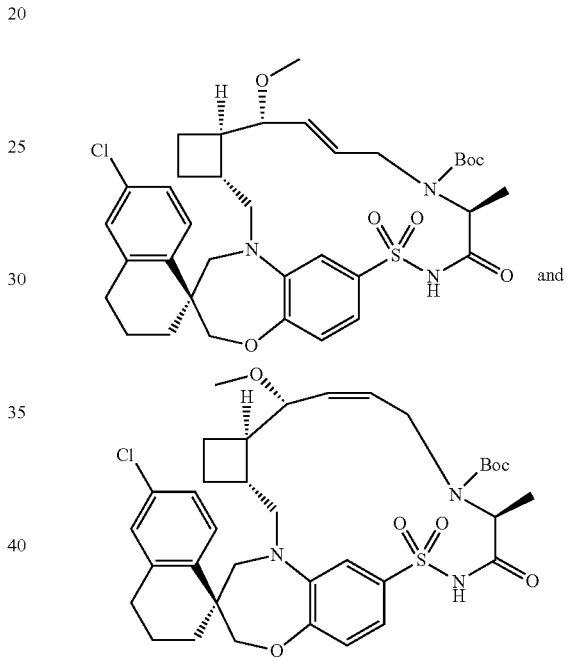

This compound was prepared using procedures analogous to those described for Example 26 Step 4 using tert-butyl N-allyl-N-[(1S)-1-methyl-2-oxo-2-[[(3S)-6'-chloro-5-[[(1R, 2R)-2-[(1R)-1-methoxyallyl]cyclobutyl]methyl]spiro[2,4-dihydro-1,5-benzoxazepine-3,1'-tetralin]-7-yl]sulfonylamino]ethyl]carbamate (81.3 mg, 0.11 mmol) in DCE (110 mL) at 80° C. overnight and purified by flash chromatography on a silica gel column (12 g) with EtOAc/Heptanes (2% to 50%) to afford two products: P1 (the earlier eluted product, 29.8 mg, 38.1% yield) and P2 (the latter eluted product, 21.7 mg, 27% yield).

P1 was assigned to tert-butyl (3R,6R,7R,8Z,12S,22S)-6'-chloro-7-methoxy-12-methyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-11-carboxylate, and P2 was assigned to tert-butyl (3R,6R,7R,8E,12S,22S)-6'-chloro-7-methoxy-12-methyl-13,15,15-trioxo-spiro[20-oxa-15-thia-1,11,14-triazatetracyclo[14.7.2.03,6.019,24]pentacosa-8,16(25),17, 19(24)-tetraene-22,1'-tetralin]-11-carboxylate.

Step 5: (3R,6R,7R,8E,12S,22S)-6'-chloro-7-methoxy-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one tert-butyl (3R,6R,7R,8E,12S,22S)-6'-chloro-7-methoxy-12-methyl-13,15,15-trioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-11-carboxylate (21.7 mg, 0.03 mmol, P2 Step 4) was treated with 2 N HCl in EA (0.5 mL). The reaction mixture was stirred at r.t. overnight and quenched with sat. NaHCO₃ aq. solution. The mixture was extracted with DCM (2 mL×2). The combined organic layers were dried over Na₂SO₄, filtered and concentrated under reduced pressure. The residue was purified by prep-HPLC on C18 column (30×250 mm, 10 m) using MeCN/H₂O (20% to 100%) to afford (3R,6R,7R,8E,12S,22S)-6'-chloro-7-methoxy-12-methyl-15,15-dioxo-spiro[20-oxa-15-thia-1,11,14-triazatetracyclo[14.7.2.0³,⁶.0¹⁹,²⁴]pentacosa-8,16(25),17, 19(24)-tetraene-22,1'-tetralin]-13-one (9.4 mg, 48.7% yield). LC-MS calc. for $C_{31}H_{39}ClN_3O_5S$ [M+H]⁺: m/z=600.22/602.22; Found=599.9/601.7. ¹H NMR (400 MHz, CDCl₃) δ 7.71 (d, J=8.5 Hz, 1H), 7.32 (s, 1H), 7.15 (s, 1H), 7.10 (d, J=1.8 Hz, 1H), 6.93 (d, J=8.1 Hz, 1H), 5.45 (dd, J=15.3, 8.8 Hz, 2H), 5.39-5.24 (m, 2H), 4.13 (d, J=12.0 Hz, 1H), 4.01 (d, J=12.3 Hz, 1H), 3.87-3.65 (m, 2H), 3.65-3.48 (m, 2H), 3.48-3.38 (m, 1H), 3.32 (d, J=14.6 Hz, 2H), 3.23 (s, 1H), 3.13 (d, J=8.2 Hz, 1H), 3.03 (dd, J=15.2, 6.0 Hz, 2H), 2.87-2.68 (m, 1H), 2.64 (s, 4H), 2.31 (d, J=3.4 Hz, 2H), 2.02 (d, J=13.6 Hz, 2H), 1.97-1.53 (m, 3H), 1.53-1.22 (m, 2H), 1.16 (dd, J=6.0, 3.4 Hz, 2H).

Example 118

(3R,6R,7R,8Z,12S,22S)-6'-Chloro-7-methoxy-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one

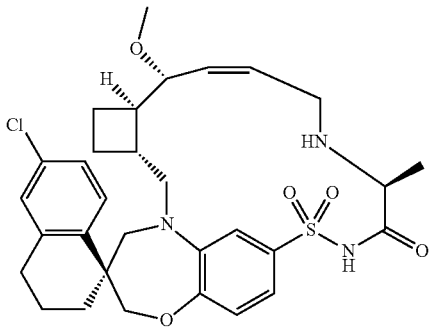 [SMILES: CO[C@@H]1/C=C\CN[C@@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 117 using tert-butyl (3R,6R,7R,8Z,12S,22S)-6'-chloro-7-methoxy-12-methyl-13,15,15-trioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-1-carboxylate (P1, Example 117, step 4) in Step 5. LC-MS calc. for $C_{31}H_{39}ClN_3O_5S$ [M+H]⁺: m/z=600.9/602.22; Found: 600.9/602.1. ¹H NMR (400 MHz, CDCl₃) δ 7.68 (d, J=8.5 Hz, 1H), 7.41 (dd, J=8.3, 1.7 Hz, 1H), 7.18 (dd, J=8.8, 2.4 Hz, 2H), 7.08 (d, J=2.1 Hz, 1H), 6.94 (d, J=8.3 Hz, 1H), 5.58 (d, J=5.1 Hz, 2H), 4.08 (s, 2H), 3.78-3.55 (m, 3H), 3.48-3.25 (m, 4H), 3.22 (s, 2H), 3.07 (dd, J=15.2, 8.0 Hz, 1H), 2.85-2.65 (m, 2H), 2.65-2.50 (m, 5H), 2.40-2.30 (m, 1H), 2.01 (d, J=14.6 Hz, 1H), 1.87 (ddd, J=32.6, 16.9, 6.0 Hz, 4H), 1.65-1.49 (m, 2H), 1.49-1.34 (m, 3H).

Example 119

(3R,6R,7R,8E,22S)-6'-Chloro-7-methoxy-12,12-ethylene-15,15-dioxo-spiro[20-oxa-15-thia-1,11,14-triazatetracyclo[14.7.2.0³,⁶.0¹⁹,²⁴]pentacosa[8,16(25),17,19(24)]tetraene-22,1'-tetralin]-13-one

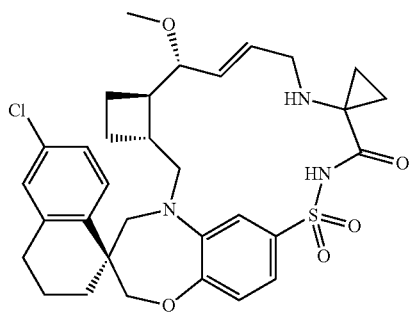 [SMILES: CO[C@@H]1/C=C/CNC2(CC2)C(=O)NS(=O)(=O)c2ccc3c(c2)N(C[C@@H]2CC[C@H]21)C[C@@]1(CCCc2cc(Cl)ccc21)CO3]

Step 1: 1-(allyl(tert-butoxycarbonyl)amino)cyclopropane-1-carboxylic acid

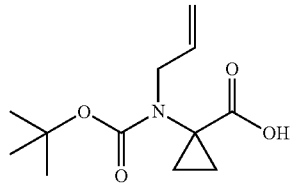 [SMILES: C=CCN(C(=O)OC(C)(C)C)C1(C(=O)O)CC1]

This compound was prepared using procedures analogous to those described for Example 116 Step 2-3 using ethyl 1-(tert-butoxycarbonylamino)cyclopropanecarboxylate to replace ethyl 1-(tert-butoxycarbonylamino)cyclobutanecarboxylate in Step 2.

Step 2. (3R,6R,7R,8E,22S)-6'-chloro-7-methoxy-12,12-ethylene-15,15-dioxo-spiro[20-oxa-15-thia-1,11,14-triazatetracyclo[14.7.2.0³,⁶.0¹⁹,²⁴]pentacosa[8,16(25),17,19(24)]tetraene-22,1'-tetralin]-13-one This compound was prepared using procedures analogous to those described for Example 26 Step 3-5 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and 1-(allyl(tert-butoxycarbonyl)amino)cyclopropane-1-carboxylic acid in Step 3. LC-MS calc. for $C_{32}H_{39}ClN_3O_5S$ [M+H]⁺: m/z=612.22/614.22; Found: 611.9/614.2. ¹H NMR (600 MHz, CDCl₃) δ 7.69 (d, J=8.5 Hz, 1H), 7.46 (d, J=7.9 Hz, 1H), 7.31 (s, 1H), 7.18 (dd, J=8.5, 2.0 Hz, 1H), 7.08 (d, J=2.0 Hz, 1H), 6.98 (d, J=8.3 Hz, 1H), 5.40 (d, J=4.0 Hz, 2H), 4.08 (dd, J=37.7, 12.1 Hz, 2H), 3.79-3.67 (m, 2H), 3.29 (dd, J=34.7, 13.2 Hz, 2H), 3.20-3.07 (m, 5H), 3.04 (dd, J=15.2, 6.4 Hz, 1H), 2.84-2.63 (m, 3H), 2.37 (s, 1H), 2.00

(d, J=13.3 Hz, 1H), 1.95-1.72 (m, 4H), 1.69-1.49 (m, 4H), 1.44-1.35 (m, 2H), 1.17-1.11 (m, 1H), 1.08 (dd, J=12.8, 8.7 Hz, 1H), 0.95 (tdd, J=15.5, 9.4, 6.0 Hz, 1H).

Example 120

(3R,6R,7R,8E,22S)-6'-Chloro-7-methoxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

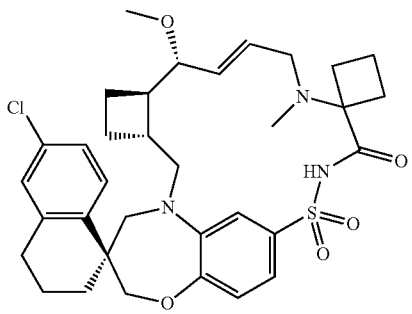 [SMILES: CO[C@@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 27 using (3R,6R,7R,8E,22S)-6'-chloro-7-methoxy-12,12-(1,3-propylene)-15,15-dioxo-spiro[20-oxa-15-thia-1,11,14-triazatetracyclo[14.7.2.03,6.019,24]pentacosa-[8,16(25),17,19(24)]tetraene-22,1'-tetralin]-13-one (Example 116) and formaldehyde aqueous solution (37%). LC-MS calc. for $C_{34}H_{43}ClN_3O_5S$ [M+H]$^+$: m/z=640.25/642.25; Found: 640.0/642.2. $^1$H NMR (600 MHz, CDCl$_3$) δ 7.67 (d, J=8.5 Hz, 1H), 7.45 (d, J=16.9 Hz, 1H), 7.16 (d, J=7.7 Hz, 1H), 7.08 (t, J=4.6 Hz, 1H), 6.90 (s, 2H), 5.41 (dd, J=14.8, 9.0 Hz, 1H), 4.07 (dd, J=33.9, 11.7 Hz, 2H), 3.71 (d, J=14.7 Hz, 1H), 3.48 (s, 1H), 3.34 (d, J=15.0 Hz, 1H), 3.26 (s, 3H), 2.97 (dd, J=34.6, 21.1 Hz, 1H), 2.85-2.66 (m, 2H), 2.49 (s, 1H), 2.42 (s, 3H), 2.29 (s, 1H), 2.17 (s, 1H), 2.11-1.88 (m, 6H), 1.83 (d, J=8.0 Hz, 1H), 1.65 (s, 9H), 1.40 (t, J=12.9 Hz, 1H), 0.95-0.73 (m, 1H).

Example 121

(3R,6R,7R,8E,12R,22S)-6'-Chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one

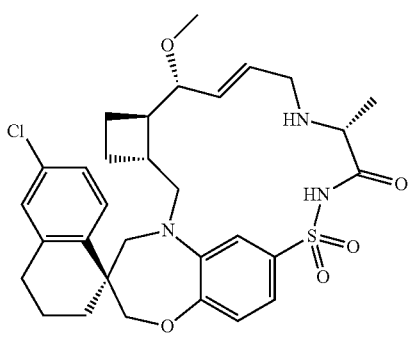 [SMILES: CO[C@@H]1/C=C/CN[C@H](C)C(=O)NS(=O)(=O)c2ccc3c(c2)N(C[C@@H]2CC[C@H]21)C[C@@]1(CCCc2cc(Cl)ccc21)CO3]

Step 1: (2R)-2-[allyl(tert-butoxycarbonyl)amino] propanoic acid

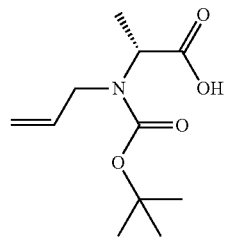 [SMILES: C=CCN(C(=O)OC(C)(C)C)[C@H](C)C(=O)O]

This compound was prepared using procedures analogous to those described for Example 116 Step 2-3 using methyl (2R)-2-(tert-butoxycarbonylamino)propanoate to replace ethyl 1-(tert-butoxycarbonylamino)cyclobutanecarboxylate in Step 2.

Step 2: tert-butyl (3R,6R,7R,8E,12R,22S)-6'-chloro-7-methoxy-12-methyl-13,15,15-trioxo-spiro[20-oxa-15-thia-1,11,14-triazatetracyclo[14.7.2.03,6.019,24] pentacosa-8,16(25),7,19(24)-tetraene-22,1'-tetralin]-11-carboxylate and tert-butyl (3R,6R,7R,8Z,12R,22S)-6'-chloro-7-methoxy-12-methyl-13,15,15-trioxo-spiro[20-oxa-15-thia-1,11,14-triazatetracyclo [14.7.2.03,6.019,24]pentacosa-8,16(25),7,19(24)-tetraene-22,1'-tetralin]-11-carboxylate

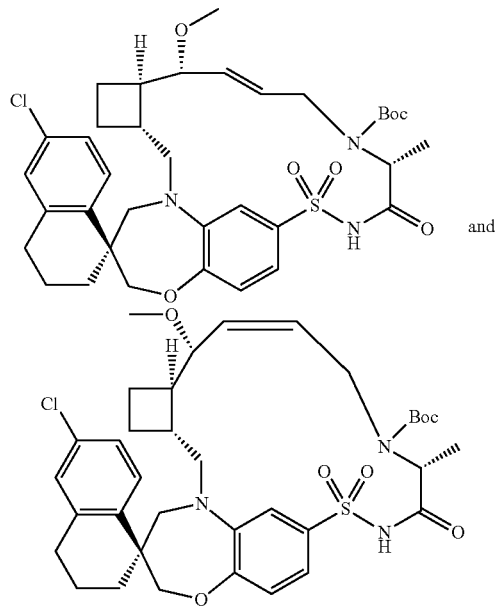

These two compounds were prepared using procedures analogous to those described for Example 117 Step 2-3 using (2R)-2-[allyl(tert-butoxycarbonyl)amino]propanoic acid to replace (2S)-2-[allyl(tert-butoxycarbonyl)amino] propanoic acid in Step 2. P1 (the earlier eluted product) was assigned to the cis-isomer and P2 (the earlier eluted product) was assigned to the trans-isomer.

Step 3: (3R,6R,7R,8E,12R,22S)-6'-chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one This compound was prepared using procedures analogous to those described for Example 117 Step 5 using tert-butyl (3R,6R,7R,8E,12R,22S)-6'-chloro-7-methoxy-12-methyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-11-carboxylate (P2). LC-MS calc. for $C_{31}H_{39}ClN_3O_5S$ [M+H]$^+$: m/z=600.22/602.22; Found: 599.9/602.0. $^1$H NMR (600 MHz, CDCl$_3$) δ 7.68 (d, J=8.5 Hz, 1H), 7.34 (d, J=8.3 Hz, 1H), 7.30 (s, 1H), 7.16 (d, J=8.4 Hz, 1H), 7.08 (s, 1H), 6.95 (d, J=8.3 Hz, 1H), 5.42-5.26 (m, 2H), 4.12 (d, J=12.1 Hz, 1H), 4.04 (d, J=12.1 Hz, 1H), 3.77-3.63 (m, 3H), 3.31 (d, J=14.5 Hz, 1H), 3.16 (d, J=6.9 Hz, 1H), 3.12 (s, 3H), 3.03 (dd, J=15.1, 6.4 Hz, 3H), 2.85-2.71 (m, 2H), 2.71-2.59 (m, 1H), 2.28 (td, J=14.0, 9.1 Hz, 1H), 2.00 (t, J=6.8 Hz, 2H), 1.94-1.69 (m, 7H), 1.64 (dd, J=19.0, 9.5 Hz, 2H), 1.40 (d, J=7.0 Hz, 2H).

Example 122

(3R,6R,7R,8Z,12R,22S)-6'-Chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one

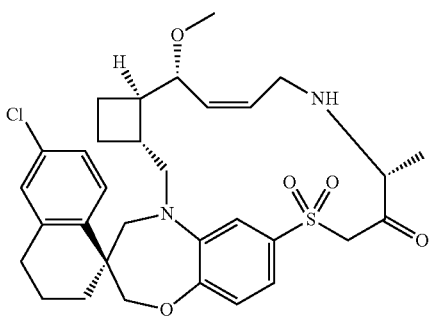 [SMILES: CO[C@@H]1/C=C\CN[C@H](C)C(=O)CS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 117 Step 5 using tert-butyl (3R,6R,7R,8Z,12R,22S)-6'-chloro-7-methoxy-12-methyl-13,15,15-trioxo-spiro[20-oxa-15-thia-1,11,14-triazatetracyclo[14.7.2.03,6.019,24]-pentacosa-8,16(25),17,19(24)-tetraene-22,1'-tetralin]-11-carboxylate (P1, Example 121 Step 2). LC-MS calc. for $C_{31}H_{39}ClN_3O_5S$ [M+H]$^+$: m/z=600.22/602.22; Found: 599.9/602.0. $^1$H NMR (600 MHz, CDCl$_3$) δ 7.68 (d, J=8.5 Hz, 1H), 7.44 (d, J=7.9 Hz, 1H), 7.17 (d, J=6.6 Hz, 2H), 7.08 (d, J=1.7 Hz, 1H), 6.94 (d, J=8.2 Hz, 1H), 5.53 (s, 2H), 4.11-4.03 (m, 2H), 3.75 (d, J=9.6 Hz, 1H), 3.69 (d, J=14.5 Hz, 1H), 3.53 (d, J=14.6 Hz, 1H), 3.33 (dd, J=42.0, 19.1 Hz, 4H), 3.21 (s, 3H), 3.06 (dd, J=14.8, 7.7 Hz, 1H), 2.82-2.69 (m, 2H), 2.60-2.51 (m, 1H), 2.40-2.32 (m, 1H), 2.01 (dd, J=15.3, 8.8 Hz, 1H), 1.86 (ddd, J=42.9, 24.7, 5.6 Hz, 5H), 1.65-1.53 (m, 2H), 1.41 (t, J=9.9 Hz, 4H), 1.27 (d, J=18.2 Hz, 1H).

Example 123

(3R,6R,7R,8E,12R,22S)-6'-Chloro-7-methoxy-11,12-dimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one

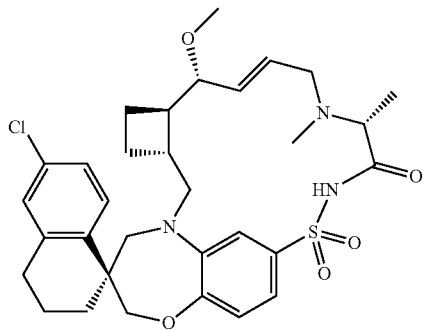 [SMILES: CO[C@@H]1/C=C/CN(C)[C@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 27 using (3R,6R,7R,8E,12R,22S)-6'-chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 121). LC-MS calc. for $C_{32}H_{41}ClN_3O_5S$ [M+H]$^+$: m/z=614.24/616.24; Found: 614.0/615.8. $^1$H NMR (600 MHz, CDCl$_3$) δ 7.68 (d, J=8.5 Hz, 1H), 7.50 (dd, J=8.4, 2.0 Hz, 1H), 7.18 (dd, J=8.5, 2.1 Hz, 1H), 7.08 (d, J=2.1 Hz, 1H), 6.97 (d, J=8.4 Hz, 2H), 5.74-5.67 (m, 1H), 5.44 (dd, J=15.7, 8.7 Hz, 1H), 4.09 (dd, J=24.3, 12.1 Hz, 2H), 3.71 (d, J=14.6 Hz, 1H), 3.50 (d, J=8.8 Hz, 1H), 3.44-3.37 (m, 1H), 3.35 (d, J=14.7 Hz, 1H), 3.23 (d, J=15.4 Hz, 2H), 3.09-3.02 (m, 2H), 2.97 (dd, J=14.9, 7.3 Hz, 1H), 2.87 (dd, J=14.9, 4.3 Hz, 1H), 2.81 (s, 1H), 2.80-2.72 (m, 2H), 2.55-2.46 (m, 2H), 2.37 (d, J=10.0 Hz, 2H), 2.15 (dd, J=15.0, 7.4 Hz, 1H), 2.06-1.89 (m, 4H), 1.83 (d, J=7.6 Hz, 2H), 1.72-1.36 (m, 2H), 1.35-1.19 (m, 2H), 0.97-0.76 (m, 2H).

Example 124

(3R,6R,7R,8Z,12R,22S)-6'-Chloro-7-methoxy-11,12-dimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one

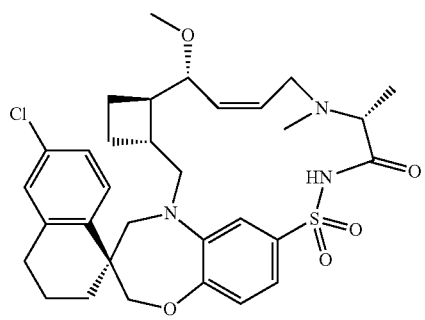 [SMILES: CO[C@@H]1/C=C\CN(C)[C@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 27 using (3R,6R,7R,8Z,12R,22S)-6'-chloro-7-methoxy-12-methyl-15,15-dioxo-spiro

[20-oxa-15-thia-1,11,14-triazatetracyclo[14.7.2.03,6.019, 24]pentacosa-8,16(25),17,19(24)-tetraene-22,1'-tetralin]-13-one (Example 122). LC-MS calc. for C$_{32}$H$_{41}$ClN$_3$O$_5$S [M+H]$^+$: m/z=614.24/616.24; Found: 614.0/615.8. $^1$H NMR (600 MHz, CDCl$_3$) δ 7.93 (d, J=7.9 Hz, 1H), 7.70 (d, J=8.7 Hz, 2H), 7.45 (dd, J=15.8, 7.4 Hz, 2H), 7.35 (d, J=8.5 Hz, 1H), 7.18 (dd, J=27.6, 9.5 Hz, 3H), 7.06 (dd, J=16.6, 8.7 Hz, 3H), 6.97 (s, 2H), 6.77 (dd, J=28.8, 20.2 Hz, 4H), 6.61 (s, 1H), 6.05 (s, 1H), 5.80-5.61 (m, 3H), 5.46 (s, 1H), 5.31 (dd, J=15.4, 8.3 Hz, 1H), 5.19 (s, 1H), 5.07 (s, 2H), 4.29 (d, J=11.2 Hz, 2H), 4.06 (d, J=10.7 Hz, 3H), 3.85-3.71 (m, 3H), 3.71-3.18 (m, 20H), 2.87 (ddt, J=92.3, 76.4, 36.2 Hz, 20H), 2.47 (d, J=30.6 Hz, 4H), 2.23 (t, J=38.8 Hz, 10H), 2.11-1.74 (m, 20H), 1.74-1.45 (m, 10H), 1.45-1.18 (m, 12H), 1.18-0.95 (m, 10H), 0.89 (ddd, J=29.8, 15.5, 8.0 Hz, 4H).

Example 125

(3R,6R,7R,8E,12S,22S)-6'-Chloro-7-methoxy-12-(methoxymethyl)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one

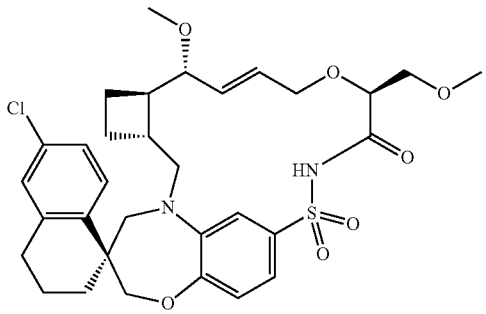 [SMILES: COC[C@@H]1OC/C=C/[C@@H](OC)[C@@H]2CC[C@H]2CN2C[C@@]3(CCCc4cc(Cl)ccc43)COc3ccc(cc32)S(=O)(=O)NC1=O]

Step 1: methyl (2S)-2-hydroxy-3-methoxy-propanoate

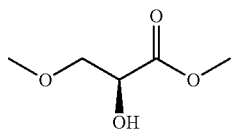

Mg(ClO$_4$)$_2$ (819 mg, 3.67 mmol) was added to methyl (2S)-oxirane-2-carboxylate (1.5 g, 14.69 mmol) in methanol (2 mL) under stirring vigorously. The reaction mixture was heated to 80° C. for 20 h. After the reaction was completed (monitored by GC, GC:SM Rt=4.68 min, product Rt=6.0 min), the mixture was cooled to r.t., filtered and concentrated under reduced pressure. The residue was re-dissolved in heptane, filtered again and concentrated to remove MeOH completely. The residue (1.97 g) was used for next step directly.

Step 2: methyl (2S)-2-allyloxy-3-methoxy-propanoate

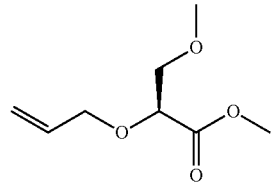

Allyl bromide (3.55 g, 29 mmol) was added to methyl (2S)-2-hydroxy-3-methoxy-propanoate (1.97 g, 14 mmol) in tert-butyl methyl ether (40 mL) and followed by addition of silver(I) oxide (6.8 g, 29 mmol) for 3 d. The reaction was filtered through a pad of Celite and the filtrate was concentrated under reduced pressure. The residue was purified by flash chromatography on a silica gel column (20 g) using EtOAc/Heptanes (2% to 30%) to afford methyl (2S)-2-allyloxy-3-methoxy-propanoate (810.9 mg, 31.7% yield).

Step 3. (2S)-2-allyloxy-3-methoxy-propanoic acid

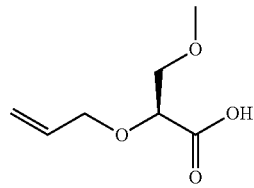

This compound was prepared using procedures analogous to those described for Example 86 Step 2 using methyl (2S)-2-allyloxy-3-methoxy-propanoat and LiOH.

Step 3. (3R,6R,7R,8E,12S,22S)-6'-chloro-7-methoxy-12-(methoxymethyl)-15,15-dioxo-spiro[11, 20-dioxa-15-thia-1,14-diazatetracyclo[14.7.2.03, 6.019,24]pentacosa-8,16(25), 17, 19(24)-tetraene-22,1'-tetralin]-13-one This compound was prepared using procedures analogous to those described for Example 26 Step 3-4 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide and (2S)-2-allyloxy-3-methoxy-propanoic acid. LC-MS calc. for C$_{32}$H$_{40}$ClN$_2$O$_7$S [M+H]$^+$: m/z=631.22/633.21; Found: 631.0/632.8. $^1$H NMR (600 MHz, CDCl$_3$) δ 7.67 (d, J=8.5 Hz, 1H), 7.41 (d, J=7.8 Hz, 1H), 7.24 (s, 1H), 7.18 (d, J=8.2 Hz, 1H), 7.09 (d, J=1.8 Hz, 1H), 6.99 (d, J=8.2 Hz, 1H), 5.46 (d, J=15.6 Hz, 1H), 5.39 (dd, J=15.6, 8.3 Hz, 1H), 4.51-4.43 (m, 1H), 4.12 (dd, J=23.8, 11.9 Hz, 2H), 3.84-3.75 (m, 2H), 3.69 (d, J=13.8 Hz, 2H), 3.60 (dd, J=10.3, 5.6 Hz, 1H), 3.56-3.46 (m, 1H), 3.40 (s, 3H), 3.35 (d, J=14.6 Hz, 1H), 3.23-3.13 (m, 2H), 3.11 (s, 3H), 2.83-2.63 (m, 3H), 2.35-2.25 (m, 1H), 2.06-1.97 (m, 1H), 1.97-1.77 (m, 4H), 1.77-1.66 (m, 1H), 1.63 (dt, J=18.8, 9.5 Hz, 2H), 1.45 (t, J=12.5 Hz, 1H).

Example 126

(3R,6R,7R,8E,12S,22S)-6'-Chloro-7-methoxy-12-cyclopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

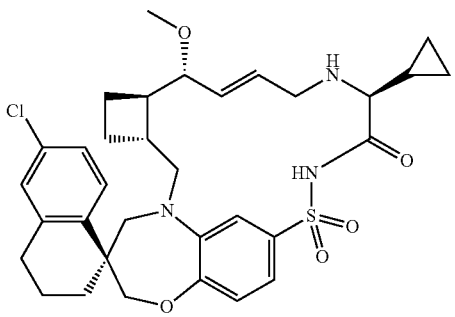 [SMILES: CO[C@@H]1/C=C/CN[C@@H](C2CC2)C(=O)NS(=O)(=O)c2ccc3c(c2)N(C[C@@H]2CC[C@H]21)C[C@@]1(CCCc2cc(Cl)ccc21)CO3]

Step 1: (S)-2-(allyl(tert-butoxycarbonyl)amino)-2-cyclopropylacetic Acid

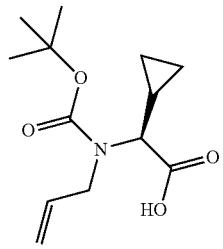 [SMILES: C=CCN(C(=O)OC(C)(C)C)[C@H](C(=O)O)C1CC1]

To a suspension of (2S)-2-(tert-butoxycarbonylamino)-2-cyclopropyl-acetic acid (1500 mg, 6.97 mmol) in THF (20 mL) was added sodium hydride (60% in oil) (351 mg, 14.6 mmol) and the reaction mixture was stirred at r.t. for 20 min. Allyl bromide (927 mg, 7.67 mmol) was added drop-wise. After addition, the reaction was stirred at 50° C. overnight. The reaction was quenched with 10 mL saturated aqueous NH$_4$Cl and extracted with EtOAc (2×20 mL). The combined organic extracts were washed with water and brine, dried over Na$_2$SO$_4$, filtered and concentrated under reduced pressure. The residue was purified by flash chromatography on a silica gel column with EtOAc/Hept (3% to 8%) to afford (2S)-2-[allyl(tert-butoxycarbonyl)amino]-2-cyclopropyl-acetic acid (840 mg, 47% yield) as a colorless oil.

Step 2: (3R,6R,7R,8E,12S,22S)-6'-chloro-7-methoxy-12-cyclopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one This compound was prepared using procedures analogous to those described for Example 26 Step 3-5 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (S)-2-(allyl(tert-butoxycarbonyl)amino)-2-cyclopropylacetic acid in Step 3. LC-MS calc. for C$_{33}$H$_{41}$ClN$_3$O$_5$S [M+H]$^+$: m/z=626.24/628.23; Found: 626.0/628.2. $^1$H NMR (600 MHz, CDCl$_3$) δ 7.68 (d, J=8.5 Hz, 1H), 7.37 (dd, J=8.3, 2.1 Hz, 1H), 7.32 (s, 1H), 7.17 (dd, J=8.5, 2.3 Hz, 1H), 7.11-7.06 (m, 1H), 6.97 (d, J=8.3 Hz, 1H), 5.39-5.32 (m, 1H), 5.28 (d, J=5.6 Hz, 1H), 4.14-4.01 (m, 2H), 3.71 (d, J=14.6 Hz, 1H), 3.69-3.59 (m, 2H), 3.31 (d, J=14.6 Hz, 1H), 3.12 (s, 3H), 3.02 (dd, J=14.9, 6.7 Hz, 2H), 2.88 (d, J=13.5 Hz, 1H), 2.83-2.70 (m, 2H), 2.65 (q, J=8.3 Hz, 1H), 2.32-2.18 (m, 2H), 2.00 (d, J=13.5 Hz, 2H), 1.94-1.78 (m, 4H), 1.80-1.69 (m, 2H), 1.64 (p, J=11.1, 10.4 Hz, 2H), 1.46-1.37 (m, 1H), 1.02 (d, J=7.2 Hz, 1H), 0.73-0.54 (m, 3H).

Example 127

(3R,6R,7R,8E,12S,22S)-6'-Chloro-12-cyclopropyl-7-methoxy-11-methyl-15,15-dioxo-spiro[20-oxa-15-thia-1,11,14-triazatetracyclo[14.7.2.0~3,6.0~19,24]pentacosa-8,16,18,24-tetraene-22,1'-tetralin]-13-one

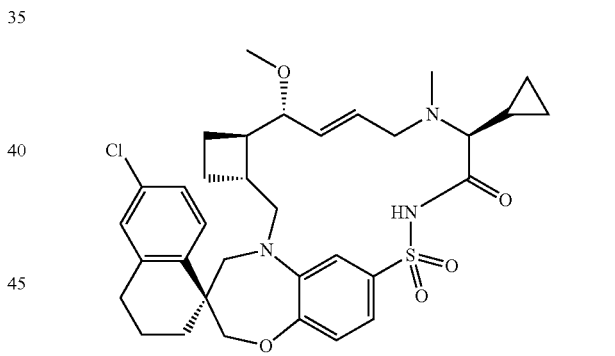

This compound was prepared using procedures analogous to those described for Example 27 using (3R,6R,7R,8E,12S,22S)-6'-chloro-12-cyclopropyl-7-methoxy-15,15-dioxo-spiro[20-oxa-15-thia-1,11,14-triazatetracyclo[14.7.2.0~3,6.0~19,24]pentacosa-8,16,18,24-tetraene-22,1'-tetralin]-13-one (Example 126). LC-MS calc. for C$_{34}$H$_{42}$ClN$_3$O$_5$S [M+H]$^+$: m/z=640.3/642.3; Found: 640.0/642.2. $^1$H NMR (600 MHz, DMSO-d$_6$) δ 7.65 (d, J=8.5 Hz, 1H), 7.26 (dd, J=8.5, 2.3 Hz, 1H), 7.17 (d, J=2.3 Hz, 1H), 7.13 (dd, J=8.2, 1.9 Hz, 1H), 6.85 (d, J=8.1 Hz, 1H), 6.82 (d, J=2.0 Hz, 1H), 6.08 (dd, J=13.4, 6.9 Hz, 1H), 5.70-5.58 (m, 1H), 4.00 (s, 2H), 3.55 (t, J=12.7 Hz, 2H), 3.33 (s, 6H), 3.19 (s, 3H), 3.04 (dd, J=15.2, 10.0 Hz, 1H), 2.78 (s, 4H), 2.13-2.04 (m, 1H), 2.04-1.94 (m, 2H), 1.94-1.87 (m, 2H), 1.84 (dq, J=10.2, 5.5, 4.7 Hz, 2H), 1.69 (p, J=10.2 Hz, 2H), 1.39 (q, J=6.9 Hz, 1H), 1.04 (ddt, J=13.4, 9.2, 4.5 Hz, 1H), 0.89-0.83 (m, 1H), 0.70 (td, J=8.6, 7.5, 4.0 Hz, 1H), 0.60 (tt, J=8.8, 3.4 Hz, 1H), 0.56-0.47 (m, 2H).

Example 128

(3R,6R,7R,8E,12S,22S)-6'-Chloro-7-methoxy-12-isopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

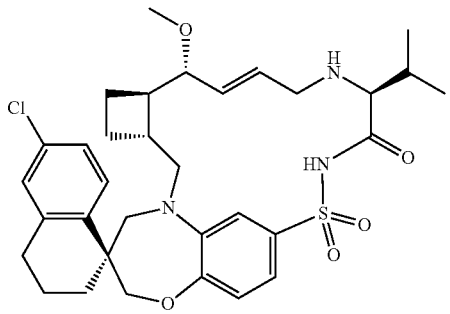

Step 1: (S)-2-(allyl(tert-butoxycarbonyl)amino)-3-methyl-butanoic acid

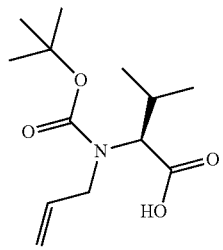 [SMILES: C=CCN(C(=O)OC(C)(C)C)[C@H](C(=O)O)C(C)C]

This compound was prepared using procedures analogous to those described for Example 116 Step 2-3 using methyl (2S)-2-(tert-butoxycarbonylamino)-3-methyl-butanoate to replace ethyl 1-(tert-butoxycarbonylamino)cyclobutanecarboxylate in Step 2.

Step 2: (3R,6R,7R,8E,12S,22S)-6'-chloro-7-methoxy-12-isopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one This compound was prepared using procedures analogous to those described for Example 26 Step 3-5 using (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (Intermediate 8) and (S)-2-(allyl(tert-butoxycarbonyl)amino)butanoic acid in Step 3. LC-MS calc. for $C_{33}H_{43}ClN_3O_5S$ [M+H]$^+$: m/z=628.25/630.25; Found: 628.1/629.8. $^1$H NMR (600 MHz, CDCl$_3$) δ 7.68 (dd, J=8.6, 3.9 Hz, 1H), 7.38 (s, 1H), 7.26 (s, 1H), 7.16 (d, J=9.6 Hz, 1H), 7.11-7.01 (m, 1H), 6.91 (s, 1H), 5.58-5.17 (m, 2H), 4.19-3.92 (m, 2H), 3.77-3.60 (m, 2H), 3.32 (d, J=14.6 Hz, 1H), 3.15 (d, J=25.0 Hz, 3H), 3.02 (dd, J=15.0, 6.7 Hz, 1H), 2.94 (s, 1H), 2.86-2.69 (m, 2H), 2.65 (s, 1H), 2.23 (dd, J=18.4, 10.8 Hz, 1H), 2.11-1.95 (m, 2H), 1.95-1.69 (m, 4H), 1.62 (dq, J=28.8, 9.6 Hz, 2H), 1.45-1.35 (m, 1H), 1.35-1.21 (m, 3H), 1.09-0.97 (m, 4H), 0.94 (d, J=6.9 Hz, 1H), 0.88 (t, J=6.9 Hz, 1H).

Example 129

(3R,6R,7R,8E,12S,22S)-6'-Chloro-7-methoxy-11-methyl-12-isopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

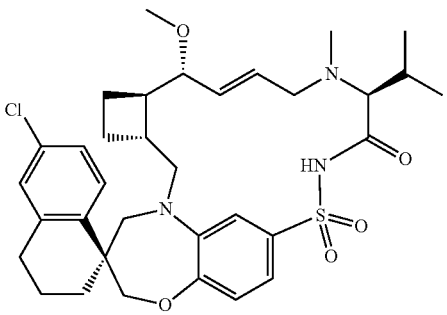 [SMILES: CO[C@@H]1/C=C/CN(C)[C@@H](C(C)C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 27 using (3R,6R,7R,8E,12S,22S)-6'-chloro-7-methoxy-12-isopropyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 128). LC-MS calc. for $C_{34}H_{45}ClN_3O_5S$ [M+H]$^+$: m/z=642.27/644.27; Found: 642.0/643.8. $^1$H NMR (400 MHz, CDCl$_3$) δ 7.70 (d, J=8.5 Hz, 1H), 7.52 (dd, J=8.4, 2.1 Hz, 1H), 7.28 (s, 1H), 7.20 (dd, J=8.5, 2.4 Hz, 1H), 7.10 (d, J=2.3 Hz, 1H), 7.05-6.93 (m, 1H), 6.07-5.16 (m, 2H), 4.28-3.97 (m, 2H), 3.82-3.68 (m, 1H), 3.53-3.26 (m, 4H), 3.20-2.91 (m, 2H), 2.91-2.66 (m, 3H), 2.58-2.14 (m, 4H), 2.14-1.90 (m, 5H), 1.91-1.54 (m, 5H), 1.54-1.37 (m, 3H), 1.32-1.20 (m, 6H).

Example 130

(3R,6R,7R,8Z,21S)-6'-Chloro-7-methoxy-14,14-dioxo-spiro[19-oxa-14-thia-1,11,13-triazatetracyclo[13.7.2.03,6.018,23]tetracosa-8,15,17,23-tetraene-21,1'-tetralin]-12-one and Example 131

(3R,6R,7R,8E,21S)-6'-chloro-7-methoxy-14,14-dioxo-spiro[19-oxa-14-thia-1,11,13-triazatetracyclo[13.7.2.03,6.018,23]tetracosa-8,15,17,23-tetraene-21,1'-tetralin]-12-one Example 130

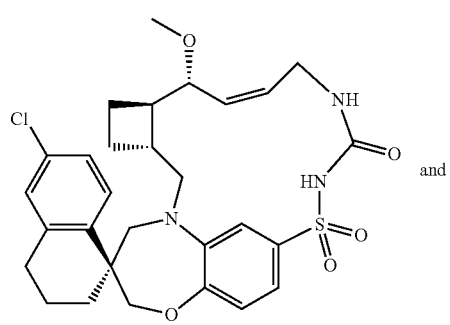

and

Example 131

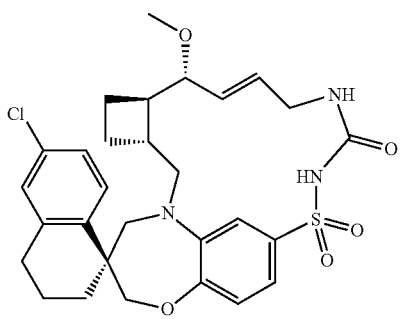

Step 1: 1-allyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea

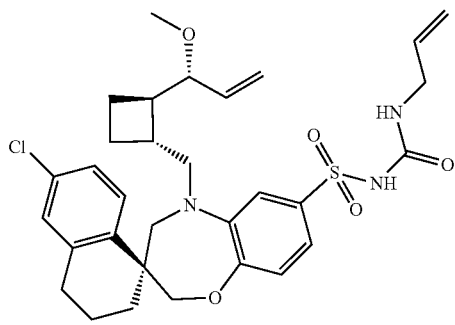 [SMILES: C=CCNC(=O)NS(=O)(=O)c1ccc2c(c1)N(C[C@@H]1CC[C@H]1[C@@H](C=C)OC)C[C@@]1(CCCc3cc(Cl)ccc31)CO2]

To a stirred solution of (3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-sulfonamide (120.0 mg, 0.23 mmol, Intermediate 8) in MeCN (5 mL) was added triethylamine (0.19 mL, 1.39 mmol) followed by phenyl chloroformate (0.09 mL, 0.70 mmol). The resulting mixture was stirred at r.t. for 20 min. LC-MS showed the consumption of starting material. Allylamine (0.35 mL, 4.6 mmol) was added and the reaction was stirred at r.t. overnight. Water (10 mL) was added, and extracted with EtOAc (10 mL×3). The combined organic layers were dried over sodium sulfate, filtered and concentrated under reduced pressure. The residue was purified by flash chromatography on a silica gel column (12 g) with EtOAc/Heptanes (20% to 100%) to afford 1-allyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea (127 mg, 91% yield) as a white solid. LC-MS calc. for $C_{31}H_{39}ClN_3O_5S$ [M+H]$^+$: m/z=600.2/602.2; Found: 599.9/602.0.

Step 2: (3R,6R,7R,8Z,21S)-6'-chloro-7-methoxy-14,14-dioxo-spiro[19-oxa-14-thia-1,11,13-triazatetracyclo[13.7.2.0³,⁶.0¹⁸,²³]tetracosa-8,15,17,23-tetraene-21,1'-tetralin]-12-one and (3R,6R,7R,8E,21S)-6'-chloro-7-methoxy-14,14-dioxo-spiro[19-oxa-14-thia-1,11,13-triazatetracyclo[13.7.2.0³,⁶.0¹⁸,²³]tetracosa-8,15,17,23-tetraene-21,1'-tetralin]-12-one To a stirred solution of 1-allyl-3-[(3S)-6'-chloro-5-[[(1R,2R)-2-[(1R)-1-methoxyallyl]cyclobutyl]methyl]spiro[2,4-dihydro-1,5-benzoxazepine-3,1'-tetralin]-7-yl]sulfonyl-urea (108.0 mg, 0.18 mmol) in DCE (180 mL) was bubbled with nitrogen for 20 min. Then Hoveyda-Grubbs II (22.5 mg, 0.04 mmol) was added under nitrogen. The reaction was further bubbled with nitrogen for 10 min. The reaction was stirred at 80° C. under nitrogen overnight. The reaction was cooled to r.t. and bubbled with air for 30 min. to deactivate the catalyst. The residue was purified by flash chromatography on a silica gel column (12 g) using EtOAc/Heptanes (20% to 100%). The desired fractions were collected, concentrated and re-purified by prep-HPLC on C18 column (30×250 mm, 10 m) using MeCN/H$_2$O (20% to 100%) to afford two products: P1 as a white solid (the earlier eluted product, 7.4 mg, 7.2%) and P2 as a white solid (the latter eluted product, 32.4 mg, 31% yield).

P1 was assigned to the cis-isomer Example 130 (3R,6R,7R,8Z,21S)-6'-chloro-7-methoxy-14,14-dioxo-spiro[19-oxa-14-thia-1,11,13-triazatetracyclo[13.7.2.0³,⁶.0¹⁸,²³]tetracosa-8,15,17,23-tetraene-21,1'-tetralin]-12-one. LC-MS calc. for $C_{29}H_{35}ClN_3O_5S$ [M+H]$^+$: m/z=572.2/574.2; Found: 572.0/573.8. HPLC (cis isomer): C18 column (4.6×150 mm, 5 m); flow rate=1 mL/min; mobile phase: 60% MeCN/H$_2$O (with 0.1% TFA) 1 min, 60% to 95% 7 min, 95% 7 min; λ=220 nm. tR=6.7 min. $^1$H NMR (600 MHz, DMSO-d$_6$) δ 10.58 (s, 1H), 7.63 (d, J=8.6 Hz, 1H), 7.33 (d, J=7.8 Hz, 1H), 7.29-7.24 (m, 1H), 7.19 (dd, J=8.5, 2.7 Hz, 1H), 7.12-7.05 (m, 1H), 7.02-6.94 (m, 2H), 5.76-5.71 (m, 1H), 5.42 (dd, J=15.9, 7.8 Hz, 1H), 4.22 (q, J=11.5, 11.0 Hz, 1H), 4.14-3.96 (m, 3H), 3.67 (d, J=14.5 Hz, 1H), 3.54-3.47 (m, 1H), 3.47-3.39 (m, 2H), 3.11 (s, 3H), 2.80 (dq, J=16.4, 6.6, 5.5 Hz, 1H), 2.72 (ddt, J=16.6, 10.9, 4.9 Hz, 2H), 2.07-1.95 (m, 3H), 1.95-1.82 (m, 4H), 1.73-1.59 (m, 2H), 1.46 (t, J=12.1 Hz, 2H).

P2 was assigned to the trans-isomer Example 131 and (3R,6R,7R,8E,21S)-6'-chloro-7-methoxy-14,14-dioxo-spiro[19-oxa-14-thia-1,11,13-triazatetracyclo[13.7.2.0³,⁶.0¹⁸,²³]tetracosa-8,15,17,23-tetraene-21,1'-tetralin]-12-one. LC-MS calc. for $C_{29}H_{35}ClN_3O_5S$ [M+H]$^+$: m/z=572.2/574.2; Found: 571.9/573.7. HPLC (trans isomer): C18 column (4.6×150 mm, 5 m); flow rate=1 mL/min; mobile phase: 60% MeCN/H$_2$O (with 0.1% TFA) 1 min, 60% to 95% 7 min, 95% 7 min; λ=220 nm. tR=9.6 min. $^1$H NMR (600 MHz, DMSO-d$_6$) δ 10.54 (s, 1H), 7.68 (d, J=8.6 Hz, 1H), 7.27 (dd, J=8.5, 2.4 Hz, 1H), 7.21-7.11 (m, 3H), 7.05 (d, J=8.3 Hz, 1H), 6.99 (d, J=2.2 Hz, 1H), 5.66 (dt, J=15.8, 3.9 Hz, 1H), 5.40 (ddt, J=15.7, 7.5, 1.9 Hz, 1H), 4.20 (d, J=12.2 Hz, 1H), 4.07 (d, J=12.1 Hz, 1H), 3.88-3.73 (m, 2H), 3.63 (d, J=14.5 Hz, 1H), 3.52 (dd, J=7.4, 5.1 Hz, 1H), 3.42-3.30 (m, 3H), 3.25 (dd, J=14.9, 9.2 Hz, 1H), 3.11 (s, 3H), 2.85-2.77 (m, 1H), 2.73 (q, J=8.3 Hz, 1H), 2.22 (dq, J=8.8, 3.6 Hz, 1H), 2.03 (dt, J=13.5, 4.2 Hz, 1H), 1.92-1.83 (m, 4H), 1.71-1.60 (m, 1H), 1.56-1.42 (m, 2H).

Example 132

(3R,6R,7R,8E,12R,22S)-6'-Chloro-7-methoxy-11-ethyl-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one

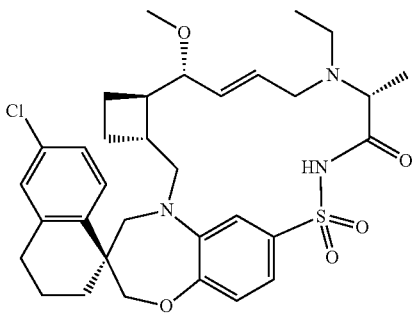 [SMILES: CCN1C/C=C/[C@@H](OC)[C@@H]2CC[C@H]2CN2C[C@@]3(CCCc4cc(Cl)ccc43)COc3ccc(cc32)S(=O)(=O)NC(=O)[C@H]1C]

This compound was prepared using procedures analogous to those described for Example 27 using (3R,6R,7R,8E,12R,22S)-6'-chloro-7-methoxy-12-methyl-15,15-dioxo-spiro[20-oxa-15-thia-1,11,14-triazatetracyclo[14.7.2.0³,⁶.0¹⁹,24]pentacosa-8,16(25),17,19(24)-tetraene-22,1'-tetralin]-13-one (Example 121) and acetaldehyde. LC-MS calc. for $C_{33}H_{43}ClN_3O_5S$ [M+H]⁺: m/z=628.25/630.25; Found: 628.0/630.2. ¹H NMR (300 MHz, CDCl₃) δ 7.70 (d, J=8.5 Hz, 1H), 7.54 (dd, J=8.4, 2.0 Hz, 1H), 7.19 (dd, J=8.5, 2.3 Hz, 1H), 7.09 (d, J=2.0 Hz, 1H), 7.03 (s, 1H), 6.99 (d, J=8.4 Hz, 1H), 5.84-5.68 (m, 1H), 5.48 (dd, J=15.4, 8.5 Hz, 1H), 4.10 (s, 2H), 3.81-3.67 (m, 1H), 3.59 (d, J=14.6 Hz, 2H), 3.48-3.37 (m, 1H), 3.37-3.28 (m, 2H), 3.26 (s, 3H), 3.23-3.13 (m, 1H), 3.05 (dd, J=15.2, 9.3 Hz, 1H), 2.88 (d, J=5.5 Hz, 1H), 2.85-2.64 (m, 4H), 2.51 (d, J=4.0 Hz, 1H), 2.30-2.14 (m, 1H), 1.90 (ddd, J=16.7, 13.7, 6.3 Hz, 4H), 1.74-1.53 (m, 2H), 1.48-1.36 (m, 1H), 1.28 (d, J=7.0 Hz, 4H), 1.10 (t, J=7.1 Hz, 3H).

Example 133

(3R,6R,7R,8E,12R,22S)-6'-Chloro-7-methoxy-11-acetyl-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one

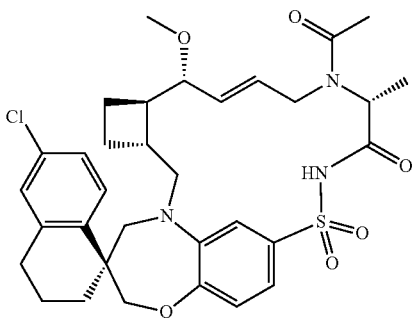 [SMILES: CO[C@@H]1/C=C/CN(C(C)=O)[C@H](C)C(=O)NS(=O)(=O)c2ccc3c(c2)N(C[C@@H]2CC[C@H]21)C[C@@]1(CCCc2cc(Cl)ccc21)CO3]

To a solution of (3R,6R,7R,8E,12R,22S)-6'-chloro-7-methoxy-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one (Example 87) (32.4 mg, 0.04 mmol) in DCM (0.50 mL) was added acetyl chloride (10.0 μL, 0.14 mmol) at r.t. The mixture was stirred for 10 min. and LC-MS indicated the reaction was completed. The mixture was concentrated under reduced pressure. The residue was purified by prep-HPLC on C18 column (30×250 mm, 10 m) with MeCN/H₂O (20% to 100%) (w/0.1% TFA) to afford the title product (9.9 mg, 35% yield). LC-MS calc. for $C_{33}H_{41}ClN_3O_6S$ [M+H]: m/z=642.23/644.23; Found: 642.0/644.2. ¹H NMR (300 MHz, CDCl₃) δ 9.62 (d, J=13.2 Hz, 1H), 7.69 (d, J=8.5 Hz, 1H), 7.50 (d, J=8.3 Hz, 1H), 7.37 (d, J=1.9 Hz, 1H), 7.19 (dd, J=8.5, 2.2 Hz, 1H), 7.10 (d, J=2.0 Hz, 1H), 7.01 (d, J=8.4 Hz, 1H), 5.44 (dd, J=15.3, 7.2 Hz, 1H), 5.20 (d, J=4.2 Hz, 1H), 5.00 (s, 1H), 4.14 (d, J=9.1 Hz, 2H), 3.84 (ddd, J=23.1, 15.6, 9.4 Hz, 3H), 3.66 (t, J=14.1 Hz, 2H), 3.40-3.19 (m, 3H), 3.19-3.04 (m, 4H), 2.89-2.50 (m, 4H), 2.36 (d, J=5.5 Hz, 1H), 2.15 (d, J=20.1 Hz, 3H), 2.08-1.54 (m, 4H), 1.45 (t, J=11.1 Hz, 4H).

Example 134

Methyl (3R,6R,7R,8E,12R,22S)-6'-Chloro-7-methoxy-12-methyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-11-carboxylate

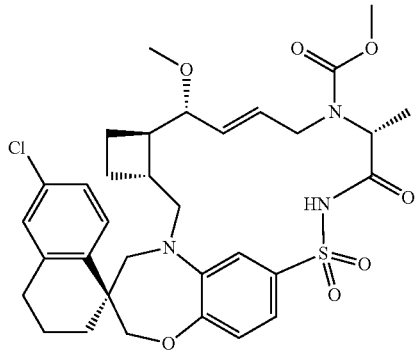 [SMILES: COC(=O)N1C/C=C/[C@@H](OC)[C@@H]2CC[C@H]2CN2C[C@@]3(CCCc4cc(Cl)ccc43)COc3ccc(cc32)S(=O)(=O)NC(=O)[C@H]1C]

This compound was prepared using procedures analogous to those described for Example 133 using (3R,6R,7R,8E,12R,22S)-6'-chloro-7-methoxy-12-methyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one (Example 121) and methyl chloroformate. LC-MS calc. for $C_{33}H_{41}ClN_3O_7S$ [M+H]⁺: m/z=658.23/660.23; Found: 658.4/660.3. ¹H NMR (600 MHz, CDCl₃) δ 7.68 (d, J=8.5 Hz, 1H), 7.49 (s, 1H), 7.29 (d, J=15.1 Hz, 1H), 7.17 (d, J=8.5 Hz, 1H), 7.08 (d, J=1.9 Hz, 1H), 6.99 (s, 1H), 5.48 (s, 1H), 4.57 (s, 1H), 4.09 (dd, J=30.4, 11.9 Hz, 2H), 3.90-3.80 (m, 1H), 3.80-3.60 (m, 6H), 3.25 (dd, J=27.0, 13.3 Hz, 2H), 3.19-3.09 (m, 2H), 3.07 (s, 1H), 2.84-2.69 (m, 2H), 2.65 (s, 1H), 2.35 (d, J=21.3 Hz, 2H), 1.99 (d, J=11.0 Hz, 1H), 1.97-1.86 (m, 1H), 1.80 (ddd, J=19.4, 16.4, 9.7 Hz, 2H), 1.64 (ddd, J=36.5, 19.0, 9.2 Hz, 5H), 1.45-1.36 (m, 3H), 1.35-1.28 (m, 1H).

Example 135

(3R,6R,7R,8E,12R,22S)-6'-Chloro-7-methoxy-12-methyl-11-methylsulfonyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

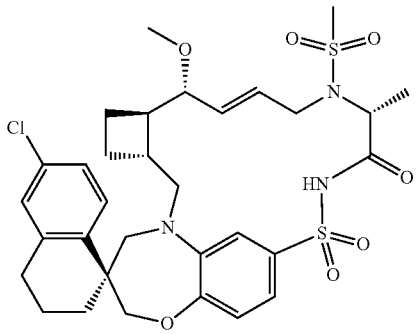 [SMILES: CO[C@@H]1/C=C/CN(S(C)(=O)=O)[C@H](C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 133 using (3R,6R,7R,8E,12R,22S)-6'-chloro-7-methoxy-12-methyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 121) and methanesulfonyl chloride. LC-MS calc. for $C_{32}H_{41}ClN_3O_7S_2$ [M+H]$^+$: m/z=678.2/680.2; Found: 678.4/680.3.

Example 136

(3R,6R,7S,8E,22S)-6'-Chloro-7-methoxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

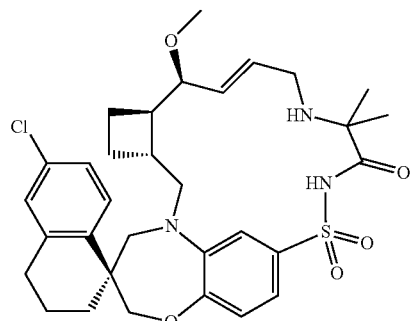

Step 1: 2-(allylamino)-N-[(3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-yl]sulfonyl-2-methyl-propanamide

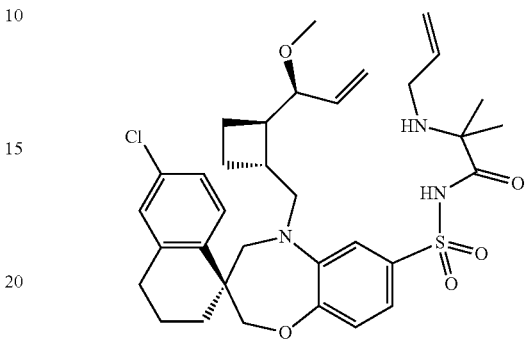

This compound was prepared using procedures analogous to those described for Example 43 Step 2 using (3R)-6'-chloro-5-[[(1R,2R)-2-[(1S)-1-methoxyallyl]cyclobutyl]methyl]spiro[2,4-dihydro-1,5-benzoxazepine-3,1'-tetralin]-7-sulfonamide (Intermediate 7) and 3-allyl-4,4-dimethyl-oxazolidine-2,5-dione (Example 43 Step 1). LC-MS calc. for $C_{34}H_{45}ClN_3O_5S$ [M+H]$^+$: m/z=642.28/644.28; Found: 642.9/644.8.

Step 2: (3R,6R,7S,8E,22S)-6'-chloro-7-methoxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one This compound was prepared using procedures analogous to those described for Example 26 Step 4 using 2-(allylamino)-N-[(3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-yl]sulfonyl-2-methyl-propanamide.- LC-MS calc. for $C_{32}H_{41}ClN_3O_5S$ [M+H]$^+$: m/z=614.24/616.24; Found: 614.8/616.7. $^1$H NMR (600 MHz, DMSO-$d_6$) δ 7.60 (d, J=8.5 Hz, 1H), 7.22 (dd, J=8.5, 2.3 Hz, 1H), 7.17 (d, J=2.2 Hz, 1H), 7.16 (d, J=1.8 Hz, 1H), 6.96 (s, 1H), 6.85 (d, J=8.2 Hz, 1H), 5.74 (s, 1H), 5.58 (dd, J=15.8, 6.0 Hz, 1H), 4.08-3.85 (m, 3H), 3.48 (d, J=14.3 Hz, 2H), 3.38 (dd, J=14.6, 7.9 Hz, 1H), 3.29-3.24 (m, 2H), 3.20 (s, 3H), 3.15 (dt, J=14.5, 5.0 Hz, 1H), 2.83-2.76 (m, 1H), 2.75-2.68 (m, 1H), 2.64-2.56 (m, 1H), 2.41-2.29 (m, 1H), 2.01 (ddt, J=13.7, 9.0, 4.5 Hz, 2H), 1.91-1.77 (m, 3H), 1.75-1.41 (m, 4H), 1.32 (s, 3H), 1.23 (s, 3H).

Example 137

(3R,6R,7S,8E,22S)-6'-Chloro-7-methoxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

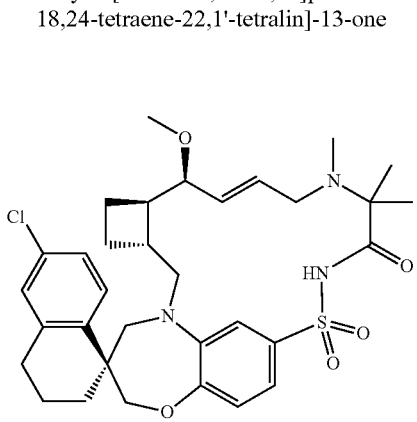

This compound was prepared using procedures analogous to those described for Example 27 using (3R,6R,7S,8E,22S)-6'-chloro-7-methoxy-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 136) and formaldehyde aqueous solution (37%). LC-MS calc. for $C_{33}H_{43}ClN_3O_5S$ [M+H]$^+$: m/z=628.25/630.25; Found: 628.7/630.5. $^1$H NMR (600 MHz, CDCl$_3$) δ 7.66 (d, J=8.5 Hz, 1H), 7.53-7.43 (m, 1H), 7.16 (dd, J=8.5, 2.3 Hz, 1H), 7.07 (d, J=2.3 Hz, 1H), 6.95 (d, J=8.3 Hz, 1H), 6.92-6.85 (m, 1H), 5.83 (s, 1H), 5.54 (dd, J=15.6, 5.3 Hz, 1H), 5.45-5.19 (m, 1H), 4.07 (q, J=11.9 Hz, 2H), 3.71 (d, J=14.8 Hz, 1H), 3.63 (d, J=5.1 Hz, 1H), 3.35 (s, 4H), 3.07 (dd, J=15.1, 10.3 Hz, 1H), 2.78 (dqt, J=22.2, 10.8, 5.1 Hz, 5H), 2.28 (s, 3H), 2.22 (t, J=7.7 Hz, 1H), 2.03-1.89 (m, 6H), 1.89-1.80 (m, 2H), 1.76 (q, J=8.9 Hz, 2H), 1.63 (ddd, J=18.1, 11.7, 5.4 Hz, 2H), 1.49-1.39 (m, 2H).

Example 138

(3R,6R,7R,8E,22S)-6'-Chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

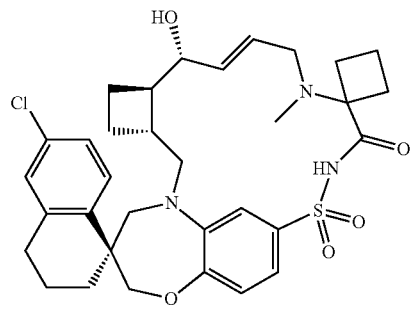 [SMILES: CN1C/C=C/[C@@H](O)[C@@H]2CC[C@H]2CN2C[C@@]3(CCCc4cc(Cl)ccc43)COc3ccc(cc32)S(=O)(=O)NC(=O)C12CCC2]

Step 1: (3R,6R,7R,8E,22S)-6'-chloro-7-acetoxy-11-tert-butoxycarbonyl-12,12-(1,3-propylene)-15,15-dioxo-spiro[20-oxa-15-thia-1,11,14-triazatetracyclo[14.7.2.03,6.019,24-]pentacosa[8,16(25),17,19(24)]tetraene-22,1'-tetralin]-13-one

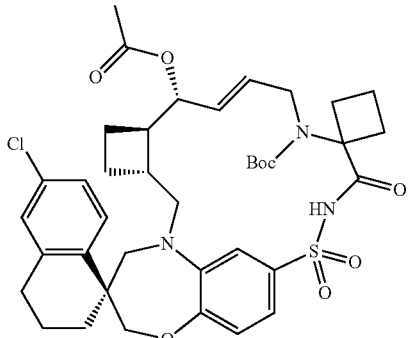

This compound was prepared using procedures analogous to those described for Example 26 Step 3-4 using [(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] acetate (Intermediate 6) and 1-[allyl(tert-butoxycarbonyl)amino]cyclobutanecarboxylic acid (Example 116 Step 3) in Step 3. LC-MS calc. for $C_{39}H_{49}ClN_3O_8S$ [M+H]$^+$: m/z=754.29/756.28; Found: 754.0/756.4.

Step 2: (3R,6R,7R,8E,22S)-6'-chloro-7-acetoxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

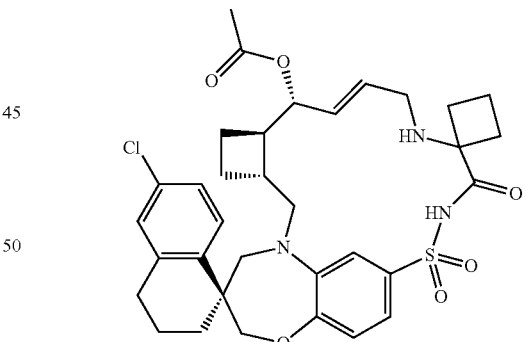

(3R,6R,7R,8E,22S)-6'-chloro-7-acetoxy-11-tert-butoxycarbonyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (40 mg, 0.05 mmol) was stirred in 2 N HCl in EtOAc (3 mL) at r.t. overnight. The reaction was diluted with EtOAc, washed with saturated aqueous NaHCO$_3$ solution and brine. The organic layer was dried over Na$_2$SO$_4$, filtered and concentrated under reduced pressure to afford (3R,6R,7R,8E,22S)-6'-chloro-7-acetoxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'- tetralin]-13-one (35 mg, 100% yield) which was used for the next step without further purification. LC-MS calc. for $C_{34}H_{41}ClN_3O_6S$ [M+H]$^+$: m/z=654.23/656.23; Found 654.0/656.2.

Step 3: (3R,6R,7R,8E,22S)-6'-chloro-7-acetoxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one

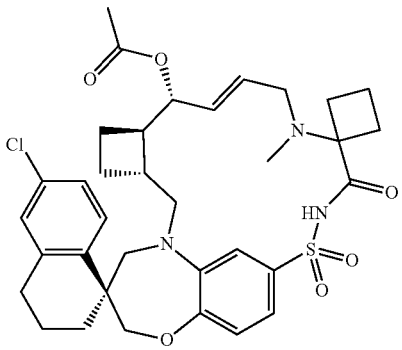 [SMILES: CC(=O)O[C@@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3]

To a solution of (3R,6R,7R,8E,22S)-6'-chloro-7-acetoxy-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (35 mg, 0.05 mmol) in DCE (2 mL) was added two drops of formaldehyde aqueous solution (37% wt %, ca. 22 mg, 0.26 mmol HCHO). After 30 min., sodium cyanoborohydride (16.8 mg, 0.27 mmol) was added in one portion, and stirred at r.t. for 4 h. The reaction was diluted with DCM and water, and filtered through a pad of Celite. The organic layer was washed with saturated aqueous NaHCO$_3$ solution and brine, dried over Na$_2$SO$_4$, filtered and concentrated under reduced pressure. The residue was purified by Prep-HPLC on C18 column (30×250 mm, 10 m) with 20 to 100% ACN/H$_2$O (t$_R$=24 min) to afford (3R,6R,7R,8E,22S)-6'-chloro-7-acetoxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (14 mg, 39% yield) as a white product. LC-MS calc. for $C_{35}H_{43}ClN_3O_6S$ [M+H]$^+$: m/z=668.26/670.25; Found: 668.0/670.3.

Step 4: (3R,6R,7R,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one To a solution of (3R,6R,7R,8E,22S)-6'-chloro-7-acetoxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (14.0 mg, 0.02 mmol) in MeOH (0.5 mL) and THF (0.2 mL) was added a solution of potassium carbonate (28.95 mg, 0.21 mmol) in water (0.5 mL) at r.t. After 16 h, LC-MS indicated the completion of reaction. The reaction was extracted with DCM, washed with brine, dried over Na$_2$SO$_4$, filtered and concentrated under reduced pressure to afford (3R,6R,7R,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa[8,16(25),17,19(24)]tetraene-22,1'-tetralin]-13-one (10 mg, 76% yield), which was sufficiently pure without further purifications. LC-MS calc. for $C_{33}H_{41}ClN_3O_5S$ [M+H]$^+$: m/z=626.25/628.24; Found: 626.0/628.2. $^1$H NMR (600 MHz, CDCl$_3$) δ 7.67 (d, J=8.5 Hz, 1H), 7.51 (dd, J=8.4, 2.2 Hz, 1H), 7.17 (dd, J=8.5, 2.4 Hz, 1H), 7.08 (d, J=2.3 Hz, 1H), 6.98 (app d, J=8.3 Hz, 2H), 5.70 (app s, 1H), 5.64-5.55 (m, 1H), 4.12 (d, J=12.2 Hz, 1H), 4.07 (d, J=12.1 Hz, 1H), 4.00 (t, J=7.8 Hz, 1H), 3.73 (d, J=14.7 Hz, 1H), 3.51 (app s, 1H), 3.33 (d, J=14.8 Hz, 1H), 3.05 (dd, J=15.2, 10.0 Hz, 1H), 2.90-2.64 (m, 4H), 2.49 (s, 1H), 2.42 (s, 3H), 2.31-2.23 (m, 1H), 2.18-2.09 (m, 3H), 2.04-1.91 (m, 5H), 1.88-1.78 (m, 1H), 1.75-1.60 (m, 3H), 1.49-1.39 (m, 1H).

Example 139

[(3R,6R,7R,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

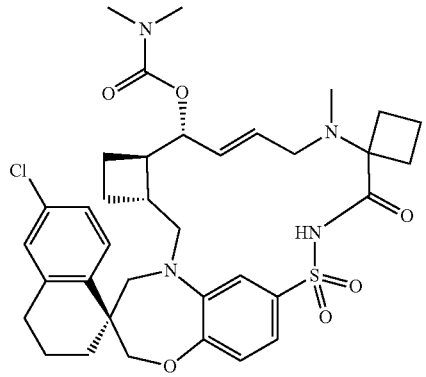 [SMILES: CN(C)C(=O)O[C@@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 34 using (3R,6R,7R,8E,22S)-6'-Chloro-7-hydroxy-11-methyl-12,12-(1,3-propylene)-15,15-dioxo-spiro[20-oxa-15-thia-1,11,14-triazatetracyclo[14.7.2.03,6.019,24]tetraene-22,1'-tetralin]-13-one (Example 138) and N,N-dimethylcarbamoyl chloride. LC-MS calc. for $C_{36}H_{46}ClN_4O_6S$ [M+H]$^+$: m/z=697.27/699.27; Found 697.9/699.7. $^1$H NMR (600 MHz, CDCl$_3$) δ 7.70 (d, J=8.5 Hz, 1H), 7.50 (d, J=8.3 Hz, 1H), 7.18 (dd, J=8.5, 2.3 Hz, 1H), 7.07 (d, J=2.3 Hz, 1H), 6.99 (d, J=8.4 Hz, 2H), 5.75 (s, 1H), 5.57 (s, 1H), 5.38-5.31 (m, 1H), 5.01 (s, 1H), 4.12-4.02 (m, 2H), 3.78 (d, J=14.5 Hz, 1H), 3.67 (s, 1H), 3.26 (d, J=14.6 Hz, 1H), 3.02 (dd, J=15.2, 9.9 Hz, 2H), 2.92 (d, J=13.5 Hz, 5H), 2.80-2.71 (m, 2H), 2.52 (s, 1H), 2.37 (s, 3H), 2.27 (s, 1H), 2.22 (t, J=7.7 Hz, 1H), 2.15 (d, J=20.7 Hz, 1H), 2.07-1.98 (m, 4H), 1.98-1.90 (m, 3H), 1.90-1.76 (m, 4H), 1.41 (t, J=12.7 Hz, 2H).

Example 140

2-[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxy-N,N-dimethyl-acetamide

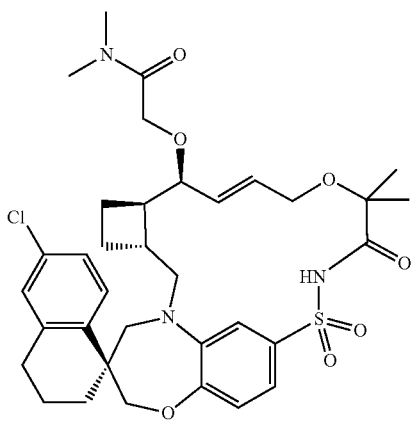 [SMILES: CN(C)C(=O)CO[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (20 mg, 0.03 mmol, Example 32) in THF (0.25 mL) was added NaH (5.3 mg, 0.13 mmol, 60% suspension on mineral oil). The reaction was stirred at 0° C. for 30 min., and 2-bromo-N,N-dimethyl-acetamide (33 mg, 0.20 mmol) was added. The reaction was slowly warmed to r.t. over 4 h. The reaction was quenched with saturated NH$_4$Cl and diluted with EtOAc (3.0 mL). The organic layer separated, washed with water and brine, dried over Na$_2$SO$_4$, filtered and concentrated under reduced pressure. The residue was purified by Prep-HPLC on a C18 column with H$_2$O:MeCN (20% to 100%) to afford 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxy-N,N-dimethyl-acetamide (12 mg, 52% yield). LC-MS calc. for C$_{35}$H$_{45}$ClN$_3$O$_7$S [M+H]$^+$: m/z=686.2/688.2; Found: 686.8/688.8.

Example 141

2-[(3R,6R,7R,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxy-N,N-dimethyl-acetamide

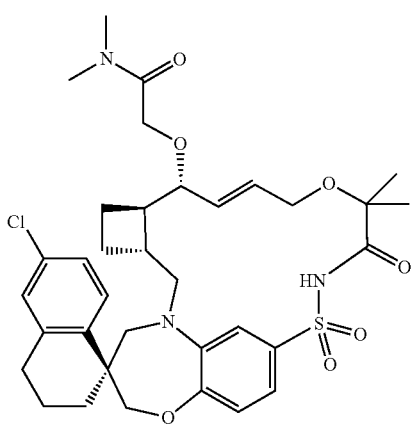 [SMILES: CN(C)C(=O)CO[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 140 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 36). LC-MS calc. for C$_{35}$H$_{45}$ClN$_3$O$_7$S [M+H]$^+$: m/z=686.2/688.2; Found: 686.7/688.8.

Example 142

2-[(3R,6R,7S,8E,22S)-6'-Chloro-12,12-ethylene-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxy-N,N-dimethyl-acetamide

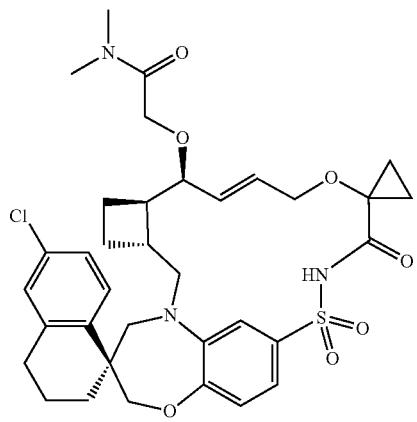 [SMILES: CN(C)C(=O)CO[C@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 140 using (3R,6R,7S,8E,22S)-6'-chloro-7-hydroxy-12,12-ethylene-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 40). LC-MS calc. for C$_{35}$H$_{43}$ClN$_3$O$_7$S [M+H]$^+$: m/z=684.2/686.2; Found: 684.7/686.9.

Example 143

2-[(3R,6R,7R,8E,22S)-6'-Chloro-12,12-ethylene-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxy-N,N-dimethyl-acetamide

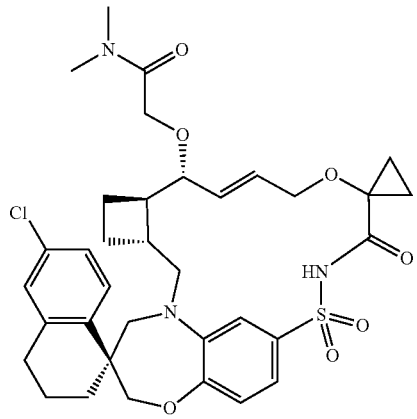 [SMILES: CN(C)C(=O)CO[C@@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 140 using (3R,6R,7R,8E, 22S)-6'-chloro-7-hydroxy-12,12-ethylene-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 38). LC-MS calc. for C₃₅H₄₃ClN₃O₇S [M+H]⁺: m/z=684.2/686.2; Found: 684.7/687.0.

Example 144

(3R,6R,7S,8E,12R,22S)-6'-Chloro-7-hydroxy-11,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

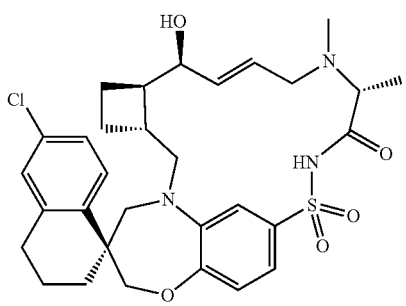 [SMILES: C[C@@H]1C(=O)NS(=O)(=O)c2ccc3c(c2)N(C[C@@H]2CC[C@H]2[C@@H](O)/C=C/CN1C)C[C@@]1(CCCc2cc(Cl)ccc21)CO3]

Step 1: (3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-sulfonamide

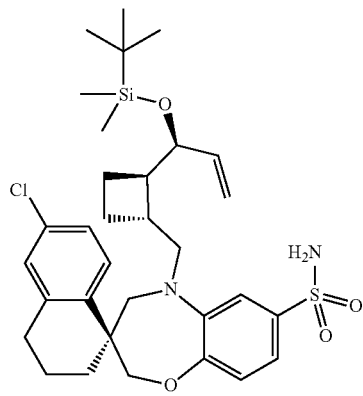 [SMILES: C=C[C@H](O[Si](C)(C)C(C)(C)C)[C@@H]1CC[C@H]1CN1C[C@@]2(CCCc3cc(Cl)ccc32)COc2ccc(S(N)(=O)=O)cc21]

To a stirred solution of (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (300 mg, 0.60 mmol, Intermediate 3) in DMF (5 mL) was added TBSCl (224 mg, 1.49 mmol) and imidazole (203 mg, 2.98 mmol). The resulting solution was stirred at 20° C. overnight. The reaction was quenched with water (15 mL), and extracted with EtOAc (20 mL×3). The combined organic layers were dried over sodium sulfate, filtered and concentrated under reduced pressure. The residue was purified by flash chromatography on a silica gel column (12 g) with EtOAc/Heptanes (2% to 75%) to afford (3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-sulfonamide (315 mg, 85% yield) as a white solid. LC-MS calc. for C₃₂H₄₆ClN₂O₄SiS [M+H]⁺: m/z=617.3/619.3; Found 617.5/619.8.

Step 2: tert-butyl N-allyl-N-[(1R)-2-[[(3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-yl]sulfonylamino]-1-methyl-2-oxo-ethyl]carbamate

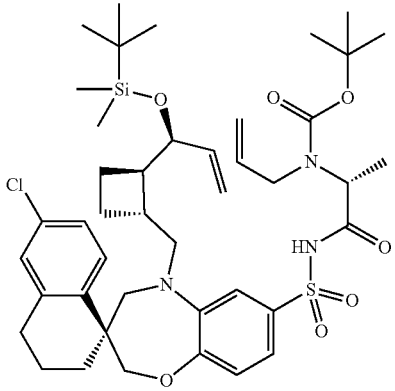 [SMILES: C=CCN(C(=O)OC(C)(C)C)[C@H](C)C(=O)NS(=O)(=O)c1ccc2c(c1)N(C[C@@H]1CC[C@H]1[C@H](C=C)O[Si](C)(C)C(C)(C)C)C[C@@]1(CCCc3cc(Cl)ccc31)CO2]

A solution of (3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-sulfonamide (315 mg, 0.51 mmol), (2R)-2-[allyl(tert-butoxycarbonyl)amino]propanoic acid (233 mg, 1.02 mmol, Example 121 Step 1) in DCM (3 mL) was added DMAP (206 mg, 2.04 mmol) and EDCI (195 mg, 1.02 mmol) at r.t. The mixture was stirred for 3 h. The reaction was diluted with DCM (10 mL), washed with 1 N HCl (3 mL) and brine, dried over Na₂SO₄, filtered and concentrated under reduced pressure. The residue was purified by flash chromatography on a silica gel column (12 g) with EtOAc/Heptanes (2% to 50%) to afford tert-butyl N-allyl-N-[(1R)-2-[[(3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-yl]sulfonylamino]-1-methyl-2-oxo-ethyl]carbamate (264 mg, 62% yield) as a white solid. LC-MS calc. for C₄₃H₆₃ClN₃O₇SiS [M+H]⁺: m/z=828.4/830.4; Found 828.9/830.9.

Step 3: tert-butyl N-allyl-N-[(1R)-2-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylamino]-1-methyl-2-oxo-ethyl]carbamate

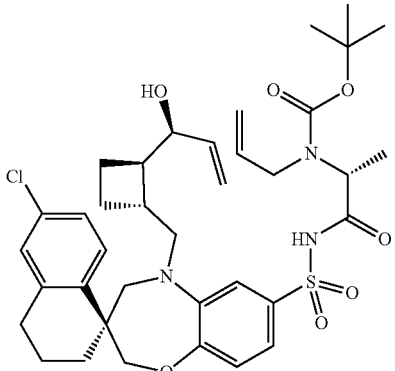

To a stirred solution of tert-butyl N-allyl-N-[(1R)-2-[[(3S)-5-[[(1R,2R)-2-[(1S)-1-[tert-butyl(dimethyl)silyl]oxyallyl]cyclobutyl]methyl]-6'-chloro-spiro[2,4-dihydro-1,5-benzoxazepine-3,1'-tetralin]-7-yl]sulfonylamino]-1-methyl-2-oxo-ethyl]carbamate (230 mg, 0.28 mmol) in THF (10 mL) was added TBAF (725 mg, 2.78 mmol, 1 M in THF, pre-treated with molecular sieve). The resulting solution was stirred at 20° C. overnight. The reaction was quenched with sat. NH$_4$Cl aq. Solution (10 mL), and extracted with EtOAc (20 mL×3). The combined organic layers were dried over sodium sulfate, filtered and concentrated under reduced pressure. The residue was purified by flash chromatography on a silica gel column (12 g) with EtOAc/Heptanes (2% to 60%) to afford tert-butyl N-allyl-N-[(1R)-2-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylamino]-1-methyl-2-oxo-ethyl]carbamate (190 mg, 95% yield). LC-MS calc. for C$_{37}$H$_{49}$ClN$_3$O$_7$S [M+H]$^+$: m/z=714.3/716.3; Found 714.8/717.0.

Step 4: tert-butyl (3R,6R,7S,8E,12R,22S)-6'-chloro-7-hydroxy-12-methyl-13,15,15-trioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-11-carboxylate

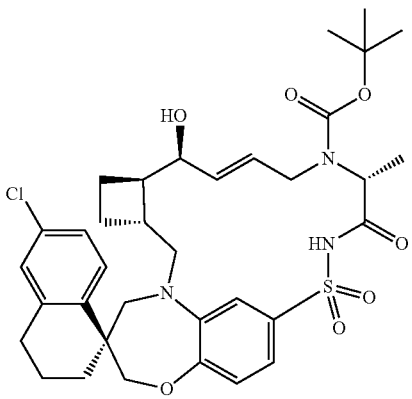 [SMILES: C[C@@H]1C(=O)NS(=O)(=O)c2ccc3c(c2)N(C[C@@H]2CC[C@H]2[C@@H](O)/C=C/CN1C(=O)OC(C)(C)C)C[C@@]1(CCCc2cc(Cl)ccc21)CO3]

A solution of tert-butyl N-allyl-N-[(1R)-2-[[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonylamino]-1-methyl-2-oxo-ethyl]carbamate (260 mg, 0.36 mmol) in DCE (200 mL) was bubbled with N$_2$ for 30 min. 1,3-Bis(2,4,6-trimethylphenyl)-4,5-dihydroimidazol-2-ylidene[2-(i-propoxy)-5-(N,N-dimethylaminosulfonyl)phenyl]-methyleneruthenium(II)dichloride (Zhan-catalyst-1B) (53.42 mg, 0.07 mmol) was added and the reaction mixture was further bubbled with N$_2$ for 30 min, and was heated to 40° C. under N$_2$ for 3 h. LC-MS analysis indicated the completion of reaction. The reaction was cool to r.t. while being exposed to air. The reaction was concentrated under reduced pressure, and the residue was purified by flash chromatography on a silica gel column (12 g) with EtOAc/Hetpanes (2% to 50%) to afford two products: P1 (the earlier eluted product, 110 mg, 44.0% yield) as a light brown colored solid and P2 (the latter eluted product, 90 mg, 0.13 mmol, 36% yield) as a light brown colored solid.

P1 was assigned to the trans-isomer tert-butyl (3R,6R,7S,8E,12R,22S)-6'-chloro-7-hydroxy-12-methyl-13,15,15-trioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-11-carboxylate. LC-MS calc. for C$_{35}$H$_{45}$ClN$_3$O$_7$S [M+H]$^+$: m/z=686.3/688.3; Found: 686.8/688.3.

And P2 was assigned to the cis-isomer tert-butyl (3R,6R,7S,8Z,12R,22S)-6'-chloro-7-hydroxy-12-methyl-13,15,15-trioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-11-carboxylate. LC-MS calc. for C$_{35}$H$_{45}$ClN$_3$O$_7$S [M+H]$^+$: m/z=686.3/688.3; Found: 686.8/688.3.

Step 5: (3R,6R,7S,8E,12R,22S)-6'-chloro-7-hydroxy-12-methyl-15,15-dioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-13-one

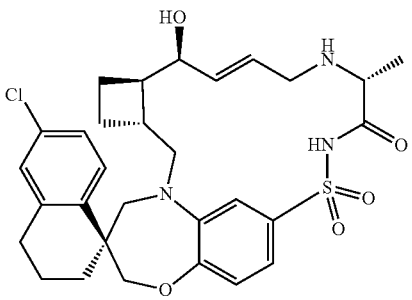 [SMILES: C[C@H]1NC/C=C/[C@H](O)[C@@H]2CC[C@H]2CN2C[C@@]3(CCCc4cc(Cl)ccc43)COc3ccc(cc32)S(=O)(=O)NC1=O]

A solution of tert-butyl (3R,6R,7S,8E,12R,22S)-6'-chloro-7-hydroxy-12-methyl-13,15,15-trioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-11-carboxylate (110.0 mg, 0.16 mmol, P1 from Step 4) in DCE (2 mL) was added phosphoric acid (3.0 mL, 51 mmol) and the resulting solution was stirred at 20° C. overnight. LC-MS analysis indicated the completion of reaction. The reaction was quenched with aq. 1M NaOH solution (20 mL) and extracted with DCM (10 mL×2). The combined organic layers were concentrated under reduced pressure to afford (3R,6R,7S,8E,12R,22S)-6'-chloro-7-hydroxy-12-methyl-15,15-dioxo-spiro[20-oxa-15-thia-1,11,14-triazatetracyclo[14.7.2.0~3,6.0~19,24]pentacosa-8,16,18,24-tetraene-22,1'-tetralin]-13-one (87 mg, 92% yield) as a light brown colored solid. LC-MS calc. for C$_{30}$H$_{37}$ClN$_3$O$_5$S [M+H]$^+$: m/z=586.2/588.2; Found: 586.7/588.6.

Step 6: (3R,6R,7S,8E,12R,22S)-6'-chloro-7-hydroxy-11,12-dimethyl-15,15-dioxo-spiro[20-oxa-15-thia-1,11,14-triazatetracyclo[14.7.2.0$^{3,6}$.0$^{19,24}$]pentacosa-8,16,18,24-tetraene-22,1'-tetralin]-13-one This compound was prepared using procedures analogous to those described for Example 27 using (3R,6R,7S,8E,12R,22S)-6'-chloro-7-hydroxy-12-methyl-15,15-dioxo-spiro[20-oxa-15-thia-1,11,14-triazatetracyclo[14.7.2.03,6.019,24]pentacosa-8,16,18,24-tetraene-22,1'-tetralin]-13-one and formaldehyde aqueous solution (37%). LC-MS calc. for C$_{31}$H$_{39}$ClN$_3$O$_5$S [M+H]$^+$: m/z=600.2/602.2; Found: 600.6/602.8. $^1$H NMR (600 MHz, CDCl$_3$) δ 7.69 (s, 1H), 7.01 (d, J=28.3 Hz, 2H), 6.69 (d, J=141.3 Hz, 2H), 6.20 (s, 1H), 5.63 (d, J=15.5 Hz, 1H), 5.43-5.24 (m, 1H), 4.11 (s, 1H), 4.05-3.69 (m, 3H), 3.59-3.46 (m, 1H), 3.25-3.06 (m, 2H), 2.79 (d, J=83.6 Hz, 5H), 2.31 (s, 3H), 2.24-2.19 (m, 1H), 2.08-1.93 (m, 3H), 1.83 (s, 3H), 1.59 (d, J=56.9 Hz, 4H), 1.44 (d, J=7.6 Hz, 2H).

Example 145

[(3R,6R,7S,8E,12R,22S)-6'-Chloro-11,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

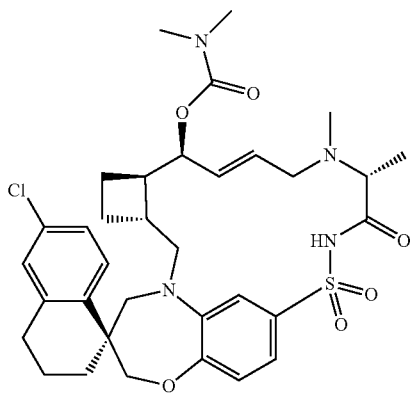 [SMILES: C[C@@H]1C(=O)NS(=O)(=O)c2ccc3c(c2)N(C[C@@H]2CC[C@H]2[C@@H](OC(=O)N(C)C)/C=C/CN1C)C[C@@]1(CCCc2cc(Cl)ccc21)CO3]

This compound was prepared using procedures analogous to those described for Example 34 using (3R,6R,7S,8E,12R,22S)-6'-chloro-7-hydroxy-11,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one and N,N-dimethylcarbamoyl chloride. LC-MS calc. for $C_{34}H_{44}ClN_4O_6S$ $[M+H]^+$: m/z=671.3/673.3; Found: 671.7/673.9. $^1$H NMR (300 MHz, CDCl$_3$) δ 7.65 (d, J=8.6 Hz, 1H), 7.51 (d, J=8.3 Hz, 1H), 7.18 (dd, J=8.5, 2.3 Hz, 1H), 7.13-6.88 (m, 3H), 5.84-5.46 (m, 2H), 5.30 (d, J=4.3 Hz, 1H), 4.32-3.97 (m, 3H), 3.67 (d, J=14.5 Hz, 2H), 3.42-3.28 (m, 2H), 2.95 (d, J=6.1 Hz, 6H), 2.79 (p, J=6.2, 4.7 Hz, 3H), 2.64 (s, 3H), 2.54-2.36 (m, 2H), 2.16-1.73 (m, 7H), 1.68-1.48 (m, 3H), 1.35 (s, 3H).

Example 146

[(3R,6R,7S,8E,12R,22S)-6'-Chloro-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

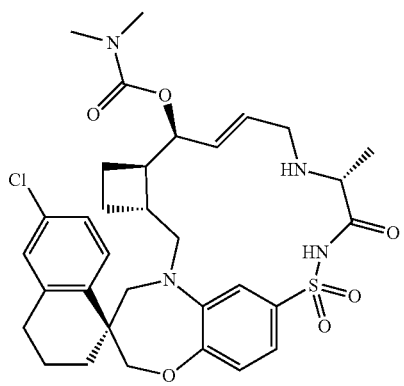 [SMILES: C[C@H]1NC/C=C/[C@H](OC(=O)N(C)C)[C@@H]2CC[C@H]2CN2C[C@@]3(CCCc4cc(Cl)ccc43)COc3ccc(cc32)S(=O)(=O)NC1=O]

Step 1: tert-butyl (3R,6R,7S,8E,12R,22S)-6'-chloro-7-(dimethylcarbamoyloxy)-12-methyl-13,15,15-trioxo-spiro[20-oxa-15-thia-1,11,14-triazatetracyclo[14.7.2.0~3,6.0~19,24]pentacosa-8,16,18,24-tetraene-22,1'-tetralin]-11

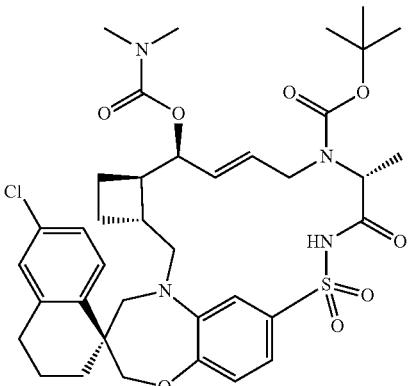

This compound was prepared using procedures analogous to those described for Example 34 using tert-butyl (3R,6R,7S,8E,12R,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-1-carboxylate (P1 Example 144 Step 4) and N,N-dimethylcarbamoyl chloride. LC-MS calc. for $C_{38}H_{50}ClN_4O_8S$ $[M+H]^+$: m/z=757.30/759.30; Found: 758.04/760.12.

Step 2: [(3R,6R,7S,8E,12R,22S)-6'-chloro-12-methyl-13,15,15-trioxo-spiro[20-oxa-15-thia-1,11,14-triazatetracyclo[14.7.2.0-3,6.0-19,24]pentacosa-8,16,18,24-tetraene-22,1'-tetralin]-7-yl] N,N-dimethylcarbamate This compound was prepared using procedures analogous to those described for Example 144 Step 5 using tert-butyl (3R,6R,7S,8E,12R,22S)-6'-chloro-7-(dimethylcarbamoyloxy)-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate and phosphoric acid. LC-MS calc. for $C_{33}H_{42}ClN_4O_6S$ $[M+H]^+$: m/z=657.24/659.24; Found: 657.73/659.70. $^1$H NMR (300 MHz, CDCl$_3$) δ 7.67 (dd, J=8.6, 4.5 Hz, 1H), 7.43-7.33 (m, 1H), 7.29 (s, 1H), 7.20-7.06 (m, 3H), 6.94 (dd, J=8.4, 4.6 Hz, 1H), 5.76-5.52 (m, 2H), 5.15 (t, J=4.6 Hz, 1H), 4.23-3.97 (m, 2H), 3.63 (dd, J=14.5, 9.7 Hz, 2H), 3.54-3.25 (m, 5H), 2.86 (s, 3H), 2.80-2.72 (m, 4H), 2.67-2.47 (m, 3H), 2.23 (t, J=7.4 Hz, 2H), 2.02-1.75 (m, 6H), 1.47 (d, J=6.7 Hz, 4H).

Example 147

[(3R,6R,7S,8E,12S,22S)-6'-Chloro-11,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

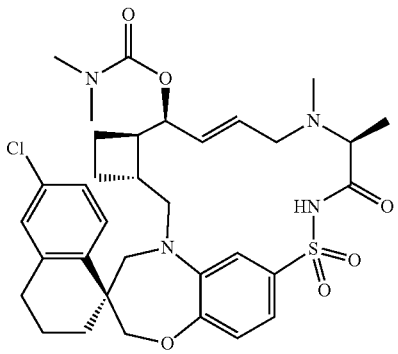 [SMILES: C[C@H]1C(=O)NS(=O)(=O)c2ccc3c(c2)N(C[C@@H]2CC[C@H]2[C@@H](OC(=O)N(C)C)/C=C/CN1C)C[C@@]1(CCCc2cc(Cl)ccc21)CO3]

Step 1: tert-butyl (3R,6R,7S,8E,12S,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate and tert-butyl (3R,6R,7S,8Z,12S,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate

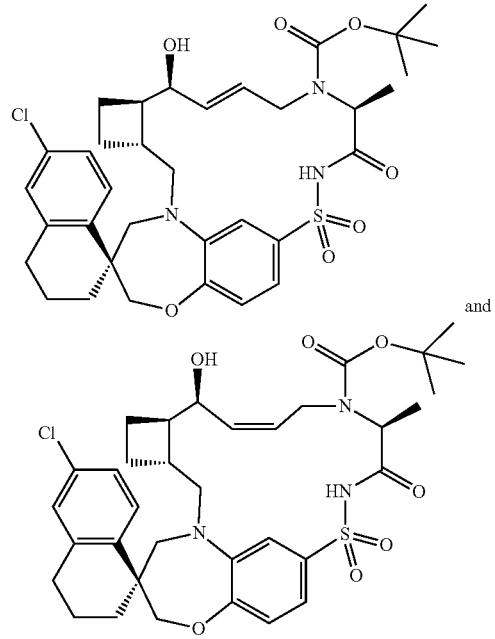

and

The compounds were prepared using procedures analogous to those described for Example 32 Step 1-3 using (3S)6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Intermediate 3) and (2S)-2-[allyl(tert-butoxycarbonyl)amino]propanoic acid (Example 85 Step 1) in Step 1. The reaction mixture was purified by flash chromatography on a silica gel column with EtOAc/Heptanes (3% to 50%) to afford two products: P1 (the earlier eluted product) was assigned to the Z-isomer tert-butyl (3R,6R,7S,8Z,12S,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate and P2 (the latter eluted product) was assigned to the E-isomer tert-butyl (3R,6R,7S,8E,12S,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate. LC-MS calc. for $C_{35}H_{45}ClN_3O_7S$ $[M+H]^+$: m/z=686.2/688.2; Found: 686.7/688.1.

Step 2: (3R,6R,7S,8E,12S,22S)-6'-chloro-7-hydroxy-12-methyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

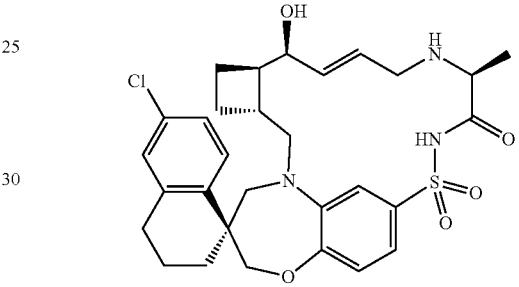

This compound was prepared using procedures analogous to those described for Example 144 Step 5 using tert-butyl (3R,6R,7S,8E,12S,22S)-6'-chloro-7-hydroxy-12-methyl-13,15,15-trioxo-spiro[20-oxa-15-thia-1,11,14-triazatetracyclo[14.7.2.03,6.019,24]pentacosa-8,16,18,24-tetraene-22,1'-tetralin]-11-carboxylate (P2 Step 1) and phosphoric acid (85% solution in water). LC-MS calc. for $C_{30}H_{37}ClN_3O_5S$ $[M+H]^+$: m/z=586.2/588.2; Found: 586.6/588.6.

Step 3: (3R,6R,7S,8E,12S,22S)-6'-chloro-7-hydroxy-11,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

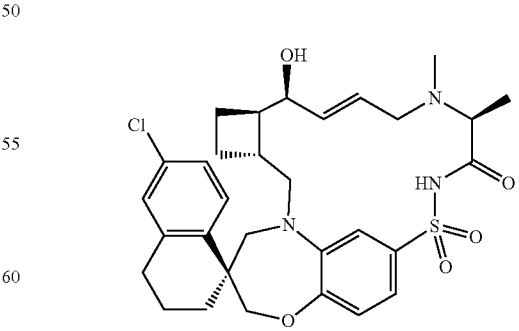

The compounds were prepared using procedures analogous to those described for Example 27 using (3R,6R,7S,8E,12S,22S)-6'-chloro-7-hydroxy-12-methyl-15,15-dioxo-spiro[20-oxa-15-thia-1,11,14-triazatetracyclo[14.7.2.03, 6.019,24]pentacosa-8,16,18,24-tetraene-22,1'-tetralin]-13-one and formaldehyde aqueous solution (37%). LC-MS calc. for $C_{31}H_{39}ClN_3O_5S$ [M+H]$^+$: m/z=600.2/602.2; Found: 600.8/602.6.

Step 4: [(3R,6R,7S,8E,12S,22S)-6'-chloro-11,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate The compounds were prepared using procedures analogous to those described for Example 34 using (3R,6R,7S,8E,12S,22S)-6'-chloro-7-hydroxy-11,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one and N,N-dimethylcarbamoyl chloride. LC-MS calc. for $C_{34}H_{44}ClN_4O_6S$ [M+H]$^+$: m/z=671.26/673.26; Found: 671.7/673.8.

Example 148

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 4-(2-hydroxyethyl)piperazine-1-carboxylate

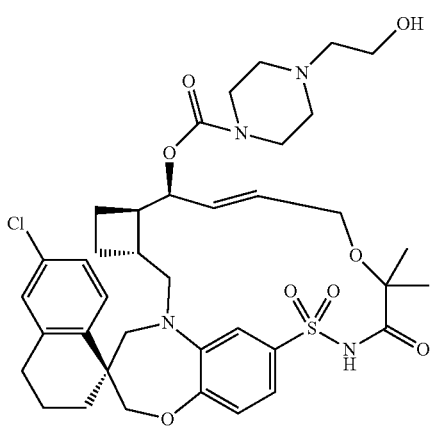 [SMILES: CC1(C)OC/C=C/[C@H](OC(=O)N2CCN(CCO)CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 Step 1-2 using (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (2.8 g, 4.66 mmol, Example 32) in Step 1 and 2-piperazin-1-ylethanol in Step 2. LC-MS calc. for $C_{38}H_{50}ClN_4O_8S$ [M+H]$^+$: m/z=757.30/759.30; Found: 757.7/759.7. $^1$H NMR (300 MHz, CDCl$_3$) δ 7.68 (d, J=8.5 Hz, 1H), 7.50 (dd, J=8.3, 2.0 Hz, 1H), 7.19 (dd, J=8.5, 2.2 Hz, 1H), 7.10 (d, J=2.0 Hz, 1H), 6.98 (dd, J=7.6, 5.2 Hz, 2H), 5.91-5.78 (m, 1H), 5.71 (dd, J=15.7, 4.9 Hz, 1H), 5.33 (d, J=9.1 Hz, 1H), 4.12 (dt, J=13.9, 9.6 Hz, 4H), 3.80-3.67 (m, 2H), 3.67-3.61 (m, 2H), 3.47 (d, J=4.4 Hz, 1H), 3.41 (s, 1H), 3.37 (d, J=14.6 Hz, 1H), 3.21 (dd, J=15.0, 9.3 Hz, 2H), 2.87-2.67 (m, 5H), 2.61-2.55 (m, 3H), 2.45-2.33 (m, 3H), 1.99 (dd, J=24.2, 8.9 Hz, 4H), 1.89-1.72 (m, 4H), 1.64 (t, J=9.4 Hz, 2H), 1.50 (d, J=12.7 Hz, 1H), 1.45 (s, 3H), 1.37 (s, 3H).

Example 149

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[2-(4-methylpiperazin-1-yl)ethyl]carbamate

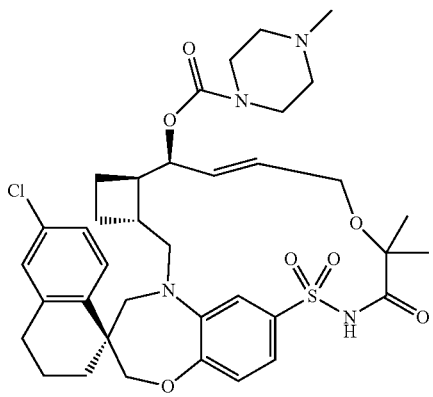 [SMILES: CN1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using 2-(4-methylpiperazin-1-yl)ethanamine to replace 1-(2-methoxyethyl)piperazine in Step 2. LC-MS calc. for $C_{39}H_{53}ClN_5O_7S$ [M+H]$^+$: m/z=770.34/772.34; Found: 770.7/772.7. $^1$H NMR (300 MHz, CDCl$_3$) δ 7.71 (d, J=8.5 Hz, 1H), 7.39 (d, J=8.3 Hz, 1H), 7.19 (dd, J=8.5, 2.1 Hz, 1H), 7.09 (s, 2H), 6.93 (d, J=8.3 Hz, 1H), 6.82 (d, J=8.3 Hz, 1H), 6.49 (s, 1H), 6.18 (d, J=15.2 Hz, 1H), 5.58 (d, J=15.6 Hz, 1H), 5.18 (s, 1H), 4.20-4.02 (m, 4H), 3.66 (dd, J=34.7, 13.8 Hz, 3H), 3.30 (dd, J=17.0, 9.0 Hz, 2H), 3.01 (d, J=14.9 Hz, 5H), 2.80 (d, J=12.3 Hz, 7H), 2.39 (s, 3H), 2.32-2.18 (m, 2H), 1.88 (ddd, J=27.1, 21.1, 12.4 Hz, 6H), 1.59 (dd, J=18.3, 8.8 Hz, 3H), 1.39 (d, J=2.5 Hz, 6H).

Example 150

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[2-(4-hydroxy-1-piperidyl)ethyl]carbamate

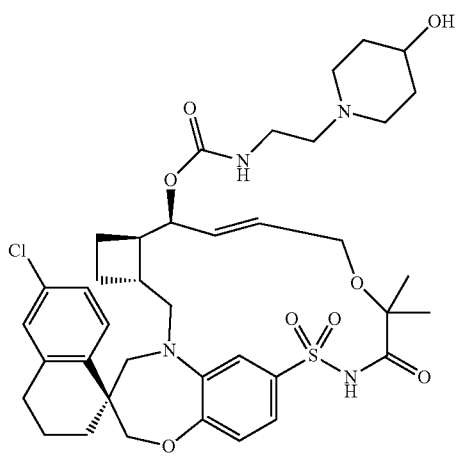 [SMILES: CC1(C)OC/C=C/[C@H](OC(=O)NCCN2CCC(O)CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 1-(2-aminoethyl)piperidin-4-ol to replace 1-(2-methoxyethyl)piperazine in Step 2. LCMS calc. for $C_{39}H_{52}ClN_4O_8S$ [M+H]$^+$: m/z=771.32/773.32; Found: 771.8/773.8. 1H NMR (300 MHz, CDCl$_3$) δ 7.73 (d, J=8.5 Hz, 1H), 7.30 (d, J=8.4 Hz, 1H), 7.18 (dd, J=8.4, 2.1 Hz, 2H), 7.14-7.06 (m, 2H), 6.88 (d, J=8.2 Hz, 1H), 6.82 (d, J=8.0 Hz, 1H), 6.41-6.26 (m, 1H), 5.50 (d, J=15.8 Hz, 1H), 5.14 (s, 1H), 4.30 (dd, J=14.9, 4.9 Hz, 1H), 4.23-4.08 (m, 2H), 4.04 (d, J=12.6 Hz, 2H), 3.84 (dd, J=15.6, 10.5 Hz, 2H), 3.77-3.63 (m, 3H), 3.30 (dd, J=39.0, 12.7 Hz, 3H), 2.97 (dt, J=25.5, 13.4 Hz, 5H), 2.85-2.32 (m, 4H), 2.19 (dd, J=17.7, 8.8 Hz, 2H), 1.94 (dt, J=22.0, 14.6 Hz, 6H), 1.85-1.68 (m, 4H), 1.67-1.48 (m, 3H), 1.37 (d, J=8.6 Hz, 6H).

Example 151

[(3R,6R,7S,8E,22S)-6'-Chloro-12,12-dimethyl-13,15,15-triox-spiro[11,20-dioxa-15-thia-1,14-diazatetracyclo[14.7.2.03,6.019,24]pentacosa-8,16,18,24-tetraene-22,1'-tetralin]-7-yl] N-[(3S)-1-methylpyrrolidin-3-yl]carbamate

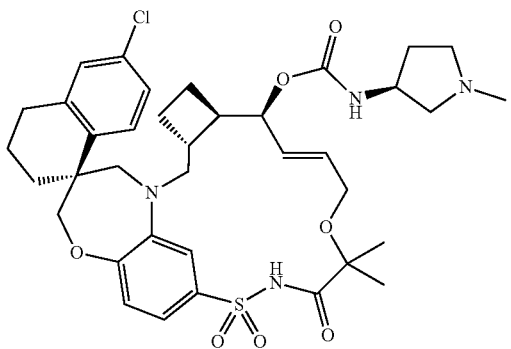 [SMILES: CN1CC[C@H](NC(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3S)-1-methylpyrrolidin-3-amine to replace 1-(2-methoxyethyl)piperazine in Step 2. LCMS calc. for $C_{37}H_{48}ClN_4O_7S$ [M+H]$^+$: m/z=727.3/729.3; Found: 727.5/729.2. $^1$H NMR (300 MHz, CDCl$_3$) δ 7.71 (d, J=8.5 Hz, 1H), 7.31 (dd, J=8.3, 2.0 Hz, 1H), 7.17 (dd, J=8.5, 2.2 Hz, 1H), 7.07 (dd, J=4.2, 2.2 Hz, 2H), 6.87 (d, J=8.2 Hz, 1H), 6.42-6.12 (m, 1H), 5.47 (dd, J=15.8, 2.6 Hz, 1H), 5.08 (s, 1H), 4.47-4.28 (m, 2H), 4.13-4.00 (m, 3H), 3.87 (d, J=11.6 Hz, 1H), 3.77-3.59 (m, 2H), 3.21 (d, J=14.3 Hz, 1H), 3.07-2.85 (m, 6H), 2.80-2.66 (m, 7H), 2.48 (ddd, J=14.3, 7.1, 3.1 Hz, 1H), 2.21-2.13 (m, 2H), 2.05-1.85 (m, 3H), 1.77 (td, J=9.3, 8.9, 3.0 Hz, 2H), 1.59-1.48 (m, 1H), 1.36 (s, 3H), 1.33 (s, 3H).

Example 152

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[(3R)-1-methylpyrrolidin-3-yl]carbamate

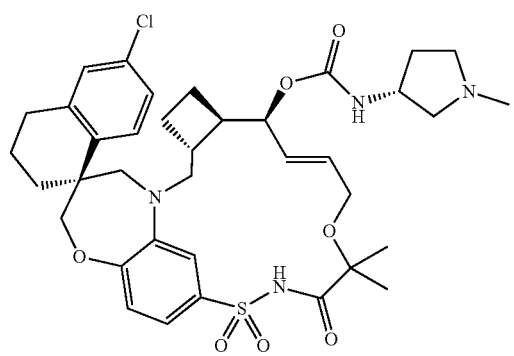 [SMILES: CN1CC[C@@H](NC(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3R)-1-methylpyrrolidin-3-amine to replace 1-(2-methoxyethyl)piperazine in Step 2. LCMS calc. for $C_{37}H_{48}ClN_4O_7S$ [M+H]$^+$: m/z=727.3/729.3; Found: 727.6/729.3. $^1$H NMR (300 MHz, CDCl$_3$) δ 7.71 (d, J=8.4 Hz, 1H), 7.32 (dd, J=8.1, 2.1 Hz, 1H), 7.17 (dd, J=8.5, 2.4 Hz, 1H), 7.11-7.03 (m, 2H), 6.87 (d, J=8.2 Hz, 1H), 6.27 (dd, J=14.3, 6.9 Hz, 1H), 5.63-5.38 (m, 1H), 5.06 (s, 1H), 4.31 (td, J=13.4, 12.5, 5.2 Hz, 2H), 4.19-3.97 (m, 3H), 3.81-3.57 (m, 3H), 3.22 (d, J=14.4 Hz, 1H), 3.03-2.33 (m, 17H), 2.18 (q, J=8.9, 7.3 Hz, 1H), 2.04-1.72 (m, 5H), 1.54 (p, J=9.2 Hz, 1H), 1.37 (s, 3H), 1.34 (s, 3H).

Example 153

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[(3R)-1-methylpyrrolidin-3-yl]carbamate

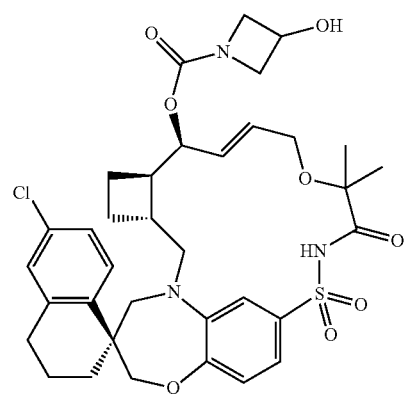 [SMILES: CC1(C)OC/C=C/[C@H](OC(=O)N2CC(O)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 3-hydroxyazetidine-1-carboxylate to replace 1-(2-methoxyethyl)piperazine in Step 2. LCMS calc. for $C_{35}H_{43}ClN_3O_8S$ [M+H]+: m/z=700.24/702.24; Found: 700.3/702.0. $^1$H NMR (300 MHz, CDCl$_3$) δ 7.66 (d, J=8.5 Hz, 1H), 7.48-7.31 (m, 1H), 7.20-7.02 (m, 2H), 6.99-6.75 (m, 2H), 6.26 (s, 1H), 5.64 (d, J=15.2 Hz, 1H), 5.09 (s, 1H), 4.55 (s, 1H), 4.43-4.16 (m, 2H), 4.10-4.00 (m, 4H), 3.81 (d, J=12.8 Hz, 1H), 3.70 (d, J=14.7 Hz, 1H), 3.62-3.44 (m, 1H), 3.41-3.34 (m, 2H), 3.01 (q, J=7.4 Hz, 2H), 2.75 (d, J=10.5 Hz, 4H), 2.20 (q, J=7.3, 5.5 Hz, 1H), 1.99-1.75 (m, 4H), 1.61 (q, J=9.3 Hz, 1H), 1.40-1.27 (m, 9H).

Example 154

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3S)-3-(dimethylamino)pyrrolidine-1-carboxylate

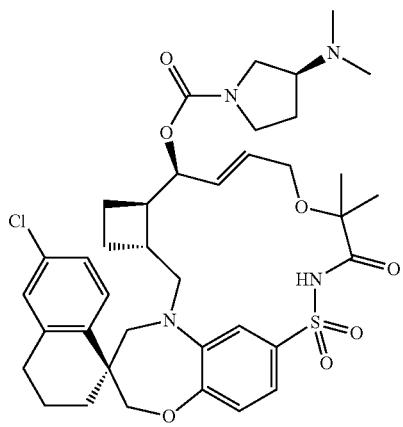 [SMILES: CN(C)[C@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3S)-N,N-dimethylpyrrolidin-3-amine to replace 1-(2-methoxyethyl)piperazine in Step 2. LCMS calc. for $C_{38}H_{50}ClN_4O_7S$ [M+H]+: m/z=741.3/743.3; Found: 741.4/743.2. $^1$H NMR (499 MHz, DMSO-d$_6$) δ 7.67 (dd, J=8.6, 3.4 Hz, 1H), 7.27 (dt, J=8.6, 2.0 Hz, 1H), 7.18 (d, J=2.4 Hz, 1H), 7.10 (dd, J=8.2, 2.0 Hz, 1H), 6.92-6.79 (m, 2H), 6.22 (s, 1H), 5.71-5.21 (m, 2H), 5.10 (d, J=32.3 Hz, 1H), 4.02 (d, J=5.9 Hz, 2H), 3.87 (d, J=9.4 Hz, 1H), 3.57 (d, J=13.5 Hz, 6H), 3.13-2.99 (m, 2H), 2.86-2.64 (m, 4H), 2.29 (d, J=35.6 Hz, 5H), 2.13-1.91 (m, 4H), 1.86 (d, J=7.5 Hz, 4H), 1.67 (dd, J=21.5, 12.4 Hz, 3H), 1.45 (q, J=12.9, 10.8 Hz, 2H), 1.22 (s, 3H), 1.12 (s, 3H).

Example 155

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[2-(dimethylamino)ethyl]carbamate

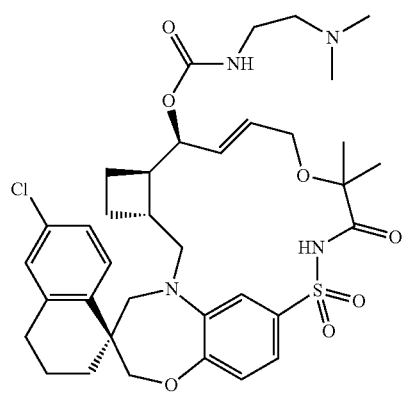 [SMILES: CN(C)CCNC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using N',N'-dimethylethane-1,2-diamine to replace 1-(2-methoxyethyl)piperazine in Step 2. LCMS calc. for $C_{36}H_{48}ClN_4O_7S$ [M+H]+: m/z=715.29/717.29; Found: 715.4/717.2. 1H NMR (499 MHz, DMSO-d$_6$) δ 7.67 (d, J=8.6 Hz, 1H), 7.28 (dd, J=8.5, 2.4 Hz, 1H), 7.18 (d, J=2.4 Hz, 1H), 7.15-7.00 (m, 2H), 6.95 (d, J=2.1 Hz, 1H), 6.85 (d, J=8.1 Hz, 1H), 6.28 (s, 1H), 5.48 (dd, J=16.1, 3.7 Hz, 1H), 4.92 (s, 1H), 4.10-3.95 (m, 2H), 3.89 (dd, J=14.0, 7.7 Hz, 1H), 3.77 (s, 1H), 3.55 (d, J=14.2 Hz, 2H), 3.27-3.12 (m, 4H), 3.12-3.00 (m, 2H), 2.86-2.56 (m, 7H), 2.44-2.24 (m, 2H), 2.15-1.90 (m, 2H), 1.84 (dd, J=14.0, 7.6 Hz, 3H), 1.67 (ddd, J=43.0, 21.1, 12.2 Hz, 3H), 1.45 (dt, J=26.0, 9.4 Hz, 2H), 1.21 (s, 3H), 1.13 (s, 3H).

Example 156

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-(methylamino)azetidine-1-carboxylate

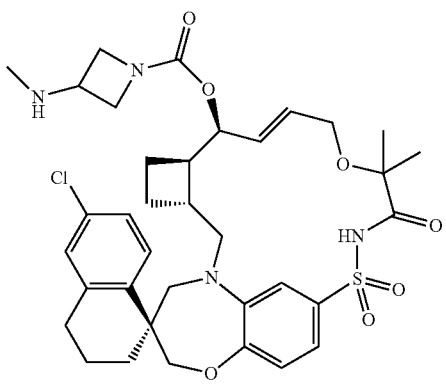 [SMILES: CNC1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

415

Step 1: [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-[tert-butoxycarbonyl(methyl)amino]azetidine-1-carboxylate

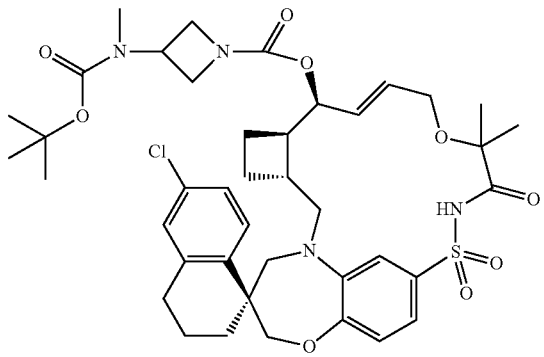 [SMILES: CN(C(=O)OC(C)(C)C)C1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using tert-butyl N-(azetidin-3-yl)-N-methyl-carbamate to replace 1-(2-methoxyethyl)piperazine in Step 2. The reaction mixture was concentrated under reduced pressure and the residue was directly used for the next step. LC-MS: calcd. for $C_{41}H_{54}ClN_4O_9S$ $[M+H]^+$: m/z=813.3/815.3; Found: 813.7/815.5.

Step 2: [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-(methylamino)azetidine-1-carboxylate To a solution of [(3R,6R,7S,8E,22S)-6'-chloro-12,12-dimethyl-13,15,15-trioxo-spiro[11,20-dioxa-15-thia-1,14-diazatetracyclo[14.7.2.0-3,6.0-19,24]pentacosa-8,16,18,24-tetraene-22,1'-tetralin]-7-yl] 3-[tert-butoxycarbonyl(methyl)amino]azetidine-1-carboxylate (30.0 mg, 0.04 mmol) in IPA (1 mL) and DCM (0.10 mL) was added phosphoric acid (0.5 mL, 8.6 mmol). The resulting solution was vigorously stirred at 20° C. for 3 h. The reaction mixture was quenched with 1M NaOH aqueous solution and extracted with DCM (2×2 mL). The combined organic layers were concentrated under reduced pressure. The residue was purified by prep-HPLC on C18 column (30×250 mm, 10 μm) with MeOH/H2O (15% to 100%) to afford [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-(methylamino)azetidine-1-carboxylate (16.8 mg, 63.9% yield) as a white solid. LCMS calc. for $C_{36}H_{46}ClN_4O_7S$ $[M+H]^+$: m/z=713.28/715.28; Found: 713.4/715.3. $^1H$ NMR (300 MHz, $CDCl_3$) δ 7.69 (d, J=8.5 Hz, 1H), 7.53-7.37 (m, 1H), 7.22-7.05 (m, 3H), 7.00-6.78 (m, 2H), 5.67 (dd, J=15.9, 4.2 Hz, 1H), 5.11 (s, 1H), 4.32-4.00 (m, 6H), 3.85-3.66 (m, 3H), 3.59 (s, 2H), 3.39 (t, J=17.0 Hz, 3H), 3.22-3.07 (m, 3H), 2.79 (s, 3H), 2.56-2.35 (m, 3H), 2.23 (t, J=7.6 Hz, 1H), 2.09-1.72 (m, 6H), 1.45 (s, 3H), 1.33 (s, 3H).

Example 157

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-[2-(methylamino)ethyl]carbamate

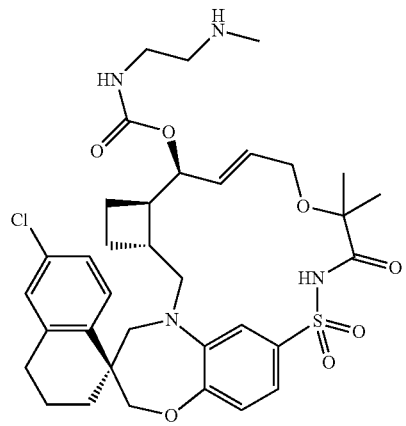 [SMILES: CNCCNC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 156 using tert-butyl N-(2-aminoethyl)-N-methyl-carbamate to replace 4-amino-1-boc-piperidine in Step 1. LCMS calc. for $C_{35}H_{46}ClN_4O_7S$ $[M+H]^+$: m/z=701.28/703.28; Found 701.4/703.3. $^1H$ NMR (499 MHz, DMSO-$d_6$) δ 7.65 (dd, J=8.8, 4.1 Hz, 1H), 7.27 (dd, J=8.5, 2.4 Hz, 1H), 7.17 (d, J=2.2 Hz, 1H), 7.06 (dd, J=8.2, 1.9 Hz, 1H), 7.02-6.87 (m, 2H), 6.84 (d, J=8.1 Hz, 1H), 6.55-6.15 (m, 1H), 5.65-4.77 (m, 2H), 4.00 (s, 2H), 3.89 (d, J=6.0 Hz, 2H), 3.66-3.50 (m, 2H), 3.19 (dd, J=24.7, 13.1 Hz, 3H), 3.11-2.93 (m, 3H), 2.80 (d, J=18.4 Hz, 2H), 2.76-2.59 (m, 4H), 2.29 (d, J=8.7 Hz, 1H), 2.00 (ddd, J=21.8, 12.3, 6.1 Hz, 2H), 1.90-1.76 (m, 3H), 1.76-1.56 (m, 3H), 1.49-1.34 (m, 2H), 1.23-1.18 (m, 3H), 1.12 (s, 3H).

Example 185

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 2,2-dimethylmorpholine-4-carboxylate

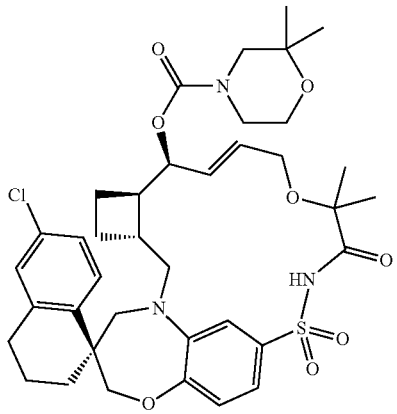 [SMILES: CC1(C)CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CCO1]

This compound was prepared using procedures analogous to those described for Example 46 using 2,2-dimethylmorpholine to replace 1-(2-methoxyethyl)piperazine in Step 2. LCMS calc. for $C_{37}H_{45}ClN_3O_8S$ [M+H]$^+$: m/z=742.29/744.29; Found: 742.6/744.6. 1H NMR (499 MHz, DMSO-d6) δ 7.64 (d, J=8.6 Hz, 1H), 7.25 (ddd, J=8.5, 6.1, 2.3 Hz, 2H), 7.18 (d, J=2.4 Hz, 1H), 7.06-6.92 (m, 2H), 6.51 (s, 1H), 5.67 (s, 1H), 5.33 (td, J=4.5, 2.2 Hz, 1H), 5.18 (s, 1H), 4.18-4.03 (m, 3H), 4.01-3.86 (m, 1H), 3.64-3.49 (m, 4H), 3.31-3.15 (m, 2H), 2.83-2.62 (m, 3H), 2.41-2.14 (m, 1H), 2.05-1.94 (m, 4H), 1.83 (d, J=4.7 Hz, 3H), 1.68 (ddt, J=44.8, 18.3, 8.4 Hz, 3H), 1.55-1.43 (m, 3H), 1.39 (s, 2H), 1.22 (s, 3H), 1.14-1.07 (m, 5H).

Example 159

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] N-(2-methoxyethyl)-N-methyl-carbamate

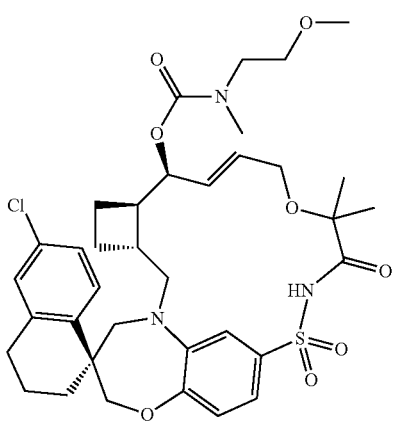 [SMILES: COCCN(C)C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using 2-methoxy-N-methyl-ethanamine to replace 1-(2-methoxyethyl)piperazine in Step 2. LCMS calc. for $C_{36}H_{47}ClN_3O_8S$ [M+H]$^+$: m/z=716.27/718.27; Found: 716.6/718.6. $^1$H NMR (499 MHz, DMSO-d$_6$) δ 7.69-7.62 (m, 1H), 7.33-7.23 (m, 2H), 7.20 (dd, J=5.6, 2.4 Hz, 2H), 6.94 (s, 2H), 5.73 (d, J=39.4 Hz, 1H), 5.39-5.05 (m, 1H), 4.23-3.83 (m, 3H), 3.66-3.52 (m, 2H), 3.46 (s, 3H), 3.25 (d, J=12.2 Hz, 4H), 3.16-3.07 (m, 1H), 2.97 (d, J=21.7 Hz, 1H), 2.91-2.63 (m, 5H), 2.60 (s, 1H), 2.47-2.20 (m, 2H), 2.01 (dt, J=18.3, 7.8 Hz, 3H), 1.86 (s, 3H), 1.78-1.59 (m, 3H), 1.57-1.42 (m, 2H), 1.42-1.33 (m, 2H), 1.20-1.12 (m, 2H).

Example 160

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (2S)-2-(methoxymethyl)pyrrolidine-1-carboxylate

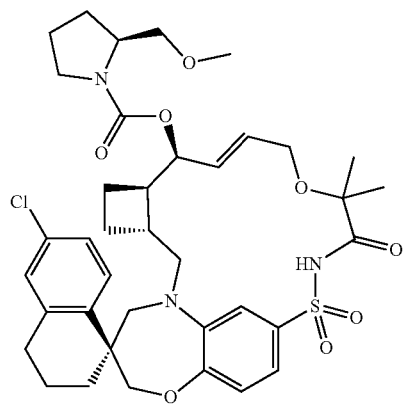 [SMILES: COC[C@@H]1CCCN1C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using (2S)-2-(methoxymethyl)pyrrolidine to replace 1-(2-methoxyethyl)piperazine in Step 2. LCMS calc. for $C_{38}H_{49}ClN_3O_8S$ [M+H]$^+$: m/z=742.29/744.28; Found: 742.5/744.5. $^1$H NMR (499 MHz, DMSO-d$_6$) δ 7.64 (d, J=8.5 Hz, 1H), 7.28-7.21 (m, 2H), 7.19-7.16 (m, 1H), 7.02 (d, J=8.3 Hz, 1H), 6.98-6.94 (m, 1H), 6.65 (s, 1H), 5.72-5.67 (m, 1H), 5.21-5.15 (m, 1H), 4.09 (t, J=15.3 Hz, 2H), 3.94 (d, J=15.4 Hz, 1H), 3.86-3.83 (m, 1H), 3.56 (d, J=14.9 Hz, 1H), 3.28-3.15 (m, 7H), 2.80-2.72 (m, 2H), 2.04-1.94 (m, 5H), 1.83-1.77 (m, 6H), 1.49-1.46 (m, 2H), 1.42-1.38 (m, 2H), 1.28-1.22 (m, 10H).

Example 161

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (2R)-2-(methoxymethyl)pyrrolidine-1-carboxylate

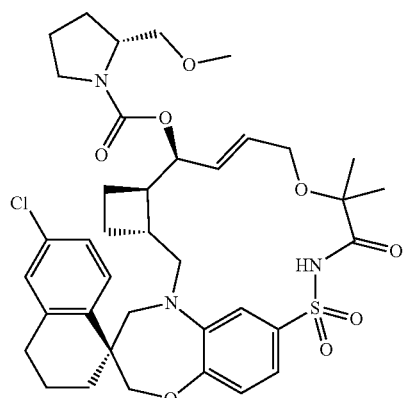

This compound was prepared using procedures analogous to those described for Example 46 using (2R)-2-(methoxymethyl)pyrrolidine to replace 1-(2-methoxyethyl)piperazine in Step 2. LCMS calc. for $C_{38}H_{49}ClN_3O_8S$ [M+H]$^+$: m/z=742.29/744.28; Found: 742.5/744.5.

Example 162

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3S)-3-ethoxypyrrolidine-1-carboxylate

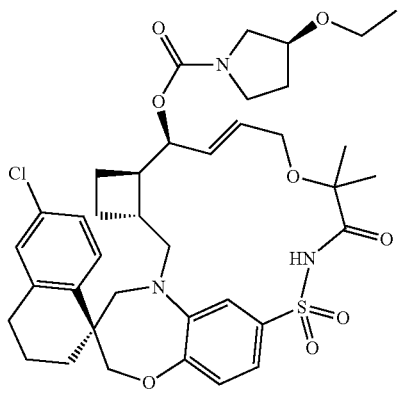 [SMILES: CCO[C@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3S)-3-ethoxypyrrolidine to replace 1-(2-methoxyethyl)piperazine in Step 2. LCMS calc. for $C_{38}H_{49}ClN_3O_8S$ [M+H]$^+$: m/z=742.29/744.28; Found: 742.6/744.6. $^1$H NMR (300 MHz, CDCl$_3$) δ 7.69 (d, J=8.5 Hz, 1H), 7.34 (t, J=7.2 Hz, 1H), 7.13 (dt, J=8.6, 2.2 Hz, 1H), 7.06 (d, J=2.2 Hz, 1H), 6.99 (s, 1H), 6.84 (dd, J=8.3, 4.0 Hz, 1H), 6.13 (s, 1H), 5.70 (dt, J=14.7, 6.4 Hz, 1H), 5.17 (d, J=4.6 Hz, 1H), 4.08-3.93 (m, 4H), 3.84 (d, J=13.0 Hz, 1H), 3.67 (d, J=14.4 Hz, 1H), 3.50-3.42 (m, 7H), 3.25 (d, J=14.3 Hz, 1H), 3.15-3.01 (m, 1H), 2.75 (q, J=5.2 Hz, 2H), 2.37-2.30 (m, 1H), 2.21 (t, J=7.6 Hz, 1H), 2.02-1.86 (m, 5H), 1.81-1.75 (m, 3H), 1.62-1.54 (m, 1H), 1.34-1.15 (m, 11H).

Example 163

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3S)-3-(methylamino)pyrrolidine-1-carboxylate

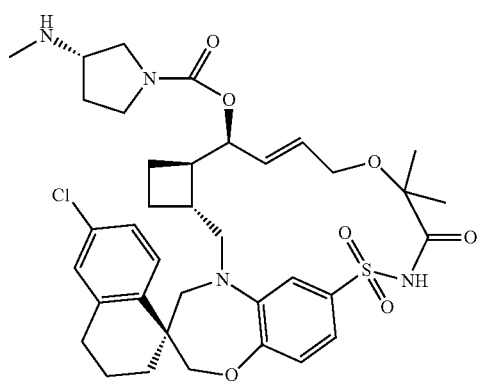 [SMILES: CN[C@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 156 using tert-butyl N-methyl-N-[(3S)-pyrrolidin-3-yl]carbamate to replace 4-amino-1-boc-piperidine in Step 1. LCMS calc. for $C_{37}H_{48}ClN_4O_7S$ [M+H]$^+$: m/z=727.3/729.3; Found: 727.5/729.3. $^1$H NMR (300 MHz, CDCl$_3$) δ 7.70 (d, J=8.5 Hz, 1H), 7.40 (dd, J=8.3, 2.0 Hz, 1H), 7.16 (dd, J=8.5, 2.3 Hz, 1H), 7.06 (d, J=2.3 Hz, 1H), 6.89 (d, J=8.3 Hz, 1H), 6.81 (d, J=2.2 Hz, 1H), 6.29 (td, J=10.4, 9.0, 4.9 Hz, 1H), 5.64 (dt, J=15.9, 2.7 Hz, 1H), 5.09 (s, 1H), 4.36 (d, J=12.4 Hz, 1H), 4.17-3.97 (m, 3H), 3.84 (d, J=13.4 Hz, 1H), 3.76-3.07 (m, 14H), 2.98-2.89 (m, 1H), 2.78 (d, J=8.6 Hz, 3H), 2.34-2.11 (m, 3H), 1.92-1.85 (m, 5H), 1.61 (d, J=6.6 Hz, 1H), 1.38 (s, 3H), 1.32 (s, 3H).

Example 164

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3R)-3-(methylamino)pyrrolidine-1-carboxylate

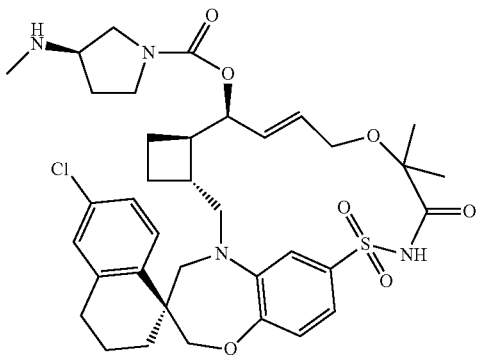 [SMILES: CN[C@@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 156 using tert-butyl N-methyl-N-[(3R)-pyrrolidin-3-yl]carbamate to replace 4-amino-1-boc-piperidine in Step 1. LCMS calc. for $C_{37}H_{48}ClN_4O_7S$ [M+H]$^+$: m/z=727.3/729.3; Found: 727.3/729.1. $^1$H NMR (499 MHz, DMSO-d$_6$) δ 7.65 (d, J=8.5 Hz, 1H), 7.26 (dd, J=8.5, 2.4 Hz, 1H), 7.20-7.13 (m, 1H), 7.10-6.99 (m, 1H), 6.91-6.73 (m, 2H), 6.22-6.17 (m, 1H), 5.54-5.46 (m, 1H), 4.91 (s, 1H), 4.11-3.94 (m, 3H), 3.90-3.78 (m, 2H), 3.70-3.65 (m, 4H), 3.01 (dd, J=16.0, 10.5 Hz, 2H), 2.88-2.67 (m, 4H), 2.67-2.55 (m, 3H), 2.29 (dq, J=15.3, 7.5, 6.3 Hz, 1H), 2.22-2.07 (m, 2H), 2.03-1.92 (m, 2H), 1.89-1.81 (m, 3H), 1.70-1.63 (m, 3H), 1.47-1.34 (m, 1H), 1.24 (s, 3H), 1.18 (s, 3H), 1.08 (d, J=8.4 Hz, 2H) ppm.

Example 165

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3-fluoroazetidine-1-carboxylate

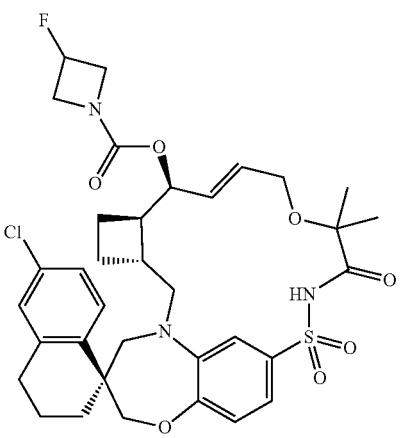 [SMILES: CC1(C)OC/C=C/[C@H](OC(=O)N2CC(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 3-Fluoroazetidine hydrochloride and Hunig's Base to replace 1-(2-methoxyethyl)piperazine in Step 2. LCMS calc. for $C_{35}H_{42}ClFN_3O_7S$ [M+H]$^+$: m/z=702.23/704.23; Found: 702.7/704.7. $^1$H NMR (300 MHz, CDCl$_3$) δ 9.13 (s, 1H, NH), 7.69 (d, J=8.5 Hz, 1H), 7.51 (dd, J=8.3, 2.1 Hz, 1H), 7.19 (dd, J=8.5, 2.2 Hz, 1H), 7.10 (d, J=2.1 Hz, 1H), 7.02-6.98 (m, 1H), 6.96 (d, J=1.8 Hz, 1H), 5.88-5.79 (m, 1H), 5.70 (dd, J=15.6, 4.9 Hz, 1H), 5.38 (m, 1H), 5.23 (m, 2H), 4.14 (m, 4H), 3.74 (dd, J=14.1, 8.3 Hz, 2H), 3.37 (d, J=14.5 Hz, 2H), 3.22 (dd, J=15.0, 9.3 Hz, 1H), 2.79 (d, J=4.1 Hz, 3H), 2.41-2.33 (m, 1H), 2.16 (s, 4H), 2.01 (dd, J=16.7, 9.0 Hz, 3H), 1.83 (d, J=8.4 Hz, 2H), 1.64 (dt, J=18.8, 9.3 Hz, 2H), 1.46 (s, 3H), 1.37 (s, 3H).

Example 166

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] 3,3-difluoropyrrolidine-1-carboxylate

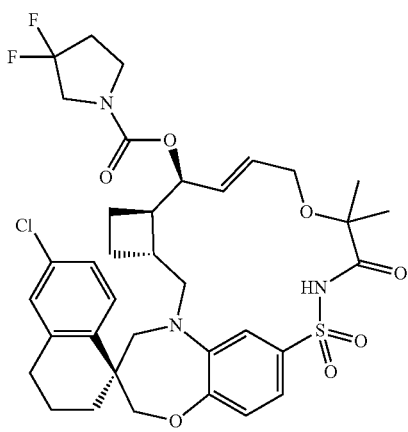 [SMILES: CC1(C)OC/C=C/[C@H](OC(=O)N2CCC(F)(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 3,3-Difluoropyrrolidine hydrochloride and Hunig's base to replace 1-(2-methoxyethyl)piperazine in Step 2. LCMS calc. for $C_{36}H_{43}ClF_2N_3O_7S$ [M+H]$^+$: m/z=734.24/736.24; Found: 734.7/735.7. $^1$H NMR (600 MHz, DMSO-d$_6$) δ 7.64 (d, J=8.5 Hz, 1H), 7.25 (d, J=8.3 Hz, 2H), 7.18 (s, 1H), 7.05-6.99 (m, 1H), 6.91 (s, 1H), 6.69-6.48 (m, 1H), 5.92-5.62 (m, 2H), 4.15-3.98 (m, 4H), 3.81 (m, 2H), 2.80 (d, J=16.8 Hz, 2H), 2.75-2.64 (m, 6H), 2.44 (s, 2H), 2.06-1.93 (m, 3H), 1.84 (d, J=4.0 Hz, 2H), 1.72 (s, 1H), 1.65 (s, 2H), 1.52-1.44 (m, 2H), 1.38 (s, 3H), 1.22 (s, 3H).

Example 167

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methoxycarbamate

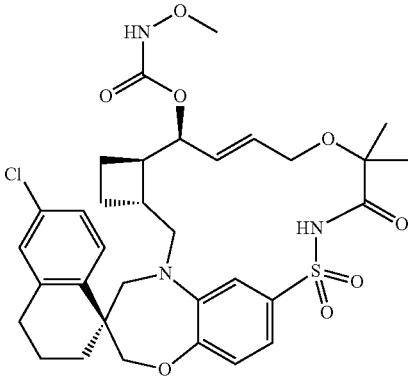 [SMILES: CONC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

To a solution of (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (30.0 mg, 0.10 mmol, Example 32) in MeCN (3 mL) was added 1,1'-carbonyldiimidazole (24.23 mg, 0.30 mmol). The mixture was stirred at 45° C. for 3 h. LCMS showed that the starting material was consumed. The mixture was concentrated, and the residue was re-dissolved in MeCN (1 mL) and water (1 mL). To the solution was added methoxyamine which was in-situ generated from methoxyamine hydrochloride (10.15 mg, 0.22 mmol) by treatment with 2 drops of 2N NaOH solution. The mixture was stirred at 45° C. overnight. The mixture was cooled down to r.t., 2 drops of 2 N HCl in EA was added and concentrated under reduced pressure. The residue was purified by prep-HPLC on a C18 column using H$_2$O/ACN (20-100%) to afford the desired product [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]N-methoxycarbamate (7.8 mg, 26.8% yield). LCMS calc. for $C_{33}H_{41}ClN_3O_8S$ [M+H]$^+$: m/z=674.22/675.23; Found: 674.3/674.2; $^1$H NMR (300 MHz, CDCl$_3$) δ 9.13 (s, 1H, NH), 7.68 (d, J=8.5 Hz, 1H), 7.52 (dt, J=8.5, 2.5 Hz, 1H), 7.19 (d, J=8.5 Hz, 1H), 7.10 (d, J=2.0 Hz, 1H), 7.07-6.97 (m, 2H), 5.78 (t, J=5.8 Hz, 1H), 4.15 (m, 3H), 4.02-3.83 (m, 2H), 3.75 (d, J=8.2 Hz, 2H), 3.50-3.23 (m, 3H), 2.88-2.70 (m, 3H), 2.45-2.33 (m, 1H), 2.10-1.95 (m, 3H), 1.91 (dd, J=12.9, 6.4 Hz, 2H), 1.87-1.80 (m, 3H), 1.69-1.59 (m, 2H), 1.58-1.49 (m, 2H), 1.44 (d, J=3.4 Hz, 3H), 1.38 (d, J=6.2 Hz, 3H).

Example 168

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (2S)-2-[(dimethylamino)methyl]pyrrolidine-1-carboxylate

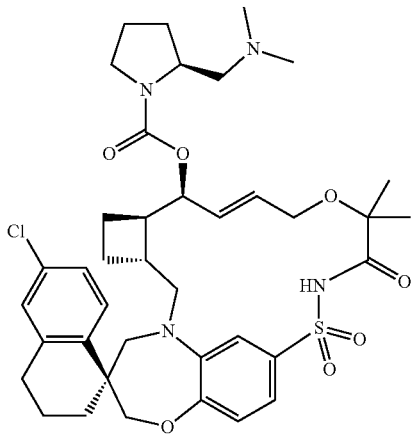 [SMILES: CN(C)C[C@@H]1CCCN1C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using N,N-dimethyl-1-[(2S)-pyrrolidin-2-yl]methanamine to replace 1-(2-methoxyethyl)piperazine in Step 2. LCMS calc. for $C_{39}H_{52}ClN_4O_7S$ [M+H]$^+$: m/z=755.32/757.31; Found: 755.5/757.4. $^1$H NMR (600 MHz, DMSO-d$_6$) δ 9.11 (s, 1H, NH), 7.70 (d, J=8.6 Hz, 1H), 7.32 (td, J=8.0, 2.1 Hz, 2H), 7.25 (d, J=2.2 Hz, 1H), 7.08 (d, J=8.3 Hz, 1H), 7.01 (d, J=19.4 Hz, 1H), 5.75 (s, 2H), 5.24 (s, 1H), 4.17 (dd, J=27.1, 12.1 Hz, 3H), 3.99 (d, J=13.3 Hz, 1H), 3.59 (m, 3H), 3.36-3.22 (m, 5H), 3.15 (s, 1H), 2.92 (s, 3H), 2.87 (s, 3H), 2.85-2.71 (m, 4H), 2.05 (dt, J=12.0, 7.2 Hz, 2H), 1.93 (m, 4H), 1.80 (dd, J=24.4, 7.6 Hz, 2H), 1.69 (m, 2H), 1.62-1.49 (m, 2H), 1.43 (s, 3H), 1.28 (s, 3H).

Example 169

[(3R,6R,7S,8E,22S)-6'-Chloro-12,12-dimethyl-13,15,15-trioxo-spiro[11,2-dioxa-15-thia-1,14-diazatetracyclo[14.7.2.03,6.019,24]pentacosa-8,16,18,24-tetraene-22,1'-tetralin]-7-yl] (2R)-2-[(dimethylamino)methyl]pyrrolidine-1-carboxylate

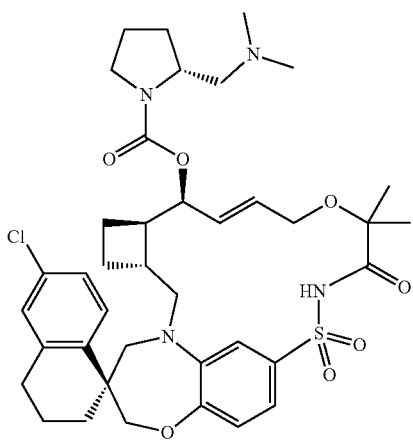 [SMILES: CN(C)C[C@H]1CCCN1C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using N,N-dimethyl-1-[(2R)-pyrrolidin-2-yl]methanamine to replace 1-(2-methoxyethyl)piperazine in Step 2. LCMS calc. for $C_{39}H_{52}ClN_4O_7S$ [M+H]$^+$: m/z=755.32/757.31; Found: 755.6/757.5. $^1$H NMR (600 MHz, DMSO-d$_6$) δ 9.14 (s, 1H, NH), 7.65 (d, J=8.5 Hz, 1H), 7.26 (d, J=8.4 Hz, 2H), 7.19 (d, J=1.5 Hz, 1H), 7.02 (d, J=8.4 Hz, 1H), 6.92 (s, 1H), 5.84-5.66 (m, 2H), 5.12 (s, 1H), 4.10 (dd, J=23.8, 12.3 Hz, 3H), 3.96 (dt, J=28.1, 14.1 Hz, 1H), 3.62-3.53 (m, 2H), 3.32-3.20 (m, 6H), 3.14-3.10 (m, 1H), 2.88 (t, J=8.8 Hz, 3H), 2.86-2.82 (m, 3H), 2.80 (dd, J=12.3, 4.1 Hz, 2H), 2.76-2.69 (m, 2H), 2.05-1.96 (m, 2H), 1.86 (m, 6H), 1.76-1.69 (m, 2H), 1.65 (dd, J=18.7, 9.5 Hz, 1H), 1.52-1.46 (m, 1H), 1.38 (d, J=8.7 Hz, 3H), 1.23 (s, 3H).

Example 170

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] 8-oxa-3-azabicyclo[3.2.1]octane-3-carboxylate

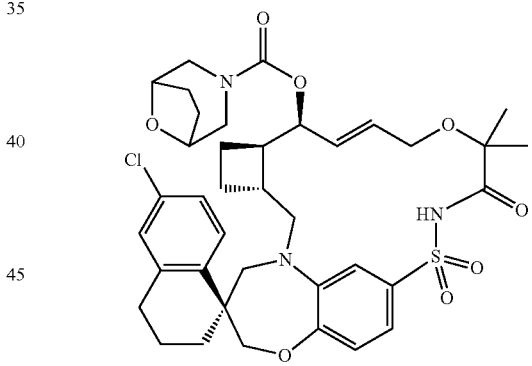

This compound was prepared using procedures analogous to those described for Example 46 using (1R,5 S)-3-oxa-8-azabicyclo[3.2.1]octane hydrochloride and N,N-diisopropylethylamine to replace 1-(2-methoxyethyl)piperazine in Step 2. LCMS calc. for $C_{38}H_{47}ClN_3O_8S$ [M+H]$^+$: m/z=740.27/742.27; Found: 740.5/742.3. $^1$H NMR (600 MHz, DMSO-d$_6$) δ 7.63 (t, J=8.3 Hz, 1H), 7.25 (d, J=8.2 Hz, 2H), 7.19 (s, 1H), 6.98 (m, 2H), 6.60 (d, J=77.3 Hz, 1H), 5.84-5.51 (m, 2H), 4.26 (m, 2H), 4.09 (dd, J=38.2, 12.5 Hz, 2H), 4.03-3.85 (m, 1H), 3.71-3.46 (m, 4H), 3.25 (s, 3H), 3.06-2.96 (m, 1H), 2.80 (d, J=16.6 Hz, 1H), 2.76-2.64 (m, 2H), 2.05-1.94 (m, 3H), 1.83 (s, 3H), 1.75 (t, J=20.1 Hz, 2H), 1.68-1.57 (m, 4H), 1.52-1.44 (m, 2H), 1.24 (s, 6H).

Example 171

[(3R,6R,7S,8E,22S)-6'-Chloro-12,12-dimethyl-13,15,15-trioxo-spiro[11,20-dioxa-15,6-thia-1,14-diaza-tetracyclo[14.7.2.0³,⁶.0¹⁹,²⁴]pentacosa-8,16,18,24-tetraene-22,1'-tetralin]-7-yl](9aS)-3,4,6,7,9,9a-hexahydro-1H-pyrazino[2,1-c][1,4]oxazine-8-carboxylate

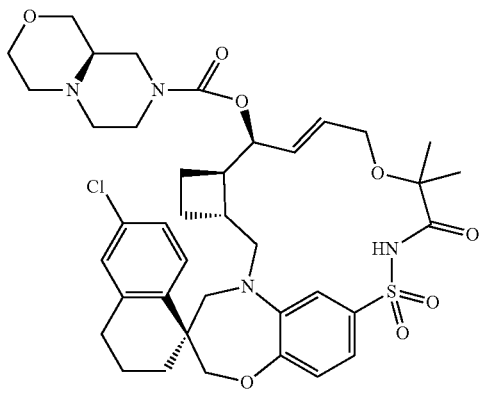 [SMILES: CC1(C)OC/C=C/[C@H](OC(=O)N2CCN3CCOC[C@H]3C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using (9aS)-1,3,4,6,7,8,9,9a-octahydropyrazino[2,1-c][1,4]oxazine; dihydrochloride and diisopropylethylamine to replace 1-(2-methoxyethyl)piperazine in Step 2. LCMS calc. for $C_{39}H_{50}ClN_4O_8S$ [M+H]$^+$: m/z=769.3/771.3; Found 769.5/771.5. $^1$H NMR (300 MHz, CDCl$_3$) δ 7.69 (d, J=8.5 Hz, 1H), 7.50 (dd, J=8.4, 2.2 Hz, 1H), 7.18 (d, J=8.5 Hz, 1H), 7.09 (d, J=2.3 Hz, 1H), 6.99 (d, J=8.4 Hz, 2H), 5.90-5.62 (m, 2H), 5.43-5.27 (m, 1H), 4.16-4.00 (m, 4H), 3.95-3.63 (m, 6H), 3.40 (dd, J=22.9, 15.5 Hz, 2H), 3.21 (dd, J=15.4, 9.0 Hz, 2H), 3.06 (t, J=12.7 Hz, 1H), 2.84-2.62 (m, 6H), 2.38 (qd, J=8.9, 3.4 Hz, 2H), 2.25 (q, J=9.2, 7.1 Hz, 2H), 1.99 (tdd, J=14.5, 11.1, 6.4 Hz, 3H), 1.89-1.78 (m, 3H), 1.65 (q, J=9.1 Hz, 2H), 1.44 (s, 3H), 1.37 (s, 3H).

Example 172

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl]morpholine-4-carboxylate

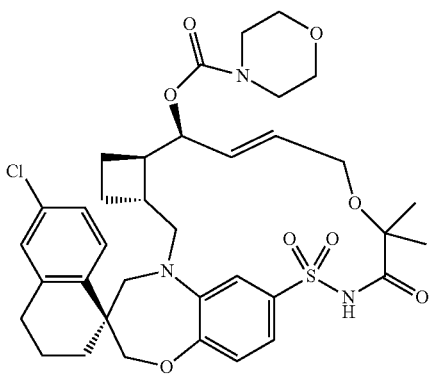 [SMILES: CC1(C)OC/C=C/[C@H](OC(=O)N2CCOCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using morpholine to replace 1-(2-methoxyethyl)piperazine in Step 2. LCMS calc. for $C_{36}H_{45}ClN_3O_8S$ [M+H]$^+$: m/z=714.26/716.26; Found: 714.7/716.7. $^1$H NMR (600 MHz, CDCl$_3$) δ 9.03 (s, 1H), 7.67 (d, J=8.5 Hz, 1H), 7.49 (dd, J=8.3, 2.1 Hz, 1H), 7.18 (dd, J=8.5, 2.2 Hz, 1H), 7.09 (d, J=2.0 Hz, 1H), 6.97 (dd, J=17.3, 5.2 Hz, 2H), 5.91-5.63 (m, 2H), 5.35 (s, 1H), 4.27-4.03 (m, 3H), 3.87-3.11 (m, 12H), 2.77 (dd, J=11.1, 5.2 Hz, 3H), 2.39 (dd, J=8.7, 3.3 Hz, 1H), 2.09-1.91 (m, 3H), 1.81 (ddd, J=29.9, 18.4, 9.7 Hz, 3H), 1.70-1.58 (m, 3H), 1.44 (s, 3H), 1.36 (s, 3H).

Example 173

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl]pyrrolidine-1-carboxylate

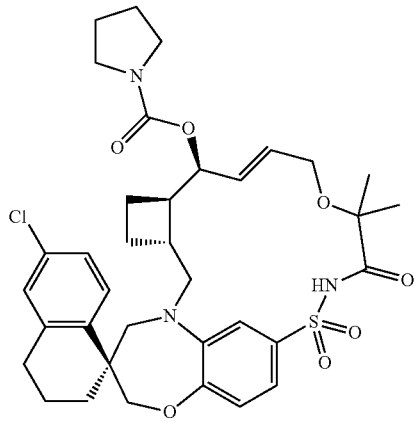 [SMILES: CC1(C)OC/C=C/[C@H](OC(=O)N2CCCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using pyrrolidine to replace 1-(2-methoxyethyl)piperazine in Step 2. LCMS calc. for $C_{36}H_{45}ClN_3O_7S$ [M+H]$^+$: m/z=698.26/700.26; Found: 698.4/700.4. $^1$H NMR (500 MHz, CDCl$_3$) δ 9.07 (s, 1H), 7.67 (d, J=8.5 Hz, 1H), 7.52-7.44 (m, 1H), 7.17 (dd, J=8.5, 2.3 Hz, 1H), 7.08 (d, J=2.3 Hz, 1H), 6.98 (dd, J=5.3, 3.0 Hz, 2H), 5.77 (ddd, J=20.5, 16.0, 8.3 Hz, 2H), 5.37-5.33 (m, 2H), 5.30 (s, 1H), 4.07 (dd, J=13.7, 5.9 Hz, 1H), 3.84-3.65 (m, 2H), 3.51-3.44 (m, 2H), 3.37 (d, J=14.9 Hz, 2H), 3.21 (dd, J=14.9, 9.3 Hz, 1H), 2.85-2.71 (m, 3H), 2.36 (dd, J=9.0, 3.7 Hz, 1H), 2.26-2.17 (m, 2H), 2.01 (d, J=6.5 Hz, 4H), 1.89-1.80 (m, 6H), 1.65 (d, J=5.7 Hz, 2H), 1.43 (s, 3H), 1.35 (s, 3H).

Example 174

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] azetidine-1-carboxylate

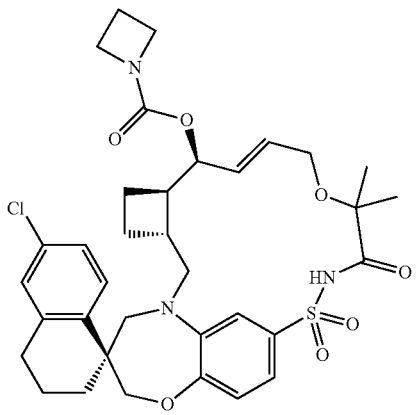 [SMILES: CC1(C)OC/C=C/[C@H](OC(=O)N2CCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using azetidine hydrochloride and hunig's base to replace 1-(2-methoxyethyl)piperazine in Step 2. LCMS calc. for $C_{35}H_{41}ClN_3O_7S$ [M−H]⁺: m/z=682.24/684.24; Found: 682.7/684.7. ¹H NMR (600 MHz, CDCl₃) δ 7.69 (d, J=8.5 Hz, 1H), 7.41 (d, J=28.7 Hz, 1H), 7.15 (d, J=8.4 Hz, 1H), 7.07 (d, J=1.6 Hz, 1H), 6.99 (s, 1H), 6.88 (s, 1H), 6.02 (s, 1H), 5.69 (dd, J=15.6, 5.6 Hz, 1H), 5.34 (d, J=2.9 Hz, 1H), 5.16 (s, 1H), 4.02 (ddd, J=21.9, 18.8, 7.6 Hz, 6H), 3.82 (s, 1H), 3.68 (d, J=14.5 Hz, 1H), 3.49 (s, 1H), 3.39-2.96 (m, 2H), 2.81-2.72 (m, 2H), 2.63 (d, J=10.3 Hz, 1H), 2.34 (qd, J=9.5, 3.2 Hz, 1H), 2.26-2.18 (m, 2H), 2.03-1.96 (m, 4H), 1.91 (dd, J=8.8, 4.0 Hz, 2H), 1.82-1.74 (m, 3H), 1.38 (s, 3H), 1.25 (s, 3H).

Example 175

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (3R)-3-methylpiperazine-1-carboxylate

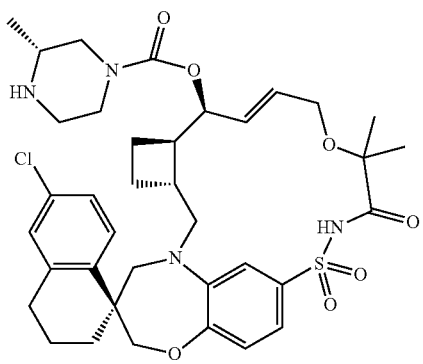 [SMILES: C[C@@H]1CN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CCN1]

This compound was prepared using procedures analogous to those described for Example 46 using (2R)-2-methylpiperazine to replace 1-(2-methoxyethyl)piperazine in Step 2. LCMS calc. for $C_{37}H_{48}ClN_4O_7S$ [M+H]⁺: m/z=727.29/729.28; Found: 727.5/729.5. ¹H NMR (600 MHz, CDCl₃) δ 9.65 (s, 1H), 7.63 (dd, J=34.1, 7.2 Hz, 1H), 7.41 (d, J=25.4 Hz, 1H), 7.19-7.04 (m, 2H), 6.93 (d, J=35.6 Hz, 2H), 5.85 (dd, J=202.2, 33.8 Hz, 1H), 5.48-5.05 (m, 1H), 4.31-3.64 (m, 7H), 3.61-3.41 (m, 1H), 3.31 (d, J=14.6 Hz, 1H), 3.19-2.98 (m, 2H), 2.76 (ddd, J=22.2, 17.3, 4.6 Hz, 5H), 2.34 (d, J=7.6 Hz, 2H), 2.27-2.18 (m, 1H), 2.03-1.88 (m, 4H), 1.84-1.70 (m, 4H), 1.63 (d, J=9.9 Hz, 2H), 1.38 (s, 3H), 1.26 (d, J=8.7 Hz, 3H), 1.10 (s, 3H).

Example 176

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (3S)-3-methylpiperazine-1-carboxylate

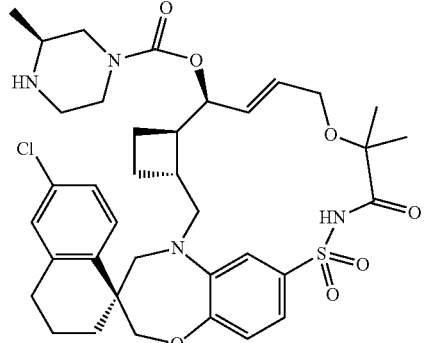

This compound was prepared using procedures analogous to those described for Example 46 using (2S)-2-methylpiperazine to replace 1-(2-methoxyethyl)piperazine in Step 2. LCMS calc. for $C_{37}H_{48}ClN_4O_7S$ [M+H]⁺: m/z=727.29/729.28; Found: 727.5/729.5. ¹H NMR (500 MHz, CDCl₃) δ 7.67 (d, J=8.5 Hz, 1H), 7.48 (d, J=7.1 Hz, 1H), 7.16 (d, J=8.4 Hz, 1H), 7.09 (dd, J=6.9, 2.2 Hz, 1H), 6.97 (d, J=8.1 Hz, 2H), 5.71 (s, 2H), 5.35 (dd, J=5.7, 3.9 Hz, 2H), 4.13 (t, J=11.9 Hz, 2H), 4.03 (dd, J=22.2, 8.6 Hz, 2H), 3.83-3.64 (m, 2H), 3.44 (d, J=14.9 Hz, 1H), 3.35 (d, J=14.6 Hz, 1H), 3.26-3.12 (m, 1H), 3.00 (d, J=15.0 Hz, 1H), 2.82-2.72 (m, 4H), 2.54 (s, 1H), 2.38 (s, 1H), 2.26-2.15 (m, 1H), 1.97 (dd, J=42.5, 8.6 Hz, 4H), 1.86-1.74 (m, 4H), 1.63 (dd, J=19.1, 9.7 Hz, 2H), 1.48 (t, J=12.2 Hz, 1H), 1.42 (s, 3H), 1.35 (s, 3H), 1.07 (s, 3H).

Example 177

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] 4-(2-pyridyl)piperazine-1-carboxylate

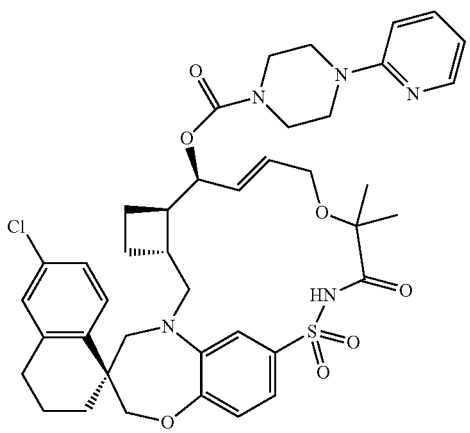 [SMILES: CC1(C)OC/C=C/[C@H](OC(=O)N2CCN(c3ccccn3)CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 1-(2-pyridyl)piperazine to replace 1-(2-methoxyethyl)piperazine in Step 2. LCMS calc. for $C_{41}H_{49}ClN_5O_7S$ [M+H]$^+$: m/z=790.3/792.3; Found: 790.3/792.3. $^1$H NMR (600 MHz, CDCl$_3$) δ 9.13 (s, 1H), 8.28 (d, J=4.8 Hz, 1H), 7.82-7.73 (m, 1H), 7.67 (d, J=8.5 Hz, 1H), 7.49 (dd, J=8.3, 2.2 Hz, 1H), 7.18 (dd, J=8.5, 2.2 Hz, 1H), 7.09 (d, J=2.2 Hz, 1H), 7.00 (d, J=8.3 Hz, 1H), 6.94 (d, J=2.0 Hz, 1H), 6.90-6.77 (m, 2H), 6.01-5.67 (m, 2H), 5.56-5.21 (m, 2H), 4.29-4.02 (m, 3H), 3.83-3.70 (m, 6H), 3.51-3.31 (m, 2H), 3.21 (dd, J=15.1, 9.7 Hz, 1H), 2.84-2.73 (m, 4H), 2.48-2.31 (m, 1H), 2.28-2.19 (m, 1H), 2.10-1.91 (m, 4H), 1.83 (ddd, J=25.5, 18.9, 9.2 Hz, 3H), 1.72-1.59 (m, 2H), 1.44 (s, 3H), 1.36 (s, 3H).

Example 178

[(3R,6R,7S,8E,22S)-6'-Chloro-12,12-dimethyl-13, 15,15-trioxo-spiro[11,20-dioxa-15λ^6-thia-1,14-diazatetracyclo[14.7.2.0^3,6.0^19,24]pentacosa-8,16, 18,24-tetraene-22,1'-tetralin]-7-yl] N-[2-(3-pyridyl)ethyl]carbamate

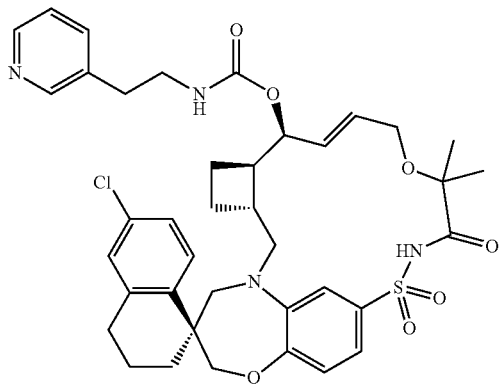 [SMILES: CC1(C)OC/C=C/[C@H](OC(=O)NCCc2cccnc2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 3-(2-aminoethyl)pyridine to replace 1-(2-methoxyethyl)piperazine in Step 2. LCMS calc. for $C_{39}H_{46}ClN_4O_7S$ [M+H]$^+$: m/z=749.28/751.28; Found: 749.5/751.4. $^1$H NMR (500 MHz, DMSO-d$_6$) δ 8.58 (s, 2H), 7.96 (d, J=7.4 Hz, 1H), 7.62 (dd, J=22.2, 7.3 Hz, 2H), 7.33-7.23 (m, 2H), 7.19 (d, J=1.9 Hz, 1H), 7.12 (t, J=5.6 Hz, 1H), 7.06-6.96 (m, 2H), 6.92 (s, 1H), 5.81-5.26 (m, 2H), 5.01 (d, J=91.1 Hz, 1H), 4.11 (dd, J=43.7, 12.2 Hz, 3H), 3.90 (dd, J=14.3, 5.9 Hz, 2H), 2.95-2.60 (m, 6H), 2.17-1.45 (m, 10H), 1.40 (s, 3H), 1.24 (s, 6H).

Example 179

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] N-(2,2-difluoroethyl) carbamate

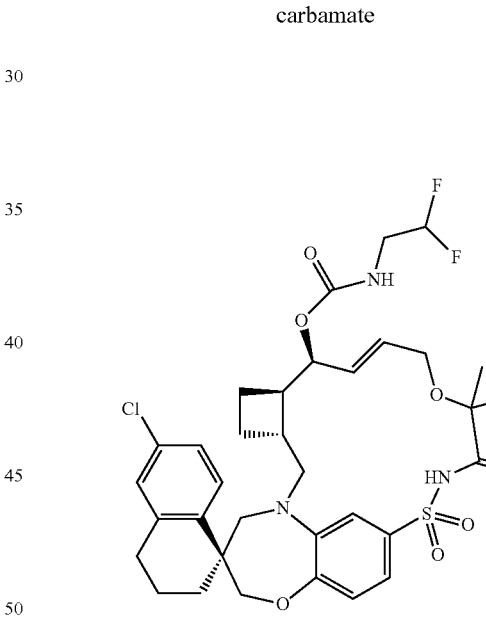

This compound was prepared using procedures analogous to those described for Example 46 using 2,2-difluoroethanamine to replace 1-(2-methoxyethyl)piperazine in Step 2. LCMS calc. for $C_{34}H_{41}ClF_2N_3O_7S$ [M+H]$^+$: m/z=708.23/710.23; Found: 708.4/710.3. $^1$H NMR (500 MHz, DMSO-d$_6$) δ 11.66 (s, 1H), 7.65 (d, J=8.4 Hz, 1H), 7.44 (d, J=7.2 Hz, 1H), 7.35-7.13 (m, 4H), 7.05 (t, J=19.8 Hz, 2H), 6.51 (s, 1H), 6.27-5.57 (m, 2H), 5.33 (t, J=4.7 Hz, 1H), 5.04 (s, 1H), 4.33-3.72 (m, 3H), 2.85-2.64 (m, 3H), 2.15-1.44 (m, 10H), 1.39 (s, 2H), 1.24 (s, 8H).

Example 180

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-(2-morpholinoethyl)carbamate

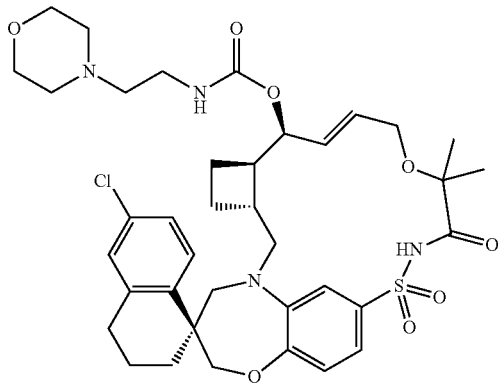 [SMILES: CC1(C)OC/C=C/[C@H](OC(=O)NCCN2CCOCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 4-(2-aminoethyl)morpholine to replace 1-(2-methoxyethyl)piperazine in Step 2. LCMS calc. for $C_{38}H_{50}ClN_4O_8S$ [M+H]$^+$: m/z=757.31/759.30; Found: 757.5/759.2.

Example 181

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-isopropylcarbamate

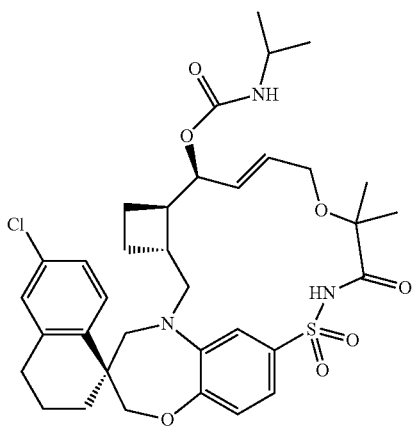 [SMILES: CC(C)NC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using isopropylamine to replace 1-(2-methoxyethyl)piperazine in Step 2. LCMS calc. for $C_{35}H_{45}ClN_3O_7S$ [M+H]$^+$: m/z=686.26/688.26; Found: 686.8/688.8. $^1$H NMR (600 MHz, CDCl$_3$) δ 8.97 (s, 1H), 7.67 (d, J=8.5 Hz, 1H), 7.50 (dd, J=8.3, 2.1 Hz, 1H), 7.17 (dd, J=8.5, 2.2 Hz, 1H), 7.08 (d, J=1.7 Hz, 2H), 6.99 (d, J=8.3 Hz, 1H), 5.82-5.60 (m, 2H), 5.15 (s, 1H), 4.64 (d, J=7.0 Hz, 1H), 4.13 (dd, J=26.0, 12.2 Hz, 3H), 3.80 (s, 3H), 3.52-3.07 (m, 3H), 2.86-2.63 (m, 3H), 2.35 (d, J=40.1 Hz, 1H), 2.07-1.71 (m, 7H), 1.64 (d, J=10.1 Hz, 1H), 1.42 (s, 3H), 1.37 (s, 3H), 1.17 (d, J=6.3 Hz, 6H).

Example 182

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-isobutylcarbamate

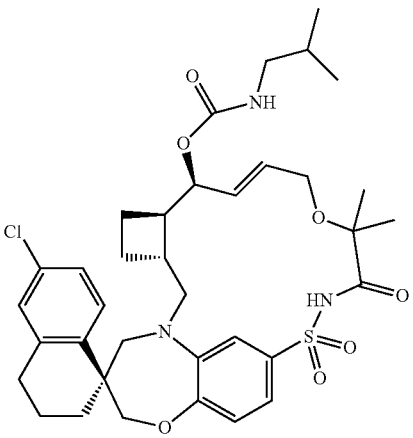 [SMILES: CC(C)CNC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using isobutylamine to replace 1-(2-methoxyethyl)piperazine in Step 2. LCMS calc. for $C_{36}H_{47}ClN_3O_7S$ [M+H]$^+$: m/z=700.27/702.27; Found: 700.8/702.6. $^1$H NMR (600 MHz, CDCl$_3$) δ 9.00 (s, 1H), 7.66 (d, J=8.5 Hz, 1H), 7.50 (dd, J=8.3, 2.1 Hz, 1H), 7.17 (dd, J=8.5, 2.2 Hz, 1H), 7.07 (dd, J=10.3, 1.9 Hz, 2H), 6.99 (d, J=8.3 Hz, 1H), 5.88-5.57 (m, 2H), 5.20 (s, 1H), 4.91 (t, J=5.6 Hz, 1H), 4.27-4.04 (m, 3H), 3.85-3.64 (m, 2H), 3.52-3.28 (m, 2H), 3.23-3.12 (m, 1H), 3.01 (dd, J=13.5, 6.9 Hz, 2H), 2.77 (dd, J=10.5, 5.2 Hz, 3H), 2.37 (dd, J=8.7, 3.9 Hz, 1H), 2.08-1.70 (m, 7H), 1.62 (d, J=9.6 Hz, 2H), 1.42 (s, 3H), 1.37 (s, 3H), 0.92 (d, J=6.7 Hz, 6H).

Example 183

[(3R,6R,7S,8E,22S)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-(cyclopropylmethyl)carbamate

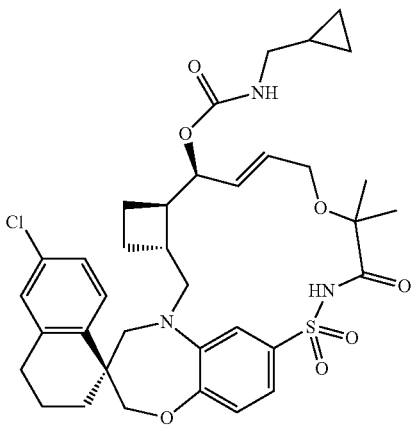 [SMILES: CC1(C)OC/C=C/[C@H](OC(=O)NCC2CC2)[C@@H]2CC[C@H]2CN2C[C@@]3(CCCc4cc(Cl)ccc43)COc3ccc(cc32)S(=O)(=O)NC1=O]

433

This compound was prepared using procedures analogous to those described for Example 46 using cyclopropylmethylamine to replace 1-(2-methoxyethyl)piperazine in Step 2. LCMS calc. for $C_{36}H_{45}ClN_3O_7S$ [M+H]$^+$: m/z=698.27/700.27; Found: 698.3/700.1.

Example 184

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-cyclobutylcarbamate

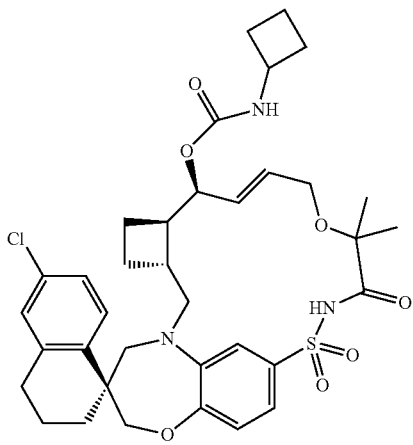 [SMILES: CC1(C)OC/C=C/[C@H](OC(=O)NC2CCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using cyclobutylamine to replace 1-(2-methoxyethyl)piperazine in Step 2. LCMS calc. for $C_{36}H_{45}ClN_3O_7S$ [M+H]$^+$: m/z=698.27/700.27; Found: 698.4/700.3. $^1$H NMR (600 MHz, CDCl$_3$) δ 9.00 (s, 1H), 7.66 (d, J=8.5 Hz, 1H), 7.50 (dd, J=8.3, 2.1 Hz, 1H), 7.17 (dd, J=8.5, 2.2 Hz, 1H), 7.07 (dd, J=10.3, 1.9 Hz, 2H), 6.99 (d, J=8.3 Hz, 1H), 5.88-5.57 (m, 2H), 5.20 (s, 1H), 4.91 (t, J=5.6 Hz, 1H), 4.27-4.04 (m, 3H), 3.85-3.64 (m, 2H), 3.52-3.28 (m, 2H), 3.23-3.12 (m, 1H), 3.01 (dd, J=13.5, 6.9 Hz, 2H), 2.77 (dd, J=10.5, 5.2 Hz, 3H), 2.37 (dd, J=8.7, 3.9 Hz, 1H), 2.08-1.70 (m, 7H), 1.62 (d, J=9.6 Hz, 2H), 1.42 (s, 3H), 1.37 (s, 3H), 0.92 (d, J=6.7 Hz, 6H).

Example 185

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-tetrahydropyran-4-ylcarbamate

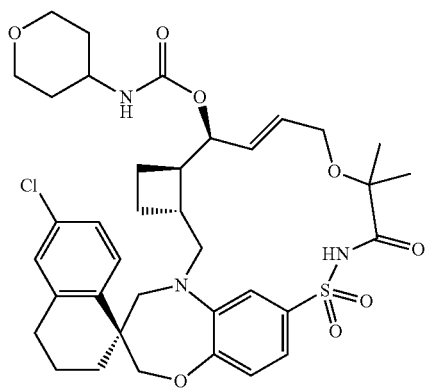 [SMILES: CC1(C)OC/C=C/[C@H](OC(=O)NC2CCOCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 4-aminotetrahydropyran to replace 1-(2-methoxyethyl)piperazine in Step 2. LCMS calc. for $C_{37}H_{47}ClN_3O_8S$ [M+H]: m/z=728.28/730.28; Found: 728.3/730.0. $^1$H NMR (600 MHz, DMSO-d$_6$) δ 11.66 (s, 1H), 7.65 (d, J=8.5 Hz, 1H), 7.40-6.73 (m, 7H), 6.53 (s, 1H), 5.51 (dd, J=178.9, 11.3 Hz, 2H), 5.02 (s, 1H), 4.28-3.72 (m, 6H), 3.55 (s, 1H), 2.73 (dd, J=24.8, 16.6 Hz, 3H), 2.12-1.49 (m, 12H), 1.43-1.09 (m, 11H).

Example 186

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] 4-isopropylpiperazine-1-carboxylate

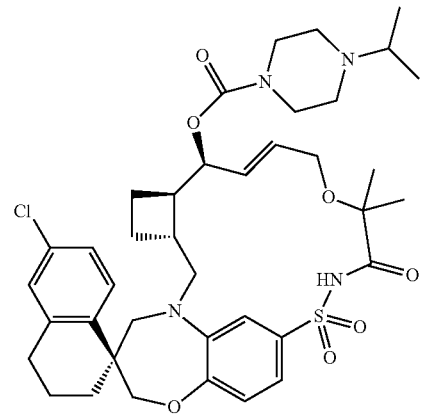 [SMILES: CC(C)N1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using 1-isopropylpiperazine to replace 1-(2-methoxyethyl)piperazine in Step 2. LCMS calc. for $C_{39}H_{52}ClN_4O_7S$ [M+H]$^+$: m/z=755.32/757.31; Found: 755.5/757.4. $^1$H NMR (600 MHz, CDCl$_3$) δ 12.87 (s, 1H), 9.15 (s, 1H), 7.67 (d, J=8.5 Hz, 1H), 7.47 (d, J=7.6 Hz, 1H), 7.18 (dd, J=8.5, 2.0 Hz, 1H), 7.09 (d, J=2.2 Hz, 1H), 7.00 (d, J=8.3 Hz, 1H), 6.86 (s, 1H), 5.90 (t, J=20.4 Hz, 2H), 5.43-5.18 (m, 1H), 4.47-4.01 (m, 5H), 3.89-3.28 (m, 9H), 3.25-2.59 (m, 6H), 2.29 (dt, J=15.3, 8.3 Hz, 2H), 2.17-1.91 (m, 4H), 1.89-1.80 (m, 4H), 1.35 (s, 10H).

Example 187

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] 4-(oxetan-3-yl)piperazine-1-carboxylate

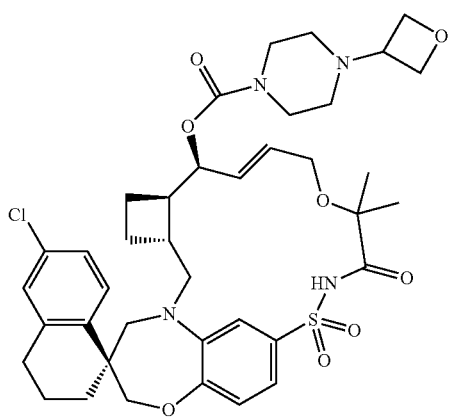 [SMILES: CC1(C)OC/C=C/[C@H](OC(=O)N2CCN(C3COC3)CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 1-(oxetan-3-yl)piperazine to replace 1-(2-methoxyethyl)piperazine in Step 2. LCMS calc. for $C_{39}H_{50}ClN_4O_8S$ [M+H]$^+$: m/z=769.30/71.29; Found: 769.7/771.6. $^1$H NMR (600 MHz, CDCl$_3$) δ 9.13 (s, 1H), 7.67 (d, J=8.5 Hz, 1H), 7.52-7.40 (m, 1H), 7.18 (dd, J=8.5, 2.2 Hz, 1H), 7.09 (d, J=2.3 Hz, 1H), 6.99 (d, J=8.3 Hz, 1H), 6.88 (d, J=2.0 Hz, 1H), 6.01-5.74 (m, 2H), 5.54-5.25 (m, 4H), 4.77 (ddd, J=42.9, 9.0, 4.2 Hz, 3H), 4.31-4.07 (m, 4H), 3.93 (dd, J=33.3, 27.0 Hz, 3H), 3.82-3.29 (m, 7H), 3.19 (dd, J=15.2, 10.0 Hz, 1H), 3.03-2.57 (m, 7H), 2.44-2.18 (m, 5H), 1.45 (s, 6H).

Example 188

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-cyclopropylcarbamate

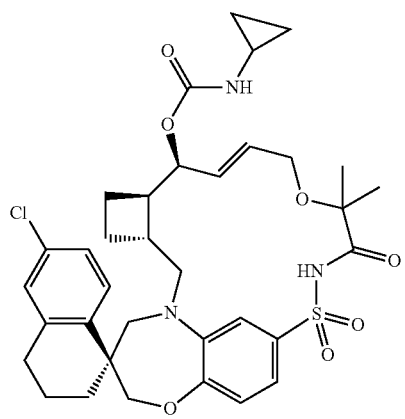 [SMILES: CC1(C)OC/C=C/[C@H](OC(=O)NC2CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using cyclopropylamine to replace 1-(2-methoxyethyl)piperazine in Step 2. LCMS calc. for $C_{35}H_{43}ClN_3O_7S$ [M+H]$^+$: m/z=684.24/686.24; Found: 684.4/686.1. $^1$H NMR (300 MHz, CDCl$_3$) δ 9.04 (s, 1H), 7.66 (d, J=8.5 Hz, 1H), 7.49 (dd, J=8.3, 2.1 Hz, 1H), 7.17 (dd, J=8.5, 2.3 Hz, 1H), 7.11-6.89 (m, 3H), 5.67 (dd, J=16.0, 3.5 Hz, 2H), 5.10 (d, J=55.9 Hz, 1H), 4.32-3.97 (m, 3H), 3.90-3.01 (m, 6H), 2.93-2.16 (m, 5H), 2.08-1.72 (m, 7H), 1.64 (s, 1H), 1.43 (s, 3H), 1.36 (s, 3H), 0.72 (dd, J=6.7, 5.0 Hz, 2H), 0.54 (s, 2H).

Example 189

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] 4-methylpiperazine-1-carboxylate

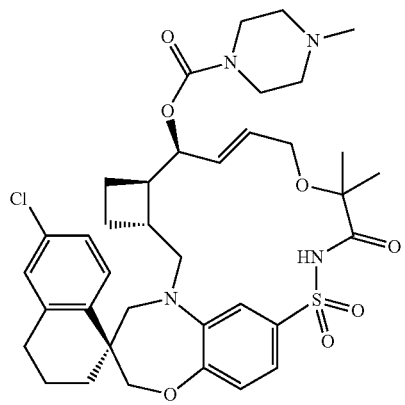 [SMILES: CN1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 using methylpiperazine to replace 1-(2-methoxyethyl)piperazine in Step 2. LCMS calc. for $C_{37}H_{48}ClN_4O_7S$ [M+H]$^+$: m/z=727.30/729.29; Found: 727.6/729.2. $^1$H NMR (499 MHz, CDCl$_3$) δ 7.67 (d, J=8.5 Hz, 1H), 7.54-7.41 (m, 1H), 7.17 (dd, J=8.5, 2.3 Hz, 1H), 7.13-7.04 (m, 1H), 6.98 (t, J=6.1 Hz, 2H), 6.17-5.55 (m, 2H), 5.32 (s, 2H), 4.12 (dd, J=25.4, 12.1 Hz, 3H), 3.85-3.08 (m, 9H), 2.93-2.64 (m, 3H), 2.60-2.14 (m, 9H), 2.09-1.92 (m, 5H), 1.82 (s, 2H), 1.43 (s, 3H), 1.36 (s, 3H).

Example 190

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] 4-hydroxypiperidine-1-carboxylate

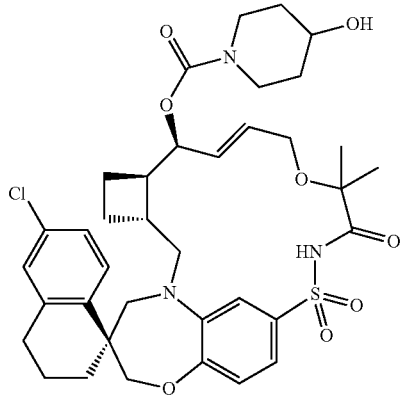 [SMILES: CC1(C)OC/C=C/[C@H](OC(=O)N2CCC(O)CC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using piperidin-4-ol to replace 1-(2-methoxyethyl)piperazine in Step 2. LCMS calc. for $C_{37}H_{47}ClN_3O_8S$ [M+H]$^+$: m/z=728.28/730.28; Found: 728.4/729.9. $^1$H NMR (500 MHz, DMSO-d$_6$) δ 11.69 (s, 1H), 7.70 (d, J=8.6 Hz, 1H), 7.20 (ddd, J=109.1, 20.0, 12.8 Hz, 6H), 6.57 (s, 1H), 5.74 (s, 2H), 5.20 (s, 1H), 4.77 (d, J=3.5 Hz, 1H), 3.92 (ddd, J=188.7, 35.2, 15.1 Hz, 8H), 2.96-2.68 (m, 4H), 1.84 (dd, J=111.2, 52.7 Hz, 11H), 1.31 (t, J=57.5 Hz, 10H).

Example 191

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-(2-methoxyethyl)carbamate

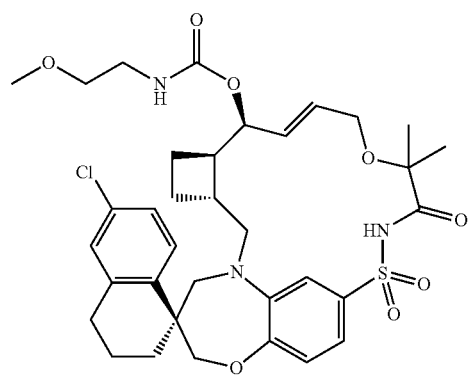 [SMILES: COCCNC(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using 2-methoxyethylamine to replace 1-(2-methoxyethyl)piperazine in Step 2. LCMS calc. for $C_{35}H_{45}ClN_3O_8S$ [M+H]$^+$: m/z=702.26/704.26; Found: 702.4/704.3. $^1$H NMR (500 MHz, DMSO-d$_6$) δ 11.72 (s, 1H), 7.70 (d, J=8.6 Hz, 1H), 7.40-7.19 (m, 3H), 7.05 (d, J=48.1 Hz, 3H), 6.57 (s, 1H), 5.95-5.33 (m, 2H), 5.07 (s, 1H), 4.39-3.76 (m, 4H), 3.59 (d, J=14.9 Hz, 2H), 3.28 (s, 3H), 3.16 (s, 2H), 2.96-2.64 (m, 3H), 2.16-1.50 (m, 9H), 1.44 (s, 2H), 1.25 (d, J=43.6 Hz, 7H).

Example 192

[(3R,6R,7S,8E,22S)-6'-Chloro-12,12-dimethyl-13,15,15-trioxo-spiro[11,20-dioxa-15-thia-1,14-diaza-tetracyclo[14.7.2.0³,⁶.0¹⁹,²⁴]pentacosa-8,16,18,24-tetraene-22,1'-tetralin]-7-yl] N-(oxetan-3-yl)carbamate

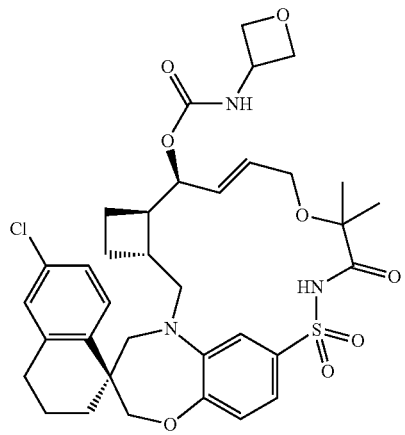 [SMILES: CC1(C)OC/C=C/[C@H](OC(=O)NC2COC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using oxetan-3-amine to replace 1-(2-methoxyethyl)piperazine in Step 2. LCMS calc. for $C_{35}H_{43}ClN_3O_8S$ [M+H]$^+$: m/z=700.24/702.24; Found: 700.3/702.3. $^1$H NMR (600 MHz, CDCl$_3$) δ 8.97 (s, 1H), 7.66 (d, J=8.5 Hz, 1H), 7.49 (dd, J=26.7, 25.2 Hz, 1H), 7.18 (dd, J=8.5, 2.2 Hz, 1H), 7.07 (d, J=13.5 Hz, 2H), 7.01 (d, J=8.3 Hz, 1H), 5.94-5.64 (m, 2H), 5.56-5.12 (m, 4H), 4.98-4.79 (m, 3H), 4.56 (d, J=6.0 Hz, 2H), 4.13 (dd, J=27.7, 12.2 Hz, 3H), 3.75 (dd, J=53.1, 12.3 Hz, 2H), 3.53-3.10 (m, 2H), 2.90-2.65 (m, 3H), 2.49-2.28 (m, 1H), 2.29-2.14 (m, 2H), 2.01 (d, J=5.4 Hz, 4H), 1.86 (d, J=10.0 Hz, 1H), 1.43 (s, 3H), 1.37 (s, 3H).

Example 193

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] N-[2-(1-piperidyl)ethyl] carbamate

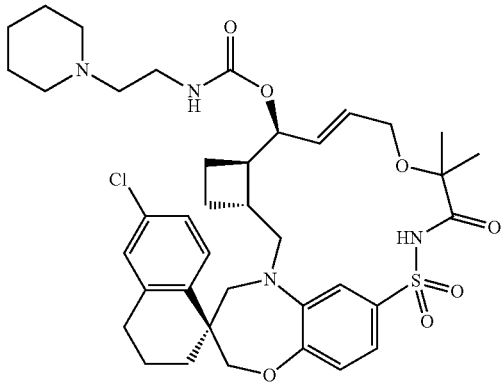 [SMILES: CC1(C)OC/C=C/[C@H](OC(=O)NCCN2CCCCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 46 using 1-(2-aminoethyl)-piperidine to replace 1-(2-methoxyethyl)piperazine in Step 2. LCMS calc. for $C_{39}H_{52}ClN_4O_7S$ [M+H]$^+$: m/z=755.33/757.32; Found: 755.5/757.4. $^1$H NMR (600 MHz, CDCl$_3$) δ 12.22 (s, 1H), 7.67 (d, J=8.5 Hz, 1H), 7.49 (d, J=7.7 Hz, 1H), 7.17 (dd, J=8.5, 2.2 Hz, 1H), 7.08 (s, 1H), 7.03-6.86 (m, 2H), 5.81 (s, 1H), 5.63 (dd, J=15.4, 4.6 Hz, 1H), 5.42-5.24 (m, 2H), 5.18 (s, 1H), 4.12 (dd, J=24.6, 12.2 Hz, 3H), 4.04-3.79 (m, 2H), 3.78-3.55 (m, 5H), 3.50-2.98 (m, 5H), 2.93-2.53 (m, 6H), 2.49-2.28 (m, 1H), 2.28-2.12 (m, 2H), 2.08-1.96 (m, 6H), 1.40 (s, 4H), 1.36 (s, 5H).

Example 194

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] N-methyl-N-[2-(methylamino)ethyl]carbamate

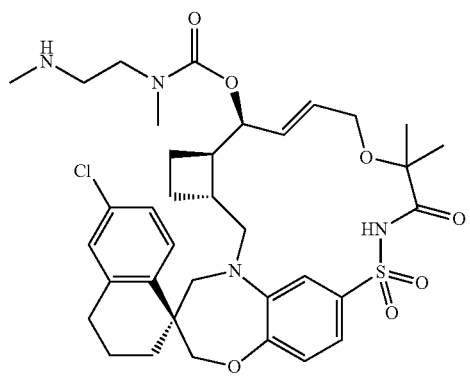 [SMILES: CNCCN(C)C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using N$^1$,N$^2$-dimethyl-ethane-1,2-diamine to replace 1-(2-methoxyethyl)piperazine in Step 2. LCMS calc. for $C_{36}H_{48}ClN_4O_7S$ [M+H]$^+$: m/z=715.30/717.29; Found: 715.5/717.5. $^1$H NMR (500 MHz, DMSO-d$_6$) δ 11.61 (s, 1H), 8.42 (s, 2H), 7.65 (d, J=8.3 Hz, 1H), 7.26 (dd, J=8.4, 2.3 Hz, 2H), 7.19 (d, J=2.0 Hz, 1H), 7.02 (d, J=8.2 Hz, 1H), 6.95 (s, 1H), 5.69 (s, 2H), 5.29 (dd, J=49.6, 44.7 Hz, 1H), 4.32-3.87 (m, 3H), 3.56 (d, J=14.5 Hz, 2H), 2.82 (ddd, J=56.1, 35.7, 24.1 Hz, 9H), 2.59 (s, 3H), 2.16-1.57 (m, 8H), 1.39 (s, 4H), 1.23 (d, J=10.5 Hz, 6H).

Example 195

[(3R,6R,7S,8E,22S)-6'-Chloro-12,12-dimethyl-13, 15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] (3S)-3-methoxypyrrolidine-1-carboxylate

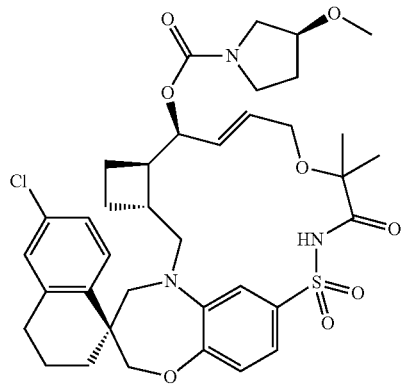 [SMILES: CO[C@H]1CCN(C(=O)O[C@H]2/C=C/COC(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 using (3S)-3-methoxypyrrolidine to replace 1-(2-methoxyethyl)piperazine in Step 2. LCMS calc. for $C_{37}H_{47}ClN_3O_8S$ $[M+H]^+$: m/z=728.27/730.27; Found: 728.5/730.5. $^1$H NMR (300 MHz, CDCl$_3$) δ 7.68 (d, J=8.5 Hz, 1H), 7.36 (d, J=8.5 Hz, 1H), 7.13 (dd, J=8.4, 2.4 Hz, 1H), 7.06 (d, J=2.2 Hz, 1H), 6.97 (d, J=2.2 Hz, 1H), 6.85 (d, J=8.2 Hz, 1H), 6.10 (br, 1H), 5.70 (ddd, J=15.8, 10.4, 5.4 Hz, 1H), 5.22-5.14 (m, 1H), 4.12-3.92 (m, 4H), 3.86 (d, J=16.1 Hz, 2H), 3.66 (t, J=13.7 Hz, 2H), 3.52-3.40 (m, 4H), 3.34 (s, 3H), 3.28 (s, 2H), 3.09 (q, J=12.3 Hz, 2H), 2.78-2.70 (m, 4H), 2.31 (d, J=8.0 Hz, 1H), 2.01-1.92 (m, 4H), 1.80-1.72 (m, 3H), 1.36 (s, 3H), 1.31 (s, 3H).

Example 196

(3R,6R,12S,22S)-6'-Chloro-11,12-dimethyl-15,15-dioxo-spiro[8,20-dioxa-15-thia-1,11,14-triazatetracyclo[14.7.2.0$^{3,6}$.0$^{19,24}$]pentacosa-16,18,24-triene-22,1'-tetralin]-10,13-dione

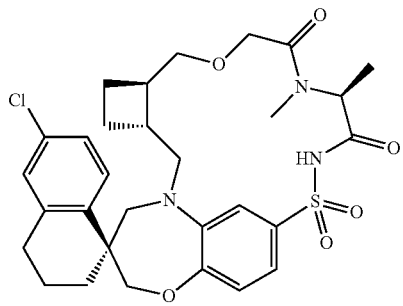 [SMILES: C[C@H]1C(=O)NS(=O)(=O)c2ccc3c(c2)N(C[C@@H]2CC[C@H]2COCC(=O)N1C)C[C@@]1(CCCc2cc(Cl)ccc21)CO3]

Step 1: tert-butyl 2-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]acetate

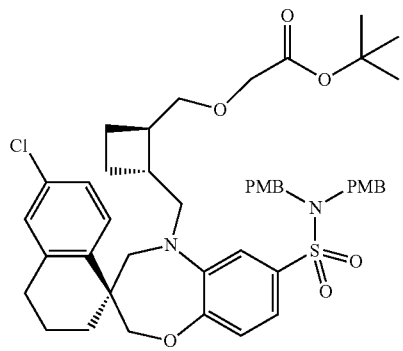

To a solution of (3S)-6'-chloro-5-[[(1R,2R)-2-(hydroxymethyl)cyclobutyl]methyl]-N,N-bis[(4-methoxyphenyl) methyl]spiro[2,4-dihydro-1,5-benzoxazepine-3,1'-tetralin]-7-sulfonamide (300.0 mg, 0.42 mmol, Intermediate 3 Step 2) in THF (15 mL) was added potassium tert-butoxide (93.86 mg, 0.84 mmol) at 20° C. The mixture was stirred at r.t. for 30 min., and t-butyl bromoacetate (163.15 mg, 0.84 mmol) was then added. The resulting mixture was stirred at r.t. overnight. LCMS showed full conversion of starting material. The reaction was quenched by water (5 mL), and extracted with EtOAc (20 mL×3). The combined organic layers were dried over sodium sulfate, filtered and concentrated under reduced pressure. The residue was purified by flash chromatography on a silica gel column (12 g) with EtOAc/Heptanes (3% to 40%) to afford tert-butyl 2-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]acetate (280 mg, 80.5% yield) as a white solid. LCMS calc. for $C_{46}H_{56}ClN_2O_8S$ $[M+H]^+$: m/z=831.34/833.34; Found: 831.06/832.45.

Step 2: 2-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]acetic acid

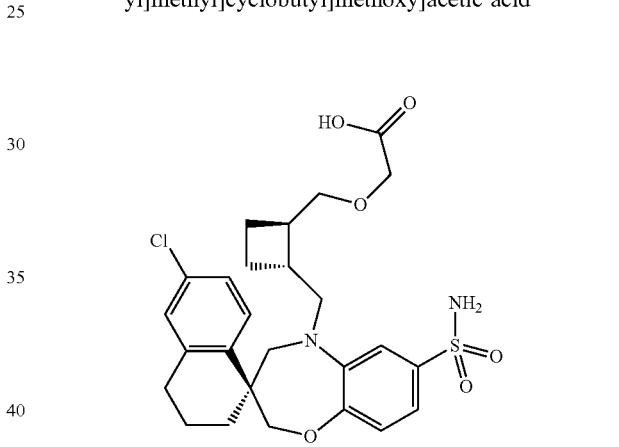

To a solution of tert-butyl 2-[[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]methoxy]acetate (280.0 mg, 0.34 mmol) in DCM (3 mL) was added TFA (3.0 mL, 39.2 mmol) at 40° C. The reaction mixture was stirred for 4 h. LCMS analysis indicated the completion of reaction. The reaction was diluted with EtOAc (10 mL), and adjusted to 7-8 pH with saturated aqueous Na$_2$CO$_3$ solution. The layers were separated, and the aqueous layer was extracted with EtOAc (10 mL×3). The combined organic layers were dried over sodium sulfate, filtered and concentrated under reduced pressure. The resulting solution was concentrated under reduced pressure and the residue was purified by flash chromatography system on a silica gel column (12 g) with EtOAc/Heptanes (3% to 60%) to afford 2-[[(1R,2R)-2-[[(3S)-6'-chloro-7-sulfamoyl-spiro[2,4-dihydro-1,5-benzoxazepine-3,1'-tetralin]-5-yl] methyl]cyclobutyl]methoxy]acetic acid (152 mg, 84.4% yield) as a white solid. LCMS calc. for $C_{26}H_{32}ClN_2O_6S$ $[M+H]^+$: m/z=535.16/537.16; Found: 534.8/536.6.

Step 3: methyl 2-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]acetate

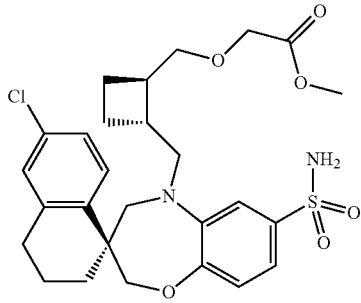 [SMILES: COC(=O)COC[C@@H]1CC[C@H]1CN1C[C@@]2(CCCc3cc(Cl)ccc32)COc2ccc(S(N)(=O)=O)cc21]

To a stirred solution of 2-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]acetic acid (195.0 mg, 0.36 mmol) in DMF (5 mL) was added $K_2CO_3$ (100.59 mg, 0.73 mmol) and iodomethane (103.46 mg, 0.73 mmol). The resulting mixture was stirred at r.t. for 4 h. LCMS showed full conversion of starting material. EtOAc (10 mL) was added and the layers were separated, then the aqueous layer was adjusted pH to 1-2 with aq. HCl (1 N), and extracted with EtOAc (20 mL×2). The combined organic layers were dried over $Na_2SO_4$, filtered and concentrated under reduced pressure. The residue was purified by flash chromatography on a silica gel column (12 g) with EtOAc/Hetpanes (2% to 50%) to afford methyl 2-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]acetate (159 mg, 79.5% yield) as a white solid. LCMS calc. for $C_{27}H_{34}ClN_2O_6S$ $[M+H]^+$: m/z=549.17/551.17; Found: 548.9/550.6.

Step 4: methyl 2-[[(1R,2R)-2-[[(3S)-7-[[(2S)-2-[tert-butoxycarbonyl(methyl)amino]propanoyl]sulfamoyl]-6'-chloro-spiro[2,4-dihydro-1,5-benzoxazepine-3,1'-tetralin]-5-yl]methyl]cyclobutyl]methoxy]acetate

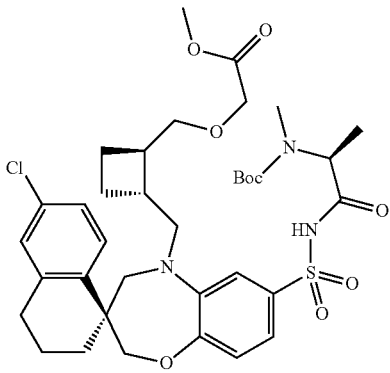 [SMILES: COC(=O)COC[C@@H]1CC[C@H]1CN1C[C@@]2(CCCc3cc(Cl)ccc32)COc2ccc(S(=O)(=O)NC(=O)[C@H](C)N(C)C(=O)OC(C)(C)C)cc21]

A mixture of (2S)-2-[tert-butoxycarbonyl(methyl)amino]propanoic acid (77.73 mg, 0.38 mmol), methyl 2-[[(1R,2R)-2-[[(3S)-6'-chloro-7-sulfamoyl-spiro[2,4-dihydro-1,5-benzoxazepine-3,1'-tetralin]-5-yl]methyl]cyclobutyl]methoxy]acetate (70.0 mg, 0.13 mmol), EDCI (73.32 mg, 0.38 mmol) and DMAP (77.4 mg, 0.76 mmol) in DCM (3 mL) was stirred at r.t. overnight. LCMS analysis indicated the completion of reaction. The reaction was diluted with DCM (10 mL), washed with 1 N HCl (2 mL) and brine, dried over $Na_2SO_4$, filtered and concentrated under reduced pressure. The residue was purified by flash chromatography on a silica gel column (12 g) with EtOAc/Heptanes (3% to 60%) to afford methyl 2-[[(1R,2R)-2-[[(3S)-7-[[(2S)-2-[tert-butoxycarbonyl(methyl)amino]propanoyl]sulfamoyl]-6'-chloro-spiro[2,4-dihydro-1,5-benzoxazepine-3,1'-tetralin]-5-yl]methyl]cyclobutyl]methoxy]acetate (75 mg, 80.1% yield) as a white solid. LCMS calc. for $C_{36}H_{49}ClN_3O_9S$ $[M+H]^+$: m/z=734.28/736.28; Found: 733.9/736.3.

Step 5: 2-[[(1R,2R)-2-[[(3S)-7-[[(2S)-2-[tert-butoxycarbonyl(methyl)amino]propanoyl]sulfamoyl]-6'-chloro-spiro[2,4-dihydro-1,5-benzoxazepine-3,1'-tetralin]-5-yl]methyl]cyclobutyl]methoxy]acetic acid

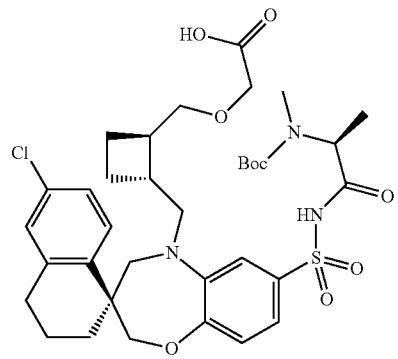 [SMILES: C[C@@H](C(=O)NS(=O)(=O)c1ccc2c(c1)N(C[C@@H]1CC[C@H]1COCC(=O)O)C[C@@]1(CCCc3cc(Cl)ccc31)CO2)N(C)C(=O)OC(C)(C)C]

To a stirred solution of methyl 2-[[(1R,2R)-2-[[(3S)-7-[[(2S)-2-[tert-butoxycarbonyl(methyl)amino]propanoyl]sulfamoyl]-6'-chloro-spiro[2,4-dihydro-1,5-benzoxazepine-3,1'-tetralin]-5-yl]methyl]cyclobutyl]methoxy]acetate (75.0 mg, 0.10 mmol) in THF (0.50 mL) and methanol (0.50 mL) was added lithium hydroxide monohydrate (12.87 mg, 0.31 mmol) in water (0.50 mL). The resulting mixture was stirred at r.t. for 4 h. LCMS showed full conversion of starting material. THF and MeOH were partially removed on a rotary evaporator, and the aqueous layer was adjusted pH to 1-2 with aq. HCl (1 N) and extracted with EtOAc (10 mL×3). The combined organic layers were dried over sodium sulfate, filtered and concentrated under reduced pressure to afford 2-[[(1R,2R)-2-[[(3S)-7-[[(2S)-2-[tert-butoxycarbonyl(methyl)amino]propanoyl]sulfamoyl]-6'-chloro-spiro[2,4-dihydro-1,5-benzoxazepine-3,1'-tetralin]-5-yl]methyl]cyclobutyl]methoxy]acetic acid (64 mg, 87% yield) as a white solid. LCMS calc. for $C_{35}H_{47}ClN_3O_9S$ $[M+H]^+$: m/z=720.26/722.26; Found: 720.0/721.6.

Step 6: 2-[[(1R,2R)-2-[[(3S)-6'-chloro-7-[[(2S)-2-(methylamino)propanoyl]sulfamoyl]spiro[2,4-dihydro-1,5-benzoxazepine-3,1'-tetralin]-5-yl]methyl]cyclobutyl]methoxy]acetic acid

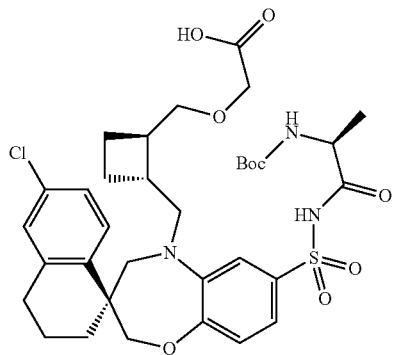 [SMILES: C[C@H](NC(=O)OC(C)(C)C)C(=O)NS(=O)(=O)c1ccc2c(c1)N(C[C@@H]1CC[C@H]1COCC(=O)O)C[C@@]1(CCCc3cc(Cl)ccc31)CO2]

2-[[(1R,2R)-2-[[(3S)-7-[[(2S)-2-tert-butoxycarbonyl(methyl)amino]propanoyl]-sulfamoyl]-6'-chloro-spiro[2,4-dihydro-1,5-benzoxazepine-3,1'-tetralin]-5-yl]methyl]-cyclobutyl]methoxy]acetic acid (64.0 mg, 0.09 mmol) was dissolved in 2N HCl in EtOAc solution (0.0 mL, 0.09 mmol), and stirred at r.t. for 6 h. The reaction was concentrated under reduced pressure, and the residue was added lithium hydroxide monohydrate (3.73 mg, 0.09 mmol) in THF (0.50 mL), water (0.50 mL) and methanol (0.50 mL). After 2 h, LCMS analysis indicated the completion of reaction. The reaction mixture was concentrated under reduced pressure to afford 2-[[(1R,2R)-2-[[(3S)-6'-chloro-7-[[(2S)-2-(methylamino)propanoyl]sulfamoyl]spiro[2,4-dihydro-1,5-benzoxazepine-3,1'-tetralin]-5-yl]methyl]cyclobutyl]methoxy]acetic acid (51 mg, 92.6% yield) as a white solid. LCMS calc. for $C_{30}H_{39}ClN_3O_7S$ [M+H]$^+$: m/z=620.22/622.22; Found: 619.9/622.1.

Step 7: (3R,6R,12S,22S)-6'-chloro-11,12-dimethyl-15,15-dioxo-spiro[8,20-dioxa-15-thia-1,11,14-triazatetracyclo[14.7.2.03,6.019,24]pentacosa-16,18,24-triene-22,1'-tetralin]-10,13-dione To a stirred solution of 2-[[(1R,2R)-2-[[(3S)-6'-chloro-7-[[(2S)-2-(methylamino)-propanoyl]sulfamoyl]spiro[2,4-dihydro-1,5-benzoxazepine-3,1'-tetralin]-5-yl]methyl]-cyclobutyl]methoxy]acetic acid (26.0 mg, 0.04 mmol) in DMF (2 mL) was added HATU (31.88 mg, 0.08 mmol) and DIPEA (0.01 mL, 0.08 mmol) at 20° C. After 1 h, LCMS analysis indicated the full conversion of starting material to the desired product. The reaction was quenched by water (5 mL), and extracted with EtOAc (10 mL×3). The combined organic layers were dried over sodium sulfate, filtered and concentrated under reduced pressure. The residue was purified by flash chromatography on a silica gel column (12 g) with EtOAc/Heptanes (2% to 60%). The desired fractions were collected, and further purified by prep-HPLC on a C18 column (30×250 mm, 10 m) with MeCN/H$_2$O (20 to 100%) to afford (3R,6R,12S,22S)-6'-chloro-11,12-dimethyl-15,15-dioxo-spiro[8,20-dioxa-15-thia-1,11,14-triazatetracyclo-[14.7.2.03,6.019,24]pentacosa-16,18,24-triene-22,1'-tetralin]-10,13-dione (6.2 mg, 0.0103 mmol, 24.56% yield) as a white solid. LCMS calc 602.20/604.20; Found 602.28/604.25.

Example 197

(3R,6R,12S,22S)-6'-Chloro-12-methyl-15,15-dioxo-spiro[8,20-dioxa-15-thia-1,11,14-triazatetracyclo[14.7.2.0~3,6.0~19,24]pentacosa-16,18,24-triene-22,1'-tetralin]-10,13-dione

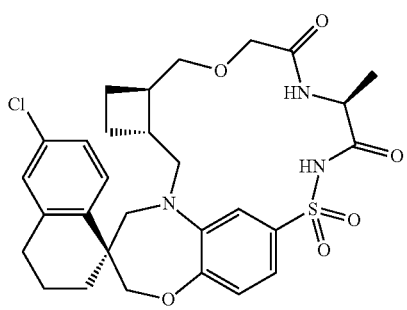 [SMILES: C[C@@H]1NC(=O)COC[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 196 Step 4-7 using (2S)-2-(tert-butoxycarbonylamino)propanoic acid to replace (2S)-2-[tert-butoxycarbonyl(methyl)amino]propanoic acid in Step 4. LCMS calc. for $C_{29}H_{35}ClN_3O_6S$ [M+H]$^+$: m/z=588.19/590.19; Found 588.6/590.6. $^1$H NMR (400 MHz, CDCl$_3$) δ 7.68 (d, J=8.5 Hz, 1H), 7.52 (d, J=8.1 Hz, 1H), 7.22 (s, 1H), 7.13 (dd, J=8.2, 2.2 Hz, 1H), 7.08 (d, J=2.3 Hz, 1H), 6.80 (d, J=8.1 Hz, 1H), 5.48-5.23 (m, 1H), 4.39 (d, J=8.6 Hz, 1H), 4.06-3.82 (m, 4H), 3.75 (d, J=14.2 Hz, 2H), 3.46 (s, 2H), 3.34 (d, J=14.4 Hz, 1H), 3.09 (d, J=13.5 Hz, 1H), 2.81 (d, J=25.2 Hz, 2H), 1.97 (s, 3H), 1.72 (ddd, J=42.0, 16.7, 8.4 Hz, 5H), 1.37 (d, J=7.2 Hz, 5H).

Example 198

[(3R,6R,7R,8E,22S)-6'-Chloro-12,12-dimethyl-13,15,15-trioxo-spiro[20-oxa-15-thia-1,11,14-triazatetracyclo[14.7.2.0~3,6.0~19,24]pentacosa-8,16,18,24-tetraene-22,1'-tetralin]-7-yl] N,N-dimethylcarbamate

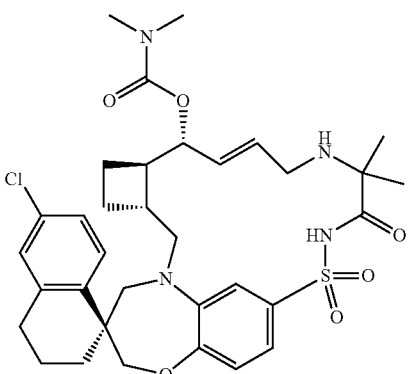

447

Step 1: [(1R)-1-[(1R,2R)-2-[[(3S)-7-[[2-(ally-lamino)-2-methyl-propanoyl]sulfamoyl]-6'-chloro-spiro[2,4-dihydro-1,5-benzoxazepine-3,1'-tetralin]-5-yl]methyl]cyclobutyl]allyl] N,N-dimethylcarbamate

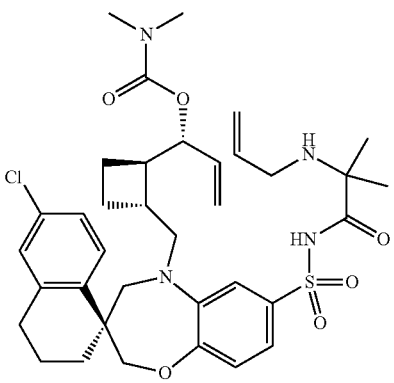 [SMILES: C=CCNC(C)(C)C(=O)NS(=O)(=O)c1ccc2c(c1)N(C[C@@H]1CC[C@H]1[C@@H](C=C)OC(=O)N(C)C)C[C@@]1(CCCc3cc(Cl)ccc31)CO2]

This compound was prepared using procedures analogous to those described for Example 42 Step 2 using [(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate (Intermediate 10) and 3-allyl-4,4-dimethyl-oxazolidine-2,5-dione (Example 42 Step 1). LC-MS: calc. for $C_{36}H_{48}ClN_4O_6S$ [M+H]$^+$: m/z=699.3/701.3; Found: 699.5/701.5.

Step 2: [(3R,6R,7R,8E,22S)-6'-chloro-12,12-dimethyl-13,15,15-trioxo-spiro[20-oxa-15-thia-1,11,14-triazatetracyclo[14.7.2.0~3,6.0~19,24]pentacosa-8,16,18,24-tetraene-22,1'-tetralin]-7-yl] N,N-dimethylcarbamate

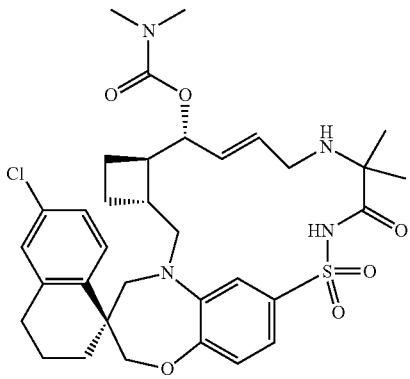 [SMILES: CN(C)C(=O)O[C@@H]1/C=C/CNC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 26 Step 4 using [(1R)-1-[(1R,2R)-2-[[(3S)-7-[[2-(allylamino)-2-methyl-propanoyl]sulfamoyl]-6'-chloro-spiro[2,4-dihydro-1,5-benzoxazepine-3,1'-tetralin]-5-yl]methyl]cyclobutyl]allyl] N,N-dimethylcarbamate. LCMS calc. for $C_{34}H_{44}ClN_4O_6S$ [M+H]$^+$: m/z=671.3/673.3; Found: 671.9/673.8.

448

Example 199

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl]morpholine-4-carboxylate

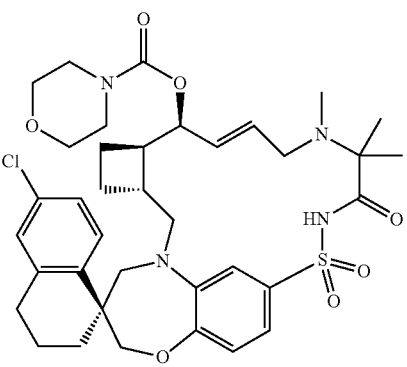 [SMILES: CN1C/C=C/[C@H](OC(=O)N2CCOCC2)[C@@H]2CC[C@H]2CN2C[C@@]3(CCCc4cc(Cl)ccc43)COc3ccc(cc32)S(=O)(=O)NC(=O)C1(C)C]

Step 1: [(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl] phenyl carbonate

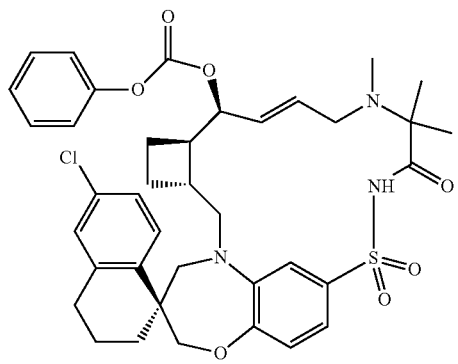 [SMILES: CN1C/C=C/[C@H](OC(=O)Oc2ccccc2)[C@@H]2CC[C@H]2CN2C[C@@]3(CCCc4cc(Cl)ccc43)COc3ccc(cc32)S(=O)(=O)NC(=O)C1(C)C]

To a solution of (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (680.0 mg, 1.11 mmol, Example 43) in pyridine (0.89 mL, 11.07 mmol) was added phenyl chloroformate (0.69 mL, 5.54 mmol). The mixture was stirred at r.t. for 1 h. LCMS showed the full conversion of the starting material into the desired product. The mixture was concentrated under reduced pressure and the residue was purified by flash chromatography on a silica gel column with EA:Hep (50% to 100%) to afford [(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl] phenyl carbonate (810 mg, 99.6% yield).

Step 2: [(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl]morpholine-4-carboxylate To a solution of [(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl] phenyl carbonate (40.0 mg, 0.05 mmol) in MeCN (1 mL) was added morpholine (47.46 mg, 0.54 mmol). Reaction was stirred for 14 h at 75° C. LCMS showed the conversion of the starting material into the desired product. The mixture was concentrated and purified by prep-HPLC on a C18 column (15% to 100% MeCN/H$_2$O) to afford [(3R,6R,7S,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] morpholine-4-carboxylate (15 mg, 37.9% yield). LCMS calcd. for C$_{37}$H$_{48}$ClN$_4$O$_7$S [M+H]$^+$: m/z=727.29/729.29; Found 727.4/729.4. $^1$H NMR (300 MHz, CDCl$_3$) δ 7.69 (d, J=8.5 Hz, 1H), 7.53-7.43 (m, 1H), 7.19 (dd, J=8.5, 2.4 Hz, 1H), 7.09 (d, J=2.3 Hz, 1H), 6.96 (d, J=8.3 Hz, 1H), 6.83 (s, 1H), 5.86 (s, 1H), 5.70 (d, J=15.7 Hz, 1H), 5.39 (s, 1H), 4.17 (d, J=12.2 Hz, 1H), 4.06 (d, J=12.1 Hz, 1H), 3.72 (d, J=5.6 Hz, 6H), 3.50 (m, 6H), 3.35 (d, J=14.8 Hz, 1H), 3.09 (dd, J=15.0, 10.9 Hz, 1H), 2.87-2.73 (m, 3H), 2.29 (s, 3H), 1.99 (d, J=12.4 Hz, 2H), 1.83 (q, J=10.1, 9.5 Hz, 2H), 1.68 (dt, J=18.6, 9.5 Hz, 1H), 1.45 (d, J=12.8 Hz, 1H), 1.31 (d, J=24.9 Hz, 6H), 1.12 (s, 3H).

Example 200

[(3R,6R,7R,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

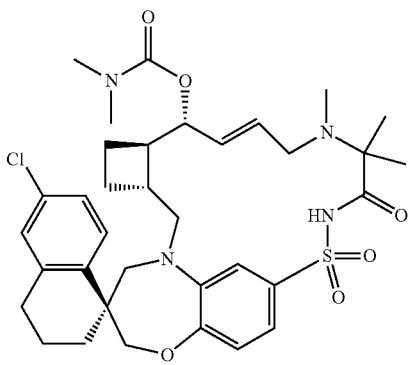 [SMILES: CN(C)C(=O)O[C@@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3]

To a solution of [(3R,6R,7R,8E,22S)-6'-chloro-12,12-dimethyl-13,15,15-trioxo-spiro[20-oxa-15-thia-1,11,14-triazatetracyclo[14.7.2.0~3,6.0~19,24]pentacosa-8,16,18,24-tetraene-22,1'-tetralin]-7-yl] N,N-dimethylcarbamate (10.0 mg, 0.01 mmol, Example 197) in DCE (0.50 mL) was added 37% formaldehyde aqueous solution (0.01 mL, 0.30 mmol). The mixture was stirred at r.t. for 2 h., then NaBH$_3$CN (11.27 mg, 0.30 mmol) in methanol (0.10 mL) was added.

The reaction mixture was stirred at r.t. for 6 h. The reaction was quenched by sat. NH$_4$Cl aqueous solution (5 mL), and extracted with EtOAc (10 mL×3). The combined organic layers were dried over sodium sulfate, filtered and concentrated under reduced pressure. The residue was purified by prep-HPLC on a C18 column with MeCN/H$_2$O (20% to 100%) to afford [(3R,6R,7R,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate (6.3 mg, 61.7% yield) as a white solid. LCMS calc. for C$_{35}$H$_{46}$ClN$_4$O$_6$S [M+H]$^+$: m/z=685.3/687.3; Found 685.8/687.3. $^1$H NMR (600 MHz, CDCl$_3$) δ 7.68 (d, J=8.5 Hz, 1H), 7.52 (d, J=15.5 Hz, 1H), 7.18 (dd, J=8.6, 2.3 Hz, 1H), 7.07 (d, J=2.3 Hz, 1H), 6.97 (d, J=8.3 Hz, 1H), 6.83 (s, 1H), 5.92 (dt, J=12.7, 6.0 Hz, 1H), 5.41-5.25 (m, 1H), 5.07 (s, 1H), 4.08 (t, J=16.8 Hz, 2H), 3.73 (d, J=14.7 Hz, 1H), 3.36 (s, 1H), 3.06 (dd, J=15.2, 10.7 Hz, 1H), 2.92 (s, 4H), 2.84-2.72 (m, 3H), 2.52 (s, 1H), 2.28 (s, 2H), 2.22 (t, J=7.7 Hz, 1H), 2.08-1.90 (m, 5H), 1.83 (s, 3H), 1.72-1.61 (m, 3H), 1.43 (t, J=13.1 Hz, 2H), 1.32 (d, J=12.4 Hz, 3H), 1.26 (d, J=8.6 Hz, 3H).

Example 201

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-cyclobutylcarbamate

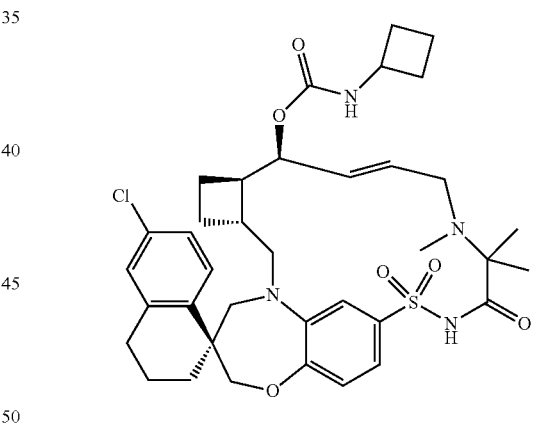

This compound was prepared using procedures analogous to those described for Example 199 Step 2 using cyclobutylamine to replace morpholine. LCMS calc. for C$_{37}$H$_{48}$ClN$_4$O$_6$S [M+H]$^+$: m/z=711.30/713.30; Found: 711.7/713.8. $^1$H NMR (300 MHz, CDCl$_3$) δ 7.69 (d, J=8.5 Hz, 1H), 7.52 (dd, J=8.3, 2.0 Hz, 1H), 7.19 (dd, J=8.5, 2.2 Hz, 1H), 7.09 (d, J=2.1 Hz, 1H), 6.98 (d, J=8.4 Hz, 1H), 6.89 (s, 1H), 5.89 (d, J=15.5 Hz, 1H), 5.67 (d, J=14.4 Hz, 1H), 5.44 (s, 1H), 5.28 (d, J=17.7 Hz, 1H), 4.14 (dt, J=35.4, 10.4 Hz, 3H), 3.70 (d, J=14.7 Hz, 1H), 3.39 (dd, J=28.7, 14.8 Hz, 2H), 3.14-2.97 (m, 1H), 2.81 (dd, J=15.8, 8.0 Hz, 5H), 2.46-2.13 (m, 5H), 2.09-1.89 (m, 5H), 1.89-1.77 (m, 4H), 1.77-1.52 (m, 4H), 1.45 (d, J=12.6 Hz, 1H), 1.35 (s, 3H), 1.11 (s, 3H).

Example 202

[(3R,6R,7S,8E,22S)-6'-Chloro-12,12-dimethyl-13,15,15-trioxo-spiro[11,20-dioxa-15-thia-1,14-diaza-tetracyclo[14.7.2.03,6.019,24]pentacosa-8,16,18,24-tetraene-22,1'-tetralin]-7-yl] N-methyl-N-[(3S)-tetrahydrofuran-3-yl]carbamate

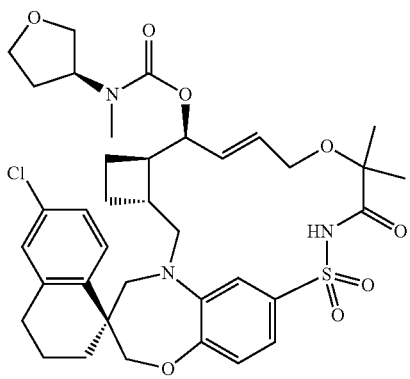 [SMILES: CN(C(=O)O[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3)[C@H]1CCOC1]

This compound was prepared using procedures analogous to those described for Example 63 using (3R,6R,7S,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 32) in Step 2 and (3S)-N-methyltetrahydrofuran-3-amine hydrochloride in Step 1. LCMS calc. for $C_{37}H_{47}ClN_3O_8S$ [M+H]$^+$: m/z=728.27/730.27; Found: 728.4/730.1. $^1$H NMR (300 MHz, CDCl$_3$) δ 9.12 (s, 1H), 7.69 (d, J=8.5 Hz, 1H), 7.50 (dd, J=8.3, 2.1 Hz, 1H), 7.19 (dd, J=8.6, 2.2 Hz, 1H), 7.10 (d, J=2.3 Hz, 1H), 7.01 (s, 1H), 6.99-6.95 (m, 1H), 5.83 (dd, J=5.9, 3.4 Hz, 1H), 5.73 (dd, J=15.7, 5.2 Hz, 1H), 5.33 (q, J=4.3, 3.9 Hz, 1H), 4.91 (s, 1H), 4.12 (t, J=6.3 Hz, 2H), 4.09-4.04 (m, 1H), 3.78 (s, 2H), 3.69 (d, J=8.3 Hz, 1H), 3.50-3.32 (m, 2H), 3.23 (dd, J=15.1, 9.3 Hz, 1H), 2.90 (s, 3H), 2.81-2.76 (m, 3H), 2.40 (dd, J=8.9, 3.5 Hz, 1H), 2.24 (dd, J=9.5, 5.5 Hz, 1H), 2.04 (d, J=8.6 Hz, 1H), 1.95 (d, J=10.1 Hz, 2H), 1.87-1.74 (m, 5H), 1.71-1.62 (m, 3H), 1.51 (d, J=12.6 Hz, 1H), 1.44 (s, 3H), 1.37 (s, 3H).

Example 203

[(3R,6R,7S,8E,22S)-6'-Chloro-11,12,12-trimethyl-13,15,15-trioxo-spiro[20-oxa-15-thia-1,11,14-triaza-tetracyclo[14.7.2.03,6.019,24]pentacosa-8,16,18,24-tetraene-22,1'-tetralin]-7-yl] N-methylcarbamate

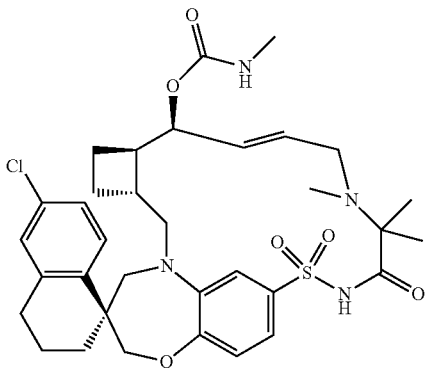 [SMILES: CNC(=O)O[C@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 199 Step 2 using methylamine (40% in water) to replace morpholine. LCMS calc. for $C_{34}H_{44}ClN_4O_6S$ [M+H]$^+$: m/z=671.27/673.27; Found: 671.7/673.6. $^1$H NMR (499 MHz, DMSO-d$_6$) δ 7.63 (dd, J=8.5, 2.5 Hz, 1H), 7.25 (dd, J=8.5, 2.4 Hz, 1H), 7.19-7.07 (m, 2H), 6.88-6.84 (m, 2H), 6.07 (br, 1H), 5.81-5.66 (m, 1H), 5.17-5.12 (m, 1H), 3.58-3.49 (m, 1H), 3.31-3.25 (m, 6H), 3.19-3.06 (m, 1H), 2.86-2.64 (m, 4H), 2.60 (d, J=4.6 Hz, 2H), 2.55 (s, 3H), 2.37 (dt, J=3.8, 2.0 Hz, 1H), 2.00 (dt, J=12.2, 3.9 Hz, 1H), 1.85 (s, 3H), 1.77-1.61 (m, 3H), 1.48-1.44 (m, 1H), 1.35 (s, 3H), 1.28-1.10 (m, 5H).

Example 204

[(3R,6R,7S,8E,22S)-6'-Chloro-11,12,12-trimethyl-13,15,15-trioxo-spiro[20-oxa-15-thia-1,11,14-triaza-tetracyclo[14.7.2.03,6.019,24]pentacosa-8,16,18,24-tetraene-22,1'-tetralin]-7-yl] N-ethylcarbamate

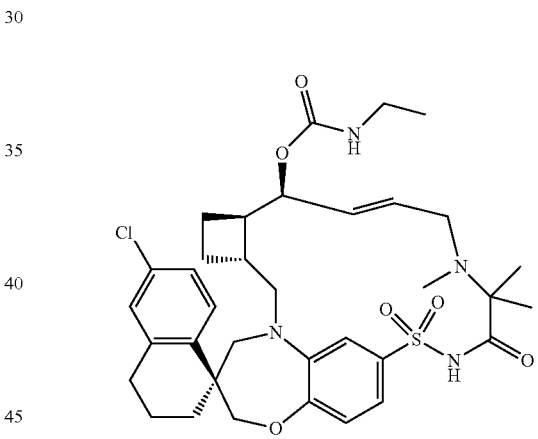

This compound was prepared using procedures analogous to those described for Example 199 Step 2 using ethylamine (66-72% in water) to replace morpholine. LCMS calc. for $C_{35}H_{46}ClN_4O_6S$ [M+H]$^+$: m/z=685.28/687.28; Found: 685.7/687.7. $^1$H NMR (300 MHz, CDCl$_3$) δ 7.69 (d, J=8.5 Hz, 1H), 7.51 (dd, J=8.3, 2.1 Hz, 1H), 7.19 (dd, J=8.5, 2.2 Hz, 1H), 7.09 (d, J=2.0 Hz, 1H), 6.98 (d, J=8.3 Hz, 1H), 6.88 (s, 1H), 5.90 (d, J=15.4 Hz, 1H), 5.68 (d, J=15.7 Hz, 1H), 5.28 (s, 1H), 5.21 (s, 1H), 4.12 (dd, J=36.0, 12.1 Hz, 2H), 3.70 (d, J=14.5 Hz, 1H), 3.50-3.35 (m, 2H), 3.27 (dd, J=13.5, 7.0 Hz, 2H), 3.16-2.97 (m, 1H), 2.81 (dd, J=14.7, 8.2 Hz, 4H), 2.28 (s, 4H), 2.06-1.92 (m, 4H), 1.85 (s, 4H), 1.63 (dd, J=18.6, 9.6 Hz, 1H), 1.45 (d, J=12.8 Hz, 1H), 1.35 (s, 3H), 1.22 (dd, J=16.2, 9.0 Hz, 3H), 1.11 (s, 3H).

Example 205

[(3R,6R,7S,8E,22S)-6'-Chloro-11,12,12-trimethyl-13,15,15-trioxo-spiro[20-oxa-15-thia-1,11,14-triaza-tetracyclo[14.7.2.0³,⁶.0¹⁹,²⁴]pentacosa-8,16,18,24-tetraene-22,1'-tetralin]-7-yl] N-(cyclopropylmethyl) carbamate

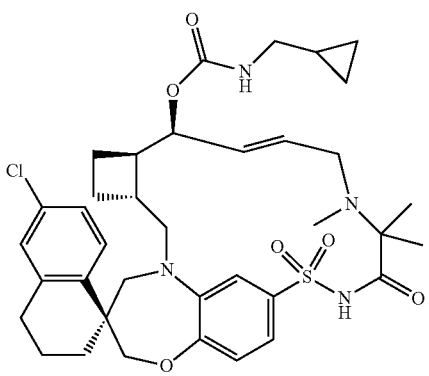 [SMILES: CN1C/C=C/[C@H](OC(=O)NCC2CC2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 Step 2 using cyclopropyl methylamine to replace morpholine. LCMS calc. for $C_{37}H_{48}ClN_4O_6S$ [M+H]⁺: m/z=711.30/713.30; Found: 711.8/713.8. ¹H NMR (300 MHz, CDCl₃) δ 7.69 (d, J=8.5 Hz, 1H), 7.51 (dd, J=8.3, 2.0 Hz, 1H), 7.19 (dd, J=8.5, 2.2 Hz, 1H), 7.09 (d, J=2.0 Hz, 1H), 6.98 (d, J=8.3 Hz, 1H), 6.89 (s, 1H), 5.93 (d, J=15.4 Hz, 1H), 5.68 (d, J=15.4 Hz, 1H), 5.40 (s, 1H), 5.26 (s, 1H), 4.12 (dd, J=36.4, 12.1 Hz, 2H), 3.70 (d, J=14.8 Hz, 1H), 3.39 (dd, J=25.6, 14.9 Hz, 3H), 3.17-2.98 (m, 3H), 2.92-2.68 (m, 4H), 2.29 (s, 4H), 1.99 (d, J=11.2 Hz, 4H), 1.87 (d, J=16.2 Hz, 4H), 1.63 (dd, J=18.8, 9.3 Hz, 1H), 1.45 (d, J=12.4 Hz, 1H), 1.35 (s, 3H), 1.10 (d, J=10.9 Hz, 3H), 0.57-0.47 (m, 2H), 0.27 (q, J=4.7 Hz, 2H).

Example 206

[(3R,6R,7S,8E,22S)-6'-Chloro-11,12,12-trimethyl-13,15,15-trioxo-spiro[20-oxa-15-thia-1,11,14-triaza-tetracyclo[14.7.2.0³,⁶.0¹⁹,²⁴]pentacosa-8,16,18,24-tetraene-22,1'-tetralin]-7-yl] N-(cyclopropylmethyl) carbamate

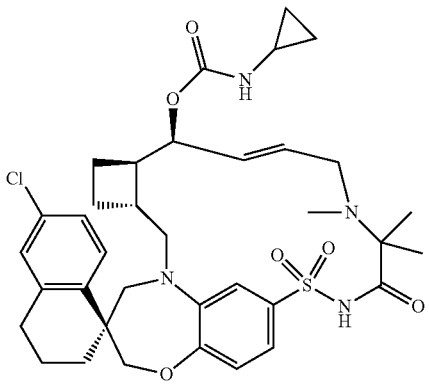 [SMILES: CN1C/C=C/[C@H](OC(=O)NC2CC2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 Step 2 using cyclopropylamine to replace morpholine. LCMS calc. for $C_{36}H_{46}ClN_4O_6S$ [M+H]⁺: m/z=697.28/699.28; Found: 697.7/699.8. ¹H NMR (300 MHz, CDCl₃) δ 7.69 (d, J=8.5 Hz, 1H), 7.50 (dd, J=8.3, 2.0 Hz, 1H), 7.19 (dd, J=8.5, 2.2 Hz, 1H), 7.09 (d, J=2.0 Hz, 1H), 6.97 (d, J=8.3 Hz, 1H), 6.85 (d, J=1.7 Hz, 1H), 5.85 (s, 1H), 5.68 (d, J=16.0 Hz, 1H), 5.43 (s, 1H), 5.29 (s, 1H), 4.11 (dd, J=35.5, 12.1 Hz, 2H), 3.70 (d, J=14.2 Hz, 1H), 3.38 (dd, J=25.8, 14.4 Hz, 2H), 3.15-2.99 (m, 2H), 2.96-2.73 (m, 4H), 2.67 (s, 1H), 2.29 (s, 4H), 2.07-1.89 (m, 4H), 1.85 (d, J=8.6 Hz, 4H), 1.63 (d, J=8.2 Hz, 1H), 1.45 (d, J=12.5 Hz, 1H), 1.36 (s, 3H), 1.11 (s, 3H), 0.77 (d, J=5.4 Hz, 2H), 0.59 (d, J=4.8 Hz, 2H).

Example 207

[(3R,6R,7S,8E,22S)-6'-Chloro-11,12,12-trimethyl-13,15,15-trioxo-spiro[20-oxa-15-thia-1,11,14-triaza-tetracyclo[14.7.2.0³,⁶.0¹⁹,²⁴]pentacosa-8,16,18,24-tetraene-22,1'-tetralin]-7-yl] N-isopropylcarbamate

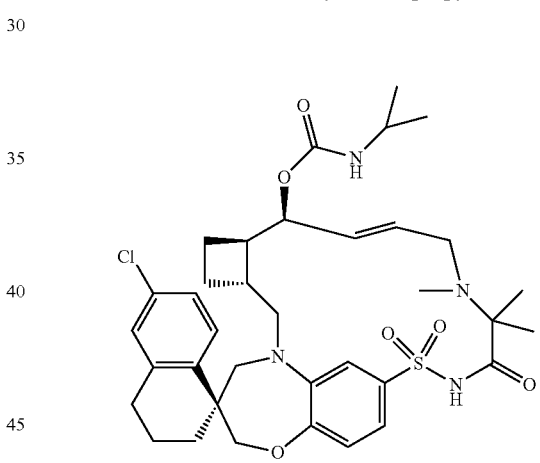

This compound was prepared using procedures analogous to those described for Example 199 Step 2 using propan-2-amine to replace morpholine. LCMS calc. for $C_{36}H_{48}ClN_4O_6S$ [M+H]⁺: m/z=699.30/701.30; Found: 699.8/701.7. ¹H NMR (300 MHz, CDCl₃) δ 7.69 (d, J=8.5 Hz, 1H), 7.51 (dd, J=8.3, 2.0 Hz, 1H), 7.19 (dd, J=8.6, 2.1 Hz, 1H), 7.09 (d, J=1.9 Hz, 1H), 6.98 (d, J=8.4 Hz, 1H), 6.89 (s, 1H), 5.89 (d, J=15.6 Hz, 1H), 5.68 (d, J=14.9 Hz, 1H), 5.24 (s, 1H), 5.12 (s, 1H), 4.12 (dd, J=35.8, 12.1 Hz, 2H), 3.86 (dd, J=13.6, 6.5 Hz, 1H), 3.70 (d, J=14.6 Hz, 1H), 3.39 (dd, J=28.1, 14.5 Hz, 2H), 3.13-2.99 (m, 1H), 2.80 (t, J=10.4 Hz, 6H), 2.28 (s, 3H), 2.08-1.91 (m, 3H), 1.84 (d, J=4.3 Hz, 3H), 1.63 (dd, J=18.9, 9.6 Hz, 1H), 1.45 (d, J=13.0 Hz, 1H), 1.35 (s, 3H), 1.23 (dd, J=11.4, 6.6 Hz, 7H), 1.11 (s, 3H).

Example 208

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] (9aS)-3,4,6,7,9,9a-hexahydro-1H-pyrazino[2,1-c][1,4]oxazine-8-carboxylate

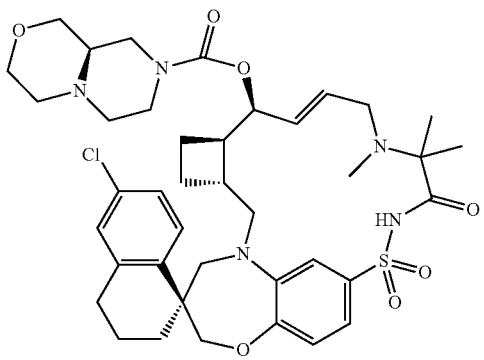 [SMILES: CN1C/C=C/[C@H](OC(=O)N2CCN3CCOC[C@H]3C2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 Step 2 by replacement of morpholine with (9aS)-1,3,4,6,7,8,9,9a-octahydropyrazino[2,1-c][1,4]oxazine which was prepared in THF solution as following: a solution of (9aS)-1,3,4,6,7,8,9,9a-octahydropyrazino[2,1-c][1,4]oxazine dihydrochloride (500.0 mg, 2.32 mmol) in methanol (1 mL) was treated NaOMe (105.9 mg, 1.96 mmol) for 30 min. at r.t., concentrated under reduced pressure, re-dissolved in THF (1 mL) and filtered. LCMS calc. for $C_{40}H_{53}ClN_5O_7S$ [M+H]$^+$: m/z=782.33/784.33; Found 782.5/784.4. $^1$H NMR (300 MHz, CDCl$_3$) δ 7.69 (dd, J=7.8, 4.1 Hz, 1H), 7.50 (dd, J=8.3, 2.1 Hz, 1H), 7.19 (dd, J=8.6, 2.4 Hz, 1H), 7.09 (d, J=2.2 Hz, 1H), 6.97 (d, J=8.3 Hz, 1H), 6.81 (s, 1H), 5.91-5.62 (m, 2H), 5.40 (s, 1H), 4.22-4.00 (m, 4H), 3.88-3.65 (m, 5H), 3.48-3.22 (m, 4H), 3.10 (q, J=13.6, 11.8 Hz, 3H), 2.89-2.70 (m, 7H), 2.28 (d, J=9.6 Hz, 6H), 1.99 (d, J=12.2 Hz, 4H), 1.91-1.75 (m, 4H), 1.35 (s, 3H), 1.10 (s, 3H).

Example 209

[(3R,6R,7S,8E,22S)-6'-Chloro-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

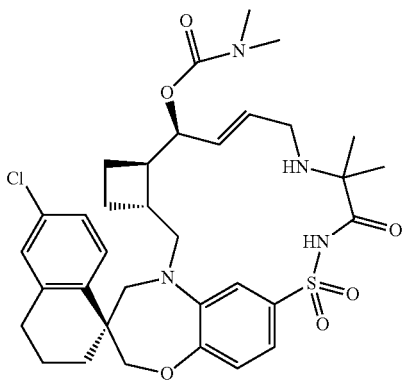 [SMILES: CN(C)C(=O)O[C@H]1/C=C/CNC(C)(C)C(=O)NS(=O)(=O)c2ccc3c(c2)N(C[C@@H]2CC[C@H]21)C[C@@]1(CCCc2cc(Cl)ccc21)CO3]

Step 1: [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate

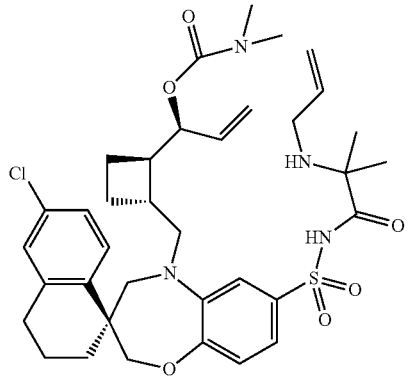 [SMILES: C=CCNC(C)(C)C(=O)NS(=O)(=O)c1ccc2c(c1)N(C[C@@H]1CC[C@H]1[C@H](C=C)OC(=O)N(C)C)C[C@@]1(CCCc3cc(Cl)ccc31)CO2]

This compound was prepared using procedures analogous to those described for Example 42 Step 2 using [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate (Intermediate 9) and 3-allyl-4,4-dimethyl-oxazolidine-2,5-dione (Example 42 Step 1). LCMS calc. for $C_{36}H_{48}ClN_4O_6S$ [M+H]$^+$: m/z=699.3/701.3; Found: 699.9/701.8.

Step 2: [(3R,6R,7S,8E,22S)-6'-chloro-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate This compound was prepared using procedures analogous to those described for Example 26 Step 4 using [(1S)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl] N,N-dimethylcarbamate. LCMS calc. for $C_{34}H_{44}ClN_4O_6S$ [M+H]$^+$: m/z=671.3/673.3; Found: 671.8/673.2.

Example 210

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

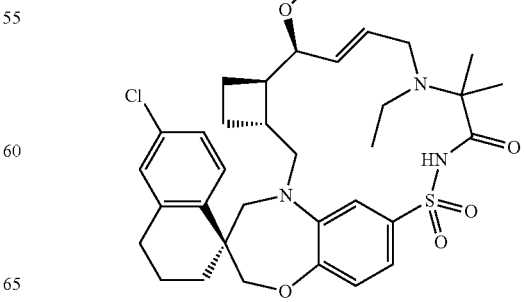

This compound was prepared using procedures analogous to those described for Example 27 using [(3R,6R,7S,8E,22S)-6'-chloro-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate (Example 204) and acetaldehyde. LCMS calc. for $C_{36}H_{48}ClN_4O_6S$ $[M+H]^+$: m/z=699.30/701.30; Found: 699.69/701.66. $^1$H NMR (300 MHz, CDCl$_3$) δ 7.69 (d, J=8.5 Hz, 1H), 7.50 (dd, J=8.3, 2.1 Hz, 1H), 7.19 (dd, J=8.5, 2.2 Hz, 1H), 7.09 (d, J=2.1 Hz, 1H), 6.97 (d, J=8.3 Hz, 1H), 6.84 (d, J=2.0 Hz, 1H), 5.90 (dd, J=15.5, 8.3 Hz, 1H), 5.67 (d, J=15.5 Hz, 1H), 5.28 (s, 1H), 4.12 (dd, J=37.4, 12.1 Hz, 2H), 3.73 (d, J=14.7 Hz, 1H), 3.41 (dd, J=20.8, 15.1 Hz, 2H), 3.12 (s, 3H), 3.00 (d, J=7.3 Hz, 3H), 2.93-2.74 (m, 4H), 2.73-2.58 (m, 1H), 2.29-2.14 (m, 2H), 1.99 (d, J=10.6 Hz, 4H), 1.91-1.74 (m, 4H), 1.66 (dd, J=18.7, 9.3 Hz, 2H), 1.41 (d, J=7.3 Hz, 5H), 1.18 (s, 3H), 1.06 (t, J=7.1 Hz, 3H).

Example 211

[(3R,6R,7S,8E,22S)-6'-Chloro-12,12-dimethyl-13,15,15-trioxo-11-propyl-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate

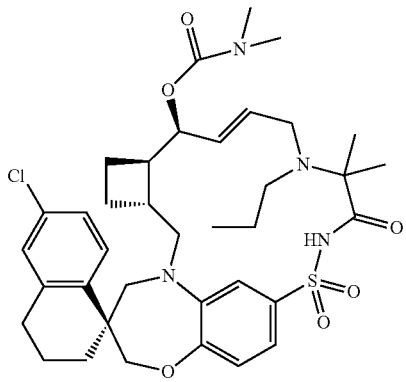 [SMILES: CCCN1C/C=C/[C@H](OC(=O)N(C)C)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 27 using [(3R,6R,7S,8E,22S)-6'-chloro-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N,N-dimethylcarbamate (Example 204) and propionaldehyde. LCMS calc. for $C_{36}H_{48}ClN_4O_6S$ $[M+H]^+$: m/z=699.30/701.30; Found: 699.7/701.7. $^1$H NMR (300 MHz, CDCl$_3$) δ 7.69 (d, J=8.5 Hz, 1H), 7.50 (dd, J=8.3, 1.9 Hz, 1H), 7.19 (dd, J=8.5, 2.1 Hz, 1H), 7.09 (d, J=1.9 Hz, 1H), 6.97 (d, J=8.3 Hz, 1H), 6.84 (d, J=1.9 Hz, 1H), 5.93 (dd, J=15.4, 8.5 Hz, 1H), 5.65 (d, J=15.7 Hz, 1H), 5.28 (s, 1H), 4.12 (dd, J=37.7, 12.1 Hz, 2H), 3.73 (d, J=14.7 Hz, 1H), 3.41 (t, J=16.2 Hz, 3H), 3.08 (dd, J=20.9, 10.1 Hz, 4H), 3.02-2.90 (m, 4H), 2.78 (dt, J=15.9, 14.5 Hz, 4H), 2.48-2.36 (m, 1H), 2.22 (d, J=8.4 Hz, 1H), 1.99 (d, J=10.9 Hz, 3H), 1.83 (dd, J=8.8, 4.5 Hz, 3H), 1.68-1.59 (m, 2H), 1.48 (dt, J=11.9, 6.1 Hz, 3H), 1.38 (s, 3H), 1.16 (s, 3H), 0.90 (t, J=7.3 Hz, 3H).

Example 212

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-[(3S)-tetrahydrofuran-3-yl]carbamate

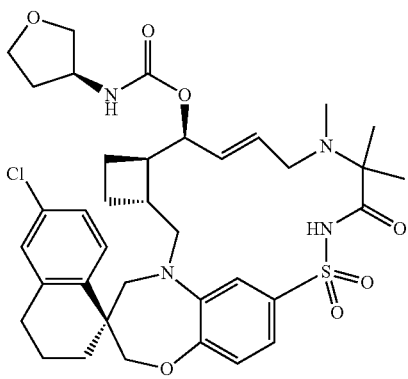 [SMILES: CN1C/C=C/[C@H](OC(=O)N[C@H]2CCOC2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 Step 2 using (3S)-tetrahydrofuran-3-amine to replace morpholine. LCMS calc. for $C_{37}H_{48}ClN_4O_7S$ $[M+H]^+$: m/z=727.29/729.29; Found: 727.4/729.5. $^1$H NMR (300 MHz, CDCl$_3$) δ 7.69 (d, J=8.5 Hz, 1H), 7.51 (dd, J=8.3, 2.1 Hz, 1H), 7.19 (dd, J=8.5, 2.4 Hz, 1H), 7.08 (d, J=2.3 Hz, 1H), 7.02-6.87 (m, 2H), 6.09 (t, J=11.5 Hz, 1H), 5.90 (s, 1H), 5.66 (d, J=16.1 Hz, 1H), 5.19 (s, 1H), 4.40-4.13 (m, 4H), 4.04 (d, J=12.1 Hz, 1H), 3.95 (d, J=9.5 Hz, 1H), 3.85-3.60 (m, 3H), 3.42 (d, J=13.5 Hz, 1H), 3.31 (d, J=14.7 Hz, 1H), 3.10-2.67 (m, 6H), 2.43-2.13 (m, 4H), 2.09-1.70 (m, 5H), 1.61 (q, J=9.0 Hz, 1H), 1.33 (d, J=38.8 Hz, 5H), 1.12 (s, 3H).

Example 213

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-[2-(dimethylamino)ethyl]-N-methyl-carbamate

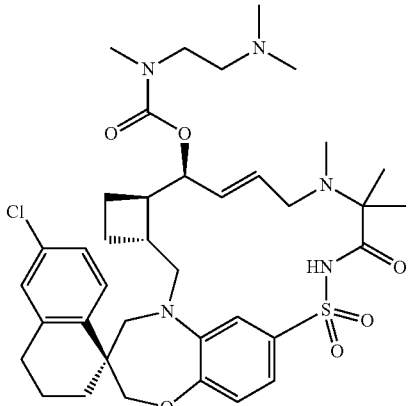

459

This compound was prepared using procedures analogous to those described for Example 199 Step 2 using N,N,N'-trimethylethylenediamine to replace morpholine. LCMS calc. for $C_{38}H_{53}ClN_5O_6S$ [M+H]$^+$: m/z=742.33/744.33; Found: 742.8/744.8. $^1$H NMR (300 MHz, CDCl$_3$) δ 7.70 (d, J=8.5 Hz, 1H), 7.50 (dd, J=8.3, 2.1 Hz, 1H), 7.19 (dd, J=8.5, 2.4 Hz, 1H), 7.09 (d, J=2.3 Hz, 1H), 6.96 (dd, J=8.3, 2.3 Hz, 1H), 6.84 (d, J=2.3 Hz, 1H), 6.06-5.85 (m, 1H), 5.78-5.65 (m, 1H), 5.31 (d, J=16.4 Hz, 1H), 4.16 (d, J=12.2 Hz, 1H), 4.11-4.00 (m, 1H), 3.78-3.56 (m, 2H), 3.51-3.23 (m, 3H), 3.15-2.86 (m, 10H), 2.88-2.73 (m, 6H), 2.64-2.38 (m, 1H), 2.35-2.17 (m, 6H), 2.01 (dt, J=10.8, 5.6 Hz, 3H), 1.66 (q, J=8.9, 8.5 Hz, 1H), 1.51-1.23 (m, 6H), 1.13 (d, J=3.5 Hz, 3H).

Example 214

[(3R,6R,7S,8E,22S)-6'-Chloro-11,12,12-trimethyl-13,15,15-trioxo-spiro[20-oxa-15-thia-1,11,14-triaza-tetracyclo[14.7.2.03,6.019,24]pentacosa-8,16,18,24-tetraene-22,1'-tetralin]-7-yl] 3-(dimethylamino)azetidine-1-carboxylate

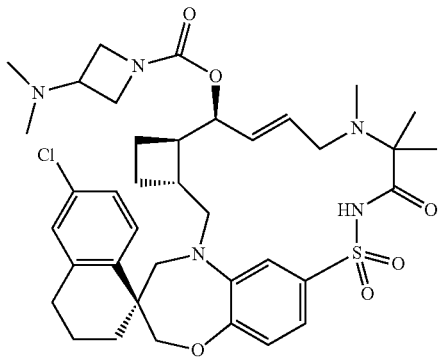

This compound was prepared using procedures analogous to those described for Example 199 using 3-dimethylamino azetidine 2HCl salt and Hunig's base to replace morpholine. LCMS calc. for $C_{38}H_{51}ClN_5O_6S$ [M+H]$^+$: m/z=740.32/742.31; Found: 740.6/742.6. $^1$H NMR (300 MHz, CDCl$_3$) δ 7.69 (d, J=8.5 Hz, 1H), 7.51 (dd, J=8.3, 2.0 Hz, 1H), 7.19 (dd, J=8.6, 2.3 Hz, 1H), 7.08 (d, J=2.1 Hz, 1H), 6.95 (d, J=8.3 Hz, 1H), 6.82 (s, 1H), 6.05-5.78 (m, 1H), 5.68 (dd, J=15.7, 2.8 Hz, 1H), 5.25 (s, 1H), 4.22-3.99 (m, 3H), 3.99-3.85 (m, 3H), 3.71 (d, J=14.7 Hz, 2H), 3.38 (dd, J=14.9, 8.9 Hz, 2H), 3.20-2.67 (m, 6H), 2.32-2.15 (m, 8H), 2.04-1.90 (m, 3H), 1.83 (dq, J=9.4, 4.9 Hz, 3H), 1.65 (q, J=9.4 Hz, 1H), 1.52-1.23 (m, 6H), 1.12 (d, J=6.4 Hz, 3H).

460

Example 215

[(3R,6R,7S,8E,22S)-6'-Chloro-11,12,12-trimethyl-13,15,15-trioxo-spiro[20-oxa-15-thia-1,11,14-triaza-tetracyclo[14.7.2.03,6.019,24]pentacosa-8,16,18,24-tetraene-22,1'-tetralin]-7-yl] (3R)-3-methoxypyrrolidine-1-carboxylate

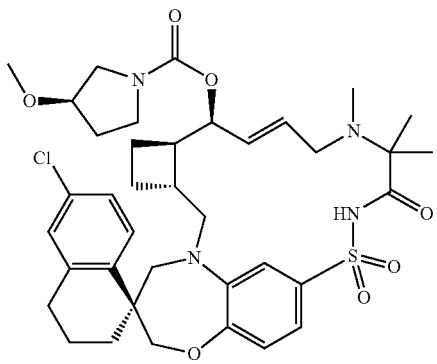

This compound was prepared using procedures analogous to those described for Example 199 Step 2 using (3R)-3-methoxypyrrolidine to replace morpholine. LCMS calc. for $C_{38}H_{50}ClN_4O_7S$ [M+H]$^+$: m/z=741.33/743.33; Found: 741.5/743.5. $^1$H NMR (300 MHz, CDCl$_3$) δ 7.69 (d, J=8.5 Hz, 1H), 7.63-7.45 (m, 1H), 7.19 (dd, J=8.5, 2.4 Hz, 1H), 7.09 (d, J=2.2 Hz, 1H), 6.96 (dd, J=8.4, 1.1 Hz, 1H), 6.85 (dd, J=5.4, 2.2 Hz, 1H), 6.00-5.62 (m, 2H), 5.40-5.25 (m, 1H), 4.17 (d, J=12.2 Hz, 1H), 4.12-3.94 (m, 2H), 3.86 (d, J=13.2 Hz, 1H), 3.72 (d, J=14.7 Hz, 1H), 3.67-3.26 (m, 8H), 3.09 (ddd, J=14.7, 11.0, 3.2 Hz, 1H), 2.82 (ddd, J=15.4, 10.3, 5.9 Hz, 6H), 2.28 (s, 3H), 1.95 (dddd, J=46.8, 27.6, 9.1, 5.6 Hz, 6H), 1.79-1.54 (m, 1H), 1.50-1.23 (m, 6H), 1.11 (s, 3H).

Example 216

[(3R,6R,7S,8E,22S)-6'-Chloro-11,12,12-trimethyl-13,15,15-trioxo-spiro[20-oxa-15-thia-1,11,14-triaza-tetracyclo[14.7.2.03,6.019,24]pentacosa-8,16,18,24-tetraene-22,1'-tetralin]-7-yl]azetidine-1-carboxylate

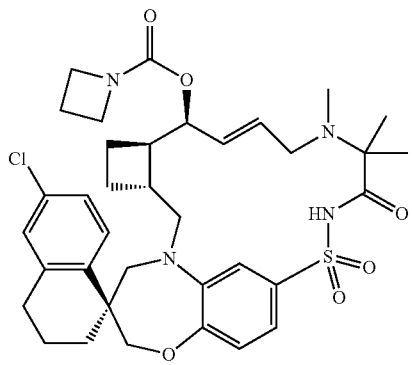 [SMILES: CN1C/C=C/[C@H](OC(=O)N2CCC2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 Step 2 using azetidine hydrochloride salt and Hunig's base to replace morpholine. LCMS calc. for $C_{36}H_{46}ClN_4O_6S$ $[M+H]^+$: m/z=697.27/699.27; Found: 697.4/699.5. $^1$H NMR (300 MHz, CDCl$_3$) δ 7.70 (d, J=8.5 Hz, 1H), 7.52-7.42 (m, 1H), 7.24-7.05 (m, 2H), 7.01-6.90 (m, 1H), 6.86 (s, 1H), 5.92 (s, 1H), 5.72-5.60 (m, 1H), 5.22 (s, 1H), 4.39-3.87 (m, 4H), 3.72 (d, J=14.6 Hz, 1H), 3.47 (d, J=15.0 Hz, 1H), 3.34 (d, J=14.8 Hz, 1H), 3.15-2.98 (m, 1H), 2.89 (s, 2H), 2.78 (d, J=10.5 Hz, 3H), 2.28 (s, 6H), 1.99 (d, J=12.0 Hz, 2H), 1.84 (d, J=15.0 Hz, 4H), 1.65 (q, J=9.5 Hz, 1H), 1.30 (d, J=22.5 Hz, 5H), 1.17-0.98 (m, 4H).

Example 217

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 3-methoxyazetidine-1-carboxylate

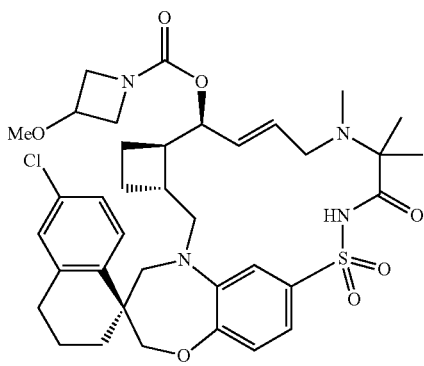 [SMILES: COC1CN(C(=O)O[C@H]2/C=C/CN(C)C(C)(C)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 199 Step 2 using 3-methoxyazetidine hydrochloride salt and Hunig's base to replace morpholine. LCMS calc. for $C_{37}H_{48}ClN_4O_7S$ $[M+H]^+$: m/z=727.29/729.29; Found: 727.4/729.5. $^1$H NMR (300 MHz, CDCl$_3$) δ 7.69 (d, J=8.5 Hz, 1H), 7.51 (dd, J=8.3, 2.1 Hz, 1H), 7.19 (dd, J=8.5, 2.4 Hz, 1H), 7.09 (d, J=2.3 Hz, 1H), 6.97 (d, J=8.3 Hz, 1H), 6.82 (d, J=2.2 Hz, 1H), 5.86 (s, 1H), 5.67 (d, J=15.9 Hz, 1H), 5.26 (s, 1H), 4.24 (s, 3H), 4.18 (d, J=12.2 Hz, 1H), 4.05 (d, J=12.1 Hz, 1H), 3.97 (d, J=7.9 Hz, 2H), 3.72 (d, J=14.7 Hz, 1H), 3.37 (d, J=14.7 Hz, 3H), 3.35-3.27 (m, 3H), 3.07 (dd, J=15.0, 11.1 Hz, 1H), 2.81 (s, 5H), 2.88-2.73 (m, 1H), 2.28 (s, 3H), 2.01 (s, 1H), 1.82 (s, 4H), 1.65 (q, J=9.4 Hz, 1H), 1.37 (s, 3H), 1.27 (d, J=4.3 Hz, 1H), 1.11 (s, 3H).

Example 218

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-[(3R)-tetrahydrofuran-3-yl]carbamate

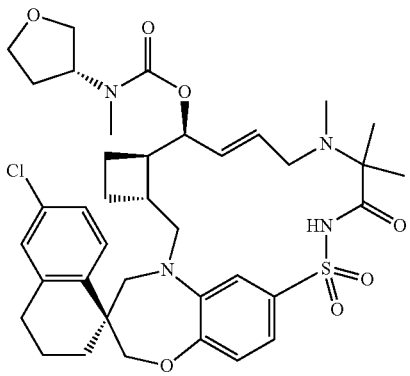 [SMILES: CN(C(=O)O[C@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3)[C@@H]1CCOC1]

This compound was prepared using procedures analogous to those described for Example 63 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 43) in Step 2 and (3R)-N-methyltetrahydrofuran-3-amine hydrochloride in Step 1. LCMS calc. for $C_{38}H_{50}ClN_4O_7S$ $[M+H]^+$: m/z=741.30/743.30; Found: 741.4/743.3. $^1$H NMR (300 MHz, CDCl$_3$) δ 7.69 (d, J=8.5 Hz, 1H), 7.51 (dd, J=8.4, 2.1 Hz, 1H), 7.19 (dd, J=8.6, 2.4 Hz, 1H), 7.09 (d, J=2.3 Hz, 1H), 6.98 (d, J=8.3 Hz, 1H), 6.84 (d, J=2.2 Hz, 1H), 5.85-5.77 (m, 1H), 5.76-5.67 (m, 1H), 5.36 (s, 1H), 5.00 (s, 1H), 4.18 (d, J=12.2 Hz, 1H), 4.10-4.03 (m, 2H), 3.74 (d, J=15.1 Hz, 2H), 3.46 (d, J=14.8 Hz, 1H), 3.37 (d, J=14.7 Hz, 1H), 3.15-3.08 (m, 1H), 3.06-2.95 (m, 3H), 2.82 (t, J=9.4 Hz, 4H), 2.28 (s, 6H), 1.99 (d, J=11.0 Hz, 2H), 1.90-1.61 (m, 9H), 1.35 (s, 3H), 1.27 (s, 3H).

Example 219

(3R,6R,7S,8E,22S)-6'-Chloro-7-hydroxy-11-ethyl-12,12-dimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

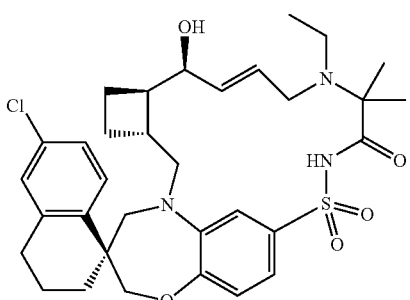

This compound was prepared using procedures analogous to those described for Example 27 using (3R,6R,7S,8E,22S)-6'-chloro-7-hydroxy-12,12-dimethyl-15,15-dioxo-spiro[20-oxa-15-thia-1,11,14-triazatetracyclo[14.7.2.0 3,6 .0 19,24 ]pentacosa-8,16,18,24-tetraene-22,1'-tetralin]-13-one (Example 43, Step 3) and acetaldehyde. LCMS calc. for $C_{33}H_{43}ClN_3O_5S$ [M+H]$^+$: m/z=628.25/630.25; Found: 628.4/630.4. $^1$H NMR (600 MHz, DMSO-d$_6$) δ 7.64 (d, J=8.6 Hz, 1H), 7.25 (dd, J=8.4, 2.4 Hz, 1H), 7.25-7.15 (m, 3H), 7.10 (d, J=8.1 Hz, 1H), 6.76 (s, 1H), 5.72 (s, 1H), 5.33 (t, J=5.0 Hz, 1H), 4.88-4.84 (m, 1H), 3.99 (t, J=10.4 Hz, 2H), 3.51 (s, 1H), 3.02 (s, 2H), 2.80 (d, J=16.8 Hz, 1H), 2.72 (dd, J=11.1, 6.1 Hz, 1H), 2.54 (s, 4H), 2.00 (dt, J=19.0, 7.0 Hz, 5H), 1.85 (s, 5H), 1.85-1.81 (m, 1H), 1.64 (d, J=8.2 Hz, 2H), 1.56 (s, 1H), 1.46 (p, J=7.2 Hz, 2H), 1.39 (s, 2H), 1.30 (s, 2H), 1.15 (s, 1H), 0.86 (t, J=6.8 Hz, 3H).

Example 220

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.0 3,6 .0 19,24 ]pentacosa-8,16,18,24-tetraene-22,1'-tetralin]-7-yl]N-tetrahydropyran-4-ylcarbamate

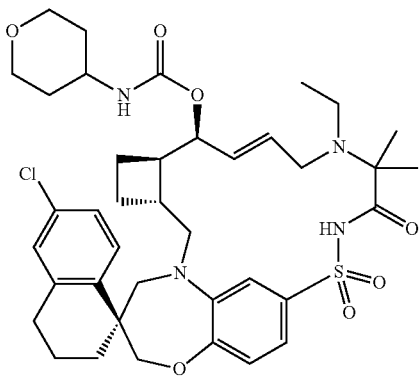 [SMILES: CCN1C/C=C/[C@H](OC(=O)NC2CCOCC2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.0 3,6 .0 19,24 ]pentacosa-8,16(25),17,19(24)-tetraene-22,1'-tetralin]-13-one (Example 219) in Step 1 and 4-aminotetrahydropyran in Step 2. LCMS calcd. for $C_{39}H_{52}ClN_4O_7S$ [M+H]$^+$: m/z=755.32/757.32; Found: 755.5/757.6. $^1$H NMR (600 MHz, DMSO-d$_6$) δ 7.65 (d, J=8.5 Hz, 1H), 7.26 (dd, J=8.5, 2.4 Hz, 1H), 7.19 (dd, J=9.9, 5.1 Hz, 2H), 6.96 (dd, J=14.4, 7.0 Hz, 2H), 5.59 (s, 1H), 4.99 (d, J=4.0 Hz, 1H), 4.11 (d, J=12.3 Hz, 1H), 4.05 (d, J=11.6 Hz, 1H), 3.68 (s, 3H), 3.58-3.12 (m, 9H), 2.82-2.76 (m, 1H), 2.72 (q, J=8.4 Hz, 2H), 2.65 (s, 7H), 2.43 (s, 1H), 1.98 (dt, J=13.8, 4.6 Hz, 1H), 1.83 (h, J=6.0, 4.9 Hz, 3H), 1.71 (q, J=8.6 Hz, 2H), 1.63-1.53 (m, 1H), 1.48 (dd, J=14.5, 7.6 Hz, 1H), 1.31 (s, 3H), 1.27-1.21 (m, 2H), 1.19 (s, 3H).

Example 221

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.0 3,6 .0 19,24 ]pentacosa-8,16,18,24-tetraene-22,1'-tetralin]-7-yl]morpholine-4-carboxylate

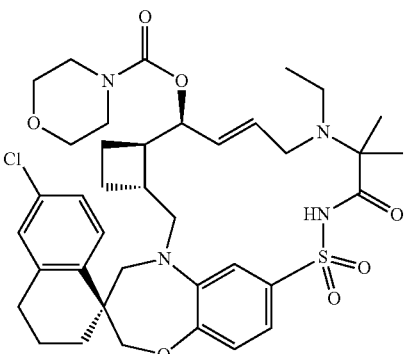

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.0 3,6 .0 19,24 ]pentacosa-8,16(25),17,19(24)-tetraene-22,1'-tetralin]-13-one (Example 219) in Step 1 and morpholine in Step 2. LCMS calc. for $C_{38}H_{49}ClN_4O_7S$ [M+H]$^+$: m/z=741.3/743.37; Found 741.6/741.6. $^1$H NMR (300 MHz, CDCl$_3$) δ 7.67 (d, J=8.5 Hz, 1H), 7.59-7.47 (m, 1H), 7.24-7.07 (m, 2H), 7.05-6.90 (m, 2H), 5.89 (s, 1H), 5.64 (d, J=16.5 Hz, 1H), 5.36 (s, 1H), 4.19 (d, J=12.2 Hz, 1H), 4.06 (d, J=12.0 Hz, 1H), 3.70 (d, J=13.1 Hz, 6H), 3.35 (d, J=14.6 Hz, 3H), 3.09 (s, 6H), 2.81 (m, 10H), 2.31 (d, J=9.3 Hz, 1H), 2.07-1.94 (m, 3H), 1.84 (t, J=9.2 Hz, 2H), 1.31 (s, 6H).

Example 222

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.0 3,6 .0 19,24 ]pentacosa-8,16,18,24-tetraene-22,1'-tetralin]-7-yl] 4-methoxypiperidine-1-carboxylate

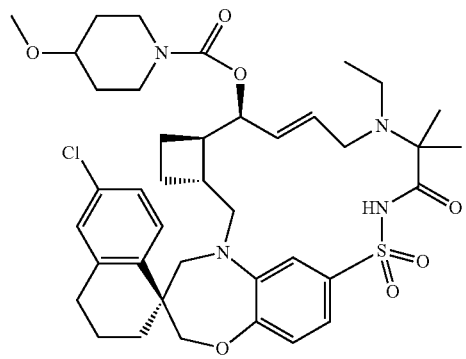

465

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one (Example 219) in Step 1 and 4-methoxypiperidine in Step 2. LCMS calc. for $C_{40}H_{54}ClN_4O_7S$ [M+H]⁺: m/z=769.34/771.34; Found 769.7/771.8. ¹H NMR (300 MHz, CDCl₃) δ 7.63 (dd, J=19.7, 8.5 Hz, 1H), 7.52 (dd, J=8.3, 2.1 Hz, 1H), 7.24-7.06 (m, 3H), 7.00 (d, J=8.4 Hz, 1H), 5.86 (s, 2H), 5.61 (s, 1H), 4.19 (d, J=12.1 Hz, 1H), 5.32 (s, 2H), 4.06 (d, J=12.1 Hz, 1H), 3.90 (m, 16H), 3.70 (d, J=14.7 Hz, 1H), 3.35 (d, J=16.0 Hz, 7H), 3.11 (s, 1H), 1.97 (t, J=10.3 Hz, 1H), 1.80 (dt, J=18.6, 8.5 Hz, 1H), 1.67-1.54 (m, 1H), 1.36-1.21 (m, 10H).

Example 223

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 3-(methylamino)azetidine-1-carboxylate

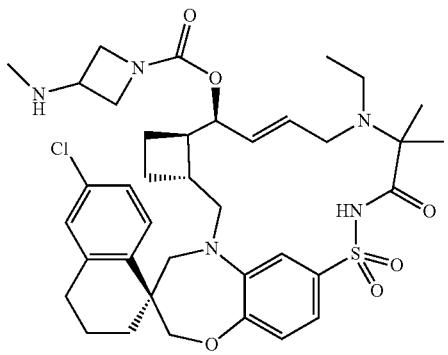

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (30.0 mg, Example 219) in Step 1 and tert-butyl N-(azetidin-3-yl)-N-methyl-carbamate (74.67 mg, 0.40 mmol) in Step 2. The reaction mixture was concentrated under reduced pressure The residue was dissolved in IPA (0.50 mL) and DCM (0.50 mL), and treated with phosphoric acid (0.5 mL, 8.6 mmol). The resulting mixture was stirred for 16 h., and quenched with sat. NaHCO₃(aq) (1 mL). The mixture was extracted with DCM (1 mL×3). The organic layer was concentrated and the residue was purified by prep-HPLC on a C18 column with MeCN/H₂O (15% to 100%) to afford the title compound (6 mg, 20.2% yield). LCMS calc. for $C_{35}H_{51}ClN_5O_6S$ [M+H]⁺: m/z=740.32/742.32; Found 740.5/742.6. ¹H NMR (600 MHz, DMSO-d₆) δ 7.64 (d, J=8.5 Hz, 1H), 7.26 (dd, J=8.5, 2.3 Hz, 1H), 7.17 (d, J=2.3 Hz, 1H), 7.09 (d, J=8.4 Hz, 1H), 6.84 (d, J=8.2 Hz, 1H), 6.72 (s, 1H), 6.41 (t, J=12.5 Hz, 1H), 5.80 (d, J=15.7 Hz, 1H), 5.11 (s, 1H), 3.99 (q, J=12.2 Hz, 3H), 3.74-3.65 (m, 2H), 3.56 (d, J=14.5 Hz, 1H), 3.31-3.24 (m, 1H), 3.03 (dd, J=15.2, 11.1 Hz, 1H), 2.96 (dd, J=12.6, 6.8 Hz, 1H), 2.83-2.76 (m, 1H), 2.70 (ddd, J=17.2, 11.3, 6.2 Hz, 2H), 2.51 (s, 1H), 2.32 (q, J=8.8 Hz, 1H), 2.24 (s, 3H), 1.99 (ddt, J=17.6, 12.2, 5.6 Hz, 2H), 1.93-1.77 (m, 3H), 1.73-1.63 (m, 3H), 1.41 (s, 3H), 1.32-1.28 (m, 1H), 1.30-1.18 (m, 10H), 0.86 (t, J=6.9 Hz, 1H).

466

Example 224

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 3-(dimethylamino)azetidine-1-carboxylate

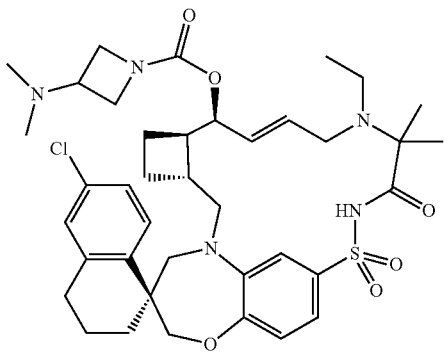

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 219) in Step 1 and N,N-dimethylazetidin-3-amine in Step 2. LCMS calc. for $C_{39}H_{53}ClN_5O_6S$ [M+H]⁺: m/z=754.33/756.43; Found 756.5/758.6. ¹H NMR (300 MHz, CDCl₃) δ 7.70 (d, J=8.5 Hz, 1H), 7.63-7.45 (m, 1H), 7.19 (dd, J=8.5, 2.4 Hz, 1H), 7.10 (dd, J=9.3, 2.2 Hz, 1H), 6.94 (d, J=8.4 Hz, 1H), 6.80 (s, 1H), 6.18 (s, 1H), 5.69 (d, J=14.6 Hz, 1H), 5.18 (s, 1H), 4.38 (s, 1H), 4.16 (d, J=12.3 Hz, 1H), 4.03 (d, J=10.9 Hz, 2H), 3.86 (s, 1H), 3.71 (d, J=14.6 Hz, 1H), 3.36 (d, J=14.7 Hz, 1H), 3.25-3.09 (m, 1H), 3.01 (m, 15H), 2.79 (m, 4H), 2.20 (d, J=16.2 Hz, 7H), 1.98 (d, J=12.3 Hz, 1H), 1.64 (q, J=9.3 Hz, 1H), 1.46 (d, J=30.9 Hz, 3H), 1.23 (q, J=7.8, 7.2 Hz, 3H).

Example 225

[(3R,6R,7S,8E,22S)-6'-Chloro-11-ethyl-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 4-(2-methoxyethyl)piperazine-1-carboxylate

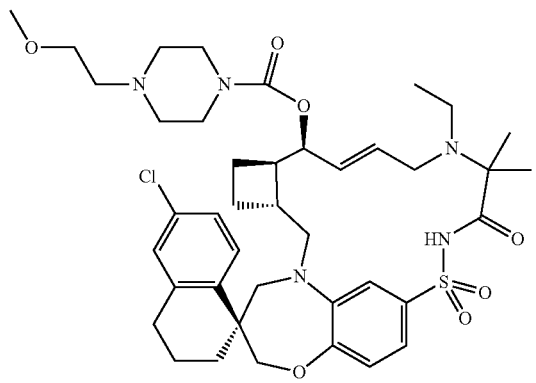

This compound was prepared using procedures analogous to those described for Example 199 using (3R,6R,7S,8E,22S)-6'-chloro-11-ethyl-7-hydroxy-12,12-dimethyl-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 219) in Step 1 and 1-(2-methoxyethyl)piperazine in Step 2. LCMS calc. for $C_{41}H_{57}ClN_5O_7S$ [M+H]$^+$: m/z=798.36/800.36; Found: 799.1/801.1.

Example 226

[(3R,6R,7S,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-[(3S)-tetrahydrofuran-3-yl]carbamate

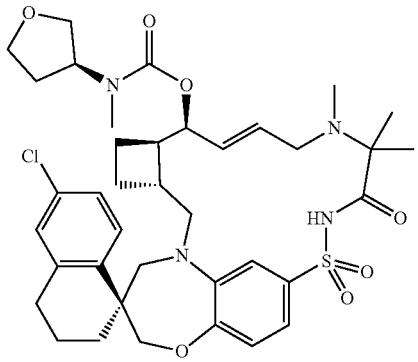 [SMILES: CN(C(=O)O[C@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3)[C@H]1CCOC1]

This compound was prepared using procedures analogous to those described for Example 63 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 43) in Step 2 and (3S)-N-methyltetrahydrofuran-3-amine hydrochloride in Step 1. LCMS calc. for $C_{38}H_{50}ClN_4O_7S$ [M+H]$^+$: m/z=741.30/743.30; Found: 741.4/743.3. $^1$H NMR (300 MHz, CDCl$_3$) δ 7.69 (d, J=8.5 Hz, 1H), 7.51 (d, J=8.5 Hz, 1H), 7.19 (dd, J=8.5, 2.3 Hz, 1H), 7.09 (d, J=2.3 Hz, 1H), 7.03-6.95 (m, 1H), 6.89-6.75 (m, 1H), 5.94-5.62 (m, 2H), 5.38 (s, 1H), 4.97 (s, 1H), 4.18 (d, J=12.1 Hz, 1H), 4.13-3.96 (m, 2H), 3.90-3.62 (m, 4H), 3.41 (dd, J=25.6, 15.3 Hz, 2H), 3.06 (dd, J=39.0, 17.3 Hz, 4H), 2.81 (t, J=12.5 Hz, 5H), 2.26 (d, J=14.2 Hz, 5H), 2.12-1.56 (m, 10H), 1.35 (s, 4H), 1.27 (s, 2H).

Example 227

[(3R,6R,7S,8E,22S)-6'-Chloro-12,12-ethylene-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methylcarbamate

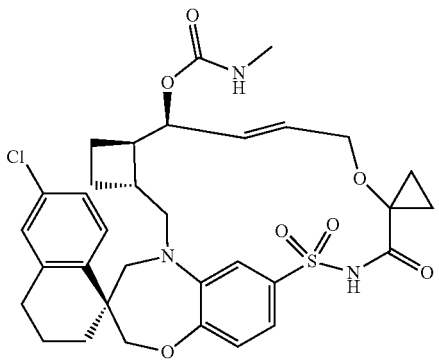 [SMILES: CNC(=O)O[C@H]1/C=C/COC2(CC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 using (3R,6R,7S,8E,22S)-6'-chloro-7-hydroxy-12,12-ethylene-15,15-dioxo-spiro[11,20-dioxa-15-thia-1,14-diazatetracyclo[14.7.2.0~3,6.0~19,24]pentacosa[8,16(25),17,19(24)]tetraene-22,1'-tetralin]-13-one (Example 40) in Step 1 and methylamine (40% in water) in Step 2. LCMS calc. for $C_{33}H_{39}ClN_3O_7S$ [M+H]$^+$: m/z=656.22/658.22; Found: 656.6/658.5. $^1$H NMR (300 MHz, CDCl$_3$) δ 9.02 (s, 1H), 7.64 (d, J=8.5 Hz, 1H), 7.50 (dd, J=8.3, 2.0 Hz, 1H), 7.37 (d, J=1.6 Hz, 1H), 7.17 (dd, J=8.5, 2.1 Hz, 1H), 7.09 (d, J=2.1 Hz, 1H), 7.00 (d, J=8.3 Hz, 1H), 5.81-5.56 (m, 2H), 5.09 (d, J=6.6 Hz, 1H), 4.46 (s, 1H), 4.14 (s, 2H), 4.07 (dd, J=13.3, 5.2 Hz, 1H), 3.95 (dd, J=13.0, 7.5 Hz, 1H), 3.67 (t, J=10.3 Hz, 1H), 3.60 (d, J=7.4 Hz, 1H), 3.30 (d, J=14.6 Hz, 1H), 3.17 (dd, J=15.3, 4.7 Hz, 1H), 2.76 (d, J=4.8 Hz, 4H), 2.72-2.61 (m, 1H), 2.56 (dd, J=16.5, 8.3 Hz, 1H), 2.05-1.85 (m, 3H), 1.81 (dd, J=10.7, 7.7 Hz, 1H), 1.70 (dd, J=11.7, 7.0 Hz, 2H), 1.62 (d, J=12.4 Hz, 2H), 1.55-1.30 (m, 3H), 1.22 (ddd, J=13.3, 11.2, 4.6 Hz, 2H).

Example 228

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3R)-3-ethoxypyrrolidine-1-carboxylate

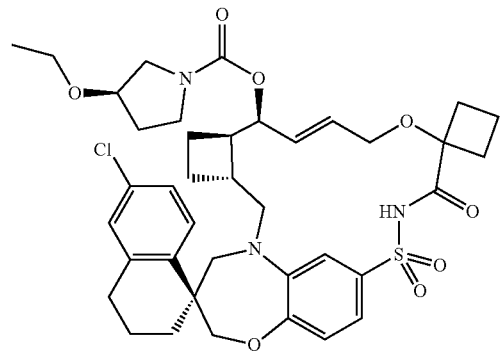 [SMILES: CCO[C@@H]1CCN(C(=O)O[C@H]2/C=C/COC3(CCC3)C(=O)NS(=O)(=O)c3ccc4c(c3)N(C[C@@H]3CC[C@H]32)C[C@@]2(CCCc3cc(Cl)ccc32)CO4)C1]

Step 1: 1-allyloxy-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-cyclobutanecarboxamide

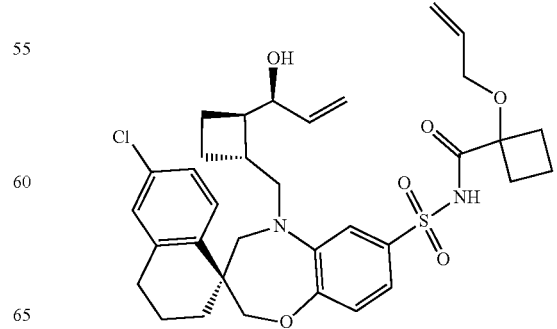

A mixture of (3S)-6'-chloro-5-[[(1R,2R)-2-[1S)-1-hydroxyallyl]cyclobutyl]methyl]spiro[2,4-dihydro-1,5-benzoxazepine-3,1'-tetralin]-7-sulfonamide (3.0 g, 5.96 mmol), 1-allyloxycyclobutanecarboxylic acid (3.26 g, 20.87 mmol), DMAP (5.83 g, 47.71 mmol) and EDC (5.72 g, 29.82 mmol) in DCM (30 mL) was stirred at 30° C. for 2 h. LCMS showed the conversion of the starting material into the desired product. The mixture was quenched with sat. NH$_4$Cl (aq) (20 mL) and extracted with DCM (20 mL×3). The combined organic layers were dried over Na$_2$SO$_4$, filtered and concentrated under reduced pressure. The residue was dissolved in THF (10 mL), water (10 mL) and methanol (10 mL), and treated with LiOH (1.29 g, 30.79 mmol). The mixture was stirred at 30° C. overnight, and quenched with 1M HCl (20 mL). The mixture was extracted with EtOAc (20 mL×3). The combined organic layers were washed with sat. NaHCO$_3$(aq) (20 mL) and brine (20 mL), dried over Na$_2$SO$_4$, filtered and concentrated under reduced pressure. The residue was purified by flash chromatography on a silica gel column with EA:Hep (5% to 30%) to afford 1-allyloxy-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-cyclobutanecarboxamide (2.35 g, 71.4% yield).

Step 2: (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),7,19(24)-tetraene-22,1'-tetralin]-13-one

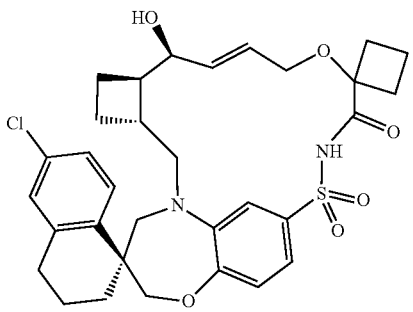 [SMILES: O=C1NS(=O)(=O)c2ccc3c(c2)N(C[C@@H]2CC[C@H]2[C@@H](O)/C=C/COC12CCC2)C[C@@]1(CCCc2cc(Cl)ccc21)CO3]

A solution of 1-allyloxy-N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-cyclobutanecarboxamide (2.35 g, 3.66 mmol) in DCE (2.5 L) was bubbled with N$_2$ gas for 15 min., then Hoveyda-Grubbs II (0.46 g, 0.73 mmol) was added and the mixture was bubbled with N$_2$ gas for an additional 15 min. The mixture was stirred for 2 h. at 40° C. under N$_2$. LCMS showed the conversion of the starting material into the desired product. The mixture was then exposed to air and stirred for 30 min before it was concentrated under reduced pressure. The reside was purified by flash chromatography on a silica gel column eluting with EA:Hep (10% to 60%) to afford (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (1.49 g, 66.3% yield).

Step 3: [(3R,6R,7S,8E,22S)-6'-chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl](3R)-3-ethoxypyrrolidine-1-carboxylate This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one in Step 1 and (3R)-3-ethoxypyrrolidine in Step 2. LCMS calc. for C$_{39}$H$_{49}$ClN$_3$O$_8$S [M+H]$^+$: m/z=754.29/756.29; Found: 754.4/756.4. $^1$H NMR (300 MHz, CDCl$_3$) δ 7.70 (dd, J=8.5, 4.3 Hz, 1H), 7.51 (d, J=8.2 Hz, 1H), 7.18 (d, J=8.4 Hz, 1H), 7.10-6.91 (m, 3H), 5.96 (s, 1H), 5.62 (ddd, J=15.6, 9.3, 5.4 Hz, 1H), 5.17 (d, J=4.8 Hz, 1H), 4.08 (m, 4H), 3.76-3.60 (m, 3H), 3.59-3.32 (m, 3H), 3.32-3.12 (m, 2H), 2.81-2.63 (m, 2H), 2.44 (m, 1H), 2.09 (dd, J=58.7, 11.5 Hz, 7H), 1.82 (t, J=8.0 Hz, 3H), 1.63 (q, J=9.4 Hz, 1H), 1.33-1.18 (m, 9H), 1.09 (dd, J=8.8, 6.3 Hz, 3H).

Example 229

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] (3S)-3-methoxypyrrolidine-1-carboxylate

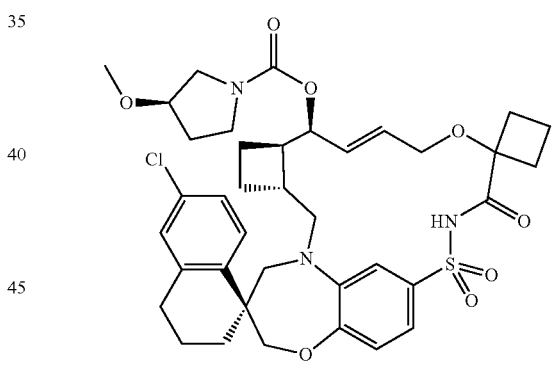

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 1 and (3R)-3-methoxypyrrolidine HCl and DIPEA in Step 2. LCMS calc. for C$_{39}$H$_{53}$ClN$_5$O$_6$S [M+H]$^+$: m/z=740.28/742.27; Found: 740.4/742.5. $^1$H NMR (300 MHz, CDCl$_3$) δ 7.68 (dd, J=8.5, 5.3 Hz, 1H), 7.48 (dd, J=8.3, 2.1 Hz, 1H), 7.18 (d, J=8.8 Hz, 1H), 7.13-6.99 (m, 2H), 6.97 (dd, J=8.3, 2.6 Hz, 1H), 5.80 (d, J=15.9 Hz, 1H), 5.64 (td, J=15.6, 13.8, 5.0 Hz, 1H), 5.23 (s, 1H), 4.23-4.01 (m, 3H), 3.75-3.46 (m, 2H), 3.47-3.29 (m, 5H), 3.29-3.08 (m, 1H), 2.78 (s, 3H), 2.67-2.48 (m, 1H), 2.42 (d, J=7.4 Hz, 2H), 2.35-2.17 (m, 1H), 2.10 (q, J=10.4, 9.9 Hz, 1H), 1.97 (dd, J=14.7, 6.0 Hz, 2H), 1.87 (dd, J=27.0, 5.2 Hz, 2H), 1.70-1.40 (m, 2H), 1.29 (d, J=16.4 Hz, 3H), 1.10 (d, J=6.6 Hz, 8H).

Example 230

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]-N,N-1,3-(2-ethoxy)propylene carbamate

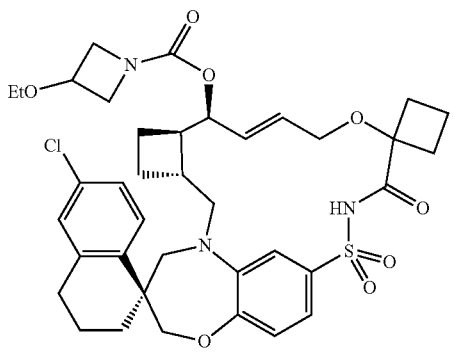 [SMILES: CCOC1CN(C(=O)O[C@H]2/C=C/COC3(CCC3)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 1 and 3-ethoxyazetidine in Step 2. LCMS calc. for $C_{38}H_{47}ClN_3O_8S$ $[M+H]^+$: m/z=740.27/742.27; Found: 740.4/742.4; $^1H$ NMR (300 MHz, CDCl$_3$) δ 7.68 (d, J=8.5 Hz, 1H), 7.45 (dd, J=8.3, 2.0 Hz, 1H), 7.16 (dd, J=8.5, 2.4 Hz, 1H), 7.05 (dd, J=13.4, 2.3 Hz, 2H), 6.94 (d, J=8.3 Hz, 1H), 5.83 (s, 1H), 5.60 (dd, J=15.7, 5.4 Hz, 1H), 5.12 (s, 1H), 4.28-3.98 (m, 7H), 3.67 (m, 3H), 3.48-3.37 (m, 4H), 3.29 (d, J=14.5 Hz, 1H), 2.76 (d, J=5.0 Hz, 2H), 2.27-2.16 (m, 3H), 2.10-1.93 (m, 7H), 1.80-1.64 (m, 6H), 1.21-1.18 (m, 3H).

Example 231

[(3R,6R,7S,8E,22S)-7'-Chloro-12,12-(1,3-propylene)-13,15,15-trioxo-spiro[11,20-dioxa-15λ6-thia-1,14-diazatetracyclo[14.7.2.03,6.019,24]pentacosa-8,16,18,24-tetraene-22,4'-chromane]-7-yl] N,N-dimethyl-1-carboxylate

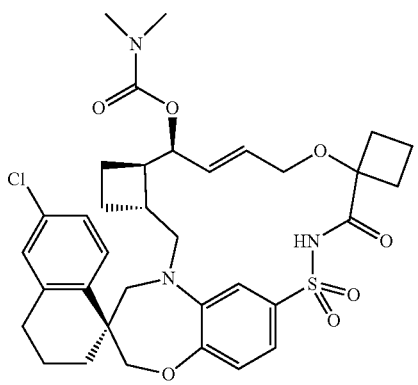 [SMILES: CN(C)C(=O)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 1 and dimethylamine (2.0 M in THF) in Step 2. LCMS calc. for $C_{35}H_{43}ClN_3O_7S$ $[M+H]^+$: m/z=684.24/686.24; Found: 684.3/686.2; $^1H$ NMR (300 MHz, CDCl$_3$) δ 7.69 (d, J=8.5 Hz, 1H), 7.45 (dd, J=8.3, 2.0 Hz, 1H), 7.16 (dd, J=8.5, 2.4 Hz, 1H), 7.04 (dd, J=18.7, 2.2 Hz, 2H), 6.93 (d, J=8.3 Hz, 1H), 6.10-5.97 (m, 1H), 5.62 (dd, J=15.7, 5.8 Hz, 1H), 5.13 (t, J=5.0 Hz, 1H), 4.07 (d, J=3.8 Hz, 1H), 3.99 (dd, J=14.0, 6.3 Hz, 1H), 3.80-3.68 (m, 2H), 3.65 (s, 1H), 3.51 (d, J=14.1 Hz, 1H), 3.24 (d, J=14.4 Hz, 1H), 3.14 (dd, J=15.0, 8.8 Hz, 1H), 2.94-2.82 (m, 6H), 2.75-2.69 (m, 3H), 2.67 (s, 3H), 2.14-1.92 (m, 6H), 1.76-1.66 (m, 6H).

Example 232

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl] N,N-1,3-propylene carbamate

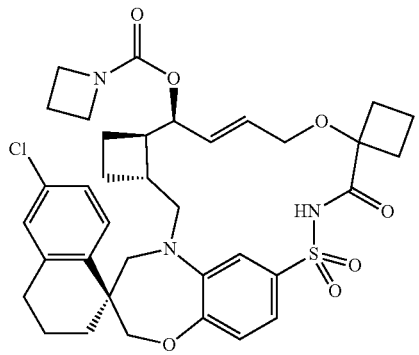 [SMILES: O=C(O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3)N1CCC1]

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 1 and azetidine hydrochloride and DIPEA in Step 2. LCMS calc. for $C_{37}H_{45}ClN_3O_6S$ $[M+H]^+$: m/z=696.24/698.24; Found: 696.3/698.4; $^1H$ NMR (300 MHz, CDCl$_3$) δ 7.69 (d, J=8.5 Hz, 1H), 7.15 (dd, J=8.5, 2.3 Hz, 2H), 7.09-7.00 (m, 2H), 6.91 (d, J=8.3 Hz, 1H), 5.63 (dd, J=15.4, 5.8 Hz, 1H), 5.37-5.31 (m, 1H), 5.12 (s, 1H), 4.10-3.88 (m, 7H), 3.66-3.64 (m, 2H), 3.24-3.20 (m, 1H), 2.76 (s, 2H), 2.40-2.31 (m, 4H), 2.21-2.08 (m, 5H), 2.06-1.93 (m, 6H), 1.76-1.62 (m, 7H).

Example 233

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl] N-[2-(dimethylamino)ethyl]-N-methyl-carbamate

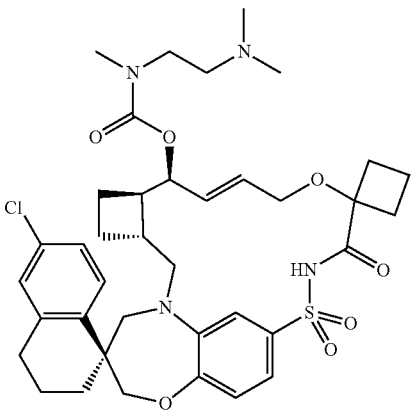 [SMILES: CN(C)CCN(C)C(=O)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 1 and N,N,N'-trimethylethylenediamine in Step 2. LCMS calc. for $C_{38}H_{50}ClN_4O_7S$ [M+H]$^+$: m/z=741.30/743.30; Found: 741.4/743.3; $^1$H NMR (300 MHz, CDCl$_3$) δ 7.71 (d, J=8.5 Hz, 1H), 7.46 (d, J=8.2 Hz, 1H), 7.18 (dd, J=8.5, 2.4 Hz, 2H), 7.09 (s, 1H), 6.94 (d, J=8.3 Hz, 1H), 6.41 (s, 1H), 6.07 (s, 1H), 5.66 (d, J=15.0 Hz, 1H), 5.34 (d, J=11.5 Hz, 1H), 4.98 (s, 1H), 4.69 (s, 1H), 4.20-4.00 (m, 4H), 3.71 (d, J=15.5 Hz, 3H), 3.50 (d, J=14.1 Hz, 2H), 3.37-3.26 (m, 2H), 3.03-2.95 (m, 4H), 2.85 (s, 3H), 2.78 (s, 2H), 2.74 (s, 1H), 2.41 (s, 3H), 2.23-2.20 (m, 4H), 1.99-1.87 (m, 4H), 1.82-1.75 (m, 4H).

Example 234

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methyl-N-[(3R)-tetrahydrofuran-3-yl]carbamate

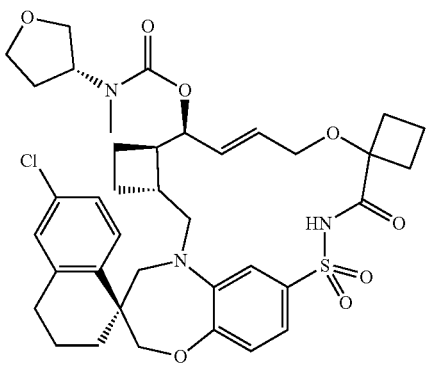 [SMILES: CN(C(=O)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3)[C@@H]1CCOC1]

This compound was prepared using procedures analogous to those described for Example 63 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 2 and (3R)-N-methyltetrahydrofuran-3-amine hydrochloride in Step 1. LCMS calc. for $C_{38}H_{47}ClN_3O_8S$ [M+H]$^+$: m/z=740.27/742.27; Found: 740.4/742.4. $^1$H NMR (300 MHz, CDCl$_3$) δ 7.67 (d, J=8.5 Hz, 1H), 7.51 (dd, J=8.3, 2.1 Hz, 1H), 7.18 (dd, J=8.5, 2.4 Hz, 1H), 7.10 (d, J=2.3 Hz, 1H), 7.05 (d, J=2.2 Hz, 1H), 7.00 (d, J=8.3 Hz, 1H), 5.66 (d, J=2.8 Hz, 2H), 5.30-5.19 (m, 1H), 4.89 (s, 1H), 4.20 (d, J=12.1 Hz, 1H), 4.12 (s, 1H), 4.08 (d, J=3.4 Hz, 1H), 4.01 (dd, J=8.6, 4.8 Hz, 1H), 3.76 (d, J=5.9 Hz, 2H), 3.70 (d, J=7.5 Hz, 1H), 3.66 (s, 1H), 3.56 (d, J=13.8 Hz, 1H), 3.38 (s, 1H), 3.32 (d, J=6.5 Hz, 2H), 2.86 (s, 3H), 2.79-2.72 (m, 4H), 2.04-1.70 (m, 12H), 1.67-1.49 (m, 4H).

Example 235

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methyl-N-(oxetan-3-yl)carbamate

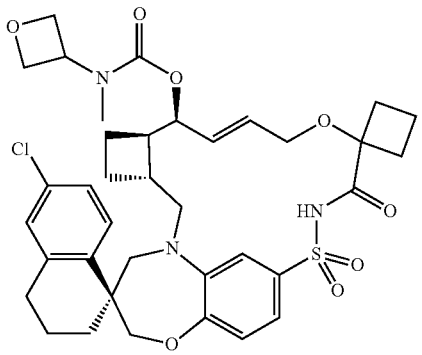 [SMILES: CN(C(=O)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3)C1COC1]

This compound was prepared using procedures analogous to those described for Example 63 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 2 and N-methyloxetan-3-amine in Step 1. LCMS calc. for $C_{37}H_{45}ClN_3O_8S$ [M+H]$^+$: m/z=726.26/728.26; Found: 726.4.4/728.6. $^1$H NMR (300 MHz, CDCl$_3$) δ 7.68 (dq, J=12.6, 8.1 Hz, 2H), 7.51 (dd, J=8.3, 2.1 Hz, 1H), 7.18-7.00 (m, 3H), 5.88 (tdd, J=16.8, 10.4, 5.5 Hz, 1H), 5.64 (s, 2H), 5.38-5.01 (m, 3H), 4.77 (dt, J=13.4, 7.0 Hz, 2H), 4.25-4.02 (m, 3H), 3.97-3.84 (m, 1H), 3.83-3.52 (m, 3H), 3.29 (d, J=20.3 Hz, 3H), 3.06 (s, 3H), 2.78 (s, 4H), 2.57-2.05 (m, 3H), 2.09-1.77 (m, 2H), 1.60 (dd, J=20.4, 10.9 Hz, 2H), 1.47-1.23 (m, 5H).

Example 236

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N-methyl-N-tetrahydropyran-4-yl-carbamate

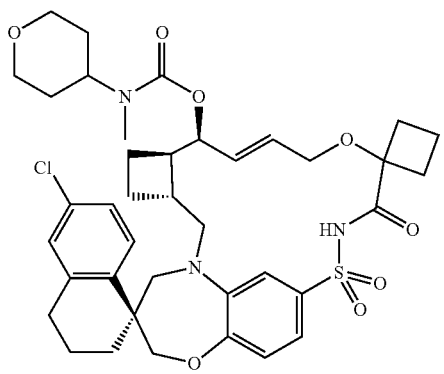 [SMILES: CN(C(=O)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3)C1CCOCC1]

This compound was prepared using procedures analogous to those described for Example 63 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 2 and N-methyltetrahydropyran-4-amine in Step 1. LCMS calc. for $C_{39}H_{49}ClN_3O_8S$ $[M+H]^+$: m/z=754.29/756.29; Found: 754.4/756.5. $^1$H NMR (300 MHz, CDCl$_3$) δ 8.81 (s, 1H), 7.67 (d, J=8.5 Hz, 1H), 7.51 (dd, J=8.4, 2.1 Hz, 1H), 7.21-6.92 (m, 4H), 5.64 (s, 2H), 5.25 (s, 1H), 4.25-4.05 (m, 2H), 4.01 (d, J=10.4 Hz, 6H), 3.73 (dd, J=30.6, 14.2 Hz, 1H), 3.56 (d, J=13.7 Hz, 1H), 3.48-3.29 (m, 8H), 2.84-2.68 (m, 7H), 2.56-2.44 (m, 1H), 2.45-2.20 (m, 1H), 2.24-1.98 (m, 1H), 2.04-1.83 (m, 1H), 1.82 (q, J=10.4, 7.9 Hz, 4H), 1.57 (s, 1H), 1.29 (d, J=16.1 Hz, 3H).

Example 237

[(3R,6R,7S,8E,22S)-6'-Chloro-12,12-(1,3-propylene)-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl] N-[(3S)-tetrahydrofuran-3-yl]carbamate

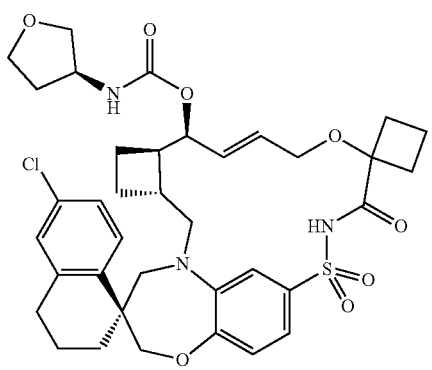 [SMILES: O=C(N[C@H]1CCOC1)O[C@H]1/C=C/COC2(CCC2)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 46 Step 1-2 using (3R,6R,7S,8E,22S)-6'-chloro-7-hydroxy-12,12-(1,3-propylene)-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 228 Step 2) in Step 2 and (3S)-tetrahydrofuran-3-amine in Step 1. LCMS calc. for $C_{37}H_{45}ClN_3O_8S$ $[M+H]^+$: m/z=726.26/728/26; Found: 726.4/728.4.

Example 238

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 3-methoxyazetidine-1-carboxylate

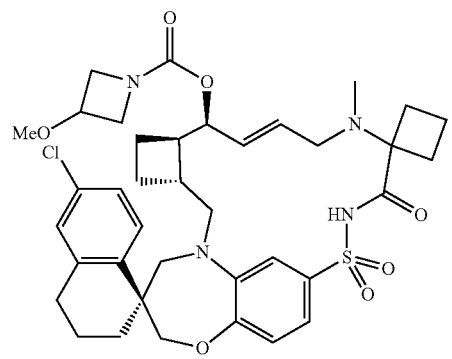 [SMILES: COC1CN(C(=O)O[C@H]2/C=C/CN(C)C3(CCC3)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 1 and 3-methoxyazetidine hydrochloride and DIPEA in Step 2. LCMS calc. for $C_{38}H_{48}ClN_4O_7S$ $[M+H]^+$: m/z=739.2/741.2; Found: 739.4/741.5. $^1$H NMR (300 MHz, CDCl$_3$) δ 7.70 (d, J=8.5 Hz, 1H), 7.53 (dd, J=8.4, 2.3, 1H), 7.23-7.18 (m, 1H), 7.10 (d, J=2.3 Hz, 1H), 7.00 (dd, J=8.3, 1.0 Hz, 1H), 6.87 (d, J=2.2 Hz, 1H), 5.72-5.67 (m, 2H), 5.24 (br, 1H), 4.23-4.06 (m, 4H), 3.96 (d, J=8.3 Hz, 1H), 3.73 (d, J=14.8 Hz, 1H), 3.45-3.40 (m, 2H), 3.33 (s, 3H), 3.12 (dd, J=14.9, 10.6 Hz, 1H), 2.89-2.66 (m, 5H), 2.44 (s, 3H), 2.35-2.15 (m, 4H), 2.04-1.92 (m, 4H), 1.85-1.64 (m, 7H), 1.34-1.30 (m, 3H).

Example 239

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-tetrahydropyran-4-yl-carbamate

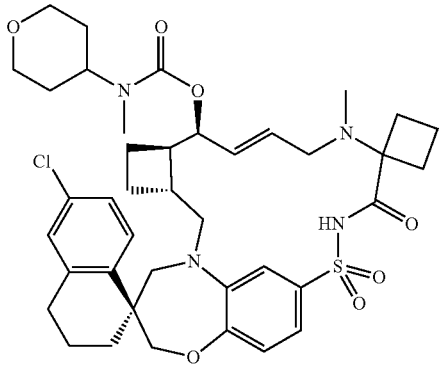 [SMILES: CN(C(=O)O[C@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3)C1CCOCC1]

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.3,6.019,24]pentacosa-8,16(25),17,19(24)-tetraene-22,1'-tetralin]-13-one (Example 48 Step 8) in Step 2 and N-methyltetrahydropyran-4-amine in Step 1. LCMS calc. for $C_{40}H_{52}ClN_4O_7S$ [M+H]$^+$: m/z=767.32/769.32; Found: 767.5/769.8. $^1$H NMR (300 MHz, CDCl$_3$) δ 7.69 (d, J=8.5 Hz, 1H), 7.52 (dd, J=8.3, 2.1 Hz, 1H), 7.19 (dd, J=8.5, 2.4 Hz, 1H), 7.09 (d, J=2.3 Hz, 1H), 6.99 (d, J=8.3 Hz, 1H), 6.86 (d, J=2.2 Hz, 1H), 5.72 (s, 2H), 5.33 (s, 1H), 4.27 (s, 1H), 4.17 (d, J=12.2 Hz, 1H), 4.06 (d, J=12.2 Hz, 1H), 3.73 (d, J=14.7 Hz, 1H), 3.55-3.40 (m, 4H), 3.36 (d, J=14.4 Hz, 1H), 3.13 (t, J=12.8 Hz, 1H), 2.90 (d, J=11.8 Hz, 3H), 2.89-2.63 (m, 7H), 2.58-2.43 (m, 1H), 2.42 (s, 3H), 2.36-2.05 (m, 1H), 2.01 (s, 2H), 2.00-1.84 (m, 1H), 1.85-1.52 (m, 8H), 1.44 (t, J=12.0 Hz, 1H), 1.36-1.20 (m, 4H).

Example 240

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-(oxetan-3-yl)carbamate

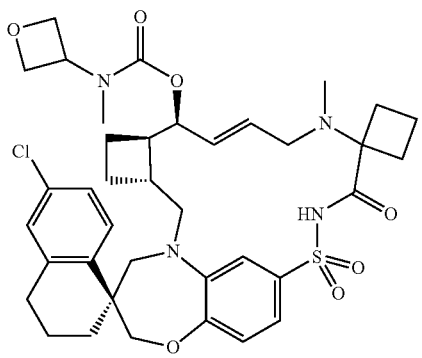 [SMILES: CN(C(=O)O[C@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3)C1COC1]

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 2 and N-methyloxetan-3-amine in Step 1. LCMS calc. for $C_{38}H_{48}ClN_4O_7S$ [M+H]$^+$: m/z=739.29/741.29; Found: 739.5/741.5.

Example 241

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-[(3S)-tetrahydrofuran-3-yl]carbamate

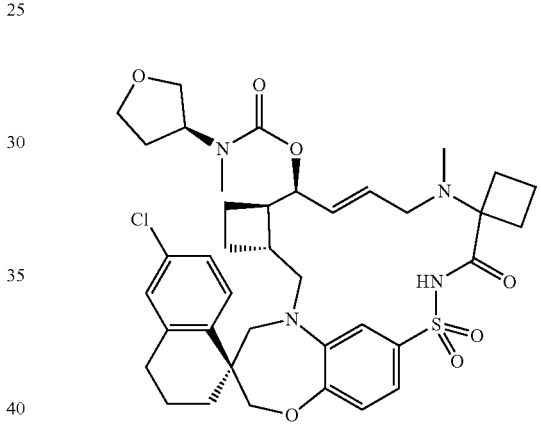

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 2 and (3S)-N-methyltetrahydrofuran-3-amine hydrochloride in Step 1. LCMS calc. for $C_{39}H_{49}ClN_3O_8S$ [M+H]$^+$: m/z=753.31/755.31; Found: 753.4/755.4. $^1$H NMR (300 MHz, Chloroform-d) δ 7.69 (d, J=8.6 Hz, 1H), 7.52 (dd, J=8.4, 2.1 Hz, 1H), 7.24-7.16 (m, 1H), 7.09 (d, J=2.3 Hz, 1H), 6.99 (d, J=8.4 Hz, 1H), 6.86 (d, J=2.2 Hz, 1H), 5.72 (d, J=2.7 Hz, 2H), 5.33 (s, 1H), 4.96 (s, 1H), 4.17 (d, J=12.2 Hz, 1H), 4.10-3.98 (m, 2H), 3.85-3.67 (m, 5H), 3.50-3.41 (m, 1H), 3.36 (d, J=14.8 Hz, 1H), 3.13 (dd, J=15.0, 10.5 Hz, 1H), 2.94 (d, J=8.5 Hz, 3H), 2.79 (q, J=6.1, 5.7 Hz, 4H), 2.72 (s, 2H), 2.43 (s, 3H), 2.08-1.92 (m, 7H), 1.85-1.62 (m, 7H), 1.46 (d, J=12.9 Hz, 1H).

Example 242

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-methyl-N-[(3R)-tetrahydrofuran-3-yl]carbamate

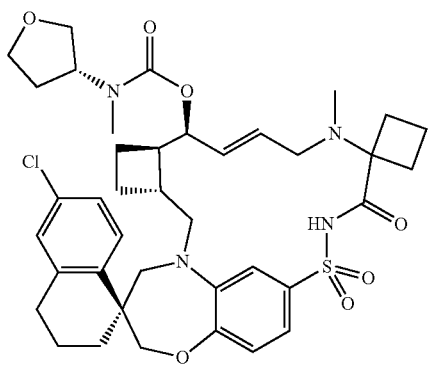 [SMILES: CN(C(=O)O[C@H]1/C=C/CN(C)C2(CCC2)C(=O)NS(=O)(=O)c2ccc3c(c2)N(C[C@@H]2CC[C@H]21)C[C@@]1(CCCc2cc(Cl)ccc21)CO3)[C@@H]1CCOC1]

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 2 and (3R)-N-methyltetrahydrofuran-3-amine hydrochloride in Step 1. LCMS calc. for $C_{39}H_{50}ClN_4O_7S$ [M+H]$^+$: m/z=753.31/755.31; Found: 753.4/755.4. $^1$H NMR (300 MHz, Chloroform-d) δ 7.69 (d, J=8.5 Hz, 1H), 7.52 (dd, J=8.4, 2.1 Hz, 1H), 7.19 (dd, J=8.5, 2.4 Hz, 1H), 7.09 (d, J=2.3 Hz, 1H), 6.99 (d, J=8.3 Hz, 1H), 6.86 (d, J=2.3 Hz, 1H), 5.72 (d, J=1.8 Hz, 2H), 5.40-5.29 (m, 1H), 4.97 (s, 1H), 4.17 (d, J=12.1 Hz, 1H), 4.06 (d, J=12.1 Hz, 2H), 3.86-3.74 (m, 3H), 3.71 (s, 2H), 3.50-3.40 (m, 1H), 3.36 (d, J=14.7 Hz, 1H), 3.12 (dd, J=15.0, 10.6 Hz, 1H), 2.95 (d, J=8.1 Hz, 3H), 2.79 (q, J=5.8, 5.1 Hz, 4H), 2.71 (s, 1H), 2.43 (s, 3H), 2.09-1.89 (m, 7H), 1.89-1.76 (m, 4H), 1.75-1.61 (m, 4H), 1.46 (d, J=13.0 Hz, 1H).

Example 243

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-[(3R)-tetrahydrofuran-3-yl]carbamate

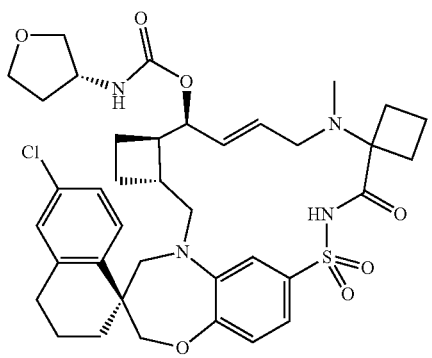 [SMILES: CN1C/C=C/[C@H](OC(=O)N[C@@H]2CCOC2)[C@@H]2CC[C@H]2CN2C[C@@]3(CCCc4cc(Cl)ccc43)COc3ccc(cc32)S(=O)(=O)NC(=O)C12CCC2]

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 2 and (3R)-tetrahydrofuran-3-amine in Step 1. LCMS calc. for $C_{38}H_{48}ClN_4O_7S$ [M+H]$^+$: m/z=739.29/741.29; Found: 739.3/741.3.

Example 244

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] 3-ethoxyazetidine-1-carboxylate

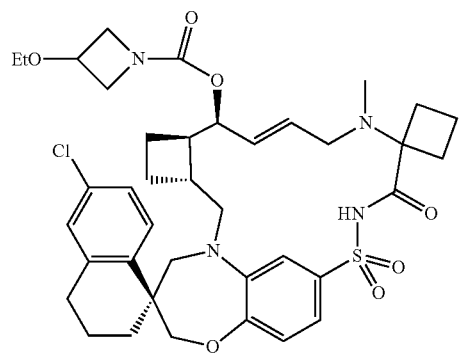 [SMILES: CCOC1CN(C(=O)O[C@H]2/C=C/CN(C)C3(CCC3)C(=O)NS(=O)(=O)c3ccc4c(c3)N(C[C@@H]3CC[C@H]32)C[C@@]2(CCCc3cc(Cl)ccc32)CO4)C1]

This compound was prepared using procedures analogous to those described for Example 46 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 1 and 3-ethoxyazetidine; hydrochloride and DIPEA in Step 2. LCMS calc. for $C_{39}H_{50}ClN_4O_7S$ [M+H]$^+$: m/z=753.30/755.30; Found: 753.6/755.3. $^1$H NMR (300 MHz, CDCl$_3$) δ 7.70 (d, J=8.5 Hz, 1H), 7.52 (dd, J=8.4, 2.0 Hz, 1H), 7.20 (dd, J=8.5, 2.4 Hz, 1H), 7.10 (d, J=2.3 Hz, 1H), 6.99 (d, J=8.3 Hz, 1H), 6.88 (d, J=2.2 Hz, 1H), 5.72-5.66 (m, 2H), 5.24 (br, 1H), 4.22-4.13 (m, 6H), 3.73 (d, J=14.7 Hz, 1H), 3.48-3.33 (m, 4H), 3.12 (dd, J=15.0, 10.5 Hz, 1H), 2.84-2.71 (m, 4H), 2.44 (s, 3H), 2.32-2.27 (m, 3H), 2.06-1.95 (m, 4H), 1.85-1.80 (m, 3H), 1.67-1.61 (m, 2H), 1.45 (t, J=11.8 Hz, 1H), 1.27-1.16 (m, 8H).

Example 245

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] 4-methoxypiperidine-1-carboxylate

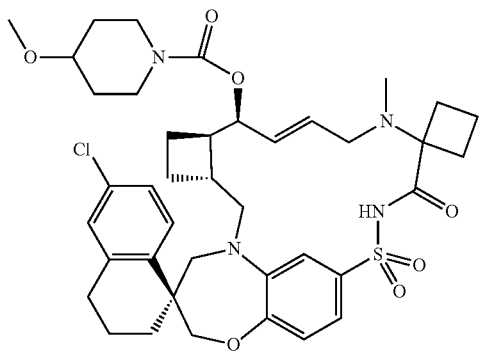 [SMILES: COC1CCN(C(=O)O[C@H]2/C=C/CN(C)C3(CCC3)C(=O)NS(=O)(=O)c3ccc4c(c3)N(C[C@@H]3CC[C@H]32)C[C@@]2(CCCc3cc(Cl)ccc32)CO4)CC1]

This compound was prepared using procedures analogous to those described for Example 46 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one (Example 48 Step 8) in Step 1 and 4-methoxypiperidine in Step 2. LC-MS: calc. for $C_{40}H_{52}ClN_4O_7S$ [M+H]⁺: m/z=767.32/769.32; Found 767.4/769.4.

Example 246

(3R,6R,7S,8E,22S)-7'-Chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one

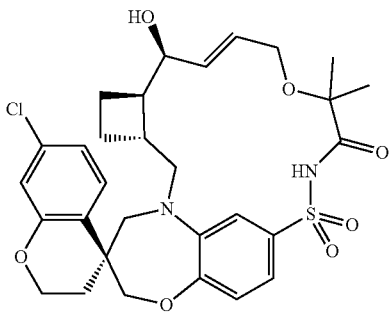 [SMILES: CC1(C)OC/C=C/[C@H](O)[C@@H]2CC[C@H]2CN2C[C@@]3(CCOc4cc(Cl)ccc43)COc3ccc(cc32)S(=O)(=O)NC1=O]

This compound was prepared using procedures analogous to those described for Example 32 Step 1-3 using (3S)-7'-chloro-5-[[(1R,2R)-2-[(1S)-1-hydroxyallyl]cyclobutyl]methyl]spiro[2,4-dihydro-1,5-benzoxazepine-3,4'-chromane]-7-sulfonamide (Intermediate 12) and 2-allyloxy-2-methyl-propanoic acid (Example 30 Step1). LC-MS: calc. for $C_{30}H_{36}ClN_2O_7S$ [M+H]⁺: m/z=603.2/605.2; Found: 603.2/605.2. HPLC: C18 column (4.6×150 mm, 100 Å); flow rate=1 mL/min; mobile phase: 5% MeCN/H₂O (with 0.1% TFA) 2 min, 5% to 95% 6 min, 95% 2 min. λ=220 nm.

tR=6.813 min. ¹H NMR (499 MHz, DMSO-d₆) δ 11.71 (s, 1H), 7.55 (d, J=8.5 Hz, 1H), 7.38-7.20 (m, 1H), 7.15-7.00 (m, 2H), 6.97 (dd, J=8.5, 2.3 Hz, 1H), 6.89 (t, J=2.4 Hz, 1H), 5.67-5.37 (m, 2H), 4.69 (d, J=4.1 Hz, 1H), 4.33-4.17 (m, 3H), 4.05 (d, J=12.1 Hz, 1H), 3.97-3.82 (m, 2H), 3.59 (d, J=14.5 Hz, 1H), 3.45 (t, J=15.4 Hz, 2H), 3.17 (dd, J=14.5, 7.4 Hz, 1H), 2.60 (q, J=7.8, 6.0 Hz, 1H), 2.34-2.20 (m, 1H), 2.17-1.95 (m, 2H), 1.84 (tdt, J=25.5, 16.6, 7.4 Hz, 3H), 1.73-1.51 (m, 2H), 1.36 (s, 3H), 1.23 (s, 3H).

Example 247

[(3R,6R,7S,8E,22S)-7'-Chloro-12,12-dimethyl-13,5,5-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N,N-dimethylcarbamate

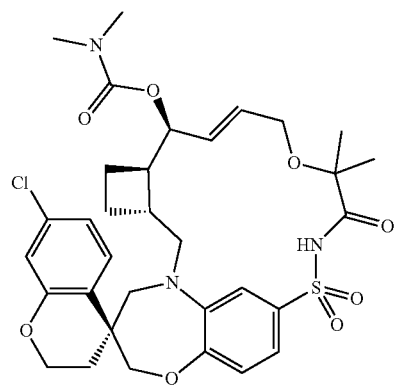 [SMILES: CN(C)C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3]

To a stirred solution of (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (22.0 mg, 0.04 mmol, Example 246) in MeCN (10 ml) was added CDI (18.11 mg, 0.11 mmol). The mixture was stirred at 45° C. for 2 h. LCMS analysis indicated the starting material was fully consumed. Dimethylamine in THF (35 uL, 0.07 mmol, 2.0 N) was added. The reaction mixture was stirred at 45° C. for 2 h. HCl (1.0 M, 2 mL) was added. The mixture was extracted with DCM (5 mL×3). The combined organic layers were dried over sodium sulfate, filtered and concentrated under reduced pressure. The residue was purified by prep-HPLC on a C₁₈ column to afford [(3R,6R,7S,8E,22S)-7'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N,N-dimethylcarbamate (5.8 mg, 23.6% yield) as a white solid. LCMS calc. for $C_{33}H_{41}ClN_3O_8S$ [M-H]⁺: m/z=674.2/676.2; Found: 674.4/676.4. ¹H NMR (499 MHz, DMSO-d₆) δ 11.69 (s, 1H), 7.57 (d, J=8.5 Hz, 1H), 7.33-7.18 (m, 1H), 7.05-6.94 (m, 3H), 6.88 (d, J=2.2 Hz, 1H), 5.66 (s, 2H), 5.10 (t, J=3.5 Hz, 1H), 4.35-4.15 (m, 3H), 4.07 (d, J=12.1 Hz, 1H), 3.94 (d, J=13.7 Hz, 1H), 3.63 (d, J=14.5 Hz, 1H), 3.41 (d, J=14.5 Hz, 1H), 3.25 (d, J=6.7 Hz, 2H), 2.92 (s, 3H), 2.83 (s, 3H), 2.69 (q, J=7.9 Hz, 1H), 2.43 (s, 1H), 2.11-1.97 (m, 1H), 1.89-1.79 (m, 2H), 1.77-1.60 (m, 3H), 1.37 (s, 3H), 1.21 (s, 3H).

Example 248

[(3R,6R,7S,8E,22S)-7'-Chloro-12,12-dimethyl-13, 15,15-trioxo-spiro[11,20-dioxa-15-thia-1,14-diazatetracyclo[14.7.2.03,6.019,24]pentacosa-8,16,18,24-tetraene-22,4'-chromane]-7-yl]morpholine-4-carboxylate

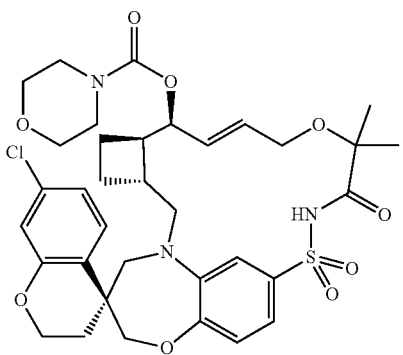 [SMILES: CC1(C)OC/C=C/[C@H](OC(=O)N2CCOCC2)[C@@H]2CC[C@H]2CN2C[C@@]3(CCOc4cc(Cl)ccc43)COc3ccc(cc32)S(=O)(=O)NC1=O]

This compound was prepared using procedures analogous to those described for Example 46 Step 1-2 using (3R,6R, 7S,8E,22S)-7'-chloro-7-hydroxy-12,12-dimethyl-15,15-dioxo-spiro[11,20-dioxa-15-thia-1,14-diazatetracyclo[14.7. 2.03,6.019,24]pentacosa-8,16,18,24-tetraene-22,4'-chromane]-13-one (Example 246) in Step 1 and morpholine in Step 2. LC-MS: calc. for $C_{35}H_{43}ClN_3O_9S$ [M+H]$^+$: m/z=716.2/718.2; Found: 716.3/718.3. $^1$H NMR (300 MHz, CDCl$_3$) δ 7.78 (d, J=7.5 Hz, 1H), 7.57 (dd, J=8.4, 1.1 Hz, 1H), 7.39 (d, J=7.6 Hz, 1H), 7.13-7.01 (m, 2H), 6.94 (ddd, J=8.4, 2.3, 1.2 Hz, 1H), 5.97-5.64 (m, 2H), 5.34 (t, J=4.3 Hz, 1H), 4.57 (td, J=11.5, 10.4, 6.4 Hz, 1H), 4.40-3.94 (m, 5H), 3.80-3.62 (m, 4H), 3.54-3.26 (m, 4H), 3.03-2.87 (m, 1H), 2.80 (d, J=7.1 Hz, 3H), 2.08-1.80 (m, 6H), 1.65 (dd, J=12.2, 6.6 Hz, 2H), 1.46 (s, 3H), 1.37 (s, 3H).

Example 249

(3R,6R,7S,8E,22R)-6'-Chloro-7-hydroxy-12,12-dimethyl-15,15-dioxo-spiro[11,20-dioxa-15-thia-1, 14-diazatetracyclo[14.7.2.03,6.019,24]pentacosa-8, 16,18,24-tetraene-22,1'-isochromane]-13-one

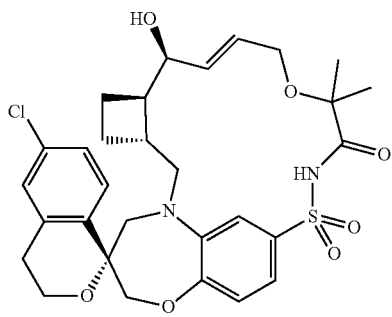 [SMILES: CC1(C)OC/C=C/[C@H](O)[C@@H]2CC[C@H]2CN2C[C@]3(COc4ccc(cc42)S(=O)(=O)NC1=O)OCCc1cc(Cl)ccc13]

This compound was prepared using procedures analogous to those described for Example 32 Step 1-3 using (3R)-6'-chloro-5-[[(1R,2R)-2-[(1S)-1-hydroxyallyl]cyclobutyl] methyl]spiro[2,4-dihydro-1,5-benzoxazepine-3,1'-isochromane]-7-sulfonamide (Intermediate 15) and 2-allyloxy-2-methyl-propanoic acid (Example 30 Step1). LC-MS: calc. for $C_{30}H_{36}ClN_2O_7S$ [M+H]$^+$: m/z=603.2/605.2; Found: 603.2/605.2. $^1$H NMR (300 MHz, CDCl$_3$) δ 7.60-7.45 (m, 2H), 7.25-7.14 (m, 3H), 7.02 (dd, J=8.4, 1.4 Hz, 1H), 5.86-5.51 (m, 2H), 4.38-4.29 (m, 1H), 4.17 (d, J=12.1 Hz, 2H), 4.09-3.96 (m, 2H), 3.84-3.52 (m, 6H), 3.28 (dd, J=14.8, 7.3 Hz, 1H), 2.94 (ddt, J=24.3, 16.0, 7.8 Hz, 2H), 2.80-2.68 (m, 1H), 2.40 (q, J=9.1 Hz, 1H), 2.14-1.78 (m, 4H), 1.42 (s, 3H), 1.39 (s, 3H).

Example 250

[(3R,6R,7S,8E,22R)-6'-Chloro-12,12-dimethyl-13, 15,15-trioxo-spiro[11,20-dioxa-15-thia-1,14-diazatetracyclo[14.7.2.03,6.019,24]pentacosa-8,16,18,24-tetraene-22,1'-isochromane]-7-yl] N,N-dimethylcarbamate

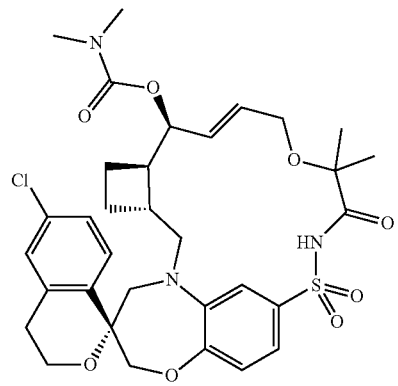 [SMILES: CN(C)C(=O)O[C@H]1/C=C/COC(C)(C)C(=O)NS(=O)(=O)c2ccc3c(c2)N(C[C@@H]2CC[C@H]21)C[C@]1(CO3)OCCc2cc(Cl)ccc21]

This compound was prepared using procedures analogous to those described for Example 46 Step 1-2 using (3R,6R, 7S,8E,22R)-6'-Chloro-7-hydroxy-12,12-dimethyl-15,15-dioxo-spiro[11,20-dioxa-15-thia-1,14-diazatetracyclo[14.7. 2.03,6.019,24]pentacosa-8,16,18,24-tetraene-22,1'-isochromane]-13-one (Example 249) in Step 1 and dimethylamine in THF solution (2.0 N) in Step 2. LC-MS: calc. for $C_{33}H_{41}ClN_3O_8S$ [M+H]$^+$: m/z=674.2/676.2; Found: 674.3/676.3. $^1$H NMR (300 MHz, CDCl$_3$) δ 7.50 (d, J=8.5 Hz, 1H), 7.43 (dd, J=8.3, 2.0 Hz, 1H), 7.27-7.21 (m, 1H), 7.16 (d, J=2.2 Hz, 1H), 7.10 (d, J=2.2 Hz, 1H), 6.94 (dd, J=8.3, 0.9 Hz, 1H), 6.09 (ddd, J=15.8, 6.4, 4.1 Hz, 1H), 5.69 (dd, J=15.7, 5.5 Hz, 1H), 5.25 (t, J=4.2 Hz, 1H), 4.31 (d, J=11.8 Hz, 1H), 4.13 (d, J=11.8 Hz, 1H), 4.02-3.95 (m, 2H), 3.80-3.71 (m, 1H), 3.66 (d, J=11.6 Hz, 2H), 3.50-3.38 (m, 2H), 3.03 (s, 3H), 2.95 (s, 3H), 2.72 (s, 5H), 2.37 (qd, J=9.0, 2.9 Hz, 1H), 2.04 (qt, J=7.5, 3.0 Hz, 1H), 1.84 (q, J=9.0 Hz, 2H), 1.71-1.57 (m, 1H), 1.40 (s, 3H), 1.33 (s, 3H).

Example 251

Methyl N-[(3R,6R,7R,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl] carbamate

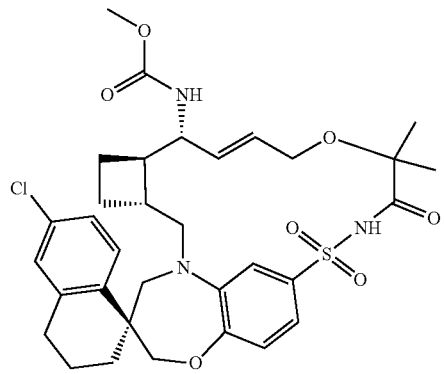 [SMILES: COC(=O)N[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: (3S)-6'-chloro-N,N-bis[(4-methoxyphenyl)methyl]-5-[[(1R,2R)-2-[(E)-[(S)-tert-butylsulfinyl]iminomethyl]cyclobutyl]methyl]spiro[2,4-dihydro-1,5-benzoxazepine-3,1'-tetralin]-7-sulfonamide

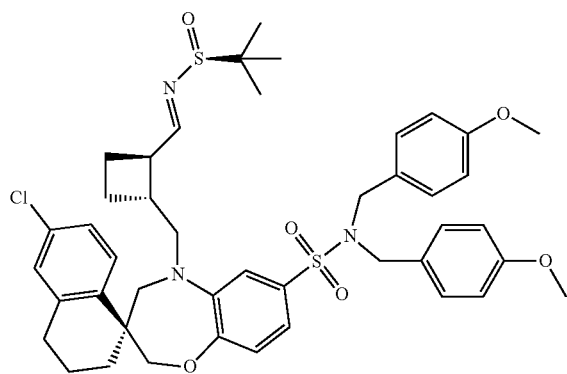 [SMILES: COc1ccc(CN(Cc2ccc(OC)cc2)S(=O)(=O)c2ccc3c(c2)N(C[C@@H]2CC[C@H]2/C=N/[S@@](=O)C(C)(C)C)C[C@@]2(CCCc4cc(Cl)ccc42)CO3)cc1]

To a solution of (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide (1000.0 mg, 1.4 mmol, Intermediate 3 Step 3) in DCM (20 mL) was added copper sulfate (669.41 mg, 4.19 mmol) followed by the addition of (S)-2-methylpropane-2-sulfinamide (254.16 mg, 2.1 mmol). The reaction mixture was stirred at r.t. overnight. The reaction was filtered through a pad of Celite and washed with DCM. The filtrate was concentrated under reduced pressure. The residue was purified by flash chromatography on a silica gel column EtOAc/Hep (3% to 60%) to afford (3S)-6'-chloro-N,N-bis[(4-methoxyphenyl)methyl]-5-[[(1R,2R)-2-[(E)-[(S)-tert-butylsulfinyl]iminomethyl]cyclobutyl]methyl]spiro[2,4-dihydro-1,5-benzoxazepine-3,1'-tetralin]-7-sulfonamide (980 mg, 85.6% yield). LCMS calcd. for $C_{44}H_{53}ClN_3O_6S_2$ $[M+H]^+$: m/z=818.31/820.30; Found: 819.0/821.0.

Step 2: (3S)-6'-chloro-N,N-bis[(4-methoxyphenyl)methyl]-5-[[(1R,2R)-2-[(1R)-1-[[(S)-tert-butylsulfinyl]amino]allyl]cyclobutyl]methyl]spiro[2,4-dihydro-1,5-benzoxazepine-3,1'-tetralin]-7-sulfonamide and (3S)-6'-chloro-N,N-bis[(4-methoxyphenyl)methyl]-5-[[(1R,2R)-2-[(1S)-1-[[(S)-tert-butylsulfinyl]amino]allyl]cyclobutyl]methyl]spiro[2,4-dihydro-1,5-benzoxazepine-3,1'-tetralin]-7-sulfonamide

P1

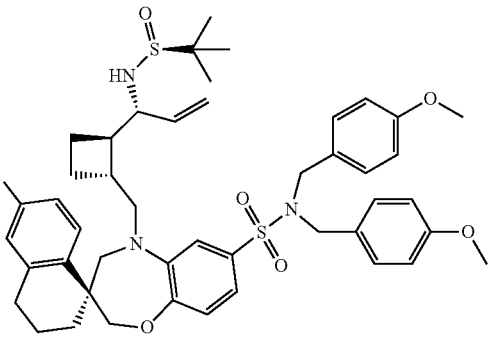

and

P2

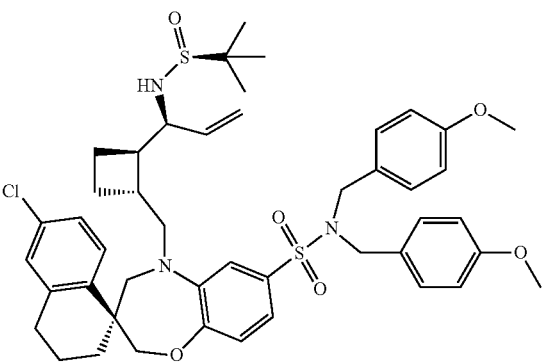

To a cooled (−78° C.) solution of (3S)-6'-chloro-N,N-bis[(4-methoxyphenyl)methyl]-5-[[(1R,2R)-2-[(E)-[(S)-tert-butylsulfinyl]iminomethyl]cyclobutyl]methyl]spiro[2,4-dihydro-1,5-benzoxazepine-3,1'-tetralin]-7-sulfonamide (980.0 mg, 1.2 mmol) in THF (20 mL) was added dropwise vinylmagnesium bromide (1.8 mL, 1.8 mmol, 1.0M THF solution) over 10 min. After addition, the reaction mixture was allowed to warm to r.t. over 1 h. LCMS showed full conversion of starting material and the formation of desired product. The reaction was quenched with sat. NH₄Cl(aq) (20 mL) and extracted with EtOAc (20 mL×3). The organic layer was dried over NaSO₄, filtered and concentrated under reduced pressure. The residue was purified by flash chromatography on a silica gel column EA:Hep (3% to 100%) to afford two products: P1 (the earlier eluted product, 410 mg, 40.4%) which was assigned to (3S)-6'-chloro-N,N-bis[(4-methoxyphenyl)methyl]-5-[[(1R,2R)-2-[(1R)-1-[[(S)-tert-butylsulfinyl]amino]allyl]cyclobutyl]methyl]spiro[2,4-dihydro-1,5-benzoxazepine-3,1'-tetralin]-7-sulfonamide and P2 (the latter eluted product, 190 mg, 18.7%) which was assigned to (3S)-6'-chloro-N,N-bis[(4-methoxyphenyl)methyl]-5-[[(1R,2R)-2-[(1S)-1-[[(S)-tert-butylsulfinyl]amino]allyl]cyclobutyl]methyl]spiro[2,4-dihydro-1,5-benzoxazepine-3,1'-tetralin]-7-sulfonamide. LCMS calcd. for $C_{46}H_{57}ClN_3O_6S_2$ [M+H]$^+$: m/z=846.34/848.33; Found: 847.1/849.2.

Step 3. (3S)-6'-chloro-N,N-bis[(4-methoxyphenyl)methyl]-5-[[(1R,2R)-2-[(1R)-1-[[(S)-tert-butylsulfinyl]amino]allyl]cyclobutyl]methyl]spiro[2,4-dihydro-1,5-benzoxazepine-3,1'-tetralin]-7-sulfonamide

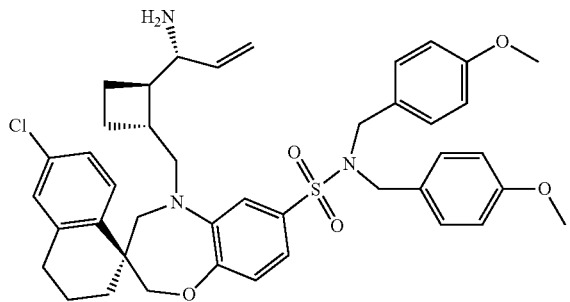 [SMILES: C=C[C@@H](N)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

(3S)-6'-chloro-N,N-bis[(4-methoxyphenyl)methyl]-5-[[(1R,2R)-2-[(1R)-1-[[(S)-tert-butylsulfinyl]amino]allyl]cyclobutyl]methyl]spiro[2,4-dihydro-1,5-benzoxazepine-3,1'-tetralin]-7-sulfonamide (400.0 mg, 0.47 mmol, P1 Step 2) in 1,4-dioxane (10 mL) was treated with 6 M HCl in IPA solution (1.5 mL, 9.45 mmol). The reaction mixture was stirred for 1 h. LCMS showed full consume of starting material. The reaction was quenched with sat. NaHCO$_3$(a$_q$) (10 mL) and extracted with EtOAc (10 mL×3). The combined organic layers were dried over Na$_2$SO$_4$, filtered and concentrated under reduced pressure to yield (3S)-6'-chloro-N,N-bis[(4-methoxyphenyl)methyl]-5-[[(1R,2R)-2-[(1R)-1-aminoallyl]cyclobutyl]methyl]spiro[2,4-dihydro-1,5-benzoxazepine-3,1'-tetralin]-7-sulfonamide (312 mg, 88.9% yield) which was used in the next step without further purification. LCMS calc. for $C_{42}H_{48}ClN_3O_5S$ [M+H]$^+$: m/z=742.31/744.31; Found: 742.7/744.1.

Step 4. (3S)-6'-chloro-N,N-bis[(4-methoxyphenyl)methyl]-5-[[(1R,2R)-2-[(1R)-1-aminoallyl]cyclobutyl]methyl]spiro[2,4-dihydro-1,5-benzoxazepine-3,1'-tetralin]-7-sulfonamide

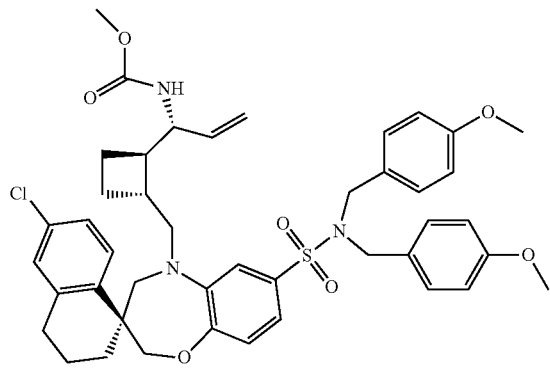 [SMILES: C=C[C@@H](NC(=O)OC)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

To a solution of (3S)-6'-chloro-N,N-bis[(4-methoxyphenyl)methyl]-5-[[(1R,2R)-2-[(1R)-1-aminoallyl]cyclobutyl]methyl]spiro[2,4-dihydro-1,5-benzoxazepine-3,1'-tetralin]-7-sulfonamide (312.0 mg, 0.42 mmol) in DCM (5 mL) was added methyl chloroformate (0.05 mL, 0.63 mmol) and triethylamine (0.09 mL, 0.67 mmol). The mixture was stirred for 4 h. The reaction was quenched with MeOH (1 mL) and concentrated under reduced pressure. The residue was purified by flash chromatography on a silica gel column EtOAc/Heptanes (3% to 50%) to afford methyl N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate (252 mg, 74.9% yield). LCMS calc. for $C_{44}H_{51}ClN_3O_7S$ [M+H]$^+$: m/z=800.31/802.31; Found: 800.8/803.0.

Step 5: methyl N-[(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl]carbamate

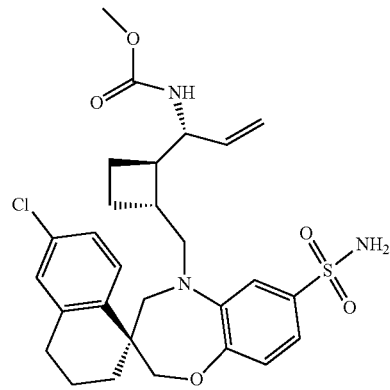 [SMILES: C=C[C@@H](NC(=O)OC)[C@@H]1CC[C@H]1CN1C[C@@]2(CCCc3cc(Cl)ccc32)COc2ccc(S(N)(=O)=O)cc21]

Methyl N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate (180.0 mg, 0.22 mmol) was dissolved in 2,2,2-trifluoroacetic acid (2.0 mL, 25.96 mmol) and DCM (8 mL). The mixture was stirred at r.t. overnight 16 h. The mixture was quenched by sat. NaHCO$_3$(a$_q$) (10 mL) and extracted with EtOAc (10 mL×3). The combined organic layers were concentrated under reduced pressure. The residue was purified by flash chromatography on a silica gel column EtOAc/Heptanes (10% to 50%) to afford methyl N-[(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl]carbamate (116 mg, 92.1% yield). LCMS calc. for $C_{28}H_{35}ClN_3O_5S$ [M+H]$^+$: m/z=560.20/562.20; Found: 560.8/562.7.

Step 6: methyl N-[(1R)-1-[(1R,2R)-2-[[(3S)-7-[(2-allyloxy-2-methyl-propanoyl) sulfamoyl]-6'-chloro-spiro[2,4-dihydro-1,5-benzoxazepine-3,1'-tetralin]-5-yl]methyl]cyclobutyl]allyl]carbamate

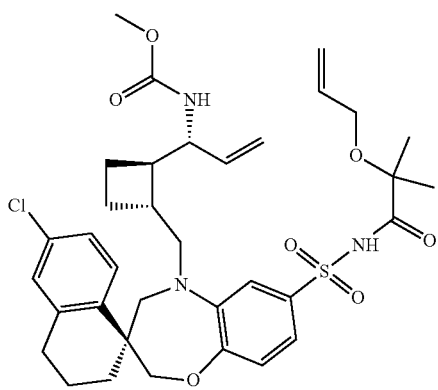 [SMILES: C=CCOC(C)(C)C(=O)NS(=O)(=O)c1ccc2c(c1)N(C[C@@H]1CC[C@H]1[C@@H](C=C)NC(=O)OC)C[C@@]1(CCCc3cc(Cl)ccc31)CO2]

To a solution of methyl N-[(1R)-1-[(1R,2R)-2-[[(3S)-6'-chloro-7-sulfamoyl-spiro[2,4-dihydro-1,5-benzoxazepine-3,1'-tetralin]-5-yl]methyl]cyclobutyl]allyl]carbamate (48.0 mg, 0.09 mmol) and 2-allyloxy-2-methyl-propanoic acid (24.71 mg, 0.17 mmol, Example 30 Step 1) in DCM (2 mL) was added sequentially DMAP (41.88 mg, 0.34 mmol), and EDCI (32.86 mg, 0.17 mmol). The mixture was stirred at r.t. overnight. The mixture was diluted with DCM (1 mL) and washed with 1 M HCl(aq) (1 mL). The organic layer was concentrated under reduced pressure. The residue was purified by flash chromatography on a silica gel column EtOAc/Heptanes (10% to 50%) to afford methyl N-[(1R)-1-[(1R,2R)-2-[[(3S)-7-[(2-allyloxy-2-methyl-propanoyl) sulfamoyl]-6'-chloro-spiro[2,4-dihydro-1,5-benzoxazepine-3,1'-tetralin]-5-yl]methyl]cyclobutyl]allyl]carbamate (51 mg, 86.7% yield). LCMS calc. for $C_{35}H_{46}ClN_4O_6S$ [M+H]$^+$: m/z=685.28/687.28; Found: 685.8/687.2.

Step 7: methyl N-[(3R,6R,7R,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl] carbamate A solution of methyl N-[(1R)-1-[(1R,2R)-2-[[(3S)-7-[(2-allyloxy-2-methyl-propanoyl) sulfamoyl]-6'-chloro-spiro[2,4-dihydro-1,5-benzoxazepine-3,1'-tetralin]-5-yl]methyl]cyclobutyl]allyl]carbamate (51.07 mg, 0.07 mmol) in DCE (60 mL) was bubbled with $N_2$ gas for 10 min., then Hoveyda-Grubbs II (9.33 mg, 0.01 mmol) was added. The reaction mixture was re-bubbled with $N_2$ for an additional 10 min. The mixture was then stirred at 40° C. under $N_2$ overnight. The reaction was exposed to air for 30 min. before concentrated under reduced pressure. The residue was purified by flash chromatography on a silica gel column EA:Hep (5% to 60%), and further purified by prep-HPLC $H_2O$:MeCN (10% to 100%) to afford methyl N-[(3R,6R,7R,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]carbamate (9 mg, 18.4% yield). LCMS calc. for $C_{33}H_{41}ClN_3O_7S$ [M+H]$^+$: m/z=658.24/660.23; Found: 658.68/660.8. HPLC: C18 column (4.6×150 mm, 5 m); flow rate=1 mL/min; mobile phase: MeCN/$H_2O$ (with 0.1% TFA) 50% to 95% 6 min, 95% 4 min; λ=220 nm. tR=6.741 min. $^1$H NMR (300 MHz, CDCl$_3$) δ 7.68 (d, J=8.5 Hz, 1H), 7.52 (d, J=8.4 Hz, 1H), 7.09-6.98 (m, 4H), 5.62 (dd, J=15.4, 7.2 Hz, 1H), 4.11-3.92 (m, 3H), 3.81-3.72 (m, 5H), 3.54 (d, J=14.6 Hz, 1H), 3.33 (d, J=14.5 Hz, 1H), 3.16 (t, J=12.2 Hz, 1H), 2.79 (s, 2H), 2.57 (s, 1H), 2.22 (q, J=6.8, 6.0 Hz, 1H), 2.04-1.89 (m, 4H), 1.65 (s, 3H), 1.50-1.23 (m, 7H), 0.89 (t, J=6.5 Hz, 1H).

Example 252

Methyl N-[(3R,6R,7R,8E,22S)-6'-Chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl] carbamate

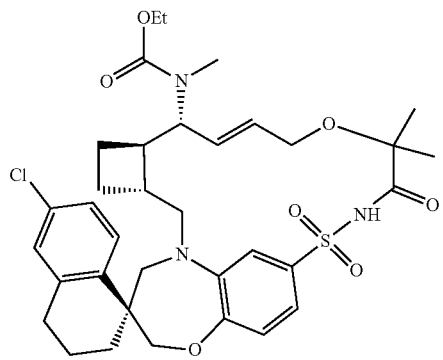 [SMILES: CCOC(=O)N(C)[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: ethyl N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate

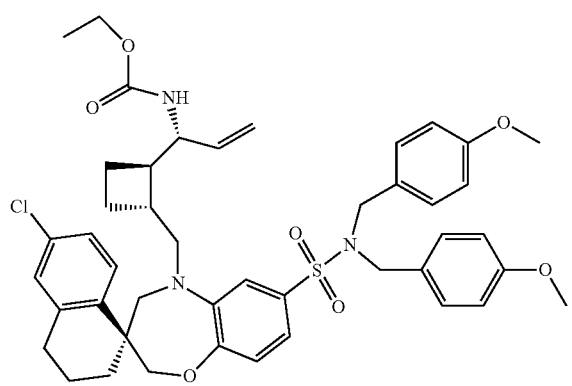 [SMILES: C=C[C@@H](NC(=O)OCC)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

This compound was prepared using procedures analogous to those described for Example 251 Step 4 using ethyl chloroformate to replace methyl chloroformate. LCMS calc. for $C_{45}H_{53}ClN_3O_7S$ [M+H]$^+$: m/z=814.33/816.33; Found: 815.0/816.9.

491

Step 2: ethyl N-methyl-N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate

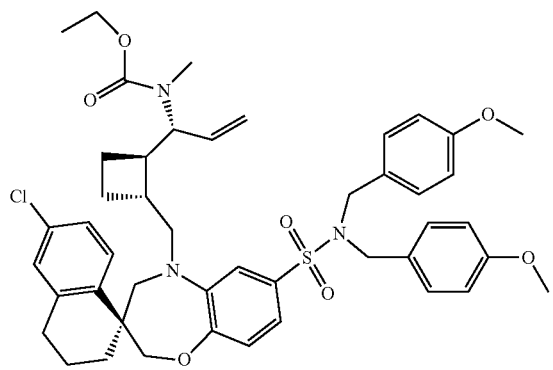 [SMILES: C=C[C@H]([C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21)N(C)C(=O)OCC]

To a solution of ethyl N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate (371.0 mg, 0.46 mmol) in DMF (6 mL) was added sodium hydride (60%, dispersion in paraffin liquid) (54.66 mg, 1.37 mmol), followed by iodomethane (0.11 mL, 1.82 mmol). The reaction was stirred at r.t. for 4 h. The reaction was quenched with sat. NH$_4$Cl (aq) and extracted with EtOAc (10 mL×3). The combined organic layers were dried over Na$_2$SO$_4$, filtered and concentrated under reduced pressure to afford the crude product which was used in the next step without further purification. LCMS calc. for $C_{46}H_{55}ClN_3O_7S$ [M+H]$^+$: m/z=828.34/830.33; Found: 828.8/830.2.

Step 3: methyl N-[(3R,6R,7R,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl]carbamate This compound was prepared using procedures analogous to those described for Example 251 Step 5-7 using ethyl N-methyl-N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate in Step 5 and 2-allyloxy-2-methyl-propanoic acid (Example 30 Step 1) in Step 6. LCMS calcd. for $C_{35}H_{45}ClN_3O_7S$ (M+H)$^+$: m/z=686.27/688.26; Found: 686.3/688.3. HPLC: C18 column (4.6×150 mm, 5 μm); flow rate=1 mL/min; mobile phase: MeCN/H$_2$O (with 0.1% TFA) 50% to 95% 6 min, 95% 4 min; λ=220 nm. tR=8.004 min.

Example 253

Ethyl N-methyl-N-[(3R,6R,7R,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl]carbamate

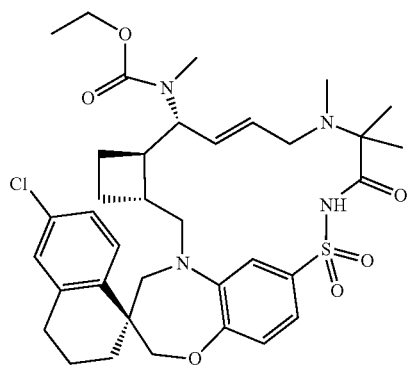 [SMILES: CCOC(=O)N(C)[C@@H]1/C=C/CN(C)C(C)(C)C(=O)NS(=O)(=O)c2ccc3c(c2)N(C[C@@H]2CC[C@H]21)C[C@@]1(CCCc2cc(Cl)ccc21)CO3]

Step 1: ethyl N-methyl-N-[(3R,6R,7R,8E,22S)-6'-chloro-12,12-dimethyl-13,15,15-trioxo-spiro[20-oxa-15-thia-1,11,14-triazatetracyclo[14.7.2.03,6.019,24]pentacosa-8,16(25),17,19(24)-tetraene-22,1'-tetralin]-7-yl]carbamate

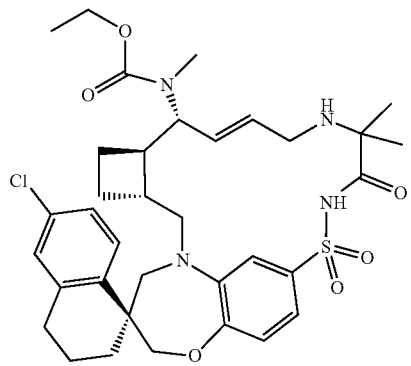

This compound was prepared using procedures analogous to those described for Example 251 Step 5-7 using ethyl N-methyl-N-[(1R)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]carbamate (Example 252, Step 2) in Step 5 and 3-allyl-4,4-dimethyl-oxazolidine-2,5-dione (Example 43 Step 1) in Step 6. LCMS calcd. for $C_{35}H_{46}ClN_4O_6S$ (M+H)$^+$: m/z=685.27/686.26; Found: 685.3/687.3.

Step 2: ethyl N-methyl-N-[(3R,6R,7R,8E,22S)-6'-chloro-11,12,12-trimethyl-13,15,15-trioxo-spiro[20-oxa-15-thia-1,11,14-triazatetracyclo[14.7.2.03,6.019,24]pentacosa-8,16(25), 17, 19(24)-tetraene-22,1'-tetralin]-7-yl]carbamate This compound was prepared using procedures analogous to those described for Example 138 Step 3 using ethyl N-methyl-N-[(3R,6R,7R,8E,22S)-6'-chloro-12,12-dimethyl-13,15,15-trioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-7-yl]carbamate and formaldehyde aqueous solution (37%). LCMS calcd. for $C_{36}H_{48}ClN_4O_6S$ [M+H]⁺: m/z=699.30/701.30; Found: 699.4/701.5.

Example 254

Methyl N-methyl-N-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl]carbamate

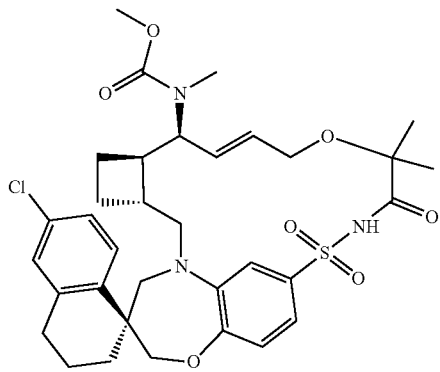 [SMILES: COC(=O)N(C)[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: (3S)-6'-chloro-N,N-bis[(4-methoxyphenyl)methyl]-5-[[(1R,2R)-2-[(1S)-1-aminoallyl]cyclobutyl]methyl]spiro[2,4-dihydro-1,5-benzoxazepine-3,1'-tetralin]-7-sulfonamide

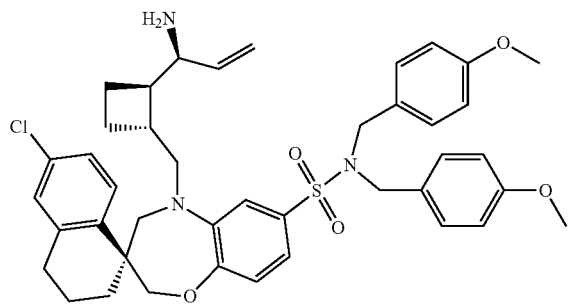 [SMILES: C=C[C@H](N)[C@@H]1CC[C@H]1CN1C[C@@]2(CCCc3cc(Cl)ccc32)COc2ccc(S(=O)(=O)N(Cc3ccc(OC)cc3)Cc3ccc(OC)cc3)cc21]

This compound was prepared using procedures analogous to those described for Example 251 Step 3 using (3S)-6'-chloro-N,N-bis[(4-methoxyphenyl)methyl]-5-[[(1R,2R)-2-[(1S)-1-[[(S)-tert-butylsulfinyl]amino]allyl]cyclobutyl]methyl]spiro[2,4-dihydro-1,5-benzoxazepine-3,1'-tetralin]-7-sulfonamide (P2 Example 251 Step 2). LCMS calc. for $C_{42}H_{48}ClN_3O_5S$ [M+H]⁺: m/z=742.31/744.31; Found: 742.7/744.1.

Step 2: 2,2,2-trifluoro-N-[(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]acetamide

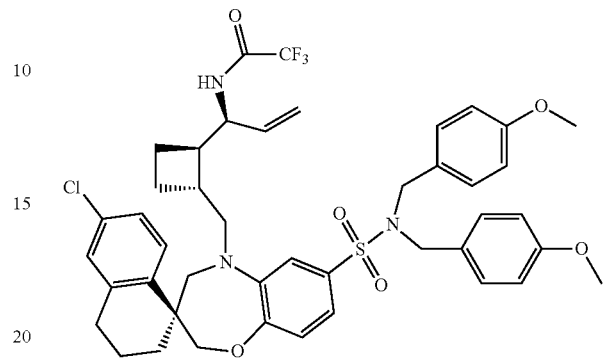

To a solution of 2,2,2-trifluoro-N-[(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]acetamide (0.82 g, 1.1 mmol) in DCM (10 mL) was added trifluoroacetic anhydride (0.28 mL, 2.21 mmol) and triethylamine (0.62 mL, 4.42 mmol). The mixture was stirred for 16 h. The reaction was concentrated under reduced pressure to afford 2,2,2-trifluoro-N-[(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]acetamide (1.6 g) which was used in the next step without further purification. LCMS calc. for $C_{44}H_{48}ClF_3N_3O_6S$ [M+H]⁺: m/z=838.29/840.29; Found: 838.8/840.0.

Step 3: 2,2,2-trifluoro-N-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),7,19(24)-tetraene-22,1'-tetralin]-7-yl]acetamide

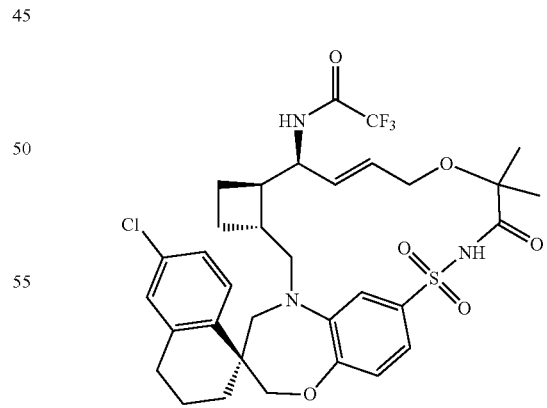

This compound was prepared using procedures analogous to those described for Example 251 Step 5-7 using 2,2,2-trifluoro-N-[(1S)-1-[(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutyl]allyl]acetamide in Step 5 and 2-allyloxy-2-methyl-propanoic acid (Example 30 Step 1) in Step 6. LCMS calc. for $C_{33}H_{38}ClF_3N_3O_6S$ [M+H]⁺: m/z=696.21/698.21; Found: 696.3/698.3.

Step 4: (3R,6R,7S,8E,22S)-7-amino-6'-chloro-12, 12-dimethyl-15,15-dioxo-spiro[11,20-dioxa-15-thia-1,14-diazatetracyclo[14.7.2.0³,⁶.0¹⁹,²⁴]pentacosa-8, 16(25),17,19(24)-tetraene-22,1'-tetralin]-13-one

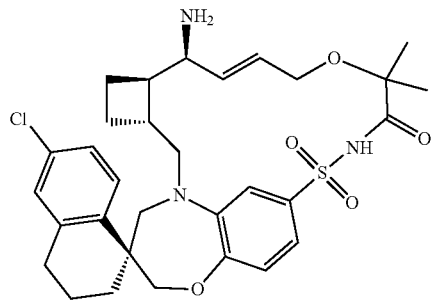 [SMILES: CC1(C)OC/C=C/[C@H](N)[C@@H]2CC[C@H]2CN2C[C@@]3(CCCc4cc(Cl)ccc43)COc3ccc(cc32)S(=O)(=O)NC1=O]

To a solution of 2,2,2-trifluoro-N-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl]acetamide (134.0 mg, 0.19 mmol) in methanol (10 mL) and water (5 mL) was added potassium carbonate (265.62 mg, 1.92 mmol). The mixture was stirred at 50° C. overnight. The mixture was quenched with NH₄Cl(aq) (10 mL) and extracted with EtOAc (10 mL×3). The combined organic layers were concentrated under reduced pressure. The residue was purified by flash chromatography on a silica gel column EA:Hep (10% to 100%) to afford (3R,6R,7S,8E, 22S)-7-amino-6'-chloro-12,12-dimethyl-15,15-dioxo-spiro[11,20-dioxa-15-thia-1,14-diazatetracyclo[14.7.2.0³,⁶.0¹⁹, ²⁴]pentacosa-8,16(25),17,19(24)-tetraene-22,1'-tetralin]-13-one (120 mg). LCMS calc. for $C_{31}H_{39}ClN_3O_5S$ [M+H]⁺: m/z=600.22/602.22; Found: 600.5/602.5.

Step 5: methyl N-[(3R,6R,7S,8E,22S)-6'-chloro-12, 12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl] carbamate

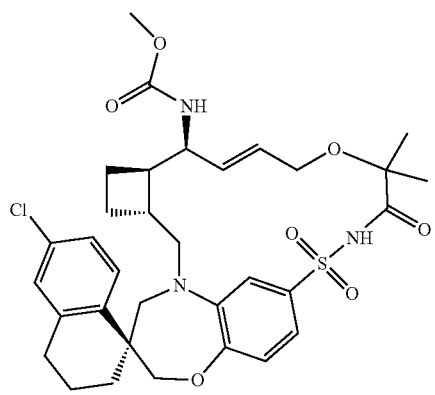 [SMILES: COC(=O)N[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 251 Step 4 using (3R,6R, 7S,8E,22S)-7-amino-6'-chloro-12,12-dimethyl-15,15-dioxo-spiro[11,20-dioxa-15-thia-1,14-diazatetracyclo[14.7. 2.0³,⁶.0¹⁹,²⁴]pentacosa-8,16(25),17,19(24)-tetraene-22,1'-tetralin]-13-one and methyl chloroformate. LCMS calc. for $C_{33}H_{40}ClN_3O_7S$ [M+H]⁺: m/z=658.23/660.22; Found: 658.4/660.4.

Step 6: methyl N-methyl-N-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹, ²⁴]pentacosa-8,16(25),17,19(24)-tetraene-22,1'-tetralin]-7-yl]carbamate

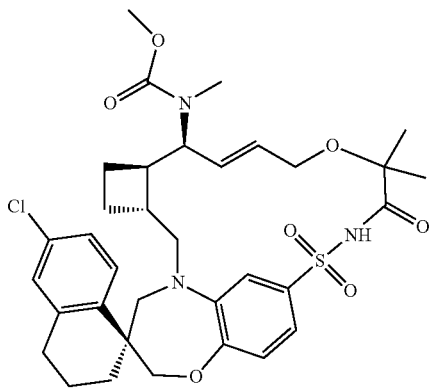 [SMILES: COC(=O)N(C)[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 252 Step 2 using methyl N-[(3R,6R,7S,8E,22S)-6'-chloro-12,12-dimethyl-13,15,15-trioxo-spiro[11,20-dioxa-15-thia-1,14-diazatetracyclo[14. 7.2.0³,⁶.0¹⁹,²⁴]pentacosa-8,16(25),17,19(24)-tetraene-22, 1'-tetralin]-7-yl]carbamate and iodomethane. LCMS calc. for $C_{34}H_{43}ClN_3O_7S$ [M+H]⁺: m/z=672.25/674.25; Found: 672.4/674.4; HPLC: C18 column (4.6×150 mm, 5 μm); flow rate=1 mL/min; mobile phase: MeCN/H₂O (with 0.1% TFA) 50% to 95% 6 min, 95% 4 min; λ=220 nm. tR=7.321 min. ¹H NMR (600 MHz, DMSO-d₆) δ 7.65 (d, J=8.5 Hz, 1H), 7.30 (s, 1H), 7.23-7.18 (m, 2H), 7.09 (s, 1H), 6.85 (s, 1H), 6.66 (s, 1H), 5.63 (s, 1H), 5.33 (t, J=4.9 Hz, 1H), 4.17 (s, 1H), 3.96 (d, J=12.7 Hz, 1H), 3.89 (s, 1H), 3.70 (s, 1H), 3.52 (s, 3H), 2.80-2.70 (m, 1H), 2.65 (s, 2H), 2.00 (tt, J=13.1, 5.7 Hz, 3H), 1.86 (s, 2H), 1.80 (s, 3H), 1.54 (d, J=9.6 Hz, 1H), 1.46 (t, J=7.1 Hz, 2H), 1.29 (d, J=6.4 Hz, 1H), 1.26-1.19 (m, 4H), 1.14 (d, J=10.6 Hz, 3H), 0.86 (t, J=6.8 Hz, 3H).

Example 255

N-Methyl-N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]acetamide

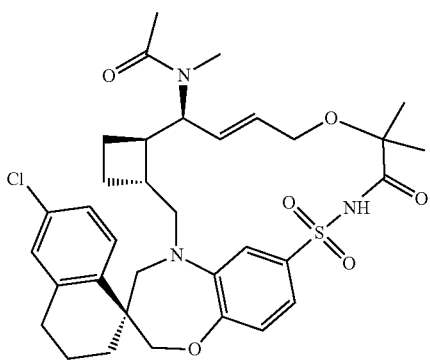 [SMILES: CC(=O)N(C)[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]acetamide

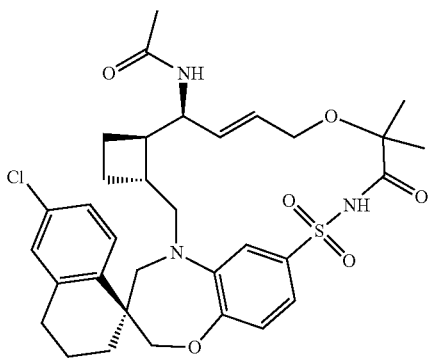 [SMILES: CC(=O)N[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 251 Step 4 using (3R,6R,7S,8E,22S)-7-amino-6'-chloro-12,12-dimethyl-15,15-dioxo-spiro[11,20-dioxa-15-thia-1,14-diazatetracyclo[14.7.2.03,6.019,24]pentacosa-8,16(25),17,19(24)-tetraene-22,1'-tetralin]-13-one (Example 254 Step 4) and acetyl chloride. LCMS calcd. for $C_{33}H_{41}ClN_3O_6S$ [M+H]$^+$: m/z=642.24/644.24; Found: 642.4/642.3.

Step 2: N-methyl-N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),7,19(24)-tetraene-22,1'-tetralin]-7-yl]acetamide This compound was prepared using procedures analogous to those described for Example 252 Step 2 using N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]acetamide and iodomethane. LCMS calcd. for $C_{34}H_{43}ClN_3O_6S$ (M+H)$^+$: m/z=656.26/658.25; Found: 656.4/658.5. $^1$H NMR (600 MHz, CDCl$_3$) δ 7.75-7.70 (m, 1H), 7.60-7.38 (m, 1H), 7.16 (dd, J=8.7, 2.4 Hz, 1H), 7.13-7.06 (m, 2H), 7.02 (s, 1H), 6.91 (s, 1H), 5.82 (s, 1H), 5.39 (s, 1H), 5.25 (s, 1H), 5.03 (s, 1H), 4.18 (d, J=13.7 Hz, 2H), 4.07 (s, 3H), 3.94 (dd, J=13.6, 8.5 Hz, 1H), 3.70 (s, 2H), 3.23 (d, J=14.3 Hz, 1H), 2.79 (d, J=5.9 Hz, 1H), 2.78-2.69 (m, 4H), 2.52-2.32 (m, 1H), 2.24-2.19 (m, 3H), 2.06-1.94 (m, 4H), 1.92-1.87 (m, 1H), 1.86-1.81 (m, 4H), 1.45 (d, J=9.8 Hz, 2H), 0.87 (h, J=7.5, 6.5 Hz, 3H).

Example 256

N-Methyl-N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]methanesulfonamide

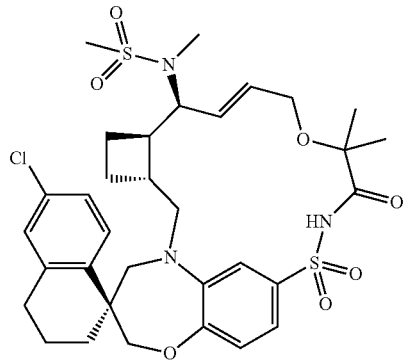 [SMILES: CN([C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3)S(C)(=O)=O]

Step 1: N-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16(25),17,19(24)-tetraene-22,1'-tetralin]-7-yl]methanesulfonamide

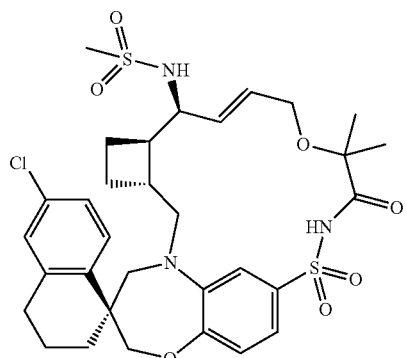

This compound was prepared using procedures analogous to those described for Example 251 Step 4 using (3R,6R,7S,8E,22S)-7-amino-6'-chloro-12,12-dimethyl-15,15-dioxo-spiro[11,20-dioxa-15-thia-1,14-diazatetracyclo

[14.7.2.0³,⁶.0¹⁹,²⁴]pentacosa-8,16(25),17,19(24)-tetraene-22,1'-tetralin]-13-one (Example 254 Step 4) and methanesulfonyl chloride. LCMS calcd. for $C_{32}H_{41}ClN_3O_7S_2$ (M+H)⁺: m/z=678.21/680.20; found: 678.4/660.1.

Step 2: N-methyl-N-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),7,19(24)-tetraene-22,1'-tetralin]-7-yl]methanesulfonamide This compound was prepared using procedures analogous to those described for Example 252 Step 2 using N-[(3R,6R,7S,8E,22S)-6'-chloro-12,12-dimethyl-13,15,15-trioxo-spiro[11,20-dioxa-15-thia-1,14-diazatetracyclo[14.7.2.0³,6.0¹⁹,²⁴]pentacosa-8,16(25),17,19(24)-tetraene-22,1'-tetralin]-7-yl]methanesulfonamide and iodomethane. LCMS calcd. for $C_{33}H_{43}ClN_3O_7S_2$ [M+H]⁺: m/z=692.22/692.42; found: 692.7/694.7. ¹H NMR (300 MHz, CDCl₃) δ 8.81 (s, 1H), 7.64 (d, J=8.6 Hz, 1H), 7.49 (d, J=8.4 Hz, 1H), 7.21-6.91 (m, 4H), 5.84 (dd, J=15.3, 8.7 Hz, 1H), 5.33 (s, 1H), 4.17 (s, 3H), 3.95 (s, 2H), 3.69-3.52 (m, 3H), 3.37 (d, J=14.4 Hz, 1H), 3.23 (s, 1H), 2.75 (m, 8H), 2.37-1.61 (m, 5H), 1.45 (d, J=12.0 Hz, 6H), 1.36-1.23 (m, 3H).

Example 257

1,1,3-Trimethyl-3-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl]urea

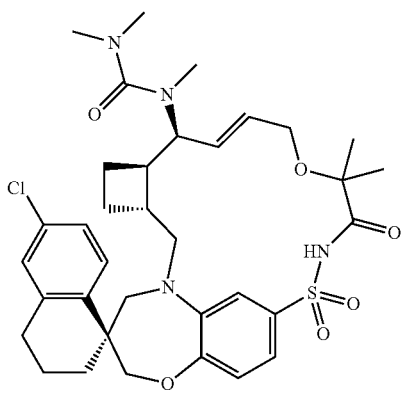 [SMILES: CN(C)C(=O)N(C)[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: 1,1-dimethyl-3-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,24]pentacosa-8,16(25), 17, 19(24)-tetraene-22,1'-tetralin]-7-yl]urea

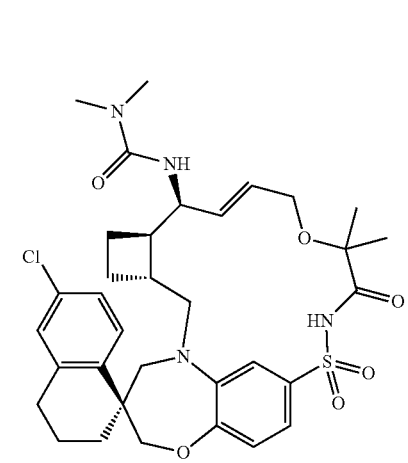 [SMILES: CN(C)C(=O)N[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 251 Step 4 using (3R,6R,7S,8E,22S)-7-amino-6'-chloro-12,12-dimethyl-15,15-dioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-13-one (Example 254 Step 4) and N,N-dimethylcarbamoyl chloride. LCMS calcd. for $C_{34}H_{44}ClN_4O_6S$ (M+H)⁺: m/z=671.27/673.26; found: 671.5/673.4.

Step 2: 1,1,3-trimethyl-3-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,24]pentacosa-8,16(25), 17, 19(24)-tetraene-22,1'-tetralin]-7-yl]urea This compound was prepared using procedures analogous to those described for Example 252 Step 2 using 1,1-dimethyl-3-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl]urea and iodomethane. LCMS calcd. for $C_{35}H_{46}ClN_4O_6S$ [M+H]⁺: m/z=685.28/687.28; found: 685.7/687.7. ¹H NMR (500 MHz, CDCl₃) δ 9.07 (s, 1H), 7.67-7.55 (m, 2H), 7.18-7.10 (m, 1H), 7.03 (s, 2H), 6.84 (d, J=8.4 Hz, 1H), 5.89 (d, J=10.0 Hz, 1H), 5.56 (d, J=15.1 Hz, 1H), 5.42 (s, 1H), 4.14 (d, J=10.7 Hz, 3H), 4.06 (d, J=11.8 Hz, 1H), 4.01-3.89 (m, 3H), 3.86 (d, J=12.9 Hz, 2H), 3.47 (d, J=15.2 Hz, 2H), 3.26 (d, J=19.2 Hz, 2H), 2.98 (d, J=14.6 Hz, 1H), 2.66 (s, 2H), 2.58 (s, 3H), 2.37 (d, J=8.4 Hz, 1H), 2.13 (s, 1H), 2.06-1.99 (m, 2H), 1.85 (s, 3H), 1.44 (d, J=14.9 Hz, 4H), 1.31 (s, 6H).

Example 258

(3R,6R,7S,8E,22S)-6'-Chloro-7-[2-(3,3-difluoroazetidin-1-yl)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

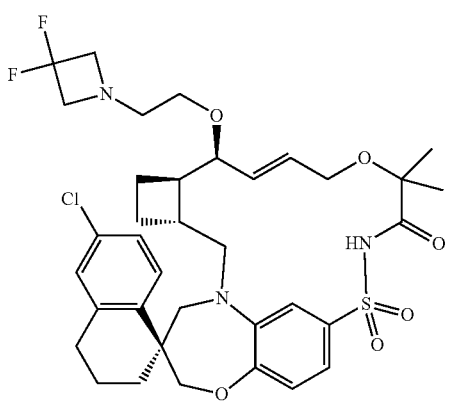 [SMILES: CC1(C)OC/C=C/[C@H](OCCN2CC(F)(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using 3,3-difluoroazetidine hydrochloride to replace dimethylamine in THF (2.0 M) in Step 5. LCMS calc. for $C_{36}H_{45}ClN_3O_6S$ [M+H]$^+$: m/z=720.26/722.26; Found: 720.5/722.6.

Example 259

(3R,6R,7S,8E,22S)-6'-Chloro-12,12-dimethyl-7-[2-(4-methylpiperazin-1-yl)ethoxy]-15,15-dioxo-spiro[11,20-dioxa-15-thia-1,14-diazatetracyclo[14.7.2.03,6.019,24]pentacosa-8,16,18,24-tetraene-22,1'-tetralin]-13-one

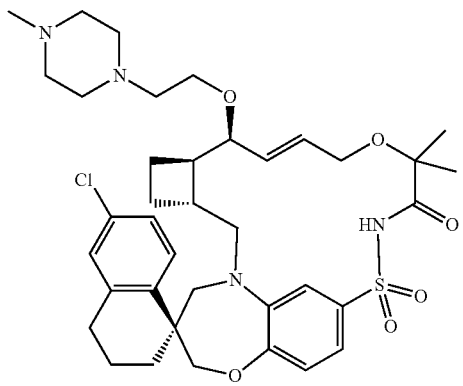

This compound was prepared using procedures analogous to those described for Example 65 using methylpiperazine to replace dimethylamine in THF (2.0 M) in Step 5. LCMS calc. for $C_{38}H_{52}ClN_4O_6S$ [M+H]$^+$: m/z=727.32/729.32; Found: 727.5/729.7; $^1$H NMR (600 MHz, DMSO-d6) δ 7.63-7.59 (m, 1H), 7.30 (dd, J=8.3, 2.1 Hz, 1H), 7.24 (d, J=8.5, 2.3 Hz, 1H), 7.20 (d, J=2.3 Hz, 1H), 7.07-7.04 (m, 2H), 5.56 (dd, J=15.7, 7.2 Hz, 1H), 5.36 (s, 1H), 4.07 (dt, J=27.4, 13.7 Hz, 3H), 3.91-3.85 (m, 2H), 3.32 (m, 6H), 3.15 (m, 3H), 2.80-2.76 (m, 2H), 2.74 (s, 4H), 2.65 (dd, J=3.9, 1.9 Hz, 1H), 2.47-2.38 (m, 2H), 2.34-2.23 (m, 1H), 2.04-1.93 (m, 3H), 1.91-1.76 (m, 5H), 1.74-1.69 (m, 1H), 1.61-1.55 (m, 2H), 1.47 (d, J=6.6 Hz, 1H), 1.38 (s, 3H), 1.26 (s, 3H).

Example 260

(3R,6R,7S,8E,22S)-6'-Chloro-7-[2-[(3R)-3-methoxypyrrolidin-1-yl]ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

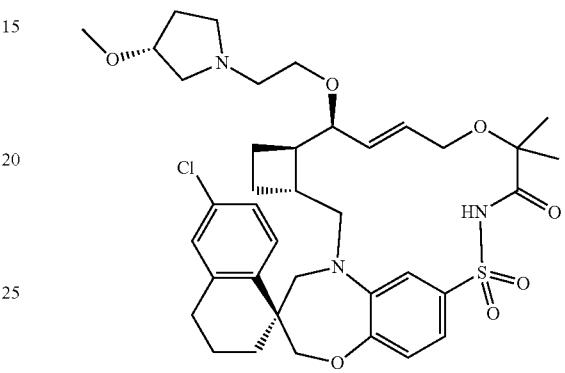

This compound was prepared using procedures analogous to those described for Example 65 using (R)-3-methoxypyrrolidine to replace dimethylamine in THF (2.0 M) in Step 5. LCMS calc. for $C_{38}H_{51}ClN_3O_7S$ [M+H]$^+$: m/z=728.31/730.30; Found: 728.5/730.7; $^1$H NMR (300 MHz, DMSO-d$_6$) δ 9.95 (s, 1H, NH), 7.61 (d, J=8.5 Hz, 1H), 7.32-7.17 (m, 3H), 7.03 (t, J=7.7 Hz, 2H), 5.57 (dd, J=15.7, 6.8 Hz, 1H), 5.46-5.31 (m, 1H), 4.08 (m, 3H), 3.87 (dd, J=14.2, 5.8 Hz, 1H), 3.68-3.58 (m, 3H), 3.32 (m, 6H), 3.23 (m, 4H), 3.20-3.08 (m, 4H), 2.79-2.62 (m, 3H), 2.28-2.18 (m, 1H), 1.96 (dd, J=18.5, 9.0 Hz, 2H), 1.84 (s, 4H), 1.77-1.61 (m, 2H), 1.58 (d, J=8.2 Hz, 2H), 1.37 (s, 3H), 1.24 (s, 3H).

Example 261

(3R,6R,7S,8E,22S)-6'-Chloro-7-[2-(3-methoxyazetidin-1-yl)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

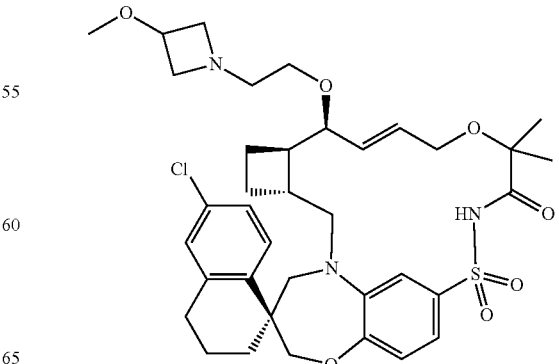

This compound was prepared using procedures analogous to those described for Example 65 using -methoxyazetidine hydrochloride to replace dimethylamine in THF (2.0 M) in Step 5. LCMS calc. for $C_{37}H_{49}ClN_3O_7S$ [M+H]$^+$: m/z=714.29/716.29; Found: 714.5/716.7; $^1$H NMR (300 MHz, DMSO-d$_6$) δ 7.61 (d, J=8.5 Hz, 1H), 7.31-7.15 (m, 3H), 7.02 (dd, J=9.3, 5.7 Hz, 2H), 5.56 (dd, J=15.6, 6.1 Hz, 1H), 5.48 (s, 1H), 4.36 (s, 1H), 4.27-4.13 (m, 2H), 4.11-4.02 (m, 2H), 3.90 (m, 2H), 3.63 (s, 1H), 3.53 (d, J=8.2 Hz, 2H), 3.32 (m, 5H), 3.22 (d, J=7.3 Hz, 4H), 3.19-3.09 (m, 2H), 2.76 (dd, J=21.0, 12.7 Hz, 2H), 2.66 (s, 1H), 2.41 (s, 2H), 1.96 (d, J=13.3 Hz, 1H), 1.84 (d, J=4.1 Hz, 4H), 1.71 (d, J=8.3 Hz, 1H), 1.55 (d, J=7.0 Hz, 2H), 1.37 (s, 3H), 1.24 (s, 3H).

Example 262

(3R,6R,7S,8E,22S)-7-[2-(Azetidin-1-yl)ethoxy]-6'-chloro-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

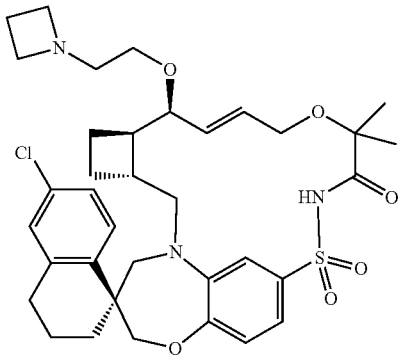 [SMILES: CC1(C)OC/C=C/[C@H](OCCN2CCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using azetidine hydrochloride to replace dimethylamine in THF (2.0 M) in Step 5. LCMS calc. for $C_{37}H_{47}ClN_3O_6S$ [M+H]$^+$: m/z=684.28/686.28; Found: 684.4/686.2; $^1$H NMR (300 MHz, CDCl$_3$) δ 10.60 (s, 1H, NH), 7.68 (d, J=8.5 Hz, 1H), 7.50 (dd, J=8.3, 2.0 Hz, 1H), 7.18 (dd, J=8.5, 2.0 Hz, 1H), 7.09 (d, J=2.0 Hz, 1H), 7.01-6.96 (m, 1H), 6.87 (t, J=4.3 Hz, 1H), 6.01 (dd, J=15.7, 3.9 Hz, 1H), 5.70 (dd, J=15.6, 5.4 Hz, 1H), 4.14-3.94 (m, 5H), 3.76 (dd, J=14.2, 5.2 Hz, 3H), 3.57-3.45 (m, 3H), 3.38 (d, J=14.9 Hz, 3H), 3.11 (dd, J=15.0, 11.0 Hz, 2H), 2.76 (M, 4H), 2.28 (d, J=7.5 Hz, 1H), 2.23-2.05 (m, 2H), 2.00 (dd, J=14.1, 5.9 Hz, 4H), 1.81 (dd, J=16.2, 8.1 Hz, 2H), 1.73-1.58 (m, 2H), 1.50 (d, J=10.2 Hz, 3H), 1.34 (s, 3H).

Example 263

(3R,6R,7S,8E,22S)-6'-Chloro-12,12-dimethyl-15,15-dioxo-7-[2-(1-piperidyl)ethoxy]spiro[11,20-dioxa-15-thia-1,14-diazatetracyclo[14.7.2.03,6.019,24]pentacosa-8,16,18,24-tetraene-22,1'-tetralin]-13-one

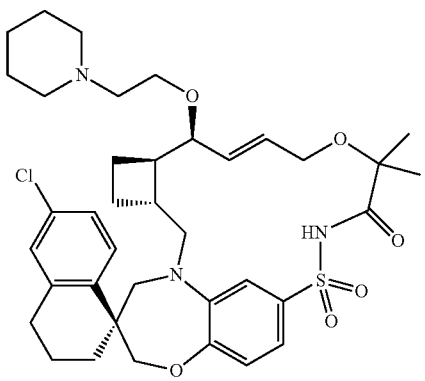 [SMILES: CC1(C)OC/C=C/[C@H](OCCN2CCCCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using piperidine to replace dimethylamine in THF (2.0 M) in Step 5. LCMS calc. for $C_{37}H_{51}ClN_3O_6S$ [M+H]$^+$: m/z=712.31/714.31; Found: 712.4/714.3; $^1$H NMR (300 MHz, CDCl$_3$) δ 9.53 (s, 1H, NH), 7.67 (d, J=8.5 Hz, 1H), 7.50 (dd, J=8.3, 2.0 Hz, 1H), 7.18 (dd, J=8.5, 2.1 Hz, 1H), 7.10 (d, J=2.0 Hz, 1H), 7.02-6.98 (m, 1H), 6.94 (t, J=3.4 Hz, 1H), 5.89 (dd, J=15.6, 3.3 Hz, 1H), 5.64 (dd, J=15.6, 6.1 Hz, 1H), 4.12 (d, J=5.8 Hz, 2H), 4.03 (dd, J=13.0, 5.2 Hz, 2H), 3.71 (d, J=15.0 Hz, 6H), 3.36 (d, J=14.5 Hz, 4H), 3.18 (dd, J=15.1, 9.6 Hz, 1H), 2.79 (d, J=4.0 Hz, 5H), 2.27-2.18 (m, 1H), 2.02-1.77 (m, 12H), 1.66 (dd, J=17.9, 8.9 Hz, 2H), 1.47 (s, 3H), 1.36 (s, 3H).

Example 264

(3R,6R,7S,8E,22S)-6'-Chloro-7-[2-[(3R)-3-fluoropyrrolidin-1-yl]ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

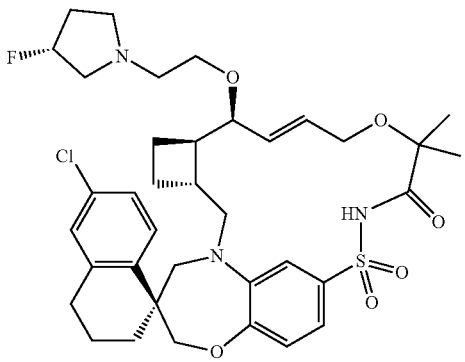 [SMILES: CC1(C)OC/C=C/[C@H](OCCN2CC[C@@H](F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using (3R)-3-fluoropyrrolidine hydrochloride to replace dimethylamine in THF (2.0 M) in Step 5. LCMS calc. for $C_{37}H_{48}ClFN_3O_6S$ [M+H]$^+$: m/z=716.3/718.3. Found: 716.4/718.2. $^1$H NMR (300 MHz, CDCl$_3$) δ 7.70 (d, J=8.5 Hz, 1H), 7.47 (dd, J=8.3, 2.1 Hz, 1H), 7.19 (dd, J=8.5, 2.4 Hz, 1H), 7.09 (d, J=2.3 Hz, 1H), 6.99 (d, J=8.3 Hz, 1H), 6.83 (d, J=2.2 Hz, 1H), 6.08-5.89 (m, 1H), 5.75 (dd, J=15.6, 6.7 Hz, 1H), 5.36 (d, J=53.3 Hz, 1H), 4.66-4.24 (m, 2H), 4.20-3.96 (m, 4H), 3.84-3.69 (m, 3H), 3.46 (qd, J=24.9, 22.1, 13.2 Hz, 7H), 3.14 (dd, J=15.0, 10.7 Hz, 2H), 2.85-2.65 (m, 3H), 2.36-2.09 (m, 5H), 1.89-1.66 (m, 5H), 1.49 (s, 3H), 1.32 (s, 3H).

Example 265

(3R,6R,7S,8E,22S)-6'-Chloro-7-[2-[(3S)-3-fluoropyrrolidin-1-yl]ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one

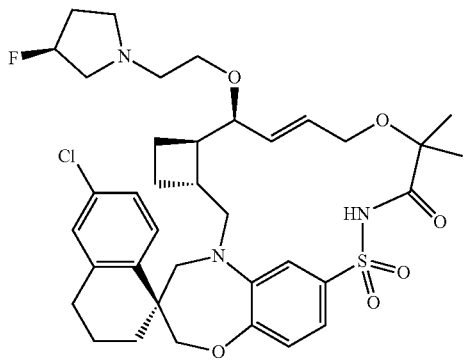 [SMILES: CC1(C)OC/C=C/[C@H](OCCN2CC[C@H](F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using (3S)-3-fluoropyrrolidine hydrochloride to replace dimethylamine in THF (2.0 M) in Step 5. LCMS calc. for $C_{37}H_{48}ClFN_3O_6S$ [M+H]$^+$: m/z=716.3/718.3. Found: 716.4/718.2. $^1$H NMR (300 MHz, CDCl$_3$) δ 7.68 (d, J=8.5 Hz, 1H), 7.48 (dd, J=8.3, 2.1 Hz, 1H), 7.18 (dd, J=8.5, 2.4 Hz, 1H), 7.09 (d, J=2.3 Hz, 1H), 6.99 (d, J=8.3 Hz, 1H), 6.89 (d, J=2.2 Hz, 1H), 6.08-5.84 (m, 1H), 5.72 (dd, J=15.7, 6.3 Hz, 1H), 5.33 (d, J=53.0 Hz, 1H), 4.26 (t, J=9.1 Hz, 2H), 4.17-4.02 (m, 4H), 3.77 (t, J=14.1 Hz, 3H), 3.59-3.33 (m, 7H), 3.16 (dd, J=15.1, 10.3 Hz, 2H), 2.82-2.74 (m, 3H), 2.28 (ddd, J=35.2, 19.4, 11.1 Hz, 5H), 1.95-1.64 (m, 5H), 1.49 (s, 3H), 1.35 (s, 3H).

Example 266

[(3R,6R,7S,8E,22S)-7'-Chloro-12,12-dimethyl-13,155-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] (3R)-3-methoxypyrrolidine-1-carboxylate

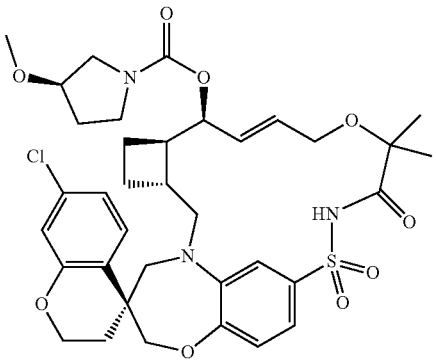

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and (3R)-3-methoxypyrrolidine hydrochloride in Step 2. LC-MS: calc. for $C_{36}H_{43}ClN_3O_9S$ [M+H]$^+$: m/z=728.2/730.2; Found: 728.5/730.5. $^1$H NMR (300 MHz, CDCl$_3$) δ 7.56 (d, J=8.5 Hz, 1H), 7.48 (ddd, J=7.8, 5.4, 2.1 Hz, 1H), 7.05 (dd, J=4.8, 2.2 Hz, 1H), 6.97 (d, J=8.3 Hz, 1H), 6.92 (dd, J=8.4, 2.2 Hz, 1H), 6.85 (d, J=2.1 Hz, 1H), 6.15-5.77 (m, 1H), 5.77-5.51 (m, 1H), 5.23 (d, J=8.3 Hz, 1H), 4.24 (dtd, J=31.1, 11.4, 8.1 Hz, 3H), 4.11-3.91 (m, 4H), 3.74-3.62 (m, 4H), 3.44 (q, J=7.4, 6.2 Hz, 3H), 3.36 (s, 3H), 3.32 (s, 2H), 3.20-3.09 (m, 1H), 2.79 (q, J=7.2 Hz, 2H), 2.06-1.95 (m, 3H), 1.85-1.77 (m, 2H), 1.60 (p, J=9.2 Hz, 1H), 1.42 (s, 3H), 1.33 (s, 3H).

Example 267

(3R,6R,7S,8E,22S)-6'-Chloro-7-[2-[methoxy(methyl)amino]ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one

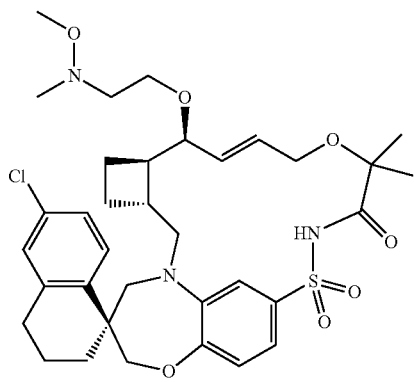 [SMILES: CON(C)CCO[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 65 using N,O-dimethylhydroxylamine hydrochloride to replace dimethylamine in THF (2.0 M) in Step 5. LCMS calc. for $C_{35}H_{47}ClFN_3O_6S$ [M+H]$^+$: m/z=688.3/690.3; Found: 688.3/690.3. $^1$H NMR (300 MHz, CDCl$_3$) δ 7.66 (d, J=8.5 Hz, 1H), 7.50 (dd, J=8.3, 2.1 Hz, 1H), 7.19 (dd, J=8.5, 2.4 Hz, 1H), 7.10 (d, J=2.3 Hz, 1H), 7.03-6.92 (m, 2H), 5.87 (d, J=16.2 Hz, 1H), 5.66 (dd, J=15.6, 6.5 Hz, 1H), 5.36 (d, J=1.0 Hz, 1H), 4.37 (s, 3H), 4.18-3.99 (m, 4H), 3.84 (s, 3H), 3.74 (d, J=5.3 Hz, 1H), 3.68 (s, 1H), 3.62-3.54 (m, 1H), 3.47-3.32 (m, 4H), 3.20 (dd, J=15.0, 9.5 Hz, 1H), 3.09 (s, 3H), 2.79 (d, J=4.5 Hz, 3H), 2.32-2.21 (m, 1H), 2.01-1.90 (m, 3H), 1.79 (q, J=9.4, 8.9 Hz, 2H), 1.47 (s, 3H), 1.37 (s, 3H).

Example 268

(3R,6R,7S,8E,22S)-6'-Chloro-7-[2-(diethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

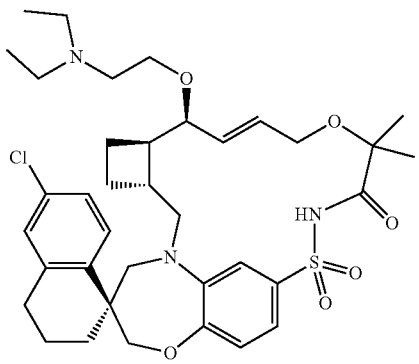 [SMILES: CCN(CC)CCO[C@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 65 using diethylamine in THF (2.0 M) to replace dimethylamine in THF (2.0 M) in Step 5. LCMS calc. for $C_{37}H_{51}ClFN_3O_6S$ [M+H]$^+$: m/z=700.3/702.3. Found: 700.3/702.3.

Example 269

(3R,6R,7S,8E,22S)-6'-Chloro-7-[2-[(3R,4S)-3,4-difluoropyrrolidin-1-yl]ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

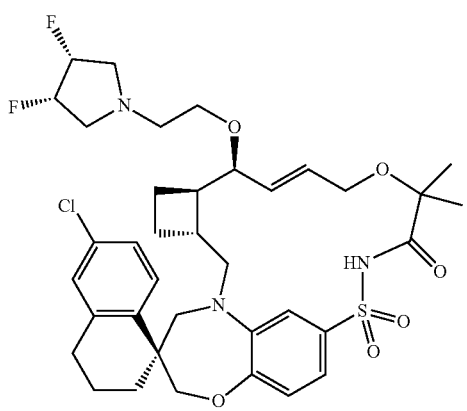 [SMILES: CC1(C)OC/C=C/[C@H](OCCN2C[C@@H](F)[C@@H](F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 using (3S,4R)-3,4-difluoropyrrolidine hydrochloride to replace dimethylamine in THF (2.0 M) in Step 5. LCMS calc. for $C_{37}H_{47}ClF_2N_3O_6S$ [M+H]$^+$: m/z=734.3/736.3. Found: 734.3/736.3.

Example 270

(3R,6R,7S,8E,22S)-6'-Chloro-12,12-dimethyl-7-(2-morpholinoethoxy)-15,15-dioxo-spiro[11,20-dioxa-15-thia-1,14-diazatetracyclo[14.7.2.03,6.019,24]pentacosa-8,16,18,24-tetraene-22,1'-tetralin]-13-one

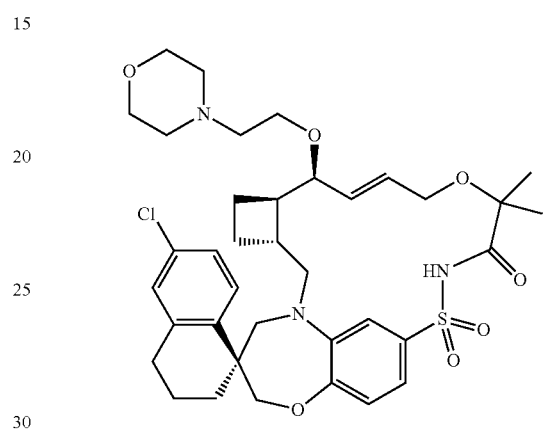

This compound was prepared using procedures analogous to those described for Example 65 using morpholine to replace dimethylamine in THF (2.0 M) in Step 5. LCMS calc. for $C_{37}H_{49}ClN_3O_7S$ [M+H]$^+$: m/z=714.29/716.29; Found: 714.7/716.8.

Example 271

(3R,6R,7R,8E,22S)-6'-Chloro-12,12-dimethyl-7-(2-morpholinoethoxy)-15,15-dioxo-spiro[11,20-dioxa-15-thia-1,14-diazatetracyclo[14.7.2.03,6.019,24]pentacosa-8,16,18,24-tetraene-22,1'-tetralin]-13-one

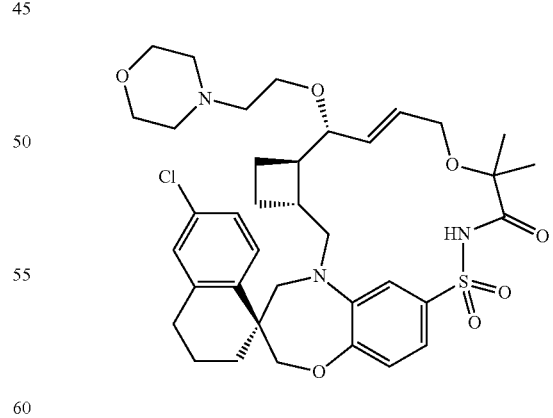

This compound was prepared using procedures analogous to those described for Example 65 Step 1-5 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (Example 36) in Step 1 and morpholine in Step 5. LCMS calc. for $C_{37}H_{49}ClN_3O_7S$ [M+H]$^+$: m/z=714.29/

716.29; Found: 714.7/716.8. $^1$H NMR (300 MHz, CDCl$_3$) δ 9.43 (s, 1H), 7.70 (d, J=8.5 Hz, 1H), 7.54 (dd, J=8.3, 2.1 Hz, 1H), 7.19 (dd, J=8.5, 2.4 Hz, 1H), 7.10 (d, J=2.2 Hz, 1H), 7.05-6.93 (m, 2H), 5.92 (dt, J=15.7, 4.5 Hz, 1H), 5.73 (dd, J=15.7, 8.5 Hz, 1H), 4.10 (d, J=2.0 Hz, 2H), 3.99 (m, 2H), 3.87 (d, J=6.5 Hz, 1H), 3.71 (dt, J=24.9, 14.9 Hz, 6H), 3.36-3.22 (m, 4H), 3.01 (m, 3H), 2.79 (m, 2H), 2.45 (m, 1H), 2.40-2.32 (m, 1H), 2.24 (m, 1H), 1.99 (m, 3H), 1.84 (m, 3H), 1.71-1.62 (m, 1H), 1.47 (m, 1H), 1.41 (d, J=15.2 Hz, 6H), 1.35-1.25 (m, 2H).

Example 272

(3R,6R,7R,8E,22S)-6'-Chloro-7-[2-(3,3-difluoroazetidin-1-yl)ethoxy]-12,12-dimethyl-15,15-dioxo-spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one

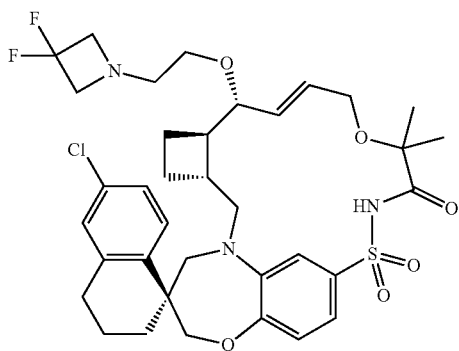 [SMILES: CC1(C)OC/C=C/[C@@H](OCCN2CC(F)(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 Step 1-5 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one (Example 36) in Step 1 and 3,3-difluoroazetidine hydrochloride in Step 5. LCMS calc. for C$_{36}$H$_{45}$ClF$_2$N$_3$O$_6$S [M+H]$^+$: m/z=720.27/722.27; Found: 720.7/722.7. $^1$H NMR (300 MHz, CDCl$_3$) δ 9.47 (s, 1H), 7.70 (d, J=8.5 Hz, 1H), 7.54 (dd, J=8.3, 2.1 Hz, 1H), 7.19 (dd, J=8.5, 2.4 Hz, 1H), 7.10 (d, J=2.3 Hz, 1H), 7.01 (d, J=8.3 Hz, 1H), 6.93 (d, J=2.2 Hz, 1H), 5.91 (dt, J=15.7, 4.6 Hz, 1H), 5.71 (dd, J=15.7, 8.6 Hz, 1H), 4.11 (s, 2H), 3.99 (m, 2H), 3.91 (m, 1H), 3.87 (d, J=6.5 Hz, 1H), 3.77 (d, J=14.4 Hz, 1H), 3.70 (dd, J=8.6, 4.9 Hz, 1H), 3.60 (m, 2H), 3.52 (m, 3H), 3.27 (m, 2H), 3.07 (dd, J=15.1, 10.1 Hz, 1H), 2.78 (m, 2H), 2.46 (t, J=9.1 Hz, 1H), 2.31 (dt, J=15.5, 9.8 Hz, 1H), 2.11-1.92 (m, 3H), 1.91-1.79 (m, 2H), 1.68 (m, 2H), 1.50 (m, 1H), 1.41 (d, J=11.1 Hz, 6H), 1.30 (m, 2H).

Example 273

(3R,6R,7R,8E,22S)-6'-Chloro-7-[2-(dimethylamino)ethoxy]-12,12-dimethyl-15,15-dioxo-spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one

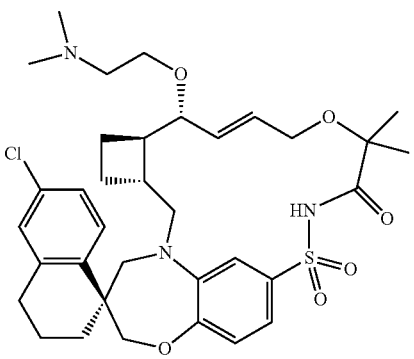 [SMILES: CN(C)CCO[C@@H]1/C=C/COC(C)(C)C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 65 Step 1-5 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one (Example 36) in Step 1 and dimethylamine in THF (2 M) in Step 5. LCMS calc. for C$_{35}$H$_{47}$ClN$_3$O$_6$S [M+H]$^+$: m/z=672.3/674.3; Found: 672.4/674.3. $^1$H NMR (600 MHz, DMSO-d$_6$) δ 9.24 (s, 1H), 7.63 (d, J=8.6 Hz, 1H), 7.26 (dd, J=8.5, 2.3 Hz, 2H), 7.19 (d, J=2.4 Hz, 1H), 7.02 (d, J=8.4 Hz, 1H), 6.82 (d, J=2.3 Hz, 1H), 6.08 (d, J=13.9 Hz, 1H), 5.43 (dd, J=16.0, 8.7 Hz, 1H), 4.14-4.03 (m, 3H), 3.74-3.66 (m, 2H), 3.61 (d, J=14.6 Hz, 1H), 3.54 (m, 1H), 3.47 (m, 2H), 3.24 (m, 3H), 3.11 (dd, J=15.3, 10.2 Hz, 1H), 2.79 (m, 7H), 2.73 (m, 1H), 2.39 (d, J=1.9 Hz, 1H), 2.10 (m, 1H), 1.98 (m, 4H), 1.85 (m, 2H), 1.73-1.69 (m, 1H), 1.47 (m, 1H), 1.35 (s, 3H), 1.23 (s, 3H).

Example 274

(3R,6R,7R,8E,22S)-6'-Chloro-12,12-dimethyl-15,15-dioxo-7-(2-pyrrolidin-1-ylethoxy)spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one

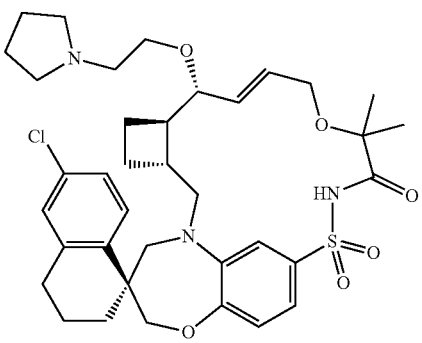 [SMILES: CC1(C)OC/C=C/[C@@H](OCCN2CCCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 65 Step 1-5 using (3R,6R,7R,8E,22S)-6'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one (Example 36) in Step 1 and pyrrolidine in Step 5. LCMS calc. for $C_{37}H_{48}ClN_3O_6S$ [M+H]⁺: m/z=698.3/700.3; Found: 698.4/700.3. ¹H NMR (600 MHz, DMSO-d₆) δ 9.37 (s, 1H), 7.64 (d, J=8.5 Hz, 1H), 7.26 (dd, J=8.5, 2.3 Hz, 2H), 7.23-7.16 (m, 1H), 7.05-6.99 (m, 1H), 6.83 (d, J=2.2 Hz, 1H), 6.07 (d, J=16.2 Hz, 1H), 5.44 (dd, J=15.9, 8.8 Hz, 1H), 4.09 (m, 3H), 3.67 (m, 1H), 3.61 (d, J=14.6 Hz, 1H), 3.55-3.41 (m, 6H), 3.19-2.95 (m, 5H), 2.89-2.64 (m, 3H), 2.13-2.06 (m, 1H), 1.99 (m, 6H), 1.84 (m, 4H), 1.71 (m, 2H), 1.47 (d, J=7.9 Hz, 1H), 1.36 (s, 3H), 1.23 (s, 3H).

Example 275

(3R,6R,7S,8E,22S)-6'-Chloro-7-[2-(3-fluoroazetidin-1-yl)ethoxy]-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one

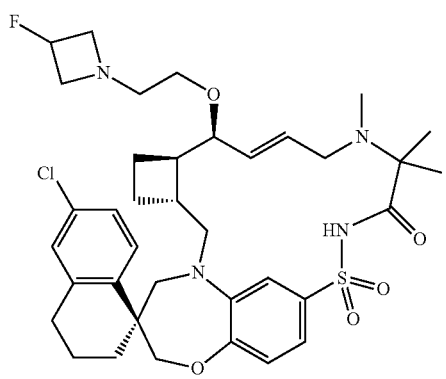 [SMILES: CN1C/C=C/[C@H](OCCN2CC(F)C2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one (Example 43) in Step 1 and 3-fluoroazetidine hydrochloride in Step 5. LCMS calc. for $C_{37}H_{49}ClFN_4O_5S$ [M+H]⁺: m/z=715.31/717.31; Found: 715.4/717.4.

Example 276

(3R,6R,7S,8E,22S)-6'-Chloro-7-[2-[(3R)-3-fluoropyrrolidin-1-yl]ethoxy]-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one

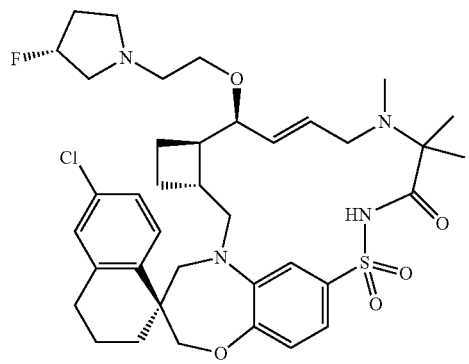 [SMILES: CN1C/C=C/[C@H](OCCN2CC[C@@H](F)C2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one (Example 43) in Step 1 and (3R)-3-fluoropyrrolidine hydrochloride in Step 5. LCMS calc. for $C_{38}H_{51}ClFN_4O_5S$ [M+H]⁺: m/z=729.32/731.31; Found: 729.5/731.5.

Example 277

(3R,6R,7S,8E,22S)-6'-Chloro-7-[2-[4-(2-methoxyethyl)-1,4-diazepan-1-yl]ethoxy]-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one

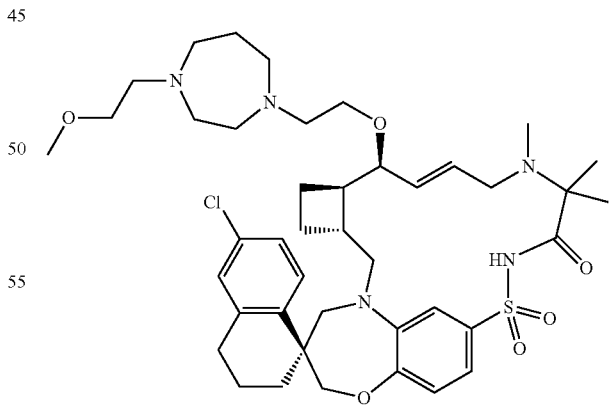

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one (Example 43) in Step 1 and 1-(2-methoxyethyl)-1,

Example 278

(3R,6R,7S,8E,22S)-6'-Chloro-7-[2-(3,3-difluoroazetidin-1-yl)-2-oxo-ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

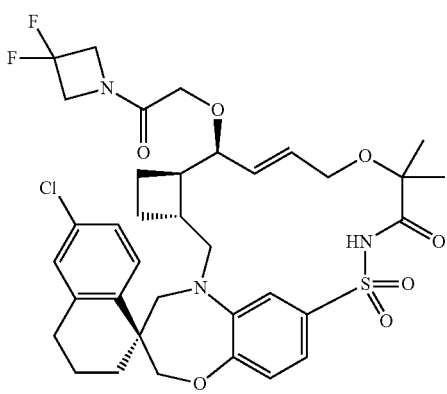 [SMILES: CC1(C)OC/C=C/[C@H](OCC(=O)N2CC(F)(F)C2)[C@@H]2CC[C@H]2CN2C[C@@]3(CCCc4cc(Cl)ccc43)COc3ccc(cc32)S(=O)(=O)NC1=O]

To a solution of isobutoxycarbonyl 2-[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl]oxyacetate (40.0 mg, 0.05 mmol, Example 65 Step 3) in THF (4 mL) was added triethylamine (0.07 mL, 0.50 mmol). The mixture was stirred at r.t. for 5 min, followed by adding of 3,3-difluoroazetidine hydrochloride (65.2 mg, 0.50 mmol). The mixture was then stirred at r.t. for an additional 4 h. LCMS showed that the starting material was consumed. The reaction was quenched by 1N HCl (2 mL), and extracted with DCM (3 mL×2). The combined organic layers were dried over Na$_2$SO$_4$, filtered and concentrated under reduced pressure. The residue was purified by prep-HPLC on a C18 column using H$_2$O/ACN (20-100%) to afford (3R,6R,7S,8E,22S)-6'-chloro-7-[2-(3,3-difluoroazetidin-1-yl)-2-oxo-ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (9 mg, 21% yield). LCMS calc. for C$_{36}$H$_{43}$ClF$_2$N$_3$O$_7$S [M+H]$^+$: m/z=734.2; Found: 734.5. $^1$H NMR (300 MHz, CDCl$_3$) δ 9.08 (s, 1H), 7.72-7.58 (m, 1H), 7.52 (m, 1H), 7.37 (dd, J=4.3, 2.0 Hz, 1H), 7.20 (dd, J=8.5, 2.4 Hz, 1H), 7.12 (d, J=2.9 Hz, 1H), 7.02 (dd, J=8.5, 3.4 Hz, 1H), 5.85-5.48 (m, 2H), 4.66 (m, 2H), 4.39 (m, 2H), 4.27-4.07 (m, 3H), 4.03-3.90 (m, 2H), 3.88-3.64 (m, 3H), 3.52 (m, 1H), 3.42-3.28 (m, 2H), 2.89-2.63 (m, 3H), 2.41 (m, 1H), 2.11-1.76 (m, 6H), 1.72-1.53 (m, 2H), 1.49-1.33 (m, 6H).

Example 279

(3R,6R,7S,8E,22S)-7-[2-(Azetidin-1-yl)-2-oxo-ethoxy]-6'-chloro-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

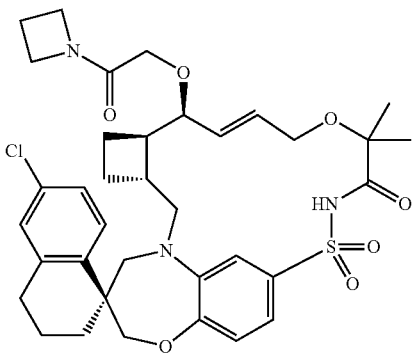 [SMILES: CC1(C)OC/C=C/[C@H](OCC(=O)N2CCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using azetidine hydrochloride to replace 3,3-difluoroazetidine hydrochloride. LCMS calc. for C$_{36}$H$_{45}$ClN$_3$O$_7$S [M+H]$^+$: m/z=698.2; Found: 698.3. $^1$H NMR (300 MHz, CDCl$_3$) δ 9.17 (s, 1H), 7.67 (d, J=8.5 Hz, 1H), 7.52 (dd, J=8.3, 2.1 Hz, 1H), 7.20 (dd, J=8.5, 2.3 Hz, 1H), 7.13 (m, 2H), 7.00 (m, 1H), 6.83 (d, J=8.2 Hz, 1H), 5.77 (m, 1H), 5.61 (dd, J=15.7, 6.4 Hz, 1H), 4.48-4.26 (m, 2H), 4.23-4.03 (m, 5H), 4.01-3.65 (m, 5H), 3.46-3.33 (m, 2H), 3.26 (m, 2H), 2.80 (m, 2H), 2.33 (m, 2H), 2.06-1.91 (m, 3H), 1.86 (m, 2H), 1.64 (s, 3H), 1.43 (d, J=20.2 Hz, 6H).

Example 280

(3R,6R,7S,8E,22S)-6'-Chloro-7-[2-(3-methoxyazetidin-1-yl)-2-oxo-ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

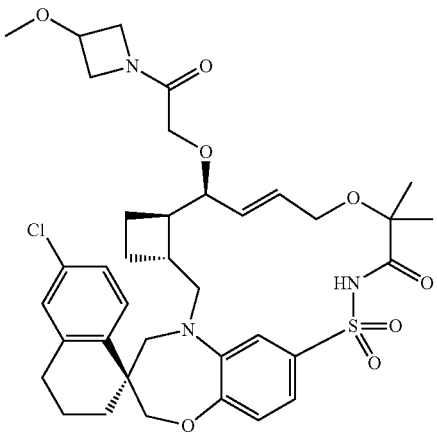

This compound was prepared using procedures analogous to those described for Example 278 using 3-methoxyazetidine hydrochloride to replace 3,3-difluoroazetidine hydrochloride. LCMS calc. for $C_{37}H_{47}ClN_3O_7S$ [M+H]$^+$: m/z=728.2; Found: 728.3. 1H NMR (300 MHz, CDCl$_3$) δ 9.17 (s, 1H), 7.67 (dd, J=8.5, 3.9 Hz, 1H), 7.52 (dd, J=8.4, 1.9 Hz, 1H), 7.20-7.10 (m, 2H), 7.08-6.94 (m, 2H), 6.83 (d, J=8.3 Hz, 1H), 5.85-5.46 (m, 2H), 4.65-4.39 (m, 1H), 4.39-4.17 (m, 3H), 4.15-3.84 (m, 6H), 3.82-3.67 (m, 2H), 3.55 (q, J=6.9 Hz, 1H), 3.45-3.33 (m, 2H), 3.31 (d, J=10.4 Hz, 3H), 3.23 (d, J=15.0 Hz, 1H), 2.83-2.69 (m, 2H), 2.45-2.29 (m, 1H), 2.29-2.14 (m, 1H), 2.07-1.78 (m, 7H), 1.59-1.50 (m, 1H), 1.52-1.33 (m, 6H).

Example 281

(3R,6R,7S,8E,22S)-6'-Chloro-7-[2-(3-fluoroazetidin-1-yl)-2-oxo-ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

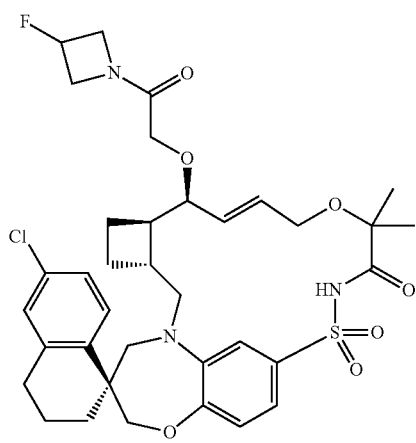 [SMILES: CC1(C)OC/C=C/[C@H](OCC(=O)N2CC(F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using 3-fluoroazetidine hydrochloride to replace 3,3-difluoroazetidine hydrochloride. LCMS calc. for $C_{36}H_{44}ClFN_3O_7S$ [M+H]$^+$: m/z=716.2; Found: 716.3. $^1$H NMR (300 MHz, CDCl$_3$) δ 9.16 (d, J=22.6 Hz, 1H), 7.67 (t, J=7.7 Hz, 1H), 7.52 (dd, J=8.3, 2.0 Hz, 1H), 7.23-7.11 (m, 2H), 7.11-6.93 (m, 2H), 6.83 (d, J=7.8 Hz, 1H), 5.94-5.52 (m, 2H), 5.33 (d, J=57.0 Hz, 1H), 4.89-4.57 (m, 1H), 4.46 (m, 2H), 4.25-4.01 (m, 5H), 3.94-3.54 (m, 4H), 3.49-3.09 (m, 3H), 2.79 (m, 2H), 2.36 (m, 1H), 2.12-1.76 (m, 5H), 1.65 (m, 3H), 1.56-1.34 (m, 6H).

Example 282

2-[(3R,6R,7S,8E,22S)-6'-Chloro-12,12-dimethyl-13,15,15-trioxo-spiro[11,20-dioxa-15λ6-thia-1,14-diazatetracyclo[14.7.2.03,6.019,24]pentacosa-8,16,18,24-tetraene-22,1'-tetralin]-7-yl]oxy-N-tetrahydropyran-4-yl-acetamide

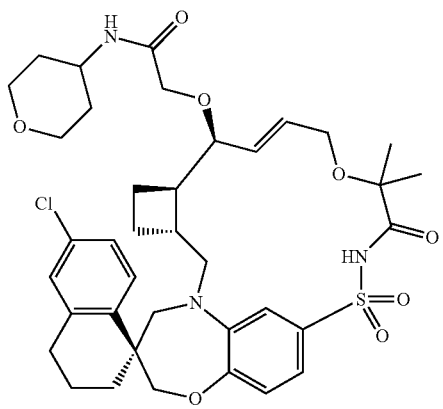 [SMILES: CC1(C)OC/C=C/[C@H](OCC(=O)NC2CCOCC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using 4-aminotetrahydropyran to replace 3,3-difluoroazetidine hydrochloride. LCMS calc. for $C_{38}H_{49}ClN_3O_8S$ [M+H]$^+$: m/z=742.29/744.28; Found: 742.4/744.3; $^1$H NMR (300 MHz, CDCl$_3$) δ 7.65 (d, J=8.4 Hz, 1H), 7.43 (s, 1H), 7.15 (d, J=8.7 Hz, 1H), 7.10 (d, J=2.2 Hz, 1H), 7.03 (d, J=2.1 Hz, 1H), 6.89 (s, 1H), 6.46 (s, 1H), 5.60 (dd, J=15.4, 6.6 Hz, 1H), 4.10-3.78 (m, 10H), 3.68 (d, J=14.4 Hz, 1H), 3.40-3.36 (m, 5H), 2.75 (d, J=18.9 Hz, 3H), 2.37 (d, J=9.6 Hz, 1H), 1.91-1.84 (m, 9H), 1.66 (d, J=9.1 Hz, 1H), 1.50-1.48 (m, 2H), 1.39 (s, 3H), 1.35 (s, 3H).

Example 283

(3R,6R,7S,8E,22S)-6'-Chloro-12,12-dimethyl-15,15-dioxo-7-(2-oxo-2-pyrrolidin-1-yl-ethoxy)spiro[11,20-dioxa-15-thia-1,14-diazatetracyclo[14.7.2.03,6.019,24]pentacosa-8,16,18,24-tetraene-22,1'-tetralin]-13-one

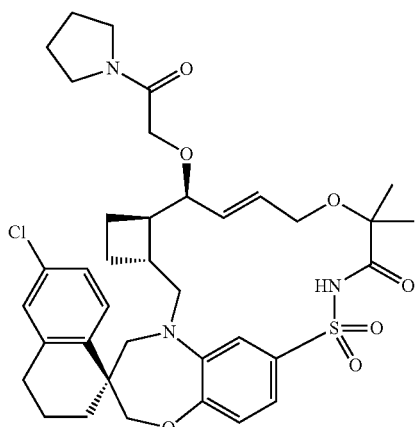

This compound was prepared using procedures analogous to those described for Example 278 using pyrrolidine to replace 3,3-difluoroazetidine hydrochloride. LCMS calc. for $C_{36}H_{43}ClF_2N_3O_7S$ [M+H]$^+$: m/z=712.2; Found: 712.4. $^1$H NMR (300 MHz, CDCl$_3$) δ 9.16 (s, 1H), 7.66 (d, J=8.5 Hz, 1H), 7.52 (dd, J=8.3, 2.1 Hz, 1H), 7.23-7.16 (m, 1H), 7.11 (d, J=2.3 Hz, 1H), 7.08-6.95 (m, 2H), 5.74 (dt, J=15.7, 4.6 Hz, 1H), 5.62 (dd, J=15.7, 6.7 Hz, 1H), 4.19 (m, 2H), 4.13 (m, 2H), 4.01 (d, J=14.0 Hz, 1H), 3.92-3.84 (m, 2H), 3.70 (d, J=14.6 Hz, 1H), 3.51 (m, 3H), 3.41 (m, 1H), 3.29 (dd, J=14.9, 8.4 Hz, 1H), 2.87-2.63 (m, 3H), 2.44 (dt, J=9.6, 4.8 Hz, 1H), 1.92 (m, 8H), 1.60 (m, 2H), 1.42 (d, J=9.5 Hz, 6H).

Example 284

2-[(3R,6R,7S,8E,22S)-6'-Chloro-12,12-dimethyl-13, 15,15-trioxo-spiro[11,20-dioxa-15λ6-thia-1,14-diazatetracyclo[14.7.2.03,6.019,24]pentacosa-8,16,18, 24-tetraene-22,1'-tetralin]-7-yl]oxy-N-[(3R)-tetrahydrofuran-3-yl]acetamide

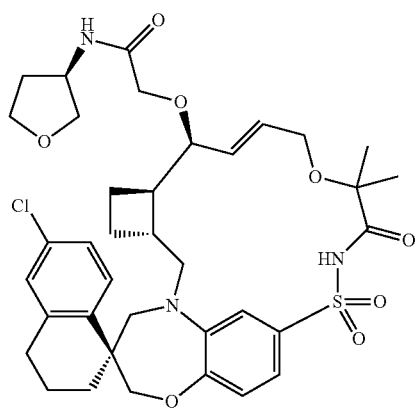 [SMILES: CC1(C)OC/C=C/[C@H](OCC(=O)N[C@@H]2CCOC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using (3R)-tetrahydrofuran-3-amine to replace 3,3-difluoroazetidine hydrochloride. LCMS calc. for $C_{37}H_{47}ClN_3O_8S$ [M+H]$^+$: m/z=728.3/730.3; Found: 728.4/730.4. $^1$H NMR (300 MHz, CDCl$_3$) δ 9.38 (s, 1H), 7.67 (d, J=8.5 Hz, 1H), 7.53 (dd, J=8.3, 2.1 Hz, 1H), 7.20 (dd, J=8.5, 2.3 Hz, 1H), 7.11 (d, J=2.3 Hz, 1H), 7.05-6.98 (m, 2H), 6.89 (d, J=7.7 Hz, 1H), 5.80 (ddd, J=16.0, 6.9, 3.3 Hz, 1H), 5.63 (dd, J=15.8, 5.9 Hz, 1H), 4.56 (ddt, J=10.5, 7.5, 3.2 Hz, 1H), 4.19-3.95 (m, 6H), 3.87-3.74 (m, 6H), 3.42-3.20 (m, 3H), 2.80 (dt, J=12.3, 6.4 Hz, 3H), 2.41-2.19 (m, 2H), 2.09-1.80 (m, 7H), 1.67 (t, J=9.3 Hz, 1H), 1.47 (s, 3H), 1.39 (s, 3H).

Example 285

2-[(3R,6R,7S,8E,22S)-6'-Chloro-12,12-dimethyl-13, 15,15-trioxo-spiro[11,20-dioxa-15λ6-thia-1,14-diazatetracyclo[14.7.2.03,6.019,24]pentacosa-8,16,18, 24-tetraene-22,1'-tetralin]-7-yl]oxy-N-[(3S)-tetrahydrofuran-3-yl]acetamide

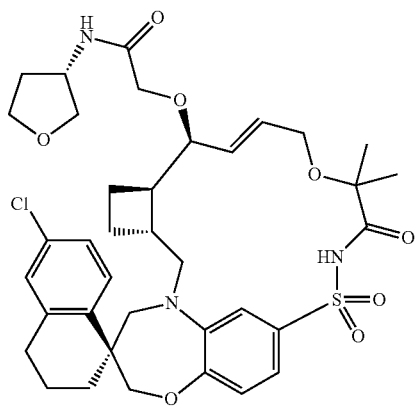 [SMILES: CC1(C)OC/C=C/[C@H](OCC(=O)N[C@H]2CCOC2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using (3S)-tetrahydrofuran-3-amine to replace 3,3-difluoroazetidine hydrochloride. LCMS calc. for $C_{37}H_{47}ClN_3O_8S$ [M+H]$^+$: m/z=728.3/730.3; Found: 728.4/730.4. $^1$H NMR (300 MHz, CDCl$_3$) δ 9.44 (s, 1H), 7.66 (d, J=8.5 Hz, 1H), 7.53 (dd, J=8.4, 2.0 Hz, 1H), 7.20 (dd, J=8.5, 2.2 Hz, 1H), 7.11 (d, J=2.2 Hz, 1H), 7.04-6.98 (m, 2H), 5.81 (ddd, J=15.9, 6.7, 3.6 Hz, 1H), 5.66 (dd, J=15.9, 6.1 Hz, 1H), 5.35-5.27 (m, 1H), 4.58 (tt, J=7.3, 3.7 Hz, 1H), 4.19-3.94 (m, 6H), 3.88-3.65 (m, 6H), 3.47-3.21 (m, 3H), 2.78 (dt, J=19.1, 5.7 Hz, 3H), 2.45-2.23 (m, 2H), 2.10-1.80 (m, 7H), 1.67 (t, J=9.3 Hz, 1H), 1.46 (s, 3H), 1.39 (s, 3H).

Example 286

[(3R,6R,22S)-6'-Chloro-12,12-dimethyl-13,15,15-trioxo-spiro[11,20-dioxa-15-thia-1,14-diazatetracyclo[14.7.2.03,6.019,24]pentacosa-16,18,24-triene-22,1'-tetralin]-7-yl] N,N-dimethylcarbamate

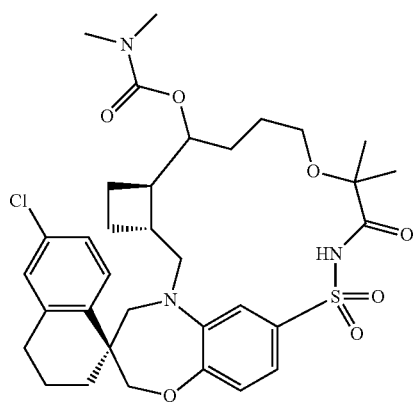 [SMILES: CN(C)C(=O)OC1CCCOC(C)(C)C(=O)NS(=O)(=O)c2ccc3c(c2)N(C[C@@H]2CC[C@@H]12)C[C@@]1(CCCc2cc(Cl)ccc21)CO3]

To a solution of (3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate (35.0 mg, 0.05 mmol, Example 34) in ethyl acetate (3 mL) was added platinum(IV) oxide (2.36 mg, 0.01 mmol). The mixture was then purged by H$_2$ gas in balloon for 2 times, and stirred at r.t. for 2 h under H$_2$ atmosphere. LCMS showed that most of the starting material was consumed. The mixture was filtered through Celite and concentrated under reduced pressure. The resulting residue was then purified by prep-HPLC on a C18 column using H$_2$O/ACN (20-100%) to provide [(3R,6R,22S)-6'-chloro-12,12-dimethyl-13,15,15-trioxo-spiro[11,20-dioxa-15-thia-1,14-diazatetracyclo[14.7.2.03,6.019,24]pentacosa-16,18,24-triene-22,1'-tetralin]-7-yl] N,N-dimethylcarbamate (7.4 mg, 21.1% yield) as a white solid. LCMS calc. for $C_{34}H_{43}ClN_3O_7S$ [M+H]$^+$: m/z=674.26/677.26; Found: 674.7/679.6; $^1$H NMR (600 MHz, DMSO-d6) δ 7.61 (q, J=8.0 Hz, 1H), 7.31-7.16 (m, 4H), 7.00 (dt, J=17.3, 8.5 Hz, 1H), 4.76-4.64 (m, 1H), 4.14-4.09 (m, 1H), 4.06-4.00 (m, 1H), 3.54-3.43 (m, 3H), 3.25 (t, J=14.6 Hz, 2H), 3.10-2.96 (m, 2H), 2.85-2.74 (m, 3H), 2.74-2.65 (m, 3H), 2.58 (d, J=14.1 Hz, 2H), 2.24 (s, 1H), 1.96-1.89 (m, 2H), 1.85-1.73 (m, 3H), 1.73-1.52 (m, 5H), 1.49-1.35 (m, 2H), 1.28 (s, 3H), 1.23 (d, J=16.5 Hz, 3H).

Example 287

(3R,6R,7S,8E,22S)-6'-Chloro-7-[2-(3,3-difluoroazetidin-1-yl)ethoxy]-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

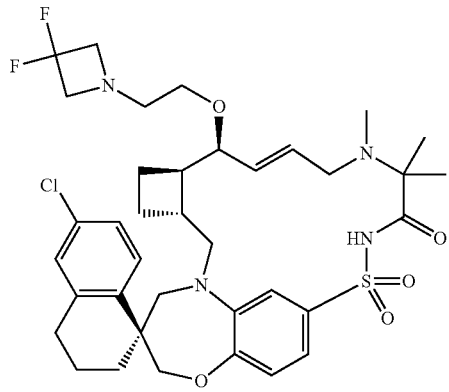 [SMILES: CN1C/C=C/[C@H](OCCN2CC(F)(F)C2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 43) in Step 1 and 3,3-difluoroazetidine hydrochloride in Step 5. LCMS calc. for $C_{37}H_{48}ClF_2N_4O_5S$ [M+H]$^+$: m/z=733.30/735.30; Found: 733.3/735.1. $^1$H NMR (300 MHz, CDCl$_3$) δ 7.74-7.45 (m, 2H), 7.22-7.18 (m, 2H), 7.09 (s, 1H), 7.03-6.89 (m, 1H), 6.02 (s, 1H), 5.71-5.46 (m, 1H), 5.36 (s, 1H), 4.23-3.94 (m, 4H), 3.87 (d, J=18.4 Hz, 1H), 3.69 (s, 3H), 3.33 (d, J=15.2 Hz, 2H), 3.06 (s, 1H), 2.79 (s, 3H), 2.46 (s, 2H), 2.25 (t, J=7.7 Hz, 2H), 1.64 (d, J=7.4 Hz, 1H), 1.46 (s, 3H), 1.33 (s, 16H).

Example 288

(3R,6R,7S,8E,22S)-6'-Chloro-7-[2-(3,3-difluoropyrrolidin-1-yl)ethoxy]-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one

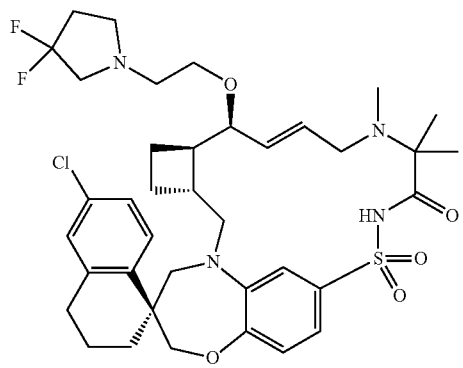 [SMILES: CN1C/C=C/[C@H](OCCN2CCC(F)(F)C2)[C@@H]2CC[C@H]2CN2C[C@@]3(CCCc4cc(Cl)ccc43)COc3ccc(cc32)S(=O)(=O)NC(=O)C1(C)C]

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one (Example 43) in Step 1 and 3,3-difluoropyrrolidine hydrochloride in Step 5. LCMS calc. for $C_{38}H_{50}ClF_2N_4O_5S$ [M+H]$^+$: m/z=747.32/749.31; Found: 747.4/749.3. $^1$H NMR (300 MHz, CDCl$_3$) δ 7.71-7.49 (m, 1H), 7.39-7.12 (m, 4H), 7.08-6.84 (m, 1H), 6.00 (s, 2H), 5.61 (d, J=17.9 Hz, 2H), 5.37 (s, 2H), 3.72 (d, J=14.2 Hz, 4H), 3.52 (s, 3H), 3.11 (s, 1H), 2.80 (s, 1H), 2.62 (m, 15H), 2.54 (s, 2H), 2.39-2.21 (m, 3H), 2.04 (s, 5H), 1.66 (d, J=7.4 Hz, 2H).

Example 289

(3R,6R,7S,8E,22S)-6'-Chloro-11,12,12-trimethyl-15,15-dioxo-7-[2-(1-piperidyl)ethoxy]spiro[20-oxa-15-thia-1,11,14-triazatetracyclo[14.7.2.03,6.019,24]pentacosa-8,16,18,24-tetraene-22,1'-tetralin]-13-one

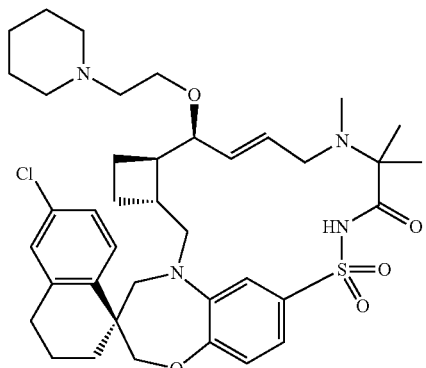

This compound was prepared using procedures analogous to those described for Example 65 Step 1-5 using (3R,6R,7S,8E,22S)-6'-chloro-7-hydroxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one (Example 43) in Step 1 and piperidine in Step 5. LCMS calc. for C₃₉H₅₄ClN₄O₅S [M+H]⁺: m/z=725.35/727.35; Found: 725.3/727.6. ¹H NMR (300 MHz, CDCl₃) δ 11.57 (s, 1H), 7.67 (d, J=8.5 Hz, 1H), 7.52 (dd, J=8.3, 2.0 Hz, 1H), 7.09 (d, J=2.3 Hz, 2H), 7.02-6.88 (m, 2H), 5.95 (d, J=45.7 Hz, 2H), 5.60 (d, J=15.9 Hz, 1H), 5.42-5.28 (m, 1H), 4.20-4.00 (m, 3H), 3.72 (dd, J=24.6, 13.3 Hz, 4H), 3.31 (d, J=14.6 Hz, 1H), 3.06 (s, 2H), 2.53 (s, 3H), 2.38-2.20 (m, 2H), 2.00 (d, J=7.1 Hz, 1H), 1.84 (s, 3H), 1.69-1.24 (m, 23H).

Example 290

(3R,6R,7S,8E,22S)-6'-Chloro-7-[2-[(3R,4R)-3,4-difluoropyrrolidin-1-yl]-2-oxo-ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one

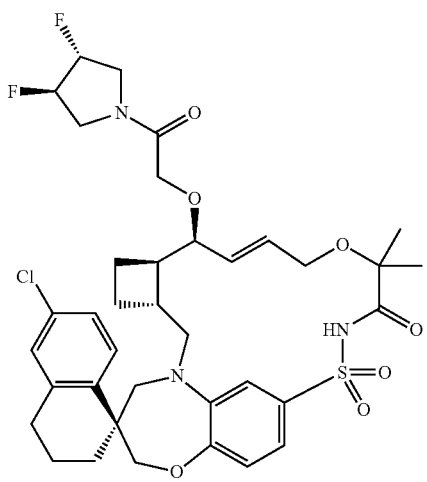 [SMILES: CC1(C)OC/C=C/[C@H](OCC(=O)N2C[C@@H](F)[C@H](F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using (3R,4R)-3,4-difluoropyrrolidine to replace 3,3-difluoroazetidine hydrochloride. LCMS calc. for C₃₇H₄₅ClF₂N₃O₇S [M+H]⁺: m/z=748.3/750.3; Found: 748.4/750.4. ¹H NMR (300 MHz, CDCl₃) δ 7.66 (d, J=8.5 Hz, 1H), 7.49 (dt, J=8.4, 1.7 Hz, 1H), 7.18 (dt, J=8.5, 1.8 Hz, 1H), 7.09 (t, J=1.8 Hz, 1H), 7.05-6.95 (m, 2H), 5.82-5.53 (m, 2H), 5.19 (ddd, J=50.3, 15.9, 4.2 Hz, 2H), 4.11-3.64 (m, 12H), 3.44-3.22 (m, 3H), 2.84-2.69 (m, 3H), 2.37 (dd, J=9.2, 3.1 Hz, 1H), 2.03-1.78 (m, 7H), 1.63 (d, J=17.3 Hz, 1H), 1.42 (s, 3H), 1.37 (s, 3H).

Example 291

(3R,6R,7S,8E,22S)-6'-Chloro-7-[2-[(3R,4S)-3,4-difluoropyrrolidin-1-yl]-2-oxo-ethoxy]-12,12-dimethyl-15,15-dioxo-spiro[11,20-dioxa-15λ⁶-thia-1,14-diazatetracyclo[14.7.2.0³,⁶.0¹⁹,²⁴]pentacosa-8,16,18,24-tetraene-22,1'-tetralin]-13-one

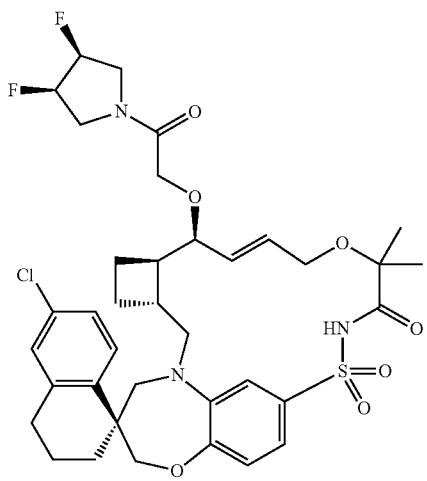 [SMILES: CC1(C)OC/C=C/[C@H](OCC(=O)N2C[C@@H](F)[C@@H](F)C2)[C@@H]2CC[C@H]2CN2C[C@@]3(CCCc4cc(Cl)ccc43)COc3ccc(cc32)S(=O)(=O)NC1=O]

This compound was prepared using procedures analogous to those described for Example 278 using (3R,4S)-3,4-difluoropyrrolidine to replace 3,3-difluoroazetidine hydrochloride. C₃₇H₄₅ClF₂N₃O₇S [M+H]⁺: m/z=748.3/750.3; Found: 748.4/750.4. ¹H NMR (300 MHz, CDCl₃) δ 7.65 (dd, J=8.5, 2.7 Hz, 1H), 7.48 (dt, J=8.4, 1.7 Hz, 1H), 7.18 (dt, J=8.5, 1.9 Hz, 1H), 7.09 (d, J=2.1 Hz, 1H), 7.00 (ddd, J=8.4, 4.1, 1.7 Hz, 2H), 5.85-5.56 (m, 2H), 5.26-4.95 (m, 2H), 4.17-3.66 (m, 12H), 3.45-3.17 (m, 3H), 2.85-2.66 (m, 3H), 2.38 (dq, J=10.6, 5.4, 3.0 Hz, 1H), 2.07-1.78 (m, 7H), 1.64 (t, J=8.7 Hz, 1H), 1.43 (s, 3H), 1.38 (s, 3H).

Example 292

[(3R,6R,7S,8E,22S)-6'-Chloro-10,12,12-trimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate

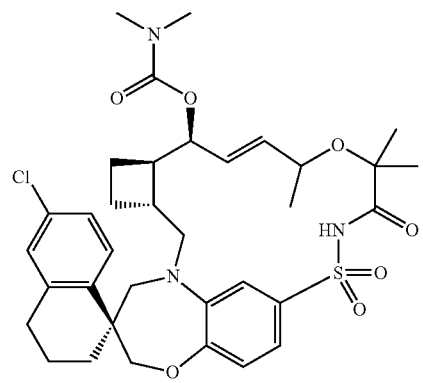 [SMILES: CC1/C=C/[C@H](OC(=O)N(C)C)[C@@H]2CC[C@H]2CN2C[C@@]3(CCCc4cc(Cl)ccc43)COc3ccc(cc32)S(=O)(=O)NC(=O)C(C)(C)O1]

523

Step 1:2-methyl-2-(1-methylallyloxy)propanoic acid

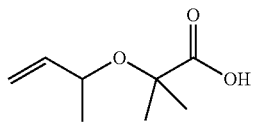

To a solution of but-3-en-2-ol (410.0 mg, 5.69 mmol) and DIPEA (1.98 mL, 11.37 mmol) in MeCN (5 mL) was added 2-bromo-2-methyl-propanoic acid (636.18 mg, 3.81 mmol). The reaction mixture was stirred at 50° C. overnight. Upon completion, the solvent was removed under reduced pressure. The residue was dissolved in DCM (10 mL) and washed with 1 N HCl solution (10 mL). The organic layer was dried over $Na_2SO_4$, filtered and concentrated under reduced pressure to yield 2-methyl-2-(1-methylallyloxy) propanoic acid (450 mg, 50.0% yield), which was used for the next reaction without further purification. TLC: $R_f$=0.1 (Heptane:EtOAc=1:1).

Step 2:[1-[(1R,2R)-2-[[(3S)-6'-chloro-7-[[2-methyl-2-(1-methylallyloxy)propanoyl]sulfamoyl]spiro[2,4-dihydro-1,5-benzoxazepine-3,1'-tetralin]-5-yl]methyl]cyclobutyl]-1-methyl-allyl] 2-methyl-2-(1-methylallyloxy)propanoate

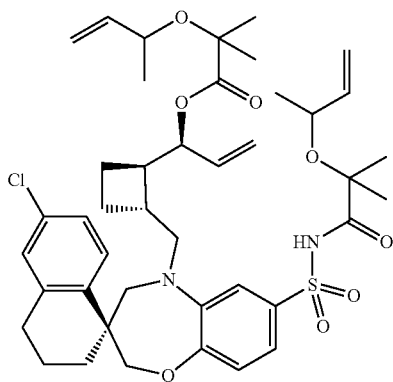 [SMILES: C=CC(C)OC(C)(C)C(=O)NS(=O)(=O)c1ccc2c(c1)N(C[C@@H]1CC[C@H]1[C@H](C=C)OC(=O)C(C)(C)OC(C)C=C)C[C@@]1(CCCc3cc(Cl)ccc31)CO2]

To a solution of (3S)-6'-chloro-5-[[(1R,2R)-2-[(1S)-1-hydroxyallyl]cyclobutyl]-methyl]spiro[2,4-dihydro-1,5-benzoxazepine-3,1'-tetralin]-7-sulfonamide (180.0 mg, 0.36 mmol, Intermediate 3) and 2-methyl-2-(1-methylallyloxy) propanoic acid (169.81 mg, 1.07 mmol) in DCM (4 mL) was added 4-(dimethylamino)pyridine (262.28 mg, 2.15 mmol), followed by the addition of EDCI (274.37 mg, 1.43 mmol). The reaction mixture was stirred at r.t. overnight. The reaction was diluted with DCM (5 mL) and washed with 1N HCl solution (5 mL). The organic layer was dried over $Na_2SO_4$, filtered and concentrated under reduced pressure to yield [1-[(1R,2R)-2-[[(3S)-6'-chloro-7-[[2-methyl-2-(1-methylallyloxy)propanoyl]sulfamoyl]spiro[2,4-dihydro-1,5-benzoxazepine-3,1'-tetralin]-5-yl]methyl]cyclobutyl]-1-methyl-allyl] 2-methyl-2-(1-methylallyloxy)propanoate (295 mg, 103.4% yield), which was used for the next reaction without further purification. LCMS calc. for $C_{43}H_{58}ClN_2O_8S$ $[M+H]^+$: m/z=783.34/785.34; Found: 783.6/785.5.

524

Step 3: N-[(3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-yl]sulfonyl-2-methyl-2-(1-methylallyloxy)propanamide

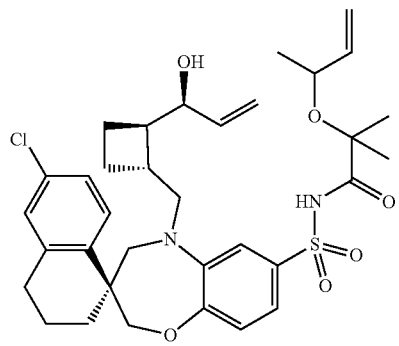 [SMILES: C=CC(C)OC(C)(C)C(=O)NS(=O)(=O)c1ccc2c(c1)N(C[C@@H]1CC[C@H]1[C@@H](O)C=C)C[C@@]1(CCCc3cc(Cl)ccc31)CO2]

To a solution of [(1S)-1-[(1R,2R)-2-[[(3S)-6'-chloro-7-[[2-methyl-2-(1-methylallyloxy)propanoyl]sulfamoyl]spiro[2,4-dihydro-1,5-benzoxazepine-3,1'-tetralin]-5-yl]methyl]cyclobutyl]allyl] 2-methyl-2-(1-methylallyloxy)propanoate (295.0 mg, 0.38 mmol) in THF (0.50 mL), methanol (0.50 mL) and water (0.50 mL) was added lithium hydroxide monohydrate (158.15 mg, 3.77 mmol). The reaction mixture was stirred at 45° C. for 2 h. The solvent was removed under reduced pressure. The residue was dissolved in DCM (5 mL) and washed with sat. $NaHCO_3$ solution (5 mL) and brine (5 mL). The organic layer was dried over $Na_2SO_4$, filtered and concentrated under reduced pressure. The residue was purified by flash chromatography on a silica gel column eluting with EtOAc/Heptanes (5-30%) to afford the desired product N-[(3S)-6'-chloro-5-[[(1R,2R)-2-[(1S)-1-hydroxyallyl]cyclobutyl]methyl]-spiro[2,4-dihydro-1,5-benzoxazepine-3,1'-tetralin]-7-yl]sulfonyl-2-methyl-2-(1-methylallyloxy) propanamide (124 mg, 51.2% yield). LCMS calc. for $C_{34}H_{44}ClN_2O_6S$ $[M+H]^+$: m/z=643.24/645.24; Found: 643.4/645.3.

Step 4: (3R,6R,7S,8E,22S)-6'-chloro-7-hydroxy-10,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

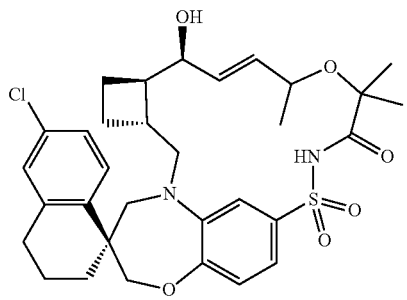 [SMILES: CC1/C=C/[C@H](O)[C@@H]2CC[C@H]2CN2C[C@@]3(CCCc4cc(Cl)ccc43)COc3ccc(cc32)S(=O)(=O)NC(=O)C(C)(C)O1]

To a solution of N-[(3S)-6'-chloro-5-[[(1R,2R)-2-[(1S)-1-hydroxyallyl]cyclobutyl]-methyl]spiro[2,4-dihydro-1,5-benzoxazepine-3,1'-tetralin]-7-yl]sulfonyl-2-methyl-2-(1-methylallyloxy)propanamide (124.0 mg, 0.19 mmol) in DCE (90 mL) was bubbled with $N_2$ for 20 min. Then Zhan catalyst (28.26 mg, 0.04 mmol) was added and was bubbled with $N_2$ for another 5 min. The reaction mixture was stirred at 45° C. for 2 h. The solvent was removed under reduced pressure. The residue was purified by flash chromatography on a silica gel column eluting with EtOAc/Heptanes with 0.2% HOAc (5-65%) to afford two products: P1 (18 mg, the earlier eluted product) and P2 (74 mg, the latter eluted product). The first fraction P1 was assigned to cis-isomer (3R,6R,7 S, 8Z,22S)-6'-chloro-7-hydroxy-10,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (18 mg, 15.2% yield). The P2 was assigned to the trans-isomer (3R,6R,7S,8E,22S)-6'-chloro-7-hydroxy-10,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (74 mg, 62.4% yield). LCMS calc. for $C_{32}H_{40}ClN_2O_6S$ $[M+H]^+$: m/z=615.22/617.22; Found: 615.3/617.2.

Step 5: [(3R,6R,7S,8E,22S)-6'-chloro-10,12,12-trimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate To a solution of (3R,6R,7S,8E,22S)-6'-chloro-7-hydroxy-10,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (15.0 mg, 0.02 mmol) in MeCN (1 mL) was added CDI (11.86 mg, 0.07 mmol). The reaction mixture was stirred at 45° C. for 2 h., and then cooled to r.t. Dimethylamine (0.025 mL, 0.05 mmol) (2.0 M in THF solution) was added. The reaction mixture was stirred at r.t. for 2 h. The reaction was concentrated under reduced pressure. The residue was purified by Prep-HPLC on a C18 column eluting with ACN/$H_2O$ (20%-100%) to afford a mixture of the two desired products: Fraction 1 (3.8 mg) contained about 39% of Product 2 (Product 1/Product 2=55:35, Rt (P1)=8.02 min, Rt (P2)=8.18 min), and Fraction 2 (3.6 mg) contained 30% of Product 1 (Product 1/Product 2=29:67, Rt (P1)=8.02 min, Rt (P2)=8.18 min). [(3R,6R,7S,8E,22S)-6'-chloro-10,12,12-trimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate (3.8 mg, 21.8% yield). LCMS calc. for $C_{35}H_{45}ClN_3O_7S$ $[M+H]^+$: m/z=686.26/688.26; Found: 686.4/688.4. $^1$H NMR (600 MHz, DMSO-$d_6$) δ 7.64 (dd, J=8.6, 4.5 Hz, 1H), 7.29-7.26 (m, 1H), 7.25 (d, J=2.5 Hz, 1H), 7.24 (d, J=2.4 Hz, 1H), 7.18 (dd, J=5.9, 2.4 Hz, 1H), 7.04 (s, 1H), 5.66 (d, J=14.2 Hz, 1H), 5.17 (s, 1H), 4.19 (s, 1H), 4.00 (d, J=12.2 Hz, 1H), 3.59 (d, J=14.3 Hz, 3H), 3.12 (s, 1H), 2.98 (s, 1H), 2.85 (s, 2H), 2.75 (s, 6H), 2.62 (s, 1H), 2.03-1.95 (m, 2H), 1.89-1.79 (m, 3H), 1.77-1.69 (m, 2H), 1.66-1.59 (m, 1H), 1.52-1.50 (m, 1H), 1.47-1.40 (m, 1H), 1.32 (s, 6H), 1.24 (s, 3H).

Example 293

[(3R,6R,7S,8E,22S)-6'-Chloro-7,12,12-trimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate

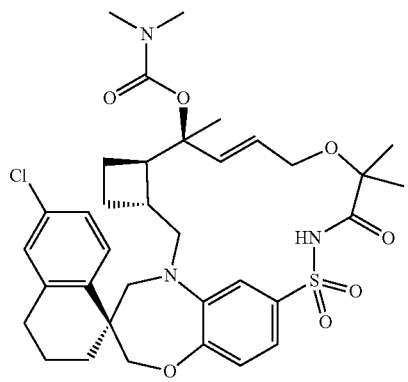 [SMILES: CN(C)C(=O)O[C@@]1(C)/C=C/COC(C)(C)C(=O)NS(=O)(=O)c2ccc3c(c2)N(C[C@@H]2CC[C@H]21)C[C@@]1(CCCc2cc(Cl)ccc21)CO3]

Step 1: [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarbonyl]oxysodium

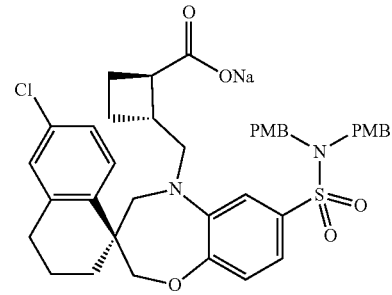

To a suspension of (3S)-6'-chloro-N,N-bis[(4-methoxyphenyl)methyl]-5-[[(1R,2R)-2-formylcyclobutyl]methyl]spiro[2,4-dihydro-1,5-benzoxazepine-3,1'-tetralin]-7-sulfonamide (1450.0 mg, 2.03 mmol, Intermediate 3 Step 3) in 1-butanol (5 mL) and 2-methylbut-2-ene (5.0 mL, 47.2 mmol) was added sodium chlorite (458.34 mg, 4.05 mmol) and the solution of sodium phosphate monobasic monohydrate (559.45 mg, 4.05 mmol) in water (5 mL). The reaction was stirred at r.t. for 3 h. LCMS showed reaction was completed. The reaction was quenched with aq. 10% $Na_2S_2O_3$ (5 mL) and the mixture was extracted with ethyl acetate (2 mL×2). The combined organic layers were dried over $Na_2SO_4$, filtered and concentrated under reduced pressure. The residue was used directly without further purification. LCMS calc. for $C_{40}H_{42}ClN_2O_7S$ $[M-H]^-$: m/z=730.24/732.24; Found: 730.8/732.7.

Step 2: (1R, 2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]-N-methoxy-N-methyl-cyclobutanecarboxamide

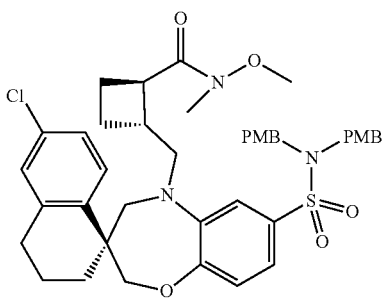

To a solution of [(1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]cyclobutanecarbonyl]oxysodium (300.0 mg, 0.40 mmol) and N,O-dimethylhydroxylamine hydrochloride (77.69 mg, 0.80 mmol) in DCM (4 mL) was added DIPEA (0.28 mL, 1.59 mmol), followed by the addition of 1-[bis(dimethylamino)methylene]-1H-1,2,3-triazolo[4,5-b]pyridinium 3-oxid hexafluorophosphate (302.86 mg, 0.80 mmol) at 0° C. The reaction mixture was stirred at r.t. for 2 h. The reaction was diluted with DCM (5 mL) and washed with 1 N HCl solution (5 mL). The organic layer was dried over $Na_2SO_4$, filtered and concentrated under reduced pressure. The residue was purified by flash chromatography on a silica gel column eluting with EtOAc/Heptanes (5-50%) to afford the desired product (1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]-N-methoxy-N-methyl-cyclobutanecarboxamide (232 mg, 75.2% yield). LCMS calc. for $C_{42}H_{49}ClN_3O_7S$ $[M+H]^+$: m/z=774.29/776.29; Found: 774.5/776.3.

Step 3: (3S)-5-[[(1R,2R)-2-acetylcyclobutyl]methyl]-6'-chloro-N,N-bis[(4-methoxyphenyl)methyl]spiro[2,4-dihydro-1,5-benzoxazepine-3,1'-tetralin]-7-sulfonamide

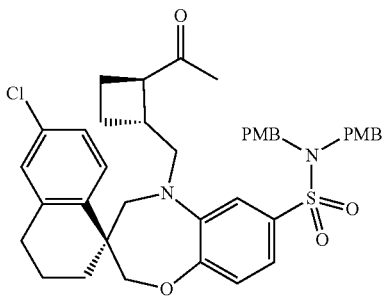

To a solution of methylmagnesium chloride THF solution (3 M in THF, 1.0 mL, 3 mmol) was added a solution of (1R,2R)-2-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]-N-methoxy-N-methyl-cyclobutanecarboxamide (232.0 mg, 0.30 mmol) in THF (2 mL) dropwise at 0° C. After addition, the reaction mixture was stirred at r.t. for 2 h. The reaction was quenched with aq. $NH_4Cl$ solution (5 mL) at 0° C. and extracted with ethyl acetate (5 mL×3). The combined organic layers were dried over $Na_2SO_4$, filtered and concentrated under reduced pressure to afford the crude (3S)-5-[[(1R,2R)-2-acetylcyclobutyl]methyl]-6'-chloro-N,N-bis[(4-methoxyphenyl)methyl]spiro[2,4-dihydro-1,5-benzoxazepine-3,1'-tetralin]-7-sulfonamide (300 mg) which contaminated with some inorganic salt and was used for the next reaction without further purification. LCMS calc. for $C_{41}H_{46}ClN_2O_6S$ $[M+H]^+$: m/z=729.27/731.27; Found: 729.5/731.4.

Step 4: (3S)-5-[[(1R,2R)-2-acetylcyclobutyl]methyl]-6'-chloro-spiro[2,4-dihydro-1,5-benzoxazepine-3,1'-tetralin]-7-sulfonamide

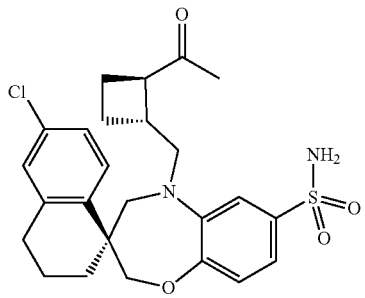 [SMILES: CC(=O)[C@@H]1CC[C@H]1CN1C[C@@]2(CCCc3cc(Cl)ccc32)COc2ccc(S(N)(=O)=O)cc21]

To a solution of (3S)-5-[[(1R,2R)-2-acetylcyclobutyl]methyl]-6'-chloro-N,N-bis[(4-methoxyphenyl)methyl]spiro[2,4-dihydro-1,5-benzoxazepine-3,1'-tetralin]-7-sulfonamide (300.0 mg, 0.41 mmol) in DCM (3 mL) was added Anisole (0.3 mL, 2.76 mmol) and TFA (3.0 mL, 39.2 mmol). The reaction mixture was stirred at r.t. overnight. The solvent was removed under reduced pressure. The residue was dissolved in DCM (5 mL) and washed with sat. $NaHCO_3$ solution (5 mL). The organic layer was dried over $Na_2SO_4$, filtered and concentrated under reduced pressure. The residue was purified by flash chromatography on a silica gel column eluting with EtOAc/Heptanes (5-70%) to afford the desired product (3S)-5-[[(1R,2R)-2-acetylcyclobutyl]methyl]-6'-chloro-spiro[2,4-dihydro-1,5-benzoxazepine-3,1'-tetralin]-7-sulfonamide (220 mg). LCMS calc. for $C_{25}H_{30}ClN_2O_4S$ $[M+H]^+$: m/z=489.15/491.15; Found: 489.2/491.4.

Step 5: (3S)-6'-chloro-5-[[(1R,2R)-2-[(1S)-1-hydroxy-1-methyl-allyl]cyclobutyl]methylspiro[2,4-dihydro-1,5-benzoxazepine-3,1'-tetralin]-7-sulfonamide

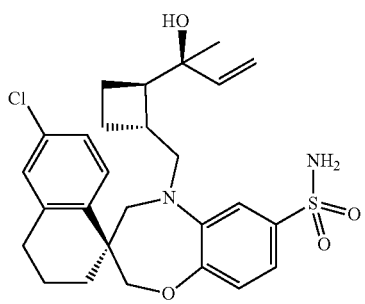 [SMILES: C=C[C@](C)(O)[C@@H]1CC[C@H]1CN1C[C@@]2(CCCc3cc(Cl)ccc32)COc2ccc(S(N)(=O)=O)cc21]

To a solution of vinylmagnesium bromide THF solution (1.0 M in THF, 4.5 mL, 4.5 mmol) was added a solution of (3S)-5-[[(1R,2R)-2-acetylcyclobutyl]methyl]-6'-chloro-spiro[2,4-dihydro-1,5-benzoxazepine-3,1'-tetralin]-7-sulfonamide (220.0 mg, 0.45 mmol) in THF (1 mL) dropwise at 0° C. After addition, the reaction mixture was stirred at r.t. for 2 h. The reaction was quenched by aq. NH$_4$Cl (5 mL) and extracted with ethyl acetate (5 mL×3). The combined organic layers were dried over Na$_2$SO$_4$, filtered and concentrated under reduced pressure. The residue was purified by flash chromatography on a silica gel column eluting with EtOAc/Heptanes (5-70%) to afford the desired product (3S)-6'-chloro-5-[[(1R,2R)-2-[(1S)-1-hydroxy-1-methyl-allyl]cyclobutyl]methyl]spiro[2,4-dihydro-1,5-benzoxazepine-3,1'-tetralin]-7-sulfonamide (85 mg, 36.5% yield). LCMS calc. for C$_{27}$H$_{33}$ClN$_2$O$_4$S [M+H]$^+$: m/z=517.18/519.18; Found: 517.2/519.3.

Step 6: [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]-1-methyl-allyl] 2-allyloxy-2-methyl-propanoate

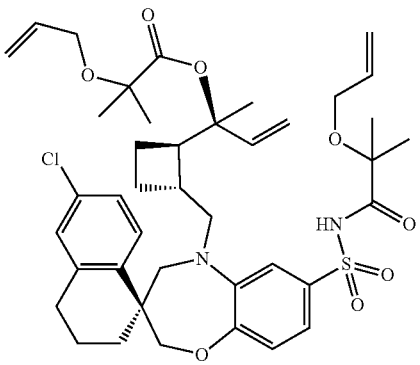 [SMILES: C=CCOC(C)(C)C(=O)NS(=O)(=O)c1ccc2c(c1)N(C[C@@H]1CC[C@H]1[C@](C)(C=C)OC(=O)C(C)(C)OCC=C)C[C@@]1(CCCc3cc(Cl)ccc31)CO2]

To a mixture of (3S)-6'-chloro-5-[[(1R,2R)-2-[(1S)-1-hydroxy-1-methyl-allyl]-cyclobutyl]methyl]spiro[2,4-dihydro-1,5-benzoxazepine-3,1'-tetralin]-7-sulfonamide (85.0 mg, 0.16 mmol) and 2-allyloxy-2-methyl-propanoic acid (71.1 mg, 0.49 mmol, Example 30 Step 1) in DCM (1 mL) was added DMAP (120.5 mg, 0.99 mmol), followed by the addition of EDCI (126.05 mg, 0.66 mmol). The reaction mixture was stirred at r.t. overnight, and then diluted with DCM (5 mL). The mixture was and washed with 1N HCl solution (5 mL). The organic layer was dried over Na$_2$SO$_4$, filtered and concentrated under reduced pressure to yield [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]-1-methyl-allyl] 2-allyloxy-2-methyl-propanoate (136 mg) which was directly used for the next reaction without further purification. LCMS calc. for C$_{41}$H$_{54}$ClN$_2$O$_8$S [M+H]$^+$: m/z=769.32/771.32; Found: 769.5/771.5.

Step 7: 2-allyloxy-N-[(3S)-6'-chloro-5-[[(1R,2R)-2-[(1S)-1-hydroxy-1-methyl-allyl]cyclobutyl]methyl]spiro[2,4-dihydro-1,5-benzoxazepine-3,1'-tetralin]-7-yl]sulfonyl-2-methyl-propanamide

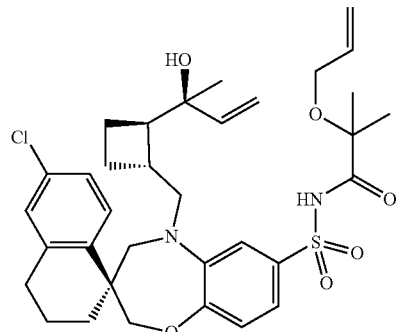

To a solution of [(1S)-1-[(1R,2R)-2-[[(3S)-7-[(2-allyloxy-2-methyl-propanoyl)sulfamoyl]-6'-chloro-spiro[2,4-dihydro-1,5-benzoxazepine-3,1'-tetralin]-5-yl]methyl]cyclobutyl]-1-methyl-allyl] 2-allyloxy-2-methyl-propanoate (136.0 mg, 0.18 mmol) in THF (0.50 mL), methanol (0.50 mL) and water (0.50 mL) was added lithium hydroxide monohydrate (74.24 mg, 1.77 mmol). The reaction mixture was stirred at 45° C. for 6 h. The solvent was removed under reduced pressure. The residue was dissolved in DCM (5 mL) and washed with 1N HCl solution (5 mL). The organic layer was dried over Na$_2$SO$_4$, filtered and concentrated under reduced pressure. The residue was purified by flash chromatography on a silica gel column eluting with EtOAc/Heptanes (5-60%) to afford the desired product 2-allyloxy-N-[(3S)-6'-chloro-5-[[(1R,2R)-2-[(1S)-1-hydroxy-1-methyl-allyl]cyclobutyl]methyl]spiro[2,4-dihydro-1,5-benzoxazepine-3,1'-tetralin]-7-yl]sulfonyl-2-methyl-propanamide (83 mg, 73.0% yield). LCMS calc. for C$_{34}$H$_{44}$ClN$_2$O$_6$S [M+H]$^+$: m/z=643.25/645.25; Found: 643.4/645.5.

Step 8: (3R,6R,7S,8E,22S)-6'-chloro-7-hydroxy-7,12,12-trimethyl-15,15-dioxo-spiro[11,20-dioxa-15-thia-1,14-diazatetracyclo[14.7.2.0$^{3,6}$.0$^{19,24}$]pentacosa-8,16,18,24-tetraene-22,1'-tetralin]-13-one

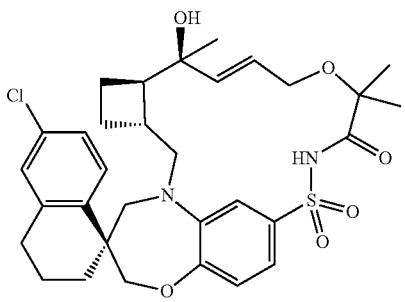 [SMILES: CC1(C)OC/C=C/[C@](C)(O)[C@@H]2CC[C@H]2CN2C[C@@]3(CCCc4cc(Cl)ccc43)COc3ccc(cc32)S(=O)(=O)NC1=O]

To a solution of 2-allyloxy-N-[(3S)-6'-chloro-5-[[(1R,2R)-2-[(1S)-1-hydroxy-1-methyl-allyl]cyclobutyl]methyl]spiro[2,4-dihydro-1,5-benzoxazepine-3,1'-tetralin]-7-yl]sulfonyl-2-methyl-propanamide (83.0 mg, 0.13 mmol) in DCE (80 mL) was bubbled with N$_2$ for 20 min. Then Zhan catalyst (18.92 mg, 0.03 mmol) was added and was bubbled with $N_2$ for another 5 min. The reaction mixture was stirred at 45° C. for 2h. Upon completion, the solvent was removed under reduced pressure. The residue was purified by flash chromatography on a silica gel column eluting with EtOAc/Heptanes (5-60%), and further purified with Prep-HPLC on a C18 column eluting with ACN/$H_2O$ (20%-100%) to afford the desired product (3R,6R,7S,8E,22S)-6'-chloro-7-hydroxy-7,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one (2.6 mg, 3.3% yield). LCMS calc. for $C_{32}H_{40}ClN_2O_6S$ $[M+H]^+$: m/z=615.23/617.23; Found: 615.4/617.5. $^1$H NMR (300 MHz, $CDCl_3$) δ 7.68 (d, J=8.5 Hz, 1H), 7.47 (s, 1H), 7.18 (d, J=9.2 Hz, 1H), 7.07 (d, J=2.3 Hz, 1H), 6.95 (s, 1H), 6.89 (d, J=2.2 Hz, 1H), 6.05 (s, 1H), 5.78 (d, J=15.4 Hz, 1H), 4.09 (s, 3H), 3.85-3.67 (m, 2H), 3.46 (d, J=14.5 Hz, 1H), 3.39-3.29 (m, 1H), 3.02 (d, J=14.2 Hz, 1H), 2.74 (d, J=19.5 Hz, 3H), 2.03-1.89 (m, 3H), 1.81 (t, J=8.5 Hz, 2H), 1.69 (s, 4H), 1.41 (s, 3H), 1.36 (s, 3H), 1.24 (d, J=7.2 Hz, 3H).

Step 9: [(3R,6R,7S,8E,22S)-6'-chloro-7,12,12-trimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate This compound was prepared using procedures analogous to those described for Example 34 using (3R,6R,7S,8E,22S)-6'-chloro-7-hydroxy-7,12,12-trimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one and dimethylcarbamoyl chloride. LCMS calc. for $C_{35}H_{45}ClN_3O_7S$ $[M+H]^+$: m/z=686.26/688.26; Found: 686.4/688.4. $^1$H NMR (300 MHz, $CDCl_3$) δ 7.70 (d, J=8.5 Hz, 1H), 7.48 (dd, J=8.3, 2.2 Hz, 1H), 7.19 (dd, J=8.5, 2.4 Hz, 1H), 7.10 (d, J=2.2 Hz, 1H), 6.98 (d, J=8.4 Hz, 1H), 6.93 (d, J=2.1 Hz, 1H), 6.04 (d, J=15.8 Hz, 1H), 5.85-5.71 (m, 1H), 4.09 (d, J=3.7 Hz, 2H), 3.92-3.83 (m, 1H), 3.78 (d, J=14.6 Hz, 1H), 3.59 (d, J=15.1 Hz, 1H), 3.34 (d, J=14.3 Hz, 1H), 3.10 (dd, J=15.1, 10.8 Hz, 1H), 2.94 (d, J=5.1 Hz, 6H), 2.79 (s, 2H), 2.24 (t, J=9.1 Hz, 1H), 2.01 (d, J=6.3 Hz, 2H), 1.85 (d, J=8.9 Hz, 1H), 1.65 (d, J=8.8 Hz, 7H), 1.61 (s, 3H), 1.43 (s, 3H), 1.36 (s, 3H).

Example 294

[(3R,6R,7S,8E,15S,25S)-6'-Chloro-16,18,18-trioxo-spiro[23-oxa-18-thia-1,11,17-triazapentacyclo[17.7.2.03,6.011,15.022,27]octacosa-8,19,21,27-tetraene-25,1'-tetralin]-7-yl] N,N-dimethylcarbamate

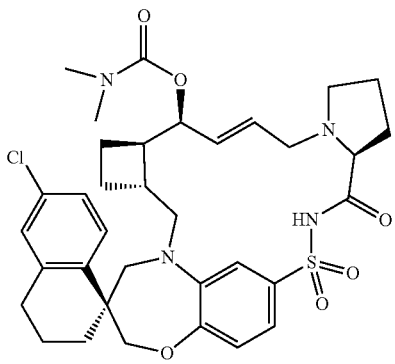 [SMILES: CN(C)C(=O)O[C@H]1/C=C/CN2CCC[C@H]2C(=O)NS(=O)(=O)c2ccc3c(c2)N(C[C@@H]2CC[C@H]21)C[C@@]1(CCCc2cc(Cl)ccc21)CO3]

This compound was prepared using procedures analogous to those described for Example 292 Step 2-5 using (2S)-1-allylpyrrolidine-2-carboxylic acid HCl (Example 100 Step 2) and (3S)-6'-chloro-5-[[(1R,2R)-2-[(1S)-1-hydroxyallyl]cyclobutyl]methyl]spiro[2,4-dihydro-1,5-benzoxazepine-3,1'-tetralin]-7-sulfonamide (Intermediate 3) in Step 2, and dimethylcarbamoyl chloride in Step 5. LCMS calc. for $C_{35}H_{44}ClN_5O_6S$ $[M+H]^+$: m/z=683.26/685.26; Found: 683.4/685.4. $^1$H NMR (300 MHz, DMSO-$d_6$) δ 8.96 (s, 1H), 7.62 (dd, J=8.6, 1.8 Hz, 1H), 7.29 (dd, J=8.5, 2.3 Hz, 1H), 7.16 (dd, J=3.7, 2.1 Hz, 2H), 6.99 (dd, J=8.1, 1.8 Hz, 1H), 6.76 (dd, J=8.2, 1.7 Hz, 1H), 5.88 (dd, J=15.6, 3.0 Hz, 1H), 5.18 (d, J=10.9 Hz, 1H), 5.08-4.93 (m, 1H), 4.05 (d, J=12.2 Hz, 1H), 3.92 (d, J=12.3 Hz, 1H), 3.75-3.58 (m, 3H), 3.57-3.42 (m, 3H), 3.17 (s, 1H), 3.14-3.08 (m, 1H), 3.05 (d, J=4.4 Hz, 1H), 2.96 (d, J=6.6 Hz, 1H), 2.78-2.70 (m, 1H), 2.66 (s, 3H), 2.51 (s, 3H), 2.41 (t, J=8.0 Hz, 2H), 2.33-2.24 (m, 1H), 2.15-1.85 (m, 5H), 1.79-1.59 (m, 5H), 1.38 (d, J=10.2 Hz, 1H).

Example 295

[(3R,6R,7S,8E,22S)-6'-Chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl] N-[(3S)-tetrahydrofuran-3-yl]carbamate

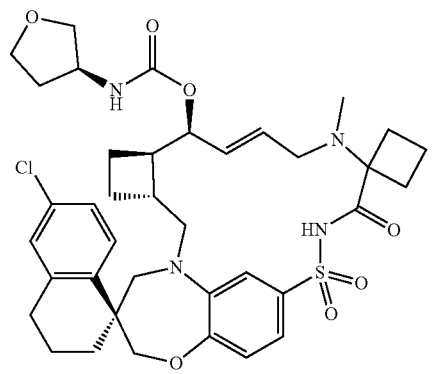 [SMILES: CN1C/C=C/[C@H](OC(=O)N[C@H]2CCOC2)[C@@H]2CC[C@H]2CN2C[C@@]3(CCCc4cc(Cl)ccc43)COc3ccc(cc32)S(=O)(=O)NC(=O)C12CCC2]

This compound was prepared using procedures analogous to those described for Example 63 Step 1-2 using (3R,6R,7S,8E,22S)-6'-chloro-7-hydroxy-11-methyl-12,12-(1,3-propylene)-15,15-dioxo-spiro[20-oxa-15-thia-1,11,14-triazatetracyclo[14.7.2.03,6.019,24]pentacosa-8,16(25),17,19(24)-tetraene-22,1'-tetralin]-13-one (Example 48 Step 8) in Step 2 and (3S)-tetrahydrofuran-3-amine in Step 1. LCMS calc. for $C_{38}H_{48}ClN_4O_7S$ $[M+H]^+$: m/z=739.29/741.29; Found: 739.3/741.4.

Example 296

(23S)-6'-Chloro-16,16-dioxo-spiro[21-oxa-16-thia-1,6,12,15,27-pentazapentacyclo[15.7.2.13,6.19,12.020,25]octacosa-9(27),10,17,19,25-pentaene-23,1'-tetralin]-7,14-dione

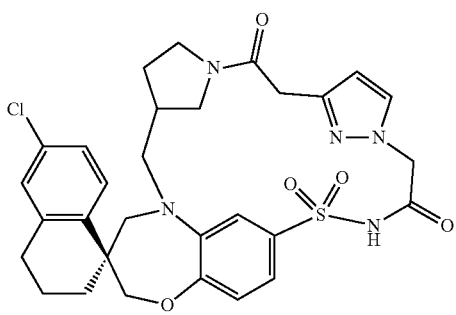 [SMILES: O=C1Cn2ccc(n2)CC(=O)N2CCC(C2)CN2C[C@@]3(CCCc4cc(Cl)ccc43)COc3ccc(cc32)S(=O)(=O)N1]

Step 1: ethyl 2-[1-(2-tert-butoxy-2-oxo-ethyl)pyrazol-3-yl]acetate

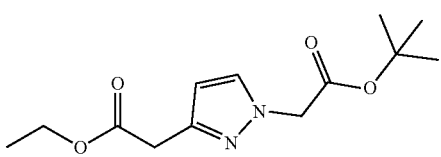 [SMILES: CCOC(=O)Cc1ccn(CC(=O)OC(C)(C)C)n1]

To a mixture of ethyl 2-(1H-pyrazol-3-yl)acetate (1.0 g, 6.49 mmol) and cesium carbonate (4.25 g, 12.97 mmol) in DMF (35 mL) was added t-butyl bromoacetate (1.9 g, 9.73 mmol) dropwise. The mixture was stirred at r.t. overnight. The mixture was diluted with ethyl acetate (50 mL), washed with water (30 mL×3). The organic layer was dried over $Na_2SO_4$, filtered, and concentrated. The residue was purified with reverse phase HPLC (0.01% ammonia in water and acetonitrile) to get ethyl 2-[1-(2-tert-butoxy-2-oxo-ethyl)pyrazol-3-yl]acetate (370.5 mg, 20.6% yield) as a pale yellow oil. LCMS calc. for $C_{13}H_{21}N_2O_4$ $[M+H]^+$: m/z=269.14; Found: 269.1. $^1$H NMR (400 MHz, $CDCl_3$-d) δ 1.26 (t, J=7.2 Hz, 3H), 1.47 (s, 9H), 3.69 (s, 2H), 4.17 (q, J=6.8 Hz, 2H), 4.77 (s, 2H), 6.30 (d, J=2.4 Hz, 1H), 7.41 (d, J=2.4 Hz, 1H).

Step 2: 2-[1-(2-tert-butoxy-2-oxo-ethyl)pyrazol-3-yl]acetic acid

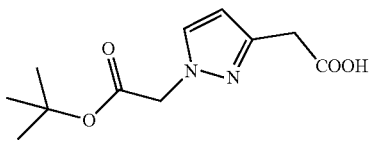 [SMILES: CC(C)(C)OC(=O)Cn1ccc(CC(=O)O)n1]

To a stirred solution of ethyl 2-[1-(2-tert-butoxy-2-oxo-ethyl)pyrazol-3-yl]acetate (128.0 mg, 0.48 mmol) in THF (1 mL), water (1 mL) and methanol (1 mL) was added lithium hydroxide monohydrate (22.02 mg, 0.52 mmol). The resulting mixture was stirred at r.t. overnight. LCMS indicated the consumption of starting material and the formation of desired product. Water (5 mL) was added followed by 5 mL of DCM. The pH of aqueous layer was adjusted to 2-3 by adding 0.1 M HCl. The layers were separated, and the aqueous layer was extracted with EtOAc (10 mL×3). The combined organic layers were dried over $Na_2SO_4$, filtered, and concentrated under reduced pressure. The residue was purified by flash chromatography on a silica gel column (12 g) with EtOAc/Heptanes (20% to 100%) to afford 2-[1-(2-tert-butoxy-2-oxo-ethyl)pyrazol-3-yl]acetic acid (115 mg) as a light yellow solid. LCMS calc. for $C_{11}H_{15}N_2O_4S$ $[M-H]^-$: m/z=239.1; Found: 239.2.

Step 3: tert-butyl 3-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]pyrrolidine-1-carboxylate

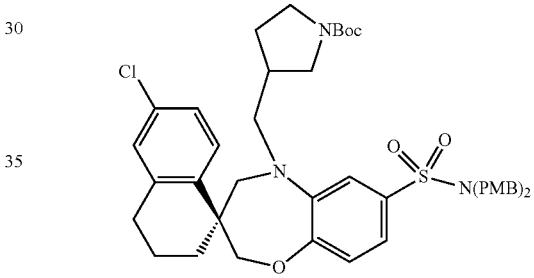

To a stirred solution of (3S)-6'-chloro-N,N-bis[[(4-methoxyphenyl)methyl]spiro[4,5-dihydro-2H-1,5-benzoxazepine-3,1'-tetralin]-7-sulfonamide (1.0 g, 1.62 mmol, Intermediate 2) in DCM (3 mL) was added tert-butyl 3-formylpyrrolidine-1-carboxylate (0.39 g, 1.94 mmol). The resulting mixture was then cooled to 0° C. TFA (1.24 mL, 16.15 mmol) was added to this solution followed by sodium borohydride (1.22 g, 32.3 mmol). The resulting mixture was further stirred at 0° C. for 30 min., then slowly warmed up to r.t. LCMS showed the consumption of starting material and the formation of desired product. MeOH (2 mL) was added to quench the reaction. Water (10 mL) was added followed by 10 mL of DCM. The pH of aqueous layer was adjusted to 7-8 by adding saturated sodium bicarbonate solution. The layers were separated, and the aqueous layer was extracted with DCM (10 mL×2). The combined organic layers were dried over $Na_2SO_4$, filtered and concentrated to afford tert-butyl 3-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]pyrrolidine-1-carboxylate (660 mg, 50.9% yield) which was used in next step without further purification. LCMS calc. for $C_{44}H_{53}ClN_3O_7S$ $[M+H]^+$: m/z=802.3/804.3; Found: 802.5/804.6.

Step 4: (3S)-6'-chloro-5-(pyrrolidin-3-ylmethyl)spiro[2,4-dihydro-1,5-benzoxazepine-3,1'-tetralin]-7-sulfonamide

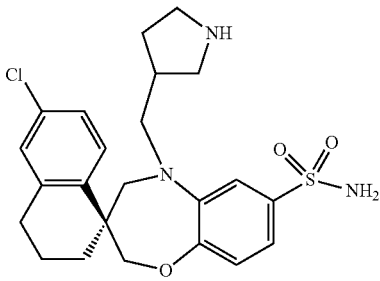 [SMILES: NS(=O)(=O)c1ccc2c(c1)N(CC1CCNC1)C[C@@]1(CCCc3cc(Cl)ccc31)CO2]

To a stirred solution of tert-butyl 3-[[(3S)-7-[bis[(4-methoxyphenyl)methyl]sulfamoyl]-6'-chloro-spiro[2,4-dihydro-1,5-benzoxazepine-3,1'-tetralin]-5-yl]methyl]pyrrolidine-1-carboxylate (0.66 g, 0.82 mmol) in DCM (10 mL) was added TFA slowly. The resulting mixture was kept stirring at r.t. overnight. The reaction was slowly poured into 100 mL of saturated sodium carbonate solution under an ice bath. Then the mixture was extracted with DCM (50 mL×3). The combined organic layers were dried over Na$_2$SO$_4$, filtered and concentrated to afford (3S)-6'-chloro-5-(pyrrolidin-3-ylmethyl)spiro[2,4-dihydro-1,5-benzoxazepine-3,1'-tetralin]-7-sulfonamide (400 mg) as a white solid. The crude product was used in next step without further purification. LCMS calc. for C$_{23}$H$_{29}$ClN$_3$O$_3$S [M+H]$^+$: m/z=462.2/464.2; Found: 462.6/464.5.

Step 5: tert-butyl 3-[[(3S)-6'-chloro-7-sulfamoyl-spiro[2,4-dihydro-1,5-benzoxazepine-3,1'-tetralin]-5-yl]methyl]pyrrolidine-1-carboxylate

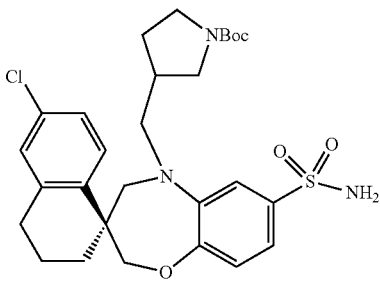 [SMILES: CC(C)(C)OC(=O)N1CCC(CN2C[C@@]3(CCCc4cc(Cl)ccc43)COc3ccc(S(N)(=O)=O)cc32)C1]

To a solution of (3S)-6'-chloro-5-(pyrrolidin-3-ylmethyl)spiro[2,4-dihydro-1,5-benzoxazepine-3,1'-tetralin]-7-sulfonamide (160.0 mg, 0.35 mmol) in methanol (5 mL) was added di-tert butyl dicarbonate (113.38 mg, 0.52 mmol). The resulting mixture was stirred at r.t. LCMS indicated the consumption of starting material and the formation of desired product. Water (20 mL) was added and extracted with DCM (20 mL×3). The combined organic layers were dried over Na$_2$SO$_4$, filtered and concentrated. The residue was purified by flash chromatography on a silica gel column (12 g) with EtOAc/Heptanes (20% to 100%) to afford tert-butyl 3-[[(3S)-6'-chloro-7-sulfamoyl-spiro[2,4-dihydro-1,5-benzoxazepine-3,1'-tetralin]-5-yl]methyl]pyrrolidine-1-carboxylate (103 mg, 52.9% yield) as a colorless oil. LCMS calc. for C$_{28}$H$_{37}$ClN$_3$O$_5$S [M+H]$^+$: m/z=562.2/564.2; Found: 562.5/564.7.

Step 6: tert-butyl 3-[[(3S)-6'-chloro-7-sulfamoyl-spiro[2,4-dihydro-1,5-benzoxazepine-3,1'-tetralin]-5-yl]methyl]pyrrolidine-1-carboxylate

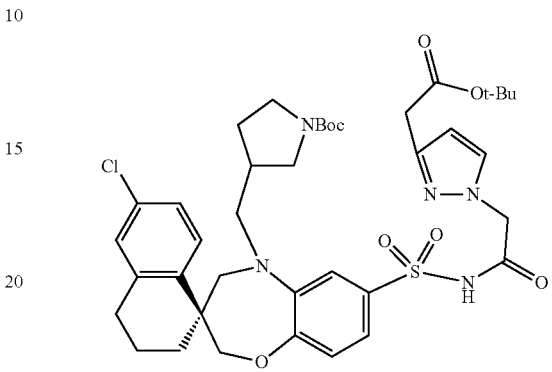

To a stirred solution of tert-butyl 3-[[(3S)-6'-chloro-7-sulfamoyl-spiro[2,4-dihydro-1,5-benzoxazepine-3,1'-tetralin]-5-yl]methyl]pyrrolidine-1-carboxylate (80.0 mg, 0.14 mmol) in DCM (2 mL) was added 2-[1-(2-tert-butoxy-2-oxo-ethyl)pyrazol-3-yl]acetic acid (68.39 mg, 0.28 mmol) followed by EDCI (0.06 mL, 0.28 mmol) and DMAP (69.55 mg, 0.57 mmol). The resulting mixture was stirred at r.t. overnight. The reaction was quenched by adding 5 mL of 1 M HCl (5 mL) and extracted with DCM (5 mL×3). The combined organic layers were dried over Na$_2$SO$_4$, filtered and concentrated under reduced pressure. The residue was purified by prep-HPLC on a C18 column (30×250 mm, 10 m) with MeCN/H$_2$O (20% to 100%) to afford tert-butyl 3-[[(3S)-7-[[2-[1-(2-tert-butoxy-2-oxo-ethyl)pyrazol-3-yl]acetyl]sulfamoyl]-6'-chloro-spiro[2,4-dihydro-1,5-benzoxazepine-3,1'-tetralin]-5-yl]methyl]pyrrolidine-1-carboxylate (62 mg, 55.5% yield) as a white solid. LCMS calc. for C$_{39}$H$_{51}$ClN$_5$O$_8$S [M+H]$^+$: m/z=784.3/786.3; Found: 784.5/786.5.

Step 7: 2-[3-[2-oxo-2-[[(3S)-6'-chloro-5-(pyrrolidin-3-ylmethyl)spiro[2,4-dihydro-1,5-benzoxazepine-3,1'-tetralin]-7-yl]sulfonylamino]ethyl]pyrazol-1-yl]acetic acid

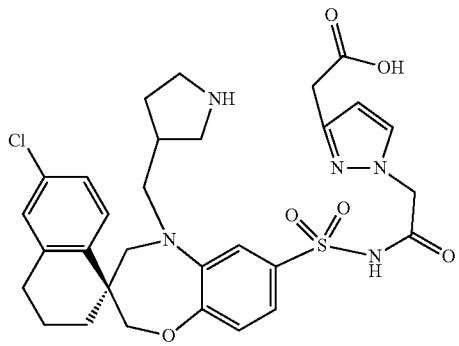 [SMILES: O=C(O)Cc1ccn(CC(=O)NS(=O)(=O)c2ccc3c(c2)N(CC2CCNC2)C[C@@]2(CCCc4cc(Cl)ccc42)CO3)n1]

To a stirred solution of tert-butyl 3-[[(3S)-7-[[2-[1-(2-tert-butoxy-2-oxo-ethyl)pyrazol-3-yl]acetyl]sulfamoyl]-6'-chloro-spiro[2,4-dihydro-1,5-benzoxazepine-3,1'-tetralin]-5-yl]methyl]pyrrolidine-1-carboxylate (62.0 mg, 0.08 mmol) in DCM (2 mL) was added phosphoric acid (0.05 mL, 0.79 mmol). The resulting mixture was stirred at r.t. for 24 h. The solution was slowly poured into a 30 mL of saturated sodium bicarbonate solution and the pH of aqueous layer was adjusted to ~4-5 by adding 1 M HCl. The mixture was extracted with EtOAc (10 mL×3). The combined organic layers were dried over Na$_2$SO$_4$, filtered and concentrated. The residue was purified by prep-HPLC on a C18 column (30×250 mm, 10 m) with MeCN/H$_2$O (20% to 100%) to afford 2-[3-[2-oxo-2-[[(3S)-6'-chloro-5-(pyrrolidin-3-ylmethyl)spiro[2,4-dihydro-1,5-benzoxazepine-3,1'-tetralin]-7-yl]sulfonylamino]ethyl]pyrazol-1-yl]acetic acid (31 mg, 50.0% yield) as a white solid. LCMS calc. for C$_{30}$H$_{35}$ClN$_5$O$_6$S [M+H]$^+$: m/z=628.2/630.2; Found: 628.4/630.5.

Step 8: (23S)-6'-chloro-16,16-dioxo-spiro[21-oxa-16-thia-1,6,12,15,27-pentazapentacyclo[15.7.2.13, 6.19,12.020,25]octacosa-9(27),10,17,19,25-pentaene-23,1'-tetralin]-7,14-dione To a stirred solution of 2-[3-[2-oxo-2-[[(3S)-6'-chloro-5-(pyrrolidin-3-ylmethyl)spiro[2,4-dihydro-1,5-benzoxazepine-3,1'-tetralin]-7-yl]sulfonylamino]ethyl]pyrazol-1-yl]acetic acid (31.0 mg, 0.05 mmol) in DMF (25 mL) was added HATU (56.3 mg, 0.15 mmol) followed by DIPEA (0.03 mL, 0.15 mmol). The resulting solution was stirred at r.t. for 2 h. Water (50 mL) was added, and extracted with ethyl acetate (25 mL×3). The combined organic layers were washed with water (25 mL), dried over Na$_2$SO$_4$, filtered and concentrated under reduced pressure. The residue was purified by prep-HPLC on a C18 column (30×250 mm, 10 m) with MeCN/H$_2$O (20% to 100%) to afford (23 S)-6'-chloro-16,16-dioxo-spiro[21-oxa-16-thia-1,6,12,15,27-pentazapentacyclo[15.7.2.13,6.19,12.020,25]octacosa-9(27), 10,17,19, 25-pentaene-23,1'-tetralin]-7,14-dione (9.1 mg, 30.2% yield) as a white solid. LCMS calc. for C$_{30}$H$_{33}$ClN$_5$O$_5$S [M+H]$^+$: m/z=610.2/612.2; Found: 610.4/612.3.

Example 297

(23S)-6'-Chloro-16,16-dioxo-spiro[21-oxa-thia-1,6,9,15,27-pentazapentacyclo[15.7.2.13,6.19,12.020, 25]octacosa-10,12(27),17,19,25-pentaene-23,1'-tetralin]-7,14-dione

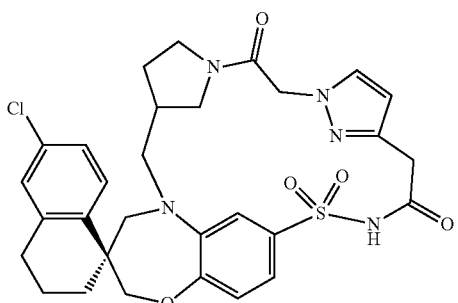

Step 1: 2-[1-(2-ethoxy-2-oxo-ethyl)pyrazol-3-yl] acetic acid

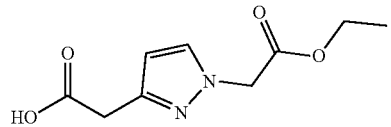

This compound was prepared using procedures analogous to those described for Example 296 Step 1-2 using tert-butyl 2-(1H-pyrazol-3-yl)acetate and ethyl bromoacetate in Step 1. LCMS calc. for C$_9$H$_{14}$N$_2$O$_4$ [M+H]$^+$: m/z=213.1; Found: 213.2.

Step 2: ethyl 2-[3-[2-[[(3S)-6'-chloro-5-(pyrrolidin-3-ylmethyl)spiro[2,4-dihydro-1,5-benzoxazepine-3, 1'-tetralin]-7-yl]sulfonylamino]-2-oxo-ethyl]pyrazol-1-yl]acetate

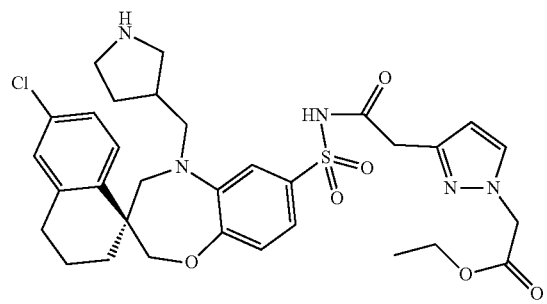 [SMILES: CCOC(=O)Cn1ccc(CC(=O)NS(=O)(=O)c2ccc3c(c2)N(CC2CCNC2)C[C@@]2(CCCc4cc(Cl)ccc42)CO3)n1]

This compound was prepared using procedures analogous to those described for Example 296 Step 6-7 using 2-[1-(2-ethoxy-2-oxo-ethyl)pyrazol-3-yl]acetic acid to replace 2-[1-(2-tert-butoxy-2-oxo-ethyl)pyrazol-3-yl]acetic acid in Step 6. LCMS calc. for C$_{32}$H$_{39}$ClN$_5$O$_6$S [M+H]$^+$: m/z=656.2/658.2; Found: 656.4/658.4.

Step 3: 2-[3-[2-[[(3S)-6'-chloro-5-(pyrrolidin-3-ylmethyl)spiro[2,4-dihydro-1,5-benzoxazepine-3,1'-tetralin]-7-yl]sulfonylamino]-2-oxo-ethyl]pyrazol-1-yl]acetic acid

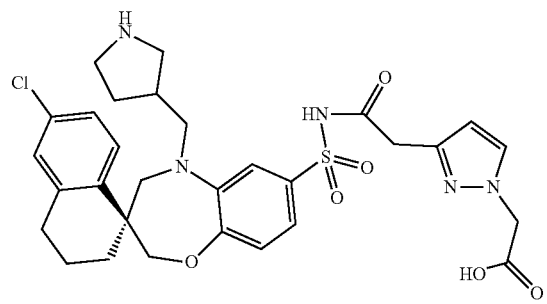 [SMILES: O=C(O)Cn1ccc(CC(=O)NS(=O)(=O)c2ccc3c(c2)N(CC2CCNC2)C[C@@]2(CCCc4cc(Cl)ccc42)CO3)n1]

To a solution of ethyl 2-[3-[2-[[(3S)-6'-chloro-5-(pyrrolidin-3-ylmethyl)spiro[2,4-dihydro-1,5-benzoxazepine-3,1'-tetralin]-7-yl]sulfonylamino]-2-oxo-ethyl]pyrazol-1-yl]acetate (25.0 mg, 0.04 mmol) in methanol (0.50 mL) and THF (0.50 mL) was added lithium hydroxide monohydrate (4.8 mg, 0.11 mmol) in water (0.50 mL). The resulting solution was stirred at 40° C. for 2 h. The reaction mixture was quenched with 1M HCl aqueous solution to pH 5-6 and extracted with EtOAc. The combined organic layers were concentrated under reduced pressure to afford 2-[3-[2-[[(3S)-6'-chloro-5-(pyrrolidin-3-ylmethyl)spiro[2,4-dihydro-1,5-benzoxazepine-3,1'-tetralin]-7-yl]sulfonylamino]-2-oxo-ethyl]pyrazol-1-yl]acetic acid (21 mg, 87.7% yield) as a white solid. LC-MS: calc. for $C_{30}H_{35}ClN_5O_6S$ [M+H]$^+$: m/z=628.1/630.2; Found: 628.3/630.2.

Step 4: (23S)-6'-chloro-16,16-dioxo-spiro[21-oxa-thia-1,6,9,15,27-pentazapentacyclo[15.7.2.13,6.19,12.020,25]octacosa-10,12(27),17,19,25-pentaene-23,1'-tetralin]-7,14-dione This compound was prepared using procedures analogous to those described for Example 296 Step. LCMS calc. for $C_{30}H_{33}ClN_5O_5S$ [M+H]$^+$: m/z=610.2/612.2; Found 610.2/612.2.

Example 298

[(3R,6R,7S,8E,22R)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-isochromane]-7-yl] N-methyl-N-(oxetan-3-yl)carbamate

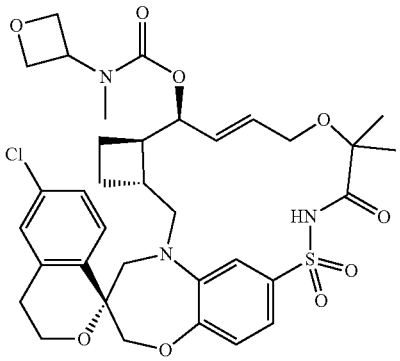 [SMILES: CN(C(=O)O[C@H]1/C=C/COC(C)(C)C(=O)NS(=O)(=O)c2ccc3c(c2)N(C[C@@H]2CC[C@H]21)C[C@]1(CO3)OCCc2cc(Cl)ccc21)C1COC1]

This compound was prepared using procedures analogous to those described for Example 63 Step 1-2 using (3R,6R,7S,8E,22R)-6'-Chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-isochromane]-13-one (Example 249) in Step 2 and N-methyl-oxetan-3-amine in Step 1. LCMS calc. for $C_{35}H_{43}ClN_3O_9S$ [M+H]$^+$: m/z=716.23/718.23; Found: 716.0/718.1. $^1$H NMR (300 MHz, Chloroform-d) δ 7.54 (dd, J=8.3, 2.1 Hz, 1H), 7.49 (d, J=8.5 Hz, 1H), 7.25 (d, J=2.3 Hz, 1H), 7.17 (d, J=2.2 Hz, 1H), 7.10 (d, J=2.3 Hz, 1H), 7.01 (dd, J=8.4, 1.1 Hz, 1H), 5.93-5.83 (m, 1H), 5.67 (dd, J=15.6, 5.9 Hz, 1H), 4.92-4.74 (m, 5H), 4.33 (d, J=11.8 Hz, 1H), 4.16 (d, J=11.8 Hz, 1H), 4.05-3.93 (m, 3H), 3.66 (td, J=15.5, 14.8, 4.6 Hz, 4H), 3.34 (dd, J=15.0, 5.2 Hz, 1H), 3.16 (s, 3H), 2.96 (dd, J=9.1, 6.0 Hz, 1H), 2.83-2.70 (m, 2H), 2.47-2.35 (m, 1H), 2.16-2.05 (m, 1H), 1.88 (q, J=10.6, 9.9 Hz, 2H), 1.65 (d, J=9.5 Hz, 2H), 1.43 (s, 3H), 1.35 (s, 3H).

Example 299

[(3R,6R,7S,8E,22R)-6'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-isochromane]-7-yl] N-methyl-N-[(3R)-tetrahydrofuran-3-yl]carbamate

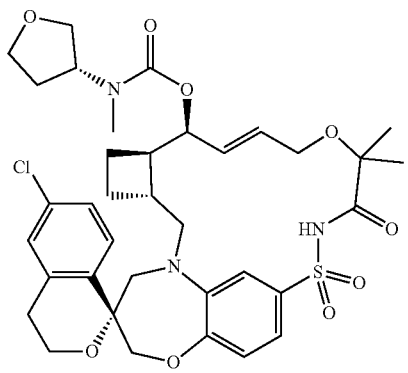 [SMILES: CN(C(=O)O[C@H]1/C=C/COC(C)(C)C(=O)NS(=O)(=O)c2ccc3c(c2)N(C[C@@H]2CC[C@H]21)C[C@]1(CO3)OCCc2cc(Cl)ccc21)[C@@H]1CCOC1]

This compound was prepared using procedures analogous to those described for Example 63 Step 1-2 using (3R,6R,7S,8E,22R)-6'-Chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-isochromane]-13-one (Example 249) in Step 2 and (3R)-N-methyltetrahydrofuran-3-amine hydrochloride in Step 1. LCMS calc. for $C_{36}H_{45}ClN_3O_9S$ [M+H]$^+$: m/z=730.25/732.25; Found: 730.0/732.2. $^1$H NMR (300 MHz, Chloroform-d) δ 7.53 (dd, J=8.3, 2.1 Hz, 1H), 7.49 (d, J=8.4 Hz, 1H), 7.26 (dd, J=8.4, 2.2 Hz, 1H), 7.17 (d, J=2.2 Hz, 1H), 7.10 (d, J=2.2 Hz, 1H), 7.01 (d, J=8.4 Hz, 1H), 5.93-5.82 (m, 1H), 5.67 (dd, J=15.7, 5.6 Hz, 1H), 5.34 (s, 1H), 4.96 (s, 1H), 4.33 (d, J=11.8 Hz, 1H), 4.16 (d, J=11.8 Hz, 1H), 4.10-3.91 (m, 4H), 3.80 (s, 2H), 3.74-3.50 (m, 5H), 3.37 (d, J=5.1 Hz, 1H), 2.95 (s, 3H), 2.90-2.82 (m, 1H), 2.81-2.69 (m, 1H), 2.48-2.36 (m, 1H), 2.26 (ddd, J=13.1, 8.9, 4.8 Hz, 1H), 2.17-2.00 (m, 2H), 1.89 (dq, J=19.4, 9.4 Hz, 3H), 1.66 (t, J=9.4 Hz, 2H), 1.44 (s, 3H), 1.35 (s, 3H).

Example 300

[(3R,6R,7S,8E,22R)-6'-Chloro-12,12-dimethyl-13,15,15-trio-spiro[11,20-dioxa-15-thia-1,14-diazatetracyclo[14.7.2.03,6.019,24]pentacosa-8,16,18,24-tetraene-22,1'-isochromane]-7-yl] N-methyl-N-tetrahydropyran-4-yl-carbamate

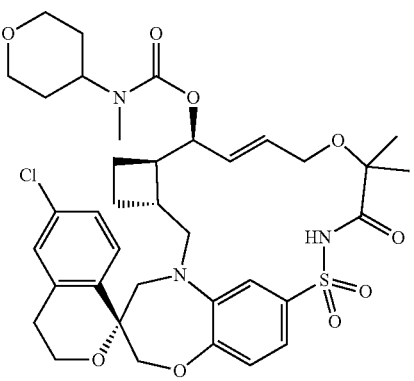 [SMILES: CN(C(=O)O[C@H]1/C=C/COC(C)(C)C(=O)NS(=O)(=O)c2ccc3c(c2)N(C[C@@H]2CC[C@H]21)C[C@]1(CO3)OCCc2cc(Cl)ccc21)C1CCOCC1]

541

This compound was prepared using procedures analogous to those described for Example 63 Step 1-2 using (3R,6R,7S,8E,22R)-6'-Chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-isochromane]-13-one (Example 249) in Step 2 and N-methyltetrahydropyran-4-amine in Step 1. LCMS calc. for $C_{37}H_{47}ClN_3O_9S$ [M+H]$^+$: m/z=744.26/746.26; Found: 744.1/746.2. $^1$H NMR (300 MHz, Chloroform-d) δ 7.59-7.44 (m, 2H), 7.26 (dd, J=8.4, 2.2 Hz, 1H), 7.17 (d, J=2.2 Hz, 1H), 7.12 (d, J=2.3 Hz, 1H), 7.01 (d, J=8.4 Hz, 1H), 5.86 (d, J=16.0 Hz, 1H), 5.66 (d, J=16.1 Hz, 1H), 5.34 (s, 1H), 4.33 (d, J=11.8 Hz, 1H), 4.17 (d, J=11.9 Hz, 1H), 4.10-3.88 (m, 5H), 3.75-3.59 (m, 4H), 3.46 (d, J=11.9 Hz, 1H), 3.35 (dd, J=15.0, 5.4 Hz, 1H), 3.05-2.95 (m, 1H), 2.88 (d, J=17.0 Hz, 3H), 2.76 (dt, J=16.3, 3.8 Hz, 1H), 2.50-2.34 (m, 1H), 2.15-1.99 (m, 1H), 1.88 (dd, J=21.4, 10.2 Hz, 4H), 1.66 (t, J=9.0 Hz, 6H), 1.43 (s, 3H), 1.35 (s, 3H).

Example 301

[(3R,6R,7S,8E,22S)-7'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,4'-chromane]-7-yl] N-methyl-N-[(3R)-tetrahydrofuran-3-yl]carbamate

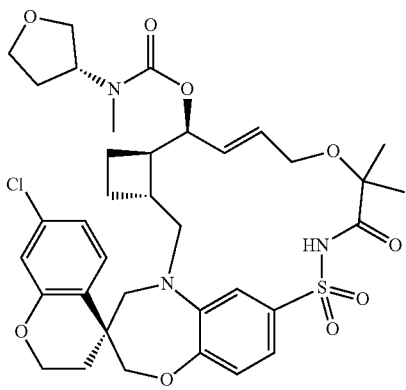 [SMILES: CN(C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3)[C@@H]1CCOC1]

This compound was prepared using procedures analogous to those described for Example 63 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one (Example 246) in Step 2 and (3R)-N-methyltetrahydrofuran-3-amine hydrochloride in Step 1. LCMS calc. for $C_{36}H_{45}ClN_3O_9S$ [M+H]$^+$: m/z=730.25/732.25; Found: 730.1/732.1. $^1$H NMR (300 MHz, CDCl$_3$) δ 9.10 (s, 1H), 7.60-7.48 (m, 2H), 7.06-6.99 (m, 2H), 6.93 (dt, J=8.5, 1.6 Hz, 1H), 6.86 (d, J=2.1 Hz, 1H), 5.87-5.63 (m, 2H), 5.27 (d, J=16.4 Hz, 2H), 4.91 (s, 1H), 4.36-4.00 (m, 7H), 3.84-3.68 (m, 5H), 3.49-3.32 (m, 2H), 3.23 (dd, J=15.0, 8.9 Hz, 1H), 2.91 (s, 3H), 2.41 (qd, J=9.3, 3.3 Hz, 1H), 2.27 (dtd, J=13.3, 8.4, 4.8 Hz, 1H), 2.09-1.98 (m, 2H), 1.91-1.77 (m, 3H), 1.66 (q, J=9.4 Hz, 1H), 1.44 (s, 3H), 1.36 (s, 3H).

Example 302

[(3R,6R,7S,8E,22S)-7'-Chloro-12,12-dimethyl-13,15,15-trioxo-spiro[11,20-dioxa-15-dioxa-15-thia-1,14-diazatetracyclo[14.7.2.03,6.019,24]pentacosa-8,16,18,24-tetraene-22,4'-chromane]-7-yl] N-[(3R)-tetrahydrofuran-3-yl]carbamate

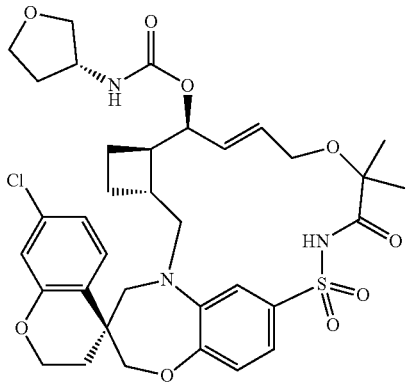 [SMILES: CC1(C)OC/C=C/[C@H](OC(=O)N[C@@H]2CCOC2)[C@@H]2CC[C@H]2CN2C[C@@]3(CCOc4cc(Cl)ccc43)COc3ccc(cc32)S(=O)(=O)NC1=O]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one (Example 246) in Step 1 and (3R)-tetrahydrofuran-3-amine in Step 2. LCMS calc. for $C_{35}H_{43}ClN_3O_9S$ [M+H]$^+$: m/z=716.23/718.23; Found: 716.52/718.09. $^1$H NMR (300 MHz, CDCl$_3$) δ 9.05 (s, 1H), 7.54 (t, J=14.5 Hz, 2H), 7.14 (s, 1H), 7.05 (d, J=8.3 Hz, 1H), 6.95 (dd, J=8.4, 2.0 Hz, 1H), 6.88 (d, J=1.9 Hz, 1H), 5.83-5.64 (m, 2H), 5.18 (s, 1H), 4.26 (m, 3H), 4.16-4.07 (m, 2H), 4.03-3.95 (m, 1H), 3.86 (d, J=5.8 Hz, 2H), 3.77 (d, J=13.5 Hz, 2H), 3.44 (t, J=12.4 Hz, 2H), 3.22 (d, J=6.9 Hz, 3H), 2.79 (d, J=6.4 Hz, 1H), 2.40 (s, 1H), 2.32-2.20 (m, 1H), 2.11-1.99 (m, 2H), 1.83 (dd, J=32.2, 8.6 Hz, 4H), 1.69-1.60 (m, 1H), 1.44 (s, 3H), 1.39 (s, 3H).

Example 303

[(3R,6R,7S,8E,22S)-7'-Chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,4'-chromane]-7-yl] N-methyl-N-(oxetan-3-yl)carbamate

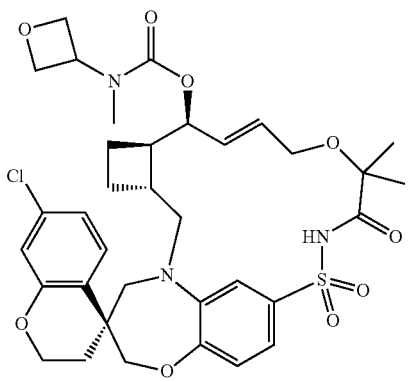 [SMILES: CN(C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3)C1COC1]

This compound was prepared using procedures analogous to those described for Example 63 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 2 and N-methyloxetan-3-amine in Step 1. LCMS calc. for $C_{35}H_{41}ClN_3O_9S$ [M−H]⁻: m/z=714.2/716.2; Found 713.8/715.8. ¹H NMR (300 MHz, CDCl₃) δ 7.56 (dd, J=8.4, 2.1 Hz, 2H), 7.05 (dd, J=8.3, 1.8 Hz, 2H), 6.95 (dd, J=8.6, 2.2 Hz, 1H), 6.88 (d, J=2.2 Hz, 1H), 5.74 (t, J=8.0 Hz, 2H), 5.28 (d, J=4.6 Hz, 1H), 4.89-4.73 (m, 3H), 4.43-3.98 (m, 6H), 3.87-3.69 (m, 3H), 3.50-3.20 (m, 3H), 3.12 (s, 3H), 2.50-2.32 (m, 1H), 2.25 (t, J=7.6 Hz, 1H), 2.17-1.76 (m, 7H), 1.46 (s, 3H), 1.37 (s, 3H).

Example 304

[(3R,6R,7S,8E,22S)-7'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N-methyl-N-tetrahydropyran-4-yl-carbamate

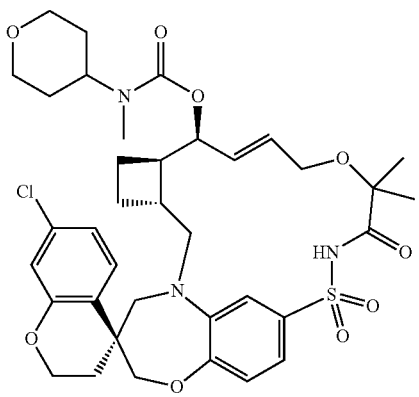 [SMILES: CN(C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3)C1CCOCC1]

This compound was prepared using procedures analogous to those described for Example 63 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 2 and N-methyltetrahydropyran-4-amine in Step 1. LCMS calc. for $C_{37}H_{47}ClN_3O_9S$ [M+H]⁺: m/z=744.26/746.26; Found: 744.2/746.2. ¹H NMR (300 MHz, CDCl₃) δ 9.04 (s, 1H), 7.60-7.46 (m, 2H), 7.09-6.99 (m, 2H), 6.93 (dd, J=8.4, 2.2 Hz, 1H), 6.86 (d, J=2.1 Hz, 1H), 5.84-5.63 (m, 2H), 5.31 (t, J=4.3 Hz, 1H), 4.39-3.92 (m, 9H), 3.76 (t, J=12.2 Hz, 2H), 3.52-3.34 (m, 4H), 3.27 (d, J=8.8 Hz, 1H), 2.85 (s, 3H), 2.51-2.35 (m, 1H), 2.12-1.98 (m, 2H), 1.81 (q, J=12.0, 10.8 Hz, 4H), 1.65 (d, J=6.8 Hz, 4H), 1.44 (s, 3H), 1.36 (s, 3H).

Example 305

[(3R,6R,7S,8E,22S)-7'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N-tetrahydropyran-4-yl-carbamate

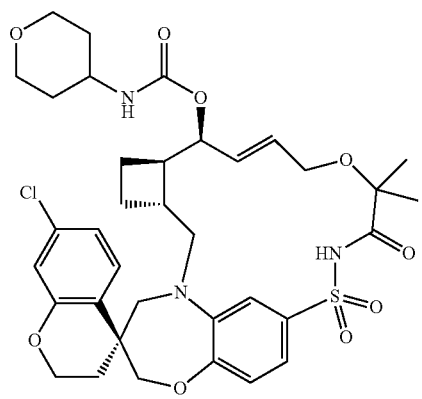 [SMILES: CC1(C)OC/C=C/[C@H](OC(=O)NC2CCOCC2)[C@@H]2CC[C@H]2CN2C[C@@]3(CCOc4cc(Cl)ccc43)COc3ccc(cc32)S(=O)(=O)NC1=O]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and tetrahydropyran-4-amine in Step 2. LCMS calc. for $C_{36}H_{45}ClN_3O_9S$ [M+H]⁺: m/z=730.25/732.25; Found: 730.2/732.2. ¹H NMR (300 MHz, CDCl₃) δ 9.02 (s, 1H), 7.61-7.53 (m, 2H), 7.15 (s, 1H), 7.05 (d, J=8.3 Hz, 1H), 6.94 (dd, J=8.4, 2.1 Hz, 1H), 6.88 (d, J=2.0 Hz, 1H), 5.79-5.67 (m, 2H), 5.18 (s, 1H), 4.30 (d, J=7.7 Hz, 1H), 4.22 (d, J=16.7 Hz, 2H), 4.14 (d, J=12.0 Hz, 2H), 4.02 (d, J=11.3 Hz, 2H), 3.84-3.74 (m, 2H), 3.54-3.43 (m, 4H), 3.19 (m, 2H), 2.83-2.72 (m, 1H), 2.41 (s, 1H), 2.04 (dd, J=10.7, 6.1 Hz, 2H), 2.00-1.80 (m, 6H), 1.54 (dd, J=12.4, 3.9 Hz, 2H), 1.45 (s, 3H), 1.39 (s, 3H).

Example 306

[(3R,6R,7S,8E,22S)-7'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N-methoxy-N-methyl-carbamate

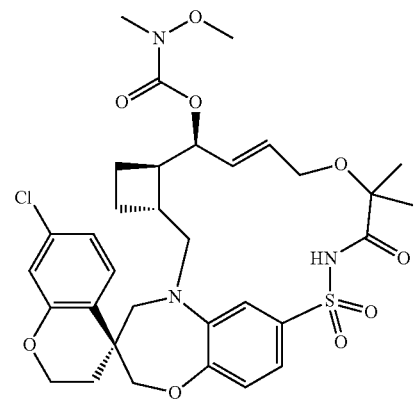 [SMILES: CON(C)C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3]

This compound was prepared using procedures analogous to those described for Example 63 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 2 and N,O-dimethylhydroxylamine hydrochloride in Step 1. LCMS calc. for $C_{33}H_{41}ClN_3O_9S$ $[M+H]^+$: m/z=690.22/692.22; Found: 690.0/692.0. $^1$H NMR (300 MHz, CDCl$_3$) δ 9.05 (s, 1H), 7.56 (dd, J=8.4, 2.0 Hz, 2H), 7.10 (d, J=2.2 Hz, 1H), 7.04 (dd, J=8.4, 0.9 Hz, 1H), 6.94 (dd, J=8.5, 2.2 Hz, 1H), 6.88 (d, J=2.2 Hz, 1H), 5.82-5.61 (m, 2H), 5.35-5.17 (m, 1H), 4.30-3.99 (m, 5H), 3.77 (dd, J=14.7, 6.0 Hz, 2H), 3.71 (s, 3H), 3.51-3.30 (m, 3H), 3.19 (s, 3H), 2.80 (d, J=7.9 Hz, 1H), 2.47 (tt, J=8.9, 4.9 Hz, 1H), 2.01-1.81 (m, 4H), 1.66 (q, J=9.6 Hz, 2H), 1.45 (s, 3H), 1.38 (s, 3H).

Example 307

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[2-(dimethylamino)ethyl]-N-methyl-carbamate

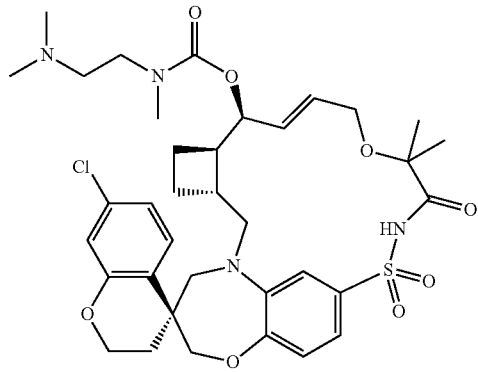 [SMILES: CN(C)CCN(C)C(=O)O[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and N,N,N'-trimethylethylenediamine in Step 2. LCMS calc. for $C_{36}H_{49}ClN_4O_8S$ $[M+H]^+$: m/z=731.28/733.28; Found: 731.2/733.3. $^1$H NMR (300 MHz, CDCl$_3$) δ 7.57 (d, J=8.4 Hz, 2H), 7.04 (d, J=8.1 Hz, 2H), 6.95 (dd, J=8.3, 1.9 Hz, 1H), 6.88 (d, J=2.0 Hz, 1H), 5.80 (d, J=37.2 Hz, 2H), 5.26 (s, 1H), 4.32 (s, 1H), 4.25-4.17 (m, 2H), 4.13 (d, J=12.2 Hz, 2H), 3.79 (d, J=14.5 Hz, 2H), 3.44 (d, J=14.7 Hz, 2H), 3.26 (s, 2H), 3.02 (s, 3H), 2.94 (s, 4H), 2.51-2.34 (m, 2H), 2.05 (d, J=8.3 Hz, 2H), 1.97-1.77 (m, 4H), 1.65 (s, 2H), 1.47 (m, 3H), 1.37 (s, 3H), 1.28 (s, 3H).

Example 308

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-ethoxypyrrolidine-1-carboxylate

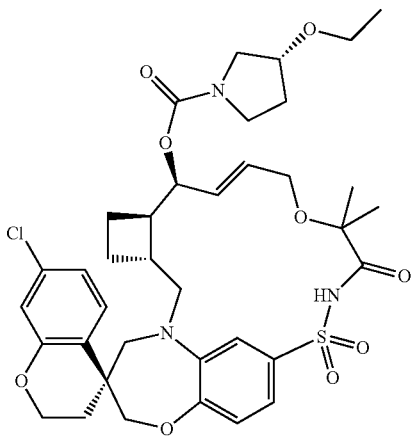 [SMILES: CCO[C@@H]1CCN(C(=O)O[C@H]2/C=C/COC(C)(C)C(=O)NS(=O)(=O)c3ccc4c(c3)N(C[C@@H]3CC[C@H]32)C[C@@]2(CCOc3cc(Cl)ccc32)CO4)C1]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and (3R)-3-ethoxypyrrolidine in Step 2. LCMS calc. for $C_{37}H_{47}ClN_3O_9S$ $[M+H]^+$: m/z=744.26/746.26; Found: 744.15/746.26; $^1$H NMR (300 MHz, CDCl$_3$) δ 9.49-9.09 (m, 1H), 7.55 (dd, J=8.4, 3.0 Hz, 2H), 7.02 (d, J=6.3 Hz, 2H), 6.93 (d, J=8.4 Hz, 1H), 6.86 (d, J=1.9 Hz, 1H), 5.82 (d, J=14.2 Hz, 1H), 5.73-5.62 (m, 1H), 5.27 (s, 1H), 4.29 (d, J=10.0 Hz, 1H), 4.25-4.15 (m, 2H), 4.08 (dd, J=16.0, 9.3 Hz, 3H), 3.82-3.72 (m, 2H), 3.71-3.61 (m, 4H), 3.42 (dd, J=13.4, 5.8 Hz, 4H), 3.25-3.17 (m, 1H), 2.83 (s, 1H), 2.38 (d, J=8.2 Hz, 1H), 2.13-1.98 (m, 4H), 1.86 (dd, J=14.6, 5.6 Hz, 3H), 1.67-1.60 (m, 1H), 1.45 (s, 3H), 1.35 (s, 3H), 1.29-1.22 (m, 3H).

Example 309

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 3-methoxyazetidine-1-carboxylate

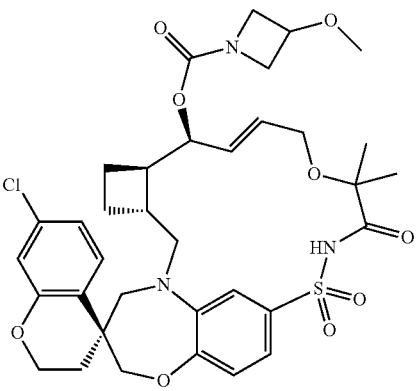 [SMILES: COC1CN(C(=O)O[C@H]2/C=C/COC(C)(C)C(=O)NS(=O)(=O)c3ccc4c(c3)N(C[C@@H]3CC[C@H]32)C[C@@]2(CCOc3cc(Cl)ccc32)CO4)C1]

547

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and 3-methoxyazetidine in Step 2. LCMS calc. for $C_{35}H_{43}ClN_3O_9S$ [M+H]⁺: m/z=716.23/718.23; Found: 716.2/718.3. ¹H NMR (300 MHz, CDCl₃) δ 9.12 (s, 1H), 7.55 (d, J=8.4 Hz, 2H), 7.02 (d, J=8.3 Hz, 2H), 6.93 (dd, J=8.5, 2.0 Hz, 1H), 6.86 (d, J=1.9 Hz, 1H), 5.79 (d, J=15.5 Hz, 1H), 5.70-5.60 (m, 1H), 5.21 (s, 1H), 4.31-4.27 (m, 1H), 4.20 (d, J=8.4 Hz, 3H), 4.13 (s, 1H), 4.10-4.01 (m, 2H), 3.91 (d, J=6.8 Hz, 1H), 3.75 (t, J=12.1 Hz, 2H), 3.42 (s, 2H), 3.38 (s, 1H), 3.31 (s, 3H), 3.22 (dd, J=14.9, 8.9 Hz, 2H), 2.79 (d, J=6.1 Hz, 1H), 2.37 (d, J=5.7 Hz, 1H), 2.09-1.98 (m, 2H), 1.95-1.78 (m, 3H), 1.68-1.59 (m, 1H), 1.45 (s, 3H), 1.36 (s, 3H).

Example 310

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-(dimethylamino)pyrrolidine-1-carboxylate

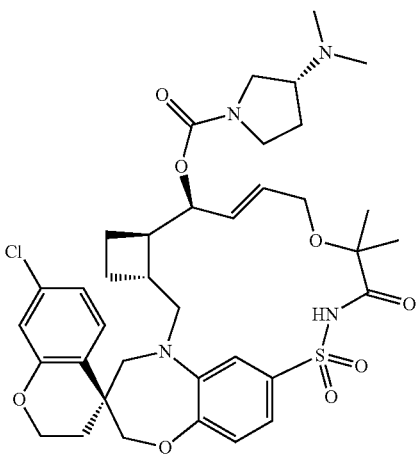 [SMILES: CN(C)[C@@H]1CCN(C(=O)O[C@H]2/C=C/COC(C)(C)C(=O)NS(=O)(=O)c3ccc4c(c3)N(C[C@@H]3CC[C@H]32)C[C@@]2(CCOc3cc(Cl)ccc32)CO4)C1]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and (3R)-N,N-dimethylpyrrolidin-3-amine in Step 2. LCMS calc. for $C_{37}H_{48}ClN_4O_8S$ [M+H]⁺: m/z=743.28/745.28; Found: 743.2/745.2. ¹H NMR (300 MHz, CDCl₃) δ 9.20 (s, 1H), 7.53 (dd, J=16.3, 8.7 Hz, 2H), 7.03 (d, J=8.3 Hz, 1H), 6.97-6.88 (m, 2H), 6.86 (d, J=2.0 Hz, 1H), 6.00-5.73 (m, 2H), 5.30 (s, 1H), 4.33 (d, J=11.4 Hz, 1H), 4.29-4.13 (m, 4H), 4.09 (d, J=12.0 Hz, 1H), 3.88 (d, J=14.8 Hz, 1H), 3.75 (d, J=12.1 Hz, 3H), 3.63 (s, 2H), 3.44 (d, J=14.7 Hz, 2H), 3.17-3.06 (m, 1H), 2.87 (d, J=18.8 Hz, 7H), 2.45-2.24 (m, 3H), 2.18 (s, 1H), 2.02 (d, J=14.3 Hz, 1H), 1.88 (s, 3H), 1.71-1.62 (m, 1H), 1.44 (s, 3H), 1.35 (s, 3H).

548

Example 311

[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 3-(dimethylamino)azetidine-1-carboxylate

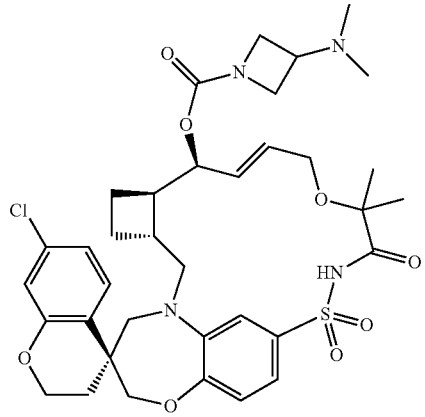 [SMILES: CN(C)C1CN(C(=O)O[C@H]2/C=C/COC(C)(C)C(=O)NS(=O)(=O)c3ccc4c(c3)N(C[C@@H]3CC[C@H]32)C[C@@]2(CCOc3cc(Cl)ccc32)CO4)C1]

This compound was prepared using procedures analogous to those described for Example 46 Step 1-2 using (3R,6R,7S,8E,22S)-7'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one (Example 246) in Step 1 and N,N-dimethylazetidin-3-amine dihydrochloride salt and Hunig's base in Step 2. LCMS calc. for $C_{36}H_{46}ClN_4O_8S$ [M+H]⁺: m/z=729.26/731.26; Found: 729.2/731.5. ¹H NMR (300 MHz, CDCl₃) δ 7.53 (dd, J=18.2, 10.3 Hz, 2H), 7.02 (d, J=8.2 Hz, 1H), 6.97-6.89 (m, 2H), 6.86 (d, J=1.7 Hz, 1H), 6.10 (s, 1H), 5.71 (s, 1H), 5.30 (s, 1H), 4.34 (d, J=11.2 Hz, 2H), 4.26 (d, J=12.1 Hz, 2H), 4.20 (d, J=10.9 Hz, 2H), 4.07 (d, J=12.0 Hz, 2H), 3.80 (d, J=14.7 Hz, 2H), 3.73 (s, 2H), 3.43 (d, J=14.4 Hz, 2H), 3.02 (s, 2H), 2.83 (s, 6H), 2.27 (s, 1H), 2.02 (d, J=14.1 Hz, 2H), 1.85 (s, 3H), 1.65 (d, J=9.2 Hz, 2H), 1.36 (s, 3H), 1.27 (s, 3H).

Example 312

[(3R,6R,7S,8E,22S)-6'-Chloro-10,10-dideuterio-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate

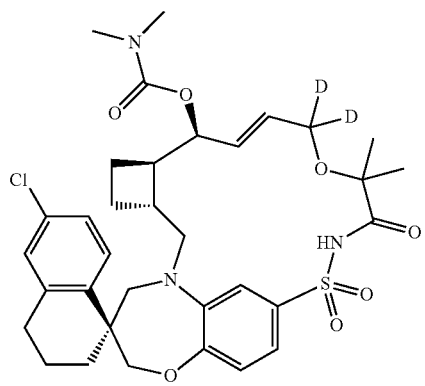 [SMILES: [2H]C1([2H])/C=C/[C@H](OC(=O)N(C)C)[C@@H]2CC[C@H]2CN2C[C@@]3(CCCc4cc(Cl)ccc43)COc3ccc(cc32)S(=O)(=O)NC(=O)C(C)(C)O1]

Step 1:
2-(1,1-dideuterioallyloxy)-2-methyl-propanoic acid

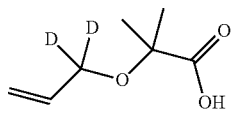

A suspension of lithium aluminium deuteride (2.0 g, 46.5 mmol) in ether (20 mL) was cooled at −78° C. under $N_2$. 2-Propenoyl chloride (4.0 mL, 39.44 mmol) in ether (20 mL) was added dropwise over 1 h. at −78° C. The mixture was then allowed to slowly warm to r.t. and stirred overnight. The mixture was carefully quenched at −10° C. with water (4 mL), followed by 15% NaOH (4 mL). The mixture was diluted with water (12 mL), and stirred for 1 h. The mixture was filtered. The filtrate was dried over $Na_2SO_4$, filtered and the solvent was partially removed under reduced pressure. The crude product (0.25 g, 4.19 mmol) and 2-bromo-2-methyl-propanoic acid (1.0 g, 5.99 mmol) was dissolved in MeCN (3 mL). DIPEA (2.3 g, 18 mmol) was added and the mixture was stirred at 50° C. overnight. The mixture was quenched with 1 M HCl (20 mL) and extracted with EtOAc (20 mL×2). The organic layer was concentrated. The residue was purified with flash chromatography on a silica gel column with EtOAc:Heptane (0% to 40%) to afford 2-(1,1-dideuterioallyloxy)-2-methyl-propanoic acid (500 mg, 40.% yield).

Step 2: (3R,6R,7S,8E,22S)-6'-Chloro-10,10-dideuterio-7-hydroxy-12,12-dimethyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one

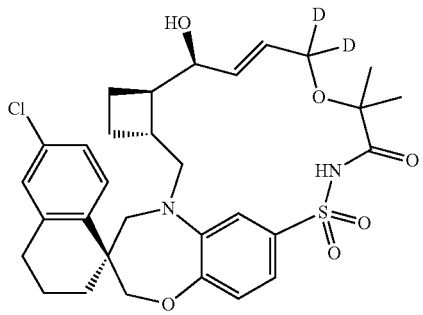 [SMILES: [2H]C1([2H])/C=C/[C@H](O)[C@@H]2CC[C@H]2CN2C[C@@]3(CCCc4cc(Cl)ccc43)COc3ccc(cc32)S(=O)(=O)NC(=O)C(C)(C)O1]

This compound was prepared using procedures analogous to those described for Example 32 Step 1-2 using 2-(1,1-dideuterioallyloxy)-2-methyl-propanoic acid to replace 2-allyloxy-2-methyl-propanoic acid in Step 1. LCMS calc. for $C_{31}H_{36}D_2ClN_2O_6S$ $[M+H]^+$: m/z=603.23/604.23; Found: 602.9.1/604.4.

Step 3: [(3R,6R,7S,8E,22S)-6'-Chloro-10,10-dideuterio-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate This compound was prepared using procedures analogous to those described for Example 34. LCMS calc. for $C_{34}H_{41}D_2ClN_3O_7S$ $[M+H]^+$: m/z=674.26/675.26; Found: 674.1/675.4.

Example 313

(3R,6R,7S,8E,22S)-7'-chloro-7-[2-(dimethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one

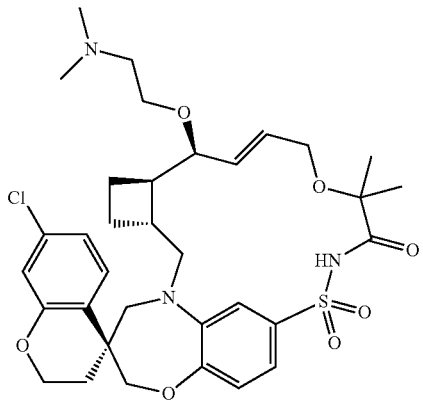 [SMILES: CN(C)CCO[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3]

Step 1: (3R,6R,7S,8E,22S)-7-(2-bromoethoxy)-7'-chloro-12,12-dimethyl-15,15-dioxo-spiro[11,20-dioxa-15-thia-1,14-diazatetracyclo[14.7.2.03,6.019,24]pentacosa-8,16(25), 17, 19(24)-tetraene-22,4'-chromane]-13-one

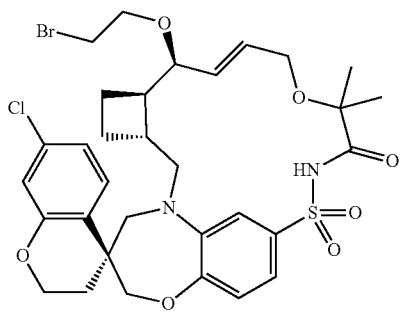 [SMILES: CC1(C)OC/C=C/[C@H](OCCBr)[C@@H]2CC[C@H]2CN2C[C@@]3(CCOc4cc(Cl)ccc43)COc3ccc(cc32)S(=O)(=O)NC1=O]

To a solution of (3R,6R,7S,8E,22S)-7'-chloro-7-hydroxy-12,12-dimethyl-15,15-dioxo-spiro[11,20-dioxa-15-thia-1,14-diazatetracyclo[14.7.2.03,6.019,24]pentacosa-8,16(25), 17,19(24)-tetraene-22,4'-chromane]-13-one (130 mg, 0.22 mmol, Example 246) in toluene (4 mL) was added 2,6-ditert-butylpyridine (412 mg, 2.2 mmol) followed by 2-bromoethyl trifluoromethanesulfonate (554 mg, 2.2 mmol). The resulting mixture was stirred at 90° C. overnight. The reaction was quenched with 1N HCl aq. solution (1 mL) and extracted with EtOAc. The combined organic extracts were washed with water and brine, dried over $Na_2SO_4$, and concentrated under reduced pressure. The residue was purified by flash chromatography on a silica gel column with EtOAc/Heptanes (3% to 60%) to afford (3R,6R,7S,8E,22S)-7-(2-bromoethoxy)-7'-chloro-12,12-dimethyl-15,15-dioxo-spiro[11,20-dioxa-15-thia-1,14-diazatetracyclo[14.7.2.03,6.019,24]pentacosa-8,16(25),17,19(24)-tetraene-22,4'-chromane]-13-one (105 mg, 68.6% yield) as a white solid. LC-MS: calc. for $C_{32}H_{39}BrClN_2O_7S$ $[M+H]^+$: m/z=709.1/711.1; Found: 709.0/710.8.

Step 2. (3R,6R,7S,8E,22S)-7'-chloro-7-[2-(dimethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one To a stirred solution of (3R,6R,7S,8E,22S)-7-(2-bromoethoxy)-7'-chloro-12,12-dimethyl-15,15-dioxo-spiro[11,20-dioxa-15-thia-1,14-diazatetracyclo[14.7.2.03,6.019,24]pentacosa-8,16(25),17,19(24)-tetraene-22,4'-chromane]-13-one (30 mg, 0.04 mmol) in DMSO (1 mL) was added potassium iodide (35 mg, 0.21 mmol) and dimethylamine (2 M in THF) (9.5 mg, 0.21 mmol). The resulting solution was stirred at 35° C. for 1 h. The reaction mixture was directly purified by prep-HPLC on C18 column (30×250 mm, 10 μm) with MeOH/$H_2O$ (15% to 100%) to afford (3R,6R,7S,8E,22S)-7'-chloro-7-[2-(dimethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one (11 mg, 38.6% yield) as a white solid. LC-MS calc. for $C_{34}H_{45}ClN_3O_7S$ $[M+H]^+$: m/z=674.26/676.26; Found: 674.2/676.4.

Example 314

(3R,6R,7S,8E,22S)-7'-chloro-7-[2-(diethylamino)ethoxy]-12,12-dimethyl-15,15-dioxo-spiro[11,20-dioxa-15-thia-1,14-diazatetracyclo[14.7.2.03,6.019,24]pentacosa-8,16,18,24-tetraene-22,4'-chromane]-13-one

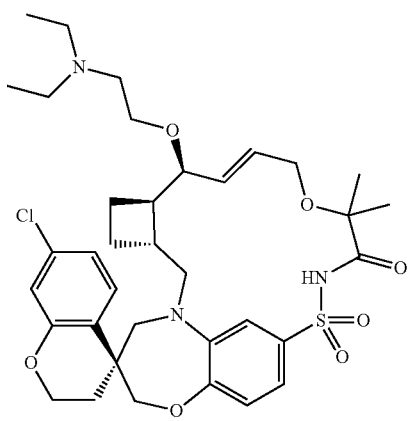 [SMILES: CCN(CC)CCO[C@H]1/C=C/COC(C)(C)C(=O)NS(=O)(=O)c2ccc3c(c2)N(C[C@@H]2CC[C@H]21)C[C@@]1(CCOc2cc(Cl)ccc21)CO3]

This compound was prepared using procedures analogous to those described for Example 313 Step 2 using diethylamine (2 M in THF) to replace dimethylamine (2 M in THF). LC-MS calc. for $C_{36}H_{49}ClN_3O_7S$ [M+H]: m/z=702.29/704.29; Found: 702.0/703.5.

Example 315

(3R,6R,7S,8E,22S)-7'-chloro-12,12-dimethyl-15,15-dioxo-7-(2-(pyrrolidin-1-yl)ethoxy)spiro[11,20-dioxa-15-thia-1,14-diazatetracyclo[14.7.2.03,6.019,24]pentacosa-8,16,18,24-tetraene-22,4'-chromane]-13-one

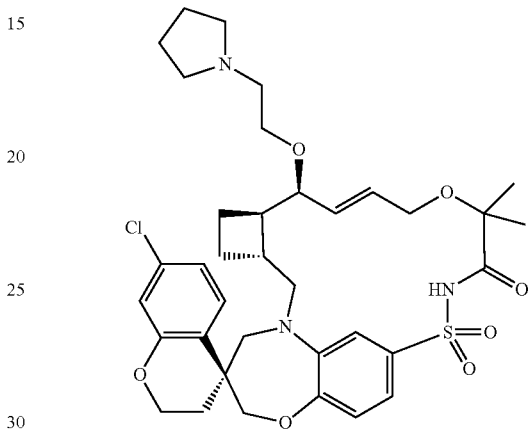

This compound was prepared using procedures analogous to those described for Example 313 Step 2 using pyrrolidine to replace dimethylamine (2 M in THF). LC-MS calc. for $C_{36}H_{47}ClN_3O_7S$ [M+H]: m/z=700.27/702.27; Found: 700.2/702.6.

Single-Crystal X-ray Analysis of Example 34

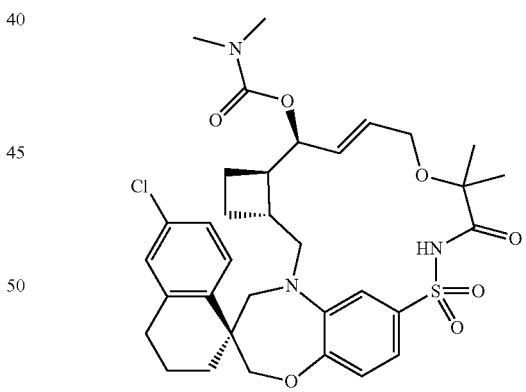

A saturated solution of Example 34 in ethanol/methyl tert-butyl ether (4/1) was stored at 23-25° C., and after 4 days, cubic crystals were observed. A crystal of approximate dimensions 0.197 mm×0.250 mm×0.345 mm, was used for the X-ray crystallographic analysis. The X-ray intensity data were measured.

The total exposure time was 3.45 hours. The frames were integrated with the Bruker SAINT software package using a narrow-frame algorithm. The integration of the data using an orthorhombic unit cell yielded a total of 26210 reflections to a maximum θ angle of 75.55° (0.80 Å resolution), of which 8525 were independent (average redundancy 3.074, completeness=98.9%, $R_{int}$=4.77%, $R_{sig}$=4.89%) and 7840 (91.96%) were greater than 2σ($F^2$). The final cell constants of a=9.1529(13) Å, b=11.1812(17) Å, c=41.054(7) Å, volume=4201.5(11) Å$^3$, are based upon the refinement of the XYZ-centroids of 9678 reflections above 20 σ(I) with 6.463°<2θ<150.8°. Data were corrected for absorption effects using the Multi-Scan method (SADABS). The ratio of minimum to maximum apparent transmission was 0.838. The calculated minimum and maximum transmission coefficients (based on crystal size) are 0.5830 and 0.7240.

FIG. 1 shows an ORTEP representation of the compound of Example 34. The structure was solved and refined using the Bruker SHELXTL Software Package, using the space group P 21 21 21, with Z=4 for the formula unit, $C_{40}H_{60}ClN_3O_{10}S$. The final anisotropic full-matrix least-squares refinement on $F^2$ with 504 variables converged at R1=7.06%, for the observed data and wR2=20.53% for all data. The goodness-of-fit was 1.151. The largest peak in the final difference electron density synthesis was 0.445 e/Å$^3$ and the largest hole was −0.447 e/Å$^3$ with an RMS deviation of 0.091 e$^−$/Å$^3$. On the basis of the final model, the calculated density was 1.281 g/cm$^3$ and F (000), 1736 e$^−$.

TABLE E1

Sample and crystal data for Example 34.

| | |
|---|---|
| Identification code | Example 34 |
| Chemical formula | $C_{40}H_{60}ClN_3O_{10}S$ (includes 3 ethanols) |
| Formula weight | 810.42 g/mol |
| Temperature | 150(2) K |
| Wavelength | 1.54178 Å |
| Crystal size | 0.197 × 0.250 × 0.345 mm |
| Crystal system | orthorhombic |
| Space group | P 21 21 21 |
| Unit cell dimensions | a = 9.1529(13) Å    α = 90° |
| | b = 11.1812(17) Å    β = 90° |
| | c = 41.054(7) Å    γ = 90° |
| Volume | 4201.5(11) Å$^3$ |
| Z | 4 |
| Density (calculated) | 1.281 g/cm$^3$ |
| Absorption coefficient | 1.752 mm$^{-1}$ |
| F(000) | 1736 |

TABLE E2

Data collection and structure refinement for Example 34.

| | |
|---|---|
| Theta range for data collection | 2.15 to 75.55° |
| Index ranges | −11 <= h <= 11, −13 <= k <= 13, −51 <= l <= 51 |
| Reflections collected | 26210 |
| Independent reflections | 8525 [R(int) = 0.0477] |
| Coverage of independent reflections | 98.9% |
| Absorption correction | Multi-Scan |
| Max. and min. transmission | 0.7240 and 0.5830 |
| Structure solution technique | direct methods |
| Structure solution program | XT, VERSION 2014/5 |
| Refinement method | Full-matrix least-squares on $F^2$ |
| Refinement program | SHELXL-2018/3 (Sheldrick, 2018) |
| Function minimized | Σ w($F_o^2$ − $F_c^2$)$^2$ |
| Data/restraints/parameters | 8525/0/504 |
| Goodness-of-fit on $F^2$ | 1.151 |
| Δ/σ$_{max}$ | 0.001 |
| Final R indices | 7840 data; I > 2σ(I)    R1 = 0.0706, wR2 = 0.2010 |
| | all data    R1 = 0.0740, wR2 = 0.2053 |
| Weighting scheme | w = 1/[σ$^2$($F_o^2$) + (0.1199P)$^2$ + 1.8325P] where P = ($F_o^2$ + 2$F_c^2$)/3 |
| Absolute structure parameter | 0.002 (11) |
| Extinction coefficient | 0.0048(6) |
| Largest diff. peak and hole | 0.445 and −0.447 eÅ$^{-3}$ |
| R.M.S. deviation from mean | 0.091 eÅ$^{-3}$ |

The binding affinity of each compound was measured via a fluorescence polarization competition assay, in which the compound competes for the same binding site with the ligand, and thus leads to a dose-dependent anisotropy reduction. The tracer ligand utilized was a fluorescein isothiocyanate labelled peptide (FITC-ARIAQELRRIGDEFNETYTR) derived from Bim (GenScript).

The assay was carried out in black half-area 96-well NBS plate (Corning), containing 15 nM of MCL-1 (BPS Bioscience), 5 nM of FITC-Bim and 3-fold serial diluted test compounds in a total volume of 50 μL of assay buffer (20 mM HEPES, 50 mM NaCl, 0.002% Tween 20, 1 mM TCEP, and 1% DMSO). The reaction plate was incubated for 1 hour at room temperature. The change of anisotropy is measured with an Envision multimode plate reader (PerkinElmer) at emission wavelength 535 nm. Fluorescence polarization was calculated in mP unit and the percentage inhibition was calculated by % inhibition=100×(mP$_{DMSO}$−mP)/(mP$_{DMSO}$−mP$_{PC}$), in which mPDMSO is the DMSO control, and mPpc is the positive control. IC$_{50}$ values were determined from a 10-point dose response curve by fitting the percent inhibition against compound concentration using the GraphPad Prism software. The inhibition constant K$_i$ was subsequently calculated according to the Nikolovska-Coleska's equation (*Anal. Biochem.*, 2004, 332, 261), $$K_i = \frac{[I]_{50}}{\frac{[L]_{50}}{K_d} + \frac{[P]_0}{K_d} + 1}$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, and K$_d$ is the dissociation constant of the protein-ligand complex. See Table F.

Caspase 3/7 Activity Assay

Dispense 10 μL aliquot of prepared H929 cells (1:1 ratio of cells:Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 2000 cells/well @ 5 μL/well. Transfer H929 cells to 50 mL conical (#430290, Corning) for each of the FBS concentration to be assayed (10%, 0.1%). Spin down at 1000 rpm for 5 min. using tabletop centrifuge (SPINCHRON 15, Beckman). Discard supernatant and resuspend cell pellet in modified RPMI 1640 (#10-040-CV, Corning) cell culture media containing sodium pyruvate (100 mM) (#25-000-CL, Corning), HEPES buffer (1 M) (#25-060-CL, Corning) and glucose (200 g/L) (A24940-01, Gibco) with appropriate FBS (F2422-500ML, Sigma) concentration to a cell density of 400,000 cells/mL. Dispense 5 μL of resuspended H929 cells per well in 384-well small volume TC treated plate (#784080, Greiner Bio-one) using standard cassette (#50950372, Thermo Scientific) on Multidrop Combi (#5840310, Thermo Scientific) in laminar flow cabinet. Dispense compounds onto plates using digital liquid dispenser (D300E, Tecan). Incubate plates in humidified tissue culture incubator @ 37° C. for 4 hours. Add 5 µL of prepared Caspase-Glo® 3/7 detection buffer (G8093, Promega) to each well of 384-well plate using small tube cassette (#24073295, Thermo Scientific) on Combi multidrop, incubate @ RT for 30-60 min. Read plates with microplate reader (PheraStar, BMG Labtech) using 384 well luminescence mode.

Cell Viability Assay (H929 10 FBS)

Dispense 10 µL aliquot of prepared H929 cells (1:1 ratio of cells:Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 4000 cells/well @ 10 µL/well. Transfer H929 cells to 50 mL conical (#430290, Corning). Spin down at 1000 rpm for 5 min using tabletop centrifuge (SPINCHRON 15, Beckman). Discard supernatant and resuspend cell pellet in modified RPMI 1640 (#10-040-CV, Corning) cell culture media containing 10% FBS (F2422-500 ML, Sigma), sodium pyruvate (100 mM) (#25-000-CL, Corning), HEPES buffer (1 M) (#25-060-CL, Corning) and glucose (200 g/L) (A24940-01, Gibco) to a cell density of 400,000 cells/mL. Dispense 10 µL of resuspended H929 cells per well in 384-well small volume TC treated plate (#784080, Greiner Bio-one) using standard cassette (#50950372, Thermo Scientific) on Multi-drop Combi (#5840310, Thermo Scientific) in laminar flow cabinet. Dispense compounds onto plates using digital liquid dispenser (D300E, Tecan). Incubate plates in humidified tissue culture incubator @ 37° C. for 24 hours. Add 10 µL of prepared CellTiTer-Glo® detection buffer (G7570, Promega) or ATPlite 1 Step detection reagent (#6016731, Perkin Elmer) to each well of 384-well plate using small tube cassette (#24073295, Thermo Scientific) on Combi multi drop, incubate @ RT for 30-60 min. Read plates with microplate reader (PheraStar, BMG Labtech) using 384 well luminescence mode.

Cytotoxicity Studies in NCI-H929 Cells

Cytotoxicity studies were conducted in NCI-H929 multiple myeloma cell line. Cells were maintained in RPMI 1640 (Corning Cellgro, Catalog #: 10-040-CV) supplemented with 10% v/v FBS (GE Healthcare, Catalog #: SH30910.03), 10 mM HEPES (Corning, Catalog #: 25-060-CI), 1 mM sodium pyruvate (Corning Cellgro, Catalog #: 25-000-CI and 2500 mg/L glucose (Gibco, Catalog #: A24940-01). Cells were seeded in 96-well plates at a density of 75000 cells/well. Compounds dissolved in DMSO were plated in duplicate using a digital dispenser (Tecan D300E) and tested on a 9-point 3-fold serial dilution. Cells were incubated for 24 hr in a 37° C. incubator at 5% $CO_2$. Cell viability was measured using the Cell Counting Kit-8 (CCK-8, Jojindo, CK04-13) as per manufacturer's instructions. Cells were incubated for 4 hours at 37° C. 5% $CO_2$ following addition of reagent and $OD_{450}$ values were measured with a microplate reader (iMark microplate reader, Bio-Rad). Background from media only wells were averaged and subtracted from all readings. $OD_{450}$ values were then normalized to DMSO controls to obtain percentage of viable cells, relative to DMSO vehicle control and plotted in Graphpad Prism ([Inhibitor] vs. normalized response–Variable slope; equation: $Y=100/(1+(X\hat{\ }HillSlope)/(IC_{50}\hat{\ }HillSlope)))$ to determine $IC_{50}$ values (the concentration of compound inhibiting half of the maximal activity).

TABLE F

Cell free Mcl-1:Bim affinity assay (Mcl-1 Bim) and Cell viability assay (H929_10FBS)

| Ex. No. | BIM_Ki (nM) | H929_10FBS $IC_{50}$ (nM) |
|---|---|---|
| 1 | 45.6 | # |
| 2 | 179 | # |
| 3 | 143 | # |
| 4 | 207 | # |
| 5 | 37.3 | # |
| 6 | 35.7 | # |
| 7 | 227 | NT |
| 8 | 424 | # |
| 9 | 1640 | # |
| 10 | 1430 | # |
| 11 | 503 | # |
| 12 | 15.8 | # |
| 13 | 22 | # |
| 14 | 222 | NT |
| 15 | 8.7 | # |
| 16 | 9 | # |
| 17 | 7.4 | # |
| 18 | 1.4 | # |
| 19 | 9.3 | # |
| 20 | 21.8 | # |
| 21 | 53.3 | # |
| 22 | 57 | # |
| 23 | 73.6 | # |
| 24 | 6.0 | # |
| 25 | 9.0 | # |
| 26 | ++ | # |
| 27 | ++ | # |
| 28 | +++ | # |
| 29 | +++ | ## |
| 30 | +++ | ## |
| 31 | ++ | # |
| 32 | +++ | ### |
| 33 | +++ | ### |
| 34 | +++ | ### |
| 35 | ++ | # |
| 36 | +++ | ## |
| 37 | +++ | ### |
| 38 | +++ | ### |
| 39 | +++ | ## |
| 40 | +++ | ### |
| 41 | +++ | ### |
| 42 | ++ | ### |
| 43 | ++ | # |
| 44 | +++ | ### |
| 45 | +++ | ### |
| 46 | +++ | ### |
| 47 | +++ | ### |
| 48 | +++ | ### |
| 49 | +++ | ### |
| 50 | +++ | ### |
| 51 | +++ | ### |
| 52 | +++ | ### |
| 53 | +++ | ### |
| 54 | +++ | ### |
| 55 | +++ | ### |
| 56 | +++ | ### |
| 57 | +++ | ### |
| 58 | +++ | ### |
| 59 | +++ | ### |
| 60 | +++ | ### |
| 61 | +++ | ### |
| 62 | +++ | ### |
| 63 | +++ | ### |
| 64 | +++ | ### |
| 65 | +++ | ### |
| 66 | +++ | ### |
| 67 | ++ | # |
| 68 | ++ | # |
| 69 | ++ | # |
| 70 | ++ | # |

TABLE F-continued

Cell free Mcl-1:Bim affinity assay (Mcl-1 Bim) and Cell viability assay (H929_10FBS)

| Ex. No. | BIM_Ki (nM) | H929_10FBS IC$_{50}$ (nM) |
|---|---|---|
| 71 | ++ | # |
| 72 | ++ | # |
| 73 | ++ | # |
| 74 | +++ | # |
| 75 | ++ | # |
| 76 | ++ | # |
| 77 | ++ | # |
| 78 | ++ | # |
| 79 | ++ | # |
| 80 | ++ | # |
| 81 | ++ | # |
| 82 | ++ | # |
| 83 | ++ | # |
| 84 | ++ | # |
| 85 | ++ | # |
| 86 | ++ | # |
| 87 | +++ | ## |
| 88 | +++ | ## |
| 89 | ++ | # |
| 90 | +++ | # |
| 91 | ++ | # |
| 92 | +++ | ## |
| 93 | ++ | # |
| 94 | +++ | # |
| 95 | ++ | # |
| 96 | +++ | # |
| 97 | +++ | # |
| 98 | ++ | # |
| 99 | ++ | # |
| 100 | ++ | # |
| 101 | +++ | # |
| 102 | ++ | # |
| 103 | +++ | # |
| 104 | +++ | # |
| 105 | ++ | # |
| 106 | ++ | ## |
| 107 | ++ | ## |
| 108 | ++ | # |
| 109 | ++ | # |
| 110 | ++ | # |
| 111 | ++ | # |
| 112 | ++ | # |
| 113 | +++ | ## |
| 114 | +++ | ## |
| 115 | ++ | # |
| 116 | ++ | ## |
| 117 | ++ | # |
| 118 | ++ | # |
| 119 | ++ | ## |
| 120 | ++ | ## |
| 121 | ++ | # |
| 122 | ++ | # |
| 123 | ++ | ## |
| 124 | ++ | ## |
| 125 | +++ | # |
| 126 | ++ | # |
| 127 | ++ | ## |
| 128 | ++ | # |
| 129 | ++ | # |
| 130 | ++ | # |
| 131 | ++ | # |
| 132 | ++ | ### |
| 133 | ++ | # |
| 134 | ++ | # |
| 135 | ++ | # |
| 136 | ++ | # |
| 137 | ++ | ## |
| 138 | ++ | ## |
| 139 | ++ | ## |
| 140 | +++ | ### |
| 141 | +++ | ### |
| 142 | +++ | ## |
| 143 | +++ | ### |
| 144 | ++ | # |
| 145 | +++ | ### |
| 146 | ++ | ### |
| 147 | +++ | ### |
| 148 | +++ | ### |
| 149 | +++ | ### |
| 150 | +++ | ## |
| 151 | +++ | ### |
| 152 | +++ | ### |
| 153 | +++ | ### |
| 154 | +++ | ### |
| 155 | +++ | ### |
| 156 | +++ | ### |
| 157 | +++ | ### |
| 158 | +++ | ### |
| 159 | +++ | ### |
| 160 | +++ | ### |
| 161 | +++ | ## |
| 162 | +++ | ### |
| 163 | +++ | ### |
| 164 | +++ | ### |
| 165 | +++ | ### |
| 166 | +++ | ### |
| 167 | +++ | ### |
| 168 | +++ | ### |
| 169 | +++ | ### |
| 170 | +++ | ## |
| 171 | +++ | ### |
| 172 | +++ | ### |
| 173 | +++ | ### |
| 174 | +++ | ### |
| 175 | +++ | ### |
| 176 | +++ | ### |
| 177 | ++ | ### |
| 178 | +++ | ### |
| 179 | +++ | ### |
| 180 | +++ | ### |
| 181 | +++ | ### |
| 182 | +++ | ### |
| 183 | +++ | ### |
| 184 | +++ | ### |
| 185 | +++ | ### |
| 186 | +++ | ### |
| 187 | +++ | ### |
| 188 | +++ | ### |
| 189 | +++ | ### |
| 190 | +++ | ### |
| 191 | +++ | ### |
| 192 | +++ | ### |
| 193 | ++ | ### |
| 194 | +++ | ### |
| 195 | +++ | ### |
| 196 | ++ | # |
| 197 | ++ | # |
| 198 | +++ | ### |
| 199 | +++ | ### |
| 200 | ++ | ### |
| 201 | +++ | ### |
| 202 | +++ | ### |
| 203 | +++ | ### |
| 204 | +++ | ### |
| 205 | ++ | ### |
| 206 | +++ | ### |
| 207 | +++ | ### |
| 208 | ++ | ### |
| 209 | +++ | ### |
| 210 | +++ | ### |
| 211 | +++ | ### |
| 212 | +++ | ### |
| 213 | +++ | ### |
| 214 | +++ | ### |
| 215 | +++ | ### |
| 216 | +++ | ### |
| 217 | +++ | ### |
| 218 | +++ | ### |

TABLE F-continued

Cell free Mcl-1:Bim affinity assay (Mcl-1 Bim) and Cell viability assay (H929_10FBS)

| Ex. No. | BIM_Ki (nM) | H929_10FBS IC$_{50}$ (nM) |
|---|---|---|
| 219 | ++ | ### |
| 220 | +++ | ### |
| 221 | +++ | ### |
| 222 | +++ | ### |
| 223 | +++ | ### |
| 224 | +++ | ### |
| 225 | ++ | ### |
| 226 | +++ | ### |
| 227 | +++ | ### |
| 228 | +++ | ### |
| 229 | +++ | ### |
| 230 | +++ | ### |
| 231 | +++ | ### |
| 232 | +++ | ### |
| 233 | +++ | ### |
| 234 | +++ | ### |
| 235 | +++ | ### |
| 236 | +++ | ### |
| 237 | +++ | ### |
| 238 | +++ | ### |
| 239 | +++ | ### |
| 240 | +++ | ### |
| 241 | +++ | ### |
| 242 | +++ | ### |
| 243 | +++ | ### |
| 244 | +++ | ### |
| 245 | +++ | ### |
| 246 | ++ | # |
| 247 | +++ | ### |
| 248 | +++ | # |
| 249 | ++ | # |
| 250 | +++ | ### |
| 251 | ++ | # |
| 252 | ++ | # |
| 253 | ++ | # |
| 254 | ++ | # |
| 255 | ++ | # |
| 256 | ++ | # |
| 257 | ++ | # |
| 258 | +++ | ### |
| 259 | +++ | ### |
| 260 | +++ | ### |
| 261 | +++ | ### |
| 262 | +++ | ### |
| 263 | +++ | ### |
| 264 | +++ | ### |
| 265 | ++ | ### |
| 266 | +++ | ### |
| 267 | ++ | ## |
| 268 | +++ | ### |
| 269 | +++ | ### |
| 270 | +++ | ### |
| 271 | +++ | ### |
| 272 | +++ | ### |
| 273 | +++ | ## |
| 274 | +++ | ## |
| 275 | ++ | ### |
| 276 | +++ | ## |
| 277 | ++ | # |
| 278 | +++ | ### |
| 279 | +++ | ### |
| 280 | +++ | ### |
| 281 | +++ | ### |
| 282 | +++ | ### |
| 283 | +++ | ### |
| 284 | +++ | ### |
| 285 | +++ | ### |
| 286 | ++ | # |
| 287 | +++ | ### |
| 288 | ++ | # |
| 289 | ++ | # |
| 290 | +++ | ### |
| 291 | +++ | ## |
| 292 | +++ | ### |
| 293 | +++ | ### |
| 294 | ++ | ### |
| 295 | ++ | # |
| 296 | ++ | ### |
| 297 | ++ | # |
| 298 | +++ | ## |
| 299 | +++ | ## |
| 300 | +++ | ## |
| 301 | +++ | ### |
| 302 | +++ | ### |
| 303 | +++ | ### |
| 304 | +++ | ### |
| 305 | +++ | ### |
| 306 | +++ | ### |
| 307 | +++ | ### |
| 308 | +++ | ### |
| 309 | +++ | ## |
| 310 | +++ | ### |
| 311 | +++ | ### |
| 312 | +++ | ### |
| 313 | NT | NT |
| 314 | NT | NT |
| 315 | NT | NT |

+++ Ki < 1 nM; ++ Ki = 1 nM-100 nM; ### IC$_{50}$ < 500 nM; ## IC$_{50}$ < 1000 nM; # IC$_{50}$ > 1000 nM; NT = not tested In some embodiments, the invention is directed to the following aspects:

Aspect 1. A compound of Formula I:

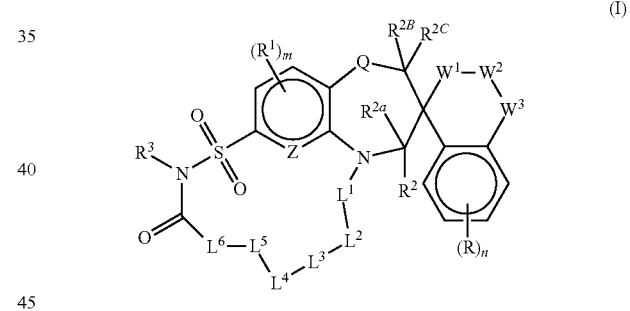

(I)

or a pharmaceutically acceptable salt or solvate thereof; wherein

Z is CH or N;

Q is —O—, —S—, —S(O)—, or —S(O)$_2$—;

the moiety —W$^1$—W$^2$—W$^3$— is —CR$^2$R$^{2A}$—CR$^2$R$^{2A}$—CR$^2$R$^{2A}$—, —O—CR$^{2B}$R$^{2C}$—CR$^2$R$^{2A}$—, —CR$^2$R$^{2A}$—CR$^{2B}$R$^{2C}$—O—, —NR$^{2B}$—CR$^{2B}$R$^{2C}$—CR$^2$R$^{2A}$—, —CR$^2$R$^{2A}$—CR$^{2B}$R$^{2C}$—NR$^{2B}$—, —S—CR$^{2B}$R$^{2C}$—CR$^2$R$^{2A}$—, or —CR$^2$R$^{2A}$—CR$^{2B}$R$^{2C}$—S—;

L$^1$ is absent or is optionally substituted —C$_1$-C$_6$alkylene-;

L$^2$ is absent or is optionally substituted cycloalkylene, optionally substituted heterocycloalkylene, optionally substituted arylene, or optionally substituted heteroarylene;

L$^3$ is absent, or is —(CR$^4$R$^5$)$_p$—, —(CR$^4$R$^5$)$_p$O—, —O—, —S—, —S(O)—, —S(O)$_2$—, —C(=O)—, —NR$^6$—, —OC(=O)—, —C(=O)O—, —NR$^{6A}$C(O)—, —C(=O)NR$^{6A}$—, —OC(=O)N(R$^{6A}$)—, —NR$^{6A}$C(O)O—, —S(=O)NR$^{6A}$—, —NR$^{6A}$S(O)—, —S(=O)$_2$NR$^{6A}$—, or —NR$^{6A}$S(O)$_2$—;

$L^4$ is absent, or is —$(CR^4R^5)_pQ^1(CR^4R^5)_q$—, wherein $Q^1$ is absent, —$CR^{4A}$=$CR^{4B}$—, —O—, —S—, —S(O)—, —S(O)$_2$—, —C(=O)—, —NR$^6$—, —OC(=O)—, —C(=O)O—, —NR$^{6A}$C(O)—, —C(=O)NR$^{6A}$—, —NR$^{6A}$C(O)R$^{6B}$—, —OC(=O)N(R$^{6A}$)—, —NR$^{6A}$C(O)O—, —S(=O)NR$^{6A}$—, —NR$^{6A}$S(O)—, —S(=O)$_2$NR$^{6A}$—, or —NR$^{6A}$S(O)$_2$—; or is —$(CR^4R^5)_p$—$(CR^{4A}$=$CR^{4B})$—$(CR^4R^5)_q$—O—;

$L^5$ is absent, or is —$C_1$-$C_6$ alkylene-, —$C_2$-$C_6$ alkenylene-, —$C_2$-$C_6$ alkynylene-, -arylene-, -heteroarylene-, -cycloalkenylene-, -cycloalkylene-, -heterocycloalkylene-, wherein said $C_1$-$C_6$ alkylene, $C_2$-$C_6$ alkenylene, $C_2$-$C_6$ alkynylene, arylene, heteroarylene, cycloalkenylene, cycloalkylene, or heterocycloalkylene groups are optionally substituted;

$L^6$ is absent, or is —$(CR^7R^8)_s$—, —$(CR^7R^8)_sO(CR^7R^8)_t$—, —$(CR^7R^8)_sNR^9(CR^7R^8)_t$—, —$(CR^7R^8)_sS(CR^7R^8)_t$—, —$(CR^7R^8)_sS(O)(CR^7R^8)_t$—, —$(CR^7R^8)_sS(O)_2(CR^7R^8)_t$—, —$(CR^7R^8)_sNR^{9A}C(O)(CR^7R^8)_t$—, —$(CR^7R^8)_sOC(O)NR^{9A}(CR^7R^8)_t$—, —$(CR^7R^8)_sNR^{9A}C(O)O(CR^7R^8)_t$—, —$(CR^7R^8)_sNR^{9A}C(O)NR^{9B}(CR^7R^8)_t$—, —$(CR^7R^8)_sNR^{9A}S(O)(CR^7R^8)_t$—, —$(CR^7R^8)_sNR^{9A}S(O)_2(CR^7R^8)_t$—; —$(CR^7R^8)_s$—$CR^{4A}$=$CR^{4B}$—$(CR^7R^8)_t$—, —$(CR^7R^8)_sC(=O)(CR^7R^8)_t$—; —$(CR^7R^8)_sC(=O)(CR^7R^8)t$-O—, or —$(CR^7R^8)_sC(=O)(CR^7R^8)t$-NR$^6$—;

each n is independently 0-3;
each m is independently 0-2;
each p is independently 0-4;
each q is independently 0-4;
each s is independently 0-3;
each t is independently 0-4;

each R is independently -D, -halo, —CN, —NO$_2$, —$C_1$-$C_6$alkyl, —$C_2$-$C_6$alkenyl, —$C_1$-$C_6$alkoxy, -cycloalkyl, —OR$^a$, —SR$^a$, —C(O)R$^b$, —C(O)OR$^a$, —NR$^cR^d$, —C(O)NR$^cR^d$, or —S(O)$_2$R$^a$; wherein said —$C_1$-$C_6$alkyl, —$C_2$-$C_6$alkenyl, —$C_1$-$C_6$alkoxy, or -cycloalkyl is optionally substituted;

each $R^1$ is independently -D, -halo, —CN, —NO$_2$, —$C_1$-$C_6$alkyl, —$C_2$-$C_6$alkenyl, —$C_2$-$C_6$alkynyl, —OR$^a$, —SR$^a$, —NR$^cR^d$, —C(O)R$^b$, —OC(O)R$^b$, —C(O)OR$^a$, —C(O)NR$^cR^d$, —S(O)$_2$R$^a$; -aryl, -heteroaryl, -cycloalkyl, or -heterocycloalkyl, wherein said —$C_1$-$C_6$alkyl, —$C_2$-$C_6$alkenyl, —$C_2$-$C_6$alkynyl, -cycloalkyl, -heterocycloalkyl, -aryl, or -heteroaryl is optionally substituted;

each $R^2$, $R^{2A}$, or $R^{2a}$ is independently H, D, halo, OR$^a$, optionally substituted $C_1$-$C_6$alkyl, or $R^2$ and $R^{2A}$ that are attached to the same carbon atom may, together with the carbon atom to which they are both attached, form an optionally substituted cycloalkyl ring;

each $R^{2B}$ and $R^{2C}$ is independently H, D, optionally substituted $C_1$-$C_6$alkyl, or $R^{2B}$ and $R^{2C}$ may, together with the carbon atom to which they are both attached, form an optionally substituted cycloalkyl ring;

$R^3$ is H, D, —$C_1$-$C_6$alkyl, —$C_3$-$C_6$alkenyl, —$C_3$-$C_6$alkynyl, cycloalkyl, heterocycloalkyl, C(O)R$^b$, C(O)OR$^a$, or C(O)NR$^cR^d$; wherein said $C_1$-$C_6$alkyl, —$C_3$-$C_6$alkenyl, —$C_3$-$C_6$alkynyl, cycloalkyl, or heterocycloalkyl is optionally substituted; or $R^3$ is —$C_1$-$C_6$alkyl substituted at the $C_1$ carbon atom with —OR$^{3A}$ wherein $R^{3A}$ is $C_1$-$C_6$alkyl, —PO$_3$H, —C(O)OR$^{2C}$, or —C(O)NR$^{3A}R^{3B}$ wherein $R^{3A}$ and $R^{3B}$ are each independently H, D, optionally substituted $C_1$-$C_6$alkyl;

each $R^4$ or $R^7$ is independently H, D, halo, —OH, —CN, —NO$_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —OR$^a$, —SR$^a$, —NR$^cR^d$, —NR$^aR^c$, —C(O)R$^b$, —OC(O)R$^a$, —C(O)OR$^a$, —C(O)NR$^cR^d$, —S(O)R$^b$, or —S(O)$_2$R$^b$, wherein said $C_1$-$C_6$alkyl, —$C_2$-$C_6$alkenyl, —$C_2$-$C_6$alkynyl, aryl, heteroaryl, cycloalkyl, cycloalkenyl, heterocycloalkenyl, or heterocycloalkyl is optionally substituted;

each $R^{4A}$ or $R^{4B}$ is independently H, D, -Me, —CF$_3$ or —F;

each $R^5$ or $R^8$ is independently H, D, fluoro, —$C_1$-$C_6$alkyl, —$C_2$-$C_6$alkenyl, —$C_2$-$C_6$alkynyl, —C(O)R$^b$, —C(O)OR$^a$, —C(O)NR$^cR^d$, aryl, heteroaryl, cycloalkyl, cycloalkenyl, heterocycloalkyl, or heterocycloalkenyl, wherein said $C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl is optionally substituted;

or $R^4$ and $R^5$ together with the C atom to which they are attached form a cycloalkyl, cycloalkenyl, heterocycloalkyl, or heterocycloalkenyl ring, each optionally substituted;

or an $R^4$ and an $R^5$ attached to adjacent carbon atoms, together with the C atoms to which they are attached, form a cycloalkyl, cycloalkenyl, heterocycloalkyl, or heterocycloalkenyl ring, each optionally substituted;

or $R^7$ and $R^8$ together with the C atom to which they are both attached form a cycloalkyl, cycloalkenyl, heterocycloalkyl, or heterocycloalkenyl ring, each optionally substituted, each optionally substituted;

or an $R^7$ and an $R^8$ attached to adjacent carbon atoms, together with the C atoms to which they are attached, form a cycloalkyl, cycloalkenyl, heterocycloalkyl, or heterocycloalkenyl ring, each optionally substituted;

each $R^6$ or $R^9$ is independently H, D, —$C_1$-$C_6$alkyl, —$C_2$-$C_6$alkenyl, —$C_2$-$C_6$alkynyl, —OC$_1$-$C_6$alkyl, —C(O)R$^b$, —C(O)OR$^a$, —C(O)NR$^cR^d$, —S(O)R$^b$ or —S(O)$_2$R$^b$, aryl, heteroaryl, cycloalkyl, cycloalkenyl, heterocycloalkyl, or heterocycloalkenyl group, wherein said $C_1$-$C_6$alkyl, —$C_2$-$C_6$alkenyl, —$C_2$-$C_6$alkynyl, —OC$_1$-$C_6$alkyl, aryl, heteroaryl, cycloalkyl, cycloalkenyl, heterocycloalkyl, or heterocycloalkenyl ring, is optionally substituted;

or $R^9$ together with either an $R^7$ or an $R^8$ forms an optionally substituted heterocyclic alkylene;

each $R^{6A}$, $R^{6B}$, $R^{9A}$, or $R^{9B}$ is independently H, D, —$C_1$-$C_6$alkyl, —$C_2$-$C_6$alkenyl, —$C_2$-$C_6$alkynyl, cycloalkyl, cycloalkenyl, heterocycloalkyl, or heterocycloalkenyl, wherein said $C_1$-$C_6$alkyl, —$C_2$-$C_6$alkenyl, —$C_2$-$C_6$alkynyl, cycloalkyl, cycloalkenyl, heterocycloalkyl, or heterocycloalkenyl is optionally substituted;

or $R^{6A}$ and $R^{6B}$ together with the N atoms to which they are attached form an optionally substituted heterocycloalkyl or heterocycloalkenyl ring;

or $R^{9A}$ and $R^{9B}$ together with the N atoms to which they are attached form an optionally substituted heterocycloalkyl or heterocycloalkenyl ring;

each $R^a$ is independently H, D, —C(O)R$^b$, —C(O)OR$^c$, —C(O)NR$^cR^d$, —P(OR$^c$)$_2$, —P(O)R$^cR^b$, P(O)OR$^c$OR$^b$, —S(O)R$^b$, —S(O)NR$^cR^d$, —S(O)$_2$R$^b$, —S(O)$_2$NR$^cR^d$, —B(OR$^c$)(OR$^b$), SiR$^b_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl wherein said $C_1$-$C_{10}$ alkyl, $C_2$-$C_{10}$ alkenyl, $C_2$-$C_{10}$ alkynyl, aryl, cycloalkyl, cycloalkenyl, heteroaryl, heterocycloalkyl, or heterocycloalkenyl is optionally substituted;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl wherein said —$C_1$-$C_6$ alkyl, —$C_2$-$C_6$ alkenyl, —$C_2$-$C_6$ alkynyl, aryl, cycloalkyl, cycloalkeneyl, heteroaryl, heterocycloalkyl, or heterocycloalkenyl is optionally substituted;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl, wherein said $C_1$-$C_{10}$ alkyl, $C_2$-$C_6$ alkenyl, $C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl are each optionally substituted;

or $R^c$ and $R^d$, together with the N atom to which they are both attached, form an optionally substituted monocyclic or multicyclic heterocycloalkyl, or optionally substituted monocyclic or multicyclic heterocycloalkenyl group.

Aspect 2. The compound according to aspect 1 having the Formula IA-0,

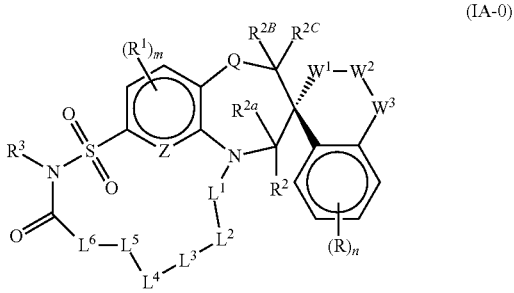

(IA-0)

or a pharmaceutically acceptable salt or solvate thereof; wherein

Z is CH or N;

Q is —O—, —S—, —S(O)—, or —S(O)$_2$—;

the moiety —$W^1$—$W^2$—$W^3$ is —$CR^2R^{2A}$—$CR^2R^{2A}$—$CR^2R^{2A}$—, —O—$CR^{2B}R^{2C}CR^2R^{2A}$—, —$CR^2R^{2A}$—$CR^{2B}R^{2C}$—O—, —$NR^{2B}$—$CR^{2B}R^{2C}$—$CR^2R^{2A}$—, —$CR^2R^{2A}$—$CR^{2B}R^{2C}$—$NR^{2B}$, —S—$CR^{2B}R^{2C}$—$CR^2R^{2A}$—, or —$CR^2R^{2A}$—$CR^{2B}R^{2C}$—S—;

$L^1$ is optionally substituted —$C_1$-$C_6$alkylene-;

$L^2$ is optionally substituted 3-7 membered cycloalkylene, optionally substituted 4-7 membered heterocycloalkylene, optionally substituted arylene, or optionally substituted heteroarylene;

$L^3$ is absent, or is —$(CR^4R^5)_p$—, —$(CR^4R^5)_pO$—, —O—, —S—, —S(O)—, —S(O)$_2$—, —C(=O)—, —$NR^6$—, —OC(=O)—, —C(=O)O—, —$NR^{6A}$C(O)—, —C(=O)$NR^{6A}$—, —OC(=O)N($R^{6A}$)—, —$NR^{6A}$C(O)O—, —S(=O)$NR^{6A}$—, —$NR^{6A}$S(O)—, —S(=O)$_2NR^{6A}$—, or —$NR^{6A}$S(O)$_2$—;

$L^4$ is absent, or is —$(CR^4R^5)_pQ^1(CR^4R^5)_q$—, wherein $Q^1$ is absent, —$CR^{4A}$=$CR^{4B}$—, —O—, —S—, —S(O)—, —S(O)$_2$—, —C(=O)—, —$NR^6$—, —OC(=O)—, —C(=O)O—, —$NR^{6A}$C(O)—, —C(=O)$NR^{6A}$—, —$NR^{6A}$C(O)$R^{6B}$—, —OC(=O)N($R^{6A}$)—, —$NR^{6A}$C(O)O—, —S(=O)$NR^{6A}$—, —$NR^{6A}$S(O)—, —S(=O)$_2NR^{6A}$—, or —$NR^{6A}$S(O)$_2$—; or is —$(CR^4R^5)_p$—$(CR^{4A}$=$CR^{4B})$—$(CR^4R^5)_q$—O—;

$L^5$ is absent, or is —$C_1$-$C_6$ alkylene-, —$C_2$-$C_6$ alkenylene-, —$C_2$-$C_6$ alkynylene-, a 6- to 10-membered arylene, 5- to 10-membered heteroarylene, a 3- to 12-membered cycloalkenylene, a 3- to 7-membered monocyclic cycloalkylene, or 6- to 12 bicyclic cycloalkylene, a 3- to 7-membered monocyclic heterocycloalkylene, or 6- to 12-membered bicyclic heterocycloalkylene group, wherein said $C_1$-$C_6$ alkylene, $C_2$-$C_6$ alkenylene, $C_2$-$C_6$ alkynylene, a 6- to 10-membered arylene, 5- to 10-membered heteroarylene, a 3- to 12-membered cycloalkenylene, a 3- to 7-membered monocyclic cycloalkylene, or 6- to 12 bicyclic cycloalkylene, a 3- to 7-membered monocyclic heterocycloalkylene, or 6- to 12-membered bicyclic heterocycloalkylene groups are optionally substituted;

$L^6$ is absent, or is —$(CR^7R^8)_s$—, —$O(CR^7R^8)_t$—, —$NR^9(CR^7R^8)_t$—, —$S(CR^7R^8)_t$—, —$S(O)(CR^7R^8)_t$—, —$S(O)_2(CR^7R^8)_t$—, —$NR^{9A}C(O)(CR^7R^8)_t$—, —C(O)$NR^{9A}(CR^7R^8)_t$—, —$R^{9A}C(O)O(CR^7R^8)_t$—, —$NR^{9A}C(O)NR^{9B}(CR^7R^8)_t$—, —$NR^{9A}S(O)(CR^7R^8)_t$—, —$NR^{9A}S(O)_2(CR^7R^8)_t$—; —$CR^{4A}$=$CR^{4B}$—$(CR^7R^8)_t$—, —C(=O)$(CR^7R^8)_t$—; —C(=O)$(CR^7R^8)_t$—O—, or —C(=O)$(CR^7R^8)$t-$NR^6$—;

each n is independently 0-3;

each m is independently 0-2;

each p is independently 0-4;

each q is independently 0-4;

each s is independently 0-3;

each t is independently 0-4;

each R is independently D, halo, —CN, —NO$_2$, $C_1$-$C_6$alkyl, $C_2$-$C_6$alkenyl, $C_1$-$C_6$alkoxy, $C_3$-$C_6$cycloalkyl, —OR$^a$, —SR$^a$, —C(O)R$^b$, —C(O)OR$^a$, —NR$^cR^d$, —C(O)NR$^cR^d$, or —S(O)$_2R^a$; wherein said $C_1$-$C_6$alkyl, $C_2$-$C_6$alkenyl, $C_1$-$C_6$alkoxy, or $C_3$-$C_6$cycloalkyl is optionally substituted;

each $R^1$ is independently D, halo, —CN, —NO$_2$, —$C_1$-$C_6$alkyl, —$C_2$-$C_6$alkenyl, —$C_2$-$C_6$alkynyl, —OR$^a$, —SR$^a$, —NR$^cR^d$, —C(O)R$^b$, —OC(O)R$^b$, —C(O)OR$^a$, —C(O)NR$^cR^d$, —S(O)$_2R^a$; aryl, heteroaryl, cycloalkyl, or heterocycloalkyl, wherein said $C_1$-$C_6$alkyl, —$C_2$-$C_6$alkenyl, —$C_2$-$C_6$alkynyl, cycloalkyl, heterocycloalkyl, aryl, or heteroaryl, is optionally substituted;

each $R^2$, $R^{2A}$, or $R^{2a}$ is independently H, D, halo, —OR$^a$, optionally substituted —$C_1$-$C_6$alkyl, or $R^2$ and $R^{2A}$, that are attached to the same carbon atom may, together with the carbon atom to which they are both attached, form an optionally substituted 3-7 membered cycloalkyl ring;

$R^{2B}$ and $R^{2C}$ are each independently H, D, optionally substituted $C_1$-$C_6$alkyl, or $R^{2B}$ and $R^{2C}$ may, together with the carbon atom to which they are both attached, form an optionally substituted 3-7 membered cycloalkyl ring;

$R^3$ is H, D, —$C_1$-$C_6$alkyl, —$C_3$-$C_6$alkenyl, —$C_3$-$C_6$alkynyl, 3-7 membered cycloalkyl, -4-7 membered heterocycloalkyl, —C(O)R$^b$, —C(O)OR$^a$, or —C(O)NR$^cR^d$; wherein said $C_1$-$C_6$alkyl, —$C_3$-$C_6$alkenyl, —$C_3$-$C_6$alkynyl, cycloalkyl, and heterocycloalkyl is optionally substituted; or $R^3$ is —$C_1$-$C_6$alkyl substituted at the $C_1$ carbon atom with —OR$^{3A}$ wherein $R^{3A}$ is $C_1$-$C_6$alkyl, —PO$_3$H, —C(O)OR$^{2C}$, or —C(O)NR$^{3A}R^{3B}$ wherein $R^{3A}$ and $R^{3B}$ are each independently H, D, optionally substituted $C_1$-$C_6$alkyl;

each $R^4$ or $R^7$ is independently H, D, halo, —OH, —CN, —NO$_2$, —$C_1$-$C_6$alkyl, —$C_2$-$C_6$alkenyl, —$C_2$-$C_6$alkynyl, 3-7 membered cycloalkyl, —OR$^a$, —SR$^a$, —NR$^c$R$^d$, —NR$^a$R$^c$, —C(O)R$^b$, —OC(O)R$^a$, —C(O)OR$^a$, —C(O)NR$^c$R$^d$, —S(O)R$^b$, —S(O)$_2$R$^b$, aryl, heteroaryl, or heterocycloalkyl, wherein said C$_1$-C$_6$alkyl, —C$_2$-C$_6$alkenyl, —C$_2$-C$_6$alkynyl, aryl, heteroaryl, cycloalkyl, or heterocycloalkyl is optionally substituted;

each R$^{4A}$ or R$^{4B}$ is independently H, D, -Me, —CF$_3$ or —F;

each R$^5$ or R$^8$ is independently H, D, fluoro, —C$_1$-C$_6$alkyl, —C$_2$-C$_6$alkenyl, —C$_2$-C$_6$alkynyl, —C(O)R$^c$, —C(O)OR$^c$, —C(O)NR$^c$R$^d$, aryl, heteroaryl, cycloalkyl, or heterocycloalkyl, wherein said C$_1$-C$_6$alkyl, —C$_2$-C$_6$alkenyl, —C$_2$-C$_6$alkynyl, aryl, heteroaryl, cycloalkyl, or heterocycloalkyl is optionally substituted;

or R$^4$ and R$^5$ together with the C atom to which they are attached form a cycloalkyl or heterocycloalkyl ring, each optionally substituted;

or R$^7$ and R$^8$ together with the C atom to which they are attached form a cycloalkyl or heterocycloalkyl ring, each optionally substituted;

each R$^6$ or R$^9$ is independently H, D, —C$_1$-C$_6$alkyl, —C$_2$-C$_6$alkenyl, —C$_2$-C$_6$alkynyl, —OC$_1$-C$_6$alkyl, —C(O)R$^b$, —C(O)OR$^a$, —C(O)NR$^c$R$^d$, —S(O)R$^b$ or —S(O)$_2$R$^b$, aryl, heteroaryl, cycloalkyl, or heterocycloalkyl group, wherein said C$_1$-C$_6$alkyl, —C$_2$-C$_6$alkenyl, —C$_2$-C$_6$alkynyl, —OC$_1$-C$_6$alkyl, -aryl, heteroaryl, cycloalkyl, or heterocycloalkyl is optionally substituted;

each R$^{6A}$, R$^{6B}$, R$^{9A}$, or R$^{9B}$ is independently H, D, C$_1$-C$_6$alkyl, —C$_2$-C$_6$alkenyl, —C$_2$-C$_6$alkynyl, 3-7 membered cycloalkyl, 4-7 membered heterocycloalkyl, wherein said C$_1$-C$_6$alkyl, —C$_2$-C$_6$alkenyl, —C$_2$-C$_6$alkynyl, 3-7 membered cycloalkyl, or 4-7 membered heterocycloalkyl is optionally substituted;

or R$^{6A}$ and R$^{6B}$ together with the atoms to which they are attached form an optionally substituted heterocycloalkyl ring;

or R$^{9A}$ and R$^{9B}$ together with the N atom to which they are attached form an optionally substituted heterocycloalkyl ring;

each R$^a$ is independently H, D, —C(O)R$^b$, —C(O)OR$^e$, —C(O)NR$^c$R$^d$, —P(OR$^c$)$_2$, —P(O)R$^c$R$^b$, P(O)OR$^c$OR$^b$, —S(O)R$^b$, —S(O)NR$^c$R$^d$, —S(O)$_2$R$^b$, —S(O)$_2$NR$^c$R$^d$, —B(OR$^c$)(OR$^b$), —SiR$^b$$_3$, —C$_1$-C$_{10}$alkyl, —C$_2$-C$_{10}$ alkenyl, —C$_2$-C$_{10}$ alkynyl, aryl, cycloalkyl, heteroaryl, heterocycloalkyl, wherein said C$_1$-C$_{10}$ alkyl, C$_2$-C$_{10}$ alkenyl, C$_2$-C$_{10}$ alkynyl, aryl, cycloalkyl, heteroaryl, or heterocycloalkyl is optionally substituted;

each R$^b$ is independently H, D, C$_1$-C$_6$ alkyl, C$_2$-C$_6$ alkenyl, C$_2$-C$_6$ alkynyl, aryl, cycloalkyl, heteroaryl, heterocycloalkyl, wherein said C$_1$-C$_6$ alkyl, C$_2$-C$_6$ alkenyl, C$_2$-C$_6$ alkynyl, aryl, cycloalkyl, heteroaryl, or heterocycloalkyl is optionally substituted;

each R$^c$ or R$^d$ is independently H, D, C$_1$-C$_{10}$ alkyl, C$_2$-C$_6$ alkenyl, C$_2$-C$_6$ alkynyl, —OC$_1$-C$_6$alkyl, —O-cycloalkyl, aryl, heteroaryl, cycloalkyl, heterocycloalkyl, wherein said C$_1$-C$_{10}$ alkyl, C$_2$-C$_6$ alkenyl, C$_2$-C$_6$ alkynyl, —OC$_1$-C$_6$alkyl, —O-cycloalkyl, aryl, heteroaryl, cycloalkyl, or heterocycloalkyl, is optionally substituted;

or R$^c$ and R$^d$, together with the N atom to which they are both attached, form an optionally substituted monocyclic or multicyclic-4-10 membered heterocycloalkyl group.

Aspect 3. The compound according to either aspect 1 or aspect 2, or a pharmaceutically acceptable salt or solvate thereof, wherein said compound has the Formula IA:

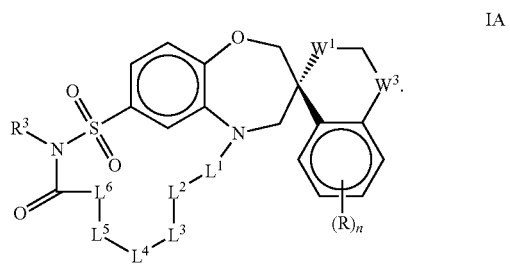

(IA)

wherein W$^1$ is —CH$_2$— and W$^3$ is —O—, or W$^1$ is —O— and W$^3$ is —CH$_2$—, or W$^1$ is —CH$_2$— and W$^3$ is —S—, or W$^1$ is —S— and W$^3$ is —CH$_2$—, or W$^1$ is —CH$_2$— and W$^3$ is —NR$^{2B}$—, or W$^1$ is —NR$^{2B}$— and W$^3$ is —CH$_2$—, or W$^1$ is —CH$_2$— and W$^3$ is —CH$_2$—.

Aspect 4. The compound according to aspect 3, or a pharmaceutically acceptable salt or solvate thereof, wherein said compound has the Formula IA-1:

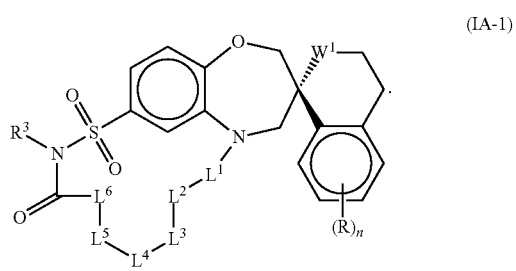

(IA-1)

Aspect 5. The compound according to aspect 4, wherein W$^1$ is —CH$_2$— or —O—.

Aspect 6. A compound according to aspect 3, or a pharmaceutically acceptable salt or solvate thereof, wherein said compound has the Formula IA-2:

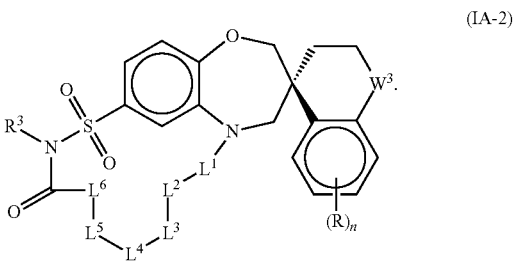

(IA-2)

Aspect 7. The compound according to aspect 6, wherein W$^3$ is —CH$_2$— or —O—.

Aspect 8. The compound according to aspect 3, or a pharmaceutically acceptable salt or solvate thereof, wherein said compound has the Formula IA-3:

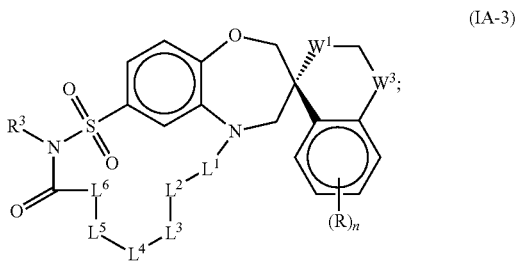

(IA-3)

wherein W¹ is —CH₂— and W³ is O, or W¹ is —O— and W³ is —CH₂—, or W¹ is —CH₂— and W³ is —CH₂—.

Aspect 9. The compound according to any one of aspects 1-8, wherein L¹ is optionally substituted C₁alkylene.

Aspect 10. The compound according to aspect 9, wherein L¹ is —CH₂—.

Aspect 11. The compound according to any one of aspects 1-10, wherein L² is optionally substituted cycloalkylene or optionally substituted heterocycloalkylene.

Aspect 12. The compound according to aspect 11, wherein L¹ is —CH₂—; and L² is optionally substituted cyclobutylene or optionally substituted pyrrolidine.

Aspect 13. The compound according to any one of aspects 1-12, wherein said compound is a compound of Formula IA-4:

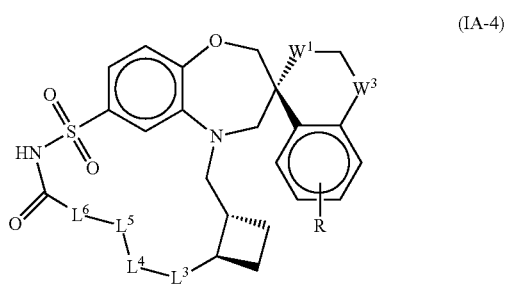

(IA-4)

or a pharmaceutically acceptable salt or solvate thereof; wherein

W¹ is —CH₂— and W³ is O, or W¹ is —O— and W³ is —CH₂—, or W¹ is —CH₂— and W³ is —CH₂—;

L³ is absent, or is —(CR⁴R⁵)$_p$—, —(CR⁴R⁵)$_p$O—, —S(O)—, —S(O)₂—, —C(=O)—, —C(=O)O—, —C(=O)NR⁶ᴬ—, —NR⁶ᴬC(O)O—, —S(=O)NR⁶ᴬ—, —NR⁶ᴬS(O)—, —S(=O)₂NR⁶ᴬ—, or —NR⁶ᴬS(O)₂—;

L⁴ is absent, or —(CR⁴R⁵)$_p$Q¹(CR⁴R⁵)$_q$—, wherein Q¹ is absent, —CR⁴ᴬ=CR⁴ᴮ—, —O—, —S—, —S(O)—, —S(O)₂—, —C(=O)—, —NR⁶—, —OC(=O)—, —C(=O)O—, —NR⁶ᴬC(O), —C(=O)NR⁶ᴬ—, NR⁶ᴬC(O)R⁶ᴮ—, —OC(=O)N(R⁶ᴬ)—, —NR⁶ᴬC(O)O—, —S(=O)NR⁶ᴬ—, —NR⁶ᴬS(O)—, —S(=O)₂NR⁶ᴬ—, or —NR⁶ᴬS(O)₂—;

L⁵ is absent, or is a 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group, wherein the 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group is optionally substituted; and L⁶ is absent, or is —(CR⁷R⁸)$_s$—, —O(CR⁷R⁸)$_t$—, —NR⁹(CR⁷R⁸)$_t$—, —S(CR⁷R⁸)$_t$—, —S(O)(CR⁷R⁸)$_t$—, —S(O)₂(CR⁷R⁸)$_t$—, —NR⁹ᴬC(O)(CR⁷R⁸)$_t$—, —C(O)NR⁹ᴬ(CR⁷R⁸)$_t$—, —R⁹ᴬC(O)O(CR⁷R⁸)$_t$—, —NR⁹ᴬC(O)NR⁹ᴮ(CR⁷R⁸)$_t$—, —NR⁹ᴬS(O)(CR⁷R⁸)$_t$—, —NR⁹ᴬS(O)₂(CR⁷R⁸)$_t$—; —CR⁴ᴬ=CR⁴ᴮ—(CR⁷R⁸)$_t$—, —C(=O)(CR⁷R⁸)$_t$—; —C(=O)(CR⁷R⁸)t-O—, or —C(=O)(CR⁷R⁸)t-NR⁶—.

Aspect 14. The compound according to any one of aspects 1-13, or a pharmaceutically acceptable salt or solvate thereof; wherein L³ absent;

L⁴ is —(CR⁴R⁵)$_p$Q¹(CR⁴R⁵)$_q$—, wherein Q¹ is absent, —CR⁴ᴬ=CR⁴ᴮ—, —O—, —S—, —S(O)—, —S(O)₂—, —C(=O)—, —NR⁶—, —OC(=O)—, —C(=O)O—, —NR⁶ᴬC(O), —C(=O)NR⁶ᴬ—, —NR⁶ᴬC(O)R⁶ᴮ—, —OC(=O)N(R⁶ᴬ)—, —NR⁶ᴬC(O)O—, —S(=O)NR⁶ᴬ—, —NR⁶ᴬS(O)—, —S(=O)₂NR⁶ᴬ—, or —NR⁶ᴬS(O)₂—;

L⁵ is absent; and

L⁶ is absent, or is —(CR⁷R⁸)$_s$—, —O(CR⁷R⁸)$_t$—, —NR⁹(CR⁷R⁸)$_t$—, —S(CR⁷R⁸)$_t$—, —S(O)(CR⁷R⁸)$_t$—, —S(O)₂(CR⁷R⁸)$_t$—, —NR⁹ᴬC(O)(CR⁷R⁸)$_t$—, —C(O)NR⁹ᴬ(CR⁷R⁸)$_t$—, —R⁹ᴬC(O)O(CR⁷R⁸)$_t$—, —NR⁹ᴬC(O)NR⁹ᴮ(CR⁷R⁸)$_t$—, —NR⁹ᴬS(O)(CR⁷R⁸)$_t$—, —NR⁹ᴬS(O)₂(CR⁷R⁸)$_t$—; —CR⁴ᴬ=CR⁴ᴮ—(CR⁷R⁸)$_t$—, —C(=O)(CR⁷R⁸)$_t$—; —C(=O)(CR⁷R⁸)t-O—, or —C(=O)(CR⁷R⁸)t-NR⁶—.

Aspect 15. The compound according to any one of aspects 1-14, wherein

L⁴ is —(CR⁴R⁵)$_p$Q¹(CR⁴R⁵)$_q$—, wherein Q¹ is —CR⁴ᴬ=CR⁴ᴮ—; and

L⁶ is absent, —O(CR⁷R⁸)$_t$—, or —NR⁹(CR⁷R⁸)$_t$—.

Aspect 16. The compound according to any one of aspects 1-15, wherein p=1;

q=1-4; and t=1.

Aspect 17. The compound according to any one of aspects 1-13, or a pharmaceutically acceptable salt or solvate thereof; wherein L³ absent;

L⁴ is —(CR⁴R⁵)$_p$Q¹(CR⁴R⁵)$_q$—, wherein Q¹ is absent, —CR⁴ᴬ=CR⁴ᴮ—, —O—, —S—, —S(O)—, —S(O)₂—, —C(=O)—, —NR⁶—, —OC(=O)—, —C(=O)O—, —NR⁶ᴬC(O), —C(=O)NR⁶ᴬ—, —NR⁶ᴬC(O)R⁶ᴮ—, —OC(=O)N(R⁶ᴬ)—, —NR⁶ᴬC(O)O—, —S(=O)NR⁶ᴬ—, —NR⁶ᴬS(O)—, —S(=O)₂ NR⁶ᴬ—, or —NR⁶ᴬS(=O)₂—;

L⁵ is a 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group, wherein the 6- to 10-membered arylene, 5- to 10-membered heteroarylene, a 3- to 12-membered cycloalkenylene, a 3- to 12-membered cycloalkenylene, a 3- to 7-membered monocyclic cycloalkylene, a 6- to 12 bicyclic cycloalkylene, a 3- to 7-membered monocyclic heterocycloalkylene, or 6- to 12-membered bicyclic heterocycloalkylene group is optionally substituted; and $L^6$ is absent, or is —$(CR^7R^8)_s$—.

Aspect 18. The compound according to any one of aspects 1-13 or 17, wherein $L^4$ is —$(CR^4R^5)_pQ^1(CR^4R^5)_q$—, wherein $Q^1$ is —$CR^{4A}$=$CR^{4B}$—, —O—, —S—, —S(O)—, —S(O)_2$—, —C(=O)—, —OC(=O)—, —C(=O)O—, —OC(=O)N($R^{6A}$)—, or —$NR^{6A}$C(O)O—;

$L^5$ is a 6- to 10-membered arylene, 5- to 10-membered heteroarylene, a 3- to 7-membered monocyclic cycloalkylene, a 3- to 7-membered monocyclic heterocycloalkylene, wherein the 6- to 10-membered arylene, 5- to 10-membered heteroarylene, a 3- to 7-membered monocyclic cycloalkylene, a 3- to 7-membered monocyclic heterocycloalkylene is optionally substituted; and $L^6$ is absent, or is —$(CR^7R^8)_s$—.

Aspect 19. The compound according to any one of aspects 1 to 14, or a pharmaceutically acceptable salt or solvate thereof; wherein $L^4$ is —$(CR^4R^5)_pQ^1(CR^4R^5)_q$— wherein p=1; q=1-3, $Q^1$ is absent, or —$CR^{4A}$=$CR^{4B}$—; $L^6$ is $(CR^7R^8)_s$, wherein s=1-2, —O$(CR^7R^8)_t$—, —$NR^9(CR^7R^8)_t$—, —S$(CR^7R^8)_t$—, —S(O)$(CR^7R^8)_t$—, or —S(O)_2(CR^7R^8)_t$—, wherein t=1.

Aspect 20. The compound according to any one of aspects 1-14 or 19, or a pharmaceutically acceptable salt or solvate thereof, wherein said compound is a compound of Formula IA-8:

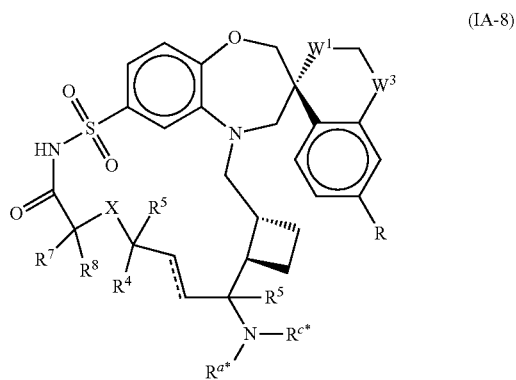

(IA-8)

wherein X is O, $NR^9$, $CR^7R^8$, S, S(O), $SO_2$;
R is halo or $C_1$-$C_6$alkyl;
----- represents a carbon-carbon single bond in which each carbon atom in the bond is substituted with $R^4$ and $R^5$, an (E)-carbon-carbon double bond, or a (Z)-carbon-carbon double bond;
$R^{a*}$ is $R^a$ wherein $R^a$ is H, —C(O)$R^b$, —C(O)O$R^c$, —C(O)N$R^cR^d$, P(OR)_2, P(O)$R^cR^b$, P(O)O$R^cOR^b$, S(O)$R^b$, S(O)N$R^cR^d$, S(O)_2$R^b$, S(O)_2N$R^cR^d$, B(O$R^c$)(O$R^b$), Si$R^b_3$, $C_1$-$C_{10}$alkyl, $C_2$-$C_{10}$ alkenyl, $C_2$-$C_{10}$ alkynyl, aryl, cycloalkyl, heteroaryl, or heterocycloalkyl, wherein said $C_1$-$C_{10}$ alkyl, $C_2$-$C_{10}$alkenyl, $C_2$-$C_{10}$ alkynyl, aryl, cycloalkyl, heteroaryl, or heterocycloalkyl is optionally substituted;
$R^{c*}$ is $R^c$ wherein $R^c$ is H, D, —$C_1$-$C_{10}$ alkyl, —$C_2$-$C_6$ alkenyl, —$C_2$-$C_6$ alkynyl, —O$C_1$-$C_6$alkyl, —O-cycloalkyl, aryl, heteroaryl, cycloalkyl, cycloalkenyl, heterocycloalkyl, or heterocycloalkenyl, wherein said $C_1$-$C_{10}$ alkyl, $C_2$-$C_6$ alkenyl, $C_2$-$C_6$ alkynyl, —O$C_1$-$C_6$alkyl, —O-cycloalkyl, aryl, heteroaryl, cycloalkyl, cycloalkenyl, heterocycloalkyl, or heterocycloalkenyl are each optionally substituted.

Aspect 21. The compound according to aspect 20, wherein ----- represents a carbon-carbon single bond in which each carbon atom in the bond is substituted with $R^4$ and $R^5$.

Aspect 22. The compound according to aspect 20, wherein ----- represents a carbon-carbon double bond substituted with $R^{4A}$ and $R^{4B}$.

Aspect 23. The compound according to aspect 22, wherein ----- represents a (E)-carbon-carbon double bond substituted with $R^{4A}$ and $R^{4B}$.

Aspect 24. The compound according to any one of aspects 20-23, wherein X is —O—, —$NR^9$—, or —$CR^7R^8$—.

Aspect 25. The compound according to any one of aspects 20-24, wherein $R^{a*}$ is $R^a$ wherein $R^a$ is H, —C(O)$R^b$, —C(O)O$R^c$, —C(O)N$R^cR^d$, —S(O)_2$R^b$, or optionally substituted $C_1$-$C_{10}$alkyl; and $R^{c*}$ is $R^c$ wherein $R^c$ is H or optionally substituted $C_1$-$C_{10}$alkyl.

Aspect 26. The compound according to any one of aspects 20-25, wherein R is —$C_1$.

Aspect 27. The compound according to any one of aspects 20-26, wherein each $R^4$ and $R^5$ is independently H or $C_1$-$C_6$alkyl.

Aspect 28. The compound according to any one of aspects 1-14 or 19, or a pharmaceutically acceptable salt or solvate thereof, wherein said compound is a compound of Formula IA-5:

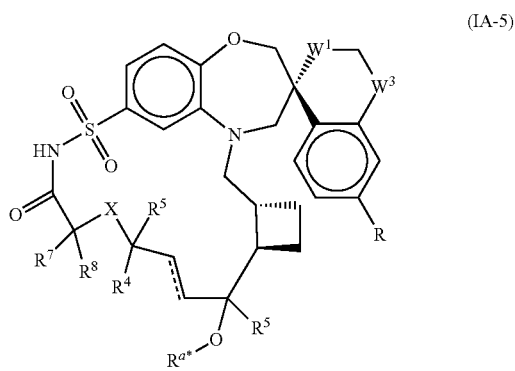

(IA-5)

wherein X is —O—, —$NR^9$—, —$CR^7R^8$—, —S—, —S(O)—, —$SO_2$—; R is halo or $C_1$-$C_6$alkyl;
----- represents a carbon-carbon single bond in which each carbon atom in the bond is substituted with $R^4$ and $R^5$, an (E)-carbon-carbon double bond substituted with $R^{4A}$ and $R^{4B}$, or a (Z)-carbon-carbon double bond substituted with $R^{4A}$ and $R^{4B}$; and $R^{a*}$ is $R^a$ wherein $R^a$ is H, —C(O)$R^b$, —C(O)O$R^c$, —C(O)N$R^cR^d$, P(OR)_2, P(O)$R^cR^b$, P(O)O$R^cOR^b$, S(O)$R^b$, S(O)N$R^cR^d$, S(O)_2$R^b$, S(O)_2N$R^cR^d$, B(O$R^c$)(O$R^b$), Si$R^b_3$, $C_1$-$C_{10}$alkyl, $C_2$-$C_{10}$ alkenyl, $C_2$-$C_{10}$ alkynyl, aryl, cycloalkyl, heteroaryl, or heterocycloalkyl, wherein said $C_1$-$C_{10}$ alkyl, $C_2$-$C_{10}$alkenyl, $C_2$-$C_{10}$ alkynyl, aryl, cycloalkyl, heteroaryl, or heterocycloalkyl is optionally substituted.

Aspect 29. The compound according to aspect 28, wherein ----- represents a carbon-carbon single bond in which each carbon atom in the bond is substituted with $R^4$ and $R^5$.

Aspect 30. The compound according to aspect 28, wherein ----- represents a carbon-carbon double bond substituted with $R^{4A}$ and $R^{4B}$.

Aspect 31. The compound according to any one of aspects 28-30 wherein X is —O—, —NR$^9$—, or —CR$^7$R$^8$—.

Aspect 32. The compound according to any one of aspects 28-31, wherein R$^{a*}$ is R$^a$ wherein R$^a$ is H, —C(O)R$^b$, —C(O)NR$^c$R$^d$, optionally substituted C$_1$-C$_{10}$alkyl, optionally substituted C$_2$-C$_{10}$alkenyl, optionally substituted C$_2$-C$_{10}$ alkynyl, optionally substituted aryl, optionally substituted cycloalkyl, optionally substituted heteroaryl, or optionally substituted heterocycloalkyl.

Aspect 33. The compound according to aspect 30, having the structure IA-6:

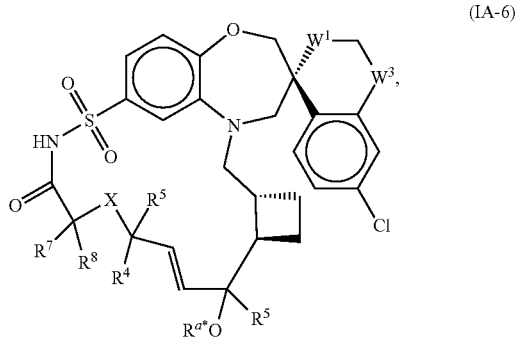

(IA-6)

or a pharmaceutically acceptable salt or solvate thereof; wherein X is —O—, —NR$^9$—, or —CR$^7$R$^8$—; and W$^1$ is —CH$_2$— and W$^3$ is O, or W$^1$ is —O— and W$^3$ is —CH$_2$—, or W$^1$ is —CH$_2$— and W$^3$ is —CH$_2$—.

Aspect 34. The compound according to any one of aspects 28-33, wherein each R$^4$ or R$^5$ is independently H, D, or C$_1$-C$_6$alkyl.

Aspect 35. The compound according to any one of aspects 20-34, wherein X is —CR$^7$R$^8$—.

Aspect 36. The compound according to any one of aspects 20-34, wherein X is —O—.

Aspect 37. The compound according to any one of aspects 20-34, wherein X is —NR$^9$—.

Aspect 38. The compound according to aspect 37, wherein X is —NR$^9$— wherein R$^9$ is H; optionally substituted —C$_1$-C$_6$alkyl; optionally substituted —C(O)OC$_1$-C$_6$alkyl; optionally substituted —SO$_2$C$_1$-C$_6$alkyl; optionally substituted —C(O)C$_1$-C$_6$alkyl; optionally substituted —C(O)NR$^c$R$^d$; or wherein R$^9$ together with either R$^7$ or R$^8$ form an optionally substituted C$_1$-C$_6$alkylene group.

Aspect 39. The compound according to aspect 38, wherein X is —NR$^9$— wherein R$^9$ is H; —C$_1$-C$_6$alkyl, optionally substituted with deuterium; —C(O)OC$_1$-C$_6$alkyl; —SO$_2$C$_1$-C$_6$alkyl; —C(O)C$_1$-C$_6$alkyl; or wherein R$^9$ together with either R$^7$ or R$^8$ form a C$_1$-C$_6$alkylene group.

Aspect 40. The compound according to aspect 39, wherein X is —NR$^9$— wherein R$^9$ is H; —CH$_3$; —CH$_2$CH$_3$, —CH$_2$CH$_2$CH$_3$, -CD$_3$, —C(O)OCH$_3$; —C(O)OC(CH$_3$)$_3$, —SO$_2$CH$_3$; or —C(O)CH$_3$.

Aspect 41. The compound according to anyone of aspects 20-40, wherein each R$^7$ and each R$^8$ is independently H, optionally substituted cycloalkyl, optionally substituted heterocycloalkyl, or optionally substituted —C$_1$-C$_6$alkyl; or R$^7$ and R$^8$ attached to the same carbon atom, together with that carbon atom, form an optionally substituted cycloalkyl ring or an optionally substituted heterocycloalkyl ring; or R$^7$ and R$^8$ attached to adjacent carbon atoms, together with those carbon atoms, form an optionally substituted cycloalkyl ring or an optionally substituted heterocycloalkyl ring.

Aspect 42. The compound of aspect 41, wherein each R$^7$ and each R$^8$ is independently H, optionally substituted 3-7 membered cycloalkyl, 4-7 membered heterocycloalkyl, or optionally substituted —C$_1$-C$_6$alkyl;
or wherein R$^7$ and R$^8$ attached to the same carbon atom, together with that carbon atom, form an optionally substituted 3-7 membered cycloalkyl ring or an optionally substituted 4-7 membered heterocycloalkyl ring;
or R$^7$ and R$^8$ attached to adjacent carbon atoms, together with those carbon atoms, form an optionally substituted 3-7 membered cycloalkyl ring or an optionally substituted 4-7 membered heterocycloalkyl ring.

Aspect 43. The compound of aspect 42, wherein R$^7$ and R$^8$ attached to the same carbon atom, together with that carbon atom, form a 3-7 membered cycloalkyl ring or 4-7 membered heterocycloalkyl ring;
or R$^7$ and R$^8$ attached to adjacent carbon atoms, together with the atoms to which they are attached, form a 3-7 membered cycloalkyl ring or 4-7 membered heterocycloalkyl ring.

Aspect 44. The compound of aspect 42, wherein R$^7$ or R$^8$ are each independently H, —CH$_3$, -cyclopropyl, —CH$_2$CH$_3$, or —CH(CH$_3$)$_2$.

Aspect 45. The compound of aspect 42, wherein R$^7$ and R$^8$ attached to the same carbon atom, together with that carbon atom, form a cyclopropyl ring, a cyclobutyl ring, or azetidinyl ring.

Aspect 46. The compound of aspect 41, wherein each R$^7$ and each R$^8$ is independently H, or a —C$_1$-C$_6$alkyl group optionally substituted with —OH; optionally substituted —OC$_1$-C$_6$alkyl; optionally substituted —(CH$_2$CH$_2$O)$_o$C$_1$-C$_6$alkyl wherein o is 1-10; or —C(O)NR$^{c1}$R$^{d1}$ wherein R$^{c1}$ and R$^{d1}$ are independently H, optionally substituted —C$_1$-C$_6$alkyl, optionally substituted cycloalkyl, or optionally substituted heterocycloalkyl; or wherein or R$^{c1}$ and R$^{d1}$, together with the N atom to which they are both attached, form an optionally substituted monocyclic or multicyclic heterocycloalkyl ring.

Aspect 47. The compound of aspect 46, wherein the —C$_1$-C$_6$alkyl group is optionally substituted with —OH; —OC$_1$-C$_6$alkyl; —(CH$_2$CH$_2$O)$_o$C$_1$-C$_6$alkyl wherein o is 1-10; or —C(O)NR$^{c1}$R$^{d1}$ wherein R$^{c1}$ and R$^{d1}$ are independently H, C$_1$-C$_6$alkyl, or 4-7 membered heterocycloalkyl; or wherein or R$^{c1}$ and R$^{d1}$, together with the N atom to which they are both attached, form a monocyclic or multicyclic 4-7 membered heterocycloalkyl ring optionally substituted with halo; —OC$_1$-C$_6$alkyl; or —C$_1$-C$_6$alkyl optionally substituted with —OH or —OC$_1$-C$_6$alkyl.

Aspect 48. The compound of any one of aspects 28-47, wherein R$^{a*}$ is R$^a$ wherein R$^a$ is H.

Aspect 49. The compound of any one of aspects 28-47, wherein R$^{a*}$ is R$^a$ wherein R$^a$ is —C(O)R$^b$.

Aspect 50. The compound of any one of aspects 28-47, wherein R$^{a*}$ is R$^a$ wherein R$^a$ is —C(O)R$^b$ wherein R$^b$ is optionally substituted —C$_1$-C$_6$alkyl.

Aspect 51. The compound of aspect 50, wherein R$^{a*}$ is R$^a$ wherein R$^a$ is —C(O)R$^b$ wherein R$^b$ is —C$_1$-C$_6$alkyl.

Aspect 52. The compound of aspect 51, wherein R$^{a*}$ is R$^a$ wherein R$^a$ is —C(O)R$^b$ wherein R$^b$ is —CH$_3$.

Aspect 53. The compound of any one of aspects 28-47, wherein R$^{a*}$ is R$^a$ wherein R$^a$ is —C(O)NR$^c$R$^d$.

Aspect 54. The compound of any one of aspects 28-47, wherein R$^{a*}$ is R$^a$ wherein R$^a$ is —C(O)NR$^c$R$^d$ wherein R$^c$ and R$^d$ are independently H; optionally substituted —OC₁-C₆alkyl; optionally substituted cycloalkyl; optionally substituted —C₁-C₆alkyl, or optionally substituted heterocycloalkyl.

Aspect 55. The compound of aspect 54, wherein $R^{a*}$ is $R^a$ wherein $R^a$ is —C(O)NR$^c$R$^d$ wherein R$^c$ and R$^d$ are independently H; optionally substituted 3-7 membered cycloalkyl; —OC₁-C₆alkyl; —C₁-C₆alkyl (optionally substituted with deuterium, halo, optionally substituted cycloalkyl, optionally substituted —OC₁-C₆alkyl, —NR$^{c1}$R$^{d1}$ wherein R$^{c1}$ and R$^{d1}$ are independently H or optionally substituted —C₁-C₆alkyl, optionally substituted 4-7 membered heterocycloalkyl, or optionally substituted 5-6 membered heteroaryl); or optionally substituted 4-7 membered heterocycloalkyl.

Aspect 56. The compound aspect 54, wherein $R^{a*}$ is $R^a$ wherein $R^a$ is —C(O)NR$^c$R$^d$ wherein R$^c$ and R$^d$ are independently H; 3-7 membered cycloalkyl; —C₁-C₆alkyl (optionally substituted with deuterium, halo, —OC₁-C₆alkyl, cycloalkyl, —NR$^{c1}$R$^{d1}$ wherein R$^{c1}$ and R$^{d1}$ are independently H or —C₁-C₆alkyl, 4-7 membered heterocycloalkyl (optionally substituted with halo, —C₁-C₆alkyl, —OH, or —OC₁-C₆alkyl), or -5-6 membered heteroaryl), —OC₁-C₆alkyl; or -4-7 membered heterocycloalkyl optionally substituted with —C₁-C₆alkyl or —OH.

Aspect 57. The compound of any one of aspects 33-39, wherein $R^{a*}$ is $R^a$ wherein $R^a$ is —C(O)NR$^c$R$^d$ wherein R$^c$ and R$^d$, together with the nitrogen atom to which they are both attached, form an optionally substituted monocyclic or multicyclic heterocycloalkyl group.

Aspect 58. The compound of aspect 47, wherein $R^{a*}$ is $R^a$ wherein $R^a$ is —C(O)NR$^c$R$^d$ wherein R$^c$ and R$^d$, together with the nitrogen atom to which they are both attached, form a monocyclic or multicyclic heterocycloalkyl group optionally substituted with -halo, —OH, optionally substituted -4-7 membered heterocycle, optionally substituted 5-6 membered heteroaryl, optionally substituted —OC₁-C₆alkyl, optionally substituted —C₁-C₆alkyl; or —NR$^{c1}$R$^{d1}$ wherein R$^{c1}$ and R$^{d1}$ are independently H or optionally substituted C₁-C₆alkyl.

Aspect 59. The compound of aspect 28-47, wherein $R^{a*}$ is $R^a$ wherein $R^a$ is —C(O)NR$^c$R$^d$ wherein R$^c$ and R$^d$, together with the nitrogen atom to which they are both attached, form a monocyclic or multicyclic-4-10 membered heterocycloalkyl group optionally substituted with -halo, —OH, -4-7 membered heterocycle, 5-6 membered heteroaryl, —OC₁-C₆alkyl, —C₁-C₆alkyl (optionally substituted with —OH, —OC₁-C₆alkyl, or NR$^{c1}$R$^{d1}$ wherein R$^{c1}$ and R$^{d1}$ are independently H or C₁-C₆alkyl); or —NR$^{c1}$R$^{d1}$ wherein R$^{c1}$ and R$^{d1}$ are independently H or C₁-C₆alkyl.

Aspect 60. The compound according to any one of aspects 28-47, wherein $R^{a*}$ is $R^a$ wherein $R^a$ is optionally substituted —C₁-C₁₀alkyl.

Aspect 61. The compound of aspect 60, wherein $R^{a*}$ is $R^a$ wherein $R^a$ is —C₁-C₁₀alkyl optionally substituted with —C(O)NR$^{c1}$R$^{d1}$, wherein R$^{c1}$ and R$^{d1}$ are independently H, optionally substituted C₁-C₆alkyl, or optionally substituted heterocyclyl; or wherein or R$^{c1}$ and R$^{d1}$ together with the N atom to which they are both attached, form an optionally substituted monocyclic or multicyclic-4-10 membered heterocycloalkyl group; —NR$^{c1}$R$^{d1}$ wherein R$^{c1}$ and R$^{d1}$ are independently H, optionally substituted C₁-C₆alkyl, optionally substituted cycloalkyl, or optionally substituted heterocycloalkyl; optionally substituted heteroaryl; —C(O)OH; or optionally substituted -heterocycloalkyl.

Aspect 62. The compound of aspect 61, wherein $R^{a*}$ is $R^a$ wherein $R^a$ is —C₁-C₁₀alkyl optionally substituted with —C(O)NR$^{c1}$R$^{d1}$, wherein R$^{c1}$ and R$^{d1}$ are independently H, C₁-C₆alkyl (optionally substituted with —OC₁-C₆alkyl), or 4-7 membered heterocycloalkyl; or wherein or R$^{c1}$ and R$^{d1}$, together with the N atom to which they are both attached, form a monocyclic or multicyclic-4-10 membered heterocycloalkyl group (optionally substituted with halo, —OC₁-C₆alkyl, or —C₁-C₆alkyl (optionally substituted with —OH or —OC₁-C₆alkyl)); —NR$^{c1}$R$^{d1}$ wherein R$^{c1}$ and R$^{d1}$ are independently H, or optionally substituted C₁-C₆alkyl; —C₄-C₅heteroaryl; —C(O)OH; or -4-7 membered heterocycloalkyl optionally substituted with halo, C₁-C₆alkyl, or —OC₁-C₆alkyl.

Aspect 63. The compound according to any one of aspects 28-62, wherein the compound has the structure (IA-7):

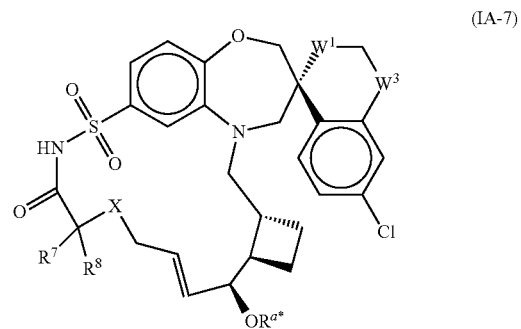

(IA-7)

wherein W¹ is —CH₂— and W³ is —O—; or W¹ is —O— and W³ is —CH₂—; or W¹ is —CH₂— and W³ is —CH₂—.

Aspect 64. The compound according to aspect 63, wherein W¹ is —CH₂— and W³ is —CH₂—.

Aspect 65. A compound, or a pharmaceutically acceptable salt or solvate thereof, wherein said compound is:

(3R,6R,7R,8E,22S)-6'-chloro-7-methoxy-12,12-ethylene-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7R,8E,12 S,22S)-6'-chloro-7-methoxy-12-methyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7R,8E,12R,22S)-6'-chloro-7-methoxy-11,12-dimethyl-15,15-dioxo-spiro[20-oxa-15-thia-1,11,14-triazatetracyclo[14.7.2.0³,⁶.0¹⁹,²⁴]pentacosa-8,16(25),17,19(24)-tetraene-22,1'-tetralin]-13-one;

(3R,6R,7R,8E,22S)-6'-chloro-7-methoxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7R,8E,22S)-6'-chloro-7-hydroxy-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7R,8E,22S)-6'-chloro-7-methoxy-11,12,12-trimethyl-15,15-dioxo-spiro[20-oxa-15-thia-1,11,14-triazatetracyclo[14.7.2.0³,⁶.0¹⁹,²⁴]pentacosa-8,16,18,24-tetraene-22,1'-tetralin]-13-one;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-Chloro-12,12-ethylene-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methylcarbamate;

[(3R,6R,7S,8E,22S)-6'-chloro-12,12-dimethyl-13,15,15-trioxo-11-(trideuteriomethyl)spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 3-(dimethylamino)azetidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-(dimethylamino)pyrrolidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 4-methyl-1,4-diazepane-1-carboxylate;

[(3R,6R,7S,8E,22S)-6'-chloro-11-ethyl-12,12-dimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-12,12-dimethyl-13,15,15-trioxo-11-propyl-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 4-methoxypiperidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[2-(dimethylamino)ethyl]-N-methyl-carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 3-methoxyazetidine-1-carboxylate;

[(3R,6R,7S,8E,22S)-6'-chloro-12,12-dimethyl-13,15,15-trioxo-spiro[11,20-dioxa-1-thia-1,14-diazatetracyclo[14.7.2.0³,⁶.0¹⁹,²⁴]pentacosa-8,16,18,24-tetraene-22,1'-tetralin]-7-yl] 3-ethoxyazetidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-methoxypyrrolidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-ethoxypyrrolidine-1-carboxylate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl]morpholine-4-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 4-(2-methoxyethyl)-1,4-diazepane-1-carboxylate;

[(3R,6R,7S,8E,22S)-7'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N,N-dimethylcarbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[(3R)-tetrahydrofuran-3-yl]carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[(3S)-tetrahydrofuran-3-yl]carbamate;

(3R,6R,7S,8E,22S)-6'-chloro-7-[2-(dimethylamino)ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7S,8E,22S)-6'-chloro-12,12-dimethyl-15,15-dioxo-7-(2-pyrrolidin-1-ylethoxy)spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-methoxypyrrolidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methoxy-N-methyl-carbamate;

[(3R,6R,7S,8E,22S)-6'-chloro-12,12-1,3-propylene-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl] N-methyl-N[2-(dimethylamino)ethyl] carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-bis(trideuteriomethyl)carbamate;

2-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl]oxy-N-tetrahydropyran-4-yl-acetamide;

[(3R,6R,7S,8E,22S)-6'-chloro-12,12-(1,3-propylene)-13,15,15-trioxo-spiro[11,20-dioxa-15-thia-1,14-diazatetracyclo

[14.7.2.0³,⁶.0¹⁹,²⁴]pentacosa-8,16,18,24-tetraene-22,1'-tetralin]-7-yl] N-methyl-N-(oxetan-3-yl)carbamate;
[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-tetrahydropyran-4-yl-carbamate;
[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-tetrahydropyran-4-yl-carbamate;
[(3R,6R,7S,8E,22S)-6'-chloro-10,12,12-trimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;
[(3R,6R,7S,8E,22S)-6'-chloro-7,12,12-trimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;
[(3R,6R,7S,8E,22S)-7'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N-methyl-N-[(3R)-tetrahydrofuran-3-yl] carbamate;
[(3R,6R,7S,8E,22S)-7'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl] N-methoxy-N-methyl-carbamate;
[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[2-(dimethylamino)ethyl]-N-methyl-carbamate;
[(3R,6R,7S,8E,22S)-6'-Chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-ethoxypyrrolidine-1-carboxylate;
[(3R,6R,7S,8E,22S)-6'-Chloro-10,10-dideuterio-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;
(3R,6R,7S,8E,22S)-7'-chloro-7-[2-(dimethylamino)ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one;
(3R,6R,7S,8E,22S)-7'-chloro-7-[2-(diethyl amino)ethoxy]-12,12-dimethyl-15,15-dioxo-spiro[11,20-dioxa-15-thia-1,14-diazatetracyclo[14.7.2.0³,⁶.0¹⁹,²⁴]pentacosa-8,16,18,24-tetraene-22,4'-chromane]-13-one;
(3R,6R,7S,8E,22S)-7'-chloro-12,12-dimethyl-15,15-dioxo-7-(2-pyrrolidin-1-ylethoxy)spiro[11,20-dioxa-15-thia-1,14-diazatetracyclo[14.7.2.0³,⁶.0¹⁹,²⁴]pentacosa-8,16,18,24-tetraene-22,4'-chromane]-13-one;
[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-(oxetan-3-yl)carbamate; or
[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate.

Aspect 66. A pharmaceutical composition comprising a compound according to any one of aspects 1 to 65 and a pharmaceutically acceptable excipient.

Aspect 67. A method of inhibiting an MCL-1 enzyme comprising contacting the MCL-1 enzyme with an effective amount of a compound of any one of aspects 1 to 65.

Aspect 68. A method of treating a disease or disorder associated with aberrant MCL-1 activity in a subject comprising administering to the subject, a compound of any one of aspects 1 to 65.

Aspect 69. The method of aspect 68, wherein the disease or disorder associated with aberrant MCL-1 activity is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

What is claimed:

1. A compound of Formula IA-5:

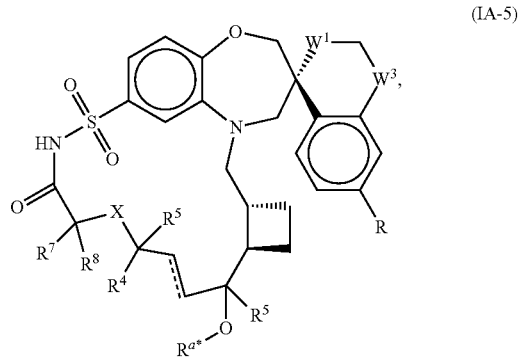

(IA-5)

or a pharmaceutically acceptable salt thereof, wherein
$W^1$ is —$CH_2$— and $W^3$ is —O—, or $W^1$ is —O— and $W^3$ is —$CH_2$—, or $W^1$ is —$CH_2$— and $W^3$ is —S—, or $W^1$ is —S— and $W^3$ is —$CH_2$— or $W^1$ is —$CH_2$— and $W^3$ is —$NR^{2B}$—, or $W^1$ is —$NR^{2B}$— and $W^3$ is —$CH_2$—, or $W^1$ is —$CH_2$— and $W^3$ is —$CH_2$—;
X is —O—, —$NR^9$—, —$CR^7R^8$—, —S—, —S(O)—, —$SO_2$—;
R is halo or $C_1$-$C_6$alkyl;
each $R^{2B}$ is independently H, D, optionally substituted $C_1$-$C_6$alkyl;
------ represents a carbon-carbon single bond in which each carbon atom in the bond is substituted with $R^4$ and $R^5$, an (E)-carbon-carbon double bond substituted with $R^{4A}$ and $R^{4B}$, or a (Z)-carbon-carbon double bond substituted with $R^{4A}$ and $R^{4B}$;
$R^{a*}$ is H, —C(O)$R^b$, —C(O)O$R^c$, —C(O)N$R^cR^d$, P(O$R^c$)$_2$, P(O)$R^cR^b$, P(O)O$R^c$O$R^b$, S(O)$R^b$, S(O)N$R^cR^d$, S(O)$_2R^b$, S(O)$_2$N$R^cR^d$, B(O$R^c$)(O$R^b$), Si$R^b_3$, $C_2$-$C_{10}$ alkenyl, $C_2$-$C_{10}$ alkynyl, aryl, cycloalkyl, heteroaryl, or heterocycloalkyl, wherein said $C_1$-$C_{10}$ alkyl, $C_2$-$C_{10}$alkenyl, $C_2$-$C_{10}$ alkynyl, aryl, cycloalkyl, heteroaryl, or heterocycloalkyl is optionally substituted;
each $R^4$ or $R^7$ is independently H, D, halo, —CN, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —O$R^a$, —S$R^a$, —N$R^cR^d$, —N$R^aR^c$, —C(O)$R^b$, —OC(O)$R^a$, —C(O)O$R^a$, —C(O)N$R^cR^d$, —S(O)$R^b$, or —S(O)$_2R^b$, wherein said $C_1$-$C_6$alkyl, —$C_2$-$C_6$alkenyl, —$C_2$-$C_6$alkynyl, aryl, heteroaryl, cycloalkyl, cycloalkenyl, heterocycloalkenyl, or heterocycloalkyl is optionally substituted;

each $R^{4A}$ or $R^{4B}$ is independently H, D, -Me, —CF$_3$ or —F;

each $R^5$ or $R^8$ is independently H, D, fluoro, —C$_1$-C$_6$alkyl, —C$_2$-C$_6$alkenyl, —C$_2$-C$_6$alkynyl, —C(O)R$^b$, —C(O)OR$^a$, —C(O)NR$^c$R$^d$, aryl, heteroaryl, cycloalkyl, cycloalkenyl, heterocycloalkyl, or heterocycloalkenyl, wherein said C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl is optionally substituted;

or $R^4$ and $R^5$ together with the C atom to which they are attached form a cycloalkyl, cycloalkenyl, heterocycloalkyl, or heterocycloalkenyl ring, each optionally substituted;

or an $R^4$ and an $R^5$ attached to adjacent carbon atoms, together with the C atoms to which they are attached, form a cycloalkyl, cycloalkenyl, heterocycloalkyl, or heterocycloalkenyl ring, each optionally substituted;

or $R^7$ and $R^8$ together with the C atom to which they are both attached form a cycloalkyl, cycloalkenyl, heterocycloalkyl, or heterocycloalkenyl ring, each optionally substituted, each optionally substituted;

or an $R^7$ and an $R^8$ attached to adjacent carbon atoms, together with the C atoms to which they are attached, form a cycloalkyl, cycloalkenyl, heterocycloalkyl, or heterocycloalkenyl ring, each optionally substituted;

each $R^9$ is independently H, D, —C$_1$-C$_6$alkyl, —C$_2$-C$_6$alkenyl, —C$_2$-C$_6$alkynyl, —OC$_1$-C$_6$alkyl, —C(O)R$^b$ —C(O)OR$^a$, —C(O)NR$^c$R$^d$, —S(O)R$^b$ or —S(O)$_2$R$^b$ aryl, heteroaryl, cycloalkyl, cycloalkenyl, heterocycloalkyl, or heterocycloalkenyl group, wherein said C$_1$-C$_6$alkyl, —C$_2$-C$_6$alkenyl, —C$_2$-C$_6$alkynyl, —OC$_1$-C$_6$alkyl, aryl, heteroaryl, cycloalkyl, cycloalkenyl, heterocycloalkyl, or heterocycloalkenyl ring, is optionally substituted;

or $R^9$ together with an $R^7$ or $R^8$ forms an optionally substituted heterocyclic alkylene;

each $R^a$ is independently H, D, alkenyl, alkynyl, aryl, cycloalkyl, cycloalkenyl, heteroaryl, heterocycloalkyl, or heterocycloalkenyl wherein said C$_1$-C$_{10}$ alkyl, C$_2$-C$_{10}$ alkenyl, C$_2$-C$_{10}$ alkynyl, aryl, cycloalkyl, cycloalkenyl, heteroaryl, heterocycloalkyl, or heterocycloalkenyl is optionally substituted;

each $R^b$, is independently H, D, —C$_1$-C$_6$ alkyl, —C$_2$-C$_6$ alkenyl, —C$_2$-C$_6$ alkynyl, aryl, cycloalkyl, cycloalkenyl, heteroaryl, heterocycloalkyl, or heterocycloalkenyl wherein said —C$_1$-C$_6$ alkyl, —C$_2$-C$_6$ alkenyl, —C$_2$-C$_6$ alkynyl, aryl, cycloalkyl, cycloalkeneyl, heteroaryl, heterocycloalkyl, or heterocycloalkenyl is optionally substituted;

each $R^c$ or $R^d$ is independently H, D, —C$_1$-C$_{10}$ alkyl, —C$_2$-C$_6$ alkenyl, —C$_2$-C$_6$ alkynyl, —O-cycloalkyl, aryl, heteroaryl, cycloalkyl, cycloalkenyl, heterocycloalkyl, or heterocycloalkenyl, wherein said C$_1$-C$_{10}$ alkyl, C$_2$-C$_6$ alkenyl, C$_2$-C$_6$ alkynyl, —O-cycloalkyl, aryl, heteroaryl, cycloalkyl, cycloalkenyl, heterocycloalkyl, or heterocycloalkenyl are each optionally substituted;

or $R^c$ and $R^d$, together with the N atom to which they are both attached, form an optionally substituted monocyclic or multicyclic heterocycloalkyl, or optionally substituted monocyclic or multicyclic heterocycloalkenyl group.

2. The compound according to claim 1, wherein ------ represents a carbon-carbon single bond in which each carbon atom in the bond is substituted with $R^4$ and $R^5$.

3. The compound according to claim 1, wherein ------ represents a carbon-carbon double bond substituted with $R^{4A}$ and $R^{4B}$.

4. The compound according to claim 1 wherein X is —O—, —NR$^9$—, or —CR$^7$R$^8$—.

5. The compound according to claim 1, wherein $R^{a*}$ is H, —C(O)R$^b$, —C(O)NR$^c$R$^d$, optionally substituted C$_1$-C$_{10}$alkyl, optionally substituted C$_2$-C$_{10}$alkenyl, optionally substituted C$_2$-C$_{10}$ alkynyl, optionally substituted aryl, optionally substituted cycloalkyl, optionally substituted heteroaryl, or optionally substituted heterocycloalkyl.

6. The compound according to claim 1, having the structure IA-6:

(IA-6)

or a pharmaceutically acceptable salt thereof; wherein
X is —O—, —NR$^9$—, or —CR$^7$R$^8$—; and
W$^1$ is —CH$_2$— and W$^3$ is O, or W$^1$ is —O— and W$^3$ is —CH$_2$—, or W$^1$ is —CH$_2$— and W$^3$ is —CH$_2$—.

7. The compound according to claim 6, wherein each $R^4$ or $R^5$ is independently H or C$_1$-C$_6$alkyl.

8. The compound according to claim 6, wherein X is —CR$^7$R$^8$—.

9. The compound according to claim 6, wherein X is —O—.

10. The compound according to claim 6, wherein X is —NR$^9$—.

11. The compound according to claim 10, wherein X is —NR$^9$— wherein $R^9$ is H;
optionally substituted —C$_1$-C$_6$alkyl; optionally substituted —C(O)OC$_1$-C$_6$alkyl; optionally substituted —SO$_2$C$_1$-C$_6$alkyl; optionally substituted —C(O)C$_1$-C$_6$alkyl; optionally substituted —C(O)NR$^c$R$^d$; or wherein $R^9$ together with either $R^7$ or $R^8$ form an optionally substituted heterocyclic alkylene.

12. The compound according to claim 6, wherein each $R^7$ and each $R^8$ is independently H, optionally substituted cycloalkyl, optionally substituted heterocycloalkyl, or optionally substituted —C$_1$-C$_6$alkyl;
or $R^7$ and $R^8$ attached to the same carbon atom, together with that carbon atom, form an optionally substituted cycloalkyl ring or an optionally substituted heterocycloalkyl ring;
or $R^7$ and $R^8$ attached to adjacent carbon atoms, together with those carbon atoms, form an optionally substituted cycloalkyl ring or and optionally substituted heterocycloalkyl ring.

13. The compound of claim 12, wherein $R^7$ or $R^8$ are each independently H, —CH$_3$, -cyclopropyl, —CH$_2$CH$_3$, or —CH(CH$_3$)$_2$.

14. The compound of claim 12, wherein $R^7$ and $R^8$ attached to the same carbon atom, together with that carbon atom, form a cyclopropyl ring, a cyclobutyl ring, or azetidinyl ring.

15. The compound of claim 12, wherein each $R^7$ and each $R^8$ is independently H or an optionally substituted —$C_1$-$C_6$alkyl group wherein the optional sub substituents are:
—OH,
optionally substituted —$OC_1$-$C_6$alkyl,
optionally substituted —$(CH_2CH_2O)_oC_1$-$C_6$alkyl wherein o is 1-10, or
—$C(O)NR^{c1}R^{d1}$ wherein $R^{c1}$ and $R^{d1}$ are independently H, optionally substituted —$C_1$-$C_6$alkyl, optionally substituted cycloalkyl, or optionally substituted heterocycloalkyl; or wherein $R^{c1}$ and $R^{d1}$, together with the N atom to which they are both attached, form an optionally substituted monocyclic or multicyclic heterocycloalkyl ring.

16. The compound of claim 1, wherein $R^{a*}$ is H.

17. The compound of claim 1, wherein $R^{a*}$ is —$C(O)R^b$.

18. The compound of claim 1, wherein $R^{a*}$ is —$C(O)NR^cR^d$.

19. The compound of claim 18, wherein $R^{a*}$ is —$C(O)NR^cR^d$ wherein $R^c$ and $R^d$ are independently H; optionally substituted —$OC_1$-$C_6$alkyl; optionally substituted cycloalkyl; optionally substituted —$C_1$-$C_6$alkyl, or optionally substituted heterocycloalkyl.

20. The compound of claim 18, wherein $R^{a*}$ —$C(O)NR^cR^d$ wherein $R^c$ and $R^d$, together with the nitrogen atom to which they are both attached, form an optionally substituted monocyclic or multicyclic heterocycloalkyl group.

21. The compound according to claim 1, wherein $R^{a*}$ is optionally substituted —$C_1$-$C_{10}$alkyl.

22. The compound according to claim 6, wherein the compound has the structure (IA-7):

(IA-7)

wherein $W^1$ is —$CH_2$— and $W^3$ is —O—; or $W^1$ is —O— and $W^3$ is —$CH_2$—; or $W^1$ is —$CH_2$— and $W^3$ is —$CH_2$—.

23. The compound according to claim 22, wherein $W^1$ is —$CH_2$— and $W^3$ is —$CH_2$—.

24. A compound, or a pharmaceutically acceptable salt thereof, wherein said compound is:
(3R,6R,7R,8E,22S)-6'-chloro-7-methoxy-12,12-ethylene-15,15-dioxo-spiro[11,20-dioxa-15-thia-1,14-diazatetracyclo[14.7.2.03,6.019,24]pentacosa-8,16,18, 24-tetraene-22,1'-tetralin]-13-one;
(3R,6R,7R,8E,12S,22S)-6'-chloro-7-methoxy-12-methyl-15,15-dioxo-spiro[11,20-dioxa-15-thia-1,14-diazatetracyclo[14.7.2.03,6.019,24]pentacosa-8,16,18,24-tetraene-22,1'-tetralin]-13-one;
(3R,6R,7R,8E,12R,22S)-6'-chloro-7-methoxy-11,12-dimethyl-15,15-dioxo-spiro[20-oxa-15-thia-1,11,14-triazatetracyclo[14.7.2.03,6.019,24]pentacosa-8,16(25), 17,19(24)-tetraene-22,1'-tetralin]-13-one;
(3R,6R,7R,8E,22S)-6'-chloro-7-methoxy-12,12-dimethyl-15,15-dioxo-spiro[11,20-dioxa-15-thia-1,14-diazatetracyclo[14.7.2.03,6.019,24]pentacosa-8,16,18, 24-tetraene-22,1'-tetralin]-13-one;
(3R,6R,7R,8E,22S)-6'-chloro-7-hydroxy-12,12-dimethyl-15,15-dioxo-spiro[11,20-dioxa-15-thia-1,14-diazatetracyclo[14.7.2.03,6.019,24]pentacosa-8,16,18, 24-tetraene-22,1'-tetralin]-13-one;
(3R,6R,7R,8E,22S)-6'-chloro-7-methoxy-11,12,12-trimethyl-15,15-dioxo-spiro[20-oxa-15-thia-1,11,14-triazatetracyclo[14.7.2.03,6.019,24]pentacosa-8,16,18,24-tetraene-22,1'-tetralin]-13-one;
[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl]N,N-dimethylcarbamate;
[(3R,6R,7S,8E,22S)-6'-Chloro-12,12-ethylene-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl]N,N-dimethylcarbamate;
[(3R,6R,7S,8E,22S)-6'-chloro-11,12,12-trimethyl-13,15, 15-trioxo-spiro[20-oxa-15-thia-1,11,14-triazatetracyclo[14.7.2.03,6.019,24]pentacosa-8,16,18,24-tetraene-22,1'-tetralin]-7-yl]N,N-dimethylcarbamate;
[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.03,6.019,24]pentacosa-8,16,18, 24-tetraene-22,1'-tetralin]-7-yl]N,N-dimethylcarbamate;
[(3R,6R,7S,8E,22S)-6'-chloro-11,12,12-trimethyl-13,15, 15-trioxo-spiro[20-oxa-15-thia-1,11,14-triazatetracyclo[14.7.2.03,6.019,24]pentacosa-8,16,18,24-tetraene-22,1'-tetralin]-7-yl]N-methylcarbamate;
[(3R,6R,7S,8E,22S)-6'-chloro-12,12-dimethyl-13,15,15-trioxo-11-(trideuteriomethyl)spiro[20-oxa-15-thia-1, 11,14-triazatetracyclo[14.7.2.03,6.019,24]pentacosa-8, 16,18,24-tetraene-22,1'-tetralin]-7-yl]N,N-dimethylcarbamate;
[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl]3-(dimethylamino)azetidine-1-carboxylate;
[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl] (3R)-3-(dimethylamino)pyrrolidine-1-carboxylate;
[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl]4-methyl-1,4-diazepane-1-carboxylate;
[(3R,6R,7S,8E,22S)-6'-chloro-11-ethyl-12,12-dimethyl-13,15,15-trioxo-spiro[20-oxa-15-thia-1,11,14-triazatetracyclo[14.7.2.03,6.019,24]pentacosa-8,16,18,24-tetraene-22,1'-tetralin]-7-yl]N,N-dimethylcarbamate;
[(3R,6R,7S,8E,22S)-6'-chloro-12,12-dimethyl-13,15,15-trioxo-11-propyl-spiro[20-oxa-15-thia-1,11,14-triazatetracyclo[14.7.2.03,6.019,24]pentacosa-8,16,18,24-tetraene-22,1'-tetralin]-7-yl]N,N-dimethylcarbamate;
[(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22, 1'-tetralin]-7-yl]4-methoxypiperidine-1-carboxylate;
[(3R,6R,7S,8E,22S)-6'-chloro-12,12-dimethyl-13,15,15-trioxo-spiro[11,20-dioxa-15-thia-1,14-diazatetracyclo

[14.7.2.0³,⁶.0¹⁹,²⁴]pentacosa-8,16,18,24-tetraene-22,1'-tetralin]-7-yl]N-[2-(dimethylamino)ethyl]-N-methyl-carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 3-methoxyazetidine-1-carboxylate;

[(3R,6R,7S,8E,22S)-6'-chloro-12,12-dimethyl-13,15,15-trioxo-spiro[11,20-dioxa-1-thia-1,14-diazatetracyclo[14.7.2.0³,⁶.0¹⁹,²⁴]pentacosa-8,16,18,24-tetraene-22,1'-tetralin]-7-yl] 3-methoxyazetidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-methoxypyrrolidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-ethoxypyrrolidine-1-carboxylate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] morpholine-4-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] 4-(2-methoxyethyl)-1,4-diazepane-1-carboxylate;

[(3R,6R,7S,8E,22S)-7'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,4'-chromane]-7-yl]N,N-dimethylcarbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[(3R)-tetrahydrofuran-3-yl]carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-[(3S)-tetrahydrofuran-3-yl]carbamate;

(3R,6R,7S,8E,22S)-6'-chloro-7-[2-(dimethylamino)ethoxy]-12,12-dimethyl-15,15-dioxo-spiro[1 1,20-dioxa-15-thia-1,14-diazatetracyclo[14.7.2.0³,⁶.0¹⁹,²⁴]pentacosa-8,16,18,24-tetraene-22,1'-tetralin]-13-one;

(3R,6R,7S,8E,22S)-6'-chloro-12,12-dimethyl-15,15-dioxo-7-(2-pyrrolidin-1-ylethoxy)spiro[11,20-dioxa-15-thia-1,14-diazatetracyclo[14.7.2.0³,⁶.0¹⁹,²⁴]pentacosa-8,16,18,24-tetraene-22,1'-tetralin]-13-one;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] (3R)-3-methoxypyrrolidine-1-carboxylate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methoxy-N-methyl-carbamate;

[(3R,6R,7S,8E,22S)-6'-chloro-12,12-1,3-propylene-13,15,15-trioxo-spiro[11,20-dioxa-15-thia-1,14-diazatetracyclo[14.7.2.0³,⁶.0¹⁹,²⁴]pentacosa-8,16(25),17,19(24)-tetraene-22,1'-tetralin]-7-yl] N-methyl-N[2-(dimethylamino)ethyl] carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-11,12,12-trimethyl-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate;

[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-bis(trideuteriomethyl)carbamate;

2-[(3R,6R,7S,8E,22S)-6'-chloro-12,12-dimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl]oxy-N-tetrahydropyran-4-yl-acetamide;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-(oxetan-3-yl)carbamate;

[(3R,6R,7S,8E,22S)-6'-chloro-12,12-(1,3-propylene)-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N-methyl-N-tetrahydropyran-4-yl-carbamate;

[(3R,6R,7S,8E,22S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-tetrahydropyran-4-yl-carbamate;

[(3R,6R,7S,8E,22S)-6'-chloro-10,12,12-trimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7S,8E,22S)-6'-chloro-7,12,12-trimethyl-13,15,15-trioxo-spiro[11,20-dioxa-15-thia-1,14-diazatetracyclo[14.7.2.0³,⁶.0¹⁹,²⁴]pentacosa-8,16,18,24-tetraene-22,1'-tetralin]-7-yl] N,N-dimethylcarbamate;

[(3R,6R,7 S, 8E,22 S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-(oxetan-3-yl)carbamate; or

[(3R,6R,7 S, 8E,22 S)-6'-chloro-11-methyl-12,12-(1,3-propylene)-13,15,15-trioxo-spiro[20-oxa-15-thia-1,11,14-triazatetracyclo[14.7.2.0³,⁶.0¹⁹,²⁴]pentacosa-8,16,18,24-tetraene-22,1'-tetralin]-7-yl] N-methyl-N-[(3R)-tetrahydrofuran-3-yl]carbamate.

25. A pharmaceutical composition comprising a compound according to claim 1 and a pharmaceutically acceptable excipient.

26. A method of treating colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer in a subject comprising administering to the subject, a compound of claim 1.

27. The compound according to claim 24, or a pharmaceutically acceptable salt thereof, wherein said compound is [(3R,6R,7S,8E,22S)-6'-chloro-12, 12-dimethyl-13,15,15-trioxo-spiro[11,20-dioxa-15-thia-1,14-diazatetracyclo [14.7.2.03,6.019,24]pentacosa-8,16,18,24-tetraene-22,1'-tetralin]-7-yl] N,N-dimethylcarbamate.

28. A pharmaceutical composition comprising a compound according to claim 24 and a pharmaceutically acceptable excipient.

29. The pharmaceutical composition according to claim 28, wherein said compound is [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate, or a pharmaceutically acceptable salt thereof.

30. A method of treating colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer in a subject comprising administering to the subject, a compound of claim 24.

31. The method according to claim 30, wherein said compound is [(3R,6R,7S,8E,22S)-6'-chloro-12,12-dimethyl-13,15,15-trioxo-spiro[11,20-dioxa-15-thia-1,14-diazatetracyclo[14.7.2.03,6.019,24]pentacosa-8,16,18,24-tetraene-22,1'-tetralin]-7-yl] N,N-dimethylcarbamate, or a pharmaceutically acceptable salt thereof.

* * * * *